(12) United States Patent
Wan et al.

(10) Patent No.: US 11,639,350 B2
(45) Date of Patent: May 2, 2023

(54) HETEROARYLDIHYDROPYRIMIDINE DERIVATIVES AND METHODS OF TREATING HEPATITIS B INFECTIONS

(71) Applicant: Janssen Pharmaceutica NV, Beerse (BE)

(72) Inventors: Zhao-Kui Wan, Lexington, MA (US); Yimin Jiang, Londonderry, NH (US); Xuedong Dai, Shanghai (CN); Qian Liu, Shanghai (CN); Wing Shun Cheung, Hoboken, NJ (US); Gang Deng, Shanghai (CN); Liqiang Fu, Shanghai (CN)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/624,140

(22) PCT Filed: Jun. 26, 2018

(86) PCT No.: PCT/CN2018/092849
§ 371 (c)(1),
(2) Date: Dec. 18, 2019

(87) PCT Pub. No.: WO2019/001420
PCT Pub. Date: Jan. 3, 2019

(65) Prior Publication Data
US 2020/0172532 A1 Jun. 4, 2020

(30) Foreign Application Priority Data
Jun. 27, 2018 (WO) ................ PCT/CN2017/090266

(51) Int. Cl.
*C07D 401/04* (2006.01)
*C07D 417/04* (2006.01)
*C07D 417/14* (2006.01)
*A61P 31/20* (2006.01)

(52) U.S. Cl.
CPC ............ *C07D 417/14* (2013.01); *A61P 31/20* (2018.01); *C07D 401/04* (2013.01); *C07D 417/04* (2013.01)

(58) Field of Classification Search
CPC ................ C07D 401/04; C07D 417/04; C07D 417/14
See application file for complete search history.

(56) References Cited

U.S. PATENT DOCUMENTS

| 6,696,451 B1 | 2/2004 | Stoltefuss |
| 8,802,669 B2 | 8/2014 | Li |
| 9,938,301 B2 | 4/2018 | He |
| 2003/0232842 A1 | 12/2003 | Goldmann et al. |
| 2015/0252057 A1 | 9/2015 | Guo |
| 2016/0083383 A1 | 3/2016 | Guo |
| 2020/0115381 A1 | 4/2020 | Ren et al. |

FOREIGN PATENT DOCUMENTS

| CN | 1305471 | 7/2001 |
| CN | 103626752 | 3/2014 |
| CN | 103664897 A | 3/2014 |
| CN | 103664899 A | 3/2014 |
| CN | 103664925 A | 3/2014 |
| CN | 104144924 | 11/2014 |
| CN | 104302626 | 1/2015 |
| CN | 107501257 A | 12/2017 |
| CN | 108947996 | 12/2018 |
| WO | 199954326 A1 | 10/1999 |
| WO | 200145712 | 6/2001 |
| WO | 200168641 A1 | 9/2001 |
| WO | 2008154817 A1 | 12/2008 |
| WO | 2009016225 | 2/2009 |
| WO | 2010/069147 A1 | 6/2010 |
| WO | 2010148631 A1 | 12/2010 |
| WO | 2013006394 A1 | 1/2013 |
| WO | 2013019967 A1 | 2/2013 |
| WO | 2013/096744 A1 | 6/2013 |
| WO | 2013102655 A1 | 7/2013 |

(Continued)

OTHER PUBLICATIONS

Bourne, et al., "Small-Molecule Effectors of Hepatitis B Virus Capsid Assembly Give Insight into Virus Life Cycle", Journal of Virology, vol. 82(20): pp. 10262-10270 (Oct. 2008).
Qui, et al., "Discovery and Pre-Clinical Characterization of Third-Generation 4-H Heteroaryldihydropyrimidine (HAP) Analogues as Hepatitis B Virus (HBV) Capsid Inhibitors", Journal of Medicinal Chemistry, vol. 60 (8); pp. 3352-3371 (2017).

(Continued)

*Primary Examiner* — Brian E McDowell
(74) *Attorney, Agent, or Firm* — Ice Miller LLP

(57) ABSTRACT

Provided herein are compounds useful for the treatment of HBV infection in a subject in need thereof, pharmaceutical compositions thereof, and methods of inhibiting, suppressing, or preventing HBV infection in the subject, and the compound has the structure of Formula I

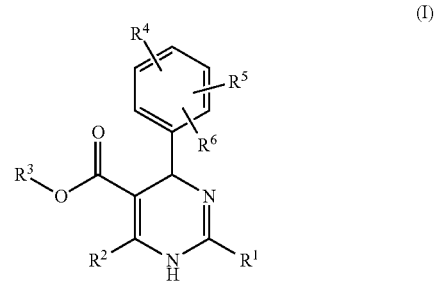

(I)

including any possible deuterated isomers, stereoisomers or tautomeric forms thereof.

23 Claims, No Drawings
Specification includes a Sequence Listing.

(56) References Cited

FOREIGN PATENT DOCUMENTS

| WO | 2014/029193 A1 | 2/2014 |
|---|---|---|
| WO | 2014037480 A1 | 3/2014 |
| WO | 2014106019 A2 | 7/2014 |
| WO | 2014184328 A1 | 11/2014 |
| WO | 2015074546 | 5/2015 |
| WO | 2015078392 | 6/2015 |
| WO | 2015132276 A1 | 9/2015 |
| WO | 2015144093 A1 | 10/2015 |
| WO | 2015180631 A1 | 12/2015 |
| WO | 2016/016316 | 2/2016 |
| WO | 2016146508 | 9/2016 |
| WO | 2016146598 A1 | 9/2016 |
| WO | 2017011552 A1 | 1/2017 |
| WO | 2017/064156 A1 | 4/2017 |
| WO | 2017064156 A1 | 4/2017 |
| WO | 2017076791 A1 | 5/2017 |
| WO | 2017108630 A1 | 6/2017 |
| WO | 2017140750 A1 | 8/2017 |
| WO | 2018036941 A1 | 3/2018 |
| WO | 2018045911 | 3/2018 |
| WO | 2018050571 A1 | 3/2018 |
| WO | 2008070707 | 6/2018 |
| WO | 2019001420 A1 | 1/2019 |
| WO | 2020001448 A1 | 6/2019 |
| WO | 2019/214610 A1 | 11/2019 |
| WO | 2020125729 A1 | 6/2020 |
| WO | 2020125730 A1 | 6/2020 |

OTHER PUBLICATIONS

Ren, et al., "Discovery of hepatitis B virus capsid assembly inhibitors leading to a heteroaryldihydropyrimidine based clinical candidate (GLS4)", Bioorganic & Medicinal Chemistry, vol. 25; pp. 1042-1056 (2017).
Tu, et al., "Exploring the binding mechanism of Heteroaryldihydropyrimidines and Hepatitis B Virus capsid combined 3D-QSAR and molecular dynamics", Antiviral Research, vol. 137: pp. 151-164 (2017).
International Search Report and Written Opinion dated Sep. 27, 2018 for PCT Application No. PCT/CN2018/092849.
F. Z. Dorwald, Side Reactions in Organic Synthesis: A Guide to Successful Synthesis Design, WILEY-VCH, pp. 1-6 (2005).
Shlenev, et al., "2-Halobenzoyl Chlorides in the Synthesis of (1,3,4) Thiadiazolo (3,2,-a) quinazolin-5-one Derivatives", Russian Journal of Organic Chemistry, (2017), pp. 1870-1877, vol. 53(12).
V. C. Jordan, "Tamoxifen: A Most Unlikely Pioneering Medicine", Nature Reviews Drug Discovery, vol. 2; pp. 205-213, (Mar. 2003).
Vippagunta, et al., "Crystalline solids", Advanced Drug Delivery Reviews, vol. 48 (1); pp. 3-26 (2001).
PubChem "Ethyl 4-(2-bromo-4-fluorophenyl)-6-[4-(diethylcarbamoyl)piperazin-1-yl]-2-(1,3-thiazol-2-yl)-1,4-dihydropyrimidine-5-carboxylate", XP055806417, Database Accession No. 46852028 (Aug. 30, 2010).
Pubchem, "Ethyl 4-(2-bromo-4-fluorophenyl)-6-[4-(dimethylcarbamoyl)piperazin-1-yl]-2-(1,3-thiazol-2-yl)-1,4-dihydropyrimidine-5-carboxylate", Database Accession No. 46852027 XP055806416 (Aug. 30, 2010).
Zhang, et al., "Direct Amination of Y-Halo-B-ketoesters with Anilines", The Journal of Organic Chemistry, vol. 77: pp. 3462-3467 (2012).
International Search Report and Written Opinion dated Jul. 25, 2019 for PCT Application No. PCT/CN2019/085838.
International Search Report and Written Opinion dated Mar. 19, 2020 for International PCT Application No. PCT/CN2019/1267353.
International Search Report dated Nov. 3, 2020 in corresponding PCT/CN2020/105764.
International Search Report dated Nov. 3, 2020 in corresponding PCT/CN2020/105765.
International Search Report dated Nov. 3, 2020 in corresponding PCT/CN2020/105767.

HETEROARYLDIHYDROPYRIMIDINE DERIVATIVES AND METHODS OF TREATING HEPATITIS B INFECTIONS

This application is a national stage under 35 U.S.C. § 371 of PCT Application No. PCT/CN2018/092849, filed on Jun. 26, 2018, which claims priority under 35 U.S.C. § 365(b) to PCT/CN2017/090266, filed Jun. 27, 2017.

BACKGROUND

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to sub-optimal treatment options and sustained rates of new infections in most parts of the developing world. Current treatments do not provide a cure and are limited to only two classes of agents (interferon alpha and nucleoside analogues/inhibitors of the viral polymerase); drug resistance, low efficacy, and tolerability issues limit their impact. The low cure rates of HBV are attributed at least in part to the fact that complete suppression of virus production is difficult to achieve with a single antiviral agent. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

The HBV capsid protein plays essential functions during the viral life cycle. HBV capsid/core proteins form metastable viral particles or protein shells that protect the viral genome during intercellular passage, and also play a central role in viral replication processes, including genome encapsidation, genome replication, and virion morphogenesis and egress. Capsid structures also respond to environmental cues to allow un-coating after viral entry. Consistently, the appropriate timing of capsid assembly and disassembly, the appropriate capsid stability and the function of core protein have been found to be critical for viral infectivity.

There is a need in the art for therapeutic agents that can increase the suppression of virus production and that can treat, ameliorate, or prevent HBV infection. Administration of such therapeutic agents to an HBV infected patient, either as monotherapy or in combination with other HBV treatments or ancillary treatments, will lead to significantly reduced virus burden, improved prognosis, diminished progression of the disease and enhanced seroconversion rates.

Background art on dihydropyrimidines for use in the treatment of HBV includes WO2013/102655 and WO9954326.

SUMMARY

Provided herein are compounds useful for the treatment of HBV infection in a subject in need thereof. Thus, in an aspect, provided herein is a compound of Formula I:

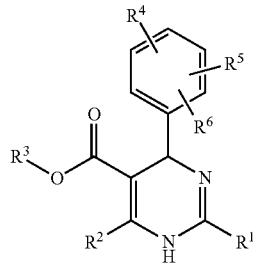

including any possible deuterated isomers, stereoisomers or tautomeric forms thereof, wherein:

$R^1$ is selected from aryl or heteroaryl, each optionally substituted with one or more halogen;

$R^2$ is selected from the group consisting of a 4-7 membered unsubstituted saturated ring, a 3-7 membered substituted saturated ring and a 5-12 membered fused, spiro or bridged bicyclic unsubstituted or substituted saturated ring, such saturated rings each optionally comprising one or more heteroatoms and wherein said substituted saturated rings are substituted with one or more substituents each independently selected from the group consisting of halogen, oxo, hydroxyl, cyano, $C_1$-$C_3$alkyl, $C_1$-$C_3$alkyloxy, hydroxyC$_1$-$C_3$alkyl or —X—$R^7$.

$R^3$ is $C_1$-$C_4$alkyl;

$R^4$, $R^5$ and $R^6$ independently are selected from the group consisting of hydrogen, $C_1$-$C_3$alkyl and halogen;

—X—$R^7$ is selected from the group consisting of —SO$_2$—$R^7$, —SO$_2$—R—(CH$_2$)$_n$—$R^7$, —SO$_2$NR$^8$R$^7$, —NR$^8$S(=O)(=NH)—$R^7$, —NR$^8$S(=O)NR$^8$—$R^7$, —NR$^8$C(=O)NR$^8$—$R^7$, —S(=O)(=NH)NR$^8$—$R^7$, —S(=O)(=NH)—$R^7$, —NR$^8$—(CH$_2$)$_n$—SO$_2$—$R^7$, —NR$^8$SO$_2$—NR$^8$R$^7$, —OC(=O)—$R^7$, —C(=O)—$R^7$, —(CH$_2$)$_n$—C(=O)O—$R^7$, —C(=O)NR$^8$—$R^7$, —NR$^8$C(=O)—$R^7$, —NR$^8$C(=O)O—$R^7$, —OC(=O)NR$^8$—$R^7$ and —NR$^8$—$R^7$;

$R^7$ and $R^8$ each independently are selected from hydrogen or a substituent selected from the group consisting of $C_1$-$C_4$alkyl, aryl, heteroaryl and a 3-7 membered saturated ring optionally containing one or more heteroatoms, each of such substituents from this group may optionally be substituted with one or more $R^9$ and $R^{10}$;

or $R^7$ and $R^8$ when attached to a nitrogen can be taken together to form a 3-7 membered saturated ring;

$R^9$ and $R^{10}$ each independently are selected from —OR$^{11}$, oxo, $C_1$-$C_4$alkyl optionally substituted with one or two $R^{11}$, —NHC(=O)OR$^{11}$, —C(=O)R$^{11}$, —(CH$_2$)$_n$—C(=O)OR$^{11}$, —C(=O)NH$_2$, —CN, halogen (more particularly fluoro), or Phenyl;

each $R^{11}$ independently is $C_1$-$C_4$ alkyl, —(CH$_2$)$_n$—OR$^{11}$, or hydrogen;

each n independently being an integer of from 0 to 4;

or a pharmaceutically acceptable salt or a solvate thereof.

In an embodiment, $R^2$ is selected from the group consisting of a 3-7 membered saturated ring and a 5-12 membered fused, spiro or bridged bicyclic saturated ring, such saturated rings each optionally comprising one or more heteroatoms and each such saturated ring optionally substituted with one or more substituents each independently selected from the group consisting of halogen, oxo, hydroxyl, cyano, $C_1$-$C_3$alkyl, $C_1$-$C_3$alkyloxy, hydroxyC$_1$-$C_3$alkyl or —X—$R^7$;

—X—R$^7$ is selected from the group consisting of —SO$_2$—R$^7$, —SO$_2$NR$^8$R$^7$, —NR$^8$S(=O)(=NH)—R$^7$, —NR$^8$SO$_2$NR$^8$R$^7$, —NR$^8$C(=O)NR$^8$—R$^7$, —S(=O)(=NH)NR$^8$—R$^7$, —S(=O)(=NH)—R$^7$, —NR$^8$SO$_2$—R$^7$, —OC(=O)—R$^7$, —C(=O)O—R$^7$, —C(=O)O—R$^7$, —C(=O)NR$^8$—R$^7$, —NR$^8$C(=O)—R$^7$, —NR$^8$C(=O)O—R$^7$, —OC(=O)NR$^8$—R$^7$ and —NR$^8$—R$^7$;

R$^9$ represents —OR$^{10}$, oxo, C$_1$-C$_4$alkyl, —NHC(=O)OR$^{10}$, —C(=O)R$^{10}$, —C(=O)OR$^{10}$;

R$^{10}$ is C$_1$-C$_4$ alkyl or hydrogen.

In another aspect, provided herein is a pharmaceutical composition comprising at least one compound of Formula I, or a pharmaceutically acceptable salt thereof, together with a pharmaceutically acceptable carrier.

In another aspect, provided herein is a pharmaceutical composition comprising at least one disclosed compound, together with a pharmaceutically acceptable carrier. In another aspect, provided herein is a method of treating an HBV infection in an individual in need thereof, comprising administering to the individual a therapeutically effective amount of a compound of Formula I or a pharmaceutically acceptable salt thereof.

In another aspect, provided herein is a method of inhibiting or reducing the formation or presence of HBV DNA-containing particles or HBV RNA-containing particles in an individual in need thereof, comprising administering to the individual a therapeutically effective amount of a compound of Formula I, or a pharmaceutically acceptable salt thereof.

In an embodiment, any of the methods provided herein can further comprising administering to the individual at least one additional therapeutic agent selected from the group consisting of an HBV polymerase inhibitor, immunomodulatory agents, interferon, viral entry inhibitor, viral maturation inhibitor, capsid assembly modulator, reverse transcriptase inhibitor, a cyclophilin/TNF inhibitor, a TLR-agonist, an HBV vaccine, and any combination thereof.

DETAILED DESCRIPTION

Provided herein are compounds, e.g., the compounds of I, or pharmaceutically acceptable salts thereof, that are useful in the treatment and prevention of HBV infection in subject.

Without being bound to any particular mechanism of action, these compounds are believed to modulate or disrupt HBV assembly and other HBV core protein functions necessary for HBV replication or the generation of infectious particles and/or may disrupt HBV capsid assembly leading to empty capsids with greatly reduced infectivity or replication capacity. In other words, the compounds provided herein may act as capsid assembly modulators.

The compounds provided herein have potent antiviral activity, exhibit favorable metabolic properties, tissue distribution, safety and pharmaceutical profiles, and are suitable for use in humans. Disclosed compounds may modulate (e.g., accelerate, delay, inhibit, disrupt or reduce) normal viral capsid assembly or disassembly, bind capsid or alter metabolism of cellular polyproteins and precursors. The modulation may occur when the capsid protein is mature, or during viral infectivity. Disclosed compounds can be used in methods of modulating the activity or properties of HBV cccDNA, or the generation or release of HBV RNA particles from within an infected cell.

In one embodiment, the compounds described herein are suitable for monotherapy and are effective against natural or native HBV strains and against HBV strains resistant to currently known drugs. In another embodiment, the compounds described herein are suitable for use in combination therapy.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used herein, the term "capsid assembly modulator" refers to a compound that disrupts or accelerates or inhibits or hinders or delays or reduces or modifies normal capsid assembly (e.g., during maturation) or normal capsid disassembly (e.g., during infectivity) or perturbs capsid stability, thereby inducing aberrant capsid morphology and function. In one embodiment, a capsid assembly modulator accelerates capsid assembly or disassembly, thereby inducing aberrant capsid morphology. In another embodiment, a capsid assembly modulator interacts (e.g. binds at an active site, binds at an allosteric site, modifies or hinders folding and the like) with the major capsid assembly protein (CA), thereby disrupting capsid assembly or disassembly. In yet another embodiment, a capsid assembly modulator causes a perturbation in structure or function of CA (e.g., ability of CA to assemble, disassemble, bind to a substrate, fold into a suitable conformation, or the like), which attenuates viral infectivity or is lethal to the virus.

As used herein, the term "treatment" or "treating" is defined as the application or administration of a therapeutic agent, i.e., a disclosed compound (alone or in combination with another pharmaceutical agent), to a patient, or application or administration of a therapeutic agent to an isolated tissue or cell line from a patient (e.g., for diagnosis or ex vivo applications), who has an HBV infection, a symptom of HBV infection or the potential to develop an HBV infection, with the purpose to cure, heal, alleviate, relieve, alter, remedy, ameliorate, improve or affect the HBV infection, the symptoms of HBV infection, or the potential to develop an HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e., $C_1$-$C_3$alkyl means an alkyl having one to three carbon atoms, $C_1$-$C_4$alkyl means an alkyl having one to four carbon) and includes straight and branched chains. Examples include methyl, ethyl, propyl, isopropyl, butyl, isobutyl, tert-butyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "3-7 membered saturated ring" refers to a mono cyclic non-aromatic saturated radical, wherein each of the atoms forming the ring (i.e., skeletal atoms) is a carbon atom, unless such ring contains one or more heteroatoms if so further defined. 3-7 Membered saturated rings include groups having 3 to 7 ring atoms. Monocyclic 3-7 membered saturated rings include, but are not limited to, cyclopropyl, cyclobutyl, cyclopentyl, cyclohexyl, cycloheptyl.

As used herein, 3-7 membered saturated ring optionally comprising one or more heteroatoms refers to a heteroalicyclic group containing one or more, more in particular, one, two or three, even more in particular, one or two, and most particular, one ring heteroatoms each selected from O, S, and N. In one embodiment, each heterocyclyl group has from 3 to 7 atoms in its ring system, with the proviso that the ring of said group does not contain two adjacent O or S atoms. The heterocyclic system may be attached to the remainder of the molecule, unless otherwise stated, at any heteroatom or carbon atom that affords a stable structure.

An example of a 3-membered heterocyclyl group includes, and is not limited to, aziridine. Examples of 4-membered heterocycloalkyl groups include, and are not limited to, azetidine and a beta lactam. Examples of 5-membered heterocyclyl groups include, and are not limited to, pyrrolidine, oxazolidine and thiazolidinedione. Examples of 6-membered heterocycloalkyl groups include, and are not limited to, piperidine, morpholine, and piperazine.

Other non-limiting examples of heterocyclyl groups include monocyclic groups such as aziridine, oxirane, thiirane, azetidine, oxetane, thietane, pyrrolidine, pyrroline, pyrazolidine, imidazoline, dioxolane, sulfolane, tetrahydrofuran, thiophane, piperidine, piperazine, morpholine, thiomorpholine.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. Preferred examples are phenyl (e.g., $C_6$-aryl) and biphenyl (e.g., $C_{12}$-aryl). In some embodiments, aryl groups have from six to sixteen carbon atoms. In some embodiments, aryl groups have from six to twelve carbon atoms (e.g., $C_6$-$C_{12}$-aryl). In some embodiments, aryl groups have six carbon atoms (e.g., $C_6$-aryl).

As used herein, the term "heteroaryl" or "heteroaromatic" refers to a heterocycle having aromatic character. Heteroaryl substituents may be defined by the number of carbon atoms, e.g., $C_1$-$C_9$-heteroaryl indicates the number of carbon atoms contained in the heteroaryl group without including the number of heteroatoms. For example, a $C_1$-$C_9$-heteroaryl will include an additional one to four heteroatoms. A polycyclic heteroaryl may include one or more rings that are partially saturated. Non-limiting examples of heteroaryls include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3-, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including, e.g., 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group.

As used herein, the terminology "selected from . . ." (e.g., "$R^4$ is selected from A, B and C") is understood to be equivalent to the terminology "selected from the group consisting of . . ." (e.g., "$R^4$ is selected from the group consisting of A, B and C").

One embodiment relates to a compound of Formula I as defined herein wherein —X—$R^7$ represents —$SO_2$—$R^7$, —$SO_2NH$—$R^7$ or —C(=O)O—$R^7$.

One embodiment relates to a compound of Formula I as defined herein wherein $R^4$, $R^5$ and $R^6$ are independently selected from Fluoro, Chloro or Bromo.

One embodiment relates to a compound of Formula I as defined herein wherein wherein at least one of $R^4$ and $R^5$ is Fluoro and $R^6$ is Hydrogen.

One embodiment relates to a compound of Formula I as defined herein wherein $R^1$ is thiazolyl.

One embodiment relates to a compound of Formula I as defined herein wherein $R^2$ is selected from the group comprising a 3-7 membered saturated ring optionally containing one or more heteroatoms and optionally substituted with one or more halogen, oxo, hydroxyl or —X—$R^7$.

One embodiment relates to a compound of Formula I as defined herein wherein $R^2$ is selected from the group comprising a 4-6 membered saturated ring optionally containing one or more heteroatoms and optionally substituted with one or more halogen, oxo, hydroxyl or —X—$R^7$.

One embodiment relates to a compound of Formula I as defined herein wherein $R^2$ is a 5 or 6 membered saturated ring optionally containing one or more heteroatoms, such ring further substituted with —X—$R^7$, more in particular wherein such saturated ring contains a nitrogen or an oxygen.

One embodiment relates to a compound of Formula I as defined herein wherein $R^3$ is methyl.

One embodiment relates to a compound selected from the group consisting of compound satisfying the following formulae:

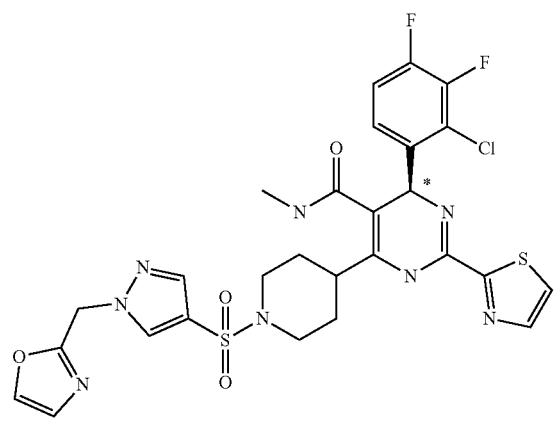

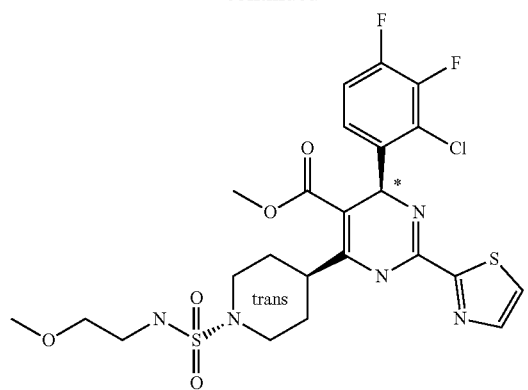
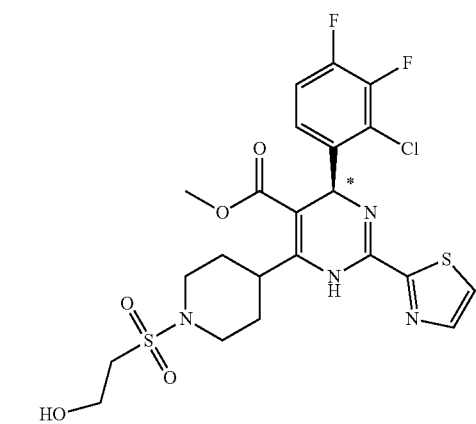
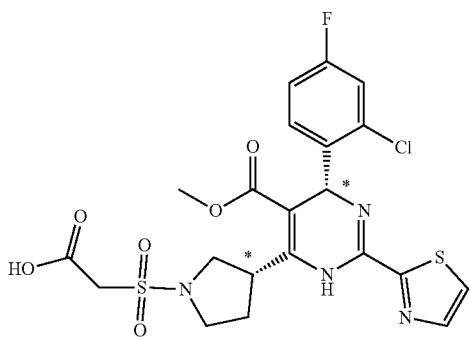
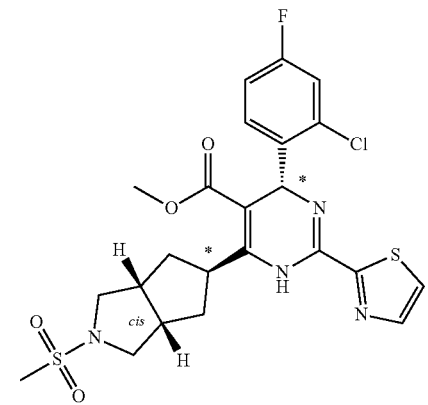
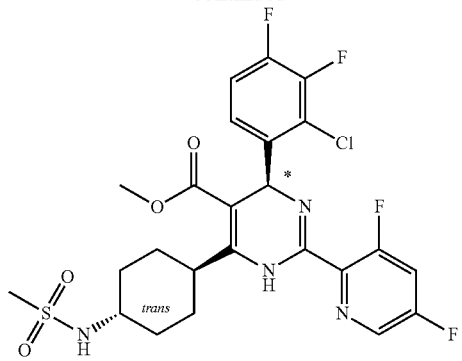
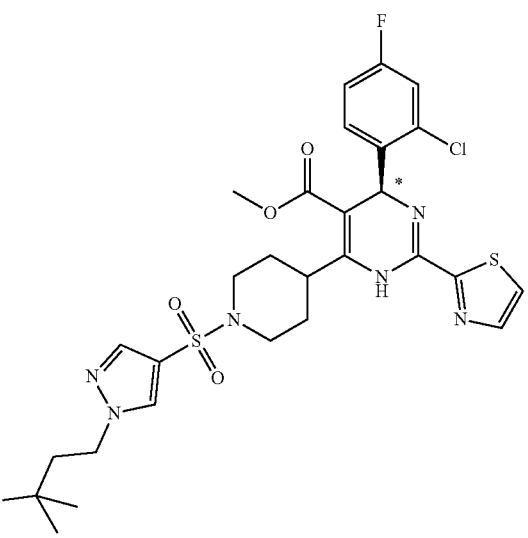
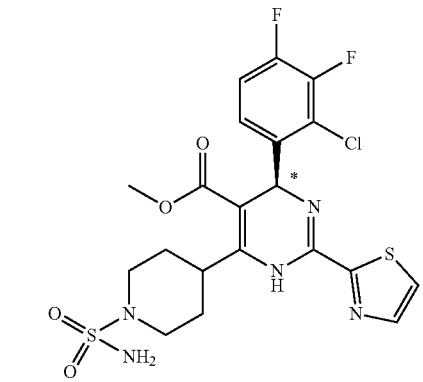
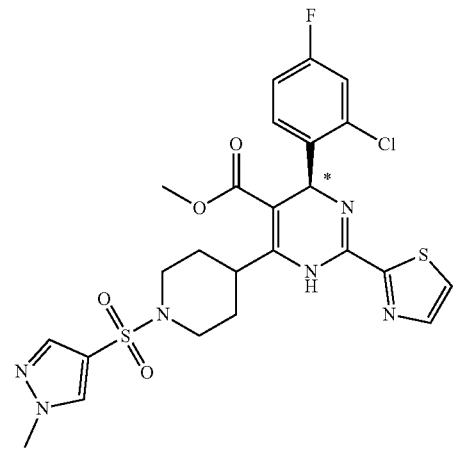

11
-continued
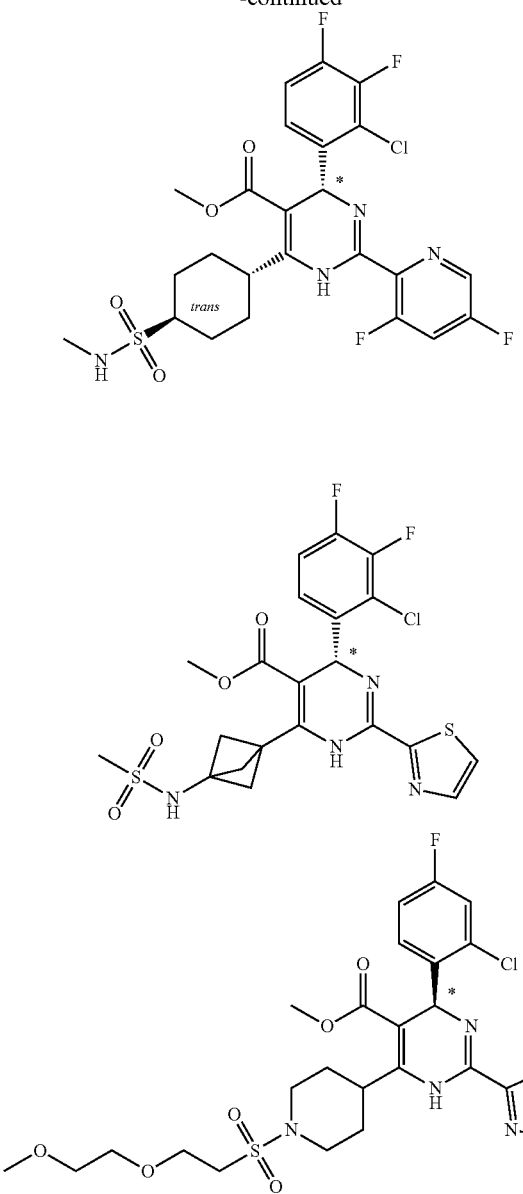
12
-continued
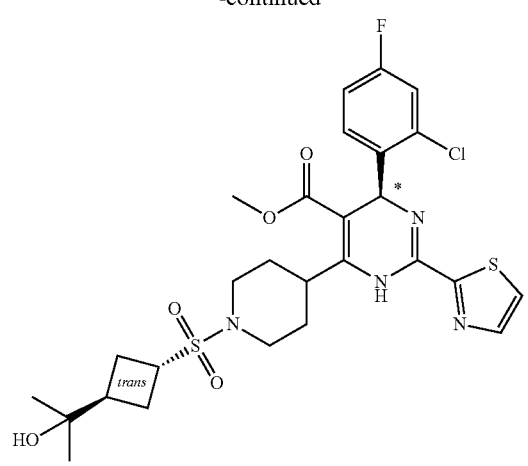
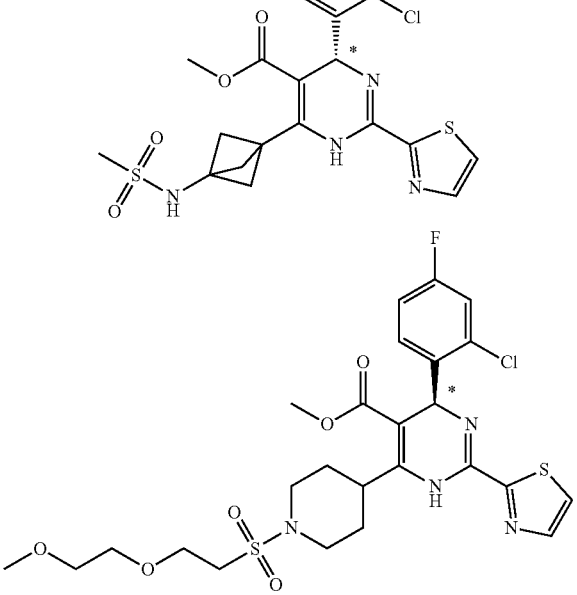
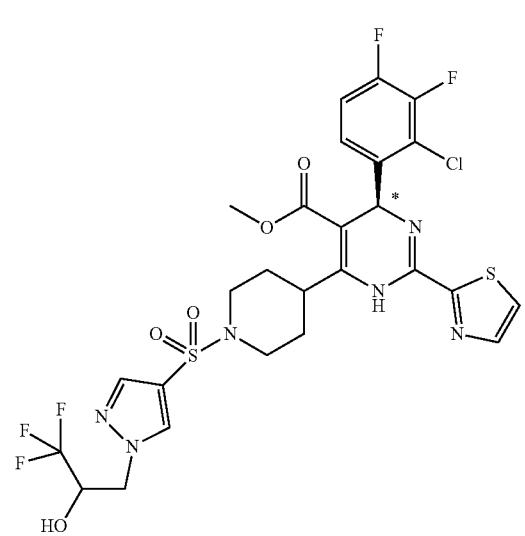
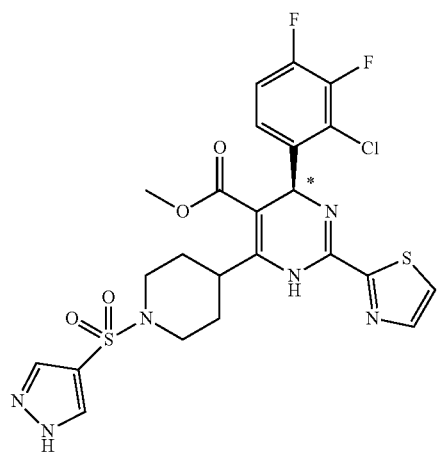
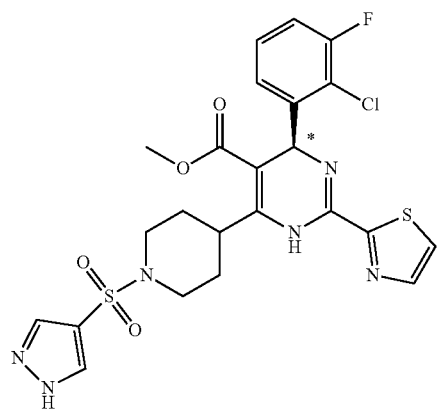

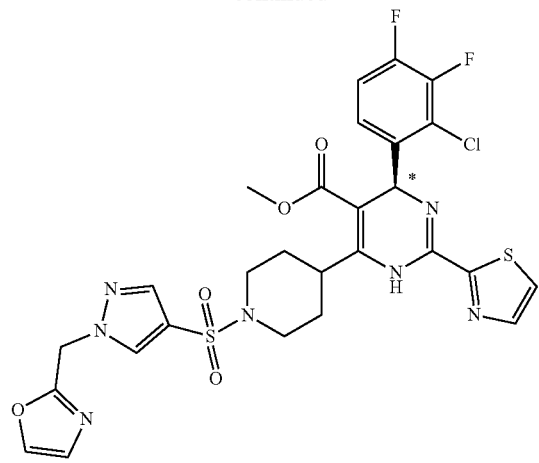
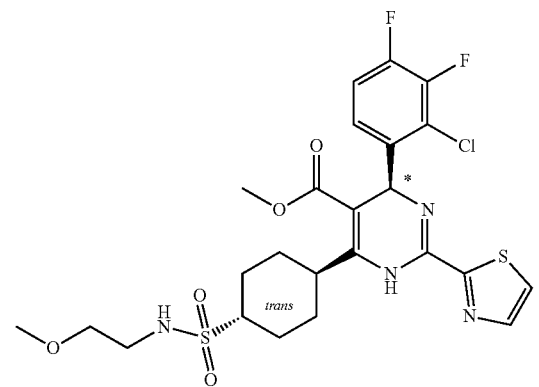
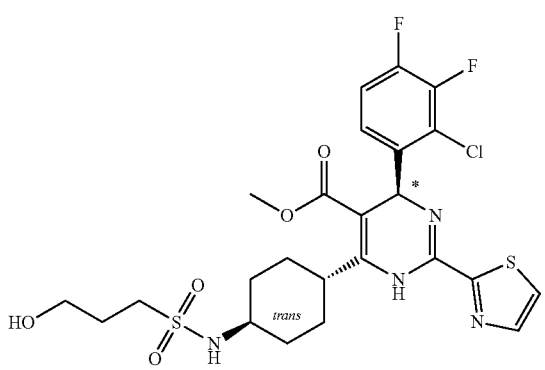
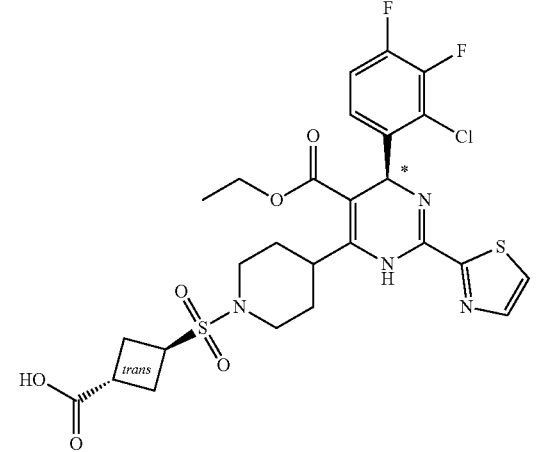
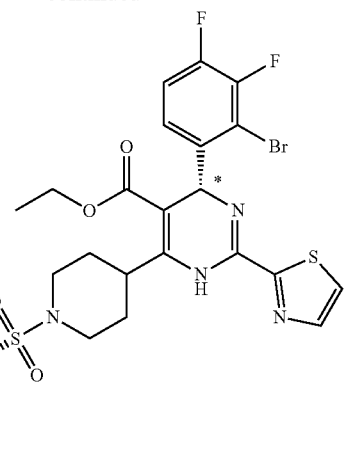

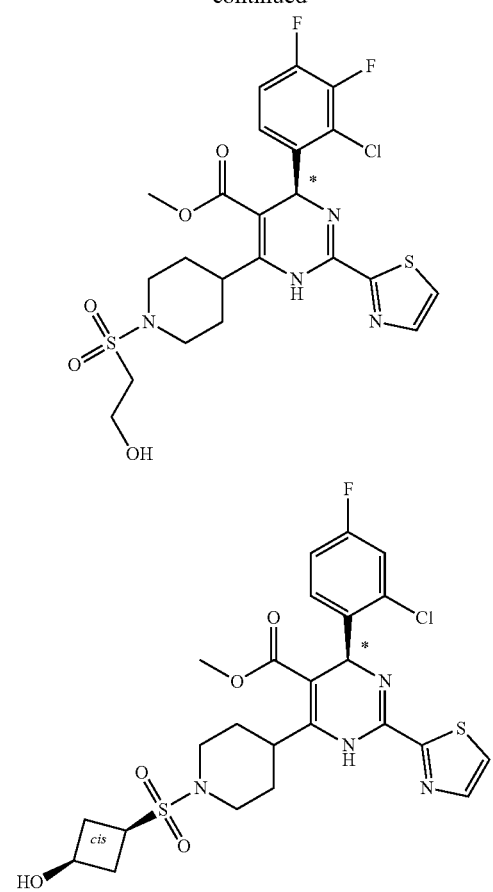
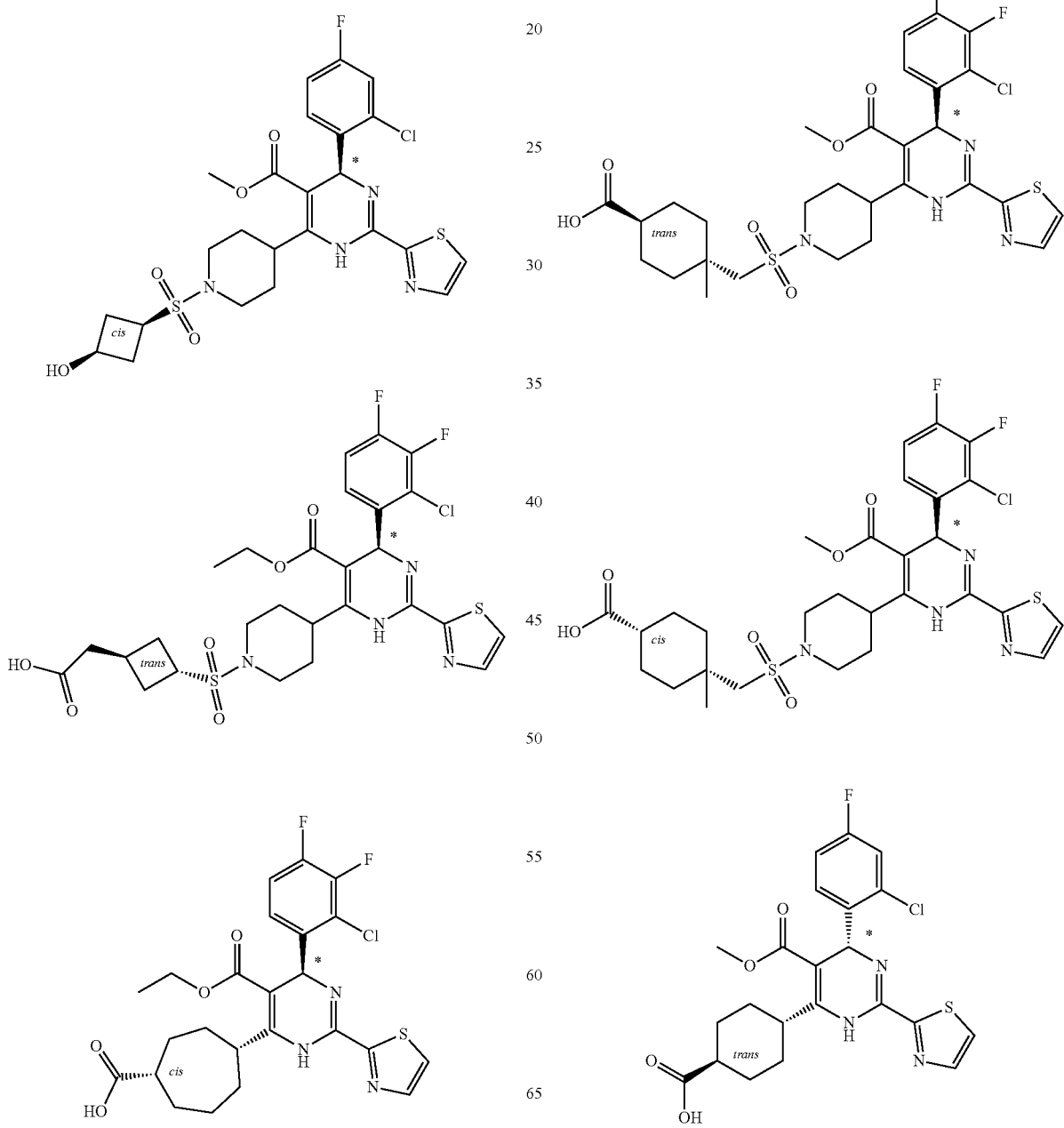

17
-continued
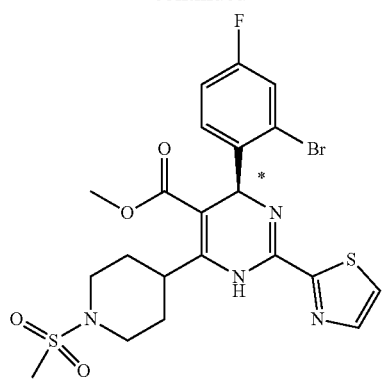
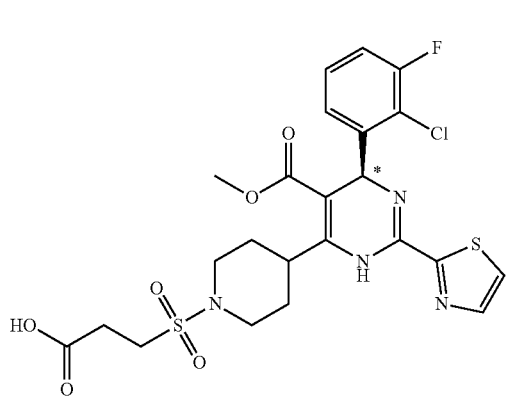 [SMILES: COC(=O)C1=C(C2CCN(S(=O)(=O)CCC(=O)O)CC2)NC(c2nccs2)=N[C@@H]1c1cccc(F)c1Cl]
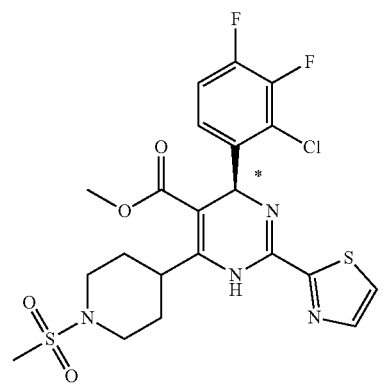
18
-continued
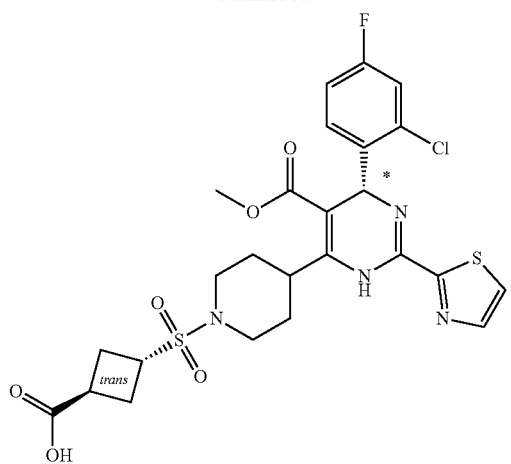
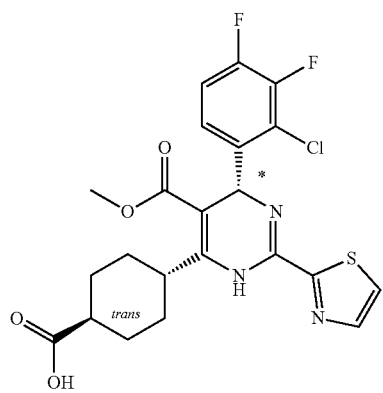
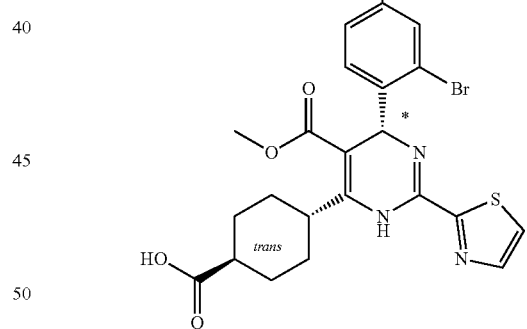

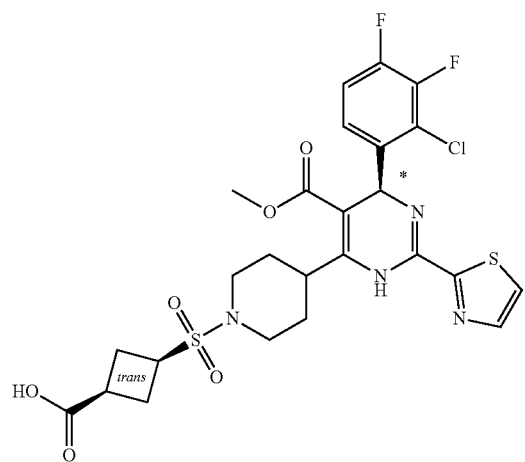
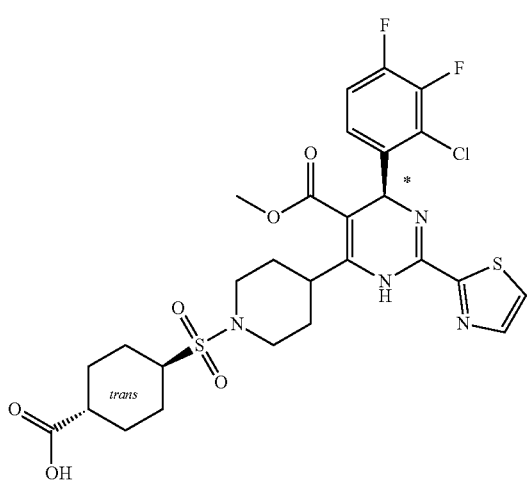
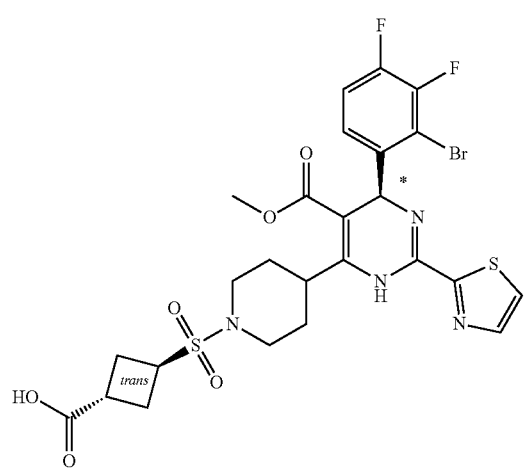
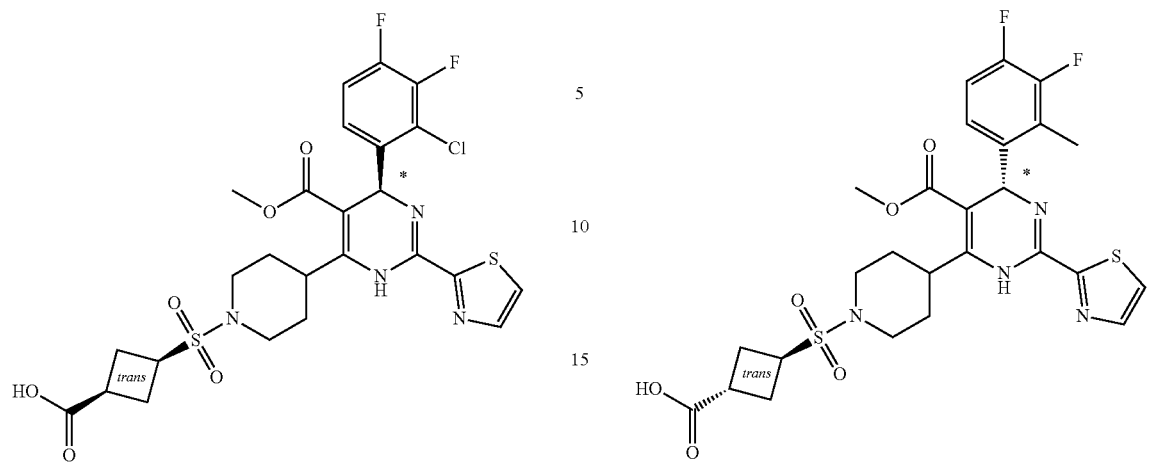
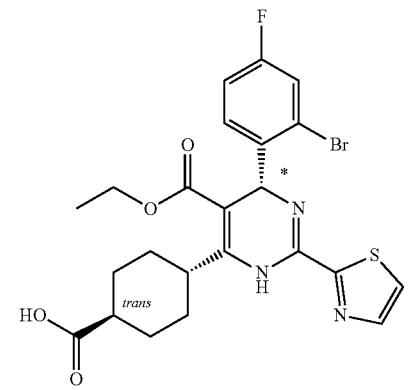
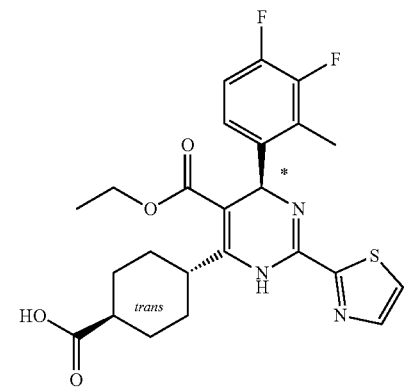
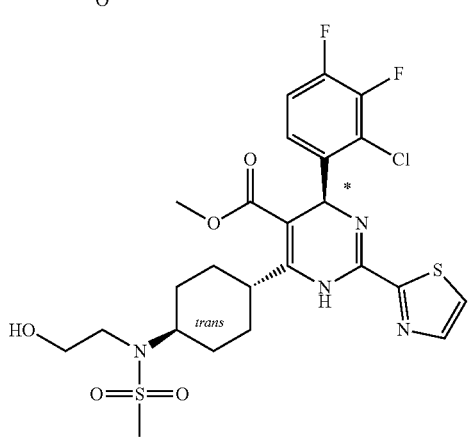

21
-continued
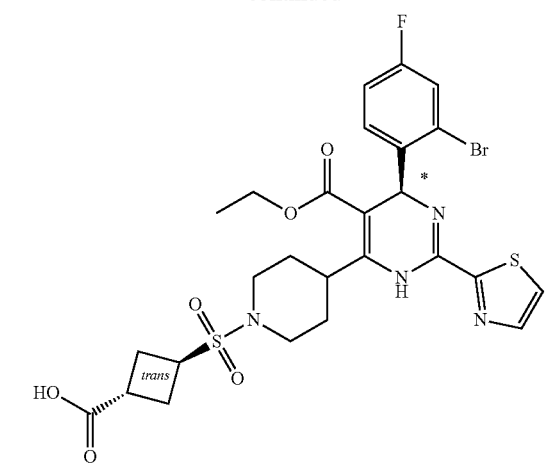
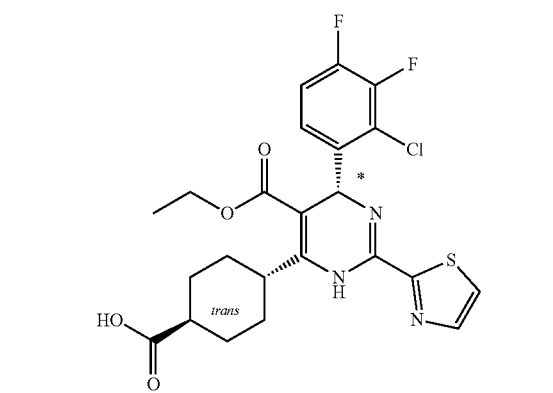
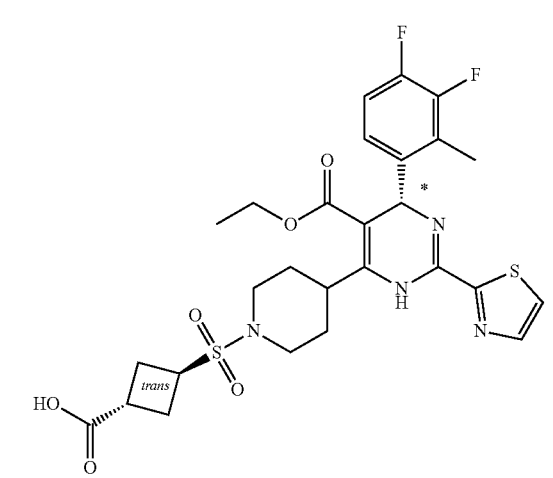
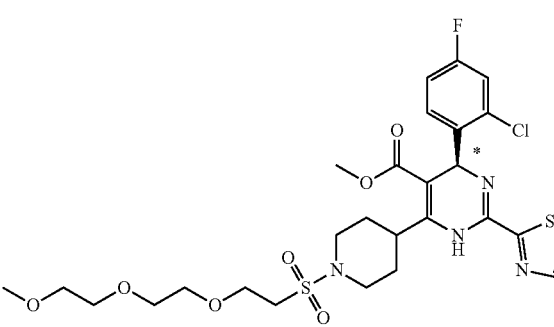
22
-continued
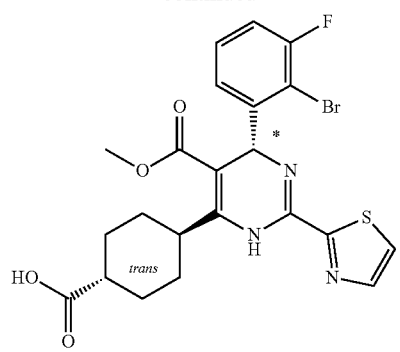
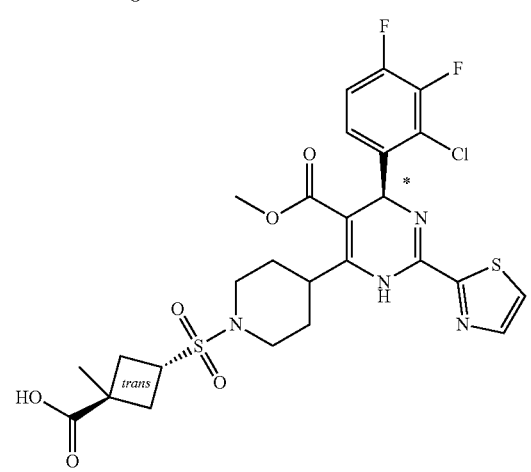
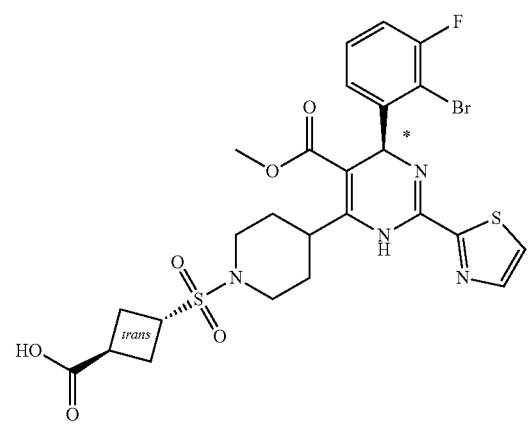
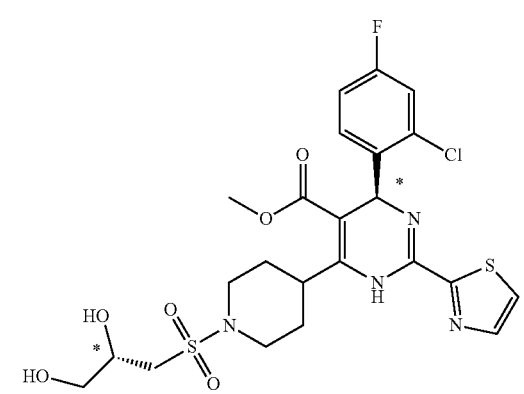

23
-continued
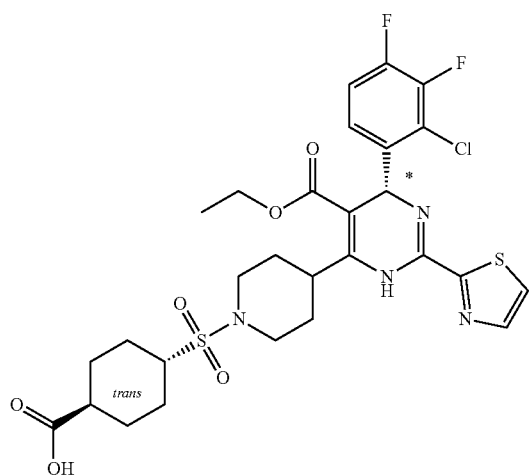
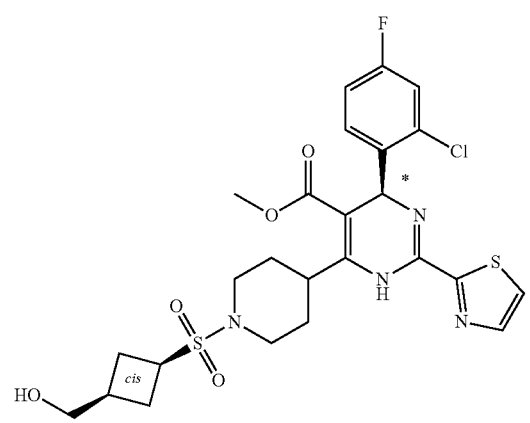
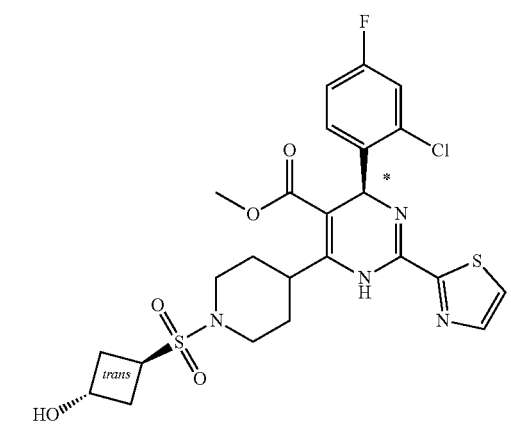
24
-continued
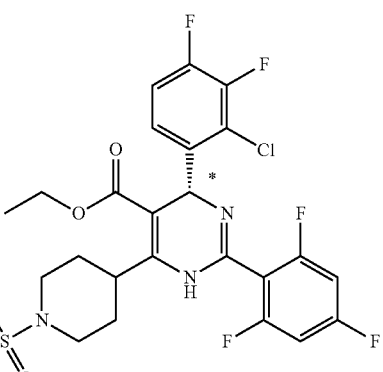
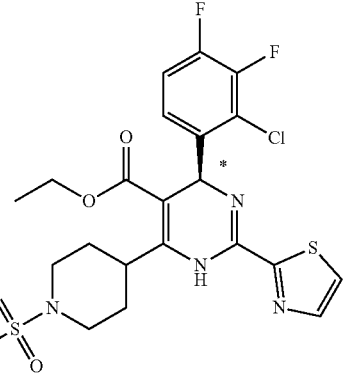
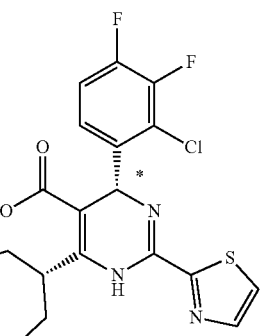
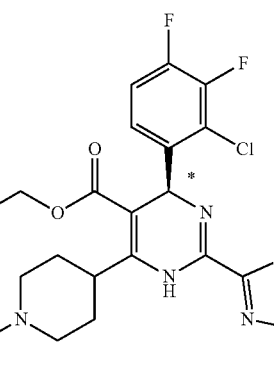

25
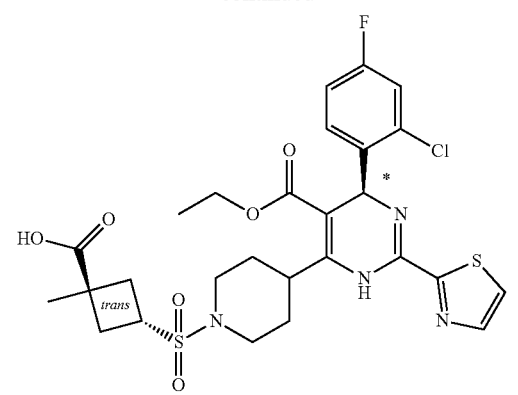
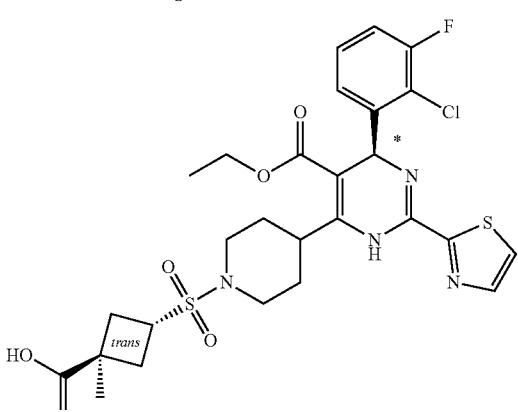
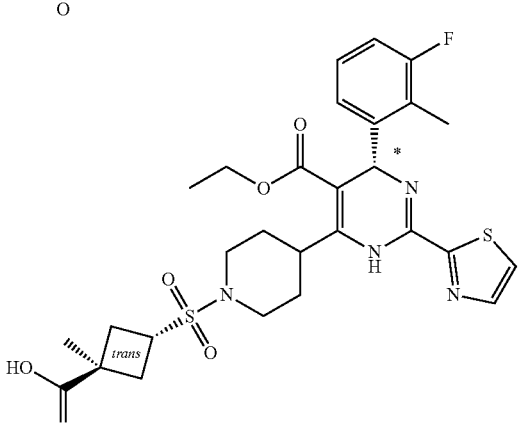
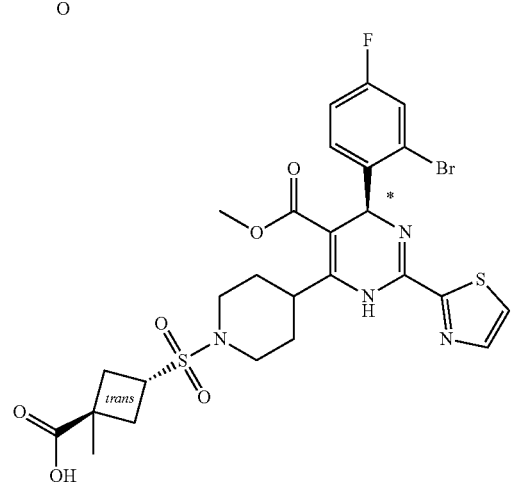
26
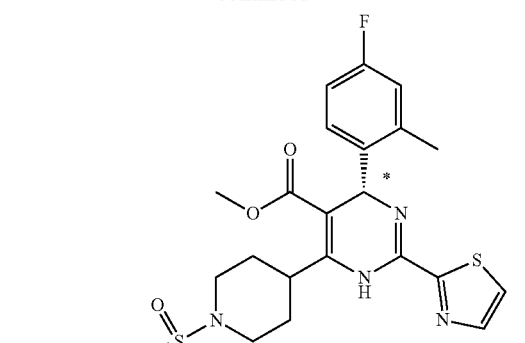
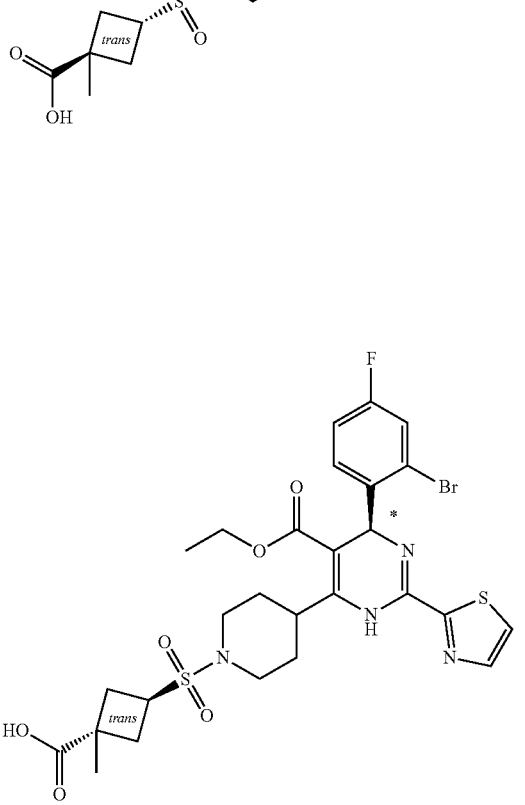
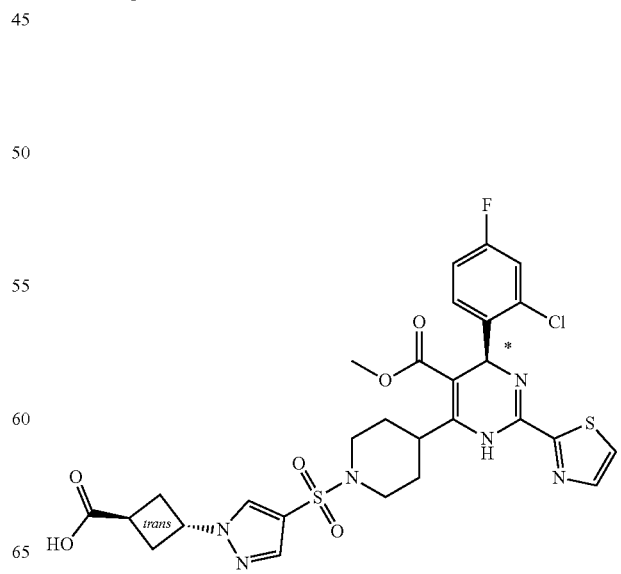

27
-continued

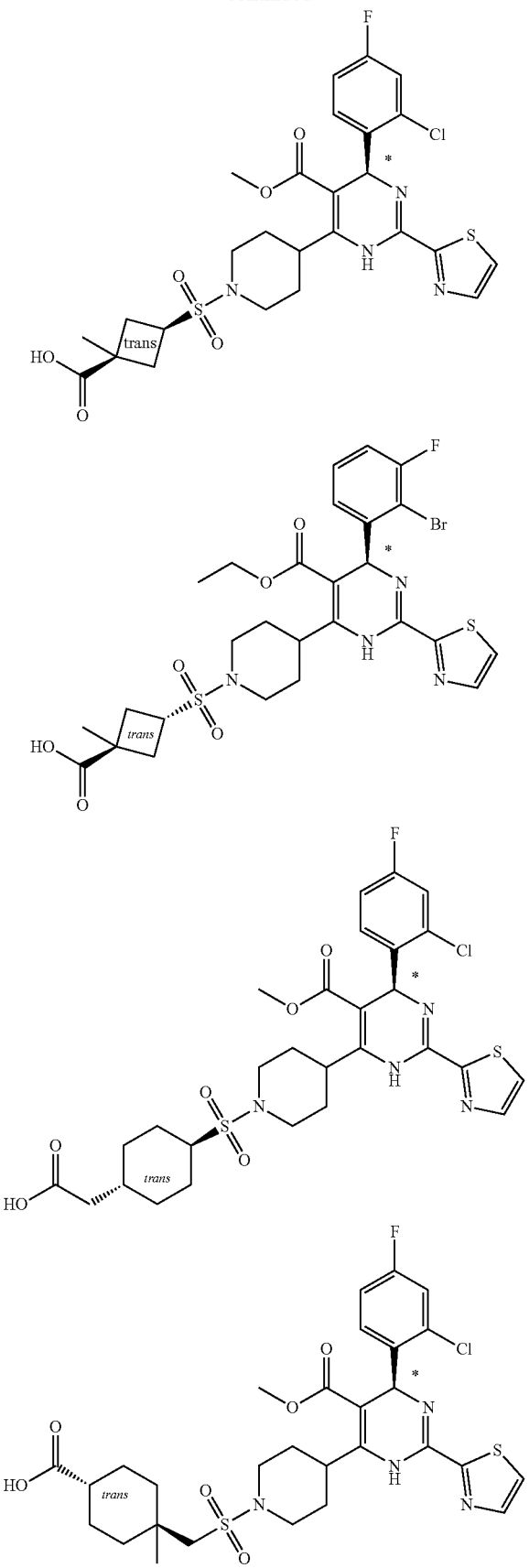

28
-continued

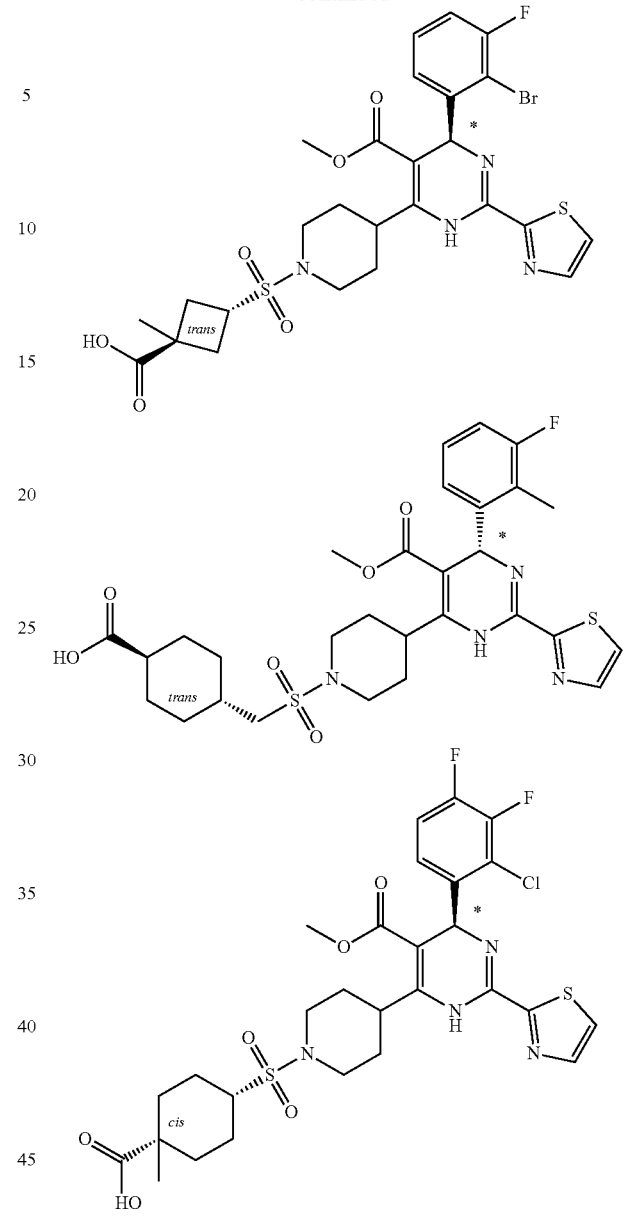

The disclosed compounds may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the disclosed compound described herein. In another embodiment, compounds described herein contain one or more chiral centers. These compounds are prepared by any means, including stereoselective synthesis, enantioselective synthesis or separation of a mixture of enantiomers or diastereomers. Resolution of compounds and isomers thereof is achieved by any means including, by way of non-limiting example, chemical processes, enzymatic processes, fractional crystallization, distillation, and chromatography.

When the absolute R or S stereochemistry of a compound cannot be determined, it can be identified by the retention time after chromatography under particular chromatographic conditions as determined by chromatography column, eluent etc.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements).

In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and techniques known to a person skilled in the art. General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

Methods

Provided herein is a method of treating an HBV infection in an individual in need thereof, comprising administering to the individual a therapeutically effective amount of a disclosed compound.

Also provided herein is a method of eradicating an HBV infection in an individual in need thereof, comprising administering to the individual a therapeutically effective amount of a disclosed compound.

Provided herein is a method of reducing viral load associated with an HBV infection in an individual in need thereof, comprising administering to the individual a therapeutically effective amount of a disclosed compound.

Further, provided herein is a method of reducing reoccurrence of an HBV infection in an individual in need thereof, comprising administering to the individual a therapeutically effective amount of a disclosed compound.

Provided herein is a method of inhibiting or reducing the formation or presence of HBV DNA-containing particles or HBV RNA-containing particles in an individual in need thereof, comprising administering to the individual a therapeutically effective amount of a disclosed compound.

In certain aspects, the methods and/or compositions described herein are effective for inhibiting or reducing the formation or presence of HBV-associated particles in vitro or in vivo (e.g., in a cell, in a tissue, in an organ (e.g., in the liver), in an organism or the like). HBV-associated particles may contain HBV DNA (i.e., linear and/or covalently closed circular DNA (cccDNA)) and/or HBV RNA (i.e., pre-genomic RNA and/or sub-genomic RNA). Accordingly, HBV-associated particles include HBV DNA-containing particles or HBV RNA-containing particles.

As used herein, "HPV-associated particles" refer to both infectious HBV virions (i.e., Dane particles) and non-infectious HBV subviral particles (i.e., HBV filaments and/or HBV spheres). HBV virions comprise an outer envelope including surface proteins, a nucleocapsid comprising core proteins, at least one polymerase protein, and an HBV genome. HBV filaments and HBV spheres comprise HBV surface proteins, but lack core proteins, polymerase and an HBV genome. HBV filaments and HBV spheres are also known collectively as surface antigen (HBsAg) particles. HBV spheres comprise middle and small HBV surface proteins. HBV filaments also include middle, small and large HBV surface proteins.

HBV subviral particles can include the nonparticulate or secretory HBeAg, which serves as a marker for active replication of HBV.

Provided herein is a method of reducing an adverse physiological impact of an HBV infection in an individual in need thereof, comprising administering to the individual a therapeutically effective amount of a disclosed compound.

Also provided herein is a method of reducing, slowing, or inhibiting an HBV infection in an individual in need thereof, comprising administering to the individual a therapeutically effective amount of a disclosed compound.

Provided herein is a method of inducing reversal of hepatic injury from an HBV infection in an individual in need thereof, comprising administering to the individual a therapeutically effective amount of a disclosed compound.

Provided herein is a method of reducing the physiological impact of long-term antiviral therapy for HBV infection in an individual in need thereof, comprising administering to the individual a therapeutically effective amount of a disclosed compound.

Provided herein is a method of prophylactically treating an HBV infection in an individual in need thereof, wherein the individual is afflicted with a latent HBV infection, comprising administering to the individual a therapeutically effective amount of a disclosed compound.

In one embodiment, the individual is refractory to other therapeutic classes of HBV drugs (e.g, HBV polymerase inhibitors, interferons, viral entry inhibitors, viral maturation inhibitors, literature-described capsid assembly modulators, antiviral compounds of distinct or unknown mechanism, and the like, or combinations thereof). In another embodiment, the disclosed method reduces viral load in an individual suffering from an HBV infection to a greater extent or at a faster rate compared to the extent that other therapeutic classes of HBV drugs reduce viral load in the individual.

In one embodiment, the administering of a disclosed compound, or a pharmaceutically acceptable salt thereof, allows for administering of the at least one additional therapeutic agent at a lower dose or frequency as compared to the administering of the at least one additional therapeutic agent alone that is required to achieve similar results in prophylactically treating an HBV infection in an individual in need thereof.

In one embodiment, the administering of a disclosed compound, or a pharmaceutically acceptable salt thereof, reduces the viral load in the individual to a greater extent or at a faster rate compared to the administering of a compound selected from the group consisting of an HBV polymerase inhibitor, interferon, viral entry inhibitor, viral maturation inhibitor, distinct capsid assembly modulator, antiviral compounds of distinct or unknown mechanism, and any combination thereof.

In one embodiment, the disclosed method reduces viral load in an individual suffering from an HBV infection, thus allowing lower doses or varying regimens of combination therapies to be used.

In one embodiment, the disclosed method causes a lower incidence of viral mutation or viral resistance compared to other classes of HBV drugs, thereby allowing for long term therapy and minimizing the need for changes in treatment regimens.

In one embodiment, the administering of a compound the invention, or a pharmaceutically acceptable salt thereof, causes a lower incidence of viral mutation or viral resistance than the administering of a compound selected from the group consisting of an HBV polymerase inhibitor, interferon, viral entry inhibitor, viral maturation inhibitor, distinct capsid assembly modulator, antiviral compounds of distinct or unknown mechanism, and combination thereof.

In one embodiment, the disclosed method increases the seroconversion rate from HBV infected to non-HBV infected or from detectable HBV viral load to non-detectable HBV viral load beyond that of current treatment regimens. As used herein, "seroconversion" refers to the period of time during which HBV antibodies develop and become detectable.

In one embodiment, the disclosed method increases or normalizes or restores normal health, elicits full recovery of normal health, restores life expectancy, or resolves the viral infection in the individual in need thereof.

In one embodiment, the disclosed method eliminates or decreases the number of HBV RNA particles that are released from HBV infected cells thus enhancing, prolonging, or increasing the therapeutic benefit of the disclosed compounds.

In one embodiment, the disclosed method eradicates HBV from an individual infected with HBV, thereby obviating the need for long term or life-long treatment, or shortening the duration of treatment, or allowing for reduction in dosing of other antiviral agents.

In another embodiment, the disclosed method further comprises monitoring or detecting the HBV viral load of the subject, and wherein the method is carried out for a period of time including until such time that the HBV virus is undetectable.

Accordingly, in one embodiment, provided herein is a method of treating an HBV infection in an individual in need thereof, comprising administering to the individual a therapeutically effective amount of a compound of Formula I, or a pharmaceutically acceptable salt thereof.

Accordingly, in one embodiment, provided herein is a method of treating an HBV infection in an individual in need thereof, comprising administering to the individual a therapeutically effective amount of a compound of Formula I, or a pharmaceutically acceptable salt thereof.

In another embodiment, provided herein is a method of treating an HBV infection in an individual in need thereof, comprising administering to the individual a therapeutically effective amount of a compound of Table 1, or a pharmaceutically acceptable salt thereof.

In an embodiment of any of the methods provided herein, the method can further comprise monitoring the HBV viral load of the subject, wherein the method is carried out for a period of time such that the HBV virus is undetectable.

Combination Therapies

The disclosed compounds may be useful in combination with one or more additional compounds useful for treating HBV infection. These additional compounds may comprise other disclosed compounds and/or compounds known to treat, prevent, or reduce the symptoms or effects of HBV infection. Such compounds include, but are not limited to, HBV polymerase inhibitors, interferons, viral entry inhibitors, viral maturation inhibitors, literature-described capsid assembly modulators, reverse transcriptase inhibitors, immunomodulatory agents, TLR-agonists, and other agents with distinct or unknown mechanisms that affect the HBV life cycle or affect the consequences of HBV infection.

In non-limiting examples, the disclosed compounds may be used in combination with one or more drugs (or a salt thereof) selected from the group comprising:

HBV reverse transcriptase inhibitors, and DNA and RNA polymerase inhibitors including, but not limited to, lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons including, but not limited to, interferon alpha (IFN-α), interferon beta (IFN-β), interferon lambda (IFN-λ), and interferon gamma (IFN-γ);

viral entry inhibitors;

viral maturation inhibitors;

literature-described capsid assembly modulators, such as, but not limited to, BAY 41-4109;

reverse transcriptase inhibitors;

immunomodulatory agents such as TLR-agonists; and agents of distinct or unknown mechanisms, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and similar analogs.

In one embodiment, the additional therapeutic agent is an interferon. The term "interferon" or "IFN" refers to any member of the family of highly homologous species-specific proteins that inhibit viral replication and cellular proliferation and modulate immune response. Human interferons are grouped into three classes: Type I, which includes interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons may include pegylated interferons and glycosylated interferons. Examples of interferons also include, but are not limited to, interferon-alpha-2a, interferon-alpha-2b, interferon-alpha-n1, interferon-beta-1a, interferon-beta-1b, interferon-lamda- 1, interferon-lamda-2, and interferon-lamda-3. Examples of pegylated interferons include pegylated interferon-alpha-2a and pegylated interferon alpha-2b.

Accordingly, in one embodiment, the compounds of Formula I can be administered in combination with an interferon selected from the group consisting of interferon alpha (IFN-α), interferon beta (IFN-β), interferon lambda (IFN-λ), and interferon gamma (IFN-γ). In one specific embodiment, the interferon is interferon-alpha-2a, interferon-alpha-2b, or interferon-alpha-n1. In another specific embodiment, the interferon-alpha-2a or interferon-alpha-2b is pegylated. In a preferred embodiment, the interferon-alpha-2a is pegylated interferon-alpha-2a (PEGASYS).

In another embodiment, the additional therapeutic agent is selected from immune modulator or immune stimulator therapies, which includes biological agents belonging to the interferon class.

Further, the additional therapeutic agent may be an agent of distinct or unknown mechanism including agents that disrupt the function of other essential viral protein(s) or host proteins required for HBV replication or persistence.

In another embodiment, the additional therapeutic agent is an antiviral agent that blocks viral entry or maturation or targets the HBV polymerase such as nucleoside or nucleotide or non-nucleos(t)ide polymerase inhibitors. In a further embodiment of the combination therapy, the reverse transcriptase inhibitor or DNA or RNA polymerase inhibitor is Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In an embodiment, the additional therapeutic agent is an immunomodulatory agent that induces a natural, limited immune response leading to induction of immune responses against unrelated viruses. In other words, the immunomodulatory agent can effect maturation of antigen presenting cells, proliferation of T-cells and cytokine release (e.g., IL-12, IL-18, IFN-alpha, -beta, and -gamma and TNF-alpha among others), In a further embodiment, the additional therapeutic agent is a TLR modulator or a TLR agonist, such as a TLR-7 agonist or TLR-9 agonist. In further embodiment of the combination therapy, the TLR-7 agonist is selected from the group consisting of SM360320 (9-benzyl-8-hydroxy-2-(2-methoxy-ethoxy)adenine) and AZD 8848 (methyl[3-({[3-(6-amino-2-butoxy-8-oxo-7,8-dihydro-9H-purin-9-yl)propyl] [3-(4-morpholinyl)propyl]amino}methyl)phenyl]acetate).

In any of the methods provided herein, the method may further comprise administering to the individual at least one HBV vaccine, a nucleoside HBV inhibitor, an interferon or any combination thereof. In an embodiment, the HBV vaccine is at least one of RECOMBIVAX HB, ENGERIX-B, ELOVAC B, GENEVAC-B, or SHANVAC B.

In one embodiment, the methods described herein further comprise administering at least one additional therapeutic agent selected from the group consisting of nucleotide/nucleoside analogs, entry inhibitors, fusion inhibitors, and any combination of these or other antiviral mechanisms.

In another aspect, provided herein is method of treating an HBV infection in an individual in need thereof, comprising reducing the HBV viral load by administering to the individual a therapeutically effective amount of a disclosed compound alone or in combination with a reverse transcriptase inhibitor; and further administering to the individual a therapeutically effective amount of HBV vaccine.

The reverse transcriptase inhibitor may be at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another aspect, provided herein is a method of treating an HBV infection in an individual in need thereof, comprising reducing the HBV viral load by administering to the individual a therapeutically effective amount of a disclosed compound alone or in combination with a antisense oligonucleotide or RNA interference agent that targets HBV nucleic acids; and further administering to the individual a therapeutically effective amount of HBV vaccine. The antisense oligonucleotide or RNA interference agent possesses sufficient complementarity to the the target HBV nucleic acids to inhibit replication of the viral genome, transcription of viral RNAs, or translation of viral proteins.

In another embodiment, the disclosed compound and the at least one additional therapeutic agent are co-formulated. In yet another embodiment, the disclosed compound and the at least one additional therapeutic agent are co-administered.

For any combination therapy described herein, synergistic effect may be calculated, for example, using suitable methods such as the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In an embodiment of any of the methods of administering combination therapies provided herein, the method can further comprise monitoring or detecting the HBV viral load of the subject, wherein the method is carried out for a period of time including until such time that the HBV virus is undetectable.

Administration/Dosage/Formulations

In another aspect, provided herein is a pharmaceutical composition comprising at least one disclosed compound, or a pharmaceutically acceptable salt thereof, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms of the invention are dictated by and directly dependent on (a) the unique characteristics of the disclosed compound and the particular therapeutic effect to be achieved, and (b) the limitations inherent in the art of compounding/formulating such a disclosed compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a disclosed compound and a pharmaceutically acceptable carrier.

In some embodiments, the dose of a disclosed compound is from about 1 mg to about 2,500 mg. In some embodiments, a dose of a disclosed compound used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a disclosed compound, alone or in combination with a second pharmaceutical agent; and instructions for using the compound to treat, prevent, or reduce one or more symptoms of HBV infection in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Preparative Examples

Exemplary compounds useful in methods of the invention will now be described by reference to the illustrative synthetic schemes for their general preparation below and the specific examples to follow.

General Scheme

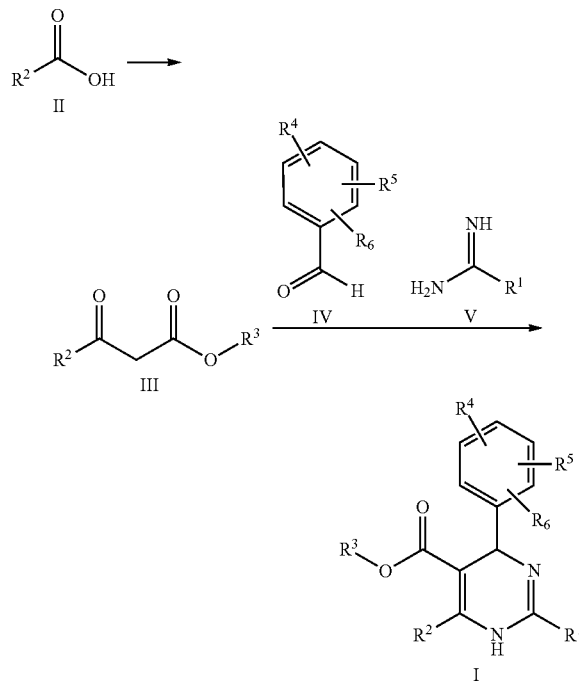

The general synthesis of compound of general formula I is described in scheme 1 and scheme 2. Compound of general formula III can be synthesized as described in Scheme 1 (Method A or Method B), the conditions used are depending on the substituents $R_2$ and $R_3$ on compound of general formula III. As described in Method A, an acid of general formula II is converted by reacting with N,N-carbonyldiimidazole CDI to an activated ester which then couples with malonic acid monomethyl ester potassium salt under basic condition to generate an intermediate which in turn undergoes decarboxylation to yield the ketoester of general formula III. Alternatively, as described in Method B, the compound of general formula III can be prepared from the acid of general formula II and 2,2-dimethyl-1,3-dioxane-4,6-dione via similar transformative sequences as Method A. The final product of general formula I can be synthesized as described in Scheme 2 (Method C or Method D). The former is the commonly utilized chemical methodology of multiple component reaction with compounds of general formula III, IV and V in the presence of base (but not limited to sodium acetate NaOAc) in solvent of choice (but not limited to ethanol EtOH). Alternatively, a stepwise approach is provided as described in Method D. Compounds of general formula III and IV undergo condensation to yield the conjugated intermediate of formula X, which then reacts with the compound of general formula V under a basic reaction medium at high temperature to generate the final product dihydropyrimidine of general formula I.

Scheme 1
Method $A_1$

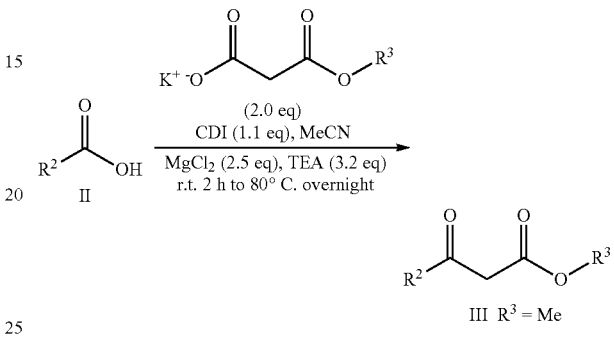

To a solution of the acid of general formula II (1 equivalent) in acetonitrile was added N,N-carbonyldiimidazole (1.1 equivalents) at room temperature. The mixture was stirred at room temperature under nitrogen atmosphere for 2 hours (mixture A). To a suspension of malonic acid monomethyl ester potassium salt (2 equivalents) in acetonitrile was added magnesium chloride (2.5 equivalents) and triethylamine (3.2 equivalents) at room temperature. After stirred under nitrogen atmosphere for 2 hours, it was added mixture A and stirred at 80-100° C. overnight. The resulting reaction mixture was cooled down to room temperature and concentrated to give a residue, which was purified by silica gel column chromatography to afford the ketoester of general formula III.

Method $A_2$ malonic acid monoethyl ester potassium salt was engaged to replace malonic acid monomethyl ester potassium salt in Method $A_1$.

Method B

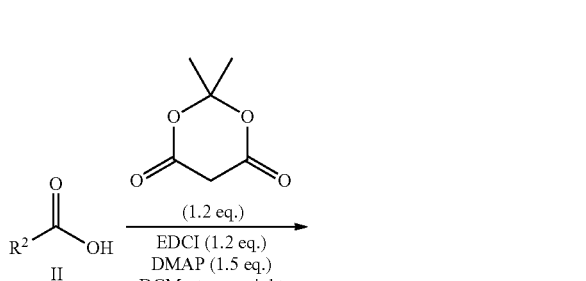

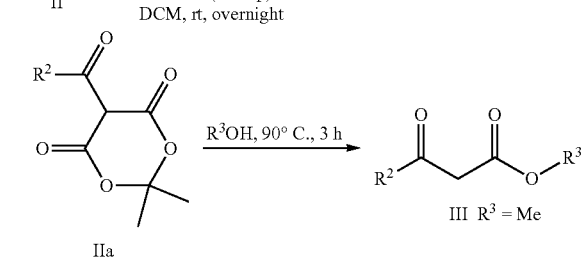

To a solution of the acid of general formula II (1 equivalent), 2,2-dimethyl-1,3-dioxane-4,6-dione (1.2 equivalents) and 4-dimethylaminopyridine (1.5 equivalents) in dichloromethane was added N-ethyl-N'-(3-dimethylaminopropyl)carbodiimide hydrochloride (1.2 equivalents) at room temperature. After stirred overnight under nitrogen atmosphere, the mixture was diluted with dichloromethane, washed with 5% wt potassium bisulfate aqueous solution followed with brine, dried over anhydrous Na₂SO₄ and filtered. The filtrate was concentrated under reduced pressure to afford the intermediate of general formula IIa.

A solution of the intermediate of general formula IIa in methanol was stirred at 90° C. for 3 hours. After cooled down to room temperature, the mixture was concentrated under reduced pressure to afford the ketoester of general formula III.

Scheme 2
Method C

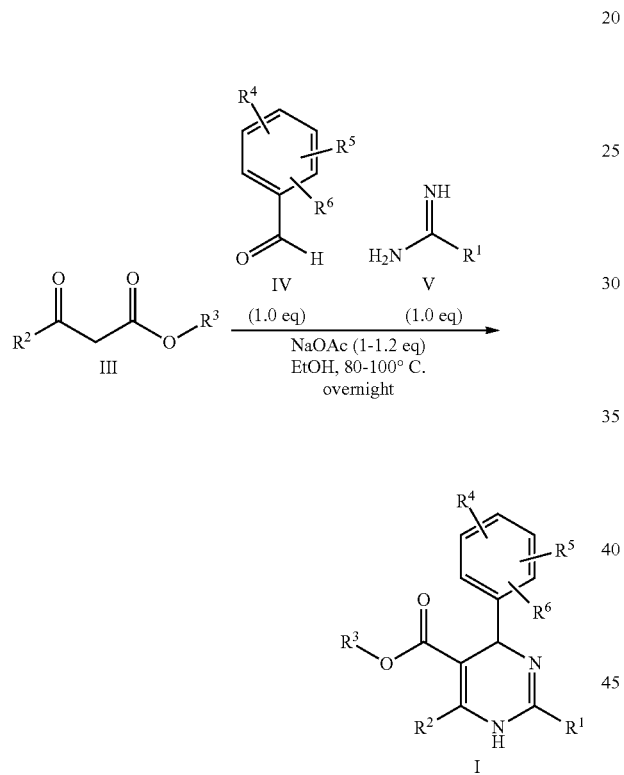

Method D

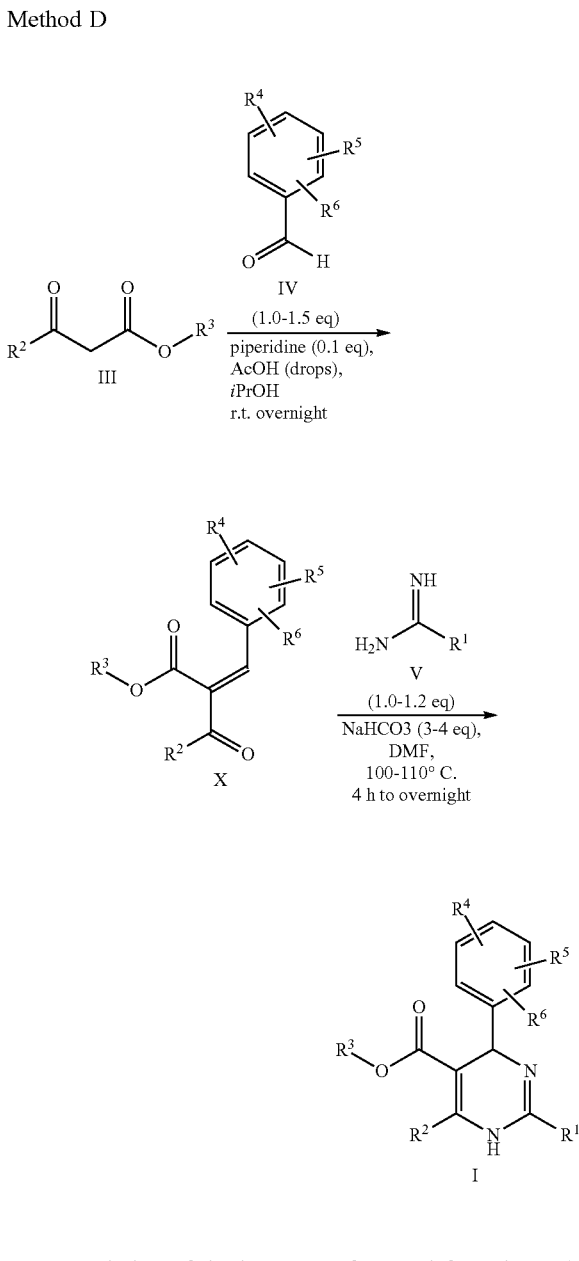

To a solution of the ketoester of general formula III (1 equivalent) in ethanol was added the aldehyde of general formula IV (1 equivalent), the carboxamidine hydrochloride of general formula V (1 equivalent) and sodium acetate (1-1.2 equivalents). The mixture was brought up to 80-100° C. and stirred under nitrogen atmosphere overnight. After cooled down to room temperature, it was concentrated to dryness. The residue was taken up in dichloromethane, washed with water, brine, dried over anhydrous Na₂SO₄ and filtered. The filtrate was concentrated under reduced pressure to give a residue, which was purified by silica gel column chromatography to afford the dihydropyrimidine product of general formula I. When applicable, the stereoisomers of the dihydropyrimidine product of general formula I were isolated and purified using chiral chromatography.

To a solution of the ketoester of general formula III (1 equivalent) in isopropanol was added the aldehyde of general formula IV (1-1.5 equivalents), piperidine (0.1 equivalent) and acetic acid glacial (drops) at room temperature under nitrogen atmosphere. After stirred overnight, the mixture was concentrated under reduced pressure to leave a residue, which was purified by silica gel column chromatography to afford the intermediate of general formula X.

To a solution of the intermediate of general formula X in N,N-dimethylformamide was added the carboxamidine hydrochloride of general formula V (1-1.2 equivalents) and sodium bicarbonate (3-4 equivalents). After stirred at 100-110° C. for reaction time ranging from 4 hours to overnight, the mixture was cooled down to room temperature and concentrated under reduced pressure to leave a residue, which was purified by silica gel column chromatography to yield the dihydropyrimidine product of general formula I.

When applicable, the stereoisomers of the dihydropyrimidine product of general formula I were isolated and purified using chiral chromatography.

Preparation of Acids of General Formula II, Aryl Aldehydes (P1) and Carboxamidines (P2)

Part I: Preparation of Acids of General Formula II

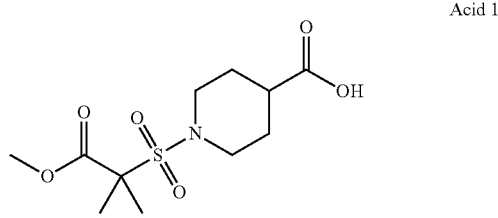

Acid 1

Intermediate A1: tert-Butyl 1-((2-methoxy-2-oxo-ethyl)sulfonyl)piperidine-4-carboxylate To a solution of piperidine-4-carboxylic acid hydrochloride (500 mg, 2.26 mmol) and triethylamine (2.29 g, 22.6 mmol) in 1,2-dichloroethane (50 mL) was added methyl 2-(chlorosulfonyl)acetate (1.17 g, 6.78 mmol) at 0° C. under nitrogen atmosphere. After stirred at 0° C. for 4 hours, the mixture was poured into water (40 mL) and extracted with dichloromethane (50 mL) for three times. The combined organic layers were washed with brine (100 mL) twice, dried over $Na_2SO_{4(s)}$, filtered and concentrated under reduced pressure to give a residue, which was purified by silica gel column chromatography (petroleum ether:ethyl acetate=9:1 to 3:1) to give the title compound (475 mg, 65% yield) as yellow solids. $^1$H NMR (400 MHz, CDCl$_3$) δ 3.92 (s, 2H), 3.79 (s, 3H), 3.75-3.70 (m, 2H), 3.04-2.98 (m, 2H), 2.39-2.32 (m, 1H), 1.98-1.92 (m, 2H), 1.81-1.71 (m, 2H), 1.44 (s, 9H).

Intermediate A2: 1-(2-Methoxycarbonyl-propane-2-sulfonyl)-piperidine-4-carboxylic Acid Tert-butyl Ester To a solution of tert-butyl 1-((2-methoxy-2-oxoethyl) sulfonyl)piperidine-4-carboxylate Intermediate A1 (100 mg, 0.312 mmol) in N,N-dimethylformamide (5 mL) was added 60% wt sodium hydride in mineral oil (31 mg, 0.780 mmol) and iodomethane (111 mg, 0.780 mmol) at 0° C. under nitrogen atmosphere. After stirred at room temperature for 4 hours, the mixture was poured into water (20 mL) and subsequently extracted with ethyl acetate (20 mL) for four times. The combined organic layers were washed with brine (30.0 mL) twice, dried over $Na_2SO_{4(s)}$, filtered, and concentrated under reduced pressure to give a residue, which was purified by silica gel column chromatography (petroleum ether:ethyl acetate=4:1) to give the title compound (114 mg, >100% yield) as brown oil. LC-MS (ESI): $R_T$=1.71 min, mass calcd. for $C_{15}H_{27}NO_6S$ 349.2, m/z found 294.1 [M+H−56]$^+$. $^1$H NMR (400 MHz, CDCl$_3$) δ 3.77 (s, 3H), 3.73-3.70 (m, 2H), 3.02 (t, J=13.2 Hz, 2H), 2.38-2.31 (m, 1H), 1.91-1.87 (m, 2H), 1.76-1.68 (m, 2H), 1.60 (s, 6H), 1.43 (s, 9H).

Acid 1: 1-((1-Methoxy-2-methyl-1-oxopropan-2-yl)sulfonyl)piperidine-4-carboxylic Acid To a solution of 1-(2-methoxycarbonyl-propane-2-sulfonyl)-piperidine-4-carboxylic acid tert-butyl ester Intermediate A2 (1.23 g, 3.52 mmol) in dichloromethane (50 mL) was added trifluoroacetic acid (50 mL) at room temperature. After stirred at room temperature for 1 hour, the mixture was concentrated under reduced pressure to give the crude title compound (1.20 g, >100% yield) as yellow solids, which was used directly in the next step. LC-MS (ESI): $R_T$=0.26 min, mass calcd. For $C_{11}H_{19}NO_6S$ 293.1, m/z found 294.0 [M+H]$^+$.

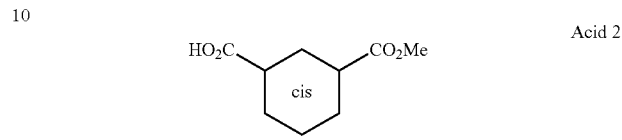

Acid 2

Intermediate A3: 3-Oxabicyclo[3.3.1]nonane-2,4-dione

A solution of cyclohexane-1,3-dicarboxylic acid (10.0 g, 58.1 mmol) in acetic anhydride (100 mL) was stirred at 120° C. for 1.5 hours. The solvent was removed to give a residue (11.8 g, crude) as yellow solids. The residue was used in the next step without further purification. $^1$H NMR (400 MHz, DMSO-d$_6$) δ 2.35-2.27 (m, 1H), 2.26-2.22 (m, 1H), 1.88-1.85 (m, 2H), 1.82-1.70 (m, 4H), 1.66-1.60 (m, 0.5H), 1.53-1.44 (m, 0.5H), 1.30-1.17 (m, 1H).

Acid 2: cis-3-(Methoxycarbonyl)cyclohexanecarboxylic Acid

A solution of 3-oxabicyclo[3.3.1]nonane-2,4-dione Intermediate A3 (12.9 g, 83.8 mmol) in methanol (100 mL) was stirred at 70° C. overnight. The solvent was removed to give a residue, which was purified by silica gel column chromatography (petroleum ether:ethyl acetate=10:1 to 3:1) to give the title compound (8.3 g, 54% yield) as yellow solids. $^1$H NMR (400 MHz, CDCl$_3$) δ 3.68 (s, 3H), 2.38-2.30 (m, 2H), 2.28-2.25 (m, 1H), 2.05-1.98 (m, 2H), 1.93-1.89 (m, 1H), 1.62-1.52 (m, 1H), 1.42-1.30 (m, 3H).

Similarly utilizing analogous procedures, the acid ester was prepared as shown:

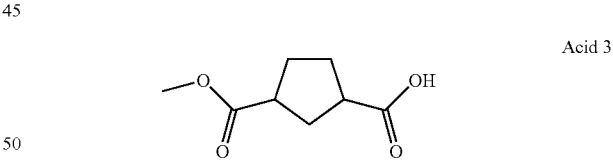

Acid 3

Acid 3: 3-(Methoxycarbonyl)cyclopentanecarboxylic Acid $^1$H NMR (400 MHz, DMSO-d$_6$) δ 12.10 (s, 1H), 3.60 (s, 3H), 2.90-2.70 (m, 2H), 2.16-1.65 (m, 6H).

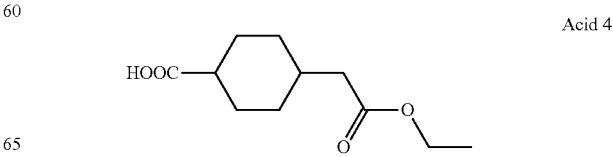

Acid 4

Intermediate A4: 4-(2-Ethoxy-2-oxoethylidene)cyclohexanecarboxylic Acid

To a solution of 4-oxocyclohexanecarboxylic acid (2.0 g, 14 mmol) in anhydrous ethanol (100 mL) was added sodium methoxide (0.9 g, 16 mmol) followed by ethyl 2-(diethoxyphosphoryl)acetate (3.5 g, 15 mmol) at room temperature under nitrogen atmosphere. The reaction mixture was cooled in an ice bath to 4° C. and another batch of sodium methoxide (800 mg, 15 mmol) was subsequently added. After stirring for 1 hour at 4° C. under nitrogen atmosphere, the reaction mixture was brought up to room temperature and adjusted to pH 5 with glacial acetic acid (3 ml). The acidified mixture was concentrated and the remaining oil was partitioned between ethyl acetate (100 ml) and 1 M hydrochloric acid in water (100 mL). The organic phase was separated, washed with water (100 mL) twice, dried over anhydrous $Na_2SO_{4(s)}$, filtered and concentrated to afford the title compound (3.0 g, 100% yield) as yellow oil, used directly to the next reaction without further purification. $^1$H NMR (400 MHz, DMSO-$d_6$) δ 12.12 (s, 1H), 5.65 (s, 1H), 4.06 (q, J=7.2 Hz, 2H), 3.45 (dt, J=13.6, 4.0 Hz, 1H), 2.54-2.50 (m, 1H), 2.36-2.26 (m, 1H), 2.24-2.15 (m, 2H), 1.97-1.94 (m, 2H), 1.57-1.41 (m, 2H), 1.19 (t, J=7.2 Hz, 3H).

Acid 4: 4-(2-Ethoxy-2-oxoethyl)cyclohexanecarboxylic Acid

To a solution of 4-(2-ethoxy-2-oxoethylidene)cyclohexanecarboxylic acid Intermediate A4 (3.2 g, 14 mmol) in ethanol (150 mL) was added 10% wt palladium on charcoal (0.4 g). Ammonium formate (2.4 g, 37 mmol) was subsequently added at 30° C. The mixture was stirred at 50° C. for 1 hour. Then it was cooled down to room temperature and the catalyst was removed by filtering through a celite. The filtrate was concentrated to give a residue, which was partitioned between ethyl acetate (100 mL) and 1 M hydrochloric acid in water (30 mL). The organic phase was separated, washed with water (100 mL) for three times, dried over anhydrous $Na_2SO_{4(s)}$, filtered and concentrated to afford the title compound (3.1 g, 96% yield) as yellow oil, used directly to the next reaction without further purification. LC-MS (ESI): $R_T$=0.266 min, mass calcd. for $C_{11}H_{18}O_4$ 214.1, m/z found 213.0 [M–H]$^+$. $^1$H NMR (400 MHz, DMSO-$d_6$) δ 12.02 (s, 1H), 4.04 (q, J=7.2 Hz, 2H), 2.46-2.42 (m, 0.3H), 2.20-2.15 (m, 2H), 2.10 (tt, J=12.0, 3.6 Hz, 0.7H), 1.91-1.81 (m, 2H), 1.73-1.70 (m, 2H), 1.66-1.60 (m, 1H), 1.54-1.46 (m, 1H), 1.35-1.22 (m, 2H), 1.17 (t, J=7.2 Hz, 3H), 0.98 (tq, J=12.0, 3.2 Hz, 1H).

Intermediate A5: 3-Methanesulfonyl-3-aza-bicyclo[3.2.1]octane-8-carboxylic Acid Methyl Ester To a solution of methyl 3-azabicyclo[3.2.1]octane-8-carboxylate hydrochloride (600 mg, 2.93 mmol) in dichloromethane (10 mL) was added triethylamine (1.18 g, 11.7 mmol) and methanesulfonyl chloride (500 mg, 4.39 mmol) at 0° C. After stirred at room temperature overnight, the mixture was quenched with water (40 mL) and extracted with dichloromethane (30 mL) twice. The combined organic layers were washed with brine (50 mL) twice, dried over $Na_2SO_{4(s)}$ and filtered. The filtrate was concentrated under reduced pressure to give the title compound (700 mg, 97% yield) as white solids. LC-MS (ESI): $R_T$=1.37 min for MS, mass calcd. for $C_{10}H_{17}NO_4S$ 247.1, m/z found 248.4 [M+H]$^+$. $^1$HNMR (400 MHz, DMSO-$d_6$) δ 3.67 (s, 1.6H), 3.61 (s, 1.4H), 3.31 (d, J=2.4 Hz, 1H), 3.21 (d, J=4.0 Hz, 0.4H), 3.18 (d, J=3.2 Hz, 0.6H), 3.04 (s, 0.6H), 3.01 (s, 0.4H), 2.92 (s, 0.5H), 2.89 (s, 0.5H), 2.84 (s, 1.4H), 2.81 (s, 1.6H), 2.70 (t, J=4.0 Hz, 0.6H), 2.62 (s, 0.4H), 2.56 (br s, 1H), 2.47 (br s, 1H), 1.74-1.50 (m, 4H).

Acid 5: 3-(Methylsulfonyl)-3-azabicyclo[3.2.1]octane-8-carboxylic Acid

To a solution of 3-methanesulfonyl-3-aza-bicyclo[3.2.1]octane-8-carboxylic acid methyl ester Intermediate A5 (440 mg, 1.76 mmol) in tetrahydrofuran (3 mL), methanol (1 mL) and water (1 mL) was added lithium hydroxide hydrate (150 mg, 3.57 mmol) at room temperature. After stirred overnight, the mixture was concentrated under reduced pressure to give a residue, which was diluted in water (6 mL) and extracted with ethyl acetate (6 mL). The remaining aqueous layer was adjusted to pH 1-2 with 1 M hydrochloric acid aqueous solution and extracted with ethyl acetate (20 mL) for three times. The combined latter organic layers were concentrated under reduced pressure to give the title compound (400 mg, 98% yield) as white solids. $^1$H NMR (400 MHz, DMSO-$d_6$) δ 12.33 (s, 1H), 3.32 (d, J=4.0 Hz, 0.6H), 3.30 (d, J=3.2 Hz, 0.4H), 3.20 (d, J=3.2 Hz, 0.4H), 3.17 (d, J=3.6 Hz, 0.6H), 3.08 (s, 0.6H), 3.05 (s, 0.4H), 2.90 (s, 0.5H), 2.87 (s, 0.5H), 2.83 (s, 1.5H), 2.80 (s, 1.5H), 2.62 (t, J=4.8 Hz, 0.5H), 2.54 (br s, 1H), 2.51-2.50 (m, 0.5H), 2.43 (br s, 1H), 1.72-1.64 (m, 2H), 1.58-1.48 (m, 2H).

Similarly utilizing analogous procedure, the following acids were prepared:

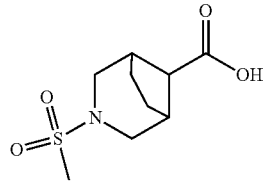

| Starting | Acid |
|---|---|
| (structure) | Acid 6 |
| (structure) | Acid 7 |

Acid 6: 8-Methanesulfonyl-8-aza-bicyclo[3.2.1]octane-3-carboxylic Acid

LC-MS (ESI): $R_T$=0.29 min, mass calcd. for $C_9H_{15}NO_4S$ 233.1, m/z found 233.8 [M+H]$^+$. $^1$H NMR (300 MHz, CDCl$_3$) δ 4.31 (s, 2H), 2.94 (s, 3H), 2.82-2.71 (m, 1H), 2.13-2.09 (m, 2H), 2.02-1.92 (m, 4H), 1.79-1.72 (m, 2H).

Acid 7: (methylsulfonyl)proline $^1$H NMR (300 MHz, DMSO-d$_6$) δ 12.70 (br s, 1H), 4.23-4.19 (m, 1H), 3.37-3.35 (m, 1H), 3.32-3.29 (m, 1H), 2.95 (s, 3H), 2.26-2.19 (m, 1H), 1.95-1.81 (m, 3H)

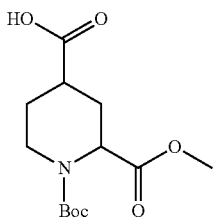

Acid 8

Intermediate A6: 2-(Methoxycarbonyl)piperidine-4-carboxylic Acid

To a solution of 2-(methoxycarbonyl)isonicotinic acid (4.20 g, 23.2 mmol) in methanol (500 mL) was added 10% palladium on charcoal wt. (420 mg) under nitrogen atmosphere at room temperature. After replacing the innert nitrogen atmosphere with hydrogen gas, the mixture was stirred at 40° C. under hydrogen atmosphere (50 psi) overnight. After cooling down to room temperature and releasing the inside pressure into normal pressure, evacuates the flask and fill in with nitrogen atmosphere for 3 times. The catalyst was filtered off and the filtrate was concentrated under reduced pressure to give the title compound (4.30 g, 99% yield) as gray solids. LC-MS (ESI): $R_T$=0.31 min, mass calcd. for $C_8H_{13}NO_4$ 187.1, m/z found 185.9 [M–H]$^-$. $^1$H NMR (400 MHz, D$_2$O) δ 4.13 (dd, J=12.4, 2.8 Hz, 1H), 3.87 (s, 3H), 3.63-3.60 (m, 1H), 3.16-3.09 (m, 1H), 2.64-2.56 (m, 2H), 2.20-2.17 (m, 1H), 1.83-1.72 (m, 2H).

Acid 8: 1-(tert-Butoxycarbonyl)-2-(methoxycarbonyl)piperidine-4-carboxylic Acid To a solution of 2-(methoxycarbonyl)piperidine-4-carboxylic acid Intermediate A6 (4.30 g, 23.0 mmol) in 1,4-dioxane (60 mL) was added water (60 mL), sodium bicarbonate (5.80 g, 69.0 mmol) and di-tert-butyl dicarbonate (10.0 g, 46.0 mmol) at room temperature. After stirring at room temperature overnight, the reaction mixture was partitioned in ethyl acetate (50 mL) and saturated sodium bicarbonate aqueous solution (100 mL). The aqueous layer was extracted with ethyl acetate (100 mL) for three times, and then it was added dropwise 0.5 N hydrochloric acid aqueous solution to adjust the pH value to 4-5. The aqueous layer was concentrated to dryness under reduced pressure to give a residue, which was purified by C18 (acetonitrile:water=5% to 50%, Wavelength: 205 nm) to give the title compound (5.24 g, 79% yield) as colorless oil. LC-MS (ESI): $R_T$=1.610 min, mass calcd. for $C_{13}H_{21}NO_6$ 287.1, m/z found 286.1 [M–H]$^-$. $^1$H NMR (400 MHz, CDCl$_3$) δ 4.63-4.56 (m, 1H), 3.87-3.80 (m, 1H), 3.69 (s, 3H), 3.37- 3.28 (m, 1H), 2.73-2.69 (m, 1H), 2.54-2.45 (m, 1H), 2.09-2.03 (m, 2H), 1.82-1.71 (m, 1H), 1.43 (s, 9H).

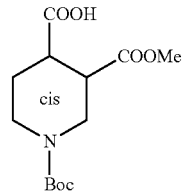

Acid 9

Intermediate A7: Pyridine-3,4-dicarboxylic Acid Dimethyl Ester

To a solution of pyridine-3,4-dicarboxylic acid (7.00 g, 41.9 mmol) and 4-dimethylaminopyridine (80 mg, 0.65 mmol) in methanol (230 mL) was added thionyl chloride (24.9 g, 210 mmol) at 0° C. The mixture was stirred at 0° C. for 30 minutes. Reaction temperature was then raised up to reflux with constant stirring overnight. Having cooled down to room temperature, the reaction mixture was concentrated under reduced pressure to give a residue, which was re-dissolved in water (200 mL). The prepared solution was adjusted to pH 8-9 with saturated sodium bicarbonate aqueous solution at 0° C. Then the aqueous was extracted with ethyl acetate (150 mL) for three times. The combined organic layers were washed with brine (200 mL), dried over Na$_2$SO$_{4(s)}$ and filtered. The filtrate was concentrated under reduced pressure to give the title compound (5.26 g, 64% yield) as yellow oil. LC-MS (ESI): $R_T$=1.27 min, mass calcd. for $C_9H_9NO_4$ 195.1, m/z found 196.4 [M+H]$^+$. $^1$H NMR (400 MHz, DMSO-d$_6$) δ 9.02 (d, J=0.8 Hz, 1H), 8.91 (d, J=5.2 Hz, 1H), 7.70 (d, J=5.2, 0.8 Hz, 1H), 3.87 (s, 6H).

Intermediate A8: Pyridine-3,4-dicarboxylic Acid 3-methyl Ester

To a suspension of pyridine-3,4-dicarboxylic acid dimethyl ester Intermediate A7 (5.26 g, 27.0 mmol) in water (50 mL) was added a solution of sodium hydroxide (1.08 g, 27.0 mmol) in water (16 mL) at 0° C. The mixture was stirred at room temperature overnight during which time the mixture became homogeneous. Extraction with chloroform removed unconsumed diester and the remained aqueous layer was acidified to pH~1 with concentrated hydrochloric acid. The resulting solution was evaporated to dryness under reduced pressure at 30° C. Extraction of the generated residue with hot tetrahydrofuran gave the crude mono-ester, which was recrystallized from methanol (1.0 g crude mono-ester in 3 mL methanol from 80° C. to room temperature) to give the title compound (2.0 g, 34% yield) as gray solids. LC-MS (ESI): $R_T$=0.25 min, mass calcd. for $C_8H_7NO_4$ 181.0, m/z found 182.3 [M+H]$^+$. $^1$H NMR (300 MHz, DMSO-d$_6$) δ 8.94 (s, 1H), 8.86 (d, J=4.8 Hz, 1H), 7.68 (d, J=4.8 Hz, 1H), 3.85 (s, 3H).

Intermediate A9: cis-Piperidine-3,4-dicarboxylic Acid 3-methyl Ester Hydrochloride To a solution of pyridine-3,4-dicarboxylic acid 3-methyl ester Intermediate A8 (1.04 g, 4.79 mmol) in methanol (30 mL) was added platinum (IV) oxide (0.12 g, 0.53 mmol) and 7 M hydrochloric acid in methanol solution (1.0 mL, 7.0 mmol). The mixture was stirred at room temperature for 24 hours under hydrogen atmosphere (50 psi). The catalyst was filtered off and the filtrate was concentrated under reduced pressure to give the title compound (1.26 g, >100% yield) as white solids. LC-MS (ESI): $R_T$=0.25 min, mass calcd. for $C_8H_{13}NO_4$ 187.1, m/z found 188.5 [M+H]$^+$. $^1$H NMR (400 MHz, D$_2$O) δ 3.80 (s, 3H), 3.75-3.62 (m, 1H), 3.57-3.46 (m, 1H), 3.42-3.39 (m, 1H), 3.34-3.22 (m, 2.7H), 3.18-3.11 (m, 0.3H), 2.27-2.16 (m, 1.8H), 1.98-1.91 (m, 0.2H).

Acid 9: cis-Piperidine-1,3,4-tricarboxylic Acid 1-tert-butyl Ester 3-methyl Ester To a solution of cis-piperidine-3,4-dicarboxylic acid 3-methyl ester hydrochloride Intermediate A9 (1.26 g, 5.65 mmol) in water (19 mL) was added a solution of sodium carbonate (1.50 g, 14.1 mmol) in water (5 ml) followed by di-tert-butyl pyrocarbonate (2.46 g, 11.3 mmol) in 1,4-dioxane (6 ml) at 0° C. The mixture was stirred at room temperature for 20 hours. It was diluted with water (20 mL) and extracted with ethyl acetate (20 mL) twice. The separated aqueous layer was acidified with 2 M citric acid in water to pH 1-2 and then extracted with ethyl acetate (40 mL) for three times. The combined organic layers were washed with water (50 mL), brine (50 mL), dried over Na$_2$SO$_{4(s)}$ and filtered. The filtrate was concentrated under reduced pressure to give the title compound (1.37 g, 85% yield) as colorless oil. LC-MS (ESI): $R_T$=1.49 min, mass calcd. for $C_{13}H_{21}NO_6$ 287.1, m/z found 233.5 [M+H−55]$^+$. $^1$H NMR (300 MHz, CDCl$_3$) δ 4.13-4.07 (m, 1H), 3.70-3.63 (m, 4H), 3.45 (dd, J=13.8, 3.3 Hz, 1H), 3.22-3.13 (m, 1H), 2.96-2.79 (m, 2H), 2.21-2.08 (m, 1H), 1.94-1.80 (m, 1H), 1.46 (s, 1.4H), 1.44 (s, 7.6H).

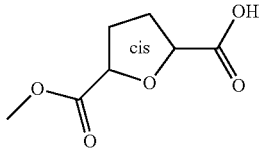

Acid 10

Intermediate A10: cis-Tetrahydrofuran-2,5-dicarboxylic Acid

To a solution of furan-2,5-dicarboxylic acid (8.0 g, 51.3 mmol) in acetic acid (150 mL) was added 10% wt palladium on charcoal (1.0 g) under nitrogen atmosphere at room temperature. After stirred at 140° C. under hydrogen atmosphere (5 MPa) overnight, the mixture was cooled down to room temperature and filtered off the catalyst. The filtrate was concentrated under reduced pressure to give the title compound (7.1 g, 87% yield) as green solids. LC-MS (ESI): $R_T$=0.30 min, mass calcd. for $C_6H_8O_5$ 160.0, m/z found 161.1 [M+H]$^+$. $^1$H NMR (300 MHz, DMSO-d$_6$) δ 12.85 (br s, 2H), 4.47 (s, 2H), 2.26-2.16 (m, 2H), 2.02-1.90 (m, 2H).

Intermediate A11: cis-3,8-Dioxabicyclo[3.2.1]octane-2,4-dione

A solution of cis-tetrahydrofuran-2,5-dicarboxylic acid Intermediate A10 (8.67 g, 54.2 mmol) in trifluoroacetic anhydride (60 mL) was stirred at 45° C. overnight and then at 55° C. for 2 days. After cooling down to room temperature, the mixture was concentrated under reduced pressure to give the title compound (8.8 g, >100% yield) as green solids. $^1$H NMR (300 MHz, DMSO-d$_6$) δ 5.18 (s, 2H), 2.27-2.14 (m, 4H).

Intermediate A12: cis-5-(Methoxycarbonyl)tetrahydrofuran-2-carboxylic Acid

To a solution of cis-3,8-dioxabicyclo[3.2.1]octane-2,4-dione Intermediate A11 (8.8 g, 54.2 mmol) in methanol (170 mL) was added triethylamine (7.12 g, 70.5 mmol) at 0° C. The mixture was stirred at room temperature for 20 hours. Then it was concentrated under reduced pressure to dryness. The residue was dissolved in water (40 mL), adjusted to pH 1-2 with 2M hydrochloric acid aqueous solution, and extracted with ethyl acetate (300 mL) for three times. The combined organic layers were washed with water (200 mL) twice, brine (200 mL) twice, dried over Na$_2$SO$_{4(s)}$ and filtered. The filtrate was concentrated under reduced pressure to give the title compound (6.19 g, 66% yield) as yellow oil. LC-MS (ESI): $R_T$=0.27 min, mass calcd. for $C_7H_{10}O_5$ 174.1, m/z found 175.1 [M+H]$^+$. $^1$H NMR (400 MHz, DMSO-d$_6$) δ 11.61 (br s, 1H), 4.53-4.50 (m, 1H), 4.43-4.40 (m, 1H), 3.64 (s, 3H), 2.22-2.11 (m, 2H), 2.03-1.94 (m, 2H).

Intermediate A13: cis-2-Benzyl 5-methyl tetrahydrofuran-2,5-dicarboxylate

To a solution of cis-5-(methoxycarbonyl)tetrahydrofuran-2-carboxylic acid Intermediate A12 (5.0 g, 28.7 mmol) in N,N-dimethylformamide (50 mL) was added potassium carbonate (15.8 g, 114 mmol) and (bromomethyl)benzene (9.8 g, 57.3 mmol) at room temperature. After stirred at 30° C. overnight, the mixture was poured into water (200 mL) and extracted with ethyl acetate (200 mL) twice. The combined organic layers were washed with water (200 mL) twice, followed with brine (200 mL) twice, dried over Na$_2$SO$_{4(s)}$, filtered and concentrated. The residue was purified by C18 column (acetonitrile:water=60%) to give the title compound (5 g, 66% yield) as colorless oil. LC-MS (ESI): $R_T$=1.54 min, mass calcd. for $C_{14}H_{16}O_5$ 264.1, m/z found 265.1 [M+H]$^+$. $^1$H NMR (300 MHz, CDCl$_3$) δ 7.37-7.35 (m, 5H), 5.25-5.15 (m, 2H), 4.66-4.59 (m, 2H), 3.70 (s, 3H), 2.32-2.17 (m, 4H).

Acid 10: cis-5-(Methoxycarbonyl)tetrahydrofuran-2-carboxylic Acid

To a solution of cis-2-benzyl 5-methyl tetrahydrofuran-2,5-dicarboxylate Intermediate A13 (5.0 g, 18.9 mmol) in methanol (60 mL) was added 10% wt palladium on charcoal (500 mg) under nitrogen at room temperature. After stirred at 25° C. under balloon pressure of hydrogen overnight, the mixture was filtered and the filtrate was concentrated under reduced pressure to give the title compound (3.2 g, 97% yield) as colorless oil. LC-MS (ESI): $R_T$=0.24 min, mass calcd. for $C_7H_{10}O_5$ 174.1, m/z found 175.1 [M+H]$^+$. $^1$H NMR (300 MHz, DMSO-d$_6$) δ 12.56 (br s, 1H), 4.51 (t, J=6.3 Hz, 1H), 4.41 (t, J=6.3 Hz, 1H), 3.64 (s, 3H), 2.17-1.91 (m, 4H).

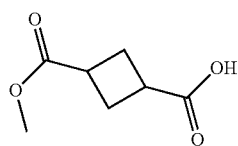

Acid 11

Intermediate A14: 3-Methylene-cyclobutanecarboxylic Acid

To a solution of 3-methylene-cyclobutanecarbonitrile (11.2 g, 120 mmol) in ethanol (30 mL) and water (30 mL) was added potassium hydroxide (33.7 g, 602 mmol). The mixture was stirred at 105° C. overnight. After cooled down, it was concentrated. The aqueous residue was neutralized with concentrated hydrochloric acid and extracted with ethyl acetate (50 mL) for three times. The combined organic layers were washed with brine (20 mL) twice, dried over $Na_2SO_{4(s)}$ and filtered. The filtrate was concentrated under reduced pressure to give the title compound (13.0 g, 96% yield) as colorless oil. $^1$H NMR (400 MHz, DMSO-d$_6$) δ 12.21 (s, 1H), 4.79-4.76 (m, 2H), 3.10-3.01 (m, 1H), 2.85-2.82 (m, 4H).

Intermediate A15: 3-Methylene-cyclobutanecarboxylic Acid Tert-butyl Ester

To a solution of 3-methylene-cyclobutanecarboxylic acid Intermediate A14 (13.0 g, 116 mmol) in tetrahydrofuran (150 mL) was added di-t-butyldicarbonate (33.0 g, 151 mmol) and 4-dimethylaminepyridine (2.83 g, 23.2 mmol). After stirred at room temperature overnight, the mixture was diluted with ethyl acetate (200 mL), washed with water (50 mL), brine (50 mL), dried over $Na_2SO_{4(s)}$ and filtered. The filtrate was concentrated under reduced pressure to give a residue, which was purified by silica gel column chromatography (100% petroleum ether) to give the title compound (9.4 g, 48% yield) as colorless oil. $^1$H NMR (400 MHz, DMSO-d$_6$) δ 4.79-4.77 (m, 2H), 3.07-2.99 (m, 1H), 2.88-2.77 (m, 4H), 1.40 (s, 9H).

Intermediate A16: 3-Hydroxymethyl-cyclobutanecarboxylic Acid Tert-butyl Ester A solution of 3-methylene-cyclobutanecarboxylic acid tert-butyl ester Intermediate A15 (2.0 g, 11.9 mmol) in tetrahydrofuran (20 mL) was cooled to −20° C. Then 10 M borane-methyl sulfide complex in dimethyl sulfide (0.36 mL, 3.57 mmol) was added slowly under nitrogen atmosphere. After stirred at room temperature for 4 hours, the mixture was cooled to −20° C.~−10° C. Methanol (2 mL) and 30% hydrogen peroxide aqueous solution (400 mg, 11.9 mmol) were added in sequence. After stirring for 15 minutes, 3 M sodium hydroxide aqueous solution (1.59 mL, 4.76 mmol) was added. The obtained mixture was stirred at −20° C.~−10° C. for 2 hours. A saturated aqueous solution of sodium sulfite (20 mL) was added. The mixture was diluted with water (20 mL) and then extracted with ethyl acetate (30 mL) for three times. The combined organic layers were washed with brine (30 mL), dried over $Na_2SO_{4(s)}$ and filtered. The filtrate was concentrated under reduced pressure to give a residue, which was purified by silica gel column chromatography (petroleum ether:ethyl acetate=10:1) to give the title compound (1.53 g, 69% yield) as colorless oil. $^1$H NMR (300 MHz, DMSO-d$_6$) δ 3.38 (d, J=6.6 Hz, 0.8H), 3.28 (d, J=6.0 Hz, 1.2H), 2.99-2.81 (m, 1H), 2.34-2.24 (m, 1H), 2.15-2.04 (m, 2H), 1.94-1.77 (m, 2H), 1.40 (s, 3.6H), 1.38 (s, 5.4H).

Intermediate A17: Cyclobutane-1,3-dicarboxylic Acid

To a hot concentrated nitric acid (5 mL) which contained one drop of fuming nitric acid was added a solution of 3-hydroxymethyl-cyclobutanecarboxylic acid tert-butyl ester Intermediate A16 (1.0 g, 5.38 mmol) in 2 M nitric acid aqueous solution (1.0 mL) dropwise. The mixture was heated to 120° C. and stirred for 3 hours until the solution turned nearly colorless and the gas evolution ceased. The completed reaction mixture was cooled down to room temperature. Most of excess nitric acid was removed under reduced pressure and the residual trace of nitric acid was destroyed by addition of formic acid (2 mL). The resulting solution was concentrated to give the title compound (800 mg, crude) as yellow oil which was directly used in next step without further purification. LC-MS (ESI): $R_T$=0.28 min, mass calcd. for $C_6H_8O_4$ 144.0, m/z found 145.0 [M+H]$^+$.

Intermediate A18: Cyclobutane-1,3-dicarboxylic Acid Dimethyl Ester

To a solution of cyclobutane-1,3-dicarboxylic acid Intermediate A17 (560 mg, 3.9 mmol) in methanol (10 mL) was added one drop of concentrated sulfuric acid. The mixture was heated to 75° C. and stirred overnight. It was then cooled down to room temperature and concentrated under reduced pressure. The residue was dissolved in ethyl acetate (50 mL) and washed with saturated sodium bicarbonate aqueous solution (20 mL) followed by brine (20 mL). The remaining organic layer was dried over $Na_2SO_4$(s), filtered, and concentrated to give the title compound (600 mg, 90% yield) as colorless oil. $^1$H NMR (300 MHz, CDCl$_3$) δ 3.71 (s, 6H), 3.28-3.17 (m, 2H), 2.53 (t, J=7.8 Hz, 4H).

Acid 11: Cyclobutane-1,3-dicarboxylic Acid Monomethyl Ester

To a solution of cyclobutane-1,3-dicarboxylic acid dimethyl ester Intermediate A18 (600 mg, 3.49 mmol) in methanol (15 mL) and water (1.5 mL) was added sodium hydroxide (142 mg, 3.55 mmol). The mixture was stirred at room temperature overnight. It was then concentrated under reduced pressure and the residue was dissolved in water (15 mL). The resulting solution was extracted with ethyl ether (15 mL). The aqueous layer was acidified to pH-2 with 2 M hydrochloric acid aqueous solution and subsequently extracted with ethyl acetate (20 mL) for three times. The combined organic layers were dried over $Na_2SO_4$(s) and concentrated to give the title compound (478 mg, 87% yield) as colorless oil. LC-MS (ESI): $R_T$=0.26 min, mass calcd. for $C_7H_{10}O_4$ 158.1, m/z found 157.4 [M−H]$^-$. $^1$H NMR (300 MHz, DMSO-d$_6$) δ 12.19 (br s, 1H), 3.62 (s, 3H), 3.16-3.00 (m, 2H), 2.37 (t, J=7.8 Hz, 4H).

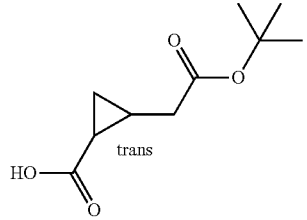

Acid 12

Intermediate A19: trans-Methyl 2-(2-(tert-butoxy)-2-oxoethyl)cyclopropane-1-carboxylate To a solution of diisopropylamine (7.80 g, 77.4 mmol) in anhydrous tetrahydrofuran (40 mL) was added n-butyllithium (31 mL, 77.4 mmol, 2 M in hexane) at −78° C. under nitrogen atmosphere. After stirring at −78° C. for 1 hour, tert-butyl acetate (10.0 g, 86.0 mmol) was added. The reaction mixture was stirred for another 1 hour, and then a solution of methyl 4-bromobut-2-enoate (14.3 g, 60.2 mmol) in anhydrous tetrahydrofuran (20 mL) was added to the reaction mixture at −78° C. The resulting mixture was brought up to room temperature and stirred overnight. It was then quenched with aqueous saturated ammonium chloride solution (100 mL), extracted with ethyl acetate (500 mL) twice. The combined organic layers were washed with brine (400 mL) for three times, dried over anhydrous $Na_2SO_{4(s)}$ and concentrated to give the title compound (12.8 g, 100% yield) as brown oil. $^1$H NMR (400 MHz, $CDCl_3$) δ 3.67 (s, 3H), 2.24-2.21 (m, 2H), 1.70-1.60 (m, 1H), 1.45-1.44 (m, 10H), 1.27-1.23 (m, 1H), 0.87-0.75 (m, 1H).

Acid 12: trans-2-(2-(tert-Butoxy)-2-oxoethyl)cyclopropane-1-carboxylic Acid

To a solution of trans-methyl 2-(2-(tert-butoxy)-2-oxoethyl)cyclopropane-1-carboxylate Intermediate A19 (5.00 g, 23.3 mmol) in tetrahydrofuran/methanol/water (60 mL/30 mL/30 mL) was added lithium hydroxide hydrate (980 mg, 23.3 mmol). The reaction mixture was stirred at room temperature for 2 hours. Then it was concentrated to remove most of the solvents at room temperature under reduced pressure. The aqueous residue was diluted with water (60 mL) and adjusted pH to 3 with aqueous hydrochloric acid (1 M). The obtained mixture was extracted with ethyl acetate (200 mL) for three times, dried over anhydrous $Na_2SO_{4(s)}$ and concentrated to give the title compound (3.30 g, 70% yield) as colorless oil. $^1$H NMR (400 MHz, DMSO-$d_6$) δ 12.14 (br s, 1H), 2.42-2.38 (m, 1H), 2.34-2.28 (m, 1H), 2.25-2.15 (m, 1H), 1.78-1.74 (m, 1H), 1.40 (s, 9H), 1.01-0.96 (m, 1H), 0.78-0.73 (m, 1H).

Acid 13:4-(Methoxycarbonyl)cycloheptanecarboxylic Acid

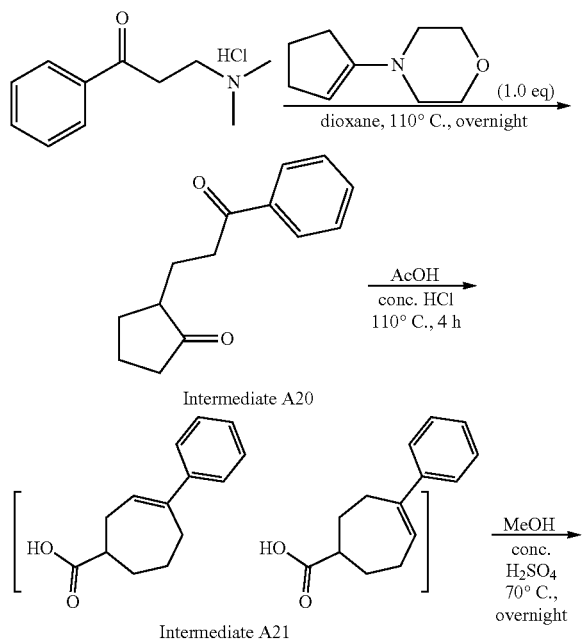

Intermediate A20:2-(3-Oxo-3-phenylpropyl)cyclopentanone To a suspension of 3-(dimethylamino)-1-phenylpropan-1-one hydrochloride (5.00 g, 23.4 mmol) in dioxane (50 mL) was added 4-(cyclopent-1-en-1-yl)morpholine (3.58 g, 23.4 mmol) at room temperature. The mixture was heated to 110° C. and stirred under nitrogen atmosphere overnight. Then it was cooled down and concentrated. The residue was dissolved in ethyl acetate (100 mL) and washed with 1 N hydrochloric acid aqueous solution (50 mL). The aqueous layer was extracted with ethyl acetate (100 mL) for three times. The combined organic layers were washed with brine (100 mL), dried over $Na_2SO_4$(s) and filtered. The filtrate was concentrated and purified by silica gel column chromatography (petroleum ether:ethyl acetate=10:1) to give the title compound (2.3 g, 46% yield) as yellow solids. LC-MS (ESI): $R_T$=1.36 min, mass calcd. for $C_{14}H_{16}O_2$ 216.1, m/z found 217.1 [M+H]$^+$. $^1$H NMR (300 MHz, $CDCl_3$) δ 7.98 (d, J=7.5 Hz, 2H), 7.57 (t, J=7.5 Hz, 1H), 7.47 (d, J=7.5 Hz, 2H), 3.22-3.05 (m, 2H), 2.38-1.99 (m, 6H), 1.88-1.73 (m, 2H), 1.63-1.53 (m, 1H).

Intermediate A21: Mixture of 4-Phenylcyclohept-3-enecarboxylic Acid and 4-phenylcyclohept-4-enecarboxylic Acid

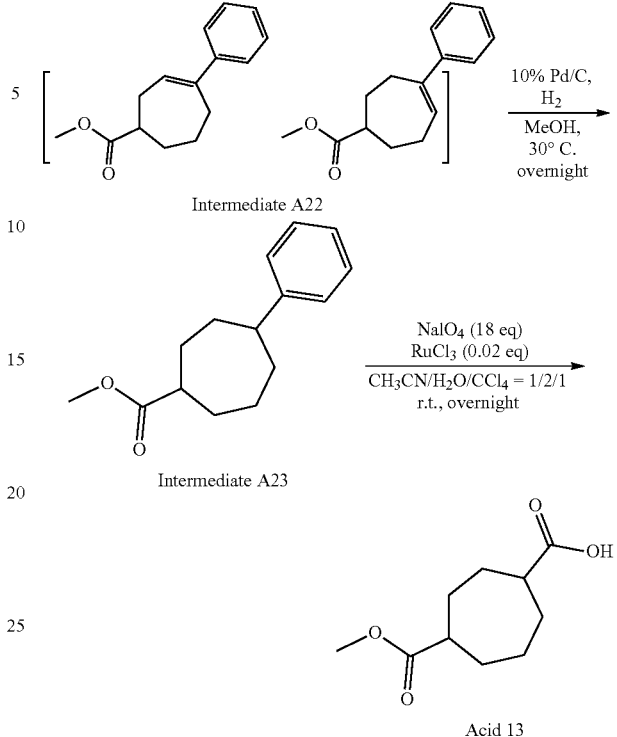

To a solution of 2-(3-oxo-3-phenylpropyl)cyclopentanone Intermediate A20 (1.00 g, 4.63 mmol) in acetic acid (8 mL) was added concentrated hydrochloric acid (2 mL) at room temperature. The mixture was heated to 110° C. and stirred for 4 hours. After cooling down, the mixture was concentrated under reduced pressure. The residue was dissolved in water (30 mL) and extracted with diethyl ether (30 mL). The isolated ethereal layer was extracted with 6 N sodium hydroxide aqueous solution (10 mL). The separated aqueous layer was acidified to pH~1 with concentrated hydrochloric acid and then extracted with diethyl ether (30 mL) twice.

The combined organic layers were dried over $Na_2SO_4(s)$ and filtered. The filtrate was concentrated to give a mixture of title compounds (750 mg, 75% yield) as yellow oil. LC-MS (ESI): $R_T$=1.24 min, mass calcd. for $C_{14}H_{16}O_2$ 216.1, m/z found 215.3 $[M-H]^-$. $^1H$ NMR (400 MHz, DMSO-$d_6$) δ 12.12 (br s, 1H), 7.31-7.28 (m, 4H), 7.25-7.20 (m, 1H), 6.08-6.02 (m, 1H), 2.68-2.54 (m, 2H), 2.46-2.33 (m, 2H), 2.27-2.20 (m, 0.5H), 2.11-1.78 (m, 3H), 1.61-1.42 (m, 1.5H).

Intermediate A22: Mixture of methyl 4-phenylcyclohept-3-enecarboxylate and Methyl 4-phenylcyclohept-4-enecarboxylate To a solution of the mixture of 4-phenylcyclohept-3-enecarboxylic acid and 4-phenylcyclohept-4-enecarboxylic acid Intermediate A21 (750 mg, 3.47 mmol) in dry methanol (10 mL) was added one drop of concentrated sulfuric acid. The mixture was heated to 70° C. and stirred overnight. After cooling down, the mixture was concentrated and the residue was dissolved in ethyl acetate (50 mL). The resulting solution was washed with saturated sodium bicarbonate aqueous solution (30 mL) and brine (30 mL), dried over $Na_2SO_4(s)$ and filtered. The filtrate was concentrated to give a mixture of title compounds (740 mg, 93% yield) as yellow oil. LC-MS (ESI): $R_T$=1.83 min, mass calcd. for $C_{15}H_{18}O_2$ 230.1, m/z found 231.3 $[M+H]^+$. $^1H$ NMR (400 MHz, $CD_3OD$) δ 7.29-7.15 (m, 5H), 6.05 (t, J=6.0 Hz, 0.5H), 6.00 (t, J=6.4 Hz, 0.5H), 3.66 (s, 1.5H), 3.65 (s, 1.5H), 2.74-2.38 (m, 4.5H), 2.30-1.84 (m, 3H), 1.72-1.49 (m, 1.5H).

Intermediate A23: Methyl 4-phenylcycloheptanecarboxylate

To a solution of the mixture of methyl 4-phenylcyclohept-3-enecarboxylate and methyl 4-phenylcyclohept-4-enecarboxylate Intermediate A22 (1.64 g, 7.13 mmol) in methanol (50 mL) were added 10% wt. palladium on charcoal (160 mg). The resulting reaction mixture was then stirred at 30° C. under hydrogen atmosphere overnight. Then the catalyst was filtered. The filtrate was concentrated to give the title compound (1.6 g, 97% yield) as yellow oil. $^1H$ NMR (400 MHz, $CD_3OD$) δ 7.25-7.09 (m, 5H), 3.66 (s, 3H), 2.74-2.63 (m, 2H), 2.09-1.46 (m, 10H).

Acid 13: 4-(Methoxycarbonyl)cycloheptanecarboxylic Acid

To a solution of sodium periodate (26.6 g, 124 mmol) in acetonitrile (13 mL) and water (26 mL) was added the solution of methyl 4-phenylcycloheptanecarboxylate Intermediate A23 (1.6 g, 6.90 mmol) in carbon tetrachloride (13 mL) and ruthenium trichloride (29 mg, 0.14 mmol). After stirred at room temperature overnight, the mixture was filtered and the filtrate was adjusted to pH 8-9 using saturated sodium bicarbonate aqueous solution. The resulting solution was rinsed with dichloromethane (20 mL), acidified to pH 2-3 with 1 N hydrochloric acid aqueous solution, and extracted with ethyl acetate (30 mL) twice. The combined organic layers were washed with brine (30 mL), dried over $Na_2SO_4(s)$ and filtered. The filtrate was concentrated to give the title compound (1.2 g, 87% yield) as yellow oil. LC-MS (ESI): $R_T$=0.29 min (MS peak), mass calcd. for $C_{10}H_{16}O_4$ 200.1, m/z found 199.1 $[M-H]^-$. $^1H$ NMR (300 MHz, $CD_3OD$) δ 3.66 (s, 3H), 2.59-2.47 (m, 2H), 2.07-1.44 (m, 10H).

Acid 36: 4-(N-Methylsulfamoyl)cyclohexanecarboxylic Acid

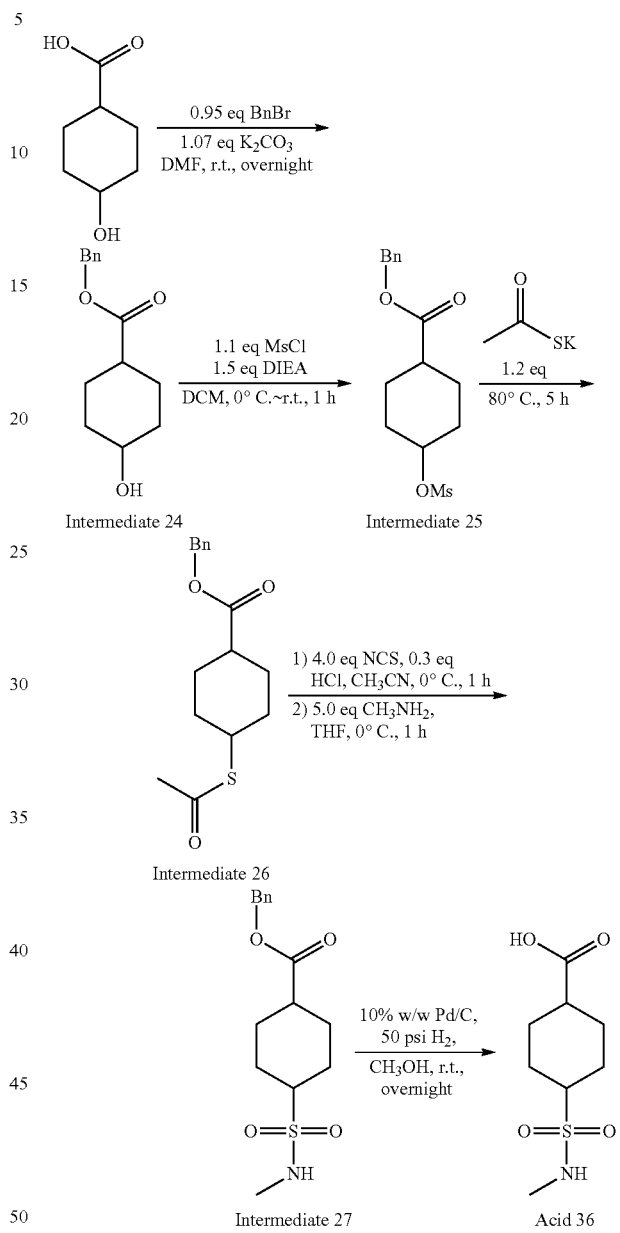

Intermediate 24: Benzyl 4-hydroxycyclohexane-1-carboxylate

To a solution of 4-hydroxycyclohexanecarboxylic acid (24.8 g, 172 mmol) in N,N-dimethylformamide (125 mL) was added potassium carbonate (25.0 g, 184 mmol) and benzyl bromide (28.0 g, 163 mmol) at room temperature. After stirring overnight under nitrogen atmosphere, the mixture was poured into water (200 mL), extracted with ethyl acetate (150 mL) twice. The combined organic layers were washed with brine (100 mL), dried over $Na_2SO_{4(s)}$, filtered and concentrated to give a residue, which was purified by silica gel column chromatography (petroleum ether:ethyl acetate=5:1) to afford the title compound (36.0 g, 89% yield) as colorless oil. LC-MS (ESI): R$_T$=1.50 min, mass calcd. for C$_{14}$H$_{18}$O$_3$ 234.1, m/z found 235.3 [M+H]$^+$.

Intermediate 25: Benzyl 4-((methylsulfonyl)oxy)cyclohexanecarboxylate

To a solution of benzyl 4-hydroxycyclohexanecarboxylate intermediate 24 (27.0 g, 115 mmol) and N-ethyl-N-isopropylpropan-2-amine (22.3 g, 173 mmol) in dichloromethane (300 mL) was added methanesulfonyl chloride (14.5 g, 127 mmol) slowly at 0° C. After stirring for 1 hour at room temperature, the mixture was diluted in dichloromethane (500 mL), washed with water (100 mL), brine (100 mL), dried over Na$_2$SO$_{4(s)}$, filtered and concentrated to give the title compound (36.5 g, crude) as light yellow solids. $^1$H NMR (400 MHz, DMSO-d$_6$) δ 7.40-7.31 (m, 5H), 5.11 (s, 1H), 5.09 (s, 1H), 4.88-4.78 (m, 0.4H), 4.64-4.53 (m, 0.6H), 3.17 (s, 3H), 2.57-2.52 (m, 0.4H), 2.45-2.37 (m, 0.6H), 2.11-2.03 (m, 1H), 2.00-1.92 (m, 1H), 1.88-1.80 (m, 1H), 1.75-1.69 (m, 3H), 1.60-1.47 (m, 2H).

Intermediate 26: Benzyl 4-(acetylthio)cyclohexanecarboxylate

To a solution of benzyl 4-((methylsulfonyl)oxy)cyclohexanecarboxylate intermediate 25 (36.5 g, crude, ~115 mmol) in N,N-dimethylformamide (350 mL) was added potassium ethanethioate (15.8 g, 139 mmol). The mixture was stirred at 80° C. under nitrogen atmosphere for 5 hours. After cooling down to room temperature, the mixture was diluted in water (500 mL). The obtained mixture was extracted with ethyl acetate (200 mL) for three times. The combined organic layers were washed with water (100 mL), brine (100 mL), dried over Na$_2$SO$_{4(s)}$, filtered and concentrated to give a residue, which was purified by silica gel column chromatography (petroleum ether:ethyl acetate=5:1) to afford the title compound (26.0 g, 77% yield) as brown oil. $^1$H NMR (400 MHz, DMSO-d$_6$) δ 7.40-7.30 (m, 5H), 5.10 (s, 1.4H), 5.09 (s, 0.6H), 3.71-3.65 (m, 0.8H), 3.30-3.23 (m, 0.2H), 2.58-2.52 (m, 1H), 2.30 (s, 2H), 2.29 (s, 1H), 1.97-1.88 (m, 1H), 1.84-1.72 (m, 3H), 1.69-1.57 (m, 3H), 1.50-1.37 (m, 1H).

Intermediate 27: Benzyl 4-(N-methylsulfamoyl)cyclohexanecarboxylate

To a solution of benzyl 4-(acetylthio)cyclohexanecarboxylate intermediate 26 (2.00 g, 6.85 mmol) in acetonitrile (20 mL) was added 2 M hydrochloride aqueous solution (1 mL) at 0° C. Then 1-chloropyrrolidine-2,5-dione (3.66 g, 27.4 mmol) was added. After stirred at 0° C. under nitrogen atmosphere for 1 hour, the mixture was diluted in ether (100 mL), washed with water (30 mL), brine (30 mL), dried over Na$_2$SO$_{4(s)}$, filtered and concentrated to give a residue, which was dissolved in tetrahydrofuran (10 mL) and cooled to 0° C. Then 2 M methanamine in tetrahydrofuran (17 mL, 34.3 mmol) was added. After stirred at 0° C. for 1 hour, the mixture was diluted in water (50 mL) and extracted with ethyl acetate (50 mL) for three times. The combined organic layers were washed with water (20 mL), 0.5 M hydrochloride aqueous solution (20 mL), brine (20 mL), dried over Na$_2$SO$_{4(s)}$, filtered and concentrated to give a residue which was purified by silica gel column chromatography (petroleum ether:ethyl acetate=2:1) to afford the title compound (2.00 g, 94% yield) as white solids. $^1$H NMR (300 MHz, DMSO-d$_6$) δ 7.43-7.29 (m, 5H), 6.91-6.81 (m, 1H), 5.13 (s, 1H), 5.19 (s, 1H), 3.13-2.96 (m, 1H), 2.77-2.70 (m, 0.5H), 2.57-2.53 (m, 3H), 2.44-2.32 (m, 0.5H), 2.18-2.05 (m, 3H), 1.92-1.79 (m, 1H), 1.65-1.34 (m, 4H).

Acid 36: 4-(N-Methylsulfamoyl)cyclohexanecarboxylic Acid

To a solution of benzyl 4-(N-methylsulfamoyl)cyclohexanecarboxylate intermediate 27 (2.45 g, 7.88 mmol) in methanol (50 mL) was added 10% palladium on charcoal wt. (245 mg). The reaction mixture was stirred at room temperature under hydrogen atmosphere (50 psi) overnight. The completed reaction mixture was filtered and the cake was washed with methanol (20 mL). The filtrate was concentrated to give the title compound (1.50 g, 86% yield) as light yellow solids. $^1$H NMR (300 MHz, DMSO-d$_6$) δ 6.89-6.77 (m, 1H), 3.04-2.89 (m, 1H), 2.57-2.55 (m, 3H), 2.20-1.79 (m, 4H), 1.62-1.28 (m, 4H).

Acid 37: 4-(pyrrolidin-1-ylsulfonyl)cyclohexane-1-carboxylic Acid

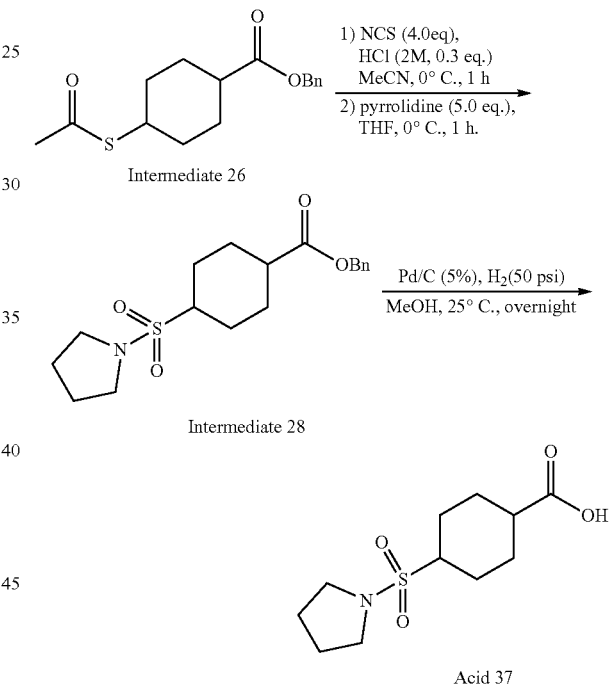

Intermediate 28: Benzyl 4-(pyrrolidin-1-ylsulfonyl)cyclohexanecarboxylate

To a solution of benzyl 4-(acetylthio)cyclohexanecarboxylate Intermediate 26 (2.70 g, 9.25 mmol) in acetonitrile (40 mL) was added 2 M hydrochloride aqueous solution (1.4 mL, 2.78 mmol), 1-chloro-pyrrolidine-2,5-dione (4.90 g, 37.0 mmol) at 0° C. After stirred at 0° C. for 1 hour, the reaction mixture was poured into water (200 mL), extracted with ethyl acetate (100 mL) twice. The combined organic layers were washed with water (100 mL), brine (100 mL), dried over Na$_2$SO$_{4(s)}$, filtered and concentrated to give the crude product (3.37 g), which was used in the next step without further purification. To a solution of the crude product (1.70 g) in tetrahydrofuran (20 mL) was added pyrrolidine (1.60 g, 23.2 mmol) at 0° C. After stirring at 0°

C. for 1 hour, the solvent was removed to give a residue, which was purified by silica gel column chromatography (petroleum ether:ethyl acetate=10:1 to 3:1) to give the title compound (1.60 g, 99% yield) as yellow solids. LC-MS (ESI): $R_T$=1.89 min, mass calcd. for $C_{18}H_{25}NO_4S$ 351.2, m/z found 352.4 [M+H]$^+$. $^1$H NMR (300 MHz, CDCl$_3$) δ 7.42-7.31 (m, 5H), 5.17 (s, 0.9H), 5.13 (s, 1.1H), 3.42-3.35 (m, 4H), 3.03-2.90 (m, 1H), 2.75-2.67 (m, 0.4H), 2.41-2.33 (m, 1.4H), 2.25-2.17 (m, 2.2H), 2.07-2.00 (m, 1H), 1.96-1.88 (m, 4H), 1.85-1.71 (m, 1H), 1.67-1.47 (m, 3H).

Acid 37: 4-(pyrrolidin-1-ylsulfonyl)cyclohexane-1-carboxylic Acid

To a solution of benzyl 4-(pyrrolidin-1-ylsulfonyl)cyclohexanecarboxylate intermediate 28 (1.60 g, 4.56 mmol) in methanol (40 mL) was added 5% palladium on charcoal wt. (160 mg). After stirred at 25° C. under hydrogen (50 psi) atmosphere overnight, the reaction mixture was filtered through the celite. The filtrate was concentrated to give the title compound (1.40 g, crude) as yellow solids, which was used in the next step without further purification. $^1$H NMR (300 MHz, DMSO-d$_6$) δ 12.12 (br s, 1H), 3.33-3.11 (m, 6H), 2.60-2.54 (m, 0.4H), 2.28-2.14 (m, 0.6H), 2.10-1.95 (m, 3H), 1.89-1.80 (m, 4H), 1.60-1.34 (m, 4H).

Acid 38: 3-(N-Methylacetamido)cyclopentanecarboxylic Acid

Intermediate 29: Benzyl 3-oxocyclopentanecarboxylate

To a solution of 3-oxocyclopentanecarboxylic acid (5.00 g, 39.1 mmol) in N,N-dimethylformamide (50 mL) was added potassium carbonate (16.2 g, 117 mmol) and benzyl bromide (13.4 g, 78.2 mmol). After stirred at room temperature overnight, the mixture was poured into water (200 mL) and extracted with ethyl acetate (200 mL) twice. The combined organic layers were washed with water (200 mL) and brine (200 mL), dried over Na$_2$SO$_{4(s)}$ and filtered. The filtrate was concentrated and purified by silica gel column chromatography (petroleum ether:ethyl acetate=10:1 to 8:1) to give the title compound (8.00 g, 94% yield) as colorless oil. $^1$H NMR (300 MHz, CDCl$_3$) δ 7.43-7.33 (m, 5H), 5.18 (s, 2H), 3.25-3.14 (m, 1H), 2.61-2.10 (m, 6H).

Intermediate 30: Benzyl 3-((tert-butoxycarbonyl)(methyl)amino)cyclopentanecarboxylate To a solution of benzyl 3-oxocyclopentanecarboxylate EO8495_514.2 (4.20 g, 19.3 mmol) in 1,2-dichloroethane (50 mL) was added methylamine hydrochloride (1.90 g, 28.6 mmol) and N,N-diisopropylethylamine (3.70 g, 28.7 mmol). The mixture was stirred at room temperature for 1 hour, and then sodium cyanoborohydride (3.00 g, 47.8 mmol) was added. After the reaction mixture was stirred at room temperature overnight, N,N-diisopropylethylamine (7.40 g, 57.4 mmol) and di-tert-butyl dicarbonate (10.5 g, 48.2 mmol) was added. After stirred at room temperature for 3 hours, the mixture was diluted with dichloromethane (100 mL) and washed with water (100 mL) twice and brine (100 mL), dried over Na$_2$SO$_{4(s)}$ and filtered. The filtrate was concentrated and purified by C18 column (acetonitrile:water=70% to 75%) to give the title compound (1.70 g, 22% yield) as yellow oil. LC-MS (ESI): $R_T$=1.52 min, mass calcd. for $C_{19}H_{27}NO_4$ 333.2, m/z found 334.3 [M+H]$^+$. $^1$H NMR (300 MHz, CDCl$_3$) δ 7.40-7.30 (m, 5H), 5.13 (s, 2H), 2.96-2.77 (m, 1H), 2.73 (s, 3H), 2.20-2.03 (m, 2H), 1.95-1.67 (m, 5H), 1.45 (s, 9H).

Intermediate 31: Benzyl 3-(N-methylacetamido)cyclopentanecarboxylate

To a solution of benzyl 3-((tert-butoxycarbonyl) methylamino)cyclopentanecarboxylate intermediate 30 (1.70 g, 5.04 mmol) in dichloromethane (15 mL) was added trifluoroacetic acid (15 mL). After stirred at room temperature for 1 hour, the mixture was concentrated under reduced pressure to remove volatiles. The residue was dissolved in dichloromethane (20 mL) and triethylamine (1.27 g, 12.6 mmol) and acetic anhydride (771 mg, 7.56 mmol) was added. After stirred at room temperature for 2 hours, the mixture was diluted with dichloromethane (30 mL) and washed with water (30 mL) and brine (30 mL), dried over Na$_2$SO$_{4(s)}$ and filtered. The filtrate was concentrated and purified by C18 column (acetonitrile:water=55% to 60%) to give the title compound (1.07 g, 76% yield) as colorless oil. LC-MS (ESI): $R_T$=1.49 min, mass calcd. for $C_{16}H_{21}NO_3$ 275.2, m/z found 276.4 [M+H]$^+$. $^1$H NMR (300 MHz, DMSO-d$_6$) δ 7.51-7.30 (m, 5H), 5.11 (s, 2H), 4.91-4.82 (m, 0.5H), 4.33-4.22 (m, 0.5H), 3.04-2.86 (m, 1H), 2.79 (s, 1.5H), 2.65 (s, 1.5H), 2.03-1.52 (m, 9H).

Acid 38: 3-(N-Methylacetamido)cyclopentanecarboxylic Acid

To a solution of benzyl 3-(N-methylacetamido)cyclopentanecarboxylate intermediate 31 (1.07 g, 3.89 mmol) in

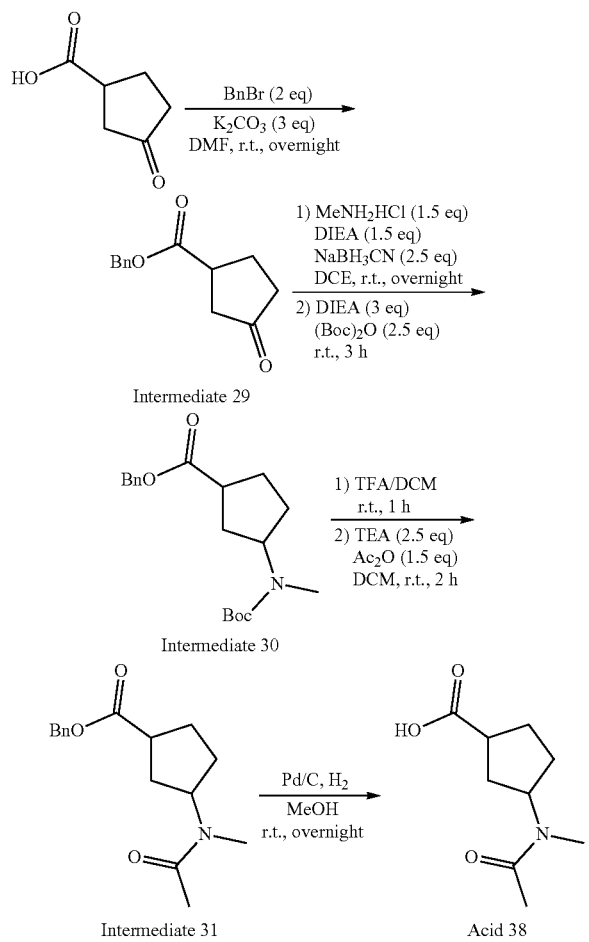

methanol (10 mL) was added 10% palladium on charcoal wt. (107 mg). After stirred at room temperature under hydrogen atmosphere overnight, the mixture was filtered. The filtrate was concentrated to give the title compound (710 mg, 99% yield) as white solids. $^1$H NMR (300 MHz, DMSO-$d_6$) δ 12.13 (s, 1H), 4.91-4.78 (m, 0.5H), 4.32-4.17 (m, 0.5H), 2.87-2.67 (m, 4H), 2.03-1.50 (m, 9H).

Acid 39: (cis)-4-Methyltetrahydrofuran-2-carboxylic Acid

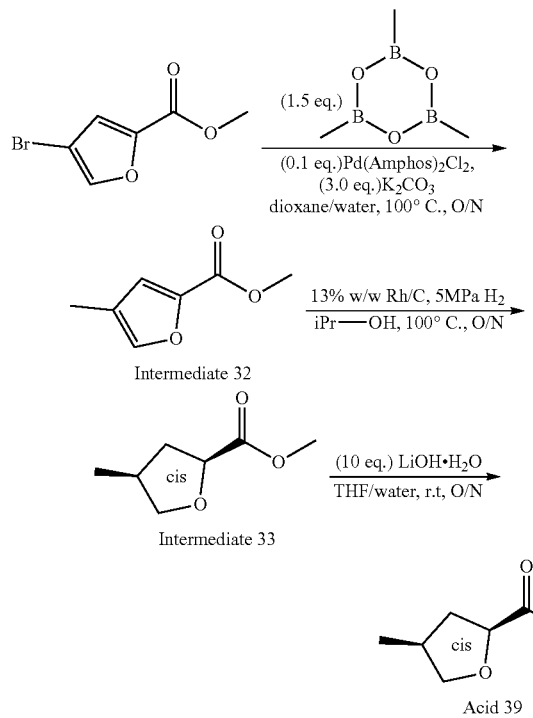

Intermediate 32

Intermediate 33

Acid 39

Intermediate 32: Methyl 4-methylfuran-2-carboxylate

To a solution of methyl 4-bromofuran-2-carboxylate (2.00 g, 9.75 mmol) in 1,4-dioxane (50 mL) were added 2,4,6-trimethyl-1,3,5,2,4,6-trioxatriborinane (1.84 g, 14.6 mmol) and a solution of potassium carbonate (4.04 g, 29.3 mmol) in water (10 mL) at room temperature under nitrogen atmosphere. The mixture was degassed with nitrogen for 10 minutes, then bis(di-tert-butyl(4-dimethylaminophenyl)phosphine)-dichloropalladium(II) (690 mg, 0.975 mmol) was added at room temperature. After stirred at 100° C. overnight under nitrogen atmosphere, the mixture was cooled down to room temperature and diluted in ethyl acetate (100 mL). The separated organic layer was washed with water (60 mL) for three times, dried over Na$_2$SO$_{4(s)}$, filtered and concentrated under reduced pressure to give a residue, which was purified by silica gel column chromatography (petroleum ether:ethyl acetate=8:1) to give the title compound (760 mg, 56% yield) as yellow oil. $^1$H NMR (400 MHz, DMSO-$d_6$) δ 7.72 (s, 1H), 7.18 (s, 1H), 3.80 (s, 3H), 2.03 (s, 3H).

Intermediate 33: (cis)-Methyl 4-methyltetrahydrofuran-2-carboxylate

To a solution of methyl 4-methylfuran-2-carboxylate 32 (760 mg, 5.42 mmol)) in propan-2-ol (50 mL) was added 5% ruthenium on charcoal wt. (100 mg) under nitrogen atmosphere at room temperature. After replacing the inert nitrogen atmosphere with hydrogen gas, the mixture was stirred at 100° C. under hydrogen atmosphere with a balloon overnight. The catalyst was filtered off and the filtrate was concentrated under reduced pressure to give the title compound (780 mg, 99% yield) as yellow oil. $^1$H NMR (300 MHz, DMSO-$d_6$) δ 4.43-4.38 (m, 1H), 3.92-3.87 (m, 1H), 3.64 (s, 3H), 3.33-3.28 (m, 1H), 2.45-2.19 (m, 2H), 1.52-1.42 (m, 1H), 0.97 (d, J=6.6 Hz, 3H).

Acid 39: (cis)-4-Methyltetrahydrofuran-2-carboxylic Acid

To a solution of (cis)-methyl 4-methyltetrahydrofuran-2-carboxylate 33 (780 mg, 5.42 mmol) in tetrahydrofuran (20 mL) was added a solution of lithium hydroxide monohydrate (2.27 g, 54.2 mmol) in water (20 mL). The reaction mixture was stirred at room temperature for 2 hours. Then reaction mixture was diluted in ethyl acetate (100 mL) and acidified with concentrated hydrochloride aqueous solution (about 20 mL) to pH=1. The aqueous phase was separated and extracted with ethyl acetate (20 mL) for three times. The combined organic layers were dried over anhydrous Na$_2$SO$_4$ $_{(s)}$, filtered and concentrated to give the title compound (300 mg, 43% yield) as yellow oil. $^1$H NMR (300 MHz, DMSO-$d_6$) δ 12.28 (s, 1H), 4.29 (t, J=7.8 Hz, 1H), 3.88 (t, J=7.2 Hz, 1H), 3.30 (t, J=8.1 Hz, 1H), 2.43-2.36 (m, 1H), 2.26-2.16 (m, 1H), 1.50-1.41 (m, 1H), 0.97 (d, J=6.6 Hz, 3H).

Acid 40: 4-((tert-Butoxycarbonyl)amino)cycloheptanecarboxylic Acid

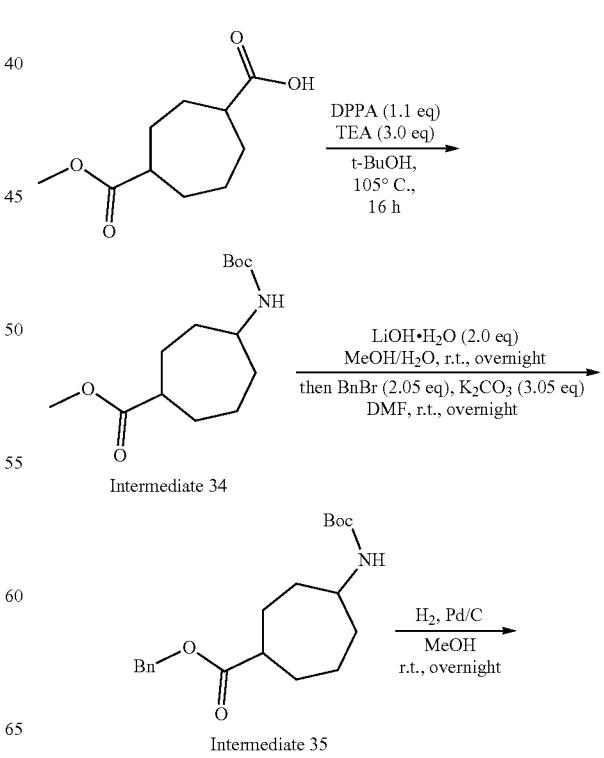

Intermediate 34

Intermediate 35

-continued

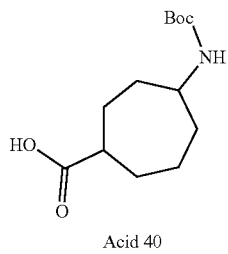

Acid 40

Intermediate 34: Methyl 4-((tert-butoxycarbonyl)amino)cycloheptanecarboxylate To a solution of 4-(methoxycarbonyl)cycloheptanecarboxylic acid EO8495_393.7 (6.10 g, 30.5 mmol) in tert-butanol (300 mL) was added triethylamine (9.20 g, 91.4 mmol) and diphenylphosphoryl azide (9.10 g, 33.5 mmol) at room temperature. The mixture was heated to 105° C. and stirred at 105° C. for 16 hours under nitrogen atmosphere. After cooling down to room temperature, the mixture was concentrated and the residue was added saturated sodium bicarbonate aqueous solution (300 mL) and extracted with ethyl acetate (200 mL) for three times. The combined organic layers were dried over $Na_2SO_{4(s)}$ and filtered. The filtrate was concentrated to give a residue, which was purified by silica gel column chromatography (petroleum ether:ethyl acetate=5:1) to give the title compound (6.20 g, 75% yield) as yellow oil. LC-MS (ESI): $R_T$=2.220 min, mass calcd. for $C_{14}H_{25}NO_4$ 271.2, m/z found 216.1 [M+H−56]$^+$ and 172.1 [M+H−Boc]$^+$.

Intermediate 35: Benzyl 4-((tert-butoxycarbonyl)amino)cycloheptanecarboxylate To a solution of methyl 4-((tert-butoxycarbonyl)amino)cycloheptanecarboxylate 34 (6.20 g, 22.8 mmol) in methanol (40 mL) was added a solution of lithium hydroxide monohydrate (1.90 g, 45.6 mmol) in water (10 mL) at 0° C. After stirred at room temperature overnight, the mixture was concentrated under reduced pressure to remove the volatile and added water (30 mL), extracted with ethyl acetate (30 mL) for three times. The aqueous layer was acidified to pH 2-3 with saturated citric acid (20 mL), extracted with ethyl acetate (30 mL) for three times. The latter organic layers were washed with brine (30 mL), dried over $Na_2SO_{4(s)}$ and filtered. The filtrate was concentrated to give a residue, which was dissolved in N,N-dimethylformamide (50 mL), then added potassium carbonate (8.00 g, 58.0 mmol) and benzyl bromide (6.70 g, 39.0 mmol) at 0° C. After stirred at room temperature overnight, the mixture was added water (500 mL), and extracted with ethyl acetate (50 mL) for four times. The combined organic layers were dried over $Na_2SO_{4(s)}$, filtered and concentrated to give a residue, which was purified by silica gel column chromatography (petroleum ether:ethyl acetate=50:1 to 30:1 to 20:1) to give the title compound (3.50 g, 53% yield) as light yellow oil. LC-MS (ESI): $R_T$=2.516 min, mass calcd. for $C_{20}H_{29}NO_4$ 347.2, m/z found 292.1 [M+H−56]$^+$, 248.1 [M+H−100]$^+$. $^1$H NMR (300 MHz, CDCl$_3$) δ 7.48-7.30 (m, 5H), 5.14 (s, 2H), 4.64-4.30 (m, 1H), 3.77-3.49 (m, 1H), 2.69-2.43 (m, 1H), 2.20-1.54 (m, 8H), 1.45 (s, 9H), 1.40-1.20 (m, 2H).

Acid 40:4-((tert-Butoxycarbonyl)amino)cycloheptanecarboxylic Acid

To a solution of benzyl 4-((tert-butoxycarbonyl)amino)cycloheptanecarboxylate 35 (3.50 g, 10.0 mmol) in methanol (50 mL) was added 10% palladium on charcoal wt. (350 mg), the mixture was stirred at room temperature under hydrogen atmosphere overnight. After filtration, the filtrate was concentrated to give the title compound (2.58 g, 100% yield) as light yellow oil. LC-MS (ESI): $R_T$=1.67 min, mass calcd. for $C_{13}H_{23}NO_4$ 257.2, m/z found 202.4 [M+H−56]$^+$. $^1$H NMR (300 MHz, CDCl$_3$) δ 4.74-4.30 (m, 1H), 3.76-3.52 (m, 1H), 2.74-2.39 (m, 1H), 2.13-1.60 (m, 8H), 1.49 (s, 9H), 1.41-1.28 (m, 2H).

Acid 41:3-((tert-Butoxycarbonyl)amino)bicyclo[1.1.1]pentane-1-carboxylic Acid

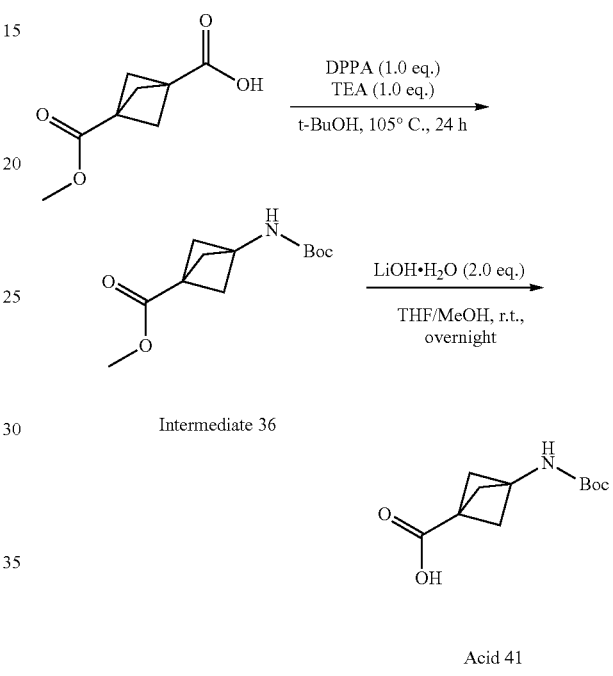

Intermediate 36

Acid 41

Intermediate 36: Methyl 3-((tert-butoxycarbonyl)amino)bicyclo[1.1.1]pentane-1-carboxylate To a solution of 3-(methoxycarbonyl)bicyclo[1.1.1]pentane-1-carboxylic acid (1.00 g, 5.90 mmol) in tert-butanol (10 mL) was added diphenylphosphoryl azide (1.60 g, 5.90 mmol) and triethylamine (596 mg, 5.90 mmol) at room temperature. After stirred at 105° C. for 24 hours under nitrogen atmosphere and then cooling down to room temperature, the reaction mixture was concentrated under reduced pressure to give a residue, which was diluted with ethyl acetate (20 mL). The mixture was washed with saturated ammonium chloride aqueous solution (20 mL), saturated sodium bicarbonate aqueous solution (20 mL) and brine (20 mL) for three times, then dried over $Na_2SO_{4(s)}$, filtered and concentrated to give a residue, which was purified by silica gel column chromatography (petroleum ether:ethyl acetate=5:1) to give the title compound (0.91 g, 76% yield) as white solids. LC-MS (ESI): $R_T$=1.844 min, mass calcd. for $C_{12}H_{19}NO_4$ 241.1, m/z found 242.2 [M+H]$^+$. $^1$H NMR (300 MHz, CDCl$_3$) δ 4.96 (br s, 1H), 3.70 (s, 3H), 2.30 (s, 6H), 1.46 (s, 9H).

Acid 41:3-((tert-Butoxycarbonyl)amino)bicyclo[1.1.1]pentane-1-carboxylic Acid To a solution of methyl 3-((tert-butoxycarbonyl)amino)bicyclo[1.1.1]pentane-1-carboxylate intermediate 36 (850 mg, 3.52 mmol) in tetrahydrofuran (10 mL), methanol (3 mL) and water (3 mL) was added lithium hydroxide monohydrate (296 mg, 7.04 mmol). After stirred at room temperature overnight, the mixture was poured into water (30 mL) and adjusted pH to 3-4 with 1 M hydrochloride aqueous solution (8 mL). The obtained aqueous solution was extracted with ethyl acetate (20 mL) for three times. The combined organic layers were dried over $Na_2SO_{4(s)}$, filtered and concentrated to give the title product (720 mg, 90% yield) as white solids. LC-MS (ESI): $R_T$=0.661 min, mass calcd. for $C_{11}H_{17}NO_4$ 227.1, m/z found 226.0 [M−H]−. $^1$H NMR (300 MHz, DMSO-$d_6$) δ 12.35 (s, 1H), 7.58 (s, 1H), 2.10 (s, 6H), 1.37 (s, 9H).

Acid 42: (cis)-5-(Ethoxycarbonyl)tetrahydrofuran-3-carboxylic Acid

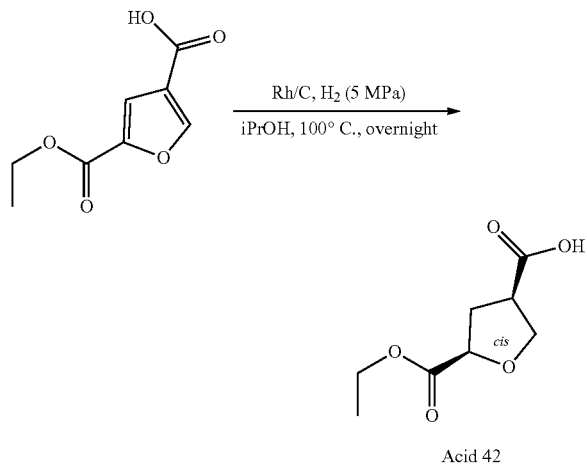

Acid 42

To a solution of 5-(ethoxycarbonyl)furan-3-carboxylic acid (7.00 g, 38 mmol) in isopropanol (50 mL) was added 5% ruthenium on charcoal wt. (1.40 g) at room temperature. The mixture was stirred at 100° C. overnight under hydrogen atmosphere (5.0 MPa). After cooling down to room temperature, the suspension was filtered and the filtrate was concentrated in vacuo to give the desired product (7.10 g, crude) as colourless oil. LC-MS (ESI): $R_T$=0.710 min, mass calcd. for $C_8H_{12}O_5$ 188.1, m/z found 187.1 [M−H]−. $^1$H NMR (300 MHz, CDCl$_3$) δ 9.15 (br s, 1H), 4.55-4.50 (m, 1H), 4.25-4.14 (m, 4H), 3.25-3.15 (m, 1H), 2.59-2.40 (m, 2H), 1.29 (t, J=7.2 Hz, 3H).

Acid 43:1,4-Dioxaspiro[4.5]decane-7-carboxylic Acid

Intermediate 37: Ethyl 1,4-dioxaspiro[4.5]decane-7-carboxylate

To a solution of ethyl 3-oxocyclohexanecarboxylate1 (5.00 g, 29.4 mmol) in toluene (15 mL) was added ethane-1,2-diol (6.38 g, 103 mmol) and 4-methylbenzenesulfonic acid hydrate (67 mg, 0.353 mmol) at room temperature. After stirred at 25° C. for 20 hours, the reaction mixture was concentrated under reduced pressure and the residue was redissolved in ethyl acetate (50 mL) and water (60 mL). The organic layer was separated and the aqueous phase was extracted with ethyl acetate (150 mL). The combined organic layers were washed with with saturated sodium carbonate aqueous solution (100 mL), brine (50 mL) twice, dried over $Na_2SO_{4(s)}$, filtered and concentrated under reduced pressure to give the title compound (5.50 g, 87% yield) as colorless oil. $^1$H NMR (300 MHz, CDCl$_3$) δ 4.15-4.08 (m, 2H), 3.94 (s, 4H), 2.62-2.53 (m, 1H), 2.04-1.34 (m, 8H), 1.26-1.21 (m, 3H).

Acid 43:1,4-Dioxaspiro[4.5]decane-7-carboxylic Acid

To a solution of ethyl 1,4-dioxaspiro[4.5]decane-7-carboxylate intermediate 37 (2.00 g, 9.35 mmol) in tetrahydrofuran (15 mL) and methanol (5 mL) was added a solution of lithium hydroxide monohydrate (1.18 g, 28.1 mmol) in water (5 mL) at room temperature. After stirred at room temperature overnight under nitrogen atmosphere, the reaction mixture was concentrated under reduced pressure, acidified with 2 M hydrochloride aqueous solution till pH=3-4 and extracted with ethyl acetate (20 mL) twice. The combined organic layers were washed with brine (10 mL) twice, dried over $Na_2SO_{4(s)}$ and filtered. The filtrate was concentrated under reduced pressure to give a residue, which was purified by silica gel column chromatography (petroleum ether:ethyl acetate=8:1 to 3:1) to give the title compound (1.70 g, 98% yield) as white solids. $^1$H NMR (300 MHz, DMSO-$d_6$) δ 12.12 (s, 1H), 3.85-3.83 (m, 4H), 2.41-2.33 (m, 1H), 1.86-1.21 (m, 8H).

Acid 44: (cis)-4-(((tert-butyldiphenylsilyl)oxy)methyl)tetrahydrofuran-2-carboxylic Acid

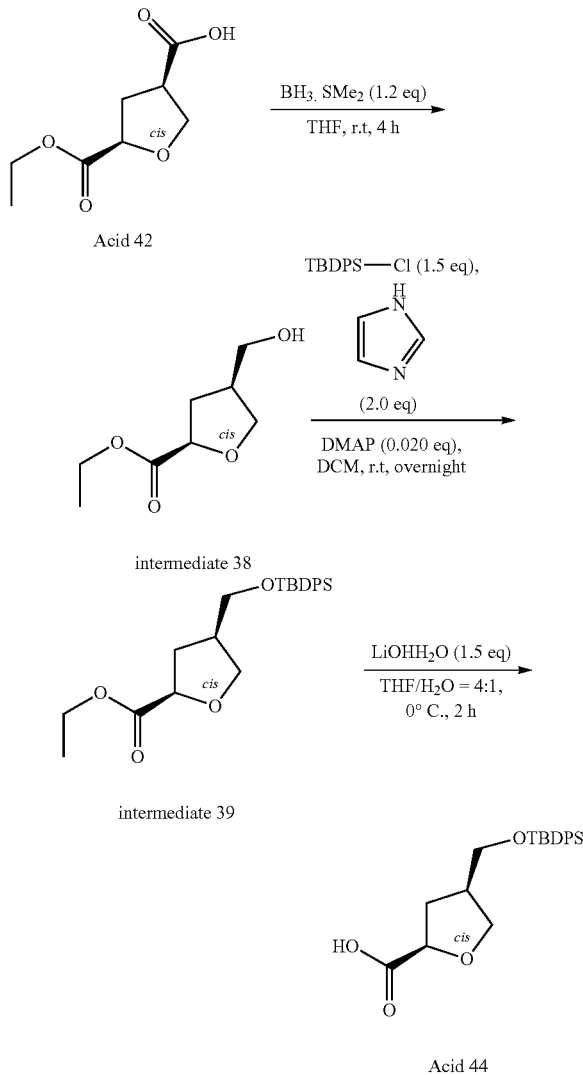

Intermediate 38: (cis)-Ethyl 4-(hydroxymethyl)tetrahydrofuran-2-carboxylate

To a solution of (cis)-5-(ethoxycarbonyl)tetrahydrofuran-3-carboxylic acid 42 (4.50 g, 24.0 mmol) in tetrahydrofuran (150 mL) was added 10 M borane-methyl sulfide complex in tetrahydrofuran (2.9 mL, 28.8 mmol) at 0° C. After stirred at room temperature under nitrogen atmosphere for 4 hours, the mixture was quenched with methanol (30 mL) and concentrated in vacuo to give a residue, which was purified by silica gel column chromatography (dichloromethane:methanol=100:1) to give the desired product (3.77 g, 90% yield) as colourless oil. LC-MS (ESI): $R_T$=1.115 min, mass calcd. for $C_8H_{14}O_4$ 174.1, m/z found 175.1 [M+H]$^+$. $^1$H NMR (300 MHz, CDCl$_3$) δ 4.47-4.42 (m, 1H), 4.24-4.12 (m, 2H), 4.03-3.98 (m, 1H), 3.87-3.83 (m, 1H), 3.66-3.57 (m, 2H), 2.58-2.37 (m, 2H), 1.84-1.76 (m, 1H), 1.29 (t, J=6.9 Hz, 3H).

Intermediate 39: (cis)-Ethyl 4-(((tert-butyldiphenylsilyl)oxy)methyl)-tetrahydrofuran-2-carboxylate To a solution of (cis)-ethyl 4-(hydroxymethyl)tetrahydrofuran-2-carboxylate 38 (3.77 g, 21.7 mmol), imidazole (2.95 g, 43.4 mmol) and 4-dimethylaminopyridine (53 mg, 0.434 mmol) in dichloromethane (100 mL) was added tert-butylchlorodiphenylsilane (8.95 g, 32.6 mmol). After stirred at room temperature under nitrogen atmosphere overnight, the mixture was concentrated in vacuo to give a residue, which was purified by silica gel column chromatography (petroleum ether:ethyl acetate=10:1) to give the desired product (3.28 g, 37% yield) as yellow oil. LC-MS (ESI): $R_T$=2.901 min, mass calcd. for $C_{24}H_{32}O_4Si$ 412.2, m/z found 430.2 [M+NH$_4$]+. $^1$H NMR (400 MHz, CDCl$_3$) δ 7.73-7.65 (m, 4H), 7.47-7.38 (m, 6H), 4.46 (t, J=7.8 Hz, 1H), 4.20 (q, J=7.2 Hz, 2H), 4.07-4.02 (m, 1H), 3.87 (t, J=7.8 Hz, 1H), 3.65 (d, J=6.0 Hz, 2H), 2.62-2.53 (m, 1H), 2.43-2.33 (m, 1H), 1.85-1.75 (m, 1H), 1.28 (t, J=7.2 Hz, 3H), 1.06 (s, 9H).

Acid 44: (cis)-4-(((tert-Butyldiphenylsilyl)oxy)methyl)tetrahydrofuran-2-carboxylic Acid To a solution of (cis)-ethyl 4-(((tert-butyldiphenylsilyl)oxy)methyl)tetrahydrofuran-2-carboxylate intermediate 39 (3.28 g, 7.96 mmol) in tetrahydrofuran (40 mL) and water (5 mL) was added a solution of lithium hydroxide monohydrate (504 mg, 12.0 mmol) in water (5 mL) at 0° C. After stirred at 0° C. for 2 hours, the mixture was poured into water (20 mL) and adjusted pH to 5-6 with 2 M hydrochloride aqueous solution (6 mL). The obtained aqueous solution was extracted with ethyl acetate (30 mL) for three times. The combined organic layers were concentrated to give the desired product (2.75 g, 90% yield) as yellow oil. $^1$H NMR (300 MHz, CDCl$_3$) δ 7.66-7.63 (m, 4H), 7.48-7.37 (m, 6H), 4.52-4.47 (m, 1H), 4.15-4.03 (m, 1H), 3.92-3.87 (m, 1H), 3.69-3.56 (m, 2H), 2.63-2.55 (m, 1H), 2.51-2.41 (m, 1H), 1.92-1.83 (m, 1H), 1.06 (s, 9H).

Acid 45: 4-(N,N-Dimethylsulfamoyl)cyclohexanecarboxylic Acid

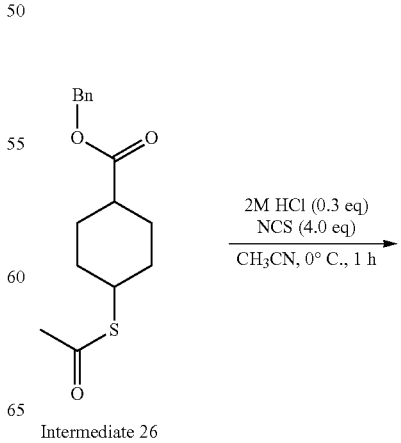

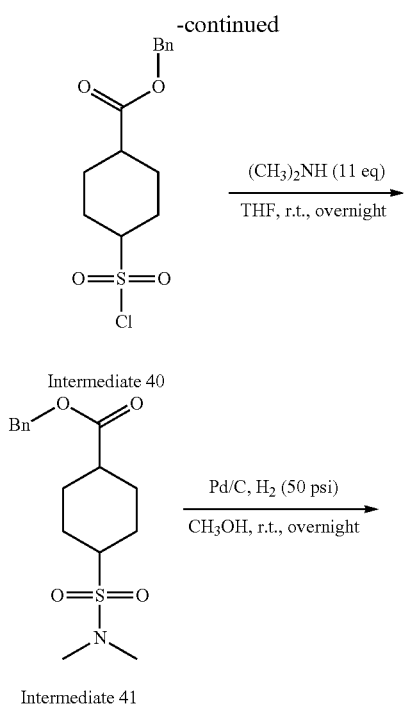

CDCl$_3$) δ 7.36-7.34 (m, 5H), 5.16 (s, 0.9H), 5.11 (s, 1.1H), 3.02-2.95 (m, 1H), 2.91 (s, 3.5H), 2.87 (s, 2.5H), 2.39-2.32 (m, 1.5H), 2.19-2.17 (m, 2.5H), 2.00-1.96 (m, 1H), 1.81-1.71 (m, 1H), 1.67-1.60 (m, 1H), 1.55-1.43 (m, 2H).

Acid 45: 4-(N,N-Dimethylsulfamoyl)cyclohexanecarboxylic Acid

To the solution of benzyl 4-(N,N-dimethylsulfamoyl)cyclohexanecarboxylate Intermediate 41 (810 mg, 2.49 mmol) in methanol (20 mL) was added 10% palladium on charcoal wt. (81 mg). After stirred at room temperature under hydrogen atmosphere of balloon overnight, the reaction mixture was filtered. The filtrate was concentrated under reduced pressure to give the title compound (500 mg, 85% yield) as white solids. $^1$H NMR (400 MHz, CDCl$_3$) δ 3.04-2.96 (m, 1H), 2.93-2.92 (m, 6H), 2.37-2.31 (m, 1.5H), 2.22-2.19 (m, 2.5H), 2.02-1.98 (m, 1H), 1.87-1.76 (m, 1H), 1.68-1.47 (m, 3H).

Acid 46: 4-(N-Isopropylsulfamoyl)cyclohexanecarboxylic Acid

Intermediate 40: Benzyl 4-(chlorosulfonyl)cyclohexanecarboxylate

To a solution of benzyl 4-(acetylthio)cyclohexanecarboxylate intermediate 26 (1.70 g, 5.82 mmol) in acetonitrile (30 mL) were added 2 M hydrochloride aqueous solution (1 mL) and 1-chloropyrrolidine-2,5-dione (3.10 g, 23.3 mmol) at 0° C. under nitrogen atmosphere. After stirred at room temperature for 1 hour, the mixture was concentrated under reduced pressure at room temperature to give a residue, which was diluted with water (50 mL) and extracted with ethyl acetate (50 mL) for three times. The combined organic layers were washed with brine (50 mL) twice, dried over Na$_2$SO$_{4(s)}$, filtered and concentrated under reduced pressure to give a residue, which was purified by silica gel column chromatography (petroleum ether:ethyl acetate=4:1) to give the title compound (2.80 g, 65% purity from $^1$H NMR, 66% yield) as white solids. $^1$H NMR (400 MHz, CDCl$_3$) δ 7.40-7.33 (m, 5H), 5.17 (s, 2H), 3.56-3.48 (m, 1H), 2.43-2.38 (m, 2H), 2.29-2.24 (m, 2H), 2.04-1.93 (m, 2H), 1.69-1.57 (m, 3H).

Intermediate 41: Benzyl 4-(N,N-dimethylsulfamoyl)cyclohexanecarboxylate

To a solution of benzyl 4-(chlorosulfonyl)cyclohexanecarboxylate intermediate 40 (1.40 g, 65% purity, 2.88 mmol) in dry tetrahydrofuran (20 mL) were added 2 M dimethylamine in tetrahydrofuran (16 mL, 32 mmol) at 0° C. under nitrogen atmosphere. After stirred at room temperature overnight, the mixture was quenched with water (50 mL) and extracted with ethyl acetate (50 mL) for three times. The combined organic layers were washed with brine (50 mL), dried over Na$_2$SO$_{4(s)}$ and filtered. The filtrate was concentrated under reduced pressure to give a residue, which was purified by silica gel column chromatography (petroleum ether:ethyl acetate=2:1) to give the title compound (810 mg, 77% yield) as white solids. $^1$H NMR (400 MHz,

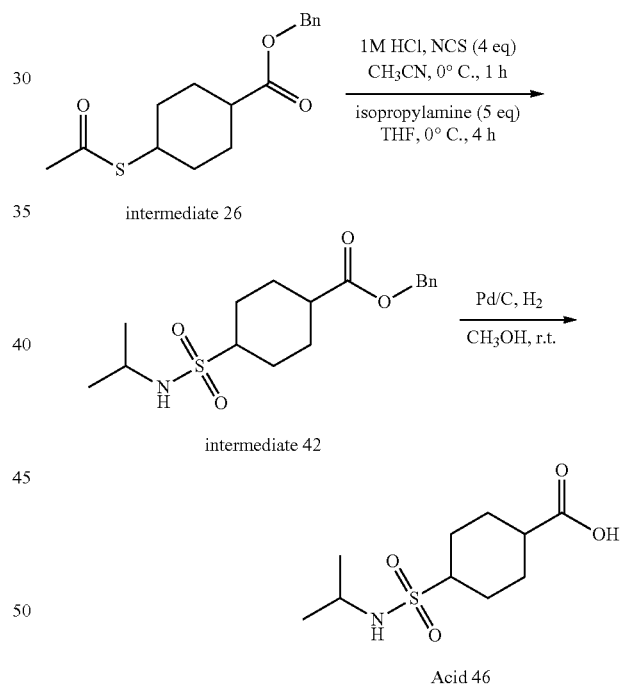

Intermediate 42: Benzyl 4-(N-isopropylsulfamoyl)cyclohexanecarboxylate

To a solution of benzyl 4-(acetylthio)cyclohexanecarboxylate intermediate 26 (700 mg, 2.40 mmol) in acetonitrile (12 mL) were added 2 M hydrochloride aqueous solution (0.4 mL) and 1-chloropyrrolidine-2,5-dione (1.28 g, 9.60 mmol) at 0° C. under nitrogen atmosphere. After stirred at room temperature for 1 hour, the mixture was concentrated under reduced pressure to give a residue at room temperature. It was diluted with water (10 mL) and extracted with ethyl acetate (10 mL) for three times. The combined organic layers were washed with brine (10 mL) twice, dried over Na$_2$SO$_{4(s)}$, filtered and concentrated under reduced pressure to give a residue, which was diluted in dry tetrahydrofuran (20 mL), then 2 M isopropylamine (709 mg, 12.0 mmol) in tetrahydrofuran (6 mL) was added into the resulted solution and stirred at 0° C. for 4 hours. The mixture was concentrated under reduced pressure, quenched with water (10 mL) and extracted with ethyl acetate (10 mL) for three times. The combined organic layers were washed with brine (10 mL), dried over Na$_2$SO$_{4(s)}$ and filtered. The filtrate was concentrated under reduced pressure to give a residue, which was purified by silica gel column chromatography (petroleum ether:ethyl acetate=4:1 to 2:1) to give the title compound (630 mg, 77% yield) as white solids. $^1$H NMR (300 MHz, CDCl$_3$) δ 7.42-7.33 (m, 5H), 5.16 (s, 0.7H), 5.13 (s, 1.3H), 3.88-3.73 (m, 1H), 3.67-3.57 (m, 1H), 2.91-2.78 (m, 1H), 2.76-2.69 (m, 0.3H), 2.42-2.18 (m, 4H), 2.11-2.06 (m, 0.7H), 1.84-1.70 (m, 0.7H), 1.66-1.45 (m, 3.3H), 1.26-1.21 (m, 6H).

Acid 46: 4-(N-Isopropylsulfamoyl)cyclohexanecarboxylic Acid

To the solution of benzyl 4-(N-isopropylsulfamoyl)cyclohexanecarboxylate (630 mg, 1.86 mmol) in methanol (20 mL) was added 10% palladium on charcoal wt. (70 mg). After stirred at room temperature under hydrogen atmosphere of balloon overnight, the reaction mixture was filtered. The filtrate was concentrated under reduced pressure to give the title compound (440 mg, 95% yield) as white solids. $^1$H NMR (400 MHz, CDCl$_3$) δ 4.10-3.99 (m, 1H), 3.67-3.57 (m, 1H), 2.91-2.79 (m, 1H), 2.73-2.70 (m, 0.3H), 2.37-2.19 (m, 4H), 2.11-2.06 (m, 0.7H), 1.84-1.73 (m, 0.7H), 1.64-1.44 (m, 3.3H), 1.25-1.22 (m, 6H).

Acid 47: (cis)-4-((tert-Butoxycarbonyl)amino)tetrahydrofuran-2-carboxylic Acid

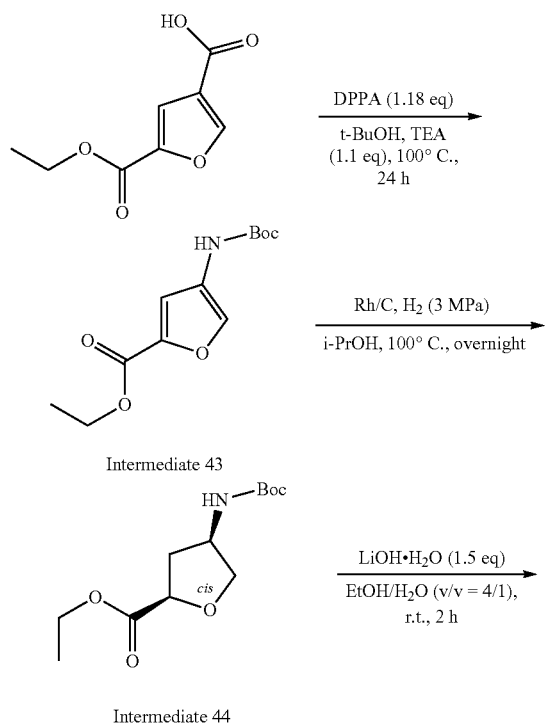

Intermediate 43

Intermediate 44

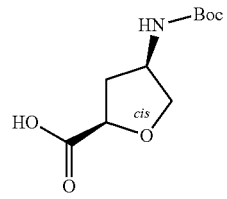

Acid 47

Intermediate 43: Ethyl 4-((tert-butoxycarbonyl)amino)furan-2-carboxylate

To a solution of 5-(ethoxycarbonyl)furan-3-carboxylic acid (4.00 g, 21.7 mmol) in tert-butanol (100 mL) was added triethylamine (2.40 g, 23.8 mmol) and diphenylphosphoryl azide (7.00 g, 25.5 mmol). After stirred at 100° C. under nitrogen atmosphere for 24 hours, it was cooled down to room temperature and concentrated under reduced pressure to give a residue, which was suspended in ethyl acetate (50 mL) and saturated sodium bicarbonate aqueous solution (50 mL). The organic layer was separated and the aqueous phase was extracted with ethyl acetate (50 mL). The combined organic layers were washed with saturated ammonium chloride aqueous solution (50 mL) and brine (50 mL), dried over Na$_2$SO$_{4(s)}$, and filtered. The filtrate was concentrated under reduced pressure to give the crude product, which was purified by silica gel column chromatography (petroleum ether:ethyl acetate=20:1) to give the desired product (4.00 g, 73% yield) as pale yellow solids. LC-MS (ESI): R$_T$=2.179 min, mass calcd. for C$_{12}$H$_{17}$NO$_5$ 255.11, m/z found 200.1 [M+H−56]$^+$. $^1$H NMR (300 MHz, CDCl$_3$) δ 7.88 (br s, 1H), 7.03 (s, 1H), 6.35 (br s, 1H), 4.36 (q, J=7.2 Hz, 2H), 1.52 (s, 9H), 1.38 (t, J=7.2 Hz, 3H).

Intermediate 44: (cis)-Ethyl 4-((tert-butoxycarbonyl)amino)tetrahydrofuran-2-carboxylate To a solution of ethyl 4-((tert-butoxycarbonyl)amino) furan-2-carboxylate Intermediate 43 (4.00 g, 15.7 mmol) in isopropanol (80 mL) was added 5% ruthenium on charcoal wt. (200 mg). After stirring at 100° C. under hydrogen atmosphere (3 Mpa) overnight, the reaction mixture was cooled down to room temperature and filtered by celite. The cake was washed with isopropanol (200 mL) and methanol (100 mL). The filtrate was concentrated to afford the desired product (4.00 g, 98.5% yield) as black solids. LC-MS (ESI): R$_T$=2.001 min, mass calcd. for C$_{12}$H$_{21}$NO$_5$ 259.14, m/z found 160.1 [M+H−100]$^+$. $^1$H NMR (300 MHz, DMSO-d$_6$) δ 6.97 (br s, 1H), 4.41 (t, J=7.2 Hz, 1H), 4.11 (q, J=7.2 Hz, 2H), 4.03-3.94 (m, 1H), 3.87 (t, J=6.9 Hz, 1H), 3.54 (t, J=6.9 Hz, 1H), 2.47-2.40 (m, 1H), 1.91-1.82 (m, 1H), 1.37 (s, 9H), 1.20 (t, J=6.9 Hz, 3H).

Acid 47: (cis)-4-((tert-Butoxycarbonyl)amino)tetrahydrofuran-2-carboxylic Acid

To a solution of (cis)-ethyl 4-((tert-butoxycarbonyl) amino)tetrahydrofuran-2-carboxylate Intermediate 44 (4.00 g, 15.4 mmol) in ethanol (40 mL) was added a solution of lithium hydroxide monohydrate (970 mg, 23.1 mmol) in water (10 mL). After stirred at room temperature for 2 hours, the solution was poured into water (100 mL) and proton-type cation exchange resin (Amberlyst 15 ion-exchange resin, 3 g) was added to acidify to pH=5-6. Then the resin was filtered and washed with acetonitrile (100 mL) for three times. The filtrate was concentrated to give the desired product (3.60 g, crude) as yellow solid. $^1$H NMR (400 MHz, DMSO-d$_6$) δ 7.06-7.04 (m, 1H), 4.28-4.24 (m, 1H), 4.02-3.97 (m, 1H), 3.84-3.80 (m, 1H), 3.53-3.49 (m, 1H), 2.42-2.35 (m, 1H), 1.81-1.75 (m, 1H), 1.37 (s, 9H).

Acid 48: (cis)-4-(Methylcarbamoyl)tetrahydrofuran-2-carboxylic Acid

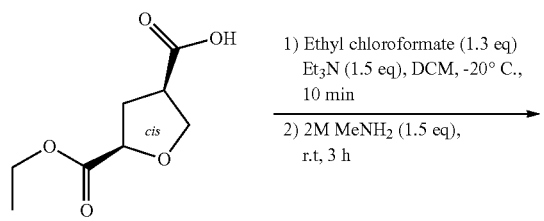

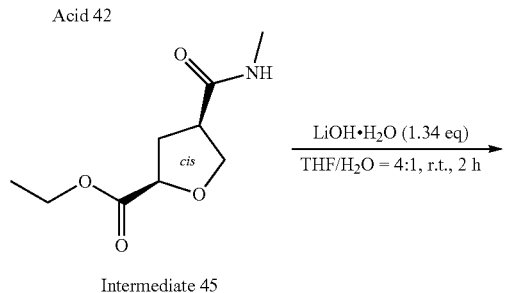

Intermediate 45: (cis)-Ethyl 4-(methylcarbamoyl)tetrahydrofuran-2-carboxylate

To a solution of (cis)-5-(ethoxycarbonyl)tetrahydrofuran-3-carboxylic acid (2.50 g, 13.3 mmol) and triethylamine (2.01 g, 20.0 mmol) in dichloromethane (60 mL) was added ethyl chloroformate (1.87 g, 17.3 mmol) under nitrogen atmosphere at −20° C. After stirring at −20° C. for 10 minutes, 2 M methylamine in tetrahydrofuran (10 mL, 20.0 mmol) was added at −20° C. and the mixture was stirred at room temperature for 3 hours. Then it was concentrated to give a residue, which was purified by silica gel column chromatography (dichloromethane:methanol=50:1) to give the title compound (1.70 g, 66% yield) as yellow oil. LC-MS (ESI): $R_T$=0.716 min, mass calcd. for $C_9H_{15}NO_4$ 201.1, m/z found 202.1 [M+H]$^+$. $^1$H NMR (300 MHz, CDCl$_3$) δ 6.23 (br s, 1H), 4.50-4.45 (m, 1H), 4.23 (q, J=6.9 Hz, 2H), 4.12-4.00 (m, 2H), 3.04-2.94 (m, 1H), 2.80 (s, 1.5H), 2.78 (s, 1.5H), 2.60-2.49 (m, 1H), 2.35-2.27 (m, 1H), 1.29 (t, J=7.2 Hz, 3H).

Acid 48: (cis)-4-(Methylcarbamoyl)tetrahydrofuran-2-carboxylic Acid

To a solution of (cis)-ethyl 4-(methylcarbamoyl)tetrahydrofuran-2-carboxylate Intermediate 45 (1.07 g, 5.32 mmol) in tetrahydrofuran (20 mL) and water (5 mL) was added lithium hydroxide monohydrate (300 mg, 7.14 mmol) at room temperature. After stirred at room temperature under nitrogen atmosphere for 2 hours, the mixture was concentrated to give a residue, which was diluted with water (10 mL). The aqueous solution was adjusted pH to 5-6 with 2 M hydrochloride aqueous solution (4 mL) and extracted with ethyl acetate (20 mL) for three times. The combined organic layers were concentrated to give the desired product (660 mg, crude) as white solids. LC-MS (ESI): $R_T$=0.273 min, mass calcd. for $C_7H_{11}NO_4$ 173.1, m/z found 174.1 [M+H]$^+$. $^1$H NMR (300 MHz, DMSO-d$_6$) δ 7.99-7.95 (m, 1H), 4.36-4.31 (m, 1H), 3.97-3.90 (m, 1H), 3.71-3.64 (m, 1H), 2.95-2.89 (m, 1H), 2.57 (s, 1.5H), 2.55 (s, 1.5H), 2.41-2.31 (m, 1H), 2.11-2.01 (m, 1H).

Acid 49: 6-(tert-Butoxycarbonyl)tetrahydro-2H-pyran-3-carboxylic Acid

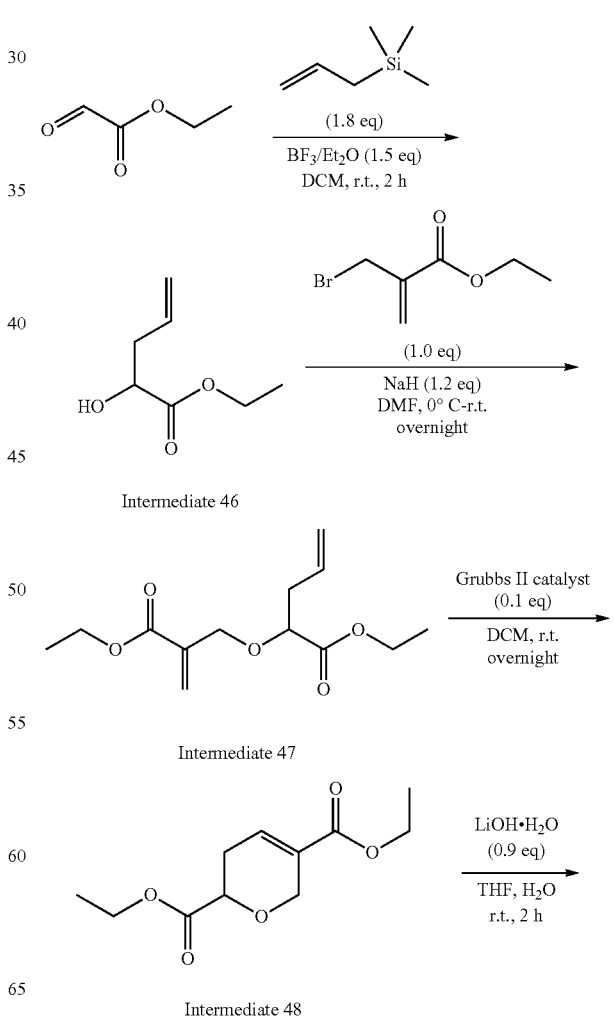

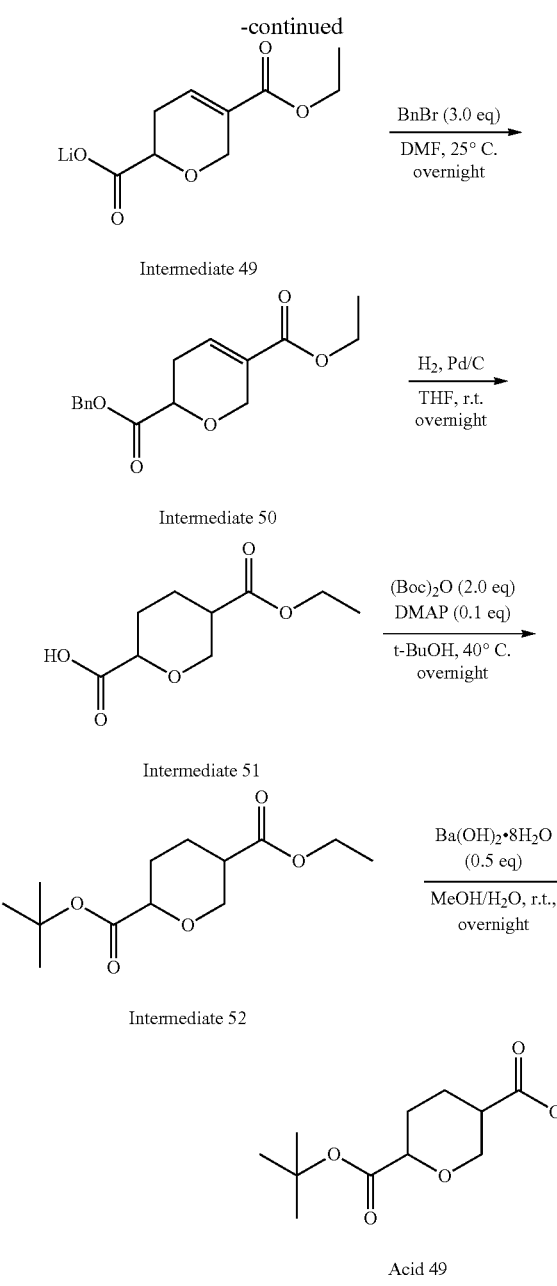

Intermediate 47: Ethyl 2-((2-(ethoxycarbonyl)allyl)oxy)pent-4-enoate

To a solution of ethyl 2-hydroxypent-4-enoate Intermediate 46 (41.0 g, 285 mmol) in N,N-dimethylformide (500 mL) was added 60% wt. sodium hydride in mineral oil (13.7 g, 342 mmol) at 0° C. Then ethyl 2-(bromomethyl)acrylate (55.0 g, 285 mmol) was added dropwise. After stirring at room temperature overnight, water (500 mL) was added, then the organic layer was separated, dried over $Na_2SO_{4(s)}$, filtered and concentrated under reduced pressure to give a residue, which was purified by silica gel column chromatography (petroleum ether:ethyl acetate=5:1) to afford the title product (16.0 g, 22% yield) as white oil. $^1$HNMR (400 MHz, $CDCl_3$) δ 6.31 (d, J=1.2 Hz, 1H), 5.94 (d, J=1.6 Hz, 1H), 5.88-5.78 (m, 1H), 5.16-5.08 (m, 2H), 4.39 (d, J=13.6 Hz, 1H), 4.22 (q, J=7.2 Hz, 4H), 4.14 (d, J=14.0 Hz, 1H), 4.01 (t, J=6.4 Hz, 1H), 2.56-2.52 (m, 2H), 1.32-1.27 (m, 6H).

Intermediate 48: Diethyl 3,6-dihydro-2H-pyran-2,5-dicarboxylate

To a solution of ethyl 2-((2-(ethoxycarbonyl)allyl)oxy)pent-4-enoate Intermediate 47 (15.0 g, 58.6 mmol) in dichloromethane (6 L) was added GrubbsII catalyst (4.90 g, 5.86 mmol) at room temperature. After stirring at room temperature overnight, water (3 L) was added, then the organic layer was separated, dried over $Na_2SO_{4(s)}$, filtered and concentrated under reduced pressure to give a residue, which was purified by silica gel column chromatography (petroleum ether:ethyl acetate=5:1) to afford the title product (8.9 g, 66% yield) as white oil. $^1$H NMR (400 MHz, $CDCl_3$) δ 7.05-7.03 (m, 1H), 4.64 (dd, J=16.8, 1.6 Hz, 1H), 4.37 (dd, J=16.8, 2.4 Hz, 1H), 4.29-4.15 (m, 5H), 2.56-2.54 (m, 2H), 1.33-1.26 (m, 6H).

Intermediate 49: Lithium 5-(ethoxycarbonyl)-3,6-dihydro-2H-pyran-2-carboxylate To a solution of diethyl 3,6-dihydro-2H-pyran-2,5-dicarboxylate Intermediate 48 (8.90 g, 39.0 mmol) in tetrahydrofuran (160 mL) was added a solution of lithium hydroxide hydrate (1.50 g, 35.1 mmol) in water (40 mL). The reaction mixture was stirred at room temperature for 2 hours. After that water (200 mL) and ethyl acetate (200 mL) was added, the aqueous phase was separated and concentrated under reduced pressure to give the title product (6.4 g, 80% yield) as white solids, which was used directly in the next step without further purification. LC-MS (ESI): $R_T$=0.323 min, mass calcd. for $C_9H_{11}LiO_5$ 206.1, m/z found 199.1 $[M-Li]^-$.

Intermediate 50: 2-Benzyl 5-ethyl 3,6-dihydro-2H-pyran-2,5-dicarboxylate

To a solution of lithium 5-(ethoxycarbonyl)-3,6-dihydro-2H-pyran-2-carboxylate Intermediate 49 (6.40 g, 31.0 mmol) in N,N-dimethylformide (100 mL) was added benzyl bromide (15.9 g, 93.0 mmol). After stirring at 25° C. overnight, the mixture was concentrated under reduced pressure to give a residue, which was purified by silica gel column chromatography (petroleum ether:ethyl acetate=5:1) to afford the product, which was further purified by C18 column (acetonitrile:water=10% to 95%) to give the title compound (6.4 g, 71% yield) as white solids. $^1$H NMR (400 MHz, $CDCl_3$) δ 7.36 (br s, 5H), 7.02 (s, 1H), 5.23 (s, 2H),

Intermediate 46: Ethyl 2-hydroxypent-4-enoate

To a solution of ethyl 2-oxoacetate (50.0 g, 490 mmol), allyltrimethylsilane (100 g, 882 mmol) in dichloromethane (1 L) was added boron trifluoride etherate (104 g, 735 mmol) dropwise at 0° C. After stirring at room temperature for 2 hours, saturated sodium bicarbonate aqueous solution (1 L) was added, then the organic layer was separated, dried over $Na_2SO_{4(s)}$, filtered and concentrated under reduced pressure to give a residue, which was purified by silica gel column chromatography (petroleum ether:ethyl acetate=5:1) to afford the title product (41.0 g, 58% yield) as yellow oil. $^1$H NMR (400 MHz, $CDCl_3$) δ 5.85-5.76 (m, 1H), 5.18-5.13 (m, 2H), 4.28-4.21 (m, 3H), 2.91 (d, J=6.0 Hz, 1H), 2.62-2.55 (m, 1H), 2.48-2.41 (m, 1H), 1.35-1.24 (m, 3H).

4.64 (dd, J=16.4, 1.2 Hz, 1H), 4.36 (dd, J=16.8, 2.4 Hz, 1H), 4.23-4.18 (m, 3H), 2.56-2.55 (m, 2H), 1.29 (t, J=6.8 Hz, 3H).

Intermediate 51: 5-(Ethoxycarbonyl)tetrahydro-2H-pyran-2-carboxylic Acid

To a solution of 2-benzyl 5-ethyl 3,6-dihydro-2H-pyran-2,5-dicarboxylate Intermediate 50 (6.40 g, 22.1 mmol) in tetrahydrofuran (200 mL) was added 10% palladium on charcoal wt. (1.30 g). The reaction mixture was stirred at room temperature under hydrogen atmosphere overnight. The completed reaction mixture was filtered and the filtrate was concentrated to give the title compound (4.40 g, 98% yield) as white oil. LC-MS (ESI): $R_T$=0.313 min, mass calcd. for $C_9H_{14}O_5$ 202.1, m/z found 201.1 [M−H]$^+$. $^1$H NMR (400 MHz, CDCl$_3$) δ 8.68 (br s, 1H), 4.40 (dd, J=11.2, 2.4 Hz, 0.7H), 4.31 (d, J=8.8 Hz, 0.3H), 4.23-4.13 (m, 2.7H), 3.99 (d, J=9.2 Hz, 0.3H), 3.79 (dd, J=11.6, 3.2 Hz, 0.8H), 3.56 (t, J=11.2 Hz, 0.2H), 2.64 (t, J=11.6 Hz, 0.3H), 2.55 (t, J=4.0 Hz, 0.7H), 2.35-2.14 (m, 1.5H), 1.98-1.96 (m, 1H), 1.88-1.82 (m, 1H), 1.78-1.64 (m, 0.5H), 1.27 (t, J=6.8 Hz, 3H).

Intermediate 52: 2-tert-Butyl 5-ethyl tetrahydro-2H-pyran-2,5-dicarboxylate

To a solution of 5-(ethoxycarbonyl)tetrahydro-2H-pyran-2-carboxylic acid Intermediate 51 (2.80 g, 13.9 mmol), di-tert-butyl dicarbonate (5.99 g, 27.8 mmol) in tert-butanol (20 mL) was added 4-dimethylaminopyridine (169 mg, 1.39 mmol) at room temperature. After stirring at 40° C. overnight, the mixture was allowed to cool down to room temperature. The mixture was concentrated under reduced pressure to give a residue, which was purified by silica gel column chromatography (petroleum ether:ethyl acetate=10:1) to afford the title product (3.10 g, 86% yield) as yellow oil. $^1$H NMR (400 MHz, CDCl$_3$) δ 4.31 (dd, J=11.6, 5.6 Hz, 1H), 4.18-4.12 (m, 2H), 4.01 (dd, J=7.6, 3.6 Hz, 0.8H), 3.82-3.76 (m, 1H), 3.50 (t, J=11.6 Hz, 0.2H), 2.63 (t, J=11.6 Hz, 0.3H), 2.52 (t, J=3.6 Hz, 0.7H), 2.22-2.18 (m, 0.4H), 2.07-2.05 (m, 0.6H), 2.03-1.95 (m, 1H), 1.85-1.83 (m, 1H), 1.75-1.71 (m, 0.4H), 1.64-1.58 (m, 0.6H), 1.48 (s, 9H), 1.27 (t, J=7.2 Hz, 3H).

Acid 49: 6-(tert-Butoxycarbonyl)tetrahydro-2H-pyran-3-carboxylic Acid

To a solution of 2-tert-butyl 2-tert-butyl 5-ethyl tetrahydro-2H-pyran-2,5-dicarboxylate Intermediate 52 (4.00 g, 15.5 mmol) in methanol (80 mL) and water (20 mL) was added barium hydroxide octahydrate (2.40 g, 7.75 mmol). After stirring at 25° C. overnight, the mixture was concentrated under reduced pressure to give a residue, and water (50 mL) and ethyl acetate (200 mL) was added. the separated aqueous phase was added amberlyst 15 iron-exchange resin (about 200 g) and extracted with ethyl acetate (200 mL) for three times. The separated organic layers were dried over $Na_2SO_{4(s)}$, filtered and concentrated under reduced pressure to give a residue, which was used directly in the next step without further purification. LC-MS (ESI): $R_T$=0.29 min, mass calcd. for $C_{11}H_{18}O_5$ 230.1, m/z found 229.2 [M−H]$^-$. $^1$H NMR (300 MHz, DMSO-d$_6$) δ 12.41 (br s, 1H), 4.08-3.97 (m, 2H), 3.84-3.79 (m, 0.3H), 3.68-3.60 (m, 0.7H), 2.50-2.41 (m, 1H), 2.04-1.99 (m, 1H), 1.91-1.83 (m, 1H), 1.78-1.72 (m, 2H), 1.41 (s, 9H).

Acid 50: 5-Oxo-1-(2-trimethylsilanyl-ethoxymethyl)-pyrrolidine-3-carboxylic Acid

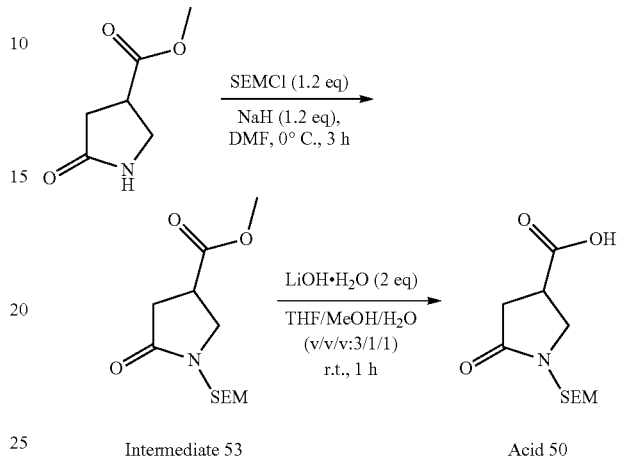

Intermediate 53    Acid 50

Intermediate 53: Methyl 5-oxo-1-((2-(trimethylsilyl)ethoxy)methyl)pyrrolidine-3-carboxylate To a solution of methyl 5-oxopyrrolidine-3-carboxylate (1.0 g, 7.0 mmol) in N,N-dimethylformamide (20 mL) was added 60% wt. sodium hydride in mineral oil (336 mg, 8.4 mmol) at 0° C. After stirring at 0° C. for 30 minutes, (2-(chloromethoxy)ethyl)trimethylsilane (1.40 g, 8.4 mmol) was added slowly, and the mixture was stirred at 0° C. under nitrogen atmosphere for 3 hours. Then it was poured into ice water (50 mL) and extracted with ethyl acetate (30 mL) for three times. The combined organic layers were washed with brine (10 mL) twice, dried over $Na_2SO_{4(s)}$, filtered and concentrated under reduced pressure to give a residue, which was purified by silica gel column chromatography (petroleum ether:ethyl acetate=2:1) to give the title compound (786 mg, 41% yield) as colorless oil. $^1$H NMR (300 MHz, CDCl$_3$) δ 4.73 (s, 2H), 3.76 (s, 3H), 3.72-3.69 (m, 2H), 3.50 (t, J=9.0 Hz, 2H), 3.30-3.21 (m, 1H), 2.82-2.64 (m, 2H), 0.92 (t, J=8.4 Hz, 2H), 0.01 (s, 9H).

Acid 50: 5-Oxo-1-(2-trimethylsilanyl-ethoxymethyl)-pyrrolidine-3-carboxylic Acid To the solution of methyl 5-oxo-1-((2-(trimethylsilyl)ethoxy)methyl)pyrrolidine-3-carboxylate Intermediate 53 (500 mg, 1.83 mmol) in methanol (1 mL), tetrahydrofuran (3 mL) and water (1 mL) was added lithium hydroxide monohydrate (154 mg, 3.66 mmol) under nitrogen atmosphere. After stirred at room temperature for 1 hour, the mixture was concentrated to give a residue, which was diluted by water (10 mL) and acidified with saturated citric acid aqueous solution to pH 5-6, extracted with ethyl acetate (50 mL) for three times. The combined organic layers were washed with brine (10 mL) twice, dried over $Na_2SO_{4(s)}$, filtered and concentrated under reduced pressure to give the title compound (470 mg, 99% yield) as colorless oil. $^1$H NMR (300 MHz, CDCl$_3$) δ 4.75 (s, 2H), 3.79-3.73 (m, 2H), 3.52 (t, J=8.4 Hz, 2H), 3.36-3.25 (m, 1H), 2.85-2.75 (m, 2H), 0.93 (t, J=8.1 Hz, 2H), 0.01 (s, 9H).

Acid 51: 4-(N-(2-Ethoxy-2-oxoethyl)sulfamoyl)cyclohexanecarboxylic Acid

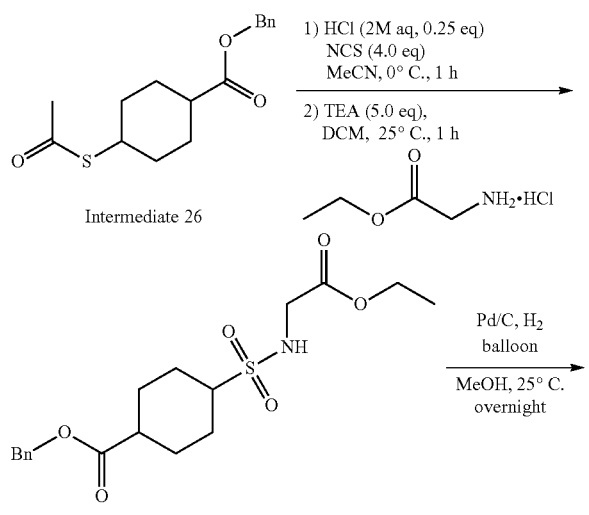

Intermediate 54

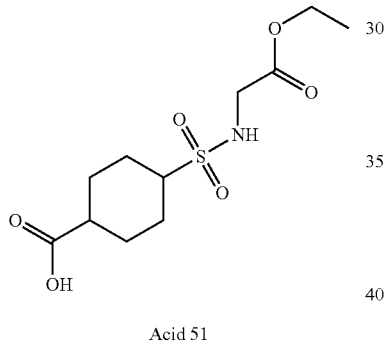

Acid 51

Intermediate 54: Benzyl 4-(N-(2-ethoxy-2-oxoethyl) sulfamoyl)-cyclohexanecarboxylate To a solution of benzyl 4-(acetylthio)cyclohexanecarboxylate (2.92 g, 10.0 mmol) in acetonitrile (30 mL) was added 2 M hydrochloride aqueous solution (1.25 mL, 2.5 mmol) and 1-chloropyrrolidine-2,5-dione (5.30 g, 40.0 mmol) at 0° C. After stirred at 0° C. for 1 hour, the mixture was quenched with water (100 mL) and extracted with ethyl ether (100 mL) twice. The combined organic layers were dried over $Na_2SO_{4(s)}$ and filtered. The filtrate was concentrated under reduced pressure at 30° C. to give a residue, which was dissolved in dry dichloromethane (20 mL). To above solution was added ethyl 2-aminoacetate hydrochloride (4.20 g, 30.0 mmol) and triethylamine (5.05 g, 50.0 mmol). After stirred at 25° C. for 1 hour, the mixture was concentrated and diluted with dichloromethane (150 mL). The resulting solution was washed with 1 M hydrochloride aqueous solution (100 mL) and brine (100 mL), dried over $Na_2SO_{4(s)}$ and filtered. The filtrate was concentrated to give a residue, which was purified by silica gel column chromatography (petroleum ether:ethyl acetate=4:1 to 2:1) to give the title compound (1.40 g, 88% yield) as light yellow oil.

LC-MS (ESI): $R_T$=1.64 min, mass calcd. for $C_{18}H_{25}NO_6S$ 383.1, m/z found 384.4 [M+H]$^+$. $^1$H NMR (300 MHz, CDCl$_3$) δ 7.42-7.31 (m, 5H), 5.15 (d, J=12.3 Hz, 2H), 4.71-4.62 (m, 1H), 4.25 (q, J=7.2 Hz, 2H), 3.91 (dd, J=13.5, 5.7 Hz, 2H), 3.00-2.87 (m, 1H), 2.75-2.69 (m, 0.5H), 2.41-2.31 (m, 2.5H), 2.23-2.16 (m, 1H), 2.13-2.08 (m, 1H), 1.84-1.67 (m, 2H), 1.56-1.49 (m, 2H), 1.33-1.27 (m, 3H).

Acid 51: 4-(N-(2-Ethoxy-2-oxoethyl)sulfamoyl) cyclohexanecarboxylic Acid

To a solution of benzyl 4-(N-(2-ethoxy-2-oxoethyl)sulfamoyl)cyclohexanecarboxylate Intermediate 54 (1.40 g, 3.65 mmol) in methanol (20 mL) was added 10% palladium on charcoal wt. (300 mg). After stirred at 25° C. under hydrogen atmosphere of balloon overnight, the mixture was filtered and the filtrate was concentrated to give the title compound (1.00 g, 94% yield) as white solids. $^1$H NMR (300 MHz, CDCl$_3$) δ 4.91-4.78 (m, 1H), 4.27-4.24 (m, 2H), 3.94 (s, 2H), 3.01-2.90 (m, 1H), 2.72-2.70 (m, 0.5H), 2.38-2.33 (m, 2H), 2.25-2.11 (m, 2H), 1.84-1.48 (m, 0.3.5H), 1.33-1.28 (m, 3H).

Acid 52: (R)-4-((3-(methoxycarbonyl)pyrrolidin-1-yl)sulfonyl)-cyclohexanecarboxylic Acid

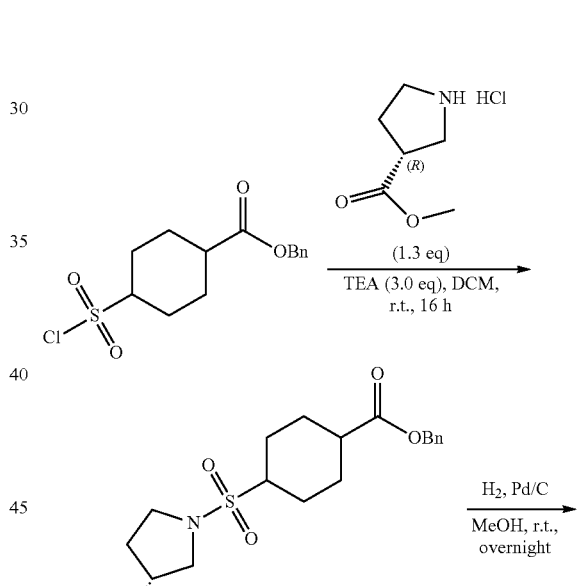

Intermediate 55

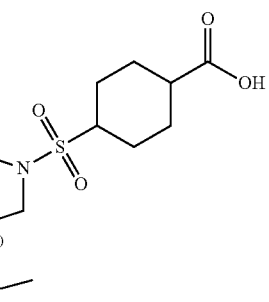

Acid 52

Intermediate 55: (R)-methyl 1-((4-((benzyloxy)carbonyl)cyclohexyl)sulfonyl)-pyrrolidine-3-carboxylate To a solution of benzyl 4-(chlorosulfonyl)cyclohexanecarboxylate (2.2 g, 6.94 mmol) and triethylamine (2.10 g, 20.8 mmol) in dichloromethane (30 mL) was added (R)-methyl pyrrolidine-3-carboxylate hydrochloride (1.50 g, 9.03 mmol) at 0° C. After stirred at room temperature for 16 hours, the mixture was washed with water (30 mL) twice followed by brine (30 mL), dried over $Na_2SO_{4(s)}$ and filtered. The filtrate was concentrated under reduced pressure to leave a residue, which was purified by silica gel column chromatography (petroleum ether:ethyl acetate=8:1 to 3:1) to give the title compound (2.30 g, 82% yield) as colorless oil. $^1H$ NMR (300 MHz, $CDCl_3$) δ 7.42-7.28 (m, 5H), 5.16 (s, 1H), 5.11 (s, 1H), 3.72 (s, 3H), 3.69-3.62 (m, 1H), 3.59-3.40 (m, 3H), 3.17-3.05 (m, 1H), 3.02-2.89 (m, 1H), 2.73-2.65 (m, 0.5H), 2.42-2.29 (m, 1.5H), 2.27-2.11 (m, 4H), 2.08-1.94 (m, 1H), 1.84-1.71 (m, 1H), 1.60-1.42 (m, 3H).

Acid 52: (R)-4-((3-(methoxycarbonyl)pyrrolidin-1-yl)sulfonyl)-cyclohexanecarboxylic Acid To a solution of (R)-methyl 1-((4-((benzyloxy)carbonyl)cyclohexyl)sulfonyl)pyrrolidine-3-carboxylate Intermediate 55 (2.30 g, 5.62 mmol) in methanol (80 mL) was added 10% wt. palladium on activated carbon (595 mg, 0.562 mmol) at room temperature. After stirred at room temperature under hydrogen atmosphere (1 atm) overnight, the mixture was filtered through a pad of celite. The filtrate was concentrated under reduced pressure to give the title compound (1.79 g, 99% yield) as white solids. $^1H$ NMR (300 MHz, $CDCl_3$) δ 3.73 (s, 3H), 3.71-3.66 (m, 1H), 3.62-3.43 (m, 3H), 3.19-3.08 (m, 1H), 3.05-2.90 (m, 1H), 2.75-2.67 (m, 0.5H), 2.40-2.28 (m, 1.5H), 2.27-2.15 (m, 4H), 2.10-1.98 (m, 1H), 1.90-1.74 (m, 1H), 1.71-1.44 (m, 3H).

Acid 53: 3-((tert-Butyldiphenylsilyl)oxy)cyclobutanecarboxylic Acid

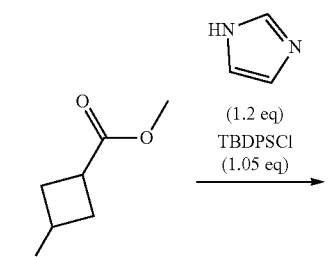

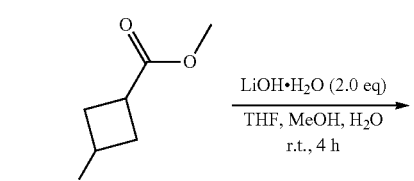

Intermediate 56

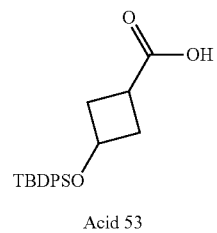

Acid 53

Intermediate 56: Methyl 3-((tert-butyldiphenylsilyl)oxy)cyclobutanecarboxylate tert-Butylchlorodiphenylsilane (8.66 g, 31.5 mmol) was added slowly to a solution of methyl 3-hydroxycyclobutanecarboxylate (3.90 g, 30.0 mmol) and 1H-imidazole (2.45 g, 36.0 mmol) in tetrahydrofuran (50 mL) at 0° C. After stirred at room temperature for 16 hours, the mixture was washed with saturated sodium bicarbonate aqueous solution (150 mL), followed with brine (150 mL), dried over $Na_2SO_{4(s)}$, filtered and concentrated to give the title compound (10.5 g, 95% yield) as colorless oil. LC-MS (ESI): $R_T$=1.87 min, mass calcd. for $C_{22}H_{28}O_3Si$ 368.2, m/z found 369.4 $[M+H]^+$. $^1H$ NMR (300 MHz, $CDCl_3$) δ 7.67-7.65 (m, 4H), 7.44-7.28 (m, 6H), 4.15-4.10 (m, 1H), 3.68 (s, 3H), 2.37-2.34 (m, 5H), 1.04 (s, 9H).

Acid 53: 3-((tert-Butyldiphenylsilyl)oxy)cyclobutanecarboxylic Acid

To the solution of methyl 3-((tert-butyldiphenylsilyl)oxy) cyclobutanecarboxylate Intermediate 56 (3.50 g, 9.50 mmol) in tetrahydrofuran (12 mL), methanol (4 mL) and water (4 mL) was added lithium hydroxide monohydrate (798 mg, 19.0 mmol) under nitrogen atmosphere at 0° C. After stirred at room temperature for 4 hours, the mixture was diluted with water (150 mL), concentrated at room temperature under reduced pressure, acidified with 1 M hydrochloride aqueous solution (20 mL) and extracted with ethyl acetate (150 mL). The organic layer was washed with brine (150 mL), dried over $Na_2SO_{4(s)}$ and filtered. The filtrate was concentrated under reduced pressure to give the crude title compound (3.10 g, 87% yield) as colorless oil, which was directly used without further purification. $^1H$ NMR (300 MHz, $CDCl_3$) δ 7.68-7.66 (m, 4H), 7.45-7.37 (m, 6H), 4.16-4.13 (m, 1H), 2.44-2.37 (m, 5H), 1.05 (s, 9H).

Acid 54: 4-(N-(2-((tert-Butyldimethylsilyl)oxy) ethyl)methylsulfonamido)-cyclohexanecarboxylic Acid

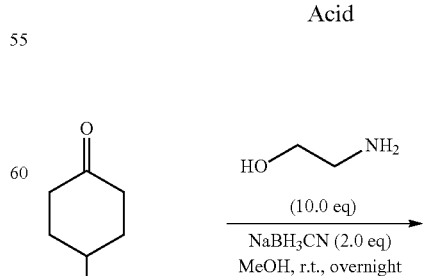

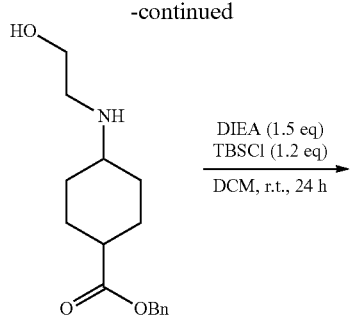

Intermediate 54a

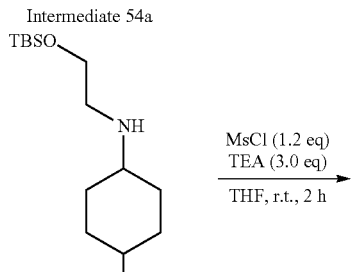

Intermediate 54b

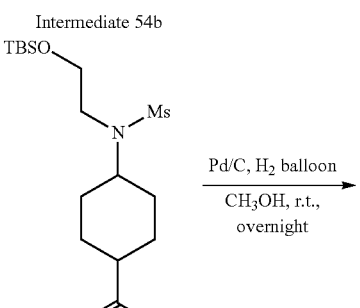

Intermediate 54c

TBSO
         \
          N—Ms
         /

/
        /
   O═══
        \
         OH

Acid 54

Intermediate 54a: Benzyl 4-((2-hydroxyethyl)amino)cyclohexanecarboxylate

To a solution of benzyl 4-oxocyclohexanecarboxylate (4.80 g, 20.7 mmol) and 2-aminoethanol (12.6 g, 210 mmol) in methanol (40 mL) was added sodium cyanoborohydride (2.60 g, 41.4 mmol) at 0° C. under nitrogen atmosphere. After stirred at room temperature overnight, the mixture was concentrated under reduced pressure to give a residue, which was dissolved in dichloromethane (50 mL), washed with water (20 mL) twice, followed with brine (20 mL) twice, dried over $Na_2SO_{4(s)}$ and filtered. The filtrate was concentrated under reduced pressure to give the title compound (5.40 g, 93% yield) as yellow oil. $^1$H NMR (400 MHz, DMSO-$d_6$) δ 7.38-7.31 (m, 5H), 5.11-5.08 (m, 2H), 4.69-4.62 (m, 0.5H), 4.45-4.31 (m, 0.5H), 3.50-3.46 (m, 1H), 3.44-3.40 (m, 2H), 2.62-2.53 (m, 2H), 2.39-2.26 (m, 1H), 2.11-1.82 (m, 4H), 1.66-1.49 (m, 2H), 1.45-1.31 (m, 2H), 1.06-0.96 (m, 1H).

Intermediate 54b: Benzyl 4-((2-((tert-butyldimethylsilyl)oxy)ethyl)amino)-cyclohexanecarboxylate To a solution of benzyl 4-((2-hydroxyethyl)amino)cyclohexanecarboxylate Intermediate 54a (5.40 g, 19.5 mmol) in dichloromethane (50 mL) was added N,N-diisopropylethylamine (3.80 g, 29.3 mmol) and tert-butyldimethylsilyl chloride (3.60 g, 23.4 mmol) at 0° C. under nitrogen atmosphere. After stirred at room temperature for 24 hours, the mixture was concentrated under reduced pressure to give a residue, which was dissolved in dichloromethane (50 mL). The solution was washed with water (20 mL) twice, followed brine (20 mL) twice, dried over $Na_2SO_{4(s)}$ and filtered. The filtrate was concentrated under reduced pressure to give the title compound (6.27 g, 70% yield) as yellow oil. $^1$H NMR (400 MHz, DMSO-$d_6$) δ 7.35-7.31 (m, 5H), 5.27 (br s, 0.3H), 5.10-5.07 (m, 1.7H), 3.65-3.58 (m, 1.5H), 3.50-3.44 (m, 1.5H), 2.64-2.55 (m, 2H), 2.45-2.24 (m, 1H), 2.11-1.83 (m, 4H), 1.57-1.24 (m, 3.5H), 1.08-0.84 (m, 1.5H), 0.86 (s, 9H), 0.03 (s, 6H).

Intermediate 54c: Benzyl 4-(N-(2-(tert-butyldimethylsilyl)ethyl)-methylsulfonamido)cyclohexanecarboxylate To a solution of benzyl 4-((2-((tert-butyldimethylsilyl)oxy)ethyl)amino)-cyclohexanecarboxylate Intermediate 54b (6.27 g, 16.0 mmol) in tetrahydrofuran (50 mL) was added triethylamine (4.85 g, 48.0 mmol) and methanesulfonyl chloride (2.21 g, 19.0 mmol) at 0° C. under nitrogen atmosphere. After stirred at room temperature for 2 hours, the mixture was concentrated under reduced pressure to give a residue, which was purified by silica gel column chromatography (petroleum ether:ethyl acetate=5:1) to afford the title compound (3.80 g, 51% yield) as yellow oil. $^1$H NMR (400 MHz, DMSO-$d_6$) δ 7.37-7.32 (m, 5H), 5.13 (s, 0.0.8H), 5.08 (s, 1.2H), 3.66-3.48 (m, 3H), 3.17-3.12 (m, 1H), 3.05-3.00 (m, 0.5H), 2.93 (s, 3H), 2.74-2.69 (m, 0.5H), 2.40-2.30 (m, 0.7H), 2.13-2.08 (m, 1H), 1.99-1.94 (m, 1.3H), 1.83-1.72 (m, 1.5H), 1.62-1.42 (m, 4.5H), 0.87 (s, 9H), 0.05-0.04 (m, 6H).

Acid 54: 4-(N-(2-((tert-Butyldimethylsilyl)oxy)ethyl)methylsulfonamido)-cyclohexanecarboxylic Acid To the solution of benzyl 4-(N-(2-((tert-butyldimethylsilyl)oxy)ethyl)-methylsulfonamido)cyclohexanecarboxylate Intermediate 54c (1.35 g, 2.87 mmol) in methanol (20 mL) was added 10% palladium on charcoal wt. (200 mg). After stirred at room temperature under hydrogen atmosphere of balloon overnight, the reaction mixture was filtered. The filtrate was concentrated under reduced pressure to give the title compound (900 mg, 82% yield) as white solids. $^1$H NMR (400 MHz, CDCl$_3$) δ 3.75-3.70 (m, 2H), 3.63-3.57 (m, 1H), 3.25-3.18 (m, 1.5H), 2.89-2.88 (s, 3H), 2.65-2.62 (m, 0.5H), 2.29-2.09 (m, 3H), 1.90-1.88 (m, 1H), 1.72-1.52 (m, 5H), 0.91-0.88 (m, 9H), 0.07 (s, 6H).

Acid 55: 4-(N-(2-Methoxyethyl)sulfamoyl)cyclohexanecarboxylic Acid

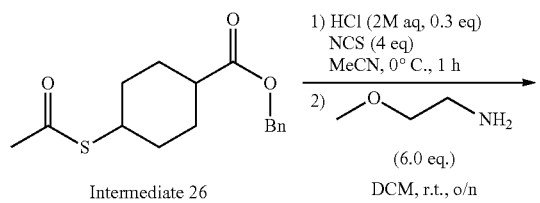

Intermediate 26

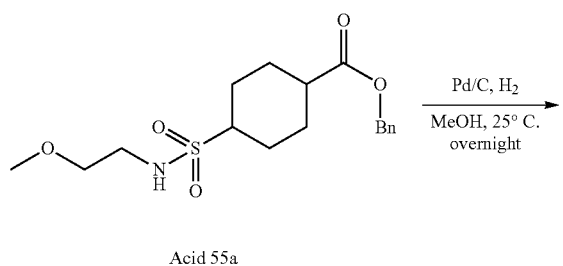

Acid 55a

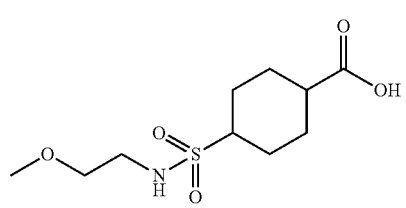

Acid 55

Intermediate 55a: Benzyl 4-(N-(2-ethoxyethyl)sulfamoyl)cyclohexanecarboxylate To the solution of benzyl 4-(acetylthio)cyclohexanecarboxylate Intermediate 26 (1.0 g, 3.42 mmol) in acetonitrile (25 mL) was added 2 M hydrochloride aqueous solution (0.5 mL, 1.0 mmol) and 1-chloropyrrolidine-2,5-dione (1.83 g, 13.7 mmol) at 0° C. After stirred at 0° C. for 1 hour, the mixture was quenched with water (50 mL), concentrated and extracted with ethyl ether (50 mL) twice. The combined organic layers were dried over $Na_2SO_{4(s)}$ and filtered. The filtrate was concentrated under reduced pressure at 30° C. to give a residue, which was dissolved in dry dichloromethane (35 mL). To above solution was added 2-methoxyethanamine (1.54 g, 20.6 mmol). After stirred at room temperature overnight, the resulting solution was washed with 1 M hydrochloride aqueous solution (30 mL) and brine (30 mL), dried over $Na_2SO_{4(s)}$ and filtered. The filtrate was concentrated to give a residue, which was purified by silica gel column chromatography (petroleum ether:ethyl acetate=10:1 to 5:1) to give the title compound (1.35 g, 92% yield) as light yellow oil. LC-MS (ESI): $R_T$=1.262 min, mass calcd. for $C_{17}H_{25}NO_5S$ 355.2, m/z found 356.1 [M+H]$^+$. $^1$H NMR (300 MHz, CDCl$_3$) δ 7.42-7.33 (m, 5H), 5.16-5.13 (m, 2H), 4.59-4.48 (m, 1H), 3.51-3.46 (m, 2H), 3.37 (s, 3H), 3.32-3.23 (m, 2H), 2.98-2.85 (m, 1H), 2.72 (br s, 0.4H), 2.39-2.18 (m, 3.6H), 2.08-2.04 (m, 1H), 1.83-1.74 (m, 1H), 1.63-1.43 (m, 3H).

Acid 55: 4-(N-(2-Methoxyethyl)sulfamoyl)cyclohexanecarboxylic Acid

To a solution of benzyl 4-(N-(2-methoxyethyl)sulfamoyl) cyclohexanecarboxylate Intermediate 55a (1.35 g, 3.79 mmol) in methanol (50 mL) was added 10% palladium on charcoal wt. (300 mg). After stirred at 25° C. under hydrogen atmosphere of balloon overnight, the mixture was filtered and the filtrate was concentrated to give the title compound (970 mg, 97% yield) as white solids. $^1$H NMR (300 MHz, CDCl$_3$) δ 4.74-4.68 (m, 0.5H), 4.65-4.61 (m, 0.5H), 3.53-3.49 (m, 2H), 3.38 (s, 3H), 3.34-3.30 (m, 2H), 3.00-2.87 (m, 1H), 2.72 (br s, 0.5H), 2.39-2.07 (m, 4.5H), 1.85-1.73 (m, 1H), 1.65-1.47 (m, 3H).

Acid 56: 4-(N-(3-(tert-butoxy)-2,2-dimethyl-3-oxopropyl)sulfamoyl)-cyclohexanecarboxylic Acid

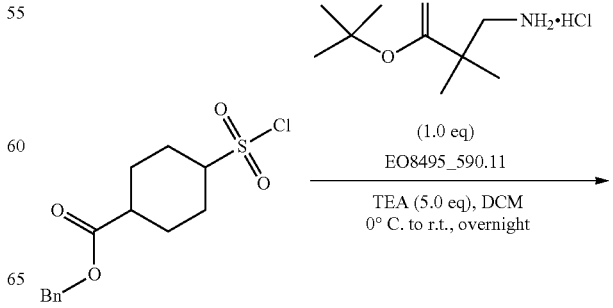

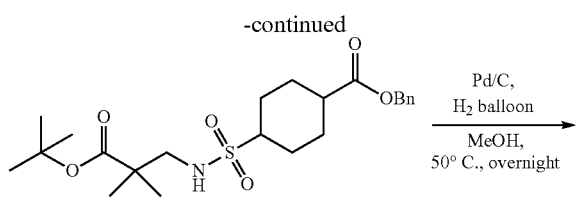

Intermediate 56a

Acid 56

Intermediate 56a: Benzyl 4-(N-(3-(tert-butoxy)-2,2-dimethyl-3-oxopropyl)sulfamoyl)cyclohexanecarboxylate To a solution of tert-butyl 3-amino-2,2-dimethylpropanoate hydrochloride (710 mg, 3.40 mmol) in dichloromethane (15 mL) was added triethylamine (1.70 g, 17.0 mmol) at 0° C. After stirring at 0° C. for 20 minutes, a solution of benzyl 4-(chlorosulfonyl)cyclohexanecarboxylate (1.06 g, 3.40 mmol) in dichloromethane (15 mL) was added. The obtained mixture was stirred at room temperature overnight. After that, it was concentrated under reduced pressure to give a residue, which was dissolved in ethyl acetate (10 mL), washed with water (8 mL) twice, brine (8 mL) twice, dried over $Na_2SO_{4(s)}$, filtered and concentrated under reduced pressure to give a residue, which was purified by silica gel column chromatography (petroleum ether:ethyl acetate=15:1 to 8:1) to give the desired compound (700 mg, 46% yield) as yellow oil. $^1$H NMR (300 MHz, $CDCl_3$) δ 7.36 (br s, 5H), 5.17 (s, 0.7H), 5.13 (s, 1.3H), 4.91-4.80 (m, 1H), 4.18-4.09 (m, 0.7H), 3.11-3.07 (m, 2H), 2.95-2.83 (m, 1H), 2.76-2.68 (m, 0.3H), 2.42-2.28 (m, 2H), 2.26-2.17 (m, 2H), 2.09-2.01 (m, 1.4H), 1.89-1.71 (m, 0.6H), 1.46 (s, 9H), 1.39-1.24 (m, 2H), 1.21 (s, 6H).

Acid 56: 4-(N-(3-(tert-butoxy)-2,2-dimethyl-3-oxopropyl)sulfamoyl)-cyclohexanecarboxylic Acid To a solution of benzyl 4-(N-(3-(tert-butoxy)-2,2-dimethyl-3-oxopropyl)sulfamoyl)cyclohexanecarboxylate Intermediate 56a (700 mg, 1.54 mmol) in methanol (20 mL) was added 10% palladium on charcoal wt. (240 mg). The reaction mixture was stirred at 50° C. under hydrogen atmosphere balloon overnight. After cooling down to room temperature, the mixture was filtered and the filtrate was concentrated to give the compound (640 mg, 80% purity, 91% yield) as white solids. $^1$H NMR (400 MHz, DMSO-$d_6$) δ 6.98-6.93 (m, 1H), 3.04-3.00 (m, 2H), 2.96-2.89 (m, 1H), 2.55-2.54 (m, 0.3H), 2.20-2.14 (m, 0.7H), 2.09-2.04 (m, 2H), 2.00-1.97 (m, 1.4H), 1.87-1.84 (m, 0.6H), 1.59-1.45 (m, 2H), 1.39 (s, 9H), 1.36-1.24 (m, 2H), 1.05 (s, 6H).

Acid 57R and 57S:
5-(Ethoxycarbonyl)tetrahydro-2H-pyran-2-carboxylic Acid

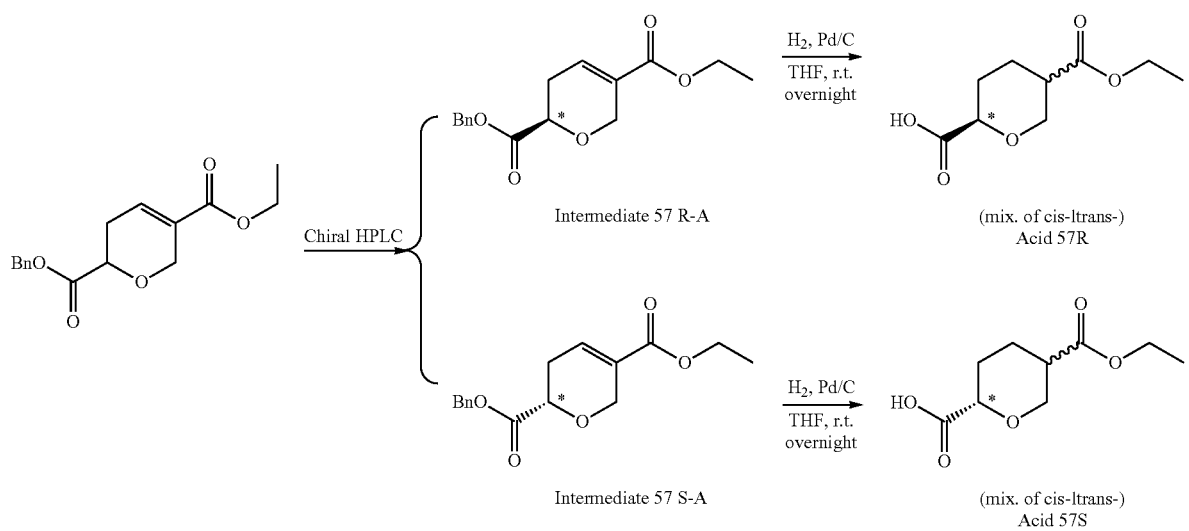 [SMILES: CCOC(=O)C1=CCC(C(=O)OCc2ccccc2)OC1 ; CCOC(=O)C1=CC[C@@H](C(=O)OCc2ccccc2)OC1 ; CCOC(=O)C1=CC[C@H](C(=O)OCc2ccccc2)OC1 ; CCOC(=O)C1CC[C@H](C(=O)O)OC1 ; CCOC(=O)C1CC[C@@H](C(=O)O)OC1]

Intermediate 57R-A and 57S-A: 2-Benzyl 5-ethyl 3,6-dihydro-2H-pyran-2,5-dicarboxylate A racemic mixture of (3.36 g, 11.6 mmol) was separated by chiral Prep. HPLC (Column: Chiralpak IF 5 μm 20*250 mm; Mobile Phase: Hex:EtOH=60:40 at 10 mL/min; Temp: 30° C.; Wavelength: 214 nm) to afford the title compounds 57R-A (1.37 g, 41% yield) and 57S-A (1.34 g, 40% yield).

Acid 57R: 5-(Ethoxycarbonyl)tetrahydro-2H-pyran-2-carboxylic Acid

To a solution of 2-benzyl 5-ethyl 3,6-dihydro-2H-pyran-2,5-dicarboxylate 57R-A (610 mg, 2.10 mmol) in tetrahydrofuran (30 mL) was added 10% palladium on charcoal wt. (180 mg). The reaction mixture was stirred at room temperature under hydrogen atmosphere of balloon overnight. Then the reaction mixture was filtered and concentrated to give the title compound (456 mg, crude) as white solids. LC-MS (ESI): no $R_T$, mass calcd. for $C_9H_{14}O_5$ 202.1, m/z found 203.1 [M+H]$^+$. $^1$H NMR (400 MHz, DMSO-$d_6$) δ 12.69 (br s, 1H), 4.13-4.02 (m, 3H), 3.88 (dd, J=11.6, 2.8 Hz, 0.6H), 3.67 (dd, J=11.6, 3.6 Hz, 1H), 3.45-3.40 (m, 0.4H), 2.59-2.53 (m, 1H), 2.06-2.01 (m, 0.2H), 1.99-1.92 (m, 0.8H), 1.88-1.82 (m, 3H), 1.21-1.16 (m, 3H).

Acid 57S: 5-(Ethoxycarbonyl)tetrahydro-2H-pyran-2-carboxylic Acid

Acid 57S was prepared analogous to Acid 57R from Intermediate 57S-A, LC-MS (ESI): no $R_T$, mass calcd. for $C_9H_{14}O_5$ 202.1, m/z found 203.1 [M+H]$^+$. $^1$H NMR (300 MHz, DMSO-$d_6$) δ 12.72 (br s, 1H), 4.15-4.03 (m, 3.6H), 3.88 (dd, J=8.1, 1.8 Hz, 0.3H), 3.67 (dd, J=8.7, 2.4 Hz, 0.7H), 3.43 (t, J=8.1 Hz, 0.4H), 2.59-2.54 (m, 1H), 2.05-2.00 (m, 0.3H), 1.91-1.88 (m, 1H), 1.80-1.44 (m, 2.7H), 1.21-1.16 (m, 3H).

Acid 58: (trans)-1-(tert-Butoxycarbonyl)-2-(((tert-butyldiphenylsilyl)oxy)methyl)-piperidine-4-carboxylic Acid

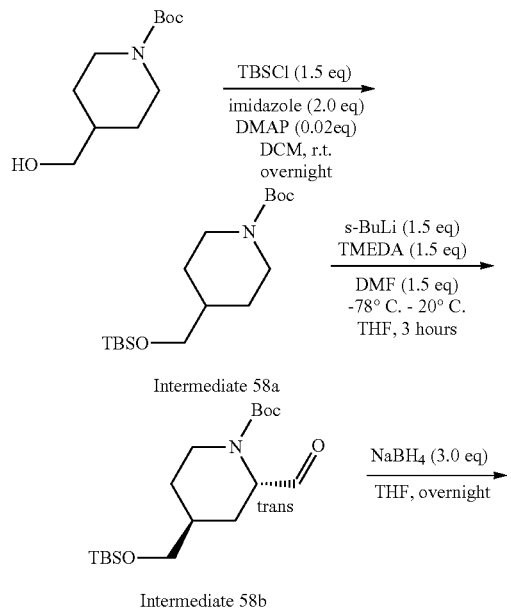

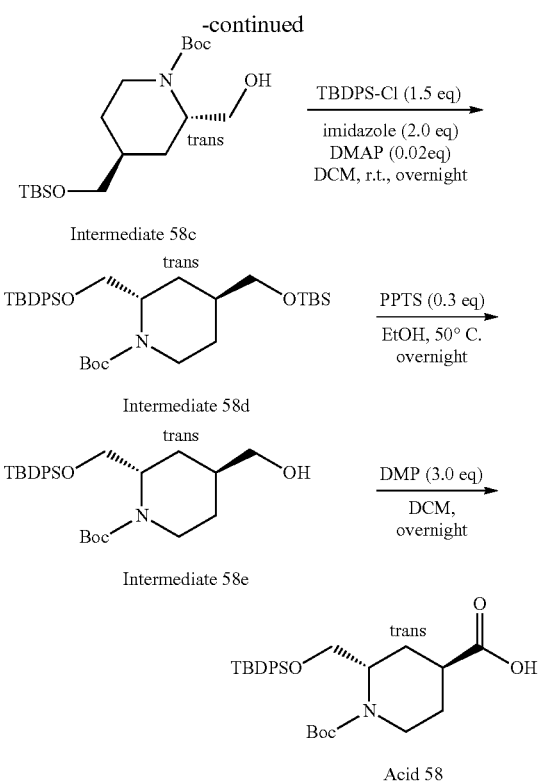

Intermediate 58a: tert-Butyl 4-(((tert-butyldimethylsilyl)oxy)methyl)piperidine-1-carboxylate To a solution of tert-butyl 4-(hydroxymethyl)piperidine-1-carboxylate (20.0 g, 93.0 mmol) in dichloromethane (200 mL) were added tert-butylchlorodimethylsilane (20.9 g, 139 mmol), imidazole (12.7 g, 186 mmol) and 4-dimethylaminopyridine (227 mg, 1.86 mmol). After stirred at room temperature under nitrogen atmosphere overnight, the mixture was quenched with water (50 mL) and extracted with dichloromethane (100 mL) twice. The combined organic layers were washed with brine (250 mL) twice, dried over Na$_2$SO$_4$(s) and filtered. The filtrate was concentrated under reduced pressure to give a residue, which was purified by silica gel column chromatography (petroleum ether:ethyl acetate=20:1) to afford the title compound (22.5 g, 74% yield) as colorless oil. LC-MS (ESI): $R_T$=2.521 min, mass calcd. for $C_{17}H_{35}NO_3Si$ 329.2, m/z found 274.2 [M+H–56]$^+$. $^1$H NMR (400 MHz, CDCl$_3$) δ 4.13-4.08 (m, 2H), 3.42 (d, J=6.4 Hz, 2H), 2.69-2.64 (m, 2H), 1.68-1.64 (m, 2H), 1.62-1.53 (m, 1H), 1.44 (s, 9H), 1.13-1.03 (m, 2H), 0.87 (s, 7H), 0.85 (s, 2H), 0.02 (s, 5H), 0.01 (s, 1H).

Intermediate 58b: (trans)-tert-Butyl 4-(((tert-butyldimethylsilyl)oxy)methyl)-2-formylpiperidine-1-carboxylate To a solution of tert-butyl 4-(((tert-butyldimethylsilyl)oxy)methyl)piperidine-1-carboxylate Intermediate 58a (15.0 g, 45.6 mmol) in anhydrous tetrahydrofuran (150 mL) was added tetramethylethylenediamine (75.6 g, 68.0 mmol). After stirring at –78° C. for 1 hour, 1.3 M sec-butyllithium in tetrahydrofuran (52.5 mL, 68.0 mmol) was added at –78° C. under nitrogen atmosphere. After stirring for 1 hour, a solution of N,N-dimethylformamide (5.25 mL, 68.0 mmol)

in anhydrous tetrahydrofuran (20 mL) was added at −78° C. The resulting mixture was stirred at −78° C. for 2 hours. Then it was brought up to room temperature and quenched with saturated ammonium chloride aqueous solution (100 mL), extracted with ethyl acetate (200 mL) twice. The combined organic layers were washed with brine (400 mL) for three times, dried over anhydrous $Na_2SO_{4(s)}$ and concentrated to give the crude compound, which was purified by silica gel column chromatography (petroleum ether:ethyl acetate=30:1) to afford the title compound (7.47 g, 40% yield) as colorless oil. LC-MS (ESI): $R_T$=2.294 min, mass calcd. for $C_{18}H_{35}NO_4Si$ 357.2, m/z found 302.2 [M+H−56]$^+$. $^1$H NMR (300 MHz, $CDCl_3$) δ 9.62-9.59 (m, 0.8H), 9.45-9.43 (m, 0.2H), 4.89-4.84 (m, 0.4H), 4.67-4.63 (m, 0.3H), 4.23-4.04 (m, 1H), 3.87-3.62 (m, 0.3H), 3.48-3.41 (m, 2H), 2.91-2.69 (m, 1H), 2.32-2.24 (m, 0.8H), 1.89-1.82 (m, 0.2H), 1.71-1.64 (m, 2H), 1.49 (s, 3H), 1.46 (s, 6H), 1.36-1.24 (m, 1H), 1.17-1.05 (m, 1H), 0.89-0.88 (m, 9H), 0.04 (s, 6H).

Intermediate 58c: (trans)-tert-Butyl 4-(((tert-butyldimethylsilyl)oxy)methyl)-2-(hydroxymethyl)piperidine-1-carboxylate To a solution of (trans)-tert-butyl 4-(((tert-butyldimethylsilyl)oxy)methyl)-2-formylpiperidine-1-carboxylate Intermediate 58b (7.47 g, 21.0 mmol) in anhydrous tetrahydrofuran (100 mL) was added sodium borohydride (2.38 g, 63.0 mmol). After stirred at room temperature under nitrogen atmosphere overnight, the reaction mixture was quenched with water (50 mL) and extracted with ethyl acetate (100 mL) for three times. The combined organic layers were washed with brine (200 mL) for three times, dried over anhydrous $Na_2SO_{4(s)}$ and concentrated to give a residue, which was purified by silica gel column chromatography (petroleum ether:ethyl acetate=3:1) to afford the title compound (6.49 g, 86% yield) as colorless oil. $^1$H NMR (400 MHz, DMSO-$d_6$) δ 4.64-4.60 (m, 1H), 4.03-3.98 (m, 1H), 3.87-3.77 (m, 1H), 3.43-3.38 (m, 2H), 3.35-3.32 (m, 1H), 2.81-2.64 (m, 1H), 1.78-1.67 (m, 2H), 1.62-1.52 (m, 1H), 1.36 (s, 9H), 1.07-0.99 (m, 1H), 0.99-0.89 (m, 1H), 0.84 (s, 9H), 0.00 (s, 6H).

Intermediate 58d: (trans)-tert-Butyl 4-(((tert-butyldimethylsilyl)oxy)methyl)-2-(((tert-butyldiphenylsilyl)oxy)methyl)piperidine-1-carboxylate To a solution of (trans)-tert-butyl 4-(((tert-butyldimethylsilyl)oxy)methyl)-2-(hydroxymethyl)piperidine-1-carboxylate Intermediate 58c (6.49 g, 18.0 mmol) in dichloromethane (200 mL) was added tert-butylchlorodiphenylsilane (7.46 g, 27.0 mmol), imidazole (2.46 g, 36.0 mmol) and 4-dimethylaminopyridine (44 mg, 0.36 mmol). After stirred at room temperature under nitrogen atmosphere overnight, the reaction mixture was quenched with water (100 mL) and extracted with dichloromethane (50 mL) twice. The combined organic layers were washed with brine (150 mL) twice, dried over $Na_2SO_4(s)$ and filtered. The filtrate was concentrated under reduced pressure to give a residue, which was purified by silica gel column chromatography (petroleum ether:ethyl acetate=30:1) to afford the title compound (9.39 g, 87% yield) as colorless oil. LC-MS (ESI): $R_T$=5.380 min, mass calcd. for $C_{34}H_{55}NO_4Si_2$ 597.4, m/z found 498.3 [M+H−Boc]$^+$. $^1$H NMR (400 MHz, DMSO-$d_6$) δ 7.68-7.65 (m, 2H), 7.61-7.59 (m, 3H), 7.45-7.35 (m, 5H), 4.35-4.21 (m, 1H), 3.88-3.79 (m, 1H), 3.70-3.51 (m, 3H), 3.43-3.39 (m, 1H), 2.69-2.57 (m, 1H), 2.03-2.00 (m, 0.5H), 1.89-1.86 (m, 0.5H), 1.68 (br s, 1H), 1.57-1.54 (m, 1H), 1.35 (s, 3H), 1.29 (s, 6H), 1.13-1.07 (m, 2H), 0.96 (s, 6H), 0.93 (s, 3H), 0.83 (s, 9H), 0.00 (s, 6H).

Intermediate 58e: (trans)-tert-Butyl 2-(((tert-butyldiphenylsilyl)oxy)methyl)-4-(hydroxymethyl)piperidine-1-carboxylate To a solution of (trans)-tert-butyl 4-(((tert-butyldimethylsilyl)oxy)methyl)-2-(((tert-butyldiphenylsilyl)oxy)methyl)piperidine-1-carboxylate Intermediate 58d (9.39 g, 15.7 mmol) in ethanol (80 mL) was added pyridinium 4-toluenesulfonate (1.15 g, 4.00 mmol). After stirred at 50° C. under nitrogen atmosphere overnight, the mixture was allowed to cool down to room temperature and concentrated under reduced pressure to give a residue, which was purified by silica gel column chromatography (petroleum ether:ethyl acetate=5:1) to afford the title compound (5.40 g, 71% yield) as colorless oil. LC-MS (ESI): $R_T$=2.173 min, mass calcd. for $C_{28}H_{41}NO_4Si$ 483.3, m/z found 384.3 [M+H]$^+$. $^1$H NMR (400 MHz, $CDCl_3$) δ 7.66 (br s, 4H), 7.43-7.37 (m, 6H), 4.59-4.56 (m, 0.5H), 4.37-4.36 (m, 0.5H), 4.15-4.07 (m, 0.5H), 3.96-3.90 (m, 0.5H), 3.72-3.61 (m, 2H), 3.48-3.35 (m, 2H), 2.71-2.60 (m, 1H), 2.05-1.97 (m, 0.5H), 1.86-1.84 (m, 0.5H), 1.74-1.64 (m, 1H), 1.60-1.52 (m, 1H), 1.42 (s, 9H), 1.37-1.17 (m, 2H), 1.05 (s, 9H).

Acid 58: (trans)-1-(tert-Butoxycarbonyl)-2-(((tert-butyldiphenylsilyl)oxy)-methyl)piperidine-4-carboxylic Acid To a solution of (trans)-tert-butyl 2-(((tert-butyldiphenylsilyl)oxy)methyl)-4-(hydroxymethyl)piperidine-1-carboxylate Intermediate 58e (4.00 g, 8.30 mmol) in dichloromethane (30 mL) was added Dess-Martin periodinane (10.4 g, 24.8 mmol). After stirred at room temperature under nitrogen atmosphere overnight, the solution was quenched with saturated sodium sulfite (250 mL) and extracted with dichloromethane (100 mL) for three times. The combined organic layers were washed with brine (150 mL) twice, dried over $Na_2SO_4(s)$ and filtered. The filtrate was concentrated under reduced pressure to give a residue, which was purified by C18 column (acetonitrile:water=50% to 95%) to afford the title compound (3.07 g, 75% yield) as light yellow oil. LC-MS (ESI): $R_T$=2.428 min, mass calcd. for $C_{28}H_{39}NO_5Si$ 497.3, m/z found 398.2 [M+H−Boc]$^+$. $^1$H NMR (400 MHz, DMSO-$d_6$) δ 12.25 (s, 1H), 7.63-7.61 (m, 4H), 7.48-7.41 (m, 6H), 4.41-4.29 (m, 1H), 3.93-3.83 (m, 1H), 3.74-3.62 (m, 2H), 3.32 (s, 1H), 2.78-2.63 (m, 1H), 2.16-2.00 (m, 1H), 1.83-1.76 (m, 1H), 1.55-1.46 (1, 1H), 1.33 (s, 9H), 1.28-1.19 (m, 1H), 0.99 (s, 9H).

Acid 59: (trans)-4-((tert-Butyldimethylsilyl)oxy) cyclohexanecarboxylic Acid

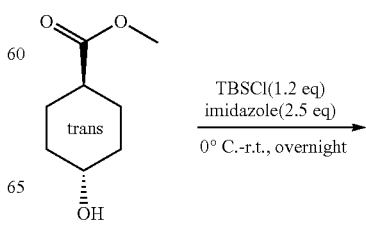

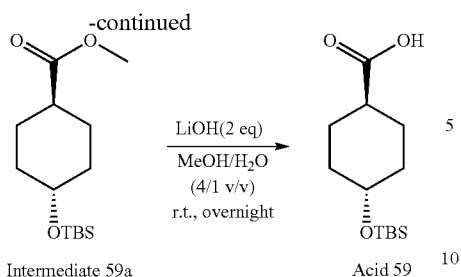

Intermediate 59a      Acid 59

Intermediate 59a: (trans)-Methyl 4-((tert-butyldimethylsilyl)oxy)-cyclohexanecarboxylate To a mixture of (trans)-methyl 4-hydroxycyclohexanecarboxylate (865 mg, 6.00 mmol) and imidazole (1.02 g, 15.0 mmol) in N,N-dimethylformamide (5 mL) was added tert-butylchlorodimethylsilane (1.09 g, 7.20 mmol) at 0° C. under nitrogen atmosphere. The reaction mixture was stirred at room temperature overnight, then poured into water (30 mL) and extracted with ethyl acetate (30 mL) for three times. The combined organic layers were washed with water (30 mL), dried over $Na_2SO_{4(s)}$ and concentrated to give a residue, which was purified by silica gel column chromatography (petroleum ether:ethyl acetate=100:1 to 20:1) to afford the title compound (1.34 g, 86% yield) as colorless oil. $^1$H NMR (400 MHz, $CD_3OD$) δ 3.58-3.51 (m, 4H), 2.24-2.17 (m, 1H), 1.91-1.81 (m, 4H), 1.45-1.36 (m, 2H), 1.29-1.20 (m, 2H), 0.82 (s, 9H), 0.01 (s, 6H).

Acid 59: (trans)-4-((tert-Butyldimethylsilyl)oxy)cyclohexanecarboxylic Acid

To a solution of (trans)-methyl 4-((tert-butyldimethylsilyl)oxy)cyclohexanecarboxylate Intermediate 59a (681 mg, 2.50 mmol) in methanol (6 mL) and water (1.5 mL) was added lithium hydroxide monohydrate (210 mg, 5.00 mmol) under nitrogen atmosphere. After stirring at room temperature overnight, the solvent was removed and the residue was diluted with water (10 mL), acidified with 1 M hydrochloride aqueous solution to pH 2, then filtered. The solid was washed with water (10 mL) and dried in vacuum to give the title compound (510 mg, 79% yield) as white solids. $^1$H NMR (300 MHz, $CD_3OD$) δ 3.64-3.59 (m, 1H), 2.24-2.19 (m, 1H), 2.03-1.86 (m, 4H), 1.50-1.27 (m, 4H), 0.90-0.89 (m, 9H), 0.08-0.01 (m, 6H).

Acid 60: 1,4-Dioxaspiro[4.5]decane-8-carboxylic Acid

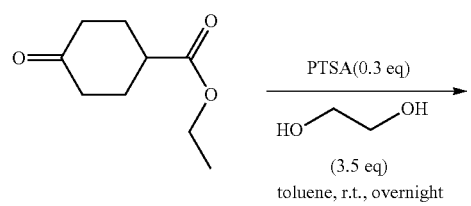

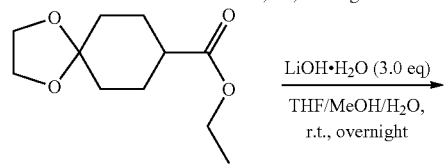

Intermediate 60a

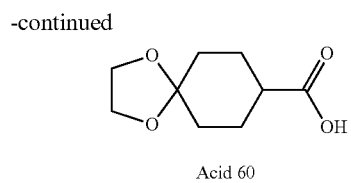

Acid 60

Intermediate 60a: Ethyl 1,4-dioxaspiro[4.5]decane-8-carboxylate

To a solution of ethyl 4-oxocyclohexanecarboxylate (5.00 g, 29.4 mmol) in toluene (20 mL) was added p-toluenesulfonic acid (1.50 g, 8.80 mmol) and ethane-1,2-diol (6.00 g, 103 mmol) at room temperature under nitrogen atmosphere. After stirred at room temperature overnight, the mixture was concentrated under reduced pressure to give a residue, which was dissolved in diethyl ether (20 mL). The above solution was washed with water (30 mL) twice, followed with saturated sodium bicarbonate aqueous solution (20 mL) twice, dried over $Na_2SO_{4(s)}$ and filtered. The filtrate was concentrated under reduced pressure to give the title compound (5.50 g, 99% yield) as yellow oil. $^1$H NMR (400 MHz, DMSO-$d_6$) δ 4.10 (q, J 9.6 Hz, 2H), 3.92 (s, 4H), 2.34-2.30 (m, 1H), 1.95-1.89 (m, 2H), 1.85-1.74 (m, 4H), 1.58-1.50 (m, 2H), 1.23 (t, J 9.6 Hz, 3H).

Acid 60: 1,4-Dioxaspiro[4.5]decane-8-carboxylic Acid

To a solution of ethyl 1,4-dioxaspiro[4.5]decane-8-carboxylate Intermediate 60a (5.60 g, 26.1 mmol) in tetrahydrofuran (56 mL), methanol (28 mL) and water (28 mL) was added lithium hydroxide monohydrate (3.29 g, 78.3 mmol). After stirred at room temperature overnight, the reaction mixture was concentrated at room temperature under reduced pressure. The obtained residue was acidified with 0.5 M hydrochloride aqueous solution to pH 3-4 and extracted with dichloromethane (200 mL) twice. The combined organic layers were washed with brine (100 mL), dried over $Na_2SO_{4(s)}$ and filtered. The filtrate was concentrated under reduced pressure to give the title compound (4.10 g, 84% yield) as yellow oil. $^1$H NMR (300 MHz, $CDCl_3$) δ 3.94 (s, 3.4H), 3.77-3.74 (m, 0.6H), 2.42-2.33 (m, 1H), 2.00-1.94 (m, 2H), 1.87-1.77 (m, 4H), 1.61-1.51 (m, 2H).

Acid 61: 4-(Azetidin-1-ylsulfonyl)cyclohexanecarboxylic Acid

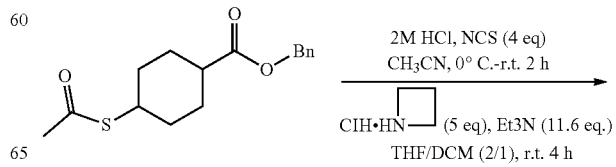

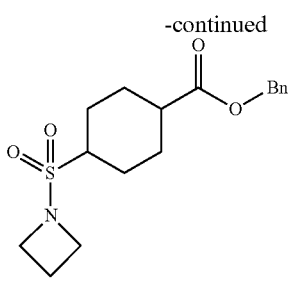

Acid 61a

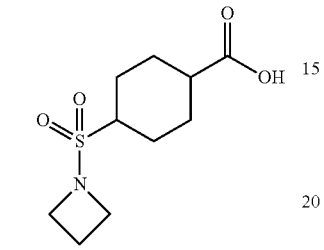

Acid 61

Intermediate 61a: Benzyl 4-(azetidin-1-ylsulfonyl)cyclohexanecarboxylate

To a solution of benzyl 4-(acetylthio)cyclohexanecarboxylate (300 mg, 1.03 mmol) in acetonitrile (10 mL) was added 2 M hydrochloride aqueous solution (0.2 mL) and 1-chloropyrrolidine-2,5-dione (550 mg, 4.12 mmol) at 0° C. under nitrogen atmosphere. After stirred at room temperature for 2 hours, the reaction mixture was concentrated under reduced pressure to give a residue. It was diluted in water (50 mL) and extracted with ether (30 mL) for three times. The combined organic layers were washed with brine (10 mL) twice, dried over $Na_2SO_{4(s)}$, filtered and concentrated under reduced pressure to give a residue. The residue was diluted in dry tetrahydrofuran (10 mL) and dichloromethane (5 mL), then azetidine hydrochloride (480 mg, 5.15 mmol) and triethylamine (1.21 g, 12.0 mmol) were added into the resulted solution and stirred at room temperature for 4 hours. The mixture was concentrated, quenched with water (50 mL) and acidified with 1 M hydrochlroide aqueous solution to pH~2, then extracted with ethyl acetate (50 mL) for three times. The combined organic layers were dried over $Na_2SO_{4(s)}$ and filtered. The filtrate was concentrated under reduced pressure to give the title compound (230 mg, 58% yield) as yellow oil. $^1$H NMR (400 MHz, $CDCl_3$) δ 7.38-7.32 (m, 5H), 5.16 (s, 1H), 5.11 (s, 1H), 3.99-3.90 (m, 4H), 2.81-2.78 (m, 1H), 2.31-2.20 (m, 5H), 2.04-1.99 (m, 1H), 1.73-1.55 (m, 5H).

Acid 61: 4-(Azetidin-1-ylsulfonyl)cyclohexanecarboxylic Acid

To a solution of benzyl 4-(azetidin-1-ylsulfonyl)cyclohexanecarboxylate Intermediate 61a (230 mg, 0.682 mmol) in methanol (5 mL) was added 10% wt. palladium on activated carbon (35 mg). After stirred at room temperature under hydrogen atmosphere overnight, the reaction mixture was filtered. The filtrate was concentrated under reduced pressure to give the title compound (160 mg, 95% yield) as white solids. $^1$H NMR (400 MHz, $CDCl_3$) δ 4.00-3.95 (m, 4H), 2.84-2.72 (m, 1H), 2.34-2.18 (m, 6H), 2.07-2.03 (m, 1H), 1.78-1.75 (m, 1H), 1.61-1.43 (m, 3H).

Acid 62: 3-((tert-Butoxycarbonyl)amino)-2,2-dimethylcyclobutanecarboxylic Acid

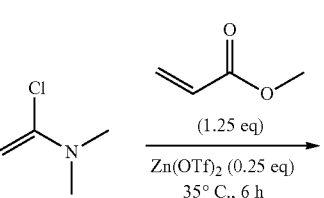

Intermediate 62a

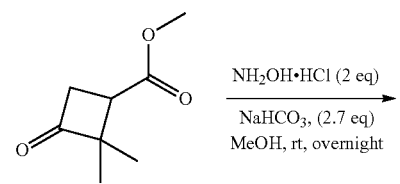

Intermediate 62b

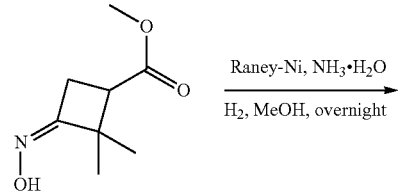

Intermediate 62c

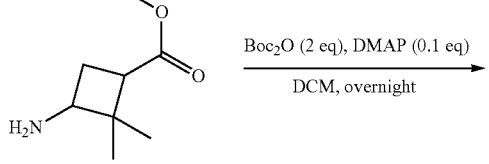

Intermediate 62d

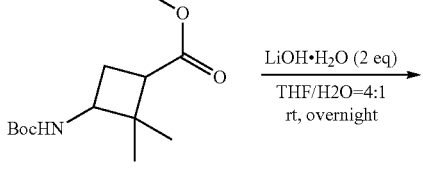

acid 62

Intermediate 62a: Methyl 2,2-dimethyl-3-oxocyclobutanecarboxylate

To a mixture of 1-chloro-N,N,2-trimethylprop-1-en-1-amine (45 mL, 0.340 mol) and methyl acrylate (384 mL, 0.425 mol) was added bis(((trifluoromethyl) sulfonyl)oxy) zinc (30.6 g, 0.084 mol) under $N_2$ atmosphere. After stirred at room temperature for 30 minutes, the mixture was stirred at 35° C. for another 6 hours, then quenched with water (400 mL) and extracted with dichloromethane (300 mL) for three times. The combined organic layers were washed with brine (100 mL), dried over Na$_2$SO$_{4(s)}$ and filtered. The filtrate was concentrated under reduced pressure to give the residue, which was purified by silica gel chromatography (petroleum:ethyl acetate=15:1 to 5:1) to give the title compound (24 g, 46% yield) as yellow oil. $^1$H NMR (300 MHz, CDCl$_3$) δ 3.76 (s, 3H), 3.59-3.51 (m, 1H), 3.15-3.06 (m, 1H), 2.99-2.93 (m, 1H), 1.32 (s, 3H), 1.12 (s, 3H).

Intermediate 62b: (Z)-3-(Hydroxyimino)-2,2-dimethylcyclobutanecarboxylic Acid

To a solution of methyl 2,2-dimethyl-3-oxocyclobutanecarboxylate Intermediate 62a (10.0 g, 64.1 mmol) in methanol (200 mL) was added hydroxylamine hydrochloride (8.80 g, 128.2 mmol) and sodium bicarbonate (14.7 g, 175 mmol) under N$_2$ atmosphere. After stirred at room temperature overnight, the mixture was filtered and concentrated under pressure to give the title compound (10.6 g, 97% yield) as colorless oil. $^1$H NMR (300 MHz, CDCl$_3$) δ 3.78 (s, 0.5H), 3.74 (s, 2.5H), 3.35-3.24 (m, 1H), 3.20-3.01 (m, 1H), 2.96-2.82 (m, 1H), 1.56-1.53 (m, 0.8H), 1.45-1.41 (m, 2.2H), 1.32-1.29 (m, 0.8H), 1.23-1.20 (m, 2.2H).

Intermediate 62c: Methyl 3-amino-2,2-dimethylcyclobutanecarboxylate

To a solution of (Z)-3-(hydroxyimino)-2,2-dimethylcyclobutanecarboxylic acid Intermediate 62b (8.60 g, 50.3 mmol) in methanol (100 mL) was added Raney-Ni (1.0 g) and ammonium hydroxide (3 mL) under nitrogen atmosphere. After stirred at room temperature under hydrogen atmosphere overnight, the mixture was filtered and concentrated to give the title compound (6.0 g, 77% yield) as colorless oil. $^1$H NMR (300 MHz, CDCl$_3$) δ 3.70 (s, 0.5H), 3.66 (s, 2.5H), 3.42-2.84 (m, 1H), 2.66-2.45 (m, 1.3H), 2.24 (br s, 0.7H), 1.90 (br s, 1H), 1.19 (s, 1.8H), 1.14 (s, 1.2H), 1.00 (s, 1H), 0.88 (s, 2H).

Intermediate 62d: Methyl 3-((tert-butoxycarbonyl)amino)-2,2-dimethylcyclobutanecarboxylate To a solution of methyl 3-amino-2,2-dimethylcyclobutanecarboxylate Intermediate 62c (6.00 g, 38.2 mmol) in dichloromethane (100 mL) was added di-tert-butyl dicarbonate (16.5 g, 76.4 mmol) and N,N-dimethylpyridin-4-amine (466 mg, 3.82 mmol) under N$_2$ atmosphere. After stirred at room temperature overnight, the mixture was concentrated to give a residue, which was washed with the mixed solvent (petroleum:ethyl acetate 10:1, 50 mL), then with petroleum (50 mL) twice to give the title compound (5.0 g, 51% yield) as white solids. $^1$H NMR (400 MHz, CDCl$_3$) δ 4.64 (br s, 1H), 3.88-3.78 (m, 1H), 3.67 (s, 3H), 2.59-2.53 (m, 1H), 2.37-2.27 (m, 1H), 2.08-1.97 (m, 1H), 1.43 (s, 9H), 1.28 (s, 3H), 0.89 (s, 3H).

Acid 62: 3-((tert-Butoxycarbonyl)amino)-2,2-dimethylcyclobutanecarboxylic acid

To a solution of methyl 3-((tert-butoxycarbonyl)amino)-2,2-dimethylcyclobutanecarboxylate Intermediate 62d (2.50 g, 9.70 mmol) in tetrahydrofuran (40 mL) was added a solution of lithium hydroxide monohydrate (817 mg, 19.4 mmol) in water (10 mL) at room temperature. After stirred at room temperature under nitrogen atmosphere overnight, the mixture was concentrated and diluted with ethyl acetate (50 mL), acidified with 2 M hydrochloride aqueous solution (5 mL) to pH~5. Then the resulting solids were collected by filtration, and washed with water (50 mL) and dried to give the title compound (2.20 g, 93% yield) as white solids. $^1$H NMR (400 MHz, DMSO-d$_6$) δ 11.96 (s, 1H), 6.97-6.94 (m, 1H), 3.65-3.56 (m, 1H), 2.45-2.42 (m, 1H), 2.08-1.99 (m, 2H), 1.38 (s, 9H), 1.16 (s, 3H), 0.82 (s, 3H).

Acid 63:4-(N-(3-methoxy-3-oxopropyl)sulfamoyl)cyclohexanecarboxylic Acid

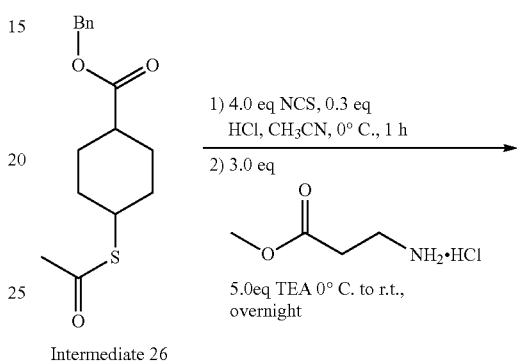

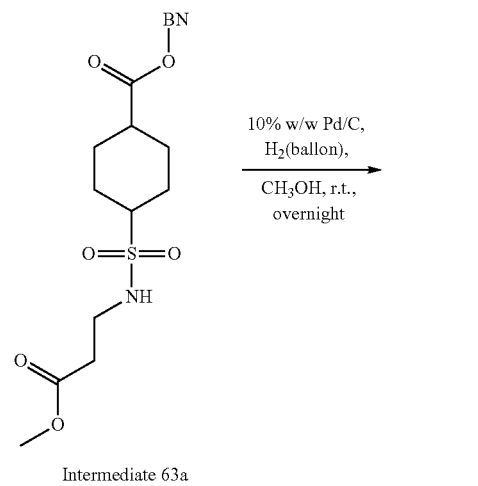

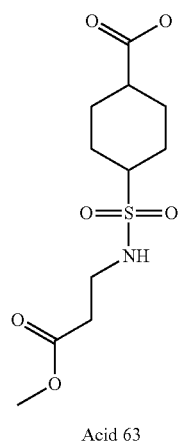

Intermediate 63a: benzyl 4-(N-(3-methoxy-3-oxopropyl)sulfamoyl)-cyclohexanecarboxylate To a solution of benzyl 4-(acetylthio)cyclohexanecarboxylate Intermediate 26 (3.00 g, 10.3 mmol) in acetonitrile (45 mL) was added 2 M hydrochloride aqueous solution (1.5 mL, 3.00 mmol) at 0° C. Then 1-chloropyrrolidine-2,5-dione (5.35 g, 40.1 mmol) was added. After stirred at 0° C. under nitrogen atmosphere for 1 hour, the mixture was diluted in ether (100 mL), washed with water (30 mL), brine (30 mL), dried over $Na_2SO_{4(s)}$, filtered and concentrated to give a residue A. To a solution of methyl 3-aminopropanoate hydrochloride in dichloromethane (40 mL) was added triethylamine (5.19 g, 51.4 mmol) and residue A (dissolved in 20 mL dichloromethane) at 0° C. The mixture was stirred under nitrogen atmosphere overnight. The mixture was added dichloromethane (200 mL) and washed with water (50 mL), 0.5 M hydrochloride aqueous solution (50 mL), brine (50 mL), dried over $Na_2SO_{4(s)}$, filtered and concentrated to give a residue which was purified by silica gel column chromatography (petroleum ether:ethyl acetate=5:1 to 3:1) to afford the title compound (2.40 g, 57% yield) as yellow oil. LC-MS (ESI): $R_T$=1.60 min, mass calcd. for $C_{18}H_{25}NO_6S$ 383.1, m/z found 384.4 [M+H]$^+$. $^1$H NMR (400 MHz, CDCl$_3$) δ 7.39-7.27 (m, 5H), 5.15 (s, 1H), 5.12 (s, 1H), 4.84-4.81 (m, 0.5H), 4.77-4.74 (m, 0.5H), 3.71 (s, 3H), 3.39-3.31 (m, 2H), 2.94-2.84 (m, 1H), 2.64-2.58 (m, 2H), 2.39-2.02 (m, 4H), 1.79-1.69 (m, 1H), 1.63-1.44 (m, 3H).

Acid 63: 4-(N-(3-methoxy-3-oxopropyl)sulfamoyl) cyclohexanecarboxylic Acid

To a solution of benzyl 4-(N-(3-methoxy-3-oxopropyl) sulfamoyl)-cyclohexanecarboxylate Intermediate 63a (2.40 g, 6.26 mmol) in methanol (25 mL) was added 10% palladium on charcoal wt. (400 mg). The reaction mixture was stirred at room temperature under hydrogen atmosphere (ballon) overnight. The completed reaction mixture was filtered and the cake was washed with methanol (20 mL). The filtrate was concentrated to give the title compound acid 63 (1.60 g, 87% yield) as light white solids. $^1$H NMR (300 MHz, DMSO-d$_6$) δ 7.10 (s, 1H), 3.60 (s, 3H), 3.21-3.12 (m, 4H), 3.05-2.89 (m, 1H), 2.59-2.52 (m, 1H), 2.18-1.84 (m, 4H), 1.59-1.33 (m, 4H).

Part II: Preparation of Aryl Aldehydes (P1)

Aldehyde 1, Al1: 2-chloro-4-fluoro-benzaldehyde
Aldehyde 2, Al2: 2-chloro-3-fluoro-benzaldehyde
Aldehyde 3, Al3: 4-chloro-2-fluorobenzaldehyde
Aldehyde 4, Al4: 2-bromo-4-fluorobenzaldehyde
Aldehyde 5, Al5: 4-chloro-3-fluorobenzaldehyde
Aldehyde 6, Al6: 2-chloro-3,4-difluorobenzaldehyde
Aldehyde 7, Al7: 2-chlorobenzaldehyde
Aldehyde 8, Al8: 2-bromobenzaldehyde
Aldehyde 9, Al9: 2-bromo-3-fluorobenzaldehyde
Aldehyde 10, Al10: 3,4-difluoro-2-methylbenzaldehyde
Aldehyde 11, Al11: 2-Bromo-3,4-difluoro-benzaldehyde
Aldehyde 12, Al12: 2-methyl-4-difluoro-benzaldehyde
Aldehyde 13: Al13: 2-methyl-3-difluoro-benzaldehyde

Intermediate B1: 2-Chloro-3,4-difluorobenzoic acid

A solution of $N^1,N^1,N^2,N^2$-tetramethylethane-1,2-diamine (3.7 g, 69.6 mmol) in tetrahydrofuran (45 mL) was cooled to −70° C. under nitrogen atmosphere before dropwise addition of 1.3 M sec-butyllithium in hexane (60 mL, 75.9 mmol) followed by a solution of 3,4-difluorobenzoic acid (5.0 g, 31.6 mmol) in tetrahydrofuran (20 mL) over 10 minutes. The resulting mixture was stirred at −70° C. for 1 hour and then a solution of 1,1,1,2,2,2-hexachloroethane (26 g, 110.8 mmol) in THF (45 mL) was added dropwise. Stirring continued at −70° C. for 2 hours. The mixture was warmed to −10° C., quenched with water (125 mL), added diethyl ether (60 mL) and then separated two phases. The aqueous layer was acidified to pH 1 by using concentrated hydrochloride aqueous solution and extracted with diethyl ether (125 mL) twice. The combined organic extracts were concentrated in vacuo to give yellow solids, which was recrystallized with ethyl acetate (30 mL) to afford the title compound (2.7 g, 45% yield) as yellow solids. $^1$H NMR (400 MHz, DMSO-d$_6$) δ 13.69 (br s, 1H), 7.75-7.71 (m, 1H), 7.55-7.48 (m, 1H).

Intermediate B2: 2-Chloro-3,4-difluoro-N-methoxy-N-methyl-benzamide

To a solution of 2-chloro-3,4-difluorobenzoic acid Intermediate B1 (1.0 g, 5.2 mmol) in N, N-dimethylformamide (10 mL) were added 1-hydroxybenzotriazole (1.1 g, 7.8 mmol), N,N-diisopropylethylamine (4.6 mL, 26 mmol) and N-(3-Dimethylamino-propyl)-N'-ethylcarbodiimide hydrochloride (1.5 g, 7.8 mmol) under nitrogen atmosphere at room temperature. The resulting mixture was stirred at room temperature for 10 minutes. 0, N-dimethyl-hydroxylamine hydrochloride (0.5 g, 5.2 mmol) was added and stirring continued at room temperature overnight. After quenched with water (20 mL), the mixture was extracted with ethyl acetate (20 mL) for three times. The combined organic layers were washed with water (20 mL), brine (20 mL), dried over $Na_2SO_{4(s)}$, filtered and concentrated to leave a residue, which was purified by silica gel column chromatography (petroleum ether:ethyl acetate=4:1 to 2:1) to give the title compound (1.06 g, 87% yield) as yellow solids. $^1$H NMR (400 MHz, DMSO-d$_6$) δ 7.60-7.53 (m, 1H), 7.42-7.38 (m, 1H), 3.80-3.45 (m, 3H), 3.39-3.06 (m, 3H).

Aldehyde 6: 2-Chloro-3,4-difluorobenzaldehyde

To a solution of 2-chloro-3,4-difluoro-N-methoxy-N-methyl-benzamide Intermediate B2 (500 mg, 2.13 mmol) in tetrahydrofuran (8 mL) was added 1 M diisobutyl-aluminium hydride in toluene (2.8 mL, 2.8 mmol) dropwise at −78° C. under nitrogen atmosphere. After the addition, the mixture was stirred at −78° C. for 1 hour. It was then quenched with water (15 mL) and extracted with ethyl acetate (25 mL) for three times. The combined organic layers were washed with 1 M hydrochloric acid aqueous solution (10 mL), dried over $Na_2SO_{4(s)}$, filtered and evaporated under reduced pressure to leave a yellow residue, which was purified by silica gel column chromatography (petroleum ether:ethyl acetate=20:1) to give the title compound (200 mg, 53% yield) as yellow solids. $^1$H NMR (400 MHz, DMSO-d$_6$) δ 10.23 (s, 1H), 7.80-7.76 (m, 1H), 7.69-7.62 (m, 1H).

Intermediate B3: 2-Bromo-3,4-difluoro-N-methoxy-N-methyl-benzamide

To a solution of 2-bromo-3,4-difluoro-benzoic acid (2.50 g, 10.6 mmol) in N,N-dimethylformamide (25 mL) was added 1-hydroxybenzotriazole (2.15 g, 15.9 mmol), N,N-diisopropylethylamine (6.84 g, 53.0 mmol) and N-ethyl-N'-

(3-dimethylaminopropyl)carbodiimide hydrochloride (3.05 g, 15.9 mmol) under nitrogen atmosphere at room temperature. The mixture was stirred for 10 minutes and N,O-dimethylhydroxylamine hydrochloride (1.04 g, 10.6 mmol) was added. After stirred at room temperature overnight, the mixture was poured into water (80 mL) and extracted with ethyl acetate (75 mL) twice. The separated organic layers were washed with water (100 mL) twice, brine (50 mL) twice, dried over $Na_2SO_{4(s)}$, filtered, concentrated and purified by silica gel column chromatography (petroleum ether: ethyl acetate=10:1 to 5:1) to give the title compound (1.9 g, 66% yield) as yellow solids. $^1$H NMR (300 MHz, $CDCl_3$) δ 7.26-7.17 (m, 1H), 7.14-7.09 (m, 1H), 3.93-3.16 (m, 6H).

Aldehyde 12: 2-Bromo-3,4-difluoro-benzaldehyde

To a solution of 2-bromo-3,4-difluoro-N-methoxy-N-methyl-benzamide intermediate B3 (1.90 g, 6.81 mmol) in tetrahydrofuran (30 mL) was added 1.5 M diisobutylaluminum hydride in toluene (5.90 mL, 8.85 mmol) at −78° C. dropwise under nitrogen atmosphere. After stirred at −78° C. for 1 hour, the mixture was quenched with water (40 mL), extracted with ethyl acetate (75 mL) three times. The separated organic layers were washed with 2 M hydrochloride aqueous solution (30 mL), water (40 mL), brine (20 mL) twice, dried over $Na_2SO_{4(s)}$ and filtered. The filtrate was concentrated under reduced pressure to give a residue, which was purified by silica gel column chromatography (petroleum ether:ethyl acetate=10:1 to 5:1) to give the title compound (1.0 g, 67% yield) as yellow solids. $^1$H NMR (300 MHz, DMSO-$d_6$) δ 10.12 (s, 1H), 7.81-7.65 (m, 2H).

Part III: Preparation of Carboxamidines (P2)

Carboxamidine 1, Ca1: thiazole-2-carboxamidine hydrochloride
Carboxamidine 2, Ca2: 2,4,6-Trifluorobenzimidamide To a solution of 2,4,6-trifluorobenzonitrile (2.00 g, 12.7 mmol) in toluene (50 mL) was added 2 M trimethylaluminum in toluene (7.00 mL, 14.0 mmol) and ammonium chloride (0.76 g, 14.0 mmol) at room temperature. After stirred at 120° C. overnight, the mixture was allowed to cool down to room temperature and filtered. The filtrate was concentrated under reduced pressure to leave a residue, which was dissolved in a mixed solvent of methanol/dichloromethane (10/1, 50 mL). The obtained mixture was added silica gel (100-200 mesh, 3 g) and stirred for another 1 hour at room temperature. Then it was filtered and the filtrate was concentrated under reduced pressure to give a residue, which was purified by re-crystallization from petroleum ether/ethyl acetate (5/1, 20 mL) to give the title compound (1.00 g, 45% yield) as white solids. LC-MS (ESI): $R_T$=0.88 min, mass calcd. for $C_7H_5F_3N_2$ 174.0, m/z found 175.0 [M+H]$^+$. $^1$H NMR (300 MHz, DMSO-$d_6$) δ 9.04 (br s, 3H), 7.55 (t, J=9.6 Hz, 2H).

Carboxamidine 3, Ca3:3,5-Difluoropicolinimidamide Hydrochloride

To a stirred suspension of ammonium chloride (1.89 g, 35.7 mmol) in toluene (100 mL) was added 2M trimethylaluminum in toluene (21 mL, 42.8 mmol) dropwise at 0° C. under nitrogen atmosphere. The resulting mixture was then brought up to room temperature and stirring continued for 30 minutes. A solution of 3,5-difluoropicolinonitrile (5.00 g, 35.7 mmol) in toluene (50 mL) was added and the reaction mixture was subsequently stirred at 80° C. overnight. After cooled down to room temperature, the mixture was poured into slurry of silica gel in dichloromethane (50 mL). After stirring for 10 minutes, the slurry was filtered and washed with methanol. The filtrate was concentrated in vacuum to give the title compound (1.90 g, 34% yield) as white solids. LC-MS (ESI): $R_T$=0.357 min, mass calcd. for $C_6H_6ClF_2N_3$ 193.0, m/z found 157.9 [M+H—HCl]$^+$. $^1$H NMR (400 MHz, DMSO-$d_6$) δ 9.77 (br s, 2H), 9.60 (br s, 2H), 8.79 (d, J=1.6 Hz, 1H), 8.41-8.35 (m, 1H).

Carboxamidine 4, Ca4:
4-Methylthiazole-2-carboximidamide Hydrochloride

To a solution of 4-methylthiazole-2-carbonitrile (3.90 g, 31.5 mmol) in methanol (30 mL) was added 1 M sodium methoxide aqueous solution (44 mL, 44.0 mmol). After stirring at room temperature for 30 minutes, the mixture was added ammonium chloride (2.50 g, 47.2 mmol) and stirring continued at room temperature for 48 hours. Then the reaction mixture was filtered and washed with methanol (50 mL). The filtrate was concentrated to give a residue, which was purified by silica gel column chromatography (dichloromethane:methanol=5:1) to afford the crude product, which was further purified by C18 column (acetonitrile:water=2% to 40%) to give the title compound (3.00 g, 54% yield) as white solids. LC-MS (ESI): $R_T$=0.409 min, mass calcd. for $C_8H_8ClN_3S$ 177.0 m/z found 142.0 [M+H−HCl]+. $^1$H NMR (300 MHz, $CD_3OD$) δ 7.78 (d, J=0.9 Hz, 1H), 2.57 (s, 3H).

Part IV: Preparation of Sulfonyl Chloride

Sulfonyl chloride 1:2-(trimethylsilyl)ethyl 4-(chlorosulfonyl)-1-methylcyclohexane-1-carboxylate

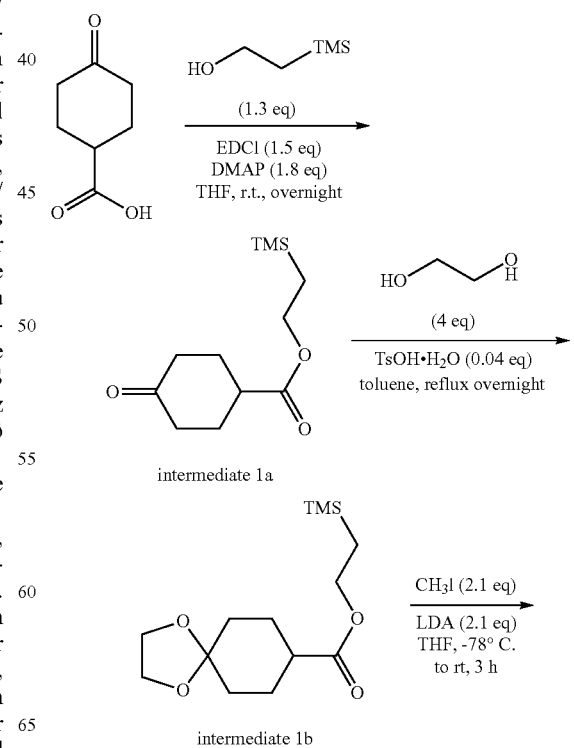

intermediate 1a intermediate 1b

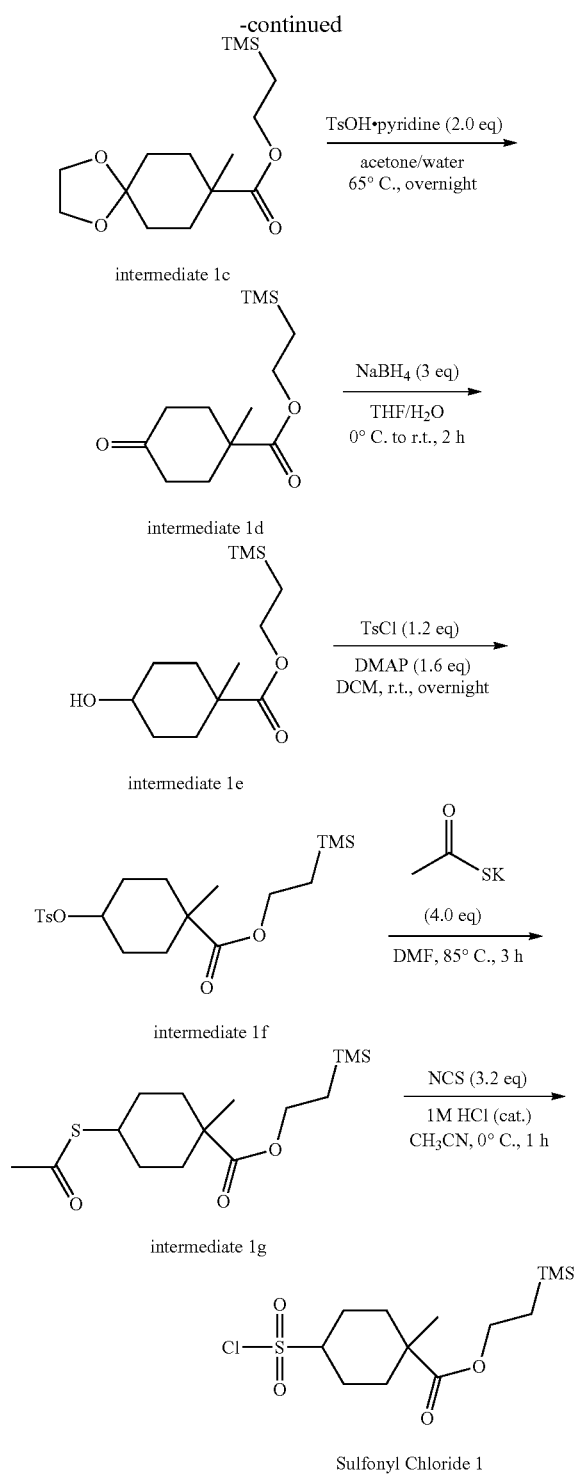

Intermediate 1a: 2-(Trimethylsilyl)ethyl 4-oxocyclohexanecarboxylate

To a solution of (10.0 g, 70.3 mmol) in tetrahydrofuran (250 mL) were added 2-(trimethylsilyl)ethanol (11.0 g, 93.0 mmol), N1-((ethylimino)methylene)-N3,N3-dimethylpropane-1,3-diamine hydrochloride (20.0 g, 104 mmol) and N,N-dimethylpyridin-4-amine (15.5 g, 127 mmol) at room temperature. After stirred overnight, the mixture was concentrated to give a residue, which was diluted with water (50 mL), extracted by ethyl acetate (150 mL) twice. The combined organic layers were washed by 2 M hydrochloride aqueous solution (150 mL), brine (150 mL), dried over $Na_2SO_{4(s)}$, filtered and concentrated to afford the desired product (14.1 g, 90% purity, 74% yield) as light yellow oil. $^1$H NMR (300 MHz, CDCl$_3$) δ 4.25-4.19 (m, 2H), 2.79-2.68 (m, 1H), 2.56-2.45 (m, 2H), 2.41-2.31 (m, 2H), 2.27-2.17 (m, 2H), 2.08-1.97 (m, 2H), 1.05-0.98 (m, 2H), 0.07 (s, 9H).

Intermediate 1b: 2-(Trimethylsilyl)ethyl 1,4-dioxaspiro[4.5]decane-8-carboxylate To a solution of 2-(trimethylsilyl)ethyl 4-oxocyclohexanecarboxylate 1a (14.1 g, 90% purity, 52.4 mmol) in toluene (180 mL) was added ethane-1,2-diol (13.0 g, 209 mmol) and p-toluenesulfonic acid monohydrate (390 mg, 2.05 mmol) at room temperature, then it was refluxed with azeotropic removal overnight. The mixture was cooled to room temperature, diluted with ethyl acetate (200 mL), washed by water (200 mL) twice, brine (200 mL), dried over $Na_2SO_{4(s)}$, filtered and concentrated to afford the desired product (11 g, 90% purity, 66% yield) as light yellow oil. $^1$H NMR (300 MHz, CDCl$_3$) δ 4.21-4.12 (m, 2H), 3.95 (s, 4H), 2.37-2.26 (m, 1H), 2.00-1.90 (m, 2H), 1.86-1.72 (m, 4H), 1.63-1.48 (m, 2H), 1.02-0.94 (m, 2H), 0.53 (s, 9H).

Intermediate 1c: 2-(Trimethylsilyl)ethyl 8-methyl-1,4-dioxaspiro[4.5]decane-8-carboxylate To a solution of 2-(trimethylsilyl)ethyl 1,4-dioxaspiro[4.5]decane-8-carboxylate 1b (4.0 g, 90% purity, 12.6 mmol) in tetrahydrofuran (60 mL) was added 2 M lithium diisopropylamide in tetrahydrofuran (13 mL, 26.0 mmol) at −78° C. After stirring at −78° C. for 2 hours, iodomethane (3.8 g, 26.8 mmol) was added. Then the mixture was warmed to room temperature and stirred for 1 hour. The mixture was poured into water (60 mL), extracted by ethyl acetate (60 mL) twice. The combined organic layers were washed by brine (60 mL), drived over $Na_2SO_{4(s)}$, filtered and concentrated. The residue was purified by silica gel column chromatography (petroleum ether:ethyl acetate=20:1) to give the desired product (3.1 g, 90% purity, 74% yield) as light yellow oil. $^1$H NMR (300 MHz, CDCl$_3$) δ 4.20-4.17 (m, 2H), 3.94 (s, 4H), 2.19-2.08 (m, 2H), 1.68-1.64 (m, 4H), 1.57-1.44 (m, 2H), 1.19 (s, 3H), 1.02-0.97 (m, 2H), 0.05 (s, 9H).

Intermediate 1d: 2-(Trimethylsilyl)ethyl 1-methyl-4-oxocyclohexanecarboxylate

To a solution of 2-(trimethylsilyl)ethyl 8-methyl-1,4-dioxaspiro[4.5]decane-8-carboxylate 1c (4.20 g, 90% purity, 12.6 mmol) in acetone (50 mL) and water (50 mL) was added pyridinium p-toluenesulfonate (6.30 g, 25.1 mmol), then the reaction was heated at 65° C. overnight. The mixture was added water (80 mL), extracted by ethyl acetate (80 mL) twice. The combined organic layers were washed by 2 M hydrochloride aqueous solution (60 mL), saturated sodium carbonate aqueous solution (40 mL), brine (60 mL), dried over $Na_2SO_{4(s)}$, filtered and concentrated to afford the desired product (3.5 g, 90% purity, 98% yield) as colorless oil. $^1$H NMR (300 MHz, CDCl$_3$) δ 4.28-4.22 (m, 2H), 2.52-2.27 (m, 6H), 1.75-1.62 (m, 2H), 1.30 (s, 3H), 1.06-1.00 (m, 2H), 0.06 (s, 9H).

Intermediate 1e: 2-(Trimethylsilyl)ethyl 4-hydroxy-1-methylcyclohexane-carboxylate To a solution of 2-(trimethylsilyl)ethyl 1-methyl-4-oxo-cyclohexanecarboxylate 1d (2.50 g, 90% purity, 8.78 mmol) in tetrahydrofuran (30 mL) and water (3 mL) was added sodium borohydride (0.996 g, 26.3 mmol) at 0° C. After stirred at room temperature for 2 hours, the reaction was concentrated to give a residue, which was added water (50 mL) and extracted by ethyl acetate (50 mL) twice. The combined organic layers were washed by 1 M hydrochloride aqueous solution (50 mL) and brine (50 mL), dried over $Na_2SO_{4(s)}$, filtered and concentrated to afford the desired product (2.30 g, 90% purity, 91% yield) as light yellow oil. $^1H$ NMR (300 MHz, $CDCl_3$) δ 4.22-4.16 (m, 2H), 3.87-3.80 (m, 0.3H), 3.65-3.56 (m, 0.7H), 2.27-2.19 (m, 2H), 1.92-1.80 (m, 2H), 1.75-1.45 (m, 2H), 1.45-1.21 (m, 2H), 1.15 (s, 3H), 1.05-0.98 (m, 2H), 0.06 (s, 9H).

Intermediate 1f: 2-(Trimethylsilyl)ethyl 1-methyl-4-(tosyloxy)cyclohexanecarboxylate To a solution of 2-(trimethylsilyl)ethyl 4-hydroxy-1-methylcyclohexanecarboxylate 1e (2.30 g, 90% purity, 8.01 mmol) in dichloromethane (30 mL) were added 4-methyl-benzene-1-sulfonyl chloride (1.83 g, 9.60 mmol), N,N-dimethylpyridin-4-amine (1.52 g, 12.4 mmol) at room temperature. After stirred overnight, the mixture was diluted with dichloromethane (80 mL), washed by water (50 mL), 2 M hydrochloride aqueous solution (50 mL), brine (50 mL), dried over $Na_2SO_{4(s)}$, filtered and concentrated. The residue was purified by silica gel column chromatography (petroleum ether:ethyl acetate=20:1) to give the desired product (3.20 g, 90% purity, 87% yield) as light yellow oil. $^1H$ NMR (300 MHz, $CDCl_3$) δ 7.79 (d, J=8.1 Hz, 2H), 7.34 (d, J=8.1 Hz, 2H), 4.67-4.61 (m, 0.2H), 4.50-4.38 (m, 0.8H), 4.19-4.14 (m, 2H), 2.46 (s, 3H), 2.24-2.19 (m, 2H), 1.94-1.73 (m, 2H), 1.65-1.51 (m, 2H), 1.25-1.12 (m, 2H), 1.12 (s, 3H), 1.01-0.95 (m, 2H), 0.06 (s, 9H).

Intermediate 1g: 2-(Trimethylsilyl)ethyl 4-(acetylthio)-1-methylcyclohexanecarboxylate To a solution of 2-(trimethylsilyl)ethyl 1-methyl-4-(tosyloxy)cyclohexanecarboxylate 1f (3.20 g, 90% purity, 6.98 mmol) in N,N-dimethylformamide (20 mL) was added potassium ethanethioate (3.20 g, 28.0 mmol) at room temperature, then the reaction was heated at 85° C. for 3 hours. After cooled to room temperature, the mixture was poured to water (100 mL), extracted by ethyl acetate (60 mL) twice. The combined extracts were washed by water (100 mL), brine (50 mL), dried over $Na_2SO_{4(s)}$, filtered and concentrated to give the desired product (2.40 g, 90% purity, 98% yield) as brown oil. $^1H$ NMR (300 MHz, $CDCl_3$) δ 4.23-4.16 (m, 2H), 3.61-3.48 (m, 1H), 2.19 (s, 3H), 2.15-2.01 (m, 4H), 1.96-1.83 (m, 4H), 1.27 (s, 3H), 1.04-0.97 (m, 2H), 0.07 (s, 9H).

Sulfonyl chloride 1: 2-(Trimethylsilyl)ethyl 4-(chlorosulfonyl)-1-methylcyclohexanecarboxylate To a solution of 2-(trimethylsilyl)ethyl 4-(acetylthio)-1-methylcyclohexanecarboxylate 1g (1.30 g, 90% purity, 3.70 mmol) in acetonitrile (15 mL) were added 1 M hydrochloride aqueous solution (0.5 mL) and 1-chloropyrrolidine-2,5-dione (1.60 g, 12.0 mmol) at 0° C. After stirred at 0° C. for 1 hour, the mixture was diluted with ethyl acetate (100 mL), washed by brine (50 mL), dried over $Na_2SO_{4(s)}$, filtered and concentrated. The residue was purified by silica gel column chromatography (petroleum ether:ethyl acetate=10:1) to give the desired product (800 mg, 90% purity, 57% yield) as light brown oil. $^1H$ NMR (300 MHz, $CDCl_3$) δ 4.28-4.08 (m, 2H), 3.96-3.80 (m, 0.3H), 3.63-3.47 (m, 0.7H), 2.53-2.24 (m, 3H), 2.14-2.06 (m, 2H), 2.01-1.78 (m, 3H), 1.28-1.24 (m, 3H), 1.03-0.96 (m, 2H), 0.07 (s, 9H).

Sulfonyl Chloride 2: tert-butyl 3-(chlorosulfonyl)-2,2-dimethylpropanoate

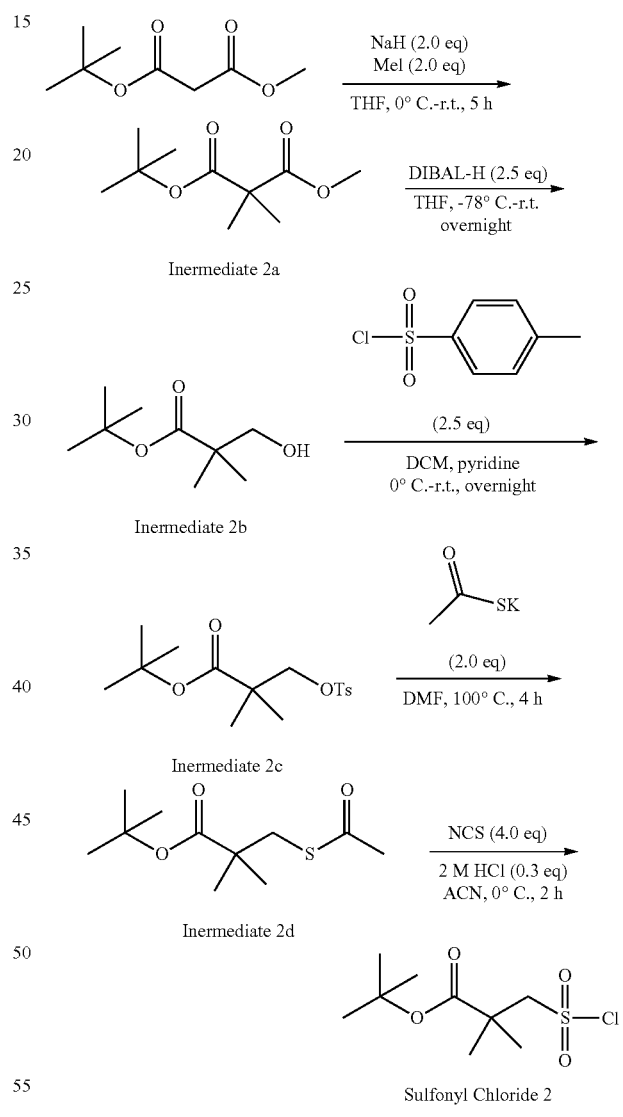

Intermediate 2a: 1-tert-Butyl 3-methyl 2,2-dimethylmalonate

To a suspension of 60% wt. sodium hydride in mineral oil (1.56 g, 39.0 mmol) in tetrahydrofuran (40 mL) was added tert-butyl methyl malonate (3.50 g, 20.0 mmol) dropwise at 0° C. After stirring at this temperature for 30 minutes, iodomethane (5.54 g, 39.0 mmol) was added dropwise and it was continued to stir at room temperature for another 5 hours. Then the mixture was quenched with water (30 mL) and extracted with ethyl acetate (50 mL) twice. The combined organic layers were washed with brine (50 mL), dried over $Na_2SO_{4(s)}$ and filtered. The filtrate was concentrated under reduced pressure to give the title compound (3.80 g, 94% yield) as brown oil. $^1H$ NMR (300 MHz, $CDCl_3$) δ 3.72 (s, 3H), 1.44 (s, 9H), 1.40 (s, 6H).

Intermediate 2b: tert-Butyl 3-hydroxy-2,2-dimethylpropanoate

To a solution of 1-tert-butyl 3-methyl 2,2-dimethylmalonate 2a (5.00 g, 24.7 mmol) in tetrahydrofuran (30 mL) was added 1.5 M diisobutylaluminum hydride in toluene (41.3 mL, 61.9 mmol) dropwise at −78° C. under nitrogen atmosphere. After stirred at this temperature under nitrogen atmosphere for 2 hours and then at room temperature overnight, the mixture was quenched with water (50 mL) and extracted with ethyl acetate (100 mL) for three times. The combined organic layers were washed with water (200 mL) for three times and brine (100 mL), dried over $Na_2SO_{4(s)}$ and filtered. The filtrate was concentrated under reduced pressure to give the title compound (2.00 g, 47% yield) as white oil. $^1H$ NMR (300 MHz, $CDCl_3$) δ 3.52 (d, J=5.4 Hz, 2H), 2.58 (br s, 1H), 1.47 (s, 9H), 1.16 (s, 6H).

Intermediate 2c: tert-Butyl 2,2-dimethyl-3-(tosyloxy)propanoate

To a solution of tert-butyl 3-hydroxy-2,2-dimethylpropanoate 2b (2.00 g, 11.5 mmol) in pyridine (8 mL) and dichloromethane (20 mL) was added tosyl chloride (5.49 g, 28.7 mmol) at 0° C. After stirred at room temperature under nitrogen atmosphere overnight, the mixture was concentrated and dissolved in ethyl acetate (40 mL) and water (40 mL), then added 0.5 M hydrochloride aqueous solution (24 mL) and separated. The aqueous layer was extracted with ethyl acetate (40 mL) twice. The combined organic layers were washed with 0.5 M hydrochloride aqueous solution (20 mL) and brine (20 mL), dried over $Na_2SO_{4(s)}$ and filtered. The filtrate was concentrated and purified by silica gel column chromatography (petroleum ether:ethyl acetate=10:1) to give the title compound (1.80 g, 48% yield) as white solids. $^1H$ NMR (300 MHz, $CDCl_3$) δ 7.79 (d, J=8.1 Hz, 2H), 7.35 (d, J=8.1 Hz, 2H), 3.98 (s, 2H), 2.46 (s, 3H), 1.40 (s, 9H), 1.14 (s, 6H).

Intermediate 2d: tert-Butyl 3-(acetylthio)-2,2-dimethylpropanoate

To a solution of tert-butyl 2,2-dimethyl-3-(tosyloxy)propanoate 2c (1.80 g, 5.49 mmol) in N,N-dimethylformamide (30 mL) was added potassium thioacetate (1.25 g, 11.0 mmol) at room temperature. After stirred at 100° C. under nitrogen atmosphere for 4 hours, the reaction mixture was cooled down to room temperature, taken up into water (100 mL), and extracted with ethyl acetate (100 mL) for three times. The combined organic layers were washed with brine (80 mL), dried over $Na_2SO_{4(s)}$ and filtered. The filtrate was concentrated under reduced pressure to give the title compound (1.2 g, 96% yield) as yellow oil. $^1H$ NMR (300 MHz, $CDCl_3$) δ 3.11 (s, 2H), 2.33 (s, 3H), 1.43 (s, 9H), 1.18 (s, 6H).

Sulfonyl Chloride 2: tert-Butyl 3-(chlorosulfonyl)-2,2-dimethylpropanoate

To a solution of tert-butyl 3-(acetylthio)-2,2-dimethylpropanoate EO8495_522.5 (1.20 g, 5.57 mmol) in acetonitrile (28 mL) was added 2 M hydrochloride aqueous solution (1 mL) and 1-chloropyrrolidine-2,5-dione (2.97 g, 22.3 mmol) at 0° C. After stirred at this temperature under nitrogen atmosphere for 2 hours, the mixture was quenched with water (30 mL) and extracted with ethyl acetate (80 mL) for three times. The combined organic layers were washed with brine (50 mL), dried over $Na_2SO_{4(s)}$ and filtered. The filtrate was concentrated and purified by silica gel column chromatography (petroleum ether:ethyl acetate=40:1) to give the title compound (250 mg, 18% yield) as white oil. $^1H$ NMR (300 MHz, $CDCl_3$) δ 4.14 (s, 2H), 1.48 (s, 9H), 1.43 (s, 6H).

Sulfonyl Chloride 3: tert-Butyl 3-(chlorosulfonyl)azetidine-1-carboxylate

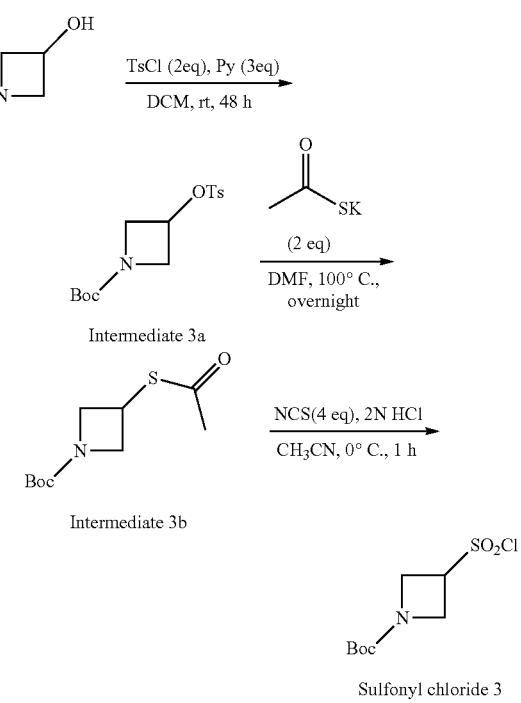

Sulfonyl chloride 3

Intermediate 3a: tert-Butyl 3-(tosyloxy)azetidine-1-carboxylate

To a solution of tert-butyl 3-hydroxyazetidine-1-carboxylate EO8495_681.1 (2.00 g, 11.5 mmol) and pyridine (2.73 g, 34.5 mmol) in dry dichloromethane (20 mL) was added a solution of tosyl chloride (4.41 g, 23.1 mmol) in dry dichloromethane (10 mL) at 0° C. under nitrogen atmosphere. The mixture was stirred at 0° C. for 30 minutes and then at room temperature for 48 hours. It was concentrated under reduced pressure to leave a residue, which was purified by silica gel column chromatography (petroleum ether:ethyl acetate=8:1) to give the title compound (3.75 g, 99% yield) as colorless oil. LC-MS (ESI): $R_T$=2.364 min, mass calcd. for $C_{15}H_{21}NO_5S$ 327.1, m/z found 349.9 $[M+Na]^+$. $^1H$ NMR (300 MHz, $CDCl_3$) δ 7.79 (d, J=8.1 Hz, 2H), 7.38 (d, J=8.1 Hz, 2H), 5.06-4.96 (m, 1H), 4.14-4.08 (m, 2H), 3.95-3.92 (m, 2H), 2.47 (s, 3H), 1.42 (s, 9H).

Intermediate 3b: tert-Butyl 3-(acetylthio)azetidine-1-carboxylate

To a solution of tert-butyl 3-(tosyloxy)azetidine-1-carboxylate EO8495_681.2 (3.25 g, 9.93 mmol) in N,N-dimethylformamide (30 mL) was added potassium thioacetate (2.27 g, 19.9 mmol). After stirred at 100° C. overnight, the mixture was cooled down to room temperature, poured into water (90 mL) and extracted with ethyl acetate (20 mL) for three times. The combined organic layers were washed with water (30 mL) for three times, dried over Na$_2$SO$_{4(s)}$ and filtered. The filtrate was concentrated to give the title compound (2.24 g, 97% yield) as brown oil. LC-MS (ESI): R$_T$=1.703 min, mass calcd. for C$_{10}$H$_{17}$NO$_3$S 231.1, m/z found 176.0 [M+H−56]$^+$. $^1$H NMR (300 MHz, CDCl$_3$) δ 4.41-4.37 (m, 2H), 4.22-4.12 (m, 1H), 3.93-3.77 (m, 2H), 2.35 (s, 3H), 1.45 (s, 9H).

Sulfonyl Chloride 3: tert-Butyl 3-(chlorosulfonyl)azetidine-1-carboxylate

To a solution of tert-butyl 3-(acetylthio)azetidine-1-carboxylate EO8495_681.3 (2.24 g, 9.69 mmol) in acetonitrile (20 mL) was added 2 M hydrochloride aqueous solution (0.8 mL) and N-chlorosuccinimide (5.17 g, 38.7 mmol) at 0° C. After stirred at 0° C. for 1 hour, the mixture was quenched with water (60 mL) and extracted with ethyl ether (30 mL) for three times. The combined organic layers were dried over Na$_2$SO$_{4(s)}$ and filtered. The filtrate was concentrated and purified by silica gel column chromatography (petroleum ether:ethyl acetate=8:1) to give the title compound (910 mg, 37% yield) as yellow solids. LC-MS (ESI): R$_T$=1.895 min, mass calcd. for C$_8$H$_{14}$ClNO$_4$S 255.0, m/z found 199.9 [M+H−56]$^+$. $^1$H NMR (300 MHz, CDCl$_3$) δ 4.59-4.47 (m, 1H), 4.43-4.31 (m, 4H), 1.47 (s, 9H).

Sulfonyl Chloride 4:1-Cyclopropyl-1H-pyrazole-4-sulfonyl Chloride

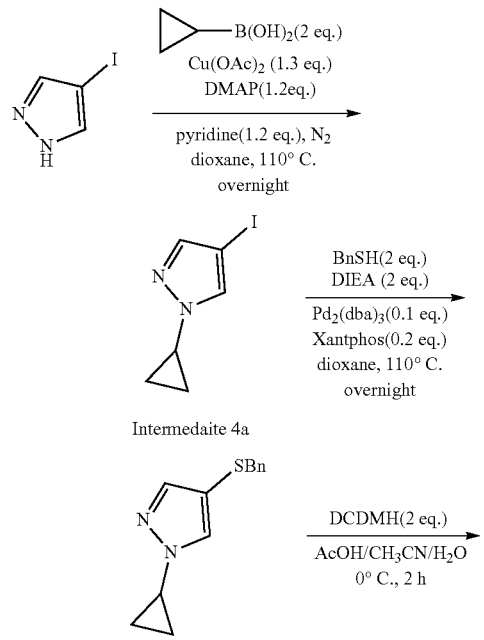

Intermedaite 4a

Intermedaite 4b

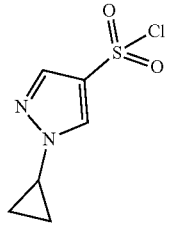

Sulfonyl chloride 4

Intermediate 4a: 1-Cyclopropyl-4-iodo-1H-pyrazole

To a solution of 4-iodo-1H-pyrazole (7.00 g, 36.0 mmol) in 1,4-dioxane (30 mL) was added cyclopropylboronic acid (6.20 g, 72.0 mmol), cupric acetate monohydrate (9.40 g, 47.0 mmol), 4-dimethylaminopyridine (108 mg, 43.0 mmol) and pyridine (3.50 g, 43.0 mmol) under nitrogen atmosphere. After stirred at 110° C. overnight, the reaction mixture was cooled down to room temperature and diluted in water (50 mL), extracted with ethyl acetate (60 mL) for three times. The combined organic layers were washed with brine (40 mL), dried over Na$_2$SO$_{4(s)}$ and filtered. The filtrate was concentrated under reduced pressure to give a crude product, which was purified by silica gel column chromatography (petroleum ether:ethyl acetate=4:1) to afford the title compound (1.80 g, 21% yield) as light yellow oil. $^1$H NMR (400 MHz, CDCl$_3$) δ 7.49 (s, 1H), 7.47 (s, 1H), 3.62-3.57 (m, 1H), 1.13-1.08 (m, 2H), 1.05-0.99 (m, 2H).

Intermediate 4b: 4-(Benzylthio)-1-cyclopropyl-1H-pyrazole

To a solution of 1-cyclopropyl-4-iodo-1H-pyrazole Intermediate 4a (500 mg, 2.13 mmol) in 1,4-dioxane (10 mL) was added benzyl mercaptan (527 mg, 4.30 mmol), N,N-diisopropylethylamine (554 g, 4.30 mmol), tris(dibenzylideneacetone)dipalladium (20 mg, 0.020 mmol) and 9,9-dimethyl-4,5-bis(diphenylphosphino)xanthene (23 mg, 0.040 mmol) under nitrogen atmosphere. After stirred at 110° C. overnight, the reaction mixture was cooled down to room temperature and diluted with water (20 mL), extracted with ethyl acetate (20 mL) for three times. The combined organic layers were washed with brine (20 mL), dried over Na$_2$SO$_{4(s)}$ and filtered. The filtrate was concentrated under reduced pressure to give a crude product, which was purified by silica gel column chromatography (petroleum ether:ethyl acetate=10:1) to to afford the title compound (330 mg, 67% yield) as colorless oil. LC-MS (ESI): R$_T$=2.358 min, mass calcd. for C$_{13}$H$_{14}$N$_2$S 230.1, m/z found 230.9 [M+H]$^+$. $^1$H NMR (300 MHz, CDCl$_3$) δ 7.32-7.17 (m, 4H), 7.13-7.07 (m, 3H), 3.78 (s, 2H), 3.57-3.46 (m, 1H), 1.07-0.92 (m, 4H).

Sulfonyl Chloride 4:1-Cyclopropyl-1H-pyrazole-4-sulfonyl Chloride

To a solution of 4-(benzylthio)-1-cyclopropyl-1H-pyrazole EO8495_729.3 (330 mg, 1.43 mmol) in acetonitrile (6 mL) was added acetic acid (0.7 mL), water (0.5 mL) and 1,3-dichloro-5,5-dimethylhydantoin (570 mg, 2.87 mmol) at 0° C. under nitrogen atmosphere. After stirred at 0° C. for 2 hours, the reaction mixture was diluted in water (10 mL) and extracted with ethyl acetate (20 mL) for three times. The combined organic layers were washed with brine (20 mL), dried over Na$_2$SO$_{4(s)}$ and filtered. The filtrate was concentrated under reduced pressure to give the title compound (320 mg, crude) as colorless oil. LC-MS (ESI): R$_T$=1.457 min, mass calcd. for C$_6$H$_7$ClN$_2$O$_2$S 206.0, m/z found 206.9 [M+H]$^+$.

Sulfonyl Chloride 5: (trans)-tert-Butyl
3-(chlorosulfonyl)cyclobutanecarboxylate

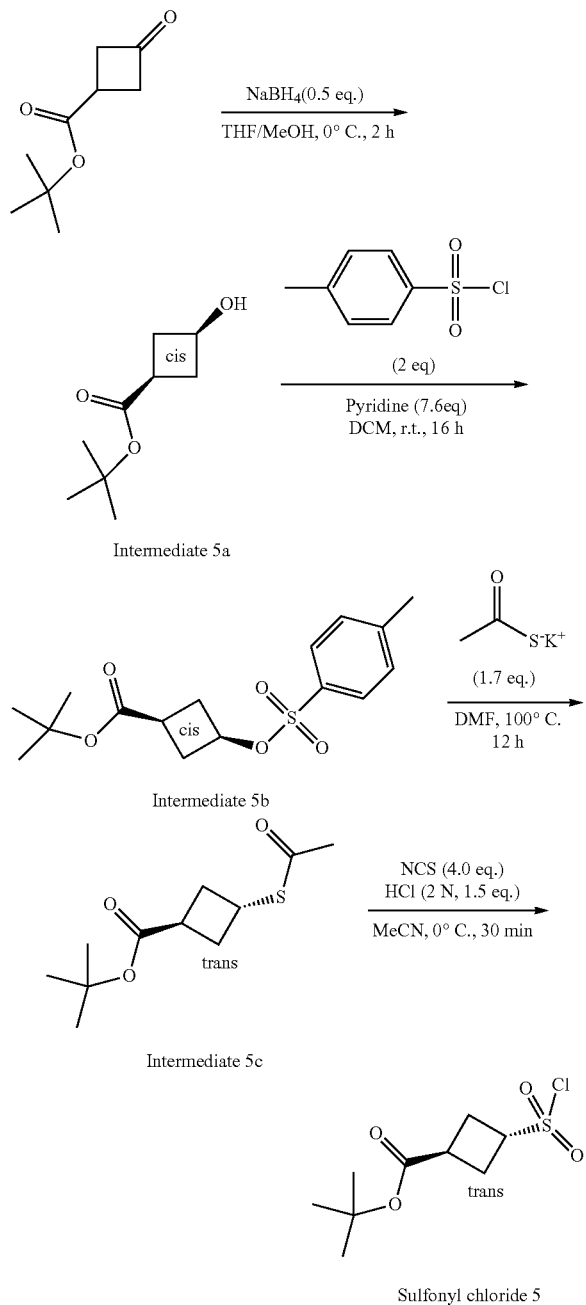

Intermediate 5a

Intermediate 5b

Intermediate 5c

Sulfonyl chloride 5

Intermediate 5a: (cis)-tert-Butyl
3-hydroxycyclobutanecarboxylate

A 1 L three-neck bottle was charged with nitrogen, 0° condition, to the suspension of Sodium borohydride (2.389 g, 63.158 mmol) in THF (108 mL, 0.886 g/mL, 1327.029 mmol) was added the solution of 3-oxocyclobutanecarboxylate (21.5 g, 126.316 mmol) in MeOH (52 mL, 0.791 g/mL, 1283.684 mmol) and THF (160 mL, 0.886 g/mL, 1965.969 mmol) drop by drop in 20 minutes under nitrogen atmosphere. [Caution! Gas emitting reaction!] [Monitor the inner reaction system temperature no more than 20°.] The reaction mixture was stirred at 00 for 2 hours, TLC (3:1=HEX: EA) to show the consumption of all starting material. The mixture was concentrated at reduced pressure to give a residue, which was added saturated Na2CO3 solution (200 mL) and extracted with EA (300 mL×3). The combined organic layers were washed with brine, dried over Na2SO4, filtered and the filtrate was concentrated to give a crude product (21.5 g, yield 98.83%) which was used without further purification for next step. $^1$H NMR (300 MHz, CDCl$_3$) δ 4.73-4.69 (m, 1H), 4.16-4.14 (m, 1H), 2.64-2.40 (m, 3H), 2.27-2.06 (m, 2H), 1.44 (s, 9H).

Intermediate 5b: (cis)-tert-Butyl
3-(tosyloxy)cyclobutanecarboxylate

4-Methyl-benzenesulfonyl chloride (93 g, 488 mmol) was added slowly to a solution of (cis)-tert-butyl 3-hydroxycyclobutanecarboxylate 5a (42 g, 244 mmol) in pyridine (150 mL) and dichloromethane (400 mL) at 0° C. After stirred at room temperature for 16 hours, the mixture was diluted with water (200 mL, 0° C.) and stirred at room temperature for 0.5 hours. The aqueous phase was extracted with dichloromethane (200 mL×2), combined the organic layer and washed with 0.5N HCl (200 mL), brine (100 mL), dried over Na$_2$SO$_{4(s)}$, filtered and concentrated to give the title compound (79.6 g, 92% yield) as white solids. $^1$H NMR (300 MHz, CDCl$_3$) δ 7.80 (d, J=8.1 Hz, 2H), 7.35 (d, J=7.5 Hz, 2H), 4.74-4.69 (m, 1H), 2.56-2.30 (m, 8H), 1.42 (s, 9H).

Intermediate 5c: (trans)-tert-Butyl
3-(acetylthio)cyclobutanecarboxylate

A 1 L three-neck bottle was charged with nitrogen, at room temperature condition, to the solution of (cis)-tert-butyl 3-(tosyloxy)cyclobutanecarboxylate 5b (41.36 g, 126.71 mmol) in DMF (400 mL, 0.944 g/mL, 5165.903 mmol) was added potassium thioacetate (24.8 g, 217.145 mmol) under nitrogen atmosphere. The reaction system was stirred at 1000 under nitrogen atmosphere overnight (12 hours). TLC (10:1=PE:EA) shows the consumption of all the starting material. Most of the solvent was evaporated at reduced pressure, the residue was re-dissolved in EA (1 L), washed with water (200 mL), saturated aqueous NaCl (100 mL×10), dried over Na2SO4, evaporated to remove the solvent to give a residue which was flash column (PE: EA=100:1 to 50:1) to give the title compound (22.5 g, yield 77.094%) as yellow oil. $^1$H NMR (300 MHz, CDCl$_3$) δ 4.16-4.06 (m, 1H), 3.19-3.11 (m, 1H), 2.79-2.70 (m, 2H), 2.29-2.20 (m, 5H), 1.46 (s, 9H).

Sulfonyl Chloride 5: (trans)-tert-Butyl
3-(chlorosulfonyl)cyclobutanecarboxylate To a solution of (trans)-tert-butyl 3-(acetylthio)cyclobutanecarboxylate 5c (25 g, 109 mmol) and 2 M hydrochloride aqueous solution (13 mL, 27 mmol) in acetonitrile (400 mL) was added 1-chloropyrrolidine-2,5-dione (58 g, 435 mmol) slowly at 0° C. After stirred at 0° C. for 30 minutes, the reaction mixture was concentrated in vacuo to remove acetonitrile (25° C. bath). And the residue was partitioned between ethyl acetate (800 mL) and saturated sodium bicarbonate aqueous solution (400 mL). The separated organic layer was washed with saturated sodium thiosulfate aqueous solution (400 mL) followed with brine (400 mL), dried over $Na_2SO_{4(s)}$ and filtered. The filtrate was concentrated and the residue was purified by silica gel column chromatography (petroleum ether:ethyl acetate=150:1) to give the title compound (19 g, 71% yield) as white solids. $^1$H NMR (400 MHz, CDCl$_3$) δ 4.49-4.41 (m, 1H), 3.29-3.21 (m, 1H), 2.93-2.86 (m, 2H), 2.80-2.73 (m, 2H), 1.47 (s, 9H).

Sulfonyl Chloride 6: 1,4-Dioxaspiro[4.5]decan-2-ylmethanesulfonyl Chloride

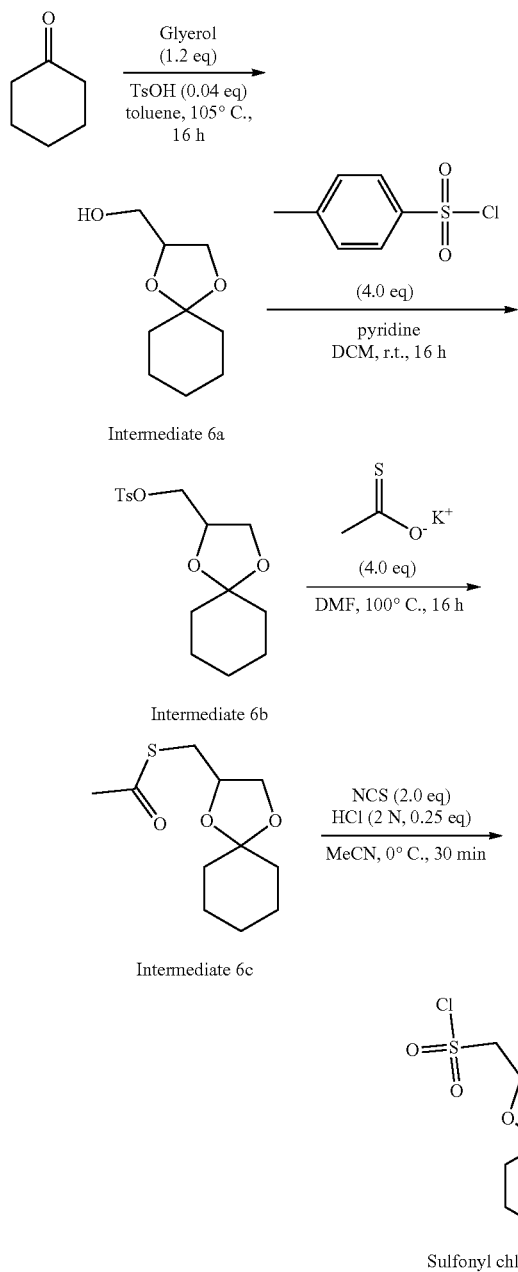

Intermediate 6a:
1,4-Dioxaspiro[4.5]decan-2-ylmethanol

To a solution of glycerol (18.2 g, 0.2 mol) and cyclohexanone (13.0 g, 0.13 mol) in toluene (13 mL) was added 4-toluenesulfonic acid (1.30 g, 7.80 mmol) at room temperature. After stirred at 105° C. for 16 hours, the reaction mixture was cooled down to room temperature. The mixture was concentrated under reduced pressure to give a residue, which was diluted with water (150 mL) and ethyl acetate (100 mL). The aqueous layer was extracted with ethyl acetate (100 mL) twice. The combined organic layers were washed with brine (250 mL), dried over $Na_2SO_{4(s)}$ and filtered. The filtrate was concentrated under reduced pressure to give the crude title compound (21.4 g, 95% yield) as yellow oil, which was directly used without further purification. $^1$H NMR (300 MHz, DMSO-d$_6$) δ 4.02-3.87 (m, 2H), 3.64-3.55 (m, 1H), 3.45-3.26 (m, 2H), 1.97-1.20 (m, 10H).

Intermediate 6b:
1,4-Dioxaspiro[4.5]decan-2-ylmethyl 4-methylbenzenesulfonate

4-Methylbenzene-1-sulfonyl chloride (44.0 g, 231 mmol) was added slowly to a solution of 1,4-dioxaspiro[4.5]decan-2-ylmethanol Intermediate 6a (10.0 g, 58 mmol) in pyridine (10 mL) and dichloromethane (100 mL) at 0° C. After stirred at room temperature for 16 hours, the mixture was diluted with water (100 mL) and stirred at room temperature for 30 minutes. The aqueous layer was extracted with dichloromethane (100 mL) twice, the combined organic layers were washed with 0.5 N hydrochloride aqueous solution (200 mL) and brine (100 mL), dried over $Na_2SO_{4(s)}$, filtered and concentrated under reduced pressure to give a residue, which was purified by silica gel column chromatography (petroleum ether:ethyl acetate=30:1) to give the title compound (15.0 g, 79% yield) as white solids. $^1$H NMR (300 MHz, CDCl$_3$) δ 7.87-7.76 (m, 2H), 7.42-7.36 (m, 2H), 4.34-4.24 (m, 1H), 4.09-3.92 (m, 3H), 3.83-3.72 (m, 1H), 2.47 (s, 3H), 1.59-1.55 (m, 10H).

Intermediate 6c:
S-(1,4-dioxaspiro[4.5]decan-2-ylmethyl) ethanethioate

To a solution of 1,4-dioxaspiro[4.5]decan-2-ylmethyl 4-methylbenzenesulfonate Intermediate 6b (15.0 g, 45.9 mmol) in N,N-dimethylformamide (150 mL) was added potassium thioacetate (21 g, 183 mmol) at room temperature. After stirred at 100° C. for 16 hours, the reaction mixture was cooled down to room temperature, concentrated under reduced pressure, added 5% sodium chloride aqueous solution (500 mL) and extracted with ethyl acetate (150 mL) twice. The combined organic layers were dried over $Na_2SO_{4(s)}$, filtered and concentrated to give a residue, which was purified by silica gel column chromatography (petroleum ether:ethyl acetate=30:1) to give the title compound (9 g, 86% yield) as yellow oil. $^1$H NMR (300 MHz, CDCl$_3$) δ 4.25-4.22 (m, 1H), 4.10-4.06 (m, 1H), 3.68-3.62 (m, 1H), 3.11-3.10 (m, 2H), 2.36 (s, 3H), 1.64-1.58 (m, 10H).

Sulfonyl Chloride 6: 1,4-Dioxaspiro[4.5]decan-2-ylmethanesulfonyl Chloride

To a solution of S-(1,4-dioxaspiro[4.5]decan-2-ylmethyl) ethanethioate Intermediate 6c (920 mg, 4 mmol) and 2 N hydrochloride aqueous solution (0.5 mL, 1.00 mmol) in acetonitrile (30 mL) was added 1-chloropyrrolidine-2,5-dione (1.07 g, 8.00 mmol) slowly at 0° C. After stirred at 0° C. for 30 minutes, the reaction mixture was concentrated in vacuo to remove acetonitrile (25° C. bath). And the residue was partitioned between ethyl acetate (50 mL) and saturated sodium bicarbonate aqueous solution (50 mL). The combined organic layer was washed with saturated sodium thiosulfate aqueous solution (50 mL), followed with brine (50 mL), dried over $Na_2SO_{4(s)}$ and filtered. The filtrate was concentrated to give a residue, which was purified by silica gel column chromatography (petroleum ether:ethyl acetate=10:1) to give the title compound (380 mg, 40% yield) as yellow oil. $^1H$ NMR (300 MHz, $CDCl_3$) δ 4.76-4.68 (m, 0.2H), 4.67-4.58 (m, 0.4H), 4.46-4.37 (m, 0.4H), 4.25-4.31 (m, 3H), 3.60-3.48 (m, 0.3H), 3.39-3.33 (m, 0.7H), 1.70-1.51 (m, 8H), 1.47-1.32 (m, 2H).

Sulfonyl Chloride 7: tert-Butyl 3-(chlorosulfonyl)cyclopentanecarboxylate

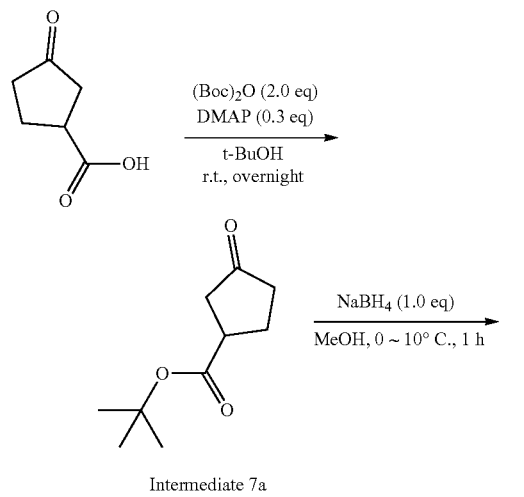

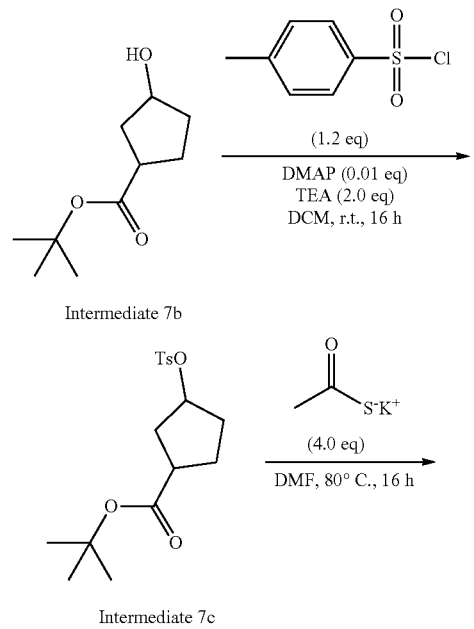

Intermediate 7c

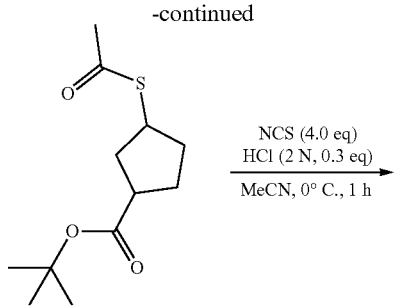

Intermediate 7d

Sulfonyl chloride 7

Intermediate 7a: tert-Butyl 3-oxocyclopentanecarboxylate

To the solution of 3-oxocyclopentanecarboxylic acid (5.00 g, 39.1 mmol) and di-tert-butyl dicarbonate (17.0 g, 78.0 mmol) in tert-butanol (100 mL) was added 4-dimethylaminopyridine (1.40 g, 11.5 mmol). After stirred at room temperature overnight, the mixture was concentrated to give a residue, which was purified by silica gel column chromatography (petroleum ether:ethyl acetate=20:1 to 10:1) to give the title compound (4.60 g, 64% yield) as yellow oil. $^1H$ NMR (300 MHz, $CDCl_3$) δ 3.09-2.99 (m, 1H), 2.54-2.07 (m, 6H), 1.47 (s, 9H).

Intermediate 7b: tert-Butyl 3-hydroxycyclopentanecarboxylate

Sodium borohydride (946 mg, 25.0 mmol) was added slowly to a solution of tert-butyl 3-oxocyclopentanecarboxylate Intermediate 7a (4.60 g, 25.0 mmol) in methanol (50 mL) at 0° C. After stirred at 10° C. for 1 hour, the mixture was diluted with water (50 mL), concentrated and extracted with ethyl acetate (80 mL) twice. The combined organic layers were dried over $Na_2SO_{4(s)}$, filtered and concentrated to afford the crude product (4.50 g, crude) as colorless oil, which was used for the next step without further purification. $^1H$ NMR (300 MHz, $CDCl_3$) δ 4.45 (br s, 0.2H), 4.30 (br s, 0.8H), 3.01-2.76 (m, 2H), 2.09-1.68 (m, 6H), 1.46-1.45 (m, 9H).

Intermediate 7c: tert-Butyl 3-(tosyloxy)cyclopentanecarboxylate

4-Methyl-benzenesulfonyl chloride (5.50 g, 29 mmol) was added slowly to a solution of tert-butyl 3-hydroxycyclopentanecarboxylate Intermediate 7b (4.50 g, 24 mmol), 4-dimethylaminopyridine (30 mg, 0.24 mmol) and triethylamine (4.9 g, 48 mmol) in dichloromethane (45 mL) at 0° C.

After stirred at room temperature for 16 hours, the mixture was washed with saturated sodium bicarbonate aqueous solution (30 mL), followed with brine (30 mL), dried over Na$_2$SO$_{4(s)}$, filtered and concentrated. The residue was purified by silica gel column chromatography (petroleum ether: ethyl acetate=20:1 to 10:1) to give the title compound (5.60 g, 68% yield) as colorless oil. $^1$H NMR (300 MHz, CDCl$_3$) δ 7.79 (d, J=7.8 Hz, 2H), 7.34 (d, J=7.8 Hz, 2H), 5.02 (s, 0.2H), 4.96-4.89 (m, 0.8H), 2.95-2.77 (m, 0.2H), 2.69-2.59 (m, 0.8H), 2.46 (s, 3H), 2.21-1.76 (m, 6H), 1.43 (s, 9H).

Intermediate 7d: tert-Butyl 3-(acetylthio)cyclopentanecarboxylate

To a solution of tert-butyl 3-(tosyloxy)cyclopentanecarboxylate Intermediate 7c (4.60 g, 13.5 mmol) in N,N-dimethylformamide (50 mL) was added potassium thioacetate (6.20 g, 54.1 mmol) at room temperature. After stirred at 80° C. for 16 hours, the reaction mixture was cooled down to room temperature, quenched with 5% sodium chloride aqueous solution (50 mL) and extracted with ethyl acetate (100 mL) twice. The combined organic layers were dried over Na$_2$SO$_{4(s)}$, filtered and concentrated. The residue was purified by silica gel column chromatography (petroleum ether:ethyl acetate=50:1 to 30:1) to give the title compound (3.50 g, 87% yield) as brown oil. $^1$H NMR (300 MHz, CDCl$_3$) δ 3.92-3.78 (m, 0.8H), 3.72-3.67 (m, 0.2H), 2.88-2.73 (m, 1H), 2.42-2.13 (m, 5H), 2.07-1.80 (m, 3H), 1.62-1.53 (m, 1H), 1.45 (s, 9H).

Sulfonyl chloride 7: tert-Butyl 3-(chlorosulfonyl)cyclopentanecarboxylate

To a solution of tert-butyl 3-(acetylthio)cyclopentanecarboxylate Intermediate 7d (3.00 g, 12 mmol) and 2 N hydrochloride aqueous solution (1.8 mL, 3.6 mmol) in acetonitrile (80 mL) was added 1-chloropyrrolidine-2,5-dione (6.60 g, 49 mmol) at 0° C. After stirred at 0° C. for 1 hour, the mixture was added to water (30 mL), concentrated under reduced pressure and extracted with ethyl acetate (50 mL) twice. The combined organic layers were washed with brine (50 mL), dried over Na$_2$SO$_{4(s)}$ and filtered. The filtrate was concentrated under reduced pressure to give a residue, which was purified by silica gel column chromatography (petroleum ether:ethyl acetate=20:1 to 10:1) to give the title compound (2.9 g, 88% yield) as white solids. $^1$H NMR (300 MHz, CDCl$_3$) δ 4.32-4.22 (m, 0.8H), 4.18-4.07 (m, 0.2H), 3.08-2.98 (m, 0.8H), 2.91-2.79 (m, 0.2H), 2.57-2.46 (m, 2H), 2.38-1.90 (m, 4H), 1.46 (s, 9H).

Sulfonyl Chloride 8: tert-Butyl 4-(chlorosulfonyl)cyclohexanecarboxylate

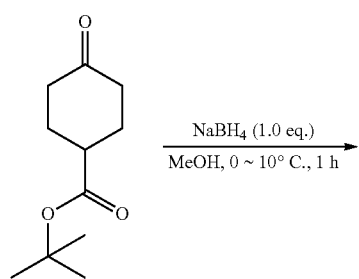

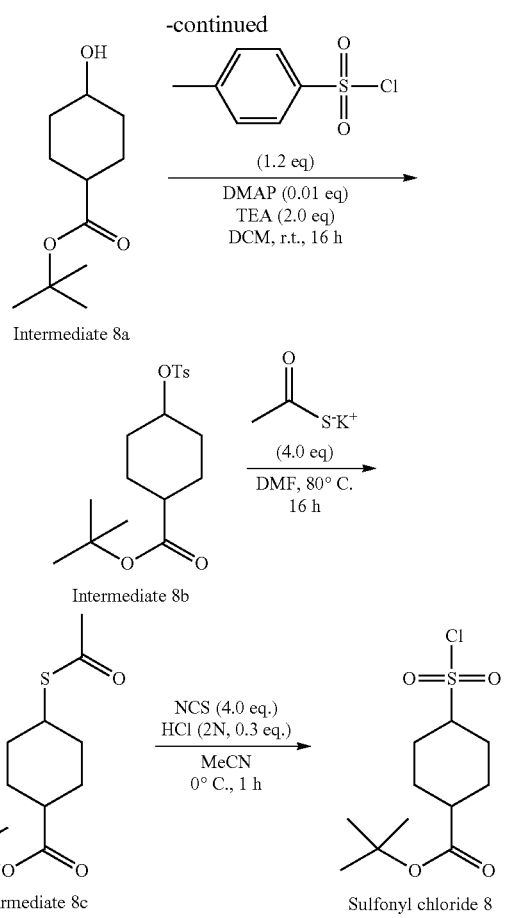

Intermediate 8a: tert-Butyl 4-hydroxycyclohexanecarboxylate

Sodium borohydride (611 mg, 16.0 mmol) was added slowly to a solution of tert-butyl 4-oxocyclohexanecarboxylate EO8495_830.1 (3.20 g, 16.0 mmol) in methanol (30 mL) at 0° C. After stirred at 10° C. for 1 hour, the mixture was added to water (50 mL), concentrated under reduced pressure and extracted with ethyl acetate (40 mL) twice. The combined organic layers were dried over Na$_2$SO$_{4(s)}$, filtered and concentrated to afford the crude product (3.20 g, crude) as colorless oil, which was used for the next step without further purification. 1H NMR (300 MHz, CDCl$_3$) δ 3.91-3.85 (m, 0.4H), 3.65-3.57 (m, 0.6H), 2.30-2.27 (m, 0.4H), 2.18-2.10 (m, 0.6H), 2.04-1.89 (m, 3H), 1.66-1.60 (m, 3H), 1.53-1.35 (m, 10H), 1.30-1.21 (m, 2H).

Intermediate 8b: tert-Butyl 4-(tosyloxy)cyclohexanecarboxylate

4-Methyl-benzenesulfonyl chloride (3.7 g, 19 mmol) was added slowly to a solution of tert-butyl 4-hydroxycyclohexanecarboxylate Intermediate 8a (3.2 g, 16 mmol), 4-dimethylaminopyridine (20 mg, 0.16 mmol) and triethylamine (3.2 g, 32 mmol) in dichloromethane (30 mL) at 0° C. After stirred at room temperature for 16 hours, the mixture was washed with saturated sodium bicarbonate aqueous solution (15 mL), followed with brine (15 mL), dried over Na$_2$SO$_{4(s)}$, filtered and concentrated. The residue was purified by silica gel column chromatography (petroleum ether:ethyl acetate=20:1 to 10:1) to give the title compound (4.0 g, 72% yield) as colorless oil. $^1$H NMR (300 MHz, CDCl$_3$) δ 7.80 (d, J=8.1 Hz, 2H), 7.34 (d, J=8.1 Hz, 2H), 4.70 (br s, 0.3H), 4.41 (br s, 0.7H), 2.46 (s, 3H), 2.25-2.13 (m, 1H), 1.98-1.79 (m, 4H), 1.71-1.42 (m, 13H).

Intermediate 8c: tert-Butyl 4-(acetylthio)cyclohexanecarboxylate

To a solution of tert-butyl 4-(tosyloxy)cyclohexanecarboxylate Intermediate 8b (3.00 g, 8.50 mmol) in N,N-dimethylformamide (30 mL) was added potassium thioacetate (3.90 g, 33.8 mmol) at room temperature. After stirred at 80° C. for 16 hours, the reaction mixture was cooled down to room temperature, quenched with 5% sodium chloride aqueous solution (50 mL) and extracted with ethyl acetate (100 mL) twice. The combined organic layers were dried over Na$_2$SO$_{4(s)}$, filtered and concentrated to give a residue, which was purified by silica gel column chromatography (petroleum ether:ethyl acetate=50:1 to 30:1) to give the title compound (1.9 g, 65% yield) as brown oil. $^1$H NMR (300 MHz, CDCl$_3$) δ 3.75 (s, 1H), 2.30-2.29 (m, 3.7H), 2.21-2.14 (m, 0.3H), 2.01-1.94 (m, 0.7H), 1.81-1.72 (m, 6.7H), 1.56-1.52 (m, 0.3H), 1.43 (s, 9H), 1.38-1.33 (m, 0.3H).

Sulfonyl Chloride 8: tert-Butyl 4-(chlorosulfonyl)cyclohexanecarboxylate

To a solution of tert-butyl 4-(acetylthio)cyclohexanecarboxylate Intermediate 8c (1.4 g, 5.4 mmol) and 2 M hydrochloride aqueous solution (0.8 mL, 1.6 mmol) in acetonitrile (50 mL) was added 1-chloropyrrolidine-2,5-dione (2.9 g, 21.7 mmol) at 0° C. After stirred at 0° C. for 1 hour, the mixture was diluted with water (20 mL), concentrated under reduced pressure and extracted with ethyl acetate (40 mL) twice. The combined organic layers were washed with brine (50 mL), dried over Na$_2$SO$_{4(s)}$ and filtered. The filtrate was concentrated to give a residue, which was purified by silica gel column chromatography (petroleum ether:ethyl acetate=20:1 to 10:1) to give the title compound (1.2 g, 78% yield) as white solids. $^1$H NMR (300 MHz, CDCl$_3$) δ 3.59-3.49 (m, 1H), 2.62-2.49 (m, 1H), 2.39-2.22 (m, 4H), 2.09-1.95 (m, 2H), 1.86-1.63 (m, 1H), 1.57-1.54 (m, 1H), 1.48-1.45 (m, 9H).

Sulfonyl chloride 9: 2-(Trimethylsilyl)ethyl 3-(chlorosulfonyl)-1-methylcyclobutanecarboxylate

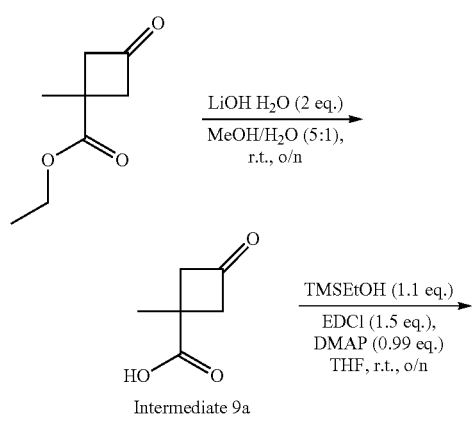

Intermediate 9a

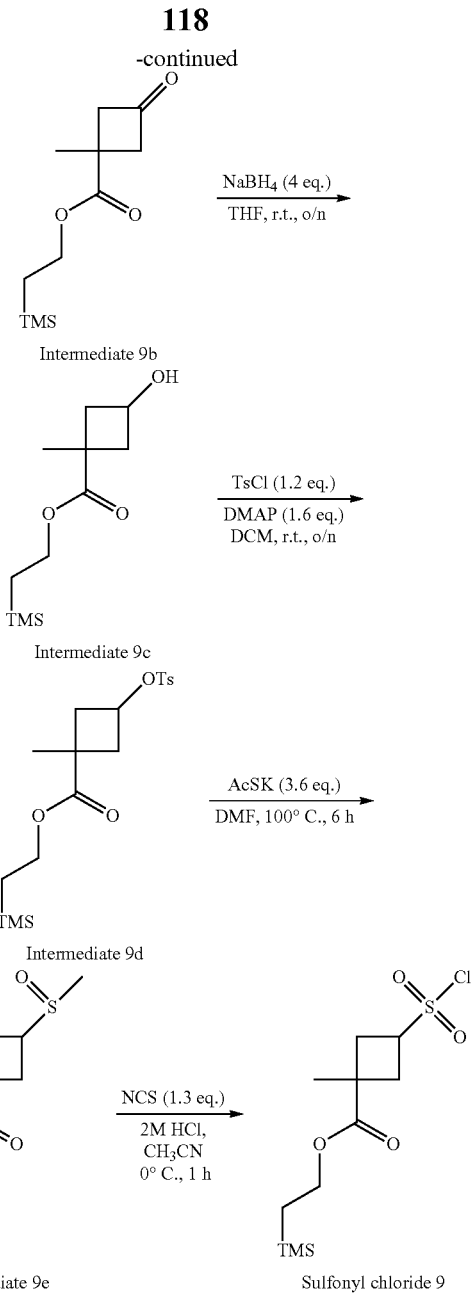

Intermediate 9a: 1-Methyl-3-oxocyclobutanecarboxylic Acid

To a solution of ethyl 1-methyl-3-oxocyclobutanecarboxylate EO8495_670.1 (4.00 g, 25.6 mmol) in methanol (50 mL) and water (10 mL) was added lithium hydroxide monohydrate (2.15 g, 51.2 mmol). After stirred at room temperature overnight, the mixture was acidified with 2 M hydrochloride aqueous solution to pH~2 and then concentrated under reduced pressure to give a residue, which was dissolved in water (50 mL) and extracted with ethyl acetate (30 mL) for three times. The combined organic layers were dried over Na$_2$SO$_{4(s)}$ and concentrated to afford the title compound (4.10 g, 90% purity, 100% yield) as yellow oil. $^1$H NMR (400 MHz, CDCl$_3$) δ 3.67-3.62 (m, 2H), 2.99-2.93 (m, 2H), 1.62 (s, 3H).

Intermediate 9b: 2-(Trimethylsilyl)ethyl 1-methyl-3-oxocyclobutanecarboxylate To a solution of 1-methyl-3-oxocyclobutanecarboxylic acid Intermediate 9a (4.10 g, purity 90%, 28.8 mmol) and 2-(trimethylsilyl)ethanol (3.75 g, 31.7 mmol), N,N-dimethylpyridin-4-amine (3.50 g, 28.6 mmol) in tetrahydrofuran (100 mL) was added 1-ethyl-3-(3-dimethylaminopropyl)carbodiimide hydrochloride (8.30 g, 43.2 mmol) under nitrogen. After stirred at room temperature overnight, the mixture was quenched with water (50 mL), then concentrated under reduced pressure to remove the volatile, extracted with ethyl acetate (80 mL) for three times. The combined organic layers were washed with 2M hydrochloride aqueous solution (100 mL), dried over $Na_2SO_{4(s)}$ and concentrated to afford the title compound (5.10 g, 80% purity, 100% yield) as yellow oil. $^1$H NMR (400 MHz, CDCl$_3$) δ 4.21-4.17 (m, 2H), 3.54-3.49 (m, 2H), 2.85-2.80 (m, 2H), 1.52 (s, 3H), 0.99-0.95 (m, 2H), 0.07 (s, 9H).

Intermediate 9c: 2-(Trimethylsilyl)ethyl 3-hydroxy-1-methylcyclobutanecarboxylate To a solution of 2-(trimethylsilyl)ethyl 1-methyl-3-oxo-cyclobutanecarboxylate Intermediate 9b (5.10 g, 80% purity, 17.9 mmol) in tetrahydrofuran (100 mL) and water (10 mL) was added portionwise sodium tetrahydroborate (2.70 g, 71.5 mmol) at room temperature. After stirred at room temperature overnight, the mixture was quenched with water (20 mL) and then concentrated under reduced pressure to give a residue. The residue was taken up with water (50 mL) and extracted with ethyl acetate (50 mL) for three times. The combined organic layers were dried over $Na_2SO_{4(s)}$ and concentrated to afford the title compound (3.80 g, 90% purity, 100% yield) as yellow oil. $^1$H NMR (400 MHz, CDCl$_3$) δ 4.38-4.22 (m, 1H), 4.16-4.10 (m, 2H), 3.71-3.67 (m, 1H), 2.80-2.71 (m, 1H), 2.32-2.21 (m, 2H), 1.85-1.77 (m, 1H), 1.35 (s, 1.5H), 1.30 (s, 1.5H), 0.97-0.89 (m, 2H), 0.07 (s, 9H).

Intermediate 9d: 2-(Trimethylsilyl)ethyl 1-methyl-3-(tosyloxy)cyclobutene-carboxylate To a solution of 2-(trimethylsilyl)ethyl 3-hydroxy-1-methylcyclobutanecarboxylate Intermediate 9c (3.70 g, 90% purity, 14.5 mmol) and N,N-dimethylpyridin-4-amine (2.90 g, 23.7 mmol) in dichloromethane (100 mL) was added 4-methylbenzene-1-sulfonyl chloride (3.3 g, 17.3 mmol) under nitrogen. After stirred at room temperature overnight, the reaction solution was washed with water (40 mL), dried over $Na_2SO_{4(s)}$ and concentrated under reduced pressure to give a residue. The residue was purified by silica gel column chromatography (petroleum ether:ethyl acetate=8:1) to afford the title compound (3.10 g, 95% purity, 48% yield) as light yellow oil. $^1$H NMR (400 MHz, CDCl$_3$) δ 7.74 (d, J=8.4 Hz, 2H), 7.30 (d, J=8.0 Hz, 2H), 4.87-4.83 (m, 1H), 4.14-4.10 (m, 1H), 2.72-2.66 (m, 0.8H), 2.56-2.52 (m, 1.2H), 2.42 (s, 3H), 2.17-2.11 (m, 1.2H), 2.08-2.03 (m, 0.8H), 1.33 (s, 1H), 1.28 (s, 2H), 0.95-0.91 (m, 2H), 0.01 (s, 9H).

Intermediate 9e: 2-(Trimethylsilyl)ethyl 3-(acetylthio)-1-methylcyclobutanecarboxylate To a solution of 2-(trimethylsilyl)ethyl 1-methyl-3-(tosyloxy)cyclobutanecarboxylate Intermediate 9d (3.10 g, 95% purity 7.26 mmol) in N,N-dimethylformamide (70 mL) was added potassium thioacetate (3.00 g, 26.3 mmol) at room temperature. After stirred at 100° C. for 6 hours, the reaction mixture was cooled down and poured into water (200 mL) and extracted with ethyl acetate (80 mL) for three times. The combined organic layers were washed with water (100 mL) for three times, dried over $Na_2SO_{4(s)}$ and concentrated to afford the title compound (2.30 g, 90% purity, 99% yield) as yellow oil. $^1$H NMR (400 MHz, CDCl$_3$) δ 4.27-4.21 (m, 2H), 4.19-4.08 (m, 1H), 3.06-3.00 (m, 1H), 2.59-2.50 (m, 1H), 2.41-2.36 (m, 1H), 2.32 (s, 3H), 2.04-1.99 (m, 1H), 1.50 (s, 1.2H), 1.44 (s, 1.8H), 1.08-1.01 (m, 2H), 0.07 (s, 9H).

Sulfonyl chloride 9: 2-(Trimethylsilyl)ethyl 3-(chlorosulfonyl)-1-methylcyclobutanecarboxylate To a solution of 2-(trimethylsilyl)ethyl 3-(acetylthio)-1-methylcyclobutane carboxylate Intermediate 9e (1.10 g, 90% purity 7.52 mmol) in acetonitrile (50 mL) was added 2M hydrochloride aqueous solution (0.2 mL) and 1-chloro-pyrrolidine-2,5-dione (1.35 g, 10.1 mmol) at 0° C. After stirred at 0° C. for 1 hour, the resulting mixture was concentrated under reduced pressure and the obtained crude product was poured in water (30 mL), extracted with ethyl acetate (30 mL) for three times The combined organic layers were washed with water (20 mL) for three times, dried over $Na_2SO_{4(s)}$ and concentrated to give a residue, which was purified by silica gel column chromatography (petroleum ether:ethyl acetate=10:1) to afford the title compound (820 mg, 95% purity, 73% yield) as light yellow oil. $^1$H NMR (400 MHz, CDCl$_3$) δ 4.48-4.33 (m, 1H), 4.26-4.19 (m, 2H), 3.16-3.10 (m, 0.8H), 2.97-2.91 (m, 1.2H), 2.63-2.57 (m, 1.2H), 2.41-2.36 (m, 0.8H), 1.48 (s, 3H), 1.04-0.99 (m, 2H), 0.07 (s, 9H).

Sulfonyl chloride 10: 3-((tert-butyldiphenylsilyl)oxy)cyclobutane-1-sulfonyl chloride

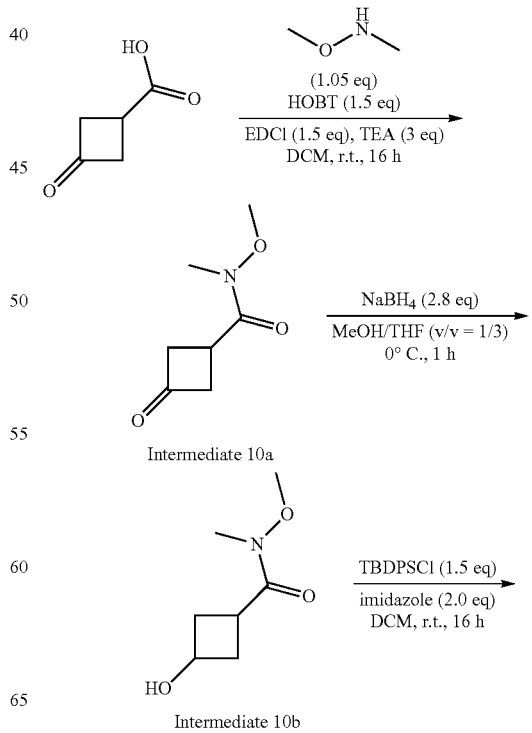

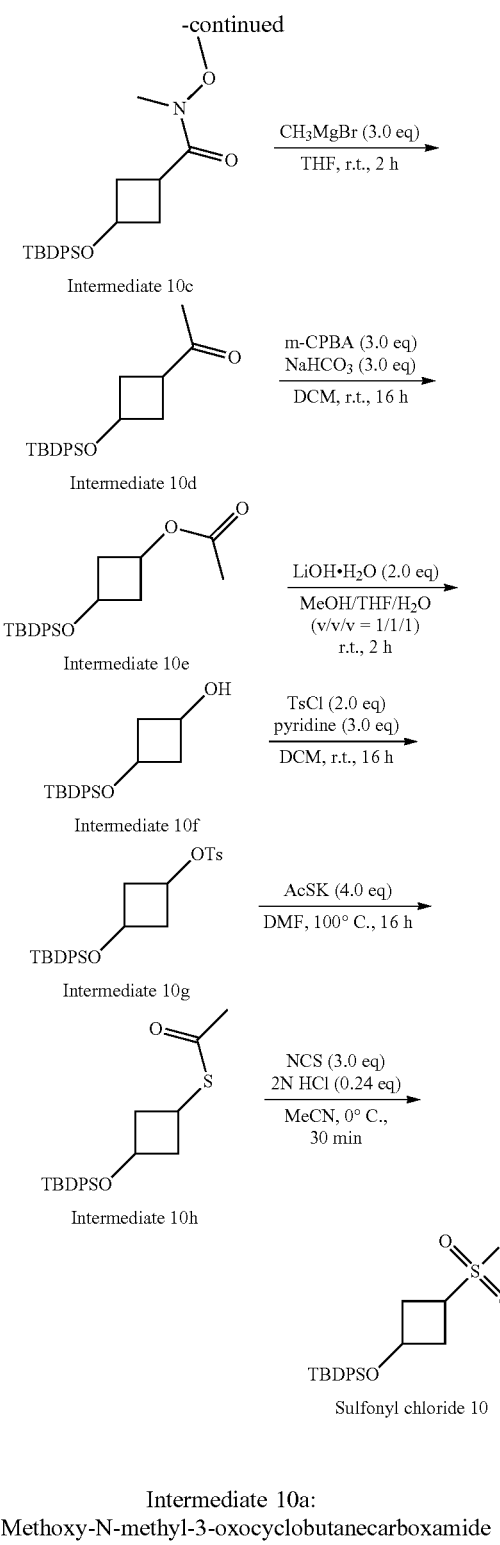

at room temperature for 0.5 hour. The organic layer was separated and the aqueous phase was extracted with dichloromethane (200 mL) twice. The combined organic layers were washed with brine (200 mL), dried over $Na_2SO_{4(s)}$, filtered and concentrated to give a residue, which was purified by silica gel column chromatography (petroleum ether:ethyl acetate=30:1) to give the title compound (13.9 g, 88% yield) as yellow oil. LC-MS (ESI): $R_T$=1.02 min, mass calcd. for $C_7H_1NO_3$ 157.1, m/z found 158.0 [M+H]$^+$. $^1$H NMR (400 MHz, CDCl$_3$) δ 3.73 (s, 3H), 3.63-3.55 (m, 1H), 3.51-3.44 (m, 2H), 3.26-3.17 (m, 5H).

Intermediate 10b:
3-Hydroxy-N-methoxy-N-methylcyclobutanecarboxamide

Sodium borohydride (3.30 g, 88.0 mmol) was added slowly to a solution of N-methoxy-N-methyl-3-oxocyclobutanecarboxamide Intermediate 10a (13.9 g, 31.6 mmol) in tetrahydrofuran (90 mL) and methanol (30 mL) at 0° C. After stirred at 0° C. for 2 hours, the mixture was diluted with water (200 mL) and extracted with ethyl acetate (300 mL). The separated organic layer was dried over $Na_2SO_{4(s)}$, filtered and concentrated to afford the crude title compound (7.20 g, 51% yield) as yellow oil which was used in the next step without further purification. $^1$H NMR (400 MHz, CDCl$_3$) δ 4.23-4.12 (m, 1H), 3.65 (s, 3H), 3.17 (s, 3H), 3.06-2.95 (m, 1H), 2.59-2.50 (m, 2H), 2.24-2.15 (m, 2H).

Intermediate 10c: 3-((tert-Butyldiphenylsilyl)oxy)-N-methoxy-N-methylcyclobutanecarboxamide tert-Butyldiphenylchlorosilane (18.5 g, 67.5 mmol) was added slowly to a solution of 3-hydroxy-N-methoxy-N-methylcyclobutanecarboxamide Intermediate 10b (7.20 g, 45.0 mmol) and imidazole (6.10 g, 90.0 mmol) in dichloromethane (100 mL) at 0° C. After stirred at room temperature for 16 hours, the mixture was washed with saturated sodium bicarbonate aqueous solution (200 mL) followed with brine (200 mL), dried over $Na_2SO_{4(s)}$, filtered and concentrated to give a residue, which was purified by silica gel column chromatography (petroleum ether:ethyl acetate=3:1) to give the title compound (15.0 g, 85% yield) as yellow oil. $^1$H NMR (400 MHz, CDCl$_3$) δ 7.68-7.62 (m, 4H), 7.43-7.33 (m, 6H), 4.19-4.10 (m, 1H), 3.60-3.57 (m, 3H), 3.18-3.12 (m, 3H), 2.76-2.72 (m, 1H), 2.37-2.29 (m, 4H), 1.03-1.00 (m, 9H).

Intermediate 10d: 1-(3-((tert-Butyldiphenylsilyl)oxy)cyclobutyl)ethanone

A solution of 1 M methyl magnesium bromide in tetrahydrofuran (53 mL, 105 mmol) was added slowly to a solution of 3-((tert-butyldiphenylsilyl)oxy)-N-methoxy-N-methylcyclobutanecarboxamide Intermediate 10c (14.0 g, 35.2 mmol) in tetrahydrofuran (100 mL) at 0° C. After stirred at room temperature for 2 hours, the mixture was diluted with water (150 mL) and extracted with ethyl acetate (150 mL). The separated organic layer was washed with brine (150 mL), dried over $Na_2SO_{4(s)}$, filtered and concentrated to give the title compound (12.0 g, 97% yield) as white solids which was used in the next step without further purification. LC-MS (ESI): $R_T$=2.09 min, mass calcd. for $C_{22}H_{28}O_2Si$ 352.2, m/z found 353.4 [M+H]$^+$. $^1$H NMR (400 MHz, CDCl$_3$) δ 7.66-7.60 (m, 4H), 7.45-7.35 (m, 6H), 4.18-4.10 (m, 1H), 2.56-2.47 (m, 1H), 2.35-2.31 (m, 2H), 2.29-2.17 (m, 2H), 2.04 (s, 3H), 1.03 (s, 9H).

Intermediate 10a:
N-Methoxy-N-methyl-3-oxocyclobutanecarboxamide

To a solution of 3-oxocyclobutanecarboxylic acid (11.4 g, 100 mmol) and 1-hydroxybenzotriazole (17.9 g, 150 mmol) in dichloromethane (200 mL) was added N-methoxymethylamine hydrochloride (9.70 g, 105 mmol), N'-(ethylkohlenstoffimidoyl)-N,N-dimethylpropan-1,3-diamine hydrochloride (28.8 g, 150 mmol) and triethylamine (30.1 g, 300 mmol) at 0° C. After stirred at room temperature for 16 hours, the mixture was diluted in water (200 mL) and stirred

Intermediate 10e: 3-((tert-Butyldiphenylsilyl)oxy)cyclobutyl Acetate

To a solution of 1-(3-((tert-butyldiphenylsilyl)oxy)cyclobutyl)ethanone Intermediate 10d (7.06 g, 20.0 mmol) and 3-chloroperoxybenzoic acid (10.3 g, 60.0 mmol) in dichloromethane (100 mL) was added sodium bicarbonate (5.04 g, 60.0 mmol) at 0° C. After stirred at room temperature for 16 hours, the mixture was diluted in water (200 mL) and stirred at room temperature for 0.5 hour. The organic layer was separated and the aqueous phase was extracted with dichloromethane (100 mL) twice. The combined organic layers were washed with brine (200 mL), dried over $Na_2SO_{4(s)}$, filtered and concentrated to give a residue, which was purified by silica gel column chromatography (petroleum ether:ethyl acetate=30:1) to give the title compound (6.00 g, 81% yield) as yellow oil. $^1H$ NMR (400 MHz, $CDCl_3$) δ 7.65-7.62 (m, 4H), 7.43-7.34 (m, 6H), 4.46-4.35 (m, 1H), 3.96-3.87 (m, 1H), 2.69-2.59 (m, 2H), 2.20-2.10 (m, 2H), 2.03 (s, 3H), 1.00 (s, 9H).

Intermediate 10f: 3-((tert-Butyldiphenylsilyl)oxy)cyclobutanol

To a solution of 3-((tert-butyldiphenylsilyl)oxy)cyclobutyl acetate Intermediate 10e (6.00 g, 16.3 mmol) in tetrahydrofuran (30 mL), methanol (30 mL) and water (30 mL) was added lithium hydroxide monohydrate (1.37 g, 32.5 mmol) under nitrogen atmosphere at 0° C. After stirred at room temperature for 2 hours, the mixture was concentrated at room temperature under reduced pressure to remove the volatile and extracted with ethyl acetate (200 mL). The separated organic layer was washed with water (150 mL) and brine (150 mL), dried over $Na_2SO_{4(s)}$, filtered and concentrated to give the title compound (4.00 g, 75% yield) as colorless oil which was used in the next step without further purification. $^1H$ NMR (400 MHz, $CDCl_3$) δ 7.66-7.63 (m, 4H), 7.40-7.37 (m, 6H), 3.87-3.78 (m, 1H), 3.77-3.67 (m, 1H), 2.64-2.56 (m, 2H), 2.07-1.97 (m, 2H), 1.04 (s, 9H).

Intermediate 10g: 3-((tert-Butyldiphenylsilyl)oxy)cyclobutyl 4-methylbenzenesulfonate 4-Methyl-benzenesulfonyl chloride (4.40 g, 22.9 mmol) was added slowly to a solution of 3-((tert-butyldiphenylsilyl)oxy)cyclobutanol Intermediate 10f (4.00 g, 11.5 mmol) in pyridine (2.70 g, 34.5 mmol) and dichloromethane (100 mL) at 0° C. After stirred at room temperature for 16 hours, the mixture was diluted in water (100 mL) and stirred at room temperature for 0.5 hour. The organic layer was separated and the aqueous phase was extracted with dichloromethane (100 mL) twice. The combined organic layers were washed with 0.5 M hydrochloride aqueous solution (200 mL), brine (100 mL), dried over $Na_2SO_{4(s)}$, filtered and concentrated to give a residue, which was purified by silica gel column chromatography (petroleum ether:ethyl acetate=20:1) to give the title compound (5.10 g, 92% yield) as yellow oil. $^1H$ NMR (400 MHz, $CDCl_3$) δ 7.77-7.69 (m, 2H), 7.61-7.44 (m, 4H), 7.35-7.27 (m, 8H), 4.25-4.16 (m, 1H), 3.82-3.72 (m, 1H), 2.53-2.37 (m, 5H), 2.29-2.19 (m, 2H), 1.01-0.96 (m, 9H).

Intermediate 10h: S-(3-((tert-Butyldiphenylsilyl)oxy)cyclobutyl)ethanethioate To a solution of 3-((tert-butyldiphenylsilyl)oxy)cyclobutyl 4-methylbenzenesulfonate Intermediate 10g (2.40 g, 5.00 mmol) in N,N-dimethylformamide (50 mL) was added potassium thioacetate (2.30 g, 20.0 mmol) at room temperature. After stirred at 100° C. for 16 hours, the reaction mixture was cooled down to room temperature and concentrated to give a residue, which was diluted with 5% wt. sodium chloride aqueous solution (200 mL) and extracted with ethyl acetate (100 mL) twice. The combined organic layers were dried over $Na_2SO_{4(s)}$, filtered and concentrated to give a residue, which was purified by silica gel column chromatography (petroleum ether:ethyl acetate=10:1) to give the title compound (1.60 g, 81% yield) as yellow oil. $^1H$ NMR (400 MHz, $CDCl_3$) δ 7.63-7.61 (m, 4H), 7.44-7.35 (m, 8H), 4.51-4.45 (m, 1H), 3.92-3.86 (m, 1H), 2.67-2.59 (m, 2H), 2.26 (s, 3H), 2.23-2.14 (m, 2H), 1.04 (s, 9H).

Sulfonyl Chloride 10:3-((tert-butyldiphenylsilyl)oxy)cyclobutane-1-sulfonyl Chloride To a solution of S-(3-((tert-butyldiphenylsilyl)oxy)cyclobutyl) ethanethioate Intermediate 10h (1.60 g, 4.20 mmol) and 2 M hydrochloride aqueous solution (0.5 mL, 1.00 mmol) in acetonitrile (20 mL) was added N-chlorosuccinimide (1.70 g, 12.5 mmol) slowly at 0° C. After stirred at 0° C. for 30 minutes, the reaction mixture was concentrated under 25° C. in vacuo to give a residue, which was partitioned between ethyl acetate (50 mL) and saturated sodium bicarbonate aqueous solution (50 mL). The separated organic layer was washed with saturated sodium thiosulfate aqueous solution (50 mL) followed with brine (50 mL), dried over $Na_2SO_{4(s)}$ and filtered. The filtrate was concentrated to give a residue, which was purified by silica gel column chromatography (petroleum ether:ethyl acetate=10:1) to give the title compound (1.20 g, 70% yield) as colorless oil. $^1H$ NMR (400 MHz, $CDCl_3$) δ 7.62-7.57 (m, 4H), 7.49-7.27 (m, 6H), 4.69-4.61 (m, 1H), 4.39-4.29 (m, 1H), 2.87-2.75 (m, 2H), 2.67-2.56 (m, 2H), 1.06 (s, 6H), 1.04 (s, 3H).

Sulfonyl chloride 11: Ethyl 4-(chlorosulfonyl)cyclohexanecarboxylate

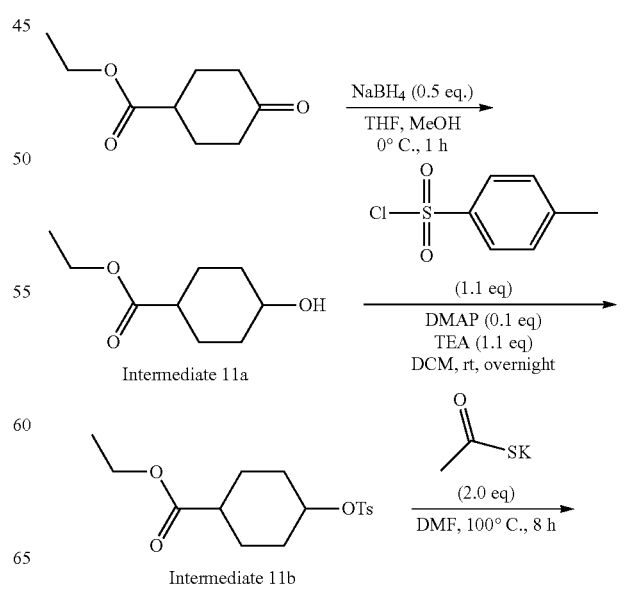

Intermediate 11a

Intermediate 11b

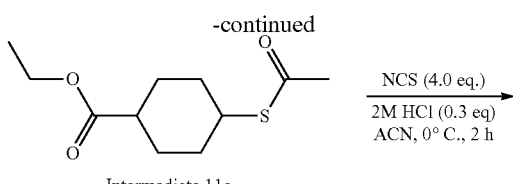

Intermediate 11c

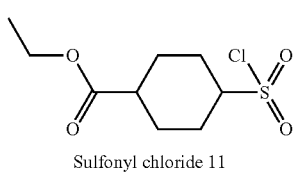

Sulfonyl chloride 11

Intermediate 1a: Ethyl 4-hydroxycyclohexanecarboxylate

To a solution of ethyl 4-oxocyclohexanecarboxylate (30.0 g, 176 mmol) in tetrahydrofuran (200 mL) and methanol (70 mL) was added sodium borohydride (3.40 g, 88.0 mmol) at 0° C. Then the mixture was stirred at 0° C. for 1 hour. After that, it was quenched with water (150 mL) and extracted with ethyl acetate (250 mL) twice. The combined organic layers were washed with brine (100 mL), dried over $Na_2SO_{4(s)}$ and filtered. The filtrate was concentrated under reduced pressure to give the title compound (29.5 g, 98% yield) as colorless oil. $^1$H NMR (300 MHz, $CDCl_3$) δ 4.14-4.05 (m, 2H), 3.89-3.81 (m, 0.3H), 3.65-3.52 (m, 0.7H), 2.39-2.31 (m, 0.3H), 2.25-2.15 (m, 0.7H), 2.02-1.90 (m, 4H), 1.69-1.60 (m, 1.7H), 1.54-1.40 (m, 1.3H), 1.31-1.19 (m, 4H).

Intermediate 1b: Ethyl 4-(tosyloxy)cyclohexanecarboxylate

To a solution of ethyl 4-hydroxycyclohexanecarboxylate Intermediate 11a (30.0 g, 174 mmol) in dichloromethane (500 mL) was added N,N-dimethylpyridin-4-amine (2.12 g, 17.4 mmol), triethylamine (20.0 g, 192 mmol) and 4-methylbenzene-1-sulfonyl chloride (36.0 g, 192 mmol) at room temperature. After stirred at room temperature under nitrogen atmosphere overnight, the mixture was washed with 0.5 M hydrochloride aqueous solution (300 mL) twice and brine (500 mL), dried over $Na_2SO_{4(s)}$ and filtered. The filtrate was concentrated under reduced pressure to give the title compound (55.0 g, 96% yield) as brown oil. $^1$H NMR (300 MHz, $CDCl_3$) δ 7.79 (d, J=8.1 Hz, 2H), 7.33 (d, J=8.4 Hz, 2H), 4.74-4.68 (m, 0.3H), 4.46-4.37 (m, 0.7H), 4.15-4.06 (m, 2H), 2.45 (s, 3H), 2.35-2.20 (m, 1H), 2.04-1.82 (m, 4.2H), 1.74-1.68 (m, 0.8H), 1.55-1.46 (m, 3H), 1.28-1.20 (m, 3H).

Intermediate 11c: Ethyl 4-(acetylthio)cyclohexanecarboxylate

To a solution of ethyl 4-(tosyloxy)cyclohexanecarboxylate Intermediate 11b (10.0 g, 31.0 mmol) in N,N-dimethylformamide (35 mL) was added potassium ethanethioate (7.00 g, 61.0 mmol) at room temperature. After stirred at 110° C. under nitrogen atmosphere for 8 hours, the mixture was cooled down to room temperature and poured into water (300 mL), extracted with ethyl acetate (150 mL) twice. The combined organic layers were washed with brine (100 mL), dried over $Na_2SO_{4(s)}$ and filtered. The filtrate was concentrated under reduced pressure to give the title compound (5.00 g, 71% yield) as brown oil. $^1$H NMR (300 MHz, $CDCl_3$) δ 4.16-4.10 (m, 2H), 3.80-3.73 (m, 1H), 2.43-2.36 (m, 1H), 2.31-2.25 (m, 4H), 1.81-1.77 (m, 5H), 1.61-1.59 (m, 2H), 1.27-1.22 (m, 3H).

Sulfonyl Chloride 11: Ethyl 4-(chlorosulfonyl)cyclohexanecarboxylate

To a solution of ethyl 4-(acetylthio)cyclohexanecarboxylate Intermediate 11c (5.00 g, 21.7 mmol) in acetonitrile (50 mL) and water (1 mL) was added 2 M hydrochloride aqueous solution (3.5 mL, 7.0 mmol) and 1-chloropyrrolidine-2,5-dione (11.6 g, 86.9 mmol) at 0° C. After stirred at 0° C. under nitrogen atmosphere for 2 hours, the mixture was quenched with water (50 mL) and extracted with ethyl acetate (50 mL) twice. The combined organic layers were washed with brine (50 mL), dried over $Na_2SO_{4(s)}$ and filtered. The filtrate was concentrated under reduced pressure to give the title compound (5.00 g, 91% yield) as colorless oil. $^1$H NMR (400 MHz, $CDCl_3$) δ 4.19 (d, J=7.2 Hz, 2H), 3.59-3.49 (m, 1H), 2.69-2.67 (m, 0.7H), 2.54-2.51 (m, 0.3H), 2.41-2.37 (m, 2H), 2.31-2.27 (m, 2H), 2.07-1.97 (m, 2H), 1.69-1.62 (m, 2H), 1.30-1.26 (t, J=7.2 Hz, 3H).

Sulfonyl Chloride 12: tert-Butyl Chlorosulfonylcarbamate

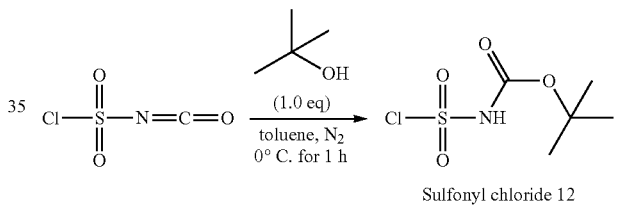

Sulfonyl chloride 12

To a solution of sulfurisocyanatidic chloride (1.14 g, 7.80 mmol) in toluene (2 mL) was added a solution of 2-methylpropan-2-ol (0.59 g, 7.80 mmol) in toluene (2 mL) at 0° C. After stirred at 0° C. for 1 hour, the mixture was diluted with petroleum ether (5 mL) and filtered. The obtained solid was dried to give the title compound (810 mg, 48% yield) as white solids. $^1$H NMR (400 MHz, DMSO-$d_6$) δ 13.49 (s, 1H), 1.62-1.25 (m, 9H).

Sulfonyl Chloride 13: trans-methyl-4-((chlorosulfonyl)methyl)cyclohexane-1-carboxylate

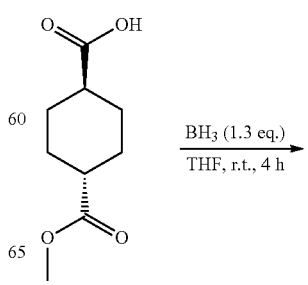

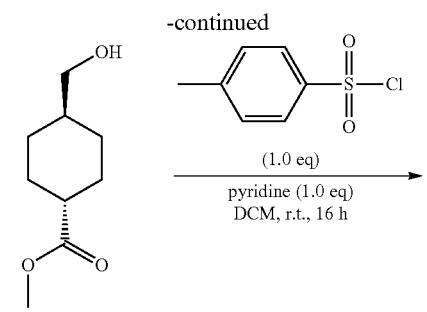

Intermediate 13a

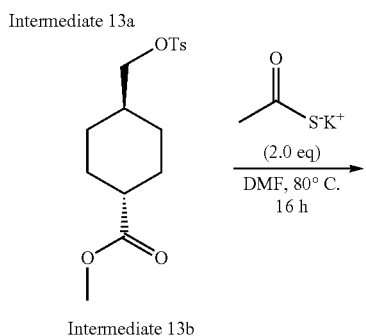

Intermediate 13b

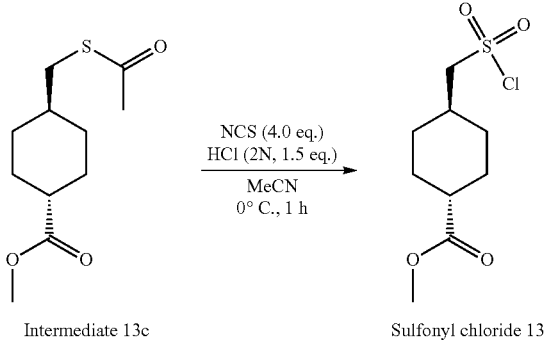

Intermediate 13c      Sulfonyl chloride 13

Intermediate 13a: trans-methyl-4-(hydroxymethyl)cyclohexane-1-carboxylate

To a solution of trans-4-(methoxycarbonyl)cyclohexane-1-carboxylic acid (5.0 g, 26.9 mmol) in THF (50 mL) was added Borane-tetrahydrofuran complex (34.9 mL, 1 M, 34.9 mmol) at −78° C. After addition, the mixture was warmed to room temperature slowly and stirred at room temperature for 4 hours. The mixture was quenched with MeOH (25 mL) and stirred at room temperature for 1 hour. Then the mixture was concentrated in vacuo to give trans-methyl-4-(hydroxymethyl)cyclohexane-1-carboxylate (6 g, crude) as colorless oil, which was used for the next step without further purification. $^{1}$H NMR (400 MHz, CDCl$_3$) δ 3.66 (s, 3H), 3.64-3.46 (m, 2H), 2.35-2.20 (m, 1H), 2.13-1.97 (m, 2H), 1.93-1.79 (m, 1H), 1.60-1.33 (m, 4H), 1.05-0.86 (m, 2H).

Intermediate 13b: trans-methyl-4-((tosyloxy)methyl)cyclohexane-1-carboxylate To a solution of trans-methyl-4-(hydroxymethyl)cyclohexane-1-carboxylate Intermediate 13a (6 g, 34.8 mmol) and 4-methylbenzenesulfonyl chloride (6.6 g, 34.8 mmol) in DCM (60 mL)) was added pyridine (2.806 mL, 0.982 g/mL, 34.8 mmol) at 0° C. After stirred at room temperature for 16 hours, the mixture was washed with saturated sodium bicarbonate aqueous solution (15 mL), followed with brine (15 mL), dried over Na$_2$SO$_{4(s)}$, filtered and concentrated. The residue was purified by silica gel column chromatography (hexane:ethyl acetate=10:1) to give the title compound (4.5 g, 39.5% yield) as colorless oil. $^{1}$H NMR (400 MHz, CDCl$_3$) δ 7.78 (d, J=8.0 Hz, 2H), 7.35 (d, J=8.0 Hz, 2H), 3.83 (d, J=8.0 Hz, 2H), 3.85 (s, 3H), 2.45 (s, 3H), 2.25-2.16 (m, 1H), 2.02-1.94 (m, 2H), 1.83-1.75 (m, 2H), 1.69-1.61 (m, 1H), 1.47-1.36 (m, 2H), 1.04-0.91 (m, 2H).

Intermediate 13c: trans-methyl-4-((acetylthio)methyl)cyclohexane-1-carboxylate To a solution of trans-methyl-4-((tosyloxy)methyl)cyclohexane-1-carboxylate Intermediate 13b (4.5 g, 13.8 mmol) in N,N-dimethylformamide (45 mL) was added potassium thioacetate (3.10 g, 27.6 mmol) at room temperature. After stirred at 80° C. for 16 hours, the reaction mixture was cooled down to room temperature, quenched with 5% sodium chloride aqueous solution (50 mL) and extracted with ethyl acetate (100 mL) twice. The combined organic layers were dried over Na$_2$SO$_{4(s)}$, filtered and concentrated to give a residue, which was purified by silica gel column chromatography (Hexane:EtOAc=20:1) to give the title compound (2.5 g, 78% yield) as brown oil. $^{1}$H NMR (400 MHz, CDCl$_3$) δ 3.66 (s, 3H), 2.80 (d, J=8.0 Hz, 2H), 2.34 (s, 3H), 2.26-2.19 (m, 1H), 2.04-1.94 (m, 2H), 1.94-1.84 (m, 2H), 1.51-1.34 (m, 3H), 1.02-0.96 (m, 2H).

Sulfonyl Chloride 13: trans-methyl-4-((chlorosulfonyl)methyl)cyclohexane-1-carboxylate To a solution of trans-methyl-4-((acetylthio)methyl)cyclohexane-1-carboxylate Intermediate 13c (2.5 g, 10.8 mmol) and 2 M hydrochloride aqueous solution (8.1 mL, 16.2 mmol) in acetonitrile (25 mL) was added 1-chloropyrrolidine-2,5-dione (5.8 g, 43.4 mmol) at 0° C. After stirred at 0° C. for 1 hour, the mixture was diluted with water (20 mL), extracted with ethyl acetate (20 mL) twice. The combined organic layers were washed with Sat. NaHCO$_3$ (100 mL), dried over Na$_2$SO$_{4(s)}$ and filtered. The filtrate was concentrated to give a residue, which was purified by silica gel column chromatography (petroleum ether:ethyl acetate=20:1 to 10:1) to give the title compound (1.5 g, 54% yield) as colorless oil. $^{1}$H NMR (400 MHz, CDCl$_3$) δ 3.68 (s, 3H), 3.63 (d, J=6.2 Hz, 2H), 2.30-2.22 (m, 1H), 2.15-2.03 (m, 4H), 1.55-1.47 (m, 2H), 1.29-1.13 (m, 3H).

Sulfonyl Chloride 14: (trans)-Methyl 4-((chlorosulfonyl)methyl)cyclohexanecarboxylate

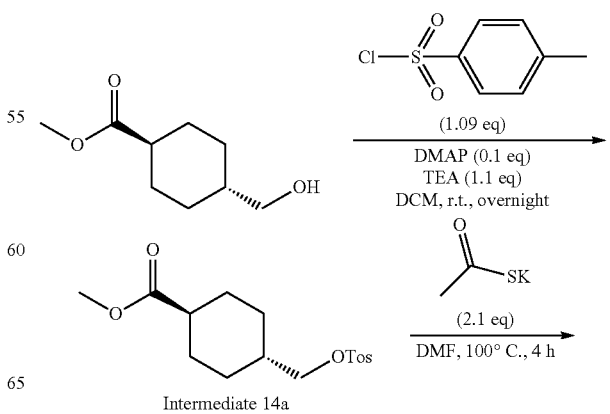

Intermediate 14a

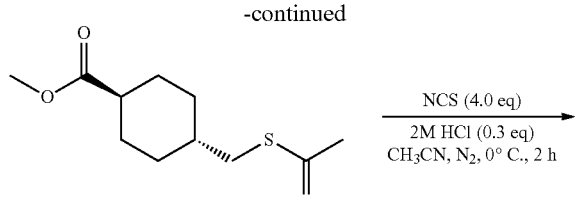

Intermediate 14b

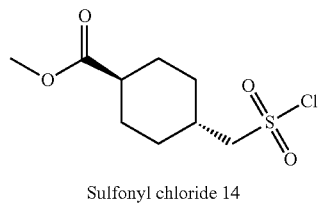

Sulfonyl chloride 14

Intermediate 14a: (trans)-Methyl 4-((tosyloxy)methyl)cyclohexanecarboxylate

To a solution of (1r, 4r)-methyl 4-(hydroxymethyl)cyclohexanecarboxylate (5.00 g, 29.0 mmol) in dichloromethane (80 mL) was added N,N-dimethylpyridin-4-amine (355 mg, 2.91 mmol), triethylamine (3.23 g, 31.9 mmol) and tosyl chloride (6.0 g, 31.5 mmol) at room temperature. After stirred at room temperature under nitrogen atmosphere overnight, the mixture was washed with 0.5 M hydrochloride aqueous solution (80 mL) twice and water (80 mL), dried over $Na_2SO_{4(s)}$ and filtered. The filtrate was concentrated under reduced pressure to give the title compound (8.0 g, 85% purity from NMR, 72% yield) as white solids. $^1$H NMR (400 MHz, $CDCl_3$) δ 7.78 (d, J=8.0 Hz, 2H), 7.35 (d, J=8.4 Hz, 2H), 3.83 (d, J=6.4 Hz, 2H), 3.65 (s, 3H), 2.46 (s, 3H), 2.04-1.77 (m, 5H), 1.49-1.34 (m, 3H), 1.04-0.92 (m, 2H).

Intermediate 14b: (trans)-Methyl 4-((acetylthio)methyl)cyclohexanecarboxylate To a solution of (1r, 4r)-methyl 4-((tosyloxy)methyl)cyclohexanecarboxylate Intermediate 14a (8.00 g, 85% purity, 20.8 mmol) in N,N-dimethylformamide (50 mL) was added potassium thioacetate (5.00 g, 43.8 mmol) at room temperature. After stirred at 100° C. under nitrogen atmosphere for 4 hours, the mixture was cooled down and taken up into water (200 mL), extracted with ethyl acetate (80 mL) twice. The combined organic layers were washed with brine (80 mL), dried over $Na_2SO_{4(s)}$ and filtered. The filtrate was concentrated under reduced pressure to give the title compound (5.40 g, 96% yield) as brown oil. $^1$H NMR (400 MHz, $CDCl_3$) δ 3.60 (s, 1.2H), 3.59 (s, 1.8H), 2.73 (d, J=6.8 Hz, 2H), 2.27 (s, 3H), 1.99-1.91 (m, 5H), 1.44-1.32 (m, 5H).

Sulfonyl Chloride 14: (trans)-Methyl 4-((chlorosulfonyl)methyl)cyclohexanecarboxylate To a solution of (1r, 4r)-methyl 4-((acetylthio)methyl)cyclohexanecarboxylate Intermediate 14b (2.0 g, 85% purity, 7.38 mmol) in acetonitrile (50 mL) was added 2 M hydrochloride aqueous solution (1.5 mL) and 1-chloropyrrolidine-2,5-dione (4.6 g, 34.4 mmol) at 0° C. After stirred at this temperature under nitrogen atmosphere for 2 hours, the mixture was quenched with water (30 mL) and extracted with ethyl acetate (30 mL) twice. The combined organic layers were washed with brine (50 mL), dried over $Na_2SO_{4(s)}$ and filtered. The filtrate was concentrated under reduced pressure to give the title compound (1.10 g, 90% purity from NMR, 53% yield) as yellow solids. 1H NMR (400 MHz, $CDCl_3$) δ 3.68 (s, 3H), 3.64 (d, J=6.0 Hz, 2H), 2.30-2.18 (m, 2H), 2.14-2.05 (m, 4H), 1.57-1.47 (m, 2H), 1.25-1.16 (m, 2H).

Sulfonyl Chloride 15: Methyl 4-((chlorosulfonyl)methyl)-4-methylcyclohexanecarboxylate

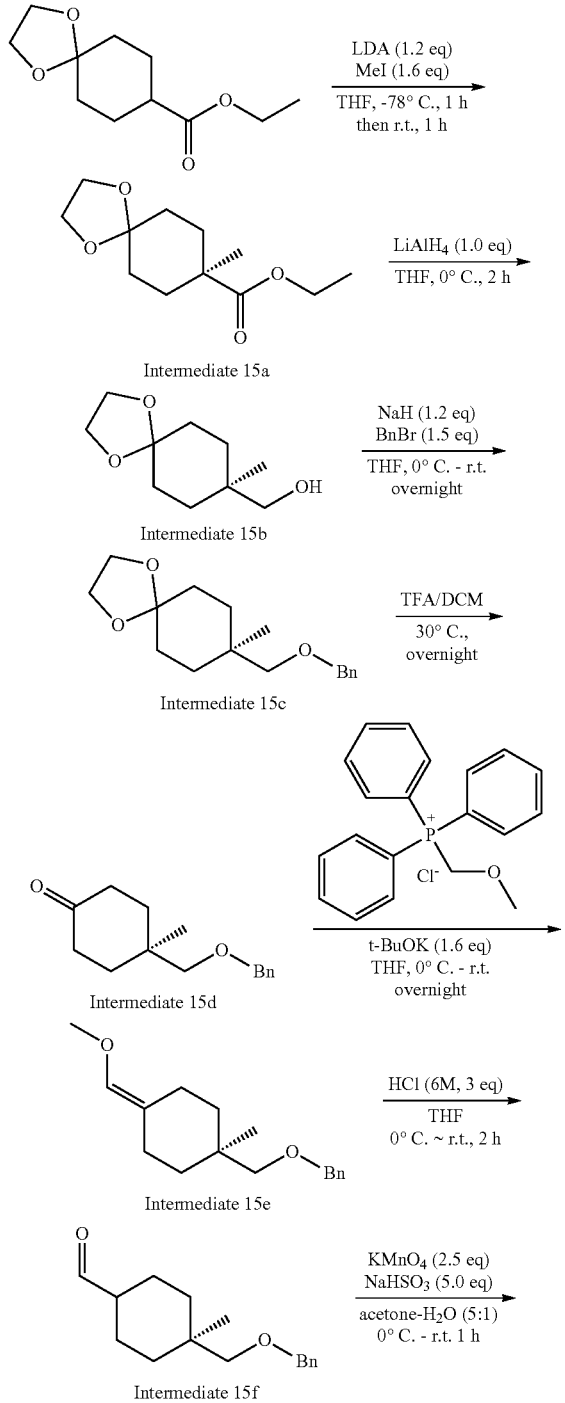

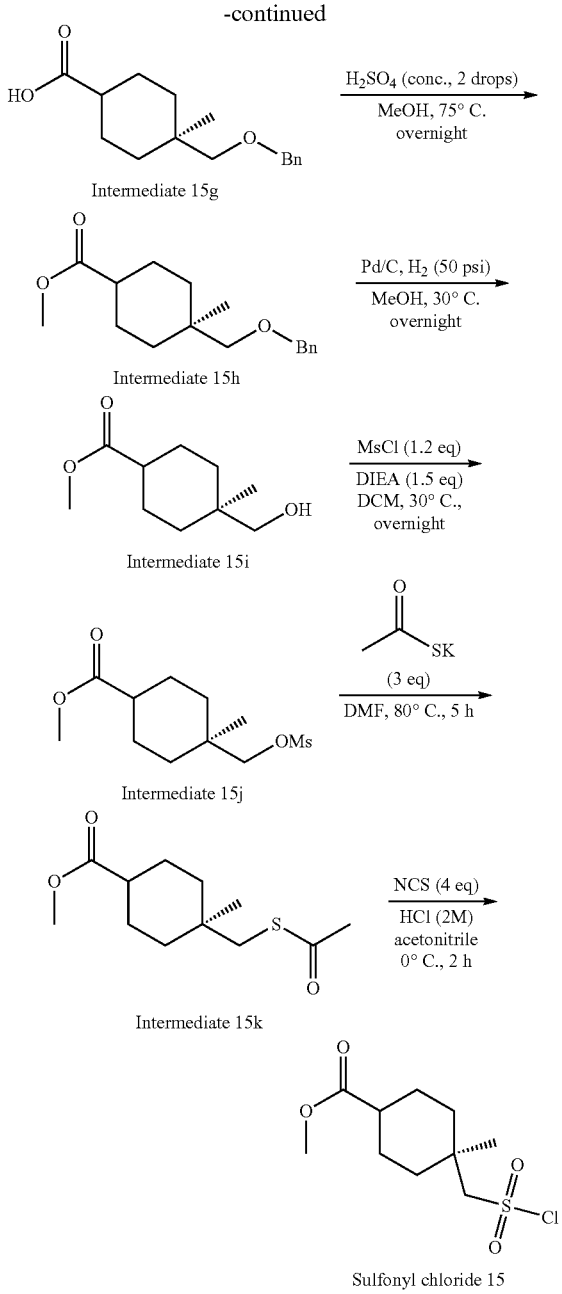

Intermediate 15a: 8-Methyl-1,4-dioxaspiro[4.5]decane-8-carboxylate

To the solution of ethyl 1,4-dioxaspiro[4.5]decane-8-carboxylate (3.00 g, 95% purity, 13.3 mmol) in dry tetrahydrofuran (30 mL) was added 2.0 M lithium diisopropylamide in tetrahydrofuran (8.0 mL, 16.0 mmol) dropwise at −78° C. under nitrogen atmosphere. After addition, the mixture was stirred at the same temperature for 30 minutes. Iodomethane (1.3 mL, 20.9 mmol) was added dropwise at −78° C. After stirred at −78° C. for 1 hour, then at room temperature for another 1 hour, the reaction was quenched with saturated ammonium chloride aqueous solution (30 mL) and extracted with ethyl acetate (30 mL) twice. The combined organic layers were washed with brine (50 mL), dried over $Na_2SO_4$ (s) and filtered. The filtrate was concentrated and purified by silica gel column chromatography (petroleum ether:ethyl acetate=20:1) to give the title compound (2.40 g, 95% purity, 75% yield) as light yellow oil. LC-MS (ESI): $R_T$=1.61 min, mass calcd. for $C_{12}H_{20}O_4$ 228.1, m/z found 229.0 [M+H]$^+$. $^1$H NMR (400 MHz, CDCl$_3$) δ 4.14 (q, J=7.2 Hz, 2H), 3.94 (s, 4H), 2.16-2.11 (m, 2H), 1.69-1.60 (m, 3.6H), 1.59-1.57 (m, 0.4H), 1.54-1.47 (m, 2H), 1.25 (t, J=7.2 Hz, 3H), 1.19 (s, 3H).

Intermediate 15b: (8-Methyl-1,4-dioxaspiro[4.5]decan-8-yl)methanol

To the solution of ethyl 8-methyl-1,4-dioxaspiro[4.5]decane-8-carboxylate Intermediate 15a (2.40 g, 95% purity, 9.99 mmol) in dry tetrahydrofuran (12 mL) was added lithium aluminum hydride (379 mg, 9.99 mmol) slowly at 0° C. Then the mixture was stirred at 0° C. for 2 hours. The reaction was quenched with water (0.38 mL) and 15% sodium hydroxide aqueous solution (0.38 mL). The resulting suspension was filtered through celite and washed with tetrahydrofuran (10 mL) and ethyl acetate (10 mL). The filtrate was concentrated to give the title compound (2.00 g, 90% purity, 97% yield) as white solids. $^1$H NMR (400 MHz, DMSO-d$_6$) δ 4.47 (t, J=5.2 Hz, 1H), 3.82 (s, 4H), 3.13 (d, J=5.2 Hz, 2H), 1.52-1.41 (m, 6H), 1.24-1.19 (m, 2H), 0.83 (s, 3H).

Intermediate 15c: 8-((Benzyloxy)methyl)-8-methyl-1,4-dioxaspiro[4.5]decane

To the solution of (8-methyl-1,4-dioxaspiro[4.5]decan-8-yl)methanol Intermediate 15b (2.00 g, 90% purity, 9.67 mmol) in dry tetrahydrofuran (15 mL) was added sodium hydride (60% in mineral oil, 464 mg, 11.6 mmol) slowly at 0° C. After addition, the suspension was stirred at 0° C. for 20 minutes. After benzyl bromide (1.7 mL, 14.3 mmol) was added dropwise, the mixture was stirred at room temperature overnight. The reaction mixture was quenched with water (30 mL) and extracted with ethyl acetate (30 mL) twice. The combined organic layers were washed with brine (30 mL), dried over $Na_2SO_4$ (s) and filtered. The filtrate was concentrated and purified by silica gel chromatography (petroleum ether:ethyl acetate=30:1 to 20:1) to give the title compound (2.20 g, 95% purity, 78% yield) as white solids. LC-MS (ESI): $R_T$=1.54 min, mass calcd. for $C_{17}H_{24}O_3$ 276.2, m/z found 277.0 [M+H]$^+$. $^1$H NMR (400 MHz, CDCl$_3$) δ 7.36-7.28 (m, 5H), 4.52 (s, 2H), 3.93 (s, 4H), 3.21 (s, 2H), 1.69-1.60 (m, 4H), 1.58-1.55 (m, 2H), 1.45-1.40 (m, 2H), 1.00 (s, 3H).

Intermediate 15d: 4-((Benzyloxy)methyl)-4-methylcyclohexanone

The solution of 8-((benzyloxy)methyl)-8-methyl-1,4-dioxaspiro[4.5]decane Intermediate 15c (2.20 g, 95% purity, 7.56 mmol) in dichloromethane (20 mL) and trifluoroacetic acid (20 mL) was stirred at 30° C. overnight. The mixture was concentrated under reduced pressure to remove the volatile. The obtained residue was dissolved in dichloromethane (50 mL) and washed with saturated sodium bicarbonate aqueous solution (50 mL) twice and brine (50 mL), dried over $Na_2SO_4$ (s) and filtered. The filtrate was concentrated and purified by silica gel column chromatography (petroleum ether:ethyl acetate=20:1) to give the title compound (1.75 g, 95% purity, 95% yield) as colorless oil. LC-MS (ESI): $R_T$=1.27 min, mass calcd. for $C_{15}H_{20}O_2$ 232.1, m/z found 233.0 [M+H]+. $^1$H NMR (400 MHz, CDCl$_3$) δ 7.38-7.27 (m, 5H), 4.54 (s, 2H), 3.31 (s, 2H), 2.41-2.28 (m, 4H), 1.85-1.81 (m, 2H), 1.71-1.65 (m, 2H), 1.14 (s, 3H).

Intermediate 15e: (((4-(Methoxymethylene)-1-methylcyclohexyl)methoxy)-methyl)benzene To the suspension of (methoxymethyl)triphenylphosphonium chloride EO8495_1093.5 (3.80 g, 11.1 mmol) in dry tetrahydrofuran (20 mL) was added potassium tert-butoxide (1.25 g, 11.1 mmol) slowly at 0° C. to keep the inter temperature below 5° C. After addition, the mixture was stirred at 0° C. for 30 minutes. A solution of 4-((benzyloxy)methyl)-4-methylcyclohexanone Intermediate 15d (1.70 g, 95% purity, 6.95 mmol) in dry tetrahydrofuran (5 mL) was added. Then the mixture was allowed to warm to room temperature and stirred at room temperature overnight. The mixture was quenched with water (30 mL) and extracted with ethyl acetate (30 mL) twice. The combined organic layers were washed with brine (50 mL), dried over Na$_2$SO$_{4(s)}$ and filtered. The filtrate was concentrated and purified by silica gel column chromatography (petroleum ether:ethyl acetate=50:1 to 30:1) to give the title compound (1.70 g, 95% purity, 89% yield) as light yellow oil. $^1$H NMR (400 MHz, CDCl$_3$) δ 7.36-7.28 (m, 5H), 5.75 (s, 1H), 4.51 (s, 2H), 3.53 (s, 3H), 3.20 (s, 2H), 2.33-2.27 (m, 1H), 2.10-1.96 (m, 2H), 1.93-1.87 (m, 1H), 1.47-1.30 (m, 4H), 1.00 (s, 3H).

Intermediate 15f: 4-((Benzyloxy)methyl)-4-methylcyclohexanecarbaldehyde

To the solution of (((4-(methoxymethylene)-1-methylcyclohexyl)methoxy)methyl)benzene Intermediate 15e (1.70 g, 95% purity, 6.20 mmol) in tetrahydrofuran (12 mL) was added 6 M hydrochloride aqueous solution (3.1 mL, 18.6 mmol) slowly at 0° C. After stirred at room temperature for 2 hours, the reaction mixture was quenched with brine (30 mL) and extracted with ethyl acetate (30 mL) twice. The combined organic layers were dried over Na$_2$SO$_{4(s)}$ and filtered. The filtrate was concentrated to give the title compound (1.60 g, 90% purity, 94% yield) as light yellow oil. $^1$H NMR (400 MHz, CDCl$_3$) δ 9.65 (d, J=1.2 Hz, 0.6H), 9.63 (d, J=0.8 Hz, 0.4H), 7.37-7.27 (m, 5H), 4.51 (s, 1.2H), 4.49 (s, 0.8H), 3.22 (s, 0.8H), 3.15 (s, 1.2H), 2.27-2.13 (m, 1H), 1.83-1.72 (m, 2H), 1.67-1.61 (m, 1H), 1.59-1.37 (m, 4H), 1.24-1.17 (m, 1H), 0.99 (s, 1.2H), 0.93 (s, 1.8H).

Intermediate 15g: 4-((Benzyloxy)methyl)-4-methylcyclohexanecarboxylic Acid

To the solution of 4-((benzyloxy)methyl)-4-methylcyclohexanecarbaldehyde Intermediate 15f (1.60 g, 90% purity, 5.85 mmol) in acetone (45 mL) and water (9 mL) was added potassium permanganate (2.30 g, 14.6 mmol) at 0° C. After stirred at 0° C. to room temperature for 1 hour, solid sodium bisulfite (3.10 g, 29.8 mmol) was added, then the mixture was diluted with acetone (50 mL) and water (50 mL). The resulting suspension was stirred at room temperature for 15 minutes and filtered through celite. The filtrate was concentrated under reduced pressure at room temperature to remove acetone. The resulting aqueous solution was acidified with solid citric acid to pH~3 and extracted with ethyl acetate (50 mL) twice. The combined organic layers were dried over Na$_2$SO$_{4(s)}$ and concentrated to give the title compound (1.5 g, 70% purity, 68% yield) as yellow oil. $^1$H NMR (400 MHz, DMSO-d$_6$) δ 12.06 (s, 1H), 7.37-7.26 (m, 5H), 4.47 (s, 0.8H), 4.46 (s, 1.2H), 3.23 (s, 0.8H), 3.11 (s, 1.2H), 2.20-2.05 (m, 1H), 1.71-1.56 (m, 3H), 1.53-1.43 (m, 2H), 1.39-1.25 (m, 2H), 1.13-1.05 (m, 1H), 0.90 (s, 1.2H), 0.89 (s, 1.8H).

Intermediate 15h: Methyl 4-((benzyloxy)methyl)-4-methylcyclohexanecarboxylate To the solution of 4-((benzyloxy)methyl)-4-methylcyclohexanecarboxylic acid Intermediate 15g (1.50 g, 70% purity, 4.00 mmol) in dry methanol (40 mL) was added 2 drops of concentrated sulfuric acid. After stirred at 75° C. overnight, the mixture was concentrated and purified by silica gel column chromatography (petroleum ether:ethyl acetate=30:1) to give the title compound (1.00 g, 95% purity, 86% yield) as light yellow oil. LC-MS (ESI): R$_T$=1.35 min, mass calcd. for C$_{17}$H$_{24}$O$_3$ 276.2, m/z found 294.0 [M+NH$_4$]+. $^1$H NMR (400 MHz, CDCl$_3$) δ 7.36-7.27 (m, 5H), 4.51 (s, 2H), 3.67 (s, 1.8H), 3.66 (s, 1.2H), 3.29 (s, 0.8H), 3.13 (s, 1.2H), 2.32-2.18 (m, 1H), 1.81-1.52 (m, 4.8H), 1.48-1.45 (m, 1.2H), 1.39-1.32 (m, 1.2H), 1.19-1.11 (m, 0.8H), 0.97 (s, 1.2H), 0.96 (s, 1.8H).

Intermediate 15i: Methyl 4-(hydroxymethyl)-4-methylcyclohexanecarboxylate

To the solution of methyl 4-((benzyloxy)methyl)-4-methylcyclohexanecarboxylate Intermediate 15h (1.00 g, 95% purity, 3.44 mmol) in methanol (30 mL) was added 10% palladium on charcoal (250 mg). After stirred at 30° C. under hydrogen atmosphere (50 psi) overnight, the mixture was filtered and the filtrate was concentrated to give the title compound (670 mg, 95% purity, 99% yield) as colorless oil. $^1$H NMR (400 MHz, CDCl$_3$) δ 3.68 (s, 1.8H), 3.67 (s, 1.2H), 3.48 (s, 0.8H), 3.31 (s, 1.2H), 2.35-2.18 (m, 1H), 1.85-1.73 (m, 2H), 1.69-1.58 (m, 2H), 1.45-1.42 (m, 1H), 1.32-1.24 (m, 2H), 1.20-1.13 (m, 1H), 0.94 (s, 1.8H), 0.93 (s, 1.2H).

Intermediate 15j: Methyl 4-methyl-4-(((methylsulfonyl)oxy)methyl)-cyclohexanecarboxylate To the solution of methyl 4-(hydroxymethyl)-4-methylcyclohexanecarboxylate Intermediate 15i (670 mg, 95% purity, 3.42 mmol) in dichloromethane (5 mL) was added N,N-diisopropylethylamine (650 mg, 5.03 mmol) and methanesulfonyl chloride (500 mg, 4.37 mmol) at room temperature. After stirred at 30° C. under nitrogen atmosphere overnight, the mixture was concentrated and diluted with water (10 mL) and extracted with ethyl acetate (20 mL) twice. The combined organic layers was washed with brine (20 mL), dried over Na$_2$SO$_{4(s)}$ and filtered. The filtrate was concentrated to give title compound (1.07 g, 80% purity, 95% yield) as brown oil. $^1$H NMR (400 MHz, CDCl$_3$) δ 4.06 (s, 0.8H), 3.89 (s, 1.2H), 3.69 (s, 1.4H), 3.68 (s, 1.6H), 3.02 (s, 3H), 2.36-2.20 (m, 1H), 1.87-1.80 (m, 1.8H), 1.69-1.63 (m, 3H), 1.52-1.49 (m, 1.2H), 1.37-1.23 (m, 2H), 1.02 (s, 1.8H), 1.01 (s, 1.2H).

Intermediate 15k: Methyl 4-((acetylthio)methyl)-4-methylcyclohexanecarboxylate To the solution of methyl 4-methyl-4-(((methylsulfonyl)oxy)methyl)cyclohexanecarboxylate Intermediate 15j (1.07 g, 80% purity, 3.24 mmol) in N,N-dimethylformamide (10 mL) was added potassium thioacetate (1.20 g, 10.5 mmol). After stirred at 80° C. under nitrogen atmosphere for 5 hours, the mixture was poured into water (40 mL) and extracted with ethyl acetate (30 mL) twice. The combined organic layers was washed with brine (50 mL), dried over Na$_2$SO$_{4(s)}$ and filtered. The filtrate was concentrated and purified by silica gel column chromatography (petroleum ether:ethyl acetate=50:1 to 20:1) to give the title compound (340 mg, 90% purity, 39% yield) as brown oil. $^1$H NMR (400 MHz, CDCl$_3$) δ 3.67 (s, 1.6H), 3.66 (s, 1.4H), 2.99 (s, 1H), 2.86 (s, 1H), 2.35 (s, 1.6H), 2.34 (s, 1.4H), 2.28-2.19 (m, 1H), 1.81-1.58 (m, 5.6H), 1.49-1.46 (m, 1.1H), 1.26-1.19 (m, 1.3H), 0.94 (s, 1.4H), 0.89 (s, 1.6H).

Sulfonyl chloride 15: Methyl 4-((chlorosulfonyl)methyl)-4-methylcyclohexanecarboxylate To the solution of methyl 4-((acetylthio)methyl)-4-methylcyclohexanecarboxylate Intermediate 15k (340 mg, 90% purity, 1.25 mmol) in acetonitrile (5 mL) was added 2M hydrochloride aqueous solution (0.2 mL) and N-chlorosuccinimide (0.68 g, 4.99 mmol) at 0° C. After stirred at 0° C. for 2 hours, the mixture was diluted with water (20 mL) and extracted with ethyl acetate (20 mL) twice. The combined organic layers were concentrated and purified by silica gel chromatography (petroleum ether:ethyl acetate=30:1 to 10:1) to give the title compound (280 mg, 90% purity, 75% yield) as yellow oil. $^1$H NMR (400 MHz, CDCl$_3$) δ 3.91 (s, 1H), 3.78 (s, 1H), 3.69 (s, 1.6H), 3.68 (s, 1.4H), 2.38-2.25 (m, 1H), 1.90-1.48 (m, 8H), 1.32 (s, 1.6H), 1.31 (s, 1.4H).

Sulfonyl Chloride 16: Methyl 3-((chlorosulfonyl)methyl)bicyclo[1.1.1]pentane-1-carboxylate

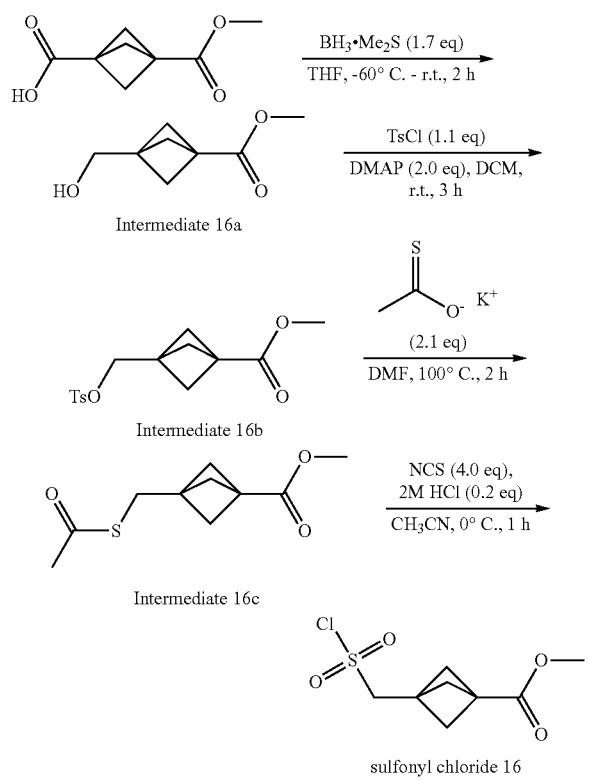

Intermediate 16a: Methyl 3-(hydroxymethyl)bicyclo[1.1.1]pentane-1-carboxylate

To a solution of 3-(methoxycarbonyl)bicyclo[1.1.1]pentane-1-carboxylic acid (5.00 g, 29.4 mmol) in tetrahydrofuran (80 mL) was added 10 M borane-dimethylsulfide complex (5 mL, 50.0 mmol) at −60° C. under nitrogen atmosphere. After stirred at room temperature for 2 hours under nitrogen atmosphere, the mixture was concentrated under reduced pressure to give a residue, which was dissolved in dichloromethane (20 mL) and washed with saturated sodium bicarbonate aqueous solution (20 mL) twice. The combined aqueous layers were extracted with dichloromethane (60 mL) twice. The combined organic layers were dried over Na$_2$SO$_{4(s)}$, filtered and concentrated under reduced pressure to give the title compound (4.00 g, 90% purity from $^1$H NMR, 78% yield) as colorless oil. $^1$H NMR (400 MHz, CDCl$_3$) δ 3.68 (s, 3H), 3.63 (s, 2H), 2.00 (s, 6H).

Intermediate 16b: Methyl 3-((tosyloxy)methyl)bicyclo[1.1.1]pentane-1-carboxylate To a solution of methyl 4-(hydroxymethyl)bicyclo[1.1.1]pentane-2-carboxylate Intermediate 16a (1.00 g, 90% purity, 5.77 mmol) in dichloromethane (10 mL) was added 4-methylbenzene-1-sulfonyl chloride (1.20 g, 6.30 mmol) and N,N-dimethylpyridin-4-amine (1.40 g, 11.5 mmol) at room temperature. After stirred at room temperature for 3 hours, the mixture was concentrated under reduced pressure to give a residue, which was diluted in water (10 mL), acidified with 1 M hydrochloride aqueous solution (2 mL) to pH~7, and extracted with ethyl acetate (50 mL) twice. The combined organic layers were washed with water (20 mL) twice and brine (20 mL), dried over Na$_2$SO$_{4(s)}$ and filtered. The filtrate was concentrated under reduced pressure to afford a residue, which was purified by silica gel column chromatography (petroleum ether:ethyl acetate=5:1 to 2:1) to give the title compound (1.70 g, 90% purity from $^1$H NMR, 86% yield) as white solids. $^1$H NMR (400 MHz, CDCl$_3$) δ 7.78 (d, J=8.4 Hz, 2H), 7.35 (d, J=8.0 Hz, 2H), 4.03 (s, 2H), 3.66 (s, 3H), 2.46 (s, 3H), 1.97 (s, 6H).

Intermediate 16c: Methyl 3-((acetylthio)methyl)bicyclo[1.1.1]pentane-1-carboxylate To a solution of methyl 4-(hydroxymethyl)bicyclo[1.1.1]pentane-2-carboxylate Intermediate 16b (1.70 g, 90% purity, 4.93 mmol) in N,N-dimethylformamide (5 mL) was added potassium thioacetate (1.20 g, 10.5 mmol) at room temperature. After stirred at 100° C. for 2 hours, the mixture was dissolved in ethyl acetate (40 mL) and washed with saturated sodium bicarbonate (60 mL) twice. The combined aqueous layers were extracted with ethyl acetate (80 mL) twice. The combined organic layers were washed with water (30 mL) twice and brine (30 mL), dried over Na$_2$SO$_{4(s)}$ and filtered. The filtrate was concentrated under reduced pressure to give the title compound (1.10 g, 90% purity from $^1$H NMR, 94% yield) as brown oil. $^1$H NMR (400 MHz, CDCl$_3$) δ 3.66 (s, 3H), 3.03 (s, 2H), 2.35 (s, 3H), 1.96 (s, 6H).

Sulfonyl Chloride 16: Methyl 3-((chlorosulfonyl)methyl)bicyclo[1.1.1]pentane-1-carboxylate To a solution of methyl 3-((acetylthio)methyl)bicyclo[1.1.1]pentane-1-carboxylate Intermediate 16c (1.10 g, 90% purity, 4.62 mmol) in acetonitrile (5 mL) was added 2 M hydrochloride aqueous solution (0.5 mL, 1.00 mmol) and 1-chloropyrrolidine-2,5-dione (2.46 g, 18.4 mmol). After stirred at 0° C. for 1 hour, the mixture was concentrated to give a residue, which was diluted water (10 mL) and extracted with ethyl acetate (40 mL) twice. The combined organic layers were washed with water (15 mL) twice and brine (15 mL), dried over Na$_2$SO$_{4(s)}$ and filtered. The filtrate was concentrated under reduced pressure to give a residue, which was purified by silica gel column chromatography (petroleum ether:ethyl acetate=10:1) to give the title compound (1.10 g, 90% purity from $^1$H NMR, 90% yield) as yellow solids. $^1$H NMR (400 MHz, CDCl$_3$) δ 3.93 (s, 2H), 3.70 (s, 3H), 2.31 (s, 6H).

Sulfonyl Chloride 17:
1-(3-Hydroxy-3-methylbutyl)-1H-pyrazole-4-sulfonyl Chloride

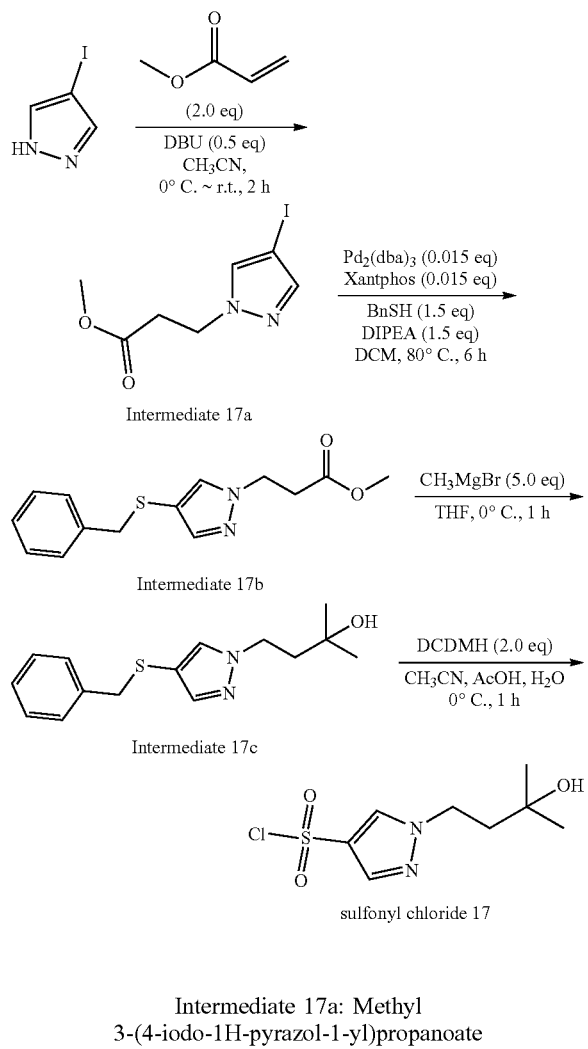

Intermediate 17a: Methyl 3-(4-iodo-1H-pyrazol-1-yl)propanoate

To a solution of methyl 4-iodo-1H-pyrazole (3.00 g, 15.5 mmol) in acetonitrile (45 mL) was added 1,8-diazabicyclo[5.4.0]undec-7-ene (1.17 g, 7.73 mmol) at 0° C., followed by methyl acrylate (2.65 g, 30.9 mmol). After stirred at room temperature for 2 hours, the reaction mixture was quenched with 1 M hydrochloride aqueous solution (30 mL) and extracted with ethyl acetate (30 mL) twice. The combined organic layers were washed with water (20 mL) and brine (20 mL) twice, dried over Na$_2$SO$_{4(s)}$ and filtered. The filtrate was concentrated under reduced pressure to give the title compound (1.00 g, 77% yield) as brown solids. $^1$H NMR (400 MHz, CDCl$_3$) δ 7.50 (s, 2H), 4.42 (t, J=6.4 Hz, 2H), 3.69 (s, 3H), 2.88 (t, J=6.4 Hz, 2H).

Intermediate 17b: Methyl 3-(4-(benzylthio)-1H-pyrazol-1-yl)propanoate

To a solution of methyl 3-(4-iodo-1H-pyrazol-1-yl)propanoate Intermediate 17a (3.30 g, 11.8 mmol) and phenylmethanethiol (2.20 g, 17.7 mmol) in 1,4-dioxane (50 mL) was added N,N-diisopropylethylamine (2.30 g, 17.8 mmol) under nitrogen atmosphere, followed by 4,5-bis(diphenylphosphino)-9,9-dimethylxanthene (102 mg, 0.177 mmol) and tris(dibenzylideneacetone)dipalladium (162 mg, 0.177 mmol) under nitrogen atmosphere. After stirred at 80° C. for 6 hours, the reaction mixture was cooled down to room temperature and concentrated under reduced pressure to give a residue, which was purified by silica gel column chromatography (petroleum ether:ethyl acetate=4:1) to give the title compound (1.60 g, 50% yield) as brown oil. LC-MS (ESI): R$_T$=2.275 min, mass calcd. for C$_{14}$H$_{16}$N$_2$O$_2$S 276.1, m/z found 277.1 [M+H]$^+$.

Intermediate 17c: 4-(4-(Benzylthio)-1H-pyrazol-1-yl)-2-methylbutan-2-ol

To a solution of methyl 3-(4-(benzylthio)-1H-pyrazol-1-yl)propanoate Intermediate 17b (500 mg, 1.80 mmol) in tetrahydrofuran (20 mL) was added 3 M methylmagnesium bromide in tetrahydrofuran (3 mL, 9.00 mmol) at 0° C. After stirred at 0° C. for 1 hour, the reaction mixture was quenched with 1 M hydrochloride aqueous solution (20 mL) and extracted with ethyl acetate (30 mL) twice. The combined organic layers were washed with brine (50 mL) twice, dried over Na$_2$SO$_{4(s)}$ and filtered. The filtrate was concentrated under reduced pressure to give the crude product, which was purified by C18 column (acetonitrile:water=40% to 60%) to give the title compound (200 mg, 40% yield) as colorless oil. LC-MS (ESI): R$_T$=2.089 min, mass calcd. for C$_{15}$H$_{20}$N$_2$OS 276.1, m/z found 277.1 [M+H]$^+$. $^1$HNMR (400 MHz, CDCl$_3$) δ 7.32 (s, 1H), 7.25-7.20 (m, 2H), 7.17-7.10 (m, 4H), 4.18 (t, J=7.2 Hz, 2H), 3.76 (s, 2H), 2.26 (br s, 1H), 1.96 (t, J=7.2 Hz, 2H), 1.24 (s, 6H).

Sulfonyl Chloride 17:
1-(3-Hydroxy-3-methylbutyl)-1H-pyrazole-4-sulfonyl Chloride To a solution of 4-(4-(benzylthio)-1H-pyrazol-1-yl)-2-methylbutan-2-ol Intermediate 17c (200 mg, 0.722 mmol) in acetonitrile (10 mL) and water (0.2 mL) were added acetic acid (0.2 mL) and 1,3-dichloro-5,5-dimethylhydantoin (284 mg, 1.44 mmol) at 0° C. under nitrogen atmosphere. After stirred at 0° C. for 1 hour, the mixture was diluted with water (20 mL) and extracted with ethyl acetate (20 mL) for three times. The combined organic layers were washed with brine (20 mL) twice, dried over Na$_2$SO$_{4(s)}$, filtered and concentrated under reduced pressure to give the title compound (200 mg, 50% purity, 55% yield) as colorless oil. LC-MS (ESI): R$_T$=2.038 min, mass calcd. for C$_8$H$_{13}$ClN$_2$O$_3$S 252.0, m/z found 252.9 [M+H]$^+$.

Sulfonyl Chloride 18:
2-(2-(2-Methoxyethoxy)ethoxy)ethanesulfonyl Chloride

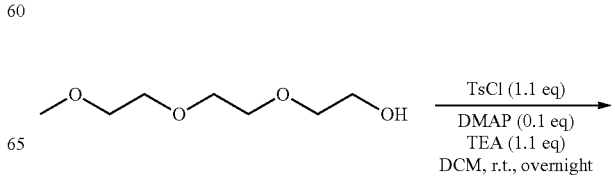

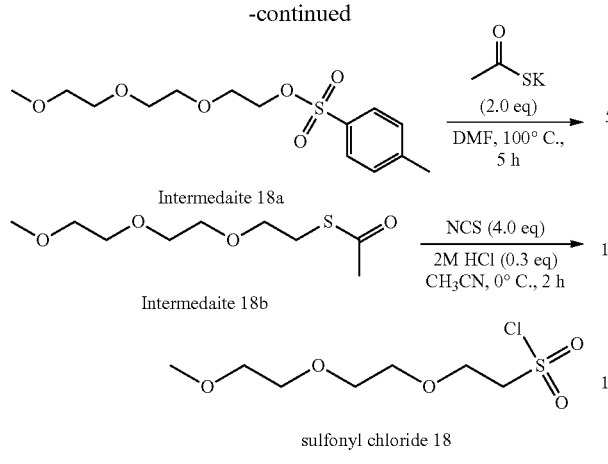

Intermediate 18a: 2-(2-(2-Methoxyethoxy)ethoxy)ethyl 4-methylbenzenesulfonate To a solution of 2-(2-(2-methoxyethoxy)ethoxy)ethanol (5.00 g, 30.5 mmol) in dichloromethane (70 mL) was added N,N-dimethylpyridin-4-amine (366 mg, 3.00 mmol), triethylamine (3.30 g, 32.7 mmol) and 4-methylbenzene-1-sulfonyl chloride (6.30 g, 33.1 mmol) at room temperature. After stirred at room temperature under nitrogen atmosphere overnight, the mixture was washed with 1 M hydrochloride aqueous solution (50 mL) for three times and brine (80 mL), dried over $Na_2SO_{4(s)}$ and filtered. The filtrate was concentrated under reduced pressure to give the title compound (8.30 g, 86% yield) as white oil. $^1$H NMR (300 MHz, $CDCl_3$) δ 7.82-7.79 (m, 2H), 7.36-7.34 (m, 2H), 4.17 (s, 2H), 3.69-3.54 (m, 10H), 3.38 (s, 3H), 2.46 (s, 3H).

Intermediate 18b: S-(2-(2-(2-Methoxyethoxy)ethoxy)ethyl) ethanethioate

To a solution of 2-(2-(2-methoxyethoxy)ethoxy)ethyl 4-methylbenzenesulfonate Intermediate 18a (1.50 g, 4.71 mmol) in N,N-dimethylformamide (25 mL) was added potassium ethanethioate (1.08 g, 9.47 mmol) at room temperature. After stirred at 100° C. under nitrogen atmosphere for 5 hours, it was cooled down to room temperature and poured into water (100 mL), extracted with ethyl acetate (50 mL) for three times. The combined organic layers were washed with brine (80 mL), dried over $Na_2SO_{4(s)}$ and filtered. The filtrate was concentrated under reduced pressure to give the title compound (1.10 g, 90% purity from $^1$H NMR, 95% yield) as brown oil. $^1$H NMR (300 MHz, $CDCl_3$) δ 3.62-3.54 (m, 10H), 3.37 (s, 3H), 3.08 (br s, 2H), 2.32 (s, 3H).

Sulfonyl Chloride 18: 2-(2-(2-Methoxyethoxy)ethoxy)ethanesulfonyl Chloride

To a solution of S-(2-(2-(2-methoxyethoxy)ethoxy)ethyl) ethanethioate Intermediate 18b (873 mg, 90% purity, 3.54 mmol) in acetonitrile (10 mL) was added 2 M hydrochloride aqueous solution (0.5 mL) and 1-chloropyrrolidine-2,5-dione (1.89 g, 14.2 mmol) at 0° C. After stirred at this temperature under nitrogen atmosphere for 2 hours, the mixture was quenched with water (30 mL) and extracted with ethyl acetate (30 mL) twice. The combined organic layers were washed with brine (50 mL), dried over $Na_2SO_{4(s)}$ and filtered. The filtrate was concentrated under reduced pressure to give the title compound (900 mg, 94% purity from $^1$H NMR, 97% yield) as white oil. $^1$H NMR (400 MHz, $CDCl_3$) δ 4.15-4.09 (m, 2H), 4.02-3.99 (m, 2H), 3.73-3.71 (m, 2H), 3.67-3.64 (m, 4H), 3.57-3.55 (m, 2H), 3.38 (d, J=1.2 Hz, 3H).

Sulfonyl Chloride 19: 2,5,8,11-Tetraoxatridecane-13-sulfonyl Chloride

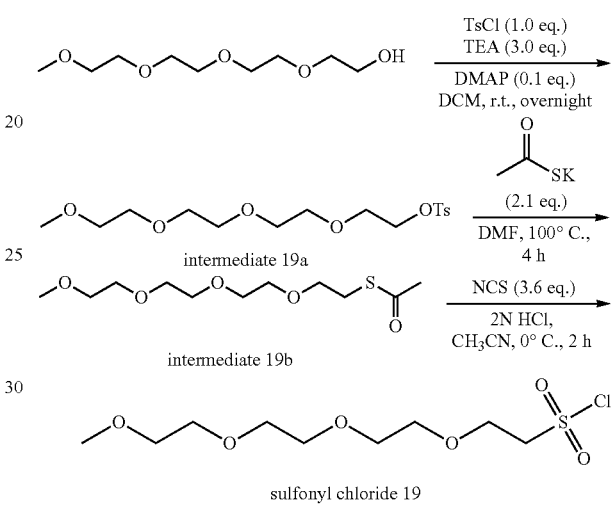

Intermediate 19a: 2,5,8,11-Tetraoxatridecan-13-yl 4-methylbenzenesulfonate

To a solution of 2,5,8,11-tetraoxatridecan-13-ol (1.50 g, 7.21 mmol), triethylamine (2.18 g, 21.6 mmol) and N,N-dimethylpyridin-4-amine (88 mg, 0.720 mmol) in dichloromethane (30 mL) was added 4-methylbenzene-1-sulfonyl chloride (1.37 g, 7.19 mmol) under nitrogen atmosphere. After stirred at room temperature overnight, the reaction mixture was washed with water (30 mL) for three times, dried over $Na_2SO_{4(s)}$ and filtered. The filtrate was concentrated under reduced pressure to afford the title compound (1.80 g, 86% yield) as colorless oil. $^1$H NMR (300 MHz, $CDCl_3$) δ 7.82-7.79 (m, 2H), 7.36-7.27 (m, 2H), 4.16 (s, 2H), 3.70-3.56 (m, 14H), 3.38 (s, 3H), 2.45 (s, 3H).

Intermediate 19b: S-2,5,8,11-Tetraoxatridecan-13-yl ethanethioate

To a solution of 2,5,8,11-tetraoxatridecan-13-yl 4-methylbenzenesulfonate Intermediate 19a (1.00 g, 2.76 mmol) in N,N-dimethylformamide (20 mL) was added potassium thioacetate (670 mg, 5.88 mmol) at room temperature. After stirring at 100° C. for 4 hours, the reaction mixture was cooled down to room temperature, poured into water (20 mL) and extracted with ethyl acetate (40 mL) for three times. The combined organic layers were washed with water (20 mL) for three times, dried over $Na_2SO_{4(s)}$ and filtered. The filtrate was concentrated to afford the title compound (800 mg, 95% yield) as colorless oil. $^1$H NMR (300 MHz, CDCl$_3$) δ 3.67-3.55 (m, 14H), 3.39-3.67 (m, 3H), 3.12-3.06 (m, 2H), 2.34-2.32 (sm, 3H).

Sulfonyl Chloride 19:
2,5,8,11-Tetraoxatridecane-13-sulfonyl Chloride

To a solution of S-2,5,8,11-tetraoxatridecan-13-yl ethanethioate Intermediate 19b (600 mg, 2.26 mmol) in acetonitrile (8 mL) was added 2 M hydrochloride aqueous solution (0.35 mL) and 1-chloropyrrolidine-2,5-dione (1.10 g, 8.24 mmol) at 0° C. After stirred at 0° C. for 2 hours, the mixture was concentrated under reduced pressure to give a residue, which was diluted with water (30 mL), extracted with ethyl acetate (20 mL) for three times. The combined organic layers were washed with water (20 mL) for three times, dried over Na$_2$SO$_{4(s)}$ and filtered. The filtrate was concentrated to afford the title compound (400 mg, 64% yield) as colorless oil. $^1$H NMR (300 MHz, CDCl$_3$) δ 4.07-3.87 (m, 4H), 3.63-3.41 (m, 12H), 3.35 (s, 3H).

Sulfonyl Chloride 20: 2,2-Dimethyl-3,3-diphenyl-4,7,10-trioxa-3-siladodecane-12-sulfonyl Chloride

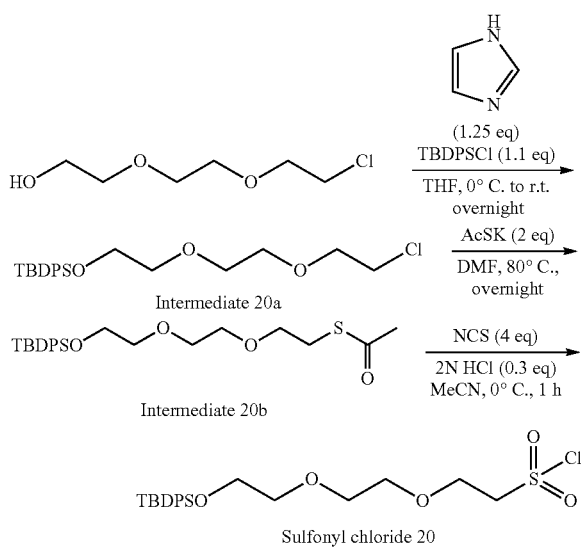

Intermediate 20a: 12-Chloro-2,2-dimethyl-3,3-diphenyl-4,7,10-trioxa-3-siladodecane To a solution of 2-(2-(2-chloroethoxy)ethoxy)ethanol (5.04 g, 29.9 mmol) in tetrahydrofuran (45 mL) was added 1H-imidazole (2.55 g, 37.5 mmol) and tert-butylchlorodiphenylsilane (9.06 g, 33.0 mmol) at 0° C. After stirred at room temperature overnight, the mixture was added water (20 mL) and extracted with ethyl acetate (20 mL) for three times. The combined organic layers were dried over Na$_2$SO$_{4(s)}$, filtered and concentrated to afford the crude product (13 g, crude) as colorless oil, which was used for the next step without further purification. LC-MS (ESI): R$_T$=2.180 min, mass calcd. for C$_{22}$H$_{31}$ClO$_3$Si 406.2, m/z found 424.1 [M+NH$_4$]$^+$.

Intermediate 20b: 12-Chloro-2,2-dimethyl-3,3-diphenyl-4,7,10-trioxa-3-siladodecane To a solution of 12-chloro-2,2-dimethyl-3,3-diphenyl-4,7,10-trioxa-3-siladodecane Intermediate 20a (12 g, 29.5 mmol) in N,N-dimethylformamide (50 mL) was added potassium ethanethioate (6.74 g, 59.1 mmol) at room temperature. After stirred at 80° C. overnight, the mixture was allowed to cool down to room temperature, poured into water (200 mL) and extracted with ethyl acetate (200 mL) twice, the combined organic layers were washed with brine (100 mL), dried over Na$_2$SO$_{4(s)}$, filtered and concentrated to give a residue, which was purified by silica gel column chromatography (petroleum ether:ethyl acetate=40:1 to 20:1) to give the title compound (7.50 g, 56% yield) as yellow oil. $^1$H NMR (400 MHz, CDCl$_3$) δ 7.70-7.67 (m, 4H), 7.42-7.36 (m, 6H), 3.81 (t, J=5.2 Hz, 2H), 3.64-3.58 (m, 8H), 3.08 (t, J=6.4 Hz, 2H), 2.32 (s, 3H), 1.05 (s, 9H).

Sulfonyl Chloride 20: 2,2-Dimethyl-3,3-diphenyl-4,7,10-trioxa-3-siladodecane-12-sulfonyl Chloride To a solution of 12-chloro-2,2-dimethyl-3,3-diphenyl-4,7,10-trioxa-3-siladodecane Intermediate 20b (2.23 g, 5.00 mmol) in acetonitrile (20 mL) was added 2 N hydrochloride aqueous solution (0.75 mL, 1.5 mmol) and N-chlorosuccinimide (2.67 g, 20.0 mmol) at 0° C. After stirred at 0° C. for 1 hour, the mixture was quenched with water (50 mL) and extracted with dichloromethane (50 mL) twice, the combined organic layers were washed with brine (50 mL), dried over Na$_2$SO$_{4(s)}$, filtered and concentrated to give a residue, which was purified by silica gel column chromatography (petroleum ether:ethyl acetate=30:1 to 20:1) to give the title compound (0.50 g, 20% yield) as yellow oil. $^1$H NMR (300 MHz, CDCl$_3$) δ 7.67-7.63 (m, 4H), 7.39-7.25 (m, 6H), 4.09-4.03 (m, 2H), 3.91-3.85 (m, 2H), 3.81-3.77 (m, 2H), 3.65-3.58 (m, 6H), 1.04 (s, 9H).

Sulfonyl Chloride 21: (trans)-tert-Butyl 3-(4-(chlorosulfonyl)-1H-pyrazol-1-yl)cyclobutanecarboxylate

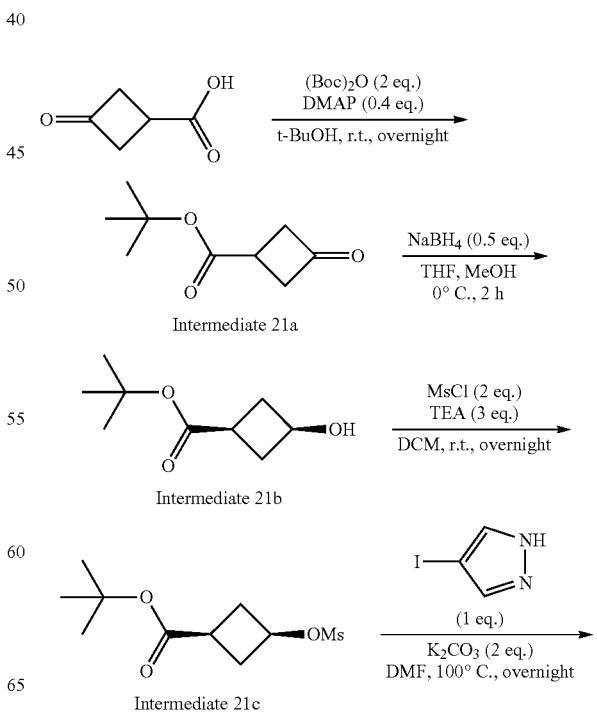

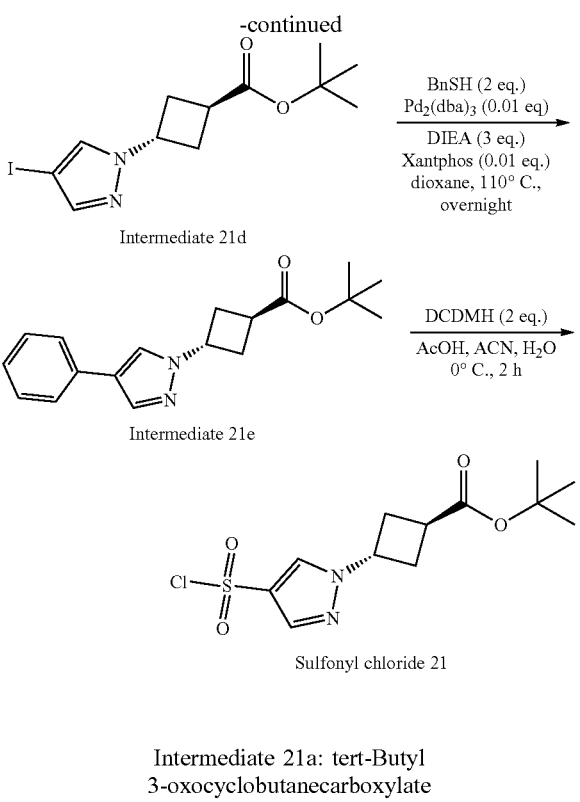

Intermediate 21a: tert-Butyl 3-oxocyclobutanecarboxylate

To a solution of 3-oxocyclobutanecarboxylic acid (8.0 g, 70 mmol) and di-tert-butyl pyrocarbonate (31.0 g, 140 mmol) in tert-butanol (150 mL) was added 4-dimethylaminopyridine (3.4 g, 28 mmol) at 0° C. under nitrogen atmosphere. After stirred at room temperature overnight, the mixture was quenched with water (80 mL), then concentrated under reduced pressure to remove the volatile, extracted with ethyl acetate (200 mL) for three times. The combined organic layers were washed with 2 M hydrochloride aqueous solution (100 mL), dried over $Na_2SO_{4(s)}$ and concentrated to give a residue, which was purified by silica gel column chromatography (petroleum ether:ethyl acetate=10:1) to afford the title compound (10 g, 70% yield) as light yellow oil. $^1$H NMR (300 MHz, $CDCl_3$) δ 3.34-2.96 (m, 5H), 1.40 (s, 9H).

Intermediate 21b: (cis)-tert-Butyl 3-hydroxycyclobutanecarboxylate

To a solution of tert-butyl 3-oxocyclobutanecarboxylate Intermediate 21a (10 g, 46.7 mmol) in tetrahydrofuran (60 mL) and methanol (20 mL) was added sodium borohydride (900 mg, 23.0 mmol) portionwise under nitrogen atmosphere. After stirred at 0° C. for 2 hours, the mixture was quenched with water (20 mL) and extracted with ethyl acetate (100 mL) for three times. The combined organic layers were dried over $Na_2SO_{4(s)}$ and concentrated to afford the title compound (7 g, 70% yield) as yellow oil. $^1$H NMR (300 MHz, DMSO-$d_6$) δ 5.22-5.14 (m, 1H), 4.04-3.92 (m, 1H), 2.55-2.31 (m, 3H), 2.08-1.88 (m, 2H), 1.43 (s, 9H).

Intermediate 21c: (cis)-tert-Butyl 3-((methylsulfonyl)oxy)cyclobutanecarboxylate To a solution of (cis)-tert-butyl 3-hydroxycyclobutanecarboxylate Intermediate 21b (5.0 g, 23 mmol) in dichloromethane (30 mL) was added methanesulfonyl chloride (5.3 g, 46 mmol) and triethylamine (7.0 g, 69 mmol) under nitrogen atmosphere. After stirred at room temperature overnight, the reaction mixture was washed with water (40 mL), dried over $Na_2SO_{4(s)}$ and concentrated under reduced pressure to afford the title compound (7 g, 85% yield) as white solids. $^1$H NMR (300 MHz, $CDCl_3$) δ 4.89-4.80 (m, 1H), 2.95 (s, 3H), 2.67-2.41 (m, 5H), 1.39 (s, 9H).

Intermediate 21d: (trans)-tert-Butyl 3-(4-iodo-1H-pyrazol-1-yl)cyclobutanecarboxylate To a solution of (cis)-tert-butyl 3-((methylsulfonyl)oxy) cyclobutanecarboxylate Intermediate 21c (3.5 g, 14 mmol) in N,N-dimethylformamide (30 mL) was added 4-iodo-1H-pyrazole (2.7 g, 14 mmol) and potassium carbonate (3.9 g, 28 mmol) at room temperature. After stirred at 100° C. overnight, the reaction mixture was cooled down to room temperature, poured into water (100 mL) and extracted with ethyl acetate (80 mL) for three times. The combined organic layers were washed with brine (80 mL) for three times, dried over $Na_2SO_{4(s)}$ and concentrated to give a residue, which was purified by silica gel column chromatography (petroleum ether:ethyl acetate=20:1) to afford the title compound (2.8 g, 60% yield) as white solids. 1H NMR (300 MHz, $CDCl_3$) δ 7.53 (s, 1H), 7.44 (s, 1H), 5.04-4.86 (m, 1H), 3.09-2.94 (m, 1H), 2.87-2.60 (m, 4H), 1.49-1.38 (m, 9H).

Intermediate 21e: (trans)-tert-Butyl 3-(4-(benzylthio)-1H-pyrazol-1-yl)cyclobutanecarboxylate To a solution of (trans)-tert-butyl 3-(4-iodo-1H-pyrazol-1-yl)cyclobutanecarboxylate Intermediate 21d (2.80 g, 7.24 mmol) in dioxane (20 mL) was treated sequentially with phenylmethanethiol (1.80 g, 14.5 mmol) and N,N-diisopropylethylamine (2.80 g, 21.7 mmol) under nitrogen atmosphere. And then the reaction mixture was added tris(dibenzylideneacetone)dipalladium (67 mg, 0.073 mmol) and 9,9-dimethyl-4,5-bis(diphenylphosphino)xanthene (42 mg, 0.073 mmol) under nitrogen atmosphere. After heated to 110° C. overnight, the reaction mixture was cooled down to room temperature, diluted with water (20 mL), extracted with ethyl acetate (20 mL) twice. The combined extracts were washed with brine (40 mL), dried over $Na_2SO_{4(s)}$, filtered and concentrated to give a residue, which was purified by silica gel column chromatography (petroleum ether:ethyl acetate=5:1) to give the desired compound (1.7 g, 90% purity, 61% yield) as white solids. $^1$H NMR (300 MHz, $CDCl_3$) δ 7.40-7.29 (m, 5H), 7.17-7.07 (m, 2H), 4.93-4.80 (m, 1H), 3.78 (s, 2H), 3.11-2.96 (m, 1H), 2.80-2.57 (m, 4H), 1.49 (s, 9H).

Sulfonyl Chloride 21: (trans)-tert-Butyl 3-(4-(chlorosulfonyl)-1H-pyrazol-1-yl)cyclobutanecarboxylate To the solution of (trans)-tert-butyl 3-(4-(benzylthio)-1H-pyrazol-1-yl)cyclobutanecarboxylate Intermediate 21e (1.5 g, 3.919 mmol) in acetonitrile (20 mL) was added acetic acid (5 mL) and water (3 mL) at 0° C. Then 1,3-dichloro-5,5-dimethylhydantoin (1.5 g, 7.613 mmol) was added in portions over 10 minutes. After stirred at 0° C. for 2 hours, the reaction mixture was quenched with water (20 mL), concentrated under reduced pressure to remove the volatile and extracted with ethyl acetate (30 mL). The organic phase was washed with brine (20 mL), dried over $Na_2SO_{4(s)}$, filtered and concentrated to give a residue, which was purified by C18 column (acetonitrile:water=60% to 80%) to give the desired compound (800 mg, 57% yield) as white solids. $^1$H NMR (300 MHz, CDCl$_3$) δ 8.05 (s, 1H), 8.02 (s, 1H), 5.10-5.00 (m, 1H), 3.21-3.05 (m, 1H), 2.91-2.69 (m, 4H), 1.49 (s, 9H).

Sulfonyl Chloride 22: (trans)-Ethyl 2-(4-(chlorosulfonyl)cyclohexyl)acetate

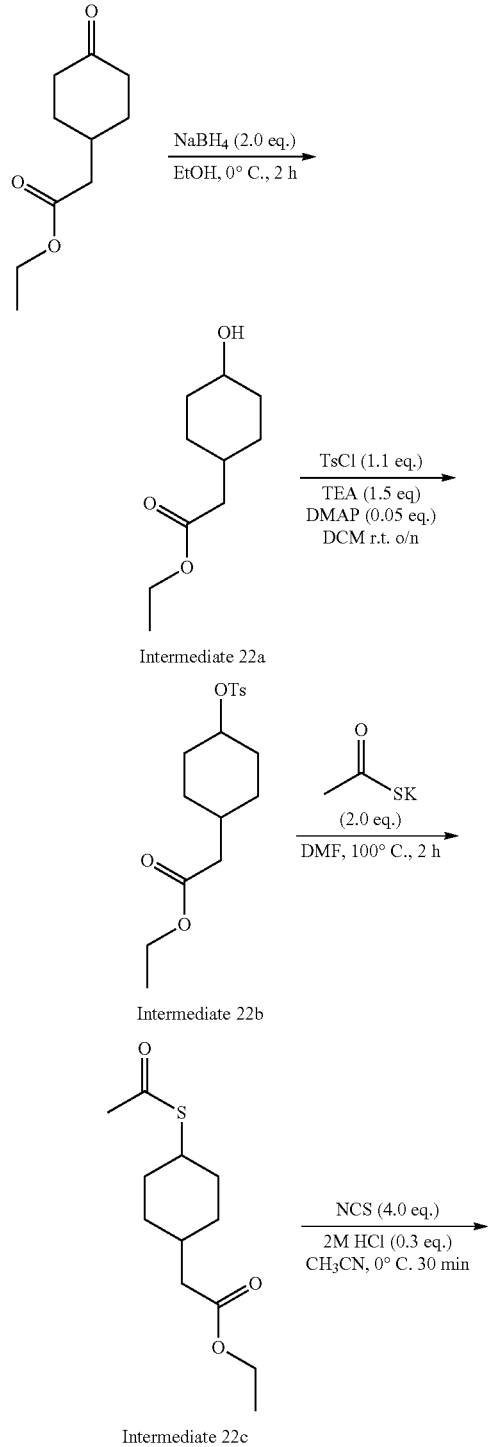

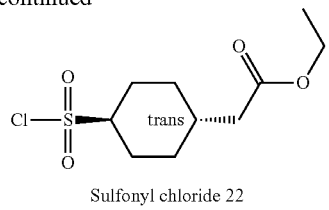

Sulfonyl chloride 22

Intermediate 22a: Ethyl 2-(4-hydroxycyclohexyl)acetate

To a solution of ethyl 2-(4-oxocyclohexyl)acetate (5.00 g, 26.6 mmol) in ethanol (50 mL) was added slowly sodium tetrahydroborate (2.10 g, 55.5 mmol) at 0° C. under nitrogen atmosphere. After stirred at 0° C. under nitrogen atmosphere for 2 hours, the reaction was quenched with saturated ammonium chloride aqueous solution (150 mL) at 0° C., then concentrated at room temperature under reduced pressure to give a residue, which was dissolved in water (100 mL) and extracted with ethyl acetate (150 mL) for three times. The combined organic layers were washed with brine (100 mL), dried over Na$_2$SO$_{4(s)}$ and filtered. The filtrate was concentrated under reduced pressure to afford the title compound Intermediate 22a (4.80 g, 95% purity from $^1$H NMR, 92% yield) as colorless oil. $^1$H NMR (300 MHz, CDCl$_3$) δ 4.15-4.07 (m, 2H), 4.00-3.92 (m, 0.3H), 3.59-3.48 (m, 0.7H), 2.24-2.08 (m, 2H), 1.98-1.40 (m, 7H), 1.35-0.96 (m, 6H).

Intermediate 22b: Ethyl 2-(4-(tosyloxy)cyclohexyl)acetate

To a solution of ethyl 2-(4-hydroxycyclohexyl)acetate Intermediate 22a (4.80 g, 95% purity, 24.5 mmol) in dichloromethane (100 mL) was added triethylamine (3.80 g, 37.6 mmol), dimethylaminopyridine (153 mg, 1.30 mmol) and tosyl chloride (5.20 g, 27.3 mmol) at 0° C. The resulting mixture was allowed to slowly warm to room temperature and stirred overnight. The reaction mixture was concentrated under reduced pressure to give a residue, which was diluted with ethyl acetate (100 mL) and washed with 20% wt. citric acid aqueous solution (55 mL) twice, water (50 mL), and brine (50 mL) and filtered. The filtrate was concentrated under reduced pressure to afford the title compound Intermediate 22b (4.70 g, 95% purity from $^1$H NMR, 53% yield) as colorless oil. $^1$H NMR (300 MHz, CDCl$_3$) δ 7.78 (d, J=8.1 Hz, 2H), 7.32 (d, J=7.8 Hz, 2H), 4.72 (br s, 0.1H), 4.41-4.31 (m, 0.9H), 4.09 (q, J=7.2 Hz, 2H), 2.43 (s, 3H), 2.20-2.12 (m, 2H), 1.98-1.85 (m, 2H), 1.82-1.69 (m, 3H), 1.56-1.43 (m, 2H), 1.24-1.20 (m, 3H), 1.06-0.82 (m, 2H).

Intermediate 22c: Ethyl 2-(4-(acetylthio)cyclohexyl)acetate

To a solution of ethyl 2-(4-(tosyloxy)cyclohexyl)acetate Intermediate 22b (1.70 g, 95% purity, 4.74 mmol) in N,N-dimethylformamide (17 mL) was added potassium thioacetate (1.09 g, 9.54 mmol) at room temperature. After stirred at 100° C. for 2 hours, the mixture was allowed to cool down to room temperature, water (50 mL) was added into the mixture and it was extracted with ethyl acetate (50 mL) for three times, the combined organic layers were washed with water (50 mL) twice, brine (50 mL), dried over Na$_2$SO$_{4(s)}$ and filtered. The filtrate was concentrated under reduced pressure to give a residue, which was purified by silica gel column chromatography (petroleum ether:ethyl acetate=100:1 to 50:1) to afford the title compound Intermediate 22c (650 mg, 95% purity, 53% yield) as brown oil. $^1$H NMR (300 MHz, CDCl$_3$) δ 4.12 (q, J=7.2 Hz, 2H), 3.91-3.86 (m, 1H), 2.31-2.30 (m, 3H), 2.22 (d, J=7.2 Hz, 2H), 1.93-1.73 (m, 5H), 1.70-1.61 (m, 2H), 1.30-1.19 (m, 5H).

Sulfonyl Chloride 22: (trans)-Ethyl 2-(4-(chlorosulfonyl)cyclohexyl)acetate

To a solution of 1-chloropyrrolidine-2,5-dione (1.35 g, 10.1 mmol) in acetonitrile (13 mL) was added 2 N hydrochloride aqueous solution (0.4 mL, 0.8 mmol) and ethyl 2-(4-(acetylthio)cyclohexyl)acetate Intermediate 22c (0.65 g, 2.5 mmol) at 0° C. After stirred at 0° C. for 30 minutes, the reaction mixture was quenched with water (10 mL) and concentrated under reduced pressure to give a residue, which was dissolved in ethyl acetate (50 mL) and washed with water (30 mL) twice, brine (30 mL), dried over Na$_2$SO$_{4(s)}$, filtered. The filtrate was concentrated under reduced pressure to give a crude product, which was purified by silica gel column chromatography (petroleum ether:ethyl acetate=10:1) to afford the title compound (600 mg, 95% purity from $^1$H NMR, 84% yield) as colorless oil. $^1$H NMR (300 MHz, CDCl$_3$) δ 4.13 (q, J=7.2 Hz, 2H), 3.69-3.61 (m, 1H), 2.36-2.31 (m, 2H), 2.24-2.08 (m, 5H), 1.81-1.63 (m, 4H), 1.25 (t, J=7.2 Hz, 3H).

Sulfonyl Chloride 23: tert-Butyl 2-(3-(chlorosulfonyl)cyclobutyl)acetate

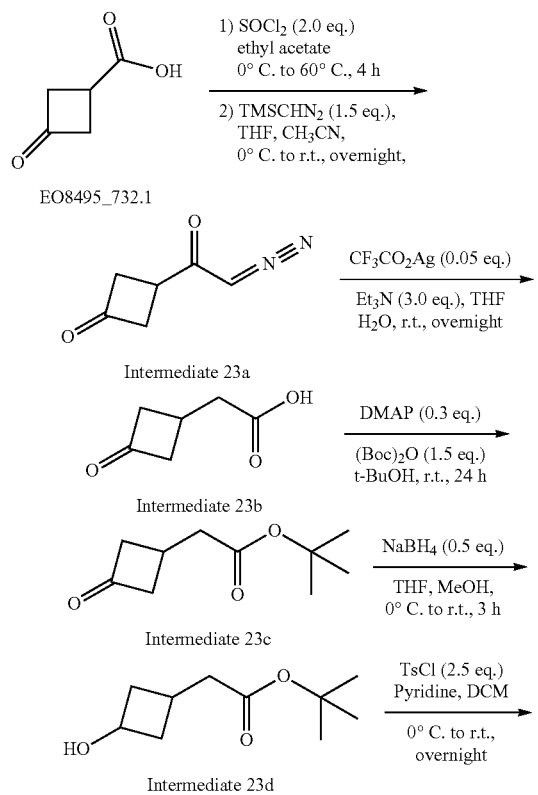

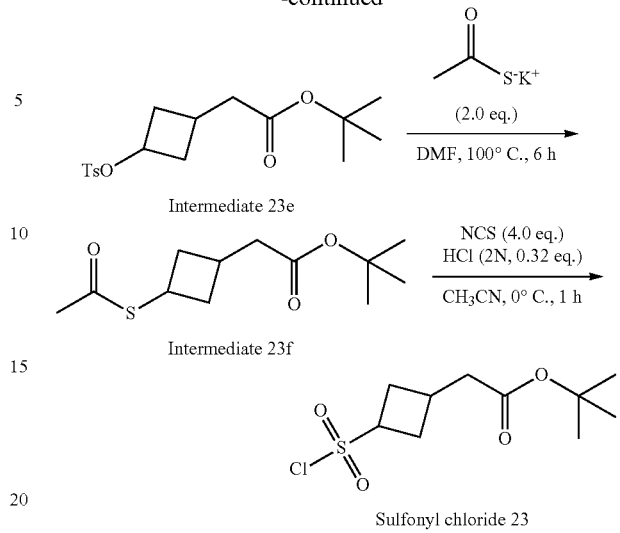

Sulfonyl chloride 23

Intermediate 23a: 3-(2-Diazoacetyl)cyclobutanone

To a solution of 3-oxocyclobutanecarboxylic acid (4.00 g, 35.1 mmol) in ethyl acetate (55 mL) was added thionyl chloride (5.1 mL, 70.1 mmol) at 0° C. and the mixture was stirred at 60° C. for 4 hours under nitrogen atmosphere. After cooled down to room temperature, the reaction was concentrated and azeotroped with toluene to give white solids, which was dissolved in tetrahydrofuran (33 mL) and acetonitrile (33 mL). To this was added a solution of 2.0 M trimethylsilyldiazomethane in hexane (26.3 mL, 52.6 mmol) in tetrahydrofuran (33 mL) and acetonitrile (33 mL) at 0° C. After stirred at room temperature overnight under nitrogen atmosphere, the mixture was quenched with acetic acid (5 mL) and water (20 mL) at 0° C. Then it was concentrated to give a residue, which was diluted with saturated sodium bicarbonate aqueous solution (100 mL). The obtained mixture was extracted with ethyl acetate (100 mL) for three times. The combined organic layers were washed with brine (100 mL), dried over Na$_2$SO$_{4(s)}$ and filtered. The filtrate was concentrated under reduced pressure to give a residue, which was purified by silica gel column chromatography (100% dichloromethane, then petroleum ether:ethyl acetate=1:1) to give the title compound (4.00 g, 90% purity from $^1$H NMR, 74% yield) as yellow oil. $^1$H NMR (300 MHz, CDCl$_3$) δ 5.38 (s, 1H), 3.51-3.38 (m, 2H), 3.30-3.12 (m, 3H).

Intermediate 23b: 2-(3-Oxocyclobutyl)acetic Acid

A solution of 3-(2-diazoacetyl)cyclobutanone Intermediate 23a (4.00 g, 90% purity, 26.1 mmol) in tetrahydrofuran (40 mL) and water (4 mL) was added dropwise to a solution of silver trifluoroacetate (288 mg, 1.30 mmol) and triethylamine (7.91 g, 78.2 mmol) in tetrahydrofuran (70 mL) and water (7 mL) at room temperature about 20 minutes. After stirred at room temperature overnight, the mixture was concentrated to give a residue, which was diluted with water (50 mL), acidified to pH 1-2 with 1 M hydrochloride aqueous solution, extracted with ethyl acetate (80 mL) for three times. The combined organic layers were washed with brine (80 mL), dried over Na$_2$SO$_{4(s)}$ and filtered. The filtrate was concentrated under reduced pressure to give the title compound (3.20 g, 80% purity from $^1$H NMR, 77% yield)

as brown oil. $^1$H NMR (300 MHz, CDCl$_3$) δ 3.46-3.20 (m, 4H), 2.88-2.75 (m, 2H), 2.70-2.68 (m, 1H).

Intermediate 23c: tert-Butyl 2-(3-oxocyclobutyl)acetate

To a solution of 2-(3-oxocyclobutyl)acetic acid Intermediate 23b (3.20 g, 80% purity, 20.0 mmol) and di-tert-butylpyrocarbonate (6.54 g, 30.0 mmol) in tert-butanol (70 mL) was added N,N-dimethylpyridin-4-amine (733 mg, 5.99 mmol) at room temperature. After stirred at room temperature for 24 hours, the reaction mixture was concentrated to give a residue, which was dissolved in ethyl acetate (150 mL). The organic phase was washed with water (80 mL), 0.2 M hydrochloride aqueous solution (80 mL), water (80 mL) and brine (80 mL), dried over Na$_2$SO$_{4(s)}$ and filtered. The filtrate was concentrated under reduced pressure to give a residue, which was purified by silica gel column chromatography (petroleum ether:ethyl acetate=40:1 to 20:1) to give the title compound (750 mg, 90% purity from $^1$H NMR, 18% yield) as colorless oil. $^1$H NMR (300 MHz, CDCl$_3$) δ 3.27-3.17 (m, 2H), 2.84-2.69 (m, 3H), 2.54-2.52 (m, 2H), 1.41 (s, 9H).

Intermediate 23d: tert-Butyl 2-(3-hydroxycyclobutyl)acetate

To a solution of tert-butyl 2-(3-oxocyclobutyl)acetate Intermediate 23c (730 mg, 90% purity, 3.57 mmol) in methanol (2 mL) and tetrahydrofuran (11 mL) was added sodium borohydride (68 mg, 1.78 mmol) at 0° C. After stirred at room temperature for 3 hours, the mixture was quenched with water (10 mL) slowly, followed by saturated sodium carbonate aqueous solution (3 mL). Then it was concentrated to give a residue, which was extracted with ethyl acetate (20 mL) for three times. The combined organic layers were washed with brine (20 mL), dried over Na$_2$SO$_{4(s)}$ and filtered. The filtrate was concentrated under reduced pressure to give the title compound (730 mg, 85% purity from $^1$H NMR, 89% yield) as colorless oil. $^1$H NMR (300 MHz, CDCl$_3$) δ 4.41-4.36 (m, 0.1H), 4.16-4.06 (m, 0.9H), 2.54-2.45 (m, 2H), 2.34-2.22 (m, 3H), 2.09-1.99 (m, 2H), 1.41 (s, 9H).

Intermediate 23e: tert-Butyl 2-(3-(tosyloxy)cyclobutyl)acetate

To a solution of tert-butyl 2-(3-hydroxycyclobutyl)acetate Intermediate 23d (730 mg, 85% purity, 3.33 mmol) in dichloromethane (14 mL) was added pyridine (2.5 mL) and 4-methylbenzene-1-sulfonyl chloride (1.59 g, 8.33 mmol) at 0° C. After stirred at room temperature overnight, the reaction mixture was concentrated under reduced pressure to give a residue, which was dissolved in ethyl acetate (30 mL), washed with 0.5 M hydrochloride aqueous solution (50 mL). The aqueous was extracted with ethyl acetate (30 mL) twice. The combined organic layers were washed with saturated sodium bicarbonate aqueous solution (30 mL), brine (30 mL), dried over Na$_2$SO$_{4(s)}$ and filtered. The filtrate was concentrated under reduced pressure to give a residue, which was purified by silica gel column chromatography (petroleum ether:ethyl acetate=20:1 to 10:1) to give the title compound (1.20 g, 90% purity from $^1$H NMR, 95% yield) as colorless oil. LC-MS (ESI): R$_T$=1.76 min, mass calcd. for C$_{17}$H$_{24}$O$_5$S 340.1, m/z found 358.5 [M+H$_2$O]$^+$. $^1$H NMR (300 MHz, CDCl$_3$) δ 7.77 (d, J=7.8 Hz, 2H), 7.33 (d, J=8.1 Hz, 2H), 4.96-4.87 (m, 0.2H), 4.70-4.61 (m, 0.8H), 2.47- 2.36 (m, 5.3H), 2.31-2.29 (m, 2H), 2.19-2.04 (m, 1H), 1.89-1.79 (m, 1.7H), 1.39 (s, 9H).

Intermediate 23f: tert-Butyl 2-(3-(acetylthio)cyclobutyl)acetate

To a solution of tert-butyl 2-(3-(tosyloxy)cyclobutyl)acetate Intermediate 23e (1.20 g, 90% purity, 3.17 mmol) in N,N-dimethylformamide (12 mL) was added potassium thioacetate (724 mg, 6.34 mmol) at room temperature. After stirred at 100° C. for 6 hours, the reaction mixture was cooled down to room temperature, diluted with water (30 mL) and extracted with ethyl acetate (30 mL) for three times. The combined organic layers were washed with water (40 mL) and brine (40 mL), dried over Na$_2$SO$_{4(s)}$ and filtered. The filtrate was concentrated under reduced pressure to give a residue, which was purified by silica gel column chromatography (petroleum ether:ethyl acetate=100:1 to 50:1) to give the title compound (680 mg, 90% purity from $^1$H NMR, 79% yield) as brown oil. LC-MS (ESI): R$_T$=1.74 min, mass calcd. for C$_{12}$H$_{20}$O$_3$S 244.1, m/z found 262.3 [M+H$_2$O]$^+$. $^1$H NMR (300 MHz, CDCl$_3$) δ 4.11-4.00 (m, 0.9H), 3.98-3.88 (m, 0.1H), 2.84-2.70 (m, 0.9H), 2.67-2.48 (m, 0.7H), 2.43-2.40 (m, 1.6H), 2.33-2.15 (m, 6.8H), 1.45-1.42 (m, 9H).

Sulfonyl Chloride 23: tert-Butyl 2-(3-(chlorosulfonyl)cyclobutyl)acetate

To a solution of tert-butyl 2-(3-(acetylthio)cyclobutyl)acetate Intermediate 23f (680 mg, 90% purity, 2.51 mmol) in acetonitrile (14 mL) was added 2 M hydrochloride aqueous solution (0.4 mL, 0.80 mmol) and 1-chloropyrrolidine-2,5-dione (1.34 g, 10.0 mmol) at 0° C. After stirred at 0° C. for 1 hour, the reaction mixture was quenched with water (30 mL) and extracted with ethyl acetate (30 mL) for three times. The combined organic layers were washed with brine (50 mL), dried over Na$_2$SO$_{4(s)}$ and filtered. The filtrate was concentrated and the residue was purified by silica gel column chromatography (petroleum ether:ethyl acetate=40:1 to 20:1) to give the title compound (600 mg, 90% purity from $^1$H NMR, 80% yield) as colorless oil. $^1$H NMR (400 MHz, CDCl$_3$) δ 4.41-4.27 (m, 1H), 2.99-2.85 (m, 2.5H), 2.73-2.65 (m, 0.5H), 2.46-2.43 (m, 2H), 2.41-2.32 (m, 2H), 1.44 (s, 9H).

Sulfonyl Chloride 24: tert-Butyl 3-((chlorosulfonyl)methyl)cyclobutanecarboxylate

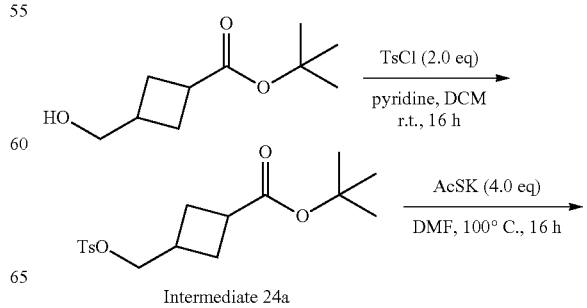

Intermediate 24a

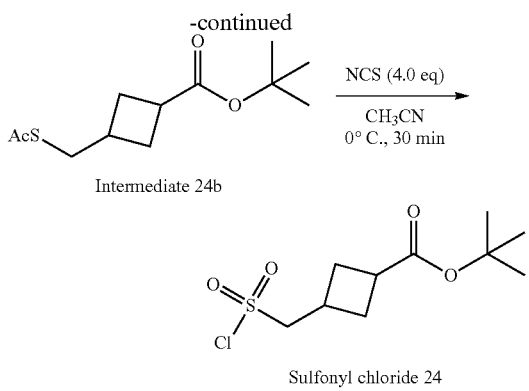

Intermediate 24a: tert-Butyl 3-((tosyloxy)methyl)cyclobutanecarboxylate

To a solution of tert-butyl 3-(hydroxymethyl)cyclobutanecarboxylate (3.50 g, 18.8 mmol) in pyridine (10 mL) and dichloromethane (50 mL) was added 4-methyl-benzenesulfonyl chloride (7.20 g, 37.6 mmol) slowly at 0° C. After stirred at room temperature for 16 hours, the mixture was diluted with water (150 mL) and stirring continued at room temperature for 0.5 hour. The resulting mixture was extracted with dichloromethane (150 mL) twice. The combined organic layers was washed with 0.5 N hydrochloride aqueous solution (200 mL), brine (150 mL), dried over $Na_2SO_{4(s)}$, filtered and concentrated to give a residue, which was purified by silica gel column chromatography (petroleum ether:ethyl acetate=30:1) to give the title compound (3.60 g, 56% yield) as white solid. $^1H$ NMR (300 MHz, $CDCl_3$) δ 7.81-7.78 (m, 2H), 7.38-7.27 (m, 2H), 4.04-3.96 (m, 3H), 2.99-2.84 (m, 1H), 2.70-2.49 (m, 1H), 2.46 (s, 3H), 2.35-2.19 (m, 2H), 2.02-1.84 (m, 2H), 1.44 (s, 9H).

Intermediate 24b: tert-Butyl 3-((acetylthio)methyl)cyclobutanecarboxylate

To a solution of tert-butyl 3-((tosyloxy)methyl)cyclobutanecarboxylate Intermediate 24a (1.10 g, 3.20 mmol) in N,N-dimethylformamide (20 mL) was added potassium thioacetate (1.50 g, 12.9 mmol) at room temperature. After stirred at 100° C. for 16 hours, the reaction mixture was cooled down to room temperature and concentrated to give a residue, which was diluted with 5% sodium chloride aqueous solution (200 mL) and extracted with ethyl acetate (100 mL) twice. The combined organic layers were dried over $Na_2SO_{4(s)}$, filtered and concentrated to give a residue, which was purified by silica gel column chromatography (petroleum ether:ethyl acetate=30:1) to give the title compound (450 mg, 62% yield) as red yellow oil. $^1H$ NMR (300 MHz, $CDCl_3$) δ 3.02-2.92 (m, 2.2H), 2.88-2.78 (m, 0.8H), 2.57-2.50 (m, 0.5H), 2.42-2.27 (m, 5.5H), 2.02-1.84 (m, 2H), 1.93-1.83 (m, 2H), 1.44 (s, 9).

Sulfonyl Chloride 24: tert-Butyl 3-((chlorosulfonyl)methyl)cyclobutanecarboxylate To a solution of tert-butyl 3-((acetylthio)methyl)cyclobutanecarboxylate Intermediate 24b (450 mg, 1.85 mmol) in 2 M hydrochloride aqueous solution (0.25 mL) and acetonitrile (10 mL) was added 1-chloropyrrolidine-2,5-dione (984 mg, 7.30 mmol) slowly at 0° C. After stirred at 0° C. for 30 minutes, the reaction mixture was concentrated in vacuo to remove acetonitrile at 25° C. The obtained residue was partitioned between ethyl acetate (50 mL) and saturated sodium bicarbonate aqueous solution (50 mL). The organic layer was separated and washed with saturated sodium thiosulfate aqueous solution (50 mL), followed with brine (50 mL), dried over $Na_2SO_{4(s)}$ and filtered. The filtrate was concentrated to give a residue, which was purified by silica gel column chromatography (petroleum ether:ethyl acetate=30:1) to give the title compound (380 mg, 80% yield) as colorless oil. $^1H$ NMR (300 MHz, $CDCl_3$) δ 3.86-3.79 (m, 2H), 3.29-3.20 (m, 0.5H), 3.10-2.94 (m, 1.5H), 2.65-2.51 (m, 2H), 2.29-2.12 (m, 2H), 1.47 (s, 9).

Sulfonyl Chloride 25: 3-(2-((tert-Butyldiphenylsilyl)oxy)ethoxy)propane-1-sulfonyl Chloride

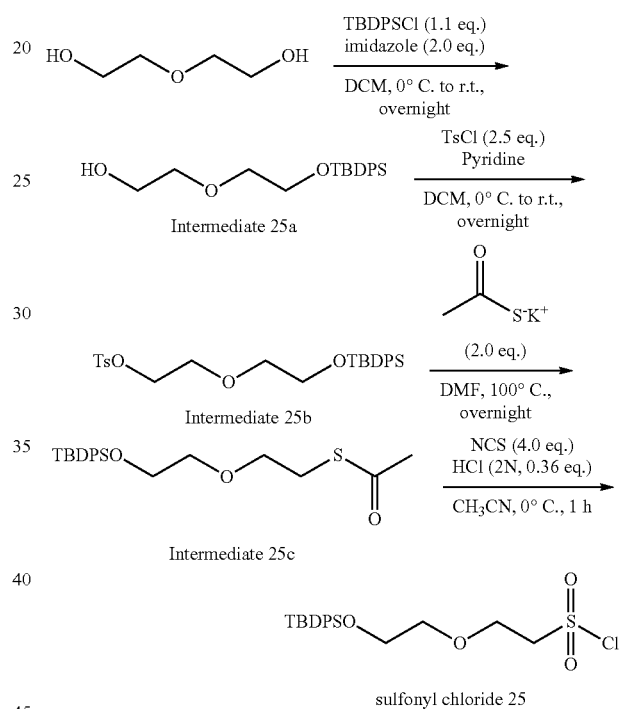

Intermediate 25a: 2-(2-((tert-Butyldiphenylsilyl)oxy)ethoxy)ethanol

To a solution of 2,2'-oxydiethanol (5.00 g, 47.2 mmol) in dichloromethane (100 mL) was added 1H-imidazole (6.42 g, 94.2 mmol) and tert-butylchlorodiphenylsilane (14.2 g, 51.8 mmol) at 0° C. After stirred at room temperature overnight, the mixture was quenched with water (100 mL) and extracted with dichloromethane (100 mL) for three times. The combined organic layers were washed with brine (100 mL), dried over $Na_2SO_{4(s)}$ and filtered. The filtrate was concentrated under reduced pressure to give a residue, which was purified by silica gel column chromatography (petroleum ether:ethyl acetate=6:1 to 3:1) to give the title compound (6.51 g, 95% purity, 38% yield) as colorless oil. LC-MS (ESI): $R_T$=1.85 min, mass calcd. for $C_{20}H_{28}O_3Si$ 344.2, m/z found 362.4 $[M+H_2O]^+$. $^1H$ NMR (300 MHz, $CDCl_3$) δ 7.72-7.67 (m, 4H), 7.46-7.35 (m, 6H), 3.84-3.79 (m, 2H), 3.73-3.67 (m, 2H), 3.64-3.56 (m, 4H), 2.22 (s, 1H), 1.06-1.05 (m, 9H).

Intermediate 25b: 2-(2-((tert-Butyldiphenylsilyl)oxy)ethoxy)ethyl 4-methylbenzenesulfonate To a solution of 2-(2-((tert-butyldiphenylsilyl)oxy) ethoxy)ethanol Intermediate 25a (6.51 g, 95% purity, 18.0 mmol) in dichloromethane (35 mL) was added pyridine (14 mL) and 4-methylbenzene-1-sulfonyl chloride (8.56 g, 44.9 mmol) at 0° C. After stirred at room temperature overnight, the reaction mixture was concentrated under reduced pressure to give a residue, which was dissolved in ethyl acetate (100 mL), washed with 0.5 M hydrochloride aqueous solution (50 mL), extracted with ethyl acetate (80 mL) twice. The combined organic layers were washed with saturated sodium bicarbonate aqueous solution (50 mL), brine (50 mL), dried over $Na_2SO_{4(s)}$ and filtered. The filtrate was concentrated under reduced pressure to give a residue, which was purified by silica gel column chromatography (petroleum ether:ethyl acetate=20:1 to 10:1) to give the title compound (7.61 g, 90% purity from $^1$H NMR, 77% yield) as colorless oil. $^1$H NMR (300 MHz, $CDCl_3$) δ 7.81-7.75 (m, 2H), 7.68-7.63 (m, 4H), 7.45-7.35 (m, 6H), 7.31-7.27 (m, 2H), 4.16-4.12 (m, 2H), 3.76-3.72 (m, 2H), 3.70-3.66 (m, 2H), 3.55-3.51 (m, 2H), 2.42 (s, 3H), 1.04 (s, 9H).

Intermediate 25c: S-(2-(2-((tert-Butyldiphenylsilyl) oxy)ethoxy)ethyl) ethanethioate To a solution of 2-(2-((tert-butyldiphenylsilyl)oxy) ethoxy)ethyl 4-methylbenzenesulfonate Intermediate 25b (7.61 g, 90% purity, 13.7 mmol) in N,N-dimethylformamide (60 mL) was added potassium thioacetate (3.14 g, 27.5 mmol) at room temperature. After stirred at 100° C. overnight, the reaction mixture was cooled down to room temperature, diluted with water (150 mL) and extracted with ethyl acetate (100 mL) for three times. The combined organic layers were washed with water (100 mL) twice, brine (100 mL), dried over $Na_2SO_{4(s)}$ and filtered. The filtrate was concentrated under reduced pressure to give a residue, which was purified by silica gel column chromatography (petroleum ether:ethyl acetate=40:1 to 30:1) to give the title compound (5.73 g, 90% purity, 93% yield) as brown oil. LC-MS (ESI): $R_T$=2.13 min, mass calcd. for $C_{22}H_{30}O_3SSi$ 402.2, m/z found 420.5 $[M+H_2O]^+$. $^1$H NMR (400 MHz, $CDCl_3$) δ 7.70-7.68 (m, 4H), 7.45-7.36 (m, 6H), 3.81-3.78 (m, 2H), 3.63-3.57 (m, 4H), 3.09-3.06 (m, 2H), 2.33 (s, 3H), 1.06 (s, 9H).

Sulfonyl Chloride 25: 3-(2-((tert-Butyldiphenylsilyl) oxy)ethoxy)propane-1-sulfonyl Chloride To a solution of S-(2-(2-((tert-butyldiphenylsilyl)oxy) ethoxy)ethyl) ethanethioate Intermediate 25c (1.00 g, 90% purity, 2.24 mmol) in acetonitrile (15 mL) was added 2 M hydrochloride aqueous solution (0.4 mL) and 1-chloropyrrolidine-2,5-dione (1.19 g, 8.94 mmol) at 0° C. After stirred at 0° C. for 1 hour, the reaction mixture was quenched with water (30 mL) and extracted with ethyl acetate (30 mL) for three times. The combined organic layers were washed with brine (50 mL), dried over $Na_2SO_{4(s)}$ and filtered. The filtrate was concentrated to give a residue, which was purified by silica gel column chromatography (petroleum ether:ethyl acetate=20:1 to 10:1) to give the title compound (350 mg, 85% purity from $^1$H NMR, 31% yield) as colorless oil. $^1$H NMR (300 MHz, $CDCl_3$) δ 7.75-7.68 (m, 4H), 7.47-7.37 (m, 6H), 4.10-4.06 (m, 2H), 3.90-3.82 (m, 4H), 3.66-3.63 (m, 2H), 1.09-1.07 (m, 9H).

Assembles of Dihydropyrimidines of General Formula I Incorporated with Acids of General Formula II, Aryl Aldehydes (P1) and Carboxamidines (P2) Via Sequential Two Reaction Steps Selected Either One Method from Scheme 1 and Scheme 2 Individually were Shown Below in Table 1:

| acid of general formula II | Method | ketoester of general formula III | Method | P1 | P2 | dihydropyrimidine of general formula I |
|---|---|---|---|---|---|---|
| Acid 14 | $A_1$ | Ketoester 1 | C | Al1 | Ca1 | Compound 1 |
| Acid 15 | B | Ketoester 2 | C | Al1 | Ca1 | Compound 2 |

-continued
| acid of general formula II | Method | ketoester of general formula III | Method | P1 | P2 | dihydropyrimidine of general formula I |
|---|---|---|---|---|---|---|
| 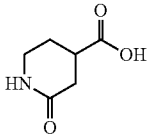<br>Acid 16 | A1 | 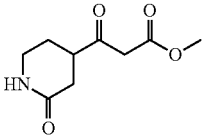<br>Ketoester 3 | C | Al1 | Ca1 | 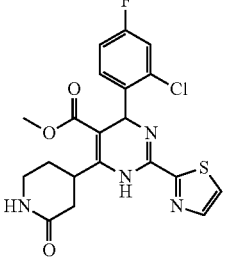<br>Compound 3 |
|  |  | 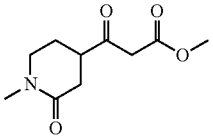<br>Ketoester 1 | C | Al2 | Ca1 | 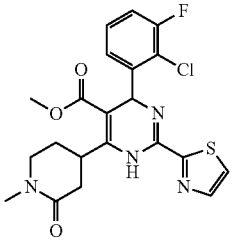<br>Compound 4 |
| 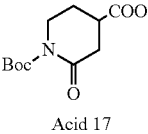<br>Acid 17 | A1 | 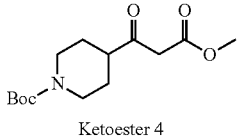 [SMILES: COC(=O)CC(=O)C1CCN(C(=O)OC(C)(C)C)CC1]<br>Ketoester 4 | C | Al1 | Ca1 | 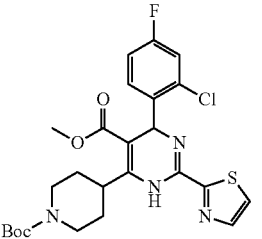<br>Compound 5 |
| 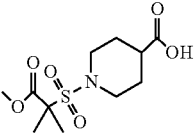<br>Acid 1 | A1 | 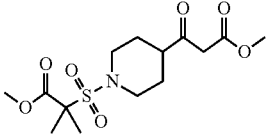<br>Ketoester 5 | C | Al1 | Ca1 | 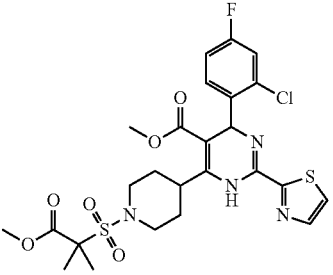<br>Compound 6 |
|  |  | 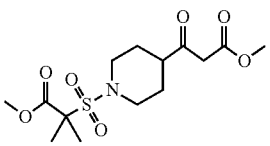<br>Ketoester 5 | C | Al2 | Ca1 | 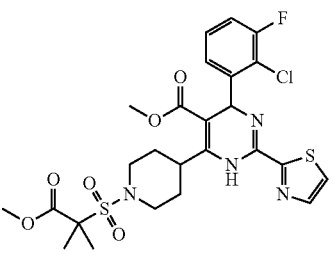<br>Compound 8 |

-continued

| acid of general formula II | Method | ketoester of general formula III | Method | P1 | P2 | dihydropyrimidine of general formula I |
|---|---|---|---|---|---|---|
| Acid 17 | A₂ | Ketoester 6 | C | Al2 | Ca1 | Compound 9 |
| | | Ketoester 4 | C | Al2 | Ca1 | Compound 10 |
| | | Ketoester 4 | C | Al3 | Ca1 | Compound 11 |
| | | Ketoester 4 | C | Al4 | Ca1 | Compound 12 |
| | | Ketoester 4 | C | Al5 | Ca1 | Compound 13 |

-continued
| acid of general formula II | Method | ketoester of general formula III | Method | P1 | P2 | dihydropyrimidine of general formula I |
|---|---|---|---|---|---|---|
| 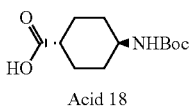<br>Acid 18 | A₁ | 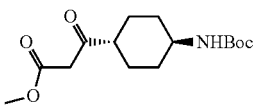<br>Ketoester 7 | C | Al1 | Ca1 | 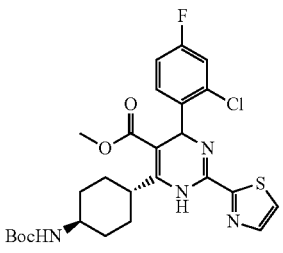<br>Compound 14 |
| 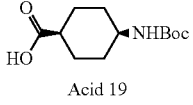<br>Acid 19 | A₁ | 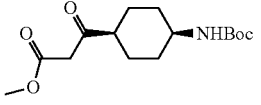<br>Ketoester 8 | C | Al1 | Ca1 | 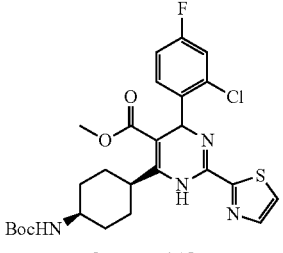<br>Compound 15 |
| 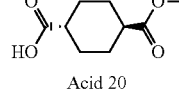<br>Acid 20 | A₁ | 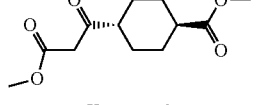<br>Ketoester 9 | C | Al2 | Ca1 | 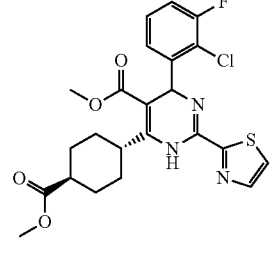<br>Compound 16 |
|  |  | 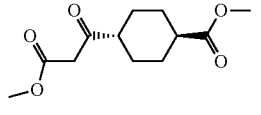<br>Ketoester 9 | C | Al1 | Ca1 | 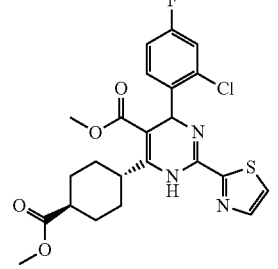<br>Compound 18 |
| 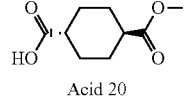<br>Acid 20 | A₂ | 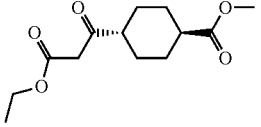<br>Ketoester 38 | C | Al1 | Ca1 | 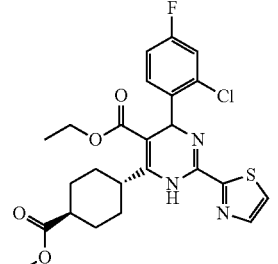<br>Compound 20 |

-continued

| acid of general formula II | Method | ketoester of general formula III | Method | P1 | P2 | dihydropyrimidine of general formula I |
|---|---|---|---|---|---|---|
| | | Ketoester 38 | C | Al2 | Ca1 | Compound 22 |
| Acid 2 | A1 | Ketoester 10 | C | Al2 | Ca1 | Compound 24 |
| Acid 4 | A1 | Ketoester 11 | C | Al2 | Ca1 | Compound 26 |
| Acid 21 | B | Ketoester 12 | C | Al2 | Ca1 | Compound 30 |
| | | Ketoester 12 | C | Al1 | Ca1 | Compound 31 |

-continued
| acid of general formula II | Method | ketoester of general formula III | Method | P1 | P2 | dihydropyrimidine of general formula I |
|---|---|---|---|---|---|---|
| 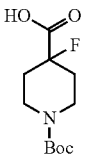 Acid 22 | A₁ | 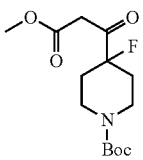 Ketoester 13 | C | Al2 | Ca1 | 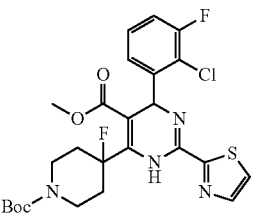 Compound 34 |
| 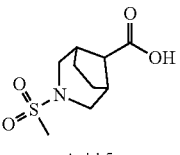 Acid 5 | A₁ | 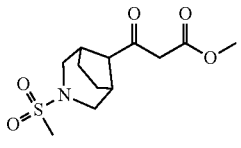 Ketoester 14 | C | Al2 | Ca1 | 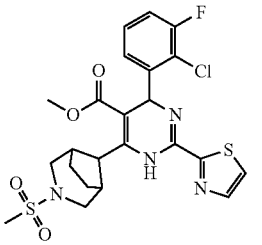 Compound 37 |
| 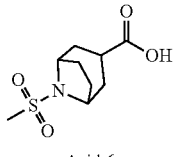 Acid 6 | A₁ | 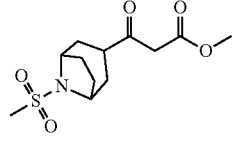 Ketoester 15 | C | Al1 | Ca1 | 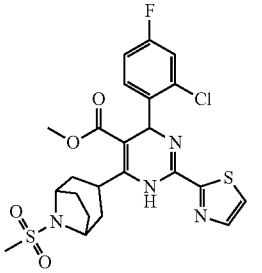 Compound 38 |
|  |  | 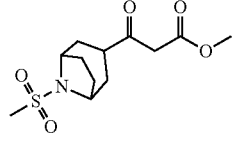 Ketoester 15 | C | Al2 | Ca1 | 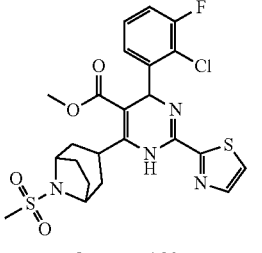 Compound 39 |
| 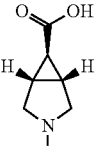 Acid 23 | A₂ | 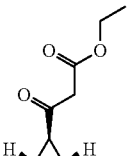 Ketoester 16 | C | Al1 | Ca1 | 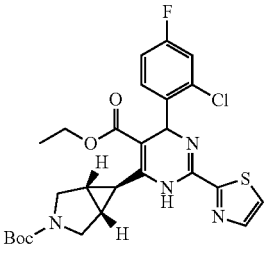 Compound 40 |

-continued
| acid of general formula II | Method | ketoester of general formula III | Method | P1 | P2 | dihydropyrimidine of general formula I |
|---|---|---|---|---|---|---|
| 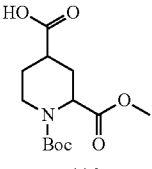<br>Acid 8 | A₁ | 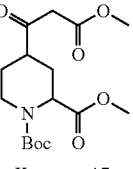<br>Ketoester 17 | D | Al1 | Ca1 | 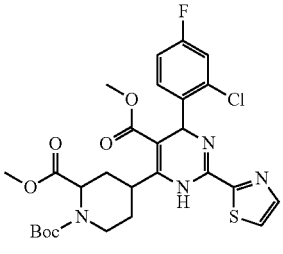<br>Compound 42 |
| 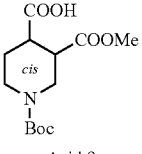<br>Acid 9 | A₁ | 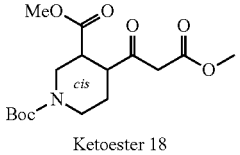<br>Ketoester 18 | C | Al1 | Ca1 | 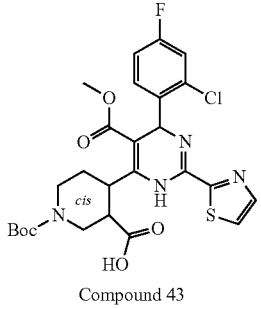 [SMILES: COC(=O)C1=C(C2CCN(C(=O)OC(C)(C)C)CC2C(=O)O)NC(c2nccs2)=NC1c1ccc(F)cc1Cl]<br>Compound 43 |
| 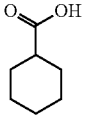<br>Acid 24 | A₂ | 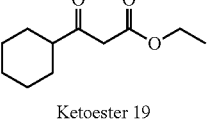<br>Ketoester 19 | C | Al1 | Ca1 | 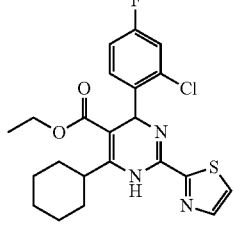<br>Compound 47 |
| 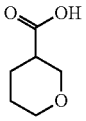<br>Acid 25 | A₁ | 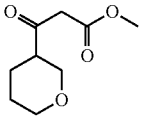<br>Ketoester 20 | C | Al1 | Ca1 | 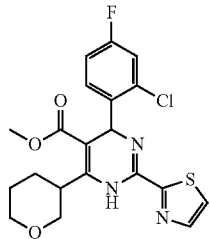<br>Compound 48 |
| 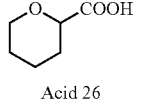<br>Acid 26 | A₁ | 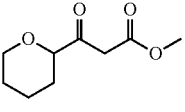<br>Ketoester 21 | C | Al1 | Ca1 | 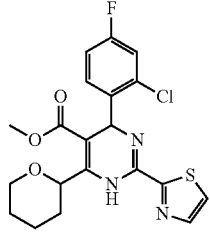<br>Compound 49 |

-continued
| acid of general formula II | Method | ketoester of general formula III | Method | P1 | P2 | dihydropyrimidine of general formula I |
|---|---|---|---|---|---|---|
| 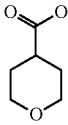<br>Acid 27 | A1 | 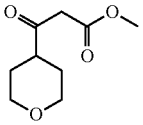<br>Ketoester 22 | C | Al2 | Ca1 | 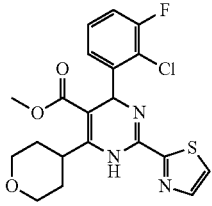<br>Compound 50 |
| | | 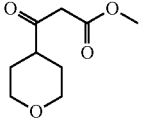<br>Ketoester 22 | C | Al1 | Ca1 | 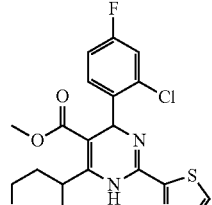<br>Compound 51 |
| | | 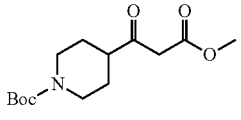<br>Ketoester 4 | D | Al1 | Ca2 | 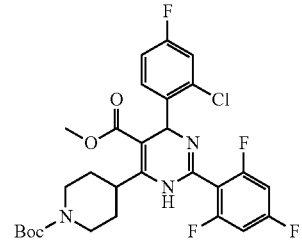<br>Compound 52 |
| | | 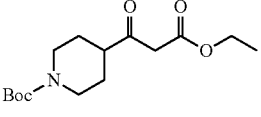<br>Ketoester 6 | C | Al1 | Ca3 | 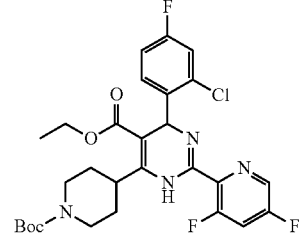<br>Compound 55 |
| | | 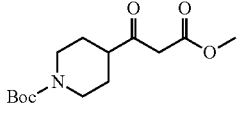<br>Ketoester 4 | C | Al6 | Ca1 | 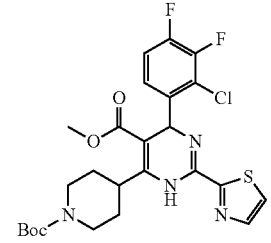<br>Compound 57 |

-continued
| acid of general formula II | Method | ketoester of general formula III | Method | P1 | P2 | dihydropyrimidine of general formula I |
|---|---|---|---|---|---|---|
| 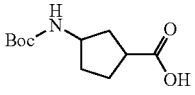 Acid 28 | A₁ | 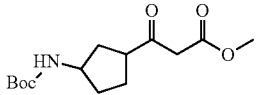 Ketoester 23 | C | Al2 | Ca1 | 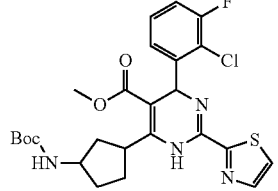 Compound 60 |
| 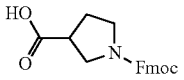 Acid 29 | B | 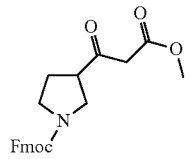 Ketoester 24 | C | Al1 | Ca1 | 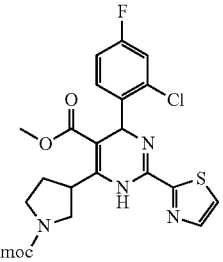 Compound 63 |
| 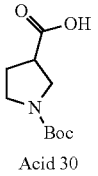 Acid 30 | A₁ | 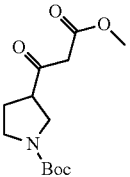 Ketoester 25 | C | Al1 | Ca1 | 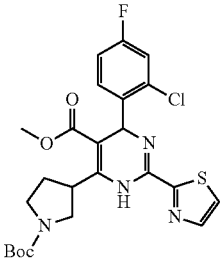 Compound 66 |
| 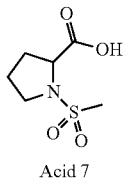 Acid 7 | A₁ | 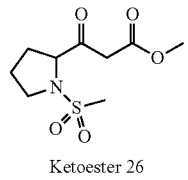 [SMILES: COC(=O)CC(=O)C1CCCN1S(C)(=O)=O] Ketoester 26 | D | Al1 | Ca1 | 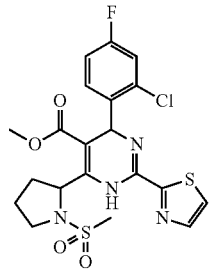 Compound 69 |
| 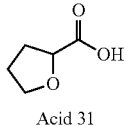 Acid 31 | A₁ | 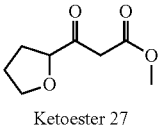 Ketoester 27 | C | Al1 | Ca1 | 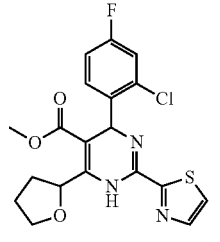 Compound 70 |

-continued
| acid of general formula II | Method | ketoester of general formula III | Method | P1 | P2 | dihydropyrimidine of general formula I |
|---|---|---|---|---|---|---|
| 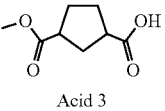<br>Acid 3 | A1 | 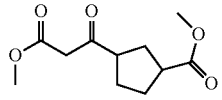<br>Ketoester 28 | C | Al1 | Ca1 | 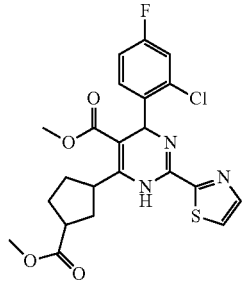<br>Compound 71 |
| 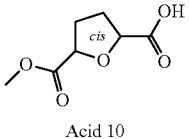<br>Acid 10 | A1 | 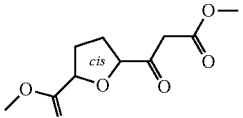<br>Ketoester 29 | C | Al2 | Ca1 | 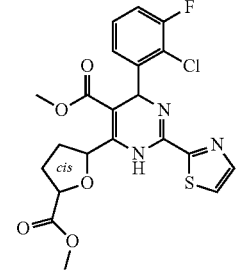<br>Compound 73 |
| <br>Acid 32 | A1 | 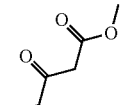<br>Ketoester 30 | C | Al2 | Ca1 | 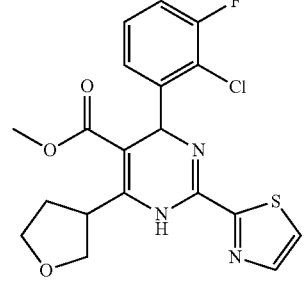 |
| 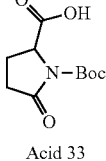<br>Acid 33 | A1 | 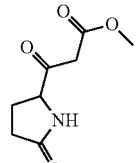<br>Ketoester 31 | C | Al2 | Ca1 | 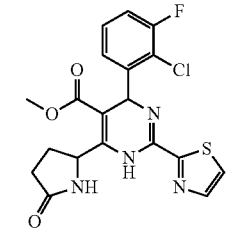<br>Compound 75 |
| 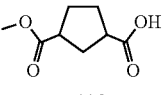<br>Acid 3 | A1 | 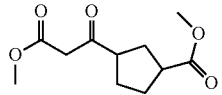<br>Ketoester 28 | C | Al2 | Ca1 | 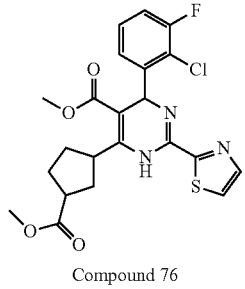 [SMILES: COC(=O)C1=C(C2CCC(C(=O)OC)C2)NC(c2nccs2)=NC1c1cccc(F)c1Cl]<br>Compound 76 |

-continued

| acid of general formula II | Method | ketoester of general formula III | Method | P1 | P2 | dihydropyrimidine of general formula I |
|---|---|---|---|---|---|---|
| 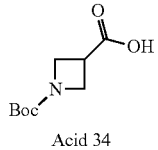<br>Acid 34 | B | 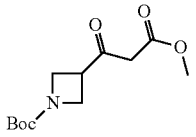<br>Ketoester 32 | C | Al1 | Ca1 | 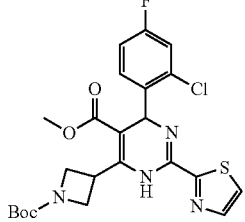<br>Compound 78 |
| 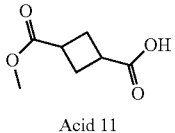<br>Acid 11 | B | 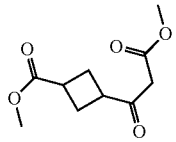<br>Ketoester 33 | C | Al1 | Ca1 | 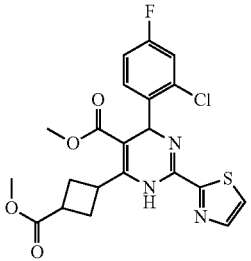<br>Compound 85 |
| 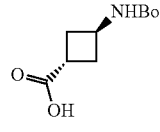<br>Acid 35 (trans) | B | 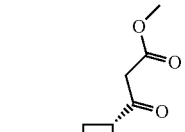<br>Ketoester 34 (trans) | C | Al1 | Ca1 | 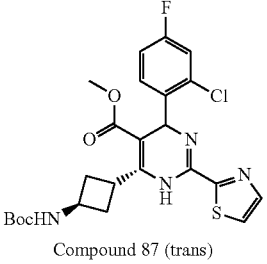<br>Compound 87 (trans) |
| 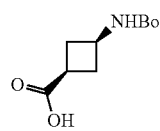<br>Acid 35 (cis) | B | 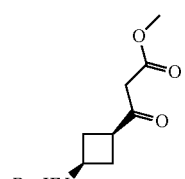<br>Ketoester 34 (cis) | C | Al1 | Ca1 | 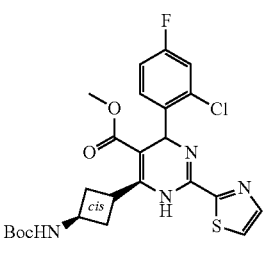<br>Compound 87 (cis) |
|  |  | 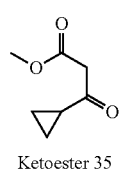<br>Ketoester 35 | C | Al1 | Ca1 | 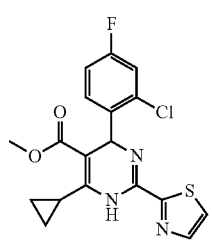<br>Compound 90 |

-continued
| acid of general formula II | Method | ketoester of general formula III | Method | P1 | P2 | dihydropyrimidine of general formula I |
|---|---|---|---|---|---|---|
| 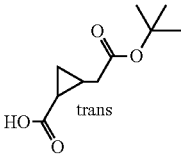 Acid 12 | A2 | 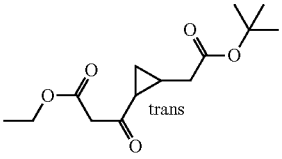 Ketoester 36 | C | Al1 | Ca1 | 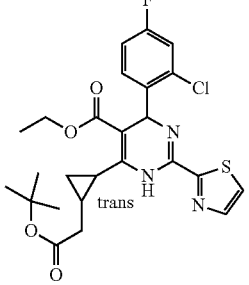 Compound 91 |
| 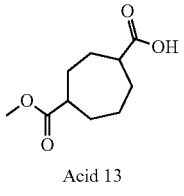 Acid 13 | A1 | 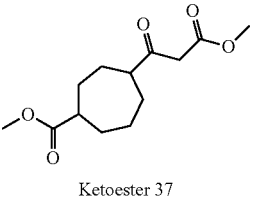 Ketoester 37 | C | Al1 | Ca1 | 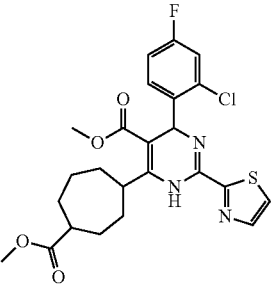 Compound 94 |
| | | 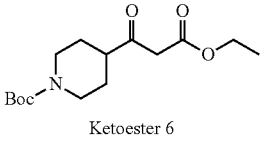 [SMILES: CCOC(=O)CC(=O)C1CCN(C(=O)OC(C)(C)C)CC1] Ketoester 6 | C | Al7 | Ca1 | 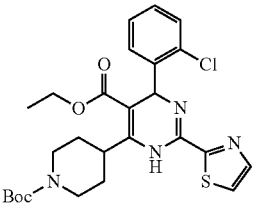 Compound 143 |
| | | 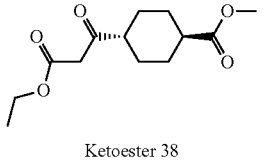 [SMILES: CCOC(=O)CC(=O)[C@H]1CC[C@H](C(=O)OC)CC1] Ketoester 38 | C | Al8 | Ca1 | 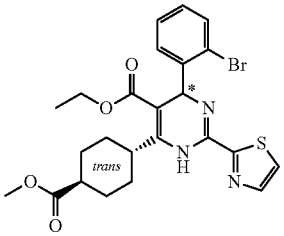 Compound 147A |
| | | 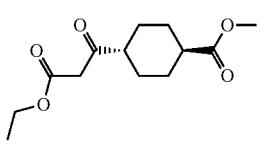 Ketoester 38 | C | Al9 | Ca1 | 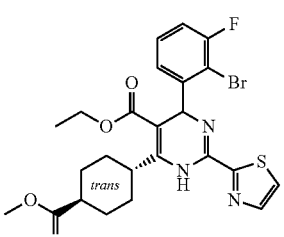 Compound 149 |

-continued

| acid of general formula II | Method | ketoester of general formula III | Method | P1 | P2 | dihydropyrimidine of general formula I |
|---|---|---|---|---|---|---|
| | | Ketoester 9 | C | Al9 | Ca1 | Compound 151 |
| | | Ketoester 9 | C | Al11 | Ca1 | Compound 159 |
| | | Ketoester 38 | C | Al10 | Ca1 | Compound 153 |
| | | Ketoester 38 | C | Al9 | Ca1 | Compound 155 |
| Acid 36 | A₁ | Ketoester 40 | D | Al6 | Ca2 | Compound 167A |

-continued

| acid of general formula II | Method | ketoester of general formula III | Method | P1 | P2 | dihydropyrimidine of general formula I |
|---|---|---|---|---|---|---|
| | | Ketoester 40 | D | Al6 | Ca3 | Compound 168A |
| Acid 37 | A₁ | Ketoester 41 | C | Al6 | Ca1 | Compound 169A |
| Acid 38 | A₁ | Ketoester 42 | D | Al2 | Ca1 | Compound 170 |
| Acid 39 | A₁ | Ketoester 43 | C | Al2 | Ca1 | Compound 171 |
| | | Ketoester 10 | C | Al1 | Ca1 | Compound 172 |

-continued

| acid of general formula II | Method | ketoester of general formula III | Method | P1 | P2 | dihydropyrimidine of general formula I |
|---|---|---|---|---|---|---|
| | | Ketoester 9 | C | Al1 | Ca3 | Compound 174A |
| | A₁ | Ketoester 44 | C | Al1 | Ca1 | Compound 175 |
| Acid 40 | A₁ | Ketoester 45 | C | Al1 | Ca1 | Compound 188 |
| | | Ketoester 6 | D | Al6 | Ca2 | Compound 191 |
| | | Ketoester 6 | C | Al11 | Ca1 | Compound 196A |

-continued
| acid of general formula II | Method | ketoester of general formula III | Method | P1 | P2 | dihydropyrimidine of general formula I |
|---|---|---|---|---|---|---|
| Acid 41 | A1 | 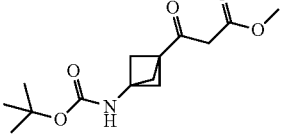 Ketoester 46 | C | Al6 | Ca1 | 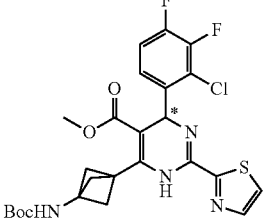 Compound 202A |
| Acid 42 | A1 | 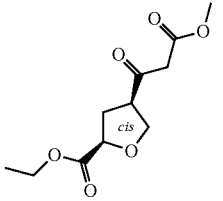 Ketoester 47 | C | Al2 | Ca1 | 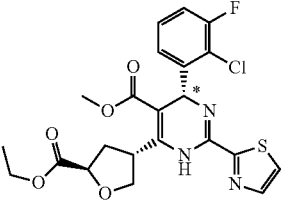 Compound 211M |
|  | A1 | 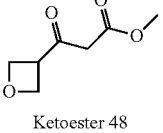 Ketoester 48 | C | Al1 | Ca1 | 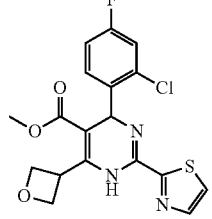 Compound 217 |
| Acid 43 | A1 | 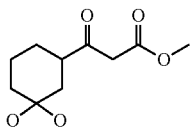 Ketoester 49 | C | Al1 | Ca1 | 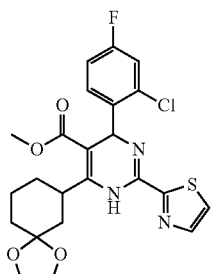 Compound 218 |
| Acid 44 | A1 | 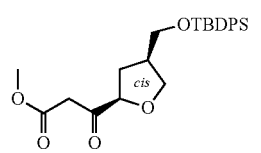 Ketoester 50 | C | Al2 | Ca1 | 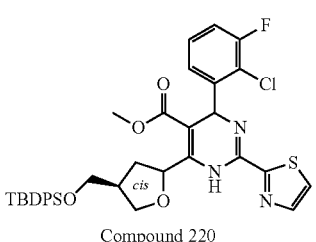 Compound 220 |
|  |  | 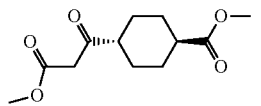 Ketoester 9 | C | Al9 | Ca1 | 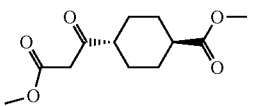 Ketoester 9 |

-continued

| acid of general formula II | Method | ketoester of general formula III | Method | P1 | P2 | dihydropyrimidine of general formula I |
|---|---|---|---|---|---|---|
| | | Ketoester 9 | C | Al10 | Ca1 | Compound 226 |
| | | Ketoester 9 | C | Al11 | Ca1 | Compound 228 |
| Acid 45 | A₁ | Ketoester 51, used as crude | C | Al6 | Ca1 | Compound 223B (cis) / Compound 223C (trans) |
| Acid 46 | A₁ | Ketoester 52 | C | Al6 | Ca1 | Compound 234B (cis) / Compound 234D (trans) |

-continued

| acid of general formula II | Method | ketoester of general formula III | Method | P1 | P2 | dihydropyrimidine of general formula I |
|---|---|---|---|---|---|---|
| | | Ketoester 7 | D | Al6 | Ca1 | Compound 235 |
| | | Ketoester 9 | C | Al4 | Ca4 | Compound 239X |
| | A₁ | Ketoester 53 | C | Al1 | Ca1 | Compound 257 |
| | | Ketoester 40 | C | Al2 | Ca1 | Compound 259C (cis)<br>Compound 259E (trans) |
| Acid 47 | A₁ | Ketoester 54 | C | Al2 | Ca1 | Compound 260 |

-continued
| acid of general formula II | Method | ketoester of general formula III | Method | P1 | P2 | dihydropyrimidine of general formula I |
|---|---|---|---|---|---|---|
| Acid 48 | A₁ | 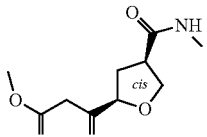<br>Ketoester 55 | C | Al2 | Ca1 | 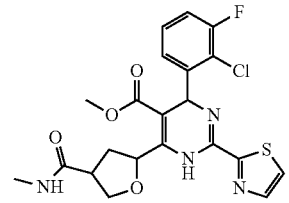<br>Compound 263 |
| Acid 49 | A₂ | 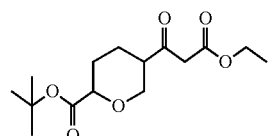<br>Ketoester 56 | C | Al1 | Ca1 | 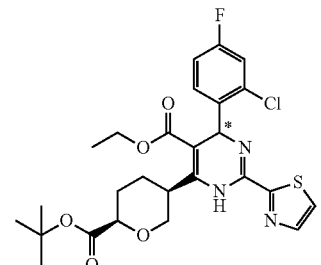<br>Compound 264 |
| | | 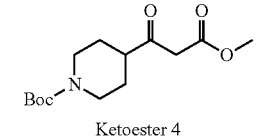 [SMILES: COC(=O)CC(=O)C1CCN(C(=O)OC(C)(C)C)CC1]<br>Ketoester 4 | C | Al9 | Ca1 | 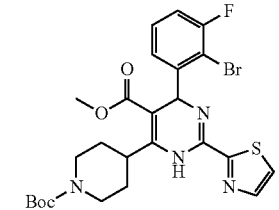<br>Compound 275 |
| | | 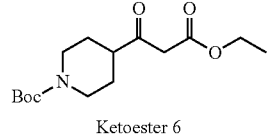 [SMILES: CCOC(=O)CC(=O)C1CCN(C(=O)OC(C)(C)C)CC1]<br>Ketoester 6 | C | Al9 | Ca1 | 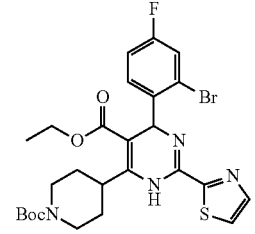<br>Compound 279 |
| Acid 50 | A₁ | 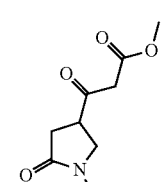<br>Ketoester 57 | C | Al2 | Ca1 | 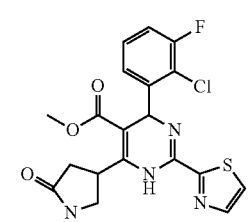<br>Compound 283 |

-continued

| acid of general formula II | Method | ketoester of general formula III | Method | P1 | P2 | dihydropyrimidine of general formula I |
|---|---|---|---|---|---|---|
| | | Ketoester 9 | C | Al6 | Ca1 | Compound 288 |
| Acid 51 | A₁ | Ketoester 58 | C | Al6 | Ca1 | Compound 290 |
| Acid 52 | A₁ | Ketoester 59 | C | Al6 | Ca1 | Compound 292 |
| Acid 53 | A₁ | Ketoester 60 | C | Al1 | Ca1 | Compound 294 |

-continued

| acid of general formula II | Method | ketoester of general formula III | Method | P1 | P2 | dihydropyrimidine of general formula I |
|---|---|---|---|---|---|---|
| | | Ketoester 7 | D | Al6 | Ca3 | Compound 296 |
| | | Ketoester 23 | D | Al6 | Ca1 | Compound 299 |
| Acid 13 | A₂ | Ketoester 61 | C | Al6 | Ca1 | Compound 301 |
| | | Ketoester 4 | C | Al10 | Ca1 | Compound 306 |
| Acid 54 | A₁ | Ketoester 62 | C | Al6 | Ca1 | Compound 314 |

-continued

| acid of general formula II | Method | ketoester of general formula III | Method | P1 | P2 | dihydropyrimidine of general formula I |
|---|---|---|---|---|---|---|
| | | Ketoester 6 | C | Al2 | Ca1 | Compound 316 |
| | | Ketoester 6 | C | Al1 | Ca1 | Compound 326 |
| | | Ketoester 6 | C | Al9 | Ca1 | Compound 336 |
| | | Ketoester 6 | C | Al10 | Ca1 | Compound 340 |
| | | Ketoester 6 | C | Al6 | Ca1 | Compound 344 |

-continued

| acid of general formula II | Method | ketoester of general formula III | Method | P1 | P2 | dihydropyrimidine of general formula I |
|---|---|---|---|---|---|---|
| | | Ketoester 6 | C | Al11 | Ca1 | Compound 346 |
| | | Ketoester 6 | C | Al6 | Ca3 | Compound 349 |
| Acid 55 | A₁ | Ketoester 63 | C | Al6 | Ca1 | Compound 359E (cis) Compound 359F (trans) |
| Acid 56 | A₁ | Ketoester 64 | C | Al6 | Ca1 | Compound 361 |
| Acid 57R | A₁ | Ketoester 65R (mixture of cis and trans) | C | Al1 | Ca1 | Compound 362a |

-continued
| acid of general formula II | Method | ketoester of general formula III | Method | P1 | P2 | dihydropyrimidine of general formula I |
|---|---|---|---|---|---|---|
| Acid 57S | A₁ | 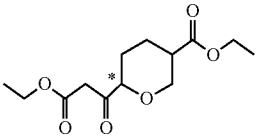<br>Ketoester 65S<br>(mixture of cis and trans) | C | Al1 | Ca1 | 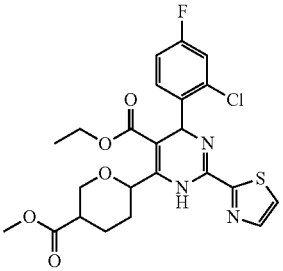<br>Compound 362R |
|  |  | 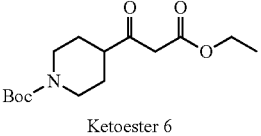 [SMILES: CCOC(=O)CC(=O)C1CCN(C(=O)OC(C)(C)C)CC1]<br>Ketoester 6 | C | Al6 | Ca1 | 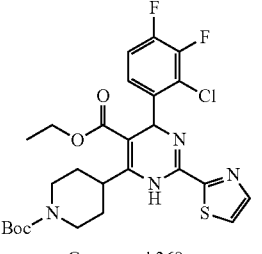<br>Compound 368 |
|  |  | 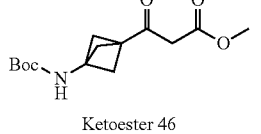<br>Ketoester 46 | C | Al1 | Ca1 | 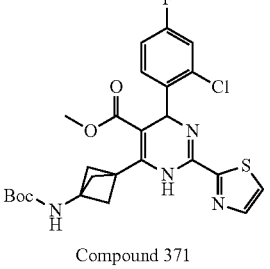<br>Compound 371 |
| Acid 58 | A₁ | 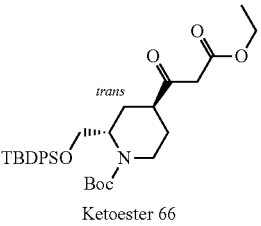<br>Ketoester 66 | C | Al1 | Ca1 | 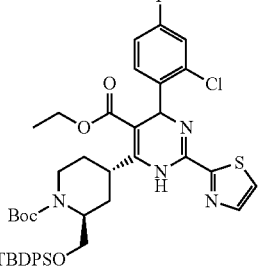<br>Compound 377 |
| Acid 59 | A₁ | 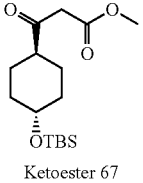<br>Ketoester 67 | C | Al2 | Ca1 | 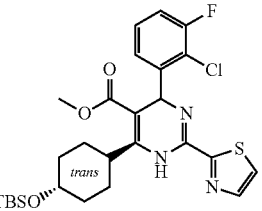<br>Compound 380 |

-continued

| acid of general formula II | Method | ketoester of general formula III | Method | P1 | P2 | dihydropyrimidine of general formula I |
|---|---|---|---|---|---|---|
| Acid (Boc-azepane-COOH) | A1 | Ketoester 68 | C | Al1 | Ca1 | Compound 382 |
| Acid 60 (dioxaspiro cyclohexane COOH) | A1 | Ketoester 69 | C | Al1 | Ca1 | Compound 385 |
|  |  | Ketoester 7 (trans) | C | Al1 | Ca3 | Compound 394 |
|  |  | Ketoester (cis) | C | Al1 | Ca3 | Compound 397 |
|  |  | Ketoester 4 | C | Al4 | Ca1 | Compound 407 |

-continued

| acid of general formula II | Method | ketoester of general formula III | Method | P1 | P2 | dihydropyrimidine of general formula I |
|---|---|---|---|---|---|---|
| | | Ketoester 6 | C | Al9 | Ca1 | Compound 411 |
| | | Ketoester 6 | C | Al12 | Ca1 | Compound 417 |
| | | Ketoester 6 | C | Al13 | Ca1 | Compound 426 |
| Acid 61 | A$_1$ | Ketoester 70 | C | Al6 | Ca1 | Compound 430 |
| | | Ketoester 69 | C | Al6 | Ca1 | Compound 432 |

-continued

| acid of general formula II | Method | ketoester of general formula III | Method | P1 | P2 | dihydropyrimidine of general formula I |
|---|---|---|---|---|---|---|
| Acid 62 | A1 | 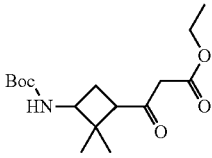<br>Ketoester 71 | C | Al1 | Ca1 | 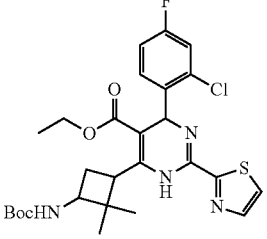<br>Compound 435 |
|  |  | 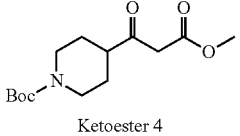 [SMILES: COC(=O)CC(=O)C1CCN(C(=O)OC(C)(C)C)CC1]<br>Ketoester 4 | C | Al13 | Ca1 | 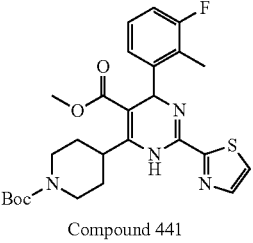<br>Compound 441 |
|  |  | 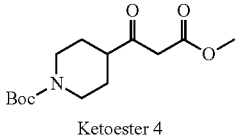<br>Ketoester 4 | C | Al12 | Ca1 | 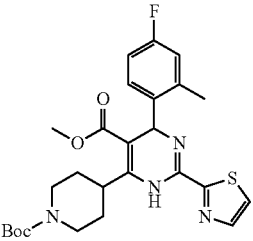<br>Compound 445 |
| Acid 63 | A1 | 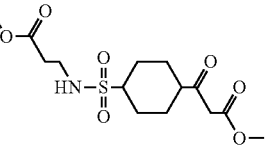<br>Ketoester 72 | D | Al6 | Ca1 | 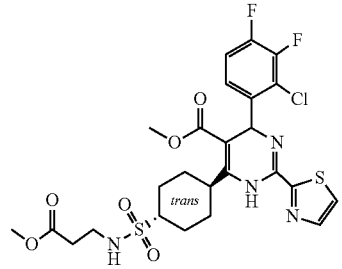<br>Compound 472 |

Ketoesters of General Formula II

Ketoester 1: Methyl 3-(1-methyl-2-oxopiperidin-4-yl)-3-oxopropanoate

LC-MS (ESI): $R_T$=1.040 min, mass calcd. for $C_{10}H_{15}NO_4$, 213.1, m/z found 213.9 [M+H]+; $^1$H NMR (300 MHz, CDCl$_3$) δ 3.84-3.74 (m, 3H), 3.66-3.55 (m, 2H), 3.42-3.33 (m, 2H), 3.13-3.07 (m, 1H), 3.03-2.94 (m, 3H), 2.59-2.45 (m, 2H), 2.22-2.17 (m, 1H), 1.92-1.83 (m, 1H).

Ketoester 2: Methyl 3-(1-acetylpiperidin-4-yl)-3-oxopropanoate

LC-MS (ESI): $R_T$=1.148 min, mass calcd. for $C_{11}H_{17}NO_4$ 227.1, m/z found 228.1 [M+H]+.

Ketoester 3: Methyl 3-oxo-3-(2-oxopiperidin-4-yl)propanoate

LC-MS (ESI): $R_T$=0.52 min, mass calcd. for $C_9H_{13}NO_4$ 199.1, m/z found 200.0 [M+H]+. $^1$H NMR (400 MHz, DMSO-d$_6$) δ 7.51 (s, 1H), 3.78 (d, J=16.8 Hz, 1H), 3.71 (d, J=16.8 Hz, 1H), 3.63 (s, 3H), 3.17-3.16 (m, 1H), 3.13-3.09 (m, 2H), 3.08-2.98 (m, 1H), 2.32-2.26 (m, 1H), 2.05-1.97 (m, 1H), 1.67-1.57 (m, 1H).

Ketoester 4: tert-Butyl 4-(3-methoxy-3-oxopropanoyl)piperidine-1-carboxylate

LC-MS (ESI): $R_T$=2.484 min, mass calcd. for $C_{14}H_{23}NO_5$ 285.2, m/z found 230.0 [M+H-t-Bu]+. $^1$H NMR (300 MHz, CDCl$_3$) δ 4.96 (s, 0.2H), 4.10-4.06 (m, 2H), 3.71 (s, 3H), 3.49 (s, 1.8H), 3.77 (t, J=16 Hz, 2H), 2.60 (tt, J=11.3, 3.83 Hz, 1H), 1.84-1.80 (m, 2H), 1.58-1.46 (m, 2H), 1.44 (s, 9H).

Ketoester 5: Methyl 3-(1-((1-methoxy-2-methyl-1-oxopropan-2-yl)sulfonyl)-piperidin-4-yl)-3-oxopropanoate LC-MS (ESI): $R_T$=1.42 min, mass calcd. for $C_{14}H_{23}NO_7S$ 349.1, m/z found 350.5 $[M+H]^+$.

Ketoester 6: 4-(2-Ethoxycarbonyl-acetyl)-piperidine-1-carboxylic acid tert-butyl ester $^1$H NMR (300 MHz, CDCl$_3$) δ 12.17 (s, 0.2H), 4.99 (s, 0.2H), 4.26-4.03 (m, 4H), 3.50 (s, 1.6H), 2.87-2.72 (m, 2H), 2.68-2.58 (m, 1H), 1.94-1.76 (m, 2H), 1.63-1.49 (m, 2H), 1.46 (s, 9H), 1.28 (t, J=10.5 Hz, 3H).

Ketoester 7: Methyl 3-(trans-4-((tert-butoxycarbonyl)amino)cyclohexyl)-3-oxopropanoate $^1$H NMR (300 MHz, CDCl$_3$) δ 4.47-4.31 (m, 1H), 3.73 (s, 3H), 3.49 (s, 2H), 3.44-3.29 (m, 1H), 2.40 (t, J=12.3 Hz, 1H), 2.09 (d, J=11.1 Hz, 2H), 1.96 (d, J=13.5 Hz, 2H), 1.65-1.47 (m, 1H), 1.43 (s, 9H), 1.11 (q, J=13.5 Hz, 2H).

Ketoester 8: Methyl 3-(cis-4-((tert-butoxycarbonyl)amino)cyclohexyl)-3-oxopropanoate $^1$H NMR (400 MHz, CDCl$_3$) δ 4.71-4.37 (m, 1H), 3.71 (s, 3H), 3.67-3.59 (m, 1H), 3.48 (s, 2H), 1.75-1.60 (m, 8H), 1.41 (s, 9H)

Ketoester 9: trans-Methyl 4-(3-methoxy-3-oxopropanoyl)cyclohexanecarboxylate $^1$H NMR (400 MHz, DMSO-d$_6$) δ 3.66-3.53 (m, 8H), 2.45-2.40 (m, 1H), 2.33-2.24 (m, 1H), 1.95-1.87 (m, 4H), 1.35-1.18 (m, 4H).

Ketoester 38: trans-Methyl 4-(3-ethoxy-3-oxopropanoyl)cyclohexane-carboxylate $^1$H NMR (300 MHz, CDCl$_3$) δ 4.20 (q, J=7.2 Hz, 2H), 3.68 (s, 3H), 3.49 (s, 2H), 2.54-2.43 (m, 1H), 2.34-2.23 (m, 1H), 2.14-1.95 (m, 5H), 1.49-1.37 (m, 3H), 1.28 (t, J=7.2 Hz, 3H).

Ketoester 10: cis-Methyl 3-(3-methoxy-3-oxopropanoyl)cyclohexanecarboxylate

LC-MS (ESI): $R_T$=1.67 min, mass calcd. for $C_{12}H_{18}O_5$ 242.1, m/z found 242.9 $[M+H]^+$. $^1$H NMR (400 MHz, CDCl$_3$) δ 12.04 (s, 0.1H), 4.98 (s, 0.1H), 3.72 (s, 2.7H), 3.71 (s, 0.3H), 3.68 (s, 0.4H), 3.66 (s, 2.6H), 3.51 (s, 0.2H), 3.50 (s, 1.4H), 2.84-2.78 (m, 0.1H), 2.75-2.72 (m, 0.1H), 2.54-2.46 (m, 0.8H), 2.38-2.26 (m, 1H), 2.21-2.10 (m, 1H), 2.03-1.87 (m, 2.7H), 1.83-1.75 (m, 0.3H), 1.54-1.43 (m, 1H), 1.39-1.24 (m, 3H).

Ketoester 11: Methyl 3-(4-(2-ethoxy-2-oxoethyl)cyclohexyl)-3-oxopropanoate

1H NMR (400 MHz, DMSO-d$_6$) δ 4.07-4.01 (m, 2H), 3.72-3.65 (m, 2H), 3.63-3.50 (m, 3H), 2.63-2.60 (m, 0.3H), 2.39 (tt, J=12.0, 3.2 Hz, 0.6H), 2.21-2.16 (m, 2H), 1.91-1.82 (m, 2H), 1.74 (dd, J=13.2, 3.2 Hz, 2H), 1.67-1.46 (m, 2H), 1.30-1.22 (m, 2H), 1.19-1.15 (m, 3H), 0.99 (tq, J=13.2, 3.2 Hz, 1H).

Ketoester 12: tert-Butyl 3-(3-methoxy-3-oxopropanoyl)piperidine-1-carboxylate LC-MS (ESI): $R_T$=1.58 min, mass calcd. For $C_{14}H_{23}NO_5$ 285.2, m/z found 286.1 $[M+H]^+$. $^1$H NMR (300 MHz, CDCl$_3$) δ 5.00-4.96 (m, 0.2H), 4.12-3.77 (m, 2H), 3.70 (s, 3H), 3.52-3.51 (m, 1.3H), 3.43 (s, 0.3H), 3.19-3.02 (m, 1H), 2.95-2.85 (m, 1H), 2.64-2.58 (m, 1H), 1.97-1.88 (m, 1H), 1.69-1.42 (m, 12H).

Ketoester 13: tert-Butyl 4-fluoro-4-(3-methoxy-3-oxopropanoyl)piperidine-1-carboxylate $^1$H NMR (400 MHz, CDCl$_3$) δ 12.10 (d, J=2.4 Hz, 0.15H), 5.39 (d, J=2.8 Hz, 0.15H), 4.04 (br s, 2H), 3.75 (d, J=6.0 Hz, 3H), 3.67 (d, J=4.4 Hz, 1.7H), 3.04 (br s, 2H), 1.99-1.82 (m, 4H), 1.45 (d, J=3.2 Hz, 9H).

Ketoester 14: Methyl 3-(3-(methylsulfonyl)-3-azabicyclo[3.2.1]octan-8-yl)-3-oxopropanoate LC-MS (ESI): $R_T$=1.32 min, mass calcd. for $C_{12}H_{19}NO_5S$ 289.1, m/z found 290.4 $[M+H]^+$. $^1$H NMR (300 MHz, CDCl$_3$) δ 3.75-3.74 (m, 3H), 3.63 (dd, J=11.1, 3.0 Hz, 1H), 3.53 (d, J=11.1 Hz, 2H), 3.38 (dd, J=10.8, 3.3 Hz, 1H), 3.18 (d, J=10.8 Hz, 1H), 2.85 (d, J=11.1 Hz, 1H), 2.76 (d, J=11.1 Hz, 3H), 2.66 (s, 1H), 2.61 (s, 2H), 1.83 (s, 2H), 1.71 (m, 2H).

Ketoester 15: 3-(8-Methanesulfonyl-8-aza-bicyclo[3.2.1]oct-3-yl)-3-oxo-propionic acid methyl ester LC-MS (ESI): $R_T$=1.26 min, mass calcd. for $C_{12}H_{19}NO_5S$ 289.1, m/z found 290.4 $[M+H]^+$. $^1$H NMR (300 MHz, CDCl$_3$) δ 4.35 (s, 2H), 3.75 (s, 3H), 3.50 (s, 2H), 2.94 (s, 3H).

Ketoester 16: (1R,5S,6r)-tert-butyl 6-(3-ethoxy-3-oxopropanoyl)-3-azabicyclo-[3.1.0]hexane-3-carboxylate LC-MS (ESI): $R_T$=1.38 min, mass calcd. for $C_{15}H_{23}NO_5$ 297.2, m/z found 242.1 $[M-56+H]^+$. $^1$H NMR (300 MHz, CDCl$_3$) δ 4.21 (q, J=7.2 Hz, 2H), 3.70-3.62 (m, 2H), 3.57 (s, 2H), 3.45-3.41 (m, 2H), 2.18 (s, 2H), 1.92 (s, 1H), 1.45 (s, 9H), 1.29 (t, J=7.2 Hz, 3H).

Ketoester 17: 1-tert-Butyl 2-methyl 4-(3-methoxy-3-oxopropanoyl)piperidine-1,2-dicarboxylate LC-MS (ESI): $R_T$=2.537 min, mass calcd. for $C_{16}H_{25}NO_7$ 343.2, m/z found 342.1 $[M-H]^-$. $^1$H NMR (400 MHz, CDCl$_3$) δ 5.06-5.02 (m, 0.5H), 4.87-4.83 (m, 0.5H), 4.18-4.12 (m, 0.5H), 4.06-4.02 (m, 0.5H), 3.75-3.71 (m, 7H), 3.55-3.48 (m, 2H), 3.03-2.96 (m, 0.5H), 2.91-2.85 (m, 0.5H), 2.51-2.41 (m, 1H), 1.94-1.72 (m, 2H), 1.47 (s, 4H), 1.44 (s, 9H).

Ketoester 18: cis-4-(2-Methoxycarbonyl-acetyl)-piperidine-1,3-dicarboxylic Acid 1-tert-butyl ester 3-methyl Ester LC-MS (ESI): $R_T$=1.59 min, mass calcd. for $C_{16}H_{25}NO_7$ 343.2, m/z found 244.0 $[M+H-100]^+$. $^1$H NMR (400 MHz, CDCl₃) δ 4.19 (dd, J=13.6, 5.6 Hz, 1H), 3.79-3.62 (m, 7H), 3.58 (s, 2H), 3.45 (dd, J=13.6, 2.8 Hz, 1H), 3.17-3.12 (m, 1H), 2.99 (q, J=4.4 Hz, 1H), 2.92-2.87 (m, 1H), 2.12-2.05 (m, 1H), 1.94-1.85 (m, 1H), 1.44 (s, 9H).

Ketoester 19: Ethyl 3-cyclohexyl-3-oxopropanoate

¹H NMR (300 MHz, CDCl₃) δ 12.15 (br s, 0.2H), 4.96 (br s, 0.2H), 4.19 (q, J=7.2 Hz, 2H), 3.48 (s, 1.6H), 2.50-2.42 (m, 1H), 1.91-1.66 (m, 5H), 1.42-1.17 (m, 8H).

Ketoester 20: Methyl 3-oxo-3-(tetrahydro-2H-pyran-3-yl)propanoate

LC-MS (ESI): $R_T$=1.15 min, mass calcd. for $C_9H_{14}O_4$ 186.1, m/z found 187.5 [M+H]⁺. ¹H NMR (300 MHz, CDCl₃) δ 12.02 (s, 0.2H), 4.99 (s, 0.2H), 4.04-3.94 (m, 1H), 3.91-3.78 (m, 1H), 3.72 (s, 2.4H), 3.71 (s, 0.6H), 3.55-3.35 (m, 3.6H), 2.81-2.72 (m, 0.8H), 2.48-2.38 (m, 0.2H), 2.04-1.91 (m, 1H), 1.76-1.62 (m, 3H).

Ketoester 21: Methyl 3-oxo-3-(tetrahydro-2H-pyran-2-yl)propanoate

LC-MS (ESI): $R_T$=1.764 min, mass calcd. for $C_9H_{14}O_4$ 186.1, m/z found 187.0 [M+H]⁺. ¹H NMR (300 MHz, CDCl₃) δ 4.01 (dd, J=11.4, 2.1 Hz, 1H), 3.84 (dd, J=10.8, 2.1 Hz, 1H), 3.71 (s, 3H), 3.65 (s, 0.2H), 3.59 (d, J=6.3 Hz, 1.6H), 3.52 (s, 0.2H), 3.49-3.41 (m, 1H), 1.91-1.88 (m, 2H), 1.59-1.36 (m, 4H).

Ketoester 22: 3-Oxo-3-(tetrahydro-pyran-4-yl)-propionic Acid Methyl Ester

¹H NMR (300 MHz, CDCl₃) δ 12.06 (s, 0.1H), 4.98 (s, 0.1H), 4.01-3.97 (m, 2H), 3.71 (s, 3H), 3.50 (s, 1.8H), 3.41 (td, J=11.4, 2.4 Hz, 2H), 2.74-2.64 (m, 0.8H), 2.40-2.30 (m, 0.2H), 1.80-1.67 (m, 4H).

Ketoester 23: 3-(3-tert-Butoxycarbonylamino-cyclopentyl)-3-oxo-propionic Acid Methyl Ester LC-MS (ESI): $R_T$=1.52 min, mass calcd. for $C_{14}H_{23}NO_5$ 285.2, m/z found 286.2 [M+H]⁺. ¹H NMR (400 MHz, CDCl₃) δ 4.85 (br s, 0.8H), 4.54 (br s, 0.2H), 4.10-3.96 (m, 1H), 3.71 (s, 3H), 3.50 (s, 1.5H), 3.47 (s, 0.5H), 3.17-3.04 (m, 1H), 2.17-2.08 (m, 1H), 1.96-1.80 (m, 3H), 1.72-1.63 (m, 1H), 1.58-1.50 (m, 1H), 1.44 (s, 9H).

Ketoester 24: (9H-Fluoren-9-yl)methyl 3-(3-methoxy-3-oxopropanoyl)pyrrolidine-1-carboxylate LC-MS (ESI): $R_T$=1.67 min, mass calcd. for $C_{23}H_{23}NO_5$ 393.2, m/z found 394.5 [M+H]⁺. ¹H NMR (300 MHz, CDCl₃) δ 12.13 (d, J=5.7 Hz, 0.2H), 7.78 (d, J=7.5 Hz, 2H), 7.62 (d, J=7.2 Hz, 2H), 7.42 (t, J=7.2 Hz, 2H), 7.33 (t, J=7.2 Hz, 2H), 5.09 (s, 0.2H), 4.48-4.35 (m, 2H), 4.28-4.24 (m, 1H), 3.78-2.95 (m, 10H), 2.24-2.15 (m, 2H).

Ketoester 25: tert-Butyl 3-(3-methoxy-3-oxopropanoyl)pyrrolidine-1-carboxylate

LC-MS (ESI): $R_T$=2.053 min, mass calcd. for $C_3H_{21}NO_5$ 271.1, m/z found 294.1 [M+Na]⁺. ¹H NMR (300 MHz, CDCl₃) δ 12.06 (s, 0.2H), 5.03 (s, 0.2H), 3.73 (s, 3H), 3.61-3.47 (m, 4.4H), 3.38-3.25 (m, 2H), 2.90 (br s, 0.2H), 2.14-2.00 (m, 2H), 1.44 (s, 9H).

Ketoester 26: Methyl 3-(1-(methylsulfonyl)pyrrolidin-2-yl)-3-oxopropanoate

¹H NMR (400 MHz, CDCl₃) δ 12.01 (s, 0.2H), 5.32 (s, 0.2H), 4.45 (dd, J=8.4, 4.8 Hz, 0.8H), 4.33 (dd, J=7.6, 3.6 Hz, 0.2H), 3.75 (s, 3H), 3.74 (s, 0.2H), 3.70 (s, 0.6H), 3.65 (s, 0.6H), 3.63 (s, 0.1H), 3.61 (s, 0.2H), 3.53-3.43 (m, 2H), 2.93 (s, 2.5H), 2.88 (s, 0.5H), 2.27-2.12 (m, 2H), 2.02-1.95 (m, 2H).

Ketoester 27: Methyl 3-oxo-3-(tetrahydrofuran-2-yl)propanoate

¹H NMR (400 MHz, DMSO-d₆) δ 4.37-4.32 (m, 1H), 3.79 (t, J=8.4 Hz, 2H), 3.68-3.62 (m, 5H), 2.16-2.05 (m, 1H), 1.92-1.76 (m, 3H).

Ketoester 29: cis-Methyl 5-(3-methoxy-3-oxopropanoyl)tetrahydrofuran-2-carboxylate ¹H NMR (300 MHz, CDCl₃) δ 11.89 (s, 0.15H), 5.69 (s, 0.15H), 4.61 (dd, J=7.2, 4.2 Hz, 1H), 4.53 (t, J=7.2 Hz, 1H), 4.00-3.76 (m, 1.7H), 3.73 (s, 6H), 2.30-2.02 (m, 4H).

Ketoester 30: Methyl 3-oxo-3-(tetrahydrofuran-3-yl)propanoate

¹H NMR (300 MHz, CDCl₃) δ 3.95-3.93 (m, 2H), 3.91-3.78 (m, 2H), 3.75 (s, 3H), 3.54 (s, 2H), 3.38-3.33 (m, 1H), 2.17-2.10 (m, 2H).

Ketoester 31: Methyl 3-oxo-3-(5-oxopyrrolidin-2-yl)propanoate

¹H NMR (300 MHz, CDCl₃) δ 11.85 (br s, 0.2H), 8.15 (br s, 0.4H), 7.34 (s, 0.4H), 7.17 (s, 0.2H), 5.19 (s, 0.2H), 4.39 (t, J=6.9 Hz, 0.6H), 4.21-4.14 (m, 0.4H), 3.73 (s, 3H), 3.57 (d, J=3.6 Hz, 1H), 3.38 (s, 0.6H), 2.54-2.36 (m, 2H), 2.26-2.10 (m, 0.9H), 1.91 (s, 0.1H), 1.47-1.42 (m, 0.4H), 1.32 (s, 0.2H), 1.11 (s, 0.2H).

Ketoester 28: Methyl 3-(3-methoxy-3-oxopropanoyl)cyclopentanecarboxylate

¹H NMR (400 MHz, DMSO-d₆) δ 3.69-3.65 (m, 1H), 3.63 (s, 1.4H), 3.60-3.59 (m, 5.6H), 3.15-3.03 (m, 0.4H), 2.92-2.78 (m, 1.6H), 2.19-2.07 (m, 1H), 1.97-1.69 (m, 5H).

Ketoester 34: trans-Methyl 3-(3-((tert-butoxycarbonyl)amino)cyclobutyl)-3-oxopropanoate ¹H NMR (400 MHz, CDCl₃) δ 4.71 (br s, 1H), 4.19-4.02 (m, 1H), 3.72 (s, 3H), 3.45 (s, 2H), 3.35-3.25 (m, 1H), 2.68-2.51 (m, 2H), 2.22-2.07 (m, 2H), 1.43 (s, 9H).

Ketoester 36: trans-Ethyl 3-(2-(2-(tert-butoxy)-2-oxoethyl)cyclopropyl)-3-oxopropanoate ¹H NMR (300 MHz, CDCl₃) δ 4.22-4.15 (m, 2H), 3.56-3.54 (m, 2H), 2.06-2.02 (m, 2H), 1.94-1.89 (m, 1H), 1.73-1.64 (m, 1H), 1.43-1.42 (m, 9H), 1.29-1.21 (m, 4H), 0.93-0.86 (m, 1H).

Ketoester 32: tert-Butyl 3-(3-methoxy-3-oxopropanoyl)azetidine-1-carboxylate LC-MS (ESI): $R_T$=1.44 min, mass calcd. for $C_{12}H_{19}NO_5$ 257.1, m/z found 258.2 [M+H]$^+$. $^1$H NMR (400 MHz, CDCl$_3$) δ 12.11 (s, 0.2H), 5.09 (s, 0.2H), 4.13-4.03 (m, 4H), 3.75 (s, 3H), 3.65-3.57 (m, 1H), 3.49 (s, 1.6H), 1.43 (s, 9H).

Ketoester 37: Methyl 4-(3-methoxy-3-oxopropanoyl)cycloheptanecarboxylate

LC-MS (ESI): $R_T$=1.28 min, mass calcd. for $C_{13}H_{20}O_5$ 256.1, m/z found 257.1 [M+H]$^+$. $^1$H NMR (300 MHz, DMSO-d$_6$) δ 3.66 (s, 2H), 3.60 (s, 3H), 3.56 (s, 3H), 2.70-2.61 (m, 1H), 2.50-2.43 (m, 1H), 1.96-1.33 (m, 10H).

Ketoester 39: 3-(2-Methoxycarbonyl-acetyl)-cyclobutanecarboxylic acid methyl ester $^1$H NMR (400 MHz, CDCl$_3$) δ 12.07 (s, 0.05H), 11.97 (s, 0.05H), 5.02 (s, 0.05H), 5.00 (s, 0.05H), 3.74-3.68 (m, 6H), 3.52-3.48 (m, 0.5H), 3.44-3.43 (m, 1.8H), 3.35-3.03 (m, 1.5H), 2.58-2.38 (m, 4H).

Ketoester 40: Methyl 3-(4-(N-methylsulfamoyl)cyclohexyl)-3-oxopropanoate $^1$H NMR (300 MHz, DMSO-d$_6$) δ 6.93-6.82 (m, 1H), 3.69 (s, 2H), 3.65 (s, 0.4H), 3.62 (s, 2.4H), 3.53 (s, 0.2H), 3.08-2.94 (m, 1H), 2.77-2.70 (m, 0.5H), 2.57-2.54 (m, 3H), 2.47-2.41 (m, 0.5H), 2.13-1.94 (m, 3H), 1.85-1.76 (m, 1H), 1.63-1.26 (m, 4H).

Ketoester 41: methyl 3-oxo-3-(4-(pyrrolidin-1-ylsulfonyl)cyclohexyl)propanoate $^1$H NMR (300 MHz, DMSO-d$_6$) δ 3.68 (s, 2H), 3.64-3.60 (m, 3H), 3.31-3.19 (m, 6H), 2.08-1.95 (m, 4H), 1.88-1.81 (m, 4H), 1.54-1.40 (m, 2H), 1.35-1.21 (m, 2H).

Ketoester 42: Methyl 3-(3-(N-methylacetamido)cyclopentyl)-3-oxopropanoate

LC-MS (ESI): $R_T$=1.17 min, mass calcd. for $C_{12}H_{19}NO_4$ 241.1, m/z found 242.3 [M+H]$^+$. $^1$H NMR (300 MHz, CDCl$_3$) δ 5.12-5.00 (m, 0.5H), 4.30-4.18 (m, 0.5H), 3.75 (s, 3H), 3.52-3.51 (m, 2H), 3.25-3.03 (m, 1H), 2.89-2.80 (m, 3H), 2.14-1.53 (m, 9H).

Ketoester 43: (cis)-Methyl 3-(4-methyltetrahydrofuran-2-yl)-3-oxopropanoate, Used as Crude

Ketoester 44: tert-butyl(cis)-5-(3-methoxy-3-oxopropanoyl)hexahydro-cyclopenta[c]pyrrole-2(1H)-carboxylate LC-MS (ESI): $R_T$=1.54 min, mass calcd. for $C_{16}H_{25}NO_5$ 311.2, m/z found 256.2 [M+H−56]$^+$. $^1$H NMR (400 MHz, CDCl$_3$) δ 12.04 (s, 0.1H), 5.01 (s, 0.1H), 3.73 (s, 2.7H), 3.72 (s, 0.3H), 3.48 (s, 1.8H), 3.47-3.43 (m, 2H), 3.28-3.07 (m, 3H), 2.77-2.71 (m, 0.2H), 2.69-2.58 (m, 1.8H), 2.21-2.04 (m, 2H), 1.68-1.56 (m, 2H), 1.44 (s, 9H).

Ketoester 45: Methyl 3-(4-((tert-butoxycarbonyl)amino)cycloheptyl)-3-oxopropanoate LC-MS (ESI): mass calcd. for $C_{16}H_{27}NO_5$ 313.2, m/z found 336.2 [M+Na]$^+$. $^1$H NMR (300 MHz, CDCl$_3$) δ 4.59-4.41 (m, 1H), 3.74 (s, 3H), 3.70-3.53 (m, 1H), 3.50 (s, 2H), 2.78-2.62 (m, 1H), 2.17-1.49 (m, 9H), 1.44 (s, 9H), 1.43-1.23 (m, 1H).

Ketoester 46: Methyl 3-(3-((tert-butoxycarbonyl)amino)bicyclo[1.1.1]pentan-1-yl)-3-oxopropanoate LC-MS (ESI): $R_T$=1.753 min, mass calcd. for $C_{14}H_{21}NO_5$ 283.1, m/z found 227.9 [M+H−56]$^+$. $^1$H NMR (400 MHz, CDCl$_3$) δ 11.78 (s, 0.2H), 4.99 (s, 0.2H), 4.96 (br s, 1H), 3.73 (s, 3H), 3.49 (s, 1.6H), 2.30 (s, 4.5H), 0.2.21 (s, 1.5H), 1.45 (s, 9H).

Ketoester 47: ethyl(cis)-4-(3-methoxy-3-oxopropanoyl)tetrahydrofuran-2-carboxylate $^1$H NMR (400 MHz, CDCl$_3$) δ 12.09 (s, 0.1H), 12.05 (s, 0.1H), 5.08 (s, 0.1H), 5.07 (s, 0.1H), 4.63-4.49 (m, 1H), 4.27-4.19 (m, 2.4H), 4.16-4.14 (m, 0.6H), 4.11-4.06 (m, 0.5H), 4.01-3.92 (m, 0.2H), 3.75 (s, 3H), 3.65-3.64 (m, 0.3H), 3.53 (s, 1.6H), 3.49-3.40 (m, 0.8H), 3.11-3.01 (m, 0.1H), 2.96-2.88 (m, 0.1H), 2.59-2.37 (m, 1.4H), 2.30-2.20 (m, 0.6H), 1.31-1.24 (m, 3H).

Ketoester 48: Methyl 3-(oxetan-3-yl)-3-oxopropanoate $^1$H NMR (300 MHz, CDCl$_3$) 12.13 (s, 0.2H), 5.06 (s, 0.2H), 4.81-4.76 (m, 2.6H), 4.15-4.05 (m, 0.5H), 3.95-3.92 (m, 0.5H), 3.90-3.76 (m, 1H), 3.73 (s, 1.5H), 3.72 (s, 1.5H), 3.71-3.63 (m, 0.7H), 3.47 (s, 1H), 3.22-3.15 (m, 0.3H).

Ketoester 49: Methyl 3-oxo-3-(1,4-dioxaspiro[4.5]decan-7-yl)propanoate $^1$H NMR (300 MHz, CDCl$_3$) δ 12.06 (s, 0.1H), 4.99 (s, 0.1H), 3.96 (s, 4H), 3.74 (s, 3H), 3.52 (s, 1.8H), 2.82-2.74 (m, 1H), 1.94-1.65 (m, 5.2H), 1.56-1.26 (m, 2.8H).

Ketoester 50: (cis)-Methyl 3-(4-(((tert-butyldiphenylsilyl)oxy)methyl)-tetrahydrofuran-2-yl)-3-oxopropanoate LC-MS (ESI): $R_T$=2.808 min, mass calcd. for $C_{25}H_{32}O_5Si$ 440.2, m/z found 458.2 [M+NH$_4$]+. $^1$H NMR (300 MHz, CDCl$_3$) δ 7.69-7.61 (m, 4H), 7.46-7.38 (m, 6H), 4.43-4.37 (m, 1H), 4.04-3.99 (m, 1H), 3.81-3.72 (m, 4H), 3.66-3.49 (m, 4H), 2.63-2.53 (m, 1H), 2.34-2.25 (m, 1H), 1.79-1.70 (m, 1H), 1.06 (s, 9H).

Ketoester 52: Methyl 3-(4-(N-isopropylsulfamoyl)cyclohexyl)-3-oxopropanoate $^1$H NMR (300 MHz, CDCl$_3$) δ 12.29 (s, 0.1H), 12.08 (s, 0.1H), 5.09 (s, 0.1H), 5.00 (s, 0.1H), 4.19-4.09 (m, 1H), 3.79 (s, 0.4H), 3.75 (s, 2.6H), 3.69-3.56 (m, 1H), 3.53 (s, 1.3H), 3.44 (s, 0.3H), 3.17-3.09 (m, 0.2H), 2.97-2.73 (m, 1.2H), 2.54-2.46 (m, 0.6H), 2.34-2.23 (m, 1.7H), 2.18-1.95 (m, 2.3H), 1.87-1.75 (m, 0.6H), 1.67-1.54 (m, 1.9H), 1.48-1.36 (m, 1.5H), 1.29-1.23 (m, 6H).

Ketoester 53: Methyl 3-(3-methoxy-3-oxopropanoyl)bicyclo[1.1.1]pentane-1-carboxylate $^1$H NMR (400 MHz, CDCl$_3$) δ 7.11 (s, 0.3H), 4.99 (s, 0.3H), 3.74 (s, 3H), 3.70 (s, 3H), 3.50 (s, 1.4H), 2.33 (s, 4H), 2.25 (s, 2H).

Ketoester 54: (cis)-Ethyl 3-(4-((tert-butoxycarbonyl) amino)tetrahydrofuran-2-yl)-3-oxopropanoate LC-MS (ESI): $R_T$=2.019 min, mass calcd. for $C_{14}H_{23}NO_6$ 301.1, m/z found 202.1. [M+H–100]$^+$. $^1$H NMR (300 MHz, CDCl3) δ 12.08 (s, 0.2H), 5.33 (s, 0.2H), 4.99 (br s, 1H), 4.57-4.52 (m, 0.2H), 4.47-4.42 (m, 0.8H), 4.25-4.21 (m, 2H), 3.98-3.93 (m, 1H), 3.82-3.71 (m, 1.6H), 3.57-3.52 (m, 1H), 2.55-2.44 (m, 1H), 2.18-2.05 (m, 1H), 1.44 (s, 9H), 1.32-1.28 (m, 3H).

Ketoester 55: (cis)-Methyl 3-(4-(methylcarbamoyl) tetrahydrofuran-2-yl)-3-oxopropanoate LC-MS (ESI): $R_T$=0.961 min and 1.236 min, mass calcd. for $C_{10}H_{15}NO_5$ 229.1, m/z found 230.1 [M+H]$^+$.

Ketoester 56: tert-Butyl 5-(3-ethoxy-3-oxopropanoyl)tetrahydro-2H-pyran-2-carboxylate $^1$H NMR (300 MHz, CD$_3$OD) δ 4.30-4.19 (m, 3H), 4.15-4.02 (m, 1H), 3.92-3.79 (m, 1H), 3.52-3.44 (m, 1H), 2.91-2.81 (m, 0.4H), 2.76-2.69 (m, 0.6H), 2.50-2.42 (m, 0.3H), 2.24-2.16 (m, 0.5H), 2.11-2.01 (m, 1.2H), 1.91-1.78 (m, 2H), 1.71-1.54 (m, 1H), 1.48 (s, 9H), 1.27 (t, J=7.2 Hz, 3H).

Ketoester 57: Methyl 3-oxo-3-(5-oxo-1-((2-trimethylsilyl)ethoxy)methyl)pyrrolidin-3-yl)propanoate $^1$H NMR (300 MHz, CDCl$_3$) δ 4.71 (s, 2H), 3.76 (s, 3.5H), 3.72-3.46 (m, 6.5H), 2.71-2.65 (m, 2H), 0.92 (t, J=8.4 Hz, 2H), 0.01 (s, 9H).

Ketoester 58: Methyl 3-(4-(N-(2-ethoxy-2-oxoethyl) sulfamoyl)cyclohexyl)-3-oxopropanoate $^1$H NMR (300 MHz, CDCl$_3$) δ 4.86-4.73 (m, 1H), 4.28-4.09 (m, 2H), 3.96-3.92 (m, 2H), 3.77 (s, 3H), 3.53 (s, 2H), 3.01-2.87 (m, 1H), 2.78-2.73 (m, 0.4H), 2.58-2.47 (m, 0.6H), 2.40-2.25 (m, 2H), 2.15-2.06 (m, 1H), 1.92-1.77 (m, 1H), 1.71-1.57 (m, 2H), 1.50-1.40 (m, 1H), 1.33-1.27 (m, 3H).

Ketoester 59: (R)-methyl 1-((4-(3-methoxy-3-oxopropanoyl)cyclohexyl)-sulfonyl)pyrrolidine-3-carboxylate $^1$H NMR (300 MHz, CDCl$_3$) δ 12.27 (s, 0.1H), 12.06 (s, 0.1H), 5.08 (s, 0.1H), 4.98 (s, 0.1H), 3.74 (s, 3H), 3.73 (m, 3H), 3.70-3.63 (m, 1H), 3.60-3.44 (m, 4.6H), 3.18-3.08 (m, 1H), 3.04-2.90 (m, 1H), 2.77-2.69 (m, 0.5H), 2.56-2.43 (m, 0.5H), 2.32-2.16 (m, 4H), 2.15-2.06 (m, 1H), 2.04-1.94 (m, 1H), 1.91-1.77 (m, 1H), 1.71-1.55 (m, 2H), 1.50-1.36 (m, 1H).

Ketoester 60: Methyl 3-(3-((tert-butyldiphenylsilyl) oxy)cyclobutyl)-3-oxopropanoate LC-MS (ESI): $R_T$=1.94 min, mass calcd. for $C_{24}H_{30}O_4Si$ 410.2, m/z found 411.5 [M+H]$^+$. $^1$H NMR (300 MHz, CDCl$_3$) δ 7.66-7.61 (m, 4H), 7.47-7.37 (m, 6H), 4.21-4.11 (m, 1H), 3.73 (s, 3H), 3.41 (s, 2H), 2.75-2.62 (m, 1H), 2.39-2.21 (m, 4H), 1.04 (s, 9H).

Ketoester 61: Methyl 4-(3-ethoxy-3-oxopropanoyl)cycloheptanecarboxylate

1H NMR (300 MHz, CDCl$_3$) δ 12.14 (s, 0.1H), 4.96 (s, 0.1H), 4.19 (q, J=6.9 Hz, 2H), 3.67 (s, 3H), 3.48 (s, 1.8H), 2.75-2.61 (m, 1H), 2.59-2.45 (m, 1H), 2.12-1.80 (m, 5.4H), 1.75-1.53 (m, 4H), 1.49-1.37 (m, 0.6H), 1.28 (t, J=6.9 Hz, 3H).

Ketoester 62: Methyl 3-(4-(N-(2-((tert-Butyldimethylsilyl)oxy)ethyl)-methylsulfonamido) cyclohexyl)-3-oxopropanoate $^1$H NMR (400 MHz, CDCl$_3$) δ 3.75-3.72 (m, 5H), 3.52-3.50 (m, 2H), 3.27-3.17 (m, 2H), 2.89 (s, 3H), 2.27-2.20 (m, 0.7H), 2.06-1.92 (m, 3.3H), 1.69-1.63 (m, 4.5H), 1.55-1.45 (m, 1.5H), 0.91 (s, 9H), 0.08 (s, 6H).

Ketoester 63: Methyl 3-(4-(N-(2-methoxyethyl) sulfamoyl)cyclohexyl)-3-oxopropanoate $^1$H NMR (300 MHz, CDCl$_3$) δ 4.55 (br s, 1H), 3.75 (s, 3H), 3.52-3.50 (m, 4H), 3.38 (s, 3H), 3.31-3.30 (m, 2H), 2.99-2.84 (m, 1H), 2.75 (br s, 0.4H), 2.56-2.48 (m, 0.6H), 2.33-2.24 (m, 2H), 2.15-2.02 (m, 2H), 1.87-1.57 (m, 3H), 1.49-1.38 (m, 1H).

Ketoester 64: tert-Butyl 3-(4-(3-methoxy-3-oxopropanoyl)-cyclohexanesulfonamido)-2,2-dimethylpropanoate $^1$H NMR (300 MHz, CDCl$_3$) δ 4.94-4.86 (m, 1H), 3.77 (s, 1.5H), 3.75 (s, 1.5H), 3.53 (s, 1.4H), 3.41 (s, 0.6H), 3.10 (d, J=6.3 Hz, 2H), 2.97-2.88 (m, 1H), 2.56-2.46 (m, 1H), 2.36-2.23 (m, 2H), 2.19-1.97 (m, 2H), 1.88-1.79 (m, 0.4H), 1.70-1.53 (m, 2H), 1.46 (s, 9H), 1.31-1.25 (m, 0.6H), 1.21 (s, 6H).

Ketoester 65R: Ethyl 6-(3-ethoxy-3-oxopropanoyl) tetrahydro-2H-pyran-3-carboxylate LC-MS (ESI): $R_T$=2.151 min, mass calcd. for $C_{13}H_{20}O_6$ 272.1, m/z found 273.1 [M+H]$^+$. $^1$H NMR (400 MHz, DMSO-d$_6$) δ 4.47-3.83 (m, 6H), 3.75-3.54 (m, 2H), 3.49-3.28 (m, 1H), 2.76-2.57 (m, 1H), 2.26-1.99 (m, 1H), 1.93-1.65 (m, 2H), 1.62-1.37 (m, 1H), 1.32-1.04 (m, 6H).

Ketoester 65S: Ethyl 6-(3-ethoxy-3-oxopropanoyl) tetrahydro-2H-pyran-3-carboxylate LC-MS (ESI): $R_T$=1.962 min, mass calcd. for $C_{13}H_{20}O_6$ 272.1, m/z found 290.2 [M+NH$_4$]+. $^1$H NMR (300 MHz, CDCl$_3$) δ 4.50-4.38 (m, 1H), 4.28-4.10 (m, 4.3H), 3.94-3.82 (m, 1H), 3.70-4.46 (m, 2.7H), 2.64-2.51 (m, 1H), 2.32-2.20 (m, 1H), 2.10-2.03 (m, 0.4H), 1.87-1.68 (m, 2.2H), 1.56-1.46 (m, 0.4H), 1.31-1.24 (m, 6H).

Ketoester 66: (trans)-tert-Butyl 2-(((tert-butyldiphenylsilyl)oxy)methyl)-4-(3-ethoxy-3-oxopropanoyl) piperidine-1-carboxylate LC-MS (ESI): $R_T$=2.574 min, mass calcd. for $C_{32}H_{45}NO_6Si$ 567.3, m/z found 468.3 [M+H–Boc]$^+$. $^1$H NMR (400 MHz, DMSO-d$_6$) δ 12.15-12.12 (m, 0.1H), 7.63 (t, J=5.6 Hz, 4H), 7.48-7.42 (m, 6H), 5.09-5.03 (m, 0.2H), 4.50-4.29 (m, 1H), 4.17-4.12 (m, 1H), 4.07-4.04 (m, 2H), 3.97-3.86 (m, 1H), 3.73-3.63 (m, 3.7H), 2.82-2.66 (m, 2H), 2.08-2.02 (m, 0.5H), 1.97-1.91 (m, 0.5H), 1.87-1.69 (m, 1H), 1.62-1.49 (m, 1H), 1.39 (s, 4H), 1.33 (s, 5H), 1.27-1.14 (m, 3H), 0.99 (s, 9H).

Ketoester 67: (trans)-Methyl 3-(4-((tert-butyldimethylsilyl)oxy)cyclohexyl)-3-oxopropanoate $^1$H NMR (300 MHz, CD$_3$OD) δ 3.70 (s, 3H), 3.65-3.57 (m, 1H), 3.34-3.29 (m, 2H), 2.51-2.44 (m, 1H), 2.00-1.86 (m, 4H), 1.45-1.27 (m, 4H), 0.90 (s, 9H), 0.08 (s, 6H).

Ketoester 68: tert-Butyl 4-(3-methoxy-3-oxopropanoyl)azepane-1-carboxylate $^1$H NMR (400 MHz, CDCl$_3$) δ 12.06 (s, 0.1H), 4.96 (s, 0.1H), 3.72 (s, 3H), 3.61-3.38 (m, 4H), 3.34-3.11 (m, 1.8H), 2.60-2.55 (m, 1H), 2.18-1.85 (m, 3H), 1.74-1.51 (m, 3H), 1.44 (s, 9H).

Ketoester 69: Methyl 3-oxo-3-(1,4-dioxaspiro[4.5]decan-8-yl)propanoate $^1$H NMR (400 MHz, CDCl$_3$) δ 3.95-3.91 (m, 4H), 3.73 (s, 3H), 3.50 (s, 2H), 2.52-2.45 (m, 1H), 1.92-1.87 (m, 2H), 1.82-1.77 (m, 2H), 1.74-1.63 (m, 2H), 1.59-1.53 (m, 2H).

Ketoester 70: Methyl 3-(4-(azetidin-1-ylsulfonyl)cyclohexyl)-3-oxopropanoate $^1$H NMR (400 MHz, CDCl$_3$) δ 12.27 (s, 0.1H), 12.06 (s, 0.1H), 5.07 (s, 0.1H), 4.97 (s, 0.1H), 4.00-3.95 (m, 4H), 3.75 (s, 2H), 3.74 (s, 1H), 3.52 (s, 0.7H), 3.50 (s, 0.7H), 2.91-2.70 (m, 1.5H), 2.53-2.44 (m, 0.5H), 2.30-2.21 (m, 4H), 2.11-2.07 (m, 1H), 2.02-1.92 (m, 1H), 1.83-1.73 (m, 2H), 1.64-1.51 (m, 2H), 1.46-1.33 (m, 1H).

Ketoester: 71: Ethyl 3-(3-((tert-butoxycarbonyl)amino)-2,2-dimethylcyclobutyl)-3-oxopropanoate LC-MS (ESI): R$_T$=1.662 min, mass calcd. for C$_{16}$H$_{27}$NO$_5$ 313.2, m/z found 258.0 [M−tBu+H]$^+$. $^1$H NMR (300 MHz, CDCl$_3$) δ 7.70 (s, 0.3H), 7.10 (s, 0.7H), 4.59 (br s, 0.5H), 4.24-4.15 (m, 2H), 3.86-3.83 (m, 0.5H), 3.38-3.27 (m, 2H), 2.89-2.83 (m, 0.6H), 2.21-2.04 (m, 1.4H), 1.69 (br s, 1H), 1.43-1.38 (m, 9H), 1.30-1.25 (m, 6H), 0.91-0.86 (s, 3H).

Ketoester 72: methyl 3-(4-(N-(3-methoxy-3-oxopropyl)sulfamoyl)cyclohexyl)-3-oxopropanoate $^1$H NMR (300 MHz, CDCl$_3$) δ 12.07 (s, 0.2H), 4.99 (s, 0.2H), 4.91-4.79 (m, 1H), 3.74 (s, 3H), 3.72 (s, 3H), 3.52 (s, 1.6H), 3.40-2.31 (m, 2H), 2.98-2.81 (m, 1H), 2.78-2.71 (m, 0.4H), 2.65-2.60 (m, 1.6H), 2.57-2.46 (m, 0.5H), 2.34-1.94 (m, 3.5H), 1.37-1.36 (m, 4H).

Dihydropyrimidines of General Formula I

Compound 1: Methyl 4-(2-chloro-4-fluorophenyl)-6-(1-methyl-2-oxopiperidin-4-yl)-2-(thiazol-2-yl)-1,4-dihydropyrimidine-5-carboxylate (a Mixture of 4 Stereoisomers)

Compound 1 (600 mg, 1.29 mmol) was further separated by chiral Prep. HPLC (the first separation condition: Column: Chiralpak IB 5 μm 20*250 mm; Mobile Phase: Hex:EtOH=90:10 at 15 mL/min; Temp: 30° C.; Wavelength: 214 nm followed by the second separation condition: Chiralpak IC 5 μm 20*250 mm; Mobile Phase: Hex:EtOH=50:50 at 10 mL/min; Temp: 30° C.; Wavelength: 214 nm) to afford stereoisomers Compound 1A (10.6 mg, 1.8% yield), Compound 1C (77.2 mg, 13% yield), Compound 1B (71.8 mg, 12% yield), and Compound 1D (117 mg, 20% yield).

Compound 1A: LC-MS (ESI): R$_T$=3.863 min, mass calcd. for C$_{21}$H$_{20}$ClFN$_4$O$_3$S, 462.1, m/z found 462.9 [M+H]$^+$. Chiral HPLC (Column: Chiralpak IC 5 μm 4.6*250 mm; Mobile Phase: Hex:EtOH=50:50 at 1.0 mL/min; Temp: 30° C.; Wavelength: 230 nm; R$_T$=9.256 min). $^1$H NMR (400 MHz, DMSO-d6) δ 9.62 (d, J=3.6 Hz, 0.9H), 9.30 (s, 0.1H), 8.02-7.99 (m, 1.9H), 7.94 (d, J=3.2 Hz, 0.1H), 7.42 (dd, J=8.8, 2.4 Hz, 1H), 7.39-7.36 (m, 1H), 7.22 (td, J=8.4, 2.8 Hz, 1H), 6.03 (s, 0.1H), 5.93 (d, J=4.0 Hz, 0.9H), 4.32-4.22 (m, 0.1H), 4.12-4.04 (m, 0.9H), 3.53 (s, 2.7H), 3.51 (s, 0.3H), 3.32-3.26 (m, 2H), 2.87 (s, 3H), 2.66-2.60 (m, 1H), 2.40-2.32 (m, 1H), 2.06-1.96 (m, 1H), 1.91-1.81 (m, 1H).

Compound 1B: LC-MS (ESI): R$_T$=3.846 min, mass calcd. for C$_{21}$H$_{20}$ClFN$_4$O$_3$S, 462.1, m/z found 462.9 [M+H]$^+$. Chiral HPLC (Column: Chiralpak IC 5 μm 4.6*250 mm; Mobile Phase: Hex:EtOH=50:50 at 1.0 mL/min; Temp: 30° C.; Wavelength: 230 nm; R$_T$=10.048 min). 1H NMR (400 MHz, DMSO-d$_6$) δ 9.59 (d, J=3.6 Hz, 0.9H), 9.26 (s, 0.1H), 8.02-8.00 (m, 1.9H), 7.93 (d, J=3.2 Hz, 0.1H), 7.43 (dd, J=8.8, 2.4 Hz, 1H), 7.40-7.37 (m, 1H), 7.22 (td, J=8.4, 2.4 Hz, 1H), 6.01 (s, 0.1H), 5.93 (d, J=3.6 Hz, 0.9H), 4.30-4.25 (m, 0.1H), 4.12-4.01 (m, 0.9H), 3.52 (s, 2.7H), 3.51 (s, 0.3H), 3.39-3.36 (m, 2H), 2.87 (s, 3H), 2.47-2.40 (m, 1H), 2.22 (dd, J=16.8, 4.0 Hz, 1H), 2.17-2.06 (m, 1H), 2.00-1.94 (m, 1H).

Compound 2: Methyl 6-(1-acetylpiperidin-4-yl)-4-(2-chloro-4-fluorophenyl)-2-(thiazol-2-yl)-1,4-dihydropyrimidine-5-carboxylate (a Mixture of 2 Stereoisomers)

Compound 2 (190 mg, 0.400 mmol) was further separated by chiral Prep. HPLC (Column: Chiralpak OD-H 5 μm 20*250 mm; Mobile Phase: Hex:EtOH=90:10 at 15 mL/min; Temp: 30° C.; Wavelength: 214 nm) followed by Prep. HPLC (Column: Xbridge C18 5 μm 19*150 mm, Mobile Phase A: Water (0.1% hydrochloric acid), Mobile Phase B: acetonitrile, Flow rate: 20 mL/min, Gradient: 30-50% (% B)) to afford stereoisomers Compound 2A (19.6 mg, 16% yield) and Compound 2B (19.4 mg, 15.4% yield) as yellow solids.

Compound 2B: LC-MS (ESI): R$_T$=4.331 min, mass calcd. for C$_{22}$H$_{22}$ClFN$_4$O$_3$S 476.1, m/z found 477.1 [M+H]$^+$. Chiral HPLC (Column: Chiralpak OD-H 5 μm 4.6*250 mm; Mobile Phase: Hex:EtOH=80:20 at 1.0 mL/min; Temp: 30° C.; Wavelength: 230 nm, 100% ee, R$_T$=7.351 min). $^1$H NMR (400 MHz, CD$_3$OD) δ 8.32 (d, J=2.8 Hz, 1H), 8.27 (d, J=3.2 Hz, 1H), 7.58-7.55 (m, 1H), 7.40 (dd, J=8.0, 2.4 Hz, 1H), 7.22 (td, J=8.4, 2.8 Hz, 1H), 6.33 (s, 1H), 4.74 (d, J=13.2 Hz, 1H), 4.21-4.14 (m, 2H), 3.69 (s, 3H), 3.31-3.24 (m, 1H), 2.83-2.74 (m, 1H), 2.23 (s, 1.5H), 2.21 (s, 1.5H), 2.15-1.85 (m, 4H).

Compound 3: Methyl 4-(2-chloro-4-fluorophenyl)-6-(2-oxopiperidin-4-yl)-2-(thiazol-2-yl)-1,4-dihydropyrimidine-5-carboxylate (a Mixture of 4 Stereoisomers)

Compound 3 (250 mg, 0.56 mmol) was further separated by chiral Prep. HPLC (separation condition: the first separation (Column: Chiralpak ID 5 μm 20*250 mm; Mobile Phase: Hex:EtOH=70:30 at 12 mL/min; Temp: 30° C.; Wavelength: 214 nm) followed by the second separation: Method A (Column: Chiralpak IC 5 μm 20*250 mm; Mobile Phase: Hex:EtOH=50:50 at 8 mL/min; Temp: 30° C.; Wavelength: 214 nm) and Method B (Column: Chiralpak IF 5 μm 20*250 mm; Mobile Phase: Hex:EtOH:DEA=60:40:0.3 at 10 mL/min; Temp: 30° C.; Wavelength: 214 nm)) to afford stereoisomers Compound 3A (20.5 mg, 8% yield), Compound 3B (41.1 mg, 16% yield), Compound 3C (24.6 mg, 10% yield) and Compound 3D (27.9 mg, 11% yield).

Compound 3A: LC-MS (ESI): $R_T$=3.647 min, mass calcd. for $C_{20}H_{18}ClFN_4O_3S$ 448.1, m/z found 448.9 [M+H]*. Chiral HPLC (Column: Chiralpak IC 5 μm 4.6*250 mm; Mobile Phase: Hex:EtOH=50:50 at 1.0 mL/min; Temp: 30° C.; Wavelength: 230 nm, $R_T$=10.135 min). $^1$H NMR (400 MHz, CDCl$_3$) δ 7.84 (d, J=3.2 Hz, 1H), 7.51 (d, J=2.8 Hz, 1H), 7.50-7.49 (m, 1H), 7.28-7.27 (m, 1H), 7.16-7.13 (m, 1H), 6.96 (td, J=8.0, 2.4 Hz, 1H), 6.07 (d, J=2.8 Hz, 1H), 5.81 (br s, 1H), 4.37-4.32 (m, 1H), 3.62 (s, 3H), 3.51-3.48 (m, 0.4H), 3.43-3.39 (m, 1.6H), 3.00-2.93 (m, 1H), 2.65-2.59 (m, 1H), 2.14-2.07 (m, 1H), 1.96-1.91 (m, 1H).

Compound 3C: LC-MS (ESI): $R_T$=3.643 min, mass calcd. for $C_{20}H_{18}ClFN_4O_3S$ 448.1, m/z found 448.9 [M+H]$^+$. Chiral HPLC (Column: Chiralpak IF 5 μm 4.6*250 mm; Mobile Phase: Hex:EtOH=60:40 at 1.0 mL/min; Temp: 30° C.; Wavelength: 230 nm, $R_T$=10.646 min). 1H NMR (400 MHz, CDCl$_3$) δ 7.83 (d, J=3.2 Hz, 1H), 7.52 (d, J=2.8 Hz, 1H), 7.46 (br s, 1H), 7.29-7.27 (m, 1H), 7.16 (dd, J=8.4, 2.8 Hz, 1H), 6.95 (td, J=8.4, 2.4 Hz, 1H), 6.11 (d, J=2.8 Hz, 1H), 5.80 (br s, 1H), 4.31-4.29 (m, 1H), 3.61 (s, 3H), 3.53-3.50 (m, 2H), 2.87-2.80 (m, 1H), 2.46-2.40 (m, 1H), 2.29-2.24 (m, 1H), 2.13-2.09 (m, 1H).

Compound 4: Methyl 4-(2-chloro-3-fluorophenyl)-6-(1-methyl-2-oxopiperidin-4-yl)-2-(thiazol-2-yl)-1,4-dihydropyrimidine-5-carboxylate (a Mixture of 4 Stereoisomers)

Compound 4 (0.51 g, 1.1 mmol) was further separated by chiral Prep. HPLC (separation condition: Column: Chiralpak IA 5 μm 20*250 mm; Mobile Phase: Hex:EtOH:DEA=80:20:0.3 at 20 mL/min; Temp: 30° C.; Wavelength: 230 nm and Column: Chiralpak IB 5 μm 20*250 mm; Mobile Phase: Hex:EtOH:DEA=90:10:0.3 at 15 mL/min; Temp: 30° C.; Wavelength: 214 nm) to afford stereoisomers Compound 4A (107 mg, 83% yield), Compound 4B (54 mg, 42% yield), Compound 4C (58 mg, 45% yield) and Compound 4D (109 mg, 85% yield).

Compound 4B: LC-MS (ESI): $R_T$=3.975 min, mass calcd. for $C_{21}H_{20}ClFN_4O_3S$, 462.1, m/z found 462.9 [M+H]$^+$. Chiral HPLC (Column: Chiralpak IB 5 μm 4.6*250 mm; Mobile Phase: Hex:EtOH:DEA=90:10:0.2 at 1.0 mL/min; Temp: 30° C.; Wavelength: 230 nm; $R_T$=11.927 min). $^1$H NMR (400 MHz, DMSO-d$_6$) δ 9.66 (br s, 0.9H), 9.32 (br s, 0.1H), 8.03-8.00 (m, 1.9H), 7.94 (d, J=3.6 Hz, 0.1H), 7.42-7.32 (m, 2H), 7.25-7.21 (m, 0.9H), 7.18-7.14 (m, 0.1H), 6.09 (s, 0.1H), 5.98 (s, 0.9H), 4.33-4.23 (m, 0.1H), 4.14-4.04 (m, 0.9H), 3.53 (s, 2.7H), 3.51 (s, 0.3H), 3.32-3.28 (m, 2H), 2.87 (s, 3H), 2.66-2.60 (m, 1H), 2.39-2.34 (m, 1), 2.07-1.97 (m, 1H), 1.90-1.81 (m, 1H).

Compound 8: Methyl 4-(2-chloro-3-fluorophenyl)-6-(1-((1-methoxy-2-methyl-1-oxopropan-2-yl)sulfonyl)piperidin-4-yl)-2-(thiazol-2-yl)-1,4-dihydropyrimidine-5-carboxylate LC-MS (ESI): $R_T$=4.436 min, mass calcd. for $C_{25}H_{28}ClFN_4O_6S_2$ 598.1, m/z found 598.9 [M+H]$^+$. Chiral HPLC (Column: Chiralpak IA 5 μm 4.6*250 mm; Mobile Phase: Hex:EtOH:DEA=70:30:0.2 at 1.0 mL/min; Temp: 30° C.; Wavelength: 230 nm, $R_T$=6.361 min and 10.935 min). $^1$H NMR (400 MHz, DMSO-d$_6$) δ 9.62 (d, J=3.6 Hz, 0.8H), 9.39 (s, 0.2H), 8.00 (m, 1.8H), 7.93 (d, J=2.8 Hz, 0.2H), 7.40-7.31 (m, 2H), 7.22-7.15 (m, 1H), 6.06 (s, 0.2H), 5.97 (d, J=3.6 Hz, 0.8H), 4.08-3.98 (m, 0.2H), 3.80-3.74 (m, 5.8H), 3.53 (s, 3H), 3.06-2.98 (m, 2H), 2.08-2.00 (m, 1H), 1.87-1.85 (m, 2H), 1.72-1.61 (m, 7H).

Compound 37: Methyl 4-(2-chloro-3-fluorophenyl)-6-(3-(methylsulfonyl)-3-azabicyclo[3.2.1]octan-8-yl)-2-(thiazol-2-yl)-1,4-dihydropyrimidine-5-carboxylate (a Mixture of 2 Stereoisomers)

Compound 37 (30 mg, 0.060 mmol) was further separated by chiral Prep. HPLC (Column: Chiralpak IF 5 μm 20*250 mm; Mobile Phase: Hex:EtOH=50:50 at 8 mL/min; Temp: 30° C.; Wavelength: 214 nm) to afford stereoisomers Compound 37A (3.1 mg, 10% yield) and Compound 37B (3.0 mg, 10% yield) as yellow solids.

Compound 37B: LC-MS (ESI): $R_T$=3.099 min, mass calcd. for $C_{23}H_{24}ClFN_4O_4S_2$ 538.1, m/z found 538.9 [M+H]$^+$. Chiral HPLC (Column: Chiralpak IF 5 μm 4.6*250 mm; Mobile Phase: Hex:EtOH=50:50 at 1.0 mL/min; Temp: 30° C.; Wavelength: 230 nm, $R_T$=14.052 min). $^1$H NMR (400 MHz, CDCl$_3$) δ 8.35 (s, 0.2H), 7.84 (d, J=3.2 Hz, 0.7H), 7.82 (d, J=3.2 Hz, 0.3H), 7.52 (d, J=3.2 Hz, 1.5H), 7.46 (d, J=2.8 Hz, 0.3H), 7.24-7.20 (m, 0.8H), 7.18-7.15 (m, 0.2H), 7.11-7.08 (m, 1.8H), 7.05-7.00 (m, 0.2H), 6.28 (s, 0.3H), 6.14 (d, J=2.8 Hz, 0.7H), 3.86 (s, 0.2H), 3.74-3.65 (m, 2.8H), 3.60 (s, 2.1H), 3.59 (s, 0.9H), 3.18-3.12 (m, 1H), 3.08-3.04 (m, 1H), 2.82 (s, 3H), 2.68 (br s, 0.7H), 2.63-2.61 (m, 0.6H), 2.55 (br s, 0.7H), 2.14-2.01 (m, 2.5H), 1.87-1.77 (m, 1.5H).

Compound 38: 4-(2-Chloro-4-fluoro-phenyl)-6-(8-methanesulfonyl-8-aza-bicyclo[3.2.1]oct-3-yl)-2-thiazol-2-yl-1,4-dihydro-pyrimidine-5-carboxylic Acid Methyl Ester (a Mixture of 2 Stereoisomers)

Compound 38 (100 mg, 0.186 mmol) was further separated by chiral Prep. HPLC (Column: Chiralpak IA 5 μm 20*250 mm, Mobile Phase: Hex:EtOH=85:15 at 20 mL/min, Temp: 30° C., Wavelength: 230 nm) to afford stereoisomers Compound 38A (19.7 mg, 20% yield) and Compound 38B (19.4 mg, 19% yield).

Compound 38B: LC-MS (ESI): $R_T$=3.995 min, mass calcd. for $C_{23}H_{24}ClFN_4O_4S_2$ 538.1, m/z found 538.9 [M+H]$^+$. Chiral HPLC (Column: Chiralpak IA 5 μm 4.6*250 mm; Mobile Phase: Hex:EtOH=85:15 at 1.0 mL/min; Temp: 30° C.; Wavelength: 230 nm, $R_T$=14.787 min). $^1$H NMR (400 MHz, DMSO-d$_6$) δ 9.52 (d, J=3.6 Hz, 0.8H), 9.05 (s, 0.2H), 8.00-7.98 (m, 1.8H), 7.93 (d, J=2.8 Hz, 0.2H), 7.44-7.40 (m, 1H), 7.34-7.28 (m, 1H), 7.23-7.16 (m, 1H), 6.01 (s, 0.2H), 5.92 (d, J=3.6 Hz, 0.8H), 4.49-4.40 (m, 0.2H), 4.27-4.15 (m, 2.8H), 3.54 (s, 3H), 2.99 (s, 3H), 2.20-1.94 (m, 4H), 1.85-1.66 (m, 3.2H), 1.52-1.49 (m, 0.8H).

Compound 39: 4-(2-Chloro-3-fluoro-phenyl)-6-(8-methanesulfonyl-8-aza-bicyclo[3.2.1]oct-3-yl)-2-thiazol-2-yl-1,4-dihydro-pyrimidine-5-carboxylic Acid Methyl Ester (a Mixture of 2 Stereoisomers)

Compound 39 (74 mg, 0.137 mmol) was further separated by chiral Prep. HPLC (Column: Chiralpak IA 5 μm 20*250 mm, Mobile Phase: Hex:IPA:DEA=90:10:0.3 at 20 mL/min, Temp: 30° C., Wavelength: 230 nm) to afford stereoisomers Compound 39A (15.8 mg, 21% yield) and Compound 39B (18.4 mg, 25% yield).

Compound 39B: LC-MS (ESI): $R_T$=3.899 min, mass calcd. for $C_{23}H_{24}ClFN_4O_4S_2$ 538.1, m/z found 538.9 [M+H]$^+$. Chiral HPLC (Column: Chiralpak IA 5 μm 4.6*250 mm; Mobile Phase: Hex:IPA:DEA=90:10:0.2 at 1.0 mL/min; Temp: 30° C.; Wavelength: 230 nm, $R_T$=17.400 min); $^1$H NMR (400 MHz, DMSO-$d_6$) δ 9.61 (d, J=3.6 Hz, 0.8H), 9.12 (s, 0.2H), 8.00-7.94 (m, 2H), 7.40-7.29 (m, 2H), 7.19-7.13 (m, 1H), 6.06 (s, 0.2H), 5.97 (d, J=3.2 Hz, 0.8H), 4.50-4.41 (m, 0.2H), 4.27-4.21 (m, 2.8H), 3.54 (s, 3H), 3.00 (s, 3H), 2.21-1.95 (m, 4H), 1.87-1.67 (m, 3.2H), 1.53-1.50 (m, 0.8H).

Compound 47: Ethyl 4-(2-chloro-4-fluorophenyl)-6-cyclohexyl-2-(thiazol-2-yl)-1,4-dihydro-pyrimidine-5-carboxylate (a Mixture of 2 Stereoisomers)

Compound 47 (150 mg, 0.33 mmol) was further separated by chiral Prep. HPLC (Column: Chiralpak IA 5 μm 20*250 mm; Mobile Phase: Hex:IPA:DEA=98:2:0.3 at 15 mL/min; Temp: 30° C.; Wavelength: 214 nm) to afford stereoisomers Compound 47A (31.4 mg, 21% yield) and Compound 47B (32.1 mg, 21% yield) as yellow solids.

Compound 47A: LC-MS (ESI): $R_T$=4.304 min, mass calcd. for $C_{22}H_{23}ClFN_3O_2S$ 447.1, m/z found 448.1 [M+H]$^+$. Chiral HPLC (Column: Chiralpak IA 5 μm 4.6*250 mm; Mobile Phase: Hex:IPA:DEA=95:5:0.2 at 1.0 mL/min; Temp: 30° C.; Wavelength: 230 nm, $R_T$=5.332 min). $^1$H NMR (400 MHz, DMSO-$d_6$) δ 9.40 (d, J=2.8 Hz, 0.5H), 8.79 (s, 0.5H), 7.99-7.94 (m, 2H), 7.44-7.41 (m, 1H), 7.36-7.32 (m, 1H), 7.24-7.19 (m, 1H), 6.02 (s, 0.5H), 5.90 (d, J=3.2 Hz, 0.5H), 3.99-3.92 (m, 2H), 3.87-3.81 (m, 0.5H), 3.61 (br s, 0.5H), 1.82-1.56 (m, 7H), 1.33-1.23 (m, 3H), 1.09-1.03 (m, 3H).

Compound 48: Methyl 4-(2-chloro-4-fluorophenyl)-6-(tetrahydro-2H-pyran-3-yl)-2-(thiazol-2-yl)-1,4-dihydropyrimidine-5-carboxylate (a Mixture of 4 Stereoisomers)

Compound 48 (300 mg, 0.690 mmol) was further separated by chiral Prep. HPLC (separation condition: Column: Chiralpak IE 5 μm 20*250 mm, Mobile Phase: Hex:EtOH=85:15 at 11 mL/min, Temp: 30° C., Wavelength: 214 nm) to afford stereoisomers Compound 48A (7.7 mg, 3% yield), Compound 48B (10.4 mg, 3% yield), Compound 48C (87.5 mg, 29% yield) and Compound 48D (88 mg, 29% yield) as yellow solids.

Compound 48A: LC-MS (ESI): $R_T$=4.273 min, mass calcd. for $C_{20}H_{19}ClFN_3O_3S$ 435.1, m/z found 435.9 [M+H]$^+$. Chiral HPLC (Chiralpak IC 5 μm 4.6*250 mm, Mobile Phase: Hex:EtOH:DEA=90:10:0.2 at 1.0 mL/min, Temp: 30° C., Wavelength: 230 nm, $R_T$=7.397 min); $^1$H NMR (400 MHz, DMSO-$d_6$) δ 9.87 (s, 0.4H), 9.48 (d, J=3.6 Hz, 0.6H), 8.00-7.98 (m, 1.5H), 7.93 (d, J=3.6 Hz, 0.5H), 7.45-7.40 (m, 1.4H), 7.35-7.31 (m, 0.6H), 7.22-7.14 (m, 1H), 6.02 (s, 0.4H), 5.91 (d, J=3.6 Hz, 0.6H), 4.17 (dd, J=11.6, 8.0 Hz, 0.5H), 3.94-3.79 (m, 3H), 3.68-3.59 (m, 1H), 3.53 (s, 1.8H), 3.50 (s, 1.2H), 3.36-3.34 (m, 0.5H), 1.99-1.86 (m, 1.5H), 1.73-1.53 (m, 2.5H).

Compound 48D: LC-MS (ESI): $R_T$=4.124 min, mass calcd. for $C_{20}H_{19}ClFN_3O_3S$ 435.1, m/z found 435.9 [M+H]$^+$. Chiral HPLC (Chiralpak IE 5 μm 4.6*250 mm, Mobile Phase: Hex:EtOH=80:20 at 1.0 mL/min, Temp: 30° C., Wavelength: 230 nm, $R_T$=9.849 min); $^1$H NMR (400 MHz, DMSO-$d_6$) δ 9.77 (d, 0.4H), 9.50 (d, J=3.6 Hz, 0.6H), 8.01-7.98 (m, 1.5H), 7.92 (d, J=3.2 Hz, 0.5H), 7.44-7.40 (m, 1H), 7.38-7.33 (m, 1H), 7.24-7.19 (m, 1H), 6.04 (s, 0.4H), 5.91 (d, J=3.6 Hz, 0.6H), 4.03 (dd, J=10.0, 3.6 Hz, 0.4H), 3.92-3.72 (m, 3H), 3.64-3.56 (m, 1H), 3.53 (s, 1.8H), 3.49 (s, 1.2H), 3.37-3.34 (m, 0.6H), 2.09-1.61 (m, 4H).

Compound 49: Methyl 4-(2-chloro-4-fluorophenyl)-6-(tetrahydro-2H-pyran-2-yl)-2-(thiazol-2-yl)-1,4-dihydropyrimidine-5-carboxylate (a Mixture of 4 Stereoisomers)

Compound 49 (450 mg, 1.03 mmol) was further separated by chiral Prep. HPLC (Column: Chiralpak IF 5 μm 20*250 mm; Mobile Phase: Hex:EtOH=90:10 at 15 mL/min; Temp: 30° C.; Wavelength: 230 nm) to afford stereoisomers Compound 49A (100 mg, 22% yield, a mixture of two stereoisomers) and Compound 49B (41.0 mg, 10% yield), Compound 49C (54.0 mg, 12% yield).

Compound 49C: LC-MS (ESI): $R_T$=4.296 min, mass calcd. for $C_{20}H_{19}ClFN_3O_3S$ 435.1, m/z found 435.9 [M+H]$^+$. Chiral HPLC (Column: Chiralpak IF 5 μm 4.6*250 mm; Mobile Phase: Hex:EtOH=90:10 at 1.0 mL/min; Temp: 30° C.; Wavelength: 230 nm, $R_T$=8.252 min). $^1$H NMR (400 MHz, DMSO-$d_6$) δ 8.91 (s, 1H), 8.00 (d, J=3.2 Hz, 1H), 7.96 (d, J=3.2 Hz, 1H), 7.43 (dd, J=8.8, 3.2 Hz, 1H), 7.32 (dd, J=8.8, 6.2 Hz, 1H), 7.23-7.18 (m, 1H), 6.06 (s, 1H), 5.15 (d, J=8.0 Hz, 1H), 4.13 (d, J=10.0 Hz, 1H), 3.63-3.57 (m, 1H), 3.53 (s, 3H), 2.01-1.99 (m, 1H), 1.94-1.88 (m, 1H), 1.70-1.56 (m, 4H).

Compound 51: Methyl 4-(2-chloro-4-fluorophenyl)-6-(tetrahydro-2H-pyran-4-yl)-2-(thiazol-2-yl)-1,4-dihydropyrimidine-5-carboxylate (a Mixture of 2 Stereoisomers)

Compound 51 (150 mg, 0.35 mmol) was further separated by chiral Prep. HPLC (Column: Chiralpak IE 5 μm 20*250 mm; Mobile Phase: Hex:EtOH=90:10 at 15 mL/min; Temp: 30° C.; Wavelength: 214 nm) to afford stereoisomers Compound 51A (45.6 mg, 30% yield) and Compound 51B (59.7 mg, 40% yield) as yellow solids.

Compound 51B: LC-MS (ESI): $R_T$=3.957 min, mass calcd. for $C_{20}H_{19}ClFN_3O_3S$ 435.1, m/z found 435.9 [M+H]$^+$. Chiral HPLC (Column: Chiralpak IE 5 μm 4.6*250 mm; Mobile Phase: Hex:EtOH=85:15 at 1.0 mL/min; Temp: 30° C.; Wavelength: 230 nm, $R_T$=9.116 min). $^1$H NMR (400 MHz, DMSO-$d_6$) δ 9.48 (d, J=3.6 Hz, 0.8H), 8.95 (s, 0.2H), 8.00 (s, 1.8H), 7.94 (d, J=3.6 Hz, 0.2H), 7.45-7.41 (m, 1H), 7.37-7.32 (m, 1H), 7.23-7.17 (m, 1H), 6.02 (s, 0.2H), 5.92 (d, J=3.2 Hz, 0.8H), 4.13-4.06 (m, 0.2H), 4.02-3.82 (m, 2.8H), 3.53 (s, 2.1H), 3.52 (s, 0.9H), 3.39 (q, J=10.4 Hz, 2H), 2.10-2.00 (m, 1H), 1.98-1.87 (m, 1H), 1.72 (d, J=11.2 Hz, 0.2H), 1.63-1.57 (m, 1H), 1.42 (d, J=13.2 Hz, 0.8H).

Compound 50: 4-(2-Chloro-3-fluoro-phenyl)-6-(tetrahydro-pyran-4-yl)-2-thiazol-2-yl-1,4-dihydro-pyrimidine-5-carboxylic acid methyl ester (a Mixture of 2 Stereoisomers)

Compound 50 (150 mg, 0.35 mmol) was further separated by chiral Prep. HPLC (Column: Chiralpak IE 5 μm 20*250 mm; Mobile Phase: Hex:EtOH=90:10 at 15 mL/min; Temp: 30° C.; Wavelength: 214 nm) to afford stereoisomers Compound 50A (54.8 mg, 37% yield) and Compound 50B (52.1 mg, 35% yield) as yellow solids.

Compound 50B: LC-MS (ESI): $R_T$=3.715 min, mass calcd. for $C_{20}H_{19}ClFN_3O_3S$ 435.1, m/z found 435.9 [M+H]$^+$. Chiral HPLC (Column: Chiralpak IE 5 μm 4.6*250 mm; Mobile Phase: Hex:EtOH=85:15 at 1.0 mL/min; Temp: 30° C.; Wavelength: 230 nm, $R_T$=9.537 min). $^1$H NMR (400

MHz, DMSO-d$_6$) δ 9.57 (d, J=3.6 Hz, 0.8H), 9.00 (s, 0.2H), 8.01 (s, 1.7H), 7.94 (d, J=3.2 Hz, 0.3H), 7.40-7.29 (m, 2H), 7.21-7.16 (m, 1H), 6.07 (s, 0.3H), 5.97 (d, J=3.6 Hz, 0.7H), 4.14-4.08 (m, 0.2H), 4.01-3.84 (m, 2.8H), 3.52 (s, 3H), 3.46-3.37 (m, 2H), 2.10-2.00 (m, 1H), 1.98-1.88 (m, 1H), 1.72 (d, J=13.2 Hz, 0.2H), 1.59 (t, J=13.4 Hz, 1H), 1.41 (d, J=15.6 Hz, 0.8H).

Compound 69: Methyl 4-(2-chloro-4-fluorophenyl)-6-(1-(methylsulfonyl)-pyrrolidin-2-yl)-2-(thiazol-2-yl)-1,4-dihydropyrimidine-5-carboxylate (a Mixture of 4 Stereoisomers)

Compound 69 was further purified by Prep. HPLC (Column: Gilson X-bridge C18 (5 μm 19*150 mm); Mobile phase A: water (0.1% ammonium bicarbonate), Mobile phase B: acetonitrile, UV: 214 nm, Flow rate: 15 mL/min Gradient: 40-70% (% B)) to get two mixtures Compound 69X (60 mg, 6% yield, a mixture of 2 stereoisomers) and Compound 69Y (60 mg, 6% yield, a mixture of 2 stereoisomers) as yellow solids.

Compound 69Y (60 mg, 0.12 mmol) was further separated by chiral Prep. HPLC (Column: Chiralpak IC 5 μm 20*250 mm; Mobile Phase: Hex:EtOH:DEA=60:40:0.3 at 12 mL/min; Temp: 30° C.; Wavelength: 214 nm) to afford stereoisomers Compound 69C (11.0 mg, 18% yield) and Compound 69D (9.6 mg, 16% yield) as yellow solids.

Compound 69C: LC-MS (ESI): R$_T$=3.901 min, mass calcd. for C$_{20}$H$_{20}$ClFN$_4$O$_4$S$_2$ 498.1, m/z found 498.9 [M+H]$^+$. Chiral HPLC (Column: Chiralpak IA 5 μm 4.6*250 mm; Mobile Phase: Hex:EtOH:DEA=80:20:0.2 at 1.0 mL/min; Temp: 30° C.; Wavelength: 230 nm, R$_T$=8.394 min); $^1$H NMR (400 MHz, DMSO-d$_6$) δ 9.62 (d, J=3.6 Hz, 0.3H), 8.89 (s, 0.6H), 7.99 (dd, J=20.4, 2.8 Hz, 2H), 7.58 (t, J=6.4 Hz, 0.3H), 7.51 (dd, J=8.2, 6.6 Hz, 0.7H), 7.43 (dd, J=8.8, 2.4 Hz, 1H), 7.10 (td, J=8.4, 2.0 Hz, 1H), 6.00 (s, 0.7H), 5.87 (d, J=3.6 Hz, 0.3H), 5.75-5.72 (m, 0.3H), 5.44 (t, J=7.2 Hz, 0.7H), 3.62-3.50 (m, 5H), 3.12 (s, 2H), 2.95 (s, 1H), 2.67-2.60 (m, 1H), 2.30-2.25 (m, 0.2H), 2.19-2.10 (m, 0.3H), 2.00-1.77 (m, 2.5H).

Compound 70: Methyl 4-(2-chloro-4-fluorophenyl)-6-(tetrahydrofuran-2-yl)-2-(thiazol-2-yl)-1,4-dihydropyrimidine-5-carboxylate (a Mixture of 4 Stereoisomers)

Compound 70 (300 mg, 0.71 mmol) was further separated by chiral Prep. HPLC (separation condition: Column: Chiralpak IE 5 μm 20*250 mm; Mobile Phase: Hex:EtOH=80:20 at 10 ml/min; Temp: 30° C.; Wavelength: 214 nm) to afford stereoisomers Compound 70C (25 mg, 8.3% yield), Compound 70D (26 mg, 8.6% yield) and a mixture of Compound 70A and Compound 70B (120 mg). The mixture (120 mg) was then separated by chiral Prep. HPLC (separation condition: Column: Chiralpak ID 5 μm 20*250 mm; Mobile Phase: Hex:IPA=80:20 at 12 mL/min; Temp: 30° C.; Wavelength: 230 nm) to afford stereoisomers Compound 70A (14 mg, 4.6% yield) and Compound 70B (20 mg, 6.6% yield).

Compound 70D: LC-MS (ESI): R$_T$=3.558 min, mass calcd. for C$_{19}$H$_7$ClFN$_3$O$_3$S 421.1, m/z found mass 421.9 [M+H]$^+$. Chiral HPLC (Column: Chiralpak IE 5 μm 4.6*250 mm; Mobile Phase: Hex:IPA=80:20 at 1.0 mL/min; Temp: 30° C.; Wavelength: 230 nm, R$_T$=11.261 min). $^1$H NMR (400 MHz, DMSO-d$_6$) δ 8.97 (s, 1H), 8.01 (d, J=2.8 Hz, 1H), 7.96 (d, J=2.8 Hz, 1H), 7.43 (dd, J=8.8, 2.4 Hz, 1H), 7.35-7.32 (m, 1H), 7.20 (td, J=8.4, 2.0 Hz, 1H), 6.06 (s, 1H), 5.40 (t, J=7.2 Hz, 1H), 4.12-4.09 (m, 1H), 3.95-3.91 (m, 1H), 3.53 (s, 3H), 2.61-2.55 (m, 1H), 2.02-1.88 (m, 3H).

Compound 74: Methyl 4-(2-chloro-3-fluorophenyl)-6-(tetrahydrofuran-3-yl)-2-(thiazol-2-yl)-1,4-dihydropyrimidine-5-carboxylate (a Mixture of 4 Stereoisomers)

Compound 74 (300 mg, 0.710 mmol) was further separated by chiral Prep. HPLC (first separation condition (Column: Chiralpak IC 5 μm 20*250 mm; Mobile Phase: Hex:EtOH:DEA=50:50:0.3 at 8 mL/min; Temp: 30° C.; Wavelength: 230 nm) followed by second separation conditions: Method A (Column: Chiralpak IA 5 μm 20*250 mm; Mobile Phase: Hex:EtOH:DEA=90:10:0.2 at 12 mL/min; Temp: 30° C.; Wavelength: 214 nm) and Method B: (Column: Chiralpak IE 5 μm 20*250 mm; Mobile Phase: Hex:EtOH:DEA=90:10:0.3 at 12 mL/min; Temp: 30° C.; Wavelength: 214 nm)) to afford stereoisomers Compound 74A (27 mg, 9% yield), Compound 74B (32 mg, 11% yield), Compound 74C (26 mg, 9% yield) and Compound 74D (23 mg, 8% yield) as yellow solids.

Compound 74A: LC-MS (ESI): R$_T$=3.603 min, mass calcd. for C$_{19}$H$_{17}$ClFN$_3$O$_3$S 421.1, m/z found 422.1 [M+H]$^+$. Chiral HPLC (Column: Chiralpak IA 5 μm 4.6*250 mm; Mobile Phase: Hex:EtOH:DEA=90:10:0.2 at 1.0 mL/min; Temp: 30° C.; Wavelength: 230 nm, R$_T$=8.120 min). $^1$H NMR (400 MHz, DMSO-d$_6$) δ 9.67 (d, J=3.6 Hz, 0.6H), 8.89 (s, 0.4H), 8.01-7.99 (m, 1.6H), 7.95-7.94 (m, 0.4H), 7.40-7.30 (m, 2H), 7.24-7.20 (m, 1H), 6.08 (s, 0.4H), 5.96 (d, J=3.6 Hz, 0.6H), 4.70-4.65 (m, 0.4H), 4.41-4.33 (m, 0.6H), 4.17-4.13 (m, 0.5H), 4.07-4.04 (m, 0.5H), 3.96-3.90 (m, 1.3H), 3.87-3.82 (m, 0.7H), 3.74-3.68 (m, 0.3H), 3.66-3.62 (m, 0.7H), 3.53-3.51 (m, 3H) 2.37-2.29 (m, 1H), 2.14-2.05 (m, 1H).

Compound 74C: LC-MS (ESI): R$_T$=3.600 min, mass calcd. for C$_{19}$H$_{17}$ClFN$_3$O$_3$S 421.1, m/z found 422.1 [M+H]$^+$. Chiral HPLC (Column: Chiralpak IA 5 μm 4.6*250 mm; Mobile Phase: Hex:EtOH:DEA=90:10:0.2 at 1.0 mL/min; Temp: 30° C.; Wavelength: 230 nm, R$_T$=10.731 min). $^1$H NMR (400 MHz, DMSO-d$_6$) δ 9.67 (s, 0.6H), 8.88 (s, 0.4H), 8.01 (s, 1.8H), 7.95 (s, 0.2H), 7.41-7.32 (m, 2H), 7.25-7.22 (m, 1H), 6.08 (s, 0.4H), 5.96 (s, 0.6H), 4.71-4.65 (m, 0.3H), 4.42-4.33 (m, 0.6H), 4.16-3.81 (m, 2.7H), 3.73-3.57 (m, 1.4H), 3.53 (s, 3H), 2.35-2.30 (m, 1H), 2.14-2.04 (m, 1H).

Compound 74D: LC-MS (ESI): R$_T$=3.704 min, mass calcd. for C$_{19}$H$_{17}$ClFN$_3$O$_3$S 421.1, m/z found 421.9 [M+H]$^+$. Chiral HPLC (Column: Chiralpak IA 5 μm 4.6*250 mm; Mobile Phase: Hex:EtOH:DEA=90:10:0.2 at 1.0 mL/min; Temp: 30° C.; Wavelength: 230 nm, R$_T$=14.190 min). $^1$H NMR (400 MHz, DMSO-d$_6$) δ 9.63 (s, 0.6H), 8.98 (s, 0.4H), 8.01 (s, 1.8H), 7.95 (s, 0.2H), 7.38-7.15 (m, 3H), 6.08 (s, 0.4H), 6.00 (s, 0.6H), 4.67-4.61 (m, 0.3H), 4.39-4.20 (m, 1H), 4.07-4.03 (m, 1H), 3.95-3.66 (m, 2.7H), 3.53 (s, 3H), 2.22-2.16 (m, 1H), 1.98-1.90 (m, 1H).

Compound 75: Methyl 4-(2-chloro-3-fluorophenyl)-6-(5-oxopyrrolidin-2-yl)-2-(thiazol-2-yl)-1,4-dihydropyrimidine-5-carboxylate (a Mixture of 4 Stereoisomers)

Compound 75 (400 mg, 0.920 mmol) was further separated by chiral Prep. HPLC (Column: Chiralpak IB, Hex: EtOH=85:15; 13 mL/min; Temp: 30° C.; Wavelength: 214 nm) to yield the product which was subsequently purified by C18 (acetonitrile:water=5% to 100%) to afford stereoisomers Compound 75A (66 mg, 17% yield), Compound 75B (20 mg, 5% yield), Compound 75C (130 mg, 33% yield) and Compound 75D (25 mg, 6% yield) as yellow solids.

Compound 75A: LC-MS (ESI): $R_T$=1.842 min, mass calcd. for $C_{19}H_{16}ClFN_4O_3S$ 434.1, m/z found 435.1 [M+H]$^+$. Chiral HPLC (Column: Chiralpak IB 5 μm 4.6*250 mm; Mobile Phase: Hex:EtOH=85:15 at 1.0 mL/min; Temp: 30° C.; Wavelength: 230 nm, $R_T$=8.614 min). $^1$H NMR (400 MHz, CDCl$_3$) δ 8.56 (s, 0.2H), 7.81 (d, J=2.8 Hz, 0.8H), 7.71 (d, J=2.8 Hz, 0.3H), 7.49 (s, 0.7H), 7.46 (d, J=3.2 Hz, 1H), 7.42 (d, J=2.8 Hz, 0.2H), 7.24-7.17 (m, 0.9H), 7.14-7.03 (m, 1.9H), 6.22 (s, 0.3H), 6.14 (d, J=7.2 Hz, 1.7H), 5.80 (t, J=8.4 Hz, 0.3H), 5.55 (d, J=6.8 Hz, 0.7H), 3.62 (d, J=4.8 Hz, 3H), 2.90-2.80 (m, 0.2H), 2.76-2.67 (m, 0.8H), 2.53-2.25 (m, 2.8H), 2.06-1.96 (m, 0.2H).

Compound 75D: LC-MS (ESI): $R_T$=2.560 min min, mass calcd. for $C_{19}H_{16}ClFN_4O_3S$ 434.1, m/z found 435.1 [M+H]$^+$. Chiral HPLC (Column: Chiralpak IB 5 μm 4.6*250 mm; Mobile Phase: Hex:EtOH=85:15 at 1.0 mL/min; Temp: 30° C.; Wavelength: 230 nm, $R_T$=15.809 min). H NMR (400 MHz, CDCl$_3$) δ 8.61 (s, 0.3H), 7.83 (d, J=2.4 Hz, 0.7H), 7.81 (s, 0.3H), 7.52 (s, 1.4H), 7.45 (s, 0.3H), 7.24-7.16 (m, 1H), 7.13-7.04 (m, 2H), 6.27 (s, 0.3H), 6.12 (s, 0.7H), 5.83-5.72 (m, 1.3H), 5.59 (d, J=7.2 Hz, 0.7H), 3.63 (s, 2H), 3.60 (s, 1H), 2.94-2.84 (m, 0.3H), 2.80-2.71 (m, 0.7H), 2.65-2.37 (m, 2.8H), 2.21-2.10 (m, 0.2H).

Compound 90: Methyl 4-(2-chloro-4-fluorophenyl)-6-cyclopropyl-2-(thiazol-2-yl)-1,4-dihydropyrimidine-5-carboxylate Compound 90 (140 mg, 0.358 mmol) was further separated by chiral Prep. HPLC (separation condition: Column: Chiralpak IA 5 μm 20*250 mm; Mobile Phase: Hex:IPA=95:5 at 11 mL/min; Temp: 30° C.; Wavelength: 230 nm) to afford stereoisomers Compound 90A (46.2 mg, 33% yield) and Compound 90B (46.6 mg, 33% yield) as yellow solids.

Compound 90A: LC-MS (ESI): $R_T$=3.429 min, mass calcd. for $C_{18}H_{15}ClFN_3O_2S$ 391.1, m/z found 391.9 [M+H]$^+$. Chiral HPLC (Column: Chiralpak IA 5 μm 4.6*250 mm; Mobile Phase: Hex:IPA=95:5 at 1.0 mL/min; Temp: 30° C.; Wavelength: 230 nm, $R_T$=7.842 min). $^1$H NMR (400 MHz, DMSO-d$_6$) δ 9.48 (d, J=3.2 Hz, 1H), 7.99-7.97 (m, 2H), 7.40 (dd, J=8.8, 2.8 Hz, 1H), 7.33 (dd, J=8.8, J=6.4 Hz, 1H), 7.21 (td, J=8.4, 2.4 Hz, 1H), 5.91 (d, J=3.2 Hz, 1H), 3.54 (s, 3H), 3.22-3.18 (m, 1H), 1.23-1.18 (m, 1H), 1.01-1.00 (m, 1H), 0.87-0.83 (m, 1H), 0.81-0.77 (m, 1H).

Conversion of Primary Dihydropyrimidines of General Formula I (from Table 1): Primary Dihydropyrimidines of General Formula I Compound 5: 6-(1-tert-Butoxycarbonyl-piperidin-4-yl)-4-(2-chloro-4-fluoro-phenyl)-2-thiazol-2-yl-1,4-dihydro-pyrimidine-5-carboxylic acid methyl ester (a Mixture of 2 Stereoisomers)

Compound 5 (7.00 g, 13.1 mmol) was further separated by chiral Prep. HPLC (Column: Chiralpak IA 5 μm 20*250 mm; Mobile Phase: Hex:EtOH=90:10 at 23 mL/min; Temp: 30° C.; Wavelength: 230 nm) to afford stereoisomers Compound 5A (2.44 g, 35% yield) and Compound 5B (1.56 g, 22% yield).

Compound 5A: SFC (analytical condition: Column: Chiralpak IG; Mobile Phase: CO$_2$:MeOH=70:30 at 1.0 mL/min; Temp: 41° C.; Wavelength: 230 nm, $R_T$=2.59 min). $^1$H NMR (400 MHz, CDCl$_3$) δ 8.12 (s, 0.5H), 7.81 (t, J=3.2 Hz, 1H), 7.48 (d, J=3.2 Hz, 0.6H), 7.44 (d, J=3.6 Hz, 0.4H), 7.41 (br s, 0.5H), 7.30-7.27 (m, 1H), 7.15-7.11 (m, 1H), 6.96-6.88 (m, 1H), 6.19 (s, 0.4H), 6.06 (d, J=2.8 Hz, 0.6H), 4.35-4.21 (m, 2H), 4.20-4.12 (m, 0.4H), 3.96-3.89 (m, 0.6H), 3.60 (s, 2.4H), 3.59 (s, 0.6H), 2.94-2.78 (m, 2H), 2.10-1.79 (m, 3H), 1.74-1.63 (m, 1H), 1.50 (s, 9H).

Compound 5B: LC-MS (ESI): $R_T$=2.191 min, mass calcd. For $C_{25}H_{28}ClFN_4O_4S$ 534.2 m/z found 534.9 [M+H]$^+$. Chiral HPLC (Column: Chiralpak IA 5 μm 4.6*250 mm; Mobile Phase: Hex:EtOH=85:15 at 1.0 mL/min; Temp: 30° C.; Wavelength: 230 nm, $R_T$=6.154 min). $^1$H NMR (400 MHz, CDCl$_3$) δ 8.12 (s, 0.5H), 7.82 (t, J=3.2 Hz, 1H), 7.47 (dd, J=20.4, 3.0 Hz, 1H), 7.41 (br s, 0.5H), 7.30-7.28 (m, 1H), 7.15-7.11 (m, 1H), 6.96-6.88 (m, 1H), 6.19 (s, 0.4H), 6.06 (d, J=2.4 Hz, 0.6H), 4.36-4.22 (m, 2H), 4.20-4.12 (m, 0.4H), 3.96-3.88 (m, 0.6H), 3.60 (s, 2.4H), 3.59 (s, 0.6H), 2.95-2.79 (m, 2H), 2.09-1.74 (m, 3H), 1.63-1.58 (m, 1H), 1.50 (s, 9H).

Compound 10: Methyl 6-(1-(tert-butoxycarbonyl)piperidin-4-yl)-4-(2-chloro-3-fluorophenyl)-2-(thiazol-2-yl)-1,4-dihydropyrimidine-5-carboxylate (a Mixture of 2 Stereoisomers)

Compound 10 (1.02 g, 1.91 mmol) was further separated by chiral Prep. HPLC (Column: Chiralpak IA 5 μm 20*250 mm; Mobile Phase: Hex:IPA=95:5 at 20 mL/min; Temp: 30° C.; Wavelength: 230 nm) to afford stereoisomers Compound 10A (420 mg, 42% yield) and Compound 10B (384 mg, 38% yield).

Compound 10A: LC-MS (ESI): $R_T$=1.68 min, mass calcd. For $C_{25}H_{28}ClFN_4O_4S$ 534.2 m/z found 535.5 [M+H]$^+$. Chiral HPLC (Column: Chiralpak IA 5 μm 4.6*250 mm; Mobile Phase: Hex:IPA:DEA=95:5:0.2 at 1.0 mL/min; Temp: 30° C.; Wavelength: 230 nm, $R_T$=10.336 min). $^1$H NMR (400 MHz, CDCl$_3$) δ 7.84 (d, J=2.8 Hz, 1H), 7.50 (d, J=2.4 Hz, 1H), 7.21-7.12 (m, 2H), 7.06 (t, J=8.4 Hz, 1H), 6.20 (s, 1H), 4.28 (br s, 2H), 4.06 (br s, 1H), 3.60 (s, 3H), 2.92-2.82 (m, 2H), 1.89-1.74 (m, 4H), 1.50 (s, 9H).

Compound 12: Methyl 4-(2-bromo-4-fluorophenyl)-6-(1-(tert-butoxycarbonyl)-piperidin-4-yl)-2-(thiazol-2-yl)-1,4-dihydropyrimidine-5-carboxylate LC-MS (ESI): $R_T$=1.61 min, mass calcd. For $C_{25}H_{28}BrFN_4O_4S$ 578.1 m/z found 579.4 [M+H]$^+$. $^1$H NMR (400 MHz, DMSO-d$_6$) δ 9.46 (d, J=3.2 Hz, 0.8H), 9.10 (s, 0.2H), 7.99-7.97 (m, 1.7H), 7.92 (d, J=3.2 Hz, 0.3H), 7.58-7.54 (m, 1H), 7.37-7.21 (m, 2H), 5.98 (s, 0.3H), 5.89 (d, J=3.2 Hz, 0.7H), 4.18-3.98 (m, 2H), 3.83-3.75 (m, 1H), 3.53 (s, 2.1H), 3.51 (s, 0.9H), 2.82-2.71 (m, 2H), 1.99-1.62 (m, 4H), 1.44 (s, 9H).

Compound 13: 6-(1-tert-Butoxycarbonyl-piperidin-4-yl)-4-(2-chloro-3-fluoro-phenyl)-2-thiazol-2-yl-1,4-dihydro-pyrimidine-5-carboxylic Acid Methyl Ester LC-MS (ESI): $R_T$=2.793 min, mass calcd. for $C_{25}H_{28}ClFN_4O_4S$, m/z found 534.7 [M+H]$^+$. $^1$HNMR (400 MHz, CDCl$_3$) δ 8.22 (s, 1H), 7.85-7.83 (m, 1H), 7.54 (d, J=2.8 Hz, 0.2H), 7.49 (d, J=3.6 Hz, 0.8H), 7.35-7.29 (m, 1H), 7.16-7.05 (m, 2H), 5.78 (s, 0.8H), 5.60 (d, J=2.8 Hz, 0.2H), 4.29 (br s, 2H), 4.15-4.08 (m, 1H), 3.67 (s, 2.4H), 3.65 (s, 0.6H), 2.91-2.80 (m, 2H), 1.90-1.82 (m, 2H), 1.73-1.65 (m, 1H), 1.59-1.54 (m, 1H), 1.50 (s, 9H).

Compound 14: Methyl 6-(trans-4-((tert-butoxycarbonyl)amino)cyclohexyl)-4-(2-chloro-4-fluorophenyl)-2-(thiazol-2-yl)-1,4-dihydropyrimidine-5-carboxylate $^1$H NMR (400 MHz, DMSO-$d_6$) δ 9.46 (d, J=3.2 Hz, 0.6H), 9.07 (s, 0.4H), 8.00-7.99 (m, 1.6H), 7.93 (d, J=3.2 Hz, 0.4H), 7.44-7.40 (m, 1H), 7.36-7.29 (m, 1H), 7.24-7.18 (m, 1H), 6.82-6.75 (m, 1H), 6.00 (s, 0.4H), 5.90 (d, J=3.6 Hz, 0.6H), 3.84-3.76 (m, 0.4H), 3.60-3.54 (m, 0.6H), 3.51 (s, 1.8H), 3.50 (s, 1.2H), 3.29-3.08 (m, 1H), 1.94-1.73 (m, 6H), 1.40 (s, 9H), 1.30-1.18 (m, 2H).

Compound 15: Methyl 6-(cis-4-((tert-butoxycarbonyl)amino)cyclohexyl-4-(2-chloro-4-fluorophenyl)-2-(thiazol-2-yl)-1,4-dihydropyrimidine-5-carboxylate LC-MS (ESI): $R_T$=3.371 min, mass calcd. for $C_{26}H_{30}ClFN_4O_4S$, 548.2, m/z found 548.8 [M+H]$^+$. $^1$H NMR (400 MHz, DMSO-$d_6$) δ 9.47-9.44 (m, 0.3H), 9.25 (s, 0.7H), 8.02-8.00 (m, 1.3H), 7.95 (d, J=3.2 Hz, 0.7H), 7.43 (dd, J=8.8, 2.8 Hz, 1H), 7.32 (dd, J=8.4, 6.0 Hz, 1H), 7.21 (td, J=8.4, 2.4 Hz, 1H), 7.17-7.15 (m, 0.3H), 6.81-6.75 (m, 0.7H), 6.01 (s, 0.7H), 5.90 (t, J=4.0 Hz, 0.3H), 3.90-3.85 (m, 1H), 3.51 (s, 0.9H), 3.50 (s, 2.1H), 3.30-3.06 (m, 1H), 1.88-1.60 (m, 8H), 1.45 (s, 9H).

Compound 16: Methyl 4-(2-chloro-3-fluorophenyl)-6-(trans-4-(methoxycarbonyl)-cyclohexyl)-2-(thiazol-2-yl)-1,4-dihydropyrimidine-5-carboxylate (a Mixture of 2 Stereoisomers)

Compound 16 (300 mg, 0.08 mmol) was further separated by chiral Prep. HPLC (separation condition: Column: Chiralpak IC 5 μm 20*250 mm; Mobile Phase: Hex:EtOH:DEA=90:10:0.2 at 12 mL/min; Temp: 30° C.; Wavelength: 214 nm) to afford stereoisomers Compound 16X (90 mg, 30% yield) and Compound 16Y (180 mg, 60% yield) as yellow solids.

Compound 16X: LC-MS (ESI): $R_T$=4.874 min, mass calcd. for $C_{23}H_{23}ClFN_3O_4S$ 491.1, m/z found 491.9 [M+H]$^+$. Chiral HPLC (Column: Chiralpak IC 5 μm 4.6*250 mm; Mobile Phase: Hex:EtOH:DEA=90:10:0.2 at 1.0 mL/min; Temp: 30° C.; Wavelength: 230 nm, $R_T$=10.425 min). $^1$H NMR (400 MHz, DMSO-$d_6$) δ 9.47 (d, J=3.2 Hz, 0.6H), 8.95 (s, 0.4H), 7.99-7.98 (m, 1.6H), 7.93 (d, J=3.2 Hz, 0.4H), 7.39-7.28 (m, 2H), 7.20-7.15 (m, 1H), 6.06 (s, 0.4H), 5.96 (d, J=3.6 Hz, 0.6H), 3.86-3.78 (m, 0.4H), 3.62-3.61 (m, 3H), 3.59-3.54 (m, 0.6H), 3.52-3.51 (m, 3H), 2.35-2.31 (m, 0.6H), 2.08-1.96 (m, 2H), 1.91-1.79 (m, 2H), 1.76-1.63 (m, 2H), 1.48-1.41 (m, 2H). (0.4H was overlapped in DMSO solvent)

Compound 18: Methyl 4-(2-chloro-4-fluorophenyl)-6-trans-4-(methoxycarbonyl)-cyclohexyl)-2-(thiazol-2-yl)-1,4-dihydropyrimidine-5-carboxylate (a Mixture of 2 Stereoisomers)

Compound 18 (459 mg, 0.93 mmol) was further separated by chiral Prep. HPLC (separation condition: Column: Chiralpak IC 5 μm 20*250 mm; Mobile Phase: Hex:EtOH=80:20 at 13 mL/min; Temp: 30° C.; Wavelength: 230 nm) to afford stereoisomers Compound 18X (194 mg, 85% yield) and Compound 18Y (172 mg, 75% yield).

Compound 18X: LC-MS (ESI): $R_T$=4.176 min, mass calcd. for $C_{23}H_{23}ClFN_3O_4S$, 491.1, m/z found 491.9 [M+H]$^+$. Chiral HPLC (Column: Chiralpak IC 5 μm 4.6*250 mm; Mobile Phase: Hex:EtOH=80:20 at 1.0 mL/min; Temp: 30° C.; Wavelength: 230 nm, $R_T$=6.660 min). $^1$H NMR (400 MHz, DMSO-$d_6$) δ 9.41 (s, 0.6H), 8.92 (s, 0.4H), 7.99 (s, 1.6H), 7.93 (s, 0.4H), 7.45-7.40 (m, 1H), 7.38-7.31 (m, 1H), 7.23-7.18 (m, 1H), 6.01 (s, 0.4H), 5.92 (s, 0.6H), 3.87-3.78 (m, 0.4H), 3.62 (s, 3H), 3.58-3.56 (m, 0.6H), 3.53-3.52 (m, 3H), 2.37-2.30 (m, 0.6H), 2.08-1.88 (m, 3H), 1.81-1.61 (m, 3H), 1.47-1.36 (m, 2H). (0.4H was overlapped in DMSO solvent)

Compound 20: Ethyl 4-(2-chloro-4-fluorophenyl)-6-(trans-4-(methoxycarbonyl)-cyclohexyl)-2-(thiazol-2-yl)-1,4-dihydropyrimidine-5-carboxylate (a Mixture of Two Stereoisomers)

Compound 20 (300 mg, 0.59 mmol) was further separated by chiral Prep. HPLC (Column: Chiralpak IC 5 μm 20*250 mm; Mobile Phase: Hex:EtOH=80:20 at 20 mL/min; Temp: 30° C.; Wavelength: 254 nm) to afford stereoisomers Compound 20X (108 mg, 36% yield) and Compound 20Y (103 mg, 34% yield) as yellow solids.

Compound 20X: LC-MS (ESI): $R_T$=3.193 min, mass calcd. for $C_{24}H_{25}ClFN_3O_4S$ 505.1 m/z found 506.1 [M+H]$^+$. Chiral HPLC (Column: Chiralpak IC 5 μm 4.6*250 mm; Mobile Phase: Hex:EtOH=80:20 at 1.0 mL/min; Temp: 30° C.; Wavelength: 230 nm, 100% ee, $R_T$=6.130 min). $^1$H NMR (400 MHz, CDCl$_3$) δ 8.09 (s, 0.6H), 7.82 (t, J=3.6 Hz, 1H), 7.49 (d, J=3.2 Hz, 0.4H), 7.45 (d, J=3.6 Hz, 0.5H), 7.33-7.28 (m, 1.5H), 7.14-7.11 (m, 1H), 6.96-6.88 (m, 1H), 6.20 (s, 0.6H), 6.07 (d, J=2.8 Hz, 0.4H), 4.06 (q, J=6.8 Hz, 2H), 4.02-3.96 (m, 0.5H), 3.79-3.72 (m, 0.5H), 3.70 (s, 3H), 2.45-2.38 (m, 1H), 2.21-1.91 (m, 4H), 1.80-1.63 (m, 3H), 1.55-1.47 (m, 1H), 1.14 (t, J=7.2 Hz, 3H).

Compound 22: Ethyl 4-(2-chloro-3-fluorophenyl)-6-(trans-4-(methoxycarbonyl)-cyclohexyl)-2-(thiazol-2-yl)-1,4-dihydropyrimidine-5-carboxylate (a Mixture of 2 Stereoisomers)

Compound 22 (290 mg, 0.574 mmol) was further separated by SFC (Column: Chiralpak IC 5 μm 20*250 mm; Mobile Phase: CO$_2$:MeOH:DEA=60:40:0.3 at 50 g/min; Co-solvent: MeOH; Col. Temp: 39.8° C.; Wavelength: 214 nm, Back pressure: 100 bar) to afford stereoisomers Compound 22X (95 mg, 22% yield) and Compound 22Y (100 mg, 34% yield) as pale yellow solids.

Compound 22Y: LC-MS (ESI): $R_T$=3.946 min, mass calcd. for $C_{24}H_{25}ClFN_3O_4S$ 505.1, m/z found 506.1 [M+H]$^+$. SFC analytical condition: (Column: Chiralpak IC 5 m 4.6*250 mm; Mobile Phase: CO$_2$:MeOH=60:40 at 3 mL/min; Co-solvent: MeOH (0.2 DEA); Col. Temp: 40.2° C.; Wavelength: 214 nm, Back pressure: 100 bar, $R_T$=3.92 min). $^1$H NMR (400 MHz, DMSO-$d_6$) δ 9.50 (d, J=3.6 Hz, 0.6H), 8.93 (s, 0.4H), 7.99 (d, J=3.2 Hz, 1.5H), 7.94 (d, J=3.6 Hz, 0.5H), 7.38-7.29 (m, 2H), 7.21-7.17 (m, 1H), 6.08 (s, 0.5H), 5.97 (d, J=3.6 Hz, 0.5H), 4.00-3.93 (m, 0.5H), 3.87-3.79 (m, 0.5H), 3.62 (s, 3.5H), 2.38-2.31 (m, 0.7H), 2.05-1.98 (m, 2H), 1.91-1.62 (m, 4.3H), 1.45-1.39 (m, 2H), 1.09-1.02 (m, 3H).

Compound 24: cis-Methyl 4-(2-chloro-3-fluorophenyl)-6-(3-(methoxycarbonyl)-cyclohexyl)-2-(thiazol-2-yl)-1,4-dihydropyrimidine-5-carboxylate (a Mixture of 4 Stereoisomers)

Compound 24 (1.91 g) was further purified by silica gel column chromatography (petroleum ether:dichloromethane:ethyl acetate=10:10:1) to give two separable groups of stereoisomers, Group 1 (964 mg) and Group 2 (942 mg). Group 1 (964 mg) was separated by chiral Prep. HPLC (the first separation condition: Column: Chiralpak IA 5 μm 20*250 mm; Mobile Phase: MeOH:DCM:DEA=60:40:0.3 at 10 mL/min; Temp: 30° C.; Wavelength: 254 nm; the second separation: Column: Chiralpak IC m 20*250 mm; Mobile Phase: Hex:EtOH:DEA=90:10:0.3 at 15 mL/min; Temp: 30° C.; Wavelength: 254 nm) followed with further purification by Prep. HPLC (Column: Xbridge C18 (5 μm 19*150 mm), Mobile Phase A: water (0.1% ammonium hydroxide), Mobile Phase B: acetonitrile, UV: 214 nm, Flow rate: 15 mL/min, Gradient: 40-80% (% B)) to afford stereoisomers Compound 24M (247 mg, 26% yield) and Compound 24N (297 mg, 31% yield). Group 2 (942 mg) was separated by chiral Prep. HPLC (the first separation condition: Column: Chiralpak IE 5 μm 20*250 mm; Mobile Phase: Hex:EtOH:DEA=90:10:0.3 at 15 mL/min; Temp: 30° C.; Wavelength: 230 nm; the second separation: Column: Chiralpak IC 5 μm 20*250 mm; Mobile Phase: Hex:IPA:DEA=80:20:0.3 at 15 mL/min; Temp: 30° C.; Wavelength: 230 nm) followed with further purification by Prep. HPLC (Column: Xbridge C18 (5 μm 19*150 mm), Mobile Phase A: water (0.1% ammonium hydroxide), Mobile Phase B: acetonitrile, UV: 214 nm, Flow rate: 15 mL/min, Gradient: 40-80% (% B)) to afford stereoisomers Compound 24P (212 mg, 23% yield) and Compound 24Q (190 mg, 20% yield).

Compound 24Q: LC-MS (ESI): $R_T$=3.789 min, mass calcd. for $C_{23}H_{23}ClFN_3O_4S$ 491.1, m/z found 491.9 [M+H]$^+$. Chiral HPLC (Column: Chiralpak IE 5 μm 4.6*250 mm; Mobile Phase: Hex:EtOH:DEA=90:10:0.2 at 1.0 mL/min; Temp: 30° C.; Wavelength: 230 nm, $R_T$=13.390 min). $^1$H NMR (400 MHz, DMSO-d$_6$) δ 9.55 (d, J=3.6 Hz, 0.6H), 9.18 (s, 0.4H), 8.00-7.98 (m, 1.6H), 7.94 (d, J=3.2 Hz, 0.4H), 7.40-7.29 (m, 2H), 7.21-7.15 (m, 1H), 6.06 (s, 0.4H), 5.96 (d, J=4.0 Hz, 0.6H), 3.99-3.91 (m, 0.4H), 3.72-3.66 (m, 0.6H), 3.61-3.59 (m, 3H), 3.52-3.51 (m, 3H), 2.44-2.37 (m, 1H), 1.94-1.86 (m, 3H), 1.79-1.69 (m, 3H), 1.50-1.30 (m, 2H).

Compound 26: Methyl 4-(2-chloro-3-fluorophenyl)-6-(4-(2-ethoxy-2-oxoethyl)-cyclohexyl)-2-(thiazol-2-yl)-1,4-dihydropyrimidine-5-carboxylate LC-MS (ESI): $R_T$=4.219 min, mass calcd. for $C_{25}H_{27}ClFN_3O_4S$ 519.1, m/z found 519.9 [M+H]$^+$. $^1$H NMR (400 MHz, DMSO-d$_6$) δ 9.51-9.39 (m, 0.6H), 8.97 (s, 0.4H), 8.00-7.97 (m, 1.6H), 7.93 (d, J=3.2 Hz, 0.4H), 7.39-7.27 (m, 2H), 7.20-7.15 (m, 1H), 6.06 (s, 0.4H), 5.96 (s, 0.6H), 4.07 (q, J=6.8 Hz, 2H), 3.87-3.77 (m, 0.6H), 3.62-3.55 (m, 0.4H), 3.51 (s, 1.6H), 3.50 (s, 1.4H), 2.25-2.19 (m, 2H), 1.96-1.51 (m, 8H), 1.20 (t, J=6.8 Hz, 3H), 1.14-1.04 (m, 1H).

Compound 27: tert-Butyl 5-methyl 6-(2-chloro-3-fluorophenyl)-4-(4-(2-ethoxy-2-oxoethyl)cyclohexyl)-2-(thiazol-2-yl)pyrimidine-1,5(6H)-dicarboxylate (a Mixture of 4 Stereoisomers)

To a solution of methyl 4-(2-chloro-3-fluorophenyl)-6-(4-(2-ethoxy-2-oxoethyl)-cyclohexyl)-2-(thiazol-2-yl)-1,4-dihydropyrimidine-5-carboxylate Compound 26 (850 mg, 2.0 mmol) in 1,4-dioxane (20 mL) was added di-tert-butyl dicarbonate (713 mg, 3.0 mmol), 4-dimethylaminopyridine (210 mg, 2.0 mmol) and triethylamine (329 mg, 3.0 mmol). After stirring at 67° C. overnight, the solvent was removed to give a residue, which was purified by Prep. HPLC (Column: waters Xbridge C18 (5 μm 19*150 mm), Mobile phase A: water (0.2% ammonium acetate), Mobile phase B: acetonitrile, UV: 214 nm, Flow rate: 15 mL/min, Gradient: 75-90% (% B)) to give the title compound (674 mg, 67% yield) as yellow solids.

Compound 27 (670 mg, 1.08 mmol) was further separated by chiral Prep. HPLC (separation condition: Column: Chiralpak IE 5 μm 20*250 mm; Mobile Phase: Hex:EtOH=90:10 at 15 ml/min; Temp: 30° C.; Wavelength: 214 nm) to afford stereoisomers Compound 27X (333 mg, 50% yield, a mixture of 3 stereoisomers) and Compound 27 Y (216 mg, 32% yield).

Compound 27 Y: LC-MS (ESI): RT=3.244 min, mass calcd. for C30H35ClFN3O6S 619.2, m/z found 620.2 [M+H]$^+$. Chiral HPLC (Column: Chiralpak IE 5 μm 4.6*250 mm; Mobile Phase: Hex:EtOH=90:10 at 1.0 mL/min; Temp: 30° C.; Wavelength: 230 nm, RT=9.770 min). 1H NMR (400 MHz, DMSO-d6) δ 7.99 (s, 2H), 7.38-7.34 (m, 1H), 7.31-7.25 (m, 1H), 6.87 (d, J=7.6 Hz, 1H), 6.59 (s, 1H), 4.07 (q, J=7.2 Hz, 2H), 3.66 (s, 3H), 3.49-3.43 (m, 1H), 2.23 (d, J=6.8 Hz, 2H), 1.95-1.50 (m, 8H), 1.21-0.99 (m, 13H).

Compound 30: Methyl 6-(1-(tert-butoxycarbonyl)piperidin-3-yl)-4-(2-chloro-3-fluorophenyl)-2-(thiazol-2-yl)-1,4-dihydropyrimidine-5-carboxylate LC-MS (ESI): $R_T$=3.002 min, mass calcd. For $C_{25}H_{28}ClFN_4O_4S$ 534.2, m/z found 534.9 [M+H]$^+$. $^1$H NMR (400 MHz, DMSO-d$_6$) δ 9.62 (d, J=3.2 Hz, 0.8H), 9.26 (d, J=18.4 Hz, 0.2H), 8.00 (s, 1.5H), 7.99-7.93 (m, 0.5H), 7.40-7.31 (m, 2H), 7.23-7.12 (m, 1H), 6.07 (s, 0.2H), 5.98 (dd, J=8.0, 3.6 Hz, 0.8H), 4.07-3.83 (m, 2H), 3.70-3.60 (m, 1H), 3.53-3.50 (m, 3H), 3.32-3.30 (m, 1H), 3.15-3.00 (m, 1H), 2.81-2.63 (m, 1H), 1.92-1.85 (m, 1H), 1.78-1.71 (m, 2H), 1.40 (s, 9H).

Compound 9: Ethyl 6-(1-(tert-butoxycarbonyl)piperidin-4-yl)-4-(2-chloro-3-fluorophenyl)-2-(thiazol-2-yl)-1,4-dihydropyrimidine-5-carboxylate $^1$H NMR (400 MHz, CDCl$_3$) δ 8.11 (brs, 0.4H), 7.82 (d, J=3.2 Hz, 1H), 7.54-7.41 (m, 1H), 7.35-7.29 (m, 0.6H), 7.25-7.12 (m, 2H), 7.10-7.00 (m, 1H), 6.27 (s, 0.5H), 6.14 (s, 0.5H), 4.38-4.18 (m, 3H), 4.08-3.90 (m, 2H), 2.95-2.76 (m, 2H), 2.01-1.61 (m, 4H), 1.50 (s, 9H), 1.11 (t, J=7.2 Hz, 3H).

Compound 11: 6-(1-tert-Butoxycarbonyl-piperidin-4-yl)-4-(4-chloro-2-fluoro-phenyl)-2-thiazol-2-yl-1,4-dihydro-pyrimidine-5-carboxylic acid methyl ester $^1$H NMR (400 MHz, DMSO-d$_6$) δ 9.46 (d, J=3.2 Hz, 0.8H), 9.08 (s, 0.2H), 8.00-7.98 (m, 1.8H), 7.92 (d, J=3.2 Hz, 0.2H), 7.44-7.42 (m, 1H), 7.37-7.31 (m, 1H), 7.23-7.18 (m, 1H), 6.01 (s, 0.2H), 5.92 (d, J=3.6 Hz, 0.8H), 4.18-3.96 (m, 2H), 3.82-3.74 (m, 1H), 3.53 (s, 2.4H), 3.52 (s, 0.6H), 2.86-2.69 (m, 2H), 1.87-1.66 (m, 3H), 1.52-1.49 (m, 1H), 1.44 (s, 9H).

Compound 31: Methyl 6-(1-(tert-butoxycarbonyl) piperidin-3-yl)-4-(2-chloro-4-fluorophenyl)-2-(thiazol-2-yl)-1,4-dihydropyrimidine-5-carboxylate LC-MS (ESI): $R_T$=2.454 min, mass calcd. For $C_{25}H_{28}ClFN_4O_4S$ 534.1 m/z found 535.0 [M+H]$^+$. $^1$H NMR (400 MHz, DMSO-d$_6$) δ 8.44 (d, J=18.4 Hz, 0.3H), 7.82 (d, J=3.2 Hz, 0.7H), 7.79-7.78 (m, 0.3H), 7.49 (d, J=2.8 Hz, 0.7H), 7.42 (d, J=5.6 Hz, 1H), 7.33-7.25 (m, 1H), 7.15-7.11 (m, 1H), 6.97-6.88 (m, 1H), 6.18 (d, J=8.0 Hz, 0.3H), 6.08 (d, J=2.8 Hz, 0.4H), 6.02 (s, 0.3H), 4.38-3.95 (m, 2H), 3.87-3.74 (m, 1H), 3.62 (s, 2.1H), 3.60 (s, 0.9H), 3.33-3.10 (m, 1H), 2.77 (br s, 1H), 2.11-1.92 (m, 1H), 1.88-1.68 (m, 3H), 1.49 (d, J=4.4 Hz, 9H).

Compound 34: Methyl 6-(1-(tert-butoxycarbonyl)-4-fluoropiperidin-4-yl)-4-(2-chloro-3-fluoro-phenyl)-2-(thiazol-2-yl)-1,4-dihydropyrimidine-5-carboxylate LC-MS (ESI): $R_T$=3.138 min, mass calcd. for $C_{25}H_{27}ClF_2N_4O_4S$ 552.1, m/z found 552.9 [M+H]$^+$. $^1$H NMR (400 MHz, DMSO-d$_6$) δ 9.24 (d, J=2.4 Hz, 1H), 8.00 (s, 2H), 7.44-7.35 (m, 2H), 7.25 (d, J=7.2 Hz, 1H), 5.82 (d, J=2.8 Hz, 1H), 4.22 (t, J=6.6 Hz, 0.1H), 3.94-3.91 (m, 1.9H), 3.50 (s, 3H), 2.95 (br s, 2H), 2.25-2.04 (m, 2H), 1.88 (t, J=12.4 Hz, 1H), 1.77 (t, J=12.4 Hz, 1H), 1.44 (s, 9H).

Compound 40: (1R,5S,6r)-tert-butyl 6-(6-(2-chloro-4-fluorophenyl)-5-(ethoxy-carbonyl)-2-(thiazol-2-yl)-3,6-dihydropyrimidin-4-yl)-3-azabicyclo[3.1.0]hexane-3-carboxylate LC-MS (ESI): $R_T$=1.78 min, mass calcd. for $C_{26}H_{28}ClFN_4O_4S$ 546.2, m/z found 547.3 [M+H]$^+$. $^1$H NMR (300 MHz, DMSO-d$_6$) δ 9.59 (s, 1H), 7.98 (s, 2H), 7.43-7.32 (m, 2H), 7.25-7.14 (m, 1H), 5.91 (s, 1H), 3.96 (q, J=6.9 Hz, 2H), 3.58-3.34 (m, 4H), 2.96 (s, 1H), 2.30 (s, 1H), 2.10 (s, 1H), 1.39 (m, 9H), 1.05 (t, J=6.3 Hz, 3H).

Compound 42: 1-tert-Butyl 2-methyl 4-(6-(2-chloro-4-fluorophenyl)-5-(methoxycarbonyl)-2-(thiazol-2-yl)-3,6-dihydropyrimidin-4-yl)piperidine-1,2-dicarboxylate (a Mixture of 4 Stereoisomers)

LC-MS (ESI): $R_T$=4.148 min, mass calcd. for $C_{27}H_{30}ClFN_4O_6S$ 592.2, m/z found 592.9 [M+H]$^+$. $^1$H NMR (400 MHz, CDCl$_3$) δ 8.09 (br s, 0.2H), 7.83-7.80 (m, 1H), 7.49 (d, J=2.8 Hz, 0.8H), 7.44-7.39 (m, 1H), 7.31-7.27 (m, 1H), 7.13 (dd, J=8.4, 2.4 Hz, 1H), 6.98-6.87 (m, 1H), 6.18 (d, J=4.0 Hz, 0.2H), 6.05 (s, 0.8H), 5.09-5.04 (m, 0.5H), 4.92-4.86 (m, 0.5H), 4.24-4.02 (m, 1H), 3.82-3.78 (m, 4H), 3.59 (s, 2.4H), 3.57 (s, 0.6H), 3.29-3.06 (m, 1H), 2.50-2.31 (m, 1H), 2.21-2.14 (m, 1H), 2.08-2.02 (m, 0.5H), 1.94-1.80 (m, 1.5H), 1.51 (s, 4H), 1.47 (s, 5H).

Compound 43: cis-4-[6-(2-Chloro-4-fluoro-phenyl)-5-methoxycarbonyl-2-thiazol-2-yl-3,6-dihydro-pyrimidin-4-yl]-piperidine-1,3-dicarboxylic Acid 1-tert-butyl Ester LC-MS (ESI): $R_T$=1.54 min, mass calcd. for $C_{26}H_{28}ClFN_4O_6S$ 578.1, m/z found 579.5 [M+H]$^+$. $^1$H NMR (400 MHz, DMSO-d$_6$) δ 12.83 (br s, 0.1H), 11.99 (br s, 0.4H), 9.56 (dd, J=11.6, 3.6 Hz, 0.7H), 9.06-8.96 (m, 0.3H), 8.01-7.91 (m, 2H), 7.59 (dd, J=8.8, 6.4 Hz, 0.3H), 7.43-7.31 (m, 1.7H), 7.25-7.06 (m, 1H), 6.06 (s, 0.2H), 5.99 (s, 0.2H), 5.94 (dd, J=5.6, 3.2 Hz, 0.6H), 4.49-4.36 (m, 0.3H), 4.23-3.78 (m, 2.7H), 3.59-3.44 (m, 3.6H), 3.40-3.34 (m, 0.4H), 3.22-3.09 (m, 0.6H), 3.00-2.92 (m, 0.4H), 2.84-2.75 (m, 0.6H), 2.68-2.63 (m, 0.4H), 2.42-2.35 (m, 0.3H), 2.14-1.94 (m, 0.7H), 1.84-1.66 (m, 0.8H), 1.60-1.55 (m, 0.2H), 1.45-1.37 (m, 9H).

Compound 44: cis-1-tert-Butyl 3-methyl 4-(6-(2-chloro-4-fluorophenyl)-5-(methoxycarbonyl)-2-(thiazol-2-yl)-3,6-dihydropyrimidin-4-yl)piperidine-1,3-dicarboxylate (a Mixture of 4 Stereoisomers)

To a solution of cis-4-[6-(2-chloro-4-fluoro-phenyl)-5-methoxycarbonyl-2-thiazol-2-yl-3,6-dihydro-pyrimidin-4-yl]-piperidine-1,3-dicarboxylic acid 1-tert-butyl ester Compound 43 (0.28 g, 0.48 mmol) in N,N-dimethylformamide (6 mL) was added potassium carbonate (74 mg, 0.53 mmol) followed by iodomethane (76 mg, 0.53 mmol) at room temperature. The mixture was stirred at room temperature for 3 hours. It was diluted with water (40 mL) and extracted with ethyl acetate (30 mL) for three times. The combined organic layers were washed with brine (50 mL), dried over Na2SO4(s) and filtered. The filtrate was concentrated under reduced pressure to give a residue, which was purified by Prep. HPLC (Column: Xbridge C18 (5 μm 19*150 mm), Mobile Phase A: water (0.1% ammonium bicarbonate), Mobile Phase B: acetonitrile, Flow rate: 15 mL/min, Gradient: 60-80% (% B)) to give two mixtures Compound 44A (104 mg, 36% yield, a mixture of 2 stereoisomers) and Compound 44B (84 mg, 29% yield, a mixture of 2 stereoisomers) as yellow solids.

Compound 44A: LC-MS (ESI): $R_T$=4.446 min, mass calcd. for $C_{27}H_{30}ClFN_4O_6S$ 592.2, m/z found 592.9 [M+H]$^+$. $^1$H NMR (400 MHz, DMSO-d$_6$) δ 9.61 (d, J=3.6 Hz, 0.8H), 8.67 (s, 0.2H), 8.01-7.99 (m, 1.8H), 7.94-7.93 (m, 0.2H), 7.75-7.67 (m, 0.1H), 7.44-7.35 (m, 1.9H), 7.25-7.14 (m, 1H), 5.99 (s, 0.2H), 5.93 (d, J=3.2 Hz, 0.8H), 4.23-4.66 (m, 2H), 3.74-3.38 (m, 9H), 2.78 (dd, J=10.8, 4.4 Hz, 1H), 2.30-2.15 (m, 1H), 1.82-1.68 (m, 1H), 1.42 (s, 9H).

Compound 52: Methyl 6-(1-(tert-butoxycarbonyl) piperidin-4-yl)-4-(2-chloro-4-fluorophenyl)-2-(2,4,6-trifluorophenyl)-1,4-dihydropyrimidine-5-carboxylate LC-MS (ESI): $R_T$=2.658 min, mass calcd. for $C_{28}H_{28}ClF_4N_3O_4$ 581.2 m/z found 581.7 [M+H]$^+$. $^1$H NMR (300 MHz, DMSO-d$_6$) δ 9.48 (s, 0.8H), 9.41 (s, 0.2H), 7.41-7.35 (m, 2H), 7.28-7.20 (m, 3H), 5.95 (s, 0.8H), 5.85 (s, 0.2H), 4.13-4.04 (m, 3H), 3.50 (s, 3H), 2.78-2.66 (m, 2H), 1.71-1.59 (m, 4H), 1.38 (s, 9H).

Compound 55: Ethyl 6-(1-(tert-butoxycarbonyl) piperidin-4-yl)-4-(2-chloro-4-fluorophenyl)-2-(3,5-difluoro-pyridin-2-yl)-1,4-dihydropyrimidine-5-carboxylate LC-MS (ESI): $R_T$=2.571 min, mass calcd. for $C_{28}H_{30}ClF_3N_4O_4$ 578.2, m/z found 578.7 [M+H]$^+$. $^1$H NMR (400 MHz, DMSO-d$_6$) δ 9.35 (d, J=3.2 Hz, 1H), 8.61 (s, 1H), 8.10-8.07 (m, 1H), 7.59-7.55 (m, 1H), 7.29-7.23 (m, 1H), 7.21-7.15 (m, 1H), 5.70 (s, 0.4H), 5.51 (d, J=3.2 Hz, 0.6H), 4.10-4.00 (m, 4.5H), 3.78-3.77 (m, 0.5H), 2.75-2.70 (m, 2H), 1.72-1.59 (m, 4H), 1.41 (s, 9H), 1.19-1.15 (m, 3H).

Compound 57: Methyl 6-(1-(tert-butoxycarbonyl) piperidin-4-yl)-4-(2-chloro-3,4-difluoro-phenyl)-2-(thiazol-2-yl)-1,4-dihydropyrimidine-5-carboxylate LC-MS (ESI): $R_T$=1.83 min, mass calcd. For $C_{25}H_{27}ClF_2N_4O_4S$ 552.1 m/z found 553.4 [M+H]$^+$. $^1$H NMR (400 MHz, DMSO-d$_6$) δ 9.64 (s, 0.8H), 9.23 (s, 0.2H), 8.00 (s, 1.8H), 7.94 (s, 0.2H), 7.48-7.42 (m, 1H), 7.21-7.15 (m, 0.8H), 6.98 (s, 0.2H), 6.01 (s, 0.2H), 5.91 (s, 0.8H), 4.08-4.00 (m, 2H), 3.82-3.76 (m, 1H), 3.52 (s, 2H), 3.48 (m, 1H), 2.82-2.69 (m, 2H), 1.86-1.63 (m, 4H), 1.43 (s, 5H), 1.39-1.38 (m, 4H).

Compound 60: Methyl 6-(3-((tert-butoxycarbonyl) amino)cyclopentyl)-4-(2-chloro-3-fluorophenyl)-2-(thiazol-2-yl)-1,4-dihydropyrimidine-5-carboxylate
(a Mixture of 8 Stereoisomers)

Compound 60 was further purified by C18 column (acetonitrile:water=75%-85%) to give two groups of stereoisomers, namely Group 1 (1.11 g) and Group 2 (2.57 g).

Group 1 (1.61 g, 3.01 mmol) was separated by chiral Prep. HPLC (Column: Chiralpak AD 5 μm 20*250 mm; Mobile Phase: Hex:EtOH:DEA=85:15:0.3 at 15 mL/min; Temp: 30° C.; Wavelength: 214 nm) to afford Fraction 1 (526 mg), Compound 60C (165 mg, 10% yield, 100% de) and Compound 60D (182 mg, 11% yield, 100% de). Fraction 1 (526 mg) was further separated by chiral Prep. HPLC (Column: Chiralpak IA 5 μm 20*250 mm; Mobile Phase: Hex:IPA:DEA=90:10:0.2 at 20 mL/min; Temp: 30° C.; Wavelength: 230 nm) to afford stereoisomers Compound 60A (150 mg, 9% yield, 96.3% de) and Compound 60B (120 mg, 7% yield, 100% de).

Group 2 (2.56 g, 4.79 mmol) was separated by chiral Prep. HPLC (Column: Chiralpak IC 5 μm 20*250 mm; Mobile Phase: CO$_2$: IPA=70:30 at 45 g/min; Co-solvent: IPA; Col. Temp: 40° C.; Wavelength: 214 nm, Back pressure: 100 bar) to afford Fraction 2 (846 mg) and Fraction 3 (1.1 g). Fraction 2 (846 mg) was further separated by chiral Prep. HPLC (Column: Chiralpak IC 5 μm 20*250 mm; Mobile Phase: CO$_2$: IPA:DEA=70:30:0.3 at 45 g/min; Co-solvent: IPA; Col. Temp: 39.6° C.; Wavelength: 214 nm, Back pressure: 100 bar) to afford stereoisomers Compound 60E (286 mg, 11% yield, 100% de) and Compound 60F (343 mg, 13% yield, 100% de). Fraction 3 (664 mg) was further separated by chiral Prep. HPLC (Column: Chiralpak AS 5 μm 20*250 mm; Mobile Phase: Hex:IPA:DEA=80:20:0.3 at 13 mL/min; Temp: 30° C.; Wavelength: 214 nm) to afford stereoisomers Compound 60G (155 mg, 10% yield, 100% de) and Compound 60H (255 mg, 17% yield, 100% de).

Compound 60B: LC-MS (ESI): $R_T$=1.72 min, mass calcd. for $C_{25}H_{28}ClFN_4O_4S$ 534.2, m/z found 535.4 [M+H]$^+$. Chiral HPLC (Column: Chiralpak AD-H 5 μm 4.6*250 mm; Mobile Phase: Hex:EtOH:DEA=85:15:0.2 at 1.0 mL/min; Temp: 30° C.; Wavelength: 230 nm, $R_T$=6.604 min). $^1$H NMR (400 MHz, CDCl$_3$) δ 8.10 (s, 0.4H), 7.81 (t, J=2.8 Hz, 1H), 7.49 (d, J=2.8 Hz, 0.6H), 7.44 (d, J=2.8 Hz, 0.4H), 7.41 (br s, 0.6H), 7.24-7.14 (m, 1H), 7.10-7.00 (m, 2H), 6.24 (s, 0.4H), 6.09 (d, J=2.4 Hz, 0.6H), 4.72-4.55 (m, 1H), 4.48-4.41 (m, 1H), 4.35-4.22 (m, 1H), 3.60 (s, 2H), 3.59 (s, 1H), 2.45-2.38 (m, 1H), 2.32-2.20 (m, 1H), 2.17-2.07 (m, 1.5H), 1.94-1.83 (m, 2.5H), 1.46 (s, 9H).

Compound 60D: LC-MS (ESI): $R_T$=1.69 min, mass calcd. for $C_{25}H_{28}ClFN_4O_4S$ 534.2, m/z found 535.8 [M+H]$^+$. Chiral HPLC (Column: Chiralpak AD-H 5 μm 4.6*250 mm; Mobile Phase: Hex:EtOH:DEA=85:15:0.2 at 1.0 mL/min; Temp: 30° C.; Wavelength: 230 nm, $R_T$=10.882 min). $^1$H NMR (400 MHz, CDCl$_3$) δ 8.10 (s, 0.4H), 7.81 (t, J=3.2 Hz, 1H), 7.49 (d, J=3.6 Hz, 0.6H), 7.44 (d, J=3.2 Hz, 0.4H), 7.41 (br s, 0.6H), 7.23-7.00 (m, 3H), 6.24 (s, 0.4H), 6.10 (d, J=2.4 Hz, 0.6H), 4.71-4.53 (m, 1H), 4.48-4.39 (m, 1H), 4.27 (br s, 1H), 3.60 (s, 2H), 3.59 (s, 1H), 2.36-2.18 (m, 2H), 2.16-1.95 (m, 2H), 1.77-1.66 (m, 2H), 1.46 (s, 9H).

Compound 60E: LC-MS (ESI): $R_T$=1.78 min, mass calcd. for $C_{25}H_{28}ClFN_4O_4S$ 534.2, m/z found 535.5 [M+H]$^+$. Chiral HPLC (Column: Chiralpak IA 5 μm 4.6*250 mm; Mobile Phase: CO$_2$:MeOH=75:25 at 3.0 mL/min; Col. Temp: 38.9° C.; Wavelength: 214 nm, Back pressure: 100 bar, $R_T$=3.22 min, 100% de). $^1$H NMR (400 MHz, CDCl$_3$) δ 8.29 (s, 0.1H), 7.86-7.81 (m, 0.9H), 7.57-7.44 (m, 2H), 7.24-7.20 (m, 1H), 7.10-7.03 (m, 2H), 6.23 (s, 0.2H), 6.13-6.10 (m, 1.8H), 4.79-4.71 (m, 0.1H), 4.55-4.47 (m, 0.9H), 4.27-4.19 (m, 0.7H), 4.13-4.05 (m, 0.3H), 3.61 (s, 2H), 3.59 (s, 1H), 2.58-2.50 (m, 0.1H), 2.39-2.31 (m, 0.7H), 2.17-2.10 (m, 0.2H), 2.02-1.67 (m, 5H), 1.45 (s, 9H).

Compound 60G: LC-MS (ESI): $R_T$=1.79 min, mass calcd. for $C_{25}H_{28}ClFN_4O_4S$ 534.2, m/z found 535.6 [M+H]$^+$. Chiral HPLC (Column: Chiralpak As-H 5 μm 4.6*250 mm; Mobile Phase: Hex:IPA:DEA=80:20:0.2 at 1.0 mL/min; Temp: 30° C.; Wavelength: 230 nm, 100% de, $R_T$=5.098 min). $^1$H NMR (400 MHz, CDCl$_3$) δ 8.24 (s, 0.1H), 7.86-7.81 (m, 0.9H), 7.56-7.44 (m, 2H), 7.24-7.20 (m, 1H), 7.13-7.07 (m, 2H), 6.25-6.23 (m, 1H), 6.13 (d, J=2.8 Hz, 1H), 4.52-4.42 (m, 1H), 4.24-4.16 (m, 0.8H), 4.11-4.03 (m, 0.2H), 3.61 (s, 2H), 3.58 (s, 1H), 2.50-2.41 (m, 0.1H), 2.26-2.08 (m, 1.9H), 2.01-1.91 (m, 2H), 1.81-1.71 (m, 2H), 1.46 (s, 9H).

Compound 63: Methyl 6-(1-(((9H-fluoren-9-yl) methoxy)carbonyl)pyrrolidin-3-yl)-4-(2-chloro-4-fluorophenyl)-2-(thiazol-2-yl)-1,4-dihydropyrimidine-5-carboxylate LC-MS (ESI): $R_T$=3.965 min, mass calcd. for $C_{34}H_{28}ClFN_4O_4S$ 642.2, m/z found 643.1 [M+H]$^+$. $^1$H NMR (400 MHz, DMSO-d$_6$) δ 9.64-9.59 (m, 1H), 8.02-7.87 (m, 4H), 7.69-7.61 (m, 2H), 7.45-7.17 (m, 7H), 6.03-5.93 (m, 1H), 4.37-4.26 (m, 4H), 3.74-3.54 (m, 6H), 3.48-3.36 (m, 1H), 2.27-2.06 (m, 2H).

Compound 64: Methyl 4-(2-chloro-4-fluorophenyl)-6-(pyrrolidin-3-yl)-2-(thiazol-2-yl)-1,4-dihydropyrimidine-5-carboxylate To a solution of methyl 6-(1-(((9H-fluoren-9-yl)methoxy) carbonyl)pyrrolidin-3-yl)-4-(2-chloro-4-fluorophenyl)-2-(thiazol-2-yl)-1,4-dihydropyrimidine-5-carboxylate Compound 63 (400 mg, 0.623 mmol) in tetrahydrofuran (10 mL) was added piperidine (2 mL). The mixture was stirred at room temperature for 2 hours. It was concentrated to give a residue, which was purified by silica gel column chromatography (dichloromethane:methanol=30:1 to 10:1) to give the title product (220 mg, 84% yield) as yellow solids. LC-MS (ESI): $R_T$=1.39 min, mass calcd. for $C_{19}H_{18}ClFN_4O_2S$ 420.1, m/z found 421.4 [M+H]$^+$.

Compound 66: Methyl 6-(1-(tert-butoxycarbonyl) pyrrolidin-3-yl)-4-(2-chloro-4-fluorophenyl)-2-(thiazol-2-yl)-1,4-dihydropyrimidine-5-carboxylate (a mixture of 4 stereoisomers)

Compound 66 (2.80 g, 5.39 mmol) was further separated by chiral Prep. HPLC (The first separation condition (column: Chiralpak IC 5 μm 20*250 mm; Mobile Phase: Hex:EtOH=90:10 at 20 mL/min, Temp: 30° C.; Wavelength: 230 nm) followed by the second separation condition (column: Chiralpak IA, 5 μm 20*250 mm; Mobile Phase: Hex:EtOH=70:30 at 10 mL/min, Temp: 30° C.; Wavelength: 214 nm)) to afford stereoisomers Compound 66A (416 mg, 15% yield), Compound 66B (474 mg, 17% yield), Compound 66C (518 mg, 19% yield), and Compound 66D (441 mg, 16% yield).

Compound 66A: LC-MS (ESI): $R_T$=4.485 min, mass calcd. for $C_{24}H_{26}ClFN_4O_4S$ 520.1, m/z found 521.0 [M+H]$^+$. Chiral HPLC (Column: Chiralpak IC 5 μm 4.6*250 mm; Mobile Phase: Hex:EtOH=90:10 at 1.0 mL/min; Temp: 30° C.; Wavelength: 230 nm, $R_T$=9.495 min). $^1$H NMR (400 MHz, DMSO-d$_6$) δ 9.56 (s, 0.8H), 9.21 (s, 0.2H), 8.05-8.00 (m, 1.8H), 7.98-7.89 (m, 0.2H), 7.42 (dd, J=9.2, 2.8 Hz, 1H), 7.38-7.34 (m, 1H), 7.24-7.19 (m, 1H), 5.94 (d, J=3.2 Hz, 0.8H), 5.75 (s, 0.2H), 4.58-4.40 (m, 0.1H), 4.34-4.23 (m, 0.9H), 3.53 (s, 5H), 3.33-3.20 (m, 2H), 2.19-1.89 (m, 2H), 1.43 (s, 9H).

Compound 66D: LC-MS (ESI): $R_T$=4.174 min, mass calcd. for $C_{24}H_{26}ClFN_4O_4S$ 520.1, m/z found 521.0 [M+H]$^+$. Chiral HPLC (Column: Chiralpak IA 5 μm 4.6*250 mm; Mobile Phase: Hex:EtOH=70:30 at 1.0 mL/min; Temp: 30° C.; Wavelength: 230 nm, $R_T$=7.464 min). $^1$H NMR (400 MHz, DMSO-d$_6$) δ 9.58 (s, 0.9H), 9.30 (s, 0.1H), 8.02-8.00 (m, 1.8H), 7.94-7.92 (m, 0.2H), 7.42 (dd, J=8.8, 2.8 Hz, 1H), 7.39-7.32 (m, 1H), 7.24-7.19 (m, 1H), 5.93 (d, J=3.2 Hz, 0.8H), 5.75 (s, 0.2H), 4.61-4.52 (m, 0.1H), 4.37-4.24 (m, 0.9H), 3.54-3.52 (m, 3H), 3.47-3.37 (m, 2H), 3.31-3.20 (m, 2H), 2.30-2.00 (m, 2H), 1.43-1.41 (m, 9H).

Compound 71: Methyl 4-(2-chloro-4-fluorophenyl)-6-(3-(methoxycarbonyl)cyclo-pentyl)-2-(thiazol-2-yl)-1,4-dihydro-pyrimidine-5-carboxylate (a Mixture of 8 Stereoisomers)

Compound 71 (2.3 g, 4.8 mmol) was further separated by chiral Prep. HPLC (separation condition: Column: Chiralpak IC 5 μm 20*250 mm; Mobile Phase: Hex:EtOH=80:20 at 15 mL/min; Temp: 30° C.; Wavelength: 214 nm) to afford stereoisomers Compound 71A (251 mg, 11% yield), Compound 71G (217 m g, 9% yield), Compound 71H (120 mg, 5% yield), a mixture of Compound 71E and Compound 71F (419 mg, 18% yield), and another mixture of Compound 71B, Compound 71C and Compound 71D (526 mg, 23% yield). The mixture of Compound 71E and Compound 71F (419 mg, 0.900 mmol) was separated by chiral Prep. HPLC (separation condition: Column: Chiralpak IA 5 μm 20*250 mm; Mobile Phase: Hex:EtOH=80:20 at 10 mL/min; Temp: 30° C.; Wavelength: 230) to afford stereoisomers Compound 71E (135 mg, 32% yield) and Compound 71F (207 mg, 49% yield). The mixture of Compound 71B, Compound 71C and Compound 71D (526 mg, 1.10 mmol) was separated by chiral Prep. HPLC (separation condition: Column: Chiralpak IA 5 μm 5.0*250 mm; Mobile Phase: EtOH=100% at 51 mL/min; Temp: 35° C.; Wavelength: 254 nm) to afford stereoisomers Compound 71d (94 mg, 18% yield) and a mixture of Compound 71B and Compound 71C (433 mg, 82% yield). The mixture of Compound 71B and Compound 71C (433 mg, 0.900 mmol) was separated by chiral Prep. HPLC (separation condition: Column: Chiralpak AS 50 mm*250 mm; Mobile Phase: MeOH=100% at 58 mL/min; Temp: 35° C.; Wavelength: UV 214 nm) to afford stereoisomers Compound 71B (105 mg, 24% yield) and Compound 71C (127 mg, 29% yield). Compound 71C: (Column: Chiralpak AS-H 5 μm 4.6*150 mm; Mobile Phase: MeOH=100% at 1.0 mL/min; Temp: 35° C.; Wavelength: 254 nm; RT=3.508 min). 1H NMR (400 MHz, DMSO-d6) δ 9.48 (d, J=3.2 Hz, 0.8H), 9.11 (s, 0.2H), 7.99 (q, J=3.2 Hz, 1.8H), 7.93 (d, J=2.8 Hz, 0.2H), 7.44-7.40 (m, 1H), 7.37-7.29 (m, 1H), 7.22 (td, J=8.4, 2.4 Hz, 1H), 6.00 (s, 0.2H), 5.90 (d, J=3.2 Hz, 0.8H), 4.35-4.29 (m, 0.2H), 4.26-4.18 (m, 0.8H), 3.64 (s, 0.6H), 3.63 (s, 2.4H), 3.52 (s, 2.4H), 3.51 (s, 0.6H), 3.17-3.09 (m, 1H), 2.26-2.19 (m, 1H), 2.12-2.02 (m, 2H), 1.90-1.72 (m, 3H). Compound 71F: LC-MS (ESI): RT=3.370 min, mass calcd. for $C_{22}H_{21}ClFN_3O_4S$ 477.1, m/z found 478.1 [M+H]$^+$. Chiral HPLC (Column: Chiralpak IA 5 μm 4.6*250 mm; Mobile Phase: Hex:EtOH=80:20 at 1.0 mL/min; Temp: 30° C.; Wavelength: 230 nm; RT=6.327 min). 1H NMR (400 MHz, DMSO-d6) δ 9.47 (d, J=3.6 Hz, 0.8H), 9.05 (s, 0.2H), 8.00 (q, J=2.8 Hz, 1.8H), 7.93 (d, J=2.8 Hz, 0.2H), 7.41 (dd, J=8.4, 2.8 Hz, 1H), 7.35-7.29 (m, 1H), 7.21 (td, J=8.4, 2.8 Hz, 1H), 6.00 (s, 0.2H), 5.91 (d, J=3.6 Hz, 0.8H), 4.36-4.30 (m, 0.2H), 4.26-4.18 (m, 0.8H), 3.63 (s, 0.6H), 3.62 (s, 2.4H), 3.52 (s, 2.4H), 3.51 (s, 0.6H), 3.14-3.07 (m, 1H), 2.17-1.99 (m, 3H), 2.03-1.88 (m, 2H), 1.85-1.76 (m, 1H).

Compound 73: cis-Methyl 4-(2-chloro-3-fluorophenyl)-6-(5-(methoxycarbonyl)-tetrahydro-furan-2-yl)-2-(thiazol-2-yl)-1,4-dihydropyrimidine-5-carboxylate (a Mixture of 4 Stereoisomers)

Compound 73 (320 mg, 0.67 mmol) was further separated by chiral Prep. HPLC (Column: Chiralpak ID 5 μm 20*250 mm; Mobile Phase: Hex:EtOH=80:20 at 15 mL/min; Temp: 30° C.; Wavelength: 214 nm) to afford stereoisomers Compound 73E (31 mg, 10% yield), Compound 73F (32 mg, 10% yield), Compound 73G (70 mg, 22% yield) and Compound 73H (83 mg, 26% yield) as yellow solids.

Compound 73H: LC-MS (ESI): $R_T$=3.649 min, mass calcd. for $C_{21}H_{19}ClFN_3O_5S$ 479.1, m/z found 479.9 [M+H]$^+$. Chiral HPLC (Column: Chiralpak ID 5 μm 4.6*250 mm; Mobile Phase: Hex:EtOH=80:20 at 1.0 mL/min; Temp: 30° C.; Wavelength: 230 nm, $R_T$=14.785 min). $^1$H NMR (400 MHz, CDCl$_3$) δ 10.05 (s, 1H), 7.89 (d, J=3.2 Hz, 1H), 7.42 (d, J=3.2 Hz, 1H), 7.18-7.09 (m, 2H), 7.05-7.01 (m, 1H), 6.29 (s, 1H), 5.83 (dd, J=9.2, 6.4 Hz, 1H), 4.74 (dd, J=9.2, 2.8 Hz, 1H), 3.89 (s, 3H), 3.58 (s, 3H), 2.75-2.68 (m, 1H), 2.53-2.43 (m, 1H), 2.28-2.23 (m, 1H), 2.01-1.90 (m, 1H).

Compound 76: Methyl 4-(2-chloro-3-fluorophenyl)-6-(3-(methoxycarbonyl)cyclo-pentyl)-2-(thiazol-2-yl)-1,4-dihydropyrimidine-5-carboxylate LC-MS (ESI): $R_T$=3.038 min, mass calcd. for $C_{22}H_{21}ClFN_3O_4S$, 477.1, m/z found 477.9 [M+H]$^+$. $^1$H NMR (400 MHz, DMSO-d$_6$) δ 9.58-9.53 (m, 0.8H), 9.21-9.11 (m, 0.2H), 8.01-7.98 (m, 1.8H), 7.95-7.93 (m, 0.2H), 7.43-7.29 (m, 2H), 7.20-7.12 (m, 1H), 6.07-6.04 (m, 0.2H), 5.97-5.93 (m, 0.8H), 4.41-4.34 (m, 0.3H), 4.26-4.20 (m, 0.3H), 4.15-4.09 (m, 0.4H), 3.68-3.59 (m, 3H), 3.51-3.49 (m, 3H), 3.16-3.09 (m, 0.4H), 3.03-2.98 (m, 0.2H), 2.92-2.85 (m, 0.4H), 2.20-1.77 (m, 6H).

Compound 78: Methyl 6-(1-(tert-butoxycarbonyl)azetidin-3-yl)-4-(2-chloro-4-fluorophenyl)-2-(thiazol-2-yl)-1,4-dihydropyrimidine-5-carboxylate (a Mixture of 2 Stereoisomers)

Compound 78 (9.00 g, 17.8 mmol) was further separated by chiral Prep. HPLC (Column: Chiralpak IC 5 μm 20*250 mm; Mobile Phase: MeOH:EtOH=70:30 at 20 mL/min; Temp: 30° C.; Wavelength: 214 nm) to afford stereoisomers Compound 78A (3.5 g, 39% yield) and Compound 78B (3.58 g, 40% yield).

Compound 78A: LC-MS (ESI): $R_T$=1.55 min, mass calcd. for $C_{23}H_{24}ClFN_4O_4S$ 506.1, m/z found 507.6 $[M+H]^+$. Chiral HPLC (Column: Chiralpak IC 5 μm 4.6*250 mm; Mobile Phase: Hex:EtOH=70:30 at 1.0 mL/min; Temp: 30° C.; Wavelength: 230 nm, $R_T$=6.015 min); $^1$H NMR (400 MHz, DMSO-$d_6$) δ 9.65 (d, J=3.6 Hz, 1H), 8.04-7.93 (m, 2H), 7.42-7.38 (m, 2H), 7.21 (dt, J=8.8, 3.2 Hz, Hz, 1H), 5.94 (d, J=3.2 Hz, 1H), 4.48-4.40 (m, 1H), 4.14-3.99 (m, 4H), 3.52 (s, 3H), 1.42 (s, 9H).

Compound 85: 4-(2-Chloro-4-fluoro-phenyl)-6-(3-methoxycarbonyl-cyclobutyl)-2-thiazol-2-yl-1,4-dihydro-pyrimidine-5-carboxylic Acid Methyl Ester
(a Mixture of 4 Stereoisomers)

Compound 85 was further purified by Prep. HPLC (Column: Gilson C18 5 μm 19*150 mm, Mobile Phase A: water (0.1% ammonium bicarbonate), Mobile Phase B: acetonitrile, Flow rate: 20 mL/min, Gradient: 35-75% (% B)) to give two mixtures Compound 85A (35 mg, 8% yield, a mixture of 2 stereoisomers) and Compound 85B (86 mg, 20% yield, a mixture of 2 stereoisomers) as yellow solids.

Compound 85A (90 mg, 0.19 mmol) was separated by chiral Prep. HPLC (separation condition: Column: Chiralpak IC 5 μm 20*250 mm; Mobile Phase: Hex:EtOH=80:20 at 15 mL/min; Temp: 30° C.; Wavelength: 214 nm) to afford stereoisomers Compound 85C (36 mg, 40% yield) and Compound 85D (40 mg, 44% yield) as yellow solids.

Compound 85C: LC-MS (ESI): $R_T$=4.350 min, mass calcd. for $C_{21}H_{19}ClFN_3O_4S$ 463.1, m/z found 463.9 $[M+H]^+$. Chiral HPLC (Column: Chiralpak IC 5 μm 4.6*250 mm; Mobile Phase: Hex:EtOH=80:20 at 1.0 mL/min; Temp: 30° C.; Wavelength: 230 nm, $R_T$=6.994 min). $^1$H NMR (400 MHz, DMSO-$d_6$) δ 9.55 (d, J=3.6 Hz, 0.9H), 9.05 (s, 0.1H), 8.02-8.01 (m, 1.8H), 7.94 (d, J=2.8 Hz, 0.2H), 7.43-7.32 (m, 2H), 7.23-7.17 (m, 1H), 5.99 (s, 0.1H), 5.91 (d, J=3.6 Hz, 0.9H), 4.63-4.57 (m, 0.1H), 4.41-4.33 (m, 0.9H), 3.68 (s, 0.5H), 3.65 (s, 2.5H), 3.51 (s, 3H), 3.29-3.24 (m, 0.9H), 3.19-3.13 (m, 0.1H), 2.67-2.52 (m, 2H), 2.49-2.32 (m, 2H).

Compound 87(trans): trans-Methyl 6-(3-((tert-butoxycarbonyl)amino)cyclobutyl)-4-(2-chloro-4-fluorophenyl)-2-(thiazol-2-yl)-1,4-dihydropyrimidine-5-carboxylate LC-MS (ESI): $R_T$=3.707 min, mass calcd. for $C_{24}H_{26}ClFN_4O_4S$ 520.1, m/z found 520.9 $[M+H]^+$. $^1$H NMR (400 MHz, CDCl$_3$) δ 8.38 (br s, 0.2H), 7.83 (d, J=3.2 Hz, 1H), 7.51 (d, J=3.2 Hz, 0.8H), 7.45 (s, 1H), 7.28-7.21 (m, 1H), 7.13 (d, J=8.4, 2.4 Hz, 1H), 6.93 (td, J=8.4, 2.4 Hz, 1H), 6.18 (s, 0.2H), 6.05 (d, J=2.4 Hz, 0.8H), 5.07-4.84 (m, 1H), 4.54-4.46 (m, 1.4H), 4.24-4.06 (m, 0.6H), 3.61 (s, 0.6H), 3.58 (s, 2.4H), 2.85-2.58 (m, 2H), 2.41-2.16 (m, 2H), 1.47 (s, 9H).

Compound 87(cis): (cis)-Methyl 6-(3-((tert-butoxycarbonyl)amino)cyclobutyl)-4-(2-chloro-4-fluorophenyl)-2-(thiazol-2-yl)-1,4-dihydropyrimidine-5-carboxylate LC-MS (ESI): $R_T$=3.379 min, mass calcd. for $C_{24}H_{26}ClFN_4O_4S$ 520.1, m/z found 520.9 $[M+H]^+$. $^1$H NMR (400 MHz, CDCl$_3$) δ 8.60 (br s, 0.2H), 7.85-7.83 (m, 1H), 7.52-7.51 (m, 0.8H), 7.45 (s, 1H), 7.28-7.22 (m, 1H), 7.13 (d, J=8.0 Hz, 1H), 6.95-6.91 (m, 1H), 6.17 (s, 0.3H), 6.05 (s, 0.7H), 5.06-4.85 (m, 1H), 4.54-4.08 (m, 2H), 3.61 (s, 2.2H), 3.59 (s, 0.8H), 2.75-2.58 (m, 2H), 2.37-2.21 (m, 2H), 1.47 (s, 9H).

Compound 91: Ethyl 6-(2-(2-(tert-butoxy)-2-oxoethyl)cyclopropyl)-4-(2-chloro-4-fluorophenyl)-2-(thiazol-2-yl)-1,4-dihydropyrimidine-5-carboxylate
(a Mixture of 4 Stereoisomers)

Compound 91 was purified by silica gel column chromatography (petroleum ether:ethyl acetate=10:1) to give two mixtures Compound 91E (360 mg, 12% yield, a mixture of 2 stereoisomers) and Compound 91F (250 mg, 8% yield, a mixture of 2 stereoisomers) as yellow solids.

Compound 91E (360 mg, 0.629 mmol) was further separated by chiral Prep. HPLC (separation condition: Column: Chiralpak IA 5 μm 20*250 mm; Mobile Phase: Hex:EtOH=90:10 at 12 mL/min; Temp: 30° C.; Wavelength: 230 nm) to afford stereoisomers Compound 91G (44 mg, 1.5% yield) and Compound 91H (46 mg, 1.5% yield).

Compound 91H: Chiral HPLC (Column: Chiralpak IA 5 μm 4.6*250 mm; Mobile Phase: Hex:EtOH=90:10 at 1.0 mL/min; Temp: 30° C.; Wavelength: 230 nm; $R_T$=7.059 min).

Compound 91F (250 mg, 0.481 mmol) was further separated by chiral Prep. HPLC (separation condition: Column: Chiralpak IA 5 μm 20*250 mm; Mobile Phase: Hex:EtOH=90:1 at 12 mL/min; Temp: 30° C.; Wavelength: 230 nm) to afford stereoisomers Compound 911 (51 mg, 1.7% yield), and Compound 91J (49 mg, 1.7% yield).

Compound 91J: Chiral HPLC (Column: Chiralpak IA 5 μm 4.6*250 mm; Mobile Phase: Hex:EtOH=90:10 at 1.0 mL/min; Temp: 30° C.; Wavelength: 230 nm; $R_T$=8.766 min).

Compound 6: Methyl 4-(2-chloro-4-fluorophenyl)-6-(1-((1-methoxy-2-methyl-1-oxopropan-2-yl)sulfonyl)piperidin-4-yl)-2-(thiazol-2-yl)-1,4-dihydropyrimidine-5-carboxylate (a Mixture of 2 Stereoisomers)

Compound 6 (230 mg, 0.385 mmol) was further separated by chiral Prep. HPLC (Column: Chiralpak IE 5 μm 20*250 mm; Mobile Phase: Hex:EtOH=60:40 at 9 mL/min; Temp: 30° C.; Wavelength: 214 nm) to afford stereoisomers Compound 6A (78 mg, 34% yield) and Compound 6B (50 mg, 22% yield).

Compound 6B: LC-MS (ESI): $R_T$=1.55 min, mass calcd. for $C_{25}H_{28}ClFN_4O_6S_2$ 598.1, m/z found 598.9. Chiral HPLC (Column: Chiralpak IE 5 μm 4.6*250 mm; Mobile Phase: Hex:EtOH=60:40 at 1.0 mL/min; Temp: 30° C.; Wavelength: 230 nm, $R_T$=13.955 min). $^1$H NMR (400 MHz, CDCl$_3$) δ 8.17 (s, 0.3H), 7.83 (t, J=2.8 Hz, 1H), 7.51 (d, J=3.2 Hz, 0.7H), 7.45-7.43 (m, 1H), 7.29-7.24 (m, 1H), 7.15-7.11 (m, 1H), 6.96-6.88 (m, 1H), 6.18 (s, 0.3H), 6.06 (d, J=2.4 Hz, 0.7H), 4.24-4.15 (m, 0.3H), 4.01-3.89 (m, 2.7H), 3.82-3.81 (m, 3H), 3.60 (s, 2H), 3.59 (s, 1H), 3.19-3.06 (m, 2H), 2.25-2.15 (m, 1H), 2.09-1.98 (m, 1H), 1.91-1.75 (m, 2H), 1.67 (s, 4H), 1.65 (s, 2H).

Compound 94: Methyl 4-(2-chloro-4-fluorophenyl)-6-(4-(methoxycarbonyl)cyclo-heptyl)-2-(thiazol-2-yl)-1,4-dihydropyrimidine-5-carboxylate LC-MS (ESI): $R_T$=3.021 min and 3.150 min, mass calcd. for $C_{24}H_{25}ClFN_3O_4S$ 505.1, m/z found 505.9 $[M+H]^+$. $^1$H NMR (400 MHz, CD$_3$OD) δ 7.93-7.87 (m, 1H), 7.74 (s, 1H), 7.40-7.36 (m, 1H), 7.24-7.20 (m, 1H), 7.07-7.01 (m, 1H), 6.12 (s, 0.6H), 6.04 (s, 0.4H), 4.12 (br s, 0.6H), 3.93 (br s, 0.4H), 3.69-3.68 (m, 3H), 3.59 (s, 1.2H), 3.58 (s, 1.8H), 2.71-2.61 (m, 1H), 2.17-1.48 (m, 10H).

A racemic mixture of 94R (870 mg, 1.72 mmol) was separated by chiral Prep. HPLC (separation condition: Column: Chiralpak IC 5 μm 20*250 mm; Mobile Phase: Hex:IPA:DEA=80:20:0.3 at 13 mL/min; Temp: 30° C.; Wavelength: 214 nm) to give two groups of stereoisomers, namely Group 1 (400 mg) and Group 2 (120 mg) as yellow solids.

Group 1 (400 mg, 0.792 mmol) was separated by chiral Prep. HPLC (separation condition: Column: Chiralpak AD-H 5 μm 20*250 mm; Mobile Phase: Hex:EtOH=90:10 at 15 mL/min; Temp: 30° C.; Wavelength: 254 nm) to give Fraction 1 (200 mg), 94P (25 mg, 3 yield, 100% stereopure) and 94Q (25 mg, 3 yield, 98.3% stereopure) as yellow solids. Fraction 1 (200 mg, 0.396 mmol) was separated by chiral Prep. HPLC (separation condition: Column: Chiralpak IC 10 m 50*250 mm; Mobile Phase: Hex:IPA:DEA=95:5:0.1 at 60 mL/min; Temp: 35° C.; Wavelength: 254 nm) to give Fraction 2 and 94J (60 mg, 7% yield, 97.8% stereopure) and pure 94N (68 mg, 8% yield, 96.7% stereopure) as yellow solids. Fraction 2 was separated by chiral Prep. HPLC (separation condition: Column: Chiralpak IE 10 μm 50*250 mm; Mobile Phase: Hex:EtOH:DEA=95:5:0.1 at 60 mL/min; Temp: 35° C.; Wavelength: 254 nm) to give the title compounds 94K (25 mg, 3 yield, 97.3% stereopure) and 94M (20 mg, 2 yield, 97.3% stereopure) as yellow solids.

Group 2 was separated by chiral Prep. HPLC (separation condition: Column: Chiralpak OJ 5 μm 20*250 mm; Mobile Phase: Hex:EtOH:DEA=97:3:0.1 at 30 mL/min; Temp: 35° C.; Wavelength: 254 nm) to give the title compounds 94S (30 mg, 3 yield, 99.4% stereopure) and 94T (25 mg, 3 yield, 98.8% stereopure) as yellow solids.

Compound 94J: Chiral analysis (Column: Chiralpak IE 4.6*150 mm; Mobile Phase: Hex:IPA:DEA=95:5:0.1 at 1 mL/min; Temp: 35° C.; Wavelength: 254 nm, R$_T$=6.900 min).

Compound 94K: Chiral analysis (Column: Chiralpak IE 4.6*150 mm; Mobile Phase: Hex:EtOH:DEA=95:5:0.1 at 1 mL/min; Temp: 35° C.; Wavelength: 254 nm, R$_T$=10.427 min).

Compound 94M: Chiral analysis (Column: Chiralpak IE 4.6*150 mm; Mobile Phase: Hex:EtOH:DEA=95:5:0.1 at 1 mL/min; Temp: 35° C.; Wavelength: 254 nm, R$_T$=13.160 min).

Compound 94N: Chiral analysis (Column: Chiralpak IE 4.6*150 mm; Mobile Phase: Hex:IPA:DEA=95:5:0.1 at 1 mL/min; Temp: 35° C.; Wavelength: 254 nm, R$_T$=12.257 min).

Compound 94P: LC-MS (ESI): R$_T$=4.480 min, mass calcd. for C$_{24}$H$_{25}$ClFN$_3$O$_4$S 505.1, m/z found 505.9 [M+H]$^+$. Chiral analysis (Column: Chiralpak AD-H 5 μm 4.6*250 mm; Mobile Phase: Hex:EtOH:DEA=90:10:0.2 at 1.0 mL/min; Temp: 30° C.; Wavelength: 230 nm, R$_T$=9.150 min). $^1$H NMR (400 MHz, DMSO-d$_6$) δ 9.41 (d, J=3.2 Hz, 0.5H), 9.07 (s, 0.5H), 7.99-7.97 (m, 1.5H), 7.93 (d, J=2.8 Hz, 0.5H), 7.44-7.40 (m, 1H), 7.36-7.29 (m, 1H), 7.24-7.18 (m, 1H), 6.00 (s, 0.4H), 5.90 (d, J=3.6 Hz, 0.6H), 4.00-3.92 (m, 0.4H), 3.84-3.75 (m, 0.6H), 3.61 (s, 1.2H), 3.60 (s, 1.8H), 3.52 (s, 1.8H), 3.51 (s, 1.2H), 2.74-2.66 (m, 0.5H), 2.59-2.55 (m, 0.5H), 2.06-1.65 (m, 9H), 1.62-1.52 (m, 1H).

Compound 94Q: LC-MS (ESI): R$_T$=4.495 min, mass calcd. for C$_{24}$H$_{25}$ClFN$_3$O$_4$S 505.1, m/z found 505.9 [M+H]$^+$. Chiral analysis (Column: Chiralpak AD-H 5 μm 4.6*250 mm; Mobile Phase: Hex:EtOH:DEA=90:10:0.2 at 1.0 mL/min; Temp: 30° C.; Wavelength: 230 nm, R$_T$=11.406 min). $^1$H NMR (400 MHz, DMSO-d$_6$) δ 9.41 (d, J=3.6 Hz, 0.5H), 9.03 (s, 0.5H), 8.00-7.97 (m, 1.5H), 7.93 (d, J=3.2 Hz, 0.5H), 7.44-7.40 (m, 1H), 7.36-7.29 (m, 1H), 7.24-7.18 (m, 1H), 5.99 (s, 0.4H), 5.89 (d, J=3.6 Hz, 0.6H), 3.99-3.91 (m, 0.4H), 3.84-3.76 (m, 0.6H), 3.63 (s, 1.2H), 3.61 (s, 1.8H), 3.52 (s, 1.8H), 3.51 (s, 1.2H), 2.70-2.63 (m, 0.5H), 2.60-2.55 (m, 0.5H), 2.07-1.60 (m, 9H), 1.50-1.40 (m, 1H).

Compound 94S: LC-MS (ESI): R$_T$=4.406 min, mass calcd. for C$_{24}$H$_{25}$ClFN$_3$O$_4$S 505.1, m/z found 505.9 [M+H]$^+$. Chiral analysis (Column: Chiralpak IC 5 μm 4.6*250 mm; Mobile Phase: Hex:EtOH:DEA=95:5:0.2 at 1.0 mL/min; Temp: 30° C.; Wavelength: 230 nm, R$_T$=17.041 min). $^1$H NMR (400 MHz, DMSO-d$_6$) δ 9.38 (d, J=3.2 Hz, 0.5H), 9.04 (s, 0.5H), 7.99-7.96 (m, 1.5H), 7.92 (d, J=3.2 Hz, 0.5H), 7.43-7.39 (m, 1H), 7.35-7.29 (m, 1H), 7.23-7.17 (m, 1H), 6.00 (s, 0.4H), 5.90 (d, J=3.6 Hz, 0.6H), 4.02-3.91 (m, 0.5H), 3.84-3.75 (m, 0.5H), 3.61 (s, 1.2H), 3.60 (s, 1.8H), 3.52 (s, 1.8H), 3.51 (s, 1.2H), 2.74-2.65 (m, 0.7H), 2.59-2.58 (m, 0.3H), 2.04-1.55 (m, 10H).

Compound 94T: LC-MS (ESI): R$_T$=4.414 min, mass calcd. for C$_{24}$H$_{25}$ClFN$_3$O$_4$S 505.1, m/z found 505.9 [M+H]$^+$. Chiral analysis (Column: Chiralpak IC 5 μm 4.6*250 mm; Mobile Phase: Hex:EtOH:DEA=95:5:0.2 at 1.0 mL/min; Temp: 30° C.; Wavelength: 230 nm, R$_T$=20.533 min). $^1$H NMR (400 MHz, DMSO-d$_6$) δ 9.39 (d, J=4.0 Hz, 0.5H), 9.01 (s, 0.5H), 7.99-7.97 (m, 1.5H), 7.92 (d, J=2.8 Hz, 0.5H), 7.43-7.39 (m, 1H), 7.36-7.31 (m, 1H), 7.24-7.18 (m, 1H), 5.99 (s, 0.4H), 5.89 (d, J=3.6 Hz, 0.6H), 3.99-3.90 (m, 0.4H), 3.84-3.75 (m, 0.6H), 3.62 (s, 1.2H), 3.61 (s, 1.8H), 3.52 (s, 1.8H), 3.51 (s, 1.2H), 2.80-2.71 (m, 0.5H), 2.62-2.58 (m, 0.5H), 2.09-1.58 (m, 10H).

Compound 143: ethyl 6-(1-(tert-butoxycarbonyl)piperidin-4-yl)-4-(2-chlorophenyl)-2-(thiazol-2-yl)-1,4-dihydropyrimidine-5-carboxylate (Mixture of Stereomers)

Compound 143 (1.10 g, 96% purity) was separated by chiral Prep. SFC (Column: chiralpak IG 5 μm 20*250 mm; Mobile Phase: CO$_2$:MeOH=70:30 at 50 g/min; Col. Temp: 30° C.; Wavelength: 230 nm; Back pressure: 100 bar) to give compound 143A (500 mg, 45% yield, 100% stereopure) and 143B (592 mg, 54% yield, 100% stereopure).

Compound 143B: Chiral analysis (Column: Chiralpak IG 5 μm 4.6*250 mm; Mobile Phase: CO$_2$:MeOH=70:30 at 3.0 g/min; Col. Temp: 40° C.; Wavelength: 230 nm; Back pressure: 100 bar, R$_T$=3.88 min). $^1$H NMR (300 MHz, DMSO-d$_6$) δ 9.35 (d, J=3.3 Hz, 0.8H), 8.97 (s, 0.2H), 7.96-7.94 (m, 1.8H), 7.90-7.88 (m, 0.2H), 7.43-7.39 (m, 1H), 7.32-7.25 (m, 3H), 6.05-6.03 (m, 0.2H), 5.94-5.91 (m, 0.8H), 4.11-3.88 (m, 4.2H), 3.81-3.73 (m, 0.8H), 2.84-2.65 (m, 2H), 1.91-1.67 (m, 3H), 1.50-1.37 (m, 10H), 1.07-1.02 (m, 3H).

Compound 147: ethyl 4-(2-bromophenyl)-6-((trans)-4-(methoxycarbonyl)cyclohexyl)-2-(thiazol-2-yl)-1,4-dihydropyrimidine-5-carboxylate LC-MS (ESI): R$_T$=8.237 min, mass calcd. for C$_{24}$H$_{26}$BrN$_3$O$_4$S 531.1, m/z found 531.8 [M+H]$^+$.

Compound 147A: (trans)-ethyl 4-(2-bromophenyl)-6-(4-(methoxycarbonyl)cyclohexyl)-2-(thiazol-2-yl)-1,4-dihydropyrimidine-5-carboxylate 147 (507 mg, 0.929 mmol) was separated by chiral SFC (Column: Chiralpak IC 5 μm 20*250 mm; Mobile Phase: CO$_2$:MeOH=70:30 at 50 g/min;

Col. Temp: 40° C.; Wavelength: 230 nm, Back pressure: 100 bar) to afford 147A (260 mg, 48% yield) and 147B (240 mg, 47% yield) as yellow solids.

Compound 147A: LC-MS (ESI): $R_T$=3.989 min, mass calcd. for $C_{24}H_{26}BrN_3O_4S$ 531.1, m/z found 534.1 $[M+H]^+$. Chiral analysis (Column: Chiralpak IC 5 μm 4.6*250 mm; Mobile Phase: $CO_2$:MeOH=70:30 at 2.999 g/min; Col. Temp: 41.2° C.; Wavelength: 230 nm, Back pressure: 100 bar, $R_T$=4.39 min). $^1$H NMR (400 MHz, DMSO-d$_6$) δ 9.23 (d, J=3.6 Hz, 0.5H), 8.84 (s, 0.5H), 7.99-7.98 (m, 1.5H), 7.93 (d, J=3.6 Hz, 0.5H), 7.61 (d, J=7.6 Hz, 1H), 7.37-7.31 (m, 2H), 7.22-7.16 (m, 1H), 6.03 (s, 0.4H), 5.92 (d, J=3.6 Hz, 0.6H), 4.01-3.93 (m, 2H), 3.86-3.82 (m, 0.5H), 3.63 (s, 3H), 3.60-3.56 (m, 0.5H), 2.57-2.54 (m, 0.4H), 2.38-2.32 (m, 0.6H), 2.08-1.99 (m, 2H), 1.91-1.63 (m, 4H), 1.50-1.37 (m, 2H), 1.10-1.03 (m, 3H).

Compound 149: ethyl 4-(2-bromo-3-fluorophenyl)-6-((1r,4r)-4-(methoxycarbonyl)cyclohexyl)-2-(thiazol-2-yl)-1,4-dihydropyrimidine-5-carboxylate LC-MS (ESI): $R_T$=4.647 min, mass calcd. for $C_{24}H_{25}BrFN_3O_4S$ 549.1, m/z found 552.0 $[M+H]^+$. Compound 149A: (trans)-ethyl 4-(2-bromo-3-fluorophenyl)-6-(4-(methoxycarbonyl)cyclohexyl)-2-(thiazol-2-yl)-1,4-dihydropyrimidine-5-carboxylate 149 (920 mg, 1.67 mmol) was separated by chiral Prep. SFC (Column: Chiralpak IC 5 μm 20*250 mm; Mobile Phase: $CO_2$:MeOH=70:30 at 50 g/min; Col. Temp: 40° C.; Wavelength: 230 nm, Back pressure: 100 bar) to afford the title compounds 149A (280 mg, 30% yield) and 149B (320 mg, 34% yield) as yellow solids.

Compound 149A: LC-MS (ESI): $R_T$=2.842 min, mass calcd. for $C_{24}H_{25}BrFN_3O_4S$ 549.1, m/z found 552.1 $[M+H]^+$. Chiral analysis (Column: Chiralpak IC 5 μm 4.6*250 mm; Mobile Phase: $CO_2$:MeOH=70:30 at 3.0 g/min; Col. Temp: 40° C.; Wavelength: 230 nm, Back pressure: 100 bar, $R_T$=4.04 min). $^1$H NMR (400 MHz, DMSO-d$_6$) δ 9.42 (s, 0.5H), 8.93 (s, 0.5H), 7.99 (d, J=2.8 Hz, 1.5H), 7.93 (d, J=2.8 Hz, 0.5H), 7.44-7.36 (m, 1H), 7.29-7.26 (m, 1H), 7.20-7.12 (m, 1H), 6.06 (s, 0.5H), 5.96 (s. 0.5H), 3.99-3.94 (m, 2H), 3.88-3.79 (m, 0.5H), 3.62 (s, 1.5H), 3.61 (s, 1.5H), 3.59-3.32 (m, 0.5H), 2.38-2.27 (m, 1H), 2.08-1.97 (m, 2H), 1.89-1.61 (m, 4H), 1.47-1.36 (m, 2H), 1.09-1.01 (m, 3H).

Compound 151: methyl 4-(2-bromo-3-fluorophenyl)-6-((1r,4r)-4-(methoxycarbonyl)cyclohexyl)-2-(thiazol-2-yl)-1,4-dihydropyrimidine-5-carboxylate LC-MS (ESI): $R_T$=1.84 min, mass calcd. for $C_{23}H_{23}BrFN_3O_4S$ 535.1, m/z found 538.8 $[M+H]^+$.

Compound 151A: (trans)-methyl 4-(2-bromo-3-fluorophenyl)-6-(4-(methoxycarbonyl)cyclohexyl)-2-(thiazol-2-yl)-1,4-dihydropyrimidine-5-carboxylate 151 (420 mg, 0.780 mmol) was separated by chiral Prep. SFC (Column: Chiralpak IC 5 μm 20*250 mm; Mobile Phase: $CO_2$:MeOH=70:30 at 50 g/min; Col. Temp: 30° C.; Wavelength: 230 nm; Back pressure: 100 bar) to afford the title compounds 151B (176 mg, 42% yield) and 151A (176 mg, 42% yield).

Compound 151A: LC-MS (ESI): $R_T$=4.439 min, mass calcd. for $C_{23}H_{23}BrFN_3O_4S$ 535.1, m/z found 535.8 $[M+H]^+$. Chiral analysis (Column: Chiralpak IC 5 μm 4.6*250 mm, Mobile Phase: Hex:EtOH:DEA=80:20:0.2 at 1.0 mL/min; Col. Temp: 30° C.; Wavelength: 230 nm, $R_T$=7.003 min). $^1$H NMR (400 MHz, CDCl$_3$) δ 8.12 (s, 0.7H), 7.83-7.80 (m, 1H), 7.49 (d, J=3.2 Hz, 0.5H), 7.47 (s, 0.3H), 7.44 (d, J=3.2 Hz, 0.5H), 7.25-7.17 (m, 1H), 7.12 (d, J=7.6 Hz, 1H), 7.06-6.98 (m, 1H), 6.24 (s, 0.5H), 6.08 (d, J=2.8 Hz, 0.5H), 4.05-3.97 (m, 0.4H), 3.81-3.73 (m, 0.6H), 3.70 (s, 3H), 3.61 (s, 1H), 3.59 (s, 2H), 2.45-2.39 (m, 1H), 2.21-1.92 (m, 4H), 1.80-1.63 (m, 3H), 1.56-1.45 (m, 1H).

Compound 153: LC-MS (ESI): $R_T$=3.874 min, mass calcd. for $C_{25}H_{27}F_2N_3O_4S$ 503.2, m/z found 504.1 $[M+H]^+$. Compound 153 (300 mg, 0.596 mmol) was separated by chiral Prep. HPLC (separation condition: Column: Chiralpak IC 5 μm 20*250 mm; Mobile Phase: Hex:EtOH=85:15 at 15 mL/min; Temp: 30° C.; Wavelength: 214 nm) to afford the title compounds 153B (125 mg, 42% yield) and 153A (120 mg, 40% yield) as yellow solids.

Compound 153A: LC-MS (ESI): $R_T$=4.904 min, mass calcd. for $C_{25}H_{27}F_2N_3O_4S$ 503.2, m/z found 504.1 $[M+H]^+$. Chiral analysis (Column: Chiralpak IC 5 μm 4.6*250 mm; Mobile Phase: Hex:EtOH=85:15 at 1.0 mL/min; Temp: 30° C.; Wavelength: 230 nm, $R_T$=6.281 min).

Compound 155: ethyl 4-(2-bromo-4-fluorophenyl)-6-(4-(methoxycarbonyl)cyclohexyl)-2-(thiazol-2-yl)-1,4-dihydropyrimidine-5-carboxylate LC-MS (ESI): $R_T$=4.000 min, mass calcd. for $C_{24}H_{25}BrFN_3O_4S$ 549.1, m/z found 552.0 $[M+H]^+$.

Compound 155 (300 mg, about 90% purity) was separated by chiral Prep. SFC (Column: chiralpak IC 5 μm 20*250 mm; Mobile Phase: $CO_2$:MeOH=70:30 at 50 g/min; Col. Temp: 30° C.; Wavelength: 230 nm, Back pressure: 100 bar) to give Group 1 (137 mg, 46% yield, 100% stereopure) and Group 2 (143 mg, 48% yield, 100% stereopure) as yellow solids. Parts of Group 1 (45 mg) and Group 2 (45 mg) were further purified by Prep. HPLC (Column: Gilson X-bridge C18 (5 μm 19*150 mm), Mobile Phase A: water (0.1% ammonium bicarbonate), Mobile Phase B: acetonitrile, UV: 254 nm, Flow rate: 15 mL/min, Gradient: 70-95% (% B)) to give the title compounds 155B (18.0 mg, 40% yield) and 155A (19.5 mg, 43% yield) as yellow solids.

Compound 155A: LC-MS (ESI): $R_T$=3.279 min, mass calcd. for $C_{24}H_{25}BrFN_3O_4S$ 549.1, m/z found 550.0 $[M+H]^+$. Chiral analysis (Column: Chiralpak IC, 5 μm 4.6*250 mm; Mobile Phase: $CO_2$:MeOH=70:30 at 2.999 g/min; Col. Temp: 40° C.; Wavelength: 230 nm; Back pressure: 100 bar, $R_T$=3.67 min).

Compound 159: methyl 4-(2-bromo-3,4-difluorophenyl)-6-(1-(tert-butoxycarbonyl)piperidin-4-yl)-2-(thiazol-2-yl)-1,4-dihydropyrimidine-5-carboxylate LC-MS (ESI): $R_T$=1.96 min, mass calcd. for $C_{25}H_{27}BrF_2N_4O_4S$ 596.1, m/z found 599.3 $[M+H]^+$.

Compound 159A: Compound 159 (950 mg, 1.59 mmol) was separated by chairl Prep.

SFC (Column: Chiralpak IG 5 μm 20*250 mm; Mobile Phase: $CO_2$:MeOH:DEA=70:30:0.2 at 50 g/min; Col. Temp 41.1° C.; Wavelength: 214 nm; Back pressure: 100 bar) to afford the title compounds 159B (450 mg, 47% yield) and 159A (460 mg, 48% yield) as yellow solids. For 159A, LC-MS (ESI): $R_T$=1.85 min, mass calcd. for $C_{25}H_{27}BrF_2N_4O_4S$ 596.1, m/z found 597.5 $[M+H]^+$. Chiral analysis (Column: Chiralpak IG 5 μm 4.6*250 mm; Mobile Phase: $CO_2$:MeOH:DEA=70:30:0.2 at 2.999 g/min; Temp: 40° C.; Wavelength: 230 nm, $R_T$=3.99 min).

Compound 167A: methyl 4-(2-chloro-3,4-difluorophenyl)-6-((trans)-4-(N-methylsulfamoyl)cyclohexyl)-2-(2,4,6-trifluorophenyl)-1,4-dihydropyrimidine-5-carboxylate Separation condition: C18 column (acetonitrile:water=20% to 95%) to give yellow solids (65 mg, 19% yield), which was separated by chiral Prep. HPLC (Column: Chiralpak IA 5 μm 20*250 mm; Mobile Phase: Hex:EtOH=90:10 at 25 mL/min; Temp: 30° C.; Wavelength: 214 nm). LC-MS (ESI): $R_T$=3.492 min, mass calcd. for $C_{25}H_{23}ClF_5N_3O_4S$ 591.1, m/z found 592.0 $[M+H]^+$. Chiral analysis (Column: Chiralpak IA 5 μm 4.6*250 mm; Mobile Phase: Hex:EtOH=85:15 at 1.0 mL/min; Temp: 30° C.; Wavelength: 230 nm, $R_T$=7.243 min). $^1$H NMR (400 MHz, DMSO-$d_6$) δ 9.44 (s, 1H), 7.57-7.44 (m, 1H), 7.30-7.24 (m, 2.3H), 7.20-7.16 (m, 0.7H), 6.99-6.95 (m, 0.8H), 6.85-6.81 (m, 0.2H), 5.96 (s, 0.8H), 5.87 (d, J=3.2 Hz, 0.2H), 3.94-3.85 (m, 0.8H), 3.64-3.57 (m, 0.2H), 3.52 (s, 1H), 3.51 (s, 2H), 3.06-2.96 (m, 0.2H), 2.88-2.79 (m, 0.8H), 2.59 (d, J=4.8 Hz, 2H), 2.57 (d, J=4.8 Hz, 1H), 2.20-2.04 (m, 2H), 1.92-1.61 (m, 4H), 1.54-1.40 (m, 2H).

Compound 168A: methyl 4-(2-chloro-3,4-difluorophenyl)-2-(3,5-difluoropyridin-2-yl)-6-((trans)-4-(N-methylsulfamoyl)cyclohexyl)-1,4-dihydropyrimidine-5-carboxylate (separation conditions: Column: Chiralpak IA 5 μm 20*250 mm; Mobile Phase: Hex:EtOH=70:30 at 25 mL/min; Temp: 30° C.; Wavelength: 214 nm) LC-MS (ESI): $R_T$=3.676 min, mass calcd. for $C_{24}H_{23}ClF_4N_4O_4S$ 574.1, m/z found 575.0 $[M+H]^+$. Chiral analysis (Column: Chiralpak IA 5 μm 4.6*250 mm; Mobile Phase: Hex:EtOH=70:30 at 1.0 mL/min; Temp: 30° C.; Wavelength: 230 nm, $R_T$=6.312 min). $^1$H NMR (400 MHz, DMSO-$d_6$) δ 9.20-9.17 (m, 1H), 8.56 (d, J=2.0 Hz, 1H), 8.09-8.04 (m, 1H), 7.51-7.42 (m, 1H), 7.25-7.16 (m, 1H), 6.98-6.94 (m, 0.7H), 6.87-6.83 (m, 0.3H), 6.04 (s, 0.7H), 5.93 (d, J=3.6 Hz, 0.3H), 3.92-3.83 (m, 0.7H), 3.62-3.57 (m, 0.3H), 3.53 (s, 1H), 3.52 (s, 2H), 3.05-2.95 (m, 1H), 2.61-2.59 (m, 3H), 2.22-2.06 (m, 2H), 2.00-1.92 (m, 0.6H), 1.88-1.66 (m, 3.4H), 1.56-1.42 (m, 2H).

Compound 169A: (trans)-Methyl 4-(2-chloro-3,4-difluorophenyl)-6-(4-(pyrrolidin-1-ylsulfonyl)cyclohexyl)-2-(thiazol-2-yl)-1,4-dihydropyrimidine-5-carboxylate (Separation condition, Column: chiralpak IE 5 μm 20*250 mm; Mobile Phase: Hex:EtOH:DEA=50:50:0.3 at 10 mL/min; Temp: 30° C.; Wavelength: 214 nm). LC-MS (ESI): $R_T$=4.293 min, mass calcd. for $C_{25}H_{27}ClF_2N_4O_4S_2$ 584.1, m/z found 584.7 $[M+H]^+$. Chiral analysis (Column: Chiralpak IE, 5 μm 4.6*250 mm; Mobile Phase: Hex:EtOH:DEA=50:50:0.2 at 1 mL/min; Temp: 30° C.; Wavelength: 230 nm; $R_T$=12.642 min). $^1$H NMR (400 MHz, DMSO-$d_6$) δ 9.55 (d, J=3.6 Hz, 0.6H), 8.89 (s, 0.4H), 8.01-7.98 (m, 1.6H), 7.95 (d, J=3.2 Hz, 0.4H), 7.48-7.42 (m, 1H), 7.20-7.14 (m, 1H), 6.02 (s, 0.4H), 5.92 (d, J=3.2 Hz, 0.6H), 3.88-3.81 (s, 0.4H), 3.61-3.57 (m, 0.6H), 3.53 (s, 1.8H), 3.52 (s, 1.2H), 3.31-3.26 (m, 4H), 3.24-3.18 (m, 1H), 2.19-2.09 (m, 2H), 1.97-1.85 (m, 7H), 1.76-1.69 (m, 1H), 1.59-1.51 (m, 2H).

Compound 170: Methyl 4-(2-chloro-3-fluorophenyl)-6-(3-(N-methylacetamido)cyclopentyl)-2-(thiazol-2-yl)-1,4-dihydropyrimidine-5-carboxylate LC-MS (ESI): $R_T$=3.858 min, mass calcd. for $C_{23}H_{24}ClFN_4O_3S$ 490.1, m/z found 491.1 $[M+H]^+$. $^1$H NMR (400 MHz, DMSO-$d_6$) δ 9.55 (s, 0.8H), 9.42-9.29 (br s, 0.2H), 8.01-7.94 (m, 2H), 7.41-7.31 (m, 2H), 7.22-7.17 (m, 1H), 6.06 (br s, 0.2H), 5.97 (s, 0.8H), 5.23 (br s, 0.2H), 4.99 (br s, 0.3H), 4.62-4.54 (m, 0.2H), 4.32-4.16 (m, 1.3H), 3.52 (s, 3H), 2.98-2.96 (m, 1H), 2.88-2.83 (m, 1.4H), 2.74-2.73 (m, 0.6H), 2.14-1.62 (m, 9H).

Compound 171: (cis)-Methyl 4-(2-chloro-3-fluorophenyl)-6-(4-methyltetrahydrofuran-2-yl)-2-(thiazol-2-yl)-1,4-dihydropyrimidine-5-carboxylate LC-MS (ESI): $R_T$=4.839 min, mass calcd. for $C_{20}H_{19}ClFN_3O_3S$ 435.1, m/z found 436.0 $[M+H]^+$. $^1$H NMR (400 MHz, DMSO-$d_6$) δ 9.27-8.90 (m, 1H), 8.02-8.00 (m, 1H), 7.98-7.95 (m, 1H), 7.43-7.29 (m, 2H), 7.25-7.18 (m, 0.4H), 7.16-7.09 (m, 0.6H), 6.11 (s, 0.7H), 6.06 (s, 0.3H), 5.58-5.53 (m, 0.2H), 5.50-5.41 (m, 0.8H), 4.26-4.18 (m, 0.2H), 4.11-4.04 (m, 0.8H), 3.64-3.58 (m, 1H), 3.52 (s, 3H), 2.82-2.69 (m, 1H), 2.47-2.36 (m, 1H), 1.63-1.53 (m, 0.6H), 1.44-1.35 (m, 0.4H), 1.08 (d, J=6.8 Hz, 2H), 1.01 (d, J=6.8 Hz, 1H).

Compound 172: Methyl 4-(2-chloro-4-fluorophenyl)-6-((cis)-3-(methoxycarbonyl) cyclohexyl)-2-(thiazol-2-yl)-1,4-dihydropyrimidine-5-carboxylate LC-MS (ESI): $R_T$=4.317 min, mass calcd. for $C_{23}H_{23}ClFN_3O_4S$ 491.1, m/z found 491.9 $[M+H]^+$. $^1$H NMR (400 MHz, CDCl$_3$) δ 8.15-8.12 (m, 0.5H), 7.82 (d, J=3.2 Hz, 1H), 7.49 (d, J=2.8 Hz, 0.5H), 7.44 (d, J=3.2 Hz, 0.5H), 7.41-7.38 (m, 0.5H), 7.32-7.28 (m, 1H), 7.15-7.11 (m, 1H), 6.97-6.88 (m, 1H), 6.18 (d, J=4.0 Hz, 0.5H), 6.04 (d, J=2.8 Hz, 0.5H), 4.11-4.04 (m, 0.5H), 3.89-3.82 (m, 0.5H), 3.76-3.67 (m, 3H), 3.63 (s, 1.5H), 3.59 (s, 1.5H), 2.63-2.50 (m, 1H), 2.26-2.11 (m, 3H), 1.96-1.84 (m, 1H), 1.72-1.62 (m, 1H), 1.57-1.40 (m, 3H).

Compound 174A: Methyl 4-(2-chloro-4-fluorophenyl)-2-(3,5-difluoropyridin-2-yl)-6-((trans)-4-(methoxycarbonyl)cyclohexyl)-1,4-dihydropyrimidine-5-carboxylate Racemic compound 174 (1.30 g, 2.50 mmol) was separated by chiral Prep. HPLC (Column: Chiralpak IG 5 μm 20*250 mm; Mobile Phase: $CO_2$:MeOH:DEA=75:25:0.2 at 50 g/min; Col. Temp: 40° C.; Wavelength: 214 nm, Back pressure: 100 bar) to afford title compound 174A (202 mg, 16% yield, 100% stereopure) and 174B (170 mg, 13% yield, 97.7% stereopure) as yellow solids.

Compound 174A: LC-MS (ESI): $R_T$=2.716 min, mass calcd. for $C_{25}H_{23}ClF_3N_3O_4$ 521.1, m/z found 521.9 $[M+H]^+$. Chiral HPLC (Column: Chiralpak IA 5 μm 4.6*250 mm; Mobile Phase: $CO_2$:MeOH:DEA=80:20:0.2 at 3.0 g/min; Col. Temp: 40.1° C.; Wavelength: 230 nm, Back pressure: 100 bar, $R_T$=3.01 min). $^1$H NMR (400 MHz, DMSO-$d_6$) δ 9.22 (br s, 0.6H), 9.03 (br s, 0.4H), 8.57 (br s, 1H), 8.06 (t, J=9.6 Hz, 1H), 7.41 (d, J=8.0 Hz, 1H), 7.35 (t, J=7.2 Hz, 1H), 7.22 (t, J=8.0 Hz, 1H), 6.03 (s, 0.7H), 5.92 (s, 0.3H), 3.90-3.79 (m, 1H), 3.61 (s, 3H), 3.52 (s, 3H), 2.39-2.29 (m, 1H), 2.08-1.98 (m, 2H), 1.89-1.66 (m, 4H), 1.50-1.35 (m, 2H).

Compound 175: (cis)-tert-Butyl 5-(3-methoxy-3-oxopropanoyl)hexahydro-cyclopenta[c]pyrrole-2(1H)-carboxylate LC-MS (ESI): $R_T$=1.54 min, mass calcd. for $C_{16}H_{25}NO_5$ 311.2, m/z found 256.2 $[M+H-56]^+$. $^1$H NMR (400 MHz, CDCl$_3$) δ 12.04 (s, 0.1H), 5.01 (s, 0.1H), 3.73 (s, 2.7H), 3.72 (s, 0.3H), 3.48 (s, 1.8H), 3.47-3.43 (m, 2H), 3.28-3.07 (m, 3H), 2.77-2.71 (m, 0.2H), 2.69-2.58 (m, 1.8H), 2.21-2.04 (m, 2H), 1.68-1.56 (m, 2H), 1.44 (s, 9H).

Compound 188: Methyl 6-(4-((tert-butoxycarbonyl) amino)cycloheptyl)-4-(2-chloro-4-fluorophenyl)-2-(thiazol-2-yl)-1,4-dihydropyrimidine-5-carboxylate LC-MS (ESI): R$_T$=2.816 min, mass calcd. for C$_{27}$H$_{32}$ClFN$_4$O$_4$S 562.2, m/z found 563.1 [M+H]$^+$. H NMR (400 MHz, CDCl$_3$) δ 8.05 (br s, 0.5H), 7.83-7.81 (m, 1H), 7.49 (d, J=2.4 Hz, 0.4H), 7.44-7.43 (m, 0.6H), 7.37-7.31 (m, 0.5H), 7.31-7.28 (m, 1H), 7.14-7.11 (m, 1H), 6.93-6.89 (m, 1H), 6.17 (s, 0.5H), 6.03 (d, J=2.8 Hz, 0.5H), 4.69-4.49 (m, 0.6H), 4.01-3.94 (m, 1H), 3.94-3.86 (m, 0.4H), 3.77-3.68 (m, 1H), 3.59 (s, 3H), 2.20-2.16 (m, 1.4H), 2.09-1.54 (m, 8.6H), 1.46 (s, 9H).

Compound 191: Ethyl 6-(1-(tert-butoxycarbonyl) piperidin-4-yl)-4-(2-chloro-3,4-difluorophenyl)-2-(2,4,6-trifluorophenyl)-1,4-dihydropyrimidine-5-carboxylate LC-MS(ESI): R$_T$=2.294 min, mass calcd. for C$_{29}$H$_{29}$ClF$_5$N$_3$O$_4$ 613.2, m/z found 614.1 [M+H]$^+$. $^1$H NMR (400 MHz, CDCl$_3$) δ 7.16-7.03 (m, 2H), 6.70-6.64 (m, 2H), 6.23 (s, 0.7H), 5.99 (d, J=2.8 Hz, 1H), 4.33-3.99 (m, 4.6H), 3.92-3.86 (m, 0.4H), 2.90-2.66 (m, 2H), 1.91-1.83 (m, 2H), 1.74-1.60 (m, 0.5H), 1.56-1.49 (m, 1H), 1.46-1.42 (m, 9.5H), 1.18-1.12 (m, 3H).

Compound 196: Ethyl 4-(2-bromo-3,4-difluorophenyl)-6-(1-(tert-butoxycarbonyl)piperidin-4-yl)-2-(thiazol-2-yl)-1,4-dihydropyrimidine-5-carboxylate LC-MS: R$_T$=2.02 min, mass calcd. for C$_{26}$H$_{29}$BrF$_2$N$_4$O$_4$S 610.1, m/z found 613.5 [M+H]$^+$. $^1$H NMR (400 MHz, DMSO-d$_6$) δ 9.53 (d, J=2.8 Hz, 0.7H), 9.08 (s, 0.3H), 7.99-7.96 (m, 1.7H), 7.92 (d, J=3.2 Hz, 0.3H), 7.52-7.44 (m, 1H), 7.22-7.14 (m, 1H), 6.02 (s, 0.3H), 5.92 (d, J=3.2 Hz, 0.7H), 4.11-3.93 (m, 4.3H), 3.82-3.76 (m, 0.7H), 2.86-2.69 (m, 2H), 1.90-1.67 (m, 3H), 1.53-1.50 (m, 1H), 1.44 (s, 9H), 1.09-1.03 (m, 3H).

Racemic compound 196 was separated by chiral Prep. HPLC (Column: Chiralpak IC 5 m 20*250 mm; Mobile Phase: Hex:EtOH:DEA=95:5:0.2 at 25 mL/min; Temp: 30° C.; Wavelength: 230 nm) to afford the title compounds 196A (400 mg, 27% yield, 100% stereopure) and 196B (500 mg, 33% yield, 97.7% stereopure) as yellow solids. Compound 196A: Chiral analysis (Column: Chiralpak IC 5 μm 4.6*250 mm; Mobile Phase: Hex:EtOH:DEA=95:5:0.2 at 1.0 mL/min; Temp: 30° C.; Wavelength: 230 nm, R$_T$=10.303 min).

Compound 202: Methyl 6-(3-((tert-butoxycarbonyl) amino)bicyclo[1.1.1]pentan-1-yl)-4-(2-chloro-3,4-difluorophenyl)-2-(thiazol-2-yl)-1,4-dihydropyrimidine-5-carboxylate LC-MS (ESI): R$_T$=2.397 min, mass calcd. for C$_{25}$H$_{25}$ClF$_2$N$_4$O$_4$S 550.1, m/z found 551.1 [M+H]$^+$. Chiral analysis (Column: Chiralpak IG 5 μm 4.6*250 mm; Mobile Phase: CO$_2$:MeOH=70:30 at 2.999 g/min; Col. Temp: 40° C.; Wavelength: 230 nm, Back pressure: 100 bar R$_T$=2.71 min and 3.94 min). $^1$H NMR (300 MHz, CDCl$_3$) δ 7.93 (br s, 0.8H), 7.84-7.81 (m, 1H), 7.51-7.50 (m, 0.2H), 7.46 (d, J=3.0 Hz, 0.8H), 7.42-7.40 (m, 0.2H), 7.09-7.02 (m, 2H), 6.16 (s, 0.8H), 6.03 (br s, 0.2H), 5.04 (br s, 1H), 3.66 (s, 0.5H), 3.61 (s, 2.5H), 2.55 (s, 5H), 2.47 (s, 1H), 1.49 (s, 9H).

Racemic compound 202 (700 mg, 1.27 mmol) was separated by chiral Prep. HPLC (Column: Chiralpak IG 5 μm 20*250 mm; Mobile Phase: CO$_2$:MeOH=70:40 at 50 g/min; Col. Temp: 40° C.; Wavelength: 214 nm, Back pressure: 100 bar) to afford the title compounds 202A (330 mg, 47% yield, 100% stereopure) and 202B (340 mg, 49% yield, 100% stereopure) as yellow solids.

Compound 202A: LC-MS (ESI): R$_T$=2.253 min, mass calcd. for C$_{25}$H$_{25}$ClF$_2$N$_4$O$_4$S 550.1, m/z found 551.0 [M+H]$^+$. Chiral analysis (Column: Chiralpak IG 5 μm 4.6*250 mm; Mobile Phase: CO$_2$:MeOH=70:30 at 2.999 g/min; Col. Temp: 39.8° C.; Wavelength: 230 nm, Back pressure: 100 bar, R$_T$=2.72 min). $^1$H NMR (300 MHz, CDCl$_3$) δ 7.92 (s, 0.8H), 7.82-7.81 (m, 1H), 7.51-7.50 (m, 0.2H), 7.46-7.45 (m, 0.8H), 7.42-7.40 (m, 0.2H), 7.09-7.02 (m, 2H), 6.16 (s, 0.8H), 6.03 (s, 0.2H), 5.06 (br s, 1H), 3.66 (s, 0.5H), 3.61 (s, 2.5H), 2.55 (s, 5H), 2.47 (s, 1H), 1.49 (s, 9H).

Compound 211: Methyl 4-(2-chloro-3-fluorophenyl)-6-(5-(ethoxycarbonyl)tetrahydrofuran-3-yl)-2-(thiazol-2-yl)-1,4-dihydropyrimidine-5-carboxylate (a Mixture of 8 Stereoisomers)

LC-MS (ESI): R$_T$=3.768, 3.851 and 3.946 min, mass calcd. for C$_{22}$H$_{21}$ClFN$_3$O$_5$S 493.1, m/z found 494.1 [M+H]$^+$. $^1$H NMR (400 MHz, CD$_3$OD) δ 7.93-7.90 (m, 0.2H), 7.89-7.88 (m, 0.8H), 7.77-7.76 (m, 0.8H), 7.75-7.73 (m, 0.2H), 7.31-7.14 (m, 3H), 6.20-6.17 (m, 0.2H), 6.16 (s, 0.3H), 6.12 (m, 0.5H), 4.88-4.79 (m, 0.5H), 4.64-4.52 (m, 1.5H), 4.29-3.94 (m, 4H), 3.60-3.57 (m, 3H), 2.96-2.83 (m, 0.4H), 2.71-2.57 (m, 1H), 2.47-2.40 (m, 0.2H), 2.32-2.18 (m, 0.4H), 1.32-1.30 (m, 2.4H), 1.29-1.19 (m, 0.6H).

A racemic mixture of 211 (810 mg, 1.64 mmol) was separated by chiral Prep. HPLC (separation condition: Column: Chiralpak IC 5 μm 20*250 mm; Mobile Phase: Hex:IPA:DEA=60:40:0.2 at 15 mL/min; Temp: 30° C.; Wavelength: 230 nm) to afford the title compounds 211S (71 mg, 9% yield, 100% stereopure), Group 1 (325 mg, 40% yield) and Group 2 (177 mg, 22% yield) as yellow solids. Group 1 (325 mg, 0.66 mmol) was separated by chiral Prep. HPLC (separation condition: Column: Chiralpak IC 5 μm 20*250 mm; Mobile Phase: Hex:IPA:DEA=80:20:0.2 at 15 mL/min; Temp: 30° C.; Wavelength: 230) to afford the title compounds 211U (32 mg, 10% yield, 97.7% stereopure), Group A (117 mg, 36% yield) and 211N (51 mg, 16% yield, containing two isomers) as yellow solids. Group 2 (177 mg, 0.36 mmol) was separated by chiral Prep. HPLC (separation condition: Column: Chiralpak IC 5 μm 20*250 mm; Mobile Phase: Hex:IPA:DEA=85:15:0.2 at 15 mL/min; Temp: 30° C.; Wavelength: 230 nm) to afford the title compounds 211V (54 mg, 31% yield, 100% stereopure) and 211T (43 mg, 24% yield, 100% stereopure) as yellow solids. Group A (117 mg, 0.24 mmol) was separated by chiral Prep. HPLC (separation condition: Column: Chiralpak IC 5 μm 20*250 mm; Mobile Phase: Hex:IPA:DEA=85:15:0.2 at 15 mL/min; Temp: 30° C.; Wavelength: 230 nm) to afford the title compounds 211M (31 mg, 26% yield, 98.7% stereopure) and 211X (38 mg, 32% yield, 100% stereopure) as yellow solids.

Intermediate 211M: LC-MS (ESI): R$_T$=4.092 min, mass calcd. for C$_{22}$H$_{21}$ClFN$_3$O$_5$S 493.1, m/z found 493.9 [M+H]$^+$. Chiral analysis (Column: Chiralpak IF 5 μm 4.6*250 mm; Mobile Phase: Hex:EtOH:DEA=80:20:0.2 at 1.0 mL/min; Temp: 30° C.; Wavelength: 230 nm; R$_T$=13.062 min). ¹H NMR (400 MHz, CD₃OD) δ 7.90 (d, J=2.4 Hz, 1H), 7.77 (d, J=2.4 Hz, 0.7H), 7.72 (d, J=2.8 Hz, 0.3H), 7.32-7.25 (m, 1.3H), 7.20-7.14 (m, 1.7H), 6.18 (s, 0.2H), 6.15 (s, 0.8H), 4.87-4.82 (m, 0.2H), 4.80-4.77 (m, 1H), 4.59-4.52 (m, 0.8H), 4.39-4.30 (m, 1H), 4.23 (q, J=7.2 Hz, 2H), 4.18-4.15 (m, 0.2H), 4.11 (t, J=6.8 Hz, 0.8H), 3.59 (s, 0.9H), 3.58 (s, 2.1H), 2.75-2.68 (m, 0.7H), 2.65-2.58 (m, 0.3H), 2.49-2.44 (m, 0.3H), 2.17-2.10 (m, 0.7H), 1.30 (t, J=7.2 Hz, 3H).

Compound 217: Methyl 4-(2-chloro-4-fluorophenyl)-6-(oxetan-3-yl)-2-(thiazol-2-yl)-1,4-dihydropyrimidine-5-carboxylate LC-MS (ESI): R$_T$=4.061 min, mass calcd. for C₁₈H₁₅ClFN₃O₃S 407.1, m/z found 407.9 [M+H]⁺. ¹H NMR (400 MHz, DMSO-d₆) 8.03 (s, 2H), 7.45-7.41 (m, 2H), 7.24-7.19 (m, 1H), 5.94 (s, 1H), 4.86-4.68 (m, 5H), 3.50 (s, 3H).

A racemic mixture of 217 (250 mg, 0.614 mmol) was separated by chiral Prep. HPLC (separation condition: column: Chiralpak IC 5 um 20*250 mm; Mobile Phase: Hex:EtOH=80:20 at 13 mL/min; Temp: 30° C.; Wavelength: 230 nm) to afford the title compounds 217A (76.9 mg, 31% yield, 100% stereopure) and 217B (53.2 mg, 21% yield, 100% stereopure) as yellow solids. Compound 217A: LC-MS (ESI): R$_T$=3.996 min, mass calcd. for C₁₈H₁₅ClFN₃O₃S 407.1, m/z found 408.1 [M+H]⁺. Chiral HPLC (Column: Chiralpak IC 5 μm 4.6*250 mm; Mobile Phase: Hex: EtOH=80:20 at 1.0 mL/min; Temp: 30° C.; Wavelength: 230 nm, R$_T$=10.020 min); ¹H NMR (400 MHz, DMSO-d₆) 9.73 (s, 0.9H), 9.28 (s, 0.1H), 8.05-7.95 (m, 2H), 7.47-7.41 (m, 2H), 7.25-7.20 (m, 1H), 6.01 (s, 0.1H), 5.93 (s, 0.9H), 4.94-4.62 (m, 5H), 3.49 (s, 3H).

Compound 218: Methyl 4-(2-chloro-4-fluorophenyl)-6-(1,4-dioxaspiro[4.5]decan-7-yl)-2-(thiazol-2-yl)-1,4-dihydropyrimidine-5-carboxylate LC-MS (ESI): R$_T$=4.437 min, mass calcd. for C₂₃H₂₃ClFN₃O₄S 491.1, m/z found 492.2 [M+H]⁺. ¹H NMR (400 MHz, DMSO-d₆) δ 9.48-9.44 (m, 0.6H), 9.20 (s, 0.2H), 9.12 (s, 0.2H), 8.00-7.99 (m, 1.6H), 7.94-7.93 (m, 0.4H), 7.44-7.41 (m, 1H), 7.36-7.29 (m, 1H), 7.25-7.20 (m, 1H), 6.01-6.00 (m, 0.3H), 5.91 (dd, J=8.4, 3.6 Hz, 0.7H), 4.14 (s, 0.3H), 3.91-3.85 (m, 4.7H), 3.53-3.51 (m, 3H), 2.12-1.87 (m, 1H), 1.83-1.42 (m, 7H).

Compound 220: (cis)-Methyl 6-(4-(((tert-butyldiphenylsilyl)oxy)methyl)-tetrahydrofuran-2-yl)-4-(2-chloro-3-fluorophenyl)-2-(thiazol-2-yl)-1,4-dihydropyrimidine-5-carboxylate LC-MS (ESI): R$_T$=2.899 min, mass calcd. for C₃₆H₃₇ClFN₃O₄SSi 689.2, m/z found 690.2 [M+H]⁺. ¹H NMR (300 MHz, CDCl₃) δ 7.76 (d, J=3.9 Hz, 0.4H), 7.70-7.60 (m, 4.6H), 7.47-7.28 (m, 8H), 7.25-7.15 (m, 1H), 7.05-7.00 (m, 2H), 6.28 (s, 0.5H), 6.23 (s, 0.5H), 5.61-5.53 (m, 1H), 4.14-4.08 (m, 2H), 3.73-3.63 (m, 2H), 3.59 (s, 3H), 2.84-2.63 (m, 2H), 1.69-1.57 (m, 0.5H), 1.53-1.49 (m, 0.5H), 1.07 (s, 5H), 1.02 (s, 4H).

Compound 224: (trans)-Methyl 4-(2-bromo-4-fluorophenyl)-6-(4-(methoxycarbonyl)cyclohexyl)-2-(thiazol-2-yl)-1,4-dihydropyrimidine-5-carboxylate LC-MS (ESI): R$_T$=2.856 min, mass calcd. for C₂₃H₂₃BrFN₃O₄S 535.1, m/z found 538.2 [M+H]⁺. ¹H NMR (400 MHz, DMSO-d₆) δ 9.47-9.39 (m, 0.5H), 8.99-8.93 (m, 0.5H), 7.99 (s, 1.5H), 7.94-7.91 (m, 0.5H), 7.57 (d, J=8.0 Hz, 1H), 7.37-7.30 (m, 1H), 7.27-7.22 (m, 1H), 5.98 (s, 0.5H), 5.88 (s, 0.5H), 3.89-3.83 (m, 0.5H), 3.78-3.69 (m, 0.5H), 3.62 (s, 3H), 3.52 (s, 3H), 2.68-2.62 (m, 0.5H), 2.37-2.29 (m, 0.5H), 2.02-1.98 (m, 2H), 1.88-1.78 (m, 3H), 1.72-1.59 (m, 1H), 1.50-1.37 (m, 2H).

A racemic mixture of 224 (450 mg, 0.840 mmol) was separated by chiral Prep. HPLC (Column: Chiralpak IC 5 μm 20*250 mm; Mobile Phase: Hex:EtOH:DEA=80:20:0.3 at 13 mL/min; Temp: 30° C.; Wavelength: 230 nm) to afford the title compounds 224X (193 mg, 43% yield, 100% stereopure) and 224Y (190 mg, 42% yield, 99.0% stereopure).

Compound 224X: LC-MS (ESI): R$_T$=3.841 min, mass calcd. for C₂₃H₂₃BrFN₃O₄S 535.1, m/z found 535.9 [M+H]⁺. Chiral analysis (Column: Chiralpak IC 5 μm 4.6*250 mm; Mobile Phase: Hex:EtOH:DEA=85:15:0.2 at 1.0 mL/min; Temp: 30° C.; Wavelength: 230 nm, R$_T$=7.151 min). ¹H NMR (400 MHz, DMSO-d₆) δ 9.47-9.41 (m, 0.5H), 9.01-8.94 (m, 0.5H), 8.00-7.99 (m, 1.5H), 7.95-7.93 (m, 0.5H), 7.57 (dd, J=8.4, 2.4 Hz, 1H), 7.39-7.30 (m, 1H), 7.28-7.23 (m, 1H), 5.98 (s, 0.5H), 5.88 (s, 0.5H), 3.87-3.79 (m, 0.5H), 3.62 (s, 3H), 3.60-3.57 (m, 0.5H), 3.52 (s, 3H), 2.40-2.29 (m, 0.8H), 2.08-1.98 (m, 2.2H), 1.91-1.79 (m, 2.2H), 1.74-1.61 (m, 1.8H), 1.50-1.36 (m, 2H).

Compound 224Y: LC-MS (ESI): R$_T$=3.847 min, mass calcd. for C₂₃H₂₃BrFN₃O₄S 535.1, m/z found 535.8 [M+H]⁺. Chiral analysis (Column: Chiralpak IC 5 μm 4.6*250 mm; Mobile Phase: Hex:EtOH:DEA=85:15:0.2 at 1.0 mL/min; Temp: 30° C.; Wavelength: 230 nm, R$_T$=10.245 min). ¹H NMR (400 MHz, DMSO-d₆) δ 9.44 (d, J=3.6 Hz, 0.6H), 8.96 (s, 0.4H), 8.00-7.99 (m, 1.5H), 7.94 (d, J=3.6 Hz, 0.5H), 7.59-7.55 (m, 1H), 7.36-7.33 (m, 1H), 7.30-7.22 (m, 1H), 5.98 (s, 0.4H), 5.88 (d, J=3.6 Hz, 0.6H), 3.88-3.78 (m, 0.5H), 3.62 (s, 1.2H), 3.61 (s, 1.8H), 3.59-3.57 (m, 0.5H), 3.53 (s, 1.6H), 3.51 (s, 1.4H), 2.38-2.30 (m, 0.7H), 2.07-1.97 (m, 2.3H), 1.91-1.82 (m, 2H), 1.79-1.60 (m, 2H), 1.51-1.36 (m, 2H).

Compound 226: (trans)-Methyl 4-(3,4-difluoro-2-methylphenyl)-6-(4-(methoxycarbonyl)cyclohexyl)-2-(thiazol-2-yl)-1,4-dihydropyrimidine-5-carboxylate LC-MS (ESI): R$_T$=4.206 min, mass calcd. for C₂₄H₂₅F₂N₃O₄S 489.2, m/z found 490.3 [M+H]⁺. ¹H NMR (400 MHz, DMSO-d₆) δ 9.53 (d, J=3.6 Hz, 0.7H), 8.96 (s, 0.3H), 7.99-7.97 (m, 1.7H), 7.92 (d, J=3.2 Hz, 0.3H), 7.25-7.17 (m, 1H), 7.10-7.07 (m, 0.7H), 6.98-6.94 (m, 0.3H), 5.81 (s, 0.3H), 5.67 (d, J=3.2 Hz, 0.7H), 3.90-3.79 (m, 0.3H), 3.62-3.53 (m, 3.7H), 3.52 (s, 3H), 2.56-2.53 (m, 0.3H), 2.47-2.43 (m, 2.7H), 2.37-2.29 (m, 1H), 2.04-1.96 (m, 2H), 1.90-1.60 (m, 4H), 1.49-1.35 (m, 2H).

Racemic 226 (200 mg, 0.410 mmol) was separated by chiral Prep. HPLC (Column: Chiralpak IC 5 μm 20*250 mm; Mobile Phase: Hex:EtOH=85:15 at 8 mL/min; Temp: 30° C.; Wavelength: 214 nm) to afford the title compounds 226M (80.0 mg, 40% yield, 100% stereopure) and 226N (90.0 mg, 45% yield, 99.8% stereopure) as yellow solids.

Compound 226M: LC-MS (ESI): R$_T$=4.302 min, mass calcd. for C₂₄H₂₅F₂N₃O₄S 489.2, m/z found 490.0 [M+H]⁺. Chiral analysis (Column: Chiralpak IC 5 μm 4.6*250 mm; Mobile Phase: Hex:EtOH=85:15 at 1.0 mL/min; Temp: 30° C.; Wavelength: 230 nm, R$_T$==6.758 min). ¹H NMR (400 MHz, DMSO-d₆) δ 9.52 (d, J=3.6 Hz, 0.7H), 8.95 (s, 0.3H), 8.00-7.97 (m, 1.7H), 7.92 (d, J=3.2 Hz, 0.3H), 7.25-7.17 (m, 1H), 7.11-7.08 (m, 0.7H), 6.98-6.94 (m, 0.3H), 5.82 (s, 0.3H), 5.68 (d, J=3.6 Hz, 0.7H), 3.90-3.80 (m, 0.3H), 3.62-3.53 (m, 3.7H), 3.52 (s, 3H), 2.55-2.53 (m, 0.3H), 2.47-2.43 (m, 2.7H), 2.38-2.30 (m, 1H), 2.08-1.97 (m, 2H), 1.94-1.60 (m, 4H), 1.49-1.36 (m, 2H).

Compound 228: (trans)-Methyl 4-(2-bromo-3,4-difluorophenyl)-6-(4-(methoxycarbonyl)cyclohexyl)-2-(thiazol-2-yl)-1,4-dihydropyrimidine-5-carboxylate LC-MS (ESI): $R_T$=4.469 min, mass calcd. for $C_{23}H_{22}BrF_2N_3O_4S$ 553.1, m/z found 553.8 [M+H]$^+$. $^1$H NMR (400 MHz, DMSO-d$_6$) δ 9.52 (d, J=4.0 Hz, 0.5H), 8.98 (s, 0.5H), 7.99-7.98 (m, 1.5H), 7.94-7.93 (m, 0.5H), 7.52-7.44 (m, 1H), 7.21-7.12 (m, 1H), 6.00 (s, 0.5H), 5.91 (d, J=3.2 Hz, 0.5H), 3.87-3.80 (m, 0.5H), 3.62-3.61 (m, 3.5H), 3.52-3.51 (m, 3H), 2.37-2.31 (m, 0.6H), 2.08-1.65 (m, 6.4H), 1.51-1.36 (m, 2H).

A racemic mixture of 228 (400 mg, 0.72 mmol) was separated by chiral Prep. HPLC (Column: Chiralpak IA 5 μm 20*250 mm; Mobile Phase: Hex:EtOH:DEA=70:30:0.3 at 25.0 mL/min; Temp: 30° C.; Wavelength: 214 nm) to afford the title compounds 228M (160 mg, 40% yield, 100% stereopure) and 228N (170 mg, 43% yield, 98.2% stereopure) as yellow solids.

Compound 228M: LC-MS (ESI): $R_T$=3.342 min, mass calcd. for $C_{23}H_{22}BrF_2N_3O_4S$ 553.1, m/z found 556.1 [M+H]$^+$. Chiral analysis (Column: Chiralpak IA 5 μm 4.6*250 mm; Mobile Phase: Hex:EtOH:DEA=70:30:0.2 at 1.0 mL/min; Temp: 30° C.; Wavelength: 230 nm, $R_T$=5.698 min). $^1$H NMR (400 MHz, DMSO-d$_6$) δ 9.53 (d, J=3.2 Hz, 0.5H), 8.99 (s, 0.5H), 8.00-7.99 (m, 1.5H), 7.94-7.93 (m, 0.5H), 7.52-7.44 (m, 1H), 7.21-7.12 (m, 1H), 6.00 (s, 0.5H), 5.91 (d, J=3.6 Hz, 0.5H), 3.87-3.80 (m, 0.5H), 3.62-3.61 (m, 3.5H), 3.52-3.51 (m, 3H), 2.37-2.31 (m, 0.7H), 2.04-1.61 (m, 6.3H), 1.50-1.39 (m, 2H).

Compound 228N: LC-MS (ESI): $R_T$=3.346 min, mass calcd. for $C_{23}H_{22}BrF_2N_3O_4S$ 553.1, m/z found 556.1 [M+H]$^+$. Chiral analysis (Column: Chiralpak IA 5 μm 4.6*250 mm; Mobile Phase: Hex:EtOH:DEA=70:30:0.2 at 1.0 mL/min; Temp: 30° C.; Wavelength: 230 nm, $R_T$=6.157 min). $^1$H NMR (400 MHz, DMSO-d$_6$) δ 9.53 (d, J=3.6 Hz, 0.5H), 8.99 (s, 0.5H), 8.00-7.99 (m, 1.5H), 7.94-7.93 (m, 0.5H), 7.52-7.44 (m, 1H), 7.22-7.12 (m, 1H), 6.00 (s, 0.5H), 5.91 (d, J=3.6 Hz, 0.5H), 3.88-3.81 (m, 0.5H), 3.62-3.57 (m, 3.5H), 3.52-3.51 (m, 3H), 2.37-2.31 (m, 0.6H), 2.07-1.64 (m, 6.4H), 1.50-1.41 (m, 2H).

Compound 233M and 233N: (cis)-Methyl 4-(2-chloro-3,4-difluorophenyl)-6-(4-(N,N-dimethylsulfamoyl)cyclohexyl)-2-(thiazol-2-yl)-1,4-dihydropyrimidine-5-carboxylate and (trans)-methyl 4-(2-chloro-3,4-difluorophenyl)-6-(4-(N,N-dimethylsulfamoyl)cyclohexyl)-2-(thiazol-2-yl)-1,4-dihydropyrimidine-5-carboxylate Compound 233M: LC-MS (ESI): $R_T$=3.477 min, mass calcd. for $C_{23}H_{25}ClF_2N_4O_4S_2$ 558.1, m/z found 559.2 [M+H]$^+$. $^1$H NMR (400 MHz, CDCl$_3$) δ 8.36 (s, 0.6H), 7.84 (d, J=3.2 Hz, 0.6H), 7.82 (d, J=3.2 Hz, 0.4H), 7.51 (d, J=3.2 Hz, 0.4H), 7.42 (d, J=3.2 Hz, 1H), 7.09-6.98 (m, 2H), 6.18 (s, 0.6H), 6.06 (d, J=2.4 Hz, 0.4H), 4.12-4.06 (m, 0.6H), 3.95-3.91 (m, 0.4H), 3.60 (s, 1.2H), 3.58 (s, 1.8H), 3.33-3.30 (m, 0.6H), 3.23-3.20 (m, 0.4H), 2.98-2.95 (m, 6H), 2.44-2.41 (m, 2.2H), 2.25-2.14 (m, 1.8H), 1.97-1.77 (m, 3.7H), 1.67-1.62 (m, 0.3H).

Compound 233N: LC-MS (ESI): $R_T$=4.172 min, mass calcd. for $C_{23}H_{25}ClF_2N_4O_4S_2$ 558.1, m/z found 559.1 [M+H]$^+$. $^1$H NMR (400 MHz, CDCl$_3$) δ 8.09 (s, 0.5H), 7.84-7.81 (m, 1H), 7.51 (d, J=3.2 Hz, 0.5H), 7.46 (d, J=3.2 Hz, 0.5H), 7.39 (s, 0.5H), 7.06-7.00 (m, 2H), 6.18 (s, 0.5H), 6.05 (d, J=2.4 Hz, 0.5H), 4.04-3.98 (m, 0.4H), 3.80-3.75 (m, 0.6H), 3.62 (s, 1.8H), 3.60 (s, 1.2H), 3.14-3.06 (m, 1H), 2.96 (d, J=4.4 Hz, 6H), 2.35-2.19 (m, 2.3H), 2.13-2.03 (m, 1H), 2.01-1.74 (m, 3.7H), 1.64-1.60 (m, 0.3H), 1.50-1.48 (m, 0.7H).

Racemic 233M (60 mg, 0.105 mmol) was separated by chiral Prep. HPLC (separation condition: Column: Chiralpak IF 5 μm 20*250 mm; Mobile Phase: Hex:EtOH:DEA=85:15:0.3 at 15 mL/min; Temp: 30° C.; Wavelength: 214 nm) to afford the title compounds 233A (5.0 mg, 8% yield, 98.8% stereopure) and 233B (5.5 mg, 9% yield, 98.2% stereopure) as yellow solids.

Compound 233A: LC-MS (ESI): $R_T$=4.329 min, mass calcd. for $C_{23}H_{25}ClF_2N_4O_4S_2$ 558.1, m/z found 558.9 [M+H]$^+$. Chiral analysis (Column: Chiralpak IF 5 μm 4.6*250 mm; Mobile Phase: Hex:EtOH=80:20 at 1.0 mL/min; Temp: 30° C.; Wavelength: 230 nm, $R_T$=10.706 min). $^1$H NMR (400 MHz, CDCl$_3$) δ 8.36 (s, 0.6H), 7.84 (d, J=3.2 Hz, 0.6H), 7.82 (d, J=3.2 Hz, 0.4H), 7.51 (d, J=3.2 Hz, 0.4H), 7.42 (d, J=3.2 Hz, 1H), 7.09-7.00 (m, 2H), 6.18 (s, 0.6H), 6.06 (d, J=2.8 Hz, 0.4H), 4.13-4.06 (m, 0.6H), 3.96-3.92 (m, 0.4H), 3.60 (s, 1.2H), 3.58 (s, 1.8H), 3.33-3.30 (m, 0.6H), 3.23-3.20 (m, 0.4H), 2.98-2.97 (m, 6H), 2.44-2.41 (m, 2.2H), 2.28-2.15 (m, 1.8H), 2.01-1.76 (m, 4H).

Compound 233B: LC-MS (ESI): $R_T$=4.329 min, mass calcd. for $C_{23}H_{25}ClF_2N_4O_4S_2$ 558.1, m/z found 558.9 [M+H]$^+$. Chiral analysis (Column: Chiralpak IF 5 μm 4.6*250 mm; Mobile Phase: Hex:EtOH=80:20 at 1.0 mL/min; Temp: 30° C.; Wavelength: 230 nm, $R_T$=13.239 min). 1H NMR (400 MHz, CDCl$_3$) δ 8.36 (s, 0.6H), 7.84 (d, J=3.2 Hz, 0.6H), 7.82 (d, J=2.8 Hz, 0.4H), 7.51 (d, J=3.2 Hz, 0.4H), 7.42 (d, J=3.2 Hz, 1H), 7.09-6.98 (m, 2H), 6.18 (s, 0.6H), 6.06 (d, J=2.8 Hz, 0.4H), 4.12-4.06 (m, 0.6H), 3.96-3.91 (m, 0.4H), 3.60 (s, 1.2H), 3.58 (s, 1.8H), 3.33-3.30 (m, 0.6H), 3.23-3.21 (m, 0.4H), 2.98-2.97 (m, 6H), 2.44-2.41 (m, 2.2H), 2.30-2.21 (m, 1.8H), 2.02-1.75 (m, 4H).

Racemic 233N (200 mg, 0.36 mmol) was separated by chiral Prep. SFC (separation condition: Column: Chiralpak IF 5 μm 20*250 mm; Mobile Phase: CO$_2$: EtOH:DEA=75:25:0.3 at 50 g/min; Col. Temp: 30° C.; Wavelength: 214 nm; Back pressure: 100 bar) to afford the title compounds 233C (46.8 mg, 23% yield, 99.4% stereopure) and 233D (40.9 mg, 21% yield, 100% stereopure) as yellow solids.

Compound 233C: LC-MS (ESI): $R_T$=4.244 min, mass calcd. for $C_{23}H_{25}ClF_2N_4O_4S_2$ 558.1, m/z found 558.9 [M+H]$^+$. Chiral analysis (Column: Chiralpak IF 5 μm 4.6*250 mm; Mobile Phase: CO$_2$: EtOH:DEA=75:25:0.2 at 3.0 g/min; Col. Temp: 41.2° C.; Wavelength: 214 nm, Back pressure: 100 bar, $R_T$=5.87 min). $^1$H NMR (400 MHz, CDCl$_3$) δ 8.10 (s, 0.5H), 7.84 (d, J=3.2 Hz, 0.5H), 7.81 (d, J=2.8 Hz, 0.5H), 7.51 (d, J=2.8 Hz, 0.5H), 7.46 (d, J=3.2 Hz, 0.5H), 7.40 (s, 0.5H), 7.07-7.01 (m, 2H), 6.18 (s, 0.5H), 6.05 (d, J=2.8 Hz, 0.5H), 4.05-3.98 (m, 0.4H), 3.80-3.78 (m, 0.6H), 3.62-3.58 (m, 3H), 3.14-3.04 (m, 1H), 2.99-2.95 (m, 6H), 2.35-2.19 (m, 2.5H), 2.12-1.96 (m, 1.5H), 1.93-1.73 (m, 3H), 1.66-1.61 (m, 0.5H), 1.53-1.47 (m, 0.5H).

Compound 233D: LC-MS (ESI): $R_T$=4.242 min, mass calcd. for $C_{23}H_{25}ClF_2N_4O_4S_2$ 558.1, m/z found 558.9 [M+H]$^+$. Chiral analysis (Column: Chiralpak IF 5 μm 4.6*250 mm; Mobile Phase: CO$_2$: EtOH:DEA=75:25:0.2 at 3.0 g/min; Col. Temp: 40.5° C.; Wavelength: 214 nm, Back pressure: 100 bar, $R_T$=7.38 min). $^1$H NMR (400 MHz, CDCl₃) δ 8.10 (s, 0.5H), 7.84 (d, J=3.2 Hz, 0.5H), 7.81 (d, J=3.2 Hz, 0.5H), 7.51 (d, J=2.8 Hz, 0.5H), 7.46 (d, J=3.2 Hz, 0.5H), 7.40 (s, 0.5H), 7.07-6.98 (m, 2H), 6.18 (s, 0.5H), 6.05 (d, J=2.4 Hz, 0.5H), 4.04-3.98 (m, 0.4H), 3.80-3.75 (m, 0.6H), 3.62 (s, 1.8H), 3.60 (s, 1.2H), 3.14-3.07 (m, 1H), 2.96 (d, J=4.8 Hz, 6H), 2.35-2.21 (m, 2.5H), 2.18-1.93 (m, 1.5H), 1.91-1.74 (m, 3H), 1.65-1.63 (m, 0.5H), 1.57-1.47 (m, 0.5H).

Compound 234M and 234N: (cis)-Methyl 4-(2-chloro-3,4-difluorophenyl)-6-(4-(N-isopropylsulfamoyl)cyclohexyl)-2-(thiazol-2-yl)-1,4-dihydropyrimidine-5-carboxylate and (trans)-methyl 4-(2-chloro-3,4-difluorophenyl)-6-(4-(N-isopropylsulfamoyl)cyclohexyl)-2-(thiazol-2-yl)-1,4-dihydropyrimidine-5-carboxylate Intermediate 234M (mixture of enantiomers): LC-MS (ESI): $R_T$=2.619 min, mass calcd. for $C_{24}H_{27}ClF_2N_4O_4S_2$ 572.1, m/z found 573.2 [M+H]⁺. ¹H NMR (400 MHz, CDCl₃) δ 8.33 (s, 0.6H), 7.83-7.81 (m, 1H), 7.49 (d, J=2.8 Hz, 0.4H), 7.42-7.41 (m, 1H), 7.09-6.97 (m, 2H), 6.17 (s, 0.7H), 6.06 (d, J=2.0 Hz, 0.3H), 4.14-4.07 (m, 0.7H), 4.00-3.91 (m, 1H), 3.86-3.84 (m, 0.3H), 3.71-3.63 (m, 1H), 3.60-3.58 (m, 3H), 3.19 (s, 0.7H), 3.10-3.03 (m, 0.3H), 2.53-2.42 (m, 2H), 2.28-2.13 (m, 1.6H), 2.08-1.91 (m, 2H), 1.87-1.73 (m, 1.4H), 1.27-1.22 (m, 6H).

Intermediate 234N (mixture of enantiomers): LC-MS (ESI): $R_T$=2.603 min, mass calcd. for $C_{24}H_{27}ClF_2N_4O_4S_2$ 572.1, m/z found 572.9 [M+H]⁺. ¹H NMR (300 MHz, CDCl₃) δ 8.12 (s, 0.4H), 7.86-7.83 (m, 1H), 7.53-7.47 (m, 1H), 7.42 (s, 0.6H), 7.10-7.02 (m, 2H), 6.19 (s, 0.5H), 6.06 (s, 0.5H), 4.09-4.03 (m, 0.4H), 3.87-3.72 (m, 2.6H), 3.67-3.61 (m, 3H), 2.99 (s, 1H), 2.44-2.30 (m, 2H), 2.24-1.94 (m, 2H), 1.84-1.75 (m, 3H), 1.30-1.28 (m, 6H).

A racemic mixture of (cis)-methyl 4-(2-chloro-3,4-difluorophenyl)-6-(4-(N-isopropylsulfamoyl)cyclohexyl)-2-(thiazol-2-yl)-1,4-dihydropyrimidine-5-carboxylate 234M (60 mg, 0.105 mmol) was separated by chiral Prep. HPLC (separation condition: Column: Chiralpak IE 5 μm 20*250 mm; Mobile Phase: Hex:EtOH:DEA=80:20:0.3 at 15 mL/min; Temp: 30° C.; Wavelength: 214 nm) to afford the title compounds 234A (20 mg, 33% yield, 100% stereopure) and 234B (20 mg, 33% yield, 99.4% stereopure) as yellow solids.

Compound 234A: LC-MS (ESI): $R_T$=4.001 min, mass calcd. for $C_{24}H_{27}ClF_2N_4O_4S_2$ 572.1, m/z found 573.1 [M+H]⁺. Chiral analysis (Column: Chiralpak IE 5 μm 4.6*250 mm; Mobile Phase: Hex:EtOH:DEA=80:20:0.2 at 1.0 mL/min; Temp: 30° C.; Wavelength: 230 nm, $R_T$=9.378 min). ¹H NMR (400 MHz, CDCl₃) δ 8.33 (s, 0.6H), 7.83-7.81 (m, 1H), 7.49 (d, J=3.2 Hz, 0.4H), 7.42-7.41 (m, 1H), 7.09-6.97 (m, 2H), 6.17 (s, 0.7H), 6.06 (d, J=2.8 Hz, 0.3H), 4.14-4.07 (m, 0.7H), 4.00-3.92 (m, 1H), 3.86-3.83 (m, 0.3H), 3.69-3.64 (m, 1H), 3.60-3.59 (m, 3H), 3.20 (s, 0.7H), 3.07 (s, 0.3H), 2.54-2.42 (m, 2H), 2.28-2.12 (m, 1.7H), 2.06-1.92 (m, 2H), 1.88-1.75 (m, 1.3H), 1.27-1.22 (m, 6H).

Compound 234B: LC-MS (ESI): $R_T$=3.998 min, mass calcd. for $C_{24}H_{27}ClF_2N_4O_4S_2$ 572.1, m/z found 573.1 [M+H]⁺. Chiral analysis (Column: Chiralpak IE 5 μm 4.6*250 mm; Mobile Phase: Hex:EtOH:DEA=80:20:0.2 at 1.0 mL/min; Temp: 30° C.; Wavelength: 230 nm, $R_T$=11.824 min). ¹H NMR (400 MHz, CDCl₃) 8.33 (s, 0.6H), 7.83-7.81 (m, 1H), 7.49 (d, J=2.8 Hz, 0.4H), 7.42-7.41 (m, 1H), 7.09-6.97 (m, 2H), 6.17 (s, 0.7H), 6.06 (d, J=2.0 Hz, 0.3H), 4.14-4.07 (m, 0.7H), 4.00-3.91 (m, 1H), 3.86-3.84 (m, 0.3H), 3.71-3.63 (m, 1H), 3.60-3.58 (m, 3H), 3.19 (s, 0.7H), 3.10-3.03 (m, 0.3H), 2.53-2.42 (m, 2H), 2.28-2.13 (m, 1.6H), 2.08-1.91 (m, 2H), 1.87-1.73 (m, 1.4H), 1.27-1.22 (m, 6H).

A racemic mixture of (trans)-methyl 4-(2-chloro-3,4-difluorophenyl)-6-(4-(N-isopropylsulfamoyl)cyclohexyl)-2-(thiazol-2-yl)-1,4-dihydropyrimidine-5-carboxylate 234N (200 mg, 0.34 mmol) was separated by chiral Prep. HPLC (separation condition: Column: Chiralpak IE 5 μm 20*250 mm; Mobile Phase: Hex:EtOH=70:30 at 12 mL/min; Temp: 30° C.; Wavelength: 214 nm) to afford the title compounds 234C (90 mg, 45% yield, 100% stereopure) and 234D (40.0 mg, 45% yield, 100% stereopure) as yellow solids.

Compound 234C: LC-MS (ESI): $R_T$=4.181 min, mass calcd. for $C_{24}H_{27}ClF_2N_4O_4S_2$ 572.1, m/z found 573.1 [M+H]⁺. Chiral analysis (Column: Chiralpak IE 5 μm 4.6*250 mm; Mobile Phase: Hex:EtOH=70:30 at 1.0 mL/min; Temp: 30° C.; Wavelength: 230 nm, $R_T$=10.101 min). ¹H NMR (400 MHz, CDCl₃) δ 8.10 (s, 0.5H), 7.84-7.81 (m, 1H), 7.51 (d, J=2.8 Hz, 0.5H), 7.46 (d, J=3.2 Hz, 0.5H), 7.40 (s, 0.5H), 7.06-6.98 (m, 2H), 6.18 (s, 0.5H), 6.05 (d, J=2.8 Hz, 0.5H), 4.04-3.97 (m, 0.5H), 3.86-3.74 (m, 1.5H), 3.72-3.65 (m, 1H), 3.64-3.60 (m, 3H), 3.01-2.92 (m, 1H), 2.48-2.29 (m, 2H), 2.23-1.91 (m, 2H), 1.83-1.70 (m, 2.7H), 1.55-1.48 (m, 0.3H), 1.28-1.26 (m, 6H).

Compound 234D: LC-MS (ESI): $R_T$=4.191 min, mass calcd. for $C_{24}H_{27}ClF_2N_4O_4S_2$ 572.1, m/z found 573.1 [M+H]⁺. Chiral analysis (Column: Chiralpak IE 5 μm 4.6*250 mm; Mobile Phase: Hex:EtOH=70:30 at 1.0 mL/min; Temp: 30° C.; Wavelength: 230 nm, $R_T$=13.624 min). ¹H NMR (400 MHz, CDCl₃) δ 8.10 (s, 0.5H), 7.84-7.81 (m, 1H), 7.51 (d, J=2.8 Hz, 0.5H), 7.46 (d, J=3.2 Hz, 0.5H), 7.40 (s, 0.5H), 7.06-6.98 (m, 2H), 6.18 (s, 0.5H), 6.05 (d, J=2.4 Hz, 0.5H), 4.05-3.98 (m, 0.5H), 3.86-3.74 (m, 1.5H), 3.73-3.67 (m, 1H), 3.64-3.60 (m, 3H), 3.00-2.92 (m, 1H), 2.42-2.29 (m, 2H), 2.23-1.92 (m, 2H), 1.87-1.64 (m, 2.6H), 1.55-1.48 (m, 0.4H), 1.28-1.26 (m, 6H).

Compound 235: (trans)-Methyl 6-(4-((tert-butoxycarbonyl)amino)cyclohexyl)-4-(2-chloro-3,4-difluorophenyl)-2-(thiazol-2-yl)-1,4-dihydropyrimidine-5-carboxylate ¹H NMR (400 MHz, DMSO-d₆) δ 9.60 (d, J=3.2 Hz, 0.7H), 9.17 (s, 0.3H), 8.00-7.98 (m, 1.7H), 7.93 (d, J=2.8 Hz, 0.3H), 7.47-7.42 (m, 1H), 7.22-7.13 (m, 1H), 6.02 (s, 0.3H), 5.93 (d, J=3.6 Hz, 0.7H), 4.07-4.02 (m, 2H), 3.94-3.89 (m, 0.2H), 3.82-3.76 (m, 0.8H), 3.53 (s, 2H), 3.52 (s, 1H), 2.83-2.71 (m, 2H), 2.01-1.94 (m, 1H), 1.89-1.81 (m, 1.5H), 1.74-1.65 (m, 1.5H), 1.53-1.49 (m, 1H), 1.44 (s, 9H).

Compound 239: (trans)-Methyl 4-(2-bromo-4-fluorophenyl)-6-(4-(methoxycarbonyl)cyclohexyl)-2-(4-methylthiazol-2-yl)-1,4-dihydropyrimidine-5-carboxylate LC-MS (ESI): $R_T$=4.219 min, mass calcd. For $C_{24}H_{25}BrFN_3O_4S$ 549.1 m/z found 549.9 [M+H]⁺. ¹H NMR (400 MHz, DMSO-d₆) δ 9.33 (d, J=2.8 Hz, 0.6H), 8.84 (s, 0.4H), 7.56-7.55 (m, 1.6H), 7.47 (s, 0.4H), 7.37-7.24 (m, 2H), 5.96 (s, 0.4H), 5.87 (d, J=3.6 Hz, 0.6H), 3.81 (br s, 0.4H), 3.62 (s, 1H), 3.61 (s, 2H), 3.58-3.56 (m, 0.6H), 3.52 (s, 2H), 3.51 (s, 1H), 2.43 (s, 1H), 2.39 (s, 2H), 2.33-2.29 (m, 1H), 2.03-1.97 (m, 2H), 1.89-1.80 (m, 1H), 1.76-1.75 (m, 2H), 1.68-1.63 (m, 1H), 1.46-1.38 (m, 2H).

A racemic mixture of 239 (350 mg, 0.638 mmol) was separated by chiral Prep. HPLC (Column: Chiralpak IC 5 μm 20*250 mm; Mobile Phase: Hex:EtOH=85:15 at 25.0 mL/min; Temp: 30° C.; Wavelength: 214 nm) and purified by Prep. HPLC (Column: Gilson X-bridge C18 (5 μm 19*150 mm), Mobile phase A: water (0.1% ammonium bicarbonate), Mobile phase B: acetonitrile, UV: 214 nm, Flowrate: 15 mL/min, Gradient: 60-95% (% B)) to give the title compounds 239X (110 mg, 31% yield, 100% stereopure) and 239Y (109 mg, 31% yield, 100% stereopure) as yellow solids.

Compound 239X: LC-MS (ESI): $R_T$=4.207 min, mass calcd. For $C_{24}H_{25}BrFN_3O_4S$ 549.1 m/z found 549.9 [M+H]$^+$. Chiral analysis (Column: Chiralpak IC 5 μm 4.6*250 mm; Mobile Phase: Hex:EtOH=85:15 at 1.0 mL/min; Temp: 30° C.; Wavelength: 230 nm, $R_T$=7.110 min). $^1$H NMR (400 MHz, DMSO-d$_6$) δ 9.33 (d, J=3.6 Hz, 0.6H), 8.83 (s, 0.4H), 7.56 (d, J=2.4 Hz, 0.6H), 7.55 (s, 1H), 7.47 (s, 0.4H), 7.36-7.30 (m, 1H), 7.28-7.21 (m, 1H), 5.96 (s, 0.4H), 5.87 (d, J=3.6 Hz, 0.6H), 3.85-3.78 (m, 0.4H), 3.62 (s, 1H), 3.61 (s, 2H), 3.59-3.55 (m, 0.6H), 3.52 (s, 2H), 3.51 (s, 1H), 2.43 (s, 1H), 2.39 (s, 2H), 2.36-2.29 (m, 1H), 2.08-1.96 (m, 2H), 1.92-1.86 (m, 1H), 1.83-1.73 (m, 2H), 1.70-1.59 (m, 1H), 1.50-1.38 (m, 2H).

Compound 239Y: LC-MS (ESI): $R_T$=4.214 min, mass calcd. For $C_{24}H_{25}BrFN_3O4S$ 549.1 m/z found 549.8 [M+H]$^+$. Chiral analysis (Column: Chiralpak IC 5 μm 4.6*250 mm; Mobile Phase: Hex:EtOH=85:15 at 1.0 mL/min; Temp: 30° C.; Wavelength: 230 nm, $R_T$=10.035 min). $^1$H NMR (400 MHz, DMSO-d$_6$) δ 9.33 (d, J=3.6 Hz, 0.6H), 8.84 (s, 0.4H), 7.56 (d, J=2.4 Hz, 0.6H), 7.54 (s, 1H), 7.47 (s, 0.4H), 7.36-7.21 (m, 2H), 5.96 (s, 0.4H), 5.87 (d, J=3.6 Hz, 0.6H), 3.85-3.80 (m, 0.4H), 3.62 (s, 1H), 3.61 (s, 2H), 3.59-3.57 (m, 0.6H), 3.52 (s, 2H), 3.51 (s, 1H), 2.43 (s, 1H), 2.39 (s, 2H), 2.37-2.29 (m, 1H), 2.07-1.96 (m, 2H), 1.92-1.86 (m, 1H), 1.83-1.73 (m, 2H), 1.70-1.59 (m, 1H), 1.49-1.38 (m, 2H).

Compound 257: Methyl 4-(2-chloro-4-fluorophenyl)-6-(3-(methoxycarbonyl)-bicyclo[1.1.1]pentan-1-yl)-2-(thiazol-2-yl)-1,4-dihydropyrimidine-5-carboxylate LC-MS (ESI): $R_T$=3.835 min, mass calcd. for $C_{22}H_{19}ClFN_3O_4S$ 475.1, m/z found 476.1 [M+H]$^+$. $^1$H NMR (400 MHz, CD$_3$OD) δ 8.02 (d, J=2.4 Hz, 1H), 7.92 (s, 1H), 7.43-7.40 (m, 1H), 7.30-7.28 (m, 1H), 7.12-7.08 (m, 1H), 6.13 (s, 1H), 3.71 (s, 3H), 3.62 (s, 3H), 2.52 (s, 6H).

A racemic mixture of methyl 4-(2-chloro-4-fluorophenyl)-6-(3-(methoxycarbonyl)bicyclo[1.1.1]pentan-1-yl)-2-(thiazol-2-yl)-1,4-dihydropyrimidine-5-carboxylate 257 (350 mg, 0.740 mmol) was separated by chiral Prep. HPLC (separation condition: Column: Chiralpak IF 5 μm 20*250 mm; Mobile Phase: Hex:EtOH:DEA=90:10:0.3 at 13 mL/min; Temp: 30° C.; Wavelength: 254 nm) and further purified by Prep. HPLC (Column: Gilson X-bridge C18 (5 μm 19*150 mm), Mobile Phase A: water (0.1% ammonium bicarbonate), Mobile Phase B: acetonitrile, UV: 214 nm, Flow rate: 15 mL/min, Gradient: 60-95% (% B)) to give the title compounds 257X (86 mg, 25% yield, 100% stereopure) and 257Y (92 mg, 26% yield, 98.1% stereopure) as yellow solids.

Compound 257X: LC-MS (ESI): $R_T$=4.141 min, mass calcd. for $C_{22}H_{19}ClFN_3O_4S$, m/z 475.1 found 476.2 [M+H]$^+$. Chiral analysis (Column: Chiralpak IF 5 μm 4.6*250 mm; Mobile Phase: Hex:EtOH:DEA=90:10:0.2 at 1.0 mL/min; Temp: 30° C.; Wavelength: 230 nm; $R_T$=8.113 min). $^1$H NMR (400 MHz, CD$_3$OD) δ 7.92 (d, J=3.2 Hz, 0.6H), 7.89 (d, J=3.2 Hz, 0.4H), 7.76-7.74 (m, 1H), 7.38-7.34 (m, 1H), 7.25-7.21 (m, 1H), 7.06-7.02 (m, 1H), 6.10 (s, 0.6H), 6.03 (s, 0.4H), 3.71 (s, 1.8H), 3.70 (s, 1.2H), 3.61 (s, 1.2H), 3.60 (s, 1.8H), 2.56 (s, 3.5H), 2.44 (s, 2.5H).

Compound 257Y: LC-MS (ESI): $R_T$=2.397 min, mass calcd. for $C_{22}H_{19}ClFN_3O_4S$, m/z 475.1 found 475.9 [M+H]$^+$. Chiral analysis (Column: Chiralpak IF 5 μm 4.6*250 mm; Mobile Phase: Hex:EtOH:DEA=90:10:0.2 at 1.0 mL/min; Temp: 30° C.; Wavelength: 230 nm; $R_T$=9.805 min). $^1$H NMR (400 MHz, CD$_3$OD) δ 7.92 (d, J=3.6 Hz, 0.6H), 7.89 (d, J=3.2 Hz, 0.4H), 7.76-7.74 (m, 1H), 7.38-7.34 (m, 1H), 7.25-7.21 (m, 1H), 7.09-7.01 (m, 1H), 6.10 (s, 0.6H), 6.03 (s, 0.4H), 3.71 (s, 1.6H), 3.70 (s, 1.4H), 3.61 (s, 1.4H), 3.60 (s, 1.6H), 2.56 (s, 3.5H), 2.44 (s, 2.5H).

Compound 259A and 259B: (cis)Methyl 4-(2-chloro-3-fluorophenyl)-6-(4-(N-methylsulfamoyl) cyclohexyl)-2-(thiazol-2-yl)-1,4-dihydropyrimidine-5-carboxylate and (trans)-methyl 4-(2-chloro-3-fluorophenyl)-6-(4-(N-methylsulfamoyl) cyclohexyl)-2-(thiazol-2-yl)-1,4-dihydropyrimidine-5-carboxylate Separation condition: Prep. HPLC (Column: Gilson X-bridge C18 (5 μm 19*150 mm), Mobile phase A: water (+0.1% ammonium bicarbonate), Mobile phase B: acetonitrile, UV: 214 nm, Flow rate: 15 mL/min, Gradient: 40-80% (% B))

Compound 259A: $^1$H NMR (400 MHz, DMSO-d$_6$) δ 9.56 (d, J=3.2 Hz, 0.7H), 8.29 (s, 0.3H), 8.01-7.97 (m, 2H), 7.41-7.29 (m, 2H), 7.22-7.15 (m, 1.4H), 6.95-6.91 (m, 0.6H), 6.08 (s, 0.3H), 5.97 (d, J=3.6 Hz, 0.7H), 3.96-3.87 (m, 0.3H), 3.73-3.66 (m, 0.7H), 3.51 (s, 3H), 3.19-3.17 (m, 0.9H), 2.67 (br s, 0.1H), 2.61-2.58 (m, 3H), 2.33-1.77 (m, 6.3H), 1.70-1.60 (m, 1H), 1.55-1.45 (m, 0.7H).

Compound 259B: $^1$H NMR (400 MHz, DMSO-d$_6$) δ 9.54 (d, J=3.6 Hz, 0.6H), 8.95 (s, 0.4H), 8.00-7.99 (m, 1.5H), 7.95-7.94 (m, 0.5H), 7.40-7.29 (m, 2H), 7.21-7.16 (m, 1H), 7.00-6.95 (m, 0.4H), 6.92-6.88 (m, 0.6H), 6.06 (s, 0.3H), 5.97 (d, J=3.6 Hz, 0.7H), 3.89-3.83 (m, 0.4H), 3.61-3.51 (m, 3.6H), 3.26-3.16 (m, 0.4H), 3.09-3.01 (m, 0.6H), 2.62 (d, J=4.4 Hz, 3H), 2.22-2.09 (m, 2H), 2.01-1.71 (m, 4H), 1.56-1.42 (m, 2H).

A racemic mixture of (cis)-methyl 4-(2-chloro-3-fluorophenyl)-6-(4-(N-methylsulfamoyl)cyclohexyl)-2-(thiazol-2-yl)-1,4-dihydropyrimidine-5-carboxylate 259A (70 mg, 0.133 mmol) was separated by chiral Prep. HPLC (Column: Chiralpak IC m 20*250 mm; Mobile Phase: Hex:EtOH: DEA=70:30:0.3 at 13 mL/min; Temp: 30° C.; Wavelength: 230 nm) to afford the title compounds 259C (7.6 mg, 11% yield, 100% stereopure) and 259D (17.1 mg, 24% yield, 100% stereopure) as yellow solids.

Compound 259C: LC-MS (ESI): $R_T$=3.455 min, mass calcd. for $C_{22}H_{24}ClFN_4O_4S_2$ 526.1, m/z found 526.9 [M+H]$^+$. Chiral analysis (Column: Chiralpak IC 5 μm 4.6*250 mm; Mobile Phase: Hex:EtOH:DEA=70:30:0.2 at 1.0 mL/min; Temp: 30° C.; Wavelength: 230 nm; $R_T$=9.436 min). $^1$H NMR (400 MHz, DMSO-d$_6$) δ 9.56 (d, J=3.6 Hz, 0.6H), 8.29 (s, 0.4H), 8.00-7.98 (m, 2H), 7.40-7.30 (m, 2H), 7.22-7.15 (m, 1.4H), 6.96-6.90 (m, 0.6H), 6.08 (s, 0.4H), 5.97 (d, J=3.2 Hz, 0.6H), 3.97-3.86 (m, 0.3H), 3.74-3.66 (m, 0.7H), 3.51 (s, 3H), 3.22-3.14 (m, 0.9H), 2.67 (br s, 0.1H), 2.59-2.58 (m, 3H), 2.30-1.77 (m, 6.3H), 1.70-1.59 (m, 1H), 1.55-1.46 (m, 0.7H).

Compound 259D: LC-MS (ESI): $R_T$=4.356 min, mass calcd. for $C_{22}H_{24}ClFN_4O_4S_2$ 526.1, m/z found 526.9 [M+H]$^+$. Chiral analysis (Column: Chiralpak IC 5 μm 4.6*250 mm; Mobile Phase: Hex:EtOH:DEA=70:30:0.2 at 1.0 mL/min; Temp: 30° C.; Wavelength: 230 nm; $R_T$=13.128 min). ¹H NMR (400 MHz, DMSO-d₆) δ 9.56 (d, J=3.2 Hz, 0.7H), 8.29 (s, 0.3H), 8.01-7.97 (m, 2H), 7.41-7.29 (m, 2H), 7.22-7.15 (m, 1.4H), 6.95-6.91 (m, 0.6H), 6.08 (s, 0.3H), 5.97 (d, J=3.6 Hz, 0.7H), 3.96-3.87 (m, 0.3H), 3.74-3.65 (m, 0.7H), 3.51 (s, 3H), 3.19-3.17 (m, 0.9H), 2.67 (br s, 0.1H), 2.61-2.58 (m, 3H), 2.30-1.78 (m, 6.3H), 1.69-1.60 (m, 1H), 1.54-1.46 (m, 0.7H).

A racemic mixture of (trans)-methyl 4-(2-chloro-3-fluorophenyl)-6-(4-(N-methylsulfamoyl)cyclohexyl)-2-(thiazol-2-yl)-1,4-dihydropyrimidine-5-carboxylate 259B (250 mg, 0.474 mmol) was separated by chiral Prep. HPLC (Column: Chiralpak IF 5 μm 20*250 mm; Mobile Phase: Hex:EtOH=50:50 at 10 mL/min; Temp: 30° C.; Wavelength: 214 nm) to afford the title compounds 259E (74.8 mg, 30% yield, 100% stereopure) and 259F (72.9 mg, 29% yield, 98.4% stereopure) as yellow solids.

Compound 259E: LC-MS (ESI): $R_T$=4.085 min, mass calcd. for $C_{22}H_{24}ClFN_4O_4S_2$ 526.1, m/z found 527.2 [M+H]⁺. Chiral analysis (Column: Chiralpak IF 5 μm 4.6*250 mm; Mobile Phase: Hex:EtOH=50:50 at 1.0 mL/min; Temp: 30° C.; Wavelength: 230 nm; $R_T$=5.843 min). ¹H NMR (400 MHz, CDCl₃) δ 8.10 (s, 0.3H), 7.83 (d, J=2.8 Hz, 0.6H), 7.81 (d, J=3.2 Hz, 0.4H), 7.50 (d, J=3.2 Hz, 0.6H), 7.46 (d, J=3.2 Hz, 0.4H), 7.43 (s, 0.7H), 7.22-7.02 (m, 3H), 6.25 (s, 0.4H), 6.11 (d, J=3.2 Hz, 0.6H), 4.09-3.95 (m, 1.3H), 3.85-3.77 (m, 0.7H), 3.61 (s, 1.8H), 3.59 (s, 1.2H), 3.11-3.01 (m, 1H), 2.88-2.86 (m, 3H), 2.41-1.76 (m, 7.3H), 1.55-1.50 (m, 0.7H).

Compound 259F: LC-MS (ESI): $R_T$=4.071 min, mass calcd. for $C_{22}H_{24}ClFN_4O_4S_2$ 526.1, m/z found 527.2 [M+H]⁺. Chiral analysis (Column: Chiralpak IF 5 μm 4.6*250 mm; Mobile Phase: Hex:EtOH=50:50 at 1.0 mL/min; Temp: 30° C.; Wavelength: 230 nm; $R_T$=7.833 min). ¹H NMR (400 MHz, DMSO-d₆) δ 9.54 (d, J=3.6 Hz, 0.6H), 8.95 (s, 0.4H), 8.00-7.99 (m, 1.5H), 7.95-7.94 (m, 0.5H), 7.40-7.29 (m, 2H), 7.21-7.16 (m, 1H), 7.00-6.95 (m, 0.4H), 6.92-6.88 (m, 0.6H), 6.06 (s, 0.3H), 5.97 (d, J=3.6 Hz, 0.7H), 3.89-3.83 (m, 0.4H), 3.61-3.51 (m, 3.6H), 3.26-3.16 (m, 0.4H), 3.09-3.01 (m, 0.6H), 2.62 (d, J=4.4 Hz, 3H), 2.22-2.09 (m, 2H), 2.01-1.71 (m, 4H), 1.56-1.42 (m, 2H).

Compound 260: (cis)-Ethyl 6-(4-((tert-butoxycarbonyl)amino)tetrahydrofuran-2-yl)-4-(2-chloro-3-fluorophenyl)-2-(thiazol-2-yl)-1,4-dihydropyrimidine-5-carboxylate LC-MS (ESI): $R_T$=2.571 min, mass calcd. for $C_{25}H_{28}ClFN_4O_5S$ 550.2, m/z found 551.2 [M+H]⁺. ¹H NMR (300 MHz, DMSO-d₆) δ 8.96 (s, 1H), 8.01-7.95 (m, 2H), 7.39-7.24 (m, 3H), 7.08-7.01 (br s, 1H), 6.08 (s, 1H), 5.48-5.42 (m, 1H), 4.09-4.02 (m, 1H), 4.00-3.92 (m, 4H), 2.83-2.74 (m, 1H), 1.89-1.80 (m, 1H), 1.40-1.32 (m, 9H), 1.05-1.01 (m, 3H).

Compound 263: Methyl 4-(2-chloro-3-fluorophenyl)-6-(4-(methylcarbamoyl)-tetrahydrofuran-2-yl)-2-(thiazol-2-yl)-1,4-dihydropyrimidine-5-carboxylate LC-MS (ESI): $R_T$=3.169, 3.328, 3.437 min, mass calcd. for $C_{21}H_{20}ClFN_4O_4S$ 478.1, m/z found 478.9 [M+H]⁺. Chiral analysis (Column: Chiralpak IG 5 μm 4.6*250 mm; Mobile Phase: CO₂:EtOH=60:40 at 2.999 g/min; Col. Temp: 40.4° C.; Wavelength: 214 nm, Back pressure: 100 bar, $R_T$=1.96, 2.24, 2.56, 2.78, 3.04, 3.19, 3.44, 3.68 min). ¹H NMR (400 MHz, CDCl₃) δ 9.14 (d, J=11.6 Hz, 0.3H), 8.93 (s, 0.1H), 8.73 (s, 0.02H), 8.67 (s, 0.05H), 8.51 (s, 0.03H), 7.88-7.78 (m, 1H), 7.55-7.39 (m, 1.5H), 7.26-6.99 (m, 3.5H), 6.92 (s, 0.2H), 6.84-6.68 (m, 0.3H), 6.28-6.22 (m, 0.5H), 6.16-6.08 (m, 0.5H), 5.71-5.52 (m, 1H), 4.77-4.69 (m, 0.3H), 4.67-4.58 (m, 0.3H), 4.57-4.48 (m, 0.4H), 4.43-4.23 (m, 1H), 4.19-3.92 (m, 1H), 3.64-3.57 (m, 3H), 3.12-3.02 (m, 0.4H), 3.02-2.92 (m, 0.6H), 2.89-2.79 (m, 3H), 2.62-2.33 (m, 0.4H), 2.27-2.14 (m, 0.4H), 2.09-2.00 (m, 0.2H).

Compound 264: Ethyl 6-(6-(tert-butoxycarbonyl) tetrahydro-2H-pyran-3-yl)-4-(2-chloro-4-fluorophenyl)-2-(thiazol-2-yl)-1,4-dihydropyrimidine-5-carboxylate Separation condition: silica gel column chromatography (petroleum ether:ethyl acetate=15:1) to afford two groups of stereoisomers, namely Group 1 (1.30 g) and Group 2 (2.10 g). Group 1 (1.30 g, 2.36 mmol) was further purified by Prep. HPLC (Column: Xtimate C18 (10 m 50*250 mm), Mobile Phase A: water (0.1% trifluoroacetic acid), Mobile Phase B: acetonitrile, UV: 214 nm, Flow rate: 80 mL/min, Gradient: 60-85% (% B)) to give two groups of stereoisomers, namely Group A (250 mg) and Group B (440 mg). Group 2 (2.10 g, 3.82 mmol) was further purified by Prep. HPLC (Column: Xtimate C18 (10 m 50*250 mm), Mobile Phase A: water (0.1% trifluoroacetic acid), Mobile Phase B: acetonitrile, UV: 214 nm, Flow rate: 80 mL/min, Gradient: 60-85% (% B)) to give two groups of stereoisomers, namely Group C (700 mg) and Group D (800 mg).

Group A (250 mg, 0.455 mmol) was separated by chiral Prep. HPLC (separation condition: Column: Chiralpak ID 5 μm 20*250 mm; Mobile Phase: Hex:EtOH:DEA=95:5:0.3 at 18 mL/min; Temp: 30° C.; Wavelength: 214 nm) to afford the title compounds 264M (70 mg, 100% ee) and 264N (58 mg, 99.1% ee), which were further purified by Prep. HPLC (Column: Gilson-2 x-bridge C18 (5 μm 15*150 mm), Mobile Phase A: water (0.1% ammonium bicarbonate), Mobile Phase B: acetonitrile, UV: 214 nm, Flow rate: 15 mL/min, Gradient: 70-95% (% B)) to give the title compounds 264M (60 mg, 24% yield, 100% ee) and 264N (48 mg, 19% yield, 99.0% ee) as yellow solids.

Group B (440 mg, 0.800 mmol) was separated by chiral Prep. HPLC (separation condition: Column: Chiralpak IC 5 μm 20*250 mm; Mobile Phase: Hex:EtOH:DEA=60:40:0.3 at 13 mL/min; Temp: 30° C.; Wavelength: 214 nm) to afford the title compounds 264U (150 mg, 100% ee) and 264V (110 mg, 100% ee), which were further purified by Prep. HPLC (Column: Gilson-2 x-bridge C18 (5 μm 15*150 mm), Mobile Phase A: water (0.1% ammonium bicarbonate), Mobile Phase B: acetonitrile, UV: 214 nm, Flow rate: 15 mL/min, Gradient: 55-95% (% B)) to give the title compounds 264U (120 mg, 27% yield, 100% ee) and 264V (110 mg, 100% ee) as yellow solids.

Group C (350 mg, 0.636 mmol) was separated by chiral Prep. HPLC (separation condition: Column: Chiralpak IE 5 μm 20*250 mm; Mobile Phase: Hex:EtOH:DEA=80:20:0.2 at 12 mL/min; Temp: 30° C.; Wavelength: 214 nm) to afford the title compounds 264S (109 mg, 100% ee) and 264T (103 mg, 100% ee), which were further purified by Prep. HPLC (Column: Gilson-2 x-bridge C18 (5 μm 19*150 mm), Mobile Phase A: water (0.1% ammonium bicarbonate), Mobile Phase B: acetonitrile, UV: 214 nm, Flow rate: 15 mL/min, Gradient: 60-95% (% B)) to give the title compounds 264S (82 mg, 23% yield, 100% ee) and 264T (91 mg, 26% yield, 100% ee) as yellow solids.

Group D (400 mg, 0.727 mmol) was separated by chiral Prep. HPLC (separation condition: Column: Chiralpak IG 5

μm 20*250 mm; Mobile Phase: Hex:EtOH:DEA=80:20:0.3 at 15 mL/min; Temp: 30° C.; Wavelength: 214 nm) to afford the title compounds 264X (130 mg, 100% ee) and 264Y (120 mg, 100% ee), which were further purified by Prep. HPLC (Column: Gilson-5 x-bridge C18 (5 μm 19*150 mm), Mobile Phase A: water (0.1% ammonium bicarbonate), Mobile Phase B: acetonitrile, UV: 214 nm, Flow rate: 15 mL/min, Gradient: 60-100% (% B)) to give the title compounds 264X (108 mg, 27% yield, 100% ee) and 264Y (93 mg, 23% yield, 100% ee) as yellow solids.

Compound 264U: LC-MS (ESI): $R_T$=3.888 min, mass calcd. for $C_{26}H_{29}ClFN_3O_5S$ 549.2, m/z found 550.2 $[M+H]^+$. Chiral HPLC (Column: Chiralpak IC 5 μm 4.6*250 mm; Mobile Phase: Hex:EtOH:DEA=60:40:0.2 at 1.0 mL/min; Temp: 30° C.; Wavelength: 230 nm, $R_T$=8.913 min). $^1$H NMR (400 MHz, DMSO-$d_6$) δ 9.50 (s, 0.8H), 9.26 (br s, 0.2H), 8.01-7.99 (m, 1.7H), 7.94 (br s, 0.3H), 7.42 (dd, J=8.8, 2.8 Hz, 1H), 7.37-7.33 (m, 1H), 7.23-7.18 (m, 1H), 6.04 (s, 0.2H), 5.92 (d, J=3.2 Hz, 0.8H), 4.16-4.13 (m, 0.3H), 4.04-3.96 (m, 3.3H), 3.87-3.70 (m, 2.4H), 2.02-1.93 (m, 2H), 1.81-1.78 (m, 1H), 1.55-1.53 (m, 1H), 1.43 (s, 9H), 1.09-1.03 (m, 3H). $^1$H NMR (400 MHz, $CD_3OD$+1 M HCl aqueous solution (1 drop)) δ 8.08 (d, J=2.8 Hz, 1H), 8.01 (d, J=3.2 Hz, 1H), 7.47 (dd, J=8.4, 5.6 Hz, 1H), 7.31 (dd, J=8.8, 2.4 Hz, 1H), 7.16-7.11 (m, 1H), 6.20 (s, 1H), 4.20 (dd, J=10.0, 2.0 Hz, 1H), 4.12-3.95 (m, 5H), 2.13-2.08 (m, 2H), 2.03-2.02 (m, 1H), 1.73-1.70 (m, 1H), 1.51 (s, 9H), 1.15 (t, J=7.2 Hz, 3H).

Compound 264Y: LC-MS (ESI): $R_T$=3.788 min, mass calcd. for $C_{26}H_{29}ClFN_3O_5S$ 549.2, m/z found 550.2 $[M+H]^+$. Chiral HPLC (Column: Chiralpak IG 5 μm 4.6*250 mm; Mobile Phase: Hex:EtOH:DEA=80:20:0.2 at 1.0 mL/min; Temp: 30° C.; Wavelength: 230 nm, $R_T$=12.361 min). $^1$H NMR (400 MHz, DMSO-$d_6$) δ 9.54 (d, J=3.6 Hz, 0.8H), 9.20 (s, 0.2H), 8.02-7.98 (m, 1.8H), 7.93 (d, J=3.2 Hz, 0.2H), 7.44-7.41 (m, 1H), 7.38-7.34 (m, 1H), 7.24-7.19 (m, 1H), 6.03 (s, 0.2H), 5.93 (d, J=3.6 Hz, 0.8H), 4.21-4.18 (m, 0.2H), 4.03-3.92 (m, 2.5H), 3.89-3.82 (m, 1.8H), 3.80-3.77 (m, 0.7H), 3.67-3.61 (m, 0.8H), 2.13-2.10 (m, 1H), 1.98-1.96 (m, 2H), 1.56-1.50 (m, 1H), 1.45 (s, 2H), 1.43 (s, 7H), 1.10-1.01 (m, 3H).

Compound 275: Methyl 4-(2-bromo-3-fluorophenyl)-6-(1-(tert-butoxycarbonyl)piperidin-4-yl)-2-(thiazol-2-yl)-1,4-dihydropyrimidine-5-carboxylate $^1$H NMR (400 MHz, $CDCl_3$) δ 8.13 (s, 0.5H), 7.85-7.80 (m, 1H), 7.52-7.47 (m, 1H), 7.47-7.43 (m, 0.5H), 7.25-7.18 (m, 1H), 7.14-6.98 (m, 2H), 6.25 (s, 0.5H), 6.12-6.07 (m, 0.5H), 4.41-4.16 (m, 2.5H), 4.01-3.90 (m, 0.5H), 3.65-3.56 (m, 3H), 2.97-2.78 (m, 2H), 2.02-1.80 (m, 2H), 1.75-1.64 (m, 2H), 1.54-1.47 (m, 9H).

Racemic compound 275 (6.40 g, 107 mmol) was separated by chiral Prep. SFC (Column: Chiralpak IG 5 μm 20*250 mm; Mobile Phase: $CO_2$:MeOH=70:30 at 50 g/min; Col. Temp: 30° C.; Wavelength: 214 nm, Back pressure: 100 bar) to afford the title compounds 275A (2.60 g, 38% yield, 100% stereopure) and 275B (2.90 g, 38% yield, 99.5% stereopure) as yellow solids.

Intermediate 275A: Chiral analysis (Column: Chiralpak IG 5 μm 4.6*250 mm; $CO_2$:MeOH=70:30 at 3.0 g/min; Col. Temp: 40° C.; Wavelength: 254 nm, Back pressure: 100 bar, $R_T$=3.25 min). $^1$H NMR (400 MHz, $CDCl_3$) δ 8.13 (s, 0.5H), 7.83-7.81 (m, 1H), 7.50-7.49 (m, 1H), 7.45-7.44 (m, 0.5H), 7.26-7.14 (m, 1H), 7.10-6.98 (m, 2H), 6.25 (s, 0.5H), 6.10 (s, 0.5H), 4.41-4.13 (m, 2.5H), 4.00-3.92 (m, 0.5H), 3.60-3.58 (m, 3H), 2.97-2.77 (m, 2H), 2.00-1.74 (m, 2H), 1.64-1.55 (m, 2H), 1.54-1.45 (m, 9H).

Intermediate 275B: Chiral analysis (Column: Chiralpak IG 5 μm 4.6*250 mm; $CO_2$:MeOH=70:30 at 3.0 g/min; Temp: 40° C.; Wavelength: 254 nm, $R_T$=4.31 min). $^1$H NMR (400 MHz, $CDCl_3$) δ 8.13 (s, 0.5H), 7.83-7.81 (m, 1H), 7.52-7.48 (m, 1H), 7.44-7.43 (m, 0.5H), 7.26-7.17 (m, 1H), 7.12-6.97 (m, 2H), 6.25 (s, 0.5H), 6.10 (s, 0.5H), 4.37-4.09 (m, 2.5H), 4.98-3.94 (m, 0.5H), 3.63-3.59 (m, 3H), 2.96-2.79 (m, 2H), 2.01-1.81 (m, 2H), 1.74-1.58 (m, 2H), 1.51-1.45 (m, 9H).

Compound 279: Ethyl 4-(2-bromo-4-fluorophenyl)-6-(1-(tert-butoxycarbonyl)piperidin-4-yl)-2-(thiazol-2-yl)-1,4-dihydropyrimidine-5-carboxylate LC-MS (ESI): $R_T$=2.252 min, mass calcd. for $C_{26}H_{30}BrFN_4O_4S$ 592.1, m/z found 593.0 $[M+H]^+$. $^1$H NMR (400 MHz, $CDCl_3$) δ 8.09 (s, 0.4H), 7.83-7.81 (m, 1H), 7.50 (d, J=3.2 Hz, 0.6H), 7.44 (d, J=3.2 Hz, 0.4H), 7.39 (s, 0.6H), 7.33-7.28 (m, 2H), 7.01-6.93 (m, 1H), 6.19 (s, 0.4H), 6.05 (d, J=2.4 Hz, 0.6H), 4.35-4.19 (m, 2.2H), 4.08-3.91 (m, 2.8H), 2.91-2.81 (m, 2H), 2.00-1.67 (m, 3H), 1.61-1.58 (m, 1H), 1.51 (s, 9H), 1.15-1.10 (m, 3H).

A racemic mixture of ethyl 4-(2-bromo-4-fluorophenyl)-6-(1-(tert-butoxycarbonyl)piperidin-4-yl)-2-(thiazol-2-yl)-1,4-dihydropyrimidine-5-carboxylate compound 279 (10.0 g, 15.2 mmol, 90% purity from $^1$H NMR) was separated by chiral Prep. SFC (separation condition: Column: Chiralpak IG 5 μm 20 mm*250 mm; Mobile Phase: $CO_2$:MeOH=75:25 at 50 g/min; Col. Temp: 40° C.; Wavelength: 214 nm, Back pressure: 100 bar) to afford the title compound 279A (4.7 g, 50% yield, 95% purity from $^1$H NMR, 100% stereopure) as yellow solids and 279B (4.9 g, 49% yield, 90% purity from $^1$H NMR, 100% stereopure) as yellow solids.

Compound 279A: LC-MS (ESI): $R_T$=2.236 min, mass calcd. for $C_{26}H_{30}BrFN_4O_4S$ 592.1, m/z found 593.0 $[M+H]^+$. Chiral analysis (Column: Chiralpak IG 5 μm 4.6 mm*250 mm; Mobile Phase: $CO_2$:MeOH=70:30 at 3.0 g/min; Col. Temp: 40° C.; Wavelength: 254 nm, Back pressure: 100 bar, $R_T$=2.86 min) $^1$H NMR (400 MHz, $CDCl_3$) δ 8.09 (s, 0.4H), 7.83-7.81 (m, 1H), 7.50 (d, J=2.8 Hz, 0.6H), 7.44 (d, J=3.2 Hz, 0.4H), 7.38 (d, J=2.0 Hz, 0.6H), 7.34-7.28 (m, 2H), 7.02-6.93 (m, 1H), 6.19 (s, 0.4H), 6.05 (d, J=2.4 Hz, 0.6H), 4.36-4.15 (m, 2.3H), 4.08-4.02 (m, 2H), 3.96-3.90 (m, 0.7H), 2.91-2.83 (m, 2H), 2.07-1.58 (m, 4H), 1.50 (s, 9H), 1.15-1.10 (m, 3H) Compound 279B: LC-MS (ESI): $R_T$=2.325 min, mass calcd. for $C_{26}H_{30}BrFN_4O_4S$ 592.1, m/z found 596.0 $[M+H]^+$. Chiral analysis (Column: Chiralpak IG 5 μm 4.6 mm*250 mm; Mobile Phase: $CO_2$:MeOH=70:30 at 3.0 g/min; Col. Temp: 40° C.; Wavelength: 254 nm, Back pressure: 100 bar, $R_T$=3.82 min) $^1$H NMR (400 MHz, $CDCl_3$) δ 8.09 (s, 0.4H), 7.83-7.81 (m, 1H), 7.50 (d, J=3.2 Hz, 0.6H), 7.44 (d, J=3.2 Hz, 0.4H), 7.38 (d, J=1.2 Hz, 0.6H), 7.33-7.28 (m, 2H), 7.02-6.93 (m, 1H), 6.18 (s, 0.4H), 6.05 (d, J=2.4 Hz, 0.6H), 4.33-4.15 (m, 2.4H), 4.08-4.02 (m, 2H), 3.96-3.90 (m, 0.6H), 2.91-2.83 (m, 2H), 2.08-1.58 (m, 4H), 1.50 (s, 9H), 1.15-1.10 (m, 3H).

Compound 283: methyl 4-(2-chloro-3-fluorophenyl)-6-(-5-oxo-1-((2-(trimethylsilyl)ethoxy)methyl)pyrrolidin-3-yl)-2-(thiazol-2-yl)-1,4-dihydropyrimidine-5-carboxylate Separation conditions: silica gel column chromatography (petroleum ether:ethyl acetate=2:1), then further purified by C18 column (acetonitrile:water=5% to 100%) to give the title compounds 283M (18 mg, 2% yield) as yellow solids and 283N (16 mg, 2% yield) as yellow solids.

Intermediate 283M: $^1$H NMR (300 MHz, CDCl$_3$) δ 7.87 (d, J=2.7 Hz, 1H), 7.55 (s, 2H), 7.28-7.22 (m, 1H), 7.17-7.10 (m, 2H), 6.19 (s, 1H), 4.84-4.75 (m, 2H), 3.96-3.90 (m, 1H), 3.83-3.78 (m, 1H), 3.66-3.56 (m, 6H), 3.03-2.95 (m, 1H), 2.68-2.59 (m, 1H), 1.03-0.95 (m, 2H), 0.04 (s, 3H), 0.00 (s, 6H).

Intermediate 283N: $^1$H NMR (300 MHz, CDCl$_3$) δ 7.87 (s 1H), 7.58 (s, 1H), 7.55 (s, 1H), 7.30-7.25 (m, 1H), 7.14 (t, J=6.9 Hz, 2H), 6.16 (s, 1H), 4.88-4.77 (m, 2H), 3.81-3.75 (m, 1H), 3.66 (s, 3H), 3.63-3.57 (m, 4H), 3.20-3.11 (m, 1H), 2.84-2.74 (m, 1H), 1.01-0.94 (m, 2H), 0.04 (s, 9H).

Compound 288: (trans)-Methyl 4-(2-chloro-3,4-difluorophenyl)-6-(4-(methoxycarbonyl)cyclohexyl)-2-(thiazol-2-yl)-1,4-dihydropyrimidine-5-carboxylate LC-MS (ESI): R$_T$=2.849 min, mass calcd. for C$_{23}$H$_{22}$ClF$_2$N$_3$O$_4$S 509.1, m/z found 509.9 [M+H]$^+$. $^1$H NMR (400 MHz, CDCl$_3$) δ 8.14 (s, 0.6H), 7.82 (s, 1H), 7.50 (s, 0.4H), 7.46 (s, 0.6H), 7.37 (s, 0.4H), 7.08-6.98 (m, 2H), 6.18 (s, 0.6H), 6.04 (s, 0.4H), 4.02-3.96 (m, 0.6H), 3.81-3.75 (m, 0.4H), 3.70 (s, 3H), 3.62 (s, 1H), 3.60 (s, 2H), 2.46-2.39 (m, 1H), 2.24-1.90 (m, 5H), 1.76-1.66 (m, 2H), 1.55-1.45 (m, 1H).

A racemic mixture of (trans)-methyl 4-(2-chloro-3,4-difluorophenyl)-6-(4-(methoxycarbonyl)cyclohexyl)-2-(thiazol-2-yl)-1,4-dihydropyrimidine-5-carboxylate 288 (420 mg, 96% purity, 0.790 mmol) was separated by chiral Prep. HPLC (separation condition: Column: Chiralpak IC 5 μm 30*250 mm; Mobile Phase: Hex:EtOH:DEA=85:15:0.3 at 23 mL/min; Temp: 30° C.; Wavelength: 230 nm) to afford the title compounds 288M (190 mg, 98% purity, 46% yield, 100% stereopure) and 288 (190 mg, 97% purity, 46% yield, 100% stereopure) as yellow solids.

Compound 288M: LC-MS (ESI): R$_T$=3.319 min, mass calcd. for C$_{23}$H$_{22}$ClF$_2$N$_3$O$_4$S 509.1, m/z found 509.9 [M+H]$^+$. Chiral analysis (Column: Chiralpak IC 5 μm 4.6*250 mm; Mobile Phase: Hex:EtOH:DEA=85:15:0.2 at 1.0 mL/min; Temp: 30° C.; Wavelength: 254 nm, R$_T$=7.204 min). 1H NMR (400 MHz, DMSO-d$_6$) δ 9.54 (s, 0.6H), 8.99 (s, 0.4H), 8.00-7.94 (m, 2H), 7.46-7.39 (m, 1H), 7.21-7.11 (m, 1H), 6.03 (s, 0.4H), 5.93 (s, 0.6H), 3.89-3.80 (m, 0.6H), 3.62 (s, 3.4H), 3.54 (s, 3H), 2.39-2.29 (m, 0.6H), 2.05-1.66 (m, 6.4H), 1.51-1.36 (m, 2H).

Compound 288N: LC-MS (ESI): R$_T$=3.313 min, mass calcd. for C$_{23}$H$_{22}$ClF$_2$N$_3$O$_4$S 509.1, m/z found 509.9 [M+H]$^+$. Chiral analysis (Column: Chiralpak IC 5 μm 4.6*250 mm; Mobile Phase: Hex:EtOH:DEA=85:15:0.2 at 1.0 mL/min; Temp: 30° C.; Wavelength: 254 nm, R$_T$=9.765 min). $^1$H NMR (400 MHz, DMSO-d$_6$) δ 9.52 (br s, 0.5H), 8.99 (s, 0.5H), 8.01-7.99 (m, 1.5H), 7.94 (d, J=3.2 Hz, 0.5H), 7.49-7.41 (m, 1H), 7.21-7.14 (m, 1H), 6.02 (s, 0.4H), 5.93 (s, 0.6H), 3.88-3.81 (m, 0.5H), 3.62-3.61 (m, 3H), 3.58-3.56 (m, 0.5H), 3.53-3.35 (m, 3H), 2.37-2.30 (m, 0.7H), 2.08-1.97 (m, 2H), 1.90-1.82 (m, 4.3H), 1.50-1.39 (m, 2H).

Compound 290: Methyl 4-(2-chloro-3,4-difluorophenyl)-6-(4-(N-(2-ethoxy-2-oxoethyl)sulfamoyl)cyclohexyl)-2-(thiazol-2-yl)-1,4-dihydropyrimidine-5-carboxylate LC-MS (ESI): R$_T$=1.76 min, mass calcd. for C$_{25}$H$_{27}$ClF$_2$N$_4$O$_6$S$_2$ 616.1, m/z found 617.3 [M+H]$^+$.

A mixture of methyl 4-(2-chloro-3,4-difluorophenyl)-6-(4-(N-(2-ethoxy-2-oxoethyl)sulfamoyl)cyclohexyl)-2-(thiazol-2-yl)-1,4-dihydropyrimidine-5-carboxylate 290 (1.20 g, 1.90 mmol) was purified by C18 column (acetonitrile:water (+0.1% ammonium bicarbonate)=49% to 70%) to give the title compounds 290R (700 mg, 58% yield) as yellow solids and 290S (40 mg, 3% yield) as yellow solids.

Compound 290R: LC-MS (ESI): R$_T$=3.603 min, mass calcd. for C$_{25}$H$_{27}$ClF$_2$N$_4$O$_6$S$_2$ 616.1, m/z found 617.0 [M+H]$^+$. $^1$H NMR (400 MHz, DMSO-d$_6$) δ 9.56 (d, J=3.6 Hz, 0.7H), 8.31 (s, 0.3H), 8.00-7.99 (m, 1.7H), 7.97-7.96 (m, 0.3H), 7.86 (t, J=6.4 Hz, 0.3H), 7.61-7.58 (m, 0.7H), 7.49-7.39 (m, 1H), 7.22-7.17 (m, 1H), 6.03 (s, 0.3H), 5.92 (d, J=3.6 Hz, 0.7H), 4.16-4.09 (m, 2H), 3.94-3.88 (m, 0.6H), 3.85-3.79 (m, 2H), 3.72-3.66 (m, 0.7H), 3.52 (s, 3H), 3.18-3.12 (m, 0.7H), 2.39-2.33 (m, 2H), 2.28-2.17 (m, 0.7H), 2.14-2.08 (m, 0.6H), 2.05-1.94 (m, 0.7H), 1.90-1.76 (m, 2.3H), 1.68-1.64 (m, 1H), 1.59-1.53 (m, 0.7H), 1.23-1.19 (m, 3H).

Compound 290S: LC-MS (ESI): R$_T$=3.447 min, mass calcd. for C$_{25}$H$_{27}$ClF$_2$N$_4$O$_6$S$_2$ 616.1, m/z found 617.0 [M+H]$^+$. $^1$H NMR (400 MHz, DMSO-d$_6$) δ 9.57 (d, J=3.6 Hz, 0.6H), 9.02 (s, 0.4H), 8.00 (s, 1H), 7.99-7.98 (m, 0.6H), 7.95-7.94 (m, 0.4H), 7.67-7.58 (m, 1H), 7.49-7.42 (m, 1H), 7.21-7.14 (m, 1H), 6.01 (s, 0.4), 5.92 (d, J=4.0 Hz, 0.6), 4.14 (q, J=7.2 Hz, 2H), 3.84-3.83 (m, 2H), 3.59-3.56 (m, 0.7H), 3.53 (s, 2H), 3.52 (s, 1H), 3.18-3.12 (m, 0.6H), 3.04-2.97 (m, 0.7H), 2.26-2.19 (m, 2H), 1.97-1.81 (m, 3H), 1.72-1.67 (m, 1H), 1.54-1.42 (m, 2H), 1.25-1.21 (m, 3H).

Compound 292: methyl 4-(2-chloro-3,4-difluorophenyl)-6-(4-(((R)-3-(methoxycarbonyl)pyrrolidin-1-yl)sulfonyl)cyclohexyl)-2-(thiazol-2-yl)-1,4-dihydropyrimidine-5-carboxylate LC-MS (ESI): R$_T$=4.523 min and 4.650 min, mass calcd. for C$_{27}$H$_{29}$ClF$_2$N$_4$O$_6$S$_2$ 642.1, m/z found 643.2 [M+H]$^+$. $^1$H NMR (400 MHz, CD$_3$OD) δ 7.94-7.91 (m, 0.5H), 7.90-7.87 (m, 0.5H), 7.77-7.73 (m, 1H), 7.26-7.17 (m, 2H), 6.14 (s, 0.2H), 6.13 (s, 0.3H), 6.07 (s, 0.2H), 6.06 (s, 0.3H), 4.12-4.04 (m, 0.2H), 4.02-3.93 (m, 0.4H), 3.90-3.81 (m, 0.2H), 3.76-3.69 (m, 3.2H), 3.67-3.62 (m, 2H), 3.61-3.57 (m, 3H), 3.53-3.46 (m, 2.4H), 3.28-3.15 (m, 1.6H), 2.50-2.39 (m, 0.5H), 2.37-2.18 (m, 4H), 2.16-2.08 (m, 0.5H), 2.04-1.91 (m, 1.6H), 1.87-1.66 (m, 3.4H).

A mixture of methyl 4-(2-chloro-3,4-difluorophenyl)-6-(4-(((R)-3-(methoxycarbonyl) pyrrolidin-1-yl)sulfonyl)cyclohexyl)-2-(thiazol-2-yl)-1,4-dihydropyrimidine-5-carboxylate 292 (1.20 g, 90% purity, 1.68 mmol) was separated by Prep. HPLC (Column: gilson X-bridge C18 (5 μm 19*150 mm), Mobile Phase A: water (0.1% ammonium bicarbonate), Mobile Phase B: acetonitrile, UV: 214 nm, Flow rate: 15 mL/min, Gradient: 60-65% (% B)) to give the title compounds 292M (247 mg, 96.3% purity, 21% yield) and 292N (762 mg, 99.4% purity, 64% yield) as yellow solids.

Compound 292M: LC-MS (ESI): R$_T$=9.612 min, mass calcd. for C$_{27}$H$_{29}$ClF$_2$N$_4$O$_6$S$_2$ 642.1, m/z found 643.2 [M+H]$^+$. $^1$H NMR (400 MHz, CDCl$_3$) δ 8.34 (s, 0.6H), 7.84-7.81 (m, 1H), 7.51 (d, J=3.2 Hz, 0.4H), 7.42-7.40 (m, 1H), 7.09-6.98 (m, 2H), 6.18 (s, 0.6H), 6.06 (d, J=2.8 Hz, 0.4H), 4.13-4.06 (m, 0.7H), 3.96-3.90 (m, 0.3H), 3.79-3.72 (m, 4H), 3.60-3.58 (m, 5H), 3.55-3.49 (m, 1.3H), 3.35-3.29 (m, 0.7H), 3.22-3.12 (m, 1H), 2.53-2.41 (m, 2H), 2.28-2.14 (m, 4H), 2.04-1.76 (m, 4H).

Compound 292N: LC-MS (ESI): R$_T$=3.593 min, mass calcd. for C$_{27}$H$_{29}$ClF$_2$N$_4$O$_6$S$_2$ 642.1, m/z found 643.2

[M+H]⁺. ¹H NMR (400 MHz, CDCl₃) δ 8.11 (s, 0.4H), 7.84-7.81 (m, 1H), 7.52-7.46 (m, 1H), 7.40 (s, 0.6H), 7.08-7.00 (m, 2H), 6.18 (s, 0.4H), 6.05 (d, J=2.8 Hz, 0.6H), 4.04-3.97 (m, 0.5H), 3.78-3.73 (m, 4.5H), 3.62-3.58 (m, 4H), 3.54-3.48 (m, 2H), 3.19-3.03 (m, 2H), 2.41-2.35 (m, 2H), 2.29-2.22 (m, 3H), 2.13-1.94 (m, 1H), 1.88-1.72 (m, 3H), 1.52-1.44 (m, 1H).

A racemic mixture of (trans)-methyl 4-(2-chloro-3,4-difluorophenyl)-6-(4-(((R)-3-(methoxycarbonyl)pyrrolidin-1-yl) sulfonyl)cyclohexyl)-2-(thiazol-2-yl)-1,4-dihydropyrimidine-5-carboxylate 292N (500 mg, 99.4% purity, 0.774 mmol) was separated by chiral Prep. SFC (separation condition: Column: Chiralpak IG 5 µm 20*250 mm; Mobile Phase: CO₂: EtOH:DEA=60:40:0.3 at 50 g/min; Col. Temp: 30° C.; Wavelength: 230 nm, Back pressure: 100 bar) to give 292W (146 mg, 29% yield, 99.3% purity, 100% stereopure) and 292Z (160 mg, 32% yield, 99.4% purity, 99.8% stereopure) as yellow solids.

Compound 292W: LC-MS (ESI): $R_T$=4.527 min, mass calcd. for $C_{27}H_{29}ClF_2N_4O_6S_2$ 642.1, m/z found 643.1 [M+H]⁺. Chiral analysis (Column: Chiralpak IG 5 µm 4.6*250 mm; Mobile Phase: CO₂: EtOH:DEA=60:40:0.2 at 2.999 g/min; Col. Temp: 40.1° C.; Wavelength: 230 nm, Back pressure: 100 bar, $R_T$=4.45 min). ¹H NMR (400 MHz, CDCl₃) δ 8.11 (s, 0.4H), 7.84-7.81 (m, 1H), 7.51 (d, J=3.2 Hz, 0.5H), 7.46 (d, J=2.8 Hz, 0.5H), 7.41 (s, 0.6H), 7.06-7.01 (m, 2H), 6.18 (s, 0.4H), 6.05 (d, J=2.4 Hz, 0.6H), 4.06-3.97 (m, 0.5H), 3.80-3.78 (m, 0.5H), 3.74-3.71 (m, 4H), 3.62-3.57 (m, 4H), 3.55-3.48 (m, 2H), 3.19-3.07 (m, 2H), 2.38-2.35 (m, 1H), 2.29-2.20 (m, 3H), 2.13-2.00 (m, 1H), 1.95-1.74 (m, 4H), 1.58-1.51 (m, 1H).

Compound 292Z: LC-MS (ESI): $R_T$=4.042 min, mass calcd. for $C_{27}H_{29}ClF_2N_4O_6S_2$ 642.1, m/z found 643.1 [M+H]⁺. Chiral analysis (Column: Chiralpak IG 5 µm 4.6*250 mm; Mobile Phase: CO₂: EtOH:DEA=60:40:0.2 at 2.999 g/min; Col. Temp: 40.1° C.; Wavelength: 230 nm, Back pressure: 100 bar, $R_T$=5.5 min). ¹H NMR (400 MHz, CDCl₃) δ 8.11 (s, 0.5H), 7.84-7.81 (m, 1H), 7.51 (d, J=2.8 Hz, 0.5H), 7.46 (d, J=3.2 Hz, 0.5H), 7.41 (s, 0.5H), 7.07-7.01 (m, 2H), 6.18 (s, 0.4H), 6.05 (d, J=2.8 Hz, 0.6H), 4.04-3.95 (m, 0.5H), 3.79-3.76 (m, 0.5H), 3.74-3.71 (m, 4H), 3.62-3.60 (m, 4H), 3.55-3.48 (m, 2H), 3.19-3.09 (m, 2H), 2.41-2.33 (m, 1H), 2.26-2.18 (m, 3H), 2.14-2.01 (m, 1H), 1.97-1.76 (m, 4H), 1.59-1.51 (m, 1H).

Compound 294: Methyl 6-(3-((tert-butyldiphenylsilyl)oxy)cyclobutyl)-4-(2-chloro-4-fluorophenyl)-2-(thiazol-2-yl)-1,4-dihydropyrimidine-5-carboxylate LC-MS (ESI): $R_T$=2.08 min, mass calcd. for $C_{35}H_{35}ClFN_3O_3SSi$ 659.2, m/z found 660.6 [M+H]⁺. ¹H NMR (300 MHz, CDCl₃) δ 8.41 (br s, 0.5H), 7.89-7.87 (m, 1H), 7.76-7.69 (m, 4H), 7.56-7.55 (m, 0.5H), 7.48-7.35 (m, 7H), 7.31-7.29 (m, 0.3H), 7.26-7.19 (m, 0.7H), 7.16-7.10 (m, 1H), 6.98-6.88 (m, 1H), 6.19-6.16 (m, 0.5H), 6.05-6.00 (m, 0.5H), 4.36-4.25 (m, 1H), 3.96-3.84 (m, 1H), 3.61-3.56 (m, 3H), 2.76-2.32 (m, 3H), 2.25-2.14 (m, 1H), 1.10 (s, 9H).

Compound 296: (trans)-Methyl 6-(4-((tert-butoxycarbonyl)amino)cyclohexyl)-4-(2-chloro-3,4-difluorophenyl)-2-(3,5-difluoropyridin-2-yl)-1,4-dihydropyrimidine-5-carboxylate LC-MS (ESI): $R_T$=1.93 min, mass calcd. for $C_{28}H_{29}ClF_4N_4O_4$ 596.2, m/z found 597.4 [M+H]⁺. ¹H NMR (300 MHz, DMSO-d₆) δ 9.30 (s, 0.8H), 9.14 (s, 0.8H), 8.58 (s, 1H), 8.10-8.03 (m, 1H), 7.51-7.42 (m, 1H), 7.20-7.13 (m, 1H), 6.83-6.73 (m, 1H), 6.03 (s, 0.8H), 5.92 (s, 0.2H), 4.04-4.01 (m, 0.5H), 3.89-3.84 (m, 0.5H), 3.51 (s, 3H), 1.90-1.65 (m, 5H), 1.39 (s, 9H), 1.35-1.23 (m, 4H).

Compound 299: Methyl 6-(−3-((tert-butoxycarbonyl)amino)cyclopentyl)-4-(2-chloro-3,4-difluorophenyl)-2-(thiazol-2-yl)-1,4-dihydropyrimidine-5-carboxylate, separation condition Prep. HPLC (Xtimate C18 (10 m 50*250 mm), Mobile Phase A: Water (0.1% ammonium bicarbonate), Mobile Phase B: acetonitrile, UV: 214 nm, Flow rate: 80 mL/min, Gradient: 60-90% (% B)) to give Group 1 (299A-D, 1.3 g, 26% yield) and Group 2 (299E-H, 1.5 g, 30% yield) as yellow oil. The Group 1 (299A-D, 1.3 g, 2.4 mmol) was separated by chiral Prep. HPLC (Column: Chiralpak IG 5 µm 20*250 mm; Mobile Phase: Hex:EtOH:DEA=80:20:0.3 at 15 mL/min; Temp: 30° C.; Wavelength: 214 nm) to give the title compounds 299A (280 mg, 22%), 299B (230 mg, 18%), 299C (320 mg, 25%) and 299D (330 mg, 25%) as yellow solids. The Group 2 (299E-H, 1.5 g, 2.7 mmol) was separated by chiral Prep. HPLC (Column: Chiralpak IG 5 µm 20*250 mm; Mobile Phase: Hex:EtOH:DEA=90:10:0.3 at 25 mL/min; Temp: 30° C.; Wavelength: 214 nm) to give the title compounds 299E (300 mg, 20%), 299F (350 mg, 23%), 299G (380 mg, 25%) and 299H (350 mg, 23%) as yellow solids.

Compound 299A: LC-MS (ESI): $R_T$=2.310 min, mass calcd. for $C_{25}H_{27}ClF_2N_4O_4S$ 552.1, m/z found 453.0 [M+H−Boc]⁺. ¹H NMR (400 MHz, CDCl₃) δ 8.11 (br s, 0.4H), 7.83-7.81 (m, 1H), 7.49 (d, J=3.2 Hz, 0.6H), 7.45 (d, J=3.2 Hz, 0.4H), 7.37 (br s, 0.6H), 7.08-7.01 (m, 2H), 6.18 (s, 0.4H), 6.04 (d, J=2.8 Hz, 0.6H), 4.69-4.54 (m, 1.4H), 4.47-4.39 (m, 0.6H), 4.32-4.25 (m, 1H), 3.61 (s, 1.8H), 3.59 (s, 1.2H), 2.45-2.06 (m, 3H), 1.98-1.82 (m, 2H), 1.67-1.61 (m, 1H), 1.47 (s, 5H), 1.46 (s, 4H).

Compound 299B: ¹H NMR (400 MHz, CDCl₃) δ 8.11 (br s, 0.4H), 7.82 (t, J=3.2 Hz, 1H), 7.50 (d, J=3.2 Hz, 0.6H), 7.45 (d, J=2.8 Hz, 0.4H), 7.38 (br s, 0.6H), 7.10-6.99 (m, 2H), 6.18 (s, 0.4H), 6.04 (d, J=2.8 Hz, 0.6H), 4.70-4.53 (m, 1.4H), 4.47-4.39 (m, 0.6H), 4.33-4.24 (m, 1H), 3.61 (s, 1.8H), 3.60 (s, 1.2H), 2.44-2.06 (m, 3H), 1.98-1.82 (m, 2H), 1.67-1.61 (m, 1H), 1.47 (s, 9H).

Compound 299C: LC-MS (ESI): $R_T$=2.324 min, mass calcd. for $C_{25}H_{27}ClF_2N_4O_4S$ 552.1, m/z found 453.0 [M+H−Boc]⁺. ¹H NMR (400 MHz, CDCl₃) δ 8.10 (br s, 0.4H), 7.82 (t, J=3.2 Hz, 1H), 7.50 (d, J=2.8 Hz, 0.6H), 7.45 (d, J=2.8 Hz, 0.4H), 7.37 (br s, 0.6H), 7.09-6.98 (m, 2H), 6.17 (s, 0.4H), 6.04 (d, J=2.8 Hz, 0.6H), 4.66-4.52 (m, 1.3H), 4.46-4.38 (m, 0.7H), 4.26 (br s, 1H), 3.61 (s, 1.8H), 3.59 (s, 1.2H), 2.33-1.96 (m, 4H), 1.74-1.63 (m, 2H) 1.46 (s, 9H).

Compound 299D: LC-MS (ESI): $R_T$=2.313 min, mass calcd. for $C_{25}H_{27}ClF_2N_4O_4S$ 552.1, m/z found 453.0 [M+H−Boc]⁺. ¹H NMR (400 MHz, CDCl₃) δ 8.11 (br s, 0.4H), 7.82 (t, J=3.2 Hz, 1H), 7.50 (d, J=3.2 Hz, 0.6H), 7.45 (d, J=2.8 Hz, 0.4H), 7.37 (br s, 0.6H), 7.09-6.98 (m, 2H), 6.17 (s, 0.4H), 6.04 (d, J=2.8 Hz, 0.6H), 4.66-4.52 (m, 1.3H), 4.46-4.38 (m, 0.7H), 4.26 (br s, 1H), 3.61 (s, 1.8H), 3.59 (s, 1.2H), 2.34-1.96 (m, 4H), 1.77-1.61 (m, 2H), 1.46 (s, 9H).

Compound 299E: LC-MS (ESI): $R_T$=2.207 min, mass calcd. for $C_{25}H_{27}ClF_2N_4O_4S$ 552.1, m/z found 453.0 [M+H−Boc]⁺. ¹H NMR (400 MHz, CDCl₃) δ 8.32 (br s, 0.2H), 7.87 (d, J=13.6 Hz, 0.8H), 7.82 (d, J=10.0 Hz, 0.2H), 7.57-7.55 (m, 1.6H), 7.47 (d, J=13.2 Hz, 0.2H), 7.11-7.01 (m, 2H), 6.17 (s, 0.2H), 6.07 (br s, 0.8H), 6.05 (d, J=2.4 Hz, 0.8H), 5.84 (br s, 0.2H), 4.72 (br s, 0.1H), 4.52-4.43 (m, 1H), 4.29 (m, 0.6H), 4.17-4.03 (m, 0.3H) 3.62 (s, 2.4H), 3.59 (s, 0.6H), 2.61-2.44 (m, 0.1H), 2.38-2.25 (m, 0.9H), 2.18-2.12 (m, 0.4H), 2.02-1.60 (m, 4.6H), 1.46 (s, 9H).

Compound 299F: LC-MS (ESI): $R_T$=2.368 min, mass calcd. for $C_{25}H_{27}ClF_2N_4O_4S$ 552.1, m/z found 453.1 [M+H−Boc]$^+$. $^1$H NMR (400 MHz, CDCl$_3$) δ 8.32 (br s, 0.2H), 7.86 (d, J=2.8 Hz, 0.8H), 7.82 (d, J=2.8 Hz, 0.2H), 7.57-7.48 (m, 1.6H), 7.45 (d, J=3.2 Hz, 0.2H), 7.11-7.01 (m, 2H), 6.16 (s, 0.2H), 6.07 (br s, 0.8H), 6.05 (d, J=2.8 Hz, 0.8H), 5.82 (br s, 0.2H), 4.80-4.70 (m, 0.1H), 4.54-4.45 (m, 1H), 4.23-4.22 (m, 0.7H), 4.12-4.05 (m, 0.2H) 3.62 (s, 2H), 3.59 (s, 1H), 2.59-2.47 (m, 0.2H), 2.38-2.29 (m, 0.8H), 2.24-2.08 (m, 0.6H), 2.03-1.89 (m, 4.4H), 1.60 (s, 9H).

Compound 299G: LC-MS (ESI): $R_T$=2.354 min, mass calcd. for $C_{25}H_{27}ClF_2N_4O_4S$ 552.1, m/z found 453.1 [M+H−Boc]$^+$. $^1$H NMR (400 MHz, CDCl$_3$) δ 8.28 (br s, 0.1H), 7.88 (d, J=14.8 Hz, 0.8H), 7.81 (d, J=5.2 Hz, 0.2H), 7.57-7.48 (m, 1.7H), 7.45 (d, J=3.6 Hz, 0.2H), 7.13-7.00 (m, 2H), 6.19-6.17 (m, 1H), 6.08-6.07 (m, 1H), 4.76-4.65 (m, 0.1H), 4.50-4.38 (m, 1H), 4.25-4.20 (m, 0.7H), 4.15-4.03 (m, 0.2H), 3.61 (s, 2.4H), 3.59 (s, 0.6H), 2.53-2.42 (m, 0.1H), 2.29-2.17 (m, 1.9H), 2.04-1.91 (m, 2H), 1.78-1.65 (m, 2H), 1.59 (s, 9H).

Compound 299H: LC-MS (ESI): $R_T$=2.177 min, mass calcd. for $C_{25}H_{27}ClF_2N_4O_4S$ 552.1, m/z found 453.0 [M+H−Boc]$^+$. $^1$H NMR (400 MHz, CDCl$_3$) δ 8.26 (br s, 0.1H), 7.86 (d, J=2.4 Hz, 0.8H), 7.81 (d, J=3.2 Hz, 0.2H), 7.57-7.54 (m, 1.7H), 7.45 (d, J=3.2 Hz, 0.2H), 7.12-7.00 (m, 2H), 6.17-6.16 (m, 1H), 6.08 (d, J=2.4 Hz, 1H), 4.78-4.69 (m, 0.1H), 4.49-4.41 (m, 1H), 4.21-4.17 (m, 0.7H), 4.10-4.05 (m, 0.2H), 3.62 (s, 2H), 3.59 (s, 1H), 2.54-2.40 (m, 0.2H), 2.23-2.08 (m, 1.8H), 1.99-1.89 (m, 2H), 1.80-1.60 (m, 2H), 1.50 (s, 9H).

Compound 301: Ethyl 4-(2-chloro-3,4-difluorophenyl)-6-(4-(methoxycarbonyl)-cycloheptyl)-2-(thiazol-2-yl)-1,4-dihydropyrimidine-5-carboxylate LC-MS (ESI): $R_T$=1.73 min, mass calcd. for $C_{25}H_{26}ClF_2N_3O_4S$ 537.1, m/z found 538.5 [M+H]$^+$. $^1$H NMR (400 MHz, DMSO-d$_6$) δ 9.50 (d, J=2.8 Hz, 0.6H), 9.09-8.96 (m, 0.4H), 8.03-7.96 (m, 1.6H), 7.93 (d, J=2.8 Hz, 0.4H), 7.52-7.41 (m, 1H), 7.24-7.13 (m, 1H), 6.01 (s, 0.4H), 5.91 (d, J=2.8 Hz, 0.6H), 4.02-3.91 (m, 2.4H), 3.86-3.76 (m, 0.6H), 3.65-3.59 (m, 3H), 2.65-2.54 (m, 1H), 2.08-1.58 (m, 9.4H), 1.49-1.37 (m, 0.6H), 1.07 (t, J=7.2 Hz, 1.8H), 1.05 (t, J=7.2 Hz, 1.2H).

The mixture of compound 301 (2.00 g, 3.72 mmol) was separated by chiral Prep. HPLC (first separation condition: Column: Chiralpak IC 5 μm 20*250 mm; Mobile Phase: CO$_2$:MeOH=75:25 at 50 g/min; Wavelength: 214 nm; second separation condition: Column: Chiralpak AD-H 5 μm 20*250 mm; Mobile Phase: Hex:EtOH:DEA=90:10:0.3 at 15 mL/min; Wavelength: 230 nm; third separation condition: Column: Superchiral S-OJ 5 Lm 21*250 mm; Mobile Phase: Hex:EtOH=95:5 at 20 mL/min; Wavelength: 254 nm; fourth separation condition: Column: Chiralpak IC 5 Lm 50*250 mm; Mobile Phase: Hex:IPA:DEA=95:5:0.1 at 60 mL/min; Wavelength: 254 nm; fifth separation condition: Column: Chiralpak IE 5 Lm 50*250 mm; Mobile Phase: Hex:IPA:DEA=95:5:0.1 at 60 mL/min; Wavelength: 254 nm) to give 301M (190 mg, 99.9% purity, 9.5% yield, 100% stereopure), 301N (185 mg, 99.9% purity, 9.3% yield, 100% stereopure), 301P (170 mg, 99.9% purity, 8.5% yield, 100% stereopure), 301Q (190 mg, 99.9% purity, 9.5% yield, 100% stereopure), 301U (150 mg, 99.9% purity, 7.5% yield, 99.8% stereopure), 301V (130 mg, 99.9% purity, 6.5% yield, 100% stereopure), 301X (245 mg, 98.5% purity, 12.3% yield, 97.8% stereopure) and 301Y (260 mg, 99.1% purity, 13.0% yield, 100% stereopure) as yellow solids.

Compound 301M: LC-MS (ESI): $R_T$=4.614 min, mass calcd. for $C_{25}H_{26}ClF_2N_3O_4S$ 537.1, m/z found 538.1 [M+H]$^+$. Chiral analysis (Column: Chiralpak IC 5 μm 4.6*250 mm; Mobile Phase: Hex:IPA:DEA=95:5:0.2 at 1.0 mL/min; Temp: 30° C.; Wavelength: 254 nm, $R_T$=10.942 min). $^1$H NMR (400 MHz, DMSO-d$_6$) δ 9.51 (d, J=2.8 Hz, 0.6H), 8.99 (s, 0.4H), 8.02-7.96 (m, 1.6H), 7.94 (s, 0.4H), 7.50-7.43 (m, 1H), 7.23-7.15 (m, 1H), 6.01 (s, 0.4H), 5.91 (d, J=2.8 Hz, 0.6H), 4.02-3.92 (m, 2.4H), 3.85-3.76 (m, 0.6H), 3.62 (s, 3H), 2.68-2.57 (m, 1H), 2.15-1.94 (m, 3H), 1.91-1.74 (m, 4H), 1.72-1.58 (m, 2H), 1.46-1.34 (m, 1H), 1.11-1.01 (m, 3H).

Compound 301N: LC-MS (ESI): $R_T$=4.615 min, mass calcd. for $C_{25}H_{26}ClF_2N_3O_4S$ 537.1, m/z found 538.1 [M+H]$^+$. Chiral analysis (Column: Chiralpak IC 5 μm 4.6*250 mm; Mobile Phase: Hex:IPA:DEA=95:5:0.2 at 1.0 mL/min; Temp: 30° C.; Wavelength: 254 nm, $R_T$=13.356 min). $^1$H NMR (400 MHz, DMSO-d$_6$) δ 9.51 (d, J=2.8 Hz, 0.6H), 8.99 (s, 0.4H), 8.02-7.96 (m, 1.6H), 7.94 (d, J=3.2 Hz, 0.4H), 7.51-7.43 (m, 1H), 7.23-7.16 (m, 1H), 6.01 (s, 0.4H), 5.91 (d, J=3.6 Hz, 0.6H), 4.00-3.94 (m, 2.4H), 3.84-3.76 (m, 0.6H), 3.62 (s, 3H), 2.65-2.57 (m, 1H), 2.15-1.94 (m, 3H), 1.91-1.74 (m, 4H), 1.72-1.58 (m, 2H), 1.45-1.35 (m, 1H), 1.11-1.03 (m, 3H).

Compound 301P: LC-MS (ESI): $R_T$=4.576 min, mass calcd. for $C_{25}H_{26}ClF_2N_3O_4S$ 537.1, m/z found 538.1 [M+H]$^+$. Chiral analysis (Column: Chiralpak IC 5 μm 4.6*250 mm; Mobile Phase: CO$_2$:MeOH=75:25 at 3 g/min; Col Temp: 40° C.; Wavelength: 214 nm; Back pressure: 100 bar; $R_T$=3.82 min). $^1$H NMR (400 MHz, DMSO-d$_6$) δ 9.50 (d, J=2.8 Hz, 0.6H), 9.04 (s, 0.4H), 8.03-7.96 (m, 1.6H), 7.93 (d, J=3.2 Hz, 0.4H), 7.50-7.43 (m, 1H), 7.22-7.16 (m, 1H), 6.01 (s, 0.4H), 5.91 (d, J=3.2 Hz, 0.6H), 4.00-3.93 (m, 2.4H), 3.85-3.77 (m, 0.6H), 3.61 (s, 3H), 2.78-2.72 (m, 0.4H), 2.61-2.55 (m, 0.6H), 2.08-1.99 (m, 1.5H), 1.95-1.85 (m, 3H), 1.81-1.56 (m, 5.5H), 1.10-1.03 (m, 3H).

Compound 301Q: LC-MS (ESI): $R_T$=4.611 min, mass calcd. for $C_{25}H_{26}ClF_2N_3O_4S$ 537.1, m/z found 538.1 [M+H]$^+$. Chiral analysis (Column: Chiralpak AD-H 5 μm 4.6*250 mm; Mobile Phase: Hex:EtOH:DEA=90:10:0.2 at 1.0 mL/min; Temp: 30° C.; Wavelength: 230 nm, $R_T$=5.704 min). $^1$H NMR (400 MHz, DMSO-d$_6$) δ 9.50 (s, 0.6H), 9.03 (s, 0.4H), 8.03-7.95 (m, 1.6H), 7.94-7.91 (m, 0.4H), 7.50-7.40 (m, 1H), 7.21-7.12 (m, 1H), 6.01 (s, 0.4H), 5.91 (s, 0.6H), 4.00-3.91 (m, 2.4H), 3.85-3.77 (m, 0.6H), 3.65-3.55 (m, 3H), 2.69-2.63 (m, 0.4H), 2.60-2.54 (m, 0.6H), 2.07-1.75 (m, 7.5H), 1.71-1.58 (m, 1.5H), 1.49-1.37 (m, 1H), 1.09-1.03 (m, 3H).

Compound 301U: LC-MS (ESI): $R_T$=3.046 min, mass calcd. for $C_{25}H_{26}ClF_2N_3O_4S$ 537.1, m/z found 538.2 [M+H]$^+$. Chiral analysis (Column: Chiralpak AD-H 5 μm 4.6*250 mm; Mobile Phase: Hex:EtOH:DEA=90:10:0.2 at 1.0 mL/min; Temp: 30° C.; Wavelength: 230 nm, $R_T$=8.566 min). $^1$H NMR (400 MHz, DMSO-d$_6$) δ 9.51 (d, J=3.6 Hz, 0.6H), 9.03 (s, 0.4H), 8.02-7.96 (m, 1.6H), 7.94 (d, J=3.2 Hz, 0.4H), 7.50-7.43 (m, 1H), 7.21-7.12 (m, 1H), 6.01 (s, 0.4H), 5.91 (d, J=3.2 Hz, 0.6H), 4.00-3.93 (m, 2.4H), 3.86-3.77 (m, 0.6H), 3.63 (s, 1.2H), 3.61 (s, 1.8H), 2.69-2.63 (m, 0.4H), 2.60-2.54 (m, 0.6H), 2.04-1.76 (m, 7.5H), 1.71-1.59 (m, 1.5H), 1.48-1.39 (m, 1H), 1.09-1.03 (m, 3H).

Compound 301V: LC-MS (ESI): $R_T$=3.113 min, mass calcd. for $C_{25}H_{26}ClF_2N_3O_4S$ 537.1, m/z found 538.1 [M+H]$^+$. Chiral analysis (Column: Chiralpak IC 5 μm 4.6*250 mm; Mobile Phase: CO₂:MeOH=75:25 at 3 g/min; Col Temp: 40° C.; Wavelength: 230 nm; Back pressure: 100 bar; $R_T$=4.06 min). ¹H NMR (400 MHz, DMSO-d₆) δ 9.51 (d, J=3.6 Hz, 0.6H), 9.08 (s, 0.4H), 8.03-7.96 (m, 1.6H), 7.93 (d, J=3.2 Hz, 0.4H), 7.50-7.43 (m, 1H), 7.21-7.13 (m, 1H), 6.01 (s, 0.4H), 5.91 (d, J=3.2 Hz, 0.6H), 4.00-3.93 (m, 2.4H), 3.84-3.77 (m, 0.6H), 3.61 (s, 1.2H), 3.60 (s, 1.8H), 2.73-2.67 (m, 0.4H), 2.59-2.54 (m, 0.6H), 2.08-1.96 (m, 1.5H), 1.95-1.80 (m, 3.5H), 1.77-1.66 (m, 4H), 1.61-1.52 (m, 1H), 1.09-1.03 (m, 3H).

Compound 301X: LC-MS (ESI): $R_T$=3.380 min, mass calcd. for $C_{25}H_{26}ClF_2N_3O_4S$ 537.1, m/z found 538.2 [M+H]⁺. Chiral analysis (Column: Chiralpak IC 5 μm 4.6*250 mm; Mobile Phase: CO₂:MeOH=75:25 at 3 g/min; Col Temp: 40° C.; Wavelength: 230 nm; Back pressure: 100 bar; $R_T$=4.62 min). ¹H NMR (400 MHz, DMSO-d₆) δ 9.51 (d, J=3.6 Hz, 0.6H), 9.08 (s, 0.4H), 8.03-7.96 (m, 1.6H), 7.93 (d, J=3.2 Hz, 0.4H), 7.50-7.43 (m, 1H), 7.21-7.13 (m, 1H), 6.01 (s, 0.4H), 5.91 (d, J=3.2 Hz, 0.6H), 4.00-3.93 (m, 2.4H), 3.84-3.77 (m, 0.6H), 3.61 (s, 1.2H), 3.60 (s, 1.8H), 2.73-2.67 (m, 0.4H), 2.59-2.54 (m, 0.6H), 2.08-1.96 (m, 1.5H), 1.95-1.80 (m, 3.5H), 1.77-1.66 (m, 4H), 1.61-1.52 (m, 1H), 1.09-1.03 (m, 3H).

Compound 301Y: LC-MS (ESI): $R_T$=3.396 min, mass calcd. for $C_{25}H_{26}ClF_2N_3O_4S$ 537.1, m/z found 538.2 [M+H]⁺. Chiral analysis (Column: Chiralpak IC 5 μm 4.6*250 mm; Mobile Phase: CO₂:MeOH=75:25 at 3 g/min; Col Temp: 40° C.; Wavelength: 214 nm; Back pressure: 100 bar; $R_T$=5.88 min). ¹H NMR (400 MHz, DMSO-d₆) δ 9.51 (d, J=2.8 Hz, 0.6H), 9.05 (s, 0.4H), 8.02-7.96 (m, 1.6H), 7.94 (d, J=2.8 Hz, 0.4H), 7.50-7.43 (m, 1H), 7.22-7.15 (m, 1H), 6.01 (s, 0.4H), 5.91 (d, J=3.2 Hz, 0.6H), 4.00-3.93 (m, 2.4H), 3.86-3.76 (m, 0.6H), 3.61 (s, 3H), 2.80-2.72 (m, 0.4H), 2.63-2.57 (m, 0.6H), 2.10-1.99 (m, 1.5H), 1.95-1.84 (m, 3H), 1.82-1.55 (m, 5.5H), 1.09-1.03 (m, 3H).

Compound 306: Methyl 6-(1-(tert-butoxycarbonyl)piperidin-4-yl)-4-(3,4-difluoro-2-methylphenyl)-2-(thiazol-2-yl)-1,4-dihydropyrimidine-5-carboxylate LC-MS (ESI): $R_T$=1.96 min, mass calcd. For $C_{26}H_{30}F_2N_4O_4S$ 532.2 m/z found 533.3 [M+H]⁺. ¹H NMR (400 MHz, DMSO-d₆) δ 9.56 (d, J=3.2 Hz, 0.8H), 9.13 (s, 0.2H), 7.99-7.91 (m, 2H), 7.25-7.18 (m, 1H), 7.11-7.08 (m, 0.8H), 6.97-6.94 (m, 0.2H), 5.82 (s, 0.2H), 5.69 (d, J=3.2 Hz, 0.8H), 4.14-4.00 (m, 2.2H), 3.81-3.75 (m, 0.8H), 3.52 (s, 3H), 2.85-2.68 (m, 2H), 2.43 (s, 3H), 1.91-1.64 (m, 3H), 1.52-1.48 (m, 1H), 1.44 (s, 9H).

A racemic mixture of 306 (600 mg, 1.13 mmol) was separated by chiral Prep. SFC (separation condition: Column: Chiralpak IG 5 μm 20*250 mm; Mobile Phase: CO₂:MeOH:DEA=80:20:0.2 at 50 g/min; Col. Temp 40° C.; Wavelength: 214 nm; Back pressure: 100 bar) to afford the title compounds 306A (260 mg, 43% yield, 100% stereopure) and 306B (270 mg, 45% yield, 98.6% stereopure) as yellow solids.

Compound 306A: LC-MS (ESI): $R_T$=1.87 min, mass calcd. For $C_{26}H_{30}F_2N_4O_4S$ 532.2 m/z found 533.6 [M+H]⁺. Chiral analysis (Column: Chiralpak IG; Mobile Phase: CO₂: MeOH:DEA=80:20:0.2 at 3.0 g/min; Col. Temp: 40.1° C.; Wavelength: 230 nm, Back pressure: 100 bar, $R_T$=3.08 min). ¹H NMR (300 MHz, CDCl₃) δ 8.10 (s, 0.7H), 7.80 (s, 1H), 7.51 (d, J=2.1 Hz, 0.3H), 7.43 (d, J=2.4 Hz, 0.7H), 7.09-7.06 (m, 0.3H), 7.04 (s, 0.2H), 6.97-6.85 (m, 1.8H), 5.93 (s, 0.8H), 5.85 (s, 0.2H), 4.39-4.16 (m, 2.8H), 3.85-3.78 (m, 0.2H), 3.60 (s, 3H), 2.94-2.79 (m, 2H), 2.57 (s, 2.3H), 2.42 (s, 0.7H), 2.00-1.97 (m, 1H), 1.87-1.63 (m, 3H), 1.50 (s, 9H).

Compound 306B: LC-MS (ESI): $R_T$=1.87 min, mass calcd. For $C_{26}H_{30}F_2N_4O_4S$ 532.2 m/z found 533.7 [M+H]⁺. Chiral analysis (Column: Chiralpak IG; Mobile Phase: CO₂: MeOH:DEA=80:20:0.2 at 3.0 g/min; Col. Temp: 39.9° C.; Wavelength: 230 nm, $R_T$=3.96 min). ¹H NMR (300 MHz, CDCl₃) δ 8.10 (s, 0.7H), 7.80-7.79 (m, 1H), 7.51 (d, J=2.1 Hz, 0.3H), 7.43 (d, J=2.1 Hz, 0.7H), 7.09-7.07 (m, 0.3H), 7.05 (s, 0.2H), 6.95-6.87 (m, 1.8H), 5.93 (s, 0.8H), 5.85 (s, 0.2H), 4.37-4.15 (m, 2.7H), 3.84-3.78 (m, 0.3H), 3.60 (s, 3H), 2.94-2.80 (m, 2H), 2.57 (s, 2.3H), 2.43 (s, 0.7H), 2.01-1.97 (m, 1H), 1.75-1.60 (m, 3H), 1.50 (s, 9H).

Compound 314: (trans)-Methyl 6-(-4-(N-(2-((tert-butyldimethylsilyl)oxy)ethyl)methylsulfonamido)cyclohexyl)-4-(2-chloro-3,4-difluorophenyl)-2-(thiazol-2-yl)-1,4-dihydropyrimidine-5-carboxylate LC-MS (ESI): $R_T$=3.077 min, mass calcd. for $C_{30}H_{41}ClF_2N_4O_5S_2Si$ 702.2, m/z found 702.8 [M+H]⁺.

Compound 316: Ethyl 6-(1-(tert-butoxycarbonyl)piperidin-4-yl)-4-(2-chloro-3-fluorophenyl)-2-(thiazol-2-yl)-1,4-dihydropyrimidine-5-carboxylate LC-MS (ESI): $R_T$=1.75 min, mass calcd. for $C_{26}H_{30}ClFN_4O_4S$ 548.2, m/z found 549.6 [M+H]⁺. ¹H NMR (300 MHz, CDCl₃) δ 8.12 (s, 0.5H), 7.83 (s, 1H), 7.51-7.50 (m, 0.5H), 7.46-7.45 (m, 0.5H), 7.38 (d, J=0.6 Hz, 0.5H), 7.19-7.05 (m, 3H), 6.29 (s, 0.5H), 6.16 (s, 0.5H), 4.32-4.03 (m, 5H), 2.90-2.84 (m, 2H), 2.05-1.86 (m, 3H), 1.62-1.52 (m, 1H), 1.50 (s, 9H), 1.15-1.10 (m, 3H).

Compound 326: Ethyl 6-(1-(tert-butoxycarbonyl)piperidin-4-yl)-4-(2-chloro-4-fluorophenyl)-2-(thiazol-2-yl)-1,4-dihydropyrimidine-5-carboxylate LC-MS (ESI): $R_T$=2.01 min, mass calcd. for $C_{26}H_{30}ClFN_4O_4S$ 548.2, m/z found 549.5 [M+H]⁺. ¹H NMR (400 MHz, DMSO-d₆) δ 9.47 (d, J=2.4 Hz, 0.7H), 9.04 (s, 0.3H), 8.01-7.99 (m, 1.7H), 7.93-7.92 (m, 0.3H), 7.43-7.34 (m, 2H), 7.24-7.18 (m, 1H), 6.03 (s, 0.2H), 5.92 (d, J=3.2 Hz, 0.8H), 4.11-4.01 (m, 2H), 3.99-3.94 (m, 2H), 3.83-3.75 (m, 1H), 2.84-2.69 (m, 2H), 1.91-1.66 (m, 3H), 1.57-1.49 (m, 1H), 1.43 (s, 9H), 1.10-1.02 (m, 3H).

A racemic mixture of ethyl 6-(1-(tert-butoxycarbonyl)piperidin-4-yl)-4-(2-chloro-4-fluorophenyl)-2-(thiazol-2-yl)-1,4-dihydropyrimidine-5-carboxylate 326 (2.50 g, 4.55 mmol) was separated by Chiral Prep. HPLC (separation condition: Column: Chiralpak IG 5 μm 20*250 mm; Mobile Phase: CO₂:MeOH=70:30 at 50 g/min; Temp: 30° C.; Wavelength: 214 nm; Back Pressure: 100 bar) to give the title compounds 326A (1.00 g, 40% yield, 100% stereopure) and 326B (1.20 g, 48% yield, 99.8% stereopure) as yellow solids.

Compound 326A: Chiral analysis (Column: Chiralpak IG 5 μm 4.6*250 mm; Mobile Phase: CO₂:MeOH=70:30 at 3 g/min; Temp: 30° C.; Wavelength: 230 nm, Back Pressure: 100 bar; $R_T$=2.5 min).

Compound 326B: Chiral analysis (Column: Chiralpak IG 5 μm 4.6*250 mm; Mobile Phase: CO₂:MeOH=70:30 at 3 g/min; Temp: 30° C.; Wavelength: 230 nm, Back Pressure: 100 bar; $R_T$=3.4 min).

Compound 336: Ethyl 4-(2-bromo-3-fluorophenyl)-6-(1-(tert-butoxycarbonyl)piperidin-4-yl)-2-(thiazol-2-yl)-1,4-dihydropyrimidine-5-carboxylate $^1$H NMR (400 MHz, DMSO-d$_6$) δ 9.48 (d, J=3.2 Hz, 0.7H), 9.06 (s, 0.3H), 8.04-7.92 (m, 2H), 7.44-7.37 (m, 1H), 7.31-7.24 (m, 1H), 7.21-7.15 (m, 1H), 6.07 (s, 0.3H), 5.97 (d, J=3.6 Hz, 0.7H), 4.16-3.93 (m, 4.3H), 3.83-3.76 (m, 0.7H), 2.85-2.67 (m, 2H), 1.96-1.64 (m, 3.3H), 1.54-1.50 (m, 0.7H), 1.44 (s, 9H), 1.08-1.01 (m, 3H).

Compound 340: Ethyl 6-(1-(tert-butoxycarbonyl)piperidin-4-yl)-4-(3,4-difluoro-2-methylphenyl)-2-(thiazol-2-yl)-1,4-dihydropyrimidine-5-carboxylate LC-MS (ESI): R$_T$=2.879 min, mass calcd. for C$_{27}$H$_{32}$F$_2$N$_4$O$_4$S 546.2, m/z found 546.9 [M+H]$^+$. $^1$H NMR (400 MHz, CDCl$_3$) δ 8.08 (s, 1H), 7.80 (d, J=3.2 Hz, 1H), 7.50 (d, J=3.2 Hz, 0.2H), 7.43 (d, J=3.2 Hz, 0.8H), 7.10-7.05 (0.4H), 6.93-6.90 (m, 1.6H), 5.95 (s, 0.8H), 5.86-5.85 (m, 0.2H), 4.36-4.28 (m, 2H), 4.21-4.05 (m, 2.7H), 3.84-3.79 (m, 0.3H), 2.92-2.83 (m, 2H), 2.57-2.56 (m, 2.3H), 2.43-2.42 (m, 0.7H), 2.01-1.98 (m, 1H), 1.86-1.83 (m, 1H), 1.77-1.68 (m, 2H), 1.50 (s, 9H), 1.13 (t, J=2.8 Hz, 3H).

Racemic 340 (2.40 g, 4.39 mmol) was separated by prep. chiral SFC (separation condition: Column: Chiralpak IG 5 μm 20*250 mm; Mobile Phase: CO$_2$:MeOH=80:20 at 50 g/min; Col. Temp 40° C.; Wavelength: 230 nm; Back pressure: 100 bar) to afford the title compounds 340A (700 mg, 29% yield, 100% stereopure) and 340B (800 mg, 33% yield, 99.4% stereopure) as yellow solids.

Compound 340A: Chiral analysis (Column: Chiralpak IG 5 μm 4.6*250 mm; Mobile Phase: CO$_2$:MeOH:DEA=80:20:0.2 at 3.0 mL/min; Temp: 40.1° C.; Wavelength: 230 nm, R$_T$=3.00 min). $^1$H NMR (300 MHz, DMSO-d$_6$) δ 9.60 (s, 0.7H), 9.12 (s, 0.3H), 8.00-7.93 (m, 2H), 7.47-7.41 (m, 1H), 7.23-7.17 (m, 1H), 6.03 (s, 0.3H), 5.93 (s, 0.7H), 4.19-3.75 (m, 5H), 2.89-2.64 (m, 2H), 2.51 (s, 2H), 2.49 (s, 1H), 2.00-1.57 (m, 4H), 1.53 (s, 9H), 1.10-1.02 (m, 3H).

Compound 340B: Chiral analysis (Column: Chiralpak IG 5 μm 4.6*250 mm; Mobile Phase: CO$_2$:MeOH:DEA=80:20:0.2 at 3.0 mL/min; Temp: 39.9° C.; Wavelength: 230 nm, R$_T$=3.85 min). $^1$H NMR (300 MHz, DMSO-d$_6$) δ 9.60 (s, 0.7H), 9.12 (s, 0.3H), 8.03-7.93 (m, 2H), 7.50-7.41 (m, 1H), 7.22-7.16 (m, 1H), 6.03 (s, 0.3H), 5.93 (s, 0.7H), 4.14-3.75 (m, 5H), 2.83-2.66 (m, 2H), 2.51 (s, 2H), 2.49 (s, 1H), 1.92-1.57 (m, 4H), 1.53 (s, 9H), 1.10-1.02 (m, 3H).

Compound 344: (trans)-Ethyl 4-(2-chloro-3,4-difluorophenyl)-6-(4-(methoxycarbonyl)cyclohexyl)-2-(thiazol-2-yl)-1,4-dihydropyrimidine-5-carboxylate LC-MS (ESI): R$_T$=3.884 min, mass calcd. for C$_{24}$H$_{24}$ClF$_2$N$_3$O$_4$S 523.1, m/z found 524.1 [M+H]$^+$. $^1$H NMR (400 MHz, DMSO-d$_6$) δ 9.51 (d, J=3.2 Hz, 0.6H), 8.92 (br s, 0.4H), 8.05-7.99 (m, 1.6H), 7.93 (d, J=3.6 Hz, 0.4H), 7.49-7.41 (m, 1H), 7.21-7.15 (m, 1H), 6.02 (s, 0.4H), 5.92 (d, J=3.6 Hz, 0.6H), 4.00-3.93 (m, 2H), 3.86-3.80 (m, 0.4H), 3.62 (s, 1.3H), 3.61 (s, 1.7H), 3.58-3.54 (m, 0.6H), 2.55-2.51 (m, 0.4H), 2.36-2.30 (m, 0.6H), 2.07-1.98 (m, 2H), 1.89-1.65 (m, 4H), 1.48-1.35 (m, 2H), 1.09-1.03 (m, 3H).

Racemic 344 (500 mg, 0.955 mmol) was separated by chiral Prep. HPLC (Column: Chiralpak IC 5 μm 20*250 mm; Mobile Phase: Hex:EtOH=85:15 at 25 mL/min; Temp: 30° C.; Wavelength: 230 nm) to afford the title compounds 344M (220 mg, 44% yield, 100% stereopure) and 344N (220 mg, 44% yield, 100% stereopure) as yellow solids.

Compound 344M: LC-MS (ESI): R$_T$=3.866 min, mass calcd. for C$_{24}$H$_{24}$ClF$_2$N$_3$O$_4$S 523.1, m/z found 524.0 [M+H]$^+$. Chiral analysis (Column: Chiralpak IC 5 μm 4.6*250 mm; Mobile Phase: Hex:EtOH=85:15 at 1.0 mL/min; Temp: 30° C.; Wavelength: 230 nm, R$_T$=6.857 min). $^1$H NMR (400 MHz, DMSO-d$_6$) δ 9.51 (br s, 0.6H), 8.92 (br s, 0.4H), 8.03-7.98 (m, 1.6H), 7.93 (d, J=3.6 Hz, 0.4H), 7.48-7.42 (m, 1H), 7.21-7.15 (m, 1H), 6.02 (s, 0.4H), 5.92 (s, 0.6H), 4.00-3.93 (m, 2H), 3.87-3.80 (m, 0.5H), 3.62 (s, 1.3H), 3.61 (s, 1.7H), 3.58-3.53 (m, 0.5H), 2.55-2.52 (m, 0.5H), 2.36-2.30 (m, 0.5H), 2.04-1.97 (m, 2H), 1.90-1.65 (m, 4H), 1.48-1.38 (m, 2H), 1.09-1.03 (m, 3H).

Compound 344N: LC-MS (ESI): R$_T$=3.859 min, mass calcd. for C$_{24}$H$_{24}$ClF$_2$N$_3$O$_4$S 523.1, m/z found 524.1 [M+H]$^+$. Chiral analysis (Column: Chiralpak IC 5 μm 4.6*250 mm; Mobile Phase: Hex:EtOH=85:15 at 1.0 mL/min; Temp: 30° C.; Wavelength: 230 nm, R$_T$=8.931 min). $^1$H NMR (400 MHz, DMSO-d$_6$) δ 9.51 (d, J=3.2 Hz, 0.6H), 8.92 (br s, 0.4H), 8.05-7.99 (m, 1.6H), 7.93 (d, J=2.8 Hz, 0.4H), 7.49-7.42 (m, 1H), 7.20-7.15 (m, 1H), 6.02 (s, 0.4H), 5.92 (d, J=2.8 Hz, 0.6H), 4.00-3.93 (m, 2H), 3.87-3.79 (m, 0.5H), 3.62 (s, 1.3H), 3.61 (s, 1.7H), 3.58-3.54 (m, 0.5H), 2.55-2.53 (m, 0.5H), 2.35-2.31 (m, 0.5H), 2.08-1.97 (m, 2H), 1.90-1.65 (m, 4H), 1.45-1.39 (m, 2H), 1.09-1.03 (m, 3H).

Compound 346: (trans)-Ethyl 4-(2-bromo-3,4-difluorophenyl)-6-(4-(methoxycarbonyl)cyclohexyl)-2-(thiazol-2-yl)-1,4-dihydropyrimidine-5-carboxylate 1H NMR (400 MHz, DMSO-d$_6$) δ 9.45 (s, 0.5H), 8.94 (s, 0.5H), 7.99-7.90 (m, 2H), 7.56-7.45 (m, 1H), 7.23-7.14 (m, 1H), 6.01 (s, 0.5H), 5.92 (s, 0.5H), 3.99-3.91 (m, 1H), 3.87-3.78 (m, 0.5H), 3.61 (s, 3H), 3.54-3.49 (m, 0.5H), 2.50-2.49 (m, 0.5H), 2.39-2.26 (m, 0.5H), 2.10-2.01 (m, 2H), 1.93-1.72 (m, 4H), 1.43-1.36 (m, 2H), 1.06-1.00 (m, 3H).

Racemic 346 (700 mg, 1.23 mmol) was separated by chiral Prep. SFC (Column: Chiralpak IC 5 μm 20*250 mm; Mobile Phase: CO$_2$:MeOH=70:30 at 50 g/min; Col. Temp: 39.9° C.; Wavelength: 214 nm, Back pressure: 100 bar) to give the title compounds 346M (300 mg, 50% yield, 100% stereopure) and 346N (200 mg, 33% yield, 100% stereopure) as yellow solids.

Compound 346M: LC-MS (ESI): R$_T$=4.110 min, mass calcd. for C$_{24}$H$_{24}$BrF$_2$N$_3$O$_4$S 567.1, m/z found 568.0 [M+H]$^+$. Chiral analysis (Column: Chiralpak IC 5 μm 4.6*250 mm, Mobile Phase: CO$_2$:MeOH=70:30 at 2.999 g/min; Col. Temp: 39.9° C.; Wavelength: 230 nm, Back pressure: 100 bar, R$_T$=3.30 min). $^1$H NMR (400 MHz, DMSO-d$_6$) δ 9.47 (s, 0.5H), 8.92 (s, 0.5H), 7.99 (s, 1.5H), 7.93 (d, J=2.8 Hz, 0.5H), 7.55-7.46 (m, 1H), 7.22-7.12 (m, 1H), 6.01 (s, 0.5H), 5.92 (s, 0.5H), 3.99-3.95 (m, 2H), 3.87-3.80 (m, 0.5H), 3.58 (s, 3H), 3.55-3.51 (m, 0.5H), 2.36-2.29 (m, 0.6H), 2.05-2.01 (m, 2.4H), 1.90-1.82 (m, 2H), 1.76-1.59 (m, 2H), 1.46-1.42 (m, 2H), 1.10-1.03 (m, 3H).

Compound 346N: LC-MS (ESI): R$_T$=4.122 min, mass calcd. for C$_{24}$H$_{24}$BrF$_2$N$_3$O$_4$S 567.1, m/z found 568.0 [M+H]$^+$. Chiral analysis (Column: Chiralpak IC 5 μm 4.6*250 mm, Mobile Phase: CO$_2$:MeOH=70:30 at 2.999 g/min; Col. Temp: 39.9° C.; Wavelength: 230 nm, Back pressure: 100 bar, R$_T$=4.78 min). $^1$H NMR (400 MHz, DMSO-d$_6$) δ 9.49 (s, 0.5H), 8.92 (s, 0.5H), 7.99 (s, 1.5H), 7.93 (d, J=3.2 Hz, 0.5H), 7.54-7.43 (m, 1H), 7.22-7.12 (m, 1H), 6.01 (s, 0.5H), 5.91 (d, J=3.2 Hz, 0.5H), 3.99-3.95 (m, 2H), 3.90-3.75 (m, 0.5H), 3.62 (s, 1.5H), 3.61 (s, 1.5H), 3.57-3.52 (m, 0.5H), 2.38-2.31 (m, 1H), 2.09-2.01 (m, 2H), 1.87-1.59 (m, 4H), 1.51-1.40 (m, 2H), 1.10-1.03 (m, 3H).

Compound 349: Ethyl 6-(1-(tert-butoxycarbonyl)piperidin-4-yl)-4-(2-chloro-3,4-difluorophenyl)-2-(3,5-difluoropyridin-2-yl)-1,4-dihydropyrimidine-5-carboxylate LC-MS (ESI): $R_T$=1.806 min, mass calcd. for $C_{28}H_{29}ClF_4N_4O_4$ 596.2, m/z found 597.2 [M+H]$^+$. $^1$H NMR (400 MHz, CDCl$_3$) δ 8.61 (s, 0.7H), 8.31 (d, J=2.4 Hz, 0.7H), 8.25 (d, J=2.0 Hz, 0.3H), 7.75 (s, 0.3H), 7.33-7.28 (m, 1H), 7.09-6.97 (m, 2H), 6.32 (s, 0.7H), 6.07 (d, J=2.4 Hz, 0.3H), 4.39-4.18 (m, 2.7H), 4.10-3.89 (m, 2.3H), 2.97-2.78 (m, 2H), 1.88-1.82 (m, 1H), 1.70-1.57 (m, 3H), 1.51 (s, 6.3H), 1.49 (s, 2.7H), 1.16-1.11 (m, 3H).

Racemic 349 (300 mg, 0.052 mmol) was separated by chiral Prep. HPLC (Column: Chiralpak IC 5 μm 20*250 mm; Mobile Phase: Hex:IPA=90:10 at 25 mL/min; Temp: 30° C.; Wavelength: 214 nm) to afford the title compounds 349A (120 mg, 40% yield, 100% stereopure) and 349A (135 mg, 45% yield, 100% stereopure).

Intermediate 349A: LC-MS (ESI): $R_T$=3.116 and 3.294 min, mass calcd. for $C_{28}H_{29}ClF_4N_4O_4$ 596.2, m/z found 597.1 [M+H]$^+$. Chiral analysis (Column: Chiralpak IC 5 μm 4.6*250 mm; Mobile Phase: Hex:IPA=90:10 at 1.0 mL/min; Temp: 30° C.; Wavelength: 230 nm; $R_T$=14.784 min). $^1$H NMR (400 MHz, DMSO-d$_6$) δ 9.27 (s, 0.6H), 9.17 (d, J=3.6 Hz, 0.4H), 8.56 (d, J=2.0 Hz, 1H), 8.08-8.02 (m, 1H), 7.49-7.43 (m, 1H), 7.24-7.18 (m, 1H), 6.04 (s, 0.6H), 5.94 (d, J=2.8 Hz, 0.4H), 4.17-3.94 (m, 4.6H), 3.82-3.75 (m, 0.4H), 2.84-2.67 (m, 2H), 1.84-1.61 (m, 3.6H), 1.53-1.46 (m, 0.4H), 1.41 (s, 9H), 1.09-1.02 (m, 3H).

Intermediate 349A: LC-MS (ESI): $R_T$=2.896 and 3.173 min, mass calcd. for $C_{28}H_{29}ClF_4N_4O_4$ 596.2, m/z found 597.1 [M+H]$^+$. Chiral analysis (Column: Chiralpak IC 5 μm 4.6*250 mm; Mobile Phase: Hex:IPA=90:10 at 1.0 mL/min; Temp: 30° C.; Wavelength: 230 nm; $R_T$=19.839 min). $^1$H NMR (400 MHz, DMSO-d$_6$) δ 9.28 (s, 0.6H), 9.17 (s, 0.4H), 8.56 (d, J=2.4 Hz, 1H), 8.07-8.02 (m, 1H), 7.51-7.43 (m, 1H), 7.24-7.17 (m, 1H), 6.04 (s, 0.6H), 5.94 (d, J=2.8 Hz, 0.4H), 4.15-3.94 (m, 4.6H), 3.82-3.73 (m, 0.4H), 2.84-2.67 (m, 2H), 1.84-1.68 (m, 3.6H), 1.52-1.46 (m, 0.4H), 1.41 (s, 9H), 1.09-1.00 (m, 3H).

Compound 359E and 359F: (cis)-Methyl 4-(2-chloro-3,4-difluorophenyl)-6-(4-(N-(2-methoxyethyl)sulfamoyl)cyclohexyl)-2-(thiazol-2-yl)-1,4-dihydropyrimidine-5-carboxylate and (trans)-methyl 4-(2-chloro-3,4-difluorophenyl)-6-(4-(N-(2-methoxyethyl)sulfamoyl)cyclohexyl)-2-(thiazol-2-yl)-1,4-dihydropyrimidine-5-carboxylate Separation condition: Prep. HPLC (separation condition: Column: Gilson X-bridge C18 (5 μm 19 mm*150 mm), Mobile Phase A: water (+0.1% ammonium bicarbonate), Mobile Phase B: acetonitrile, UV: 254 nm, Flow rate: 15 mL/min, Gradient: 50-70% (% B)) to give the title compounds 359E (130 mg, 9% yield) and 359F (430 mg, 29% yield) as yellow solids.

Compound 359E: LC-MS (ESI): $R_T$=3.771 min, mass calcd. for $C_{24}H_{27}ClF_2N_4O_5S_2$ 588.1, m/z found 589.1 [M+H]$^+$. $^1$H NMR (400 MHz, DMSO-d$_6$) δ 9.56 (s, 0.7H), 8.31 (s, 0.3H), 8.00-7.96 (m, 2H), 7.49-7.37 (m, 1.3H), 7.22-7.19 (m, 1H), 7.11 (t, J=6.0 Hz, 0.7H), 6.04 (s, 0.3H), 5.93 (s, 0.7H), 3.93-3.87 (m, 0.3H), 3.69 (br s, 0.7H), 3.52 (s, 3H), 3.41-3.37 (m, 2H), 3.27-3.25 (m, 3.3H), 3.17-3.08 (m, 2.7H), 2.37-1.78 (m, 6.3H), 1.65-1.62 (m, 1H), 1.52-1.48 (m, 0.7H).

Compound 359F: LC-MS (ESI): $R_T$=3.648 min, mass calcd. for $C_{24}H_{27}ClF_2N_4O_5S_2$ 588.1, m/z found 589.0 [M+H]$^+$. $^1$H NMR (400 MHz, DMSO-d$_6$) δ 9.57 (d, J=3.6 Hz, 0.6H), 8.99 (s, 0.4H), 8.00-7.94 (m, 2H), 7.49-7.41 (m, 1H), 7.21-7.10 (m, 2H), 6.01 (s, 0.4H), 5.92 (d, J=3.6 Hz, 0.6H), 3.89-3.81 (m, 0.4H), 3.61-3.52 (m, 3.6H), 3.41-3.37 (m, 2H), 3.29 (s, 3H), 3.16-3.10 (m, 2.4H), 3.07-2.99 (m, 0.6H), 2.20-2.13 (m, 2H), 2.01-1.68 (m, 4H), 1.56-1.41 (m, 2H).

Racemic 359E (120 mg, 0.200 mmol) was separated by chiral Prep. HPLC (separation condition: Column: Chiralpak IA 5 μm 20*250 mm; Mobile Phase: Hex:EtOH:DEA=70:30:0.3 at 25 mL/min; Temp: 30° C.; Wavelength: 214 nm) to give the title compounds 359A (40 mg, 33% yield, 100% stereopure) and 359B (45 mg, 38% yield, 100% stereopure) as yellow solids.

Compound 359A: LC-MS (ESI): $R_T$=2.375 min, mass calcd. for $C_{24}H_{27}ClF_2N_4O_5S_2$ 588.1, m/z found 589.0 [M+H]$^+$. Chiral analysis (Column: Chiralpak IA 5 μm 4.6*250 mm; Mobile Phase: Hex:EtOH:DEA=70:30:0.2 at 1.0 mL/min; Temp: 30° C.; Wavelength: 230 nm, $R_T$=7.183 min). $^1$H NMR (400 MHz, DMSO-d$_6$) δ 9.57 (s, 0.7H), 8.31 (s, 0.3H), 8.01-7.96 (m, 2H), 7.49-7.37 (m, 1.3H), 7.22-7.18 (m, 1H), 7.12 (t, J=6.0 Hz, 0.7H), 6.03 (s, 0.3H), 5.92 (s, 0.7H), 3.94-3.86 (m, 0.3H), 3.72-3.66 (m, 0.7H), 3.52 (s, 3H), 3.40-3.35 (m, 2H), 3.27-3.25 (m, 3H), 3.18-3.08 (m, 3H), 2.38-1.76 (m, 6.3H), 1.66-1.62 (m, 1H), 1.51-1.45 (m, 0.7H).

Compound 359B: LC-MS (ESI): $R_T$=2.361 min, mass calcd. for $C_{24}H_{27}ClF_2N_4O_5S_2$ 588.1, m/z found 589.0 [M+H]$^+$. Chiral analysis (Column: Chiralpak IA 5 μm 4.6*250 mm; Mobile Phase: Hex:EtOH:DEA=70:30:0.2 at 1.0 mL/min; Temp: 30° C.; Wavelength: 230 nm, $R_T$=9.264 min). $^1$H NMR (400 MHz, DMSO-d$_6$) δ 9.57 (s, 0.7H), 8.31 (s, 0.3H), 8.01-7.96 (m, 2H), 7.50-7.37 (m, 1.3H), 7.22-7.18 (m, 1H), 7.12 (t, J=6.0 Hz, 0.7H), 6.03 (s, 0.3H), 5.92 (s, 0.7H), 3.94-3.86 (m, 0.3H), 3.72-3.66 (m, 0.7H), 3.52 (s, 3H), 3.41-3.35 (m, 2H), 3.27-3.25 (m, 3H), 3.18-3.08 (m, 3H), 2.37-1.74 (m, 6.3H), 1.65-1.60 (m, 1H), 1.52-1.45 (m, 0.7H).

Racemic 359F (380 mg, 0.65 mmol) was separated by chiral Prep. HPLC (separation condition: Column: Chiralpak IE 5 μm 20*250 mm; Mobile Phase: Hex:EtOH=50:50 at 10 mL/min; Temp: 30° C.; Wavelength: 230 nm) to give the title compounds 359C (150 mg, 39% yield, 100% stereopure) and 359D (130 mg, 34% yield, 100% stereopure) as yellow solids.

Compound 359C: LC-MS (ESI): $R_T$=3.082 min, mass calcd. for $C_{24}H_{27}ClF_2N_4O_5S_2$ 588.1, m/z found 589.0 [M+H]$^+$. Chiral analysis (Column: Chiralpak IE 5 μm 4.6*250 mm; Mobile Phase: Hex:EtOH=50:50 at 1.0 mL/min; Temp: 30° C.; Wavelength: 230 nm, $R_T$=9.329 min). $^1$H NMR (400 MHz, DMSO-d$_6$) δ 9.56 (d, J=3.6 Hz, 0.6H), 8.97 (s, 0.4H), 8.00-7.94 (m, 2H), 7.48-7.41 (m, 1H), 7.21-7.15 (m, 1.4H), 7.10 (t, J=6.0 Hz, 0.6H), 6.01 (s, 0.4H), 5.92 (d, J=3.6 Hz, 0.6H), 3.88-3.80 (m, 0.4H), 3.61-3.52 (m, 3.6H), 3.41-3.37 (m, 2H), 3.28 (s, 3H), 3.18-3.11 (m, 2.4H), 3.06-2.99 (m, 0.6H), 2.20-2.09 (m, 2H), 1.98-1.67 (m, 4H), 1.55-1.41 (m, 2H).

Compound 359D: LC-MS (ESI): $R_T$=3.086 min, mass calcd. for $C_{24}H_{27}ClF_2N_4O_5S_2$ 588.1, m/z found 589.0 [M+H]$^+$. Chiral analysis (Column: Chiralpak IE 5 μm 4.6*250 mm; Mobile Phase: Hex:EtOH=50:50 at 1.0 mL/min; Temp: 30° C.; Wavelength: 230 nm, $R_T$=11.758 min). $^1$H NMR (400 MHz, DMSO-$d_6$) δ 9.56 (d, J=3.2 Hz, 0.6H), 8.97 (s, 0.4H), 8.00-7.94 (m, 2H), 7.48-7.41 (m, 1H), 7.21-7.16 (m, 1.4H), 7.10 (t, J=5.6 Hz, 0.6H), 6.02 (s, 0.4H), 5.92 (d, J=3.6 Hz, 0.6H), 3.89-3.80 (m, 0.4H), 3.62-3.52 (m, 3.6H), 3.41-3.37 (m, 2H), 3.29 (s, 3H), 3.16-3.11 (m, 2.4H), 3.06-3.00 (m, 0.6H), 2.20-2.09 (m, 2H), 1.99-1.68 (m, 4H), 1.55-1.41 (m, 2H).

Compound 361: (trans)-methyl 6-(4-(N-(3-(tert-butoxy)-2,2-dimethyl-3-oxopropyl)sulfamoyl)cyclohexyl)-4-(2-chloro-3,4-difluorophenyl)-2-(thiazol-2-yl)-1,4-dihydropyrimidine-5-carboxylate purified by Prep. HPLC (Column: Gilson Xbridge C18 (5 μm 19*150 mm), Mobile Phase A: water (0.1% ammonium bicarbonate), Mobile Phase B: acetonitrile, UV: 214 nm, Flow rate: 15 mL/min, Gradient: 70-90% (% B)) to give the title compound (200 mg, 24% yield) as yellow solids. LC-MS (ESI): $R_T$=4.561 min, mass calcd. for $C_{30}H_{37}ClF_2N_4O_6S_2$ 686.2, m/z found 686.9 [M+H]$^+$. $^1$H NMR (400 MHz, DMSO-$d_6$) δ 9.58 (d, J=3.6 Hz, 0.6H), 9.00 (s, 0.4H), 8.02-8.01 (m, 1H), 7.99 (d, J=6.4 Hz, 0.6H), 7.96-7.93 (m, 0.4H), 7.49-7.41 (m, 1H), 7.22-7.14 (m, 1H), 7.10-7.06 (m, 0.4H), 7.00-6.96 (m, 0.6H), 6.01 (s, 0.4H), 5.92 (d, J=4.0 Hz, 0.6H), 3.89-3.80 (m, 0.4H), 3.61-3.56 (m, 0.6H), 3.53 (s, 1.8H), 3.52 (s, 1.2H), 3.17-3.13 (m, 0.4H), 3.11-3.05 (m, 2H), 3.03-2.96 (m, 0.6H), 2.23-2.10 (m, 2H), 2.04-1.91 (m, 1H), 1.89-1.75 (m, 2H), 1.73-1.67 (m, 1H), 1.56-1.45 (m, 2H), 1.42 (s, 9H), 1.09 (s, 2.4H), 1.08 (s, 3.6H).

Racemic 361 (190 mg, 0.227 mmol) was separated by chiral Prep. HPLC (separation condition: Column: Chiralpak IE 5 μm 20*250 mm; Mobile Phase: Hex:EtOH:DEA=70:30:0.3 at 14 mL/min; Temp: 30° C.; Wavelength: 214 nm) to afford the title compounds 361X (65 mg, 34% yield, 100% stereopure) and 361Y (65 mg, 34% yield, 99.9% stereopure) as yellow solids.

Compound 361X: LC-MS (ESI): $R_T$=4.288 min, mass calcd. for $C_{30}H_{37}ClF_2N_4O_6S_2$ 686.2, m/z found 687.2 [M+H]$^+$. Chiral analysis (Column: Chiralpak IE 5 μm 4.6*250 mm; Mobile Phase: Hex:EtOH:DEA=70:30:0.2 at 1 mL/min; Temp: 30° C.; Wavelength: 230 nm; $R_T$=10.214 min). H NMR (400 MHz, CDCl$_3$) δ 8.10 (S, 0.5H), 7.84-7.81 (m, 1H), 7.51 (d, J=2.8 Hz, 0.5H), 7.46 (d, J=2.8 Hz, 0.5H), 7.39 (s, 0.5H), 7.07-7.01 (m, 2H), 6.18 (s, 0.5H), 6.05 (d, J=2.0 Hz, 0.5H), 4.93-4.84 (m, 1H), 4.04-3.98 (m, 0.5H), 3.80-3.75 (m, 0.5H), 3.62-3.60 (m, 3H), 3.16-3.13 (m, 2H), 3.06-3.00 (m, 1H), 2.44-1.95 (m, 4H), 1.83-1.64 (m, 3H), 1.46 (s, 9H), 1.23 (m, 6H).

Compound 361Y: LC-MS (ESI): $R_T$=3.650 min, mass calcd. for $C_{30}H_{37}ClF_2N_4O_6S_2$ 686.2, m/z found 687.2 [M+H]$^+$. Chiral analysis (Column: Chiralpak IE 5 μm 4.6*250 mm; Mobile Phase: Hex:EtOH:DEA=70:30:0.2 at 1 mL/min; Temp: 30° C.; Wavelength: 230 nm; $R_T$=13.723 min). $^1$H NMR (400 MHz, CDCl$_3$) δ 8.10 (s, 0.5H), 7.84-7.81 (m, 1H), 7.51 (d, J=3.2 Hz, 0.5H), 7.46 (d, J=3.2 Hz, 0.5H), 7.39 (s, 0.5H), 7.07-7.01 (m, 2H), 6.18 (s, 0.5H), 6.05 (d, J=2.8 Hz, 0.5H), 4.93-4.84 (m, 1H), 4.10-3.98 (m, 0.5H), 3.80-3.75 (m, 0.5H), 3.62-3.60 (m, 3H), 3.16-3.13 (m, 2H), 3.06-3.00 (m, 1H), 2.43-1.95 (m, 4H), 1.84-1.70 (m, 3H), 1.46 (s, 9H), 1.23 (m, 6H).

Compound 362a: Ethyl 4-(2-chloro-4-fluorophenyl)-6-(5-(ethoxycarbonyl)tetrahydro-2H-pyran-2-yl)-2-(thiazol-2-yl)-1,4-dihydropyrimidine-5-carboxylate LC-MS (ESI): $R_T$=2.471 min, mass calcd. for $C_{24}H_{25}ClFN_3O_5S$ 521.1, m/z found 522.1 [M+H]$^+$. $^1$H NMR (400 MHz, DMSO-$d_6$) δ 8.86 (s, 0.2H), 8.80 (s, 0.2H), 8.74 (d, J=4.8 Hz, 0.6H), 8.01-7.96 (m, 2H), 7.45-7.42 (m, 2H), 7.23-7.21 (m, 1H), 6.07 (d, J=2.8 Hz, 0.5H), 6.01 (d, J=5.6 Hz, 0.5H), 5.25-5.08 (m, 1H), 4.46-4.41 (m, 0.5H), 4.34-4.09 (m, 2.5H), 3.99-3.94 (m, 2H), 3.89-3.76 (m, 0.6H), 3.68-3.34 (m, 0.4H), 2.83-2.62 (m, 1H), 2.31-2.12 (m, 1.5H), 2.02-1.65 (m, 2H), 1.61-1.48 (m, 0.5H), 1.33-1.26 (m, 2H), 1.22-1.18 (m, 1H), 1.09-1.04 (m, 3H).

Compound 362R: Ethyl 4-(2-chloro-4-fluorophenyl)-6-(5-(ethoxycarbonyl)tetrahydro-2H-pyran-2-yl)-2-(thiazol-2-yl)-1,4-dihydropyrimidine-5-carboxylate LC-MS (ESI): $R_T$=3.606 and 3.694 min, mass calcd. for $C_{24}H_{25}ClFN_3O_5S$ 521.1, m/z found 522.2 [M+H]$^+$. $^1$H NMR (400 MHz, CD$_3$OD) δ 7.93-7.89 (m, 1H), 7.76-7.75 (m, 1H), 7.49-7.44 (m, 0.5H), 7.41-7.34 (m, 0.5H), 7.24-7.22 (m, 1H), 7.10-7.02 (m, 1H), 6.18 (d, J=4.4 Hz, 0.5H), 6.12 (d, J=3.2 Hz, 0.5H), 5.34-5.20 (m, 1H), 4.60-4.55 (m, 0.5H), 4.21-4.16 (m, 1.8H), 4.15-4.12 (m, 0.7H), 4.03 (q, J=6.8 Hz, 2H), 3.88-3.83 (m, 0.7H), 3.70-3.63 (m, 0.3H), 2.81-2.75 (m, 0.2H), 2.65 (br s, 0.6H), 2.41-2.33 (m, 0.6H), 2.28-2.13 (m, 0.6H), 1.96-1.82 (m, 2.2H), 1.79-1.56 (m, 0.8H), 1.38-1.35 (m, 2H), 1.29-1.25 (m, 1H), 1.15-1.11 (m, 3H).

362a (676 mg, 1.30 mmol) and 362R (962 mg, 1.85 mmol) was further purified by silica gel column chromatography (petroleum ether:ethyl acetate=6:1) to afford the title compound 362W (1.40 g, 2.69 mmol), which was separated by chiral Prep. HPLC (separation condition: Column: Chiralpak IC 5 μm 20*250 mm; Mobile Phase: Hex:EtOH=90:10 at 15 mL/min; Temp: 30° C.; Wavelength: 214 nm) to afford Group 1 (690 mg), Group 2 (92 mg), Group 3 (80 mg), Group 4 (146 mg) and the title compound 362Y (48 mg, 3% yield, 92.7% stereopure). Group 2 was further purified by Prep. HPLC (Column: Waters Kinete EVO C18 (5 μm 21.2*150 mm), Mobile Phase A: water (0.1% ammonia bicarbonate), Mobile Phase B: acetonitrile, UV: 214 nm, Flow rate: 15 mL/min, Gradient: 65-70% (% B)) to give the title compound 362V (50 mg, 4% yield, 100% stereopure), Group 3 was further separated by chiral Prep. HPLC (separation condition: Column: Chiralpak IC 5 μm 20*250 mm; Mobile Phase: Hex:EtOH=90:10 at 25 mL/min; Temp: 30° C.; Wavelength: 214 nm) to afford the title compound 362X (48 mg, 3% yield, 99.2% stereopure), and Group 4 was further separated by chiral Prep. HPLC (separation condition: Column: Chiralpak IC 5 μm 20*250 mm; Mobile Phase: Hex:EtOH=90:10 at 25 mL/min; Temp: 30° C.; Wavelength: 214 nm) to afford the title compound 362T (90 mg, 6% yield, 99.7% stereopure). Group 1 was further separated by chiral Prep. HPLC (separation condition: Column: Chiralpak IC 5 μm 20*250 mm; Mobile Phase: Hex:EtOH=95:5 at 25 mL/min; Temp: 30° C.; Wavelength: 214) to afford Group 5 (140 mg), Group 6 (130 mg), Group 7 (110 mg) and the title compound 362U (60 mg, 4% yield, 100% stereopure). Group 5 was further purified by Prep. HPLC (Column: Gilson X-bridge C18 (5 m 21.2*150 mm), Mobile Phase A: water (0.1% ammonia bicarbonate), Mobile Phase B: acetonitrile, UV: 214 nm, Flow rate: 15 mL/min, Gradient: 65-85% (% B) to give title compound 362M (110 mg, 8% yield, 96.9% stereopure). Group 6 was further purified by Prep. HPLC (Column: Waters kinete EVO C18 (5 μm 21.2*150 mm), Mobile Phase A: water (0.1% ammonia bicarbonate), Mobile Phase B: acetonitrile, UV: 214 nm, Flow rate: 15 mL/min, Gradient: 50-95% (% B) to give title compound 362N (88 mg, 6% yield, 96.9% stereopure), Group 7 was further purified by Prep. HPLC (Column: Waters Gemininx C18 (5 μm 19*150 mm), Mobile Phase A: water (0.1% ammonia bicarbonate), Mobile Phase B: acetonitrile, UV: 214 nm, Flow rate: 15 mL/min, Gradient: 65-95% (% B) to give title compound 362S (86 mg, 6% yield, 94.6% stereopure).

Compound 362M(cis): LC-MS (ESI): $R_T$=3.344 min, mass calcd. for $C_{24}H_{25}ClFN_3O_5S$ 521.1, m/z found 521.9 [M+H]$^+$. Chiral analysis (Column: Chiralpak IC 5 μm 4.6*250 mm; Mobile Phase: Hex:EtOH=95:5 at 1.0 mL/min; Temp: 30° C.; Wavelength: 230 nm; $R_T$=9.833 min). $^1$H NMR (400 MHz, CDCl$_3$) δ 8.92 (br s, 1H), 7.77 (d, J=2.8 Hz, 1H), 7.42-7.38 (m, 2H), 7.11 (dd, J=8.4, 2.4 Hz, 1H), 6.93-6.88 (m, 1H), 6.16 (s, 1H), 5.33 (dd, J=10.8, 2.0 Hz, 1H), 4.63-4.60 (m, 1H), 4.38-4.22 (m, 2H), 4.06-3.98 (m, 2H), 3.82-3.78 (m, 1H), 2.57 (br s, 1H), 2.40-2.37 (m, 1H), 2.02-1.88 (m, 2H), 1.78-1.65 (m, 1H), 1.37 (t, J=7.2 Hz, 3H), 1.12 (t, J=7.2 Hz, 3H).

Compound 362N(cis): LC-MS (ESI): $R_T$=3.348 min, mass calcd. for $C_{24}H_{25}ClFN_3O_5S$ 521.1, m/z found 521.9 [M+H]$^+$. Chiral analysis (Column: Chiralpak IC 5 μm 4.6*250 mm; Mobile Phase: Hex:EtOH=95:5 at 1.0 mL/min; Temp: 30° C.; Wavelength: 230 nm; $R_T$=11.383 min). $^1$H NMR (400 MHz, CDCl$_3$) δ 9.25 (br s, 1H), 7.89 (br s, 1H), 7.62 (br s, 1H), 7.46-7.42 (m, 1H), 7.14 (dd, J=8.8, 2.4 Hz, 1H), 6.96-6.93 (m, 1H), 6.25 (br s, 1H), 5.34 (d, J=10.0 Hz, 1H), 4.62 (d, J=11.6 Hz, 1H), 4.38-4.22 (m, 2H), 4.10-4.01 (m, 2H), 3.82-3.79 (m, 1H), 2.59 (br s, 1H), 2.42-2.38 (m, 1H), 2.00-1.89 (m, 2H), 1.77-1.68 (m, 1H), 1.37 (t, J=7.2 Hz, 3H), 1.14 (t, J=7.2 Hz, 3H).

Compound 362S(cis): LC-MS (ESI): $R_T$=3.334 min, mass calcd. for $C_{24}H_{25}ClFN_3O_5S$ 521.1, m/z found 521.9 [M+H]$^+$. Chiral analysis (Column: Chiralpak IC 5 μm 4.6*250 mm; Mobile Phase: Hex:EtOH=95:5 at 1.0 mL/min; Temp: 30° C.; Wavelength: 230 nm; $R_T$=13.153 min). $^1$H NMR (400 MHz, CDCl$_3$) δ 8.84 (br s, 1H), 7.80 (d, J=3.2 Hz, 1H), 7.41 (d, J=2.8 Hz, 1H), 7.29-7.28 (m, 1H), 7.12 (dd, J=8.8, 2.4 Hz 1H), 6.94-6.89 (m, 1H), 6.22 (s, 1H), 5.32-5.29 (m, 1H), 4.63 (d, J=11.6 Hz, 1H), 4.39-4.32 (m, 1H), 4.29-4.23 (m, 1H), 4.08-3.98 (m, 2H), 3.82-3.78 (m, 1H), 2.58 (br s, 1H), 2.44-2.41 (m, 1H), 2.11-2.08 (m, 1H), 1.97-1.88 (m, 2H), 1.39 (t, J=6.8 Hz, 3H), 1.14 (t, J=6.8 Hz, 3H).

Compound 362T(cis): LC-MS (ESI): $R_T$=4.093 min, mass calcd. for $C_{24}H_{25}ClFN_3O_5S$ 522.2 [M+H]$^+$. Chiral analysis (Column: Chiralpak IC 5 μm 4.6*250 mm; Mobile Phase: Hex:EtOH=90:10 at 1.0 mL/min; Temp: 30° C.; Wavelength: 230 nm; $R_T$=15.229 min). $^1$H NMR (400 MHz, CDCl$_3$) δ 8.84 (br s, 1H), 7.80 (d, J=3.2 Hz, 1H), 7.41 (d, J=3.2 Hz, 1H), 7.29-7.27 (m, 1H), 7.11 (dd, J=8.8, 2.8 Hz, 1H), 6.94-6.88 (m, 1H), 6.22 (s, 1H), 5.32-5.29 (m, 1H), 4.63 (d, J=11.2 Hz, 1H), 4.39-4.34 (m, 1H), 4.28-4.23 (m, 1H), 4.08-3.98 (m, 2H), 3.82-3.78 (m, 1H), 2.58 (br s, 1H), 2.43-2.41 (m, 1H), 2.11-2.08 (m, 1H), 1.97-1.87 (m, 2H), 1.39 (t, J=7.2 Hz, 3H), 1.14 (t, J=7.2 Hz, 3H).

Compound 362U(trans): LC-MS (ESI): $R_T$=4.304 min, mass calcd. for $C_{24}H_{25}ClFN_3O_5S$ 521.1, m/z found 522.2 [M+H]$^+$. Chiral analysis (Column: Chiralpak IC 5 μm 4.6*250 mm; Mobile Phase: Hex:EtOH=95:5 at 1.0 mL/min; Temp: 30° C.; Wavelength: 230 nm; $R_T$=8.729 min). $^1$H NMR (400 MHz, CDCl$_3$) δ 8.82 (br s, 1H), 7.84 (d, J=3.2 Hz, 1H), 7.44-7.39 (m, 2H), 7.12 (dd, J=8.4, 2.4 Hz, 1H), 6.95-6.90 (m, 1H), 6.17 (s, 1H), 5.25 (dd, J=10.8, 2.0 Hz, 1H), 4.37 (dd, J=8.4, 5.2 Hz, 1H), 4.16 (q, J=7.2 Hz, 2H), 4.05-4.00 (m, 2H), 3.67 (t, J=11.6 Hz, 1H), 2.78-2.70 (m, 1H), 2.45-2.18 (m, 2H), 1.96-1.85 (m, 1H), 1.57-1.47 (m, 1H), 1.27 (t, J=7.2 Hz, 3H), 1.12 (t, J=7.2 Hz, 3H).

Compound 362V(trans): LC-MS (ESI): $R_T$=3.711 min, mass calcd. for $C_{24}H_{25}ClFN_3O_5S$ 521.1, m/z found 522.2 [M+H]$^+$. Chiral analysis (Column: Chiralpak IC 5 μm 4.6*250 mm; Mobile Phase: Hex:EtOH=90:10 at 1.0 mL/min; Temp: 30° C.; Wavelength: 230 nm; $R_T$=9.631 min). $^1$H NMR (400 MHz, CDCl$_3$) δ 8.82 (br s, 1H), 7.83 (d, J=3.2 Hz, 1H), 7.43-7.39 (m, 2H), 7.12 (dd, J=8.8, 2.4 Hz, 1H), 6.95-6.89 (m, 1H), 6.17 (s, 1H), 5.25 (dd, J=11.2, 2.0 Hz, 1H), 4.38 (dd, J=10.0, 2.8 Hz, 1H), 4.16 (q, J=7.2 Hz, 2H), 4.03 (q, J=7.2 Hz, 2H), 3.68 (m, J=11.6 Hz, 1H), 2.78-2.70 (m, 1H), 2.25-2.18 (m, 2H), 1.96-1.85 (m, 1H), 1.58-1.47 (m, 1H), 1.27 (t, J=7.2 Hz, 3H), 1.12 (t, J=6.8 Hz, 3H).

Compound 362X(trans): LC-MS (ESI): $R_T$=4.313 min, mass calcd. for $C_{24}H_{25}ClFN_3O_5S$ 521.1, m/z found 522.2 [M+H]$^+$. Chiral analysis (Column: Chiralpak IC 5 μm 4.6*250 mm; Mobile Phase: Hex:EtOH=90:10 at 1.0 mL/min; Temp: 30° C.; Wavelength: 230 nm; $R_T$=11.369 min). $^1$H NMR (400 MHz, CDCl$_3$) δ 8.83 (br s, 1H), 7.84 (d, J=3.2 Hz, 1H), 7.43 (d, J=3.2 Hz, 1H), 7.30-7.27 (m, 1H), 7.13 (dd, J=8.8, 2.4 Hz, 1H), 6.93-6.89 (m, 1H), 6.23 (s, 1H), 5.24 (dd, J=10.8, 1.6 Hz, 1H), 4.39 (dd, J=7.6, 4.0 Hz, 1H), 4.16 (q, J=7.2 Hz, 2H), 4.07-3.97 (m, 2H), 3.69-3.63 (m, 1H), 2.78-2.68 (m, 1H), 2.30-2.25 (m, 2H), 2.00-1.89 (m, 1H), 1.73-1.66 (m, 1H), 1.27 (t, J=7.2 Hz, 3H), 1.15 (t, J=7.2 Hz, 3H).

Compound 362Y (trans): LC-MS (ESI): $R_T$=4.306 min, mass calcd. for $C_{24}H_{25}ClFN_3O_5S$ 522.2, m/z found 521.9 [M+H]$^+$. Chiral analysis (Column: Chiralpak IC 5 μm 4.6*250 mm; Mobile Phase: Hex:EtOH=90:10 at 1.0 mL/min; Temp: 30° C.; Wavelength: 230 nm; $R_T$=13.057 min). $^1$H NMR (400 MHz, CDCl$_3$) δ 8.83 (br s, 1H), 7.84 (d, J=3.2 Hz, 1H), 7.43 (d, J=3.2 Hz, 1H), 7.30-7.27 (m, 1H), 7.13 (dd, J=8.4, 2.0 Hz, 1H), 6.95-6.88 (m, 1H), 6.23 (s, 1H), 5.24-5.21 (m, 1H), 4.41-4.37 (m, 1H), 4.16 (q, J=7.2 Hz, 2H), 4.06-4.01 (m, 2H), 3.69-3.63 (m, 1H), 2.78-2.69 (m, 1H), 2.30-2.25 (m, 2H), 1.99-1.88 (m, 1H), 1.70-1.66 (m, 1H), 1.28 (t, J=7.2 Hz, 3H), 1.15 (t, J=7.2 Hz, 3H).

Compound 368: Ethyl 6-(1-(tert-butoxycarbonyl) piperidin-4-yl)-4-(2-chloro-3,4-difluorophenyl)-2-(thiazol-2-yl)-1,4-dihydropyrimidine-5-carboxylate LC-MS (ESI): $R_T$=2.05 min, mass calcd. for $C_{26}H_{29}ClF_2N_4O_4S$ 566.2, m/z found 567.7 [M+H]$^+$. $^1$H NMR (400 MHz, CDCl$_3$) δ 8.36 (s, 0.5H), 7.82 (d, J=3.2 Hz, 1H), 7.51 (d, J=2.8 Hz, 0.5H), 7.46 (d, J=3.2 Hz, 0.5H), 7.38 (s, 0.5H), 7.10-6.99 (m, 2H), 6.20 (s, 0.5H), 6.08 (s, 0.5H), 4.30 (br s, 1.5H), 4.09-3.99 (m, 2H), 3.97-3.89 (m, 0.5H), 2.91-2.79 (m, 2H), 1.80-1.74 (m, 3H), 1.61-1.58 (m, 2H), 1.50 (s, 9H), 1.13 (t, J=6.8 Hz, 3H).

Racemic 368 (13.0 g, 22.9 mmol) was separated by chiral Prep. HPLC (Column: Chiralpak IA 5 μm 20*250 mm; Mobile Phase: Hex:EtOH=95:5 at 25 mL/min, Temp: 30° C.; Wavelength: 214 nm) to afford the title compounds 368A (5 g, 38% yield, 99.7% stereopure) and 368B (5 g, 38% yield, 98.4% stereopure).

Compound 368A: LC-MS (ESI): $R_T$=2.05 min, mass calcd. for $C_{26}H_{29}ClF_2N_4O_4S$ 566.2, m/z found 567.6 [M+H]$^+$. Chiral analysis (Column: Chiralpak IA 5 μm 4.6*250 mm; Mobile Phase: Hex:EtOH=95:5 at 1.0 mL/min; Temp: 30° C.; Wavelength: 230 nm; $R_T$=7.937 min). $^1$H NMR (400 MHz, CDCl$_3$) δ 8.12 (s, 0.5H), 7.83-7.82 (m, 1H), 7.51 (d, J=3.2 Hz, 0.4H), 7.46 (d, J=3.2 Hz, 0.6H), 7.34 (s, 0.5H), 7.10-6.99 (m, 2H), 6.20 (s, 0.6H), 6.08

(d, J=2.4 Hz, 0.4H), 4.36-4.14 (m, 2.6H), 4.10-3.99 (m, 2H), 3.97-3.89 (m, 0.4H), 2.91-2.78 (m, 2H), 2.10-1.63 (m, 3.5H), 1.58-1.56 (m, 0.5H), 1.50 (s, 9H), 1.14 (t, J=7.2 Hz, 3H).

Compound 368B: LC-MS (ESI): $R_T$=2.05 min, mass calcd. for $C_{26}H_{29}ClF_2N_4O_4S$ 566.2, m/z found 567.6 [M+H]$^+$. Chiral analysis (Column: Chiralpak IA 5 μm 4.6*250 mm; Mobile Phase: Hex:EtOH=95:5 at 1.0 mL/min; Temp: 30° C.; Wavelength: 230 nm; $R_T$=8.930 min). $^1$H NMR (400 MHz, CDCl$_3$) δ 8.12 (s, 0.5H), 7.83-7.82 (m, 1H), 7.51 (d, J=3.2 Hz, 0.4H), 7.46 (d, J=3.2 Hz, 0.6H), 7.34 (s, 0.5H), 7.10-6.99 (m, 2H), 6.20 (s, 0.6H), 6.08 (d, J=2.4 Hz, 0.4H), 4.36-4.14 (m, 2.6H), 4.10-3.99 (m, 2H), 3.97-3.89 (m, 0.4H), 2.91-2.78 (m, 2H), 2.10-1.63 (m, 3.5H), 1.58-1.56 (m, 0.5H), 1.50 (s, 9H), 1.14 (t, J=7.2 Hz, 3H).

Compound 371: Methyl 6-(3-((tert-butoxycarbonyl)amino)bicyclo[1.1.1]pentan-1-yl)-4-(2-chloro-4-fluorophenyl)-2-(thiazol-2-yl)-1,4-dihydropyrimidine-5-carboxylate LC-MS (ESI): $R_T$=2.454 min, mass calcd. for $C_{25}H_{26}ClFN_4O_4S$ 532.1, m/z found 532.8 [M+H]$^+$. $^1$H NMR (400 MHz, CDCl$_3$) δ 7.91-7.86 (m, 0.8H), 7.82-7.79 (m, 1H), 7.48 (d, J=2.8 Hz, 0.2H), 7.43 (d, J=3.2 Hz, 0.8H), 7.41 (br s, 0.2H), 7.31-7.27 (m, 0.7H), 7.25-7.24 (m, 0.3H), 7.14-7.11 (m, 1H), 6.96-6.89 (m, 1H), 6.15 (s, 0.8H), 6.01 (d, J=2.8 Hz, 0.2H), 5.04 (br s, 1H), 3.64 (s, 0.7H), 3.60 (s, 2.3H), 2.53 (s, 4.6H), 2.45 (s, 1.4H), 1.47 (s, 9H).

Racemic 371 (1.20 g, 2.26 mmol) was separated by chiral Prep. SFC (Column: Chiralpak IG 5 μm 20*250 mm; Mobile Phase: CO$_2$:MeOH=70:30 at 45 g/min; Col. Temp: 39° C.; Wavelength: 214 nm, Back pressure: 100 bar) to afford the title compounds 371A (608 mg, 51% yield, 100% stereopure) and 371B (576 mg, 48% yield, 100% stereopure) as yellow solids.

Compound 371A: LC-MS (ESI): $R_T$=2.455 min, mass calcd. for $C_{25}H_{26}ClFN_4O_4S$ 532.1, m/z found 532.8 [M+H]$^+$. Chiral analysis (Column: Chiralpak IG 5 μm 4.6*250 mm; Mobile Phase: CO$_2$:MeOH=70:30 at 2.999 g/min; Col. Temp: 40° C.; Wavelength: 230 nm, Back pressure: 100 bar, $R_T$=2.92 min). $^1$H NMR (400 MHz, CDCl$_3$) δ 7.88 (br s, 0.8H), 7.81 (d, J=3.6 Hz, 0.2H), 7.80 (d, J=2.8 Hz, 0.8H), 7.48 (d, J=2.8 Hz, 0.3H), 7.43 (d, J=3.2 Hz, 0.7H), 7.40 (br s, 0.2H), 7.31-7.27 (m, 0.7H), 7.25-7.24 (m, 0.3H), 7.12 (dd, J=8.8, 2.8 Hz, 1H), 6.96-6.89 (m, 1H), 6.15 (s, 0.7H), 6.01 (s, 0.3H), 5.03 (br s, 1H), 3.64 (s, 0.7H), 3.60 (s, 2.3H), 2.53 (s, 4.3H), 2.45 (s, 1.7H), 1.47 (s, 9H).

Compound 371B: LC-MS (ESI): $R_T$=2.456 min, mass calcd. for $C_{25}H_{26}ClFN_4O_4S$ 532.1, m/z found 532.8 [M+H]$^+$. Chiral analysis (Column: Chiralpak IG 5 μm 4.6*250 mm; Mobile Phase: Hex:EtOH=70:30 at 2.999 g/min; Col. Temp: 40° C.; Wavelength: 230 nm, Back pressure: 100 bar, $R_T$=4.32 min). $^1$H NMR (400 MHz, CDCl$_3$) δ 7.88 (br s, 0.8H), 7.81 (d, J=3.2 Hz, 0.2H), 7.80 (d, J=3.2 Hz, 0.8H), 7.48 (d, J=3.2 Hz, 0.3H), 7.43 (d, J=3.2 Hz, 0.7H), 7.40 (br s, 0.2H), 7.31-7.27 (m, 0.7H), 7.25-7.24 (m, 0.3H), 7.14-7.11 (m, 1H), 6.97-6.89 (m, 1H), 6.15 (s, 0.7H), 6.01 (d, J=2.4 Hz, 0.3H), 5.03 (br s, 1H), 3.64 (s, 0.7H), 3.60 (s, 2.3H), 2.53 (s, 4.3H), 2.45 (s, 1.7H), 1.47 (s, 9H).

Compound 377: ethyl 6-(−1-(tert-butoxycarbonyl)-2-(((tert-butyldiphenylsilyl)oxy)methyl)piperidin-4-yl)-4-(2-chloro-4-fluorophenyl)-2-(thiazol-2-yl)-1,4-dihydropyrimidine-5-carboxylate Compound 377a (racemate): $^1$H NMR (400 MHz, CDCl$_3$) δ 8.09 (s, 0.2H), 7.82 (d, J=2.8 Hz, 0.8H), 7.70-7.66 (m, 4H), 7.50 (d, J=2.4 Hz, 0.6H), 7.45-7.38 (m, 6H), 7.34-7.29 (m, 1.4H), 7.13 (d, J=8.0 Hz, 1H), 6.96-6.88 (m, 1H), 6.23 (d, J=9.2 Hz, 0.4H), 6.10 (d, J=12.8 Hz, 0.6H), 4.77-4.68 (m, 0.3H), 4.54-4.37 (m, 1H), 4.26-4.13 (m, 1H), 3.99-3.94 (m, 2H), 3.89-3.79 (m, 1H), 3.72-3.65 (m, 0.7H), 2.93-2.79 (m, 1H), 2.22-2.05 (m, 1H), 1.97-1.88 (m, 1H), 1.85-1.68 (m, 2H), 1.58 (s, 3H), 1.55-1.40 (m, 9H), 1.28-1.21 (m, 1H), 1.08-0.98 (m, 9H).

Compound 377b (racemate): $^1$H NMR (400 MHz, CDCl$_3$) δ 8.14-8.11 (m, 0.3H), 7.84-7.80 (m, 0.7H), 7.73-7.65 (m, 4H), 7.50 (d, J=2.8 Hz, 0.6H), 7.45-7.26 (m, 7.4H), 7.16-7.11 (m, 1H), 6.91-6.84 (m, 1H), 6.21-6.18 (m, 0.4H), 6.07-6.04 (m, 0.6H), 4.83-4.74 (m, 0.3H), 4.58-4.32 (m, 1.2H), 4.23-4.10 (m, 1.4H), 4.04-3.96 (m, 1.6H), 3.89-3.65 (m, 1.5H), 2.93-2.65 (m, 1H), 2.38-2.18 (m, 1.6H), 2.05-2.00 (m, 0.4H), 1.98-1.84 (m, 2H), 1.63 (s, 3H), 1.49-1.42 (m, 9H), 1.28-1.24 (m, 1H), 1.08-1.00 (m, 9H).

Compound 380: (trans)-Methyl 6-(4-((tert-butyldimethylsilyl)oxy)cyclohexyl)-4-(2-chloro-3-fluorophenyl)-2-(thiazol-2-yl)-1,4-dihydropyrimidine-5-carboxylate LC-MS (ESI): $R_T$=3.152 min, mass calcd. for $C_{27}H_{35}ClFN_3O_3SSi$ 563.2, m/z found 564.2 [M+H]$^+$.

Compound 382: tert-Butyl 4-(6-(2-chloro-4-fluorophenyl)-5-(methoxycarbonyl)-2-(thiazol-2-yl)-3,6-dihydropyrimidin-4-yl)azepane-1-carboxylate LC-MS (ESI): $R_T$=1.92 min, mass calcd. for $C_{26}H_{30}ClFN_4O_4S$ 548.2, m/z found 549.4 [M+H]$^+$. 1H NMR (400 MHz, CDCl$_3$) δ 8.08-8.06 (m, 0.5H), 7.82-7.78 (m, 1H), 7.49-7.39 (m, 1.5H), 7.32-7.26 (m, 1H), 7.15-7.12 (m, 1H), 7.00-6.89 (m, 1H), 6.19-6.16 (m, 0.5H), 6.04-6.03 (m, 0.5H), 4.15-4.06 (m, 0.5H), 3.96-3.71 (m, 1.5H), 3.61-3.59 (m, 3H), 3.56-3.18 (m, 3H), 2.15-1.67 (m, 6H), 1.51 (s, 4H), 1.50 (s, 5H).

Compound 385: Methyl 4-(2-chloro-4-fluorophenyl)-6-(1,4-dioxaspiro[4.5]decan-8-yl)-2-(thiazol-2-yl)-1,4-dihydropyrimidine-5-carboxylate $^1$H NMR, 41% yield) as yellow solids. $^1$H NMR (300 MHz, CDCl$_3$) δ 8.20 (br s, 0.6H), 7.83-7.77 (m, 1H), 7.46 (br s, 0.4H), 7.43-7.40 (m, 1H), 7.33-7.28 (m, 1H), 7.15-7.07 (m, 1H), 6.95-6.86 (m, 1H), 6.18 (s, 0.7H), 6.04 (s, 0.3H), 3.99 (s, 4H), 3.94-3.90 (m, 1H), 3.63-3.58 (m, 3H), 2.06-2.00 (m, 1H), 1.91-1.88 (m, 2H), 1.83-1.75 (m, 4H), 1.66-1.55 (m, 1H).

Compound 394: (trans)-Methyl 6-(4-((tert-butoxycarbonyl)amino)cyclohexyl)-4-(2-chloro-4-fluorophenyl)-2-(3,5-difluoropyridin-2-yl)-1,4-dihydropyrimidine-5-carboxylate $^1$H NMR (300 MHz, CDCl$_3$) δ 8.67-8.64 (m, 0.7H), 8.31-8.28 (m, 0.7H), 8.25-8.22 (m, 0.3H), 7.84-7.80 (m, 0.3H), 7.33-7.28 (m, 1H), 7.15-7.11 (m, 1H), 6.97-6.82 (m, 2H), 6.29-6.26 (m, 0.7H), 6.02-6.00 (m, 0.3H), 4.51-4.42 (m, 1H), 4.05-3.96 (m, 1H), 3.60 (s, 1.2H), 3.58 (s, 1.8H), 2.21-2.07 (m, 4H), 1.98-1.90 (m, 2H), 1.61-1.54 (m, 1H), 1.46 (s, 9H), 1.32-1.28 (m, 1H).

Compound 397: (cis)-Methyl 6-(4-((tert-butoxycarbonyl)amino)cyclohexyl)-4-(2-chloro-4-fluorophenyl)-2-(3,5-difluoropyridin-2-yl)-1,4-dihydropyrimidine-5-carboxylate $^1$H NMR (300 MHz, CDCl$_3$) δ 8.67-8.61 (m, 0.7H), 8.32-8.29 (m, 0.6H), 8.26-8.23 (m, 0.4H), 7.84-7.80 (m, 0.3H), 7.30-7.28 (m, 1H), 7.13-7.11 (m, 1H), 6.98-6.96 (m, 1H), 6.90-6.87 (m, 1H), 6.30-6.26 (m, 0.7H), 6.04-6.00 (m, 0.3H), 4.46-4.39 (m, 1H), 3.99-3.94 (m, 1H), 3.58 (s, 3H), 2.13-2.07 (m, 3H), 1.98-1.91 (m, 3H), 1.71-1.67 (m, 2H), 1.48 (s, 4H), 1.45 (s, 5H).

Compound 407: Methyl 4-(2-bromo-4-fluorophenyl)-6-(1-(tert-butoxycarbonyl)piperidin-4-yl)-2-(thiazol-2-yl)-1,4-dihydropyrimidine-5-carboxylate LC-MS (ESI): R$_T$=2.207 min, mass calcd. for C$_{25}$H$_{28}$BrFN$_4$O$_4$S 578.1, m/z found 579.0 [M+H]$^+$. $^1$H NMR (400 MHz, CDCl$_3$) δ 8.12 (s, 0.4H), 7.83-7.81 (m, 1H), 7.51-7.45 (m, 1.6H), 7.34-7.30 (m, 1H), 7.01-6.94 (m, 1H), 6.17 (s, 0.4H), 6.02 (d, J=2.8 Hz, 0.6H), 4.32-4.17 (m, 2H), 3.94-3.93 (m, 0.3H), 3.61-3.60 (m, 3H), 3.50-3.49 (m, 0.7H), 2.86 (br s, 2H), 2.10-1.66 (m, 3.3H), 1.51 (s, 9H), 1.46-1.35 (m, 0.7H).

Racemic compound 407 (5.00 g, 8.65 mmol) was separated by chiral SFC (Column: Chiralpak IG 5 μm 20*250 mm; Mobile Phase: CO2:MeOH=70:30 at 50 g/min, Temp: 30° C.; Wavelength: 214 nm, Back pressure: 100 bar) to get 407A (1.6 g, 32% yield, 100% stereopure) as yellow solids and 407B (1.8 g, 36% yield, 100% stereopure) as yellow solids.

Compound 407A: Chiral HPLC analysis (Column: Chiralpak IG 5 μm 4.6*250 mm; Mobile Phase: CO$_2$:MeOH=70:30, at 3.0 g/min; Temp: 40° C.; Wavelength: 220 nm; R$_T$=2.98 min). $^1$H NMR (400 MHz, CDCl$_3$) δ 8.12 (s, 0.4H), 7.84-7.81 (m, 1H), 7.55-7.45 (m, 1.6H), 7.33-7.31 (m, 1H), 7.01-6.93 (m, 1H), 6.17 (s, 0.4H), 6.02 (d, J=2.8 Hz, 0.6H), 4.36-4.14 (m, 2.4H), 3.96-3.91 (m, 0.6H), 3.61-3.60 (m, 3H), 2.89 (br s, 2H), 2.12-1.64 (m, 3.5H), 1.58 (s, 0.5H), 1.51 (s, 9H).

Compound 407B: Chiral HPLC analysis (Column: Chiralpak IG 5 μm 4.6*250 mm; Mobile Phase: CO$_2$:MeOH=70:30 at 3.0 g/min; Temp: 40° C.; Wavelength: 230 nm; R$_T$=4.46 min). $^1$H NMR (400 MHz, CDCl$_3$) δ 8.12 (s, 0.4H), 7.83-7.81 (m, 1H), 7.50-7.44 (m, 1.6H), 7.35-7.33 (m, 1H), 7.01-6.93 (m, 1H), 6.17 (s, 0.4H), 6.02 (d, J=2.8 Hz, 0.6H), 4.37-4.14 (m, 2.4H), 3.96-3.91 (m, 0.6H), 3.61-3.60 (m, 3H), 2.96-2.77 (m, 2H), 2.11-1.63 (m, 3.5H), 1.58 (s, 0.5H), 1.51 (s, 9H).

Compound 411: Ethyl 4-(2-bromo-3-fluorophenyl)-6-(1-(tert-butoxycarbonyl)piperidin-4-yl)-2-(thiazol-2-yl)-1,4-dihydropyrimidine-5-carboxylate LC-MS (ESI): R$_T$=2.11 min, mass calcd. for C$_{26}$H$_{30}$BrFN$_4$O$_4$S 592.1, m/z found 594.9 [M+H]$^+$. $^1$H NMR (300 MHz, CDCl$_3$) δ 8.10 (s, 0.4H), 7.82-7.80 (m, 1H), 7.50-7.47 (m, 0.6H), 7.44-7.39 (m, 1H), 7.24-7.17 (m, 1H), 7.13-7.11 (m, 1H), 7.10-6.95 (m, 1H), 6.26 (s, 0.5H), 6.11 (d, J=2.4 Hz, 0.5H), 4.36-4.14 (m, 2.4H), 4.08-3.90 (m, 2.6H), 2.94-2.77 (m, 2H), 2.08-1.71 (m, 3H), 1.62-1.54 (m, 1H), 1.50 (s, 9H), 1.13-1.08 (m, 3H).

Compound 411A and 411B: Ethyl 4-(2-bromo-3-fluorophenyl)-6-(1-(tert-butoxycarbonyl)piperidin-4-yl)-2-(thiazol-2-yl)-1,4-dihydropyrimidine-5-carboxylate and Ethyl 4-(2-bromo-3-fluorophenyl)-6-(1-(tert-butoxycarbonyl)piperidin-4-yl)-2-(thiazol-2-yl)-1,4-dihydropyrimidine-5-carboxylate Racemic compound 411 (7.60 g, 95% purity, 12.2 mmol) was separated by chiral Prep. SFC (separation condition: Column: Chiralpak IG 5 μm 20*250 mm; Mobile Phase: CO$_2$:MeOH=75:25 at 50 g/min; Col. Temp.: 40° C.; Wavelength: 254 nm; Back Pressure: 100 Bar) to afford the title compounds 411A (3.20 g, 95% purity, 42% yield, 100% stereopure) as yellow solids and 411B (3.20 g, 95% purity, 42% yield, 99.3% stereopure) as yellow solids.

Compound 411A: LC-MS (ESI): R$_T$=2.268 min, mass calcd. for C$_{26}$H$_{30}$BrFN$_4$O$_4$S 592.1, m/z found 593.1 [M+H]$^+$. Chiral analysis (Column: Chiralpak IG 5 μm 20*250 mm; Mobile Phase: CO$_2$:MeOH=75:25 at 3.0 g/min; Col. Temp.: 40° C.; Wavelength: 254 nm; Back Pressure: 100 Bar, R$_T$=3.98 min). $^1$H NMR (300 MHz, CDCl$_3$) δ 8.09 (s, 0.4H), 7.82-7.80 (m, 1H), 7.49-7.40 (m, 1.6H), 7.24-7.17 (m, 1H), 7.17-7.11 (m, 1H), 7.07-6.98 (m, 1H), 6.26 (s, 0.5H), 6.12 (s, 0.5H), 4.35-3.91 (m, 5H), 2.93-2.78 (m, 2H), 2.01-1.81 (m, 2H), 1.71-1.56 (m, 2H), 1.50 (s, 9H), 1.10 (t, J=7.2 Hz, 3H).

Compound 411B: LC-MS (ESI): R$_T$=2.249 min, mass calcd. for C$_{26}$H$_{30}$BrFN$_4$O$_4$S 592.1, m/z found 593.0 [M+H]$^+$. Chiral analysis (Column: Chiralpak IG 5 μm 20*250 mm; Mobile Phase: CO$_2$:MeOH=75:25 at 3.0 g/min; Col. Temp.: 40° C.; Wavelength: 254 nm; Back Pressure: 100 Bar, R$_T$=4.84 min). $^1$H NMR (300 MHz, CDCl$_3$) δ 8.14-8.08 (m, 0.3H), 7.81 (d, J=3.0 Hz, 1H), 7.51-7.34 (m, 1.7H), 7.24-7.20 (m, 1H), 7.07-7.00 (m, 1H), 6.27-6.10 (m, 1H), 4.39-3.90 (m, 5H), 2.98-2.76 (m, 2H), 2.06-1.77 (m, 2.5H), 1.68-1.57 (m, 1.5H), 1.50 (s, 9H), 1.10 (t, J=7.2 Hz, 3H).

Compound 417: Ethyl 6-(1-(tert-butoxycarbonyl)piperidin-4-yl)-4-(4-fluoro-2-methylphenyl)-2-(thiazol-2-yl)-1,4-dihydropyrimidine-5-carboxylate LC-MS (ESI): R$_T$=2.169 min, mass calcd. for C$_{27}$H$_{33}$FN$_4$O$_4$S 528.2, m/z found 529.1 [M+H]$^+$. 1H NMR (400 MHz, CDCl$_3$) δ 8.07 (s, 1H), 7.80-7.78 (m, 1H), 7.50 (d, J=3.2 Hz, 0.3H), 7.42 (d, J=3.2 Hz, 0.7H), 7.06-6.79 (m, 3H), 5.96 (s, 0.7H), 5.87 (d, J=2.0 Hz, 0.3H), 4.34-4.15 (m, 2.7H), 4.07-4.00 (m, 2H), 3.85-3.79 (m, 0.3H), 2.89-2.86 (m, 2H), 2.63 (s, 2H), 2.48 (s, 1H), 2.03-2.00 (m, 1H), 1.87-1.83 (m, 1H), 1.70-1.55 (m, 2H), 1.50 (s, 9H), 1.14-1.10 (m, 3H).

Racemic 417 (6.00 g, 90% purity, 10.2 mmol) was separated by chiral Prep. SFC (Column: Chiralpak IG 5 μm 20 mm*250 mm; Mobile Phase: CO$_2$:MeOH:DEA=75:25:0.3 at 50 g/min; Col. Temp: 40° C.; Wavelength: 214 nm, Back pressure: 100 bar) to afford the title compounds 417A (2.70 g, 90% purity, 45% yield, 100% stereopure) and 417B (2.60 g, 90% purity, 43% yield, 99.2% stereopure) as yellow solids.

Compound 417A: Chiral analysis (Column: Chiralpak IG 5 Lm 4.6 mm*250 mm; Mobile Phase: CO$_2$:MeOH:DEA=75:25:0.2 at 3.00 g/min; Col. Temp: 40° C.; Wavelength: 214 nm, Back pressure: 100 bar, R$_T$=2.73 min). $^1$H NMR (400 MHz, CDCl$_3$) δ 8.05 (s, 0.7H), 7.80-7.79 (m, 1H), 7.50 (d, J=3.2 Hz, 0.3H), 7.42 (d, J=3.2 Hz, 0.7H), 7.32-7.28 (m, 0.3H), 7.18-7.15 (m, 0.7H), 7.00 (s, 0.3H), 6.90-6.76 (m, 2H), 5.96 (s, 0.7H), 5.87 (s, 0.3H), 4.35-4.16

(m, 2.7H), 4.09-3.99 (m, 2H), 3.84-3.79 (m, 0.3H), 2.92-2.83 (m, 2H), 2.63 (s, 2H), 2.48 (s, 1H), 2.03-2.00 (m, 1H), 1.87-1.84 (m, 1H), 1.72-1.59 (m, 2H), 1.50 (s, 9H), 1.14-1.09 (m, 3H).

Compound 417B: Chiral analysis (Column: Chiralpak IG 5 μm 4.6 mm*250 mm; Mobile Phase: $CO_2$:MeOH:DEA=75:25:0.2 at 3.00 g/min; Col. Temp: 40° C.; Wavelength: 214 nm, Back pressure: 100 bar, $R_T$=3.59 min). $^1$H NMR (400 MHz, $CDCl_3$) δ 8.05 (s, 0.7H), 7.79 (d, J=2.8 Hz, 1H), 7.50 (d, J=3.2 Hz, 0.3H), 7.42 (d, J=2.8 Hz, 0.7H), 7.32-7.28 (m, 0.3H), 7.18-7.15 (m, 0.7H), 6.99 (s, 0.3H), 6.90-6.76 (m, 2H), 5.96 (s, 0.7H), 5.87 (d, J=2.0 Hz, 0.3H), 4.36-4.16 (m, 2.7H), 4.09-3.99 (m, 2H), 3.84-3.78 (m, 0.3H), 2.92-2.83 (m, 2H), 2.63 (s, 2H), 2.49 (s, 1H), 2.03-2.00 (m, 1H), 1.87-1.79 (m, 1H), 1.73-1.69 (m, 1H), 1.61-1.56 (m, 1H), 1.50 (s, 9H), 1.15-1.10 (m, 3H).

Compound 426: Ethyl 6-(1-(tert-butoxycarbonyl)piperidin-4-yl)-4-(3-fluoro-2-methylphenyl)-2-(thiazol-2-yl)-1,4-dihydropyrimidine-5-carboxylate LC-MS (ESI): $R_T$=2.143 min, mass calcd. for $C_{27}H_{33}FN_4O_4S$ 528.2, m/z found 529.1 [M+H]$^+$. $^1$H NMR (400 MHz, $CDCl_3$) δ 8.08 (s, 1H), 7.80-7.78 (m, 1H), 7.49 (d, J=2.8 Hz, 0.3H), 7.42 (d, J=2.8 Hz, 0.7H), 7.08-7.01 (m, 2H), 6.95-6.88 (m, 1H), 6.01 (s, 0.7H), 5.92 (d, J=2.0 Hz, 0.3H), 4.31-4.17 (m, 3H), 4.08-3.99 (m, 2H), 2.89-2.82 (m, 2H), 2.54 (d, J=2.0 Hz, 2H), 2.39 (d, J=1.6 Hz, 1H), 2.03-2.00 (m, 1H), 1.87-1.84 (m, 1H), 1.69-1.56 (m. 2H), 1.50 (s, 9H), 1.13-1.09 (m, 3H).

Racemic 426 (3.0 g, 85% purity, 4.82 mmol) was separated by Chiral Prep. HPLC (Column: Chiralpak IC 5 μm 20 mm*250 mm; Mobile Phase: Hex:EtOH:DEA=98:2:0.3 at 22 mL/min; Temp: 30° C.; Wavelength: 214 nm) to afford the title compounds 426A (950 mg, 32% yield, 90% purity, 100% stereopure) and 426B (650 mg, 23% yield, 90% purity, 99.3% stereopure) as yellow solids.

Compound 426A: Chiral HPLC (Column: Chiralpak IC 5 μm 4.6 mm*250 mm; Mobile Phase: Hex:EtOH:DEA=98:2:0.2 at 1 mL/min; Col. Temp: 40° C.; Wavelength: 254 nm, $R_T$=17.28 min). $^1$H NMR (400 MHz, $CDCl_3$) δ 8.06 (s, 0.7H), 7.79 (d, J=3.2 Hz, 1H), 7.49 (d, J=3.2 Hz, 0.3H), 7.42 (d, J=3.2 Hz, 0.7H), 7.16-7.01 (m, 2.3H), 6.95-6.88 (m, 1H), 6.01 (s, 0.7H), 5.92 (d, J=2.4 Hz, 0.3H), 4.38-4.17 (m, 2.7H), 4.09-3.99 (m, 2H), 3.86-3.80 (m, 0.3H), 2.93-2.82 (m, 2H), 2.53 (s, 2.2H), 2.39 (s, 0.8H), 2.06-2.00 (m, 1H), 1.87-1.68 (m, 2H), 1.62-1.55 (m, 1H), 1.50 (s, 9H), 1.13-1.09 (m, 3H).

Compound 426B: Chiral HPLC(Column: Chiralpak IC 5 μm 4.6 mm*250 mm; Mobile Phase: Hex:EtOH:DEA=98:2:0.2 at 1 mL/min; Col. Temp: 40° C.; Wavelength: 254 nm, $R_T$=19.61 min). $^1$H NMR (400 MHz, $CDCl_3$) δ 8.06 (s, 0.7H), 7.79 (d, J=2.8 Hz, 1H), 7.50 (d, J=3.2 Hz, 0.3H), 7.42 (d, J=3.2 Hz, 0.7H), 7.15-7.01 (m, 2.3H), 6.95-6.88 (m, 1H), 6.01 (s, 0.7H), 5.92 (d, J=2.0 Hz, 0.3H), 4.35-4.17 (m, 2.7H), 4.10-3.99 (m, 2H), 3.86-3.81 (m, 0.3H), 2.89-2.83 (m, 2H), 2.54 (s, 2.2H), 2.40 (s, 0.8H), 2.03-2.00 (m, 1H), 1.87-1.84 (m, 1H), 1.73-1.68 (m, 1H), 1.62-1.56 (m, 1H), 1.50 (s, 9H), 1.14-1.09 (m, 3H)

Compounds 430: methyl 6-(4-(azetidin-1-ylsulfonyl)cyclohexyl)-4-(2-chloro-3,4-difluorophenyl)-2-(thiazol-2-yl)-1,4-dihydropyrimidine-5-carboxylate Purification conditions: purified by silica gel column chromatography (petroleum ether:ethyl acetate=3:1), then further purified by C18 column (acetonitrile:water=5% to 80%) to give 170 mg racemic product as yellow solids. The racemic mixture (170 mg, 0.298 mmol) was separated by chiral Prep. HPLC (separation condition: Column: Chiralpak ID 5 μm 20*250 mm; Mobile Phase: Hex:EtOH=70:30 at 12 mL/min; Temp: 30° C.; Wavelength: 214 nm) to afford the title compounds 430A (4.7 mg, 3% yield, 100% stereopure), 430B (5.1 mg, 3% yield, 93.7% stereopure), 430C (10 mg, 6% yield, 100% stereopure) and 430D (11 mg, 6% yield, 99.1% stereopure) as yellow solids.

Compound 430A(cis): LC-MS (ESI): $R_T$=4.455 min, mass calcd. for $C_{24}H_{25}ClF_2N_4O_4S_2$ 570.0, m/z found 570.9 [M+H]$^+$. Chiral HPLC (Column: Chiralpak ID 5 μm 4.6*250 mm; Mobile Phase: Hex:EtOH=70:30 at 1.0 mL/min; Temp: 30° C.; Wavelength: 230 nm, $R_T$=7.861 min). $^1$H NMR (400 MHz, DMSO-$d_6$) δ 9.59 (s, 0.7H), 8.22 (s, 0.3H), 8.03-8.00 (m, 1.7H), 7.97 (d, J=2.8 Hz, 0.3H), 7.50-7.40 (m, 1H), 7.22-7.18 (m, 1H), 6.03 (s, 0.3H), 5.92 (s, 0.7H), 3.91-3.84 (m, 4.2H), 3.73-3.67 (m, 0.8H), 3.51 (s, 3H), 3.21-3.15 (m, 1H), 2.35-2.17 (m, 5H), 2.14-1.97 (m, 1H), 1.93-1.77 (m, 2H), 1.71-1.62 (m, 1H), 1.56-1.41 (m, 1H).

Compound 430B(cis): LC-MS (ESI): $R_T$=4.264 min, mass calcd. for $C_{24}H_{25}ClF_2N_4O_4S_2$ 570.0, m/z found 570.9 [M+H]$^+$. Chiral HPLC (Column: Chiral HPLC (Column: Chiralpak ID 5 μm 4.6*250 mm; Mobile Phase: Hex:EtOH=70:30 at 1.0 mL/min; Temp: 30° C.; Wavelength: 230 nm, $R_T$=8.867 min). $^1$H NMR (400 MHz, DMSO-$d_6$) δ 9.59 (s, 0.7H), 8.30 (s, 0.3H), 8.04-7.96 (m, 2H), 7.48-7.46 (m, 1H), 7.22-7.18 (m, 1H), 6.03 (s, 0.3H), 5.92 (d, J=3.2 Hz, 0.7H), 3.91-3.84 (m, 4.2H), 3.72-3.69 (m, 0.8H), 3.52 (s, 1.2H), 3.51 (s, 1.8H), 3.19-3.16 (m, 1H), 2.37-2.19 (m, 5H), 2.10-1.92 (m, 1H), 1.88-1.80 (m, 2H), 1.70-1.68 (m, 1H), 1.62-1.55 (m, 1H).

Compound 430C(trans): LC-MS (ESI): $R_T$=3.966 min, mass calcd. for $C_{24}H_{25}ClF_2N_4O_4S_2$ 570.0, m/z found 571.2 [M+H]$^+$. Chiral HPLC (Column: Chiral HPLC (Column: Chiralpak IE 5 μm 4.6*250 mm; Mobile Phase: Hex:EtOH=50:50 at 1.0 mL/min; Temp: 30° C.; Wavelength: 230 nm, $R_T$=9.127 min). $^1$H NMR (400 MHz, DMSO-$d_6$) δ 9.61 (s, 0.7H), 8.95 (s, 0.3H), 8.03-7.94 (m, 2H), 7.49-7.46 (m, 1H), 7.24-7.16 (m, 1H), 6.01 (s, 0.4H), 5.93 (s, 0.6H), 3.95-3.86 (m, 4.5H), 3.53-3.51 (m, 3.5H), 3.05-2.96 (m, 0.4H), 2.87 (br s, 0.6H), 2.26-2.07 (m, 5H), 1.97-1.90 (m, 2H), 1.85-1.80 (m, 1H), 1.59-1.46 (m, 2H).

Compound 430D(trans): LC-MS (ESI): $R_T$=3.961 min, mass calcd. for $C_{24}H_{25}ClF_2N_4O_4S_2$ 570.0, m/z found 571.2 [M+H]$^+$. Chiral HPLC (Column: Chiral HPLC (Column: Chiralpak IE 5 μm 4.6*250 mm; Mobile Phase: Hex:EtOH=50:50 at 1.0 mL/min; Temp: 30° C.; Wavelength: 230 nm, $R_T$=12.662 min). $^1$H NMR (400 MHz, DMSO-$d_6$) δ 9.60 (s, 0.6H), 8.93 (s, 0.4H), 8.01-8.00 (m, 1.6H), 7.98-7.94 (m, 0.4H), 7.52-7.42 (m, 1H), 7.23-7.13 (m, 1H), 5.99 (s, 0.4H), 5.93 (s, 0.6H), 3.97-3.86 (m, 4.4H), 3.62-3.52 (m, 3.6H), 3.22-3.16 (m, 0.5H), 3.08-3.04 (m, 0.5H), 2.20-2.13 (m, 4H), 1.95-1.81 (m, 2.7H), 1.76-1.66 (m, 1.3H), 1.55-1.43 (m, 2H).

Compound 432: Methyl 4-(2-chloro-3,4-difluorophenyl)-6-(1,4-dioxaspiro[4.5]decan-8-yl)-2-(thiazol-2-yl)-1,4-dihydropyrimidine-5-carboxylate $^1$H NMR (400 MHz, DMSO-$d_6$) δ 9.53 (d, J=3.6 Hz, 0.6H), 8.63 (s, 0.4H), 8.02-7.95 (m, 2H), 7.48-7.39 (m, 1H), 7.21-7.17 (m, 1H), 6.02 (s, 0.3H), 5.92 (d, J=3.6 Hz, 0.7H), 3.93-3.86 (m, 4H), 3.63-3.57 (m, 1H), 3.53 (s, 2.7H), 3.49 (s, 0.3H), 2.07-1.97 (m, 1H), 1.94-1.88 (m, 1H), 1.82-1.68 (m, 4H), 1.57-1.52 (m, 2H).

Compound 435: Ethyl 6-(3-((tert-butoxycarbonyl)amino)-2,2-dimethylcyclobutyl)-4-(2-chloro-4-fluorophenyl)-2-(thiazol-2-yl)-1,4-dihydropyrimidine-5-carboxylate LC-MS (ESI): $R_T$=1.930 min, mass calcd. for $C_{27}H_{32}ClFN_4O_4S$ 563.1, m/z found 563.0 [M+H]$^+$. $^1$H NMR (400 MHz, CDCl$_3$) δ 7.86-7.85 (m, 1H), 7.51 (d, J=2.8 Hz, 1H), 7.41-7.37 (m, 1H), 7.15-7.11 (m, 1H), 6.99-6.90 (m, 1H), 6.18-6.14 (m, 1H), 4.23 (br s, 0.3H), 4.08-4.02 (m, 2.6H), 3.90 (br s, 1H), 3.76 (br s, 0.3H), 2.49-2.30 (m, 2H), 1.46 (s, 12H), 1.14-1.09 (m, 6H).

Racemic 435 (910 mg, 1.60 mmol) was separated by chiral Prep. SFC (separation condition: Column: Chiralpak IE 5 μm 20*250 mm, Mobile Phase: CO$_2$:MeOH=75:25 at 50 g/min; Temp: 40° C.; Wavelength: 214 nm) to afford the title compound 435b (450 mg, 49% yield) and 435a (440 mg, 48% yield) as yellow solids.

435a (cis): $^1$H NMR (400 MHz, CDCl$_3$) δ 8.14 (s, 0.2H), 7.85-7.84 (m, 0.8H), 7.52-7.51 (m, 1H), 7.45-7.38 (m, 1H), 7.36-7.34 (m, 1H), 7.15-7.11 (m, 1H), 7.00-6.91 (m, 1H), 6.24 (s, 0.2H), 6.15 (d, J=2.4 Hz, 0.8H), 4.07-4.03 (m, 2H), 3.98-3.94 (m, 1H), 3.91-3.85 (m, 0.7H), 3.81-3.67 (m, 0.3H), 2.48-2.31 (m, 2H), 1.45 (s, 13H), 1.36-1.24 (m, 2H), 1.16-1.11 (m, 3H).

435b (trans): $^1$H NMR (400 MHz, CDCl$_3$) δ 8.17 (s, 0.2H), 7.86-7.85 (m, 0.8H), 7.54-7.45 (m, 2H), 7.32-7.29 (m, 1H), 7.14-7.11 (m, 1H), 6.95-6.87 (m, 1H), 6.25 (s, 0.2H), 6.09 (d, J=2.8 Hz, 0.8H), 4.23-4.14 (m, 1.3H), 4.10-4.00 (m, 2H), 3.93-3.87 (m, 0.7H), 2.63-2.46 (m, 2H), 1.47-1.44 (m, 13H), 1.29-1.26 (m, 2H), 1.12 (t, J=7.2 Hz, 3H).

Compound 441: Methyl 6-(1-(tert-butoxycarbonyl)piperidin-4-yl)-4-(3-fluoro-2-methylphenyl)-2-(thiazol-2-yl)-1,4-dihydropyrimidine-5-carboxylate LC-MS (ESI): $R_T$=2.133 min, mass calcd. for $C_{26}H_{31}FN_4O_4S$ 514.6, m/z found 515.1 [M+H]$^+$. $^1$H NMR (400 MHz, CDCl$_3$) δ 8.10 (br s, 1H), 7.79-7.78 (m, 1H), 7.49 (d, J=3.2 Hz, 0.3H), 7.42 (d, J=3.2 Hz, 0.7H), 7.17-7.00 (m, 2H), 6.95-6.88 (m, 1H), 6.01 (s, 0.7H), 5.91 (s, 0.3H), 4.40-4.17 (m, 2.7H), 3.88-3.80 (m, 0.3H), 3.59-3.58 (m, 3H), 2.99-2.79 (m, 2H), 2.54 (d, J=2 Hz, 2.2H), 2.38 (d, J=2 Hz, 0.8H), 2.04-1.59 (m, 4H), 1.50 (s, 9H).

Racemic 441 (5.0 g, 90% purity, 8.77 mmol) was separated by chiral Prep. HPLC (separation condition: Column: Chiralpak IG 5 μm 20*250 mm; Mobile Phase: CO$_2$:MeOH:DEA=75:25:0.3 at 50 g/min; Temp: 30° C.; Wavelength: 230 nm) to give the title compounds 441a (2.2 g, 90% purity, 44% yield, 99.1% stereopure) and 441b (2.0 g, 90% purity, 40% yield, 100% stereopure) as yellow solids.

Compound 441a: chiral analytical: (Column: Chiralpak IG 5 μm 4.6*250 mm; Mobile Phase: CO$_2$:MeOH=75:25 at 3 g/min; Col. Temp: 40° C.; Wavelength: 214 nm, Back pressure: 100 bar, $R_T$=3.38 min). $^1$H NMR (400 MHz, CDCl$_3$) δ 8.09 (s, 1H), 7.79-7.78 (m, 1H), 7.50 (d, J=3.2 Hz, 0.3H), 7.42 (d, J=3.2 Hz, 0.7H), 7.16-7.04 (m, 2H), 6.99-6.88 (m, 1H), 6.00 (s, 0.7H), 5.91 (s, 0.3H), 4.43-4.16 (m, 2.7H), 3.87-3.81 (m, 0.3H), 3.59-3.58 (m, 3H), 2.98-2.78 (m, 2H), 2.54 (d, J=2 Hz, 2.2H), 2.37 (d, J=2.4 Hz, 0.8H), 2.03-1.59 (m, 4H), 1.50 (s, 9H).

Compound 441b: chiral analytical: (Column: Chiralpak IG 5 μm 4.6*250 mm; Mobile Phase: CO$_2$:MeOH=75:25 at 3 g/min; Col. Temp: 40° C.; Wavelength: 214 nm, Back pressure: 100 bar, $R_T$=2.91 min). $^1$H NMR (400 MHz, CDCl$_3$) δ 8.10 (s, 1H), 7.79-7.78 (m, 1H), 7.49 (d, J=3.2 Hz, 0.3H), 7.42 (d, J=3.2 Hz, 0.7H), 7.17-7.12 (m, 2H), 7.00-6.88 (m, 1H), 6.01 (s, 0.7H), 5.91 (d, J=3.2 Hz, 0.3H), 4.43-4.17 (m, 2.7H), 3.88-3.80 (m, 0.3H), 3.59-3.58 (m, 3H), 2.98-2.79 (m, 2H), 2.54 (d, J=2 Hz, 2.2H), 2.39 (d, J=2 Hz, 0.8H), 2.04-1.56 (m, 4H), 1.50 (s, 9H).

Compound 445: Methyl 6-(1-(tert-butoxycarbonyl)piperidin-4-yl)-4-(4-fluoro-2-methylphenyl)-2-(thiazol-2-yl)-1,4-dihydropyrimidine-5-carboxylate LC-MS (ESI): $R_T$=1.79 min, mass calcd. for $C_{26}H_{31}FN_4O_4S$ 514.2, m/z found 515.4 [M+H]$^+$. 1H NMR (400 MHz, CDCl$_3$) δ 8.09 (s, 0.7H), 7.79 (d, J=2.8 Hz, 1H), 7.49 (d, J=3.2 Hz, 0.3H), 7.42 (d, J=2.8 Hz, 0.7H), 7.32-7.28 (m, 0.3H), 7.17-7.13 (m, 0.7H), 7.07 (s, 0.3H), 6.90-6.76 (m, 2H), 5.95 (s, 0.7H), 5.85 (s, 0.3H), 4.40-4.20 (m, 2H), 3.59 (s, 2H), 3.58 (s, 1H), 2.97-2.79 (m, 2H), 2.63 (s, 2H), 2.47 (s, 1H), 2.02-1.97 (m, 1H), 1.90-1.81 (m, 1H), 1.72-1.59 (m, 3H), 1.50 (s, 9H).

Racemic 445 (2.00 g, 3.88 mmol) was separated by chiral Prep. SFC (Column: Chiralpak IG 5 Lm 20*250 mm; Mobile Phase: CO$_2$:MeOH:DEA=75:25:0.3 at 50 g/min; Col. Temp 40° C.; Wavelength: 214 nm; Back pressure: 100 bar) to afford title compounds 445A (684 mg, 34% yield, 99.3% stereopure) as yellow solids and 445B (607 mg, 30% yield, 100% stereopure) as yellow solids.

Compound 445A: LC-MS (ESI): $R_T$=1.89 min, mass calcd. for $C_{26}H_{31}FN_4O_4S$ 514.2, m/z found 515.1 [M+H]$^+$. Chiral analysis (Column: Chiralpak IG 5 μm 4.6*250 mm; Mobile Phase: CO2:MeOH:DEA=75:25:0.2 at 3.0 g/min; Col. Temp: 40° C.; Wavelength: 280 nm, Back pressure: 100 bar; $R_T$=3.81 min).

Compound 445B: LC-MS (ESI): $R_T$=1.88 min, mass calcd. for $C_{26}H_{31}FN_4O_4S$ 514.2, m/z found 515.1 [M+H]$^+$. Chiral analysis (Column: Chiralpak IG 5 μm 4.6*250 mm; Mobile Phase: CO2:MeOH:DEA=75:25:0.2 at 3.0 g/min; Col. Temp: 40° C.; Wavelength: 280 nm, Back pressure: 100 bar; $R_T$=2.93 min).

Compound 472: trans-methyl 4-(2-chloro-3,4-difluorophenyl)-6-(4-(N-(3-methoxy-3-oxopropyl)sulfamoyl)cyclohexyl)-2-(thiazol-2-yl)-1,4-dihydropyrimidine-5-carboxylate LC-MS (ESI): $R_T$=3.937 min, mass calcd. for $C_{25}H_{27}ClF_2N_4O_6S_2$ 616.1, m/z found 617.0 [M+H]$^+$. $^1$H NMR (400 MHz, DMSO-d$_6$) δ 9.57 (d, J=3.6 Hz, 0.6H), 8.97 (s, 0.4H), 7.99-7.94 (m, 2H), 7.49-7.42 (m, 1H), 7.22-7.11 (m, 2H), 6.02 (s, 0.4H), 5.92 (d, J=3.6 Hz, 0.6H), 3.90-3.80 (m, 0.4H), 3.63 (s, 3H), 3.61-3.52 (m, 3.6H), 3.26-3.14 (m, 2.4H), 3.07-2.99 (m, 0.6H), 2.57-2.54 (m, 2H), 2.22-2.11 (m, 2H), 2.00-1.70 (m, 4H), 1.56-1.40 (m, 2H).

Section I: Single Step Conversion (Deprotection and Coupling) of Primary Dihydropyrimidines of General Formula I Compound 96: Ethyl 4-(2-chloro-3-fluorophenyl)-6-(1-(methylsulfonyl)piperidin-4-yl)-2-(thiazol-2-yl)-1,4-dihydropyrimidine-5-carboxylate (a Mixture of 2 Stereoisomers)

Method O: To a solution of ethyl 6-(1-(tert-butoxycarbonyl)piperidin-4-yl)-4-(2-chloro-3-fluorophenyl)-2-(thiazol-2-yl)-1,4-dihydropyrimidine-5-carboxylate Compound 9 (200 mg, 0.340 mmol) in methanol (5 mL) was added 2 M hydrochloric acid in methanol (5 mL, 10 mmol) at 0° C. After stirred at room temperature for 2 hours, the mixture was concentrated to give a residue, which was dissolved in dichloromethane (5 mL) and added triethylamine (150 mg, 1.50 mmol) and methanesulfonyl chloride (114 mg, 1.00 mmol) under nitrogen atmosphere at room temperature. Having stirred overnight, the reaction mixture was washed with water (30 mL) twice, dried over $Na_2SO_{4(s)}$, filtered and concentrated under reduced pressure to give a residue, which was purified by C18 (acetonitrile:water=40% to 55%) to give the title compound (240 mg, 86% yield) as pale yellow solids.

Compound 96 (200 mg, 0.380 mmol) was further separated by chiral Prep. HPLC (Column: Chiralpak IA 5 μm 20*250 mm; Mobile Phase: Hex:EtOH=70:30 at 11 mL/min; Temp: 30° C.; Wavelength: 214 nm) to afford stereoisomers Compound 96A (62 mg, 31% yield) and Compound 96B (61.5 mg, 31% yield) as yellow solids.

Compound 96B: LC-MS (ESI): $R_T$=4.103 min, mass calcd. for $C_{22}H_{24}ClFN_4O_4S_2$ 526.1, m/z found 527.2 [M+H]$^+$. Chiral HPLC (Column: Chiralpak IA 5 μm 4.6*250 mm; Mobile Phase: Hex:EtOH=70:30 at 1.0 mL/min; Temp: 30° C.; Wavelength: 230 nm, $R_T$=8.673 min). $^1$H NMR (400 MHz, CDCl$_3$) δ 8.16 (br s, 0.3H), 7.83 (d, J=3.2 Hz, 1H), 7.53 (d, J=2.8 Hz, 0.7H), 7.45 (d, J=2.8 Hz, 0.3H), 7.38 (br s, 0.7H), 7.24-7.03 (m, 3H), 6.28 (br s, 0.3H), 6.15 (d, J=2.8 Hz, 0.7H), 4.23-3.88 (m, 5H), 2.89-2.76 (m, 5H), 2.34-1.72 (m, 4H), 1.13-1.07 (m, 3H).

Compound 97: 4-(4-Chloro-2-fluoro-phenyl)-6-(1-methanesulfonyl-pip-eridin-4-yl)-2-thiazol-2-yl-1,4-dihydro-pyrimidine-5-carboxylic Acid Methyl Ester (a Mixture of 2 Stereoisomers)

Method P: To a solution of 6-(1-tert-butoxycarbonyl-piperidin-4-yl)-4-(4-chloro-2-fluoro-phenyl)-2-thiazol-2-yl-1,4-dihydro-pyrimidine-5-carboxylic acid methyl ester Compound 11 (300 mg, 0.562 mmol) in dichloromethane (3 mL) was added trifluoroacetic acid (3 mL, 40.2 mmol). After stirred at room temperature for 1 hour, the mixture was concentrated to give a residue, used without further purification. To a solution of the residue (700 mg, 0.562 mmol) and triethylamine (170 mg, 1.69 mmol) in dichloromethane (6 mL) was added methanesulfonyl chloride (71 mg, 0.62 mmol). After stirred at room temperature for 2 hours, the mixture was concentrated and the residue was purified by Prep. HPLC (column: Gilson X-bridge C18 (5 μm 19*150 mm), Mobile Phase A: water (0.1% ammonium bicarbonate), Mobile Phase B: acetonitrile, Flow rate: 15 mL/min; Gradient: 15-95% (% B)) to get the title compounds (81 mg, 28% yield) as yellow solids. Compound 97 (250 mg, 0.488 mmol) was further separated by chiral Prep. HPLC (separation condition: Column: Chiralpak IA 5 μm 20*250 mm; Mobile Phase: Hex:EtOH:DEA=70:30:0.3 at 18 mL/min, Temp: 30° C.; Wavelength: 230 nm) to afford stereoisomers Compound 97A (47.0 mg, 19% yield) and Compound 97B (36.0 mg, 15% yield) as yellow solids.

Compound 97B: LC-MS (ESI): $R_T$=4.388 min, mass calcd. for $C_{21}H_{22}ClFN_4O_4S_2$ 512.1, m/z found 512.9 [M+H]$^+$. Chiral HPLC (Column: Chiralpak IA 5 μm 4.6*250 mm; Mobile Phase: Hex:EtOH:DEA=70:30:0.2 at 1.0 mL/min; Temp: 30° C.; Wavelength: 230 nm, $R_T$=11.437 min). $^1$H NMR (400 MHz, DMSO-d$_6$) δ 9.60 (br s, 0.8H), 9.26 (br s, 0.2H), 8.05-8.00 (m, 1.8H), 7.95-7.94 (m, 0.2H), 7.42 (d, J=10.4 Hz, 1H), 7.31-7.26 (m, 2H), 5.89 (s, 0.2H), 5.77 (s, 0.8H), 3.72-3.63 (m, 3H), 3.55 (s, 3H), 2.91 (s, 0.6H), 2.90 (s, 2.4H), 2.80-2.72 (m, 2H), 2.08-1.95 (m, 1H), 1.90-1.72 (m, 2H), 1.63-1.61 (m, 1H).

Similarly utilizing the analogous procedures (Method O or Method P), the following products were prepared:

| Method | Product |
|---|---|
| O<br>Compound 9 | Compound 96B |
| P<br>Compound 11 | Compound 97B |
| O<br>Compound 40 | Compound 98 |

283
-continued

| Method | Product |
|---|---|
| P<br>Compound 40 | Compound 41 |
| P<br>Compound 55 | Compound 56 |
| P<br>Compound 60B<br>Compound 60D<br>Compound 60E<br>Compound 61G | Compound 60B<br>Compound 60D<br>Compound 60E<br>Compound 61G |
| P<br>Compound 60B<br>Compound 60D<br>Compound 61G | Compound 62B<br>Compound 62D |

284
-continued

| Method | Product |
|---|---|
| | Compound 62G |
| P<br>Compound 64 | Compound 65 |
| O<br>Compound 175 | Compound 176 |
| P<br>Compound 260 | Compound 261 |
| P<br>Compound 260 | Compound 262 |

| Method | Product |
|---|---|
| P<br>Compound 299B, 299D, 299G | 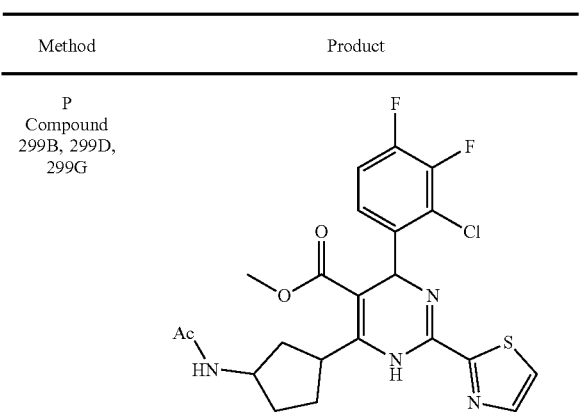<br>Compound 300B, 300D, 300G |
| P<br>Compound 371 | 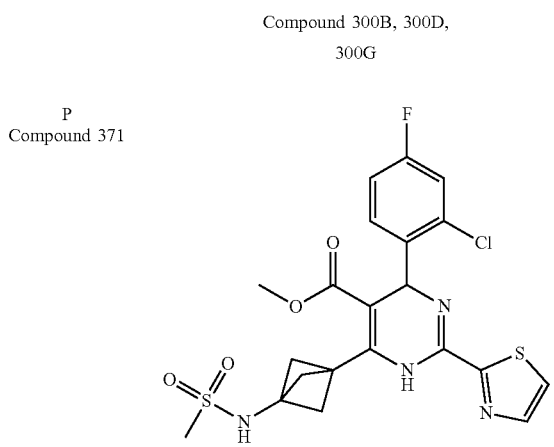<br>Compound 372 |
| P<br>Compound 377a and 377b | 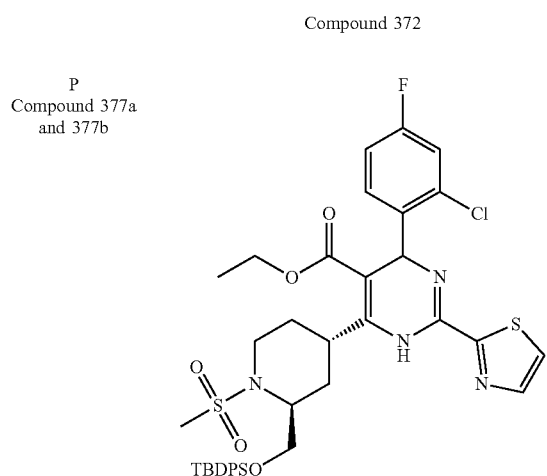<br>Compound 378a<br>Compound 378b |

| Method | Product |
|---|---|
| P<br>Compound 382 | 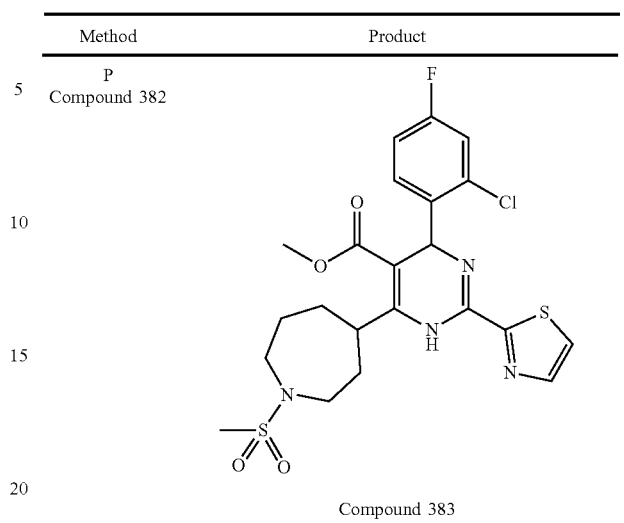<br>Compound 383 |
| O<br>Compound 14 | 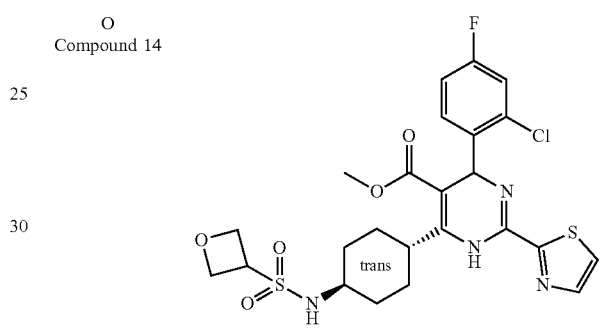<br>Compound 384 |

Compound 98: Methyl 4-(2-chloro-3-fluorophenyl)-6-(1-(methylsulfonyl)piperidin-3-yl)-2-(thiazol-2-yl)-1,4-dihydropyrimidine-5-carboxylate (a Mixture of 4 Stereoisomers)

Compound 98 (300 mg, 0.59 mmol) was further separated by chiral Prep. HPLC (the first separation condition: Column: Chiralpak IE 5 μm 20*250 mm; Mobile Phase: Hex:EtOH:DEA=70:30:0.3 at 12 mL/min; Temp: 30° C.; Wavelength: 230 nm; the second separation condition: Column: Chiralpak IC 5 μm 20*250 mm; Mobile Phase: Hex:EtOH:DEA=50:50:0.3 at 10 mL/min; Temp: 30° C.; Wavelength: 230 nm) to afford the title compounds Compound 98A (17.2 mg, 6% yield), Compound 98B (18.0 mg, 6% yield), Compound 98C (18.7 mg, 6% yield) and Compound 98D (25.9 mg, 9% yield) as yellow solids.

Compound 98A: LC-MS (ESI): $R_T$=3.335 min, mass calcd. for $C_{21}H_{22}ClFN_4O_4S_2$ 512.1, m/z found 512.9. Chiral HPLC (Column: Chiralpak IE 5 μm 4.6*250 mm; Mobile Phase: Hex:EtOH:DEA=70:30:0.2 at 1.0 mL/min; Temp: 30° C.; Wavelength: 230 nm, $R_T$=12.265 min). $^1$H NMR (400 MHz, DMSO-$d_6$) δ 9.62 (s, 0.8H), 9.36 (s, 0.2H), 8.01-7.94 (m, 2H), 7.43-7.30 (m, 2H), 7.21 (d, J=8.4 Hz, 0.8H), 7.19 (d, J=7.2 Hz, 0.2H), 6.10 (s, 0.2H), 5.99 (s, 0.8H), 4.14-4.06 (m, 0.2H), 3.84-3.74 (m, 0.8H), 3.71-3.63 (m, 1.5H), 3.53 (s, 2H), 3.51 (s, 1H), 3.49-3.43 (m, 0.5H), 3.04 (t, J=11.2 Hz, 1H), 2.97 (s, 1H), 2.93 (s, 2H), 2.75-2.67 (m, 1H), 1.85-1.69 (m, 3H), 1.62-1.53 (m, 1H).

Compound 41: ethyl 4-(2-chloro-4-fluorophenyl)-6-((1R,5S,6r)-3-(methylsulfonyl)-3-azabicyclo-[3.1.0] hexan-6-yl)-2-(thiazol-2-yl)-1,4-dihydropyrimidine-5-carboxylate (a Mixture of 2 Stereoisomers)

Compound 41 (170 mg, 0.32 mmol) was further separated by SFC (separation condition: Column: Chiralpak IA 5 μm 20*250 mm; Mobile Phase: $CO_2$: EtOH=70:30 at 45 g/min; Co-solvent: EtOH; Col. Temp: 39.8° C.; Wavelength: 214 nm, Back pressure: 100 bar) to afford stereoisomers Compound 41A (45.9 mg, 27% yield) and Compound 41B (58.8 mg, 35% yield) as pale yellow solids.

Compound 41A: LC-MS (ESI): $R_T$=3.687 min, mass calcd. for $C_{22}H_{22}ClFN_4O_4S_2$ 524.1, m/z found 525.1 [M+H]$^+$. SFC analytical method (Column: Chiralpak IA 5 μm 4.6*250 mm; Mobile Phase: $CO_2$: EtOH=70:30 at 4 mL/min; Col. Temp: 40° C.; Wavelength: 214 nm, Back pressure: 100 bar, $R_T$=2.88 min). $^1$H NMR (400 MHz, DMSO-$d_6$) δ 9.64 (d, J=2.8 Hz, 1H), 8.01 (s, 2H), 7.44-7.41 (m, 1H), 7.39-7.35 (m, 1H), 7.25-7.20 (m, 1H), 5.93 (d, J=2.8 Hz, 1H), 3.98 (q, J=7.2 Hz, 2H), 3.53-3.46 (m, 3H), 3.43 (s, 0.6H), 3.40 (s, 0.4H), 3.28 (t, J=2.8 Hz, 1H), 2.94 (s, 3H), 2.40-2.37 (m, 1H), 2.20-2.17 (m, 1H), 1.07 (t, J=6.8 Hz, 3H).

Compound 56: Ethyl 4-(2-chloro-4-fluorophenyl)-2-(3,5-difluoropyridin-2-yl)-6-(1-(methylsulfonyl) piperidin-4-yl)-1,4-dihydropyrimidine-5-carboxylate (a Mixture of 2 Stereoisomers)

Compound 56 (150 mg, 0.270 mmol) was further separated by chiral Prep. HPLC (Column: Chiralpak IC 5 μm 20*250 mm; Mobile Phase: Hex:EtOH=60:40 at 18 mL/min; Temp: 30° C.; Wavelength: 214 nm) to afford stereoisomers Compound 56A (43.2 mg, 29% yield) and Compound 56B (37.7 mg, 25% yield) as yellow solids.

Compound 56A: LC-MS (ESI): $R_T$=3.648 min, mass calcd. for $C_{24}H_{24}ClF_3N_4O_4S$ 556.1, m/z found 557.1 [M+H]$^+$. Chiral HPLC (Column: Chiralpak IC 5 μm 4.6*250 mm; Mobile Phase: Hex:EtOH=60:40 at 1.0 mL/min; Temp: 30° C.; Wavelength: 210 nm, $R_T$=9.583 min). $^1$H NMR (400 MHz, DMSO-$d_6$) δ 9.44 (s, 0.4H), 9.41 (d, J=3.2 Hz, 0.6H), 8.63-8.62 (m, 1H), 8.11-8.06 (m, 1H), 7.60-7.56 (m, 1H), 7.31-7.28 (m, 1H), 7.22-7.16 (m, 1H), 5.71 (s, 0.4H), 5.52 (d, J=3.6 Hz, 0.6H), 4.11-4.03 (m, 2H), 3.95-3.93 (m, 0.4H), 3.73-3.62 (m, 2.6H), 2.89-2.88 (m, 3H), 2.78-2.71 (m, 2H), 2.02-1.61 (m, 4H), 1.19-1.12 (m, 3H).

Compound 61B: Methyl 4-(2-chloro-3-fluorophenyl)-6-(3-(methylsulfonamido)-cyclopentyl)-2-(thiazol-2-yl)-1,4-dihydropyrimidine-5-carboxylate LC-MS (ESI): $R_T$=3.666 min, mass calcd. for $C_{21}H_{22}ClFN_4O_4S_2$ 512.1, m/z found 513.1 [M+H]$^+$. Chiral HPLC (Column: Chiralpak IA 5 μm 4.6*250 mm; Mobile Phase: $CO_2$:MeOH=70:30 at 4.0 mL/min; Col. Temp: 40.2° C.; Wavelength: 214 nm, Back pressure: 100 bar, Rt=6.50 min). $^1$H NMR (400 MHz, DMSO-$d_6$) δ 9.54 (br s, 0.7H), 9.16 (s, 0.3H), 8.00-7.99 (m, 1.7H), 7.93 (d, J=2.8 Hz, 0.3H), 7.41-7.31 (m, 2H), 7.21-7.12 (m, 2H), 6.05 (s, 0.2H), 5.94 (s, 0.8H), 4.48-4.43 (m, 0.2H), 4.33-4.25 (m, 0.8H), 4.05-3.97 (m, 1H), 3.52 (s, 3H), 2.93 (s, 3H), 2.28-2.22 (m, 1H), 2.14-2.07 (m, 1H), 1.98-1.77 (m, 2H), 1.70-1.54 (m, 2H).

Compound 61D: Methyl 4-(2-chloro-3-fluorophenyl)-6-(3-(methylsulfonamido)-cyclopentyl)-2-(thiazol-2-yl)-1,4-dihydropyrimidine-5-carboxylate LC-MS (ESI): $R_T$=3.625 min, mass calcd. for $C_{21}H_{22}ClFN_4O_4S_2$ 512.1, m/z found 513.1 [M+H]$^+$. Chiral HPLC (Column: Chiralpak IA 5 μm 4.6*250 mm; Mobile Phase: $CO_2$:MeOH=70:30 at 4.0 mL/min; Col. Temp: 40.3° C.; Wavelength: 214 nm, Back pressure: 100 bar, $R_T$=5.79 min). $^1$H NMR (400 MHz, DMSO-$d_6$) δ 9.52 (br s, 0.8H), 9.14 (s, 0.2H), 8.02-7.99 (m, 1.8H), 7.93 (d, J=3.2 Hz, 0.2H), 7.40-7.31 (m, 2H), 7.22-7.11 (m, 2H), 6.05 (s, 0.2H), 5.96 (s, 0.8H), 4.50-4.40 (m, 0.2H), 4.31-4.23 (m, 0.8H), 4.08-3.93 (m, 1H), 3.52 (s, 3H), 2.92 (s, 3H), 2.18-1.98 (m, 3H), 1.92-1.77 (m, 1H), 1.70-1.53 (m, 2H).

Compound 61E: Methyl 4-(2-chloro-3-fluorophenyl)-6-(3-(methylsulfonamido) cyclopentyl)-2-(thiazol-2-yl)-1,4-dihydropyrimidine-5-carboxylate LC-MS (ESI): $R_T$=3.976 min, mass calcd. for $C_{21}H_{22}ClFN_4O_4S_2$ 512.1, m/z found 512.9 [M+H]$^+$. Chiral HPLC (Column: Chiralpak AD-H 5 μm 4.6*250 mm; Mobile Phase: Hex:EtOH:DEA=80:20:0.2 at 1.0 mL/min; Temp: 30° C.; Wavelength: 230 nm, $R_T$=11.038 min). $^1$H NMR (400 MHz, DMSO-$d_6$) δ 9.56 (d, J=3.6 Hz, 0.7H), 8.94 (s, 0.3H), 8.03-8.01 (m, 1.5H), 7.97 (dd, J=14.0, 3.0 Hz, 0.5H), 7.41-7.29 (m, 2H), 7.19-7.14 (m, 2H), 6.06 (s, 0.3H), 5.96 (d, J=3.6 Hz, 0.7H), 4.35-4.26 (m, 0.3H), 4.17-4.08 (m, 0.7H), 3.87-3.79 (m, 0.3H), 3.76-3.66 (m, 0.7H), 3.52-3.51 (m, 3H), 2.98 (s, 1H), 2.94 (s, 2H), 2.44-2.37 (m, 0.3H), 2.24-2.18 (m, 0.7H), 2.02-1.64 (m, 5H).

Compound 61G: Methyl 4-(2-chloro-3-fluorophenyl)-6-(3-(methylsulfonamido)-cyclopentyl)-2-(thiazol-2-yl)-1,4-dihydropyrimidine-5-carboxylate LC-MS (ESI): $R_T$=3.770 min, mass calcd. for $C_{21}H_{22}ClFN_4O_4S_2$ 512.1, m/z found 512.9 [M+H]$^+$. Chiral HPLC (Column: Chiralpak IC 5 μm 4.6*250 mm; Mobile Phase: $CO_2$:MeOH=60:40 at 3.0 mL/min; Col. Temp: 40° C.; Wavelength: 214 nm, Back pressure: 100 bar, $R_T$=7.31 min). $^1$H NMR (400 MHz, DMSO-$d_6$) δ 9.58 (s, 0.7H), 8.96 (s, 0.3H), 8.04-7.95 (m, 2H), 7.41-7.29 (m, 2H), 7.20-7.14 (m, 2H), 6.06 (s, 0.3H), 5.96 (s, 0.7H), 4.34-4.25 (m, 0.3H), 4.15-4.07 (m, 0.7H), 3.82-3.75 (m, 0.3H), 3.74-3.66 (m, 0.7H), 3.52-3.50 (m, 3H), 2.96-2.93 (m, 3H), 2.29-2.23 (m, 0.3H), 2.07-1.97 (m, 2.7H), 1.89-1.65 (m, 3H).

Compound 62B: Methyl 6-(3-acetamidocyclopentyl)-4-(2-chloro-3-fluorophenyl)-2-(thiazol-2-yl)-1,4-dihydropyrimidine-5-carboxylate LC-MS (ESI): $R_T$=3.704 min, mass calcd. for $C_{22}H_{22}ClFN_4O_3S$ 476.1, m/z found 477.0 [M+H]$^+$. Chiral HPLC (Column: Chiralpak IA 5 μm 4.6*250 mm; Mobile Phase: Hex:EtOH=85:15 at 1.0 mL/min; Temp: 30° C.; Wavelength: 230 nm, $R_T$=16.977 min). $^1$H NMR (400 MHz, DMSO-$d_6$) δ 9.57 (d, J=3.6 Hz, 0.8H), 9.08 (s, 0.2H), 8.03-8.00 (m, 2H), 7.94-7.90 (m, 1H), 7.41-7.29 (m, 2H), 7.19 (d, J=7.6 Hz, 0.8H), 7.13 (d, J=7.2 Hz, 0.2H), 6.05 (s, 0.2H), 5.94 (d, J=3.6 Hz, 0.8H), 4.48-4.38 (m, 0.2H), 4.35-4.24 (m, 1.8H), 3.52-3.51 (m, 3H), 2.22-2.12 (m, 1H), 2.09-2.01 (m, 1H), 1.94-1.82 (m, 1H), 1.79 (s, 3H), 1.76-1.67 (m, 2H), 1.56-1.43 (m, 1H).

Compound 62D: Methyl 6-(3-acetamidocyclopentyl)-4-(2-chloro-3-fluorophenyl)-2-(thiazol-2-yl)-1,4-dihydropyrimidine-5-carboxylate LC-MS (ESI): $R_T$=3.675 min, mass calcd. for $C_{22}H_{22}ClFN_4O_3S$ 476.1, m/z found 477.0 [M+H]$^+$. Chiral HPLC (Column: Chiralpak IA 5 μm 4.6*250 mm; Mobile Phase: Hex:EtOH=85:15 at 1.0 mL/min; Temp: 30° C.; Wavelength: 254 nm, $R_T$=9.898 min). $^1$H NMR (400 MHz, DMSO-$d_6$) δ 9.55 (d, J=2.8 Hz, 0.8H), 9.13 (s, 0.2H), 8.00-7.88 (m, 3H), 7.40-7.31 (m, 2H), 7.20-7.12 (m, 1H), 6.05 (s, 0.2H), 5.96 (d, J=2.0 Hz, 0.8H), 4.50-4.39 (m, 0.2H), 4.33-4.22 (m, 1.8H), 3.52 (s, 3H), 2.10-1.98 (m, 3H), 1.91-1.83 (m, 1H), 1.79 (s, 3H), 1.59-1.43 (m, 2H).

Compound 62G: Methyl 6-(3-acetamidocyclopentyl)-4-(2-chloro-3-fluorophenyl)-2-(thiazol-2-yl)-1,4-dihydropyrimidine-5-carboxylate LC-MS (ESI): $R_T$=3.489 min, mass calcd. for $C_{22}H_{22}ClFN_4O_3S$ 476.1, m/z found 477.0 [M+H]$^+$. Chiral HPLC (Column: Chiralpak IB 5 μm 4.6*250 mm; Mobile Phase: Hex:EtOH=90:10 at 1.0 mL/min; Temp: 30° C.; Wavelength: 254 nm, $R_T$=11.172 min). $^1$H NMR (400 MHz, DMSO-$d_6$) δ 9.56 (d, J=3.6 Hz, 0.7H), 8.69 (s, 0.3H), 8.04-8.01 (m, 1.7H), 7.99 (d, J=3.2 Hz, 0.3H), 7.96 (d, J=3.6 Hz, 0.3H), 7.90 (d, J=7.6 Hz, 0.7H), 7.41-7.30 (m, 2H), 7.20-7.15 (m, 1H), 6.07 (s, 0.3H), 5.96 (d, J=3.6 Hz, 0.7H), 4.37-4.27 (m, 0.3H), 4.15-4.01 (m, 1.7H), 3.52-3.51 (m, 3H), 2.20-2.13 (m, 0.3H), 2.06-1.87 (m, 4.7H), 1.80 (s, 2H), 1.74-1.57 (m, 2H).

Compound 65: 4-(2-Chloro-4-fluoro-phenyl)-6-(1-methanesulfonyl-pyrrolidin-3-yl)-2-thiazol-2-yl-1,4-dihydro-pyrimidine-5-carboxylic Acid Methyl Ester (a Mixture of 4 Stereoisomers)

Compound 65 (240 mg, 0.482 mmol) was further separated by chiral Prep. HPLC (the first separation condition (Column: Chiralpak IB 5 μm 20*250 mm, Mobile Phase: Hex:EtOH:DEA=80:20:0.3 at 15 mL/min, Temp: 30° C., Wavelength: 230 nm) and the second separation condition (Column: Chiralpak IE 5 μm 20*250 mm, Mobile Phase: Hex:EtOH:DEA=50:50:0.3 at 10 mL/min, Temp: 30° C., Wavelength: 230 nm)) to afford stereoisomers Compound 65A (22.4 mg, 9% yield), Compound 65B (36.8 mg, 15% yield), Compound 65C (42.7 mg, 18% yield) and Compound 65D (23.4 mg, 10% yield).

Compound 65A: LC-MS (ESI): $R_T$=3.750 min, mass calcd. for $C_{20}H_{20}ClFN_4O_4S_2$ 498.1, m/z found 498.9 [M+H]$^+$. Chiral HPLC (Column: Chiralpak IE 5 μm 4.6*250 mm; Mobile Phase: Hex:EtOH:DEA=50:50:0.2 at 1.0 mL/min; Temp: 30° C.; Wavelength: 230 nm, $R_T$=8.523 min). $^1$H NMR (400 MHz, DMSO-$d_6$) δ 9.60 (s, 0.9H), 9.33 (s, 0.1H), 8.01 (s, 1.9H), 7.94 (s, 0.1H), 7.43-7.36 (m, 2H), 7.23-7.19 (m, 1H), 6.03 (s, 0.1H), 5.95 (s, 0.9H), 4.58-4.53 (m, 0.1H), 4.40-4.33 (m, 0.9H), 3.62-3.37 (m, 7H), 3.03 (s, 0.3H), 2.97 (s, 2.7H), 2.22-2.13 (m, 1H), 2.05-1.97 (m, 1H).

Compound 65C: LC-MS (ESI): $R_T$=3.709 min, mass calcd. for $C_{20}H_{20}ClFN_4O_4S_2$ 498.1, m/z found 498.9 [M+H]$^+$. Chiral HPLC (Column: Chiralpak IE 5 μm 4.6*250 mm; Mobile Phase: Hex:EtOH:DEA=50:50:0.2 at 1.0 mL/min; Temp: 30° C.; Wavelength: 230 nm, $R_T$=10.361 min). $^1$H NMR (400 MHz, DMSO-$d_6$) δ 9.62 (s, 0.9H), 9.28 (s, 0.1H), 8.02-7.93 (m, 2H), 7.43-7.35 (m, 2H), 7.24-7.19 (m, 1H), 6.03 (s, 0.1H), 5.94 (d, J=2.4 Hz, 0.9H), 4.59-4.55 (m, 0.1H), 4.41-4.33 (m, 0.9H), 3.59-3.34 (m, 7H), 3.03 (s, 0.3H), 2.95 (s, 2.7H), 2.33-2.24 (m, 1H), 2.18-2.11 (m, 1H).

Compound 176: Methyl 4-(2-chloro-4-fluorophenyl)-6-((cis)-2-(methylsulfonyl)-octahydrocyclopenta[c]pyrrol-5-yl)-2-(thiazol-2-yl)-1,4-dihydropyrimidine-5-carboxylate and Methyl Racemic 176 was separated using C18 column (acetonitrile:water=70%-80%) and Prep. HPLC (Column: Waters Kinate EVO C18 (5 μm 21.2*150 mm), Mobile Phase A: water (+0.1% trifluoroacetic acid), Mobile Phase B: acetonitrile, UV: 214 nm, Flow rate: 15 mL/min, Gradient: 30-60% (% B)) to give 176X (17 mg, 10% yield) and 176Y (60 mg, 35% yield) as yellow solids.

Compound 176X was then separated using chiral Prep. HPLC (Column: Chiralpak IC m 20*250 mm; Mobile Phase: $CO_2$: IPA=60:40 at 50 g/min; Co-solvent: IPA; Col. Temp: 40° C.; Wavelength: 214 nm, Back pressure: 100 bar) to afford the title compounds 176A (26 mg, 17% yield, 100% stereopure) and 176B (23 mg, 15% yield, 98.3% stereopure) as yellow solids.

Compound 176A: LC-MS (ESI): $R_T$=3.923 min, mass calcd. for $C_{23}H_{24}ClFN_4O_4S_2$ 538.1, m/z found 539.2 [M+H]$^+$. Chiral SFC (Column: Chiralpak IG 5 μm 4.6*250 mm; Mobile Phase: $CO_2$: IPA=60:40 at 2.999 g/min; Col. Temp: 40.2° C.; Wavelength: 214 nm, Back pressure: 100 bar, $R_T$=3.85 min). $^1$H NMR (400 MHz, DMSO-$d_6$) δ 9.44 (d, J=2.8 Hz, 0.8H), 9.00 (s, 0.2H), 7.99 (d, J=1.6 Hz, 1.8H), 7.93 (br s, 0.2H), 7.42 (dd, J=9.2, 2.4 Hz, 1H), 7.34-7.31 (m, 1H), 7.30-7.18 (m, 1H), 6.00 (s, 0.2H), 5.91 (d, J=2.8 Hz, 0.8H), 4.47-4.38 (m, 0.2H), 4.32-4.24 (m, 0.8H), 3.54 (s, 3H), 3.48-3.37 (m, 2H), 2.99-2.92 (m, 4H), 2.91 (s, 3H), 2.22-2.14 (m, 1H), 2.08-2.01 (m, 1H), 1.87-1.81 (m, 0.3H), 1.77-1.72 (m, 1H), 1.62-1.58 (m, 0.7H).

Compound 176Y was further separated using chiral Prep. HPLC (Column: Chiralpak IA 5 μm 20*250 mm; Mobile Phase: Hex:EtOH=70:30; Temp: 30° C.; Wavelength: 230 nm) to afford the title compounds 176C (26 mg, 17% yield, 100% stereopure) and 176D (23 mg, 15% yield, 99.5% stereopure) as yellow solids. 176D: LC-MS (ESI): $R_T$=3.686 min, mass calcd. for $C_{23}H_{24}ClFN_4O_4S_2$ 538.1, m/z found 538.9 [M+H]$^+$. Chiral SFC (Column: Chiralpak IA 5 μm 4.6*250 mm; Mobile Phase: $CO_2$:MeOH=70:30 at 2.999 g/min; Col. Temp: 39.7° C.; Wavelength: 230 nm, Back pressure: 100 bar, $R_T$=4.41 min). $^1$H NMR (400 MHz, CDCl$_3$) δ 8.25 (br s, 0.2H), 7.84-7.82 (m, 1H), 7.50 (d, J=3.2 Hz, 0.7H), 7.44 (d, J=3.2 Hz, 0.3H), 7.42 (br s, 0.8H), 7.25-7.23 (m, 1H), 7.15-7.11 (m, 1H), 6.97-6.88 (m, 1H), 6.19 (s, 0.2H), 6.05 (d, J=2.8 Hz, 0.8H), 4.44-4.27 (m, 1H), 3.60 (s, 2H), 3.59 (s, 1H), 3.45-3.41 (m, 3.5H), 3.27-3.19 (m, 0.5H), 2.90 (s, 1H), 2.88 (s, 2H), 2.87-2.77 (m, 2H), 2.53-2.43 (m, 0.3H), 2.38-2.23 (m, 1H), 2.11-2.02 (m, 2H), 1.90-1.83 (m, 0.7H).

Compound 261: (cis)-Ethyl 4-(2-chloro-3-fluorophenyl)-6-(4-(methylsulfonamido)-tetrahydrofuran-2-yl)-2-(thiazol-2-yl)-1,4-dihydropyrimidine-5-carboxylate LC-MS (ESI): $R_T$=3.735 min, mass calcd. for $C_{21}H_{22}ClFN_4O_5S_2$ 528.1, m/z found 528.9 [M+H]$^+$. $^1$H NMR (400 MHz, DMSO-$d_6$) δ 9.14 (s, 0.4H), 8.99 (s, 0.4H), 8.95 (s, 0.1H), 8.87 (s, 0.1H), 8.03-8.00 (m, 1H), 7.97-7.95 (m, 0.8H), 7.60-7.55 (m, 0.2H), 7.51 (d, J=4.4 Hz, 0.4H), 7.38-7.27 (m, 3H), 6.13 (s, 0.4H), 6.08 (s, 0.4H), 6.02-6.00 (m, 0.1H), 5.96-5.94 (m, 0.1H), 5.70-5.59 (m, 0.2H), 5.50-5.44 (m, 0.8H), 4.32-4.24 (m, 0.2H), 4.13-4.07 (m, 1.3H), 3.99-3.95 (m, 3.3H), 3.80-3.75 (m, 0.2H), 2.99-2.95 (m, 3H), 2.92-2.85 (m, 0.8H), 2.64-2.61 (m, 0.2H), 2.58-2.55 (m, 0.7H), 2.45-2.42 (m, 0.3H), 2.26-2.19 (m, 0.1H), 2.09-2.03 (m, 0.5H), 1.86-1.79 (m, 0.4H), 1.07-1.00 (m, 3H).

Compound 262: (cis)-Ethyl 6-(4-acetamidotetrahydrofuran-2-yl)-4-(2-chloro-3-fluorophenyl)-2-(thiazol-2-yl)-1,4-dihydropyrimidine-5-carboxylate LC-MS (ESI): $R_T$=3.620 min, mass calcd. for $C_{21}H_{22}ClFN_4O_4S_2$ 492.1, m/z found 492.9 [M+H]$^+$. $^1$H NMR (400 MHz, CD$_3$OD) δ 7.94-7.91 (m, 1H), 7.75-7.73 (m, 1H), 7.31-7.26 (m, 1.5H), 7.21-7.11 (m, 1.5H), 6.23 (s, 0.5H), 6.20 (s, 0.5H), 5.73-5.67 (m, 0.2H), 5.62-5.52 (m, 0.8H), 4.46-4.41 (m, 0.5H), 4.39-4.33 (m, 0.5H), 4.17-4.14 (m, 0.5H), 4.08-4.00 (m, 3.3H), 3.88-3.84 (m, 0.2H), 3.07-2.98 (m, 0.8H), 2.70-2.65 (m, 0.2H), 2.02-1.96 (m, 1H), 1.95-1.91 (m, 1.3H), 1.86-1.80 (m, 1.7H), 1.12-1.09 (m, 3H). Compound 300B, 300D and 300E: Methyl 6-(-3-acetamidocyclopentyl)-4-(2-chloro-3,4-difluorophenyl)-2-(thiazol-2-yl)-1,4-dihydropyrimidine-5-carboxylate Compound 300B: Prep. HPLC (Column: gilson X-bridge C18 (5 μm 19*150 mm), Mobile Phase A: water (0.1% ammonium bicarbonate), Mobile Phase B: acetonitrile, UV: 214 nm, Flow rate: 15 mL/min, Gradient: 35-65% (% B)) to give the title compound 300B (120 mg, 61% yield, 100% ee) as yellow solids. LC-MS (ESI): $R_T$=4.358 min, mass calcd. for C$_{22}$H$_{21}$ClF$_2$N$_4$O$_3$S 494.1, m/z found 495.0 [M+H]$^+$. Chiral HPLC (Column: Chiralpak IA 5 μm 4.6*250 mm; Mobile Phase: CO$_2$:MeOH=70:30 at 2.999 g/min; Col. Temp: 39.9° C.; Wavelength: 230 nm, Back pressure: 100 bar, $R_T$=2.85 min). $^1$H NMR (400 MHz, CDCl$_3$) δ 8.13 (br s, 0.3H), 7.83-7.81 (m, 1H), 7.50 (d, J=3.2 Hz, 0.6H), 7.45 (d, J=3.2 Hz, 0.4H), 7.39 (d, J=0.8 Hz, 0.7H), 7.08-7.01 (m, 2H), 6.18 (s, 0.4H), 6.04 (d, J=2.8 Hz, 0.6H), 5.63 (d, J=6.4 Hz, 0.4H), 5.55 (d, J=6.8 Hz, 0.6H), 4.64-4.59 (m, 1H), 4.55-4.41 (m, 1H), 3.60 (s, 2H), 3.59 (s, 1H), 2.48-2.41 (m, 0.6H), 2.39-2.24 (m, 1H), 2.19-2.05 (m, 1.4H), 2.00 (s, 3H), 1.97-1.96 (m, 0.7H), 1.91-1.81 (m, 1.3H), 1.72-1.63 (m, 0.6H), 1.54-1.51 (s, 0.4H).

Compound 300D: purified by Prep. HPLC (Column: gilson X-bridge C18 (5 μm 19*150 mm), Mobile Phase A: water (0.1% ammonium bicarbonate), Mobile Phase B: acetonitrile, UV: 214 nm, Flow rate: 15 mL/min, Gradient: 35-65% (% B)) to give the title compound 300D (210 mg, 71% yield, 100% ee) as yellow solids. LC-MS (ESI): $R_T$=3.573 min, mass calcd. for C$_{22}$H$_{21}$ClF$_2$N$_4$O$_3$S 494.1, m/z found 494.7 [M+H]$^+$. Chiral HPLC (Column: Chiralpak IE 5 μm 4.6*250 mm; Mobile Phase: Hex:EtOH=70:30 at 1.0 mL/min; Temp: 30° C.; Wavelength: 230 nm, $R_T$=7.839 min). $^1$H NMR (400 MHz, CDCl$_3$) δ 8.13 (s, 0.4H), 7.82 (d, J=3.2 Hz, 1H), 7.51 (d, J=3.2 Hz, 0.6H), 7.45 (d, J=3.2 Hz, 0.4H), 7.38 (d, J=2.0 Hz, 0.6H), 7.08-7.01 (m, 2H), 6.18 (s, 0.4H), 6.05 (d, J=2.8 Hz, 0.6H), 5.58 (d, J=10.4 Hz, 0.4H), 5.50 (d, J=6.8 Hz, 0.6H), 4.62-4.56 (m, 1H), 4.54-4.41 (m, 1H), 3.60 (s, 2H), 3.59 (s, 1H), 2.40-2.31 (m, 1H), 2.29-2.22 (m, 1H), 2.19-2.09 (m, 1H), 2.09-2.01 (m, 1H), 1.99 (s, 1H), 1.98 (s, 2H), 1.79-1.68 (m, 2H).

Compound 300G: purified by Prep. HPLC (Column: gilson X-bridge C18 (5 μm 19*150 mm), Mobile Phase A: water (0.1% ammonium bicarbonate), Mobile Phase B: acetonitrile, UV: 214 nm, Flow rate: 15 mL/min, Gradient: 35-65% (% B)) to give the title compound 300G (200 mg, 59% yield, 99.5% ee) as yellow solids. LC-MS (ESI): $R_T$=3.593 min, mass calcd. for C$_{22}$H$_{21}$ClF$_2$N$_4$O$_3$S 494.1, m/z found 494.7 [M+H]$^+$. Chiral HPLC (Column: Chiralpak IC 5 μm 4.6*250 mm; Mobile Phase: CO$_2$:MeOH=70:30 at 2.999 g/min; Col. Temp: 40° C.; Wavelength: 230 nm, Back pressure: 100 bar, $R_T$=5.77 min). H NMR (400 MHz, CDCl$_3$) δ 8.17 (s, 0.1H), 7.89 (d, J=3.2 Hz, 0.8H), 7.80 (d, J=3.2 Hz, 0.2H), 7.55 (d, J=3.2 Hz, 0.9H), 7.53 (br s, 0.9H), 7.46 (d, J=2.8 Hz, 0.1H), 7.13-7.02 (m, 2H), 6.19 (s, 0.1H), 6.09 (d, J=2.8 Hz, 0.9H), 4.49-4.43 (m, 1.8H), 4.39-4.31 (m, 0.2H), 3.61 (s, 2.5H), 3.59 (s, 0.5H), 2.51-2.43 (m, 1H), 2.34-2.27 (m, 0.9H), 2.25-2.14 (m, 0.2H), 2.13-2.11 (m, 1H), 2.00 (s, 3H), 1.97-1.93 (m, 0.8H), 1.89-1.74 (m, 3H).

Compound 372: Methyl 4-(2-chloro-4-fluorophenyl)-6-(3-(methylsulfonamido)bicyclo[1.1.1]pentan-1-yl)-2-(thiazol-2-yl)-1,4-dihydropyrimidine-5-carboxylate LC-MS (ESI): $R_T$=3.314 min, mass calcd. for C$_{21}$H$_{20}$ClFN$_4$O$_4$S$_2$ 510.1, m/z found 510.9 [M+H]$^+$. $^1$H NMR (400 MHz, DMSO-d$_6$) δ 9.46 (d, J=3.6 Hz, 0.5H), 8.35 (s, 0.5H), 8.17 (s, 0.5H), 8.02-8.00 (m, 0.5H), 8.00 (s, 1.5H), 7.96 (d, J=2.8 Hz, 0.5H), 7.46-7.41 (m, 1H), 7.35-7.30 (m, 1H), 7.25-7.19 (m, 1H), 5.97 (s, 0.5H), 5.87 (d, J=3.6 Hz, 0.5H), 3.55 (s, 1.5H), 3.53 (s, 1.5H), 2.96 (s, 1.4H), 2.93 (s, 1.6H), 2.44 (s, 3H), 2.28 (s, 3H).

Racemic 372 (180 mg, 0.353 mmol) was separated by chiral Prep. HPLC (Column: Chiralpak IG 5 μm 20*250 mm; Mobile Phase: Hex:EtOH=70:30 at 13 mL/min; Temp: 30° C.; Wavelength: 230 nm) to afford the title compounds 372X (56.3 mg, 31% yield, 100% stereopure) and 372Y (50.1 mg, 28% yield, 99.7% stereopure).

Compound 372X: LC-MS (ESI): $R_T$=3.125 min, mass calcd. for C$_{21}$H$_{20}$ClFN$_4$O$_4$S$_2$ 510.1, m/z found 511.2 [M+H]$^+$. Chiral analysis (Column: Chiralpak IG 5 μm 4.6*250 mm; Mobile Phase: Hex:EtOH=70:30 at 1.0 mL/min; Temp: 30° C.; Wavelength: 230 nm, $R_T$=8.003 min). $^1$H NMR (400 MHz, DMSO-d$_6$) δ 9.47-9.40 (m, 0.5H), 8.37-8.32 (m, 0.5H), 8.18-8.13 (m, 0.5H), 8.01-8.00 (m, 2H), 7.96-7.94 (m, 0.5H), 7.44-7.42 (m, 1H), 7.34-7.31 (m, 1H), 7.24-7.20 (m, 1H), 5.97 (s, 0.5H), 5.87 (s, 0.5H), 3.54 (s, 3H), 2.95 (s, 1.3H), 2.94 (s, 1.7H), 2.44 (s, 3H), 2.28 (s, 3H).

Compound 372Y: LC-MS (ESI): $R_T$=3.164 min, mass calcd. for C$_{21}$H$_{20}$ClFN$_4$O$_4$S$_2$ 510.1, m/z found 511.2 [M+H]$^+$. Chiral analysis (Column: Chiralpak IG 5 μm 4.6*250 mm; Mobile Phase: Hex:EtOH=70:30 at 1.0 mL/min; Temp: 30° C.; Wavelength: 230 nm, $R_T$=10.326 min). $^1$H NMR (400 MHz, DMSO-d$_6$) δ 9.47-9.41 (m, 0.5H), 8.37-8.32 (m, 0.5H), 8.18-8.13 (m, 0.5H), 8.00-7.99 (m, 2H), 7.96-7.93 (m, 0.5H), 7.44-7.42 (m, 1H), 7.34-7.30 (m, 1H), 7.24-7.20 (m, 1H), 5.97 (s, 0.5H), 5.87 (s, 0.5H), 3.54 (s, 3H), 2.95 (s, 1.3H), 2.94 (s, 1.7H), 2.44 (s, 3H), 2.28 (s, 3H).

Compound 378a: ethyl 6-((trans)-2-(((tert-butyldiphenylsilyl)oxy)methyl)-1-(methylsulfonyl)piperidin-4-yl)-4-(2-chloro-4-fluorophenyl)-2-(thiazol-2-yl)-1,4-dihydropyrimidine-5-carboxylate LC-MS (ESI): $R_T$=2.861, mass calcd. for C$_{39}$H$_{44}$ClFN$_4$O$_5$S$_2$Si 794.2, m/z found 795.3 [M+H]$^+$.

Compound 378b: ethyl 6-((trans)-2-(((tert-butyldiphenylsilyl)oxy)methyl)-1-(methylsulfonyl)piperidin-4-yl)-4-(2-chloro-4-fluorophenyl)-2-(thiazol-2-yl)-1,4-dihydropyrimidine-5-carboxylate LC-MS (ESI): $R_T$=2.831 min, mass calcd. for C$_{39}$H$_{44}$ClFN$_4$O$_5$S$_2$Si 794.2, m/z found 795.3 [M+H]$^+$.

Compound 383: Methyl 4-(2-chloro-4-fluorophenyl)-6-(1-(methylsulfonyl)azepan-4-yl)-2-(thiazol-2-yl)-1,4-dihydropyrimidine-5-carboxylate LC-MS (ESI): $R_T$=3.891 min, mass calcd. for C$_{22}$H$_{24}$ClFN$_4$O$_4$S$_2$ 526.1, m/z found 527.2 [M+H]$^+$. $^1$H NMR (400 MHz, CDCl$_3$) δ 8.12 (s, 0.4H), 7.84-7.83 (s, 1H), 7.50 (d, J=3.2 Hz, 0.6H), 7.45 (d, J=3.2 Hz, 0.4H), 7.42-7.40 (m, 0.6H), 7.32-7.29 (m, 0.6H), 7.25-7.24 (m, 0.4H), 7.15-

7.12 (m, 1H), 6.98-6.90 (m, 1H), 6.19 (s, 0.2H), 6.16 (s, 0.2H), 6.05 (s, 0.6H), 4.23-4.17 (m, 0.4H), 4.04-3.98 (m, 0.6H), 3.79-3.68 (m, 1H), 3.61-3.55 (m, 4H), 3.45-3.22 (m, 2H), 2.94-2.90 (m, 3H), 2.26-1.81 (m, 6H).

Racemic 383 (251 mg, 0.480 mmol) was separated by chiral Prep. SFC (separation condition: Column: Chiralpak IA 5 μm 20*250 mm; Mobile Phase: $CO_2$:MeOH=70:30 at 45 g/min; Col. Temp 41.1° C.; Wavelength: 214 nm; Back pressure: 100 bar; Column: Chiralpak IA 5 μm 20*250 mm; Mobile Phase: Hex:IPA:DEA=80:20:0.3 at 15 mL/min; Temp: 30° C.; Wavelength: 230 nm; Column: Chiralpak IC 5 μm 20*250 mm; Mobile Phase: Hex:EtOH:DEA=70:30: 0.3 at 15 mL/min; Temp: 30° C.; Wavelength: 230 nm) to afford the title compounds 383A (25 mg, 10% yield, 100% stereopure) and 383B (22 mg, 9% yield, 99.4% stereopure), 383C (23 mg, 32% yield, 99.2% stereopure) and 383D (31 mg, 12% yield, 100% stereopure) as yellow solids.

Compound 383A: LC-MS (ESI): $R_T$=3.909 min, mass calcd. for $C_{22}H_{24}ClFN_4O_4S_2$ 526.1, m/z found 527.2 $[M+H]^+$. Chiral analysis (Column: Chiralpak IC 5 μm 4.6*250 mm; Mobile Phase: Hex:EtOH:DEA=70:30:0.2 at 1.0 mL/min; Temp: 30° C.; Wavelength: 230 nm; $R_T$=14.425 min). $^1$H NMR (400 MHz, DMSO-$d_6$) δ 9.49 (s, 0.7H), 9.13 (s, 0.3H), 8.00 (s, 1.6H), 7.94 (s, 0.4H), 7.44-7.42 (m, 1H), 7.38-7.31 (m, 1H), 7.24-7.20 (m, 1H), 6.01 (s, 0.3H), 5.91 (s, 0.7H), 4.04 (s, 0.3H), 3.84-3.80 (m, 0.7H), 3.53-3.36 (m, 5H), 3.28-3.19 (m, 2H), 2.94 (s, 3H), 2.13-1.62 (m, 6H).

Compound 383B: LC-MS (ESI): $R_T$=3.635 min, mass calcd. for $C_{22}H_{24}ClFN_4O_4S_2$ 526.1, m/z found 526.9 $[M+H]^+$. Chiral analysis (Column: Chiralpak IC 5 μm 4.6*250 mm; Mobile Phase: Hex:EtOH:DEA=70:30:0.2 at 1.0 mL/min; Temp: 30° C.; Wavelength: 230 nm; $R_T$=16.887 min). $^1$H NMR (400 MHz, DMSO-$d_6$) δ 9.47 (d, J=3.6 Hz, 0.7H), 9.12 (s, 0.3H), 8.00-7.99 (m, 1.6H), 7.94-7.93 (m, 0.4H), 7.45-7.41 (m, 1H), 7.38-7.31 (m, 1H), 7.24-7.19 (m, 1H), 6.01 (s, 0.3H), 5.91 (d, J=3.6 Hz, 0.7H), 4.07-4.01 (m, 0.3H), 3.84-3.78 (m, 0.7H), 3.55-3.39 (m, 5H), 3.26-3.20 (m, 2H), 2.93 (s, 3H), 2.14-1.62 (m, 6H).

Compound 383C: LC-MS (ESI): $R_T$=3.619 min, mass calcd. for $C_{22}H_{24}ClFN_4O_4S_2$ 526.1, m/z found 526.9 $[M+H]^+$. Chiral analysis (Column: Chiralpak IA; Mobile Phase: $CO_2$:MeOH=70:30 at 2.999 mL/min; Col. Temp: 40° C.; Wavelength: 214 nm, Back pressure: 100 bar, $R_T$=3.73 min). $^1$H NMR (400 MHz, DMSO-$d_6$) δ 9.48 (d, J=3.6 Hz, 0.7H), 9.08 (s, 0.3H), 8.00-7.99 (m, 1.6H), 7.94-7.93 (m, 0.4H), 7.44-7.41 (m, 1H), 7.38-7.30 (m, 1H), 7.25-7.20 (m, 1H), 6.00 (s, 0.3H), 5.91 (d, J=3.2 Hz, 0.7H), 4.06-4.00 (m, 0.3H), 3.84-3.79 (m, 0.7H), 3.52-3.41 (m, 5H), 3.31-3.21 (m, 2H), 2.93 (s, 3H), 2.13-1.66 (m, 6H).

Compound 383D: LC-MS (ESI): $R_T$=3.617 min, mass calcd. for $C_{22}H_{24}ClFN_4O_4S_2$ 526.1, m/z found 526.9 $[M+H]^+$. Chiral analysis (Column: Chiralpak IA; Mobile Phase: $CO_2$:MeOH=70:30 at 2.999 mL/min; Temp: 40° C.; Wavelength: 214 nm, $R_T$=4.63 min). $^1$H NMR (400 MHz, DMSO-$d_6$) δ 9.48 (d, J=3.6 Hz, 0.7H), 9.08 (s, 0.3H), 8.00-7.99 (m, 1.6H), 7.94-7.93 (m, 0.4H), 7.44-7.41 (m, 1H), 7.38-7.33 (m, 1H), 7.25-7.19 (m, 1H), 6.00 (s, 0.3H), 5.91 (d, J=3.6 Hz, 0.7H), 4.06-4.00 (m, 0.3H), 3.84-3.79 (m, 0.7H), 3.52-3.42 (m, 5H), 3.31-3.22 (m, 2H), 2.93 (s, 3H), 2.13-1.66 (m, 6H).

Compound 384: (trans)-Methyl 4-(2-chloro-4-fluorophenyl)-6-(4-(oxetane-3-sulfonamido)cyclohexyl)-2-(thiazol-2-yl)-1,4-dihydropyrimidine-5-carboxylate LC-MS (ESI): $R_T$=3.381 min, mass calcd. for $C_{24}H_{26}ClFN_4O_5S_2$ 568.1, m/z found 569.2 $[M+H]^+$. $^1$H NMR (400 MHz, DMSO-$d_6$) δ 9.47 (d, J=3.6 Hz, 0.6H), 9.04 (s, 0.4H), 8.00-7.98 (m, 1.5H), 7.94 (d, J=3.2 Hz, 0.5H), 7.51-7.41 (m, 2H), 7.35-7.29 (m, 1H), 7.23-7.19 (m, 1H), 5.99 (s, 0.4H), 5.90 (d, J=3.6 Hz, 0.6H), 4.84-4.78 (m, 2H), 4.72-4.59 (m, 3H), 3.85-3.76 (m, 0.5H), 3.55 (br s, 0.5H), 3.51 (s, 2H), 3.50 (s, 1H), 3.32 (br s, 0.4H), 3.13-3.11 (m, 0.6H), 2.01-1.59 (m, 6H), 1.35-1.23 (m, 2H). Racemic 384 (110 mg, 0.190 mmol) was separated by chiral Prep. HPLC (Column: Chiralpak IE 5 μm 20*250 mm; Mobile Phase: Hex:EtOH=50:50 at 10.0 mL/min; Temp: 30° C.; Wavelength: 230 nm) to afford the title compounds 384A (43.1 mg, 39% yield, 100% stereopure) and 384B (42.3 mg, 38% yield, 100% stereopure).

Compound 384A: LC-MS (ESI): $R_T$=3.309 min, mass calcd. for $C_{24}H_{26}ClFN_4O_5S_2$ 568.1, m/z found 569.2 $[M+H]^+$. Chiral HPLC (Column: Chiralpak IE 5 μm 4.6*250 mm; Mobile Phase: Hex:EtOH=50:50 at 1.0 mL/min; Temp: 30° C.; Wavelength: 230 nm, $R_T$=9.233 min). $^1$H NMR (400 MHz, DMSO-$d_6$) δ 9.46 (d, J=3.2 Hz, 0.6H), 9.03 (s, 0.4H), 7.99-7.98 (m, 1.5H), 7.94 (d, J=3.2 Hz, 0.5H), 7.49-7.41 (m, 2H), 7.35-7.29 (m, 1H), 7.22-7.21 (m, 1H), 5.99 (s, 0.4H), 5.90 (d, J=2.8 Hz, 0.6H), 4.84-4.78 (m, 2H), 4.68-4.58 (m, 3H), 3.82-3.76 (m, 0.4H), 3.68 (br s, 0.6H), 3.51 (s, 2H), 3.50 (s, 1H), 3.31-3.27 (m, 0.4H), 3.14-3.09 (m, 0.6H), 1.94-1.59 (m, 6H), 1.34-1.29 (m, 2H).

Compound 384B: LC-MS (ESI): $R_T$=3.264 min, mass calcd. for $C_{24}H_{26}ClFN_4O_5S_2$ 568.1, m/z found 569.2 $[M+H]^-$. Chiral HPLC (Column: Chiralpak IE 5 μm 4.6*250 mm; Mobile Phase: Hex:EtOH=50:50 at 1.0 mL/min; Temp: 30° C.; Wavelength: 230 nm, $R_T$=13.064 min). $^1$H NMR (400 MHz, DMSO-$d_6$) δ 9.46 (d, J=3.6 Hz, 0.6H), 9.03 (s, 0.4H), 7.99-7.98 (m, 1.6H), 7.94 (d, J=2.8 Hz, 0.4H), 7.50-7.40 (m, 2H), 7.35-7.29 (m, 1H), 7.23-7.19 (m, 1H), 6.00 (s, 0.4H), 5.90 (d, J=3.6 Hz, 0.6H), 4.84-4.78 (m, 2H), 4.70-4.58 (m, 3H), 3.82-3.76 (m, 0.4H), 3.57-3.55 (m, 0.6H), 3.51 (s, 2H), 3.50 (s, 1H), 3.31-3.30 (m, 0.4H), 3.15-3.09 (m, 0.6H), 1.98-1.59 (m, 6H), 1.34-1.28 (m, 2H).

Section II: Removal of Boc Protection of Primary Dihydropyrimidines of General Formula I Hydrochloride Salts Compound 99: Methyl 4-(2-chloro-4-fluorophenyl)-6-(piperidin-4-yl)-2-(thiazol-2-yl)-1,4-dihydropyrimidine-5-carboxylate Hydrochloride To a solution of 6-(1-tert-butoxycarbonyl-piperidin-4-yl)-4-(2-chloro-4-fluoro-phenyl)-2-thiazol-2-yl-1,4-dihydropyrimidine-5-carboxylic acid methyl ester Compound 5B (1.56 g, 2.92 mmol) in methanol (15 mL) was added 4 M hydrochloric acid in methanol (15 mL, 60.0 mmol) at room temperature. After stirred at room temperature for 20 minutes, the mixture was concentrated to give the title compound (1.69 g, >100% yield) as yellow solids. LC-MS (ESI): $R_T$=1.444 min, mass calcd. For $C_{20}H_{21}Cl_2FN_4O_2S$ 470.1, m/z found 434.9 $[M-HCl+H]^+$. $^1$H NMR (400 MHz, DMSO-$d_6$) δ 9.00 (br s, 1H), 8.60 (br s, 1H), 8.02 (dd, J=4.4, 3.2 Hz, 2H), 7.43 (dd, J=8.8, 2.8 Hz, 1H), 7.36 (dd, J=8.8, 6.0 Hz, 1H), 7.21 (td, J=8.4, 2.8 Hz, 1H), 5.94 (s, 1H), 3.86-3.79 (m, 1H), 3.54 (s, 3H), 3.40-3.35 (m, 2H), 3.02-2.89 (m, 2H), 2.19-2.02 (m, 2H), 1.88 (d, J=14.4 Hz, 1H), 1.72 (d, J=14.4 Hz, 1H).

Similarly utilizing the analogous procedure, the following amine hydrochloride salts were prepared:

Compound 109: Methyl 4-(2-chloro-4-fluorophenyl)-6-(piperidin-4-yl)-2-(thiazol-2-yl)-1,4-di-hydropyrimidine-5-carboxylate Hydrochloride Compound 5 was de-Boc to afford Compound 109. LC-MS (ESI): $R_T$=0.834 min, m/z found 434.7 [M+H]$^+$.

Compound 111: Methyl 4-(2-chloro-3-fluorophenyl)-6-(piperidin-4-yl)-2-(thiazol-2-yl)-1,4-dihydropyrimidine-5-carboxylate Hydrochloride Compound 10 was de-Boc to afford Compound 111. LC-MS (ESI): $R_T$=1.33 min, mass calcd. For $C_{20}H_{21}Cl_2FN_4O_2S$ 470.1, m/z found 435.4 [M−HCl+H]$^+$.

Compound 117: 4-(2-Chloro-3-fluoro-phenyl)-6-piperidin-4-yl-2-thiazol-2-yl-1,4-dihydro-pyrimidine-5-carboxylic Acid Methyl Ester Hydrochloride Compound 10A was de-Boc to afford Compound 117. LC-MS (ESI): $R_T$=1.34 min, mass calcd. For $C_{20}H_{21}Cl_2FN_4O_2S$ 470.1, m/z found 434.9 [M−HCl+H]$^+$.

Compound 119: Methyl 4-(2-bromo-4-fluorophenyl)-6-(piperidin-4-yl)-2-(thiazol-2-yl)-1,4-dihydropyrimidine-5-carboxylate Hydrochloride Compound 12 was de-Boc to afford Compound 119. LC-MS (ESI): $R_T$=1.45 min, mass calcd. For $C_{20}H_{21}BrClFN_4O_2S$ 514.0, m/z found 479.1 [M−HCl+H]$^+$.

Compound 32: Methyl 4-(2-chloro-4-fluorophenyl)-6-(piperidin-3-yl)-2-(thiazol-2-yl)-1,4-dihydropyrimidine-5-carboxylate Compound 31 was de-Boc to afford Compound 32. LC-MS (ESI): $R_T$=3.416 min, mass calcd. for $C_{20}H_{21}Cl_2FN_4O_2S$ 470.1, m/z found 434.9 [M−HCl+H]$^+$. $^1$H NMR (400 MHz, DMSO-d$_6$) δ 9.67 (br s, 1H), 9.26 (br s, 0.4H), 9.10 (br s, 0.6H), 8.77 (br s, 1H), 8.05-8.00 (m, 2H), 7.45-7.33 (m, 2H), 7.24-7.17 (m, 1H), 5.97 (s, 0.6H), 5.94 (s, 0.4H), 4.09-3.99 (m, 1H), 3.55 (s, 3H), 3.37-3.20 (m, 3H), 2.96-2.83 (m, 1H), 1.93-1.71 (m, 4H).

Compound 35: Methyl 4-(2-chloro-3-fluorophenyl)-6-(4-fluoro-piperidin-4-yl)-2-(thiazol-2-yl)-1,4-dihydropyrimidine-5-carboxylate Compound 34 was de-Boc to afford Compound 35. LC-MS (ESI): $R_T$=1.44 min, mass calcd. for $C_{20}H_{19}ClF_2N_4O_2S$ 452.1, m/z found 453.4 [M+H]$^+$.

Compound 45: Methyl 4-(2-chloro-4-fluorophenyl)-6-(cis-3-(methoxycarbonyl)-piperidin-4-yl)-2-(thiazol-2-yl)-1,4-dihydropyrimidine-5-carboxylate hydrochloride Compound 44A was de-Boc to afford Compound 45. LC-MS (ESI): $R_T$=1.46 min, mass calcd. for $C_{22}H_{22}ClFN_4O_4S$ 492.1, m/z found 493.5 [M+H]$^+$. $^1$H NMR (400 MHz, DMSO-d$_6$) δ 9.75 (s, 1H), 9.15 (s, 1H), 8.88 (s, 1H), 8.06 (d, J=3.2 Hz, 1H), 8.03 (d, J=3.2 Hz, 1H), 7.55-7.48 (m, 0.2H), 7.44-7.36 (m, 1.8H), 7.23-7.18 (m, 1H), 5.95 (s, 1H), 3.95-3.87 (m, 1H), 3.55 (s, 3H), 3.46 (s, 3H), 3.42-3.37 (m, 1H), 3.30-3.28 (m, 0.5H), 3.24-3.17 (m, 3.5H), 2.21-2.08 (m, 2H).

Compound 53: Methyl 4-(2-chloro-4-fluorophenyl)-6-(piperidin-4-yl)-2-(2,4,6-trifluorophenyl)-1,4-dihydropyrimidine-5-carboxylate hydrochloride Compound 52 was de-Boc to afford Compound 53. LC-MS (ESI): $R_T$=0.90 min, mass calcd. for $C_{23}H_{20}ClF_4N_3O_2$ 517.1 m/z found 482.1 [M+H−HCl]$^+$.

Compound 67A: Methyl 4-(2-chloro-4-fluorophenyl)-6-(pyrrolidin-3-yl)-2-(thiazol-2-yl)-1,4-dihydropyrimidine-5-carboxylate hydrochloride Compound 66A was de-Boc to afford Compound 67. (LC-MS (ESI): $R_T$=3.198 min, mass calcd. for $C_{19}H_{19}Cl_2FN_4O_2S$ 456.1, m/z found 420.9 [M−HCl+H]$^+$. $^1$H NMR (400 MHz, DMSO-d$_6$) δ 9.46-9.07 (m, 2H), 8.06-8.03 (m, 2H), 7.45-7.41 (m, 2H), 7.23-7.18 (m, 1H), 5.95 (s, 0.8H), 5.76 (s, 0.2H), 4.44-4.32 (m, 2H), 3.54 (s, 3H), 3.33-3.34 (m, 2H), 3.28-3.17 (m, 1H), 2.13-2.08 (m, 2H).

Compound 67D: Methyl 4-(2-chloro-4-fluorophenyl)-6-(pyrrolidin-3-yl)-2-(thiazol-2-yl)-1,4-dihydropyrimidine-5-carboxylate Hydrochloride Compound 66D was e-Boc to give compound 67D, LC-MS (ESI): $R_T$=1.95 min, mass calcd. for $C_{19}H_{18}ClFN_4O_4S$ 420.9, m/z found 421.1 [M+H]$^+$.

Compound 79: Methyl 6-(azetidin-3-yl)-4-(2-chloro-4-fluorophenyl)-2-(thiazol-2-yl)-1,4-dihydropyrimidine-5-carboxylate Hydrochloride Compound 78A was de-Boc to afford Compound 79. $^1$H NMR (400 MHz, DMSO-d$_6$) δ 9.27 (br s, 2H), 8.07 (d, J=2.8 Hz, 1H), 8.04 (d, J=2.8 Hz, 1H), 7.49-7.45 (m, 1H), 7.42 (dd, J=8.8, 2.4 Hz, 1H), 7.19 (td, J=11.2, 2.4 Hz, 1H), 5.95 (s, 1H), 4.58-4.50 (m, 1H), 4.30-4.04 (m, 4H), 3.52 (s, 3H).

Compound 297: (trans)-Methyl 6-(4-aminocyclohexyl)-4-(2-chloro-3,4-difluorophenyl)-2-(3,5-difluoropyridin-2-yl)-1,4-dihydropyrimidine-5-carboxylate hydrochloride $^1$H NMR (300 MHz, DMSO-d$_6$) δ 8.78-8.73 (m, 1H), 8.38-8.20 (m, 2H), 8.12-8.01 (m, 1H), 7.67-7.52 (m, 1H), 7.43-7.27 (m, 1H), 6.23-6.15 (m, 1H), 4.16 (s, 3H), 3.79-3.71 (m, 1H), 3.60 (s, 0.5H), 3.57 (s, 2.5H), 3.08-2.90 (m, 1H), 2.09-2.01 (m, 3H), 1.93-1.78 (m, 3H), 1.54-1.46 (m, 2H).

Compound 350: Ethyl 4-(2-chloro-3,4-difluorophenyl)-2-(3,5-difluoropyridin-2-yl)-6-(piperidin-4-yl)-1,4-dihydropyrimidine-5-carboxylate Hydrochloride Compound 349 was de-Boc to give compound 350, LC-MS (ESI): $R_T$=2.05 min, mass calcd. for $C_{26}H_{29}ClF_2N_4O_4S$ 566.2, m/z found 567.7 [M+H]$^+$. $^1$H NMR (400 MHz, CDCl$_3$) δ 8.36 (s, 0.5H), 7.82 (d, J=3.2 Hz, 1H), 7.51 (d, J=2.8 Hz, 0.5H), 7.46 (d, J=3.2 Hz, 0.5H), 7.38 (s, 0.5H), 7.10-6.99 (m, 2H), 6.20 (s, 0.5H), 6.08 (s, 0.5H), 4.30 (br s, 1.5H), 4.09-3.99 (m, 2H), 3.97-3.89 (m, 0.5H), 2.91-2.79 (m, 2H), 1.80-1.74 (m, 3H), 1.61-1.58 (m, 2H), 1.50 (s, 9H), 1.13 (t, J=6.8 Hz, 3H).

Compound 350A: Ethyl 4-(2-chloro-3,4-difluorophenyl)-2-(3,5-difluoropyridin-2-yl)-6-(piperidin-4-yl)-1,4-dihydropyrimidine-5-carboxylate Hydrochloride Compound 349A was de-Boc to give compound 350A, LC-MS (ESI): $R_T$=1.512 min, mass calcd. for $C_{23}H_{22}Cl_2F_4N_4O_2$ 532.1, m/z found 497.1 [M+H−HCl]$^+$.

Compound 350B: Ethyl 4-(2-chloro-3,4-difluorophenyl)-2-(3,5-difluoropyridin-2-yl)-6-(piperidin-4-yl)-1,4-dihydropyrimidine-5-carboxylate Hydrochloride Compound 349B was de-Boc to give compound 350B, LC-MS (ESI): $R_T$=1.504 min, mass calcd. for $C_{23}H_{22}Cl_2F_4N_4O_2$ 532.1, m/z found 497.0 [M+H−HCl]$^+$.

Compound 369: Ethyl 4-(2-chloro-3,4-difluorophenyl)-6-(piperidin-4-yl)-2-(thiazol-2-yl)-1,4-dihydropyrimidine-5-carboxylate Compound 368 was de-Boc to give compound 369, LC-MS (ESI): $R_T$=1.55 min, mass calcd. for $C_{21}H_{21}ClF_2N_4O_2S$ 466.1, m/z found 467.1 [M+H]$^+$.

Compound 369A: Ethyl 4-(2-chloro-3,4-difluorophenyl)-6-(piperidin-4-yl)-2-(thiazol-2-yl)-1,4-dihydropyrimidine-5-carboxylate Compound 368A was de-Boc to give compound 369A, $^1$H NMR (400 MHz, DMSO-d$_6$) δ 8.02 (s, 2H), 7.50-7.43 (m, 1H), 7.24-7.20 (m, 1H), 5.97 (s, 1H), 3.98 (q, J=6.8 Hz, 2H), 3.88-3.75 (m, 1H), 3.32-3.23 (m, 2H), 2.89-2.77 (m, 2H), 2.10-1.79 (m, 3H), 1.67-1.64 (m, 1H), 1.08 (t, J=6.8 Hz, 3H).

Compound 369B: Ethyl 4-(2-chloro-3,4-difluorophenyl)-6-(piperidin-4-yl)-2-(thiazol-2-yl)-1,4-dihydropyrimidine-5-carboxylate Compound 368B was de-Boc to give compound 369B, $^1$H NMR (400 MHz, DMSO-d$_6$) δ 8.02 (s, 2H), 7.49-7.42 (m, 1H), 7.23-7.19 (m, 1H), 5.95 (s, 1H), 3.98 (q, J=6.8 Hz, 2H), 3.84-3.76 (m, 1H), 3.36-3.31 (m, 2H), 2.97-2.82 (m, 2H), 2.15-1.97 (m, 2H), 1.89-1.83 (m, 1H), 1.72-1.66 (m, 1H), 1.07 (t, J=6.8 Hz, 3H).

Compound 373: Methyl 6-(3-aminobicyclo[1.1.1]pentan-1-yl)-4-(2-chloro-4-fluorophenyl)-2-(thiazol-2-yl)-1,4-dihydropyrimidine-5-carboxylate Compound 371 was de-boc to give compound 373, LC-MS (ESI): $R_T$=1.41 min, mass calcd. for $C_{20}H_{18}ClFN_4O_2S$ 432.1, m/z found 433.5 [M+H]$^+$. $^1$H NMR (400 MHz, CDCl$_3$) δ 7.85 (s, 0.8H), 7.81 (d, J=3.6 Hz, 1H), 7.48 (d, J=2.8 Hz, 0.2H), 7.43 (d, J=2.8 Hz, 0.8H), 7.39 (s, 0.2H), 7.30-7.27 (m, 0.6H), 7.25-7.23 (m, 0.4H), 7.13-7.10 (m, 1H), 6.93-6.89 (m, 1H), 6.15 (s, 0.8H), 6.00 (d, J=2.4 Hz, 0.2H), 3.63 (s, 0.5H), 3.60 (m, 2.5H), 2.31 (s, 5H), 2.25 (s, 1H).

Compound 373A: Methyl 6-(3-aminobicyclo[1.1.1]pentan-1-yl)-4-(2-chloro-4-fluorophenyl)-2-(thiazol-2-yl)-1,4-dihydropyrimidine-5-carboxylate Compound 371A was de-boc to give compound 373A, LC-MS (ESI): $R_T$=0.982 min, mass calcd. for $C_{20}H_{18}ClFN_4O_2S$ 432.1, m/z found 432.8 [M+H]$^+$. $^1$H NMR (400 MHz, CDCl$_3$) δ 7.85-7.81 (m, 1.7H), 7.44-7.43 (m, 1.3H), 7.29-7.27 (m, 0.6H), 7.26-7.25 (m, 0.4H), 7.12 (dd, J=8.8, 2.8 Hz, 1H), 6.92-6.91 (m, 1H), 6.15 (s, 0.8H), 6.00 (s, 0.2H), 3.67 (s, 0.3H), 3.64 (s, 0.7H), 3.60 (s, 2H), 2.32 (s, 4H), 2.30 (s, 1H), 2.27 (s, 1H).

Compound 373B: Methyl 6-(3-aminobicyclo[1.1.1]pentan-1-yl)-4-(2-chloro-4-fluorophenyl)-2-(thiazol-2-yl)-1,4-dihydropyrimidine-5-carboxylate Compound 371B was de-boc to give compound 373B, LC-MS (ESI): $R_T$=1.883 min, mass calcd. for $C_{20}H_{18}ClFN_4O_2S$ 432.1, m/z found 432.8 [M+H]$^+$. $^1$H NMR (400 MHz, CDCl$_3$) δ 7.95 (d, J=3.2 Hz, 0.3H), 7.85 (s, 0.7H), 7.81 (d, J=2.8 Hz, 1H), 7.55-7.51 (m, 0.5H), 7.49-7.38 (m, 1.2H), 7.29-7.28 (m, 0.6H), 7.26-7.25 (m, 0.2H), 7.23-7.17 (m, 0.2H), 7.13-7.11 (m, 1H), 7.07-7.00 (m, 0.3H), 6.94-6.89 (m, 1H), 6.15 (s, 0.8H), 6.00 (s, 0.2H), 3.63-3.60 (m, 3H), 2.32-2.27 (m, 6H).

Trifluoroacetic Acid Salt

Compound 121: Methyl 4-(2-chloro-4-fluorophenyl)-6-(piperidin-4-yl)-2-(thiazol-2-yl)-1,4-dihydropyrimidine-5-carboxylate Trifluoroacetic Acid Salt To a suspension of methyl 6-(1-(tert-butoxycarbonyl)piperidin-4-yl)-4-(2-chloro-4-fluorophenyl)-2-(thiazol-2-yl)-1,4-dihydropyrimidine-5-carboxylate Compound 5 (2.00 g, 3.75 mmol) in dichloromethane (10 mL) was added 2,2,2-trifluoroacetic acid (10 mL) at room temperature. After stirred at room temperature for 2 hours, the mixture was concentrated under reduced pressure to get the title compound (2.50 g, >100% yield) as yellow solids. LC-MS (ESI): $R_T$=1.45 min, mass calcd. for $C_{22}H_{20}ClF_4N_4O_3S$ 531.1, m/z found 435.4 [M−CF$_3$COOH+H]$^+$.

Similarly utilizing the analogous procedure, the following amine trifluoroacetic acid salts were prepared:

Compound 123: 4-(4-Chloro-3-fluoro-phenyl)-6-piperidin-4-yl-2-thiazol-2-yl-1,4-dihydro-pyrimidine-5-carboxylic Acid Methyl Ester Trifluoroacetic Acid Salts Compound 13 was de-Boc to afford Compound 123. LC-MS (ESI): $R_T$=2.035 min, mass calcd. for $C_{20}H_{20}ClFN_4O_2S$ 434.1, m/z found 435.1 [M+H]$^+$.

Compound 125: Methyl 6-(trans-4-aminocyclohexyl)-4-(2-chloro-4-fluorophenyl)-2-(thiazol-2-yl)-1,4-dihydropyrimidine-5-carboxylate Trifluoroacetic Acid Salt Compound 14 was de-Boc to afford Compound 125. LC-MS (ESI): $R_T$=2.288 min, mass calcd. for $C_{23}H_{22}ClF_4N_4O_3S$, 545.1, m/z found 448.8 [M+H−TFA]$_+$.

Compound 127: Methyl 6-(cis-4-aminocyclohexyl)-4-(2-chloro-4-fluorophenyl)-2-(thiazol-2-yl)-1,4-dihydro-pyrimidine-5-carboxylate Trifluoroacetic Acid Salt Compound 15 was de-Boc to afford Compound 127. LC-MS (ESI): $R_T$=0.299 min, mass calcd. for $C_{23}H_{22}ClF_4N_4O_3S$, 545.1, m/z found 448.8 [M+H−TFA]+.

Compound 28: Methyl 4-(2-chloro-3-fluorophenyl)-6-(trans-4-(2-ethoxy-2-oxoethyl)-cyclohexyl)-2-(thiazol-2-yl)-1,4-dihydropyrimidine-5-carboxylate Compound 27Y was de-Boc to afford Compound 28. LC-MS (ESI): $R_T$=3.324 min, mass calcd. for $C_{25}H_{27}ClFN_3O_4S$ 519.1, m/z found 520.0 [M+H]$^+$. Chiral HPLC (Column: Chiralcel OJ-H 5 μm 4.6*250 mm; Mobile Phase: Hex:EtOH=80:20 at 1.0 mL/min; Temp: 30° C.; Wavelength: 230 nm; $R_T$=7.308 min). $^1$H NMR (400 MHz, DMSO-d$_6$) δ 9.46 (s, 0.5H), 8.99 (m, 0.5H), 7.99 (d, J=2.8 Hz, 1H), 7.98-7.94 (m, 1H), 7.39-7.29 (m, 2H), 7.19-7.17 (m, 1H), 6.05-5.96 (m, 1H), 4.07 (q, J=7.2 Hz, 2H), 3.81-3.58 (m, 1H), 3.51 (s, 3H), 2.22 (d, J=7.2 Hz, 2H), 1.91-1.59 (m, 8H), 1.20 (t, J=7.2 Hz, 3H), 1.12-1.08 (m, 1H).

Free Amines

Compound 58: Methyl 4-(2-chloro-3,4-difluorophenyl)-6-(piperidin-4-yl)-2-(thiazol-2-yl)-1,4-dihydro-pyrimidine-5-carboxylate To a solution of methyl 6-(1-(tert-butoxycarbonyl)piperidin-4-yl)-4-(2-chloro-3,4-difluorophenyl)-2-(thiazol-2-yl)-1,4-dihydropyrimidine-5-carboxylate Compound 57 (280 mg, 0.507 mmol) in dichloromethane (3 mL) was added trifluoroacetic acid (3 mL) at room temperature. After stirred for 1 hour, the mixture was concentrated to dryness which was then taken up to 5 M ammonia in methanol (3 mL). Stirring continued for 0.5 hour. The reaction mixture was concentrated to leave a residue, which was purified by silica gel column chromatography (dichloromethane:methanol=20:1) to give the title compound (160 mg, 70% yield) as yellow solids. LC-MS (ESI): $R_T$=1.48 min, mass calcd. For $C_{20}H_{19}ClF_2N_4O_2S$ 452.1 m/z found 453.3 [M+H]$^+$. $^1$H NMR (400 MHz, DMSO-d$_6$) δ 8.00 (s, 2H), 7.49-7.42 (m, 1H), 7.20-7.17 (m, 1H), 6.02-5.92 (m, 1H), 4.01-3.91 (m, 0.5H), 3.73-3.70 (m, 0.5H), 3.52 (s, 3H), 3.07-3.00 (m, 2H), 2.59-2.54 (m, 2H), 1.90-1.57 (m, 4H).

Compound 88(trans): trans-Methyl 6-(3-aminocyclobutyl)-4-(2-chloro-4-fluorophenyl)-2-(thiazol-2-yl)-1,4-dihydropyrimidine-5-carboxylate A solution of trans-methyl 6-(3-((tert-butoxycarbonyl)amino)cyclobutyl)-4-(2-chloro-4-fluorophenyl)-2-(thiazol-2-yl)-1,4-dihydropyrimidine-5-carboxylate Compound 87 (400 mg, 0.769 mmol) in 5 M hydrochloride acid in methanol (10 mL, 50 mmol) was stirred at room temperature for 1 hour. Then the mixture was concentrated under reduced pressure at room temperature to give a residue, which was dissolved in 4 M ammonia in methanol (20 mL, 80 mmol) and stirred at room temperature for 30 min. The resulting mixture was concentrated to give the crude title compound (283 mg, 88% yield) as yellow solids. LC-MS (ESI): $R_T$=2.178 min, mass calcd. for $C_{19}H_{18}ClFN_4O_2S$ 420.1, m/z found 420.9 [M+H]$^+$. $^1$H NMR (400 MHz, CDCl$_3$) δ 8.38 (br s, 0.3H), 7.84 (d, J=3.2 Hz, 0.7H), 7.82 (d, J=3.2 Hz, 0.3H), 7.50 (d, J=3.2 Hz, 0.7H), 7.45 (d, J=3.2 Hz, 1H), 7.30-7.25 (m, 1H), 7.13 (dt, J=8.4, 2.8 Hz, 1H), 6.96-6.88 (m, 1H), 6.18 (s, 0.3H), 6.05 (d, J=2.8 Hz, 0.7H), 4.59-4.52 (m, 0.4H), 4.48-4.40 (m, 0.6H), 3.93-3.86 (m, 0.6H), 3.80-3.72 (m, 0.4H), 3.60 (s, 2H), 3.58 (s, 1H), 2.82-2.75 (m, 0.6H), 2.63-2.46 (m, 1.4H), 2.37-2.23 (m, 0.6H), 2.21-2.03 (m, 1.4H).

Similarly utilizing the analogous procedure, the following free amines were prepared:

Compound 88(cis): (cis)-Methyl 6-(3-aminocyclobutyl)-4-(2-chloro-4-fluorophenyl)-2-(thiazol-2-yl)-1,4-dihydropyrimidine-5-carboxylate LC-MS (ESI): $R_T$=3.168 min, mass calcd. for $C_{19}H_{18}ClFN_4O_2S$ 420.1, m/z found 420.9 [M+H]$^+$. $^1$H NMR (400 MHz, CDCl$_3$) δ 9.82 (br s, 0.4H), 7.83 (d, J=3.2 Hz, 1H), 7.51-7.45 (m, 1H), 7.29-7.26 (m, 1H), 7.12 (dd, J=4.8, 2.8 Hz, 1H), 6.95-6.87 (m, 1H), 6.18-6.05 (m, 1H), 4.51-4.16 (m, 1H), 3.69-3.47 (m, 4H), 2.84-2.49 (m, 2H), 2.23-1.82 (m, 2H).

Compound 83: Methyl 6-(azetidin-3-yl)-4-(2-chloro-4-fluorophenyl)-2-(thiazol-2-yl)-1,4-dihydro-pyrimidine-5-carboxylate Compound 78 was de-Boc to afford Compound 83. LC-MS (ESI): $R_T$=1.32 min, mass calcd. for $C_{18}H_{16}ClFN_4O_2S$ 406.1, m/z found 407.4 [M+H]$^+$. $^1$H NMR (400 MHz, DMSO-d$_6$+D$_2$O) δ 8.01 (d, J=3.2 Hz, 1H), 7.95 (s, 1H), 7.44-7.40 (m, 2H), 7.20 (td, J=8.0, 2.0 Hz, 1H), 5.98 (s, 1H), 4.58 (s, 1H), 3.96-3.88 (m, 4H), 3.51 (s, 3H).

Compound 144: ethyl 4-(2-chlorophenyl)-6-(piperidin-4-yl)-2-(thiazol-2-yl)-1,4-dihydropyrimidine-5-carboxylate Compound 143B was de-Boc to afford compound 144. LC-MS (ESI): $R_T$=1.47 min, mass calcd. for $C_{21}H_{23}ClN_4O_2S$ 430.10, m/z found 431.4 [M+H]$^+$.

Compound 160: methyl 4-(2-bromo-3,4-difluorophenyl)-6-(piperidin-4-yl)-2-(thiazol-2-yl)-1,4-dihydropyrimidine-5-carboxylate Compound 159A was de-Boc to afford compound 160. LC-MS (ESI): $R_T$=1.64 min, mass calcd. for $C_{20}H_{19}BrF_2N_4O_2S$ 496.0, m/z found 499.4 [M+3]$^+$.

Compound 189: Methyl 6-(4-aminocycloheptyl)-4-(2-chloro-4-fluorophenyl)-2-(thiazol-2-yl)-1,4-dihydropyrimidine-5-carboxylate Compound 188 was de-Boc to give compound 189, LC-MS (ESI): $R_T$=2.154 min and 2.282 min, mass calcd. for $C_{22}H_{24}ClFN_4O_2S$ 462.1, m/z found 463.1 [M+H]$^+$.

Compound 192: Ethyl 4-(2-chloro-3,4-difluorophenyl)-6-(piperidin-4-yl)-2-(2,4,6-trifluorophenyl)-1,4-dihydropyrimidine-5-carboxylate Compound 191 was de-Boc to give compound 192. LC-MS(ESI): $R_T$=1.986 min, mass calcd. for $C_{24}H_{21}ClF_5N_3O_2$ 513.1, m/z found 514.0 [M+H]$^+$.

Compound 197A: Ethyl 4-(2-bromo-3,4-difluorophenyl)-6-(piperidin-4-yl)-2-(thiazol-2-yl)-1,4-dihydropyrimidine-5-carboxylate hydrochloride Compound 196A was de-Boc to give compound 197A, LC-MS: $R_T$=1.52 min, Mass calc for $C_{21}H_{21}BrF_2N_4O_2S$ 510.05, m/z found: 513.4 [M−HCl+H]$^+$.

Compound 203: Methyl 6-(3-aminobicyclo[1.1.1]pentan-1-yl)-4-(2-chloro-3,4-difluorophenyl)-2-(thiazol-2-yl)-1,4-dihydropyrimidine-5-carboxylate Compound 202 was de-Boc to give compound 203, LC-MS (ESI): $R_T$=1.844 min, mass calcd. for $C_{12}H_{19}NO_4$ 241.1, m/z found 242.2 [M+H]+. 1H NMR (300 MHz, CDCl3) δ 4.96 (br s, 1H), 3.70 (s, 3H), 2.30 (s, 6H), 1.46 (s, 9H).

Compound 202A was de-Boc to give compound 203A. LC-MS (ESI): $R_T$=1.489 min, mass calcd. for $C_{20}H_{17}ClF_2N_4O_2S$ 450.1, m/z found 450.9 [M+H]+. 1H NMR (300 MHz, CDCl3) δ 7.90 (br s, 1H), 7.82 (d, J=2.4 Hz, 1H), 7.46 (d, J=2.4 Hz, 1H), 7.06-7.03 (m, 2H), 6.14 (br s, 1H), 3.61 (s, 3H), 2.43 (s, 6H).

Compound 202B was de-Boc to give compound 203B. LC-MS (ESI): $R_T$=2.249 min, mass calcd. for $C_{25}H_{25}ClF_2N_4O_4S$ 550.1, m/z found 551.0 [M+H]+. Chiral analysis (Column: Chiralpak IG 5 μm 4.6*250 mm; Mobile Phase: CO2:MeOH=70:30 at 2.999 g/min; Col. Temp: 40.1° C.; Wavelength: 230 nm, Back pressure: 100 bar, $R_T$=3.95 min). 1H NMR (300 MHz, CDCl3) δ 7.91-7.89 (m, 0.8H), 7.81-7.78 (m, 1H), 7.49-7.48 (m, 0.2H), 7.44-7.42 (m, 0.8H), 7.40-7.38 (m, 0.2H), 7.08-7.01 (m, 2H), 6.14 (br s, 0.8H), 6.01 (br s, 0.2H), 5.03 (br s, 1H), 3.64 (s, 0.5H), 3.60 (s, 2.5H), 2.53 (s, 5H), 2.45 (s, 1H), 1.47 (s, 9H).

Compound 236: (trans)-Methyl 6-(4-aminocyclohexyl)-4-(2-chloro-3,4-difluorophenyl)-2-(thiazol-2-yl)-1,4-dihydropyrimidine-5-carboxylate Compound 235 was de-Boc to give compound 236, 1H NMR (400 MHz, CDCl3) δ 8.14 (br s, 0.7H), 7.83-7.80 (m, 1H), 7.48 (d, J=3.2 Hz, 0.3H), 7.44 (d, J=3.2 Hz, 0.7H), 7.41-7.38 (m, 0.3H), 7.08-7.05 (m, 1H), 7.04-6.97 (m, 1H), 6.17 (s, 0.7H), 6.03 (s, 0.3H), 3.97-3.89 (m, 0.7H), 3.72-3.68 (m, 0.3H), 3.61 (s, 1H), 3.59 (s, 2H), 2.79-2.72 (m, 1H), 2.05-2.02 (m, 2.5H), 1.96-1.92 (m, 1.5H), 1.65-1.50 (m, 2H), 1.36-1.26 (m, 2H).

Compound 238: (trans)-Methyl 4-(2-chloro-3,4-difluorophenyl)-6-(4-(sulfamoylamino)cyclohexyl)-2-(thiazol-2-yl)-1,4-dihydropyrimidine-5-carboxylate Compound 237 was de-Boc to give compound 238, LC-MS (ESI): $R_T$=3.924 min, mass calcd. for $C_{21}H_{22}ClF_2N_5O_4S_2$ 545.1, m/z found 546.0 [M+H]+. 1H NMR (400 MHz, DMSO-d6) δ 9.54 (br s, 0.6H), 9.05 (br s, 0.4H), 7.99-7.94 (m, 2H), 7.49-7.40 (m, 1H), 7.22-7.11 (m, 1H), 6.56-6.43 (m, 3H), 6.00 (s, 0.4H), 5.91 (s, 0.6H), 3.84-3.75 (m, 0.4H), 3.61-3.56 (m, 0.6H), 3.51 (s, 3H), 3.25-3.20 (m, 0.4H), 3.12-3.07 (m, 0.6H), 2.12-2.02 (m, 2H), 1.90-1.69 (m, 3H), 1.65-1.53 (m, 1H), 1.30-1.23 (m, 2H).

Compound 247: Methyl 6-(1-(azetidin-3-ylsulfonyl)piperidin-4-yl)-4-(2-chloro-3,4-difluorophenyl)-2-(thiazol-2-yl)-1,4-dihydropyrimidine-5-carboxylate Compound 246 was de-Boc to give compound 247, LC-MS (ESI): $R_T$=1.598 min, mass calcd. for $C_{23}H_{24}ClF_2N_5O_4S_2$ 571.1, m/z found 571.9 [M+H]+. 1H NMR (300 MHz, CDCl3) δ 8.28 (s, 0.3H), 7.85 (s, 1H), 7.56 (s, 0.7H), 7.48-7.45 (m, 1H), 7.14-7.05 (m, 2H), 6.19 (s, 0.3H), 6.08 (s, 0.7H), 4.21-4.08 (m, 4H), 4.03-3.90 (m, 4H), 3.61 (s, 3H), 3.01-2.88 (m, 2H), 2.26-2.16 (m, 1H), 2.06-1.87 (m, 2H), 1.74-1.67 (m, 1H).

Compound 250: (trans)-Methyl 6-(4-(azetidine-3-sulfonamido)cyclohexyl)-4-(2-chloro-3,4-difluorophenyl)-2-(thiazol-2-yl)-1,4-dihydropyrimidine-5-carboxylate Compound 249 wa de-Boc to give compound 250, LC-MS (ESI): $R_T$=1.589 min, mass calcd. for $C_{24}H_{26}ClF_2N_5O_4S_2$ 585.1, m/z found 585.9 [M+H]+. 1H NMR (300 MHz, CDCl3) δ 8.16 (s, 0.5H), 7.84 (s, 1H), 7.57-7.53 (m, 0.5H), 7.48-7.47 (m, 0.5H), 7.42 (s, 0.5H), 7.10-7.00 (m, 2H), 6.18 (s, 0.5H), 6.05 (s, 0.5H), 4.25-4.04 (m, 4H), 3.99-3.87 (m, 2H), 3.82-3.67 (m, 1H), 3.61 (s, 1.5H), 3.60 (s, 1.5H), 3.50-3.32 (m, 1H), 2.21-1.99 (m, 4H), 1.75-1.36 (m, 4H).

Compound 276A: methyl 4-(2-bromo-3-fluorophenyl)-6-(piperidin-4-yl)-2-(thiazol-2-yl)-1,4-dihydropyrimidine-5-carboxylate Compound 275A was de-Boc to give compound 276A, 1H NMR (400 MHz, CDCl3) δ 7.82 (d, J=6.4 Hz, 1H), 7.56-7.52 (m, 0.9H), 7.50 (d, J=2.8 Hz, 1H), 7.42-7.42 (m, 0.1H), 7.25-7.18 (m, 1H), 7.11-7.04 (m, 2H), 7.01-6.98 (m, 0.2H), 6.25 (s, 0.1H), 6.12 (d, J=2.8 Hz, 0.9H), 4.37-4.27 (m, 0.3H), 4.08-4.00 (m, 0.7H), 3.75-3.62 (m, 2H), 3.61-3.56 (m, 3H), 3.13-3.00 (m, 2H), 2.64-2.53 (m, 1H), 2.47-2.36 (m, 1H), 2.34-2.12 (m, 1H), 1.95-1.84 (m, 1H).

Compound 276B: methyl 4-(2-bromo-3-fluorophenyl)-6-(piperidin-4-yl)-2-(thiazol-2-yl)-1,4-dihydropyrimidine-5-carboxylate Compound 275B was de-Boc to give compound 276B, 1H NMR (400 MHz, CDCl3) δ 9.59-9.01 (m, 1H), 7.82 (s, 1H), 7.58-7.37 (m, 2H), 7.30-7.27 (m, 0.5H), 7.25-7.23 (m, 0.5H), 6.24 (s, 0.2H), 6.14-6.09 (m, 0.5H), 4.09-4.01 (m, 0.8H), 3.74 (s, 0.2H), 3.67-3.51 (m, 5H), 3.17-3.02 (m, 2H), 2.53-2.38 (m, 1H), 2.34-2.23 (m, 1H), 2.13-2.07 (m, 1H), 1.93-1.83 (m, 1H).

Compound 280: Ethyl 4-(2-bromo-4-fluorophenyl)-6-(piperidin-4-yl)-2-(thiazol-2-yl)-1,4-dihydropyrimidine-5-carboxylate Compound 279 was de-Boc to give compound 280, LC-MS (ESI): $R_T$=1.01 min, mass calcd. for $C_{21}H_{22}BrFN_4O_2S$ 492.1, m/z found 495.4 [M+H]+. 1H NMR (300 MHz, CDCl3) δ 8.27-8.20 (m, 0.6H), 7.85-7.78 (m, 1H), 7.50 (d, J=3.0 Hz, 0.4H), 7.46-7.43 (m, 0.6H), 7.34-7.31 (m, 2.4H), 7.04-6.91 (m, 1H), 6.19 (s, 0.6H), 6.06 (s, 0.4H), 4.25-3.88 (m, 3H), 3.35-3.15 (m, 2H), 2.93-2.74 (m, 2H), 2.24-2.06 (m, 1H), 1.90-1.60 (m, 3H), 1.19-1.07 (m, 3H).

Compound 280A: Ethyl 4-(2-bromo-4-fluorophenyl)-6-(piperidin-4-yl)-2-(thiazol-2-yl)-1,4-dihydropyrimidine-5-carboxylate Compound 279A was de-Boc to give compound 280A, LC-MS (ESI): $R_T$=1.57 min, mass calcd. for $C_{21}H_{22}BrFN_4O_2S$ 492.1, m/z found 494.9 [M+H]+. 1H NMR (400 MHz, CDCl3) δ 8.26 (br s, 1H), 7.83 (d, J=2.8 Hz, 0.6H), 7.80 (d, J=3.2 Hz, 0.4H), 7.52 (d, J=3.2 Hz, 0.6H), 7.43 (d, J=2.8 Hz, 0.4H), 7.33-7.28 (m, 2H), 7.03-6.94 (m, 1H), 6.18 (s, 0.4H), 6.06 (s, 0.6H), 4.22-4.17 (m, 0.4H), 4.08-3.97 (m, 2.6H), 3.47-3.38 (m, 1.2H), 3.30-3.23 (m, 1H), 3.02-2.84 (m, 2.8H), 2.34-2.10 (m, 1.3H), 2.00-1.97 (m, 1H), 1.88-1.73 (m, 1.7H), 1.13 (q, J=7.2 Hz, 3H).

Compound 280B: Ethyl 4-(2-bromo-4-fluorophenyl)-6-(piperidin-4-yl)-2-(thiazol-2-yl)-1,4-dihydropyrimidine-5-carboxylate Compound 279B was de-Boc to give compound 280B, LC-MS (ESI): $R_T$=1.55 min, mass calcd. for $C_{21}H_{22}BrFN_4O_2S$ 492.1, m/z found 494.9 [M+H]$^+$. $^1$H NMR (400 MHz, CDCl$_3$) δ 8.28 (br s, 1H), 7.83 (d, J=3.2 Hz, 0.6H), 7.80 (d, J=3.2 Hz, 0.4H), 7.52 (d, J=3.2 Hz, 0.6H), 7.43 (d, J=2.8 Hz, 0.4H), 7.33-7.28 (m, 2H), 7.03-6.93 (m, 1H), 6.18 (s, 0.4H), 6.07 (s, 0.6H), 4.23-4.17 (m, 0.4H), 4.07-3.99 (m, 2.6H), 3.51-3.41 (m, 1.8H), 3.32-3.25 (m, 1H), 3.05-2.83 (m, 2.2H), 2.38-2.13 (m, 1.3H), 2.02-1.98 (m, 1H), 1.89-1.76 (m, 1.7H), 1.12 (q, J=7.2 Hz, 3H).

Compound 307A: Methyl 4-(3,4-difluoro-2-methylphenyl)-6-(piperidin-4-yl)-2-(thiazol-2-yl)-1,4-dihydropyrimidine-5-carboxylate Compound 306A was de-Boc to give compound 307A, LC-MS (ESI): R$_T$=1.908 min, mass calcd. for $C_{21}H_{22}F_2N_4O_2S$ 432.1, m/z found 432.9 [M+H]$^+$.

Compound 307B: Methyl 4-(3,4-difluoro-2-methylphenyl)-6-(piperidin-4-yl)-2-(thiazol-2-yl)-1,4-dihydropyrimidine-5-carboxylate Compound 306B was de-Boc to give compound 307B, LC-MS (ESI): R$_T$=1.896 min, mass calcd. for $C_{21}H_{22}F_2N_4O_2S$ 432.1, m/z found 432.9 [M+H]$^+$.

Compound 317: Ethyl 4-(2-chloro-3-fluorophenyl)-6-(piperidin-4-yl)-2-(thiazol-2-yl)-1,4-dihydropyrimidine-5-carboxylate Compound 316 was de-Boc to give compound 317: LC-MS (ESI): R$_T$=0.85 min, mass calcd. for $C_{21}H_{22}ClFN_4O_2S$ 448.1, m/z found 449.5 [M+H]$^+$. $^1$H NMR (300 MHz, CDCl$_3$) δ 7.82 (d, J=3.6 Hz, 1H), 7.52 (d, J=3.6 Hz, 0.6H), 7.46-7.43 (m, 0.4H), 7.24-7.00 (m, 3H), 6.28 (s, 0.4H), 6.17 (s, 0.6H), 4.78-4.29 (m, 2.4H), 4.09-4.01 (m, 2.6H), 3.66-3.51 (m, 1.4H), 3.44-3.33 (m, 0.6H), 3.12-2.84 (m, 2H), 2.55-2.22 (m, 1.4H), 2.05-1.78 (m, 2.6H), 1.14-1.09 (m, 3H).

Compound 327A: Ethyl 4-(2-chloro-4-fluorophenyl)-6-(piperidin-4-yl)-2-(thiazol-2-yl)-1,4-dihydropyrimidine-5-carboxylate Compound 326A was de-Boc to give compound 327A, LC-MS (ESI): R$_T$=1.899 min, mass calcd. for $C_{21}H_{22}ClFN_4O_2S$ 448.1, m/z found 449.1 [M+H]$^+$.

Compound 327B: Ethyl 4-(2-chloro-4-fluorophenyl)-6-(piperidin-4-yl)-2-(thiazol-2-yl)-1,4-dihydropyrimidine-5-carboxylate Compound 326B was de-Boc to give compound 327B, LC-MS (ESI): R$_T$=1.897 min, mass calcd. for $C_{21}H_{22}ClFN_4O_2S$ 448.1, m/z found 449.1 [M+H]$^+$.

Compound 337: Ethyl 4-(2-bromo-3-fluorophenyl)-6-(piperidin-4-yl)-2-(thiazol-2-yl)-1,4-dihydropyrimidine-5-carboxylate Compound 336 was de-Boc to give compound 337, LC-MS (ESI): R$_T$=1.42 min, mass calcd. for $C_{21}H_{22}BrFN_4O_4S$ 492.1, m/z found 495.4 [M+H]$^+$.

Compound 341A: ethyl 4-(3,4-difluoro-2-methylphenyl)-6-(piperidin-4-yl)-2-(thiazol-2-yl)-1,4-dihydropyrimidine-5-carboxylate Compound 340A was de-Boc to give 341A, $^1$H NMR (300 MHz, DMSO-d$_6$) δ 8.63 (s, 0.2H), 7.98-7.94 (m, 1.8H), 7.25-7.19 (m, 1H), 7.10-7.00 (m, 1H), 5.82 (s, 0.3H), 5.68 (s, 0.7H), 4.02-3.94 (m, 2.3H), 3.72-3.65 (m, 0.7H), 3.08-3.00 (m, 2H), 2.62-2.55 (m, 2H), 2.44 (s, 3H), 1.92-1.78 (m, 2H), 1.63-1.59 (m, 1.3H), 1.45-1.42 (m, 0.7H), 1.07 (t, J=5.4 Hz, 3H).

Compound 341B: ethyl 4-(3,4-difluoro-2-methylphenyl)-6-(piperidin-4-yl)-2-(thiazol-2-yl)-1,4-dihydropyrimidine-5-carboxylate Compound 340B was de-Boc to give 341B, $^1$H NMR (300 MHz, DMSO-d$_6$) δ 8.63 (s, 0.2H), 7.98 (s, 1.8H), 7.25-7.18 (m, 1H), 7.09-6.99 (m, 1H), 5.82 (s, 0.3H), 5.68 (s, 0.7H), 4.00-3.94 (m, 2.2H), 3.73-3.65 (m, 0.8H), 3.08-3.01 (m, 2H), 2.61-2.55 (m, 2H), 2.45 (s, 3H), 1.89-1.75 (m, 2H), 1.66-1.58 (m, 1.2H), 1.45-1.42 (m, 0.8H), 1.06 (t, J=5.4 Hz, 3H).

Compound 395: (trans)-Methyl 6-(4-aminocyclohexyl)-4-(2-chloro-4-fluorophenyl)-2-(3,5-difluoropyridin-2-yl)-1,4-dihydropyrimidine-5-carboxylate Compound 394 was de-Boc to give compound 395, $^1$H NMR (300 MHz, CDCl$_3$) δ 8.66-8.57 (m, 0.6H), 8.34-8.29 (m, 0.6H), 8.26-8.21 (m, 0.4H), 7.86-7.80 (m, 0.2H), 7.62-7.55 (m, 0.2H), 7.34-7.28 (m, 1H), 7.16-7.10 (m, 1H), 6.93-6.84 (m, 1H), 6.32-6.27 (m, 0.6H), 6.06-5.97 (m, 0.4H), 4.13-3.94 (m, 1H), 3.77-3.64 (m, 1H), 3.56 (s, 3H), 2.14-2.05 (m, 3H), 2.00-1.93 (m, 1H), 1.62-1.37 (m, 4H).

Compound 408A: Methyl 4-(2-bromo-4-fluorophenyl)-6-(piperidin-4-yl)-2-(thiazol-2-yl)-1,4-dihydropyrimidine-5-carboxylate Compound 407A was de-Boc to give compound 408A, LC-MS (ESI): R$_T$=1.799 min, mass calcd. for $C_{20}H_{20}BrFN_4O_2S$ 478.1, m/z found 479.0 [M+H]$^+$. $^1$H NMR (400 MHz, CDCl$_3$) δ 8.28 (s, 0.4H), 7.84-7.79 (m, 1H), 7.52-7.51 (m, 0.6H), 7.44-7.43 (m, 0.5H), 7.33-7.29 (m, 1.5H), 7.02-6.93 (m, 1H), 6.16 (s, 0.4H), 6.03 (s, 0.6H), 4.20-4.11 (m, 0.5H), 4.02-3.96 (m, 0.5H), 3.61-3.60 (m, 3H), 3.44-3.35 (m, 1H), 3.28-3.23 (m, 1H), 3.01-2.81 (m, 3H), 2.32-2.23 (m, 0.6H), 2.12-2.08 (m, 0.4H), 1.98-1.94 (m, 1H), 1.88-1.72 (m, 2H).

Compound 408B: Methyl 4-(2-bromo-4-fluorophenyl)-6-(piperidin-4-yl)-2-(thiazol-2-yl)-1,4-dihydropyrimidine-5-carboxylate Compound 407B was de-Boc to give compound 408B, LC-MS (ESI): R$_T$=1.903 min, mass calcd. for $C_{20}H_{20}BrFN_4O_2S$ 478.1, m/z found 479.0 [M+H]$^+$. $^1$H NMR (400 MHz, CDCl$_3$) δ 8.34 (s, 0.3H), 7.84-7.80 (m, 1H), 7.53-7.52 (m, 1H), 7.43-7.42 (m, 0.3H), 7.34-7.31 (m, 1.2H), 7.26-7.25 (m, 0.5H), 7.03-6.93 (m, 1H), 6.16 (s, 0.3H), 6.04 (s, 0.7H), 4.25-4.21 (m, 0.3H), 4.06-4.00 (m, 0.7H), 3.61-3.60 (m, 3H), 3.56-3.49 (m, 1H), 3.37-3.30 (m, 0.7H), 3.09-2.85 (m, 3H), 2.48-2.39 (m, 1.2H), 2.35-2.21 (m, 0.8H), 2.02-1.99 (m, 0.6H), 1.92-1.81 (m, 1.4H).

Compound 398: (cis)-Methyl 6-(4-aminocyclohexyl)-4-(2-chloro-4-fluorophenyl)-2-(3,5-difluoropyridin-2-yl)-1,4-dihydropyrimidine-5-carboxylate Compound 397 was de-Boc to give compound 398, $^1$H NMR (300 MHz, CDCl$_3$) δ 8.93-8.89 (m, 0.3H), 8.76-8.73 (m, 0.1H), 8.62-8.60 (m, 0.2H), 8.33-8.28 (m, 0.7H), 8.27-

8.24 (m, 0.5H), 7.84-7.79 (m, 0.2H), 7.32-7.27 (m, 2H), 7.14-7.11 (m, 1H), 6.91-6.86 (m, 1H), 6.28 (s, 0.7H), 6.04-6.00 (m, 0.3H), 4.10-3.92 (m, 1H), 3.61 (s, 1H), 3.58 (s, 2H), 3.39-3.33 (m, 1H), 2.04-1.93 (m, 5H), 1.60-1.38 (m, 3H).

Compound 412A: Ethyl 4-(2-bromo-3-fluorophenyl)-6-(piperidin-4-yl)-2-(thiazol-2-yl)-1,4-dihydropyrimidine-5-carboxylate Compound 411A was de-Boc to give compound 412A, LC-MS (ESI): $R_T$=1.57 min, mass calcd. for $C_{21}H_{22}BrFN_4O_2S$ 492.1, m/z found 494.8 [M+H]$^+$. $^1$H NMR (300 MHz, CDCl$_3$) δ 8.23 (s, 0.5H), 7.81 (d, J=3.0 Hz, 0.4H), 7.78 (d, J=3.3 Hz, 0.6H), 7.49 (d, J=3.0 Hz, 0.4H), 7.42 (d, J=3.0 Hz, 0.6H), 7.21-7.12 (m, 1.5H), 7.07-6.98 (m, 1H), 6.25 (s, 0.6H), 6.11 (s, 0.4H), 4.22-3.92 (m, 3H), 3.33-3.18 (m, 2H), 2.88-2.77 (m, 2H), 2.10-2.04 (m, 0.3H), 1.83-1.62 (m, 3.7H), 1.11 (t, J=7.2 Hz, 3H).

Compound 412B: Ethyl 4-(2-bromo-3-fluorophenyl)-6-(piperidin-4-yl)-2-(thiazol-2-yl)-1,4-dihydropyrimidine-5-carboxylate Compound 411B was de-Boc to give compound 412B, LC-MS (ESI): $R_T$=1.58 min, mass calcd. for $C_{21}H_{22}BrFN_4O_2S$ 492.1, m/z found 494.8 [M+H]$^+$. $^1$H NMR (300 MHz, CDCl$_3$) δ 8.25 (s, 0.5H), 7.83 (d, J=3.0 Hz, 0.4H), 7.80 (d, J=2.7 Hz, 0.6H), 7.51 (d, J=3.0 Hz, 0.4H), 7.44 (d, J=3.0 Hz, 0.6H), 7.23-7.14 (m, 1.5H), 7.09-6.98 (m, 1H), 6.27 (s, 0.6H), 6.13 (s, 0.4H), 4.24-3.97 (m, 3H), 3.34-3.20 (m, 2H), 2.94-2.80 (m, 2H), 2.20-2.09 (m, 0.8H), 1.93-1.63 (m, 3.2H), 1.13 (t, J=7.2 Hz, 3H).

Compound 418B: Ethyl 4-(4-fluoro-2-methylphenyl)-6-(piperidin-4-yl)-2-(thiazol-2-yl)-1,4-dihydropyrimidine-5-carboxylate Compound 417B was de-boc to give compound 418B, LC-MS (ESI): $R_T$=1.536 min, mass calcd. for $C_{22}H_{25}FN_4O_2S$ 428.2, m/z found 429.1 [M+H]$^+$. $^1$H NMR (400 MHz, CDCl$_3$) δ 8.49 (s, 0.3H), 7.81-7.79 (m, 1H), 7.53 (d, J=3.2 Hz, 0.7H), 7.39 (d, J=2.8 Hz, 0.3H), 7.30-7.28 (m, 0.7H), 7.17-7.13 (m, 0.3H), 7.09 (s, 0.7H), 6.90-6.84 (m, 1.7H), 6.81-6.76 (m, 0.3H), 5.95 (s, 0.3H), 5.88 (d, J=1.6 Hz, 0.7H), 4.41-4.35 (m, 0.3H), 4.06-3.92 (m, 2.7H), 3.60-3.53 (m, 2H), 3.11-3.00 (m, 2H), 2.62 (s, 1H), 2.48 (s, 2H), 2.45-2.08 (m, 3H), 2.01-1.97 (m, 0.3H), 1.86-1.83 (m, 0.7H), 1.13-1.08 (m, 3H).

Compound 427A: Ethyl 4-(3-fluoro-2-methylphenyl)-6-(piperidin-4-yl)-2-(thiazol-2-yl)-1,4-dihydropyrimidine-5-carboxylate Compound 426A was de-Boc to give compound 427A, LC-MS (ESI): $R_T$=1.52 min, mass calcd. for $C_{22}H_{25}FN_4O_2S$ 428.2, m/z found 429.0 [M+H]$^+$. $^1$H NMR (400 MHz, CDCl$_3$) δ 8.48 (s, 0.3H), 7.81-7.79 (m, 1H), 7.52 (d, J=3.2 Hz, 0.7H), 7.38 (d, J=3.2 Hz, 0.3H), 7.14-7.01 (m, 2.7H), 6.97-6.88 (m, 1H), 6.01 (s, 0.3H), 5.93 (d, J=1.6 Hz, 0.7H), 4.43-4.37 (m, 0.4H), 4.06-3.94 (m, 2.7H), 3.61-3.54 (m, 2H), 3.12-3.01 (m, 2H), 2.52 (s, 1H), 2.45-2.29 (m, 4H), 2.25-2.09 (m, 1H), 2.05-2.01 (m, 0.3H), 1.87-1.83 (m, 0.7H), 1.13-1.08 (m, 3H).

Compound 427B: Ethyl 4-(3-fluoro-2-methylphenyl)-6-(piperidin-4-yl)-2-(thiazol-2-yl)-1,4-dihydropyrimidine-5-carboxylate Compound 426B was de-Boc to give compound 427B, LC-MS (ESI): $R_T$=1.53 min, mass calcd. for $C_{22}H_{25}FN_4O_2S$ 428.2, m/z found 429.0 [M+H]$^+$. $^1$H NMR (400 MHz, CDCl$_3$) δ 8.37 (s, 0.4H), 7.79 (d, J=3.2 Hz, 1H), 7.52 (d, J=3.2 Hz, 0.6H), 7.40 (d, J=3.2 Hz, 0.4H), 7.14-7.01 (m, 2.6H), 6.97-6.88 (m, 1H), 6.01 (s, 0.3H), 5.93 (s, 0.7H), 4.35-4.29 (m, 0.4H), 4.06-3.93 (m, 2.6H), 3.59-3.42 (m, 2H), 3.10-2.93 (m, 2H), 2.53 (s, 1H), 2.39 (s, 2H), 2.37-2.26 (m, 1H), 2.15-2.08 (m, 1.3H), 2.01-1.82 (m, 1.7H), 1.13-1.08 (m, 3H).

Compound 436a: (cis)-Ethyl 6-(3-amino-2,2-dimethylcyclobutyl)-4-(2-chloro-4-fluorophenyl)-2-(thiazol-2-yl)-1,4-dihydropyrimidine-5-carboxylate Compound 435a was de-Boc to give compound 436a, LC-MS (ESI): $R_T$=1.83 min, mass calcd. for $C_{22}H_{24}ClFN_4O_2S$ 462.1, m/z found 463.5 [M+H]$^+$. $^1$H NMR (400 MHz, CDCl$_3$) δ 10.8 (s, 0.7H), 7.81 (d, J=2.0 Hz, 1H), 7.63-7.37 (m, 2.3H), 7.19-7.11 (m, 1H), 6.92 (br s, 1H), 6.25 (s, 0.7H), 6.16 (s, 0.3H), 4.50-4.37 (m, 0.7H), 4.29-4.24 (m, 0.3H), 4.23-4.19 (m, 0.3H), 4.11-3.91 (m, 2.7H), 3.34-3.22 (m, 0.7H), 3.19-3.08 (m, 0.3H), 2.67-2.47 (m, 0.6H), 2.46-2.21 (m, 0.4H), 1.36 (s, 3H), 1.14-1.10 (m, 6H).

Compound 442a: Methyl-4-(3-fluoro-2-methylphenyl)-6-(piperidin-4-yl)-2-(thiazol-2-yl)-1,4-dihydropyrimidine-5-carboxylate Compound 441a was de-Boc to give compound 442a, LC-MS (ESI): $R_T$=1.481 min, mass calcd. for $C_{21}H_{23}FN_4O_2S$ 414.5, m/z found 415.1 [M+H]$^+$. $^1$HNMR (400 MHz, CDCl$_3$) δ 8.26 (s, 1H), 7.76 (d, J=2.8 Hz, 1H), 7.50 (d, J=2.8 Hz, 0.4H), 7.39 (d, J=3.2 Hz, 0.6H), 7.26-7.06 (m, 2H), 7.00-6.87 (m, 1H), 5.99 (s, 0.6H), 5.90 (s, 0.4H), 4.25-4.17 (m, 0.6H), 3.97-3.88 (m, 0.4H), 3.58 (s, 3H), 3.52-3.44 (m, 0.7H), 3.32-3.25 (m, 1.3H), 3.04-2.82 (m, 2H), 2.53 (s, 2H), 2.38 (s, 1H), 2.35-2.19 (m, 1H), 2.00-1.73 (m, 3H).

Compound 442b: Methyl-4-(3-fluoro-2-methylphenyl)-6-(piperidin-4-yl)-2-(thiazol-2-yl)-1,4-dihydropyrimidine-5-carboxylate Compound 441b was de-Boc to give compound 442b, LC-MS (ESI): $R_T$=1.47 min, mass calcd. for $C_{21}H_{23}FN_4O_2S$ 414.5, m/z found 414.9 [M+H]$^+$. $^1$H NMR (400 MHz, CDCl$_3$) δ 8.27 (s, 1H), 7.77 (d, J=2.8 Hz, 1H), 7.51 (d, J=2.8 Hz, 0.4H), 7.40 (d, J=3.2 Hz, 0.6H), 7.15-7.01 (m, 2H), 6.97-6.88 (m, 1H), 6.00 (s, 0.6H), 5.91 (s, 0.4H), 4.27-4.18 (m, 0.6H), 3.98-3.89 (m, 0.4H), 3.59 (s, 3H), 3.53-3.45 (m, 0.7H), 3.33-3.26 (m, 1.3H), 3.05-2.83 (m, 2H), 2.54 (s, 2H), 2.39 (s, 1H), 2.36-2.21 (m, 1H), 1.87-1.73 (m, 3H).

Compound 446A: Methyl 4-(4-fluoro-2-methylphenyl)-6-(piperidin-4-yl)-2-(thiazol-2-yl)-1,4-dihydropyrimidine-5-carboxylate Compound 445A was de-Boc to give compound 446A, LC-MS (ESI): $R_T$=1.40 min, mass calcd. for $C_{21}H_{23}FN_4O_2S$ 414.2, m/z found 415.1 [M+H]$^+$. $^1$H NMR (400 MHz, CD$_3$OD) δ 7.79 (d, J=3.2 Hz, 1H), 7.64 (d, J=3.2 Hz, 1H), 7.22-7.19 (m, 1H), 6.83-6.73 (m, 2H), 5.78 (s, 1H), 4.03-

3.79 (m, 1H), 3.50 (s, 3H), 3.19-3.13 (m, 2H), 2.78-2.69 (m, 2H), 2.46 (s, 3H), 2.14-1.81 (m, 3H), 1.65-1.62 (m, 1H).

Compound 446B: Methyl 4-(4-fluoro-2-methylphenyl)-6-(piperidin-4-yl)-2-(thiazol-2-yl)-1,4-dihydropyrimidine-5-carboxylate Compound 445B was de-Boc to give compound 446B, LC-MS (ESI): $R_T$=1.38 min, mass calcd. for $C_{21}H_{23}FN_4O_2S$ 414.2, m/z found 415.1 [M+H]$^+$. $^1$H NMR (400 MHz, CD$_3$OD) δ 7.80 (d, J=3.2 Hz, 1H), 7.64 (d, J=3.2 Hz, 1H), 7.22-7.19 (m, 1H), 6.83-6.73 (m, 2H), 5.78 (m, 1H), 4.00-3.80 (m, 1H), 3.50 (s, 3H), 3.19-3.13 (m, 2H), 2.78-2.69 (m, 2H), 2.46 (s, 3H), 2.12-1.81 (m, 3H), 1.65-1.62 (m, 1H).

Section III: Coupling Reaction with the Resulting Amines (Section II) of Primary Dihydropyrimidines of General Formula I Compound 100: Methyl 4-(2-chloro-4-fluorophenyl)-6-(1-(cyclopropylsulfonyl)-piperidin-4-yl)-2-(thiazol-2-yl)-1,4-dihydropyrimidine-5-carboxylate Method M: To a solution of methyl 4-(2-chloro-4-fluorophenyl)-6-(piperidin-4-yl)-2-(thiazol-2-yl)-1,4-dihydropyrimidine-5-carboxylate hydrochloride Compound 99 (80.0 mg, 0.170 mmol) and triethylamine (51.5 mg, 0.510 mmol) in dichloromethane (3 mL) was added cyclopropanesulfonyl chloride (31.1 mg, 0.221 mmol) at 20° C. After stirred at room temperature overnight, the mixture was quenched with water (10 mL) and subsequently extracted with dichloromethane (50 mL) three times. The combined organic layers were washed with water (20 mL) twice, brine (20 mL) twice, dried over Na$_2$SO$_{4(s)}$ and filtered. The filtrate was concentrated under reduced pressure to give a residue, which was purified by Prep. HPLC (Column: X-bridge C18 (5 m 19*150 mm), Mobile Phase A: water (0.1% ammonium bicarbonate), Mobile Phase B: acetonitrile, UV: 214 nm, Flow rate: 20 mL/min, Gradient: 25-75% (% B)) to give the title compound (34.0 mg, 37% yield) as yellow solids. LC-MS (ESI): $R_T$=4.061 min, mass calcd. for $C_{22}H_{24}ClFN_4O_4S_2$ 538.1, m/z found 538.9 [M+H]$^+$. Chiral HPLC (Column: Chiralpak IA 5 μm 4.6*250 mm; Mobile Phase: Hex:EtOH=60:40 at 1.0 mL/min; Temp: 30° C.; Wavelength: 230 nm, $R_T$=7.052 min). $^1$H NMR (400 MHz, DMSO-d$_6$) δ 9.51 (d, J=3.2 Hz, 0.8H), 9.11 (s, 0.2H), 8.00-7.98 (m, 1.6H), 7.92 (d, J=3.2 Hz, 0.4H), 7.42 (dd, J=8.8, 2.8 Hz, 1H), 7.39-7.32 (m, 1H), 7.24-7.19 (dd, J=8.8, 2.8 Hz, 1H), 6.02 (s, 0.2H), 5.93 (d, J=3.6 Hz, 0.8H), 4.01-3.96 (m, 0.1H), 3.81-3.69 (m, 2.9H), 3.53 (s, 2.4H), 3.52 (s, 0.6H), 2.90 (q, J=12.0 Hz, 2H), 2.68-2.59 (m, 1H), 2.12-1.98 (m, 1H), 1.93-1.76 (m, 2H), 1.63 (d, J=11.6 Hz, 1H), 1.06-1.00 (m, 2H), 0.99-0.92 (m, 2H).

Compound 108: Methyl-4-(2-chloro-4-fluorophenyl)-6-(1-(1-(methoxycarbonyl)-cyclopropane-1-carbonyl)piperidin-4-yl)-2-(thiazol-2-yl)-1,4-dihydropyrimidine-5-carboxylate Method N: To a solution of 1-(methoxycarbonyl)cyclopropanecarboxylic acid (55 mg, 0.38 mmol) in N,N-dimethylformamide (6 mL) was added N,N-diisopropylethylamine (123 mg, 0.957 mmol) and 2-(3H-[1,2,3]triazolo[4,5-b]pyridin-3-yl)-1,1,3,3-tetramethyluronium hexafluorophosphate(V) (145 mg, 0.383 mmol). After stirring at room temperature for 30 minutes, the mixture was added methyl 4-(2-chloro-4-fluorophenyl)-6-(piperidin-4-yl)-2-(thiazol-2-yl)-1,4-dihydropyrimidine-5-carboxylate hydrochloride Compound 99 (150 mg, 0.319 mmol) and continued to stir at room temperature for 2 hours. Then it was poured into water (40 mL) and extracted with ethyl acetate (40 mL) twice. The combined organic layers were washed with water (40 mL) twice and brine (40 mL) twice, concentrated and purified by Prep. HPLC (Column: Gilson X-bridge C18 (5 μm 19*150 mm), Mobile Phase A: water (0.1% ammonium bicarbonate), Mobile Phase B: acetonitrile, UV: 214 nm, Flow rate: 20 mL/min, Gradient: 25-80% (% B)) to give the title compound (105 mg, 59% yield, 100% ee) as yellow solids. LC-MS (ESI): $R_T$=3.831 min, mass calcd. for $C_{26}H_{26}ClFN_4O_5S$ 560.1, m/z found 560.9 [M+H]$^+$. Chiral HPLC (Column: Chiralpak IC 5 μm 4.6*250 mm; Mobile Phase: Hex:EtOH=70:30 at 1.0 mL/min; Temp: 30° C.; Wavelength: 230 nm, $R_T$=23.052 min). $^1$H NMR (400 MHz, DMSO-d$_6$) δ 9.48 (d, J=3.2 Hz, 0.7H), 9.03 (s, 0.2H), 8.94 (s, 0.1H), 8.00-7.98 (m, 1.8H), 7.92 (d, J=2.8 Hz, 0.2H), 7.43-7.31 (m, 2H), 7.23-7.17 (m, 1H), 6.02 (s, 0.3H), 5.92 (d, J=3.6 Hz, 0.7H), 4.58-4.46 (m, 1H), 4.10-3.82 (m, 2H), 3.72-3.70 (m, 3H), 3.54 (s, 3H), 3.14-3.05 (m, 1H), 2.70-2.61 (m, 1H), 2.01-1.56 (m, 4H), 1.43-1.27 (m, 4H).

Similarly utilizing the analogous procedures (Method M or Method N), products could be prepared as shown:

| Method & Coupling partners | Product |
|---|---|
| M<br>Compound 99<br>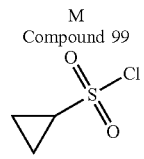 | 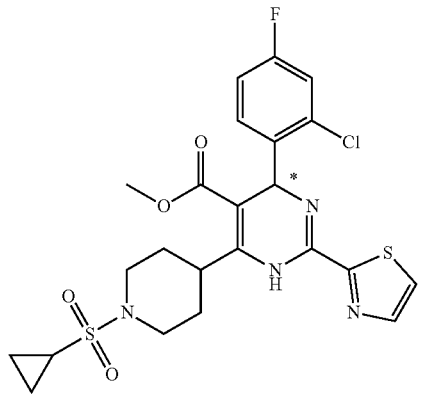 [SMILES: COC(=O)C1=C(C2CCN(S(=O)(=O)C3CC3)CC2)NC(c2nccs2)=NC1c1ccc(F)cc1Cl]<br>Compound 100 |

309 310
-continued
| Method & Coupling partners | Product |
|---|---|
| M Compound 99 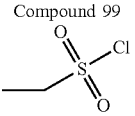 | 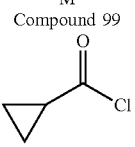 Compound 101 |
| M Compound 99 | Compound 102 |
| M Compound 99 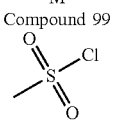 | Compound 103 |

-continued

| Method & Coupling partners | Product |
|---|---|
| M Compound 99 | Compound 104 |
| M Compound 99 | Compound 106 |
| M Compound 99 | Compound 164 |

-continued
| Method & Coupling partners | Product |
|---|---|
| M<br>Compound 99<br>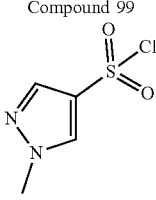 | 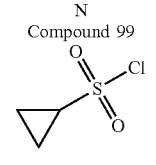<br>Compound 165 |
| N<br>Compound 99<br> | <br>Compound 108 |
| M<br>Compound 109<br> | 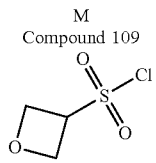<br>Compound 110 |

-continued
| Method & Coupling partners | Product |
|---|---|
| N<br>Compound 121<br>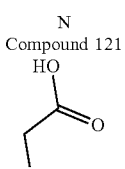 | 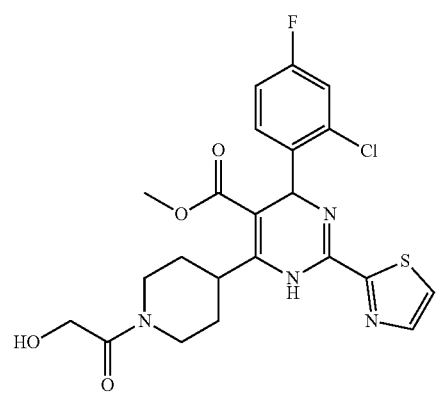 [SMILES: COC(=O)C1=C(C2CCN(C(=O)CO)CC2)NC(c2nccs2)=NC1c1ccc(F)cc1Cl]<br>Compound 122 |
| N<br>Compound 99<br>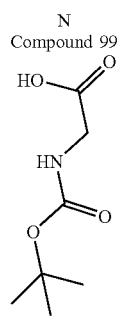 | 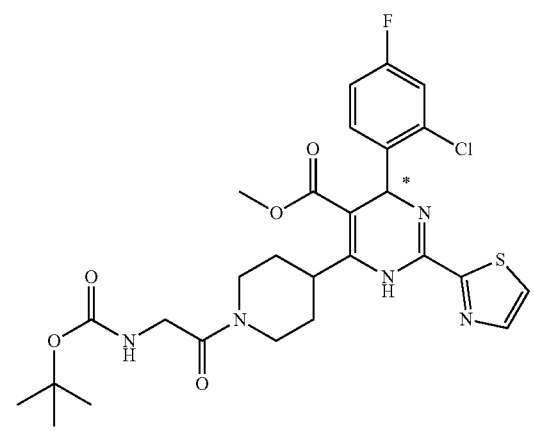 [SMILES: COC(=O)C1=C(C2CCN(C(=O)CNC(=O)OC(C)(C)C)CC2)NC(c2nccs2)=NC1c1ccc(F)cc1Cl]<br>Compound 129 |
| M<br>Compound 111<br>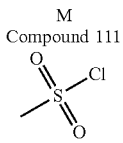 | 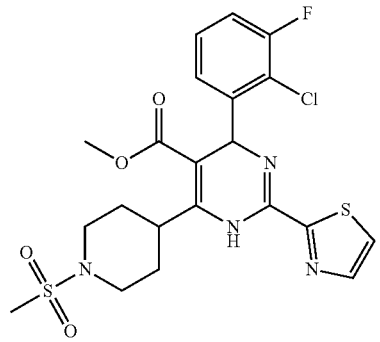 [SMILES: COC(=O)C1=C(C2CCN(S(C)(=O)=O)CC2)NC(c2nccs2)=NC1c1cccc(F)c1Cl]<br>Compound 112 |

-continued

| Method & Coupling partners | Product |
|---|---|
| M Compound 111 | Compound 113 |
| M Compound 117 | Compound 118 |
| M Compound 111 | Compound 115 |

| Method & Coupling partners | Product |
|---|---|
| M<br>Compound 119<br>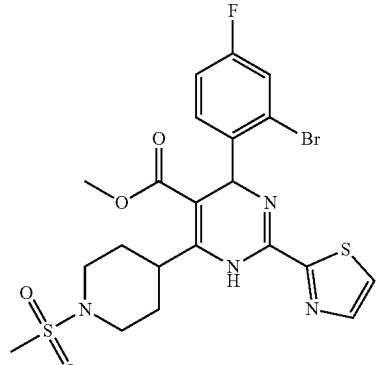 | 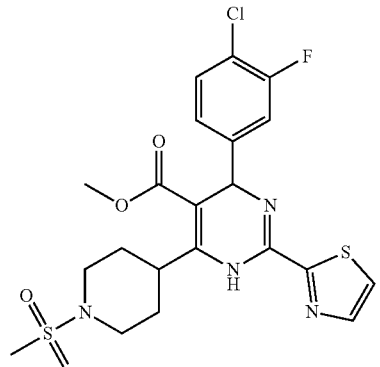<br>Compound 120 |
| M<br>Compound 123<br>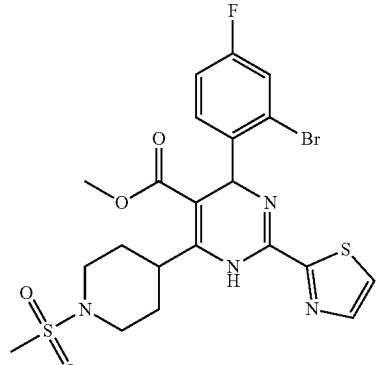 | 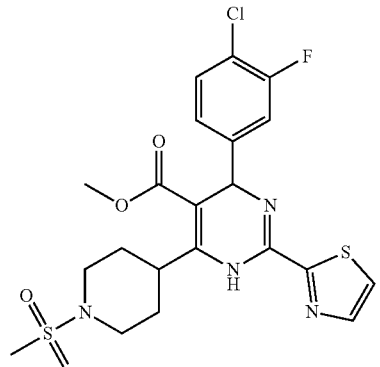<br>Compound 124 |
| M<br>Compound 125<br>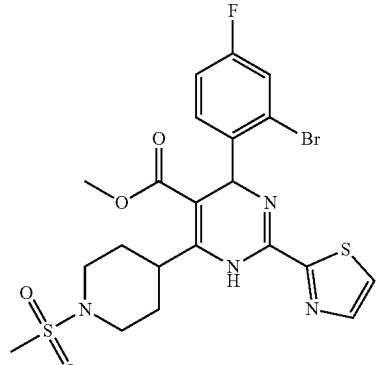 | 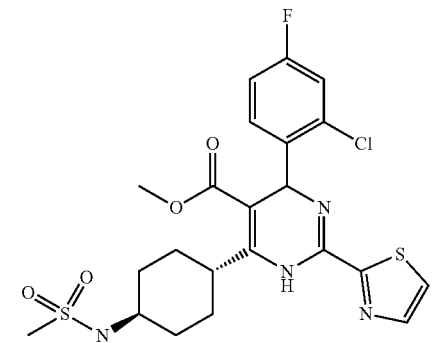<br>Compound 126 |

-continued
| Method & Coupling partners | Product |
|---|---|
| M<br>Compound 127<br>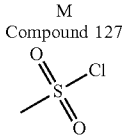 | 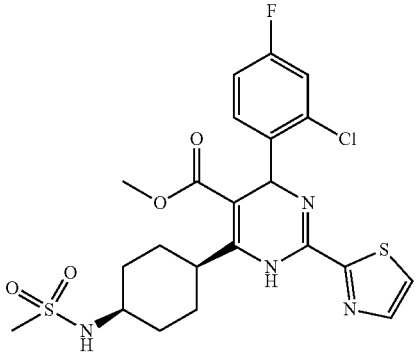 [SMILES: COC(=O)C1=C([C@H]2CC[C@@H](NS(C)(=O)=O)CC2)NC(c2nccs2)=NC1c1ccc(F)cc1Cl]<br>Compound 128 |
| M<br>Compound 32<br>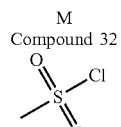 | 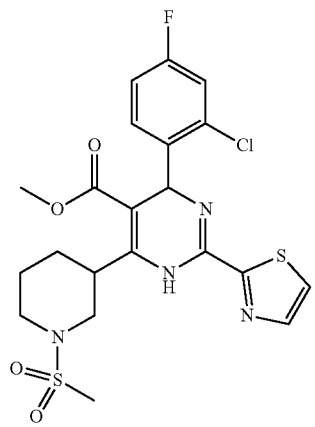 [SMILES: COC(=O)C1=C(C2CCCN(S(C)(=O)=O)C2)NC(c2nccs2)=NC1c1ccc(F)cc1Cl]<br>Compound 33 |
| M<br>Compound 35<br>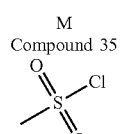 | 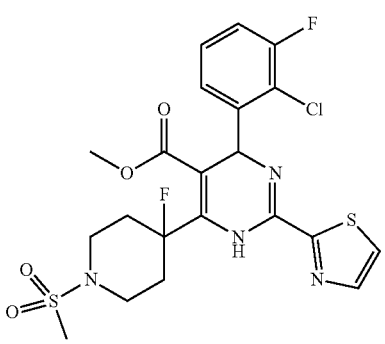 [SMILES: COC(=O)C1=C(C2(F)CCN(S(C)(=O)=O)CC2)NC(c2nccs2)=NC1c1cccc(F)c1Cl]<br>Compound 36 |

323                                                                 324
-continued
| Method & Coupling partners | Product |
|---|---|
| M<br>Compound 45<br>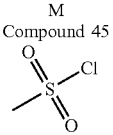 | 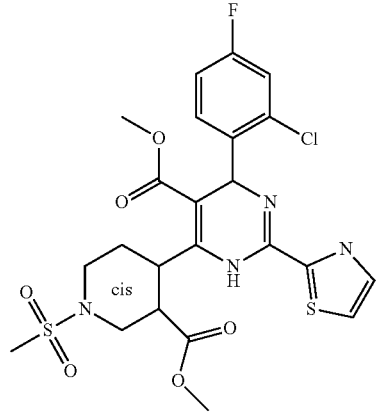<br>Compound 46 |
| M<br>Compound 53<br>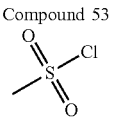 | 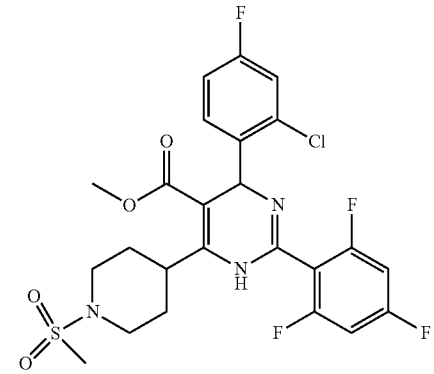 [SMILES: COC(=O)C1=C(C2CCN(S(C)(=O)=O)CC2)NC(c2c(F)cc(F)cc2F)=NC1c1ccc(F)cc1Cl]<br>Compound 54 |
| M<br>Compound 58<br>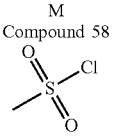 | 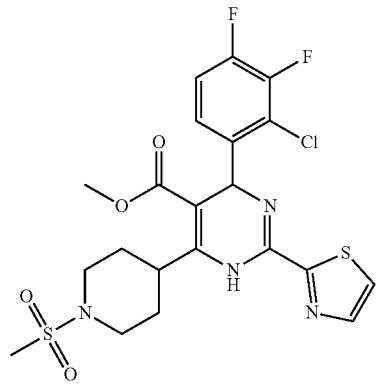 [SMILES: COC(=O)C1=C(C2CCN(S(C)(=O)=O)CC2)NC(c2nccs2)=NC1c1ccc(F)c(F)c1Cl]<br>Compound 59 |

-continued

| Method & Coupling partners | Product |
|---|---|
| M<br>Compound 67A | Compound 68 |
| M<br>Compound 58 | Compound 157A |
| M<br>Compound 117 | Compound 158A |

-continued

| Method & Coupling partners | Product |
|---|---|
| M<br>Compound 83<br>methanesulfonyl chloride | Compound 84 |
| M<br>Compound 79<br>cyclobutanesulfonyl chloride | Compound 80 |
| M<br>Compound 79<br>N-ethylsulfamoyl chloride | Compound 81 |

-continued
| Method & Coupling partners | Product |
|---|---|
| M<br>Compound 79<br>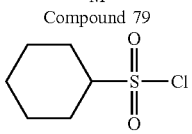 | 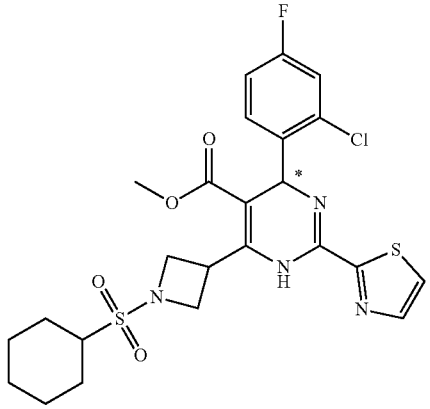 [SMILES: COC(=O)C1=C(C2CN(S(=O)(=O)C3CCCCC3)C2)NC(c2nccs2)=NC1c1ccc(F)cc1Cl]<br>Compound 82 |
| M<br>Compound 83<br>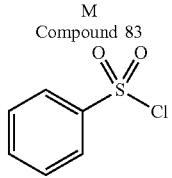 | 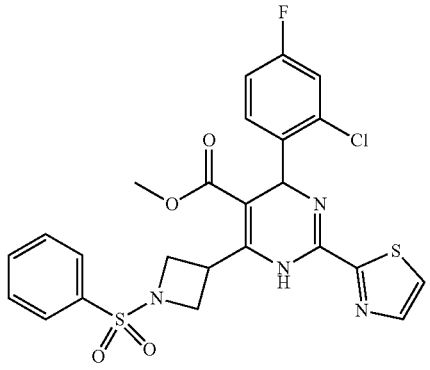 [SMILES: COC(=O)C1=C(C2CN(S(=O)(=O)c3ccccc3)C2)NC(c2nccs2)=NC1c1ccc(F)cc1Cl]<br>Compound 130 |
| M<br>Compound 88<br>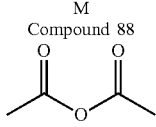 | 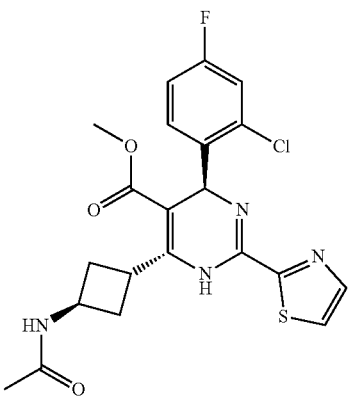<br>Compound 89 |

US 11,639,350 B2
331                                            332
-continued
| Method & Coupling partners | Product |
|---|---|
| M<br>Compound 111<br>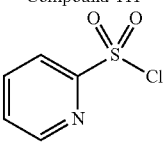 | 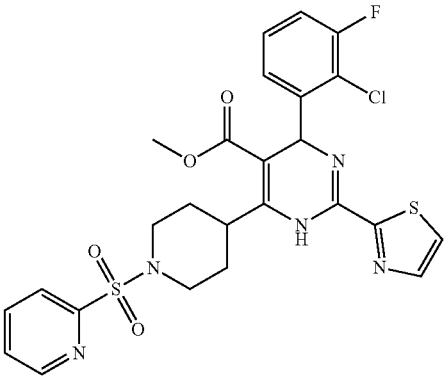 [SMILES: COC(=O)C1=C(C2CCN(S(=O)(=O)c3ccccn3)CC2)NC(c2nccs2)=NC1c1cccc(F)c1Cl]<br>Compound 116 |
| M<br>Compound 99<br>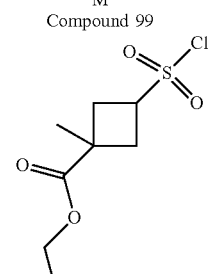<br>Sulfonyl chloride 9 | 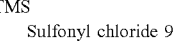<br>Compound 140 |
| M<br>Compound 144<br>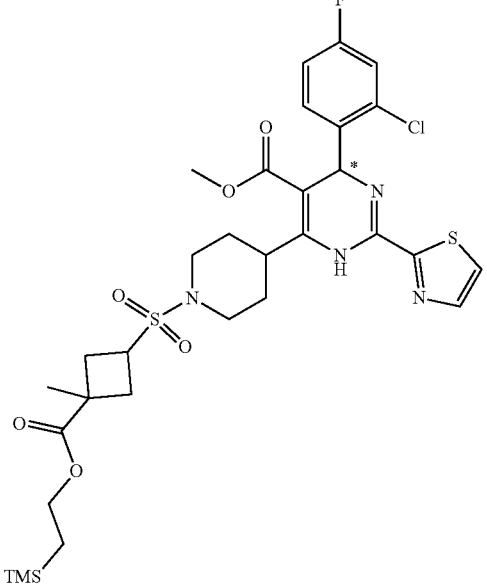<br>Sulfonyl chloride 5 | 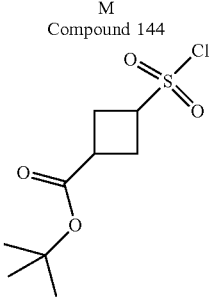<br>Compound 145 |

333                                                                                                 334
-continued
| Method & Coupling partners | Product |
|---|---|
| M<br>Compound 160<br>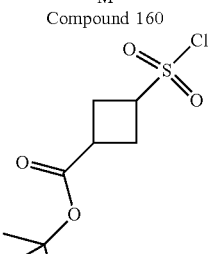<br>Sulfonyl chloride 5 | 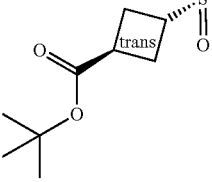<br>Compound 161 |
| N<br>Compound 21<br>NH₄Cl | 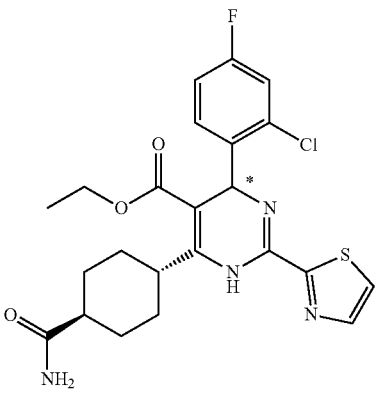 [SMILES: CCOC(=O)C1=C([C@H]2CC[C@H](C(N)=O)CC2)NC(c2nccs2)=NC1c1ccc(F)cc1Cl]<br>Compound 163 |
| M<br>Compound 58<br>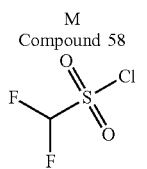 | 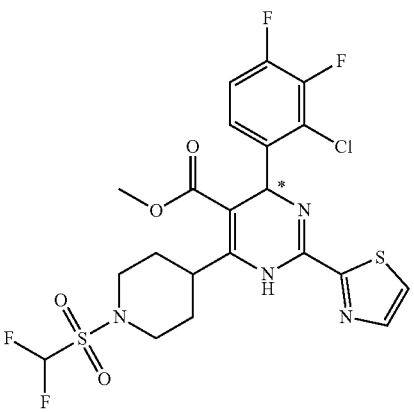 [SMILES: COC(=O)C1=C(C2CCN(S(=O)(=O)C(F)F)CC2)NC(c2nccs2)=NC1c1ccc(F)c(F)c1Cl]<br>Compound 166A |

-continued
| Method & Coupling partners | Product |
|---|---|
| M<br>Compound 189<br>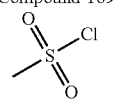 | 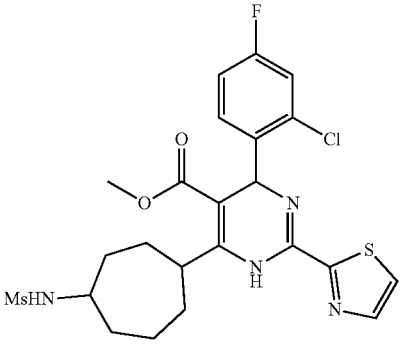<br>Compound 190 |
| M<br>Compound 193<br>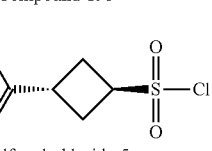<br>Sulfonyl chloride 5 | 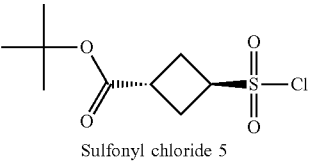<br>Compound 194A |
| M<br>Compound 197A<br>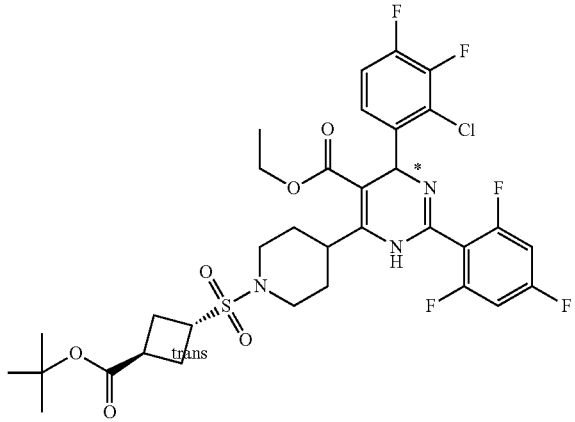 [SMILES: CCOC(=O)C1=C(C2CCN(S(=O)(=O)[C@H]3C[C@H](C(=O)OC(C)(C)C)C3)CC2)NC(c2c(F)cc(F)cc2F)=NC1c1ccc(F)c(F)c1Cl]<br>Sulfonyl chloride 5 | 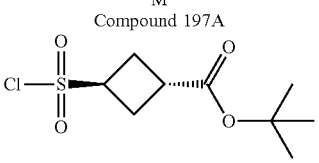<br>Compound 198A (trans)<br>Compound 198B (cis) |

-continued
| Method & Coupling partners | Product |
|---|---|
| M<br>Compound 99<br>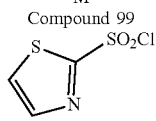 | 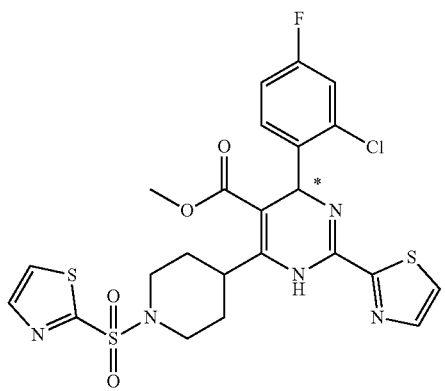 [SMILES: COC(=O)C1=C(C2CCN(S(=O)(=O)c3nccs3)CC2)NC(c2nccs2)=NC1c1ccc(F)cc1Cl]<br>Compound 200A |
| M<br>Compound 99<br>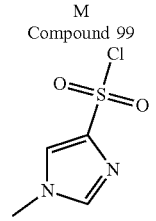 | 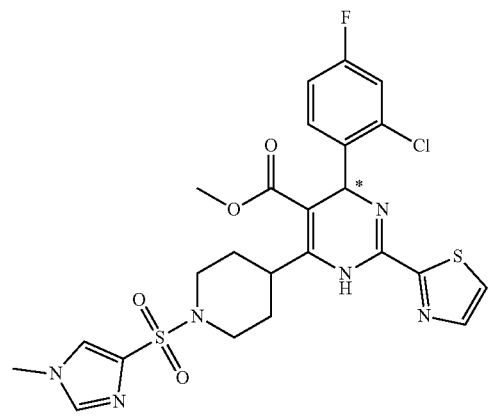 [SMILES: COC(=O)C1=C(C2CCN(S(=O)(=O)c3cn(C)cn3)CC2)NC(c2nccs2)=NC1c1ccc(F)cc1Cl]<br>Compound 201A |
| M<br>Compound 203A<br>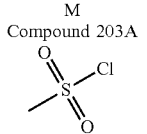 | 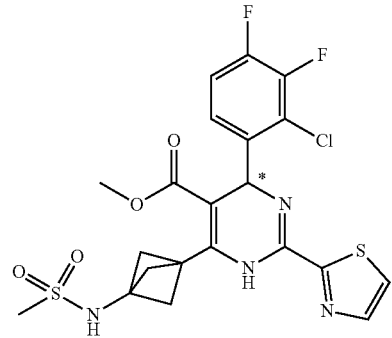 [SMILES: COC(=O)C1=C(C23CC(NS(C)(=O)=O)(C2)C3)NC(c2nccs2)=NC1c1ccc(F)c(F)c1Cl]<br>Compound 204A |

-continued
| Method & Coupling partners | Product |
|---|---|
| M<br>Compound 88(trans) and 88(cis)<br>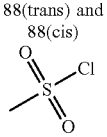 | 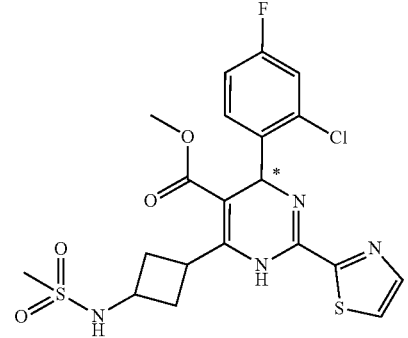 [SMILES: COC(=O)C1=C(C2CC(NS(C)(=O)=O)C2)NC(c2nccs2)=NC1c1ccc(F)cc1Cl]<br>Compound 206B, trans<br>Compound 206D, cis |
| M<br>Compound 373B<br>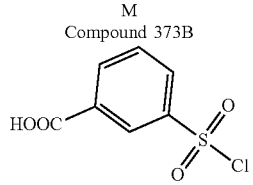 | 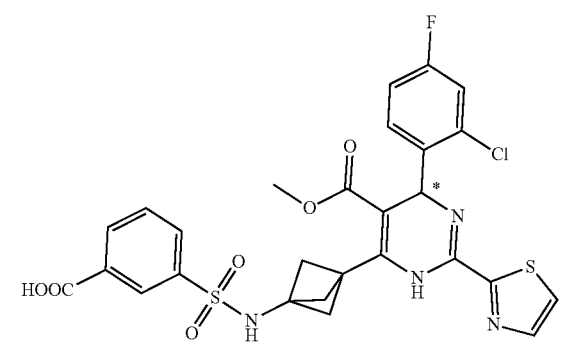 [SMILES: COC(=O)C1=C(C23CC(NS(=O)(=O)c4cccc(C(=O)O)c4)(C2)C3)NC(c2nccs2)=NC1c1ccc(F)cc1Cl]<br>Compound 208B |
| M<br>Compound 58<br>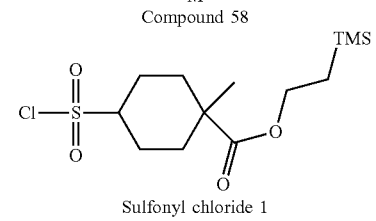<br>Sulfonyl chloride 1 | 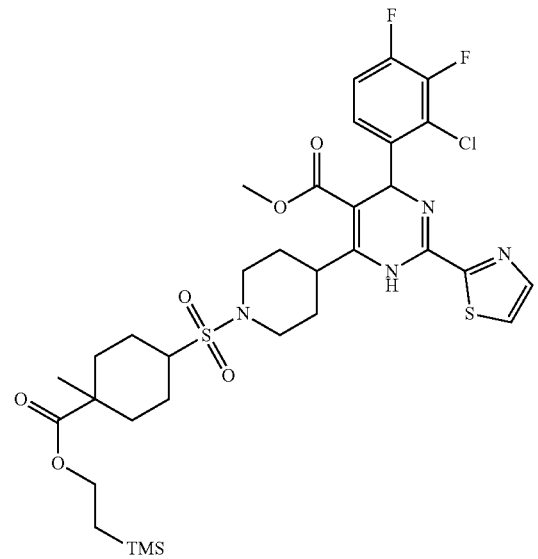 [SMILES: COC(=O)C1=C(C2CCN(S(=O)(=O)C3CCC(C)(C(=O)OCC[Si](C)(C)C)CC3)CC2)NC(c2nccs2)=NC1c1ccc(F)c(F)c1Cl]<br>Compound 209A, trans<br>Compound 209B, cis |

-continued
| Method & Coupling partners | Product |
|---|---|
| M<br>Compound 67A<br>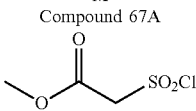 | 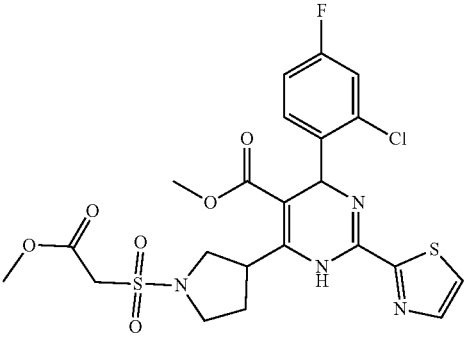 [SMILES: COC(=O)CS(=O)(=O)N1CCC(C2=C(C(=O)OC)C(c3ccc(F)cc3Cl)N=C(c3nccs3)N2)C1]<br>Compound 213 |
| M<br>Compound 99<br>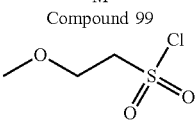 | 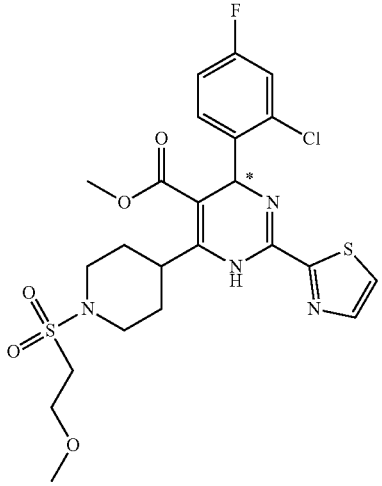 [SMILES: COCCS(=O)(=O)N1CCC(C2=C(C(=O)OC)C(c3ccc(F)cc3Cl)N=C(c3nccs3)N2)CC1]<br>Compound 215 |
| M<br>Compound 99<br>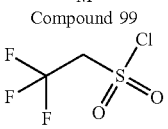 | 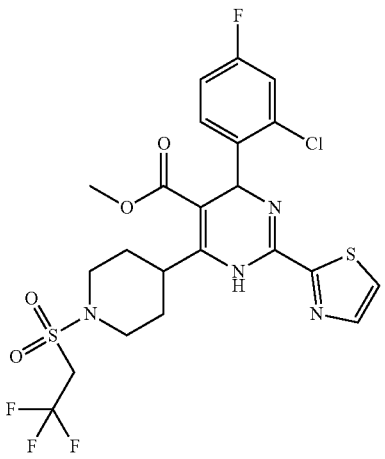 [SMILES: COC(=O)C1=C(C2CCN(S(=O)(=O)CC(F)(F)F)CC2)NC(c2nccs2)=NC1c1ccc(F)cc1Cl]<br>Compound 216 |

-continued
| Method & Coupling partners | Product |
|---|---|
| M<br>Compound 99<br>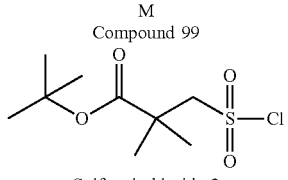<br>Sulfonyl chloride 2 | 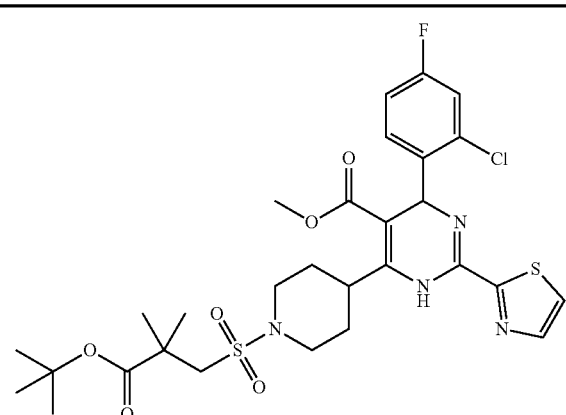<br>Compound 222 |
| M<br>Compound 58<br>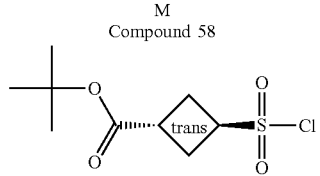<br>Sulfonyl chloride 5 | 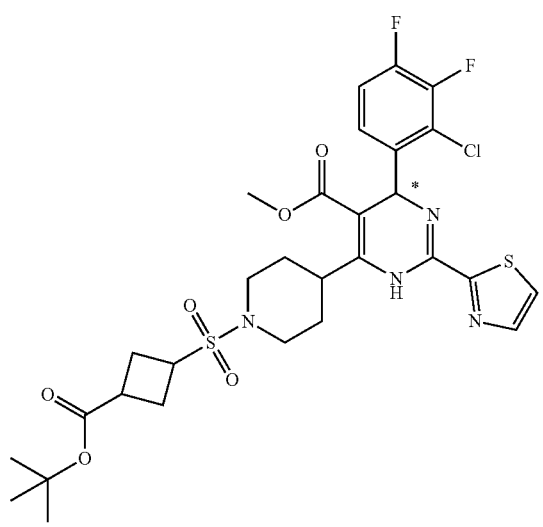 [SMILES: COC(=O)C1=C(C2CCN(S(=O)(=O)C3CC(C(=O)OC(C)(C)C)C3)CC2)NC(c2nccs2)=NC1c1ccc(F)c(F)c1Cl]<br>Compound 231B, trans<br>Compound 231D, cis |
| M<br>Compound 236<br>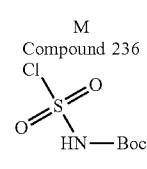 | 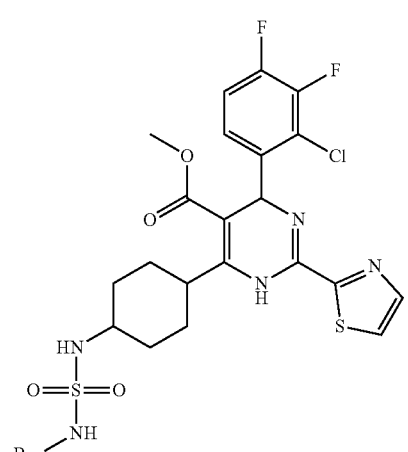<br>Compound 237 |

-continued
| Method & Coupling partners | Product |
|---|---|
| M<br>Compound 119<br>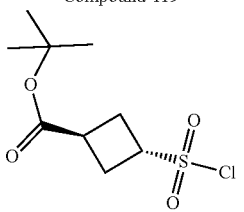<br>Sulfonyl chloride 5 | 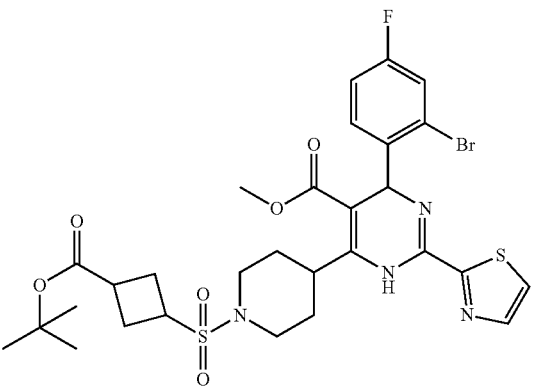 [SMILES: COC(=O)C1=C(C2CCN(S(=O)(=O)C3CC(C(=O)OC(C)(C)C)C3)CC2)NC(c2nccs2)=NC1c1ccc(F)cc1Br]<br>Compound 240 |
| M<br>Compound 99<br>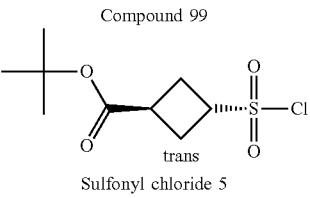<br>trans<br>Sulfonyl chloride 5 | 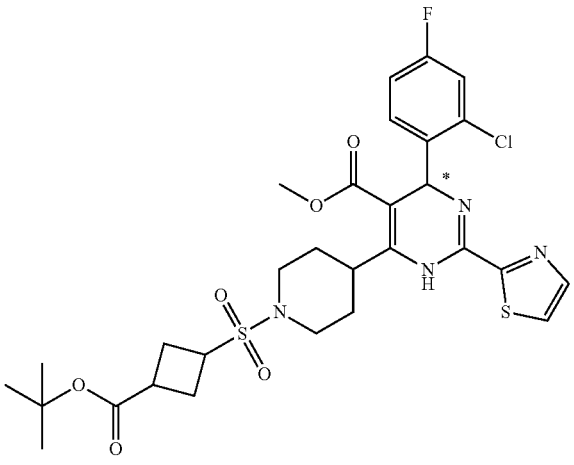 [SMILES: COC(=O)C1=C(C2CCN(S(=O)(=O)C3CC(C(=O)OC(C)(C)C)C3)CC2)NC(c2nccs2)=NC1c1ccc(F)cc1Cl]<br>Compound 242 |
| M<br>Compound 58<br>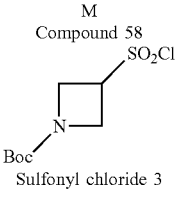<br>Sulfonyl chloride 3 | 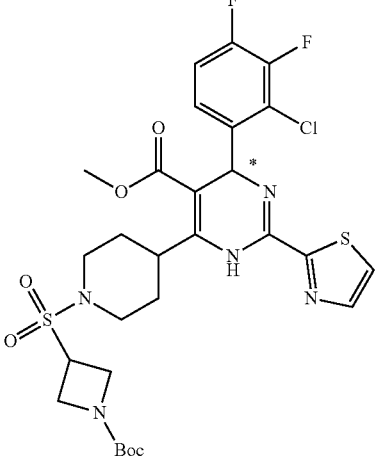<br>Compound 246 |

347 348
-continued
| Method & Coupling partners | Product |
|---|---|
| M<br>Compound 236<br>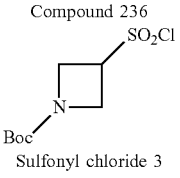<br>Sulfonyl chloride 3 | 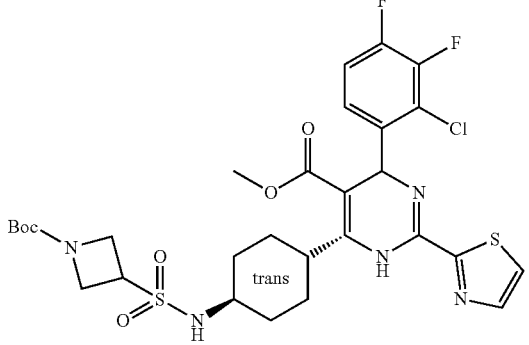<br>Compound 249 |
| M<br>Compound 236<br>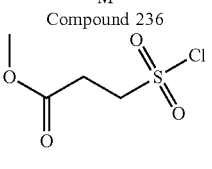 | 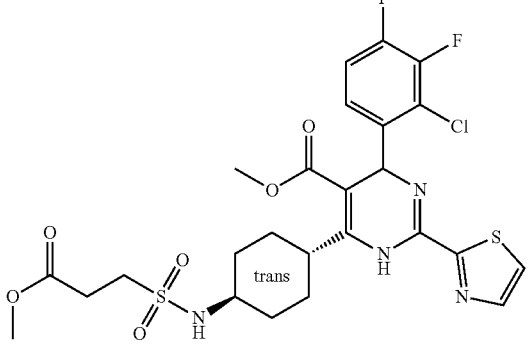<br>Compound 252 |
| M<br>Compound 99<br>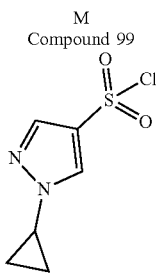 | 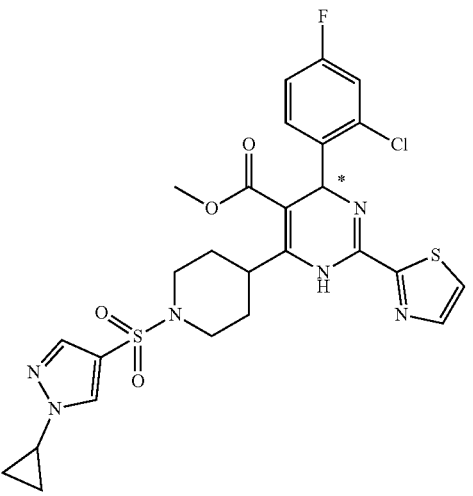 [SMILES: COC(=O)C1=C(C2CCN(S(=O)(=O)c3cnn(C4CC4)c3)CC2)NC(c2nccs2)=NC1c1ccc(F)cc1Cl]<br>Compound 254 |

-continued
| Method & Coupling partners | Product |
|---|---|
| M<br>Compound 67A<br>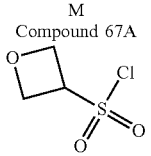 | 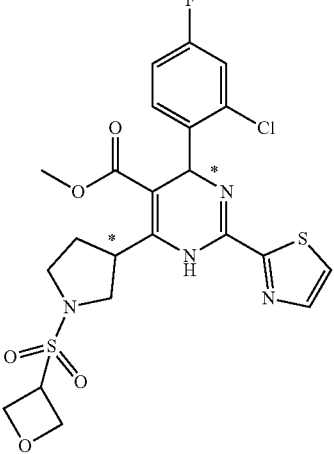<br>Compound 255 |
| M<br>Compound 67A<br>Compound 67D<br>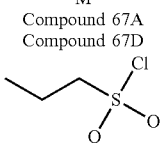 | 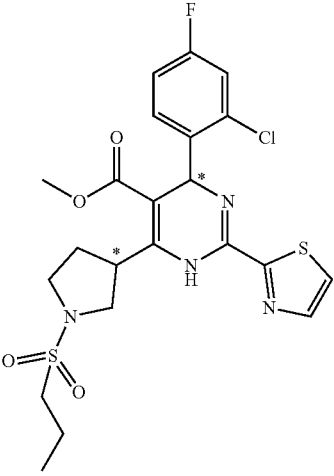 [SMILES: CCCS(=O)(=O)N1CCC(C2=C(C(=O)OC)C(c3ccc(F)cc3Cl)N=C(c3nccs3)N2)C1]<br>Compound 256A<br>Compound 256D |
| M<br>Compound 99<br>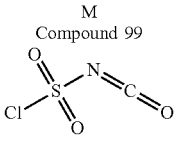 | 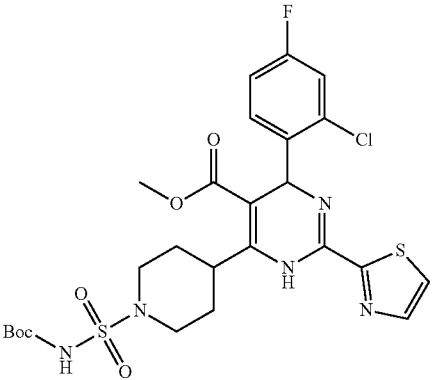 [SMILES: COC(=O)C1=C(C2CCN(S(=O)(=O)NC(=O)OC(C)(C)C)CC2)NC(c2nccs2)=NC1c1ccc(F)cc1Cl]<br>Compound 266 |

-continued
| Method & Coupling partners | Product |
|---|---|
| M<br>Compound 369<br>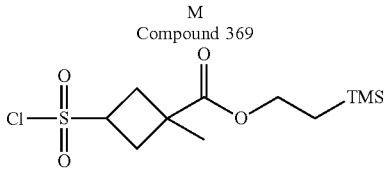<br>Sulfonyl chloride 9 | 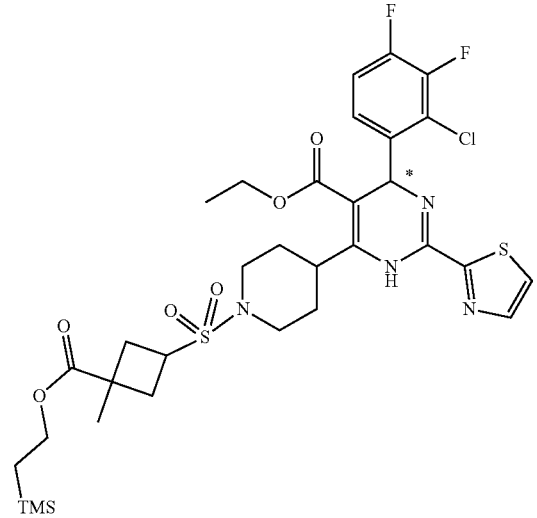 [SMILES: CCOC(=O)C1=C(C2CCN(S(=O)(=O)C3CC(C)(C(=O)OCC[Si](C)(C)C)C3)CC2)NC(c2nccs2)=NC1c1ccc(F)c(F)c1Cl]<br>Compound 269A (trans)<br>Compound 269B (cis) |
| M<br>Compound 327B<br>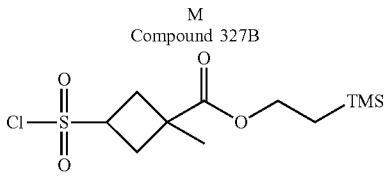<br>Sulfonyl chloride 9 | 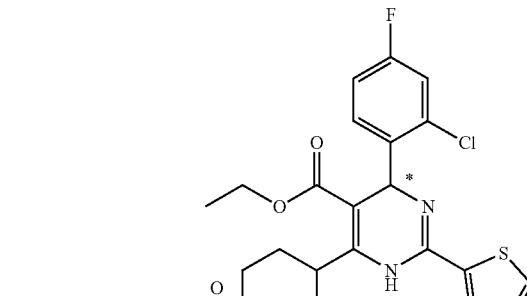<br>Compound 271A (trans)<br>Compound 271B (cis) |

-continued
| Method & Coupling partners | Product |
|---|---|
| M<br>Compound 117<br>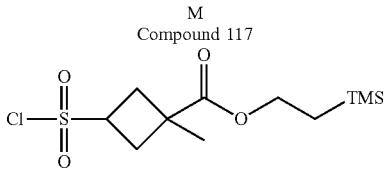<br>Sulfonyl chloride 9 | 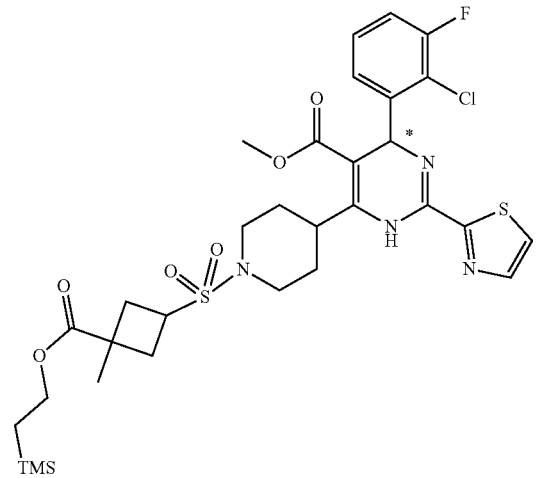 [SMILES: COC(=O)C1=C(C2CCN(S(=O)(=O)C3CC(C)(C(=O)OCC[Si](C)(C)C)C3)CC2)NC(c2nccs2)=NC1c1cccc(F)c1Cl]<br>Compound 273A (trans)<br>Compound 273B (cis) |
| M<br>Compound 276B<br>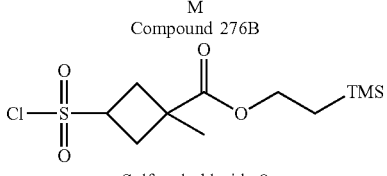<br>Sulfonyl chloride 9 | 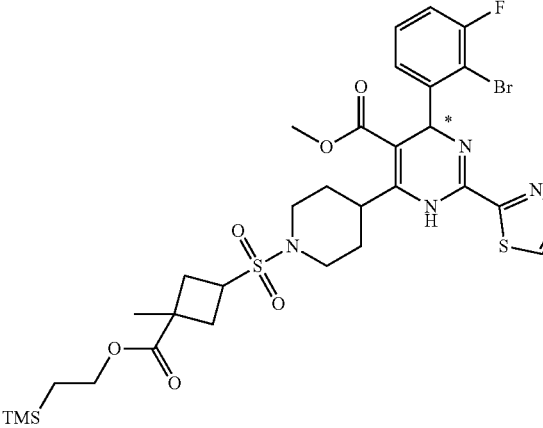<br>Compound 277C (trans)<br>Compound 277D (cis) |
| M<br>Compound 280B<br>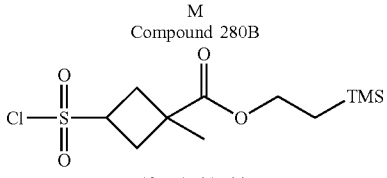<br>Sulfonyl chloride 9 | 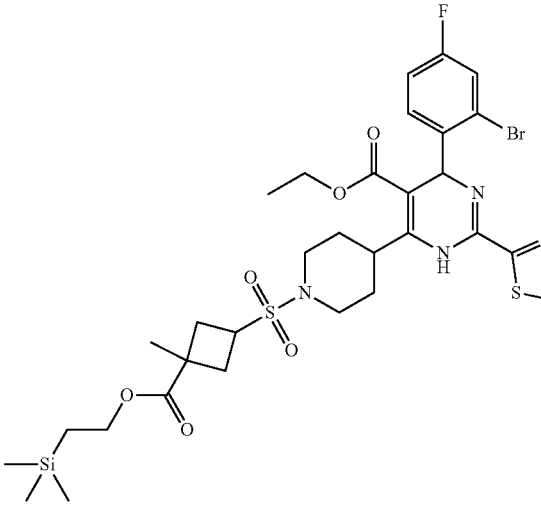<br>Compound 281C (trans) |

-continued

| Method & Coupling partners | Product |
|---|---|
| M<br>Compound 297<br>methanesulfonyl chloride | Compound 281D (cis) |
| M<br>Compound 99<br>Sulfonyl chloride 6 | Compound 298 |
| | Compound 304 |
| M<br>Compound 307B<br>Sulfonyl chloride 5 (trans) | Compound 308M (trans)<br>Compound 308N (cis) |

| Method & Coupling partners | Product |
|---|---|
| 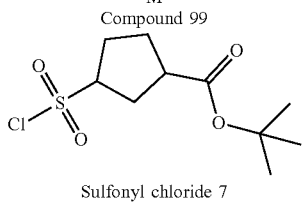<br>M<br>Compound 99<br><br>Sulfonyl chloride 7 | 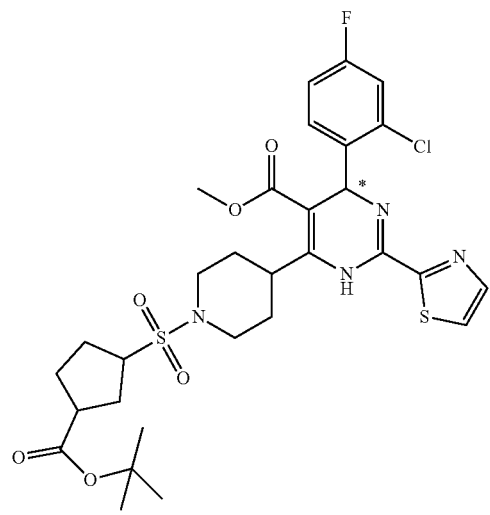 [SMILES: COC(=O)C1=C(C2CCN(S(=O)(=O)C3CCC(C(=O)OC(C)(C)C)C3)CC2)NC(c2nccs2)=NC1c1ccc(F)cc1Cl]<br>Compound 310 |
| 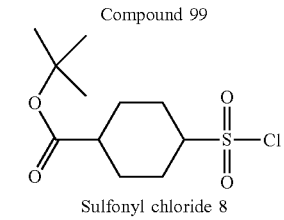<br>M<br>Compound 99<br><br>Sulfonyl chloride 8 | 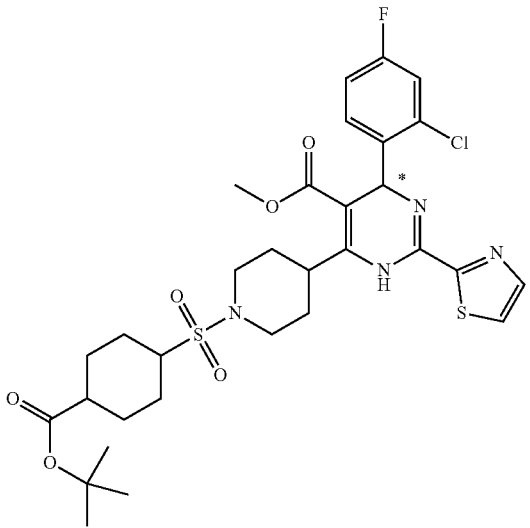 [SMILES: COC(=O)C1=C(C2CCN(S(=O)(=O)C3CCC(C(=O)OC(C)(C)C)CC3)CC2)NC(c2nccs2)=NC1c1ccc(F)cc1Cl]<br>Compound 312X(cis)<br>Compound 312Y (trans) |

-continued

| Method & Coupling partners | Product |
|---|---|
| M<br>Compound 317<br>Sulfonyl chloride 5 | Compound 318M (trans)<br>Compound 318N (cis) |
| M<br>Compound 317<br>Sulfonyl chloride 9 | Compound 320A (trans)<br>Compound 320B (cis) |
| M<br>Compound 58<br>Sulfonyl chloride 9 | Compound 322C (trans)<br>Compound 322D (cis) |

-continued
| Method & Coupling partners | Product |
|---|---|
| M<br>Compound 58<br>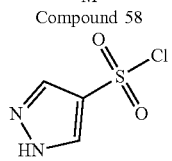 | 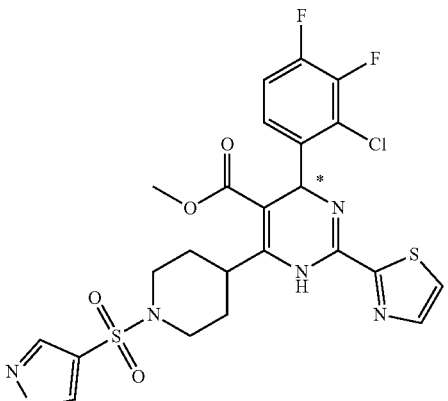<br>Compound 324 |
| M<br>Compound 327B<br>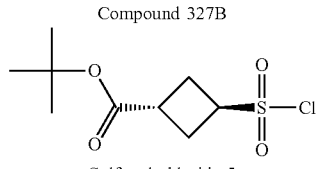<br>Sulfonyl chloride 5 | 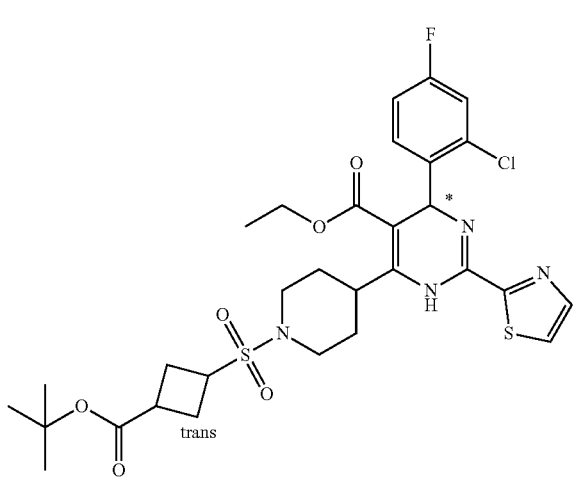 [SMILES: CCOC(=O)C1=C(C2CCN(S(=O)(=O)C3CC(C(=O)OC(C)(C)C)C3)CC2)NC(c2nccs2)=NC1c1ccc(F)cc1Cl]<br>Compound 328F (trans)<br>Compound 328H (cis) |
| M<br>Compound 117<br>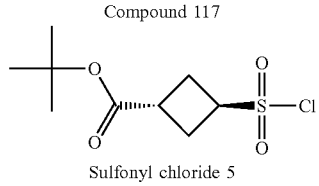<br>Sulfonyl chloride 5 | 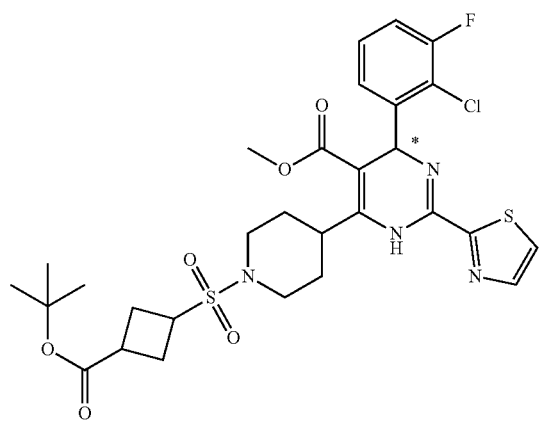 [SMILES: COC(=O)C1=C(C2CCN(S(=O)(=O)C3CC(C(=O)OC(C)(C)C)C3)CC2)NC(c2nccs2)=NC1c1cccc(F)c1Cl]<br>Compound 330P (trans)<br>Compound 330Q (cis) |

-continued
| Method & Coupling partners | Product |
|---|---|
| M<br>Compound 280B<br>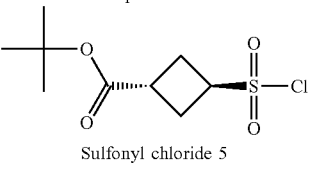<br>Sulfonyl chloride 5 | 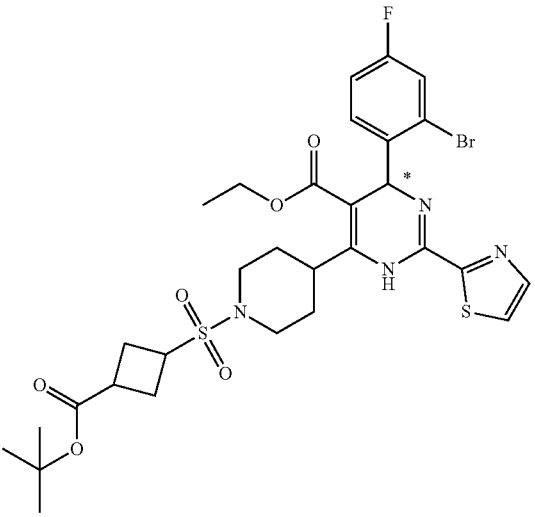 [SMILES: CCOC(=O)C1=C(C2CCN(S(=O)(=O)C3CC(C(=O)OC(C)(C)C)C3)CC2)NC(c2nccs2)=NC1c1ccc(F)cc1Br]<br>Compound 332M (trans)<br>Compound 332N (cis) |
| M<br>Compound 99<br>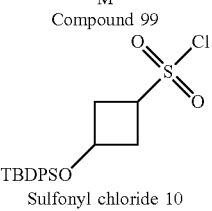<br>Sulfonyl chloride 10 | 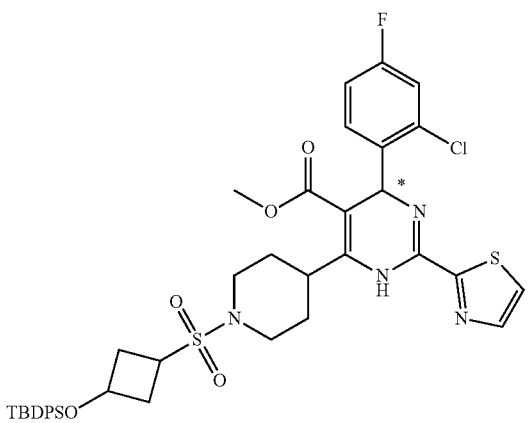<br>Compound 334 |
| M<br>Compound 337B<br>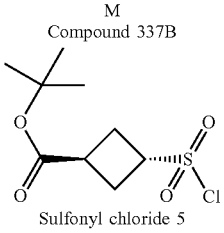<br>Sulfonyl chloride 5 | 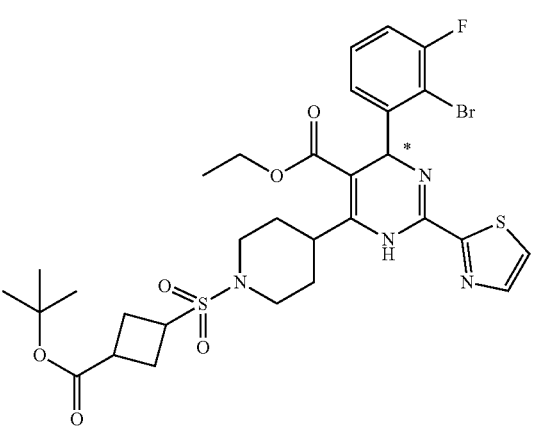 [SMILES: CCOC(=O)C1=C(C2CCN(S(=O)(=O)C3CC(C(=O)OC(C)(C)C)C3)CC2)NC(c2nccs2)=NC1c1cccc(F)c1Br]<br>Compound 338M (trans)<br>Compound 338N (cis) |

-continued

| Method & Coupling partners | Product |
|---|---|
| M<br>Compound 341A and 341B<br>Sulfonyl chloride 5 | Compound 342 |
| M<br>Compound 350B<br>Sulfonyl chloride 5 | Compound 351X (trans)<br>Compound 351Y (cis) |

-continued
| Method & Coupling partners | Product |
|---|---|
| M<br>Compound 369<br>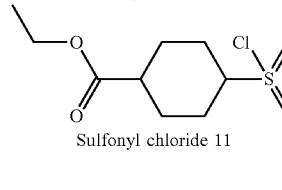<br>Sulfonyl chloride 11 | 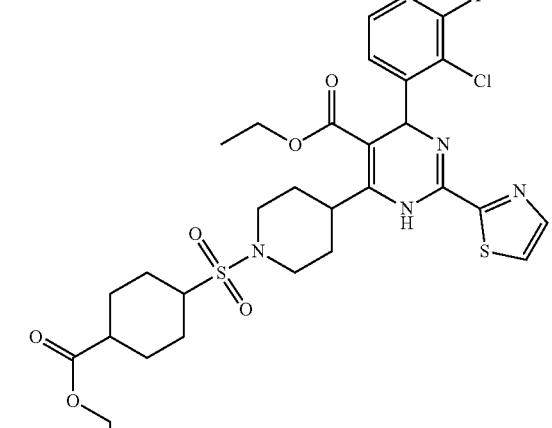<br>Compound 353 |
| M<br>Compound 369<br>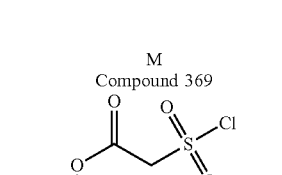 | 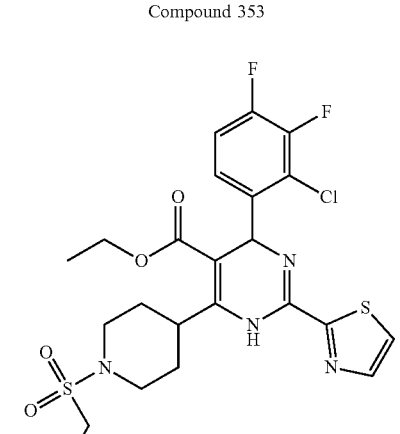<br>Compound 355 |
| M<br>Compound 67A<br>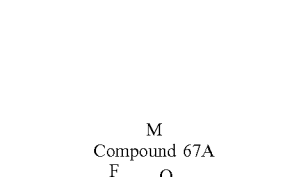 | 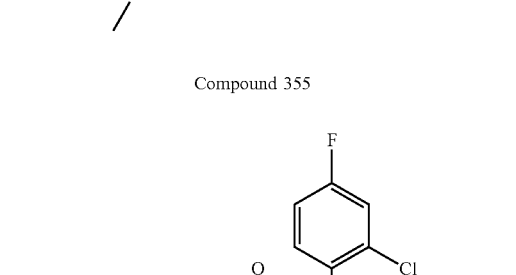<br>Compound 364 |

-continued
| Method & Coupling partners | Product |
|---|---|
| M<br>Compound 67A<br>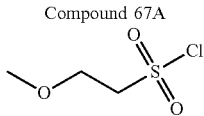 | 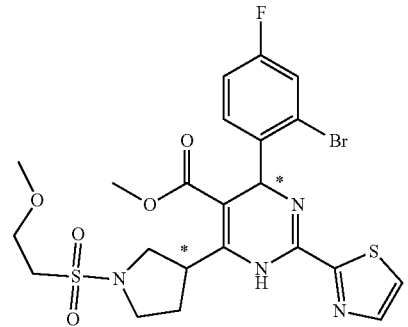 [SMILES: COCCS(=O)(=O)N1CCC(C2=C(C(=O)OC)C(c3ccc(F)cc3Br)N=C(c3nccs3)N2)C1]<br>Compound 365 |
| M<br>Compound 67A<br>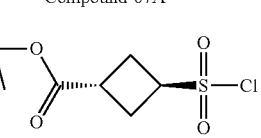<br>Sulfonyl chloride 5 | 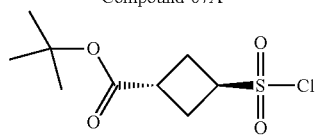<br>Compound 366X (trans)<br>Compound 366Y (cis) |
| M<br>Compound 369B<br>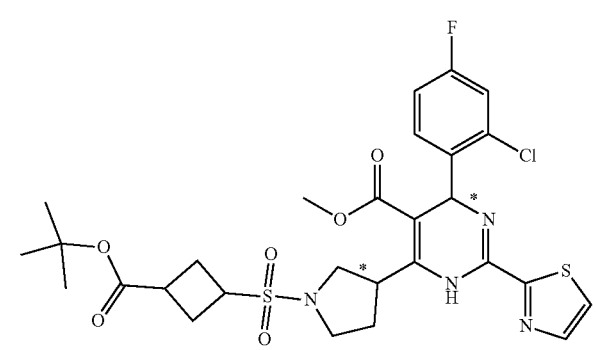 [SMILES: COC(=O)C1=C(C2CCN(S(=O)(=O)C3CC(C(=O)OC(C)(C)C)C3)C2)NC(c2nccs2)=NC1c1ccc(F)cc1Cl]<br>Sulfonyl chloride 5 | 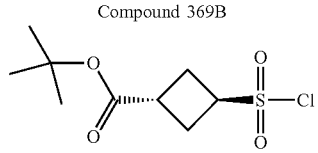<br>Compound 370B-1 (trans)<br>Compound 370D-1 (cis) |

-continued

| Method & Coupling partners | Product |
|---|---|
| M<br>Compound 373B<br>methyl 2-(chlorosulfonyl)acetate | Compound 389B |
| M<br>Compound 373B<br>AcCl | Compound 391B |
| M<br>Compound 373B<br>Sulfonyl chloride 6 (1,4-dioxaspiro[4.5]decan-2-ylmethanesulfonyl chloride) | Compound 392B |
| M<br>Compound 395<br>methanesulfonyl chloride | Compound 396 |

| Method & Coupling partners | Product |
|---|---|
| M<br>Compound 398<br>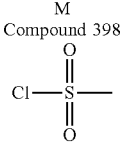 | 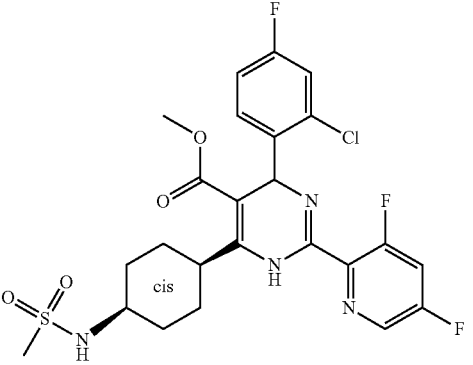 [SMILES: COC(=O)C1=C([C@H]2CC[C@@H](NS(C)(=O)=O)CC2)NC(c2ncc(F)cc2F)=NC1c1ccc(F)cc1Cl]<br>Compound 399 |
| M<br>Compound 203<br>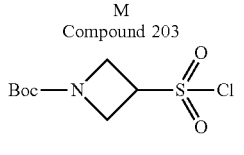 | 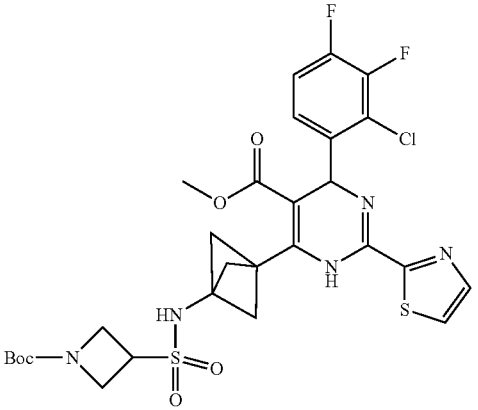 [SMILES: COC(=O)C1=C(C23CC(NS(=O)(=O)C4CN(C(=O)OC(C)(C)C)C4)(C2)C3)NC(c2nccs2)=NC1c1ccc(F)c(F)c1Cl]<br>Compound 405 |
| M<br>Compound 408B<br>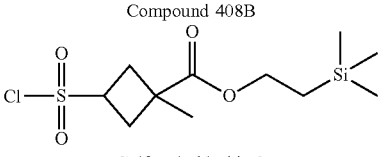<br>Sulfonyl chloride 9 | 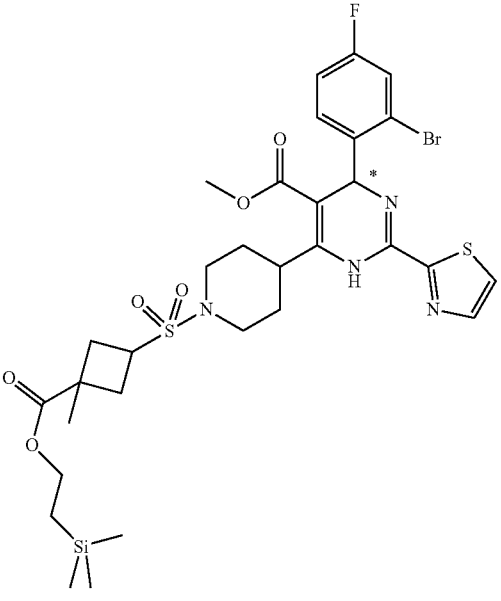 [SMILES: COC(=O)C1=C(C2CCN(S(=O)(=O)C3CC(C)(C(=O)OCC[Si](C)(C)C)C3)CC2)NC(c2nccs2)=NC1c1ccc(F)cc1Br]<br>Compound 409P (trans)<br>Compound 409QP (cis) |

-continued
| Method & Coupling partners | Product |
|---|---|
| M<br>Compound 412B<br>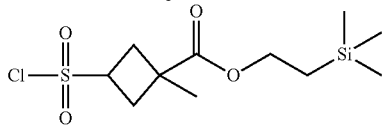<br>Sulfonyl chloride 9 | 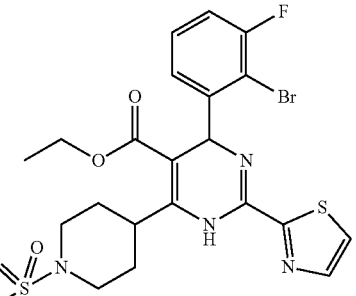<br>Compound 413C (trans)<br>Compound 413D (cis) |
| M<br>Compound 58<br>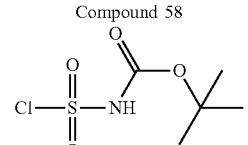<br>Sulfonyl chloride 12 | 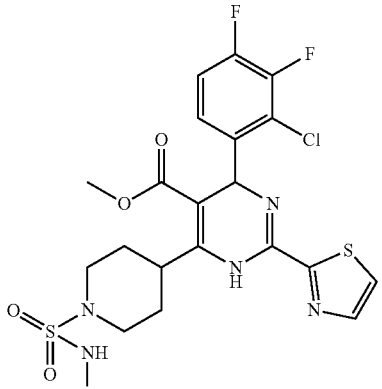<br>Compound 415 |
| M<br>Compound 418B<br>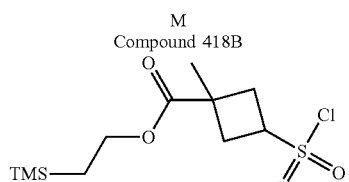<br>Sulfonyl chloride 9 | 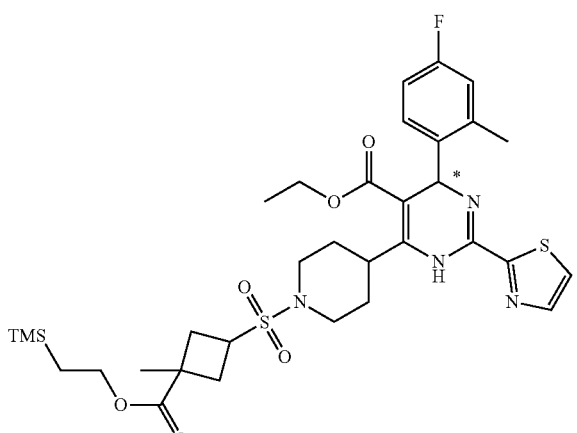<br>Compound 419A (trans)<br>Compound 419B (cis) |

US 11,639,350 B2

377 378

-continued

| Method & Coupling partners | Product |
|---|---|
| M<br>Compound 99<br>Sulfonyl chloride 13 | Compound 421 |
| M<br>Compound 368B<br>Sulfonyl chloride 13 | Compound 423 |
| M<br>Compound 427B<br>Sulfonyl chloride 9 | Compound 428C (trans)<br>Compound 428D (cis) |

-continued
| Method & Coupling partners | Product |
|---|---|
| M<br>Compound 436a<br>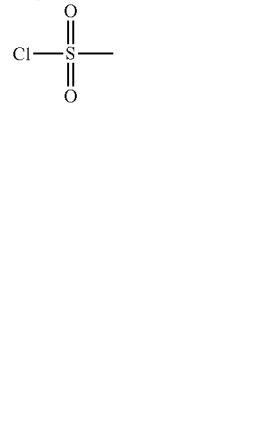 | 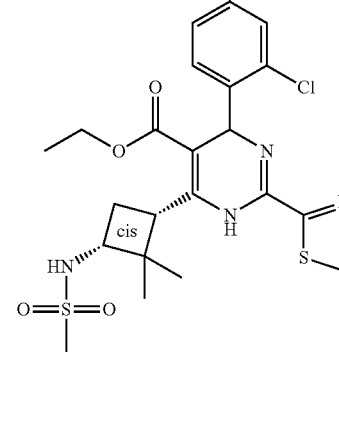<br>Compound 437 |
| M<br>Compound 276B<br>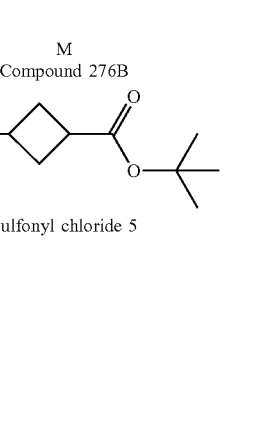<br>Sulfonyl chloride 5 | 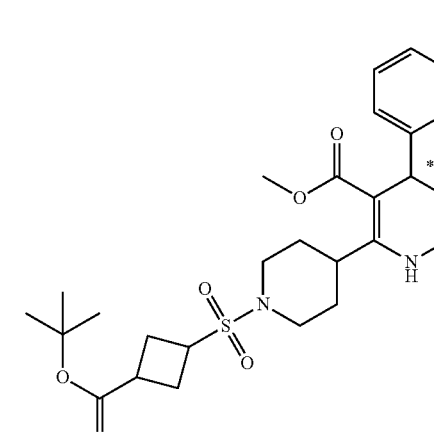<br>Compound 438F (trans)<br>Compound 438H (cis) |
| M<br>Compound 373B<br>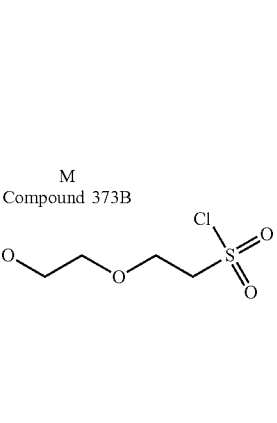 | 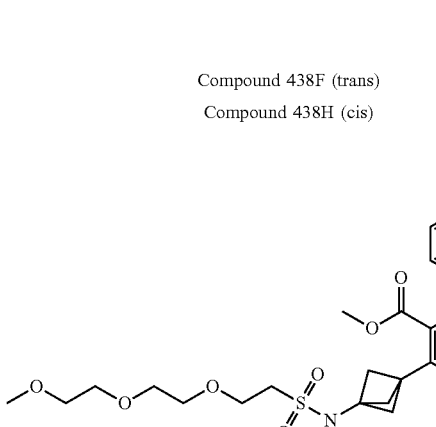<br>Compound 440B |

| Method & Coupling partners | Product |
|---|---|
| M<br>Compound 442b<br>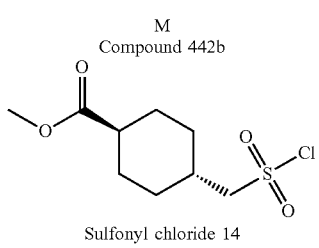<br>Sulfonyl chloride 14 | 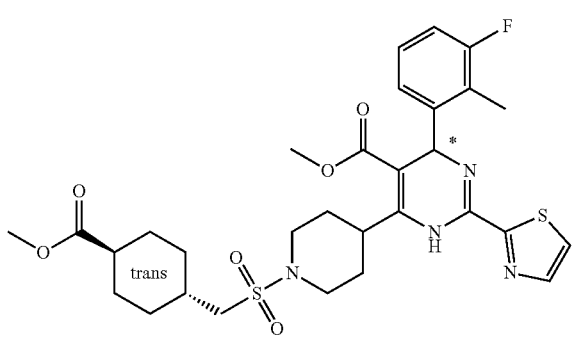 [SMILES: COC(=O)C1=C(C2CCN(S(=O)(=O)C[C@H]3CC[C@H](C(=O)OC)CC3)CC2)NC(c2nccs2)=NC1c1cccc(F)c1C]<br>Compound 443b |
| M<br>Compound 446B<br>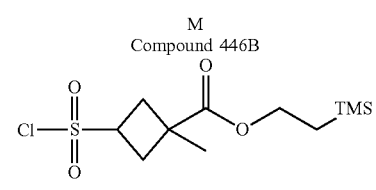<br>Sulfonyl chloride 9 | 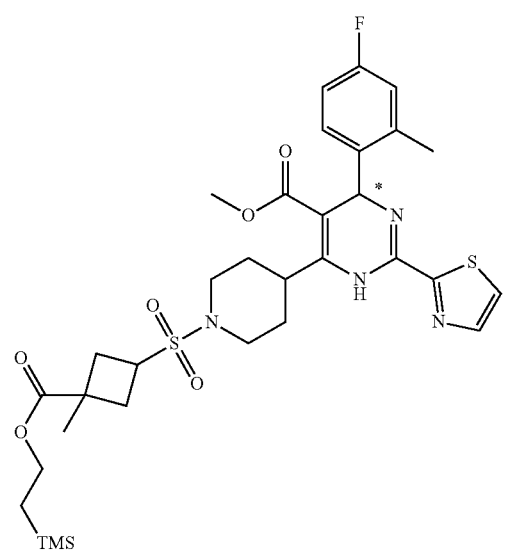 [SMILES: COC(=O)C1=C(C2CCN(S(=O)(=O)C3CC(C)(C(=O)OCC[Si](C)(C)C)C3)CC2)NC(c2nccs2)=NC1c1ccc(F)cc1C]<br>Compound 447-1C (trans)<br>Compound 447-1D (cis) |
| M<br>Compound 99<br>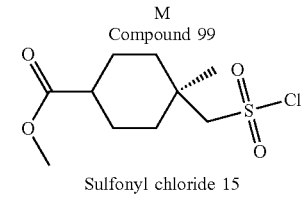<br>Sulfonyl chloride 15 | 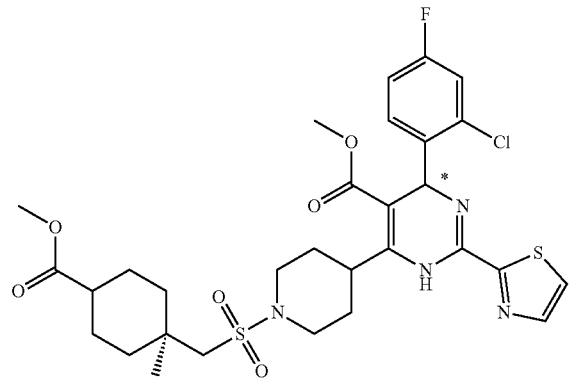<br>Compound 449A (cis)<br>Compound 449B (trans) |

-continued
| Method & Coupling partners | Product |
|---|---|
| M<br>Compound 99<br>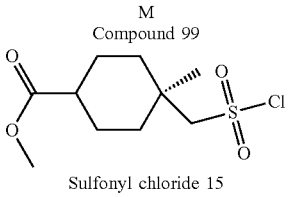<br>Sulfonyl chloride 15 | 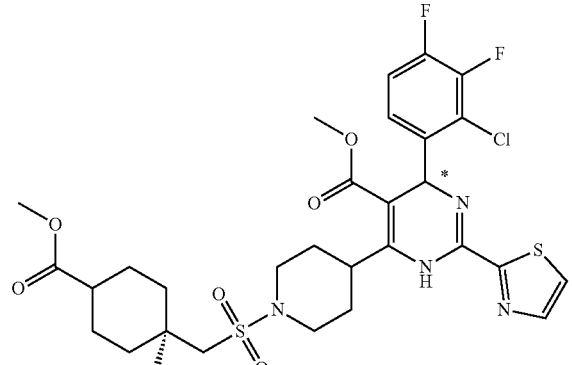<br>Compound 451A (cis)<br>Compound 451B (trans) |
| M<br>Compound 117<br>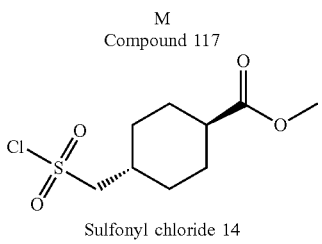<br>Sulfonyl chloride 14 | 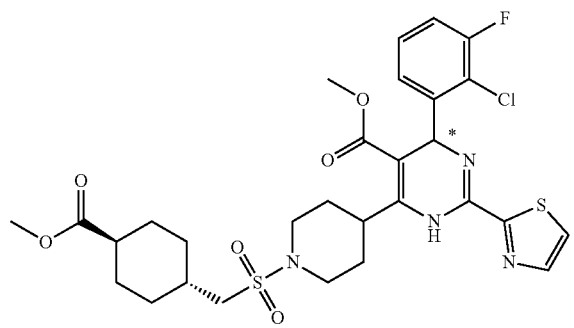 [SMILES: COC(=O)C1=C(C2CCN(S(=O)(=O)C[C@H]3CC[C@H](C(=O)OC)CC3)CC2)NC(c2nccs2)=NC1c1cccc(F)c1Cl]<br>Compound 453 |
| M<br>Compound 58<br>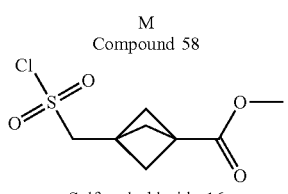<br>Sulfonyl chloride 16 | 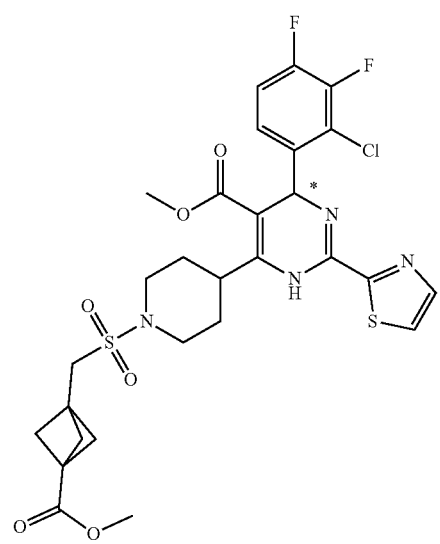 [SMILES: COC(=O)C1=C(C2CCN(S(=O)(=O)CC34CC(C(=O)OC)(C3)C4)CC2)NC(c2nccs2)=NC1c1ccc(F)c(F)c1Cl]<br>Compound 455 |

-continued
| Method & Coupling partners | Product |
|---|---|
| M<br>Compound 99<br>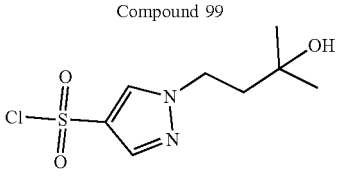<br>Sulfonyl chloride 17 | 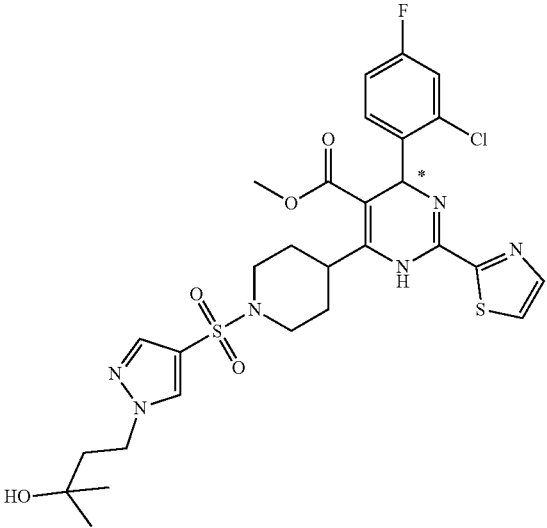 [SMILES: COC(=O)C1=C(C2CCN(S(=O)(=O)c3cnn(CCC(C)(C)O)c3)CC2)NC(c2nccs2)=NC1c1ccc(F)cc1Cl]<br>Compound 458 |
| M<br>Compound 99<br>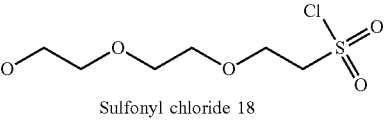<br>Sulfonyl chloride 18 | 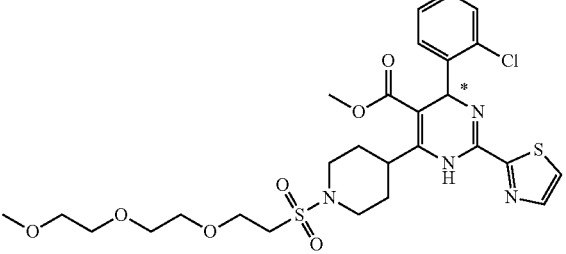<br>Compound 459 |
| Compound 99<br>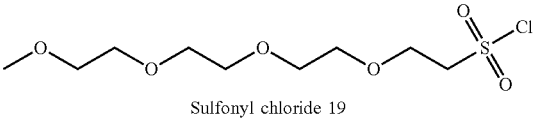<br>Sulfonyl chloride 19 | 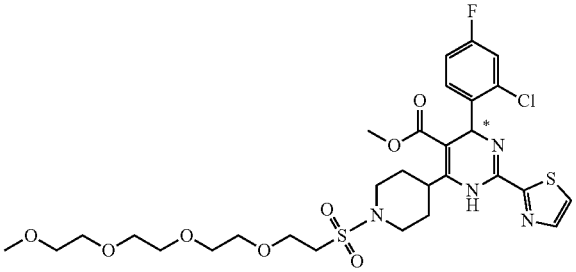 [SMILES: COCCOCCOCCOCCS(=O)(=O)N1CCC(C2=C(C(=O)OC)C(c3ccc(F)cc3Cl)N=C(c3nccs3)N2)CC1]<br>Compound 460 |

-continued
| Method & Coupling partners | Product |
|---|---|
| M<br>Compound 369B<br>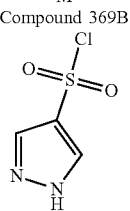 | 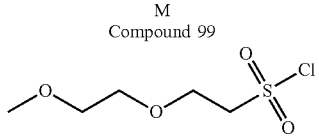<br>Compound 461 |
| M<br>Compound 99<br>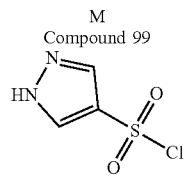 | Compound 464 |
| M<br>Compound 99 | Compound 466 |

-continued

| Method & Coupling partners | Product |
|---|---|
| M<br>Compound 99<br>Sulfonyl chloride 20 | Compound 467 |
| M<br>Compound 99<br>Sulfonyl chloride 21 | Compound 469 |
| M<br>Compound 58 | Compound 473 |

-continued
| Method & Coupling partners | Product |
|---|---|
| M<br>Compound 99<br>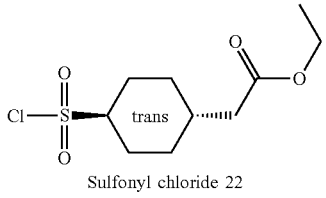<br>Sulfonyl chloride 22 | 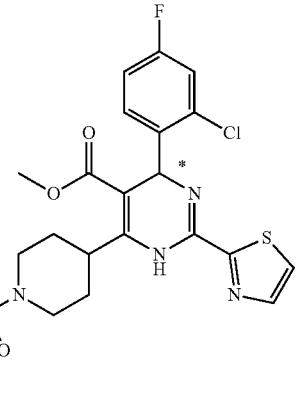<br>Compound 475 |
| M<br>Compound 58<br>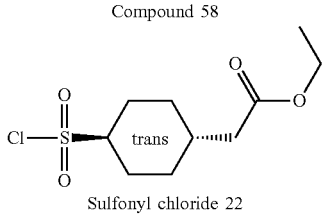<br>Sulfonyl chloride 22 | 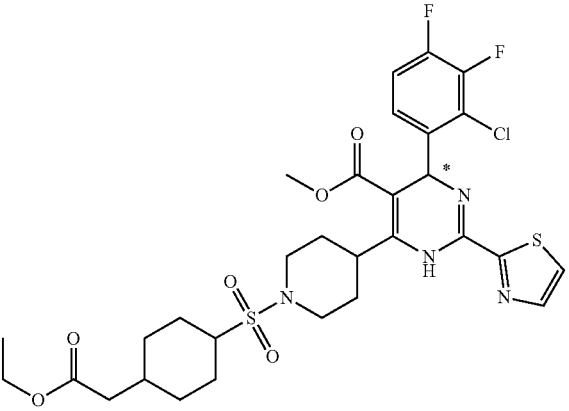 [SMILES: CCOC(=O)CC1CCC(S(=O)(=O)N2CCC(C3=C(C(=O)OC)C(c4ccc(F)c(F)c4Cl)N=C(c4nccs4)N3)CC2)CC1]<br>Compound 477 |
| M<br>Compound 369<br>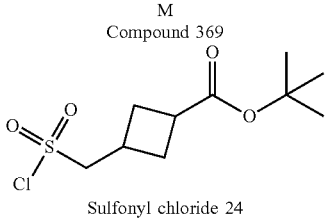<br>Sulfonyl chloride 24 | 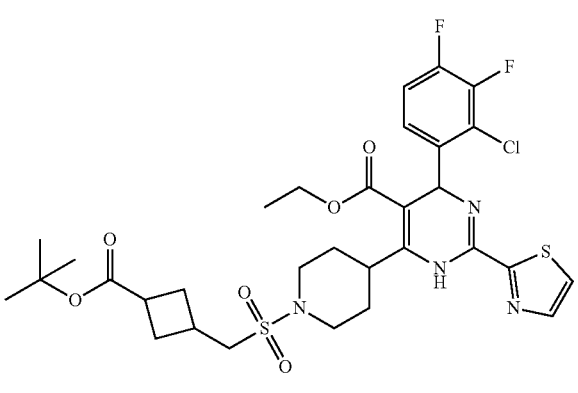 [SMILES: CCOC(=O)C1=C(C2CCN(S(=O)(=O)CC3CC(C(=O)OC(C)(C)C)C3)CC2)NC(c2nccs2)=NC1c1ccc(F)c(F)c1Cl]<br>Compound 479 |

| Method & Coupling partners | Product |
|---|---|
| M<br>Compound 369B<br>Sulfonyl chloride 23 | Compound 481A and 481B (single isomer, cis/trans unkown) |
| M<br>Compound 99<br>Sulfonyl chloride 25 | Compound 483 |

Compound 101: Methyl 4-(2-chloro-4-fluorophenyl)-6-(1-(ethylsulfonyl)piperidin-4-yl)-2-(thiazol-2-yl)-1,4-dihydropyrimidine-5-carboxylate LC-MS (ESI): $R_T$=3.991 min, mass calcd. for $C_{22}H_{24}ClFN_4O_4S_2$ 526.1, m/z found 526.9 [M+H]$^+$. Chiral HPLC (Column: Chiralpak IA 5 μm 4.6*250 mm; Mobile Phase: Hex:EtOH=60:40 at 1.0 mL/min; Temp: 30° C.; Wavelength: 230 nm, $R_T$=7.516 min). $^1$H NMR (400 MHz, DMSO-d$_6$) δ 9.51 (d, J=3.6 Hz, 0.8H), 9.14 (s, 0.2H), 8.00 (s, 1.8H), 7.93 (d, J=2.8 Hz, 0.2H), 7.42 (dd, J=9.2, 2.8 Hz, 1H), 7.38-7.34 (m, 1H), 7.23-7.18 (m, 1H), 6.02 (s, 0.2H), 5.92 (d, J=3.6 Hz, 0.8H), 4.01-3.90 (m, 0.2H), 3.79-3.69 (m, 2.8H), 3.53 (s, 3H), 3.08 (q, J=7.2 Hz, 2H), 2.94-2.80 (m, 2H), 2.10-1.95 (m, 1H), 1.91-1.75 (m, 2H), 1.65-1.60 (m, 1H), 1.25 (t, J=7.2 Hz, 3H).

Compound 102: Methyl 4-(2-chloro-4-fluorophenyl)-6-(1-(cyclopropanecarbonyl)-piperidin-4-yl)-2-(thiazol-2-yl)-1,4-dihydropyrimidine-5-carboxylate LC-MS (ESI): $R_T$=3.851 min, mass calcd. for $C_{24}H_{24}ClFN_4O_3S$ 502.1, m/z found 502.9 [M+H]$^+$. Chiral HPLC (Column: Chiralpak IC 5 μm 4.6*250 mm; Mobile Phase: Hex:EtOH=80:20 at 1.0 mL/min; Temp: 30° C.; Wavelength: 230 nm, $R_T$=15.920 min). $^1$H NMR (400 MHz, DMSO-d$_6$) δ 9.48 (d, J=3.6 Hz, 0.7H), 9.23-9.16 (m, 0.3H), 7.98 (dd, J=6.4, 3.2 Hz, 1.7H), 7.91 (d, J=3.2 Hz, 0.3H), 7.43-7.40 (m, 1H), 7.38-7.31 (m, 1H), 7.20 (dd, J=8.8, 2.8 Hz, 1H), 6.02 (s, 0.3H), 5.92 (d, J=3.6 Hz, 0.7H), 4.61-4.33 (m, 2H), 4.18-4.07 (m, 0.3H), 3.92-3.84 (m, 0.7H), 3.54 (s, 2.1H), 3.53 (s, 0.9H), 3.20-3.08 (m, 1H), 2.59-2.54 (m, 1H), 2.06-1.93 (m, 1.2H), 1.49-1.23 (m, 3.8H), 0.81-0.69 (m, 4H).

Compound 103: Methyl 4-(2-chloro-4-fluorophenyl)-6-(1-(methylsulfonyl)-piperidin-4-yl)-2-(thiazol-2-yl)-1,4-dihydropyrimidine-5-carboxylate LC-MS (ESI): $R_T$=4.495 min, mass calcd. for $C_{21}H_{22}ClFN_4O_4S_2$ 512.1, m/z found 512.9 [M+H]$^+$. Chiral HPLC (Column: Chiralpak IE 5 μm 4.6*250 mm; Mobile Phase: Hex:EtOH:DEA=50:50:0.2 at 1.0 mL/min; Temp: 30° C.; Wavelength: 230 nm, $R_T$=10.842 min). $^1$H NMR (400 MHz, DMSO-d$_6$) δ 9.51 (d, J=4.0 Hz, 0.8H), 9.14 (s, 0.2H), 8.00-7.98 (m, 1.5H), 7.93-7.92 (m, 0.5H), 7.43-7.40 (m, 1H), 7.39-7.32 (m, 1H), 7.23-7.19 (m, 1H), 6.02 (s, 0.2H), 5.93 (d, J=4.0 Hz, 0.8H), 4.00-3.91 (m, 0.2H), 3.74-3.64 (m, 2.8H), 3.53-3.52 (m, 3H), 2.91-2.90 (m, 3H), 2.82-2.73 (m, 2H), 2.15-1.80 (m, 3.2H), 1.67-1.64 (m, 0.8H).

Compound 104: Methyl 4-(2-chloro-4-fluorophenyl)-6-(1-((3-methoxy-3-oxopropyl)-sulfonyl)piperidin-4-yl)-2-(thiazol-2-yl)-1,4-dihydropyrimidine-5-carboxylate LC-MS (ESI): $R_T$=4.371 min, mass calcd. for $C_{24}H_{26}ClFN_4O_6S_2$ 584.1, m/z found 585.1 [M+H]$^+$. $^1$H NMR (400 MHz, DMSO-d$_6$) δ 9.52 (d, J=4.0 Hz, 0.8H), 9.14 (s, 0.2H), 8.00-7.89 (m, 2H), 7.42 (dd, J=8.8, 2.8 Hz, 1H), 7.38-7.32 (m, 1H), 7.24-7.19 (m, 1H), 6.02 (s, 0.2H), 5.92 (d, J=3.6 Hz, 0.8H), 3.83-3.70 (m, 2.4H), 3.66 (s, 3H), 3.63-3.61 (m, 0.6H), 3.54 (s, 2.4H), 3.53 (s, 0.6H), 3.34 (t, J=3.2 Hz, 2H), 2.94-2.85 (m, 2H), 2.76 (t, J=3.2 Hz, 2H), 2.02-1.93 (m, 1H), 1.89-1.75 (m, 2H), 1.64-1.61 (m, 1H).

Compound 106: Methyl 4-(2-chloro-4-fluorophenyl)-6-(1-((2-methoxy-2-oxoethyl)-sulfonyl)-piperidin-4-yl)-2-(thiazol-2-yl)-1,4-dihydropyrimidine-5-carboxylate LC-MS (ESI): $R_T$=3.985 min, mass calcd. for $C_{23}H_{24}ClFN_4O_6S_2$ 570.1, m/z found 570.9 [M+H]$^+$. Chiral HPLC (Chiralpak IA 5 μm 4.6*250 mm, Mobile Phase: Hex:EtOH=70:30 at 1.0 mL/min, Temp: 30° C., Wavelength: 230 nm, $R_T$=12.627 min); $^1$H NMR (400 MHz, DMSO-d$_6$) δ 9.52 (d, J=2.4 Hz, 0.8H), 9.17 (s, 0.2H), 8.05-7.96 (m, 1.8H), 7.92 (d, J=2.8 Hz, 0.2H), 7.46-7.41 (m, 1H), 7.38-7.31 (m, 1H), 7.26-7.16 (m, 1H), 6.02 (s, 0.2H), 5.92 (d, J=2.8 Hz, 0.8H), 4.30 (s, 2H), 4.00-3.91 (m, 0.2H), 3.83-3.68 (m, 5.8H), 3.53 (s, 3H), 2.99-2.83 (m, 2H), 2.06-1.93 (m, 1H), 1.91-1.75 (m, 2H), 1.65 (d, J=11.2 Hz, 1H).

Compound 110: Methyl 4-(2-chloro-4-fluorophenyl)-6-(1-(oxetan-3-ylsulfonyl)-piperidin-4-yl)-2-(thiazol-2-yl)-1,4-dihydropyrimidine-5-carboxylate (a Mixture of 2 Stereoisomers)

Compound 110 (330 mg, 0.595 mmol) was further separated by chiral Prep. HPLC (Column: Chiralpak IA 5 μm 20*250 mm; Mobile Phase: Hex:EtOH:DEA=50:50:0.3 at 8.0 mL/min; Temp: 30° C.; Wavelength: 214 nm) to afford stereoisomers Compound 110A (110 mg, 33% yield) and Compound 110B (105 mg, 32% yield). Compound 110B: LC-MS (ESI): $R_T$=2.890 min, mass calcd. for $C_{23}H_{24}ClFN_4O_5S_2$ 554.1, m/z found 554.9 [M+H]$^+$. Chiral HPLC (Column: Chiralpak IA 5 μm 4.6*250 mm; Mobile Phase: Hex:EtOH:DEA=50:50:0.2 at 1.0 mL/min; Temp: 30° C.; Wavelength: 230 nm, $R_T$=9.357 min). $^1$H NMR (400 MHz, DMSO-d$_6$) δ 9.56 (s, 0.8H), 9.18 (s, 0.2H), 8.03-7.99 (m, 1.8H), 7.93 (d, J=2.8 Hz, 0.2H), 7.43 (dd, J=8.8, 2.4 Hz, 1H), 7.38-7.34 (m, 1H), 7.23-7.18 (m, 1H), 6.01 (s, 0.2H), 5.92 (s, 0.8H), 4.89-4.86 (m, 2H), 4.83-4.79 (m, 1H), 4.76 (t, J=5.2 Hz, 2H), 3.72 (t, J=11.6 Hz, 3H), 3.52-3.51 (m, 3H), 2.88-2.79 (m, 2H), 1.95-1.89 (m, 1H), 1.80-1.75 (m, 2H), 1.62-1.59 (m, 1H).

Compound 122: Methyl 4-(2-chloro-4-fluorophenyl)-6-(1-(2-hydroxyacetyl)-piperidin-4-yl)-2-(thiazol-2-yl)-1,4-dihydropyrimidine-5-carboxylate (a Mixture of 2 Stereoisomers)

Compound 122 (340 mg, 0.690 mmol) was further separated by chiral Prep. HPLC (Column: Chiralpak IA 5 μm 20*250 mm; Mobile Phase: Hex:IPA:DEA=50:50:0.3 at 8 mL/min; Temp: 30° C.; Wavelength: 230 nm) to afford stereoisomers Compound 122A (93.9 mg, 28% yield) and Compound 122B (88.4 mg, 26% yield). Compound 122B: LC-MS (ESI): $R_T$=3.385 min, mass calcd. for $C_{22}H_{22}ClFN_4O_4S$ 492.1, m/z found 492.9 [M+H]$^+$. Chiral HPLC (Column: Chiralpak IA 5 μm 4.6*250 mm; Mobile Phase: Hex:EtOH:DEA=50:50:0.2 at 1.0 mL/min; Temp: 30° C.; Wavelength: 230 nm, $R_T$=9.523 min). $^1$H NMR (400 MHz, DMSO-d$_6$) δ 9.52 (d, J=3.6 Hz, 0.7H), 9.30 (s, 0.2H), 9.19 (s, 0.1H), 8.00-7.97 (m, 1.7H), 7.92 (d, J=3.2 Hz, 0.3H), 7.42 (dd, J=8.4, 2.4 Hz, 1H), 7.37-7.33 (m, 1H), 7.23-7.19 (m, 1H), 6.01 (s, 0.3H), 5.92 (d, J=3.6 Hz, 0.7H), 4.53-4.50 (m, 2H), 4.19-4.06 (m, 2.3H), 3.87-3.75 (m, 1.7H), 3.53 (s, 2.1H), 3.52 (s, 0.9H), 3.03-2.97 (m, 1H), 2.71-2.61 (m, 1H), 1.87-1.59 (m, 4H).

Compound 129: 6-[1-(2-tert-Butoxycarbonylaminoacetyl)-piperidin-4-yl]-4-(2-chloro-4-fluoro-phenyl)-2-thiazol-2-yl-1,4-dihydro-pyrimidine-5-carboxylic Acid Methyl Ester LC-MS (ESI): $R_T$=4.362 min, mass calcd. for $C_{27}H_{31}ClFN_5O_5S$ 591.2, m/z found 592.0 [M+H]$^+$. Chiral HPLC (Column: Chiralpak IA 5 μm 4.6*250 mm; Mobile Phase: Hex:EtOH=70:30 at 1.0 mL/min; Temp: 30° C.; Wavelength: 230 nm, $R_T$=9.371 min). $^1$H NMR (400 MHz, DMSO-d$_6$) δ 9.47 (d, J=2.8 Hz, 0.7H), 9.15-9.12 (m, 0.3H), 7.98 (d, J=4.4 Hz, 1.7H), 7.92 (s, 0.3H), 7.41 (dd, J=8.8, 2.4 Hz, 1H), 7.37-7.31 (m, 1H), 7.22-7.18 (m, 1H), 6.76-6.64 (m, 1H), 6.01 (s, 0.3H), 5.93 (d, J=3.6 Hz, 0.7H), 4.64-4.42 (m, 1H), 4.14-4.05 (m, 0.2H), 3.99-3.75 (m, 3.8H), 3.53 (s, 3H), 3.12-2.98 (m, 1H), 2.67-2.56 (m, 1H), 2.00-1.64 (m, 3.2H), 1.61-1.50 (m, 0.8H), 1.40 (s, 9H).

Compound 112: Methyl 4-(2-chloro-3-fluorophenyl)-6-(1-(methylsulfonyl)-piperidin-4-yl)-2-(thiazol-2-yl)-1,4-dihydropyrimidine-5-carboxylate (a Mixture of 2 Stereoisomers)

Compound 112 (90 mg, 0.18 mmol) was further separated by chiral Prep. HPLC (Column: Chiralpak IF 5 μm 20*250 mm; Mobile Phase: Hex:IPA=60:40 at 10 mL/min; Temp: 30° C.; Wavelength: 230 nm) to afford stereoisomers Compound 112A (24.4 mg, 27% yield) and Compound 112B (20.6 mg, 23% yield) as yellow solids. Compound 112B: LC-MS (ESI): $R_T$=2.384 min, mass calcd. For $C_{21}H_{22}ClFN_4O_4S_2$ 512.1, m/z found 512.9 [M+H]$^+$. Chiral HPLC (Column: Chiralpak IF 5 μm 4.6*250 mm; Mobile Phase: Hex:EtOH=60:40 at 1.0 mL/min; Temp: 30° C.; Wavelength: 230 nm, $R_T$=10.487 min). $^1$H NMR (400 MHz, DMSO-d$_6$) δ 9.60 (d, J=3.6 Hz, 0.8H), 9.20 (s, 0.2H), 8.02-7.99 (m, 1.8H), 7.93 (d, J=2.8 Hz, 0.2H), 7.41-7.31 (m, 2H), 7.23-7.17 (m, 1H), 6.08 (s, 0.2H), 5.98 (d, J=3.6 Hz, 0.8H), 4.01-3.92 (m, 0.2H), 3.75-3.63 (m, 2.8H), 3.53 (s, 3H), 2.90 (d, J=6.0 Hz, 3H), 2.82-2.73 (m, 2H), 2.17-1.97 (m, 1H), 1.94-1.86 (m, 1H), 1.81 (d, J=12.8 Hz, 1H), 1.66 (d, J=14.8 Hz, 1H).

Compound 113: 4-(2-Chloro-3-fluoro-phenyl)-6-[1-(2-methoxycarbonyl-ethane-sulfonyl)-piperidin-4-yl]-2-thiazol-2-yl-1,4-dihydro-pyrimidine-5-carboxylic Acid Methyl Ester (a Mixture of 2 Stereoisomers)

Compound 113 (380 mg, 0.650 mmol) was further separated by chiral Prep. HPLC (Column: Chiralpak IE 5 μm 4.6*250 mm; Mobile Phase: MeOH: EtOH:DEA=50:50:0.2: at 10 mL/min; Temp: 30° C.; Wavelength: 254 nm) to afford stereoisomers Compound 113P (170 mg, 44% yield) and Compound 113Y (180 mg, 47% yield) as yellow solids.

Compound 113Y: LC-MS (ESI): $R_T$=4.081 min, mass calcd. for $C_{24}H_{26}ClFN_4O_6S_2$ 584.1, m/z found 585.1 [M+H]*. Chiral HPLC (Column: Chiralpak IE 5 μm 4.6*250 mm; Mobile Phase: MeOH: EtOH:DEA=50:50:0.2 at 1.0 mL/min; Temp: 30° C.; Wavelength: 230 nm, $R_T$=8.353 min). $^1$H NMR (400 MHz, CDCl$_3$) δ 8.18 (br s, 0.3H), 7.83 (t, J=3.2 Hz, 1H), 7.52 (d, J=3.2 Hz, 0.7H), 7.45 (d, J=3.2 Hz, 1H), 7.23-7.02 (m, 3H), 6.25 (s, 0.3H), 6.12 (d, J=2.8 Hz, 0.7H), 4.22-3.90 (m, 3H), 3.76 (s, 3H), 3.60 (s, 2.1H), 3.59 (s, 0.9H), 3.29 (t, J=7.6 Hz, 2H), 3.00-2.84 (m, 4H), 2.27-1.71 (m, 4H).

Compound 118: 3-((4-(6-(2-Chloro-3-fluorophenyl)-5-(methoxycarbonyl)-2-(thiazol-2-yl)-3,6-dihydro-pyrimidin-4-yl)piperidin-1-yl)sulfonyl)benzoic Acid LC-MS (ESI): $R_T$=4.112 min, mass calcd. For $C_{27}H_{24}ClFN_4O_6S_2$ 618.1, m/z found 618.9 [M+H]$^+$. Chiral HPLC (Column: Chiralpak IE 5 μm 4.6*250 mm; Mobile Phase: Hex:IPA:TFA=60:40:0.2 at 1.0 mL/min; Temp: 30° C.; Wavelength: 230 nm, $R_T$=10.487 min). $^1$H NMR (400 MHz, CD$_3$OD) δ 8.41 (s, 1H), 8.33 (d, J=7.6 Hz, 1H), 8.05 (d, J=7.6 Hz, 1H), 7.92 (d, J=2.8 Hz, 1H), 7.79-7.75 (m, 2H), 7.30-7.25 (m, 1H), 7.19-7.13 (m, 2H), 6.11 (s, 1H), 4.00-3.92 (m, 2H), 3.80-3.69 (m, 1H), 3.52 (s, 3H), 2.47 (q, J=12.0 Hz, 2H), 2.17-1.95 (m, 2H), 1.90 (d, J=12.8 Hz, 1H), 1.74 (d, J=12.8 Hz, 1H).

Compound 115: 4-(2-Chloro-3-fluoro-phenyl)-6-(1-methylsulfamoyl-piperidin-4-yl)-2-thiazol-2-yl-1,4-dihydro-pyrimidine-5-carboxylic Acid Methyl Ester
(a Mixture of 2 Stereoisomers)

Compound 115 (150 mg, 0.280 mmol) was further separated by chiral Prep. HPLC (Column: Chiralpak IE 5 μm 20*250 mm; Mobile Phase: Hex:EtOH=70:30 at 12 mL/min; Temp: 30° C.; Wavelength: 214 nm) to afford stereoisomers Compound 115A (34.3 mg, 23% yield) and Compound 115B (20.6 mg, 23% yield) as yellow solids.

Compound 115B: LC-MS (ESI): $R_T$=3.935 min, mass calcd. For $C_{21}H_{23}ClFN_5O_4S_2$ 527.1, m/z found 527.9 [M+H]$^+$. Chiral HPLC (Column: Chiralpak IE 5 μm 4.6*250 mm; Mobile Phase: Hex:EtOH=70:30 at 1.0 mL/min; Temp: 30° C.; Wavelength: 230 nm, $R_T$=13.838 min). $^1$H NMR (400 MHz, DMSO-d$_6$) δ 9.61 (d, J=3.2 Hz, 0.8H), 9.09 (s, 0.2H), 8.00-7.99 (m, 1.8H), 7.93 (d, J=2.8 Hz, 0.2H), 7.40-7.29 (m, 2H), 7.22-7.05 (m, 2H), 6.07 (s, 0.2H), 5.97 (d, J=3.6 Hz, 0.8H), 3.96-3.90 (m, 0.2H), 3.72-3.60 (m, 2.8H), 3.53 (s, 2.4H), 3.52 (s, 0.6H), 2.77-2.67 (m, 2H), 2.57 (d, J=4.8 Hz, 3H), 2.10-1.76 (m, 3H), 1.62 (d, J=10.8 Hz, 1H).

Compound 120: Methyl 4-(2-bromo-4-fluorophenyl)-6-(1-(methylsulfonyl)-piperidin-4-yl)-2-(thiazol-2-yl)-1,4-dihydropyrimidine-5-carboxylate (a Mixture of 2 Stereoisomers)

Compound 120 (193 mg, 0.350 mmol) was further separated by chiral Prep. HPLC (Column: Chiralpak IF 5 μm 20*250 mm; Mobile Phase: Hex:IPA=60:40 at 10 mL/min; Temp: 30° C.; Wavelength: 230 nm) to afford stereoisomers Compound 120A (65 mg, 34% yield) and Compound 120B (64 mg, 33% yield).

Compound 120A: LC-MS (ESI): $R_T$=2.589 min, mass calcd. For $C_{21}H_{22}BrFN_4O_4S_2$ 556.0, m/z found 556.8 [M+H]$^+$. Chiral HPLC (Column: Chiralpak IF 5 μm 4.6*250 mm; Mobile Phase: Hex:EtOH=60:40 at 1.0 mL/min; Temp: 30° C.; Wavelength: 230 nm, $R_T$=8.568 min). 1H NMR (400 MHz, DMSO-d$_6$) δ 9.51 (s, 0.8H), 9.16 (s, 0.2H), 8.00 (s, 2H), 7.56 (dd, J=8.4, 2.4 Hz, 1H), 7.39-7.35 (m, 1H), 7.28-7.23 (m, 1H), 5.99 (s, 0.2H), 5.91 (s, 0.8H), 3.71-3.64 (m, 3H), 3.53 (s, 3H), 2.90 (s, 3H), 2.78 (q, J=12.0 Hz, 2H), 2.16-1.97 (m, 1H), 1.94-1.79 (m, 2H), 1.67-1.63 (m, 1H).

Compound 120B: LC-MS (ESI): $R_T$=2.539 min, mass calcd. For $C_{21}H_{22}BrFN_4O_4S_2$ 556.0, m/z found 556.8 [M+H]$^+$. Chiral HPLC (Column: Chiralpak IF 5 μm 4.6*250 mm; Mobile Phase: Hex:EtOH=60:40 at 1.0 mL/min; Temp: 30° C.; Wavelength: 230 nm, $R_T$=10.530 min). $^1$H NMR (400 MHz, DMSO-d$_6$) δ 9.51 (d, J=3.6 Hz, 0.8H), 9.16 (s, 0.2H), 8.01-7.98 (m, 1.8H), 7.93 (d, J=3.2 Hz, 0.2H), 7.59-7.55 (m, 1H), 7.37 (dd, J=8.8, 7.0 Hz, 0.7H), 7.34-7.22 (m, 1.3H), 5.99 (s, 0.2H), 5.90 (d, J=3.6 Hz, 0.8H), 4.00-3.91 (m, 0.2H), 3.76-3.63 (m, 2.8H), 3.53 (s, 2.4H), 3.52 (s, 0.6H), 2.91 (s, 1H), 2.90 (s, 2H), 2.82-2.72 (m, 2H), 2.09-1.97 (m, 1H), 1.95-1.78 (m, 2H), 1.67-1.64 (d, J=13.6 Hz, 1H).

Compound 124: 4-(4-Chloro-3-fluoro-phenyl)-6-(1-methanesulfonyl-piperidin-4-yl)-2-thiazol-2-yl-1,4-dihydro-pyrimidine-5-carboxylic Acid Methyl Ester
(a Mixture of 2 Stereoisomers)

Compound 124 (150 mg, 0.514 mmol) was further separated by chiral Prep. HPLC (separation condition: Column: Chiralpak IA 5 μm 20*250 mm; Mobile Phase: Hex:EtOH: DEA=70:30:0.2 at 12 mL/min; Temp: 30° C.; Wavelength: 214 nm) to afford stereoisomers Compound 124A (36.5 mg, 24% yield) and Compound 124B (35.3 mg, 24% yield) as yellow solids.

Compound 124B: LC-MS (ESI): $R_T$=4.261 min, mass calcd. for $C_{21}H_{22}ClFN_4O_4S_2$ 512.1, m/z found 512.9 [M+H]$^+$. Chiral HPLC (Column: Chiralpak IA 5 μm 4.6*250 mm; Mobile Phase: Hex:EtOH:DEA=70:30:0.2 at 1.0 mL/min; Temp: 30° C.; Wavelength: 230 nm, $R_T$=10.524 min). $^1$H NMR (400 MHz, DMSO-d$_6$) δ 9.78 (d, J=3.2 Hz, 1H), 8.03 (d, J=3.2 Hz, 2H), 7.58 (t, J=8.0 Hz, 1H), 7.24 (d, J=8.4 Hz, 1H), 7.14 (dd, J=8.0, 1.6 Hz, 1H), 5.50 (s, 1H), 3.77-3.63 (m, 3H), 3.59 (s, 3H), 2.90 (s, 3H), 2.76 (q, J=12.4 Hz, 2H), 2.06-1.94 (m, 1H), 1.87-1.77 (m, 2H), 1.65 (d, J=12.0 Hz, 1H).

Compound 126: Methyl 4-(2-chloro-4-fluorophenyl)-6-(trans-4-(methyl-sulfonamido)cyclohexyl)-2-(thiazol-2-yl)-1,4-dihydropyrimidine-5-carboxylate
(a Mixture of 2 Stereoisomers)

Compound 126 (280 mg, 0.530 mmol) was further separated by chiral Prep. HPLC (separation condition: Column: Chiralpak IF 5 μm 20*250 mm; Mobile Phase: Hex:EtOH: DEA=70:30:0.3 at 10 mL/min; Temp: 30° C.; Wavelength: 230 nm) to afford stereoisomers Compound 126A (26 mg, 19% yield) and Compound 126B (20 mg, 14%, yield).

Compound 126B: LC-MS (ESI): $R_T$=3.529 min, mass calcd. for $C_{22}H_{24}ClFN_4O_4S_2$ 526.1, m/z found 527.1 [M+H]$^+$. Chiral HPLC (Column: Chiralpak IF 5 μm 4.6*250 mm; Mobile Phase: Hex:EtOH:DEA=70:30:0.2 at 1.0 mL/min; Temp: 30° C.; Wavelength: 230 nm, $R_T$=10.664 min). $^1$H NMR (400 MHz, DMSO-d$_6$) δ 9.42 (d, J=3.2 Hz, 0.6H), 8.97 (s, 0.4H), 8.00-7.98 (m, 1.6H), 7.93 (d, J=3.2 Hz, 0.4H), 7.43-7.40 (m, 1H), 7.36-7.30 (m, 1H), 7.23-7.17

(m, 1H), 7.09-7.04 (m, 1H), 6.00 (s, 0.4H), 5.90 (d, J=3.6 Hz, 0.6H), 3.83-3.75 (m, 0.4H), 3.58-3.54 (m, 0.6H), 3.52 (s, 1.8H), 3.50 (s, 1.2H), 3.19-3.09 (m, 1H), 2.94 (s, 1.8H), 2.93 (s, 1.2H), 2.04-1.97 (m, 2H), 1.88-1.67 (m, 3H), 1.62-1.53 (m, 1H), 1.42-1.28 (m, 2H).

Compound 128: Methyl 4-(2-chloro-4-fluorophenyl)-6-(cis-4-(methylsulfonamido)-cyclohexyl)-2-(thiazol-2-yl)-1,4-dihydropyrimidine-5-carboxylate (a Mixture of 2 Stereoisomers)

Compound 128 (400 mg, 0.800 mmol) was further separated by chiral Prep. HPLC (separation condition: Column: Chiralpak IF 5 μm 20*250 mm; Mobile Phase: Hex:EtOH=70:30 at 10 mL/min; Temp: 30° C.; Wavelength: 214 nm) to afford stereoisomers Compound 128C (19 mg, 10% yield) and Compound 128D (37 mg, 19% yield).

Compound 128D: LC-MS (ESI): $R_T$=3.605 min, mass calcd. for $C_{22}H_{24}ClFN_4O_4S_2$, 526.1, m/z found 527.1 [M+H]$^+$. Chiral HPLC (Column: Chiralpak AS-H 5 μm 4.6*250 mm; Mobile Phase: Hex:EtOH=70:30 at 1.0 mL/min; Temp: 30° C.; Wavelength: 230 nm, $R_T$=8.617 min). $^1$H NMR (400 MHz, DMSO-d$_6$) δ 9.41 (d, J=4.0 Hz, 0.2H), 9.13 (s, 0.8H), 8.12-8.00 (m, 1.2H), 7.94 (d, J=2.8 Hz, 0.8H), 7.47 (d, J=9.6 Hz, 0.8H), 7.43 (dd, J=8.4, 2.8 Hz, 1H), 7.32 (dd, J=8.4, 6.0 Hz, 1H), 7.21 (td, J=8.4, 2.8 Hz, 1H), 6.86 (d, J=4.4 Hz, 0.2H), 6.01 (s, 0.8H), 5.91 (d, J=4.0 Hz, 0.2H), 3.96-3.84 (m, 1H), 3.72-3.63 (m, 1H), 3.52 (s, 0.6H), 3.50 (s, 2.4H), 2.98 (s, 2.4H), 2.93 (s, 0.6H), 2.11-1.80 (m, 4H), 1.68-1.49 (m, 4H).

Compound 33: Methyl 4-(2-chloro-4-fluorophenyl)-6-(1-(methylsulfonyl)piperidin-3-yl)-2-(thiazol-2-yl)-1,4-dihydropyrimidine-5-carboxylate (a Mixture of 4 Stereoisomers)

Compound 33 (210 mg, 0.410 mmol) was further separated by chiral Prep. HPLC (first separation Column: Chiralpak IE 5 μm 20*250 mm; Mobile Phase: Hex:EtOH=60:40 at 10 mL/min; Temp: 30° C.; Wavelength: 214 nm and second separation Column: Chiralpak IC 5 μm 20*250 mm; Mobile Phase: Hex:EtOH=50:50 at 10 mL/min; Temp: 30° C.; Wavelength: 214 nm) to afford stereoisomers Compound 33A (17.0 mg, 8% yield), Compound 33B (22.7 mg, 11% yield), Compound 33C (23.4 mg, 11% yield), and Compound 33D (20.1 mg, 10% yield) as yellow solids.

Compound 33A: LC-MS (ESI): $R_T$=4.383 min, mass calcd. for $C_{21}H_{22}ClFN_4O_4S_2$, 512.1, m/z found 512.9 [M+H]$^+$. Chiral HPLC (Column: Chiralpak IE 5 μm 4.6*250 mm; Mobile Phase: Hex:EtOH=60:40 at 1.0 mL/min; Temp: 30° C.; Wavelength: 230 nm, $R_T$=8.720 min). $^1$H NMR (400 MHz, DMSO-d$_6$) δ 9.55 (d, J=2.8 Hz, 0.8H), 9.33 (s, 0.2H), 8.01-7.98 (m, 1.5H), 7.94-7.93 (m, 0.5H), 7.44-7.41 (m, 1H), 7.39-7.34 (m, 1H), 7.25-7.21 (m, 1H), 6.04 (s, 0.2H), 5.94 (d, J=2.8 Hz, 0.8H), 4.16-4.03 (m, 0.2H), 3.81-3.74 (m, 0.8H), 3.72-3.63 (m, 1.6H), 3.54-3.52 (m, 3H), 3.49-3.42 (m, 0.4H), 3.06-3.03 (m, 1H), 3.01-2.93 (m, 3H), 2.75-2.67 (m, 1H), 1.85-1.68 (m, 3H), 1.64-1.54 (m, 1H).

Compound 33C: LC-MS (ESI): $R_T$=4.325 min, mass calcd. for $C_{21}H_{22}ClFN_4O_4S_2$, 512.1, m/z found 512.9 [M+H]$^+$. Chiral HPLC (Column: Chiralpak IC 5 μm 4.6*250 mm; Mobile Phase: Hex:EtOH=50:50 at 1.0 mL/min; Temp: 30° C.; Wavelength: 230 nm, $R_T$=9.380 min). $^1$H NMR (400 MHz, DMSO-d$_6$) δ 9.57 (d, J=3.6 Hz, 0.8H), 9.25 (s, 0.2H), 8.00-7.96 (m, 1.5H), 7.93-7.91 (m, 0.5H), 7.43-7.41 (m, 1H), 7.41-7.34 (m, 1H), 7.24-7.19 (m, 1H), 6.01 (s, 0.2H), 5.93 (d, J=4.0 Hz, 0.8H), 4.15-4.05 (m, 0.2H), 3.84-3.77 (m, 0.8H), 3.67-3.58 (m, 1H), 3.54-3.51 (m, 4H), 2.96-2.90 (m, 4H), 2.74-2.66 (m, 1H), 2.07-1.96 (m, 0.3H), 1.89-1.85 (m, 2.7H), 1.67-1.58 (m, 1H).

Compound 36: Methyl 4-(2-chloro-3-fluorophenyl)-6-(4-fluoro-1-(methylsulfonyl)-piperidin-4-yl)-2-(thiazol-2-yl)-1,4-dihydropyrimidine-5-carboxylate (a Mixture of 2 Stereoisomers)

LC-MS (ESI): $R_T$=3.604 min, mass calcd. for $C_{21}H_{21}ClF_2N_4O_4S_2$ 530.1, m/z found 530.9 [M+H]$^+$. $^1$H NMR (400 MHz, DMSO-d$_6$) δ 9.29 (d, J=2.8 Hz, 1H), 8.02-8.00 (m, 2H), 7.45-7.35 (m, 2H), 7.27-7.26 (m, 1H), 6.08 (s, 0.1H), 5.84 (d, J=3.2 Hz, 0.9H), 3.59-3.55 (m, 2H), 3.50 (s, 3H), 2.96-2.89 (m, 5H), 2.39-2.21 (m, 2H), 2.09-1.90 (m, 2H). Compound 36 (150 mg, 0.283 mmol) was further separated by Chiral Prep. HPLC (Column: Chiralpak IE 5 μm 20*250 mm; Mobile phase: Hex:EtOH=50:50 at 9.0 mL/min; Temp: 30° C.; Wavelength: 230 nm) to afford stereoisomers Compound 36A (13.2 mg, 9% yield) and Compound 36B (19.6 mg, 13% yield) as yellow solids.

Compound 46: Methyl 4-(2-chloro-4-fluorophenyl)-6-(cis-3-(methoxycarbonyl)-1-(methylsulfonyl)piperidin-4-yl)-2-(thiazol-2-yl)-1,4-dihydropyrimidine-5-carboxylate (a Mixture of 2 Stereoisomers)

LC-MS (ESI): $R_T$=1.65 min, mass calcd. for $C_{23}H_{24}ClFN_4O_6S_2$ 570.1, m/z found 571.5 [M+H]$^+$. $^1$H NMR (400 MHz, DMSO-d$_6$) δ 9.64 (s, 1H), 8.00 (s, 2H), 7.43-7.37 (m, 2H), 7.23 (t, J=9.2 Hz, 1H), 5.96 (s, 1H), 4.26-4.17 (m, 1H), 4.02-3.97 (m, 1H), 3.74-3.66 (m, 1H), 3.50 (s, 3H), 3.47 (s, 3H), 3.46-3.40 (m, 1H), 3.32-3.21 (m, 1H), 3.12-3.00 (m, 1H), 2.92 (s, 3H), 2.17-2.08 (m, 1H), 2.04-1.95 (m, 1H).

Compound 54: Methyl 4-(2-chloro-4-fluorophenyl)-6-(1-(methylsulfonyl)piperidin-4-yl)-2-(2,4,6-trifluorophenyl)-1,4-dihydropyrimidine-5-carboxylate (a Mixture of 2 Stereoisomers)

Compound 54 (250 mg, 0.45 mmol) was further separated by chiral prep. HPLC (Column: Chiralpak IC 5 μm 20*250 mm; Mobile Phase: Hex:EtOH=85:15 at 15 mL/min; Temp: 30° C.; Wavelength: 214 nm) to afford stereoisomers Compound 54A (51.7 mg, 21% yield) and Compound 54B (51.9 mg, 21% yield).

Compound 54A: LC-MS (ESI): $R_T$=3.004 min, mass calcd. for $C_{24}H_{22}ClF_4N_3O_4S$ 559.1 m/z found 559.9 [M+H]$^+$. Chiral HPLC (Column: Chiralpak IC 5 μm 4.6*250 mm; Mobile Phase: Hex:EtOH=85:15 at 1.0 mL/min; Temp: 30° C.; Wavelength: 230 nm, $R_T$=12.463 min). $^1$H NMR (400 MHz, DMSO-d$_6$) δ 9.57 (s, 0.7H), 9.44 (d, J=2.8 Hz, 0.3H), 7.47-7.35 (m, 2H), 7.28-7.20 (m, 3H), 5.97 (s, 0.7H), 5.87 (d, J=2.8 Hz, 0.3H), 4.04-3.98 (m, 2H), 3.74-3.63 (m, 2H), 3.52 (s, 1H), 3.51 (s, 2H), 2.89 (s, 2H), 2.86 (s, 1H), 2.78-2.73 (m, 2H), 2.01-1.95 (m, 1H), 1.88-1.73 (m, 3H).

Compound 59: Methyl 4-(2-chloro-3,4-difluorophenyl)-6-(1-(methylsulfonyl)-piperidin-4-yl)-2-(thiazol-2-yl)-1,4-dihydropyrimidine-5-carboxylate (a Mixture of 2 Stereoisomers)

Compound 59 (90 mg, 0.17 mmol) was further separated by chiral Prep. HPLC (Column: Chiralpak IE 5 μm 20*250 mm, Mobile Phase: Hex:EtOH=50:50 at 8 mL/min; Temp: 30° C.; Wavelength: 214 nm) to afford stereoisomers Compound 59A (31.5 mg, 35% yield) and Compound 59B (27.7 mg, 31% yield) as yellow solids. Compound 59B: LC-MS (ESI): RT=4.264 min, mass calcd. for $C_{21}H_{21}ClF_2N_4O_4S_2$ 530.1, m/z found 531.1 [M+H]$^+$. Chiral HPLC (Column: Chiralpak IE 5 μm 4.6*250 mm; Mobile Phase: Hex:EtOH=50:50 at 1.0 mL/min; Temp: 30° C.; Wavelength: 230 nm, $R_T$=11.213 min). $^1$H NMR (400 MHz, DMSO-d$_6$) δ 9.68 (d, J=2.8 Hz, 0.8H), 9.28 (s, 0.2H), 8.03-8.00 (m, 1.8H), 7.95 (d, J=2.8 Hz, 0.2H), 7.50-7.43 (m, 1H), 7.23-7.14 (m, 1H), 6.02 (s, 0.2H), 5.94 (d, J=3.2 Hz, 0.8H), 4.00-3.93 (m, 0.2H), 3.75-3.64 (m, 2.8H), 3.53 (s, 3H), 2.91 (s, 0.6H), 2.90 (s, 2.4H), 2.84-2.73 (m, 2H), 2.21-2.11 (m, 0.2H), 2.04-2.01 (m, 1H), 1.96-1.79 (m, 2H), 1.68-1.64 (m, 0.8H).

Compound 68: Methyl 4-(2-chloro-4-fluorophenyl)-6-(1-pivaloylpyrrolidin-3-yl)-2-(thiazol-2-yl)-1,4-dihydropyrimidine-5-carboxylate LC-MS (ESI): $R_T$=4.126 min, mass calcd. for $C_{24}H_{26}ClFN_4O_3S$ 504.1, m/z found 505.0 [M+H]$^+$. Chiral HPLC (Column: Chiralpak IC 5 μm 4.6*250 mm; Mobile Phase: Hex:EtOH=70:30 at 1.0 mL/min; Temp: 30° C.; Wavelength: 230 nm, $R_T$=7.737 min). $^1$H NMR (400 MHz, DMSO-d$_6$) δ 9.57 (d, J=3.2 Hz, 0.9H), 9.10 (s, 0.1H), 8.00 (s, 1.8H), 7.94 (d, J=9.2 Hz, 0.2H), 7.44-7.36 (m, 2H), 7.21 (t, J=11.2 Hz, 1H), 6.04 (s, 0.1H), 5.94 (d, J=5.2 Hz, 0.9H), 4.25 (br s, 1H), 4.03-3.60 (m, 3H), 3.54 (s, 3H), 2.27-1.90 (m, 2H), 1.23-1.19 (m, 9H).

Compound 84: 4-(2-Chloro-4-fluoro-phenyl)-6-(1-methanesulfonyl-azetidin-3-yl)-2-thiazol-2-yl-1,4-dihydro-pyrimidine-5-carboxylic Acid Methyl Ester (a Mixture of 2 Stereoisomers)

Compound 84 (120 mg, 0.248 mmol) was further separated by chiral Prep. HPLC (Column: Chiralpak IC 5 μm 20*250 mm, Mobile Phase: MeOH:EtOH=50:50 at 10 mL/min, Temp: 30° C., Wavelength: 214 nm) to afford stereoisomers Compound 84A (35.5 mg, 30% yield) and Compound 84B (43.2 mg, 36% yield) as yellow solids. Compound 84A: LC-MS (ESI): $R_T$=3.600 min, mass calcd. for $C_{19}H_{18}ClFN_4O_4S_2$ 484.0, m/z found 484.9 [M+H]$^+$. Chiral HPLC (Column: Chiralpak IC 5 μm 4.6*250 mm; Mobile Phase: MeOH:EtOH=50:50 at 1.0 mL/min; Temp: 30° C.; Wavelength: 230 nm, $R_T$=5.449 min). $^1$H NMR (400 MHz, DMSO-d$_6$) δ 9.73 (d, J=3.6 Hz, 1H), 8.05-8.03 (m, 2H), 7.43-7.40 (m, 2H), 7.20 (td, J=8.4, 2.4 Hz, 1H), 5.94 (d, J=3.6 Hz, 1H), 4.55-4.46 (m, 1H), 4.26-4.21 (m, 2H), 4.07 (t, J=8.4 Hz, 1H), 3.99 (t, J=8.4 Hz, 1H), 3.54 (s, 3H), 3.08 (s, 3H).

Compound 80: Methyl 4-(2-chloro-4-fluorophenyl)-6-(1-(cyclobutylsulfonyl)-azetidin-3-yl)-2-(thiazol-2-yl)-1,4-dihydropyrimidine-5-carboxylate LC-MS (ESI): $R_T$=2.758 min, mass calcd. for $C_{22}H_{22}ClFN_4O_4S_2$ 524.1, m/z found 524.9 [M+H]$^+$. Chiral HPLC (Column: Chiralpak IA 5 μm 4.6*250 mm; Mobile Phase: Hex:EtOH=60:40 at 1.0 mL/min; Temp: 30° C.; Wavelength: 230 nm, $R_T$=8.206 min); $^1$H NMR (400 MHz, DMSO-d$_6$) δ 9.72 (d, J=2.8 Hz, 0.95H), 9.21 (s, 0.05H), 8.06 (d J=3.2 Hz, 0.95H), 8.04 (d J=3.2 Hz, 0.95H), 8.00 (d J=3.2 Hz, 0.05H), 7.95 (d, J=3.2 Hz, 0.05H), 7.43-7.38 (m, 2H), 7.23-7.18 (m, 1H), 6.02 (s, 0.05H), 5.94 (d, J=3.2 Hz, 0.95H), 4.51-4.43 (m, 1H), 4.26-4.14 (m, 3H), 4.01 (t, J=8.0 Hz, 1H), 3.94 (t, J=8.0 Hz, 1H), 3.51 (d, J=6.8 Hz, 3H), 2.40-2.27 (m, 4H), 2.05-1.86 (m, 2H).

Compound 81: 4-(2-Chloro-4-fluoro-phenyl)-6-(1-ethylsulfamoyl-azetidin-3-yl)-2-thiazol-2-yl-1,4-dihydro-pyrimidine-5-carboxylic Acid Methyl Ester LC-MS (ESI): $R_T$=3.702 min, mass calcd. for $C_{20}H_{21}ClFN_5O_4S_2$ 513.1, m/z found 513.9 [M+H]$^+$. Chiral HPLC (Column: Chiralpak IB 5 μm 4.6*250 mm; Mobile Phase: Hex:EtOH=80:20 at 1.0 mL/min; Temp: 30° C.; Wavelength: 230 nm, $R_T$=8.934 min). $^1$H NMR (400 MHz, DMSO-d$_6$) δ 9.71 (d, J=3.2 Hz, 0.9H), 9.25 (s, 0.1H), 8.04 (dd, J=8.0, 3.2 Hz, 1.8H), 7.98 (dd, J=11.2, 3.2 Hz, 0.2H), 7.44-7.38 (m, 2H), 7.23-7.15 (m, 2H), 6.03 (s, 0.1H), 5.94 (d, J=3.6 Hz, 0.9H), 4.32-4.24 (m, 1H), 4.14-4.06 (m, 2H), 3.92 (t, J=8.4 Hz, 1H), 3.85 (t, J=8.4 Hz, 1H), 3.52 (d, J=7.2 Hz, 3H), 3.12-3.00 (m, 2H), 1.13-1.06 (m, 3H).

Compound 82: Methyl 4-(2-chloro-4-fluorophenyl)-6-(1-(cyclohexylsulfonyl)-azetidin-3-yl)-2-(thiazol-2-yl)-1,4-dihydropyrimidine-5-carboxylate LC-MS (ESI): $R_T$=4.108 min, mass calcd. for $C_{24}H_{26}ClFN_4O_4S_2$ 552.1, m/z found 552.9 [M+H]$^+$. Chiral HPLC (Column: Chiralpak IA 5 μm 4.6*250 mm; Mobile Phase: Hex:EtOH=50:50 at 1.0 mL/min; Temp: 30° C.; Wavelength: 230 nm, $R_T$=7.760 min). $^1$H NMR (400 MHz, DMSO-d$_6$) δ 9.71 (d, J=3.2 Hz, 0.95H), 9.25 (s, 0.05H), 8.04 (d, J=3.2 Hz, 0.95H), 8.02 (d, J=3.2 Hz, 0.95H), 7.96 (s, 0.1H), 7.43-7.38 (m, 2H), 7.20 (td, J=10.8, 2.4 Hz, 1H), 6.03 (s, 0.05H), 5.94 (d, J=3.2 Hz, 0.95H), 4.47-4.39 (m, 1H), 4.29-4.23 (m, 2H), 4.03 (t, J=8.0 Hz, 1H), 3.97 (t, J=8.0 Hz, 1H), 3.53 (s, 3H), 3.03 (tt, J=11.6, 3.6 Hz, 1H), 2.07 (d, J=11.6 Hz, 2H), 1.77 (d, J=12.4 Hz, 2H), 1.62 (d, J=12.8 Hz, 1H), 1.44-1.24 (m, 4H), 1.19-1.08 (m, 1H).

Compound 130: 6-(1-Benzenesulfonyl-azetidin-3-yl)-4-(2-chloro-4-fluoro-phenyl)-2-thiazol-2-yl-1,4-dihydro-pyrimidine-5-carboxylic acid methyl ester (a Mixture of 2 Stereoisomers)

Compound 130 (80 mg, 0.147 mmol) was further separated by chiral Prep. HPLC (separation condition: column: Chiralpak ID 5 μm 20*250 mm; Mobile Phase: Hex: EtOH=70:30 at 15 mL/min; Temp: 30° C.; Wavelength: 214 nm) to afford stereoisomers Compound 130A (17.1 mg, 21% yield) and Compound 130B (17.3 mg, 22% yield) as yellow solids.

Compound 130A: LC-MS (ESI): $R_T$=4.231 min, mass calcd. for $C_{24}H_{20}ClFN_4O_4S_2$ 546.1, m/z found 546.9 [M+H]$^+$. Chiral HPLC (Column: Chiralpak ID 5 μm 4.6*250 mm; Mobile Phase: Hex:EtOH==: 70:30 at 1.0 mL/m, in; Temp: 30° C.: Wavelength: 230 nm, $R_T$=13.425 min); $^1$H NMR (400 MHz, DMSO-d$_6$) δ 9.62 (d, J=3.6 Hz, 1H), 8.04 (d, J=3.2 Hz, 1H), 8.00 (d, J=3.2 Hz, 1H), 7.87-7.85 (m, 2H), 7.73-7.69 (m, 1H), 7.67-7.63 (m, 2H), 7.38 (dd, J=8.8, 2.0 Hz, 1H), 7.19-7.13 (m, 2H), 5.84 (d, J=3.2 Hz, 1H), 4.21-4.08 (m, 2H), 4.02 (t, J=8.0 Hz, 1H), 3.93 (t, J=7.6 Hz, 2H), 3.48 (s, 3H).

Compound 89: trans-Methyl 6-(3-acetamidocyclobutyl)-4-(2-chloro-4-fluoro-phenyl)-2-thiazol-2-yl)-1,4-dihydropyrimidine-5-carboxylate (a mixture of 2 stereoisomers)

Compound 89 (115 mg, 0.249 mmol) was further separated by chiral Prep. HPLC (Column: Chiralpak IC 5 μm 20*250 mm; Mobile Phase: Hex:EtOH:DEA=80:20:0.3 at 15 mL/min; Temp: 30° C.; Wavelength: 230 nm) to afford stereoisomers Compound 89R (39.6 mg, 34% yield) and Compound 89S (36.8 mg, 32% yield) as yellow solids.

Compound 89R: LC-MS (ESI): $R_T$=2.865 min, mass calcd. for $C_{21}H_{20}ClFN_4O_3S$ 462.1, m/z found 462.9 [M+H]$^+$. Chiral HPLC (Column: Chiralpak IA 5 μm 4.6*250 mm; Mobile Phase: Hex:EtOH:DEA=85:15:0.2 at 1.0 mL/min; Temp: 30° C.; Wavelength: 230 nm, $R_T$=9.512 min). $^1$H NMR (400 MHz, DMSO-d$_6$) δ 9.55 (d, J=3.6 Hz, 0.9H), 8.78 (s, 0.1H), 8.37 (d, J=6.4 Hz, 0.1H), 8.17 (d, J=3.2 Hz, 0.9H), 8.03-8.01 (m, 1.8H), 7.96 (s, 0.2H), 7.44-7.33 (m, 2H), 7.21 (td, J=8.8, 2.8 Hz, 1H), 6.00 (s, 0.2H), 5.91 (d, J=3.6 Hz, 0.8H), 4.42-4.48 (m, 1H), 4.33-4.26 (m, 1H), 3.50 (s, 3H), 2.67-2.59 (m, 1H), 2.49-2.44 (m, 1H), 2.29-2.12 (m, 2H), 1.83 (s, 0.3H), 1.80 (s, 2.7H).

Compound 116: Methyl 4-(2-chloro-3-fluorophenyl)-6-(1-(pyridin-2-ylsulfonyl)-piperidin-4-yl)-2-(thiazol-2-yl)-1,4-dihydropyrimidine-5-carboxylate Compound 116 (140 mg, 0.243 mmol) was separated by chiral Prep. HPLC (Column: Chiralpak IE 5 μm 20*250 mm; Mobile Phase: MeOH: EtOH:DEA=50:50:0.2 at 8 mL/min; Temp: 30° C.; Wavelength: 214 nm) to afford stereoisomers Compound 116A (34 mg, 24% yield, 100% ee) and Compound 116B (23 mg, 16% yield, 100% ee) as yellow solids.

Compound 116B: LC-MS (ESI): $R_T$=4.343 min, mass calcd. for $C_{25}H_{23}ClFN_5O_4S_2$ 575.1, m/z found 575.9 [M+H]$^+$. Chiral HPLC (Column: Chiralpak IE 5 μm 4.6*250 mm; Mobile Phase: Hex:EtOH:DEA=50:50:0.2 at 1.0 mL/min; Temp: 30° C.; Wavelength: 230 nm, $R_T$=13.410 min). $^1$H NMR (400 MHz, DMSO-d$_6$) δ 9.59 (d, J=3.6 Hz, 0.8H), 9.13 (s, 0.2H), 8.84-8.81 (m, 1H), 8.16-8.12 (m, 1H), 8.04-8.00 (m, 2H), 7.97-7.95 (m, 1H), 7.76-7.73 (m, 1H), 7.37-7.33 (m, 2H), 7.19-7.13 (m, 1H), 6.05 (s, 0.2H), 5.95 (d, J=4.0 Hz, 0.8H), 3.93-3.85 (m, 2H), 3.66-3.59 (m, 1H), 3.48 (s, 2.1H) 3.47 (s, 0.9H), 2.79-2.67 (m, 2H), 2.00-1.90 (m, 1H), 1.87-1.73 (m, 2H), 1.61-1.57 (m, 1H).

Compound 140: methyl 4-(2-chloro-4-fluorophenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate (Mixture of Diastereomers)

To a solution of methyl 4-(2-chloro-4-fluorophenyl)-6-(piperidin-4-yl)-2-(thiazol-2-yl)-1,4-dihydropyrimidine-5-carboxylate Compound 99 (300 mg, 0.648 mmol) in dichloromethane (6 mL) was added 2-(trimethylsilyl)ethyl 3-(chlorosulfonyl)-1-methylcyclobutanecarboxylate (293 mg, 0.843 mmol) and triethylamine (201 mg, 1.99 mmol) at room temperature. After stirred at 40° C. under nitrogen atmosphere overnight, the reaction mixture was diluted with water (10 mL) and extracted with ethyl acetate (10 mL) twice. The combined organic layers were washed with brine (10 mL), dried over Na$_2$SO$_{4(s)}$, filtered and concentrated. The residue was purified by silica gel column chromatography (petroleum ether:ethyl acetate=4:1) to give the title compounds 140A (160 mg, 90% purity, 31% yield) and 140B (175 mg, 90% purity, 34% yield) as yellow solids.

Compound 140A (trans): $^1$H NMR (400 MHz, DMSO-d$_6$) δ 9.53 (d, J=3.2 Hz, 0.8H), 9.13 (s, 0.2H), 7.99-7.90 (m, 2H), 7.35-7.33 (m, 1H), 7.28-7.21 (m, 1H), 7.18-7.16 (m, 1H), 5.99 (s, 0.2H), 5.89 (d, J=3.2 Hz, 0.8H), 4.16-4.12 (m, 2H), 3.97-3.88 (m, 1H), 3.76-3.65 (m, 3H), 3.50 (s, 3H), 2.89-2.72 (m, 4H), 2.29-2.23 (m, 2H), 1.94-1.85 (m, 1H), 1.83-1.69 (m, 2H), 1.63-1.55 (m, 1H), 1.33 (s, 3H), 0.99-0.92 (m, 2H), 0.01 (s, 9H).

Compound 140B (cis): $^1$H NMR (400 MHz, DMSO-d$_6$) δ 9.53 (d, J=3.6 Hz, 0.8H), 9.12 (s, 0.2H), 8.00-7.90 (m, 2H), 7.41-7.38 (m, 1H), 7.35-7.28 (m, 1H), 7.20-7.14 (m, 1H), 5.99 (s, 0.2H), 5.89 (d, J=3.6 Hz, 0.8H), 4.15-4.09 (m, 3H), 3.74-3.63 (m, 3H), 3.50 (s, 3H), 2.88-2.79 (m, 2H), 2.68-2.61 (m, 2H), 2.19-2.13 (m, 2H), 1.94-1.69 (m, 3H), 1.65-1.55 (m, 1H), 1.40 (s, 3H), 0.95-0.91 (m, 2H), 0.00 (s, 9H).

Compound 145: ethyl 6-(1-(((trans)-3-(tert-butoxycarbonyl)cyclobutyl)sulfonyl)piperidin-4-yl)-4-(2-chlorophenyl)-2-(thiazol-2-yl)-1,4-dihydropyrimidine-5-carboxylate LC-MS (ESI): $R_T$=3.573 min, mass calcd. for $C_{30}H_{37}ClN_4O_6S_2$ 648.2, m/z found 649.2 [M+H]$^+$. Chiral analysis (Column: Chiralpak IA 5 Lm 4.6*250 mm; Mobile Phase: Hex:EtOH:DEA=80:20:0.2 at 1.0 mL/min; Temp: 30° C.; Wavelength: 230 nm; $R_T$=8.109 min).

Compound 157A: Methyl 4-(2-chloro-3,4-difluorophenyl)-6-(1-((3-methoxy-3-oxopropyl)sulfonyl)piperidin-4-yl)-2-(thiazol-2-yl)-1,4-dihydropyrimidine-5-carboxylate LC-MS (ESI): $R_T$=2.05 min, mass calcd. for $C_{24}H_{25}ClF_2N_4O_6S_2$ 602.1, m/z found 603.2 [M+H]$^+$. $^1$H NMR (400 MHz, DMSO-d$_6$) δ 9.65 (d, J=3.6 Hz, 0.8H), 9.23 (s, 0.2H), 8.02-7.99 (m, 1.8H), 7.94 (d, J=3.2 Hz, 0.2H), 7.47-7.42 (m, 1H), 7.23-7.19 (m, 1H), 6.02 (s, 0.2H), 5.93 (d, J=3.6 Hz, 0.8H), 3.76-3.69 (m, 3H), 3.66 (s, 3H), 3.53 (s, 3H), 3.38-3.35 (m, 2H), 2.93-2.88 (m, 2H), 2.76 (t, J=7.2 Hz, 2H), 2.02-1.96 (m, 1H), 1.85-1.77 (m, 2H), 1.65-1.62 (m, 1H).

Compound 158A: Methyl 6-(1-((1H-pyrazol-4-yl)sulfonyl)piperidin-4-yl)-4-(2-chloro-3-fluorophenyl)-2-(thiazol-2-yl)-1,4-dihydropyrimidine-5-carboxylate LC-MS (ESI): $R_T$=3.074 min, mass calcd. for $C_{23}H_{22}ClFN_6O_4S_2$ 564.1, m/z found 564.8 [M+H]$^+$. $^1$H NMR (400 MHz, DMSO-d$_6$) δ 13.72 (br s, 1H), 9.58 (br s, 0.8H), 9.18 (s, 0.2H), 8.12-7.93 (m, 4H), 7.39-7.30 (m, 2H), 7.20-7.19 (m, 1H), 6.05 (s, 0.3H), 5.96 (s, 0.7H), 3.74-3.67 (m, 2.3H), 3.55-3.48 (m, 3.7H), 2.28-2.19 (m, 2H), 2.09-2.00 (m, 1H), 1.95-1.86 (m, 1H), 1.80-1.78 (m, 1H), 1.65-1.62 (m, 1H).

Compound 161: (trans)-methyl 4-(2-bromo-3,4-difluorophenyl)-6-(1-((3-(tert-butoxycarbonyl)cyclobutyl)sulfonyl)piperidin-4-yl)-2-(thiazol-2-yl)-1,4-dihydropyrimidine-5-carboxylate To a solution of methyl 4-(2-bromo-3,4-difluorophenyl)-6-(piperidin-4-yl)-2-(thiazol-2-yl)-1,4-dihydropyrimidine-5-carboxylate 160 (230 mg, 0.464 mmol) in dichloromethane (10 mL) was added triethylamine (141.0 mg, 1.392 mmol) and (trans)-tert-butyl 3-(chlorosulfonyl)cyclobutanecarboxylate (153 mg, 0.603 mmol) at 0° C. After stirred at room temperature for 1 hour, the mixture was concentrated under reduced pressure to give a residue, which was purified by silica gel column chromatography (petroleum ether:ethyl acetate=5:1 to 3:1) to give small polar fraction, which was further purified by Prep. HPLC (Column: gilson X-bridge C18 (5 m 19*150 mm), Mobile phase A: water (+0.1% ammonium bicarbonate), Mobile phase B: acetonitrile, UV: 214 nm, Flow rate: 15 mL/min, Gradient: 83-98% (% B)) to give title compound 161 (190 mg, 57% yield) as yellow solids and large polar fraction 161A (100 mg, 30% yield) as yellow solids.

Compound 161, LC-MS (ESI): $R_T$=3.689 min, mass calcd. for $C_{29}H_{33}BrF_2N_4O_6S_2$ 714.1, m/z found 714.8 [M+H]$^+$.

Compound 163: (trans)-ethyl 6-(-4-carbamoylcyclohexyl)-4-(2-chloro-4-fluorophenyl)-2-(thiazol-2-yl)-1,4-dihydropyrimidine-5-carboxylate LC-MS (ESI): $R_T$=4.017 min, mass calcd. for $C_{23}H_{24}ClFN_4O_3S$ 490.1, m/z found 491.0 [M+H]$^+$. Chiral analysis (Column: Chiralpak OZ-H, 5 μm 4.6*150 mm; Mobile Phase: Hex:EtOH=70:30 at 1 mL/min; Temp: 35° C.; Wavelength: 254 nm; $R_T$=5.648 min). $^1$H NMR (400 MHz, DMSO-d$_6$) δ 9.37 (d, J=3.6 Hz, 0.6H), 8.83 (s, 0.4H), 7.99-7.97 (m, 1.6H), 7.94 (d, J=3.2 Hz, 0.4H), 7.44-7.40 (m, 1H), 7.37-7.33 (m, 1H), 7.24-7.18 (m, 2H), 6.72 (br s, 0.4H), 6.67 (br s, 0.6H), 6.02 (s, 0.4H), 5.91 (d, J=3.6 Hz, 0.6H), 4.01-3.94 (m, 2H), 3.83-3.78 (m, 0.4H), 3.64-3.55 (m, 0.6H), 2.26-2.15 (m, 1H), 1.91-1.81 (m, 4H), 1.73-1.62 (m, 2H), 1.50-1.36 (m, 2H), 1.10-1.04 (m, 3H).

Compound 164: Methyl 4-(2-chloro-4-fluorophenyl)-6-(1-(morpholinosulfonyl)piperidin-4-yl)-2-(thiazol-2-yl)-1,4-dihydropyrimidine-5-carboxylate LC-MS (ESI): $R_T$=4.058 min, mass calcd. for $C_{24}H_{27}ClFN_5O_5S_2$ 583.1, m/z found 584.1 [M+H]$^+$. $^1$H NMR (400 MHz, CDCl$_3$) δ 8.16 (s, 0.3H), 7.84-7.82 (m, 1H), 7.51 (d, J=3.2 Hz, 0.7H), 7.46-7.45 (m, 0.3H), 7.43 (s, 0.7H), 7.29-7.27 (m, 0.8H), 7.25-7.24 (m, 0.2H), 7.16-7.11 (m, 1H), 6.99-6.89 (m, 1H), 6.19 (s, 0.3H), 6.07 (d, J=2.8 Hz, 0.7H), 4.21-4.13 (m, 0.3H), 3.98-3.85 (m, 2.7H), 3.78-3.75 (m, 4H), 3.61-3.59 (m, 3H), 3.30-3.24 (m, 4H), 3.07-2.95 (m, 2H), 2.25-2.15 (m, 1H), 2.09-1.98 (m, 1H), 1.96-1.78 (m, 1.4H), 1.71-1.67 (m, 0.6H).

Compound 165: Methyl 4-(2-chloro-4-fluorophenyl)-6-(1-((1-methyl-1H-pyrazol-4-yl)sulfonyl)piperidin-4-yl)-2-(thiazol-2-yl)-1,4-dihydropyrimidine-5-carboxylate LC-MS (ESI): $R_T$=3.874 min, mass calcd. for $C_{24}H_{24}ClFN_6O_4S_2$ 578.1, m/z found 578.9 [M+H]$^+$. $^1$H NMR (400 MHz, CDCl$_3$) δ 8.18 (s, 0.3H), 7.83 (d, J=3.2 Hz, 1H), 7.75-7.73 (m, 2H), 7.53 (d, J=2.8 Hz, 0.7H), 7.46 (d, J=3.2 Hz, 0.3H), 7.43 (s, 0.7H), 7.28-7.27 (m, 0.3H), 7.26-7.24 (m, 0.7H), 7.15-7.11 (m, 1H), 6.97-6.89 (m, 1H), 6.17 (s, 0.3H), 6.04 (d, J=2.8 Hz, 0.7H), 3.99 (s, 3H), 3.95-3.85 (m, 2H), 3.77-3.69 (m, 1H), 3.55 (s, 3H), 2.44-2.26 (m, 3H), 2.20-2.05 (m, 1H), 2.00-1.87 (m, 1.4H), 1.73-1.69 (m, 0.6H).

Compound 166A: Methyl 4-(2-chloro-3,4-difluorophenyl)-6-(1-((difluoromethyl)sulfonyl)piperidin-4-yl)-2-(thiazol-2-yl)-1,4-dihydropyrimidine-5-carboxylate Racemic compound 166 (70 mg, 0.124 mmol) was separated by chiral Prep. HPLC (Column: Chiralpak IG 5 μm 20*250 mm; Mobile Phase: Hex:EtOH:DEA=70:30:0.3 at 16 mL/min; Temp: 30° C.; Wavelength: 230 nm) to afford the title compounds 166B (25 mg, 25% yield, 100% stereopure) and 166A (22 mg, 23% yield, 100% stereopure) as yellow solids.

Compound 166A: LC-MS (ESI): $R_T$=2.341 min, mass calcd. for $C_{21}H_{19}ClF_4N_4O_4S_2$ 566.1, m/z found 567.1 [M+H]$^+$. Chiral analysis (Column: Chiralpak IG 5 μm 4.6*250 mm; Mobile Phase: Hex:EtOH:DEA=70:30:0.2 at 1.0 mL/min; Temp: 30° C.; Wavelength: 230 nm; $R_T$=8.619 min). $^1$H NMR (400 MHz, DMSO-d$_6$) δ 9.65 (s, 0.8H), 9.35 (s, 0.2H), 8.01 (s, 1.7H), 7.94-7.93 (m, 0.3H), 7.45 (q, J=9.2 Hz, 1H), 7.28-7.12 (m, 1.7H), 7.02-6.99 (m, 0.3H), 6.02 (s, 0.2H), 5.93 (s, 0.8H), 4.02-4.01 (m, 0.2H), 3.91-3.78 (m, 2.8H), 3.58-3.54 (m, 3H), 3.21-3.12 (m, 2H), 2.18-1.64 (m, 4H).

Compound 190: Methyl 4-(2-chloro-4-fluorophenyl)-6-(4-(methylsulfonamido)-cycloheptyl)-2-(thiazol-2-yl)-1,4-dihydropyrimidine-5-carboxylate LC-MS (ESI): $R_T$=3.016 min, mass calcd. for $C_{23}H_{26}ClFN_4O_4S_2$ 540.1, m/z found 541.0 [M+H]$^+$. $^1$H NMR (400 MHz, CDCl$_3$) δ 8.06-8.02 (br s, 0.4H), 7.85-7.81 (m, 1H), 7.50-7.49 (m, 0.5H), 7.46-7.44 (m, 0.5H), 7.40 (br s, 0.6H), 7.30-7.25 (m, 1H), 7.15-7.11 (m, 1H), 6.97-6.98 (m, 1H), 6.17 (s, 0.4H), 6.05-6.03 (m, 0.6H), 4.44-4.25 (m, 1H), 4.22-4.10 (m, 0.5H), 4.03-3.97 (m, 0.5H), 3.80-3.63 (m, 1H), 3.62 (s, 1.5H), 3.60 (s, 1.5H), 3.01 (s, 1.5H), 3.00 (s, 1.5H), 2.28-1.65 (m, 10H). $^1$H NMR (400 MHz, CD$_3$OD) δ 7.92 (d, J=3.2 Hz, 0.6H), 7.88 (d, J=2.8 Hz, 0.4H), 7.74 (d, J=2.8 Hz, 0.9H), 7.68-7.58 (m, 0.1H), 7.41-7.35 (m, 1H), 7.24-7.20 (m, 1H), 7.07-7.01 (m, 1H), 6.12 (d, J=4.0 Hz, 0.6H), 6.04 (d, J=2.4 Hz, 0.4H), 4.21-4.05 (m, 0.5H), 3.95-3.88 (m, 0.5H), 3.69-3.62 (m, 0.4H), 3.59 (s, 3H), 3.55-3.44 (m, 0.6H), 2.96-2.93 (m, 3H), 2.37-1.44 (m, 10H).

Compound 194A: (trans)-Ethyl 6-(1-((3-(tert-butoxycarbonyl)cyclobutyl)sulfonyl)-piperidin-4-yl)-4-(2-chloro-3,4-difluorophenyl)-2-(2,4,6-trifluorophenyl)-1,4-dihydropyrimidine-5-carboxylate The reaction mixture was purified by prep-thin layer chromatography (petroleum ether:ethyl acetate=1:10) to give the title compounds 194X (400 mg, 19% yield) and 194Y (600 mg, 28% yield) as white solids. For 194X: LC-MS (ESI): $R_T$=3.540 min, mass calcd. for $C_{33}H_{35}ClF_5N_3O_6S$ 731.2, m/z found 732.3 [M+H]$^+$. $^1$H NMR (400 MHz, DMSO-d$_6$) δ 9.55 (s, 0.8H), 9.45 (d, J=3.2 Hz, 0.2H), 7.57-7.45 (m, 1H), 7.27-7.19 (m, 3H), 5.98 (s, 0.8H), 5.89 (d, J=3.2 Hz, 0.2H), 4.08-3.89 (m, 4H), 3.77-3.62 (m, 2H), 3.08-2.97 (m, 1H), 2.85-2.74 (m, 2H), 2.47-2.42 (m, 4H), 2.00-1.79 (m, 3H), 1.74-1.67 (m, 1H), 1.40 (s, 9H), 1.06-1.03 (m, 3H).

Compound 194X was further separated by chiral Prep. HPLC (Column: Chiralpak OD-H 5 μm 20*250 mm; Mobile Phase: Hex:EtOH:DEA=90:10:0.3 at 15 mL/min; Temp: 30° C.; Wavelength: 214 nm) to give the title compounds 194A (200 mg, 33% yield) and 194B (100 mg, 17% yield) as colorless solids.

Compound 198A and compound 198B: (trans)-Ethyl 4-(2-bromo-3,4-difluorophenyl)-6-(1-((3-(tert-butoxycarbonyl)cyclobutyl)sulfonyl)piperidin-4-yl)-2-(thiazol-2-yl)-1,4-dihydropyrimidine-5-carboxylate and (cis)-ethyl 4-(2-bromo-3,4-difluorophenyl)-6-(1-((3-(tert-butoxycarbonyl)cyclobutyl)sulfonyl)piperidin-4-yl)-2-(thiazol-2-yl)-1,4-dihydropyrimidine-5-carboxylate Compound 198A: LC-MS: $R_T$=4.589 min, Mass calc for $C_{30}H_{35}BrF_2N_4O_6S_2$ 728.1, m/z found: 729.0 [M+1]$^+$. $^1$H NMR (400 MHz, DMSO-d$_6$) δ 9.60 (s, 0.7H), 9.12 (s, 0.3H), 8.00-7.92 (m, 2H), 7.51-7.42 (m, 1H), 7.24-7.14 (m, 1H), 6.02 (s, 0.2H), 5.95 (s, 0.8H), 4.04-3.91 (m, 3H), 3.80-3.67 (m, 3H), 3.16-3.06 (m, 1H), 2.93-2.83 (m, 2H), 2.64-2.55 (m, 3H), 2.04-1.72 (m, 4H), 1.64-1.54 (m, 1H), 1.43 (s, 9H), 1.09-1.05 (m, 3H).

Compound 198B: LC-MS: R$_T$=4.413 min, Mass calc for C$_{30}$H$_{35}$BrF$_2$N$_4$O$_6$S$_2$ 728.1, m/z found: 729.0 [M+1]$^+$. $^1$H NMR (400 MHz, DMSO-d$_6$) δ 9.58 (s, 0.8H), 9.12 (s, 0.2H), 8.00-7.93 (m, 2H), 7.54-7.46 (m, 1H), 7.27-7.14 (m, 1H), 6.02 (s, 0.2H), 5.93-5.90 (m, 0.8H), 3.97-3.93 (m, 3H), 3.76-3.65 (m, 3H), 3.11-3.04 (m, 1H), 2.90-2.74 (m, 2H), 2.48-2.35 (m, 4H), 2.01-1.77 (m, 3H), 1.67-1.59 (m, 1H), 1.41 (s, 9H), 1.09-1.05 (m, 3H).

Compound 200A: Methyl 4-(2-chloro-4-fluorophenyl)-2-(thiazol-2-yl)-6-(1-(thiazol-2-ylsulfonyl)piperidin-4-yl)-1,4-dihydropyrimidine-5-carboxylate LC-MS (ESI): R$_T$=3.868 min, mass calcd. for C$_{23}$H$_{21}$ClFN$_5$O$_4$S$_3$ 581.0, m/z found 581.9 [M+H]$^+$. $^1$H NMR (400 MHz, DMSO-d$_6$) δ 9.52 (d, J=1.2 Hz, 0.8H), 9.11 (s, 0.2H), 8.25 (d, J=2.0 Hz, 1H), 8.20 (d, J=2.8 Hz, 1H), 8.01-7.95 (m, 2H), 7.42-7.40 (m, 1H), 7.33-7.32 (m, 1H), 7.32-7.20 (m, 1H), 6.00 (s, 0.2H), 5.90 (d, J=3.2 Hz, 0.8H), 3.94-3.87 (m, 2H), 3.67-3.59 (m, 1H), 3.49 (s, 3H), 2.83-2.73 (m, 2H), 1.99-1.87 (m, 1H), 1.81-1.80 (m, 2H), 1.65-1.61 (m, 1H).

Compound 201A: Methyl 4-(2-chloro-4-fluorophenyl)-6-(1-((1-methyl-1H-imidazol-4-yl) sulfonyl)piperidin-4-yl)-2-(thiazol-2-yl)-1,4-dihydropyrimidine-5-carboxylate LC-MS (ESI): R$_T$=3.453 min, mass calcd. for C$_{24}$H$_{24}$ClFN$_6$O$_4$S$_2$ 578.1, m/z found 578.9 [M+H]$^+$. $^1$H NMR (400 MHz, DMSO-d$_6$) δ 9.51 (d, J=3.6 Hz, 0.8H), 9.00 (s, 0.2H), 8.03-8.00 (m, 1.8H), 7.94 (d, J=3.2 Hz, 0.2H), 7.86-7.82 (m, 2H), 7.44-7.39 (m, 1H), 7.36-7.29 (m, 1H), 7.23-7.16 (m, 1H), 6.00 (s, 0.2H), 5.90 (d, J=3.6 Hz, 0.8H), 3.82-3.70 (m, 5H), 3.57-3.49 (m, 1H), 3.48 (s, 3H), 2.63-2.55 (m, 2H), 2.07-1.72 (m, 3H), 1.61-1.57 (m, 1H).

Compound 204A: Methyl 4-(2-chloro-3,4-difluorophenyl)-6-(3-(methyl-sulfonamido)bicyclo[0.1.1.1]pentan-1-yl)-2-(thiazol-2-yl)-1,4-dihydropyrimidine-5-carboxylate LC-MS (ESI): R$_T$=3.326 min, mass calcd. for C$_{21}$H$_{19}$ClF$_2$N$_4$O$_4$S$_2$ 528.1 m/z found 529.1 [M+H]$^+$. $^1$H NMR (400 MHz, CDCl$_3$) δ 7.89 (s, 0.7H), 7.83 (d, J=3.2 Hz, 0.3H), 7.82 (d, J=3.2 Hz, 0.7H), 7.51 (d, J=2.8 Hz, 0.3H), 7.46 (d, J=3.2 Hz, 0.7H), 7.44 (br s, 0.3H), 7.08-7.02 (m, 2H), 6.15 (s, 0.7H), 6.03 (d, J=2.4 Hz, 0.3H), 5.14 (br s, 0.7H), 5.03 (br s, 0.3H), 3.63 (s, 0.9H), 3.60 (s, 2.1H), 3.05 (s, 0.9H), 3.04 (s, 2.1H), 2.61 (s, 4.2H), 2.53 (s, 1.8H).

Compound 206B: (trans)-Methyl 4-(2-chloro-4-fluorophenyl)-6-(3-(methylsulfonamido)cyclobutyl)-2-(thiazol-2-yl)-1,4-dihydropyrimidine-5-carboxylate (separation condition: Column: Chiralpak IE 5 μm 20*250 mm; Mobile Phase: Hex:EtOH=60:40 at 10 mL/min; Temp: 30° C.; Wavelength: 214 nm), LC-MS (ESI): R$_T$=3.925 min, mass calcd. for C$_{20}$H$_{20}$ClFN$_4$O$_4$S$_2$ 498.1, m/z found 498.9 [M+H]$^+$. Chiral analysis (Column: Chiralpak IE 5 μm 4.6*250 mm; Mobile Phase: Hex:EtOH=60:40 at 1.0 mL/min; Temp: 30° C.; Wavelength: 230 nm, R$_T$=11.912 min). $^1$H NMR (400 MHz, DMSO-d$_6$) δ 9.61 (d, J=3.2 Hz, 0.9H), 8.90 (s, 0.1H), 8.05-8.02 (m, 1.8H), 7.96 (d, J=3.2 Hz, 0.2H), 7.64-7.62 (m, 0.2H), 7.47-7.35 (m, 2.8H), 7.23-7.19 (m, 1H), 6.00 (s, 0.1H), 5.92 (d, J=3.6 Hz, 0.9H), 4.45-4.40 (m, 0.1H), 4.33-4.21 (m, 1.8H), 4.03-3.98 (m, 0.1H), 3.50 (s, 3H), 2.91 (s, 0.2H), 2.87 (s, 2.8H), 2.67-2.61 (m, 1H), 2.48-2.29 (m, 3H).

Compound 206D: (cis)-Methyl 4-(2-chloro-4-fluorophenyl)-6-(3-(methylsulfonamido)cyclobutyl)-2-(thiazol-2-yl)-1,4-dihydropyrimidine-5-carboxylate (separation condition: Column: Chiralpak IA 5 μm 20*250 mm; Mobile Phase: Hex:EtOH:DEA=70:30:0.3 at 11 mL/min; Temp: 30° C.; Wavelength: 214 nm), LC-MS (ESI): R$_T$=3.312 min, mass calcd. for C$_{20}$H$_{20}$ClFN$_4$O$_4$S$_2$ 498.1, m/z found 498.9 [M+H]$^+$. Chiral analysis (Column: Chiralpak IA 5 μm 4.6*250 mm; Mobile Phase: Hex:EtOH:DEA=70:30:0.2 at 1.0 mL/min; Temp: 30° C.; Wavelength: 254 nm, R$_T$=8.762 min). $^1$H NMR (400 MHz, DMSO-d$_6$) 9.54 (br s, 0.7H), 8.83 (br s, 0.3H), 8.04-8.02 (m, 1.6H), 7.97-7.96 (m, 0.4H), 7.53-7.51 (m, 0.4H), 7.46-7.41 (m, 1.6H), 7.33-7.28 (m, 1H), 7.23-7.18 (m, 1H), 5.99 (s, 0.3H), 5.90 (d, J=2.0 Hz, 0.7H), 4.20-4.10 (m, 0.3H), 3.91-3.83 (m, 0.7H), 3.80-3.68 (m, 1H), 3.52 (s, 2H), 3.51 (s, 1H), 2.92 (s, 1H), 2.88 (s, 2H), 2.71-2.68 (m, 0.4H), 2.59-2.58 (m, 0.6H), 2.43-2.33 (m, 2H), 2.28-2.18 (m, 1H).

Compound 208B: 3-(N-(3-(6-(2-Chloro-4-fluorophenyl)-5-(methoxycarbonyl)-2-(thiazol-2-yl)-3,6-dihydropyrimidin-4-yl)bicyclo[1.1.1]pentan-1-yl)sulfamoyl)benzoic acid LC-MS (ESI): R$_T$=4.457 min, mass calcd. for C$_{27}$H$_{22}$ClFN$_4$O$_6$S$_2$ 616.1, m/z found 616.8 [M+H]$^+$. $^1$H NMR (400 MHz, DMSO-d$_6$) δ 9.38 (d, J=2.8 Hz, 0.5H), 8.98 (s, 0.5H), 8.82 (s, 0.5H), 8.40 (s, 1H), 8.26 (s, 0.5H), 8.21-8.18 (m, 1H), 8.07-8.06 (m, 1H), 7.98-7.92 (m, 2H), 7.78-7.74 (m, 1H), 7.42-7.37 (m, 1H), 7.28-7.23 (m, 1H), 7.20-7.14 (m, 1H), 5.91 (s, 0.5H), 5.81 (d, J=3.2 Hz, 0.5H), 3.48 (s, 1.5H), 3.46 (s, 1.5H), 2.21 (s, 3H), 2.03 (s, 3H).

Compound 209A and 209B: (trans)-methyl 4-(2-chloro-3,4-difluorophenyl)-6-(1-((4-methyl-4-((2-(trimethylsilyl)ethoxy)carbonyl)cyclohexyl)sulfonyl)piperidin-4-yl)-2-(thiazol-2-yl)-1,4-dihydropyrimidine-5-carboxylate and (cis)-methyl 4-(2-chloro-3,4-difluorophenyl)-6-(1-((4-methy-4-((2-(trimethylsilyl)ethoxy)carbonyl)-cyclohexyl)sulfonyl)piperidin-4-yl)-2-(thiazol-2-yl)-1,4-dihydropyrimidine-5-carboxylate To a solution of methyl 4-(2-chloro-3,4-difluorophenyl)-6-(piperidin-4-yl)-2-(thiazol-2-yl)-1,4-dihydropyrimidine-5-carboxylate compound 58 (300 mg, 85% purity, 0.563 mmol) in dichloromethane (10 mL) were added triethylamine (800 mg, 7.906 mmol) and 2-(trimethylsilyl)ethyl 4-(chlorosulfonyl)-1-methylcyclohexanecarboxylate (400 mg, 90% purity, 1.06 mmol, Part IV) at 0° C. After stirred at 25° C. overnight, the mixture was concentrated to give a residue, which was purified by silica gel column chromatography (petroleum ether:ethyl acetate=4:1) and prep. thin-layer chromatography (petroleum ether:ethyl acetate=4:1) to afford 209A (160 mg, 60% purity, 23% yield) and 209B (70 mg, 80% purity, 13% yield) as yellow solids.

Compound 209A: ¹H NMR (400 MHz, CDCl₃) δ 8.17-8.15 (m, 0.3H), 7.81-7.77 (m, 1H), 7.50-7.48 (m, 0.7H), 7.43-7.41 (m, 0.4H), 7.39-7.35 (m, 0.6H), 7.06-6.93 (m, 2H), 6.16 (s, 0.4H), 6.02 (m, 0.6H), 4.19-4.10 (m, 2H), 4.05-3.72 (m, 3H), 3.58-3.56 (m, 3H), 3.07-2.67 (m, 3H), 2.39-2.13 (m, 2H), 2.09-1.83 (m, 5H), 1.75-1.48 (m, 5H), 1.23-1.20 (m, 3H), 1.00-0.88 (m, 2H), 0.01 (s, 9H).

Compound 209B: ¹H NMR (400 MHz, CDCl₃) δ 8.14 (s, 0.4H), 7.80-7.77 (m, 1H), 7.50-7.47 (m, 0.6H), 7.42-7.40 (m, 0.4H), 7.37-7.34 (m, 0.6H), 7.02-6.95 (m, 2H), 6.13 (s, 0.4H), 6.00 (s, 0.6H), 4.20-4.11 (m, 2H), 4.03-3.81 (m, 3H), 3.55-3.53 (m, 3H), 3.18-2.80 (m, 3H), 2.36-2.15 (m, 2H), 2.11-1.84 (m, 4H), 1.82-1.55 (m, 4H), 1.19-1.15 (m, 2H), 1.12-1.01 (m, 3H), 0.98-0.91 (m, 2H), 0.01 (s, 9H).

Compound 213: Methyl 4-(2-chloro-4-fluorophenyl)-6-(1-((2-methoxy-2-oxoethyl)sulfonyl)pyrrolidin-3-yl)-2-(thiazol-2-yl)-1,4-dihydropyrimidine-5-carboxylate ¹H NMR (400 MHz, DMSO-d₆) δ 9.68 (s, 0.9H), 9.41-9.37 (m, 0.1H), 8.04-7.98 (m, 1.8H), 7.95-7.93 (m, 0.2H), 7.45-7.43 (m, 1H), 7.40-7.35 (m, 1H), 7.24-7.19 (m, 1H), 6.02 (s, 0.1H), 5.93 (s, 0.9H), 4.48-4.34 (m, 3H), 3.72 (s, 1.2H), 3.71 (s, 1.8H), 3.67-3.56 (m, 2H), 3.54 (s, 3H), 3.51-3.38 (m, 2H), 2.33-2.12 (m, 1.6H), 2.06-1.98 (m, 0.4H).

A racemic mixture of 213 (400 mg, 0.720 mmol) was separated by Chiral Prep. HPLC (the first separation condition: Column: Chiralpak IB5 μm 20*250 mm; Mobile Phase: Hex:EtOH=85:15 at 8 mL/min; Temp: 30° C.; Wavelength: 214 nm; the second separation condition: Column: ChiralpakID 5 μm 20*250 mm; Mobile Phase: Hex:IPA:DEA=98:2:0.2 at 15 mL/min; Temp: 30° C.; Wavelength: 214 nm; Column: Chiralpak IF 5 μm 20*250 mm; Mobile Phase: Hex:EtOH=50:50 at 8 mL/min; Temp: 30° C.; Wavelength: 214 nm) to afford the title compounds 213X (40 mg, 10% yield, 100% stereopure), 213Y (45 mg, 11% yield, 100% stereopure), 213M (47 mg, 11% yield, 100% stereopure) and 213N (50 mg, 13% yield, 97.7% stereopure) as yellow solids.

Compound 213X: LC-MS (ESI): R$_T$=3.558 min, mass calcd. for C₂₂H₂₂ClFN₄O₆S₂ 556.1, m/z found 557.1 [M+H]⁺. Chiral analysis (Column: Chiralpak ID 5 μm 4.6*250 mm; Mobile Phase: Hex:IPA:DEA=50:50:0.2 at 1.0 mL/min; Temp: 30° C.; Wavelength: 230 nm, R$_T$=__=13.460 min)¹H NMR (400 MHz, DMSO-d₆) δ 9.65 (d, J=3.2 Hz, 0.9H), 9.37 (s, 0.1H), 8.04-8.01 (m, 1.8H), 7.99 (d, J=3.2 Hz, 0.1H), 7.94 (d, J=2.4 Hz, 0.1H), 7.45-7.42 (m, 1H), 7.40-7.36 (m, 1H), 7.23-7.19 (m, 1H), 6.02 (s, 0.1H), 5.94 (d, J=3.6 Hz, 0.9H), 4.47-4.34 (m, 3H), 3.73 (s, 3H), 3.72-3.65 (m, 1H), 3.63-3.56 (m, 2H), 3.54 (s, 3H), 3.45-3.38 (m, 1H), 2.25-2.16 (m, 1H), 2.06-1.98 (m, 1H).

Compound 213M: LC-MS (ESI): R$_T$=3.541 min, mass calcd. for C₂₂H₂₂ClFN₄O₆S₂ 556.1, m/z found 557.1 [M+H]⁺. Chiral analysis (Column: Chiralpak IF 5 μm 4.6*250 mm; Mobile Phase: Hex:EtOH=50:50 at 1.0 mL/min; Temp: 30° C.; Wavelength: 230 nm, R$_T$=10.289 min). ¹H NMR (400 MHz, DMSO-d₆) δ 9.68 (d, J=3.2 Hz, 0.9H), 9.40 (s, 0.1H), 8.04-8.02 (m, 1.8H), 7.99 (d, J=2.8 Hz, 0.1H), 7.93 (d, J=2.8 Hz, 0.1H), 7.45-7.42 (m, 1H), 7.39-7.36 (m, 1H), 7.25-7.20 (m, 1H), 6.02 (s, 0.1H), 5.94 (d, J=2.8 Hz, 0.9H), 4.46-4.36 (m, 3H), 3.73 (s, 3H), 3.71-3.58 (m, 1.4H), 3.55 (s, 3H), 3.53-3.49 (m, 0.6H), 3.47-3.40 (m, 2H), 2.33-2.26 (m, 1H), 2.20-2.13 (m, 1H).

Compound 215: Methyl 4-(2-chloro-4-fluorophenyl)-6-(1-((2-methoxyethyl)sulfonyl)piperidin-4-yl)-2-(thiazol-2-yl)-1,4-dihydropyrimidine-5-carboxylate LC-MS (ESI): R$_T$=2.794 min, mass calcd. for C₂₃H₂₆ClFN₄O₅S₂ 556.1, m/z found 556.9 [M+H]⁺. ¹H NMR (400 MHz, CDCl₃) δ 8.18 (s, 0.3H), 7.83 (d, J=2.8 Hz, 1H), 7.53 (d, J=3.2 Hz, 0.7H), 7.46-7.44 (m, 1H), 7.30-7.28 (m, 0.8H), 7.26 (br s, 0.2H), 7.16-7.12 (m, 1H), 6.99-6.89 (m, 1H), 6.19 (s, 0.3H), 6.07 (d, J=2.4 Hz, 0.7H), 4.20-4.14 (m, 0.3H), 4.00-3.88 (m, 2.7H), 3.83-3.76 (m, 2H), 3.60 (s, 2H), 3.59 (s, 1H), 3.41 (s, 2H), 3.40 (s, 1H), 3.25-3.22 (m, 2H), 3.00-2.88 (m, 2H), 2.31-2.21 (m, 0.7H), 2.13-2.03 (m, 1H), 1.98-1.70 (m, 2.3H).

Compound 216: Methyl 4-(2-chloro-4-fluorophenyl)-2-(thiazol-2-yl)-6-(1-((2,2,2-trifluoroethyl)sulfonyl)piperidin-4-yl)-1,4-dihydropyrimidine-5-carboxylate LC-MS (ESI): R$_T$=3.603 min, mass calcd. for C₂₂H₂₁ClF₄N₄O₄S₂ 580.1, m/z found 581.1 [M+H]⁺. ¹H NMR (400 MHz, DMSO-d₆) δ 9.55 (s, 0.7H), 9.24 (s, 0.3H), 8.01-7.93 (m, 2H), 7.44-7.35 (m, 2H), 7.23-7.19 (m, 1H), 6.02-5.93 (m, 1H), 4.56-4.49 (m, 2H), 3.96 (br s, 0.2H), 3.79-3.73 (m, 2.8H), 3.53 (s, 3H), 2.97-2.88 (m, 2H), 2.10-1.81 (m, 3.2H), 1.68-1.65 (m, 0.8H).

Compound 222: Methyl 6-(1-((3-(tert-butoxy)-2,2-dimethyl-3-oxopropyl)sulfonyl)piperidin-4-yl)-4-(2-chloro-4-fluorophenyl)-2-(thiazol-2-yl)-1,4-dihydropyrimidine-5-carboxylate LC-MS (ESI): R$_T$=3.790 min, mass calcd. for C₂₉H₃₆ClFN₄O₆S₂ 654.2, m/z found 655.2 [M+H]⁺. ¹H NMR (400 MHz, CDCl₃) δ 8.16 (s, 0.3H), 7.83-7.81 (m, 1H), 7.52 (d, J=3.2 Hz, 0.7H), 7.44 (d, J=3.2 Hz, 0.3H), 7.42 (s, 0.7H), 7.29-7.28 (m, 1H), 7.16-7.12 (m, 1H), 7.00-6.89 (m, 1H), 6.19 (s, 0.3H), 6.07 (d, J=2.8 Hz, 0.7H), 4.18-4.11 (m, 0.3H), 4.03-3.85 (m, 2.7H), 3.60 (s, 2H), 3.59 (s, 1H), 3.19 (s, 1.3H), 3.18 (s, 0.7H), 2.90-2.79 (m, 2H), 2.32-2.20 (m, 0.7H), 2.16-2.02 (m, 1H), 2.00-1.80 (m, 1.6H), 1.73-1.70 (m, 0.7H), 1.49 (s, 9H), 1.40 (s, 4H), 1.38 (s, 2H).

Compound 231X and 231Y: (trans)-Methyl 6-(1-((3-(tert-butoxycarbonyl)cyclobutyl)sulfonyl)piperidin-4-yl)-4-(2-chloro-3,4-difluorophenyl)-2-(thiazol-2-yl)-1,4-dihydropyrimidine-5-carboxylate and (cis)-methyl 6-(1-((3-(tert-butoxycarbonyl)cyclobutyl)sulfonyl)piperidin-4-yl)-4-(2-chloro-3,4-difluorophenyl)-2-(thiazol-2-yl)-1,4-dihydropyrimidine-5-carboxylate Intermediate 231X (trans, a mixture of enantiomers): LC-MS (ESI): R$_T$=3.685 min, mass calcd. for C₂₉H₃₃ClF₂N₄O₆S₂ 670.2, m/z found 671.2 [M+H]⁺. ¹H NMR (400 MHz, DMSO-d₆) δ 9.63 (d, J=3.2 Hz, 0.8H), 9.19 (s, 0.2H), 8.02-7.99 (m, 1.8H), 7.93 (d, J=2.8 Hz, 0.2H), 7.46-7.42 (m, 1H), 7.22-7.18 (m, 1H), 6.02 (s, 0.2H), 5.93 (d, J=3.6 Hz, 0.8H), 4.02-3.97 (m, 1H), 3.76-3.70 (m, 3H), 3.53 (s, 3H), 3.15-3.08 (m, 1H), 2.92-2.83 (m, 2H), 2.57-2.53 (m, 4H), 1.96-1.90 (m, 1H), 1.85-1.73 (m, 2H), 1.62-1.58 (m, 1H), 1.42 (s, 9H).

Intermediate 231Y(cis, a mixture of enantiomers): LC-MS (ESI): R$_T$=3.653 min, mass calcd. for C₂₉H₃₃ClF₂N₄O₆S₂ 670.2, m/z found 670.9 [M+H]⁺. ¹H NMR (400 MHz, DMSO-d$_6$) δ 9.63 (d, J=3.6 Hz, 0.8H), 9.20 (s, 0.2H), 8.01-7.99 (m, 1.8H), 7.93 (d, J=3.2 Hz, 0.2H), 7.46-7.42 (m, 1H), 7.23-7.19 (m, 1H), 6.02 (s, 0.2H), 5.93 (d, J=3.6 Hz, 0.8H), 3.97-3.93 (m, 1H), 3.75-3.67 (m, 3H), 3.53 (s, 3H), 3.18-3.06 (m, 1H), 2.88-2.80 (m, 2H), 2.46-2.40 (m, 4H), 1.97-1.93 (m, 1H), 1.83-1.74 (m, 2H), 1.62-1.59 (m, 1H), 1.41 (s, 9H).

A racemic mixture of (trans)-methyl 6-(1-((3-(tert-butoxycarbonyl)-cyclobutyl)sulfonyl)piperidin-4-yl)-4-(2-chloro-3,4-difluorophenyl)-2-(thiazol-2-yl)-1,4-dihydropyrimidine-5-carboxylate 231X (280 mg, 0.420 mmol) was separated by chiral Prep. HPLC (the separation condition: Column: Chiralpak IE 5 μm 20*250 mm; Mobile Phase: Hex:EtOH=60:40 at 10 mL/min; Temp: 30° C.; Wavelength: 214 nm) to give the title compounds 231A (80 mg, 29% yield, 100% stereopure) and 231B (100 mg, 36% yield, 100% stereopure) as yellow solids.

Compound 231A: LC-MS (ESI): R$_T$=1.93 min, mass calcd. for C$_{29}$H$_{33}$ClF$_2$N$_4$O$_6$S$_2$ 670.2, m/z found 671.4 [M+H]$^+$. Chiral analysis (Column: Chiralpak IE 5 μm 4.6*250 mm; Mobile Phase: Hex:EtOH=60:40 at 1.0 mL/min; Temp: 30° C.; Wavelength: 230 nm, R$_T$=9.730 min). $^1$H NMR (400 MHz, CDCl$_3$) δ 8.19 (s, 0.3H), 7.83 (d, J=3.6 Hz, 1H), 7.53 (d, J=2.8 Hz, 0.6H), 7.46 (d, J=3.2 Hz, 0.4H), 7.42 (m, 0.7H), 7.08-7.03 (m, 2H), 6.18 (s, 0.3H), 6.06 (d, J=2.4 Hz, 0.7H), 4.16-3.99 (m, 0.4H), 3.97-3.87 (m, 3.6H), 3.60 (s, 2H), 3.59 (s, 1H), 3.20-3.14 (m, 1H), 2.95-2.90 (m, 2H), 2.82-2.74 (m, 2H), 2.62-2.55 (m, 2H), 2.22-2.14 (m, 0.6H), 2.05-1.92 (m, 1.1H), 1.90-1.66 (m, 1.3H), 1.63-1.58 (m, 1H), 1.47 (s, 9H).

Compound 231B: LC-MS (ESI): R$_T$=1.93 min, mass calcd. for C$_{29}$H$_{33}$ClF$_2$N$_4$O$_6$S$_2$ 670.2, m/z found 671.4 [M+H]$^+$. Chiral analysis (Column: Chiralpak IE 5 μm 4.6*250 mm; Mobile Phase: Hex:EtOH=60:40 at 1.0 mL/min; Temp: 30° C.; Wavelength: 230 nm, R$_T$=12.613 min). $^1$H NMR (400 MHz, CDCl$_3$) δ 8.19 (s, 0.3H), 7.83 (d, J=3.6 Hz, 1H), 7.53 (d, J=2.8 Hz, 0.6H), 7.46 (d, J=3.2 Hz, 0.4H), 7.42 (s, 0.7H), 7.08-7.03 (m, 2H), 6.18 (s, 0.3H), 6.06 (d, J=2.4 Hz, 0.7H), 4.16-4.14 (m, 0.4H), 4.00-3.87 (m, 3.6H), 3.60 (s, 2H), 3.59 (s, 1H), 3.20-3.14 (m, 1H), 2.95-2.90 (m, 2H), 2.82-2.74 (m, 2H), 2.62-2.55 (m, 2H), 2.22-2.14 (m, 0.6H), 2.05-1.77 (m, 2.4H), 1.70-1.58 (m, 1H), 1.47 (s, 9H).

A racemic mixture of (cis)-methyl 6-(1-((3-(tert-butoxycarbonyl)cyclobutyl)-sulfonyl)piperidin-4-yl)-4-(2-chloro-3,4-difluorophenyl)-2-(thiazol-2-yl)-1,4-dihydropyrimidine-5-carboxylate 231Y (220 mg, 0.330 mmol) was separated by chiral Prep. HPLC (the separation condition: Column: Chiralpak IG 5 μm 20*250 mm; Mobile Phase: Hex:EtOH=50:50 at 12 mL/min; Temp: 30° C.; Wavelength: 214 nm) to give the title compounds 231C (97 mg, 44% yield, 100% stereopure) and 231D (107 mg, 49% yield, 99.7% stereopure) as yellow solids.

Compound 231C: LC-MS (ESI): R$_T$=1.90 min, mass calcd. for C$_{29}$H$_{33}$ClF$_2$N$_4$O$_6$S$_2$ 670.2, m/z found 671.4 [M+H]$^+$. Chiral analysis (Column: Chiralpak IE 5 μm 4.6*250 mm; Mobile Phase: Hex:EtOH=60:40 at 1.0 mL/min; Temp: 30° C.; Wavelength: 230 nm, R$_T$=10.809 min). $^1$H NMR (400 MHz, CDCl$_3$) δ 8.20 (s, 0.4H), 7.84-7.83 (m, 1H), 7.53 (d, J=3.2 Hz, 0.6H), 7.46 (d, J=2.8 Hz, 0.4H), 7.42 (d, J=2.4 Hz, 0.7H), 7.08-7.03 (m, 2H), 6.18 (s, 0.4H), 6.06 (d, J=1.6 Hz, 0.6H), 4.19-4.13 (m, 0.3H), 4.04-3.91 (m, 2.7H), 3.70-3.65 (m, 1H), 3.60 (s, 2H), 3.59 (s, 1H), 3.03-2.90 (m, 3H), 2.79-2.72 (m, 2H), 2.57-2.50 (m, 2H), 2.23-2.18 (m, 0.4H), 2.05-1.97 (m, 1H), 1.89-1.81 (m, 2H), 1.69-1.66 (m, 0.6H), 1.47 (s, 9H).

Compound 231D: LC-MS (ESI): R$_T$=1.90 min, mass calcd. for C$_{29}$H$_{33}$ClF$_2$N$_4$O$_6$S$_2$ 670.2, m/z found 671.4 [M+H]$^+$. Chiral analysis (Column: Chiralpak IE 5 μm 4.6*250 mm; Mobile Phase: Hex:EtOH=60:40 at 1.0 mL/min; Temp: 30° C.; Wavelength: 230 nm, R$_T$=14.521 min). $^1$H NMR (400 MHz, CDCl$_3$) δ 8.21 (s, 0.4H), 7.84-7.83 (m, 1H), 7.53 (d, J=3.2 Hz, 0.7H), 7.46 (d, J=3.2 Hz, 0.3H), 7.42-7.41 (m, 0.6H), 7.08-7.02 (m, 2H), 6.18 (s, 0.3H), 6.06 (s, 0.6H), 4.19-4.13 (m, 0.3H), 4.05-3.89 (m, 2.7H), 3.70-3.63 (m, 1H), 3.60 (s, 2H), 3.59 (s, 1H), 3.03-2.91 (m, 3H), 2.87-2.74 (m, 2H), 2.57-2.51 (m, 2H), 2.23-2.18 (m, 0.5H), 2.05-2.02 (m, 1H), 1.93-1.80 (m, 2H), 1.70-1.66 (m, 0.5H), 1.47 (s, 9H).

Compound 237: (trans)-Methyl 6-(4-((N-(tert-butoxycarbonyl)sulfamoyl)amino)-cyclohexyl)-4-(2-chloro-3,4-difluorophenyl)-2-(thiazol-2-yl)-1,4-dihydropyrimidine-5-carboxylate $^1$H NMR (300 MHz, CDCl$_3$) δ 8.13 (br s, 0.6H), 7.83-7.80 (m, 1H), 7.50 (d, J=3.0 Hz, 0.4H), 7.45 (d, J=3.0 Hz, 0.6H), 7.40-7.37 (m, 0.4H), 7.05-6.95 (m, 2H), 6.15 (s, 0.6H), 6.05-6.01 (m, 0.4H), 3.96-3.89 (m, 0.6H), 3.72-3.67 (m, 0.4H), 3.60 (s, 1.1H), 3.58 (s, 1.9H), 3.31-3.23 (m, 1H), 2.31-2.15 (m, 2H), 2.06-1.91 (m, 2H), 1.79-1.57 (m, 2H), 1.50-1.47 (m, 9H), 1.44-1.41 (m, 2H).

Compound 240M and 240N: (trans)-Methyl 4-(2-bromo-4-fluorophenyl)-6-(1-((3-(tert-butoxycarbonyl)cyclobutyl)sulfonyl)piperidin-4-yl)-2-(thiazol-2-yl)-1,4-dihydropyrimidine-5-carboxylate and (cis)-methyl 4-(2-bromo-4-fluorophenyl)-6-(1-((3-(tert-butoxycarbonyl)cyclobutyl)sulfonyl)piperidin-4-yl)-2-(thiazol-2-yl)-1,4-dihydropyrimidine-5-carboxylate Compound 240M (mixture of enantiomer): LC-MS (ESI): R$_T$=2.650 min, mass calcd. for C$_{29}$H$_{34}$BrFN$_4$O$_6$S$_2$ 696.1, m/z found 698.9 [M+H]$^+$. $^1$H NMR (400 MHz, CDCl$_3$) δ 8.15 (s, 0.2H), 7.83 (d, J=3.2 Hz, 1H), 7.52-7.44 (m, 1.8H), 7.32 (dd, J=8.4, 2.8 Hz, 1H), 7.28-7.25 (m, 1H), 7.02-6.93 (m, 1H), 6.16 (s, 0.2H), 6.03 (d, J=2.4 Hz, 0.8H), 4.20-4.08 (m, 0.3H), 4.04-3.87 (m, 3.7H), 3.60 (s, 3H), 3.22-3.13 (m, 1H), 2.99-2.87 (m, 2H), 2.82-2.72 (m, 2H), 2.63-2.53 (m, 2H), 2.25-2.15 (m, 0.8H), 2.07-1.59 (m, 3.2H), 1.47 (s, 9H).

Compound 240N (mixture of enantiomer): LC-MS (ESI): R$_T$=2.610 min, mass calcd. for C$_{29}$H$_{34}$BrFN$_4$O$_6$S$_2$ 696.1, m/z found 698.9 [M+H]$^+$. $^1$H NMR (400 MHz, CDCl$_3$) δ 8.17 (s, 0.2H), 7.83-7.82 (m, 1H), 7.52-7.44 (m, 1.8H), 7.35-7.31 (m, 1H), 7.29-7.21 (m, 1H), 7.02-6.94 (m, 1H), 6.16 (s, 0.2H), 6.03 (d, J=2.4 Hz, 0.8H), 4.21-4.08 (m, 0.2H), 4.05-3.87 (m, 2.8H), 3.73-3.64 (m, 1H), 3.59 (s, 3H), 3.06-2.87 (m, 3H), 2.82-2.71 (m, 2H), 2.59-2.47 (m, 2H), 2.26-2.14 (m, 0.7H), 2.04-1.78 (m, 2.6H), 1.70-1.66 (m, 0.7H), 1.47 (s, 9H).

A racemic mixture of (trans)-methyl 4-(2-bromo-4-fluorophenyl)-6-(1-((3-(tert-butoxycarbonyl)cyclobutyl) sulfonyl)piperidin-4-yl)-2-(thiazol-2-yl)-1,4-dihydropyrimidine-5-carboxylate 240M (480 mg, 0.69 mmol) was separated by chiral Prep. HPLC (separation condition: Column: Chiralpak ID 5 μm 20*250 mm; Mobile Phase: Hex:IPA:DEA=50:50:0.3 at 13 mL/min; Temp: 30° C.; Wavelength: 214 nm) to afford the title compounds 240P (140 mg, 29% yield, 100% stereopure) as yellow solids and 240Q (150 mg, 31% yield, 99.2% stereopure) as yellow solids.

Compound 240P: LC-MS (ESI): R$_T$=3.629 min, mass calcd. for C$_{29}$H$_{34}$BrFN$_4$O$_6$S$_2$ 696.1, m/z found 699.2

[M+H]⁺. Chiral analysis (Column: Chiralpak ID 5 μm 4.6*250 mm; Mobile Phase: Hex:IPA:DEA=50:50:0.2 at 1.0 mL/min; Temp: 30° C.; Wavelength: 230 nm, $R_T$=8.996 min). ¹H NMR (400 MHz, DMSO-d₆) δ 9.50 (d, J=3.6 Hz, 0.8H), 9.13 (s, 0.2H), 8.01-7.98 (m, 1.8H), 7.93 (d, J=3.2 Hz, 0.2H), 7.58-7.55 (m, 1H), 7.38-7.31 (m, 1H), 7.30-7.21 (m, 1H), 5.99 (s, 0.2H), 5.90 (d, J=3.6 Hz, 0.8H), 4.04-3.95 (m, 1H), 3.80-3.70 (m, 3H), 3.53 (s, 2.5H), 3.52 (s, 0.5H), 3.16-3.08 (m, 1H), 2.92-2.83 (m, 2H), 2.68-2.53 (m, 4H), 2.07-1.88 (m, 1H), 1.87-1.75 (m, 2H), 1.61-1.58 (m, 1H), 1.42 (s, 9H).

Compound 240Q: LC-MS (ESI): $R_T$=3.794 min, mass calcd. For $C_{29}H_{34}BrFN_4O_6S_2$ 696.1, m/z found 699.2 [M+H]⁺. Chiral analysis (Column: Chiralpak ID 5 μm 4.6*250 mm; Mobile Phase: Hex:IPA:DEA=50:50:0.2 at 1.0 mL/min; Temp: 30° C.; Wavelength: 230 nm, $R_T$=11.886 min). ¹H NMR (400 MHz, DMSO-d₆) δ 9.50 (d, J=3.6 Hz, 0.8H), 9.12 (s, 0.2H), 8.01-7.98 (m, 1.8H), 7.93 (d, J=3.6 Hz, 0.2H), 7.58-7.55 (m, 1H), 7.38-7.31 (m, 1H), 7.30-7.21 (m, 1H), 5.99 (s, 0.2H), 5.90 (d, J=3.6 Hz, 0.8H), 4.04-3.96 (m, 1H), 3.77-3.70 (m, 3H), 3.53 (s, 2.5H), 3.52 (s, 0.5H), 3.16-3.08 (m, 1H), 2.93-2.83 (m, 2H), 2.66-2.51 (m, 4H), 2.10-1.89 (m, 1H), 1.87-1.75 (m, 2H), 1.61-1.58 (m, 1H), 1.42 (d, J=3.6 Hz, 9H).

Compound 242: Methyl 6-(1-((3-(tert-butoxycarbonyl)cyclobutyl)sulfonyl)-piperidin-4-yl)-4-(2-chloro-4-fluorophenyl)-2-(thiazol-2-yl)-1,4-dihydropyrimidine-5-carboxylate ¹H NMR (300 MHz, CDCl₃) δ 8.18 (br s, 0.3H), 7.84-7.82 (m, 1H), 7.52-7.50 (m, 0.7H), 7.47-7.43 (m, 1H), 7.31-7.28 (m, 1H), 7.15-7.12 (m, 1H), 6.98-6.91 (m, 1H), 6.18 (s, 0.3H), 6.08-6.04 (m, 0.7H), 4.12-3.85 (m, 4H), 3.74-3.66 (m, 1H), 3.59 (s, 3H), 3.37-3.09 (m, 1H), 3.01-2.90 (m, 2H), 2.82-2.73 (m, 2H), 2.60-2.49 (m, 2H), 2.25-2.13 (m, 1H), 2.07-1.98 (m, 1H), 1.91-1.85 (m, 1H), 1.47 (s, 5H), 1.46 (s, 4H).

Compound 242 was separated by prep-HPLC using C18 column (acetonitrile:water=80% to 88%) to give compound 242A and 242B Compound 242A (trans): LC-MS (ESI): $R_T$=8.683 min, mass calcd. for $C_{29}H_{34}ClFN_4O_6S_2$ 652.2, m/z found 653.1 [M+H]⁺. ¹H NMR (400 MHz, DMSO-d₆) δ 9.52 (d, J=3.2 Hz, 0.9H), 9.13 (br s, 0.1H), 8.01-7.98 (m, 1.8H), 7.93-7.92 (m, 0.2H), 7.42 (dd, J=8.8, 2.4 Hz, 1H), 7.37-7.31 (m, 1H), 7.23-7.18 (m, 1H), 6.01 (s, 0.2H), 5.92 (d, J=3.2 Hz, 0.8H), 4.03-3.96 (m, 1H), 3.77-3.70 (m, 3H), 3.53-3.52 (m, 3H), 3.15-3.08 (m, 1H), 2.92-2.83 (m, 2H), 2.61-2.53 (m, 4H), 2.07-1.89 (m, 1.2H), 1.86-1.72 (m, 2H), 1.61-1.57 (m, 0.8H), 1.43-1.42 (m, 9H).

Compound 242B (cis): LC-MS (ESI): $R_T$=1.27 min, mass calcd. for $C_{29}H_{34}ClFN_4O_6S_2$ 652.2, m/z found 653.6 [M+H]⁺. ¹H NMR (400 MHz, DMSO-d₆) δ 9.51 (d, J=3.2 Hz, 0.8H), 9.12 (br s, 0.2H), 8.00 (s, 1.8H), 7.92 (m, 0.2H), 7.42 (dd, J=8.8, 2.4 Hz, 1H), 7.38-7.31 (m, 1H), 7.23-7.18 (m, 1H), 6.02 (s, 0.2H), 5.92 (d, J=3.6 Hz, 0.8H), 3.99-3.90 (m, 1H), 3.78-3.67 (m, 3H), 3.53 (s, 3H), 3.12-3.03 (m, 1H), 2.89-2.80 (m, 2H), 2.49-2.48 (m, 4H), 2.08-1.90 (m, 1.2H), 1.87-1.75 (m, 2H), 1.62-1.59 (m, 0.8H), 1.41 (s, 9H).

Compound 246: Methyl 6-(1-((1-(tert-butoxycarbonyl)azetidin-3-yl)sulfonyl)piperidin-4-yl)-4-(2-chloro-3,4-difluorophenyl)-2-(thiazol-2-yl)-1,4-dihydropyrimidine-5-carboxylate LC-MS (ESI): $R_T$=2.686 min, mass calcd. for $C_{28}H_{32}ClF_2N_5O_6S_2$ 671.2, m/z found 671.8 [M+H]⁺. ¹H NMR (300 MHz, CDCl₃) δ 8.21 (s, 0.3H), 7.86-7.84 (m, 1H), 7.55 (s, 0.7H), 7.49-7.45 (m, 1H), 7.11-7.01 (m, 2H), 6.19 (s, 0.3H), 6.08 (s, 0.7H), 4.35-4.13 (m, 4.2H), 4.09-3.94 (m, 3.8H), 3.61-3.60 (m, 3H), 3.04-2.91 (m, 2H), 2.20-2.16 (m, 1H), 2.06-1.86 (m, 2H), 1.74-1.70 (m, 1H), 1.47 (s, 9H).

Compound 249: (trans)-Methyl 6-(4-(1-(tert-butoxycarbonyl)azetidine-3-sulfonamido)cyclohexyl)-4-(2-chloro-3,4-difluorophenyl)-2-(thiazol-2-yl)-1,4-dihydropyrimidine-5-carboxylate LC-MS (ESI): $R_T$=2.631 min, mass calcd. for $C_{29}H_{34}ClF_2N_5O_6S_2$ 685.2, m/z found 685.8 [M+H]⁺. ¹H NMR (300 MHz, CDCl₃) δ 8.16 (s, 0.5H), 7.84 (d, J=1.8 Hz, 1H), 7.58-7.53 (m, 0.5H), 7.50-7.46 (m, 0.5H), 7.42 (s, 0.5H), 7.09-7.01 (m, 2H), 6.18 (s, 0.5H), 6.06 (s, 0.5H), 4.39-4.27 (m, 1H), 4.22-4.17 (m, 4H), 4.05-3.90 (m, 1.5H), 3.84-3.67 (m, 0.5H), 3.61 (s, 1.5H), 3.60 (s, 1.5H), 3.54-3.38 (m, 1H), 2.31-1.91 (m, 4H), 1.88-1.65 (m, 2H), 1.58-1.51 (m, 2H), 1.46 (s, 9H).

Compound 252: (trans)-Methyl 4-(2-chloro-3,4-difluorophenyl)-6-(4-(3-methoxy-3-oxopropylsulfonamido)cyclohexyl)-2-(thiazol-2-yl)-1,4-dihydropyrimidine-5-carboxylate LC-MS (ESI): $R_T$=4.182 min, mass calcd. for $C_{25}H_{27}ClF_2N_4O_6S_2$ 616.1, m/z found 617.1 [M+H]⁺. ¹H NMR (400 MHz, CDCl₃) δ 8.16 (s, 0.5H), 7.83 (d, J=3.2 Hz, 1H), 7.52 (d, J=3.2 Hz, 0.5H), 7.46 (d, J=2.8 Hz, 0.5H), 7.41 (s, 0.5H), 7.07-6.98 (m, 2H), 6.17 (s, 0.5H), 6.04 (d, J=2.8 Hz, 0.5H), 4.38-4.36 (m, 0.5H), 4.31-4.29 (m, 0.5H), 4.02-3.93 (m, 0.5H), 3.75 (s, 3H), 3.73-3.70 (m, 0.5H), 3.60-3.59 (m, 3H), 3.42-3.37 (m, 3H), 2.89-2.84 (m, 2H), 2.31-1.99 (m, 4H), 1.93-1.72 (m, 1H), 1.64-1.35 (m, 3H).

A racemic mixture of (trans)-methyl 4-(2-chloro-3,4-difluorophenyl)-6-(4-(3-methoxy-3-oxopropylsulfonamido)cyclohexyl)-2-(thiazol-2-yl)-1,4-dihydropyrimidine-5-carboxylate 252 (200 mg, 0.320 mmol) was separated by chiral Prep. SFC (Column: Chiralpak IA 5 μm 20*250 mm; Mobile Phase: CO₂:MeOH:DEA=65:35:0.3 at 45 g/min; Col. Temp: 39.9° C.; Wavelength: 230 nm, Back pressure: 100 bar) to give 252X (80 mg, 90% purity, 40% yield, 97.6% stereopure) and 252Y (70 mg, 90% purity, 45% yield, 94.2% stereopure) as yellow solids.

Intermediate 252X: LC-MS (ESI): $R_T$=2.933 min, mass calcd. for $C_{25}H_{27}ClF_2N_4O_6S_2$ 616.1, m/z found 617.1 [M+H]⁺. Chiral analysis (Column: Chiralpak IA 5 μm 4.6*250 mm; Mobile Phase: CO₂:MeOH:DEA=65:35:0.2 at 2.999 mL/min; Col. Temp: 39.9° C.; Wavelength: 230 nm, Back pressure: 100 bar, $R_T$=3.88 min). ¹H NMR (400 MHz, CDCl₃) δ 8.15 (s, 0.5H), 7.84-7.82 (m, 1H), 7.52 (d, J=3.2 Hz, 0.5H), 7.46 (d, J=3.2 Hz, 0.5H), 7.40 (s, 0.5H), 7.07-6.98 (m, 2H), 6.17 (s, 0.5H), 6.04 (d, J=2.8 Hz, 0.5H), 4.23-4.16 (m, 1H), 4.01-3.93 (m, 0.5H), 3.75 (s, 3H), 3.73-3.69 (m, 0.5H), 3.60-3.59 (m, 3H), 3.44-3.35 (m, 3H), 2.89-2.84 (m, 2H), 2.29-2.14 (m, 2H), 2.12-1.92 (m, 2H), 1.90-1.64 (m, 2H), 1.53-1.35 (m, 2H).

Intermediate 252Y: LC-MS (ESI): $R_T$=3.842 min, mass calcd. for $C_{25}H_{27}ClF_2N_4O_6S_2$ 616.1, m/z found 617.1 [M+H]⁺. Chiral analysis (Column: Chiralpak IA 5 μm 4.6*250 mm; Mobile Phase: CO₂:MeOH:DEA=65:35:0.2 at 2.999 mL/min; Col. Temp: 39.9° C.; Wavelength: 230 nm, Back pressure: 100 bar, $R_T$=4.65 min). ¹H NMR (400 MHz, CDCl₃) δ 8.15 (s, 0.5H), 7.83-7.82 (m, 1H), 7.52 (d, J=3.2 Hz, 0.5H), 7.46 (d, J=3.2 Hz, 0.5H), 7.40 (s, 0.5H), 7.07-6.98 (m, 2H), 6.17 (s, 0.5H), 6.04 (d, J=2.4 Hz, 0.5H), 4.23-4.16 (m, 1H), 4.01-3.93 (m, 0.5H), 3.75 (s, 3H), 3.73-3.70 (m, 0.5H), 3.60-3.59 (m, 3H), 3.45-3.36 (m, 3H), 2.89-2.84 (m, 2H), 2.29-2.14 (m, 2H), 2.12-1.95 (m, 2H), 1.93-1.64 (m, 2H), 1.55-1.36 (m, 2H).

Compound 254: Methyl 4-(2-chloro-4-fluorophenyl)-6-(1-((1-cyclopropyl-1H-pyrazol-4-yl)sulfonyl)piperidin-4-yl)-2-(4,5-dihydrothiazol-2-yl)-1,4-dihydropyrimidine-5-carboxylate LC-MS (ESI): $R_T$=4.252 min, mass calcd. for $C_{26}H_{26}ClFN_6O_4S_2$ 604.1, m/z found 604.9 [M+H]$^+$. $^1$H NMR (400 MHz, CDCl$_3$) δ 8.18 (s, 0.3H), 7.83 (s, 2H), 7.72-7.70 (m, 1H), 7.54-7.53 (m, 0.7H), 7.46-7.45 (m, 0.3H), 7.43 (s, 0.7H), 7.30-7.29 (m, 0.3H), 7.25-7.23 (m, 0.7H), 7.15-7.11 (m, 1H), 6.97-6.88 (m, 1H), 6.17 (s, 0.3H), 6.05 (s, 0.7H), 4.01-3.83 (m, 2H), 3.77-3.65 (m, 2H), 3.55 (s, 3H), 2.45-2.27 (m, 3H), 2.20-2.05 (m, 1H), 2.02-1.88 (m, 1.5H), 1.75-1.69 (m, 0.5H), 1.24-1.18 (m, 2H), 1.17-1.09 (m, 2H).

Compound 255: Methyl 4-(2-chloro-4-fluorophenyl)-6-(-1-(oxetan-3-ylsulfonyl)pyrrolidin-3-yl)-2-(thiazol-2-yl)-1,4-dihydropyrimidine-5-carboxylate LC-MS (ESI): $R_T$=3.777 min, mass calcd. for $C_{22}H_{22}ClFN_4O_5S_2$ 540.1, m/z found 541.1 [M+H]$^+$. $^1$H NMR (400 MHz, DMSO-d$_6$) δ 9.63 (s, 1H), 8.02 (s, 2H), 7.44-7.41 (m, 1H), 7.39-7.35 (m, 1H), 7.23-7.18 (m, 1H), 5.94 (s, 1H), 4.97-4.90 (m, 1H), 4.88-4.79 (m, 4H), 4.37-4.28 (m, 1H), 3.63-3.52 (m, 6H), 3.38-3.32 (m, 1H), 2.18-2.07 (m, 1H), 2.05-1.96 (m, 1H).

Compound 256A: Methyl 4-(2-chloro-4-fluorophenyl)-6-(-1-(propylsulfonyl)pyrrolidin-3-yl)-2-(thiazol-2-yl)-1,4-dihydropyrimidine-5-carboxylate LC-MS (ESI): $R_T$=4.129 min, mass calcd. For $C_{22}H_{24}ClFN_4O_4S_2$ 526.1, m/z found 527.2 [M+H]$^+$. $^1$H NMR (400 MHz, DMSO-d$_6$) δ 9.62 (s, 1H), 8.02 (s, 2H), 7.44-7.41 (m, 1H), 7.39-7.35 (m, 1H), 7.24-7.19 (m, 1H), 5.94 (s, 1H), 4.41-4.33 (m, 1H), 3.63-3.52 (m, 6H), 3.39-3.33 (m, 1H), 3.16-3.12 (m, 2H), 2.23-2.14 (m, 1H), 2.02 (br s, 1H), 1.81-1.71 (m, 2H), 1.01 (t, J=7.2 Hz, 3H).

Compound 256D: Methyl 4-(2-chloro-4-fluorophenyl)-6-(-1-(propylsulfonyl)pyrrolidin-3-yl)-2-(thiazol-2-yl)-1,4-dihydropyrimidine-5-carboxylate LC-MS (ESI): $R_T$=4.098 min, mass calcd. for $C_{22}H_{24}ClFN_4O_4S_2$ 526.1, m/z found 527.2 [M+H]$^+$. $^1$H NMR (400 MHz, DMSO-d$_6$) δ 9.67 (d, J=2.8 Hz, 0.9H), 9.30 (s, 0.1H), 8.05-8.02 (m, 1.8H), 7.99-7.98 (m, 0.1H), 7.94-7.93 (m, 0.1H), 7.45-7.42 (m, 1H), 7.39-7.36 (m, 1H), 7.24-7.20 (m, 1H), 6.02 (s, 0.1H), 5.93 (d, J=2.8 Hz, 0.9H), 4.61-4.54 (m, 0.1H), 4.42-4.34 (m, 0.9H), 3.62-3.36 (m, 7H), 3.20-3.04 (m, 2H), 2.35-2.26 (m, 1H), 2.18-2.10 (m, 1H), 1.78-1.68 (m, 2H), 1.03-0.95 (m, 3H).

Compound 266: Methyl 6-(1-(N-(tert-butoxycarbonyl)sulfamoyl)piperidin-4-yl)-4-(2-chloro-4-fluorophenyl)-2-(thiazol-2-yl)-1,4-dihydropyrimidine-5-carboxylate LC-MS (ESI): $R_T$=2.586 min, mass calcd. For $C_{25}H_{29}ClFN_5O_6S_2$ 613.1, m/z found 614.2 [M+H]$^+$. $^1$H NMR (400 MHz, DMSO-d$_6$) δ 10.95 (s, 1H), 9.55 (d, J=3.6 Hz, 0.8H), 9.11 (s, 0.2H), 8.01 (s, 2H), 7.44-7.35 (m, 2H), 7.23-7.19 (m, 1H), 6.02 (s, 0.2H), 5.92 (d, J=3.6 Hz, 0.8H), 3.80-3.62 (m, 3H), 3.52 (s, 3H), 2.90-2.82 (m, 2H), 1.96-1.79 (m, 3H), 1.65-1.62 (m, 1H), 1.44 (s, 9H).

Compound 269A and 269B: (trans)-Ethyl 4-(2-chloro-3,4-difluorophenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate and (cis)-ethyl 4-(2-chloro-3,4-difluorophenyl)-6-(1-((3-methyl-3-((2-(trimethylsilyl)ethoxy)carbonyl)cyclobutyl)-sulfonyl)piperidin-4-yl)-2-(thiazol-2-yl)-1,4-dihydropyrimidine-5-carboxylate Compound 269A: $^1$H NMR (400 MHz, CDCl$_3$) δ 8.10 (s, 0.4H), 7.76 (d, J=3.2 Hz, 1H), 7.47 (d, J=3.2 Hz, 0.6H), 7.39 (d, J=3.2 Hz, 0.4H), 7.29 (d, J=2.4 Hz, 0.6H), 7.02-6.98 (m, 2H), 6.13 (s, 0.4H), 6.02 (d, J=2.8 Hz, 0.6H), 4.19-4.14 (m, 2H), 4.03-3.76 (m, 6H), 2.87-2.80 (m, 2H), 2.70-2.66 (m, 2H), 2.45-2.35 (m, 2H), 2.18-2.09 (m, 0.5H), 1.98-1.58 (m, 3.5H), 1.39 (s, 2H), 1.38 (s, 1H), 1.07-1.03 (m, 3H), 0.98-0.94 (m, 2H), 0.00 (s, 9H)

Compound 269B: $^1$H NMR (400 MHz, CDCl$_3$) δ 8.12 (s, 0.4H), 7.78-7.77 (m, 1H), 7.48 (d, J=2.8 Hz, 0.6H), 7.41 (d, J=3.2 Hz, 0.4H), 7.30 (d, J=2.0 Hz, 0.6H), 7.04-7.01 (m, 2H), 6.15 (s, 0.4H), 6.04 (d, J=2.8 Hz, 0.6H), 4.17-4.13 (m, 2H), 4.01-3.84 (m, 5H), 3.75-3.65 (m, 1H), 2.96-2.78 (m, 4H), 2.20-2.11 (m, 3H), 2.01-1.62 (m, 3H), 1.43 (s, 2H), 1.42 (s, 1H), 1.11-1.04 (m, 3H), 0.99-0.94 (m, 2H), 0.00 (s, 9H).

Compound 271A and compound 271B: (trans)-Ethyl 4-(2-chloro-4-fluorophenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate and (cis)-methyl 4-(2-chloro-3,4-difluorophenyl)-6-(1-((3-methy-3-((2-(trimethylsilyl)ethoxy)carbonyl)-cyclobutyl)sulfonyl)piperidin-4-yl)-2-(thiazol-2-yl)-1,4-dihydropyrimidine-5-carboxylate Compound 271A: (trans)-Ethyl 4-(2-chloro-4-fluorophenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate Intermediate EO08495_1034.1A: $^1$H NMR (400 MHz, CDCl$_3$) δ 8.13 (br s, 0.2H), 7.83 (d, J=2.8 Hz, 1H), 7.52 (d, J=3.2 Hz, 0.7H), 7.45 (d, J=3.2 Hz, 0.3H), 7.36-7.33 (m, 0.8H), 7.31-7.26 (m, 1H), 7.15-7.11 (m, 1H), 6.98-6.89 (m, 1H), 6.20 (s, 0.3H), 6.09 (d, J=2.4 Hz, 0.7H), 4.25-4.21 (m, 2H), 4.03 (q, J=7.2 Hz, 2H), 3.98-3.80 (m, 4H), 2.95-2.73 (m, 4H), 2.51-2.44 (m, 2H), 2.24-2.18 (m, 0.5H), 2.07-2.00 (m, 1H), 1.94-1.85 (m, 1.5H), 1.78-1.66 (m, 1H), 1.46 (s, 2.5H), 1.45 (s, 0.5H), 1.12-1.08 (m, 3H), 0.87-0.86 (m, 2H), 0.07 (s, 9H).

Compound 271B: $^1$H NMR (400 MHz, CDCl$_3$) δ 8.09 (s, 0.2H), 7.78-7.77 (m, 1H), 7.46 (d, J=2.8 Hz, 0.7H), 7.39 (d, J=3.2 Hz, 0.3H), 7.29 (br s, 0.8H), 7.26-7.22 (m, 1H), 7.10-7.07 (m, 1H), 6.93-6.88 (m, 1H), 6.15 (s, 0.3H), 6.04 (d, J=2.4 Hz, 0.7H), 4.17-4.14 (m, 2H), 4.01-3.85 (m, 4H), 3.73-3.68 (m, 1H), 2.97-2.83 (m, 4H), 2.19-2.11 (m, 3H), 2.00-1.82 (m, 3H), 1.43 (s, 2.5H), 1.42 (s, 0.5H), 1.09-1.03 (m, 3H), 0.99-0.94 (m, 2H), 0.01 (s, 9H).

Compound 273A and 273B: (trans)-Methyl 4-(2-chloro-3-fluorophenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate and (cis)-methyl 4-(2-chloro-3-fluorophenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate Compound 273A: $^1$H NMR (400 MHz, CDCl$_3$) δ 8.10 (s, 0.2H), 7.77 (d, J=3.2 Hz, 1H), 7.46 (d, J=3.2 Hz, 1H), 7.38 (s, 0.8H), 7.16-7.11 (m, 1H), 7.10-6.98 (m, 2H), 6.18 (s, 0.3H), 6.05 (d, J=2.8 Hz, 0.7H), 4.18-4.14 (m, 2H), 3.95-3.73 (m, 4H), 3.53 (s, 2H), 3.52 (s, 1H), 2.90-2.82 (m, 2H), 2.76-2.70 (m, 2H), 2.43-2.42 (m, 2H), 2.17-2.10 (m, 1H), 1.98-1.61 (m, 3H), 1.39 (s, 2H), 1.38 (s, 1H), 0.98-0.94 (m, 2H), 0.00 (s, 9H)

Compound 273B: $^1$H NMR (400 MHz, CDCl$_3$) δ 8.13 (s, 0.2H), 7.78-7.77 m, 1H), 7.46 (d, J=3.2 Hz, 1H), 7.40 (d, J=2.8 Hz, 0.8H), 7.21-7.14 (m, 1H), 7.06-7.02 (m, 2H), 6.20 (s, 0.3H), 6.07 (d, J=3.2 Hz, 0.7H), 4.17-4.13 (m, 2H), 3.95-3.85 (m, 3H), 3.73-3.69 (m, 1H), 3.54 (s, 2H), 3.53 (s, 1H), 2.97-2.84 (m, 4H), 2.19-2.12 (m, 2H), 2.00-1.65 (m, 4H), 1.43 (s, 3H), 0.99-0.94 (m, 2H), 0.01 (s, 9H)

Compound 277C and 277D: (trans)-methyl 4-(2-bromo-3-fluorophenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate and (cis)-methyl 4-(2-bromo-3-fluorophenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate Compound 277C: $^1$H NMR (400 MHz, CDCl$_3$) δ 8.16 (s, 0.2H), 7.84-7.81 (m, 1H), 7.53-7.49 (m, 1.7H), 7.46-7.45 (m, 0.2H), 7.28-7.27 (m, 0.8H), 7.19-7.00 (m, 2H), 6.24 (s, 0.2H), 6.10 (s, 0.8H), 4.34-4.25 (m, 2H), 4.03-3.80 (m, 4H), 3.59 (s, 3H), 2.96-2.76 (m, 4H), 2.54-2.45 (m, 2H), 2.18-2.09 (m, 1H), 2.03-1.85 (m, 2H), 1.73-1.67 (m, 1H), 1.49-1.40 (m, 3H), 1.05-1.01 (m, 2H), 0.07 (s, 9H).

Compound 277D: $^1$H NMR (400 MHz, CDCl$_3$) δ 8.12 (s, 0.2H), 7.79-7.75 (m, 1H), 7.49-7.41 (m, 2H), 7.25-7.22 (m, 0.8H), 7.05-6.95 (m, 2H), 6.19 (s, 0.3H), 6.06-6.02 (m, 0.7H), 4.17-4.13 (m, 2H), 3.99-3.66 (m, 4H), 3.53 (s, 3H), 2.98-2.80 (m, 4H), 2.20-2.10 (m, 3H), 1.94-1.60 (m, 3H), 1.43 (s, 3H), 0.99-0.95 (m, 2H), 0.03 (s, 9H).

Compound 281C and 281D: (trans)-Ethyl 4-(2-bromo-4-fluorophenyl)-6-(1-((3-methyl-3-(((trimethylsilyl)ethoxy)carbonyl)cyclobutyl)sulfonyl)piperidin-4-yl)-2-(thiazol-2-yl)-1,4-dihydropyrimidine-5-carboxylate and (cis)-ethyl 4-(2-bromo-4-fluorophenyl)-6-(1-((3-methyl-3-(((trimethylsilyl)ethoxy)carbonyl)cyclobutyl)sulfonyl)piperidin-4-yl)-2-(thiazol-2-yl)-1,4-dihydropyrimidine-5-carboxylate compound 281C: LC-MS (ESI): R$_T$=2.24 min, mass calcd. for C$_{32}$H$_{42}$BrFN$_4$O$_6$S$_2$Si 768.2, m/z found 770.8 [M+H]$^+$. $^1$H NMR (400 MHz, CDCl$_3$) δ 8.13 (s, 0.2H), 7.83 (d, J=3.2 Hz, 1H), 7.52 (d, J=2.8 Hz, 0.8H), 7.45 (d, J=3.2 Hz, 0.3H), 7.39 (d, J=2.0 Hz, 0.7H), 7.33-7.29 (m, 1H), 7.03-6.94 (m, 1H), 6.18 (s, 0.2H), 6.06 (d, J=2.4 Hz, 0.8H), 4.25-4.20 (m, 2H), 4.06-3.83 (m, 6H), 2.94-2.77 (m, 4H), 2.52-2.46 (m, 2H), 2.24-2.18 (m, 0.8H), 2.08-2.01 (m, 1H), 1.99-1.95 (m, 0.2H), 1.92-1.89 (m, 1H), 1.84-1.77 (m, 0.3H), 1.70-1.66 (m, 0.7H), 1.45 (s, 3H), 1.13-1.08 (m, 3H), 1.05-1.01 (m, 2H), 0.07 (s, 9H).

compound 281D: LC-MS (ESI): R$_T$=2.16 min, mass calcd. for C$_{32}$H$_{42}$BrFN$_4$O$_6$S$_2$Si 768.2, m/z found 768.8 [M+H]$^+$. $^1$H NMR (400 MHz, CDCl$_3$) δ 8.13 (s, 0.2H), 7.83-7.81 (m, 1H), 7.51 (d, J=3.2 Hz, 0.8H), 7.44 (d, J=3.2 Hz, 0.3H), 7.39 (d, J=2.4 Hz, 0.7H), 7.32-7.28 (m, 2H), 7.02-6.94 (m, 1H), 6.17 (s, 0.3H), 6.05 (d, J=2.4 Hz, 0.7H), 4.22-4.18 (m, 2.2H), 4.05-3.90 (m, 4.8H), 3.77-3.73 (m, 1H), 3.01-2.88 (m, 4H), 2.24-2.16 (2.8H), 2.07-2.06 (m, 0.2H), 2.01-2.00 (m, 0.8H), 1.98-1.96 (m, 0.2H), 1.92-1.88 (m, 1H), 1.83-1.77 (m, 0.2H), 1.69-1.65 (m, 0.8H), 1.47 (s, 3H), 1.14-1.07 (m, 3H), 1.03-0.99 (m, 2H), 0.04 (s, 9H).

Compound 298: (trans)-Methyl 4-(2-chloro-3,4-difluorophenyl)-2-(3,5-difluoropyridin-2-yl)-6-4-(methylsulfonamido)cyclohexyl)-1,4-dihydropyrimidine-5-carboxylate LC-MS (ESI): R$_T$=3.182 min, mass calcd. for C$_{24}$H$_{23}$ClF$_4$N$_4$O$_4$S 574.1, m/z found 575.1 [M+H]$^+$. $^1$H NMR (400 MHz, CDCl$_3$) δ 8.34-8.31 (m, 1H), 7.34-7.29 (m, 1H), 7.07-6.98 (m, 2H), 6.20 (s, 11H), 4.42 (d, J=7.6 Hz, 1H), 3.96-3.90 (m, 1H), 3.60 (s, 3H), 3.48-3.39 (m, 1H), 3.03 (s, 3H), 2.27-2.17 (m, 3H), 2.09-2.06 (m, 1H), 1.94-1.91 (m, 1H), 1.83-1.62 (m, 2H), 1.57-1.45 (m, 2H).

A racemic mixture of (trans)-methyl 4-(2-chloro-3,4-difluorophenyl)-2-(3,5-difluoropyridin-2-yl)-6-4-(methylsulfonamido)cyclohexyl)-1,4-dihydropyrimidine-5-carboxylate 298 (120 mg, 93.5% purity, 0.195 mmol) was separated by chiral Prep. HPLC (separation condition: Column: Chiralpak IC 5 μm 20*250 mm; Mobile Phase: Hex:EtOH:DEA=50:50:0.3 at 10 mL/min; Temp: 30° C.; Wavelength: 214 nm) to give the title compounds 298A (17.3 mg, 99.9% purity, 15% yield, 100% stereopure) and 298B (17.3 mg, 99.8% purity, 15% yield, 99.7% stereopure) as yellow solids.

Compound 298A: LC-MS (ESI): R$_T$=2.652 min, mass calcd. for C$_{24}$H$_{23}$ClF$_4$N$_4$O$_4$S 574.1, m/z found 575.0 [M+H]$^+$. Chiral analysis (Column: Chiralpak IC 5 μm 4.6*250 mm; Mobile Phase: Hex:EtOH:DEA=50:50:0.2 at 1.0 mL/min; Temp: 30° C.; Wavelength: 230 nm, R$_T$=7.634 min). 1H NMR (400 MHz, DMSO-d$_6$) δ 9.23 (s, 0.7H), 9.15 (s, 0.3H), 8.57 (s, 1H), 8.08-8.03 (m, 1H), 7.48-7.42 (m, 1H), 7.21-7.01 (m, 2H), 6.03 (s, 0.7H), 5.92 (s, 0.3-), 3.85-3.81 (m, 0.7H), 3.51 (s, 3H), 3.20-3.17 (m, 1H), 3.08 (br s, 0.3H), 2.92 (s, 3H$_1$), 2.02-1.99 (m, 2H), 1.85-1.71 (m, 4H), 1.36-1.23 (m, 2H).

Compound 298B: LC-MS (ESI): R$_T$=2.650 min, mass calcd. for C$_{24}$H$_{23}$ClF$_4$N$_4$O$_4$S 574.1, m/z found 575.0 [M+H]$^+$. Chiral analysis (Column: Chiralpak IC 5 μm 4.6*250 mm; Mobile Phase: Hex:EtOH:DEA=50:50:0.2 at 1.0 mL/min; Temp: 30° C.; Wavelength: 230 nm, R$_T$=9.413 min). $^1$H NMR (400 MHz, DMSO-d$_6$) δ 9.23 (s, 0.7H), 9.15 (s, 0.3H), 8.57 (s, 1H), 8.06 (t, J=8.8 Hz, 1H), 7.48-7.42 (m, 1H), 7.22-7.02 (m, 2H), 6.03 (s, 0.711), 5.92 (s, 0.3H), 3.86-3.81 (m, 0.7H), 3.51 (s, 3H$_1$), 3.20-3.18 (m, 1H), 3.08 (br s, 0.3H), 2.92 (s, 31H), 2.03-2.00 (m, 2H), 1.85-1.71 (m, 4H), 1.36-1.26 (m, 2H).

Compound 304: Methyl 6-(1-((1,4-dioxaspiro[4.5]decan-2-ylmethyl)sulfonyl)piperidin-4-yl)-4-(2-chloro-4-fluorophenyl)-2-(thiazol-2-yl)-1,4-dihydropyrimidine-5-carboxylate To a solution of methyl 4-(2-chloro-4-fluorophenyl)-6-(piperidin-4-yl)-2-(thiazol-2-yl)-1,4-dihydropyrimidine-5- carboxylate compound 99 (434 mg, 1.00 mmol) in dichloromethane (15 mL) was added triethylamine (202 mg, 2.00 mmol) and 1,4-dioxaspiro[4.5]decan-2-ylmethanesulfonyl chloride (382 mg, 1.5 mmol) at 0° C. After stirred at room temperature for 2 hours, the mixture was diluted with dichloromethane (50 mL), washed with water (100 mL) and brine (100 mL), dried over $Na_2SO_{4(s)}$ and filtered. The filtrate was concentrated under reduced pressure to give a residue, which was purified by silica gel column chromatography (petroleum ether:ethyl acetate=10:1 to 3:1) to give small polar fraction, which was further purified by C18 column (acetonitrile:water=80% to 88%) to give the title compound (110 mg, 20% yield) as yellow solids. LC-MS (ESI): $R_T$=1.97 min, mass calcd. for $C_{29}H_{34}ClFN_4O_6S_2$ 652.2, m/z found 652.9 [M+H]$^+$. $^1$H NMR (400 MHz, CDCl$_3$) δ 8.18 (s, 0.2H), 7.86-7.82 (m, 1H), 7.52 (d, J=3.2 Hz, 0.8H), 7.47-7.42 (m, 1H), 7.31-7.24 (m, 1H), 7.17-7.11 (m, 1H), 6.99-6.89 (m, 1H), 6.19 (s, 0.3H), 6.07 (d, J=2.4 Hz, 0.7H), 4.62-4.52 (m, 1H), 4.21-4.11 (m, 0.3H), 4.04-3.75 (m, 3.7H), 3.62-3.57 (m, 3H), 3.41-3.25 (m, 2H), 3.13-2.88 (m, 3H), 2.31-2.20 (m, 0.7H), 2.13-2.04 (m, 1H), 1.98-1.84 (m, 1.3H), 1.76-1.69 (m, 1H), 1.65-1.60 (m, 8H), 1.45-1.39 (m, 2H).

Compound 304 (110 mg, 0.169 mmol) was separated by chiral Prep. HPLC (separation condition: Column: Chiralpak IC 5 μm 20*250 mm; Mobile Phase: Hex:EtOH:DEA=60:40:0.3 at 12 mL/min; Wavelength: 214 nm) to afford 304A (45 mg, 41% yield, 100% stereopure) and 304B (45 mg, 45% yield, 100% stereopure) as yellow solids.

Compound 304A: LC-MS (ESI): $R_T$=2.00 min, mass calcd. for $C_{29}H_{34}ClFN_4O_6S_2$ 652.2, m/z found 652.8 [M+H]$^+$. Chiral analysis (Column: Chiralpak IC 5 μm 4.6*250 mm; Mobile Phase: Hex:EtOH:DEA=60:40:0.2 at 1.0 mL/min; Temp: 30° C.; Wavelength: 230 nm, $R_T$=9.430 min). $^1$H NMR (400 MHz, CDCl$_3$) δ 8.18 (s, 0.3H), 7.85-7.81 (m, 1H), 7.52 (d, J=3.2 Hz, 0.7H), 7.47-7.42 (m, 1H), 7.31-7.24 (m, 1H), 7.17-7.12 (m, 1H), 7.00-6.89 (m, 1H), 6.19 (s, 0.3H), 6.07 (d, J=2.8 Hz, 0.7H), 4.61-4.51 (m, 1H), 4.26-4.14 (m, 1.3H), 4.02-3.79 (m, 2.7H), 3.63-3.57 (m, 3H), 3.35-3.26 (m, 1H), 3.13-2.92 (m, 4H), 2.32-2.21 (m, 0.7H), 2.13-2.02 (m, 1H), 1.99-1.81 (m, 1.6H), 1.76-1.69 (m, 0.7H), 1.65-1.55 (m, 8H), 1.46-1.38 (m, 2H).

Compound 304B: LC-MS (ESI): $R_T$=2.00 min, mass calcd. for $C_{29}H_{34}ClFN_4O_6S_2$ 652.2, m/z found 652.8 [M+H]$^+$. Chiral analysis (Column: Chiralpak IC 5 μm 4.6*250 mm; Mobile Phase: Hex:EtOH:DEA=60:40:0.2 at 1.0 mL/min; Temp: 30° C.; Wavelength: 230 nm, $R_T$=11.231 min). $^1$H NMR (400 MHz, CDCl$_3$) δ 8.18 (s, 0.3H), 7.83 (d, J=2.8 Hz, 1H), 7.52 (d, J=2.8 Hz, 0.7H), 7.47-7.41 (m, 1H), 7.31-7.24 (m, 1H), 7.17-7.11 (m, 1H), 7.00-6.89 (m, 1H), 6.19 (s, 0.3H), 6.07 (d, J=2.8 Hz, 0.7H), 4.62-4.52 (m, 1H), 4.26-4.13 (m, 1.3H), 4.05-3.79 (m, 2.7H), 3.63-3.57 (m, 3H), 3.35-3.25 (m, 1H), 3.12-2.87 (m, 4H), 2.31-2.20 (m, 0.7H), 2.14-2.03 (m, 1H), 1.99-1.82 (m, 1.6H), 1.76-1.69 (m, 0.7H), 1.65-1.56 (m, 8H), 1.46-1.38 (m, 2H).

Compound 308M and 308N: (trans)-Methyl 6-(1-((3-(tert-butoxycarbonyl)cyclobutyl)sulfonyl)piperidin-4-yl)-4-(3,4-difluoro-2-methylphenyl)-2-(thiazol-2-yl)-1,4-dihydropyrimidine-5-carboxylate and (cis)-methyl 6-(1-((3-(tert-butoxycarbonyl)cyclobutyl)sulfonyl)piperidin-4-yl)-4-(3,4-difluoro-2-methylphenyl)-2-(thiazol-2-yl)-1,4-dihydropyrimidine-5-carboxylate Separation condition: silica gel column chromatography (petroleum ether:ethyl acetate=5:1 to 2:1) to give a small polar fraction, which was further purified by C18 column (acetonitrile:water=70% to 75%) to give the title compounds 308M (80 mg, 23% yield) as yellow solids and 308N (70 mg, 22% yield) as yellow solids.

Intermediate 308M: LC-MS (ESI): $R_T$=4.436 min, mass calcd. for $C_{30}H_{36}F_2N_4O_6S_2$ 650.2, m/z found 651.3 [M+H]$^+$. $^1$H NMR (400 MHz, CDCl$_3$) δ 8.15 (s, 0.6H), 7.82-7.80 (m, 1H), 7.52 (d, J=3.2 Hz, 0.4H), 7.43 (d, J=3.2 Hz, 0.6H), 7.29-7.27 (m, 0.4H), 7.08-7.05 (m, 0.7H), 6.99-6.94 (m, 0.3H), 6.92-6.87 (m, 1H), 5.93 (s, 0.6H), 5.84 (d, J=2.0 Hz, 0.4H), 4.22-4.14 (m, 0.5H), 4.04-3.77 (m, 3.5H), 3.59 (s, 1.8H), 3.58 (s, 1.2H), 3.22-3.13 (m, 1H), 2.98-2.85 (m, 2H), 2.82-2.71 (m, 2H), 2.62-2.53 (m, 3.8H), 2.42 (d, J=2.4 Hz, 1.2H), 2.20-1.73 (m, 4H), 1.48 (s, 5H), 1.47 (s, 4H).

Intermediate 308N: LC-MS (ESI): $R_T$=3.620 min, mass calcd. for $C_{30}H_{36}F_2N_4O_6S_2$ 650.2, m/z found 650.9 [M+H]$^+$. $^1$H NMR (400 MHz, CDCl$_3$) δ 8.17 (s, 0.6H), 7.81 (d, J=3.2 Hz, 1H), 7.53 (d, J=2.4 Hz, 0.4H), 7.43 (d, J=3.2 Hz, 0.6H), 7.29-7.28 (m, 0.4H), 7.10-7.05 (m, 0.7H), 7.00-6.94 (m, 0.3H), 6.91-6.87 (m, 1H), 5.93 (s, 0.6H), 5.84 (d, J=2.0 Hz, 0.4H), 4.23-4.15 (m, 0.5H), 4.06-3.90 (m, 2H), 3.84-3.76 (m, 0.5H), 3.72-3.64 (m, 1H), 3.59 (s, 1.8H), 3.58 (s, 1.2H), 3.04-2.86 (m, 3H), 2.81-2.70 (m, 2H), 2.58-2.47 (m, 4H), 2.42 (d, J=2.0 Hz, 1H), 2.18-1.76 (m, 4H), 1.46 (s, 4H), 1.45 (s, 5H).

Compound 310: Methyl 6-(1-((3-(tert-butoxycarbonyl)cyclopentyl)sulfonyl)-piperidin-4-yl)-4-(2-chloro-4-fluorophenyl)-2-(thiazol-2-yl)-1,4-dihydropyrimidine-5-carboxylate LC-MS (ESI): $R_T$=5.260 min and 5.392 min, mass calcd. for $C_{30}H_{36}ClFN_4O_6S_2$ 666.2, m/z found 667.1 [M+H]$^+$. $^1$H NMR (400 MHz, DMSO-d$_6$) δ 9.52 (d, J=3.6 Hz, 0.8H), 9.15 (s, 0.2H), 8.01-7.98 (m, 1.8H), 7.93 (d, J=3.2 Hz, 0.2H), 7.44-7.31 (m, 2H), 7.23-7.17 (m, 1H), 6.02 (s, 0.2H), 5.92 (d, J=3.6 Hz, 0.8H), 4.00-3.91 (m, 0.2H), 3.79-3.69 (m, 3.8H), 3.53 (s, 2.4H), 3.52 (s, 0.6H), 2.95-2.72 (m, 3H), 2.33-1.59 (m, 10H), 1.41-1.40 (m, 9H).

A racemic mixture of methyl 6-(1-((3-(tert-butoxycarbonyl)cyclopentyl)sulfonyl)-piperidin-4-yl)-4-(2-chloro-4-fluorophenyl)-2-(thiazol-2-yl)-1,4-dihydropyrimidine-5-carboxylate 310 (500 mg, 0.750 mmol) was separated by chiral Prep. HPLC (Column: Chiralpak IB 5 μm 20*250 mm; Mobile Phase: Hex:EtOH:DEA=90:10:0.3 at 15 mL/min; Temp: 30° C.; Wavelength: 214 nm) to afford the title compounds 310X (233 mg, 47% yield) and 310Y (183 mg, 37% yield) as yellow solids.

Intermediate 310X: LC-MS (ESI): $R_T$=4.482 min, mass calcd. for $C_{30}H_{36}ClFN_4O_6S_2$ 666.2, m/z found 667.3 [M+H]$^+$. Chiral analysis (Column: Chiralpak IB 5 μm 4.6*250 mm; Mobile Phase: Hex:EtOH:DEA=85:15:0.2 at 1.0 mL/min; Temp: 30° C.; Wavelength: 230 nm, $R_T$=7.745 and 7.932 min). $^1$H NMR (400 MHz, DMSO-d$_6$) δ 9.52 (d, J=3.6 Hz, 0.8H), 9.15 (s, 0.2H), 8.01-7.92 (m, 2H), 7.43-7.34 (m, 2H), 7.23-7.18 (m, 1H), 6.02 (s, 0.2H), 5.92 (d, J=3.6 Hz, 0.8H), 4.00-3.93 (m, 0.2H), 3.79-3.72 (m, 3.8H), 3.53 (s, 2.4H), 3.52 (s, 0.6H), 2.96-2.81 (m, 3H), 2.18-1.59 (m, 10H), 1.41-1.40 (m, 9H).

Intermediate 310Y: LC-MS (ESI): $R_T$=4.285 min, mass calcd. for $C_{30}H_{36}ClFN_4O_6S_2$ 666.2, m/z found 667.2 [M+H]$^+$. Chiral analysis (Column: Chiralpak IB 5 μm 4.6*250 mm; Mobile Phase: Hex:EtOH:DEA=85:15:0.2 at 1.0 mL/min; Temp: 30° C.; Wavelength: 230 nm, $R_T$=9.191 and 9.699 min). $^1$H NMR (400 MHz, DMSO-d$_6$) δ 9.52 (d, J=3.6 Hz, 0.8H), 9.16 (s, 0.2H), 8.00-7.92 (m, 2H), 7.43-

7.31 (m, 2H), 7.23-7.18 (m, 1H), 6.02 (s, 0.2H), 5.92 (d, J=3.6 Hz, 0.8H), 4.00-3.93 (m, 0.2H), 3.79-3.67 (m, 3.8H), 3.53 (s, 2.4H), 3.52 (s, 0.6H), 2.95-2.86 (m, 2H), 2.80-2.72 (m, 1H), 2.33-2.24 (m, 1H), 2.05-1.76 (m, 8H), 1.62-1.56 (m, 1H), 1.41-1.40 (m, 9H).

Compound 312: Methyl 6-(1-((4-(tert-butoxycarbonyl)cyclohexyl)sulfonyl)-piperidin-4-yl)-4-(2-chloro-4-fluorophenyl)-2-(thiazol-2-yl)-1,4-dihydropyrimidine-5-carboxylate LC-MS (ESI): $R_T$=2.251 min, mass calcd. for $C_{31}H_{38}ClFN_4O_6S_2$ 680.2, m/z found 681.1 [M+H]$^+$. $^1$H NMR (400 MHz, DMSO-$d_6$) δ 9.51 (s, 0.8H), 9.15 (s, 0.2H), 8.01-7.92 (m, 2H), 7.44-7.31 (m, 2H), 7.23-7.17 (m, 1H), 6.02 (s, 0.2H), 5.92 (d, J=3.6 Hz, 0.8H), 4.01-3.93 (m, 0.2H), 3.79-3.72 (m, 2.8H), 3.53 (s, 2.4H), 3.52 (s, 0.6H), 3.22-3.11 (m, 1H), 3.02-2.71 (m, 2H), 2.58-2.54 (m, 1H), 2.23-1.75 (m, 7.7H), 1.64-1.37 (m, 13.3H).

A racemic mixture of methyl 6-(1-((4-(tert-butoxycarbonyl)cyclohexyl)sulfonyl)-piperidin-4-yl)-4-(2-chloro-4-fluorophenyl)-2-(thiazol-2-yl)-1,4-dihydropyrimidine-5-carboxylate Compound 312 (160 mg, 0.240 mmol) was separated by chiral Prep. HPLC (Column: Chiralpak IC 5 µm 20*250 mm; Mobile Phase: Hex:EtOH:DEA=50:50:0.3 at 10 mL/min; Temp: 30° C.; Wavelength: 230 nm) to afford the title compounds Compound 312X (40 mg, 58% yield, 100% stereopure) and Compound 312Y (45 mg, 28% yield, 100% stereopure) as yellow solids.

Intermediate Compound 312X (cis): LC-MS (ESI): $R_T$=3.906 min, mass calcd. for $C_{31}H_{38}ClFN_4O_6S_2$ 680.2, m/z found 681.1 [M+H]$^+$. Chiral analysis (Column: Chiralpak IC 5 µm 4.6*250 mm; Mobile Phase: Hex:EtOH:DEA=50:50:0.2 at 1.0 mL/min; Temp: 30° C.; Wavelength: 230 nm, $R_T$=6.838 min). $^1$H NMR (400 MHz, DMSO-$d_6$) δ 9.51 (d, J=3.2 Hz, 0.7H), 9.15 (s, 0.3H), 8.00 (s, 1.7H), 7.93 (s, 0.3H), 7.43-7.34 (m, 2H), 7.23-7.18 (m, 1H), 6.01 (s, 0.3H), 5.92 (d, J=3.2 Hz, 0.7H), 3.96 (br s, 0.3H), 3.82-3.73 (m, 2.7H), 3.53 (s, 3H), 3.22-3.17 (m, 1H), 2.93 (q, J=12.0 Hz, 2H), 2.55-2.51 (m, 1H), 2.07-1.74 (m, 7.3H), 1.64-1.51 (m, 4.7H), 1.42 (s, 9H).

Intermediate Compound 312Y(tran): LC-MS (ESI): $R_T$=5.024 min, mass calcd. for $C_{31}H_{38}ClFN_4O_6S_2$ 680.2, m/z found 681.1 [M+H]$^+$. Chiral analysis (Column: Chiralpak IC 5 µm 4.6*250 mm; Mobile Phase: Hex:EtOH:DEA=50:50:0.2 at 1.0 mL/min; Temp: 30° C.; Wavelength: 230 nm, $R_T$=8.891 min). $^1$H NMR (400 MHz, DMSO-$d_6$) δ 9.52 (d, J=3.6 Hz, 0.8H), 9.15 (s, 0.2H), 8.00-7.92 (m, 2H), 7.44-7.31 (m, 2H), 7.23-7.17 (m, 1H), 6.02 (s, 0.2H), 5.92 (d, J=3.6 Hz, 0.8H), 4.03-3.93 (m, 0.2H), 3.79-3.72 (m, 2.8H), 3.53 (s, 2.4H), 3.52 (s, 0.6H), 3.17-3.11 (m, 1H), 3.01-2.95 (m, 2H), 2.23-2.16 (m, 1H), 2.09-1.74 (m, 7H), 1.61-1.51 (m, 1H), 1.48-1.33 (m, 13H).

Compound 318M and 318N: (trans)-Ethyl 6-(1-(3-(tert-butoxycarbonyl)cyclobutyl)sulfonyl)piperidin-4-yl)-4-(2-chloro-3-fluorophenyl)-2-(thiazol-2-yl)-1,4-dihydropyrimidine-5-carboxylate and (cis)-ethyl 6-(1-(3-(tert-butoxycarbonyl)cyclobutyl)sulfonyl)piperidin-4-yl)-4-(2-chloro-3-fluorophenyl)-2-(thiazol-2-yl)-1,4-dihydropyrimidine-5-carboxylate purified by silica gel column chromatography (petroleum ether:ethyl acetate=6:1 to 3:1) to give part 1 and part 2. Part 1 was further purified by Prep. HPLC (Column: Gilson Xbridge C18 (5 µm 19*150 mm), Mobile Phase A: water (0.1% ammonium bicarbonate), Mobile Phase B: acetonitrile, UV: 214 nm, Flow rate: 15 mL/min, Gradient: 55-95% (% B)) to give the title compound 318M (380 mg, 32% yield) as yellow solids. Part 2 was further purified by Prep. HPLC (Column: Gilson Xbridge C18 (5 µm 19*150 mm), Mobile Phase A: water (0.1% ammonium bicarbonate), Mobile Phase B: acetonitrile, UV: 214 nm, Flow rate: 15 mL/min, Gradient: 60-95% (% B)) to give the title compound 318N (330 mg, 28% yield) as yellow solids.

Compound 318M: LC-MS (ESI): $R_T$=3.959 min, mass calcd. for $C_{30}H_{36}ClFN_4O_6S_2$ 666.2, m/z found 667.1 [M+H]$^+$. $^1$H NMR (400 MHz, DMSO-$d_6$) δ 9.56 (d, J=3.2 Hz, 0.8H), 9.08 (s, 0.2H), 8.00-7.98 (m, 1.8H), 7.93 (d, J=3.2 Hz, 0.2H), 7.40-7.29 (m, 2H), 7.23-7.18 (m, 1H), 6.09 (s, 0.2H), 5.99 (d, J=3.2 Hz, 0.8H), 4.04-3.92 (m, 3.2H), 3.78-3.71 (m, 2.8H), 3.16-3.08 (m, 1H), 2.91-2.83 (m, 2H), 2.61-2.53 (m, 4H), 1.99-1.76 (m, 3H), 1.62-1.59 (m, 1H), 1.43 (s, 1.8H), 1.42 (s, 7.2H), 1.08-1.01 (m, 3H).

Compound 318N: LC-MS (ESI): $R_T$=3.654 min, mass calcd. for $C_{30}H_{36}ClFN_4O_6S_2$ 666.2, m/z found 667.1 [M+H]$^+$. $^1$H NMR (400 MHz, CD$_3$OD) δ 7.93 (d, J=2.8 Hz, 0.3H), 7.88 (d, J=2.8 Hz, 0.7H), 7.75 (d, J=3.2 Hz, 0.7H), 7.73 (d, J=3.6 Hz, 0.3H), 7.32-7.11 (m, 3H), 6.21 (s, 0.3H), 6.14 (s, 0.7H), 4.07-4.00 (m, 2H), 3.97-3.82 (m, 4H), 3.16-3.06 (m, 1H), 3.00-2.89 (m, 2H), 2.68-2.50 (m, 4H), 2.16-1.85 (m, 3.3H), 1.71-1.62 (m, 0.7H), 1.46 (s, 6.3H), 1.45 (s, 2.7H), 1.13-1.09 (m, 3H).

A racemic mixture of (trans)-ethyl 6-(1-(3-(tert-butoxycarbonyl)cyclobutyl)sulfonyl)-piperidin-4-yl)-4-(2-chloro-3-fluorophenyl)-2-(thiazol-2-yl)-1,4-dihydropyrimidine-5-carboxylate 318M (200 mg, 0.30 mmol) was separated by chiral Prep. HPLC (Column: Chiralpak IE 5 µm 20*250 mm; Mobile Phase: Hex:EtOH=50:50 at 10 mL/min; Temp: 30° C.; Wavelength: 230 nm) to afford the title compounds 318X (85 mg, 43% yield, 100% stereopure) and 318Y (80 mg, 46% yield, 100% stereopure) as yellow solids.

Intermediate 318X: LC-MS (ESI): $R_T$=3.997 min, mass calcd. for $C_{30}H_{36}ClFN_4O_6S_2$ 666.2, m/z found 667.1 [M+H]$^+$. Chiral analysis (Column: Chiralpak IE 5 µm 4.6*250 mm; Mobile Phase: Hex:EtOH=50:50 at 1.0 mL/min; Temp: 30° C.; Wavelength: 254 nm; $R_T$=8.184 min). $^1$H NMR (400 MHz, CD$_3$OD) δ 7.89 (s, 1H), 7.74 (d, J=2.8 Hz, 1H), 7.30-7.14 (m, 3H), 6.20 (s, 0.3H), 6.14 (s, 0.7H), 4.06-3.86 (m, 6H), 3.31-3.14 (m, 1H), 3.00-2.90 (m, 2H), 2.73-2.58 (m, 4H), 2.14-1.86 (m, 3.3H), 1.80-1.61 (m, 0.7H), 1.47 (s, 9H), 1.11 (t, J=6.8 Hz, 3H).

Intermediate 318Y: LC-MS (ESI): $R_T$=3.992 min, mass calcd. for $C_{30}H_{36}ClFN_4O_6S_2$ 666.2, m/z found 667.1 [M+H]$^+$. Chiral analysis (Column: Chiralpak IE 5 µm 4.6*250 mm; Mobile Phase: Hex:EtOH=50:50 at 1.0 mL/min; Temp: 30° C.; Wavelength: 230 nm; $R_T$=9.519 min). $^1$H NMR (400 MHz, CD$_3$OD) δ 7.93 (s, 0.2H), 7.88 (d, J=2.4 Hz, 0.8H), 7.30-7.14 (m, 3H), 6.21 (s, 0.2H), 6.14 (s, 0.8H), 4.06-3.86 (m, 6H), 3.20-3.14 (m, 1H), 3.00-2.90 (m, 4H), 2.70-2.62 (m, 4H), 2.15-1.79 (m, 3.2H), 1.72-1.65 (m, 0.8H), 1.47 (s, 9H), 1.11 (t, J=7.2 Hz, 3H).

Compound 320A and 320B: (trans)-Ethyl 4-(2-chloro-3-fluorophenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate and (cis)ethyl 4-(2-chloro-3-fluorophenyl)-6-(1-((3-methyl-3-((2-(trimethylsilyl)ethoxy)carbonyl)cyclobutyl)-sulfonyl)piperidin-4-yl)-2-(thiazol-2-yl)-1,4-dihydropyrimidine-5-carboxylate Separation condition: purified by silica gel column chromatography (petroleum ether:ethyl acetate=5:1) to afford the title 320A (301 mg, 95% purity from 1H NMR, 37% yield) and 320B (300 mg, 95% purity from ¹H NMR, 37% yield) as yellow solids.

Compound 320A: ¹H NMR (400 MHz, CDCl₃) δ 8.15 (s, 0.3H), 7.83 (d, J=3.2 Hz, 1H), 7.52 (d, J=2.8 Hz, 0.7H), 7.45 (d, J=3.2 Hz, 0.3H), 7.39 (s, 0.7H), 7.25-7.17 (m, 1H), 7.14-7.03 (m, 2H), 6.27 (s, 0.3H), 6.15 (d, J=2.8 Hz, 0.7H), 4.25-4.21 (m, 2H), 4.07-4.00 (m, 2H), 3.97-3.80 (m, 4H), 2.95-2.87 (m, 2H), 2.83-2.74 (m, 2H), 2.52-2.44 (m, 2H), 2.25-2.15 (m, 1H), 2.09-2.02 (m, 1H), 1.97-1.68 (m, 2H), 1.48-1.46 (m, 3H), 1.13-1.08 (m, 3H), 1.05-1.01 (m, 2H), 0.07 (s, 9H).

Compound 320B: ¹H NMR (400 MHz, CDCl₃) δ 8.16 (s, 0.3H), 7.83 (d, J=3.2 Hz, 1H), 7.52 (d, J=3.2 Hz, 0.7H), 7.45 (d, J=2.8 Hz, 0.3H), 7.38 (s, 0.7H), 7.25-7.14 (m, 1H), 7.09-7.03 (m, 2H), 6.27 (s, 0.3H), 6.15 (d, J=2.8 Hz, 0.7H), 4.23-4.19 (m, 2H), 4.07-3.91 (m, 5H), 3.81-3.72 (m, 1H), 3.02-2.86 (m, 4H), 2.25-2.19 (m, 2H), 2.16-1.97 (m, 2H), 1.93-1.67 (m, 2H), 1.48 (s, 2H), 1.47 (s, 1H), 1.13-1.07 (m, 3H), 1.03-1.00 (m, 2H), 0.05 (s, 9H).

Compound 322C and 322D: (trans)-Methyl 4-(2-chloro-3,4-difluorophenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate and (cis)-methyl 4-(2-chloro-3,4-difluorophenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate Separation conditions: silica gel column chromatography (petroleum ether:ethyl acetate=5:1) to afford the title compound 322C (230 mg, 90% purity, 22% yield) and the title compound 322D (370 mg, 90% purity, 35% yield) as yellow solids.

compound 322C: ¹H NMR (400 MHz, CDCl₃) δ 8.12 (s, 0.3H), 7.76 (d, J=3.2 Hz, 1H), 7.46 (d, J=3.2 Hz, 0.7H), 7.40 (d, J=3.2 Hz, 0.3H), 7.36 (s, 0.7H), 7.34 (s, 0.4H), 7.02-6.97 (m, 2H), 6.11 (s, 0.4H), 5.99 (s, 0.6H), 4.19-4.17 (m, 2H), 4.06-3.82 (m, 4H), 3.54 (s, 2.1H), 3.52 (s, 0.9H), 2.85-2.80 (m, 2H), 2.76-2.70 (m, 2H), 2.45-2.39 (m, 2H), 2.12-2.03 (m, 1H), 1.98-1.57 (m, 3H), 1.39 (s, 3H), 0.99-0.93 (m, 2H), 0.03 (s, 9H).

322D: ¹H NMR (400 MHz, CDCl₃) δ 8.17 (s, 0.3H), 7.75 (s, 1H), 7.48 (s, 0.7H), 7.40 (s, 0.6H), 7.37 (s, 0.4H), 7.01-6.98 (m, 2H), 6.12-6.01 (m, 1H), 4.17-4.10 (m, 2H), 3.95-3.88 (m, 3H), 3.85-3.80 (m, 1H), 3.68 (s, 3H), 2.97-2.84 (m, 4H), 2.19-2.11 (m, 3H), 1.98-1.57 (m, 3H), 1.42 (s, 3H), 0.99-0.94 (m, 2H), 0.03 (s, 9H).

Compound 324: Methyl 6-(1-((1H-pyrazol-4-yl)sulfonyl)piperidin-4-yl)-4-(2-chloro-3,4-difluorophenyl)-2-(thiazol-2-yl)-1,4-dihydropyrimidine-5-carboxylate LC-MS (ESI): R_T=3.749 min, mass calcd. for C₂₃H₂₁ClF₂N₆O₄S₂ 582.1, m/z found 582.8 [M+H]⁺. ¹H NMR (400 MHz, DMSO-d₆) δ 13.77 (s, 1H), 9.63 (d, J=3.6 Hz, 0.8H), 9.23 (s, 0.2H), 8.39 (s, 1H), 8.04-7.99 (m, 1.8H), 7.94 (d, J=3.6 Hz, 0.2H), 7.85 (s, 1H), 7.49-7.40 (m, 1H), 7.23-7.12 (m, 1H), 6.00 (s, 0.2H), 5.91 (d, J=3.6 Hz, 0.8H), 3.80-3.64 (m, 2.2H), 3.56-3.50 (m, 0.8H), 3.48 (s, 2.4H), 3.47 (s, 0.6H), 2.29-2.16 (m, 2.2H), 2.10-1.98 (m, 2H), 1.95-1.84 (m, 1H), 1.82-1.73 (m, 1H), 1.67-1.60 (m, 0.8H).

Compound 328F and 328H: (trans)-Ethyl 6-(1-((3-(tert-butoxycarbonyl)cyclobutyl)sulfonyl)piperidin-4-yl)-4-(2-chloro-4-fluorophenyl)-2-(thiazol-2-yl)-1,4-dihydropyrimidine-5-carboxylate and (cis)-ethyl 6-(1-((-3-(tert-butoxycarbonyl)cyclobutyl)sulfonyl)piperidin-4-yl)-4-(2-chloro-4-fluorophenyl)-2-(thiazol-2-yl)-1,4-dihydropyrimidine-5-carboxylate Compound 328F: LC-MS (ESI): R_T=4.330 min, mass calcd. For C₃₀H₃₆ClFN₄O₆S₂ 666.2, m/z found 667.1 [M+H]⁺. Chiral analysis (Column: Chiralpak IE 5 µm 4.6*250 mm; Mobile Phase: Hex:EtOH=70:30 at 1.0 mL/min; Temp: 30° C.; Wavelength: 230 nm, R_T=15.325 min). ¹H NMR (400 MHz, DMSO-d₆) δ 9.49 (s, 0.8H), 9.07 (br s, 0.2H), 8.00-7.98 (m, 2H), 7.43-7.41 (m, 1H), 7.38-7.34 (m, 1H), 7.23-7.18 (m, 1H), 6.00 (br s, 0.2H), 5.93 (s, 0.8H), 4.02-3.95 (m, 3H), 3.77-3.71 (m, 3H), 3.17-3.08 (m, 1H), 2.91-2.83 (m, 2H), 2.60-2.51 (m, 4H), 1.96-1.93 (m, 1H), 1.84-1.76 (m, 2H), 1.61-1.58 (m, 1H), 1.42 (s, 9H), 1.07 (t, J=7.2 Hz, 3H).

Compound 328H: LC-MS (ESI): R_T=4.029 min, mass calcd. For C₃₀H₃₆ClFN₄O₆S₂ 666.2, m/z found 667.1 [M+H]⁺. Chiral analysis (Column: Chiralpak IA 5 µm 4.6*250 mm; Mobile Phase: Hex:EtOH=70:30 at 1.0 mL/min; Temp: 30° C.; Wavelength: 230 nm, R_T=7.610 min). ¹H NMR (400 MHz, DMSO-d₆) δ 9.50 (d, J=3.6 Hz, 0.8H), 9.06 (s, 0.2H), 8.00-7.98 (m, 1.8H), 7.93-7.92 (m, 0.2H), 7.43-7.40 (m, 1H), 7.38-7.34 (m, 1H), 7.24-7.19 (m, 1H), 6.03 (s, 0.2H), 5.93 (d, J=3.6 Hz, 0.8H), 4.00-3.93 (m, 3H), 3.73-3.67 (m, 3H), 3.10-3.05 (m, 1H), 2.88-2.78 (m, 2H), 2.48-2.40 (m, 4H), 2.04-1.93 (m, 1H), 1.90-1.82 (m, 2H), 1.62-1.57 (m, 1H), 1.41 (s, 9H), 1.09-1.03 (m, 3H).

Compound 330P and 330Q: (trans)-Methyl 6-(1-((3-(tert-butoxycarbonyl)cyclobutyl)sulfonyl)piperidin-4-yl)-4-(2-chloro-3-fluorophenyl)-2-(thiazol-2-yl)-1,4-dihydropyrimidine-5-carboxylate and (cis)-methyl 6-(1-((3-(tert-butoxycarbonyl)cyclobutyl)sulfonyl)piperidin-4-yl)-4-(2-chloro-3-fluorophenyl)-2-(thiazol-2-yl)-1,4-dihydropyrimidine-5-carboxylate Separation conditions: silica gel column chromatography (petroleum ether:ethyl acetate=5:1 to 3:1) followed by C18 column (acetonitrile:water=30% to 90%) to give the title compounds 330P (85 mg, 98.5% purity, 28% yield) and another crude product which was further purified by prep. HPLC (Column: Waters Kinete EVO C18 (5 µm, 21.2*150 mm), Mobile phase A: water (0.1% ammonium bicarbonate), Mobile phase B: acetonitrile, UV: 214 nm, Flow rate: 15 mL/min, 40-80% (% B)) to give 330Q (75 mg, 99.5% purity, 25% yield) as yellow solids.

Compound 330P: LC-MS (ESI): R_T=4.162 min, mass calcd. for C₂₉H₃₄ClFN₄O₆S₂ 652.2, m/z found 652.9 [M+H]⁺. ¹H NMR (400 MHz, DMSO-d₆) δ 9.57 (s, 0.8H), 9.15 (s, 0.2H), 8.04-7.93 (m, 2H), 7.41-7.27 (m, 2H), 7.24-7.15 (m, 1H), 6.07 (s, 0.2H), 5.98 (s, 0.8H), 4.05-3.93 (m, 1.2H), 3.82-3.66 (m, 2.8H), 3.52 (s, 3H), 3.18-3.07 (m, 1H), 2.95-2.81 (m, 2H), 2.63-2.50 (m, 4H), 2.12-2.03 (m, 0.2H), 2.01-1.90 (m, 1H), 1.88-1.70 (m, 2H), 1.65-1.55 (m, 0.8H), 1.42 (s, 9H).

Compound 330Q: LC-MS (ESI): R_T=4.297 min, mass calcd. for C₂₉H₃₄ClFN₄O₆S₂ 652.2, m/z found 653.3 [M+H]⁺. ¹H NMR (400 MHz, DMSO-d₆) δ 9.58 (d, J=3.6 Hz, 0.8H), 9.16 (s, 0.2H), 8.01 (s, 1.6H), 7.99 (d, J=2.8 Hz, 0.2H), 7.93 (d, J=2.8 Hz, 0.2H), 7.42-7.29 (m, 2H), 7.24-7.15 (m, 1H), 6.07 (s, 0.2H), 5.98 (d, J=3.6 Hz, 0.8H), 4.01-3.90 (m, 1.2H), 3.79-3.64 (m, 2.8H), 3.53 (s, 2.4H), 3.52 (s, 0.6H), 3.12-3.02 (m, 1H), 2.91-2.78 (m, 2H), 2.48-2.38 (m, 4H), 2.11-2.02 (m, 0.2H), 2.01-1.90 (m, 1H), 1.89-1.71 (m, 2H), 1.66-1.57 (m, 0.8H), 1.41 (s, 9H).

Compound 332M and 332N: (trans)-Ethyl 4-(2-bromo-4-fluorophenyl)-6-(1-(3-(tert-butoxycarbonyl)cyclobutyl)sulfonyl)piperidin-4-yl)-2-(thiazol-2-yl)-1,4-dihydropyrimidine-5-carboxylate and (cis)-ethyl 4-(2-bromo-4-fluorophenyl)-6-(1-(3-(tert-butoxycarbonyl)cyclobutyl)sulfonyl)piperidin-4-yl)-2-(thiazol-2-yl)-1,4-dihydropyrimidine-5-carboxylate Separation condition: silica gel column chromatography (petroleum ether:ethyl acetate=6:1 to 2:1), then further purified by Prep. HPLC (Column: Gilson X-bridge C18 (5 m 19*150 mm), Flow rate: 15 mL/min, Mobile Phase A: water (0.1% ammonium bicarbonate), Mobile Phase B: acetonitrile, Gradient: 75-85% (% B)) to give the title compound 332M (370 mg, 52% yield) and 332N (300 mg, 42% yield) as yellow solids.

Compound 332M: LC-MS (ESI): $R_T$=3.249 min, mass calcd. for $C_{30}H_{36}BrFN_4O_6S_2$ 710.1, m/z found 711.1 [M+H]$^+$. $^1$H NMR (400 MHz, CDCl$_3$) δ 8.14 (s, 0.3H), 7.82 (d, J=2.8 Hz, 1H), 7.51 (d, J=2.8 Hz, 0.7H), 7.44 (d, J=2.8 Hz, 0.3H), 7.41 (s, 0.7H), 7.33-7.27 (m, 2H), 7.03-6.94 (m, 1H), 6.18 (s, 0.3H), 6.05 (d, J=2.0 Hz, 0.7H), 4.21-4.15 (m, 0.3H), 4.09-3.84 (m, 5.7H), 3.21-3.14 (m, 1H), 2.98-2.87 (m, 2H), 2.82-2.72 (m, 2H), 2.63-2.53 (m, 2H), 2.21-2.18 (m, 0.7H), 2.17-1.77 (m, 2.6H), 1.70 (br s, 0.7H), 1.47 (s, 9H), 1.14-1.08 (m, 3H).

Compound 332N: LC-MS (ESI): $R_T$=2.896 min, mass calcd. for $C_{30}H_{36}BrFN_4O_6S_2$ 710.1, m/z found 711.1 [M+H]$^+$. $^1$H NMR (400 MHz, CDCl$_3$) δ 8.15 (s, 0.3H), 7.83-7.81 (m, 1H), 7.52 (d, J=3.2 Hz, 0.7H), 7.44 (d, J=3.2 Hz, 0.3H), 7.40 (d, J=2.0 Hz, 0.7H), 7.33-7.28 (m, 2H), 7.03-6.94 (m, 1H), 6.18 (s, 0.3H), 6.06 (d, J=2.4 Hz, 0.7H), 4.21-4.15 (m, 0.3H), 4.08-3.87 (m, 4.7H), 3.74-3.63 (m, 1H), 3.06-2.86 (m, 3H), 2.82-2.70 (m, 2H), 2.58-2.47 (m, 2H), 2.24-2.14 (m, 0.7H), 2.09-1.97 (m, 1H), 1.92-1.78 (m, 1.3H), 1.70-1.63 (m, 1H), 1.46 (s, 6.3H), 1.45 (s, 2.7H), 1.14-1.08 (m, 3H).

Racemic 332M (300 mg, 0.420 mmol) was separated by chiral Prep. HPLC (Column: Chiralpak IE 5 μm 20*250 mm; Mobile Phase: Hex:EtOH=70:30 at 14 mL/min; Temp: 30° C.; Wavelength: 214 nm) to afford the title compounds 332X (90 mg, 30% yield, 100% stereopure) and 332Y (75 mg, 25% yield, 99.5% stereopure) as yellow solids.

Compound 332X: LC-MS (ESI): $R_T$=4.122 min, mass calcd. for $C_{30}H_{36}BrFN_4O_6S_2$ 710.1, m/z found 711.0 [M+H]$^+$. Chiral analysis (Column: Chiralpak IE 5 μm 4.6*250 mm; Mobile Phase: Hex:EtOH=70:30 at 1.0 mL/min; Temp: 30° C.; Wavelength: 230 nm; $R_T$=12.685 min). $^1$H NMR (400 MHz, CD$_3$OD) δ 7.93 (d, J=3.2 Hz, 0.3H), 7.89 (d, J=3.2 Hz, 0.7H), 7.74 (d, J=3.2 Hz, 0.7H), 7.73 (d, J=3.2 Hz, 0.3H), 7.43-7.37 (m, 2H), 7.14-7.06 (m, 1H), 6.13 (s, 0.3H), 6.06 (s, 0.7H), 4.14-3.83 (m, 6H), 3.23-3.14 (m, 1H), 3.04-2.89 (m, 2H), 2.74-2.57 (m, 4H), 2.16-1.85 (m, 3.3H), 1.69-1.63 (m, 0.7H), 1.48 (s, 2.7H), 1.47 (s, 6.3H), 1.12 (t, J=7.2 Hz, 3H).

Compound 332Y: LC-MS (ESI): $R_T$=4.117 min, mass calcd. for $C_{30}H_{36}BrFN_4O_6S_2$ 710.1, m/z found 711.1 [M+H]$^+$. Chiral analysis (Column: Chiralpak IE 5 μm 4.6*250 mm; Mobile Phase: Hex:EtOH=70:30 at 1.0 mL/min; Temp: 30° C.; Wavelength: 230 nm; $R_T$=15.270 min). $^1$H NMR (400 MHz, CD$_3$OD) δ 7.93 (d, J=2.8 Hz, 0.3H), 7.89 (d, J=3.2 Hz, 0.7H), 7.74 (d, J=3.2 Hz, 0.7H), 7.73 (d, J=3.2 Hz, 0.3H), 7.43-7.37 (m, 2H), 7.13-7.06 (m, 1H), 6.13 (s, 0.3H), 6.06 (s, 0.7H), 4.13-3.85 (m, 6H), 3.22-3.14 (m, 1H), 3.04-2.90 (m, 2H), 2.74-2.56 (m, 4H), 2.16-1.85 (m, 3.3H), 1.69-1.63 (m, 0.7H), 1.48 (s, 2.7H), 1.47 (s, 6.3H), 1.12 (t, J=7.2 Hz, 3H).

Compound 334: Methyl 6-(1-((3-((tert-butyldiphenylsilyl)oxy)cyclobutyl)-sulfonyl)piperidin-4-yl)-4-(2-chloro-4-fluorophenyl)-2-(thiazol-2-yl)-1,4-dihydropyrimidine-5-carboxylate $^1$H NMR (400 MHz, CDCl$_3$) δ 8.16-8.14 (m, 1H), 7.82-7.80 (m, 1H), 7.65-7.61 (m, 4H), 7.45-7.36 (m, 8H), 7.16-7.12 (m, 1H), 7.00-6.97 (m, 1H), 6.18 (s, 0.3H), 6.06 (s, 0.7H), 4.67-4.60 (m, 0.5H), 4.16-4.14 (m, 0.5H), 3.98-3.84 (m, 2.7H), 3.79-3.74 (m, 0.3H), 3.60 (s, 1H), 3.59 (s, 2H), 3.12-3.04 (m, 0.5H), 2.92-2.42 (m, 6H), 2.21-2.14 (m, 0.5H), 2.00-1.76 (m, 2.3H), 1.67-1.64 (m, 0.7H), 1.06 (s, 4.5H), 1.04 (s, 4.5H), 0.95-0.80 (m, 1H).

Compound 338M and 338N: (trans)-Ethyl 4-(2-bromo-3-fluorophenyl)-6-(1-((3-(tert-butoxycarbonyl)cyclobutyl)sulfonyl)piperidin-4-yl)-2-(thiazol-2-yl)-1,4-dihydropyrimidine-5-carboxylate and (cis)-ethyl 4-(2-bromo-3-fluorophenyl)-6-(1-((3-(tert-butoxycarbonyl)cyclobutyl)sulfonyl)piperidin-4-yl)-2-(thiazol-2-yl)-1,4-dihydropyrimidine-5-carboxylate Compound 338M: LC-MS (ESI): $R_T$=4.457 min, mass calcd. for $C_{30}H_{36}BrFN_4O_6S_2$ 710.1, m/z found 711.0 [M+H]$^+$. $^1$H NMR (400 MHz, DMSO-d$_6$) δ 9.51 (d, J=3.2 Hz, 0.7H), 9.08 (s, 0.3H), 8.00-7.92 (m, 2H), 7.44-7.38 (m, 1H), 7.31-7.15 (m, 2H), 6.07 (s, 0.3H), 5.98 (d, J=3.6 Hz, 0.7H), 4.04-3.93 (m, 3.3H), 3.78-3.70 (m, 2.7H), 3.16-3.08 (m, 1H), 2.92-2.82 (m, 2H), 2.67-2.52 (m, 4H), 2.05-1.74 (m, 3.2H), 1.62-1.59 (m, 0.8H), 1.43-1.42 (m, 9H), 1.08-1.01 (m, 3H).

Compound 338N: LC-MS (ESI): $R_T$=4.103 min, mass calcd. for $C_{30}H_{36}BrFN_4O_6S_2$ 710.1, m/z found 711.0 [M+H]$^+$. $^1$H NMR (400 MHz, DMSO-d$_6$) δ 9.51 (d, J=3.2 Hz, 0.7H), 9.08 (s, 0.3H), 8.00-7.92 (m, 2H), 7.44-7.38 (m, 1H), 7.31-7.15 (m, 2H), 6.07 (s, 0.3H), 5.98 (d, J=3.6 Hz, 0.7H), 4.04-3.93 (m, 3.3H), 3.78-3.70 (m, 2.7H), 3.16-3.08 (m, 1H), 2.92-2.82 (m, 2H), 2.67-2.52 (m, 4H), 2.05-1.74 (m, 3.2H), 1.62-1.59 (m, 0.8H), 1.42 (s, 9H), 1.08-1.01 (m, 3H).

Racemic 338M (360 mg, 0.510 mmol) was separated by chiral Prep. HPLC (separation condition: Column: Chiralpak ID 5 Lm 20*250 mm; Mobile Phase: Hex:IPA:DEA=50:50:0.3 at 12 mL/min; Temp: 30° C.; Wavelength: 230 nm) to afford the title compounds 338A (130 mg, 36% yield, 100% stereopure) and 338B (150 mg, 42% yield, 98.1% stereopure).

Compound 338A: LC-MS (ESI): $R_T$=4.684 min, mass calcd. for $C_{30}H_{36}BrFN_4O_6S_2$ 710.1, m/z found 711.1 [M+H]$^+$. Chiral analysis (Column: Chiralpak ID 5 am 4.6*250 mm; Mobile Phase: Hex:IPA:DEA=50:50:0.2 at 1.0 mL/min; Temp: 30° C.; Wavelength: 230 nm, $R_T$=8.521 min). $^1$H NMR (400 MHz, DMSO-d$_6$) δ 9.52 (d, J=2.4 Hz, 0.7H), 9.09 (s, 0.3H), 8.00-7.93 (m, 2H), 7.44-7.38 (m, 1H), 7.29 (t, J=8.8 Hz, 1H), 7.21-7.15 (m, 1H), 6.07 (s, 0.3H), 5.98 (d, J=3.2 Hz, 0.7H), 4.04-3.95 (m, 3.3H), 3.78-3.71 (m, 2.7H), 3.16-3.08 (m, 1H), 2.91-2.83 (m, 2H), 2.61-2.53 (m, 4H), 2.08-1.77 (m, 3.3H), 1.63-1.58 (m, 0.7H), 1.42 (s, 9H), 1.06 (t, J=6.8 Hz, 3H).

Compound 338B: LC-MS (ESI): $R_T$=4.684 min, mass calcd. for $C_{30}H_{36}BrFN_4O_6S_2$ 710.1, m/z found 713.1 [M+H]$^+$. Chiral analysis (Column: Chiralpak ID 5 am 4.6*250 mm; Mobile Phase: Hex:IPA:DEA=50:50:0.2 at 1.0 mL/min; Temp: 30° C.; Wavelength: 230 nm, $R_T$=10.348 min). $^1$H NMR (400 MHz, DMSO-d$_6$) δ 9.52 (d, J=3.6 Hz, 0.7H), 9.09 (s, 0.3H), 8.00-7.92 (m, 2H), 7.44-7.37 (m, 1H), 7.32-7.24 (m, 1H), 7.21-7.15 (m, 1H), 6.07 (s, 0.3H), 5.98 (d, J=3.6 Hz, 0.7H), 4.04-3.92 (m, 3.3H), 3.81-3.70 (m, 2.7H), 3.16-3.08 (m, 1H), 2.92-2.82 (m, 2H), 2.61-2.54 (m, 4H), 2.10-1.77 (m, 3.3H), 1.62-1.59 (m, 0.7H), 1.43-1.42 (m, 9H), 1.08-1.01 (m, 3H).

Racemic 338N (280 mg, 0.390 mmol) was separated by chiral Prep. HPLC (separation condition: Column: Chiralpak ID 5 μm 20*250 mm; Mobile Phase: Hex:EtOH:DEA=60:40:0.3 at 12 mL/min; Temp: 30° C.; Wavelength: 230 nm) to afford the title compounds 338C (100 mg, 36% yield, 100% stereopure) and 338D (110 mg, 39% yield, 97.3% stereopure) as yellow solids.

Compound 338C: LC-MS (ESI): $R_T$=4.576 min, mass calcd. for $C_{30}H_{36}BrFN_4O_6S_2$ 710.1, m/z found 713.1 [M+H]$^+$. Chiral analysis (analytical condition: Column: Chiralpak ID 5 μm 4.6*250 mm; Mobile Phase: Hex:EtOH:DEA=60:40:0.2 at 1.0 mL/min; Temp: 30° C.; Wavelength: 230 nm, $R_T$=7.731 min). $^1$H NMR (400 MHz, DMSO-d$_6$) δ 9.52 (d, J=3.2 Hz, 0.7H), 9.09 (s, 0.3H), 8.01-7.92 (m, 2H), 7.44-7.37 (m, 1H), 7.31-7.24 (m, 1H), 7.21-7.15 (m, 1H), 6.07 (s, 0.3H), 5.97 (d, J=3.6 Hz, 0.7H), 4.00-3.91 (m, 3.3H), 3.76-3.67 (m, 2.7H), 3.12-3.03 (m, 1H), 2.88-2.80 (m, 2H), 2.48-2.33 (m, 4H), 2.10-1.77 (m, 3.3H), 1.63-1.57 (m, 0.7H), 1.41 (s, 9H), 1.08-1.01 (m, 3H).

Compound 338D: LC-MS (ESI): $R_T$=4.575 min, mass calcd. for $C_{30}H_{36}BrFN_4O_6S_2$ 710.1, m/z found 711.1 [M+H]$^+$. Chiral analysis (Column: Chiralpak ID 5 jam 4.6*250 mm; Mobile Phase: Hex:EtOH:DEA=60:40:0.2 at 1.0 mL/min; Temp: 30° C.; Wavelength: 230 nm, $R_T$=9.220 min). $^1$H NMR (400 MHz, DMSO-d$_6$) δ 9.52 (d, J=3.2 Hz, 0.7H), 9.09 (s, 0.3H), 8.01-7.92 (m, 2H), 7.44-7.37 (m, 1H), 7.31-7.24 (m, 1H), 7.21-7.15 (m, 1H), 6.07 (s, 0.3H), 5.97 (d, J=3.6 Hz, 0.7H), 4.00-3.91 (m, 3.3H), 3.76-3.67 (m, 2.7H), 3.12-3.03 (m, 1H), 2.88-2.80 (m, 2H), 2.48-2.33 (m, 4H), 2.10-1.77 (m, 3.3H), 1.63-1.57 (m, 0.7H), 1.41 (s, 9H), 1.08-1.01 (m, 3H).

Compound 342X and 342Y: (trans)-Ethyl 6-(1-((3-(tert-butoxycarbonyl)cyclobutyl)sulfonyl)piperidin-4-yl)-4-(3,4-difluoro-2-methylphenyl)-2-(thiazol-2-yl)-1,4-dihydropyrimidine-5-carboxylate and (cis)-ethyl 6-(1-((3-(tert-butoxycarbonyl)cyclobutyl)sulfonyl)piperidin-4-yl)-4-(3,4-difluoro-2-methylphenyl)-2-(thiazol-2-yl)-1,4-dihydropyrimidine-5-carboxylate Compound 342X: LC-MS (ESI): $R_T$=3.760 min, mass calcd. for $C_{31}H_{38}F_2N_4O_6S_2$ 664.2, m/z found 665.3 [M+H]$^+$. $^1$H NMR (400 MHz, CDCl$_3$) δ 8.11 (s, 0.6H), 7.81-7.80 (m, 1H), 7.52 (d, J=2.8 Hz, 0.4H), 7.43 (d, J=2.8 Hz, 0.6H), 7.09-7.04 (m, 0.8H), 6.99-6.95 (m, 0.4H), 6.92-6.86 (m, 1.2H), 5.94 (s, 0.6H), 5.85 (d, J=2.0 Hz, 0.4H), 4.21-4.15 (m, 0.5H), 4.10-3.76 (m, 5.5H), 3.22-3.13 (m, 1H), 2.97-2.85 (m, 2H), 2.82-2.72 (m, 2H), 2.62-2.53 (m, 3.7H), 2.42 (d, J=1.6 Hz, 1.3H), 2.20-2.01 (m, 1.5H), 1.96-1.73 (m, 2.2H), 1.70-1.67 (m, 0.3H), 1.48 (s, 9H), 1.11 (t, J=7.2 Hz, 3H).

Compound 342Y: LC-MS (ESI): $R_T$=3.747 min, mass calcd. for $C_{31}H_{38}F_2N_4O_6S_2$ 664.2, m/z found 665.3 [M+H]$^+$. $^1$H NMR (400 MHz, CDCl$_3$) δ 8.11 (s, 0.6H), 7.81-7.80 (m, 1H), 7.52 (d, J=3.2 Hz, 0.4H), 7.43 (d, J=3.2 Hz, 0.6H), 7.09-7.03 (m, 0.8H), 6.99-6.94 (m, 0.4H), 6.92-6.86 (m, 1.2H), 5.94 (s, 0.6H), 5.86 (d, J=2.0 Hz, 0.4H), 4.23-4.15 (m, 0.6H), 4.09-3.91 (m, 4H), 3.84-3.77 (m, 0.4H), 3.72-3.63 (m, 1H), 3.06-2.85 (m, 3H), 2.81-2.70 (m, 2H), 2.57-2.48 (m, 3.8H), 2.42 (d, J=2.0 Hz, 1.2H), 2.20-2.01 (m, 1.5H), 1.95-1.76 (m, 2.2H), 1.64-1.61 (m, 0.3H), 1.46 (s, 9H), 1.11 (t, J=7.2 Hz, 3H).

Compound 342M and 342N: (trans)-Ethyl 6-(1-((3-(tert-butoxycarbonyl)cyclobutyl)sulfonyl)piperidin-4-yl)-4-(3,4-difluoro-2-methylphenyl)-2-(thiazol-2-yl)-1,4-dihydropyrimidine-5-carboxylate and (cis)-ethyl 6-(1-((3-(tert-butoxycarbonyl)cyclobutyl)sulfonyl)piperidin-4-yl)-4-(3,4-difluoro-2-methylphenyl)-2-(thiazol-2-yl)-1,4-dihydropyrimidine-5-carboxylate Compound 342M: LC-MS (ESI): $R_T$=3.632 min, mass calcd. for $C_{31}H_{38}F_2N_4O_6S_2$ 664.2, m/z found 665.3 [M+H]$^+$. $^1$H NMR (400 MHz, CDCl$_3$) δ 8.11 (s, 0.6H), 7.81-7.80 (m, 1H), 7.52 (d, J=2.8 Hz, 0.4H), 7.43 (d, J=2.8 Hz, 0.6H), 7.08-7.04 (m, 0.8H), 6.99-6.93 (m, 0.4H), 6.92-6.86 (m, 1.2H), 5.94 (s, 0.6H), 5.85 (d, J=2.0 Hz, 0.4H), 4.22-4.15 (m, 0.5H), 4.10-3.76 (m, 5.5H), 3.22-3.12 (m, 1H), 2.98-2.85 (m, 2H), 2.82-2.72 (m, 2H), 2.62-2.53 (m, 3.7H), 2.42 (d, J=1.6 Hz, 1.3H), 2.20-2.01 (m, 1.5H), 1.96-1.73 (m, 2.2H), 1.70-1.67 (m, 0.3H), 1.48 (s, 9H), 1.11 (t, J=7.2 Hz, 3H).

Compound 342N: LC-MS (ESI): $R_T$=2.888 min, mass calcd. for $C_{31}H_{38}F_2N_4O_6S_2$ 664.2, m/z found 665.3 [M+H]$^+$. $^1$H NMR (400 MHz, CDCl$_3$) δ 8.13 (s, 0.6H), 7.81-7.80 (m, 1H), 7.52 (d, J=3.2 Hz, 0.4H), 7.43 (d, J=3.2 Hz, 0.6H), 7.09-7.04 (m, 0.8H), 6.99-6.94 (m, 0.4H), 6.92-6.86 (m, 1.2H), 5.94 (s, 0.6H), 5.86 (d, J=2.0 Hz, 0.4H), 4.23-4.15 (m, 0.6H), 4.09-3.91 (m, 4H), 3.85-3.77 (m, 0.4H), 3.72-3.63 (m, 1H), 3.06-2.84 (m, 3H), 2.81-2.70 (m, 2H), 2.57-2.48 (m, 3.8H), 2.42 (d, J=2.4 Hz, 1.2H), 2.20-2.01 (m, 1.5H), 1.95-1.76 (m, 2.2H), 1.69-1.64 (m, 0.3H), 1.46 (s, 9H), 1.11 (t, J=7.2 Hz, 3H).

Compound 315X and 351Y: (trans)-Ethyl 6-(3-(tert-butoxycarbonyl)cyclobutyl)sulfonyl)piperidin-4-yl)-4-(2-chloro-3,4-difluorophenyl)-2-(3,5-difluoropyridin-2-yl)-1,4-dihydropyrimidine-5-carboxylate and (cis)-ethyl 6-(3-(tert-butoxycarbonyl)cyclobutyl)sulfonyl)piperidin-4-yl)-4-(2-chloro-3,4-difluorophenyl)-2-(3,5-difluoropyridin-2-yl)-1,4-dihydropyrimidine-5-carboxylate Compound 351X: LC-MS (ESI): $R_T$=3.273 min, mass calcd. for $C_{32}H_{35}ClF_4N_4O_6S$ 714.2, m/z found 715.2 [M+H]$^+$. Chiral analysis (Column: Chiralpak ID 5 μm 4.6*250 mm; Mobile Phase: Hex:IPA=70:30 at 1.0 mL/min; Temp: 30° C.; Wavelength: 230 nm; $R_T$=10.999 min). $^1$H NMR (400 MHz, CDCl$_3$) δ 8.64 (s, 0.6H), 8.35 (d, J=2.0 Hz, 0.6H), 8.26 (d, J=2.0 Hz, 0.4H), 7.77 (s, 0.4H), 7.33-7.29 (m, 1H), 7.08-6.98 (m, 2H), 6.31 (s, 0.6H), 6.07 (d, J=2.4 Hz, 0.4H), 4.25-4.17 (m, 0.6H), 4.09-3.94 (m, 3.4H), 3.89-3.87 (m, 2H), 3.20-3.15 (m, 1H), 2.98-2.88 (m, 2H), 2.80-2.72 (m, 2H), 2.61-2.53 (m, 2H), 2.22-2.17 (m, 0.4H), 1.97-1.62 (m, 3.6H), 1.48 (s, 5.4H), 1.47 (s, 3.6H), 1.13 (t, J=7.2 Hz, 3H).

Compound 351Y: LC-MS (ESI): $R_T$=2.469 min, mass calcd. for $C_{32}H_{35}ClF_4N_4O_6S$ 714.2, m/z found 715.1 [M+H]$^+$.

Compound 353: Ethyl 4-(2-chloro-3,4-difluorophenyl)-6-(1-((4-(ethoxycarbonyl)cyclohexyl)sulfonyl)piperidin-4-yl)-2-(thiazol-2-yl)-1,4-dihydropyrimidine-5-carboxylate LC-MS (ESI): $R_T$=4.177 min, mass calcd. for $C_{30}H_{35}ClF_2N_4O_6S_2$ 684.2, m/z found 685.2 [M+H]$^+$. $^1$H NMR (400 MHz, DMSO-d$_6$) δ 9.60 (d, J=3.2 Hz, 0.7H), 9.14 (s, 0.3H), 7.98-7.97 (m, 1.7H), 7.91 (d, J=3.2 Hz, 0.3H), 7.47-7.40 (m, 1H), 7.21-7.14 (m, 1H), 6.01 (s, 0.2H), 5.92 (d, J=3.2 Hz, 0.8H), 4.11-4.01 (m, 2H), 3.98-3.92 (m, 2H), 3.80-3.71 (m, 3H), 3.23-3.11 (m, 1H), 2.98-2.86 (m, 2H), 2.11-1.72 (m, 8H), 1.58-1.36 (m, 5H), 1.19-1.14 (m, 3H), 1.07-1.01 (m, 3H).

A racemic mixture of 353 (700 mg, 1.02 mmol) was separated by chiral Prep. HPLC (Column: Chiralpak IB 5 μm 20*250 mm; Mobile Phase: Hex:EtOH:DEA=80:20:0.3 at 15 mL/min; Temp: 30° C.; Wavelength: 214 nm) to give Group 1 (360 mg) and Group 2 (230 mg) as yellow solids. The Group 1 (360 mg, 0.526 mmol) was separated by chiral Prep. HPLC (Column: Chiralpak IE 5 μm 20*250 mm; Mobile Phase: Hex:EtOH:DEA=60:40:0.3 at 12 mL/min; Temp: 30° C.; Wavelength: 214 nm) to give EO08495_837M (80 mg, 11% yield, 100% stereopure) and EO08495_837N (80 mg, 11% yield, 100% stereopure) as yellow solids. The Group 2 (230 mg, 0.336 mmol) was separated by chiral Prep. HPLC (Column: Chiralpak IC 5 μm 20*250 mm; Mobile Phase: Hex:EtOH:DEA=60:40:0.3 at 12 mL/min; Temp: 30° C.; Wavelength: 214 nm) to give 353X (90 mg, 13% yield, 100% stereopure) and 353Y (90 mg, 13% yield, 100% stereopure) as yellow solids.

Compound 353M: LC-MS (ESI): $R_T$=4.195 min, mass calcd. for $C_{30}H_{35}ClF_2N_4O_6S_2$ 684.2, m/z found 685.1 [M+H]$^+$. Chiral analysis (Column: Chiralpak IE 5 μm 4.6*250 mm; Mobile Phase: Hex:EtOH:DEA=60:40:0.2 at 1 mL/min; Temp: 30° C.; Wavelength: 230 nm; $R_T$=17.755 min). $^1$H NMR (400 MHz, DMSO-d$_6$) δ 9.61 (d, J=3.2 Hz, 0.8H), 9.15 (s, 0.2H), 8.02-7.99 (m, 1.8H), 7.93 (d, J=3.6 Hz, 0.2H), 7.49-7.42 (m, 1H), 7.24-7.16 (m, 1H), 6.03 (s, 0.2H), 5.94 (d, J=3.2 Hz, 0.8H), 4.13-4.07 (m, 2H), 4.02-3.94 (m, 2.3H), 3.82-3.72 (m, 2.7H), 3.25-3.17 (m, 1H), 2.99-2.87 (m, 2H), 2.67 (br s, 1H), 2.13-1.74 (m, 7.4H), 1.64-1.52 (m, 4.6H), 1.19 (t, J=7.2 Hz, 3H), 1.09-1.03 (m, 3H).

Compound 353N: LC-MS (ESI): $R_T$=4.191 min, calcd. for $C_{30}H_{35}ClF_2N_4O_6S_2$ 684.2, m/z found 685.1 [M+H]$^+$. Chiral analysis (Column: Chiralpak IE 5 μm 4.6*250 mm; Mobile Phase: Hex:EtOH:DEA=60:40:0.2 at 1 mL/min; Temp: 30° C.; Wavelength: 230 nm; $R_T$=19.587 min). $^1$H NMR (400 MHz, DMSO-d$_6$) δ 9.61 (d, J=3.6 Hz, 0.8H), 9.15 (s, 0.2H), 8.01-7.99 (m, 1.8H), 7.93 (d, J=3.2 Hz, 0.2H), 7.49-7.42 (m, 1H), 7.24-7.16 (m, 1H), 6.03 (s, 0.2H), 5.94 (d, J=3.6 Hz, 0.8H), 4.13-4.08 (m, 2H), 4.01-3.94 (m, 2.3H), 3.83-3.72 (m, 2.7H), 3.26-3.17 (m, 1H), 3.00-2.88 (m, 2H), 2.67 (br s, 1H), 2.14-2.02 (m, 2H), 1.98-1.74 (m, 5H), 1.65-1.53 (m, 5H), 1.19 (t, J=7.2 Hz, 3H), 1.09-1.03 (m, 3H).

Compound 353X: LC-MS (ESI): $R_T$=4.178 min, mass calcd. for $C_{30}H_{35}ClF_2N_4O_6S_2$ 684.2, m/z found 685.2 [M+H]$^+$. Chiral analysis (Column: Chiralpak IC 5 μm 4.6*250 mm; Mobile Phase: Hex:EtOH:DEA=60:40:0.2 at 1 mL/min; Temp: 30° C.; Wavelength: 230 nm; $R_T$=13.384 min). $^1$H NMR (400 MHz, DMSO-d$_6$) δ 9.60 (d, J=3.2 Hz, 0.8H), 9.14 (s, 0.2H), 7.99-7.97 (m, 1.8H), 7.92 (d, J=3.6 Hz, 0.2H), 7.47-7.40 (m, 1H), 7.22-7.14 (m, 1H), 6.02 (s, 0.2H), 5.92 (d, J=3.2 Hz, 0.8H), 4.06-4.01 (m, 2H), 3.99-3.92 (m, 2.2H), 3.81-3.71 (m, 2.8H), 3.19-3.11 (m, 1H), 3.00-2.89 (m, 2H), 2.34-2.25 (m, 1H), 2.09-1.73 (m, 7.2H), 1.61-1.54 (m, 0.8H), 1.52-1.36 (m, 4H), 1.16 (t, J=7.2 Hz, 3H), 1.07-1.01 (m, 3H).

Compound 353Y: LC-MS (ESI): $R_T$=4.180 min, mass calcd. for $C_{30}H_{35}ClF_2N_4O_6S_2$ 684.2, m/z found 685.2 [M+H]$^+$. Chiral analysis (Column: Chiralpak IC 5 μm 4.6*250 mm; Mobile Phase: Hex:EtOH:DEA=60:40:0.2 at 1 mL/min; Temp: 30° C.; Wavelength: 230 nm; $R_T$=16.644 min). $^1$H NMR (400 MHz, DMSO-d$_6$) δ 9.62 (d, J=3.2 Hz, 0.8H), 9.16 (s, 0.2H), 8.01-7.99 (m, 1.7H), 7.94 (d, J=3.2 Hz, 0.3H), 7.49-7.43 (m, 1H), 7.23-7.16 (m, 1H), 6.04 (s, 0.2H), 5.94 (d, J=3.2 Hz, 0.8H), 4.06 (q, J=7.2 Hz, 2H), 4.01-3.94 (m, 2.3H), 3.82-3.73 (m, 2.7H), 3.21-3.13 (m, 1H), 3.00-2.92 (m, 2H), 2.36-2.28 (m, 1H), 2.10-1.74 (m, 7.2H), 1.62-1.59 (m, 0.8H), 1.53-1.38 (m, 4H), 1.18 (t, J=7.2 Hz, 3H), 1.09-1.03 (m, 3H).

Compound 355: Ethyl 4-(2-chloro-3,4-difluorophenyl)-6-(1-((2-methoxy-2-oxoethyl)sulfonyl)piperidin-4-yl)-2-(thiazol-2-yl)-1,4-dihydropyrimidine-5-carboxylate LC-MS (ESI): $R_T$=4.127 min, mass calcd. for $C_{24}H_{25}ClF_2N_4O_6S_2$ 602.1, m/z found 602.9 [M+H]$^+$. $^1$H NMR (400 MHz, DMSO-d$_6$) δ 9.62 (br s, 0.8H), 9.17 (br s, 0.2H), 8.04-7.99 (m, 1.8H), 7.94-7.91 (m, 0.2H), 7.49-7.42 (m, 1H), 7.24-7.17 (m, 1H), 6.04 (s, 0.2H), 5.94-5.91 (d, J=1.6 Hz, 0.8H), 4.33 (s, 0.5H), 4.31 (s, 1.5H), 3.98 (q, J=2.8 Hz, 2H), 3.82-3.67 (m, 6H), 2.97-2.84 (m, 2H), 2.17-2.08 (m, 0.2H), 2.04-1.94 (m, 1H), 1.89-1.80 (m, 2H), 1.70-1.62 (m, 0.8H), 1.10-1.03 (m, 3H).

Compound 364: Methyl 4-(2-chloro-4-fluorophenyl)-2-(thiazol-2-yl)-6-((R)-1-((2,2,2-trifluoroethyl)sulfonyl)pyrrolidin-3-yl)-1,4-dihydropyrimidine-5-carboxylate LC-MS (ESI): $R_T$=2.458 min, mass calcd. for $C_{21}H_{19}ClF_4N_4O_4S_2$ 566.0, m/z found 566.8 [M+H]$^+$. $^1$H NMR (400 MHz, DMSO-d$_6$) 9.60-9.38 (m, 1H), 8.04-7.94 (m, 2H), 7.44-7.32 (m, 2H), 7.23-7.20 (m, 1H), 6.03 (s, 0.1H), 5.94 (s, 0.9H), 4.62-4.54 (m, 2.1H), 4.42-4.34 (m, 0.9H), 3.78-3.61 (m, 3H), 3.58 (s, 3H), 3.48-3.42 (m, 1H), 2.24-2.15 (m, 1H), 2.09-1.99 (m, 1H).

Compound 365: Methyl 4-(2-chloro-4-fluorophenyl)-6-((R*)-1-((2-methoxyethyl)sulfonyl)pyrrolidin-3-yl)-2-(thiazol-2-yl)-1,4-dihydropyrimidine-5-carboxylate LC-MS (ESI): $R_T$=4.246 min, mass calcd. for $C_{22}H_{24}ClFN_4O_5S_2$ 542.1, m/z found 543.2 [M+H]$^+$. $^1$H NMR (400 MHz, DMSO-d$_6$) δ 9.62 (d, J=3.6 Hz, 0.9H), 9.28 (s, 0.1H), 8.03-7.93 (m, 2H), 7.44-7.41 (m, 1H), 7.39-7.35 (m, 1H), 7.24-7.19 (m, 1H), 6.02 (s, 0.1H), 5.94 (d, J=3.6 Hz, 0.9H), 4.60-4.56 (m, 0.1H), 4.40-4.31 (m, 0.9H), 3.72 (t, J=6.0 Hz, 2H), 3.64-3.50 (m, 6H), 3.48-3.43 (m, 2H), 3.39-3.30 (m, 4H), 2.25-2.16 (m, 1H), 2.03-1.94 (m, 1H).

Compound 366X and 366Y: (trans)-methyl 6-(1-((3-(tert-butoxycarbonyl)cyclobutyl)sulfonyl)pyrrolidin-3-yl)-4-(2-chloro-4-fluorophenyl)-2-(thiazol-2-yl)-1,4-dihydropyrimidine-5-carboxylate and (cis)-methyl 6-(1-((3-(tert-butoxycarbonyl)cyclobutyl)sulfonyl)pyrrolidin-3-yl)-4-(2-chloro-4-fluorophenyl)-2-(thiazol-2-yl)-1,4-dihydropyrimidine-5-carboxylate Compound 366X: LC-MS (ESI): $R_T$=1.92 min, mass calcd. for $C_{28}H_{32}ClFN_4O_6S_2$ 638.1, m/z found 639.8

[M+H]⁺. ¹H NMR (400 MHz, DMSO-d₆) δ 9.60 (s, 1H), 8.01 (d, J=2.8 Hz, 1H), 7.74-7.66 (m, 1H), 7.43-7.35 (m, 2H), 7.22-7.17 (m, 1H), 5.95 (s, 1H), 4.36-4.32 (m, 1H), 4.14-4.10 (m, 1H), 3.67-3.60 (m, 2.5H), 3.53 (s, 3H), 3.50-3.48 (m, 0.5H), 3.41-3.35 (m, 1H), 3.15-3.09 (m, 1H), 2.66-2.59 (m, 2H), 2.17-2.11 (m, 1H), 2.04-1.95 (m, 1H), 1.37 (s, 9H), 1.27-1.22 (m, 2H).

Compound 366Y: LC-MS (ESI): $R_T$=1.88 min, mass calcd. for $C_{28}H_{32}ClFN_4O_6S_2$ 638.1, m/z found 638.6 [M+H]⁺. ¹H NMR (400 MHz, DMSO-d₆) δ 9.61 (s, 0.9H), 9.25 (br s, 0.1H), 8.03 (s, 1.5H), 7.75-7.69 (m, 0.5H), 7.44-7.36 (m, 2H), 7.23-7.19 (m, 1H), 5.95 (s, 0.9H), 5.79 (s, 0.1H), 4.38-4.33 (m, 0.8H), 4.13-4.01 (m, 1.2H), 3.63-3.48 (m, 6H), 3.27-3.18 (m, 1H), 3.14-3.05 (m, 1H), 2.53 (br s, 2H), 2.22-2.13 (m, 1H), 2.02-1.96 (m, 1H), 1.40 (s, 9H), 1.28-1.15 (m, 2H).

Compound 370B-1 and 370D-1: (trans)-Ethyl 6-(1-((3-(tert-butoxycarbonyl)cyclobutyl)sulfonyl)piperidin-4-yl)-4-(2-chloro-3,4-difluorophenyl)-2-(thiazol-2-yl)-1,4-dihydropyrimidine-5-carboxylate and (cis)-ethyl 6-(1-((3-(tert-butoxycarbonyl)cyclobutyl)sulfonyl)piperidin-4-yl)-4-(2-chloro-3,4-difluorophenyl)-2-(thiazol-2-yl)-1,4-dihydropyrimidine-5-carboxylate Compound 370B-1: LC-MS (ESI): $R_T$=4.718 min, mass calcd. for $C_{30}H_{35}ClF_2N_4O_6S_2$ 684.2, m/z found 685.1 [M+H]⁺. ¹H NMR (400 MHz, DMSO-d₆) δ 9.62 (s, 0.7H), 9.13 (s, 0.3H), 8.01-7.94 (m, 2H), 7.49-7.43 (m, 1H), 7.23-7.19 (m, 1H), 6.03 (s, 0.3H), 5.94 (s, 0.7H), 4.04-3.95 (m, 3.2H), 3.78-3.70 (m, 2.8H), 3.16-3.08 (m, 1H), 2.91-2.82 (m, 2H), 2.60-2.52 (m, 4H), 2.02-1.74 (m, 3H), 1.63-1.58 (m, 1H), 1.42 (s, 9H), 1.07 (t, d=6.8 Hz, 3H).

Compound 370D-1: LC-MS (ESI): $R_T$=2.812 min, mass calcd. for $C_{30}H_{35}ClF_2N_4O_6S_2$ 684.2, m/z found 685.1 [M+H]⁺. ¹H NMR (400 MHz, CDCl₃) δ 8.18 (s, 0.3H), 7.83 (d, J=3.2 Hz, 1H), 7.53 (d, J=3.2 Hz, 0.7H), 7.45 (d, J=3.6 Hz, 0.3H), 7.35 (s, 0.7H), 7.10-6.99 (m, 2H), 6.20 (s, 0.3H), 6.09 (d, J=2.8 Hz, 0.7H), 4.22-4.15 (m, 0.3H), 4.10-3.87 (m, 4.7H), 3.72-3.63 (m, 1H), 3.06-2.86 (m, 3H), 2.81-2.70 (m, 2H), 2.57-2.47 (m, 2H), 2.24-1.66 (m, 4H), 1.46 (s, 9H), 1.14-1.10 (m, 3H).

Compound 389B: Methyl 4-(2-chloro-4-fluorophenyl)-6-(3-(2-methoxy-2-oxoethylsulfonamido)bicyclo[1.1.1]pentan-1-yl)-2-(thiazol-2-yl)-1,4-dihydropyrimidine-5-carboxylate ¹H NMR (400 MHz, DMSO-d₆) 9.43 (br s, 0.3H), 8.34-8.32 (m, 0.7H), 8.01-7.98 (m, 1.5H), 7.95-7.94 (m, 0.5H), 7.44-7.40 (m, 1H), 7.35-7.30 (m, 1H), 7.25-7.18 (m, 1H), 5.97 (s, 0.5H), 5.87 (s, 0.5H), 4.20 (s, 1H), 4.15 (s, 1H), 3.72 (s, 1.2H), 3.71 (s, 1.8H), 3.55 (s, 1.5H), 3.53 (s, 1.5H), 2.45 (s, 2H), 2.42 (s, 1H), 2.29 (s, 2H), 2.25 (s, 1H).

Compound 391B: Methyl 6-(3-acetamidobicyclo[1.1.1]pentan-1-yl)-4-(2-chloro-4-fluorophenyl)-2-(thiazol-2-yl)-1,4-dihydropyrimidine-5-carboxylate LC-MS (ESI): $R_T$=2.398 min, mass calcd. for $C_{22}H_{20}ClFN_4O_3S$ 474.1, m/z found 475.1 [M+H]⁺. ¹H NMR (400 MHz, DMSO-d₆) δ 9.36 (s, J=2.8 Hz, 0.4H), 8.52 (s, 0.5H), 8.39 (s, 0.5H), 8.28 (s, 0.5H), 8.01-7.99 (m, 1.4H), 7.95 (d, J=2.8 Hz, 0.6H), 7.44-7.40 (m, 1H), 7.35-7.30 (m, 1H), 7.25-7.19 (m, 1H), 5.96 (s, 0.5H), 5.86 (d, J=3.6 Hz, 0.5H), 3.55 (s, 1.5H), 3.53 (s, 1.5H), 2.44 (s, 3.2H), 2.28 (s, 2.8H), 1.79 (s, 1.7H), 1.77 (s, 1.3H).

Compound 392B: Methyl 6-(3-(1,4-dioxaspiro[4.5]decan-2-ylmethylsulfonamido)bicyclo[1.1.1]pentan-1-yl)-4-(2-chloro-4-fluorophenyl)-2-(thiazol-2-yl)-1,4-dihydropyrimidine-5-carboxylate LC-MS (ESI): $R_T$=1.86 min, mass calcd. for $C_{29}H_{32}ClFN_4O_6S_2$ 650.1, m/z found 651.5 [M+H]⁺.

Compound 396: (trans)-Methyl 4-(2-chloro-4-fluorophenyl)-2-(3,5-difluoropyridin-2-yl)-6-(4-(methylsulfonamido)cyclohexyl)-1,4-dihydropyrimidine-5-carboxylate LC-MS (ESI): $R_T$=4.132 min, mass calcd. for $C_{24}H_{24}ClF_3N_4O_4S$ 556.1, m/z found 557.1 [M+H]⁺. ¹H NMR (400 MHz, DMSO-d₆) δ 9.18 (br s, 0.7H), 9.07-9.03 (m, 0.3H), 8.59-8.55 (m, 1H), 8.09-8.03 (m, 1H), 7.44-7.39 (m, 1H), 7.36-7.31 (m, 1H), 7.25-7.18 (m, 1H), 7.15-7.09 (m, 0.7H), 7.07-7.02 (m, 0.3H), 6.01 (s, 0.7H), 5.90 (d, J=3.2 Hz, 0.3H), 3.86-3.78 (m, 0.7H), 3.57-3.54 (m, 0.3H), 3.52 (s, 1H), 3.50 (s, 2H), 3.22-3.15 (m, 0.7H), 3.11-3.04 (m, 0.3H), 2.92 (s, 1H), 2.91 (s, 2H), 2.03-1.97 (m, 2H), 1.85-1.79 (m, 1.8H), 1.76-1.71 (m, 1.8H), 1.60-1.53 (m, 0.4H), 1.38-1.27 (m, 2H).

Racemic 396 (140 mg, 0.251 mmol) was separated by chiral Prep. HPLC (separation condition: Column: Chiralpak OD-H 5 µm 20*250 mm; Mobile Phase: Hex:EtOH:DEA=85:15:0.3 at 15 mL/min; Temp: 30° C.; Wavelength: 214 nm) to afford the title compounds 396A (25 mg, 18% yield, 100% stereopure) as yellow solids and 396B (25 mg, 18% yield, 97.3% stereopure) as yellow solids.

Compound 396A: LC-MS (ESI): $R_T$=4.016 min, mass calcd. for $C_{24}H_{24}ClF_3N_4O_4S$ 556.1, m/z found 556.9 [M+H]⁺. Chiral analysis (Column: Chiralpak OD-H 5 µm 4.6*250 mm; Mobile Phase: Hex:EtOH:DEA=85:15:0.2 at 1.0 mL/min; Temp: 30° C.; Wavelength: 230 nm, $R_T$=12.683 min). ¹H NMR (400 MHz, DMSO-d₆) δ 9.15 (br s, 0.7H), 9.02 (d, J=3.6 Hz, 0.3H), 8.57-8.55 (m, 1H), 8.08-8.02 (m, 1H), 7.44-7.39 (m, 1H), 7.36-7.31 (m, 1H), 7.24-7.18 (m, 1H), 7.10 (d, J=7.6 Hz, 0.7H), 7.01 (d, J=7.2 Hz, 0.3H), 6.02 (s, 0.7H), 5.91 (d, J=2.8 Hz, 0.3H), 3.84-3.80 (m, 0.8H), 3.56-3.54 (m, 0.2H), 3.52 (s, 1H), 3.50 (s, 2H), 3.21-3.18 (m, 0.6H), 3.10-3.05 (m, 0.4H), 2.92 (s, 1H), 2.91 (s, 2H), 2.04-1.95 (m, 2H), 1.86-1.80 (m, 1.6H), 1.77-1.71 (m, 2H), 1.59-1.54 (m, 0.4H), 1.36-1.27 (m, 2H).

Compound 396B: LC-MS (ESI): $R_T$=4.016 min, mass calcd. for $C_{24}H_{24}ClF_3N_4O_4S$ 556.1, m/z found 556.9 [M+H]⁺. Chiral analysis (Column: Chiralpak OD-H 5 µm 4.6*250 mm; Mobile Phase: Hex:EtOH:DEA=85:15:0.2 at 1.0 mL/min; Temp: 30° C.; Wavelength: 230 nm, $R_T$=15.170 min). ¹H NMR (400 MHz, DMSO-d₆) δ 9.16 (br s, 0.7H), 9.02 (d, J=3.2 Hz, 0.3H), 8.57-8.55 (m, 1H), 8.08-8.02 (m, 1H), 7.44-7.39 (m, 1H), 7.35-7.31 (m, 1H), 7.24-7.18 (m, 1H), 7.10 (d, J=7.6 Hz, 0.7H), 7.02 (d, J=7.6 Hz, 0.3H), 6.02 (s, 0.7H), 5.91 (d, J=3.2 Hz, 0.3H), 3.86-3.78 (m, 0.7H), 3.58-3.54 (m, 0.3H), 3.52 (s, 1H), 3.50 (s, 2H), 3.21-3.17 (m, 0.7H), 3.10-3.04 (m, 0.3H), 2.92 (s, 1H), 2.91 (s, 2H), 2.04-1.99 (m, 2H), 1.85-1.80 (m, 1.7H), 1.76-1.71 (m, 2H), 1.58-1.53 (m, 0.3H), 1.36-1.27 (m, 2H).

Compound 399: (cis)-Methyl 4-(2-chloro-4-fluorophenyl)-2-(3,5-difluoropyridin-2-yl)-6-(4-(methylsulfonamido)cyclohexyl)-1,4-dihydropyrimidine-5-carboxylate LC-MS (ESI): $R_T$=3.700 min, mass calcd. for $C_{24}H_{24}ClF_3N_4O_4S$ 556.1, m/z found 556.9 [M+H]⁺. ¹H NMR (400 MHz, DMSO-$d_6$) δ 9.19-9.14 (m, 0.8H), 9.08-9.02 (m, 0.2H), 8.65-8.62 (m, 0.5H), 8.58-8.55 (m, 0.5H), 8.11-8.03 (m, 1H), 7.44-7.39 (m, 1H), 7.36-7.31 (m, 1H), 7.25-7.19 (m, 1H), 7.12-7.09 (m, 0.8H), 7.05-7.02 (m, 0.1H), 6.78-6.76 (m, 0.1H), 6.05-6.00 (m, 0.8H), 5.92-5.89 (m, 0.2H), 3.94-3.88 (m, 0.6H), 3.84-3.80 (m, 0.3H), 3.69-3.62 (m, 0.5H), 3.52 (s, 1H), 3.50 (s, 2H), 3.21-3.16 (m, 0.4H), 3.11-3.04 (m, 0.2H), 2.96 (s, 1.5H), 2.92-2.91 (s, 1.3H), 2.90-2.88 (m, 0.2H), 2.07-2.00 (m, 1H), 1.94-1.80 (m, 3H), 1.73-1.51 (m, 3H), 1.36-1.24 (m, 1H).

Racemic 399 (70 mg, 0.126 mmol) was separated by chiral Prep. HPLC (separation condition: Column: Chiralpak ID 5 μm 20*250 mm; Mobile Phase: Hex:EtOH=70:30 at 13 mL/min; Temp: 30° C.; Wavelength: 254 nm) to afford the title compounds 399C (25 mg, 36% yield, 100% stereopure) as yellow solids and 399D (24 mg, 34% yield, 99.4% stereopure) as yellow solids.

Compound 399C: LC-MS (ESI): $R_T$=4.040 min, mass calcd. for $C_{24}H_{24}ClF_3N_4O_4S$ 556.1, m/z found 556.9 [M+H]$^+$. Chiral analysis (Column: Chiralpak ID 5 μm 4.6*250 mm; Mobile Phase: Hex:EtOH=70:30 at 1.0 mL/min; Temp: 30° C.; Wavelength: 230 nm, $R_T$=6.748 min). $^1$H NMR (400 MHz, DMSO-$d_6$) δ 9.17 (br s, 0.9H), 9.10-9.05 (m, 0.1H), 8.67-8.61 (m, 0.9H), 8.57-8.55 (m, 0.1H), 8.11-8.04 (m, 1H), 7.45-7.40 (m, 1H), 7.39-7.33 (m, 1H), 7.25-7.19 (m, 1H), 7.14-7.07 (m, 0.9H), 6.79-6.76 (m, 0.1H), 6.03 (s, 0.9H), 5.93-5.90 (m, 0.1H), 3.96-3.86 (m, 1H), 3.68-3.62 (m, 1H), 3.51 (s, 0.4H), 3.50 (s, 2.6H), 2.96 (s, 2.6H), 2.89 (s, 0.4H), 1.97-1.80 (m, 4H), 1.68-1.57 (m, 3H), 1.54-1.51 (m, 1H).

Compound 399D: LC-MS (ESI): $R_T$=4.018 min, mass calcd. for $C_{24}H_{24}ClF_3N_4O_4S$ 556.1, m/z found 556.9 [M+H]$^+$. Chiral analysis (Column: Chiralpak ID 5 μm 4.6*250 mm; Mobile Phase: Hex:EtOH=70:30 at 1.0 mL/min; Temp: 30° C.; Wavelength: 230 nm, $R_T$=8.621 min). $^1$H NMR (400 MHz, DMSO-$d_6$) δ 9.18 (br s, 0.7H), 9.08-9.03 (m, 0.3H), 8.59-8.54 (m, 1H), 8.09-8.03 (m, 1H), 7.44-7.40 (m, 1H), 7.36-7.31 (m, 1H), 7.25-7.18 (m, 1H), 7.15-7.10 (m, 0.7H), 7.06-7.02 (m, 0.3H), 6.01 (s, 0.7H), 5.92-5.89 (m, 0.3H), 3.86-3.79 (m, 0.7H), 3.57-3.54 (m, 0.3H), 3.51 (s, 1H), 3.50 (s, 2H), 3.20-3.15 (m, 0.7H), 3.09-3.06 (m, 0.3H), 2.92 (s, 3H), 2.02-1.98 (m, 2H), 1.85-1.80 (m, 1.8H), 1.76-1.71 (m, 2H), 1.58-1.55 (m, 0.2H), 1.33-1.24 (m, 2H).

Compound 405: Methyl 6-(3-(1-(tert-butoxycarbonyl)azetidine-3-sulfonamido)bicyclo[1.1.1]pentan-1-yl)-4-(2-chloro-3,4-difluorophenyl)-2-(thiazol-2-yl)-1,4-dihydropyrimidine-5-carboxylate LC-MS (ESI): $R_T$=1.81 min, mass calcd. for $C_{28}H_{30}ClF_2N_5O_6S_2$ 669.1, m/z found 670.2 [M+H]$^+$. $^1$H NMR (400 MHz, CDCl$_3$) δ 7.87-7.81 (m, 1.7H), 7.51-7.46 (m, 1.3H), 7.04-7.02 (m, 2H), 6.15 (s, 0.7H), 6.02 (s, 0.3H), 5.40 (s, 0.7H), 5.23 (s, 0.3H), 4.22-4.17 (m, 4H), 3.99-3.95 (m, 1H), 3.62 (s, 0.9H), 3.59 (s, 2.1H), 2.58 (s, 4.2H), 2.45 (s, 1.8H), 1.45 (s, 9H).

Compound 406: Methyl 6-(3-(azetidine-3-sulfonamido)bicyclo[1.1.1]pentan-1-yl)-4-(2-chloro-3,4-difluorophenyl)-2-(thiazol-2-yl)-1,4-dihydropyrimidine-5-carboxylate Compound 405 was de-Boc using TFA to give compound 406, LC-MS (ESI): $R_T$=3.946 min, mass calcd. for $C_{23}H_{22}ClF_2N_5O_4S_2$ 569.1, m/z found 570.2 [M+H]$^+$. $^1$H NMR (400 MHz, CDCl$_3$) δ 7.88-7.81 (m, 1.7H), 7.52-7.46 (m, 1.3H), 7.10-7.02 (m, 2H), 6.15 (s, 0.7H), 6.02 (s, 0.3H), 4.28-4.16 (m, 1H), 4.10-4.04 (m, 2H), 3.87-3.83 (m, 2H), 3.62 (s, 0.9H), 3.60 (s, 2.1H), 2.57 (s, 4H), 2.48 (s, 2H).

Compound 409P and 409Q: trans-Methyl 4-(2-bromo-4-fluorophenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate and cis-methyl 4-(2-bromo-4-fluorophenyl)-6-(1-((3-methyl-3-((2-(trimethylsilyl)ethoxy)carbonyl)cyclobutyl)-sulfonyl)piperidin-4-yl)-2-(thiazol-2-yl)-1,4-dihydropyrimidine-5-carboxylate Compound 409P (trans): LC-MS (ESI): $R_T$=3.005 min, mass calcd. for $C_{31}H_{40}BrFN_4O_6S_2Si$ 754.1, m/z found 754.7 [M+H]$^+$. $^1$H NMR (400 MHz, CDCl$_3$) δ 7.84 (d, J=3.2 Hz, 1H), 7.53-7.45 (m, 1.8H), 7.34-7.31 (m, 1.2H), 7.02-6.94 (m, 1H), 6.16 (s, 0.2H), 6.03 (d, J=2.0 Hz, 0.8H), 4.25-4.21 (m, 2.2H), 4.01-3.78 (m, 3.8H), 3.60 (s, 3H), 2.94-2.74 (m, 4H), 2.52-2.46 (m, 2H), 2.29-2.20 (m, 1H), 2.05-2.01 (m, 1H), 1.92-1.88 (m, 1H), 1.71-1.67 (m, 1H), 1.60 (s, 1H), 1.45 (m, 3H), 1.05-1.01 (m, 2H), 0.06 (s, 9H).

Compound 409Q (cis): LC-MS (ESI): $R_T$=2.952 min, mass calcd. for $C_{31}H_{40}BrFN_4O_6S_2Si$ 754.1, m/z found 754.7 [M+H]$^+$. $^1$H NMR (400 MHz, CDCl$_3$) δ 8.12 (s, 0.2H), 7.78 (d, J=2.8 Hz, 1H), 7.47-7.39 (m, 1.8H), 7.28-7.20 (m, 1H), 6.97-6.89 (m, 1H), 6.11 (s, 0.3H), 5.98 (d, J=2.0 Hz, 0.7H), 4.17-4.09 (m, 2.2H), 3.98-3.82 (m, 2.8H), 3.71-3.67 (m, 1H), 3.54 (s, 3H), 2.97-2.81 (m, 4H), 2.19-2.08 (m, 3H), 2.02-1.95 (m, 1H), 1.86-1.83 (m, 1H), 1.64-1.61 (m, 1H), 1.52 (s, 1H), 1.43 (s, 3H), 0.99-0.94 (m, 2H), 0.01 (s, 9H).

Compound 413C and 413D: (trans)-Ethyl 4-(2-bromo-3-fluorophenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate and (cis)-ethyl 4-(2-bromo-3-fluorophenyl)-6-(1-((3-methyl-3-((2-(trimethylsilyl)ethoxy)carbonyl)cyclobutyl)-sulfonyl)piperidin-4-yl)-2-(thiazol-2-yl)-1,4-dihydropyrimidine-5-carboxylate Compound 413C (trans): LC-MS (ESI): $R_T$=2.43 min, mass calcd. for $C_{32}H_{42}BrFN_4O_6S_2Si$ 768.2, m/z found 770.7 [M+H]$^+$. $^1$H NMR (400 MHz, DMSO-$d_6$) δ 9.53 (br s, 0.8H), 9.08 (br s, 0.2H), 8.01-7.97 (m, 1.9H), 7.90-7.83 (m, 0.1H), 7.38 (dd, J=13.6, 8.0 Hz, 1H), 7.28-7.24 (m, 1H), 7.17 (d, J=7.6 Hz, 1H), 6.04 (br s, 0.2H), 5.95 (br s, 0.8H), 4.14 (t, J=8.4 Hz, 2H), 3.97-3.89 (m, 3H), 3.73-3.66 (m, 3H), 2.86-2.71 (m, 4H), 2.28-2.22 (m, 2H), 1.80-1.70 (m, 3H), 1.61-1.54 (m, 1H), 1.33 (s, 3H), 1.02 (t, J=6.8 Hz, 3H), 0.94 (t, J=8.4 Hz, 2H), 0.00 (s, 9H).

Compound 413D (cis): LC-MS (ESI): $R_T$=2.32 min, mass calcd. for $C_{32}H_{42}BrFN_4O_6S_2Si$ 768.2, m/z found 770.7 [M+H]$^+$. $^1$H NMR (400 MHz, DMSO-$d_6$) δ 9.53 (d, J=3.2 Hz, 0.8H), 9.07 (br s, 0.2H), 7.99-7.95 (m, 1.8H), 7.90 (d, J=3.6 Hz, 0.2H), 7.41-7.36 (m, 1H), 7.29-7.22 (m, 1H), 7.18 (d, J=7.6 Hz, 0.8H), 7.13 (d, J=7.6 Hz, 0.2H), 6.04 (br s, 0.2H), 5.94 (d, J=3.6 Hz, 0.8H), 4.15-4.10 (m, 3H), 3.97-3.91 (m, 2H), 3.73-3.63 (m, 3H), 2.87-2.78 (m, 2H), 2.66-2.61 (m, 2H), 2.18-2.13 (m, 2H), 1.94-1.74 (m, 3H), 1.57 (d, J=12.8 Hz, 1H), 1.40 (s, 3H), 1.03 (t, J=6.8 Hz, 3H), 0.93 (t, J=8.4 Hz, 2H), 0.00 (s, 9H).

Compound 415: Methyl 6-(1-(N-(tert-butoxycarbo-nyl)sulfamoyl)piperidin-4-yl)-4-(2-chloro-3,4-difluorophenyl)-2-(thiazol-2-yl)-1,4-dihydropyrimidine-5-carboxylate LC-MS (ESI): $R_T$=1.82 min, mass calcd. for $C_{25}H_{28}ClF_2N_5O_6S_2$ 631.1, m/z found 632.3 [M+H]$^+$.

Compound 419A and 419B: (trans)-Ethyl 4-(4-fluoro-2-methylphenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate and (cis)-ethyl 4-(4-fluoro-2-methylphenyl)-6-(1-((3-methyl-3-((2-(trimethylsilyl)ethoxy)-carbonyl)cyclobutyl)sulfonyl)piperidin-4-yl)-2-(thiazol-2-yl)-1,4-dihydropyrimidine-5-carboxylate Compound 419A: LC-MS (ESI): $R_T$=2.122 min, mass calcd. for $C_{33}H_{45}FN_4O_6S_2Si$ 704.3, m/z found 705.1 [M+H]$^+$. $^1$H NMR (400 MHz, CDCl$_3$) δ 8.09 (br s, 0.5H), 7.81-7.80 (m, 1H), 7.52 (d, J=2.8 Hz, 0.5H), 7.42 (d, J=3.2 Hz, 0.5H), 7.31-7.29 (m, 0.5H), 7.16-7.13 (m, 0.5H), 7.00 (s, 0.5H), 6.90-6.77 (m, 2H), 5.95 (s, 0.5H), 5.86 (d, J=4.8 Hz, 0.5H), 4.25-4.21 (m, 2.5H), 4.03-3.77 (m, 5.5H), 2.95-2.74 (m, 4H), 2.62 (s, 1.5H), 2.52-2.43 (m, 3.5H), 2.15-2.05 (m, 1.4H), 1.96-1.77 (m, 2H), 1.67-1.63 (m, 0.6H), 1.45 (d, J=2.8 Hz, 3H), 1.10 (q, J=7.2 Hz, 3H), 1.06-0.99 (m, 2H), 0.07-0.06 (m, 9H).

Compound 419B: LC-MS (ESI): $R_T$=2.012 min, mass calcd. for $C_{33}H_{45}FN_4O_6S_2Si$ 704.3, m/z found 705.2 [M+H]$^+$. $^1$H NMR (400 MHz, CDCl$_3$) δ 8.10 (br s, 0.5H), 7.80 (d, J=3.2 Hz, 1H), 7.52 (d, J=2.8 Hz, 0.5H), 7.42 (d, J=3.2 Hz, 0.5H), 7.31-7.29 (m, 0.5H), 7.17-7.13 (m, 0.5H), 7.02-6.99 (m, 0.5H), 6.90-6.77 (m, 2H), 5.95 (s, 0.5H), 5.86 (d, J=4.8 Hz, 0.5H), 4.22-4.18 (m, 2.5H), 4.04-3.90 (m, 4H), 3.84-3.71 (m, 1.5H), 3.02-2.83 (m, 4H), 2.62 (s, 1.5H), 2.48 (s, 1.5H), 2.24-2.05 (m, 3.5H), 1.96-1.78 (m, 2H), 1.66-1.64 (m, 0.5H), 1.48 (d, J=2.0 Hz, 3H), 1.10 (q, J=7.2 Hz, 3H), 1.04-0.99 (m, 2H), 0.05 (s, 9H).

Compound 421: Methyl 4-(2-chloro-4-fluorophenyl)-6-(1-(((trans-4-(methoxycarbonyl)cyclohexyl)methyl)sulfonyl)piperidin-4-yl)-2-(thiazol-2-yl)-1,4-dihydropyrimidine-5-carboxylate LC-MS (ESI): $R_T$=3.13 min, mass calcd. for $C_{29}H_{34}ClFN_4O_6S_2$ 652.1, m/z found 653.2 [M+H]$^+$. $^1$H NMR (400 MHz, CDCl$_3$) δ 8.18 (brs, 0.2H), 7.87-7.78 (m, 1H), 7.53 (d, J=3.2 Hz, 0.8H), 7.46-7.45 (m, 1H), 7.30-7.26 (m, 1H), 7.16-7.12 (m, 1H), 7.04-6.98 (m, 1H), 6.19 (s, 0.2H), 6.07 (d, J=3.6 Hz, 0.8H), 4.03-3.86 (m, 3H), 3.67 (s, 3H), 3.60-3.59 (m, 3H), 2.94-2.84 (m, 2H), 2.81-2.78 (m, 2H), 2.31-2.20 (m, 2H), 2.16-2.09 (m, 2H), 2.04-1.98 (m, 3H), 1.99-1.80 (m, 2H), 1.74-1.70 (m, 1H), 1.57-1.47 (m, 2H), 1.19-1.09 (m, 2H).

Compound 423: Ethyl 4-(2-chloro-3,4-difluorophenyl)-6-(1-(((trans-4-(methoxycarbonyl)cyclohexyl)methyl)sulfonyl)piperidin-4-yl)-2-(thiazol-2-yl)-1,4-dihydropyrimidine-5-carboxylate LC-MS (ESI): $R_T$=3.28 min, mass calcd. for C30H35ClF2N4O6S2, 684.2, m/z found 685.4 [M+H]$^+$. $^1$H NMR (400 MHz, CD$_3$OD) 7.95 (d, J=3.2 Hz, 0.3H), 7.91 (d, J=3.2 Hz, 0.7H), 7.78 (d, J=3.2 Hz, 0.7H), 7.91 (d, J=3.2 Hz, 0.3H), 7.30-7.22 (m, 2H), 6.18 (s, 0.3H), 6.11 (s, 0.7H), 4.16-4.01 (m, 2H), 3.98-3.83 (m, 3H), 3.67 (s, 3H), 2.99-2.85 (m, 4H), 2.37-2.27 (m, 1H), 2.20-2.04 (m, 4H), 2.01-1.90 (m, 4H), 1.75-1.70 (m, 1H), 1.55-1.45 (m, 2H), 1.28-1.21 (m, 2H), 116-1.12 (m, 3H).

Compound 428C and 428D: (trans)-Ethyl 4-(3-fluoro-2-methylphenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate and (cis)-ethyl 4-(3-fluoro-2-methylphenyl)-6-(1-((3-methyl-3-((2-(trimethylsilyl)ethoxy)carbonyl)cyclobutyl)-sulfonyl)piperidin-4-yl)-2-(thiazol-2-yl)-1,4-dihydropyrimidine-5-carboxylate Compound 428C (trans): LC-MS (ESI): $R_T$=2.06 min, mass calcd. for $C_{33}H_{45}FN_4O_6S_2Si$ 704.3, m/z found 704.9 [M+H]$^+$. $^1$H NMR (400 MHz, CD$_3$OD) δ 7.92 (d, J=3.2 Hz, 0.3H), 7.88 (d, J=3.2 Hz, 0.7H), 7.75-7.72 (m, 1H), 7.18-7.08 (m, 2H), 6.97-6.92 (m, 1H), 5.96 (s, 0.3H), 5.90 (s, 0.7H), 4.26-4.22 (m, 2H), 4.06-3.80 (m, 6H), 3.00-2.79 (m, 4H), 2.50 (d, J=2.0 Hz, 1H), 2.44-2.38 (m, 4H), 2.13-2.01 (m, 2H), 1.90-1.84 (m, 1.4H), 1.68-1.63 (m, 0.6H), 1.43 (d, J=2.4 Hz, 3H), 1.12 (t, J=7.2 Hz, 3H), 1.10-1.00 (m, 2H), 0.07-0.05 (m, 9H).

Compound 428D (cis): LC-MS (ESI): $R_T$=1.99 min, mass calcd. for $C_{33}H_{45}FN_4O_6S_2Si$ 704.3, m/z found 704.9 [M+H]$^+$. $^1$H NMR (400 MHz, CD$_3$OD) δ 7.91-7.88 (m, 1H), 7.76-7.72 (m, 1H), 7.20-7.08 (m, 2H), 6.97-6.91 (m, 1H), 5.96 (s, 0.3H), 5.90 (s, 0.7H), 4.25-4.21 (m, 2H), 4.11-3.79 (m, 6H), 2.99-2.84 (m, 4H), 2.50 (d, J=2.0 Hz, 1H), 2.43 (d, J=1.6 Hz, 2H), 2.27-2.24 (m, 2H), 2.11-1.97 (m, 2H), 1.88-1.85 (m, 1.4H), 1.68-1.64 (m, 0.6H), 1.49 (s, 3H), 1.12 (t, J=7.2 Hz, 3H), 1.05-1.01 (m, 2H), 0.07-0.05 (m, 9H).

Compound 437: (cis)-Ethyl 4-(2-chloro-4-fluorophenyl)-6-(2,2-dimethyl-3-(methylsulfonamido)cyclobutyl)-2-(thiazol-2-yl)-1,4-dihydropyrimidine-5-carboxylate LC-MS (ESI): $R_T$=4.161 min, mass calcd. for $C_{23}H_{26}ClFN_4O_4S_2$ 540.1, m/z found 541.2 [M+H]$^+$. $^1$H NMR (400 MHz, DMSO-d$_6$) δ 9.40 (d, J=3.2 Hz, 0.7H), 8.30 (s, 0.3H), 8.04-7.98 (m, 2H), 7.45-7.36 (m, 2H), 7.32-7.25 (m, 2H), 6.08 (s, 0.3H), 5.95 (d, J=3.2 Hz, 0.7H), 4.20-4.15 (m, 0.3H), 3.98 (q, J=7.2 Hz, 2H), 3.84-3.80 (m, 0.7H), 3.62-3.56 (m, 0.3H), 3.50-3.43 (m, 0.7H), 2.94 (s, 0.9H), 2.91 (s, 2.1H), 2.80-2.72 (m, 0.7H), 2.40-2.34 (m, 0.3H), 2.27-2.19 (m, 0.3H), 2.12-2.05 (m, 0.7H), 1.21 (s, 0.9H), 1.18 (s, 2.1H), 1.10-1.04 (m, 6H).

Racemic 437 (200 mg, 0.37 mmol) was separated by chiral Prep. HPLC (the separation condition: Column: Chiralpak IC 5 μm 20*250 mm; Mobile Phase: Hex:EtOH=60:40 at 12 mL/min; Temp: 30° C.; Wavelength: 230 nm) to afford the title compounds 437A (85 mg, 42% yield, 100% stereopure) and 437B (87 mg, 43% yield, 100% stereopure) as yellow solids.

Compound 437A: LC-MS (ESI): $R_T$=3.661 min, mass calcd. for $C_{23}H_{26}ClFN_4O_4S_2$ 540.1, m/z found 540.9 [M+H]$^+$. Chiral HPLC (Column: Chiralpak IC 5 μm 4.6*250 mm; Mobile Phase: Hex:EtOH=60:40 at 1 mL/min; Temp: 30° C.; Wavelength: 230 nm, $R_T$=6.429 min). $^1$H NMR (400 MHz, DMSO-d$_6$) δ 9.39 (d, J=3.2 Hz, 0.7H), 8.30 (s, 0.3H), 8.03-7.98 (m, 2H), 7.45-7.36 (m, 2H), 7.32-7.25 (m, 2H), 6.08 (s, 0.3H), 5.95 (d, J=3.2 Hz, 0.7H), 4.20-4.15 (m, 0.3H), 3.98 (q, J=7.2 Hz, 2H), 3.84-3.79 (m, 0.7H), 3.62-3.56 (m, 0.3H), 3.50-3.43 (m, 0.7H), 2.94 (s, 0.9H), 2.91 (s, 2.1H), 2.79-2.72 (m, 0.7H), 2.40-2.32 (m, 0.3H), 2.27-2.18 (m, 0.3H), 2.12-2.05 (m, 0.7H), 1.21 (s, 0.9H), 1.18 (s, 2.1H), 1.10-1.04 (m, 6H).

Compound 437B: LC-MS (ESI): $R_T$=3.691 min, mass calcd. for $C_{23}H_{26}ClFN_4O_4S_2$ 540.1, m/z found 540.9 [M+H]$^+$. Chiral HPLC (Column: Chiralpak IC 5 μm 4.6*250 mm; Mobile Phase: Hex:EtOH=60:40 at 1 mL/min; Temp: 30° C.; Wavelength: 230 nm, $R_T$=9.756 min). $^1$H NMR (400 MHz, DMSO-d$_6$) δ 9.38 (d, J=3.2 Hz, 0.7H), 8.30 (s, 0.3H), 8.03-7.98 (m, 2H), 7.45-7.36 (m, 2H), 7.32-7.25 (m, 2H), 6.08 (s, 0.3H), 5.95 (d, J=3.2 Hz, 0.7H), 4.20-4.15 (m, 0.3H), 3.98 (q, J=7.2 Hz, 2H), 3.84-3.79 (m, 0.7H), 3.62-3.56 (m, 0.3H), 3.50-3.43 (m, 0.7H), 2.94 (s, 0.9H), 2.91 (s, 2.1H), 2.79-2.72 (m, 0.7H), 2.40-2.33 (m, 0.3H), 2.27-2.18 (m, 0.3H), 2.12-2.05 (m, 0.7H), 1.21 (s, 0.9H), 1.18 (s, 2.1H), 1.10-1.04 (m, 6H).

Compound 438F and 438H: (trans)-Methyl 4-(2-bromo-3-fluorophenyl)-6-(1-((3-(tert-butoxycarbonyl)cyclobutyl)sulfonyl)piperidin-4-yl)-2-(thiazol-2-yl)-1,4-dihydropyrimidine-5-carboxylate and (cis)-methyl 4-(2-bromo-3-fluorophenyl)-6-(1-((3-(tert-butoxycarbonyl)cyclobutyl)sulfonyl)piperidin-4-yl)-2-(thiazol-2-yl)-1,4-dihydropyrimidine-5-carboxylate Purification condition: purified by silica gel column chromatography (petroleum ether:ethyl acetate=4:1 to 2:1), and further purified by C18 column (acetonitrile:water=80% to 88%) to give the title compounds 438F (450 mg, 38% yield, 100% stereopure) and 438H (350 mg, 30% yield, 99.5% stereopure) as yellow solids.

Compound 438F (trans): LC-MS (ESI): $R_T$=4.235 min, mass calcd. for $C_{29}H_{34}BrFN_4O_6S_2$ 696.1, m/z found 696.8 [M+H]$^+$. Chiral analysis (Column: Chiralpak IG 5 μm 4.6*250 mm; Mobile Phase: Hex:EtOH:DEA=60:40:0.2 at 1.0 mL/min; Temp: 30° C.; Wavelength: 230 nm, $R_T$=11.290 min). $^1$H NMR (400 MHz, DMSO-d$_6$) δ 9.56 (d, J=3.2 Hz, 0.8H), 9.16 (s, 0.2H), 8.01-7.98 (m, 1.7H), 7.93 (d, J=3.2 Hz, 0.3H), 7.44-7.37 (m, 1H), 7.29 (t, J=8.4 Hz, 1H), 7.24-7.20 (m, 0.8H), 7.15 (d, J=7.2 Hz, 0.2H), 6.06 (s, 0.2H), 5.97 (d, J=3.6 Hz, 0.8H), 4.04-3.96 (m, 1H), 3.77-3.71 (m, 3H), 3.52 (s, 2.4H), 3.51 (s, 0.6H), 3.16-3.08 (m, 1H), 2.92-2.83 (m, 2H), 2.61-2.54 (m, 4H), 2.06-1.76 (m, 3H), 1.62-1.59 (m, 1H), 1.42 (s, 9H).

Compound 438H (cis): LC-MS (ESI): $R_T$=4.145 min, mass calcd. for $C_{29}H_{34}BrFN_4O_6S_2$ 696.1, m/z found 696.8 [M+H]$^+$. Chiral analysis (Column: Chiralpak IA 5 μm 4.6*250 mm; Mobile Phase: Hex:EtOH=70:30 at 1.0 mL/min; Temp: 30° C.; Wavelength: 230 nm, $R_T$=9.158 min). $^1$H NMR (400 MHz, DMSO-d$_6$) δ 9.57 (d, J=2.8 Hz, 0.8H), 9.16 (s, 0.2H), 8.01-7.98 (m, 1.7H), 7.93 (d, J=3.2 Hz, 0.3H), 7.44-7.38 (m, 1H), 7.29 (t, J=8.4 Hz, 1H), 7.24-7.20 (m, 0.8H), 7.14 (d, J=7.6 Hz, 0.2H), 6.06 (s, 0.2H), 5.97 (d, J=3.2 Hz, 0.8H), 3.99-3.91 (m, 1H), 3.76-3.67 (m, 3H), 3.52 (s, 2.4H), 3.51 (s, 0.6H), 3.12-3.03 (m, 1H), 2.89-2.80 (m, 2H), 2.49-2.40 (m, 4H), 2.07-1.76 (m, 3H), 1.63-1.57 (m, 1H), 1.41 (s, 9H).

Compound 440B: Methyl 4-(2-chloro-4-fluorophenyl)-6-(3-(2-(2-(2-methoxyethoxy)ethoxy)ethyl-sulfonamido)bicyclo[1.1.1]pentan-1-yl)-2-(thiazol-2-yl)-1,4-dihydropyrimidine-5-carboxylate LC-MS (ESI): $R_T$=4.335 min, mass calcd. for $C_{27}H_{32}ClFN_4O_7S_2$ 642.1, m/z found 643.2 [M+H]$^+$. $^1$H NMR (400 MHz, CDCl$_3$) δ 7.86 (s, 0.7H), 7.83-7.81 (m, 1H), 7.49 (d, J=3.2 Hz, 0.3H), 7.45-7.42 (m, 1H), 7.30-7.28 (m, 0.5H), 7.26-7.24 (m, 0.5H), 7.15-7.11 (m, 1H), 6.97-6.89 (m, 1H), 6.33 (s, 0.7H), 6.15 (s, 0.7H), 6.09 (s, 0.3H), 6.02 (d, J=2.8 Hz, 0.3H), 3.95-3.91 (m, 2H), 3.69-3.66 (m, 6H), 3.63 (s, 1H), 3.60-3.57 (m, 4H), 3.41 (s, 1H), 3.40 (s, 2H), 3.32-3.26 (m, 2H), 2.56 (s, 4H), 2.50 (s, 2H).

Compound 443b: Methyl 4-(3-fluoro-2-methylphenyl)-6-(1-((((trans)-4-(methoxycarbonyl)cyclohexyl)methyl)sulfonyl)piperidin-4-yl)-2-(thiazol-2-yl)-1,4-dihydropyrimidine-5-carboxylate LC-MS (ESI): $R_T$=1.86 min, mass calcd. for $C_{30}H_{37}FN_4O_6S_2$ 632.2, m/z found 632.9 [M+H]$^+$. $^1$H NMR (400 MHz, DMSO-d$_6$) δ 9.59 (d, J=3.2 Hz, 0.9H), 9.17 (s, 0.1H), 8.00-7.92 (m, 2H), 7.22-7.13 (m, 2H), 7.08-6.99 (m, 1H), 5.87 (s, 0.1H), 5.73 (d, J=3.2 Hz, 0.9H), 3.79-3.66 (m, 3H), 3.59 (s, 3H), 3.53 (s, 0.5H), 3.52 (s, 2.5H), 2.94 (d, J=6.4 Hz, 2H), 2.87-2.76 (m, 2H), 2.45 (s, 0.4H), 2.38 (s, 2.6H), 2.30-2.22 (m, 1H), 2.06-1.77 (m, 8H), 1.66-1.62 (m, 1H), 1.36-1.31 (m, 2H), 1.18-1.06 (m, 2H)

Compound 447-1C and 447-1D: (trans)-Methyl 4-(4-fluoro-2-methylphenyl)-6-(1-((3-methyl-3-((2-(trimethylsilyl)ethoxy)carbonyl)cyclobutyl)sulfonyl)piperidin-4-yl)-2-(thiazol-2-yl)-1,4-dihydropyrimidine-5-carboxylate and (cis)-methyl 4-(4-fluoro-2-methylphenyl)-6-(1-((3-methyl-3-((2-(trimethylsilyl)ethoxy)carbonyl)cyclobutyl)-sulfonyl)piperidin-4-yl)-2-(thiazol-2-yl)-1,4-dihydropyrimidine-5-carboxylate Compound 447-1C(trans): LC-MS (ESI): $R_T$=2.323 min, mass calcd. for $C_{32}H_{43}FN_4O_6S_2Si$ 690.2, m/z found 691.1 [M+H]$^+$. $^1$H NMR (400 MHz, CD$_3$OD) δ 7.92-7.87 (m, 1H), 7.76-7.69 (m, 1H), 7.34-7.30 (m, 0.7H), 7.24-7.21 (m, 0.3H), 6.90-6.78 (m, 2H), 5.90 (s, 0.3H), 5.84 (s, 0.7H), 4.26-4.22 (m, 2H), 4.17-4.06 (m, 0.4H), 3.98-3.78 (m, 3.6H), 3.58 (s, 3H), 3.00-2.79 (m, 4H), 2.60 (s, 1H), 2.52 (s, 2H), 2.46-2.38 (m, 2H), 2.10-1.97 (m, 2H), 1.90-1.83 (m, 1H), 1.65-1.62 (m, 1H), 1.43 (s, 3H), 1.06-0.98 (m, 2H), 0.07 (s, 9H).

Compound 447-1D(cis): LC-MS (ESI): $R_T$=2.301 min, mass calcd. for $C_{32}H_{43}FN_4O_6S_2Si$ 690.2, m/z found 691.1 [M+H]$^+$. $^1$H NMR (400 MHz, CD$_3$OD) δ 7.92-7.87 (m, 1H), 7.75-7.71 (m, 1H), 7.34-7.31 (m, 0.7H), 7.25-7.21 (m, 0.3H), 6.93-6.83 (m, 2H), 5.90 (s, 0.3H), 5.84 (s, 0.7H), 4.25-4.20 (m, 2H), 4.12-4.02 (m, 1H), 3.95-3.78 (m, 3H), 3.58 (s, 3H), 2.99-2.84 (m, 4H), 2.60 (s, 1H), 2.52 (s, 2H), 2.29-2.22 (m, 2H), 2.11-2.01 (m, 2H), 1.93-1.83 (m, 1.3H), 1.66-1.63 (m, 0.7H), 1.48 (s, 3H), 1.05-1.00 (m, 2H), 0.06 (s, 9H).

Compound 449: Methyl 4-(2-chloro-4-fluorophenyl)-6-(1-(((4-(methoxycarbonyl)-1-methylcyclohexyl)methyl)sulfonyl)piperidin-4-yl)-2-(thiazol-2-yl)-1,4-dihydropyrimidine-5-carboxylate LC-MS (ESI): $R_T$=1.75 min, mass calcd. for $C_{30}H_{36}ClFN_4O_6S_2$ 666.2, m/z found 666.8 [M+H]$^+$. $^1$H NMR (400 MHz, DMSO-d$_6$) δ 9.56 (d, J=3.6 Hz, 0.8H), 9.18 (s, 0.2H), 8.02-7.99 (m, 1.8H), 7.93 (d, J=3.2 Hz, 0.2H), 7.44-7.41 (m, 1H), 7.38-7.33 (m, 1H), 7.24-7.20 (m, 1H), 6.02 (s, 0.2H), 5.92 (d, J=2.8 Hz, 0.8H), 3.98-3.93 (m, 0.2H), 3.74-3.66 (m, 2.8H), 3.60 (s, 3H), 3.53 (s, 2.4H), 3.52 (s, 0.6H), 3.01 (s, 0.9H), 2.95 (s, 1.1H), 2.87-2.77 (m, 2H), 2.33-2.24 (m, 1H), 2.02-1.44 (m, 11H), 1.27-1.20 (m, 1H), 1.17 (s, 1.2H), 1.15 (m, 1.8H).

Racemic 449 (100 mg, 95% purity, 0.142 mmol) was separated by chiral Prep. HPLC (separation condition: Column: Chiralpak IC 5 μm 20*250 mm; Mobile Phase: Hex:EtOH:DEA=70:30:0.3 at 15 mL/min; Temp: 30° C.; Wavelength: 214 nm) to afford the title compounds 449A (cis) (40 mg, 90% purity, 38% yield) as yellow solids and 449B (trans) (40 mg, 90% purity, 38% yield) as yellow solids.

Compound 449A (cis): LC-MS (ESI): $R_T$=1.67 min, mass calcd. for $C_{30}H_{36}ClFN_4O_6S_2$ 666.2, m/z found 666.8 [M+H]$^+$. Chiral analysis (Column: Chiralpak IC 5 μm 4.6*250 mm; Mobile Phase: Hex:EtOH:DEA=70:30:0.2 at 1.0 mL/min; Temp: 30° C.; Wavelength: 230 nm, $R_T$=11.261 min). $^1$H NMR (400 MHz, DMSO-$d_6$) δ 9.54 (d, J=3.2 Hz, 0.8H), 9.17 (s, 0.2H), 8.01 (s, 1.6H), 7.93 (br s, 0.4H), 7.44-7.35 (m, 2H), 7.24-7.19 (m, 1H), 6.02 (s, 0.2H), 5.92 (d, J=3.6 Hz, 0.8H), 3.96 (br s, 0.2H), 3.72-3.66 (m, 2.8H), 3.59 (s, 3H), 3.53 (s, 3H), 3.01 (s, 2H), 2.90-2.82 (m, 2H), 2.35-2.27 (m, 1H), 2.02-1.96 (m, 1H), 1.91-1.81 (m, 4H), 1.74-1.56 (m, 5H), 1.27-1.21 (m, 2H), 1.17 (s, 3H).

Compound 449B (trans): LC-MS (ESI): $R_T$=1.66 min, mass calcd. for $C_{30}H_{36}ClFN_4O_6S_2$ 666.2, m/z found 666.8 [M+H]$^+$. Chiral HPLC (Column: Chiralpak IC 5 μm 4.6*250 mm; Mobile Phase: Hex:EtOH:DEA=70:30:0.2 at 1.0 mL/min; Temp: 30° C.; Wavelength: 230 nm, $R_T$=13.764 min). $^1$H NMR (400 MHz, DMSO-$d_6$) δ 9.54 (d, J=3.2 Hz, 0.8H), 9.16 (s, 0.2H), 8.02-7.98 (m, 1.6H), 7.93 (d, J=3.2 Hz, 0.4H), 7.44-7.41 (m, 1H), 7.39-7.31 (m, 1H), 7.24-7.19 (m, 1H), 6.02 (s, 0.2H), 5.92 (d, J=3.2 Hz, 0.8H), 3.98-3.92 (m, 0.2H), 3.74-3.66 (m, 2.8H), 3.60 (s, 3H), 3.53 (s, 2.4H), 3.52 (s, 0.6H), 2.95 (s, 2H), 2.85-2.77 (m, 2H), 2.33-2.24 (m, 1H), 2.02-1.95 (m, 1H), 1.90-1.72 (m, 4H), 1.65-1.62 (m, 3H), 1.57-1.44 (m, 4H), 1.15 (s, 3H).

Compound 451: Methyl 4-(2-chloro-3,4-difluorophenyl)-6-(1-(((4-(methoxycarbonyl)-1-methylcyclohexyl)methyl)sulfonyl)piperidin-4-yl)-2-(thiazol-2-yl)-1,4-dihydropyrimidine-5-carboxylate LC-MS (ESI): $R_T$=1.70 min, mass calcd. for $C_{30}H_{35}ClF_2N_4O_6S_2$ 684.2, m/z found 684.8 [M+H]$^+$. $^1$H NMR (400 MHz, DMSO-$d_6$) δ 9.66 (d, J=3.6 Hz, 0.8H), 9.24 (s, 0.2H), 8.02-7.94 (m, 2H), 7.49-7.43 (m, 1H), 7.23-7.20 (m, 1H), 6.02 (s, 0.2H), 5.93 (d, J=2.8 Hz, 0.8H), 3.96 (br s, 0.2H), 3.76-3.69 (m, 2.8H), 3.60 (s, 3H), 3.53 (s, 3H), 3.01 (s, 0.8H), 2.94 (s, 1.2H), 2.90-2.76 (m, 2H), 2.34-2.24 (m, 1H), 2.02-1.44 (m, 11H), 1.27-1.19 (m, 1H), 1.17-1.15 (m, 3H). Racemic 451 (90 mg, 90% purity, 0.118 mmol) was separated by chiral Prep. HPLC (separation condition: Column: Chiralpak IC 5 μm 20*250 mm; Mobile Phase: Hex:EtOH:DEA=70:30:0.3 at 15 mL/min; Temp: 30° C.; Wavelength: 214 nm) to afford the title compounds 451A (48 mg, 90% purity, 53% yield) as yellow solids and 451B (40 mg, 90% purity, 44% yield) as yellow solids.

Compound 451A(cis): LC-MS (ESI): $R_T$=1.71 min, mass calcd. for $C_{30}H_{35}ClF_2N_4O_6S_2$ 684.2, m/z found 684.8 [M+H]$^+$. Chiral HPLC (Column: Chiralpak IC 5 μm 4.6*250 mm; Mobile Phase: Hex:EtOH:DEA=70:30:0.2 at 1.0 mL/min; Temp: 30° C.; Wavelength: 230 nm, $R_T$=10.547 min). $^1$H NMR (400 MHz, DMSO-$d_6$) δ 9.65 (s, 0.8H), 9.23 (s, 0.2H), 8.02-7.99 (m, 1.6H), 7.94 (d, J=3.2 Hz, 0.4H), 7.50-7.43 (m, 1H), 7.24-7.16 (m, 1H), 6.03 (s, 0.2H), 5.93 (s, 0.8H), 4.00-3.95 (m, 0.2H), 3.75-3.66 (m, 2.8H), 3.59 (s, 3H), 3.53 (s, 2.4H), 3.52 (s, 0.6H), 3.00 (s, 2H), 2.87-2.82 (m, 2H), 2.34-2.29 (m, 1H), 2.03-1.04 (m, 10H), 1.28-1.21 (m, 2H), 1.07 (s, 1.8H), 1.05 (s, 1.2H).

Compound 451B(trans): LC-MS (ESI): $R_T$=1.68 min, mass calcd. for $C_{30}H_{35}ClF_2N_4O_6S_2$ 684.2, m/z found 684.8 [M+H]$^+$. Chiral HPLC (Column: Chiralpak IC 5 μm 4.6*250 mm; Mobile Phase: Hex:EtOH:DEA=70:30:0.2 at 1.0 mL/min; Temp: 30° C.; Wavelength: 230 nm, $R_T$=12.719 min). $^1$H NMR (400 MHz, DMSO-$d_6$) δ 9.65 (s, 0.8H), 9.23 (s, 0.2H), 8.03-7.99 (m, 1.6H), 7.94 (d, J=3.2 Hz, 0.4H), 7.49-7.42 (m, 1H), 7.23-7.15 (m, 1H), 6.02 (s, 0.2H), 5.93 (s, 0.8H), 3.99-3.93 (m, 0.2H), 3.74-3.66 (m, 2.8H), 3.60 (s, 3H), 3.53 (s, 2.4H), 3.52 (s, 0.6H), 2.94 (s, 2H), 2.85-2.77 (m, 2H), 2.30-2.24 (m, 1H), 2.02-1.45 (m, 12H), 1.16 (s, 1.8H), 1.15 (s, 1.2H).

Compound 453: (trans)-Methyl 4-(2-chloro-3-fluorophenyl)-6-(1-(((4-(methoxycarbonyl)cyclohexyl)methyl)sulfonyl)piperidin-4-yl)-2-(thiazol-2-yl)-1,4-dihydropyrimidine-5-carboxylate $^1$H NMR (400 MHz, DMSO-$d_6$) δ 9.62 (d, J=4.0 Hz, 0.8H), 9.19 (s, 0.2H), 8.01-7.99 (m, 1.8H), 7.94 (d, J=3.2 Hz, 0.2H), 7.41-7.32 (m, 2H), 7.23-7.16 (m, 1H), 6.07 (s, 0.2H), 5.98 (d, J=3.2 Hz, 0.8H), 3.77-3.65 (m, 3H), 3.59 (s, 3H), 3.53 (s, 2.2H), 3.52 (s, 0.8H), 2.94 (d, J=6.4 Hz, 2H), 2.86-2.78 (m, 2H), 2.30-2.22 (m, 1H), 1.97-1.78 (m, 8H), 1.66-1.62 (m, 1H), 1.41-1.31 (m, 2H), 1.12-1.08 (m, 2H).

Compound 455: Methyl 4-(2-chloro-3,4-difluorophenyl)-6-(1-(((3-(methoxycarbonyl)bicyclo[1.1.1]pentan-1-yl)methyl)sulfonyl)piperidin-4-yl)-2-(thiazol-2-yl)-1,4-dihydropyrimidine-5-carboxylate LC-MS (ESI): $R_T$=2.579 min, mass calcd. for $C_{28}H_{29}ClF_2N_4O_6S_2$ 654.1, m/z found 654.7 [M+H]$^+$. $^1$H NMR (400 MHz, CDCl$_3$) δ 8.20 (s, 0.2H), 7.84-7.83 (m, 1H), 7.54 (d, J=3.2 Hz, 0.8H), 7.47 (d, J=3.2 Hz, 0.4H), 7.42 (d, J=2.0 Hz, 0.6H), 7.08-7.03 (m, 2H), 6.18 (s, 0.3H), 6.06 (d, J=2.4 Hz, 0.7H), 4.20-4.10 (m, 0.3H), 3.99-3.88 (m, 2.7H), 3.69 (s, 3H), 3.60 (s, 2H), 3.59 (s, 1H), 3.14-3.12 (m, 2H), 2.92-2.85 (m, 2H), 2.28-2.22 (m, 6H), 2.08-2.04 (m, 2H), 1.96-1.90 (m, 1H), 1.73-1.70 (m, 0.6H), 1.56 (s, 0.4H).

Compound 458: Methyl 4-(2-chloro-4-fluorophenyl)-6-(1-((1-(3-hydroxy-3-methylbutyl)-1H-pyrazol-4-yl)sulfonyl)piperidin-4-yl)-2-(thiazol-2-yl)-1,4-dihydropyrimidine-5-carboxylate LC-MS (ESI): $R_T$=3.150 min, mass calcd. for $C_{28}H_{32}ClFN_6O_5S_2$ 650.2, m/z found 651.2 [M+H]$^+$. $^1$H NMR (400 MHz, DMSO-$d_6$) δ 9.52 (d, J=3.6 Hz, 0.8H), 9.16 (s, 0.2H), 8.40 (s, 1H), 8.02-7.99 (m, 1.6H), 7.93 (d, J=3.2 Hz, 0.4H), 7.80 (s, 1H), 7.42-7.33 (m, 2H), 7.22-7.18 (m, 1H), 6.00 (s, 0.2H), 5.90 (d, J=3.2 Hz, 0.8H), 4.45 (s, 1H), 4.29-4.25 (m, 2H), 3.76-3.65 (m, 2H), 3.55-3.51 (m, 1H), 3.47 (s, 3H), 2.27-2.18 (m, 2H), 2.09-2.01 (m, 1H), 1.95-1.89 (m, 3H), 1.81-1.78 (m, 1H), 1.65-1.62 (m, 1H), 1.11 (s, 6H).

Compound 459: Methyl 4-(2-chloro-4-fluorophenyl)-6-(1-((2-(2-(2-methoxyethoxy)ethoxy)ethyl)sulfonyl)piperidin-4-yl)-2-(thiazol-2-yl)-1,4-dihydropyrimidine-5-carboxylate LC-MS (ESI): $R_T$=4.041 min, mass calcd. for $C_{27}H_{34}ClFN_4O_7S_2$ 644.2, m/z found 645.2 [M+H]$^+$. $^1$H NMR (400 MHz, CDCl$_3$) δ 8.19 (s, 0.3H), 7.83 (d, J=2.8 Hz, 1H), 7.52 (d, J=2.4 Hz, 0.7H), 7.45 (d, J=2.8 Hz, 1H), 7.29-7.28 (m, 0.7H), 7.27 (br s, 0.3H), 7.15-7.13 (m, 1H), 6.97-6.89 (m, 1H), 6.19 (s, 0.4H), 6.07 (s, 0.7H), 4.19-4.12 (m, 0.4H), 3.97-3.87 (m, 4.6H), 3.69-3.65 (m, 6H), 3.60-3.55 (m, 5H), 3.37 (d, J=5.2 Hz, 3H), 3.29-3.26 (m, 2H), 3.03-2.89 (m, 2H), 2.30-2.20 (m, 0.8H), 2.12-1.81 (m, 3.2H).

Compound 460: Methyl 6-(1-(2,5,8,11-tetraoxatridecan-13-ylsulfonyl)piperidin-4-yl)-4-(2-chloro-4-fluorophenyl)-2-(thiazol-2-yl)-1,4-dihydropyrimidine-5-carboxylate LC-MS (ESI): $R_T$=2.853 min, mass calcd. for $C_{29}H_{38}ClFN_4O_8S_2$ 688.2, m/z found 688.9 [M+H]$^+$. $^1$H NMR (400 MHz, CDCl$_3$) δ 8.19 (s, 0.3H), 7.83 (d, J=3.2 Hz, 1H), 7.53 (d, J=3.2 Hz, 0.7H), 7.45-7.42 (m, 1H), 7.30-7.28 (m, 0.7H), 7.26-7.24 (m, 0.3H), 7.16-7.12 (m, 1H), 6.98-6.89 (m, 1H), 6.19 (s, 0.3H), 6.06 (d, J=2.4 Hz, 0.7H), 4.18-4.11 (m, 0.3H), 3.99-3.87 (m, 4.7H), 3.66-3.62 (m, 10H), 3.60-3.58 (m, 3H), 3.56-3.54 (m, 2H), 3.39 (s, 2.1H), 3.37 (s, 0.9H), 3.29-3.26 (m, 2H), 3.04-2.88 (m, 2H), 2.30-2.20 (m, 0.7H), 2.12-1.80 (m, 3H), 1.73-1.69 (m, 0.3H).

Compound 461: Ethyl 6-(1-((1H-pyrazol-4-yl)sulfonyl)piperidin-4-yl)-4-(2-chloro-3,4-difluorophenyl)-2-(thiazol-2-yl)-1,4-dihydropyrimidine-5-carboxylate LC-MS (ESI): $R_T$=1.907 min, mass calcd. for $C_{24}H_{23}ClF_2N_6O_4S_2$ 596.1, m/z found 597.0 [M+H]$^+$.

Compound 464: Methyl 4-(2-chloro-4-fluorophenyl)-6-(1-((2-(2methoxyethoxy)ethyl)sulfonyl)piperidin-4-yl)-2-(thiazol-2-yl)-1,4-dihydropyrimidine-5-carboxylate LC-MS (ESI): $R_T$=3.921 min, mass calcd. for $C_{25}H_{30}ClFN_4O_6S_2$ 600.1, m/z found 600.9 [M+H]$^+$. $^1$H NMR (400 MHz, CDCl$_3$) δ 8.17 (s, 0.3H), 7.83 (d, J=3.2 Hz, 1H), 7.52 (d, J=3.2 Hz, 0.7H), 7.45 (d, J=2.8 Hz, 0.3H), 7.43-7.41 (m, 0.7H), 7.30-7.27 (m, 0.7H), 7.25-7.24 (m, 0.3H), 7.16-7.12 (m, 1H), 6.97-6.88 (m, 1H), 6.19 (s, 0.3H), 6.06 (d, J=2.4 Hz, 0.7H), 4.20-4.12 (m, 0.3H), 3.99-3.86 (m, 4.7H), 3.68-3.65 (m, 2H), 3.60-3.56 (m, 5H), 3.41 (s, 2.1H), 3.40 (s, 0.93H), 3.30-3.26 (m, 2H), 3.04-2.89 (m, 2H), 2.30-2.19 (m, 1H), 2.12-2.02 (m, 1H), 1.96-1.80 (m, 1.5H), 1.72-1.69 (m, 0.5H).

Compound 466: Methyl 6-(1-((1H-pyrazol-4-yl)sulfonyl)piperidin-4-yl)-4-(2-chloro-4-fluorophenyl)-2-(thiazol-2-yl)-1,4-dihydropyrimidine-5-carboxylate LC-MS (ESI): $R_T$=1.55 min, mass calcd. for $C_{23}H_{22}ClFN_6O_4S_2$ 564.1, m/z found 565.3 [M+H]$^+$. H NMR (400 MHz, DMSO-d$_6$) δ 13.76 (s, 1H), 9.51 (d, J=3.6 Hz, 0.8H), 9.15 (s, 0.2H), 8.49-8.19 (m, 1H), 8.10-7.76 (m, 3H), 7.42-7.39 (m, 1H), 7.36-7.29 (m, 1H), 7.22-7.17 (m, 1H), 5.99 (s, 0.2H), 5.90 (d, J=3.6 Hz, 0.8H), 3.77-3.67 (m, 2H), 3.55-3.47 (m, 4H), 2.44-2.36 (m, 0.2H), 2.28-2.17 (m, 2H), 2.10-1.99 (m, 1H), 1.95-1.85 (m, 1H), 1.80-1.77 (m, 1H), 1.64-1.61 (m, 0.8H).

Compound 467: Methyl 4-(2-chloro-4-fluorophenyl)-6-(1-((2,2-dimethyl-3,3-diphenyl-4,7,10-trioxa-3-siladodecan-12-yl)sulfonyl)piperidin-4-yl)-2-(thiazol-2-yl)-1,4-dihydropyrimidine-5-carboxylate LC-MS (ESI): $R_T$=2.14 min, mass calcd. for $C_{42}H_5{}^°ClFN_4O_7S_2Si$ 868.3, m/z found 869.7 [M+H]$^+$. $^1$H NMR (400 MHz, CDCl$_3$) δ 7.83 (d, J=3.2 Hz, 1H), 7.68-7.66 (m, 4H), 7.50 (d, J=2.8 Hz, 1H), 7.44-7.35 (m, 6H), 7.29-7.25 (m, 1H), 7.15-7.12 (m, 1H), 6.95-6.90 (m, 1H), 6.11 (s, 1H), 3.96-3.88 (m, 5H), 3.82 (t, J=5.6 Hz, 2H), 3.69-3.61 (m, 6H), 3.57 (s, 3H), 3.24 (t, J=6.0 Hz, 2H), 2.99-2.88 (m, 2H), 2.13-1.74 (m, 5H), 1.05 (s, 9H).

Compound 469: (trans)-Methyl 6-(1-((1-(3-(tert-butoxycarbonyl)cyclobutyl)-1H-pyrazol-4-yl)sulfonyl)piperidin-4-yl)-4-(2-chloro-4-fluorophenyl)-2-(thiazol-2-yl)-1,4-dihydropyrimidine-5-carboxylate LC-MS (ESI): $R_T$=2.26 min, mass calcd. for $C_{32}H_{36}ClFN_6O_6S_2$ 718.2, m/z found 718.8 [M+H]$^+$. $^1$H NMR (400 MHz, CDCl$_3$) δ 8.19 (s, 0.3H), 7.84 (d, J=2.8 Hz, 1H), 7.81 (s, 1H), 7.79 (s, 1H), 7.55 (d, J=3.2 Hz, 0.7H), 7.46 (d, J=2.8 Hz, 0.3H), 7.45-7.43 (m, 0.7H), 7.30-7.29 (m, 0.2H), 7.26-7.24 (m, 0.8H), 7.16-7.11 (m, 1H), 6.98-6.90 (m, 1H), 6.17 (s, 0.3H), 6.05 (d, J=2.4 Hz, 0.7H), 5.09-4.99 (m, 1H), 4.02-3.70 (m, 3H), 3.55 (s, 3H), 3.18-3.10 (m, 1H), 2.95-2.86 (m, 2H), 2.81-2.71 (m, 2H), 2.46-2.23 (m, 3H), 2.14-1.89 (m, 2.4H), 1.73-1.70 (m, 0.6H), 1.51 (s, 9H).

Compound 473: Methyl 4-(2-chloro-3,4-difluorophenyl)-6-(1-((2-methoxy-2-oxoethyl)sulfonyl)piperidin-4-yl)-2-(thiazol-2-yl)-1,4-dihydropyrimidine-5-carboxylate $^1$H NMR (400 MHz, DMSO-d$_6$) δ 9.64 (s, 1H), 8.03-7.94 (m, 2H), 7.47-7.41 (m, 1H), 7.25-7.16 (m, 1H), 5.94 (s, 1H), 4.34-4.31 (m, 2H), 3.83-3.68 (m, 6H), 3.52 (s, 3H), 2.96-2.87 (m, 2H), 2.04-1.94 (m, 1H), 1.90-1.77 (m, 2H), 1.73-1.62 (m, 1H).

Compound 475: Methyl 4-(2-chloro-4-fluorophenyl)-6-(1-((4-(2-ethoxy-2-oxoethyl)cyclohexyl)sulfonyl)piperidin-4-yl)-2-(thiazol-2-yl)-1,4-dihydropyrimidine-5-carboxylate $^1$H NMR (300 MHz, CDCl$_3$) δ 7.84 (d, J=2.1 Hz, 1H), 7.56-7.42 (m, 1.6H), 7.30-7.28 (m, 0.4H), 7.16-7.13 (m, 1H), 6.96-6.92 (m, 1H), 6.10 (s, 1H), 4.17-4.10 (m, 2.4H), 4.04-3.94 (m, 2.6H), 3.60 (s, 3H), 3.09-2.93 (m, 3H), 2.29-2.17 (m, 5H), 1.98-1.89 (m, 4H), 1.82-1.73 (m, 2H), 1.29-1.25 (m, 5H), 1.09-1.05 (m, 1H), 0.93-0.83 (m, 2H).

Racemic 475 (150 mg, 94% purity, 0.214 mmol) was separated by chiral Prep. HPLC (Chiralpak IC 5 μm 20*250 mm; Mobile Phase: Hex:EtOH:DEA=40:60:0.3 at 11 mL/min; Temp: 30° C.; Wavelength: 214 nm) to give the title compounds 475A (50 mg, 95% purity from $^1$H NMR, 33% yield) and 475B (50 mg, 92% purity, 32% yield) as yellow solids.

Compound 475A(trans): LC-MS (ESI): $R_T$=1.91 min, mass calcd. for $C_{30}H_{36}ClFN_4O_6S_2$ 666.2, m/z found 666.9 [M+H]$^+$. Chiral analysis (Column: Chiralpak IC 5 μm 4.6*250 mm: Mobile Phase: Hex:EtOH:DEA. 40:60:0.2 at 1.0 mL/min; Temp: 30° C.; Wavelength: 230 nm, $R_T$=10.297 min). $^1$H NMR (300 MHz, CDCl$_3$) δ 8.17 (s, 0.3H), 7.83 (d, J=2.1 Hz, 1H), 7.54 (d, J=2.4 Hz, 0.7H), 7.45-7.42 (m, 1H), 7.30-729 (m, 1H), 7.15-7.11 (m, 1H), 6.97-6.88 (m, 1H), 6.18 (s, 0.31-), 6.06 (d, J=1.8 Hz, 0.7-1), 4.20-4.11 (m, 2.3H), 4.07-3.90 (m, 2.7H), 3.60 (s, 21-), 3.59 (s, 1H), 3.09-2.88 (m, 3H), 2.26-2.18 (in, 4.3H), 2.09-1.78 (m, 5.7H), 1.69-1.60 (m, 3H), 1.26 (t, J=5.4 Hz, 3H), 1.12-1.02 (m, 2H).

Compound 475B(cis): LC-MS (ESI): $R_T$=1.92 min, mass calcd. for $C_{30}H_{36}ClFN_4O_6S_2$ 666.2, m/z found 666.9

[M+H]⁺. Chiral analysis (Column: Chiralpak IC 5 μm 4.6*250 mm; Mobile Phase: Hex:EtOH:DEA=40:60:0.2 at 1.0 mL/min; Temp: 30° C.; Wavelength: 230 nm, $R_T$=8.298 min). ¹H NMR (300 MHz, CDCl₃) δ 8.17 (s, 0.3H), 7.83-7.81 (m, 1H), 7.52-7.50 (m, 0.7H), 7.45-7.41 (m, 1H), 7.30-7.27 (m, 0.6H), 7.25-7.22 (m, 0.4H), 7.16-7.10 (m, 1H), 6.97-6.87 (m, 1H), 6.18 (s, 0.3H), 6.06 (d, J=2.4 Hz, 0.7H), 4.18-3.87 (m, 5H), 3.59 (s, 3H), 3.09-2.95 (m, 3H), 2.39-2.36 (m, 2H), 2.29-2.11 (m, 2H), 2.02-1.98 (m, 1H), 1.95-1.69 (m, 8.6H), 1.66-1.63 (m, 1.4H), 1.25 (t, J=7.2 Hz, 3H).

Compound 477: Methyl 4-(2-chloro-4-fluorophenyl)-6-(1-((4-(2-ethoxy-2-oxoethyl)cyclohexyl)sulfonyl)piperidin-4-yl)-2-(thiazol-2-yl)-1,4-dihydropyrimidine-5-carboxylate LC-MS (ESI): $R_T$=1.93 min, mass calcd. for C₃₀H₃₅ClF₂N₄O₆S₂ 684.2, m/z found 684.9 [M+H]⁺. ¹H NMR (400 MHz, CDCl₃) δ 7.83 (d, J=3.2 Hz, 1H), 7.55-7.46 (m, 1H), 7.06-7.02 (m, 2H), 6.18 (s, 0.4H), 6.06 (s, 0.6H), 4.16-3.93 (m, 5H), 3.60 (s, 3H), 3.09-2.89 (m, 3H), 2.38-2.17 (m, 6H), 2.01-1.74 (m, 8H), 1.28-1.24 (m, 5H).

Racemic 477 (140 mg, 95% purity, 0.194 mmol) was separated by chiral Prep. HPLC (Chiralpak IC 5 Lm 30*250 mm; Mobile Phase: Hex:EtOH:DEA=50:50:0.3 at 25 mL/min; Temp: 30° C.; Wavelength: 230 nm) to give the title compounds 477A (50 mg, 95% purity from ¹H NMR, 36% yield) and 477B (30 mg, 95% purity from ¹H NMR, 21% yield) as yellow solids.

Compound 477A(trans): LC-MS (ESI): $R_T$=1.94 min, mass calcd. for C₃₀H₃₅ClF₂N₄O₆S₂ 684.2, m/z found 684.8 [M+H]⁺. Chiral analysis (Column: Chiralpak IC 5 μm 4.6*250 mm; Mobile Phase: Hex:EtOH:DEA=50:50:0.2 at 1.0 mL/min; Temp.: 30° C.; Wavelength: 230 nm, $R_T$=10.735 min). 1H NMR (400 MHz, CDCl₃) δ 8.22 (s, 0.4H), 7.84-7.82 (m, 1H), 7.55 (d, J=2.8 Hz, 0.6H), 7.46-7.43 (m, 1H), 7.08-7.00 (m, 2H), 6.17 (s, 0.4H), 6.06 (d, J=2.8 Hz, 0.6H), 4.19-4.13 (m, 2.3H), 4.06-3.90 (m, 2.7H), 3.60 (s, 1.8H), 3.59 (s, 1.2H), 3.08-2.88 (m, 3H), 2.25-2.14 (m, 4.7H), 2.04-1.77 (m, 6H), 1.69-1.66 (m, 2.3H), 1.26 (t, J=7.2 Hz, 3H), 1.11-1.01 (m, 2H).

Compound 477B(cis): LC-MS (ESI): $R_T$=1.95 min, mass calcd. for C₃₀H₃₅ClF₂N₄O₆S₂ 684.2, m/z found 684.8 [M+H]⁺. Chiral analysis (Column: Chiralpak IC 5 μm 4.6*250 mm; Mobile Phase: Hex:EtOH:DEA=50:50:0.2 at 1.0 mL/min; Temp.: 30° C.; Wavelength: 230 nm, $R_T$=8.605 min). ¹H NMR (400 MHz, CDCl₃) 8.19 (s, 0.31-), 7.83 (d, J==3.2 Hz, 1H), 7.53-7.52 (m, 0.7-), 7.46 (d, J=3.2 Hz, 0.4H), 7.41 (s, 0.6H), 7.08-7.00 (m, 2H), 6.18 (s, 0.4H), 6.06 (d, J=2.8 Hz, 0.6H), 4.22-3.89 (m, 5H), 3.60 (s, 1.8I), 3.59 (s, 12H), 3.08-2.97 (m, 3), 2.39-2.36 (m, 2H₁), 2.25-2.15 (m, 2H), 2.08-1.99 (m, 1H₁), 1.96-1.78 (in, 8H), 1.73-1.61 (m, 2H), 1.26 (t, J=7.2 Hz, 3H).

Compound 479: Ethyl 6-(1-(((3-(tert-butoxycarbonyl)cyclobutyl)methyl)sulfonyl)piperidin-4-yl)-4-(2-chloro-3,4-difluorophenyl)-2-(thiazol-2-yl)-1,4-dihydropyrimidine-5-carboxylate LC-MS (ESI): $R_T$=2.02 min, mass calcd. for C₃₁H₃₇ClF₂N₄O₆S₂ 698.2, m/z found 699.2 [M+H]⁺. ¹H NMR (400 MHz, CDCl₃) δ 8.18 (s, 0.4H), 7.83 (d, J=3.2 Hz, 1H), 7.53 (d, J=3.2 Hz, 0.6H), 7.45 (d, J=3.2 Hz, 0.4H), 7.36 (s, 0.6H), 7.11-6.98 (m, 2H), 6.20 (s, 0.4H), 6.09 (d, J=2.4 Hz, 0.6H), 4.22-3.86 (m, 5H), 3.11-2.74 (m, 6H), 2.58-2.44 (m, 2H), 2.30-2.06 (m, 3.6H), 1.97-1.77 (m, 1.8H), 1.75-1.67 (0.6H), 1.50-1.41 (m, 9H), 1.26 (t, J=7.2 Hz, 0.4H), 1.12 (t, J=7.2 Hz, 3H).

Racemic 479 (750 mg, 1.07 mmol) was separated by chiral Prep. HPLC (first separation condition: Column: Chiralpak ID 5 μm 20*250 mm; Mobile Phase: Hex:EtOH:DEA=80:20:0.3 at 15 mL/min; Wavelength: 214 nm; second separation condition: Column: Superchiral S-IC 5 μm 21*250 mm; Mobile Phase: Hex:EtOH=95:5 at 20 mL/min; Wavelength: 254 nm; third separation condition: Column: Superchiral S-IC 5 μm 21*250 mm; Mobile Phase: Hex:EtOH=95:5 at 20 mL/min; Wavelength: 254 nm) to give the title compounds 479M (170 mg, 99.8% purity, 23% yield, 100% stereopure), 479N (60 mg, 98.5% purity, 8% yield, 100% stereopure), 479P (120 mg, 99.9% purity, 16% yield, 100% stereopure) and 479Q (60 mg, 99.8% purity, 8% yield, 100% stereopure) as yellow solids.

Compound 479M: LC-MS (ESI): $R_T$=3.331 min, mass calcd. for C₃₁H₃₇ClF₂N₄O₆S₂ 698.2, m/z found 699.2 [M+H]⁺. Chiral analysis (Column: Chiralpak ID 5 μm 4.6*250 mm; Mobile Phase: Hex:EtOH:DEA=80:20:0.2 at 1.0 mL/min; Temp: 30° C.; Wavelength: 230 nm, $R_T$=12.253 min). ¹H NMR (400 MHz, DMSO-d₆) δ 9.63 (d, J=3.6 Hz, 0.8H), 9.14 (s, 0.2H), 8.04-7.99 (m, 1.8H), 7.94 (d, J=3.2 Hz, 0.2H), 7.49-7.43 (m, 1H), 7.24-7.17 (m, 1H), 6.03 (s, 0.2H), 5.94 (d, J=3.2 Hz, 0.8H), 4.01-3.94 (m, 2.2H), 3.75-3.66 (m, 2.8H), 3.16 (d, J=7.2 Hz, 2H), 3.02-2.93 (m, 1H), 2.85-2.77 (m, 2H), 2.67-2.59 (m, 1H), 2.35-2.28 (m, 2H), 2.10-1.93 (m, 3H), 1.90-1.77 (m, 2.2H), 1.65-1.62 (m, 0.8H), 1.39 (s, 9H), 1.10-1.03 (m, 3H).

Compound 479N: LC-MS (ESI): $R_T$=3.318 min, mass calcd. for C₃₁H₃₇ClF₂N₄O₆S₂ 698.2, m/z found 699.2 [M+H]⁺. Chiral analysis (Column: Chiralpak ID 5 μm 4.6*250 mm; Mobile Phase: Hex:EtOH:DEA=80:20:0.2 at 1.0 mL/min; Temp: 30° C.; Wavelength: 230 nm, $R_T$=12.963 min). ¹H NMR (400 MHz, DMSO-d₆) δ 9.63 (d, J=3.2 Hz, 0.8H), 9.14 (s, 0.2H), 8.01-7.99 (m, 1.8H), 7.94 (d, J=2.8 Hz, 0.2H), 7.49-7.43 (m, 1H), 7.24-7.17 (m, 1H), 6.04 (s, 0.2H), 5.94 (d, J=3.6 Hz, 0.8H), 4.01-3.94 (m, 2.2H), 3.75-3.66 (m, 2.8H), 3.25 (d, J=7.6 Hz, 2H), 3.09-3.01 (m, 1H), 2.86-2.73 (m, 3H), 2.33-2.27 (m, 2H), 2.15-2.08 (m, 2H), 2.04-1.97 (m, 1H), 1.95-1.78 (m, 2.2H), 1.65-1.62 (m, 0.8H), 1.41 (s, 9H), 1.10-1.03 (m, 3H).

Compound 479P: LC-MS (ESI): $R_T$=3.318 min, mass calcd. for C₃₁H₃₇ClF₂N₄O₆S₂ 698.2, m/z found 699.2 [M+H]⁺. Chiral analysis (Column: Chiralpak ID 5 μm 4.6*250 mm; Mobile Phase: Hex:EtOH:DEA=80:20:0.2 at 1.0 mL/min; Temp: 30° C.; Wavelength: 230 nm, $R_T$=15.188 min). 1H NMR (400 MHz, DMSO-d₆) δ 9.63 (d, J=3.2 Hz, 0.8H), 9.14 (s, 0.2H), 8.01-7.99 (m, 1.8H), 7.94 (d, J=2.8 Hz, 0.2H), 7.49-7.43 (m, 1H), 7.24-7.17 (m, 1H), 6.04 (s, 0.2H), 5.94 (d, J=3.6 Hz, 0.8H), 4.01-3.94 (m, 2.2H), 3.75-3.66 (m, 2.8H), 3.16 (d, J=7.6 Hz, 2H), 3.02-2.93 (m, 1H), 2.85-2.77 (m, 2H), 2.67-2.59 (m, 1H), 2.35-2.28 (m, 2H), 2.11-1.93 (m, 3H), 1.90-1.77 (m, 2.2H), 1.65-1.62 (m, 0.8H), 1.39 (s, 9H), 1.10-1.03 (m, 3H).

Compound 479Q: LC-MS (ESI): $R_T$=3.313 min, mass calcd. for C₃₁H₃₇ClF₂N₄O₆S₂ 698.2, m/z found 699.2 [M+H]⁺. Chiral analysis (Column: Chiralpak ID 5 μm 4.6*250 mm; Mobile Phase: Hex:EtOH:DEA=80:20:0.2 at 1.0 mL/min; Temp: 30° C.; Wavelength: 230 nm, $R_T$=15.206 min). ¹H NMR (400 MHz, DMSO-d₆) δ 9.63 (d, J=2.8 Hz, 0.8H), 9.14 (s, 0.2H), 8.01-7.99 (m, 1.8H), 7.94 (d, J=3.2 Hz, 0.2H), 7.49-7.43 (m, 1H), 7.24-7.17 (m, 1H), 6.04 (s, 0.2H), 5.94 (d, J=2.0 Hz, 0.8H), 4.01-3.94 (m, 2.2H), 3.75-3.66 (m, 2.8H), 3.25 (d, J=7.2 Hz, 2H), 3.08-3.01 (m, 1H), 2.86-2.73 (m, 3H), 2.33-2.27 (m, 2H), 2.15-2.05 (m, 2H), 2.02-1.94 (m, 1H), 1.90-1.77 (m, 2.2H), 1.65-1.62 (m, 0.8H), 1.41 (s, 9H), 1.10-1.03 (m, 3H).

Compound 481A and 481B: Ethyl 6-(1-((3-(2-(tert-butoxy)-2-oxoethyl)cyclobutyl)sulfonyl)piperidin-4-yl)-4-(2-chloro-3,4-difluorophenyl)-2-(thiazol-2-yl)-1,4-dihydropyrimidine-5-carboxylate Purification conditions: silica gel column chromatography (petroleum ether:ethyl acetate=4:1 to 2:1) to give the product (210 mg, 88% yield) as yellow solids, which was separated by chiral Prep. SFC (Column: Chiralpak IC 5 μm 20*250 mm; Mobile Phase: $CO_2$:IPA:DEA=60:40:0.3 at 50 g/min; Col. Temp: 40° C.; Wavelength: 230 nm; Back pressure: 100 bar) to afford the title compounds 481A (65.8 mg, 31% yield, 100% stereopure) and 481B (64.8 mg, 31% yield, 100% stereopure) as yellow solids.

Compound 481A: LC-MS (ESI): $R_T$=3.997 min, mass calcd. for $C_{31}H_{37}ClF_2N_4O_6S_2$ 698.2, m/z found 699.2 [M+H]$^+$. Chiral analysis (Column: Chiralpak IC 5 μm 4.6*250 mm; Mobile Phase: $CO_2$:IPA:DEA=60:40:0.2 at 3.0 g/min; Col. Temp: 40° C.; Wavelength: 280 nm, $R_T$=5.40 min). 1H NMR (400 MHz, $CD_3OD$) δ 7.93 (d, J=3.2 Hz, 0.3H), 7.89 (d, J=3.6 Hz, 0.7H), 7.76 (d, J=3.2 Hz, 0.7H), 7.73 (d, J=3.6 Hz, 0.3H), 7.27-7.19 (m, 2H), 6.15 (s, 0.3H), 6.08 (s, 0.7H), 4.11-3.98 (m, 3.4H), 3.95-3.82 (m, 2.6H), 2.98-2.88 (m, 2H), 2.82-2.74 (m, 1H), 2.70-2.61 (m, 2H), 2.48 (d, J=7.6 Hz, 2H), 2.22-1.85 (m, 5.3H), 1.70-1.65 (m, 0.7H), 1.44-1.43 (m, 9H), 1.14-1.10 (m, 3H).

Compound 481B: LC-MS (ESI): $R_T$=3.986 min, mass calcd. for $C_{31}H_{37}ClF_2N_4O_6S_2$ 698.2, m/z found 699.1 [M+H]$^+$. Chiral analysis (Column: Chiralpak IC 5 μm 4.6*250 mm; Mobile Phase: $CO_2$:IPA:DEA=60:40:0.2 at 3.0 g/min; Col. Temp: 40° C.; Wavelength: 280 nm, $R_T$=4.28 min). 1H NMR (400 MHz, DMSO-d6) δ 9.62 (d, J=3.2 Hz, 0.7H), 9.12 (s, 0.3H), 8.01-8.00 (m, 2H), 7.51-7.43 (m, 1H), 7.24-7.17 (m, 1H), 6.03 (s, 0.3H), 5.93 (d, J=3.2 Hz, 0.7H), 4.01-3.89 (m, 3H), 3.76-3.64 (m, 3H), 2.88-2.77 (m, 2H), 2.44-2.41 (m, 1H), 2.34 (d, J=7.2 Hz, 2H), 2.07-1.57 (m, 8H), 1.40-1.39 (m, 9H), 1.09-1.03 (m, 3H).

Compound 483: Methyl 6-(1-((2-(2-((tert-butyldiphenylsilyl)oxy)ethoxy)ethyl)sulfonyl)piperidin-4-yl)-4-(2-chloro-4-fluorophenyl)-2-(thiazol-2-yl)-1,4-dihydropyrimidine-5-carboxylate $^1$H NMR (400 MHz, $CDCl_3$) δ 8.16 (s, 0.3H), 7.82-7.81 (m, 1H), 7.69-7.67 (m, 4H), 7.48 (d, J=3.2 Hz, 0.7H), 7.44-7.34 (m, 7H), 7.30-7.27 (m, 0.6H), 7.25-7.23 (m, 0.4H), 7.16-7.12 (m, 1H), 6.97-6.88 (m, 1H), 6.19 (s, 0.3H), 6.06 (d, J=2.4 Hz, 0.7H), 4.10-4.05 (m, 0.3H), 3.99-3.82 (m, 6.7H), 3.63-3.60 (m, 2H), 3.57-3.56 (m, 3H), 3.22-3.18 (m, 2H), 2.95-2.84 (m, 2H), 2.29-2.19 (m, 0.7H), 2.11-1.99 (m, 1H), 1.92-1.89 (m, 1.2H), 1.83-1.77 (m, 0.4H), 1.71-1.67 (m, 0.7H), 1.58 (s, 9H).

Section IV: Hydrolysis of the Labile Ester of Primary Dihydropyrimidines of General Formula I Compound 105: 3-((4-(6-(2-Chloro-4-fluorophenyl)-5-(methoxycarbonyl)-2-(thiazol-2-yl)-3,6-dihydropyrimidin-4-yl)piperidin-1-yl)sulfonyl)propanoic Acid Method S: To a solution of methyl 4-(2-chloro-4-fluorophenyl)-6-(1-((3-methoxy-3-oxopropyl)sulfonyl) piperidin-4-yl)-2-(thiazol-2-yl)-1,4-dihydropyrimidine-5-carboxylate Compound 104 (63 mg, 0.11 mmol) in tetrahydrofuran (2 mL) was added a solution of lithium hydroxide monohydrate (13.4 mg, 0.33 mmol) in water (3 mL) at 0° C. After stirring at room temperature for 2 hours, the mixture was acidified to pH=3 with 1 N hydrochloric acid aqueous solution (5 mL). The obtained mixture was extracted with ethyl acetate (10 mL) for three times. The combined organic layers were washed with brine (10 mL), dried over $Na_2SO_{4(s)}$ and filtered. The filtrate was concentrated under reduced pressure to give the title compound (30 mg, 49% yield) as yellow solids. LC-MS (ESI): $R_T$=3.040 min, mass calcd. for $C_{23}H_{24}ClFN_4O_6S_2$ 570.1, m/z found 571.1 [M+H]$^+$. Chiral HPLC (Column: Chiralpak IC 5 μm 4.6*250 mm; Mobile Phase: Hex: EtOH:TFA=70:30:0.2 at 1.0 mL/min; Temp: 30° C.; Wavelength: 230 nm, $R_T$=11.155 min). $^1$H NMR (400 MHz, DMSO-d$_6$) δ 8.00-7.95 (m, 2H), 7.41 (dd, J=8.8, 2.4 Hz, 1H), 7.38-7.34 (m, 1H), 7.23-7.18 (m, 1H), 5.94 (s, 1H), 3.75-3.66 (m, 3H), 3.54 (s, 3H), 3.23 (t, J=3.6 Hz, 2H), 2.88 (q, J=12.4 Hz, 2H), 2.50-2.46 (m, 2H), 2.06-2.94 (m, 1H), 1.86-1.75 (m, 2H), 1.70-1.56 (m, 1H).

Compound 92: 2-(trans-2-(6-(2-Chloro-4-fluorophenyl)-5-(ethoxycarbonyl)-2-(thiazol-2-yl)-3,6-dihydropyrimidin-4-yl)cyclopropyl)acetic Acid Method T: A mixture of Compound 91H (46 mg, 0.09 mmol) in 4M hydrochloric acid in 1,4-dioxane (4 mL) was stirred at room temperature for 2 hours. Then it was concentrated to give a residue, which was purified by preparation thin layer chromatography (petroleum ether:ethyl acetate=1:1) to give the title compound (14.0 mg, 34% yield) as yellow solids. LC-MS (ESI): $R_T$=3.904 min, mass calcd. for $C_{21}H_{19}ClFN_3O_4S$, 463.1, m/z found 463.9 [M+H]$^+$. Chiral HPLC (Column: Chiralpak IE 5 μm 4.6*250 mm; Mobile Phase: Hex:IPA:TFA=85:15:0.2 at 1.0 mL/min; Temp: 30° C.; Wavelength: 230 nm, $R_T$=7.771 min). $^1$H NMR (400 MHz, DMSO-d$_6$) δ 9.44 (d, J=3.6 Hz, 1H), 7.99-7.96 (m, 2H), 7.44-7.36 (m, 2H), 7.20-7.15 (m, 1H), 5.90 (d, J=2.0 Hz, 1H), 4.02-3.94 (m, 2H), 3.13-3.07 (m, 1H), 2.37-2.32 (m, 3H), 1.92-1.82 (m, 1H), 1.08 (t, J=7.2 Hz, 3H), 0.78-0.71 (m, 1H).

Compound 141: (trans)-3-((4-(6-(2-chloro-4-fluorophenyl)-5-(methoxycarbonyl)-2-(thiazol-2-yl)-3,6-dihydropyrimidin-4-yl)piperidin-1-yl)sulfonyl)-1-methylcyclobutane-1-carboxylic Acid Method U: To a solution of (trans)-methyl 4-(2-chloro-4-fluorophenyl)-6-(1-((3-methyl-3-((2-(trimethylsilyl)ethoxy) carbonyl)cyclobutyl) sulfonyl)piperidin-4-yl)-2-(thiazol-2-yl)-1,4-dihydropyrimidine-5-carboxylate compound 140A (160 mg, 0.202 mmol) in dichloromethane (8 mL) was added trifluoroacetic acid (4 mL) at room temperature. After stirred at room temperature under nitrogen atmosphere for 2 hours, the reaction mixture was diluted with water (20 mL) and extracted with ethyl acetate (20 mL) twice. The combined organic layers were washed with brine (20 mL), dried over $Na_2SO_{4(s)}$, filtered and concentrated. The residue was purified by C18 column (acetonitrile:water=60% to 80%) to give the title compound (125 mg, 98% yield) as yellow solids. LC-MS (ESI): $R_T$=3.476 min, mass calcd. For $C_{26}H_{28}ClFN_4O_6S_2$ 610.1, m/z found 610.9 [M+H]$^+$. $^1$H NMR (400 MHz, DMSO-d$_6$) δ 12.58 (s, 1H), 9.55 (d, J=3.2 Hz, 0.8H), 9.15 (s, 0.2H), 8.01-7.98 (m, 1.8H), 7.93 (d, J=3.2 Hz, 0.2H), 7.45-7.41 (m, 1H), 7.37-7.30 (m, 1H), 7.24-7.17 (m, 1H), 6.01 (s, 0.2H), 5.91 (d, J=3.2 Hz, 0.8H), 4.00-3.92 (m, 1H), 3.79-3.65 (m, 3H), 3.53 (s, 2.4H), 3.52

(s, 0.6H), 2.91-2.82 (m, 2H), 2.79-2.68 (m, 2H), 2.29-2.20 (m, 2H), 2.08-1.71 (m, 3H), 1.62-1.55 (m, 1H), 1.35 (s, 3H).

Compound 270A: (trans)-3-((4-(6-(2-Chloro-3,4-difluorophenyl)-5-(ethoxycarbonyl)-2-(thiazol-2-yl)-3,6-dihydropyrimidin-4-yl)piperidin-1-yl)sulfonyl)-1-methylcyclobutanecarboxylic Acid Method W: To a solution of (trans)-ethyl 4-(2-chloro-3,4-difluorophenyl)-6-(1-((3-methyl-3-((2-(trimethylsilyl)ethoxy)carbonyl)cyclobutyl) sulfonyl)piperidin-4-yl)-2-(thiazol-2-yl)-1,4-dihydropyrimidine-5-carboxylate compound 269A (180 mg, 90% purity, 0.218 mmol) in tetrahydrofuran (5 mL) was added 1 M tetrabutylammonium fluoride in tetrahydrofuran (5 mL, 5.0 mmol). After stirred at room temperature for 2 hours, the reaction was quenched with water (5 mL) and concentrated to give a residue, which was diluted with water (5 mL) and extracted with ethyl acetate (10 mL) for three times. The combined organic layers were washed with water (10 mL) for three times, dried over $Na_2SO_{4(s)}$ and concentrated to afford a crude product, which was purified by Prep. HPLC (Column: Gilson Xbridge C18 (5 μm 19*150 mm), Mobile Phase A: water (0.1% ammonium bicarbonate), Mobile Phase B: acetonitrile, UV: 214 nm, Flow rate: 15 mL/min, Gradient: 10-80% (% B)) to give the desired product (125 mg, 99.7% purity, 89% yield) as yellow solids. LC-MS (ESI): $R_T$=3.401 min, mass calcd. For $C_{27}H_{29}ClF_2N_4O_6S_2$ 642.1 m/z found 643.0 [M+H]$^+$. $^1$H NMR (400 MHz, DMSO-d$_6$) δ 8.01-7.94 (m, 2H), 7.45 (q, J=8.4 Hz, 1H), 7.23-7.15 (m, 1H), 6.04 (s, 0.2H), 5.93 (s, 0.8H), 4.02-3.89 (m, 3H), 3.75-3.64 (m, 3H), 2.92-2.80 (m, 2H), 2.74-2.64 (m, 2H), 2.25-2.18 (m, 2H), 2.02-1.70 (m, 3H), 1.64-1.56 (m, 1H), 1.33 (s, 3H), 1.07 (t, J=7.2 Hz, 3H).

Similarly utilizing the analogous procedures (Method S or Method T, method U, or method W), the following acids could be prepared:

| Method & Ester | Acid |
|---|---|
| S Compound 104 | 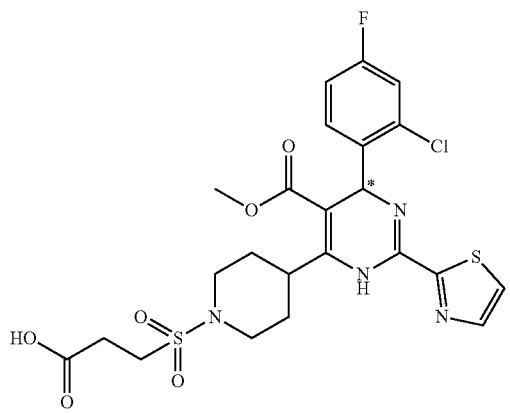<br>Compound 105 |
| S Compound 106 | 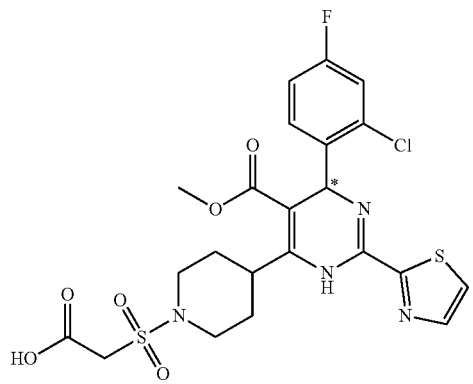<br>Compound 107 |

-continued
| Method & Ester | Acid |
|---|---|
| S Compound 6B | 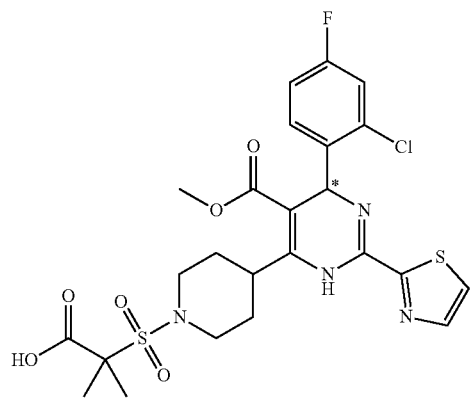<br>Compound 7 |
| S Compound 113 | 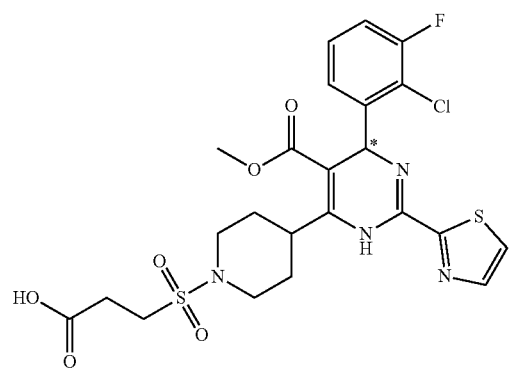<br>Compound 114 |
| S Compound 16X | 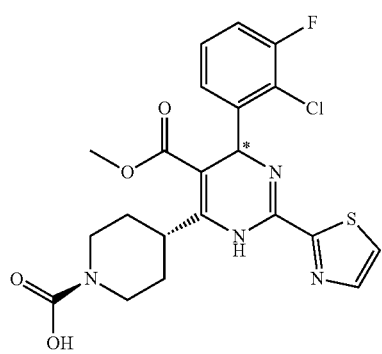<br>Compound 17 |

-continued
| Method & Ester | Acid |
|---|---|
| S Compound 18X | 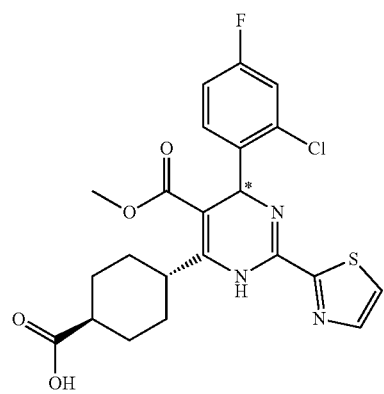<br>Compound 19 |
| S Compound 20Y | 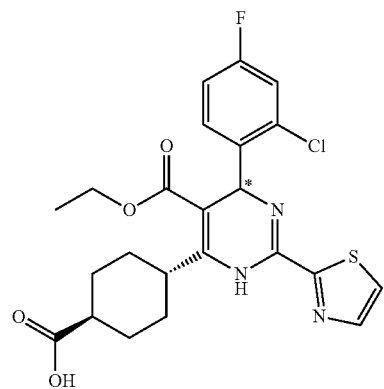<br>Compound 21 |
| S Compound 22Y | 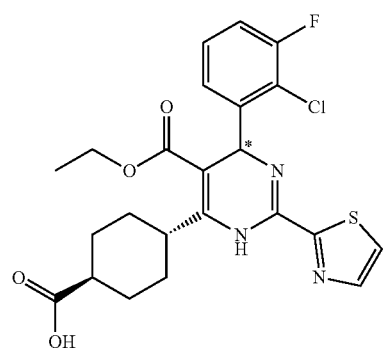<br>Compound 23 |

-continued
| Method & Ester | Acid |
|---|---|
| S Compound 24Q | 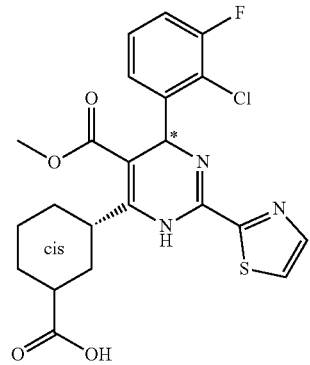
Compound 25 |
| S Compound 28 | 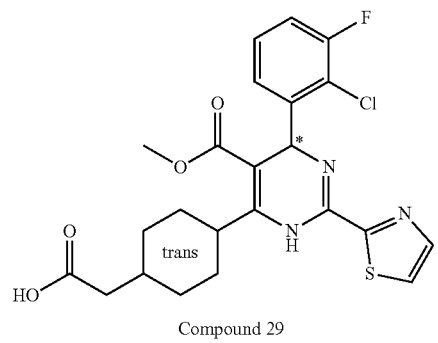 [SMILES: COC(=O)C1=C(C2CCC(CC(=O)O)CC2)NC(c2nccs2)=NC1c1cccc(F)c1Cl]
Compound 29 |
| S Compound 71C
Compound 71F | 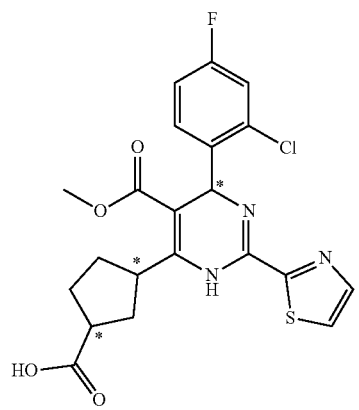
Compound 72C
Compound 72F |

-continued
| Method & Ester | Acid |
|---|---|
| S Compound 76 | 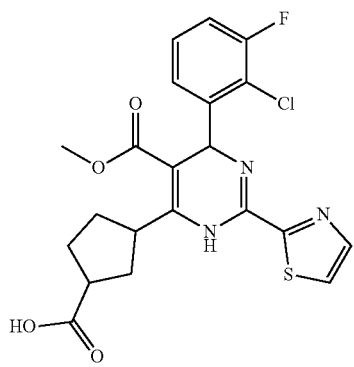<br>Compound 77 |
| S Compound 85C | 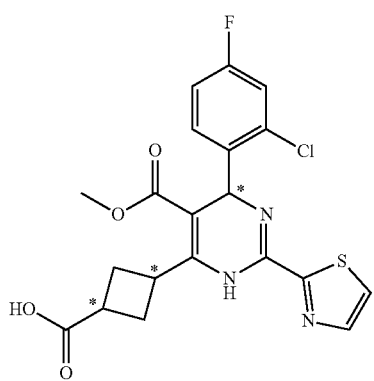<br>compound 86 |
| S Compound 91H<br>Compound 91J | 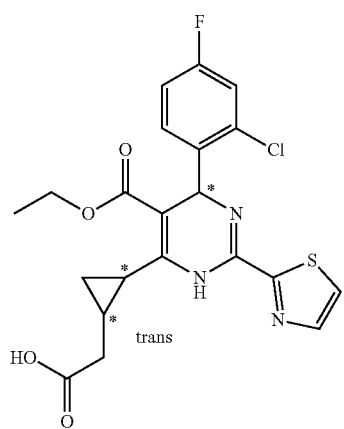<br>Compound 92<br>Compound 93 |

| Method & Ester | Acid |
|---|---|
| S Compound 94 | 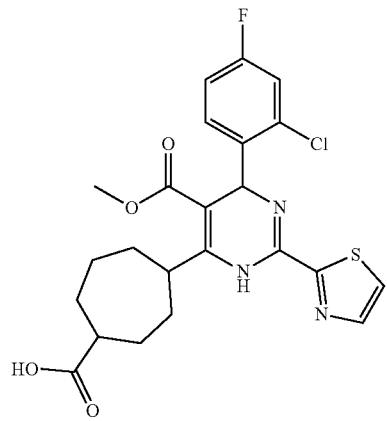<br>Compound 95 |
| U Compound 140A | 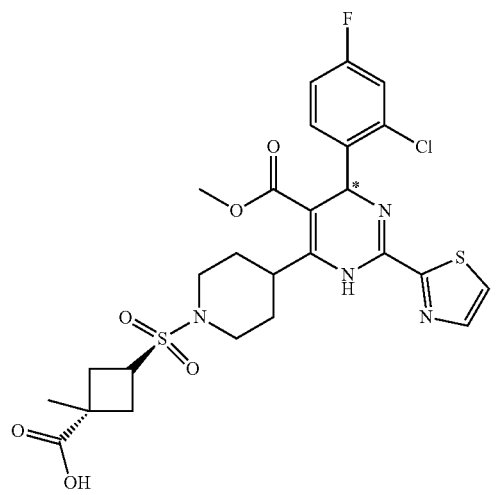<br>Compound 141 |
| U Compound 140B | 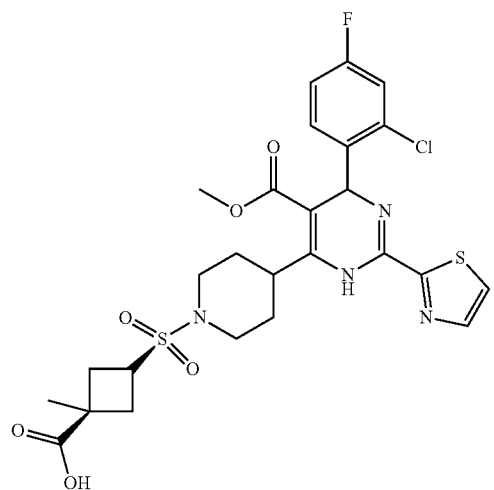<br>Compound 142 |

| Method & Ester | Acid |
|---|---|
| T Compound 145 | 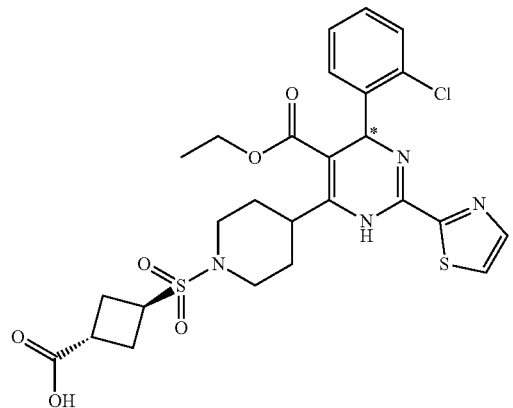<br>Compound 146 |
| S Compound 147A | 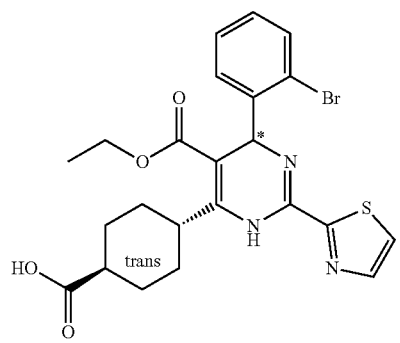<br>Compound 148A |
| S Compound 149A | 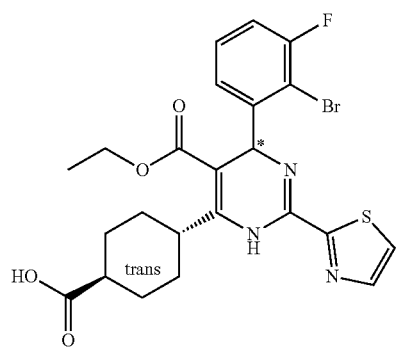<br>Compound 150A |
| S Compound 151A | 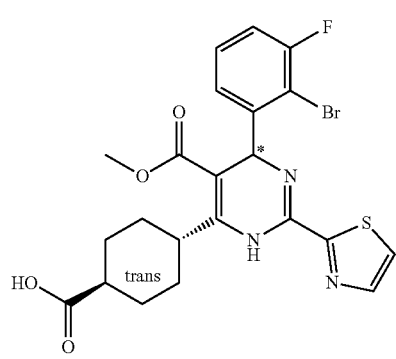<br>Compound 152A |

| Method & Ester | Acid |
|---|---|
| U compound 153A | 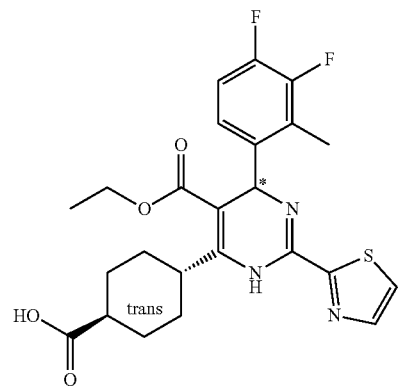
Compound 154A |
| S Compound 155A | 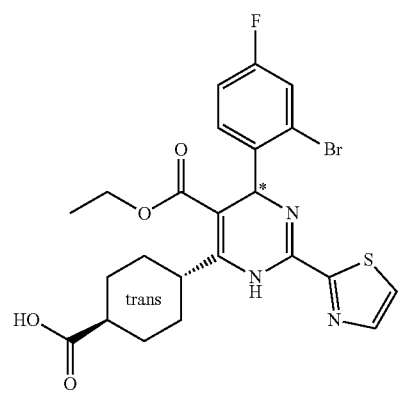
Compound 156A |
| U Compound 161 | 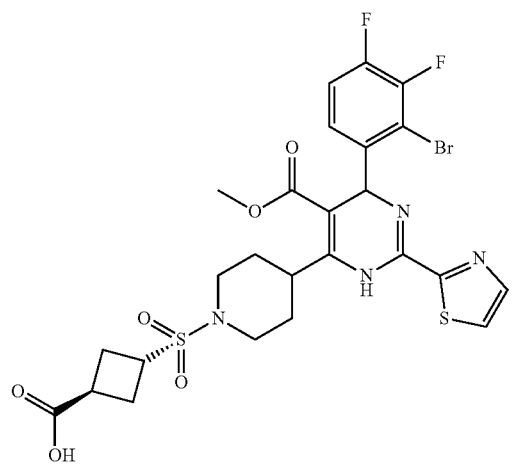
Compound 162 |

-continued
| Method & Ester | Acid |
|---|---|
| T Compound 194A | 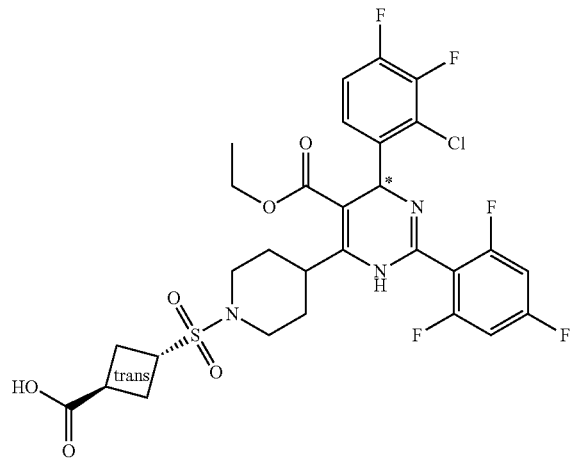<br>Compound 195A |
| T Compound 198A | 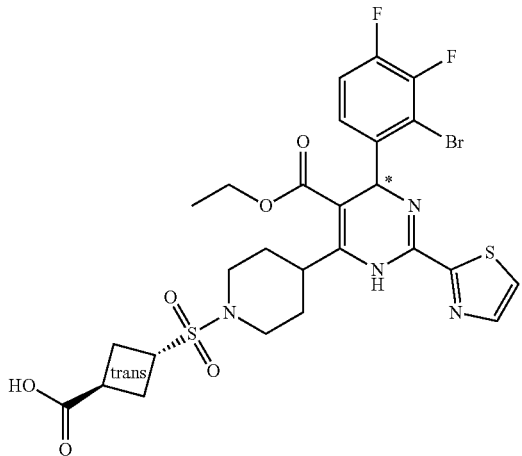<br>Compound 199A |
| T Compound 198B | 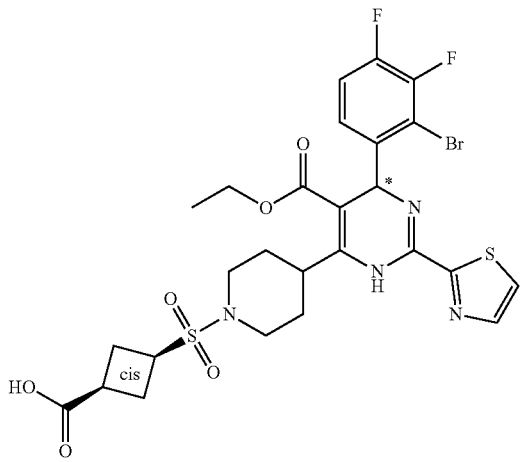<br>Compound 199B |

| Method & Ester | Acid |
|---|---|
| T Compound 209A and 209B | 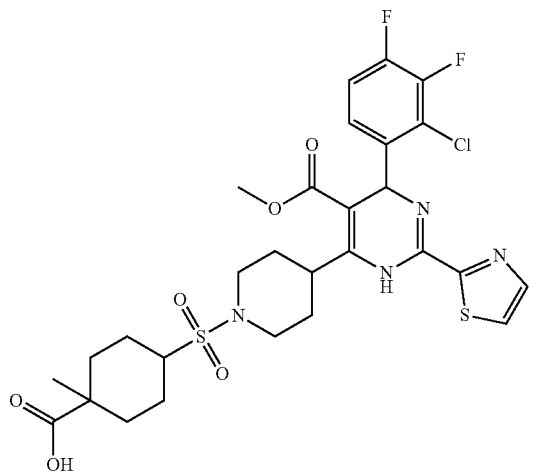<br>Compound 210A, trans<br>Compound 210B, cis |
| S Compound 211M | 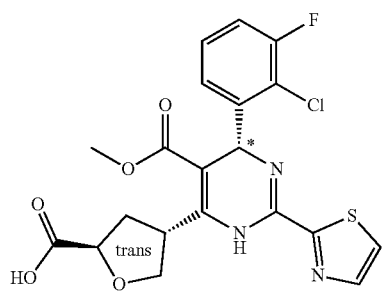<br>Compound 212M |
| S Compound 213X 213M | 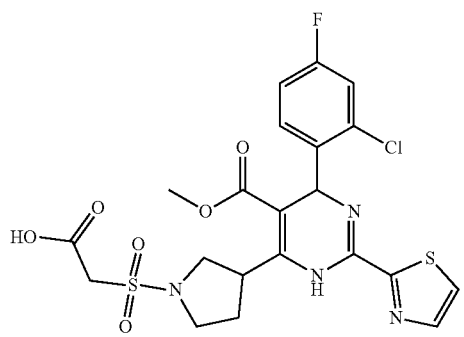<br>Compound 214A<br>Compound 214C |

| Method & Ester | Acid |
|---|---|
| U Compound 222 | 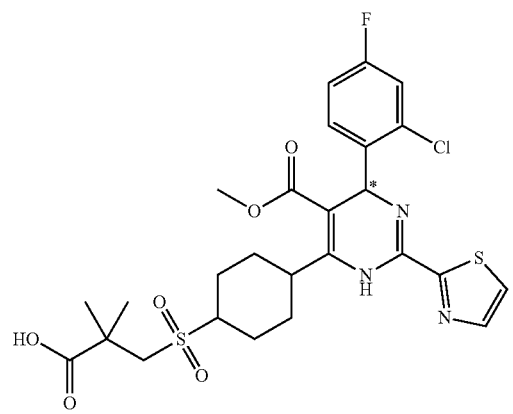<br>Compound 223 |
| S Compound 224X | 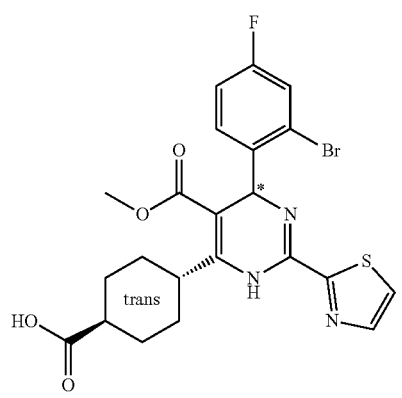<br>Compound 225 |
| S Compound 226M | 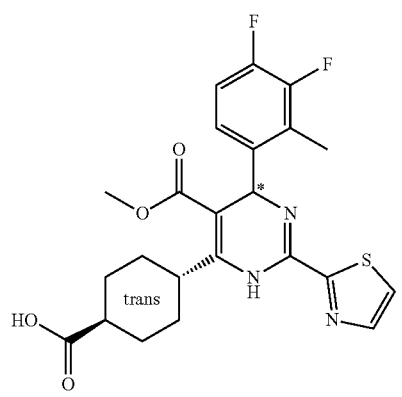<br>Compound 227A |

-continued
| Method & Ester | Acid |
|---|---|
| S Compound 228N | 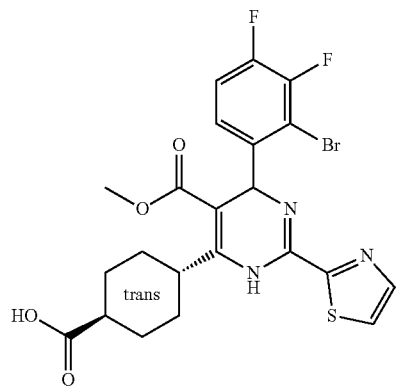<br>Compound 229B |
| S Compound 157A | 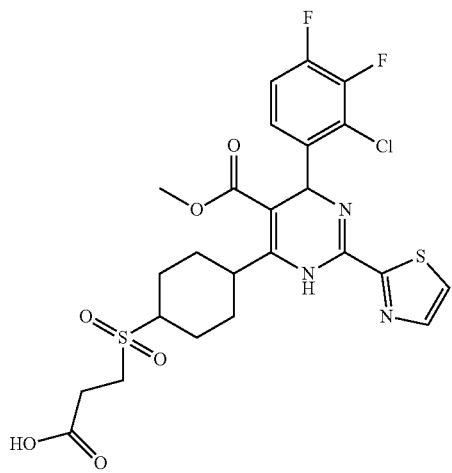<br>Compound 230 |
| T Compound 231X,<br>231B (trans) and 231D (cis) | 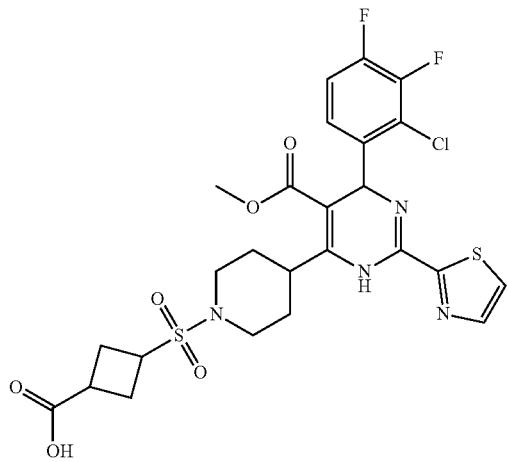<br>Compound 232X (trans)<br>Compound 232B (trans)<br>Compound 232D (cis) |

| Method & Ester | Acid |
|---|---|
| U Compound 240Q | 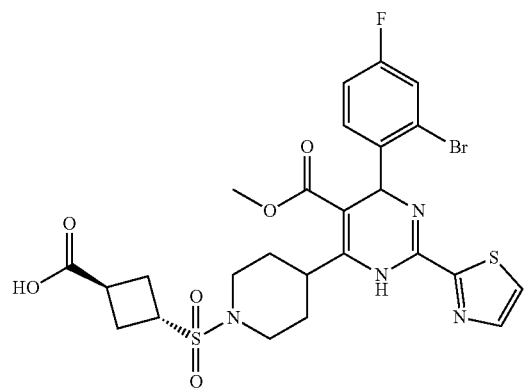<br>Compound 241B |
| S Compound 257 and 257Y | 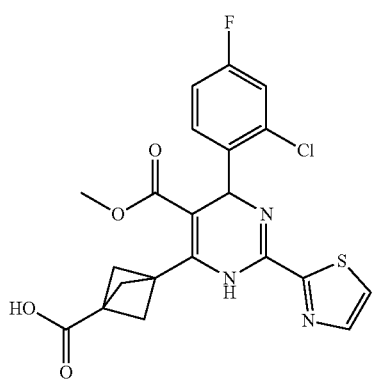<br>Compound 258 and 258B |
| U Compound 264U and 264Y | 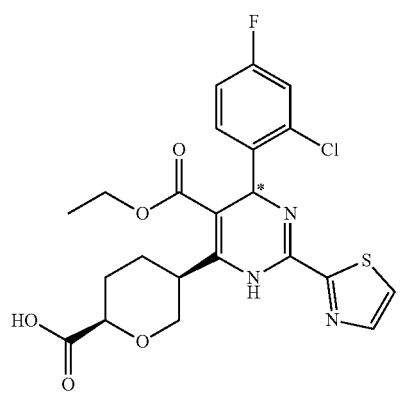<br>Compound 265E<br>Compound 265H |

| Method & Ester | Acid |
|---|---|
| W Compound 269A and compound 269B | 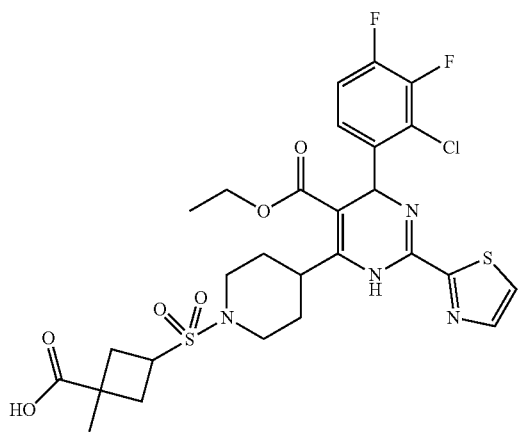  Compound 270A (trans)  Compound 270B (cis) |
| W Compound 271A and 271B | 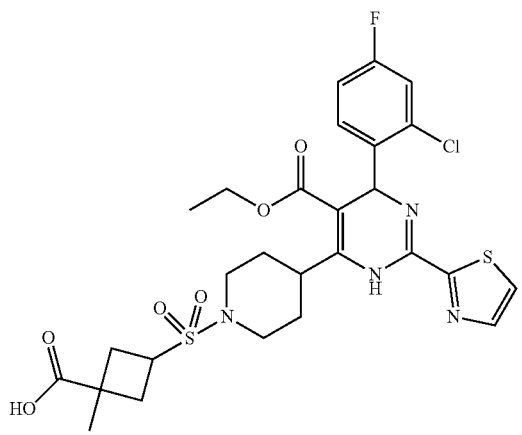  Compound 272A (trans)  Compound 272B (cis) |
| W Compound 273A and 273B | 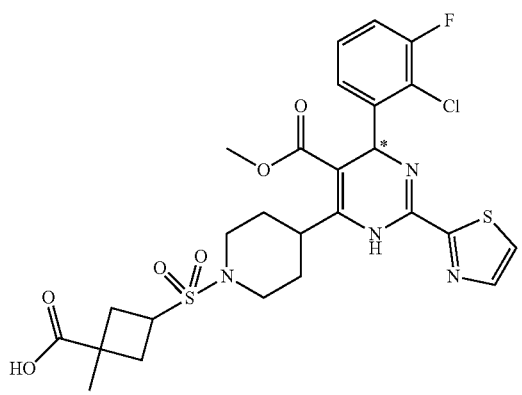  Compound 274A (trans)  Compound 274B (cis) |

| Method & Ester | Acid |
|---|---|
| W Compound 277C and 277D | 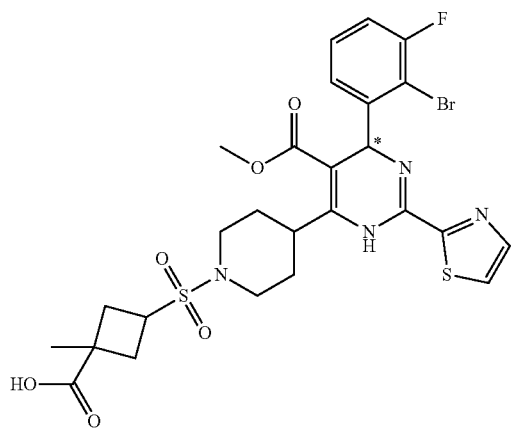<br>Compound 278C (trans)<br>Compound 278D (cis) |
| W Compound 281C and 281D | 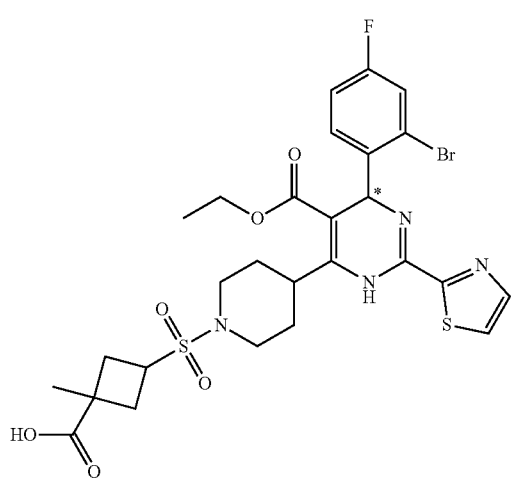<br>Compound 282C (trans)<br>Compound 282D (cis) |
| U Compound 242A | 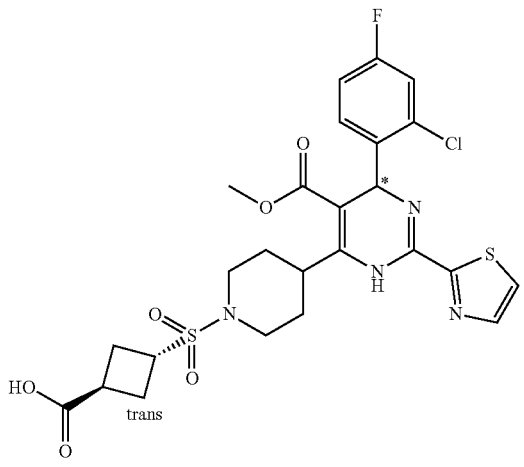<br>Compound 285A |

-continued
| Method & Ester | Acid |
|---|---|
| S Compound 288M | 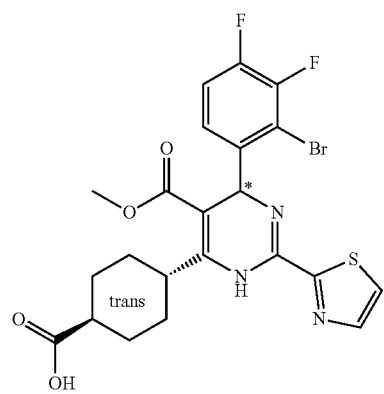<br>Compound 289A |
| S Compound 292W | 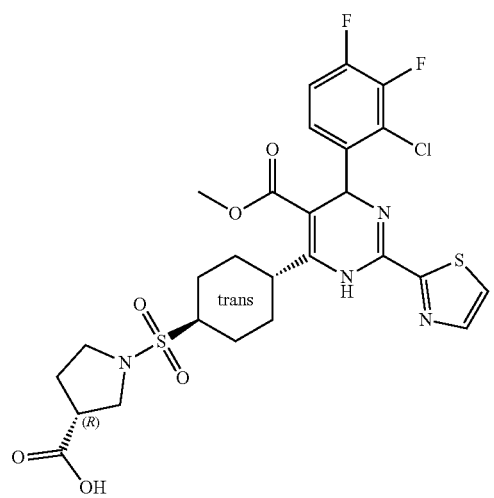<br>Compound 293C |
| S Compound 301 | 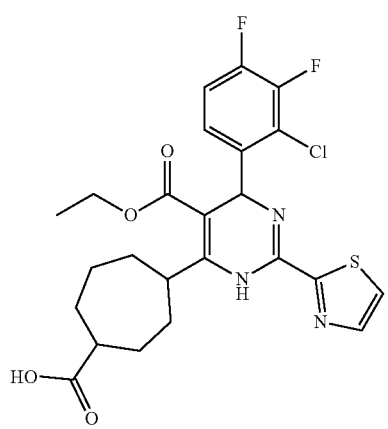<br>Compound 302 |

| Method & Ester | Acid |
|---|---|
| U Compound 308M | 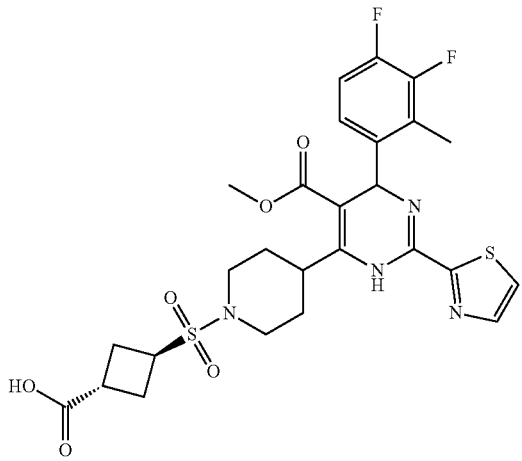<br>Compound 309C |
| U Compound 310 | 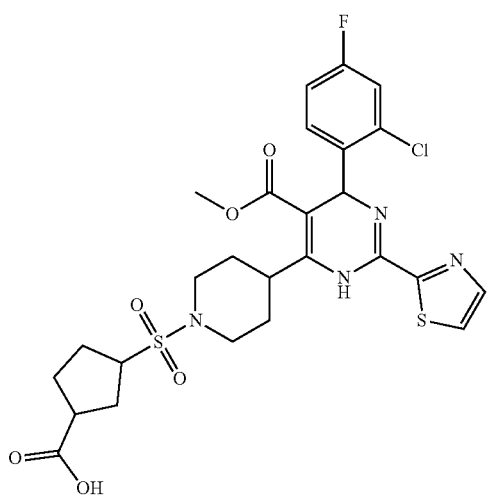<br>Compound 311 |
| U Compound 312X and 312Y | 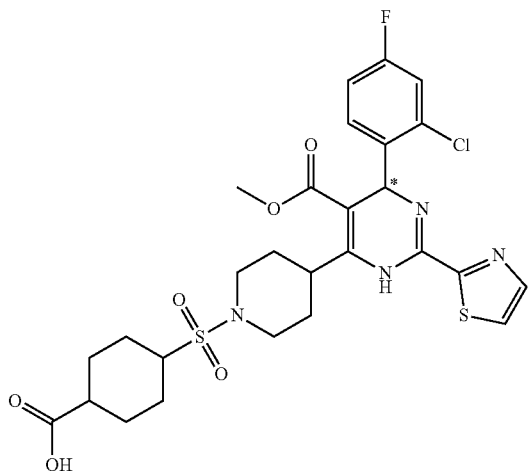<br>Compound 313A (cis)<br>Compound 313B (trans) |

-continued
| Method & Ester | Acid |
|---|---|
| U Compound 318Y | 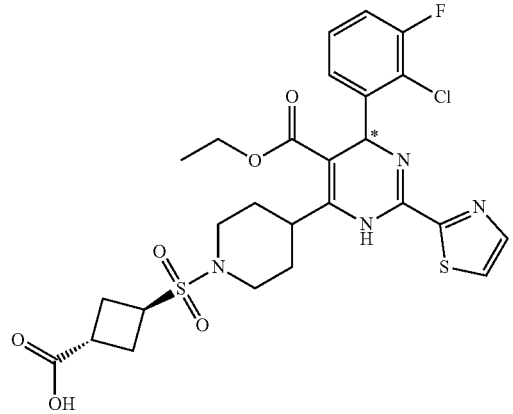<br>Compound 319B |
| U Compound 320A and 320B | 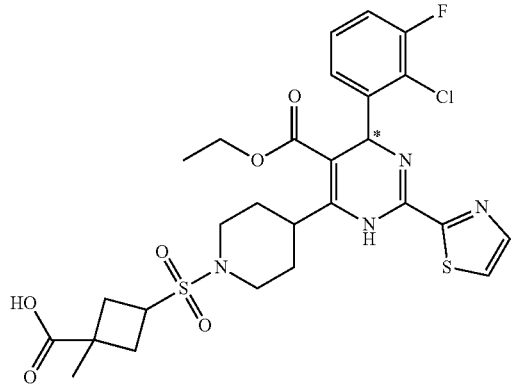<br>Compound 321A (trans)<br>Compound 321B (cis) |
| W Compound 322C and 322D | 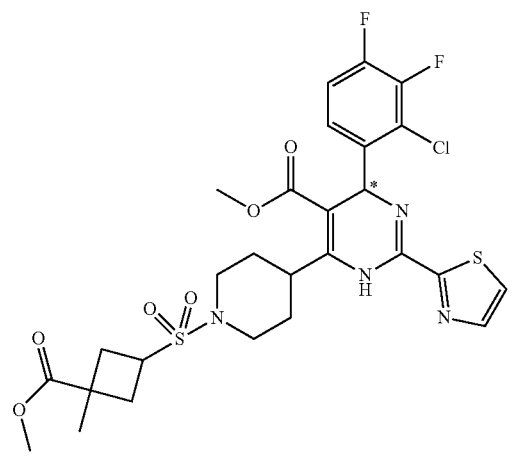<br>Compound 323C (trans)<br>Compound 323D (cis) |

| Method & Ester | Acid |
|---|---|
| U Compound 328F | 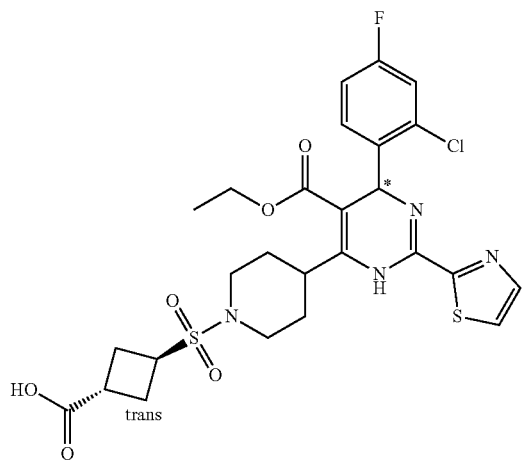Compound 329B |
| U Compound 330P | 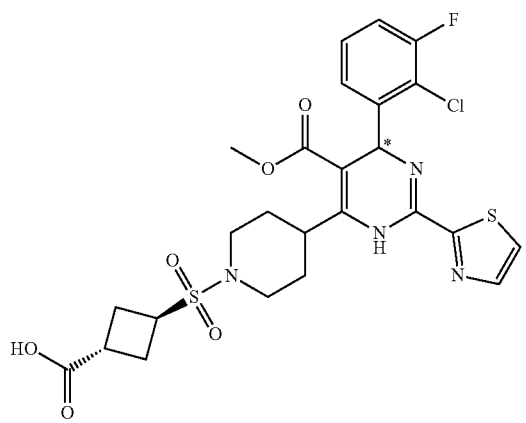Compound 331C |
| U Compound 332Y | 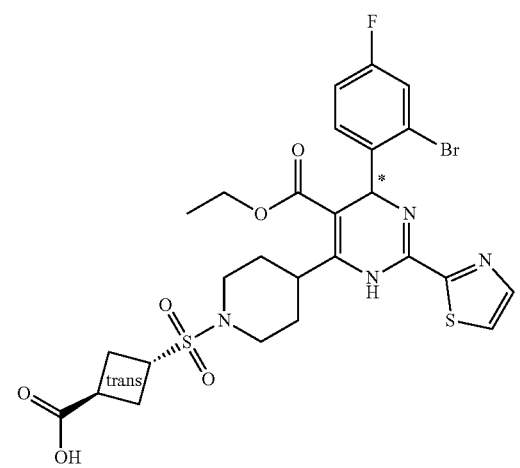Compound 333B |

| Method & Ester | Acid |
|---|---|
| U Compound 338B and 338D | 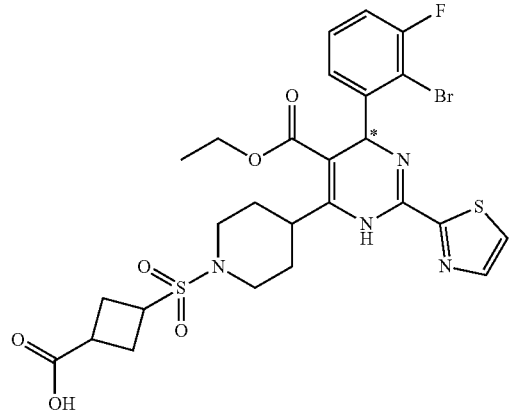<br>Compound 339B (trans)<br>Compound 339D (cis) |
| U Compound 342X, 342M and 342N | 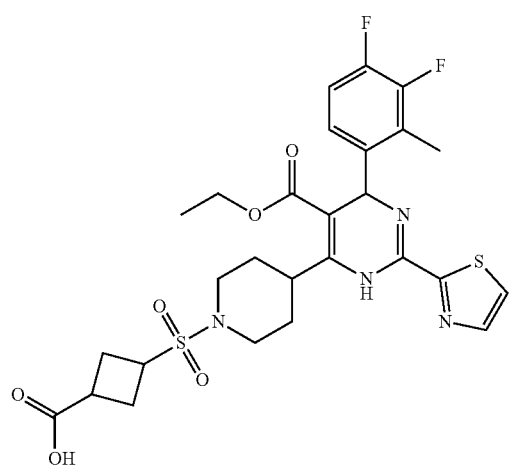<br>Compound 343A<br>Compound 343C<br>Compound 343D |
| S Compound 344M | 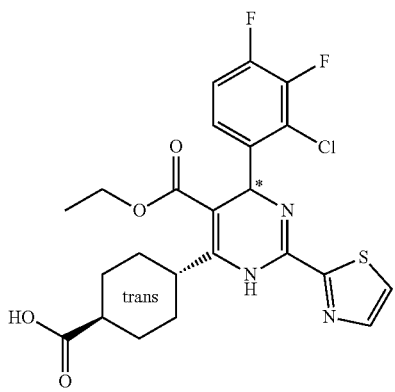<br>Compound 345A |

-continued
| Method & Ester | Acid |
|---|---|
| S Compound 346N | 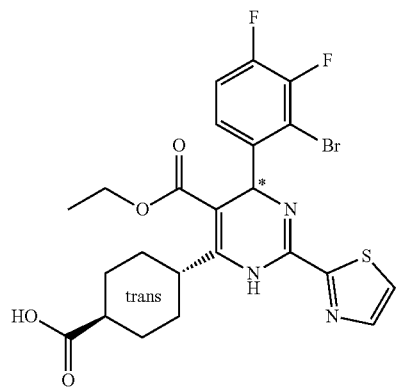<br>Compound 347B |
| U Compound 351Y | 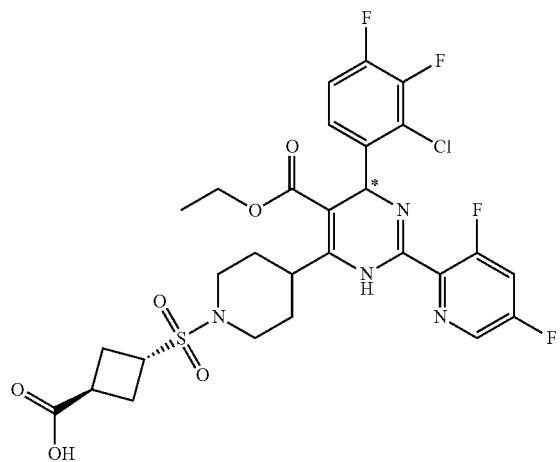<br>Compound 352B |
| S Compound 353N and 353X | 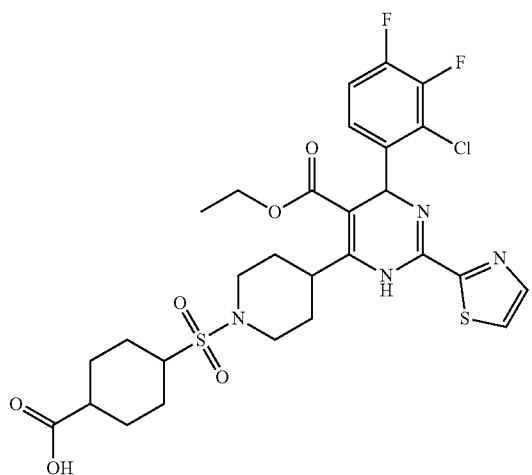<br>Compound 354B (cis)<br>Compound 354C (trans) |

| Method & Ester | Acid |
|---|---|
| S Compound 362U and 362Y | 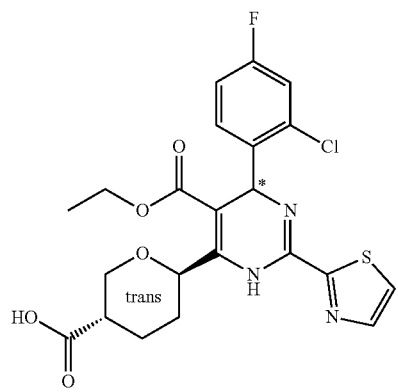<br>Compound 363E<br>Compound 363H |
| U Compound 366X and 366Y | 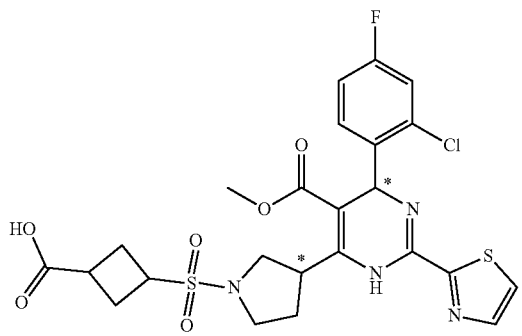<br>Compound 367A (trans)<br>Compound 367B (cis) |
| U Compound 409P and 409Q | 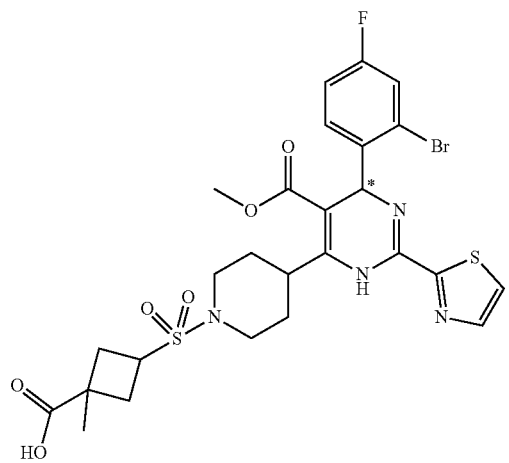<br>Compound 410 (trans)<br>Compound 410 (cis) |

| Method & Ester | Acid |
|---|---|
| U Compound 413C and 413D | 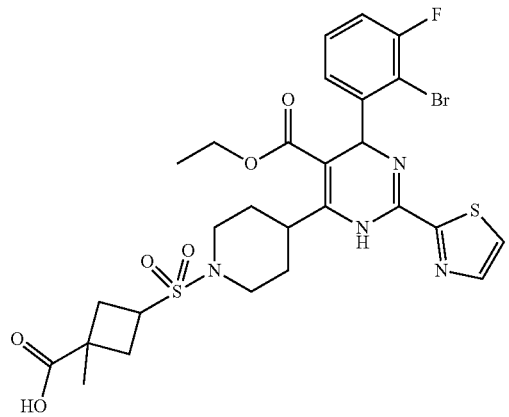<br>Compound 414C (trans)<br>Compound 414D (cis) |
| U Compound 419A | 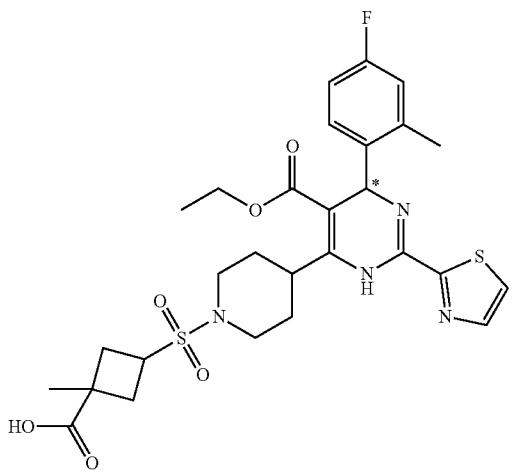<br>Compound 420A |
| S Compound 421 | 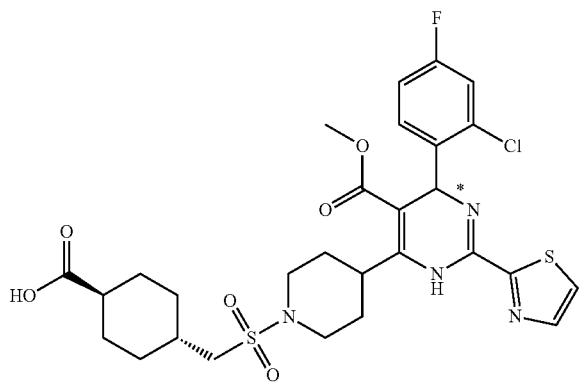<br>Compound 422 |

| Method & Ester | Acid |
|---|---|
| S Compound 423 | 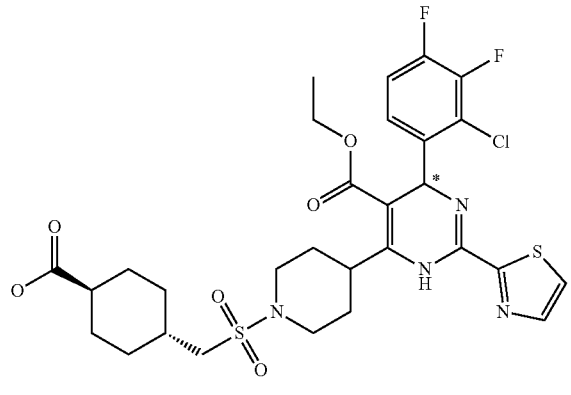<br>Compound 424 |
| S Compound 423 | 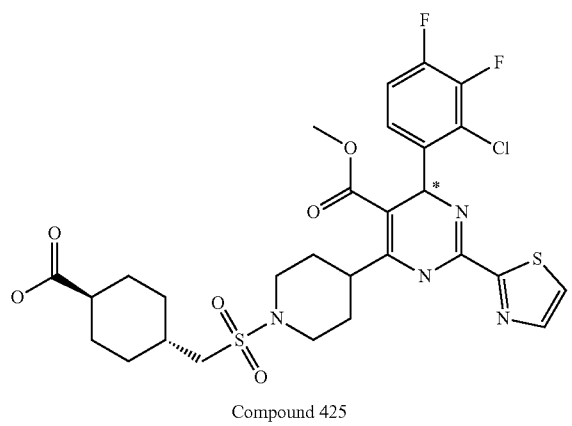 [SMILES: COC(=O)C1=C(C2CCN(S(=O)(=O)C[C@H]3CC[C@H](C(=O)O)CC3)CC2)NC(c2nccs2)=NC1c1ccc(F)c(F)c1Cl]<br>Compound 425 |
| U Compound 428C and 428D | 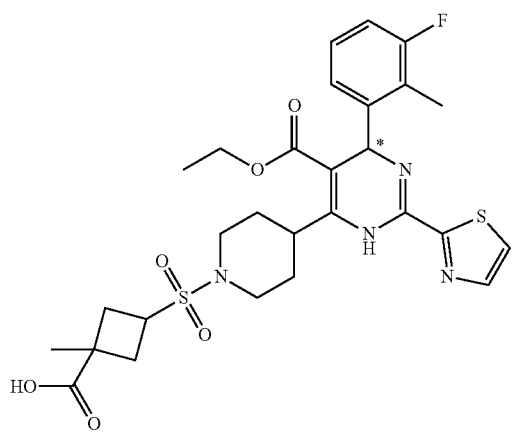<br>Compound 429C (trans)<br>Compound 429D (cis) |

-continued
| Method & Ester | Acid |
|---|---|
| U Compound 438F and 438H | 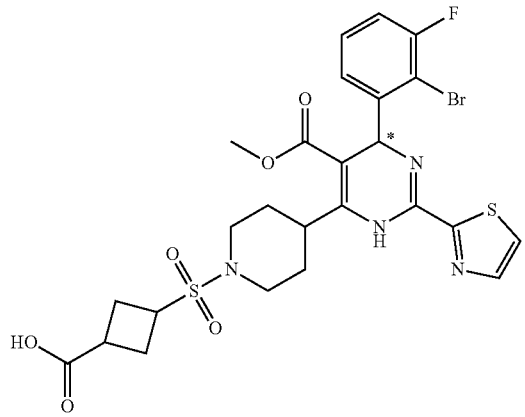<br>Compound 439B (trans)<br>Compound 439D (cis) |
| S Compound 443b | 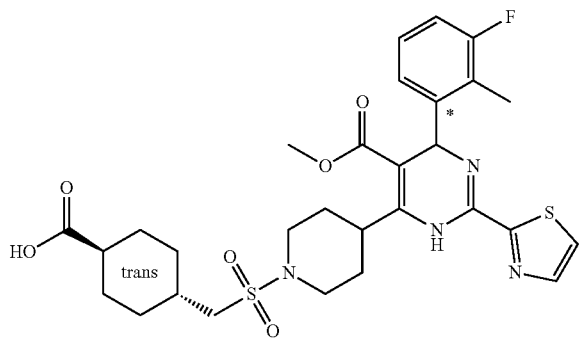<br>Compound 444b |
| U Compound 446C and 446D | 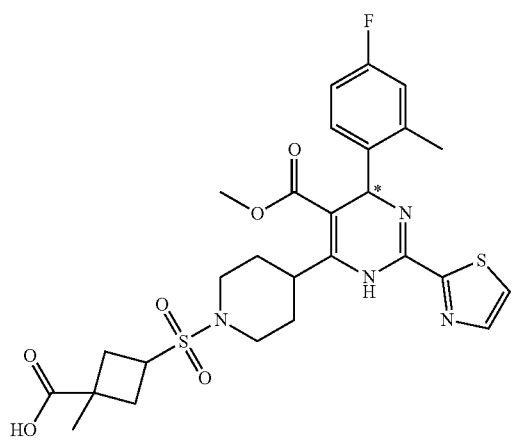<br>Compound 447C (trans)<br>Compound 447D (cis) |

| Method & Ester | Acid |
|---|---|
| S Compound 449A and 449B | 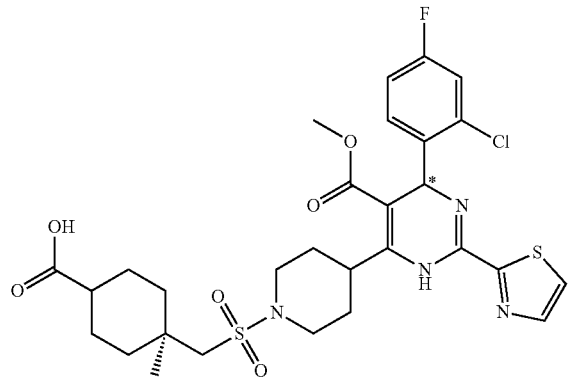<br>Compound 450A (cis)<br>Compound 450B (trans) |
| S Compound 451A and 451B | 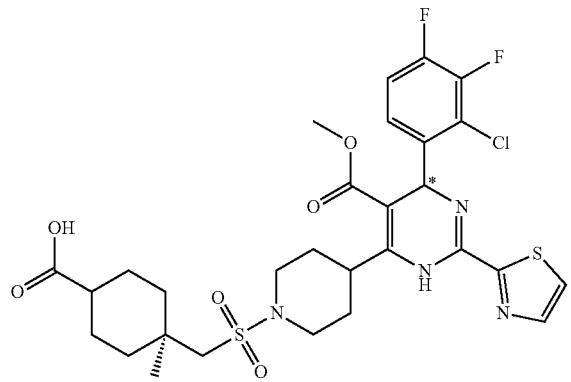<br>Compound 452A (cis)<br>Compound 452B (trans) |
| S Compound 453 | 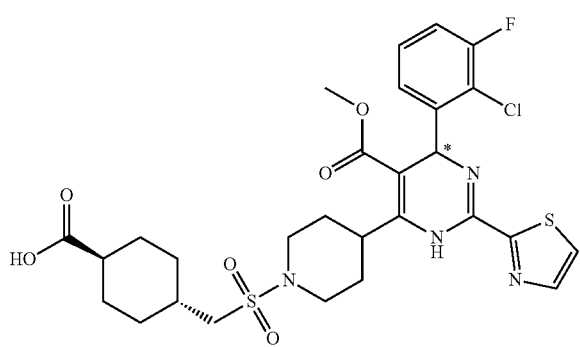<br>Compound 454 |

| Method & Ester | Acid |
|---|---|
| S Compound 455 | 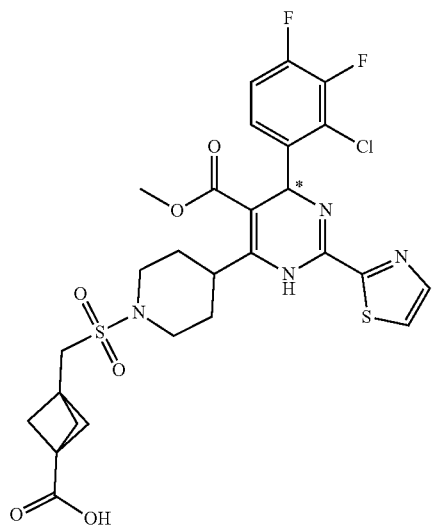<br>Compound 456 |
| U Compound 469 | 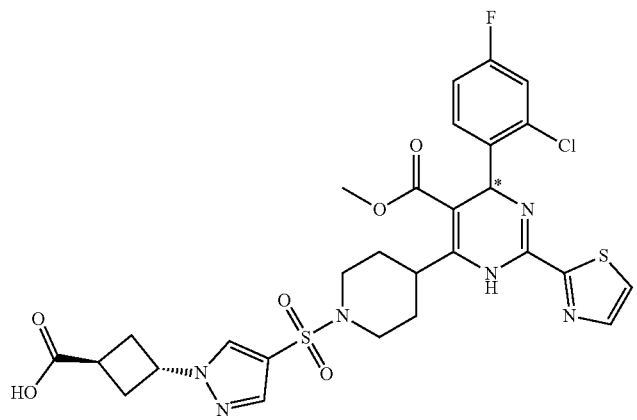<br>Compound 470 |
| S Compound 475A and 475B | 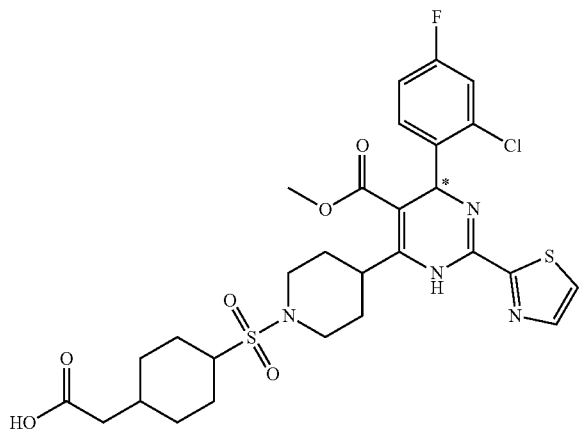<br>Compound 476A (trans)<br>Compound 476B (cis) |

| Method & Ester | Acid |
|---|---|
| S Compound 477 and 477A | 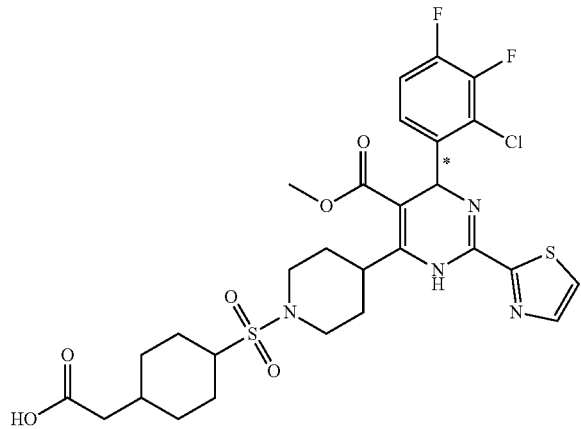<br>Compound 478 (mixture)<br>Compound 478A (trans) |
| W Compound 479P | 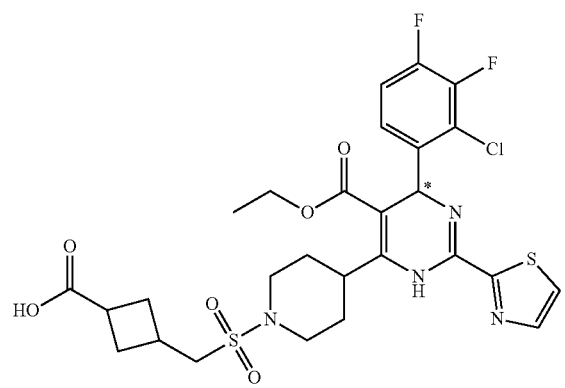<br>Compound 480B (cis/trans uknown) |
| W Compound 479Q | 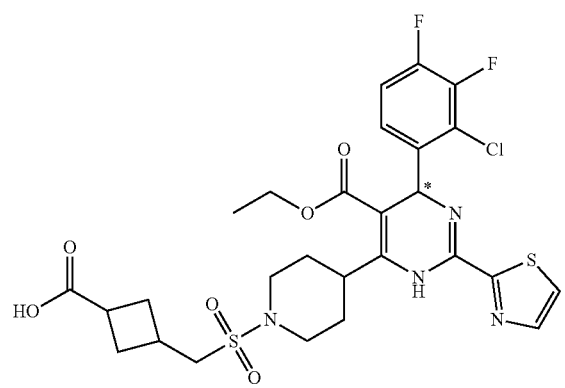<br>Compound 480Y (cis/trans uknown) |

| Method & Ester | Acid |
|---|---|
| W Compound 481A | 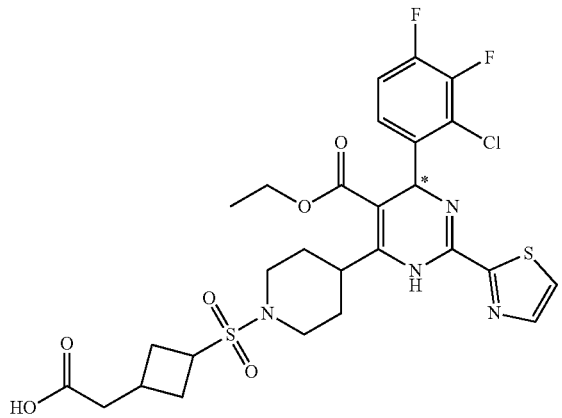<br>Compound 482A (cis/trans uknown) |
| W Compound 481B | 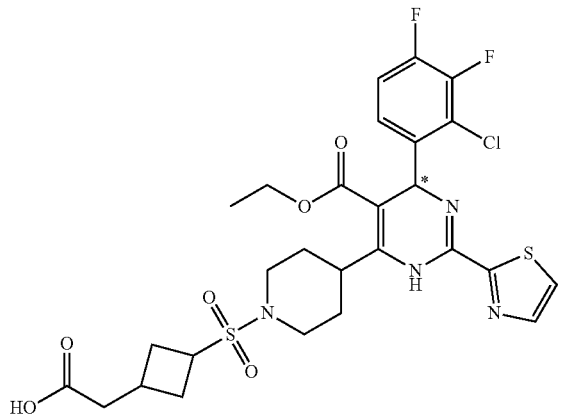<br>Compound 482B (cis/trans uknown) |
| U Copound | 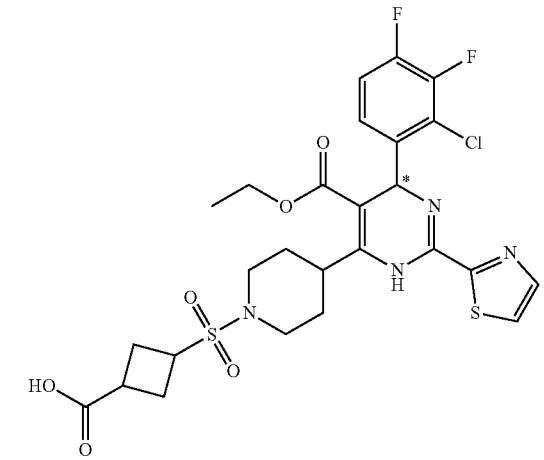<br>Compound 470B (trans)<br>Compound 370D (cis) |

Compound 107: 2-((4-(6-(2-Chloro-4-fluorophenyl)-5-(methoxycarbonyl)-2-(thiazol-2-yl)-3,6-dihydropyrimidin-4-yl)piperidin-1-yl)sulfonyl)acetic Acid LC-MS (ESI): $R_T$=3.307 min, mass calcd. for $C_{22}H_{22}ClFN_4O_6S_2$ 556.1, m/z found 556.9 [M+H]$^+$. Chiral HPLC (Chiralpak IB 5 μm 4.6*250 mm, Mobile Phase: Hex: EtOH:TFA=70:30:0.2 at 1.0 mL/min, Temp: 30° C., Wavelength: 230 nm, $R_T$=8.254 min); $^1$H NMR (400 MHz, DMSO-d$_6$) δ 8.00 (s, 1.7H), 7.92 (s, 0.3H), 7.41 (dd, J=8.8, 2.8 Hz, 1H), 7.38-7.34 (m, 1H), 7.23-7.18 (m, 1H), 6.01 (s, 0.2H), 5.92 (s, 0.8H), 3.95-3.88 (m, 2H), 3.80-3.64 (m, 3H), 3.53 (s, 3H), 2.97-2.88 (m, 2H), 2.04-1.91 (m, 1H), 1.90-1.77 (m, 2H), 1.62 (d, J=11.2 Hz, 1H).

Compound 7: 2-((4-(6-(2-Chloro-4-fluorophenyl)-5-(methoxycarbonyl)-2-(thiazol-2-yl)-3,6-dihydropyrimidin-4-yl)piperidin-1-yl)sulfonyl)-2-methylpropanoic Acid LC-MS (ESI): $R_T$=3.967 min, mass calcd. for $C_{24}H_{26}ClFN_4O_6S_2$ 584.1, m/z found 584.9 [M+H]$^+$. Chiral HPLC (Column: Chiralpak IE 5 μm 4.6*250 mm; Mobile Phase: Hex:IPA:TFA=70:30:0.2 at 1.0 mL/min; Temp: 30° C.; Wavelength: 230 nm, $R_T$=10.158 min). $^1$H NMR (400 MHz, DMSO-d$_6$ (+D$_2$O)) δ 7.98 (dd, J=12.4, 3.2 Hz, 2H), 7.41 (dd, J=8.4, 2.8 Hz, 1H), 7.34 (dd, J=9.2, 6.0 Hz, 1H), 7.22-7.17 (m, 1H), 5.93 (s, 1H), 3.85-3.82 (m, 3H), 3.52 (s, 3H), 3.06-2.98 (m, 2H), 2.01-1.92 (m, 1H), 1.88-1.80 (m, 1H), 1.75 (d, J=12 Hz, 1H), 1.60 (d, J=12.4 Hz, 1H), 1.51 (s, 6H).

Compound 114: 3-((4-(6-(2-Chloro-3-fluorophenyl)-5-(methoxycarbonyl)-2-(thiazol-2-yl)-3,6-dihydropyrimidin-4-yl)piperidin-1-yl)sulfonyl)propanoic Acid LC-MS (ESI): $R_T$=2.524 min, mass calcd. for $C_{23}H_{24}ClFN_4O_6S_2$ 570.1, m/z found 571.1 [M+H]$^+$. Chiral HPLC (Column: Chiralpak IF 5 μm 4.6*250 mm; Mobile Phase: Hex:EtOH:TFA=60:40:0.2 at 1.0 mL/min; Temp: 30° C.; Wavelength: 230 nm, $R_T$=11.664 min). $^1$H NMR (400 MHz, DMSO-d$_6$) δ 9.62 (br s, 1H), 8.00 (s, 2H), 7.41-7.31 (m, 2H), 7.21 (d, J=7.2 Hz, 1H), 5.99 (s, 1H), 3.80-3.68 (m, 3H), 3.53 (s, 3H), 3.31 (t, J=7.2 Hz, 2H), 2.95-2.86 (m, 2H), 2.67 (t, J=7.2 Hz, 2H), 2.05-1.61 (m, 4H).

Compound 17: trans-4-(6-(2-Chloro-3-fluorophenyl)-5-(methoxycarbonyl)-2-(thiazol-2-yl)-3,6-dihydropyrimidin-4-yl)cyclohexanecarboxylic Acid LC-MS (ESI): $R_T$=3.326 min, mass calcd. for $C_{22}H_{21}ClFN_3O_4S$ 477.1, m/z found mass 477.9 [M+H]$^+$. Chiral HPLC (Column: Chiralpak IE 5 μm 4.6*250 mm; Mobile Phase: Hex:EtOH:TFA=85:15:0.2 at 1.0 mL/min; Temp: 30° C.; Wavelength: 230 nm, $R_T$=11.064 min). 1H NMR (400 MHz, DMSO-d$_6$) δ 9.45 (br s, 0.6H), 8.94 (br s, 0.4H), 7.99-7.93 (m, 2H), 7.39-7.29 (m, 2H), 7.19-7.17 (m, 1H), 6.06 (br s, 0.4H), 5.97 (br s, 0.6H), 3.87-3.77 (m, 0.4H), 3.64-3.56 (m, 0.6H), 3.52 (s, 3H), 2.42-2.37 (m, 0.4H), 2.35-2.21 (m, 0.6H), 2.05-1.97 (m, 2H), 1.86-1.76 (m, 2H), 1.73-1.62 (m, 2H), 1.44-1.36 (m, 2H).

Compound 19: trans-4-(6-(2-Chloro-4-fluorophenyl)-5-(methoxycarbonyl)-2-(thiazol-2-yl)-3,6-dihydropyrimidin-4-yl)cyclohexanecarboxylic Acid LC-MS (ESI): $R_T$=3.958 min, mass calcd. for $C_{22}H_{21}ClFN_3O_4S$, 477.1, m/z found 478.1 [M+H]$^+$. Chiral HPLC (Column: Chiralpak IE 5 μm 4.6*250 mm; Mobile Phase: Hex:IPA:TFA:DEA=85:15:0.1:0.1 at 1.0 mL/min; Temp: 30° C.; Wavelength: 230 nm, $R_T$=9.501 min). $^1$H NMR (400 MHz, DMSO-d$_6$) δ 12.03 (br s, 1H), 9.40 (d, J=2.8 Hz, 0.6H), 8.92 (s, 0.4H), 7.99-7.98 (m, 1.6H), 7.94-7.93 (m, 0.4H), 7.45-7.39 (m, 1H), 7.36-7.30 (m, 1H), 7.23-7.18 (m, 1H), 6.01 (s, 0.4H), 5.91 (d, J=3.2 Hz, 0.6H), 3.89-3.75 (m, 0.4H), 3.64-3.56 (m, 0.6H), 3.53 (s, 3H), 2.44-2.32 (m, 0.4H), 2.25-2.17 (m, 0.6H), 2.09-1.97 (m, 2H), 1.88-1.58 (m, 4H), 1.49-1.34 (m, 2H).

Compound 21: trans-4-(6-(2-Chloro-4-fluorophenyl)-5-(ethoxycarbonyl)-2-(thiazol-2-yl)-3,6-dihydropyrimidin-4-yl)cyclohexanecarboxylic Acid LC-MS (ESI): $R_T$=4.156 min, mass calcd. $C_{23}H_{23}ClFN_3O_4S$ for 491.1, m/z found 491.9 [M+H]$^+$. Chiral HPLC (Column: Chiralpak IE 5 μm 4.6*250 mm; Mobile Phase: Hex:IPA:DEA:TFA=85:15:0.1:0.1 at 1.0 mL/min; Temp: 30° C.; Wavelength: 230 nm, 100% ee, $R_T$=8.533 min). $^1$H NMR (400 MHz, DMSO-d$_6$) δ 8.88 (br s, 0.2H), 7.99 (d, J=3.6 Hz, 1.8H), 7.94 (d, J=3.2 Hz, 0.2H), 7.44-7.41 (m, 1H), 7.36-7.33 (m, 1H), 7.24-7.19 (m, 1H), 6.02 (s, 0.4H), 5.91 (s, 0.6H), 4.00-3.93 (m, 2H), 3.86-3.77 (m, 0.4H), 3.61-3.54 (m, 0.6H), 2.40-2.33 (m, 0.4H), 2.25-2.18 (m, 0.6H), 2.04-1.74 (m, 6H), 1.47-1.32 (m, 2H), 1.10-1.03 (m, 3H).

Compound 23: trans-4-(6-(2-Chloro-3-fluorophenyl)-5-(ethoxycarbonyl)-2-(thiazol-2-yl)-3,6-dihydropyrimidin-4-yl)cyclohexanecarboxylic Acid LC-MS (ESI): $R_T$=3.542 min, mass calcd. for $C_{23}H_{23}ClFN_3O_4S$, m/z found 492.2 [M+H]$^+$. Chiral HPLC (Column: Chiralpak IE 5 μm 4.6*250 mm; Mobile Phase: Hex: IPA:TFA:DEA=90:10:0.1:0.1 at 1.0 mL/min; Temp: 30° C.; Wavelength: 230 nm, $R_T$=12.746 min). $^1$H NMR (400 MHz, DMSO-d$_6$) δ 9.49 (br s, 0.5H), 8.88 (s, 0.5H), 8.00-7.93 (m, 2H), 7.39-7.31 (m, 2H), 7.21-7.17 (m, 1H), 6.07 (s, 0.4H), 5.96 (s, 0.6H), 4.00-3.93 (m, 2H), 3.84-3.78 (m, 0.5H), 3.59-3.55 (m, 0.5H), 2.34-2.28 (m, 0.5H), 2.18-2.15 (m, 0.5H), 2.03-1.96 (m, 2H), 1.86-1.63 (m, 4H), 1.40-1.35 (m, 2H), 1.09-1.02 (m, 3H).

Compound 25: cis-3-(6-(2-Chloro-3-fluorophenyl)-5-(methoxycarbonyl)-2-(thiazol-2-yl)-3,6-dihydropyrimidin-4-yl)cyclohexanecarboxylic Acid LC-MS (ESI): $R_T$=4.541 min, mass calcd. for $C_{22}H_{21}ClFN_3O_4S$ 477.1, m/z found 477.9 [M+H]$^+$. Chiral HPLC (Column: Chiralpak ID 5 μm 4.6*250 mm; Mobile Phase: Hex:EtOH:TFA=85:15:0.2 at 1.0 mL/min; Temp: 30° C.; Wavelength: 230 nm, $R_T$=7.090 min). $^1$H NMR (400 MHz, DMSO-d$_6$) δ 9.12 (br s, 0.3H), 8.00-7.98 (m, 1.6H), 7.94 (d, J=2.8 Hz, 0.4H), 7.40-7.29 (m, 2H), 7.21-7.15 (m, 1H), 6.06 (s, 0.4H), 5.97 (s, 0.6H), 3.97-3.89 (m, 0.4H), 3.71-3.63 (m, 0.6H), 3.52-3.51 (m, 3H), 2.35-2.24 (m, 1H), 1.93-1.81 (m, 3H), 1.78-1.67 (m, 3H), 1.45-1.25 (m, 2H).

Compound 29: 2-(trans-4-(6-(2-Chloro-3-fluorophenyl)-5-(methoxycarbonyl)-2-(thiazol-2-yl)-3,6-dihydropyrimidin-4-yl)cyclohexyl)acetic Acid LC-MS (ESI): $R_T$=3.930 min, mass calcd. for $C_{23}H_{23}ClFN_3O_4S$ 491.1, m/z found 491.9 [M+H]$^+$. Chiral HPLC (Column: Chiralpak IA 5 μm 4.6*250 mm; Mobile Phase: Hex: EtOH:TFA=90:10:0.2 at 1.0 mL/min; Temp: 30° C.; Wavelength: 230 nm; $R_T$=9.625 min). $^1$H NMR (400 MHz, DMSO-d$_6$) δ 11.81 (br s, 1H), 9.46 (br s, 0.4H), 8.97 (s, 0.6H), 7.99-7.97 (m, 1.6H), 7.93 (d, J=3.2 Hz, 0.4H), 7.39-7.28 (m, 2H), 7.21-7.15 (m, 1H), 6.06 (s, 0.4H), 5.96 (s, 0.6H), 3.87-3.53 (m, 1H), 3.51-3.50 (m, 3H), 2.14 (d, J=6.8 Hz, 2H), 1.88-1.55 (m, 7H), 1.15-1.03 (m, 2H).

Compound 72C: 3-(6-(2-Chloro-4-fluorophenyl)-5-(methoxycarbonyl)-2-(thiazol-2-yl)-3,6-dihydropyrimidin-4-yl)cyclopentanecarboxylic Acid LC-MS (ESI): $R_T$=3.434 min, mass calcd. for $C_{20}H_{17}ClFN_3O_4S$ 463.1, m/z found 463.9 [M+H]$^+$. Chiral HPLC (Column: Chiralcel OJ-H 5 μm 4.6*250 mm; Mobile Phase: Hex:EtOH:TFA=70:30:0.2 at 1.0 mL/min; Temp: 30° C.; Wavelength: 230 nm, $R_T$=6.639 min). $^1$H NMR (400 MHz, CD$_3$OD) δ 7.93 (d, J=2.8 Hz, 1H), 7.78 (d, J=3.2 Hz, 1H), 7.38 (dd, J=8.4, 6.0 Hz, 1H), 7.25 (dd, J=8.4, 2.8 Hz, 1H), 7.07 (td, J=8.4, 2.4 Hz, 1H), 6.08 (s, 1H), 4.44-4.35 (m, 1H), 3.59 (s, 3H), 3.18-3.10 (m, 1H), 2.29-2.16 (m, 3H), 2.05-1.81 (m, 3H).

Compound 72F: 3-(6-(2-Chloro-4-fluorophenyl)-5-(methoxycarbonyl)-2-(thiazol-2-yl)-3,6-dihydropyrimidin-4-yl)cyclopentanecarboxylic Acid LC-MS (ESI): $R_T$=3.875 min, mass calcd. for $C_{21}H_{19}ClFN_3O_4S$ 463.1, m/z found 463.9 [M+H]$^+$. Chiral HPLC (Column: Chiralpak IC 5 μm 4.6*250 mm; Mobile Phase: Hex:EtOH:TFA=80:20:0.2 at 1.0 mL/min; Temp: 30° C.; Wavelength: 230 nm, $R_T$=5.240 min). $^1$H NMR (400 MHz, DMSO-d$_6$) δ 12.02 (s, 1H), 9.45 (d, J=3.6 Hz, 0.8H), 8.99 (s, 0.2H), 7.99 (q, J=3.2 Hz, 1.8H), 7.93 (d, J=3.2 Hz, 0.2H), 7.44-7.40 (m, 1H), 7.35-7.30 (m, 1H), 7.24-7.17 (m, 1H), 6.01 (s, 0.2H), 5.92 (d, J=3.6 Hz, 0.8H), 4.35-4.28 (m, 0.2H), 4.24-4.16 (m, 0.8H), 3.52 (s, 2.4H), 3.51 (s, 0.6), 3.06-2.97 (m, 1H), 2.16-1.77 (m, 6H).

Compound 77: 3-(6-(2-Chloro-3-fluorophenyl)-5-(methoxycarbonyl)-2-(thiazol-2-yl)-3,6-dihydropyrimidin-4-yl)cyclopentanecarboxylic Acid LC-MS (ESI): $R_T$=3.607 min, mass calcd. for $C_{21}H_{19}ClFN_3O_4S$, 463.1, m/z found 463.9 [M+H]$^+$. $^1$H NMR (400 MHz, DMSO-d$_6$) δ 12.09 (br s, 1H), 9.75-9.45 (m, 1H), 8.01-7.91 (m, 2H), 7.41-7.30 (m, 2H), 7.23-7.13 (m, 1H), 6.06 (s, 0.3H), 5.97-5.95 (m, 0.7H), 4.52-4.34 (m. 0.3H), 4.30-4.07 (m. 0.7H), 3.52 (s, 3H), 3.43-3.23 (m, 1H), 3.08-2.96 (m, 0.4H), 2.91-2.68 (m, 0.6H), 2.22-1.99 (m, 3H), 1.94-1.74 (m, 2H).

Compound 86: 6-(3-Carboxy-cyclobutyl)-4-(2-chloro-4-fluoro-phenyl)-2-thiazol-2-yl-1,4-dihydropyrimidine-5-carboxylic acid methyl ester LC-MS (ESI): $R_T$=4.042 min, mass calcd. for $C_{20}H_{17}ClFN_3O_4S$ 449.1, m/z found 449.9 [M+H]$^+$. Chiral HPLC (Column: Chiralpak IC 5 μm 4.6*250 mm; Mobile Phase: Hex:EtOH:TFA=80:20:0.2 at 1.0 mL/min; Temp: 30° C.; Wavelength: 230 nm, $R_T$=5.654 min). $^1$H NMR (400 MHz, CDCl$_3$) δ 8.31 (s, 0.2H), 7.85 (d, J=2.8 Hz, 0.8H), 7.83 (d, J=3.2 Hz, 0.2H), 7.53-7.50 (m, 1.6H), 7.46 (d, J=3.6 Hz, 0.2H), 7.30-7.27 (m, 1H), 7.14 (dd, J=8.4, 2.4 Hz, 1H), 6.97-6.89 (m, 1H), 6.18 (s, 0.2H), 6.06 (d, J=2.8 Hz, 0.8H), 4.75-4.69 (m, 0.2H), 4.64-4.56 (m, 0.8H), 3.61 (s, 2.5H), 3.59 (s, 0.5H), 3.47-3.39 (m, 0.8H), 3.28-3.20 (m, 0.2H), 2.85-2.69 (m, 2H), 2.67-2.60 (m, 1.7H), 2.54-2.51 (m, 0.3H).

Compound 93: 2-(trans-2-(6-(2-Chloro-4-fluorophenyl)-5-(ethoxycarbonyl)-2-(thiazol-2-yl)-3,6-dihydropyrimidin-4-yl)cyclopropyl)acetic Acid LC-MS (ESI): $R_T$=3.309 min, mass calcd. for $C_{21}H_{19}ClFN_3O_4S$, 463.1, m/z found 463.9 [M+H]$^+$. Chiral HPLC (Column: Chiralpak IA 5 μm 4.6*250 mm; Mobile Phase: Hex:EtOH:TFA=90:10:0.2 at 1.0 mL/min; Temp: 30° C.; Wavelength: 230 nm, $R_T$=10.898 min). 1H NMR (400 MHz, DMSO-d$_6$) δ 9.48 (s, J=3.2 Hz, 1H), 8.00-7.96 (m, 2H), 7.40 (dd, J=7.2, 2.4 Hz, 1H), 7.34-7.30 (m, 1H), 7.24-7.19 (m, 1H), 5.92 (d, J=3.6 Hz, 1H), 3.98 (q, J=7.2 Hz, 2H), 3.11-3.05 (m, 1H), 2.37-2.28 (m, 2H), 1.70-1.61 (m, 1H), 1.46-1.39 (m, 1H), 1.07 (t, J=7.2 Hz, 3H), 0.84-0.74 (m, 1H).

Compound 95: 4-(6-(2-Chloro-4-fluorophenyl)-5-(methoxycarbonyl)-2-(thiazol-2-yl)-3,6-dihydropyrimidin-4-yl)cycloheptanecarboxylic Acid LC-MS (ESI): $R_T$=3.860 min, mass calcd. for $C_{23}H_{23}ClFN_3O_4S$ 491.1, m/z found 491.9 [M+H]$^+$. $^1$H NMR (400 MHz, CD$_3$OD) δ 7.91 (br s, 1H), 7.74-7.73 (m, 1H), 7.41-7.36 (m, 1H), 7.23-7.21 (m, 1H), 7.06-7.02 (m, 1H), 6.11-6.05 (m, 1H), 4.11 (br s, 0.6H), 3.93 (br s, 0.4H), 3.59 (s, 3H), 2.55 (br s, 1H), 2.22-1.47 (m, 10H).

Compound 95A: LC-MS (ESI): $R_T$=3.623 min, mass calcd. for $C_{23}H_{23}ClFN_3O_4S$ 491.1, m/z found 491.9 [M+H]$^+$. $^1$H NMR (400 MHz, CD$_3$OD) δ 7.91 (s, 1H), 7.73 (d, J=3.2 Hz, 1H), 7.40-7.37 (m, 1H), 7.22-7.20 (m, 1H), 7.07-7.03 (m, 1H), 6.11 (s, 0.6H), 6.05 (s, 0.4H), 4.11 (br s, 0.6H), 3.93 (br s, 0.4H), 3.59 (s, 3H), 2.64 (s, 1H), 2.19-1.74 (m, 9H), 1.61-1.46 (m, 1H).

Compound 95C: LC-MS (ESI): $R_T$=2.621 min, mass calcd. for $C_{23}H_{23}ClFN_3O_4S$ 491.1, m/z found 492.2 [M+H]$^+$. $^1$H NMR (400 MHz, CD$_3$OD) δ 7.92 (s, 1H), 7.74 (d, J=3.2 Hz, 1H), 7.41-7.37 (m, 1H), 7.23-7.21 (m, 1H), 7.07-7.02 (m, 1H), 6.11 (s, 0.6H), 6.05 (s, 0.4H), 4.11 (br s, 0.6H), 3.93 (br s, 0.4H), 3.59 (s, 3H), 2.61 (br s, 1H), 2.22-1.75 (m, 10H).

Compound 95E: LC-MS (ESI): $R_T$=3.530 min, mass calcd. for $C_{23}H_{23}ClFN_3O_4S$ 491.1, m/z found 492.2 [M+H]$^+$. $^1$H NMR (400 MHz, CD$_3$OD) δ 7.92-7.89 (m, 1H), 7.74 (d, J=3.2 Hz, 1H), 7.39-7.36 (m, 1H), 7.23-7.21 (m, 1H), 7.06-7.01 (m, 1H), 6.12 (s, 0.6H), 6.04 (s, 0.4H), 4.12 (br s, 0.6H), 3.94 (br s, 0.4H), 3.59 (s, 3H), 2.55 (br s, 1H), 2.17-1.71 (m, 10H).

Compound 142: (cis)-3-((4-(6-(2-chloro-4-fluorophenyl)-5-(methoxycarbonyl)-2-(thiazol-2-yl)-3,6-dihydropyrimidin-4-yl)piperidin-1-yl)sulfonyl)-1-methylcyclobutane-1-carboxylic Acid LC-MS (ESI): $R_T$=3.345 min, mass calcd. for $C_{26}H_{28}ClFN_4O_6S_2$ 610.1, m/z found 610.9 [M+H]$^+$. $^1$H NMR (400 MHz, DMSO-d6) δ 9.55 (s, 0.8H), 9.15 (s, 0.2H), 8.03-8.00 (m, 1.8H), 7.93 (s, 0.2H), 7.45-7.41 (m, 1H), 7.38-7.34 (m, 1H), 7.24-7.19 (m, 1H), 6.02 (s, 0.2H), 5.92 (s, 0.8H), 4.14-4.05 (m, 1H), 3.78-3.63 (m, 3H), 3.53 (s, 3H), 2.90-2.80 (m, 2H), 2.70-2.63 (m, 2H), 2.17-2.07 (m, 2H), 2.00-1.71 (m, 3H), 1.63-1.55 (m, 1H), 1.40 (s, 3H).

Compound 146: (trans)-3-((4-(6-(2-chlorophenyl)-5-(ethoxycarbonyl)-2-(thiazol-2-yl)-3,6-dihydropyrimidin-4-yl)piperidin-1-yl)sulfonyl)cyclobutane-1-carboxylic Acid LC-MS (ESI): $R_T$=4.575 min, mass calcd. for $C_{26}H_{29}ClN_4O_6S_2$ 592.1, m/z found 592.9 [M+H]$^+$. $^1$H NMR (400 MHz, DMSO-d$_6$) δ 7.99-7.97 (m, 1.8H), 7.92 (d, J=2.8 Hz, 0.2H), 7.44-7.42 (m, 1H), 7.36-7.26 (m, 3H), 6.07 (s, 0.2H), 5.96 (s, 0.8H), 4.02-3.95 (m, 3.2H), 3.78-3.71 (m, 2.8H), 3.13-3.10 (m, 1H), 2.91-2.82 (m, 2H), 2.57-2.51 (m, 4H), 2.06-1.94 (m, 1H), 1.89-1.76 (m, 2.2H), 1.61-1.58 (m, 0.8H), 1.08-1.02 (m, 3H).

Compound 148A: (trans)-4-(6-(2-bromophenyl)-5-(ethoxycarbonyl)-2-(thiazol-2-yl)-3,6-dihydropyrimidin-4-yl)cyclohexane-1-carboxylic Acid LC-MS (ESI): $R_T$=3.561 min, mass calcd. for $C_{23}H_{24}BrN_3O_4S$ 517.1, m/z found 520.1 [M+H]$^+$. Chiral analysis (Column: Chiralpak OJ-H 5 μm 4.6*250 mm; Mobile Phase: Hex:EtOH:TFA=85:15:0.2 at 1.0 mL/min; Temp: 30° C.; Wavelength: 230 nm, $R_T$=8.374 min). $^1$H NMR (400 MHz, DMSO-$d_6$) δ 12.01 (br s, 1H), 9.23 (s, 0.6H), 8.83 (s, 0.4H), 7.99-7.97 (m, 1.5H), 7.92 (d, J=3.2 Hz, 0.5H), 7.61 (d, J=8.4 Hz, 1H), 7.38-7.32 (m, 2H), 7.22-7.16 (m, 1H), 6.03 (s, 0.4H), 5.91 (d, J=2.8 Hz, 0.6H), 4.01-3.92 (m, 2H), 3.87-3.79 (m, 0.5H), 3.61-3.56 (m, 0.5H), 2.42-2.35 (m, 0.5H), 2.25-2.19 (m, 0.5H), 2.04-1.97 (m, 2H), 1.91-1.64 (m, 4H), 1.47-1.37 (m, 2H), 1.10-1.02 (m, 3H).

Compound 150A: (trans)-4-(6-(2-bromo-3-fluorophenyl)-5-(ethoxycarbonyl)-2-(thiazol-2-yl)-3,6-dihydropyrimidin-4-yl)cyclohexane-1-carboxylic Acid LC-MS (ESI): $R_T$=3.634 min, mass calcd. for $C_{23}H_{23}BrFN_3O_4S$ 535.1, m/z found 538.1 [M+H]$^+$. $^1$H NMR (400 MHz, DMSO-$d_6$) δ 8.87 (s, 1H), 7.99 (d, J=4.0 Hz, 1.5H), 7.93 (d, J=3.2 Hz, 0.5H), 7.44-7.38 (m, 1H), 7.31-7.24 (m, 1H), 7.20-7.15 (m, 1H), 6.60 (s, 0.5H), 5.96 (s, 0.5H), 3.99-3.94 (m, 2H), 3.89-3.79 (m, 0.5H), 3.62-3.55 (m, 0.5H), 2.41-2.34 (m, 0.5H), 2.25-2.19 (m, 0.5H), 2.05-1.98 (m, 2H), 1.91-1.63 (m, 4H), 1.47-1.33 (m, 2H), 1.09-1.01 (m, 3H).

Compound 152A: LC-MS (ESI): $R_T$=3.382 min, mass calcd. for $C_{22}H_{21}BrFN_3O_4S$ 521.0, m/z found 524.0 [M+H]$^+$. Chiral analysis (Column: Chiralpak IE 5 μm 4.6*250 mm; Mobile Phase: Hex:EtOH:TFA=85:15:0.2 at 1.0 mL/min; Temp: 30° C.; Wavelength: 230 nm, $R_T$=10.792 min). $^1$H NMR (400 MHz, CDCl$_3$) δ 8.11 (s, 0.7H), 7.83 (d, J=2.8 Hz, 1H), 7.51 (s, 0.3H), 7.49 (d, J=3.2 Hz, 0.5H), 7.45 (d, J=3.2 Hz, 0.5H), 7.24-7.18 (m, 1H), 7.12 (d, J=7.6 Hz, 1H), 7.07-6.99 (m, 1H), 6.25 (s, 0.5H), 6.09 (d, J=2.8 Hz, 0.5H), 4.07-4.01 (m, 0.5H), 3.83-3.75 (m, 0.5H), 3.61 (s, 1H), 3.59 (s, 2H), 2.50-2.43 (m, 1H), 2.27-2.12 (m, 2.5H), 2.06-1.93 (m, 1.5H), 1.81-1.50 (m, 4H).

Compound 154A: LC-MS (ESI): $R_T$=3.726 min, mass calcd. for $C_{24}H_{25}F_2N_3O_4S$ 489.2, m/z found 490.1 [M+H]$^+$. $^1$H NMR (400 MHz, DMSO-$d_6$) δ 12.04 (s, 1H), 9.49 (d, J=2.8 Hz, 0.7H), 8.88 (s, 0.3H), 7.98 (d, J=3.2 Hz, 1.7H), 7.92 (d, J=3.2 Hz, 0.3H), 7.26-7.17 (m, 1H), 7.10-7.07 (m, 0.7H), 7.00-6.95 (m, 0.3H), 5.81 (s, 0.3H), 5.68 (d, J=3.2 Hz, 0.7H), 3.97 (q, J=7.2 Hz, 2H), 3.86-3.79 (m, 0.3H), 3.61-3.52 (m, 0.7H), 2.50 (s, 1H), 2.45 (s, 2H), 2.39-2.32 (m, 0.3H), 2.25-2.18 (m, 0.7H), 2.08-1.59 (m, 6H), 1.49-1.30 (m, 2H), 1.07 (t, J=6.8 Hz, 3H).

Compound 156A: LC-MS (ESI): $R_T$=3.467 min, mass calcd. for $C_{23}H_{23}BrFN_3O_4S$ 535.1, m/z found 536.0 [M+H]$^+$. Chiral analysis (Column: Chiralpak IE 5 μm 4.6*250 mm; Mobile Phase: Hex:EtOH:TFA=90:10:0.2 at 1.0 mL/min; Temp: 30° C.; Wavelength: 230 nm; $R_T$=12.600 min). $^1$H NMR (400 MHz, DMSO-$d_6$) δ 11.99 (br s, 1H), 9.31 (d, J=3.2 Hz, 0.6H), 8.85 (s, 0.4H), 7.99-7.97 (m, 1.6H), 7.93 (d, J=3.2 Hz, 0.4H), 7.56 (dd, J=8.4, 2.0 Hz, 1H), 7.36-7.31 (m, 1H), 7.28-7.22 (m, 1H), 5.99 (s, 0.4H), 5.89 (d, J=3.6 Hz, 0.6H), 4.01-3.93 (m, 2H), 3.85-3.78 (m, 0.4H), 3.61-3.54 (m, 0.6H), 2.42-2.32 (m, 0.4H), 2.26-2.19 (m, 0.6), 2.04-1.97 (m, 2H), 1.90-1.61 (m, 4H), 1.47-1.36 (m, 2H), 1.11-1.04 (m, 3H).

Compound 162: trans-3-((4-(-6-(2-Bromo-3,4-difluorophenyl)-5-(methoxycarbonyl)-2-(thiazol-2-yl)-3,6-dihydropyrimidin-4-yl)piperidin-1-yl)sulfonyl) cyclobutanecarboxylic Acid LC-MS (ESI): $R_T$=4.127 min, mass calcd. for $C_{25}H_{25}BrF_2N_4O_6S_2$ 658.0, m/z found 658.8 [M+H]$^+$. $^1$H NMR (400 MHz, CD$_3$OD) δ 7.91 (s, 1H), 7.75 (s, 1H), 7.29-7.19 (m, 2H), 6.12-6.07 (m, 1H), 4.10-3.87 (m, 4H), 3.58 (s, 3H), 3.26-3.20 (m, 1H), 3.02-2.92 (m, 2H), 2.77-2.64 (m, 4H), 2.14-1.69 (m, 4H).

Compound 195A: (trans)-3-((4-(6-(2-Chloro-3,4-difluorophenyl)-5-(ethoxycarbonyl)-2-(2,4,6-trifluorophenyl)-3,6-dihydropyrimidin-4-yl)piperidin-1-yl)sulfonyl)cyclobutanecarboxylic Acid LC-MS(ESI): $R_T$=4.267 min, mass calcd. for $C_{29}H_{27}ClF_5N_3O_6S$ 675.1, m/z found 676.1 [M+H]$^+$. Chiral analysis (Column: Chiralcel OZ-H 5 μm 4.6*150 mm, Phase: Hex:EtOH=90:10 at 1.0 mL/min, Temp: 35° C.; Wavelength: 254 nm, $R_T$=7.778 min). $^1$H NMR (400 MHz, DMSO-$d_6$) δ 9.56 (s, 1H), 7.59-7.47 (m, 1H), 7.27-7.17 (m, 3H), 5.97 (s, 0.8H), 5.88 (s, 0.2H), 4.01-3.92 (m, 4H), 3.81-3.66 (m, 2H), 3.12-3.08 (m, 1H), 2.86-2.79 (m, 2H), 2.58-2.53 (m, 4H), 1.97-1.53 (m, 4H), 1.06-1.03 (m, 3H).

Compound 199A: (trans)-3-((4-(6-(2-bromo-3,4-difluorophenyl)-5-(ethoxycarbonyl)-2-(thiazol-2-yl)-3,6-dihydropyrimidin-4-yl)piperidin-1-yl)sulfonyl) cyclobutanecarboxylic Acid LC-MS (ESI): $R_T$=3.993 min, mass calcd. for $C_{26}H_{27}BrF_2N_4O_6S_2$ 672.1, m/z found 673.0 [M+H]$^+$. Chiral analysis (Column: Chiralpak IA 5 μm 4.6*250 mm; Mobile Phase: Hex:EtOH:TFA=80:20:0.2 at 1.0 mL/min; Temp: 30° C.; Wavelength: 230 nm, $R_T$=13.117 min). $^1$H NMR (400 MHz, DMSO-$d_6$) δ 8.00-7.98 (m, 1.8H), 7.93-7.92 (m, 0.2H), 7.52-7.45 (m, 1H), 7.23-7.14 (m, 1H), 6.02 (s, 0.2H), 5.93 (s, 0.8H), 4.02-3.95 (m, 3H), 3.78-3.71 (m, 3H), 3.17-3.11 (m, 1H), 2.91-2.81 (m, 2H), 2.58-2.54 (m, 4H), 2.04-1.83 (m, 3H), 1.62-1.60 (m, 0.8H), 1.47-1.42 (m, 0.2H), 1.09-1.05 (m, 3H).

Compound 199B: (trans)-3-((4-(6-(2-bromo-3,4-difluorophenyl)-5-(ethoxycarbonyl)-2-(thiazol-2-yl)-3,6-dihydropyrimidin-4-yl)piperidin-1-yl)sulfonyl) cyclobutanecarboxylic Acid LC-MS (ESI): $R_T$=4.002 min, mass calcd. for $C_{26}H_{27}BrF_2N_4O_6S_2$ 672.1, m/z found 673.0 [M+H]$^+$. Chiral analysis (Column: Chiralpak IA 5 μm 4.6*250 mm; Mobile Phase: Hex:EtOH:TFA=80:20:0.2 at 1.0 mL/min; Temp: 30° C.; Wavelength: 230 nm, $R_T$=11.811 min). $^1$H NMR (400 MHz, DMSO-$d_6$) δ 8.00-7.98 (m, 1.8H), 7.95-7.92 (m, 0.2H), 7.52-7.45 (m, 1H), 7.25-7.17 (m, 1H), 6.02 (s, 0.2H), 5.93 (s, 0.8H), 4.02-3.96 (m, 3H), 3.77-3.71 (m, 3H), 3.16-3.10 (m, 1H), 2.91-2.82 (m, 2H), 2.57-2.53 (m, 4H), 2.03-1.74 (m, 3H), 1.63-1.58 (m, 0.8H), 1.48-1.42 (m, 0.2H), 1.07-1.05 (m, 3H).

Compound 210A: (trans)-4-((4-(6-(2-chloro-3,4-difluorophenyl)-5-(methoxycarbonyl)-2-(thiazol-2-yl)-3,6-dihydropyrimidin-4-yl)piperidin-1-yl)sulfonyl)-1-methylcyclohexanecarboxylic Acid LC-MS (ESI): $R_T$=3.66 min, mass calcd. for $C_{28}H_{31}ClF_2N_4O_6S_2$ 657.1 m/z found 656.1 [M+H]$^+$. $^1$H NMR (400 MHz, CD$_3$OD) δ 7.97-7.89 (m, 1H), 7.76-7.75 (m, 1H), 7.28-7.17 (m, 2H), 6.14 (s, 0.3H), 6.07 (s, 0.7H), 4.21-4.10 (m, 0.3H), 4.02-3.85 (m, 2.7H), 3.59 (s, 3H), 3.14-2.99 (m, 3H), 2.18-1.95 (m, 4H), 1.90-1.63 (m, 8H), 1.25 (s, 3H).

Compound 210B: (cis)-4-((4-(6-(2-chloro-3,4-difluorophenyl)-5-(methoxycarbonyl)-2-(thiazol-2-yl)-3,6-dihydropyrimidin-4-yl)piperidin-1-yl)sulfonyl)-1-methylcyclohexanecarboxylic Acid LC-MS (ESI): $R_T$=3.65 min, mass calcd. for $C_{28}H_{31}ClF_2N_4O_6S_2$ 657.1 m/z found 656.9 [M+H]$^+$. $^1$H NMR (400 MHz, CD$_3$OD) δ 7.97-7.88 (m, 1H), 7.79-7.72 (m, 1H), 7.27-7.18 (m, 2H), 6.13 (s, 0.3H), 6.07 (s, 0.7H), 4.22-4.11 (m, 0.3H), 3.99-3.83 (m, 2.7H), 3.59 (s, 3H), 3.14-2.95 (m, 3H), 2.32-2.29 (m, 2H), 2.18-1.96 (m, 4H), 1.90-1.61 (m, 4H), 1.28-1.21 (m, 2H), 1.17 (s, 3H).

Compound 212M: (trans)-4-(-6-(2-Chloro-3-fluorophenyl)-5-(methoxycarbonyl)-2-(thiazol-2-yl)-3,6-dihydropyrimidin-4-yl)tetrahydrofuran-2-carboxylic Acid LC-MS (ESI): $R_T$=2.910 min, mass calcd. for $C_{20}H_{17}ClFN_3O_5S$ 465.1, m/z found 466.1 [M+H]$^+$. $^1$H NMR (400 MHz, CDCl$_3$) δ 7.85 (d, J=2.0 Hz, 1H), 7.52 (d, J=2.8 Hz, 1H), 7.24-7.22 (m, 1H), 7.12-7.07 (m, 2H), 6.24 (brs, 0.1H), 6.17 (s, 0.9H), 4.90-4.87 (m, 1H), 4.63-4.61 (m, 1H), 4.51-4.49 (m, 1H), 4.24-4.22 (m, 1H), 3.61 (s, 3H), 2.80-2.79 (m, 1H), 2.28-2.26 (m, 1H).

Compound 214A: 2-((-3-(-6-(2-Chloro-4-fluorophenyl)-5-(methoxycarbonyl)-2-(thiazol-2-yl)-3,6-dihydropyrimidin-4-yl)pyrrolidin-1-yl)sulfonyl)acetic Acid LC-MS (ESI): $R_T$=3.127 min, mass calcd. for $C_{21}H_{20}ClFN_4O_6S_2$ 542.1, m/z found 543.0 [M+H]$^+$. Chiral analysis (Column: Chiralpak IE 5 μm 4.6*250 mm; Mobile Phase: Hex:EtOH:TFA=70:30:0.2 at 1.0 mL/min; Temp: 30° C.; Wavelength: 230 nm, $R_T$=13.322 min). $^1$H NMR (400 MHz, DMSO-d$_6$) δ 8.01 (s, 2H), 7.44-7.41 (m, 1H), 7.39-7.35 (m, 1H), 7.25-7.20 (m, 1H), 5.94 (s, 1H), 4.41-4.29 (m, 1H), 3.87 (s, 2H), 3.70-3.58 (m, 2H), 3.54 (s, 3H), 3.51-3.39 (m, 2H), 2.26-2.13 (m, 1H), 2.05-1.92 (m, 1H).

Compound 214C: 2-((-3-(-6-(2-Chloro-4-fluorophenyl)-5-(methoxycarbonyl)-2-(thiazol-2-yl)-3,6-dihydropyrimidin-4-yl)pyrrolidin-1-yl)sulfonyl)acetic Acid LC-MS (ESI): $R_T$=2.914 min, mass calcd. for $C_{21}H_{20}ClFN_4O_6S_2$ 542.1, m/z found 543.1 [M+H]$^+$. Chiral analysis (Column: Chiralpak OD-H5 μm 4.6*250 mm; Mobile Phase: Hex:EtOH:TFA=70:30:0.2 at 1.0 mL/min; Temp: 30° C.; Wavelength: 230 nm, $R_T$=7.997 min). $^1$H NMR (400 MHz, DMSO-d$_6$) δ 8.01 (s, 2H), 7.44-7.41 (m, 1H), 7.38-7.35 (m, 1H), 7.24-7.19 (m, 1H), 5.94 (s, 1H), 4.42-4.30 (m, 1H), 3.87 (s, 2H), 3.63-3.54 (m, 5H), 3.47-3.40 (m, 2H), 2.33-2.24 (m, 1H), 2.19-2.08 (m, 1H).

Compound 223: 3-((4-(6-(2-Chloro-4-fluorophenyl)-5-(methoxycarbonyl)-2-(thiazol-2-yl)-3,6-dihydropyrimidin-4-yl)piperidin-1-yl)sulfonyl)-2,2-dimethylpropanoic Acid LC-MS (ESI): $R_T$=3.326 min, mass calcd. for $C_{25}H_{28}ClFN_4O_6S_2$ 598.1, m/z found 599.2 [M+H]$^+$. $^1$H NMR (400 MHz, CD$_3$OD) δ 7.89 (br s, 1H), 7.75 (d, J=2.8 Hz, 1H), 7.41-7.37 (m, 1H), 7.24-7.22 (m, 1H), 7.07-7.03 (m, 1H), 6.14-6.07 (m, 1H), 4.09 (br s, 0.3H), 3.89-3.82 (m, 2.7H), 3.59 (s, 3H), 3.36 (s, 2H), 2.94-2.84 (m, 2H), 2.21-1.89 (m, 3.3H), 1.72-1.68 (m, 0.7H), 1.39 (s, 6H).

Compound 225: (trans)-4-(6-(2-Bromo-4-fluorophenyl)-5-(methoxycarbonyl)-2-(thiazol-2-yl)-3,6-dihydropyrimidin-4-yl)cyclohexanecarboxylic Acid $^1$H NMR (400 MHz, DMSO-d$_6$) δ 8.93 (br s, 1H), 7.99 (s, 1.5H), 7.93 (d, J=2.8 Hz, 0.5H), 7.57-7.55 (m, 1H), 7.37-7.33 (m, 1H), 7.29-7.22 (m, 1H), 5.98 (s, 0.5H), 5.88 (s, 0.5H), 3.87-3.76 (m, 0.5H), 3.65-3.58 (m, 0.5H), 3.53 (s, 1.6H), 3.51 (s, 1.4H), 2.41-2.34 (m, 0.5H), 2.25-2.16 (m, 0.5H), 2.09-1.97 (m, 2H), 1.89-1.74 (m, 3H), 1.67-1.58 (m, 1H), 1.50-1.34 (m, 2H).

Compound 227A: (trans)-4-(-6-(3,4-Difluoro-2-methylphenyl)-5-(methoxycarbonyl)-2-(thiazol-2-yl)-3,6-dihydropyrimidin-4-yl)cyclohexanecarboxylic Acid LC-MS (ESI): $R_T$=3.615 min, mass calcd. for $C_{23}H_{23}F_2N_3O_4S$ 475.1, m/z found 475.9 [M+H]$^+$. Chiral analysis (Column: Chiralpak IC m 4.6*250 mm; Mobile Phase. Hex:EtOH:TFA=90:10:0.2 at 1.0 mL/min; Temp: 30° C.; Wavelength: 230 nm, $R_T$=7.364 min). $^1$H NMR (400 MHz, DMSO-d$_6$) δ 7.99-7.97 (m, 1.7H), 7.92 (d, J=2.8 Hz, 0.3H), 7.26-7.17 (m, 1H), 7.11-7.06 (m, 0.7H), 6.98-6.95 (m, 0.3H), 5.81 (s, 0.3H), 5.68 (s, 0.7H), 3.85 (br s, 0.3H), 3.62-3.57 (m, 0.7H), 3.52 (s, 3H), 2.44-2.38 (m, 3H), 2.30-2.16 (m, 1H), 2.06-1.96 (m, 2H), 1.90-1.62 (m, 4H), 1.46-1.33 (m, 2H).

Compound 229B: (trans)-4-(6-(2-Bromo-3,4-difluorophenyl)-5-(methoxycarbonyl)-2-(thiazol-2-yl)-3,6-dihydropyrimidin-4-yl)cyclohexane-carboxylic Acid LC-MS (ESI): $R_T$=3.510 min, mass calcd. for $C_{22}H_{20}BrF_2N_3O_4S$ 539.0, m/z found 542.1 [M+H]$^+$. Chiral analysis (Column: Chiralpak IC 5 μm 4.6*250 mm; Mobile Phase: Hex:EtOH:DEA=80:20:0.2 at 1.0 mL/min; Temp: 30° C.; Wavelength: 230 nm, $R_T$=5.689 min). $^1$H NMR (400 MHz, DMSO-d$_6$) δ 11.97 (s, 1H), 9.51 (s, 0.4H), 8.98 (s, 0.6H), 8.00-7.99 (m, 1.5H), 7.94-7.93 (m, 0.5H), 7.52-7.44 (m, 1H), 7.22-7.12 (m, 1H), 6.00 (s, 0.5H), 5.91 (s, 0.5H), 3.88-3.80 (m, 0.5H), 3.65-3.51 (m, 3.5H), 2.41-2.33 (m, 0.5H), 2.25-2.19 (m, 0.5H), 2.06-2.01 (m, 2H), 1.97-1.61 (m, 4H), 1.49-1.36 (m, 2H).

Compound 230: 3-((4-(6-(2-Chloro-3,4-difluorophenyl)-5-(methoxycarbonyl)-2-(thiazol-2-yl)-3,6-dihydropyrimidin-4-yl)piperidin-1-yl)sulfonyl)propanoic Acid LC-MS (ESI): $R_T$=3.864 min, mass calcd. for $C_{23}H_{23}ClF_2N_4O_6S_2$ 588.1, m/z found mass 588.9 [M+H]$^+$.

¹H NMR (400 MHz, DMSO-d₆+one drop of D₂O) δ 8.01-7.99 (m, 1.8H), 7.93-7.92 (m, 0.2H), 7.48-7.42 (m, 1H), 7.23-7.19 (m, 1H), 6.02 (s, 0.2H), 5.94 (s, 0.8H), 3.77-3.68 (m, 3H), 3.54 (s, 3H), 3.30-3.27 (m, 2H), 2.94-2.84 (m, 2H), 2.63-2.59 (m, 2H), 2.04-1.94 (m, 1H), 1.89-1.77 (m, 2.2H), 1.66-1.61 (m, 0.8H).

Compound 232B: (trans)-3-((4-(6-(2-Chloro-3,4-difluorophenyl)-5-(methoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=3.944 min, mass calcd. for $C_{25}H_{25}ClF_2N_4O_6S_2$ 614.1, m/z found mass 615.0 [M+H]⁺. ¹H NMR (400 MHz, DMSO-d₆) δ 8.01-7.92 (m, 2H), 7.49-7.41 (m, 1H), 7.22-7.18 (m, 1H), 6.01 (s, 0.2H), 5.92 (s, 0.8H), 4.00-3.97 (m, 1H), 3.76-3.70 (m, 3H), 3.53 (s, 3H), 3.11-3.04 (m, 1H), 2.91-2.83 (m, 2H), 2.56-2.51 (m, 4H), 1.98-1.91 (m, 1H), 1.86-1.72 (m, 2H), 1.61-1.57 (m, 1H).

Compound 232D: (cis)-3-((4-(−6-(2-Chloro-3,4-difluorophenyl)-5-(methoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=3.164 min, mass calcd. for $C_{25}H_{25}ClF_2N_4O_6S_2$ 614.1, m/z found mass 615.0 [M+H]⁺. ¹H NMR (400 MHz, DMSO-d₆) δ 9.32 (s, 1H), 8.01-7.95 (m, 2H), 7.48-7.42 (m, 1H), 7.22-7.18 (m, 1H), 5.93 (s, 1H), 3.95-3.91 (m, 1H), 3.73-3.67 (m, 3H), 3.53 (s, 3H), 3.06-3.01 (m, 1H), 2.88-2.80 (m, 2H), 2.48-2.41 (m, 4H), 1.99-1.92 (m, 1H), 1.83-1.74 (m, 2.1H), 1.62-1.59 (m, 0.9H).

Compound 232X: (trans)-3-((4-(6-(2-Chloro-3,4-difluorophenyl)-5-(methoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=3.939 min, mass calcd. for $C_{25}H_{25}ClF_2N_4O_6S_2$ 614.1, m/z found mass 615.1 [M+H]⁺. ¹H NMR (400 MHz, DMSO-d₆) δ 9.63 (s, 1H), 8.01-7.97 (m, 2H), 7.48-7.41 (m, 1H), 7.22-7.18 (m, 1H), 5.94 (s, 1H), 4.03-3.99 (m, 1H), 3.77-3.71 (m, 3H), 3.53 (s, 3H), 3.17-3.14 (m, 1H), 2.92-2.84 (m, 2H), 2.59-2.55 (m, 4H), 2.07-1.96 (m, 1.2H), 1.91-1.72 (m, 2H), 1.64-1.59 (m, 0.8H).

Compound 241B: (trans)-3-((4-(−6-(2-Bromo-4-fluorophenyl)-5-(methoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=3.329 min, mass calcd. for $C_{25}H_{26}BrFN_4O_6S_2$ 640.1, m/z found 643.1 [M+H]⁺. ¹H NMR (400 MHz, DMSO-d₆) δ 8.01-7.98 (m, 1.8H), 7.93 (d, J=2.8 Hz, 0.2H), 7.58-7.55 (m, 1H), 7.38-7.30 (m, 1H), 7.28-7.21 (m, 1H), 5.99 (s, 0.2H), 5.89 (s, 0.8H), 4.04-3.95 (m, 1H), 3.77-3.70 (m, 3H), 3.53 (s, 2.5H), 3.52 (s, 0.5H), 3.18-3.10 (m, 1H), 2.88 (q, J=14.0 Hz, 2H), 2.59-2.53 (m, 4H), 2.10-1.84 (m, 1H), 1.82-1.75 (m, 2H), 1.61-1.57 (m, 1H).

Compound 258: 3-(6-(2-Chloro-4-fluorophenyl)-5-(methoxycarbonyl)-2-(thiazol-2-yl)-3,6-dihydropyrimidin-4-yl)bicyclo[1.1.1]pentane-1-carboxylic Acid LC-MS (ESI): $R_T$=2.821 min, mass calcd. for $C_{21}H_{17}ClFN_3O_4S$ 461.1, m/z found 462.1 [M+H]⁺. ¹H NMR (400 MHz, CDCl₃) δ 8.01-7.99 (m, 1.4H), 7.95 (d, J=2.8 Hz, 0.6H), 7.44-7.42 (m, 1H), 7.32-7.30 (m, 1H), 7.24-7.20 (m, 1H), 5.97 (s, 0.5H), 5.87 (s, 0.5H), 3.56 (s, 1.5H), 3.55 (s, 1.5H), 2.34 (s, 3H), 2.26 (s, 3H).

Compound 258B: 3-(6-(2-Chloro-4-fluorophenyl)-5-(methoxycarbonyl)-2-(thiazol-2-yl)-3,6-dihydropyrimidin-4-yl)bicyclo[1.1.1]pentane-1-carboxylic Acid LC-MS (ESI): $R_T$=3.399 min, mass calcd. for $C_{21}H_{17}ClFN_3O_4S$ 461.1, m/z found 461.9 [M+H]⁺. Chiral analysis (Column: Chiralpak IA 5 μm 4.6*250 mm; Mobile Phase: Hex:EtOH:TFA=80:20:0.2 at 1.0 mL/min; Temp: 30° C.; Wavelength: 230 nm, $R_T$=6.227 min). ¹H NMR (400 MHz, DMSO-d₆) δ 8.01-7.99 (m, 1.4H), 7.95-7.92 (m, 0.6H), 7.44-7.42 (m, 1H), 7.35-7.28 (m, 1H), 7.24-7.20 (m, 1H), 5.97 (s, 0.5H), 5.87 (s, 0.5H), 3.56 (s, 1.5H), 3.55 (s, 1.5H), 2.36 (s, 3H), 2.26 (s, 3H).

Compound 265E and 265H: (cis)-5-(−6-(2-Chloro-4-fluorophenyl)-5-(ethoxycarbonyl)-2-(thiazol-2-yl)-3,6-dihydropyrimidin-4-yl)tetrahydro-2H-pyran-2-carboxylic Acid Compound 265E: LC-MS (ESI): $R_T$=3.412 min, mass calcd. for $C_{22}H_{21}ClFN_3O_5S$ 493.1, m/z found 494.0 [M+H]⁺. Chiral HPLC (Column: Chiralpak IG 5 μm 4.6*250 mm; Mobile Phase: Hex:EtOH:DEA=70:30:0.2 at 1.0 mL/min; Temp: 30° C.; Wavelength: 230 nm, $R_T$=12.672 min). ¹H NMR (400 MHz, DMSO-d₆) δ 9.57 (br s, 1H), 8.00 (s, 2H), 7.43 (dd, J=8.8, 2.4 Hz, 1H), 7.38-7.34 (m, 1H), 7.24-7.20 (m, 1H), 5.96 (s, 1H), 4.03-4.01 (m, 1H), 3.98 (q, J=7.2 Hz, 2H), 3.88-3.78 (m, 3H), 2.06-1.97 (m, 2H), 1.83-1.76 (m, 1H), 1.59-1.50 (m, 1H), 1.07 (t, J=7.2 Hz, 3H). ¹H NMR (400 MHz, DMSO-d₆+D₂O) δ 8.02-8.01 (m, 1H), 7.97-7.95 (m, 1H), 7.44-7.36 (m, 2H), 7.24-7.19 (m, 1H), 5.98 (s, 1H), 4.05-3.98 (m, 4H), 3.92-3.85 (m, 2H), 2.07-2.00 (m, 2H), 1.86-1.80 (m, 1H), 1.60-1.51 (m, 1H), 1.07 (t, J=7.2 Hz, 3H).

Compound 2651H: LC-MS (ESI): $R_T$=3.153 min, mass calcd. for $C_{22}H_{21}ClFN_3O_5S$ 493.1, m/z found 493.9 [M+H]⁻. Chiral SFC (Column: Chiralpak IE 5 μm 4.6*250 mm; Mobile Phase: CO₂: ACN:TFA=60:40:0.2 at 2.999 g/min; Col. Temp: 40.1° C.; Wavelength: 214 nm, Back pressure: 100 bar; $R_T$=6.19 min). ¹H NMR (400 MHz, DMSO-d₆) δ 9.58 (br s, 1H), 8.00 (s, 2H), 7.43 (dd, J=8.8, 2.8 Hz, 1H), 7.37 (dd, J=8.8, 6.0 Hz, 1H), 7.25-7.20 (m, 1H), 5.95 (s, 1H), 3.98 (q, J=7.2 Hz, 2H), 3.90-3.82 (m, 3H), 3.75-3.70 (m, 1H), 2.15-2.09 (m, 1H), 2.04-1.97 (m, 2H), 1.62-1.53 (m, 1H), 1.07 (t, J=6.8 Hz, 3H). ¹H NMR (400 MHz, DMSO-d₆+D₂O) δ 8.01 (d, J=3.2 Hz, 1H), 7.96 (d, J=3.2 Hz, 1H), 7.43 (dd, J=8.8, 2.4 Hz, 1H), 7.37 (dd, J=8.8, 6.0 Hz, 1H), 7.25-7.20 (m, 1H), 5.98 (s, 1H), 3.99 (q, J=6.8 Hz, 2H), 3.92-3.86 (m, 3H), 3.77-3.72 (m, 1H), 2.17-2.12 (m, 1H), 2.07-1.99 (m, 2H), 1.64-1.54 (m, 1H), 1.07 (t, J=6.8 Hz, 3H).

270B: (cis)-3-((4-(6-(2-Chloro-3,4-difluorophenyl)-5-(ethoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.425 min, mass calcd. for $C_{27}H_{29}ClF_2N_4O_6S_2$ 642.1 m/z found 643.0 [M+H]⁺. ¹H NMR (400 MHz, DMSO-d₆) δ 9.71 (br s, 1H), 8.00 (s, 2H), 7.46 (q, J=8.4 Hz, 1H), 7.23-7.19 (m, 1H), 5.94 (s, 1H), 4.10-4.06 (m, 1H), 3.97 (q, J=7.2 Hz, 2H), 3.74-3.67 (m, 3H), 2.84 (q, J=10.4 Hz, 2H), 2.67-2.62 (m, 2H), 2.13-2.08 (m, 2H), 2.01-1.82 (m, 1H), 1.85-1.78 (m, 2H), 1.74-1.61 (m, 1H), 1.39 (s, 3H), 1.07 (t, J=7.2 Hz, 3H).

Compound 272A: (trans)-3-((4-(6-(2-Chloro-4-fluorophenyl)-5-(ethoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.339 min, mass calcd. for $C_{27}H_{30}ClFN_4O_6S_2$ 624.1 m/z found 625.0 [M+H]$^+$. $^1$H NMR (400 MHz, DMSO-d$_6$) δ 8.01-7.93 (m, 2H), 7.42 (dd, J=8.8, 2.8 Hz, 1H), 7.36 (dd, J=8.8, 6.0 Hz, 1H), 7.26-7.18 (m, 1H), 6.02 (s, 0.2H), 5.92 (s, 0.8H), 3.98-3.94 (m, 3H), 3.76-3.72 (m, 3H), 2.86-2.78 (m, 2H), 2.75-2.72 (m, 2H), 2.26-2.20 (m, 2H), 2.04-1.77 (m, 3H), 1.60-1.55 (m, 1H), 1.33 (s, 3H), 1.07 (t, J=7.2 Hz, 3H).

Compound 272B: (cis)-3-((4-(6-(2-Chloro-4-fluorophenyl)-5-(ethoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.321 min, mass calcd. for $C_{27}H_{30}ClFN_4O_6S_2$ 624.1 m/z found 625.0 [M+H]$^+$. $^1$H NMR (400 MHz, DMSO-d$_6$) δ 9.43 (br s, 1H), 8.01-8.00 (m, 2H), 7.42-7.38 (m, 1H), 7.38-7.35 (m, 1H), 7.24-7.19 (m, 1H), 5.93 (s, 1H), 4.10-4.06 (m, 1H), 3.97 (q, J=7.2 Hz, 2H), 3.74-3.71 (m, 3H), 2.89-2.80 (m, 2H), 2.67-2.62 (m, 2H), 2.13-2.08 (m, 2H), 1.99-1.92 (m, 1H), 1.88-1.76 (m, 2H), 1.61-1.53 (m, 1H), 1.39 (s, 3H), 1.07 (t, J=6.8 Hz, 3H).

Compound 274A: (trans)-3-((4-(-6-(2-Chloro-3-fluorophenyl)-5-(methoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.165 min, mass calcd. for $C_{26}H_{28}ClFN_4O_6S_2$ 610.1 m/z found 611.2 [M+H]$^+$. $^1$H NMR (400 MHz, DMSO-d$_6$) δ 9.42 (br s, 1H), 8.01-7.99 (m, 1.8H), 7.93 (d, J=3.2 Hz, 0.2H), 7.38-7.31 (m, 2H), 7.22-7.20 (m, 1H), 6.07 (s, 0.2H), 5.97 (s, 0.8H), 3.97-3.93 (m, 1H), 3.76-3.68 (m, 3H), 3.52 (s, 2H), 3.51 (s, 1H), 2.90-2.81 (m, 2H), 2.79-2.73 (m, 2H), 2.27-2.22 (m, 2H), 2.06-1.72 (m, 3H), 1.62-1.53 (m, 1H), 1.34 (s, 3H).

Compound 274B: (cis)-3-((4-(-6-(2-Chloro-3-fluorophenyl)-5-(methoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.142 min, mass calcd. for $C_{26}H_{28}ClFN_4O_6S_2$ 610.1 m/z found 611.2 [M+H]$^+$. $^1$H NMR (400 MHz, DMSO-d$_6$) δ 9.78 (br s, 1H), 8.03-7.92 (m, 2H), 7.39-7.34 (m, 2H), 7.22-7.20 (m, 1H), 6.07 (s, 0.2H), 5.97 (s, 0.8H), 4.21-4.06 (m, 1H), 3.81-3.62 (m, 3H), 3.52 (s, 3H), 2.94-2.80 (m, 2H), 2.68-2.62 (m, 2H), 2.16-2.10 (m, 2H), 1.99-1.90 (m, 1H), 1.82-1.70 (m, 2H), 1.65-1.52 (m, 1H), 1.40 (s, 3H)

Compound 278C: (trans)-3-((4-(6-(2-bromo-3-fluorophenyl)-5-(methoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.742 min, mass calcd. for $C_{26}H_{28}BrFN_4O_6S_2$ 654.1 m/z found 654.8 [M+H]$^+$. $^1$H NMR (400 MHz, DMSO-d$_6$) δ 12.60 (s, 1H), 9.60 (s, 0.8H), 9.18 (s, 0.2H), 8.03-7.95 (m, 1.7H), 7.95-7.91 (m, 0.2H), 7.44-7.37 (m, 1H), 7.33-7.26 (m, 1H), 7.22-7.13 (m, 1H), 6.05 (s, 0.2H), 5.96 (s, 0.8H), 3.99-3.92 (m, 1H), 3.80-3.65 (m, 3H), 3.55-3.50 (m, 3H), 2.94-2.70 (m, 4H), 2.31-2.18 (m, 2H), 2.18-2.09 (m, 1H), 2.07-1.71 (m, 3.2H), 1.63-1.55 (m, 0.8H), 1.35 (s, 3H).

Compound 278D: (cis)-3-((4-(6-(2-bromo-3-fluorophenyl)-5-(methoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.662 min, mass calcd. for $C_{26}H_{28}BrFN_4O_6S_2$ 654.1, m/z found 654.9 [M+H]$^+$. $^1$H NMR (400 MHz, DMSO-d$_6$) δ 9.61 (s, 0.8H), 9.20-9.18 (m, 0.2H), 8.05-7.98 (m, 2H), 7.45-7.39 (m, 1H), 7.31-7.24 (m, 1H), 7.19-7.15 (m, 1H), 6.07-5.54 (m, 1H), 4.19-4.09 (m, 1H), 3.79-3.65 (m, 3H), 3.55-3.50 (m, 3H), 2.93-2.80 (m, 2H), 2.71-2.62 (m, 2H), 2.18-2.13 (m, 2H), 2.04-1.74 (m, 3.2H), 1.65-1.57 (m, 0.8H), 1.41 (s, 3H).

Compound 282C: (trans)-3-((4-(-6-(2-Bromo-4-fluorophenyl)-5-(ethoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=2.852 min, mass calcd. for $C_{27}H_{30}BrFN_4O_6S_2$ 668.1, m/z found 670.9 [M+H]$^+$. $^1$H NMR (400 MHz, DMSO-d$_6$) δ 7.99 (s, 1.8H), 7.93 (s, 0.2H), 7.57 (dd, J=8.4, 2.4 Hz, 1H), 7.37-7.34 (m, 1H), 7.28-7.24 (m, 1H), 5.99 (s, 0.2H), 5.90 (s, 0.8H), 4.00-3.85 (m, 3.2H), 3.75-3.68 (m, 2.8H), 2.87-2.79 (m, 2H), 2.73-2.67 (m, 2H), 2.19-2.13 (m, 2H), 2.00-1.76 (m, 3.2H), 1.60-1.57 (m, 0.8H), 1.28 (s, 3H), 1.08 (t, J=7.2 Hz, 3H).

Compound 282D: (cis)-3-((4-(6-(2-Bromo-4-fluorophenyl)-5-(ethoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=2.746 min, mass calcd. for $C_{27}H_{30}BrFN_4O_6S_2$ 668.1, m/z found 670.9 [M+H]$^+$. $^1$H NMR (400 MHz, DMSO-d$_6$) δ 8.82 (br s, 1H), 8.01-7.99 (m, 2H), 7.57 (dd, J=8.8, 2.8 Hz, 1H), 7.38-7.34 (m, 1H), 7.29-7.24 (m, 1H), 5.99 (s, 0.2H), 5.91 (s, 0.8H), 4.08-3.95 (m, 3.2H), 3.74-3.67 (m, 2.8H), 2.89-2.80 (m, 2H), 2.66-2.61 (m, 2H), 2.10-1.78 (m, 5.2H), 1.61-1.59 (m, 0.8H), 1.37 (s, 3H), 1.08 (t, J=6.8 Hz, 3H).

Compound 285A: trans-3-((4-(6-(2-Chloro-4-fluorophenyl)-5-(methoxycarbonyl)-2-(thiazol-2-yl)-3,6-dihydropyrimidin-4-yl)piperidin-1-yl)sulfonyl)cyclobutane-carboxylic Acid LC-MS (ESI): $R_T$=8.027 min, mass calcd. for $C_{25}H_{26}ClFN_4O_6S_2$ 596.1, m/z found 596.9 [M+H]$^+$. Chiral HPLC (Column: Chiralpak IA 5 μm 4.6*250 mm; Mobile Phase: Hex:EtOH:TFA=70:30:0.2 at 1.0 mL/min; Temp: 30° C.; Wavelength: 230 nm, $R_T$=8.190 min); $^1$H NMR (400 MHz, DMSO-d$_6$) δ 12.39 (br s, 1H), 9.51 (d, J=3.6 Hz, 0.8H), 9.12 (s, 0.2H), 7.99 (dd, J=8.8, 3.2 Hz, 1.8H), 7.93 (d, J=3.2 Hz, 0.2H), 7.44-7.40 (m, 1H), 7.37-7.31 (m, 1H), 7.23-7.18 (m, 1H), 6.01 (s, 0.2H), 5.92 (d, J=3.2 Hz, 0.8H), 4.05-3.97 (m, 1H), 3.77-3.70 (m, 3H), 3.53 (s, 3H), 3.19-

3.11 (m, 1H), 2.93-2.83 (m, 2H), 2.59-2.54 (m, 4H), 2.06-1.91 (m, 1H), 1.90-1.73 (m, 2.2H), 1.60-1.57 (m, 0.8H).

Compound 289A: (trans)-4-(6-(2-chloro-3,4-difluorophenyl)-5-(methoxycarbonyl)-2-(thiazol-2-yl)-3,6-dihydropyrimidin-4-yl)cyclohexanecarboxylic Acid LC-MS (ESI): $R_T$=3.915 min, mass calcd. for $C_{22}H_{20}ClF_2N_3O_4S$ 495.1, m/z found 495.9 [M+H]$^+$. $^1$H NMR (400 MHz, DMSO-$d_6$) δ 8.00-7.90 (m, 2H), 7.48-7.41 (m, 1H), 7.18 (br s, 1H), 6.02 (s, 0.5H), 5.93 (s, 0.5H), 3.82-3.59 (m, 1H), 3.53 (s, 3H), 2.34-2.21 (m, 1H), 2.05-1.99 (m, 2H), 1.86-1.64 (m, 4H), 1.48-1.34 (m, 2H).

Compound 293C: (trans)-1-((4-((R)-6-(2-Chloro-3,4-difluorophenyl)-5-(methoxycarbonyl)-2-(thiazol-2-yl)-3,6-dihydropyrimidin-4-yl)cyclohexyl)-sulfonyl)pyrrolidine-3-carboxylic Acid Chiral analysis (Column: Chiralpak IG 5 μm 4.6*250 mm; Mobile Phase: Hex:EtOH:TFA=60:40:0.2 at 1.0 mL/min; Temp: 30° C.; Wavelength: 230 nm, $R_T$=9.720 min). LC-MS (ESI): $R_T$=2.674 min, mass calcd. for $C_{26}H_{27}ClF_2N_4O_6S_2$ 628.1, m/z found 629.1 [M+H]$^+$. $^1$H NMR (400 MHz, CD$_3$OD) δ 7.90 (s, 1H), 7.75 (d, J=2.8 Hz, 1H), 7.23-7.20 (m, 2H), 6.10 (s, 1H), 4.05-3.74 (m, 1H), 3.66-3.64 (m, 2H), 3.60 (s, 3H), 3.52-3.49 (m, 2H), 3.27-3.25 (m, 1H), 3.20-3.16 (m, 1H), 2.36-2.31 (m, 2H), 2.28-2.20 (m, 2H), 2.12-1.96 (m, 2H), 1.87-1.64 (m, 4H).

Compound 302A: (trans)-4-(-6-(2-Chloro-3,4-difluorophenyl)-5-(ethoxycarbonyl)-2-(thiazol-2-yl)-3,6-dihydropyrimidin-4-yl)cycloheptanecarboxylic Acid purified by C18 column (acetonitrile:water (+0.1% ammonium bicarbonate)=5% to 80%) to give the title compound (95 mg, 97.4% purity, 86% yield, 95.2% stereopure) as yellow solids. LC-MS (ESI): $R_T$=3.673 min, mass calcd. for $C_{24}H_{24}ClF_2N_3O_4S$ 523.1, m/z found 523.9 [M+H]$^+$. Chiral analysis (Column: Chiralpak IA 5 μm 4.6*250 mm; Mobile Phase: Hex:EtOH:TFA=90:10:0.2 at 1.0 mL/min; Temp: 30° C.; Wavelength: 230 nm, $R_T$=7.999 min). $^1$H NMR (400 MHz, CD$_3$OD) δ 7.92 (br s, 1H), 7.74 (d, J=2.8 Hz, 1H), 7.26-7.19 (m, 2H), 6.13 (s, 0.7H), 6.06 (s, 0.3H), 4.19-4.10 (m, 0.7H), 4.04 (q, J=7.2 Hz, 2H), 3.98-3.90 (m, 0.3H), 2.67-2.54 (m, 1H), 2.20-1.88 (m, 7H), 1.81-1.70 (m, 2H), 1.59-1.48 (m, 1H), 1.14 (t, J=7.2 Hz, 3H).

Compound 302C: (cis)-4-(-6-(2-Chloro-3,4-difluorophenyl)-5-(ethoxycarbonyl)-2-(thiazol-2-yl)-3,6-dihydropyrimidin-4-yl)cycloheptanecarboxylic Acid purified by C18 column (acetonitrile:water (+0.1% ammonium bicarbonate)=5% to 80%) to give the title compound (90 mg, 97.5% purity, 82% yield, 100% stereopure) as yellow solids. LC-MS (ESI): $R_T$=3.679 min, mass calcd. for $C_{24}H_{24}ClF_2N_3O_4S$ 523.1, m/z found 523.9 [M+H]$^+$. Chiral HPLC (Column: Chiralpak IA 5 μm 4.6*250 mm; Mobile Phase: Hex:EtOH:TFA=80:20:0.2 at 1.0 mL/min; Temp: 30° C.; Wavelength: 254 nm, $R_T$=5.465 min). $^1$H NMR (400 MHz, CD$_3$OD) δ 7.92 (s, 0.7H), 7.89 (s, 0.3H), 7.74 (d, J=3.2 Hz, 1H), 7.26-7.19 (m, 2H), 6.12 (s, 0.7H), 6.06 (s, 0.3H), 4.19-4.10 (m, 0.7H), 4.04 (q, J=7.2 Hz, 2H), 3.97-3.91 (m, 0.3H), 2.65-2.53 (m, 1H), 2.25-2.14 (m, 1H), 2.11-1.93 (m, 3H), 1.90-1.69 (m, 6H), 1.14 (t, J=7.2 Hz, 3H).

Compound 302E: (cis)-4-(-6-(2-Chloro-3,4-difluorophenyl)-5-(ethoxycarbonyl)-2-(thiazol-2-yl)-3,6-dihydropyrimidin-4-1)cycloheptanecarboxylic Acid purified by C18 column (acetonitrile:water (+0.1% ammonium bicarbonate)=5% to 80%) to give the title compound (72 mg, 98.1% purity, 81% yield, 98.9% stereopure) as yellow solids. LC-MS (ESI): $R_T$=3.844 min, mass calcd. for $C_{24}H_{24}ClF_2N_3O_4S$ 523.1, m/z found 523.9 [M+H]$^+$. Chiral analysis (Column: Chiralpak IE 5 μm 4.6*250 mm; Mobile Phase: Hex:EtOH:TFA=90:10:0.2 at 1.0 mL/min; Temp: 30° C.; Wavelength: 230 nm, $R_T$=10.165 min). $^1$H NMR (400 MHz, CD$_3$OD) δ 7.92 (br s, 0.7H), 7.89 (br s, 0.3H), 7.74 (d, J=3.2 Hz, 1H), 7.26-7.18 (m, 2H), 6.13 (s, 0.7H), 6.06 (s, 0.3H), 4.19-4.10 (m, 0.7H), 4.04 (q, J=7.2 Hz, 2H), 3.98-3.92 (m, 0.3H), 2.68-2.61 (m, 0.7H), 2.59-2.53 (m, 0.3H), 2.17-1.87 (m, 7H), 1.85-1.69 (m, 2H), 1.63-1.53 (m, 1H), 1.14 (t, J=7.2 Hz, 3H).

Compound 302F: (trans)-4-(-6-(2-Chloro-3,4-difluorophenyl)-5-(ethoxycarbonyl)-2-(thiazol-2-yl)-3,6-dihydropyrimidin-4-yl)cycloheptanecarboxylic Acid purified by C18 column (acetonitrile:water (+0.1% ammonium bicarbonate)=5% to 80%) to give the title compound (78 mg, 98.4% purity, 87% yield, 100% stereopure) as yellow solids. LC-MS (ESI): $R_T$=3.810 min, mass calcd. for $C_{24}H_{24}ClF_2N_3O_4S$ 523.1, m/z found 523.9 [M+H]$^+$. Chiral analysis (Column: Chiralpak IC 5 μm 4.6*250 mm; Mobile Phase: Hex:EtOH:TFA=90:10:0.2 at 1.0 mL/min; Temp: 30° C.; Wavelength: 230 nm, $R_T$=8.067 min). $^1$H NMR (400 MHz, CD$_3$OD) δ 7.95-7.87 (m, 1H), 7.74 (d, J=2.8 Hz, 1H), 7.26-7.18 (m, 2H), 6.13 (s, 0.7H), 6.06 (s, 0.3H), 4.18-4.10 (m, 0.7H), 4.04 (q, J=7.2 Hz, 2H), 3.98-3.90 (m, 0.3H), 2.62-2.49 (br s, 1H), 2.21-2.11 (m, 1H), 2.10-1.95 (m, 2.5H), 1.93-1.76 (m, 5.5H), 1.75-1.65 (m, 1H), 1.14 (t, J=7.2 Hz, 3H).

Compound 309C: (trans)-3-((4-(6-(3,4-Difluoro-2-methylphenyl)-5-(methoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=3.189 min, mass calcd. for $C_{26}H_{28}F_2N_4O_6S_2$ 594.1, m/z found 595.2 [M+H]$^+$. $^1$H NMR (400 MHz, DMSO-$d_6$) δ 8.00-7.97 (m, 1.9H), 7.92 (s, 0.1H), 7.25-7.18 (m, 1H), 7.12-7.08 (m, 1H), 5.81 (s, 0.1H), 5.69 (s, 0.9H), 4.00-3.96 (m, 1H), 3.78-3.69 (m, 3H), 3.52 (s, 3H), 3.09-3.04 (m, 1H), 2.91-2.82 (m, 2H), 2.56-2.51 (m, 4H), 2.43 (s, 3H), 2.00-1.91 (m, 1H), 1.84-1.72 (m, 2H), 1.60-1.57 (m, 1H).

Compound 311A: (trans)-3-((4-(6-(2-Chloro-4-fluorophenyl)-5-(methoxycarbonyl)-2-(thiazol-2-yl)-3,6-dihydropyrimidin-4-yl)piperidin-1-yl)sulfonyl)-cyclopentanecarboxylic Acid and LC-MS (ESI): $R_T$=3.395 min, mass calcd. for $C_{26}H_{28}ClFN_4O_6S_2$ 610.1, m/z found 611.1 [M+H]$^+$. $^1$H NMR (400 MHz, DMSO-$d_6$) δ 8.00-7.93 (m, 2H), 7.43-7.35 (m, 2H), 7.23-7.19 (m, 1H), 6.02 (s, 0.3H), 5.92 (s, 0.7H), 4.00-3.93 (m, 0.3H), 3.80-3.72 (m, 3.7H), 3.53 (s, 3H), 2.96-2.82 (m, 3H), 2.24-2.19 (m, 1H), 2.17-2.10 (m, 2H), 2.06-1.99 (m, 2H), 1.96-1.83 (m, 2H), 1.79-1.59 (m, 3H).

Compound 311B: (cis)-3-((4-(6-(2-Chloro-4-fluorophenyl)-5-(methoxycarbonyl)-2-(thiazol-2-yl)-3,6-dihydropyrimidin-4-yl)piperidin-1-yl)sulfonyl)-cyclopentanecarboxylic Acid LC-MS (ESI): $R_T$=3.340 min, mass calcd. for $C_{26}H_{28}ClFN_4O_6S_2$ 610.1, m/z found 611.1 [M+H]$^+$. $^1$H NMR (400 MHz, DMSO-d$_6$) δ 7.99 (s, 2H), 7.43-7.34 (m, 2H), 7.23-7.18 (m, 1H), 6.02 (s, 0.3H), 5.93 (s, 0.7H), 4.02-3.91 (m, 0.3H), 3.79-3.66 (m, 3.7H), 3.53 (s, 3H), 2.95-2.86 (m, 2H), 2.79-2.70 (m, 1H), 2.32-2.25 (m, 1H), 2.03-1.59 (m, 9H).

Compound 313A: (cis)-4-((4-(6-(2-Chloro-4-fluorophenyl)-5-(methoxycarbonyl)-2-(thiazol-2-yl)-3,6-dihydropyrimidin-4-yl)piperidin-1-yl)sulfonyl)-cyclohexanecarboxylic Acid LC-MS (ESI): $R_T$=3.669 min, mass calcd. for $C_{27}H_{30}ClFN_4O_6S_2$ 624.1, m/z found 625.0 [M+H]$^+$. $^1$H NMR (400 MHz, DMSO-d$_6$) δ 7.99 (d, J=3.2 Hz, 1H), 7.94 (d, J=2.4 Hz, 0.7H), 7.88 (br s, 0.3H), 7.42-7.34 (m, 2H), 7.22-7.17 (m, 1H), 6.02 (s, 0.3H), 5.94 (s, 0.7H), 3.82-3.74 (m, 3H), 3.54 (s, 3H), 3.20 (br s, 1H), 2.95 (q, J=12.0 Hz, 2H), 2.59 (s, 1H), 2.11 (br s, 2H), 1.97-1.78 (m, 5H), 1.59-1.54 (m, 5H).

Compound 313B: (trans)-4-((4-(6-(2-Chloro-4-fluorophenyl)-5-(methoxycarbonyl)-2-(thiazol-2-yl)-3,6-dihydropyrimidin-4-yl)piperidin-1-yl)sulfonyl)-cyclohexanecarboxylic Acid LC-MS (ESI): $R_T$=2.353 min, mass calcd. for $C_{27}H_{30}ClFN_4O_6S_2$ 624.1, m/z found 625.0 [M+H]$^+$. $^1$H NMR (400 MHz, DMSO-d$_6$) δ 8.00-7.93 (m, 2H), 7.43-7.31 (m, 2H), 7.23-7.18 (m, 1H), 6.02 (s, 0.3H), 5.92 (s, 0.7H), 4.01-3.94 (m, 0.3H), 3.79-3.72 (m, 2.7H), 3.53 (s, 3H), 3.18-3.12 (m, 1H), 2.97 (q, J=12.0 Hz, 2H), 2.24-2.18 (m, 1H), 2.09-1.71 (m, 7.3H), 1.61-1.35 (m, 4.7H).

Compound 319B: (trans)-3-((4-(6-(2-chloro-3-fluorophenyl)-5-(ethoxycarbonyl)-2-(thiazol-2-yl)-3,6-dihydropyrimidin-4-yl)piperidin-1-yl)sulfonyl)-cyclobutanecarboxylic Acid LC-MS (ESI): $R_T$=3.410 min, mass calcd. for $C_{26}H_{28}ClFN_4O_6S_2$ 610.1, m/z found 611.1 [M+H]$^+$. $^1$H NMR (400 MHz, CD$_3$OD) δ 7.91 (s, 1H), 7.75 (d, J=2.8 Hz, 1H), 7.34-7.14 (m, 3H), 6.16 (s, 1H), 4.07-4.02 (m, 3H), 3.96-3.87 (m 3H), 3.28-3.22 (m, 1H), 3.03-2.93 (m, 2H), 2.80-2.65 (m, 4H), 2.16-1.66 (m, 4H), 1.12 (t, J=7.2 Hz, 3H).

Compound 321A: (trans)-3-((4-(6-(2-Chloro-3-fluorophenyl)-5-(ethoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.435 min, mass calcd. for $C_{27}H_{30}ClFN_4O_6S_2$ 624.1, m/z found 625.2 [M+H]$^+$. $^1$H NMR (400 MHz, DMSO-d$_6$) δ 9.60 (s, 0.8H), 9.11 (s, 0.2H), 8.01-7.99 (m, 1.8H), 7.94 (d, J=3.2 Hz, 0.2H), 7.40-7.32 (m, 2H), 7.23-7.18 (m, 1H), 6.08 (s, 0.2H), 5.98 (d, J=2.4 Hz, 0.8H), 4.00-3.93 (m, 3H), 3.77-3.69 (m, 3H), 2.89-2.81 (m, 2H), 2.79-2.73 (m, 2H), 2.27-2.22 (m, 2H), 2.00-1.87 (m, 1H), 1.81-1.74 (m, 2H), 1.61-1.58 (m, 1H), 1.34 (s, 3H), 1.08-1.03 (m, Compound 321B: (cis)-3-((4-(6-(2-Chloro-3-fluorophenyl)-5-(ethoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.422 min, mass calcd. for $C_{27}H_{30}ClFN_4O_6S_2$ 624.1, m/z found 625.2 [M+H]$^+$. $^1$H NMR (400 MHz, DMSO-d$_6$) δ 9.60 (s, 0.8H), 9.11 (s, 0.2H), 8.03-8.00 (m, 1.8H), 7.94 (s, 0.2H), 7.41-7.32 (m, 2H), 7.23-7.21 (m, 1H), 6.09 (s, 0.2H), 5.98 (s, 0.8H), 4.14-4.05 (m, 1H), 3.97 (q, J=6.8 Hz, 2H), 3.77-3.66 (m, 3H), 2.89-2.81 (m, 2H), 2.69-2.64 (m, 2H), 2.14-2.09 (m, 2H), 1.99-1.90 (m, 1H), 1.86-1.75 (m, 2H), 1.62-1.59 (m, 1H), 1.40 (s, 3H), 1.06 (t, J=7.2 Hz, 3H).

Compound 323C: trans-methyl 4-(2-chloro-3,4-difluorophenyl)-6-(1-((3-(methoxycarbonyl)-3-methylcyclobutyl)sulfonyl)piperidin-4-yl)-2-(thiazol-2-yl)-1,4-dihydropyrimidine-5-carboxylate purified by Prep. HPLC (Column: gilson Xbridge C18 (5 μm 19*150 mm), Mobile Phase A: water (+0.1% ammonium bicarbonate), Mobile Phase B: acetonitrile, UV: 214 nm, Flow rate: 15 mL/min, Gradient: 10-80% (% B)) to give the title compound (125 mg, 98% purity, 69% yield, 100% ee) as yellow solids. LC-MS (ESI): $R_T$=3.270 min, mass calcd. for $C_{26}H_{27}ClF_2N_4O_6S_2$ 628.1, m/z found 629.0 [M+H]$^+$. Chiral HPLC (Column: Chiralpak IC 5 μm 4.6*250 mm; Mobile Phase: Hex:EtOH:TFA=80:20:0.2 at 1.0 mL/min; Temp: 30° C.; Wavelength: 230 nm; RT=9.816 min). $^1$H NMR (400 MHz, DMSO-d$_6$) δ 8.01-7.94 (m, 2H), 7.49-7.42 (m, 1H), 7.22-7.16 (m, 1H), 6.01 (s, 0.2H), 5.92 (s, 0.8H), 3.95-3.87 (m, 1H), 3.76-3.64 (m, 3H), 3.53 (s, 3H), 2.89-2.81 (m, 2H), 2.78-2.72 (m, 2H), 2.25-2.18 (m, 2H), 2.00-1.81 (m, 1H), 1.81-1.69 (m, 2H), 1.61-1.56 (m, 1H), 1.33 (s, 3H).

Compound 323D: cis-methyl 4-(2-chloro-3,4-difluorophenyl)-6-(1-((3-(methoxycarbonyl)-3-methylcyclobutyl)sulfonyl)piperidin-4-yl)-2-(thiazol-2-yl)-1,4-dihydropyrimidine-5-carboxylate purified by Prep. HPLC (Column: gilson Xbridge C18 (5 μm 19*150 mm), Mobile Phase A: water (+0.1% ammonium bicarbonate), Mobile Phase B: acetonitrile, UV: 214 nm, Flow rate: 15 mL/min, Gradient: 10-80% (% B)) to give the title compound (125 mg, 99% purity, 43% yield) as yellow solids. LC-MS (ESI): $R_T$=3.243 min, mass calcd. for $C_{26}H_{27}ClF_2N_4O_6S_2$ 628.1, m/z found 629.0 [M+H]$^+$. $^1$H NMR (400 MHz, DMSO-d$_6$) δ 8.01-8.00 (m, 2H), 7.50-7.42 (m, 1H), 7.24-7.14 (m, 1H), 5.93 (s, 1H), 4.13-4.01 (m, 1H), 3.82-3.61 (m, 3H), 3.53 (s, 3H), 2.89-2.81 (m, 2H), 2.70-2.62 (m, 2H), 2.16-2.08 (m, 2H), 2.01-1.94 (m, 1H), 1.85-1.74 (m, 2H), 1.74-1.61 (m, 1H), 1.39 (s, 3H).

Compound 329B: (trans)-3-((4-(6-(2-Chloro-4-fluorophenyl)-5-(ethoxycarbonyl)-2-(thiazol-2-yl)-3,6-dihydropyrimidin-4-yl)piperidin-1-yl)sulfonyl)cyclobutane-carboxylic Acid purified by Prep. HPLC (Column: Xbridge C18 (5 μm 10*190 mm), Mobile phase A: water (0.1% ammonium bicarbonate), Mobile phase B: acetonitrile, UV: 214 nm, Flow rate: 15 mL/min, Gradient: 30-70% (% B)) to give the title compound (58 mg, 63% yield, 100% stereopure) as a yellow solids. LC-MS (ESI): $R_T$=3.553 min, mass calcd. for $C_{26}H_{28}ClFN_4O_6S_2$ 610.1, m/z found mass 611.1 [M+H]$^+$.

Chiral analysis (Column: Chiralpak IA 5 µm 4.6*250 mm; Mobile Phase: Hex:EtOH:TFA=80:20:0.2 at 1.0 mL/min; Temp: 30° C.; Wavelength: 230 nm, $R_T$=11.296 min). $^1$H NMR (400 MHz, DMSO-$d_6$) δ 7.99-7.92 (m, 2H), 7.43-7.40 (m, 1H), 7.38-7.34 (m, 1H), 7.23-7.19 (m, 1H), 6.03 (br s, 0.2H), 5.93 (s, 0.8H), 4.00-3.92 (m, 3H), 3.74-3.67 (m, 3H), 3.07-3.00 (m, 1H), 2.88-2.79 (m, 2H), 2.46-2.44 (m, 4H), 1.97-1.91 (m, 1H), 1.83-1.76 (m, 2H), 1.63-1.57 (m, 1H), 1.07 (t, J=7.2 Hz, 3H).

Compound 331C: (trans)-3-((4-(6-(2-Chloro-3-fluorophenyl)-5-(methoxycarbonyl)-2-(thiazol-2-yl)-3,6-dihydropyrimidin-4-yl)piperidin-1-yl)sulfonyl)cyclobutane-carboxylic Acid LC-MS (ESI): $R_T$=3.780 min, mass calcd. for $C_{25}H_{26}ClFN_4O_6S_2$ 596.1, m/z found 596.9 [M+H]$^+$. $^1$H NMR (400 MHz, DMSO-$d_6$) δ 12.16 (s, 1H), 9.58 (d, J=3.2 Hz, 0.8H), 9.15 (s, 0.2H), 8.01-7.98 (m, 1.8H), 7.93 (d, J=3.2 Hz, 0.2H), 7.40-7.31 (m, 2H), 7.22-7.16 (m, 1H), 6.07 (s, 0.2H), 5.97 (d, J=3.2 Hz, 0.8H), 4.05-3.97 (m, 1H), 3.77-3.71 (m, 3H), 3.52 (s, 2.4H), 3.51 (s, 0.6H), 3.17-3.13 (m, 1H), 2.93-2.84 (m, 2H), 2.59-2.55 (m, 4H), 1.97-1.90 (m, 1H), 1.82-1.74 (m, 2.2H), 1.61-1.58 (m, 0.8H).

Compound 333B: (trans)-3-((4-(6-(2-bromo-4-fluorophenyl)-5-(ethoxycarbonyl)-2-(thiazol-2-yl)-3,6-dihydropyrimidin-4-yl)piperidin-1-yl)sulfonyl)cyclobutane-1-carboxylic Acid LC-MS (ESI): $R_T$=3.702 min, mass calcd. for $C_{26}H_{28}BrFN_4O_6S_2$ 654.1 m/z found 655.0 [M+H]$^+$. Chiral analysis (Column: Chiralpak IG 5 µm 4.6*250 mm; Mobile Phase: Hex:EtOH:TFA=70:30:0.2 at 1.0 mL/min; Temp: 30° C.; Wavelength: 230 nm; $R_T$=13.060 min). $^1$H NMR (400 MHz, CD$_3$OD) δ 7.91 (br s, 1H), 7.76 (d, J=2.8 Hz, 1H), 7.43-7.39 (m, 2H), 7.14-7.10 (m, 1H), 6.09 (s, 1H), 4.05 (q, J 7.2 Hz, 2H), 3.96-3.89 (m, 4H), 3.26-3.22 (m, 1H), 3.03-2.93 (m, 2H), 2.80-2.68 (m, 4H), 2.15-1.61 (m, 4H), 1.14 (t, J 7.2 Hz, 3H).

Compound 339B: (trans)-3-((4-(6-(2-Bromo-3-fluorophenyl)-5-(ethoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=3.933 min, mass calcd. for $C_{26}H_{28}BrFN_4O_6S_2$ 654.1, m/z found 655.0 [M+H]$^+$. $^1$H NMR (400 MHz, DMSO-$d_6$) δ 9.51 (s, 0.7H), 9.07 (s, 0.3H), 8.00-7.92 (m, 2H), 7.44-7.37 (m, 1H), 7.31-7.15 (m, 2H), 6.07 (s, 0.3H), 5.97 (s, 0.7H), 4.03-3.93 (m, 3H), 3.78-3.71 (m, 3H), 3.15-3.12 (m, 1H), 2.92-2.83 (m, 2H), 2.58-2.53 (m, 4H), 2.06-1.58 (m, 4H), 1.08-1.01 (m, 3H).

Compound 339D: (cis)-3-((4-(6-(2-Bromo-3-fluorophenyl)-5-(ethoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=4.011 min, mass calcd. for $C_{26}H_{28}BrFN_4O_6S_2$ 654.1, m/z found 655.1 [M+H]$^+$. $^1$H NMR (400 MHz, DMSO-$d_6$) δ 9.51 (s, 0.7H), 9.09 (s, 0.3H), 8.00 (s, 1.7H), 7.93 (s, 0.3H), 7.44-7.39 (m, 1H), 7.29 (d, J=7.6 Hz, 1H), 7.24-7.16 (m, 1H), 6.07 (s, 0.3H), 5.97 (s, 0.7H), 4.00-3.91 (m, 3.3H), 3.77-3.67 (m, 2.7H), 3.11-3.02 (m, 1H), 2.88-2.80 (m, 2H), 2.48-2.33 (m, 4H), 2.04-1.78 (m, 3.3H), 1.62-1.59 (m, 0.7H), 1.08-1.01 (m, 3H).

Compound 343A: (trans)-3-((4-(6-(3,4-difluoro-2-methylphenyl)-5-(ethoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=4.142 min, mass calcd. for $C_{27}H_{30}F_2N_4O_6S_2$ 608.2, m/z found 609.2 [M+H]$^+$. $^1$H NMR (400 MHz, CD$_3$OD) δ 7.89 (s, 1H), 7.73 (d, J=2.8 Hz, 1H), 7.17-6.99 (m, 2H), 5.86 (s, 1H), 4.07-3.79 (m, 6H), 3.26-3.17 (m, 1H), 3.04-2.90 (m, 2H), 2.77-2.63 (m, 4H), 2.56-2.41 (m, 3H), 2.16-1.80 (m, 3.3H), 1.70-1.61 (m, 0.7H), 1.12 (t, J=7.2 Hz, 3H).

Compound 343C: (trans)-3-((4-(6-(3,4-difluoro-2-methylphenyl)-5-(ethoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=3.310 min, mass calcd. for $C_{27}H_{30}F_2N_4O_6S_2$ 608.2, m/z found 609.2 [M+H]$^+$. $^1$H NMR (400 MHz, CD$_3$OD) δ 7.89 (d, J=2.4 Hz, 1H), 7.73 (d, J=3.2 Hz, 1H), 7.17-6.99 (m, 2H), 5.86 (s, 1H), 4.07-3.77 (m, 6H), 3.27-3.20 (m, 1H), 3.03-2.91 (m, 2H), 2.77-2.64 (m, 4H), 2.48 (s, 3H), 2.15-1.79 (m, 3.3H), 1.74-1.59 (m, 0.7H), 1.12 (t, J=7.2 Hz, 3H).

343D: (cis)-3-((4-(6-(3,4-difluoro-2-methylphenyl)-5-(ethoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=4.133 min, mass calcd. for $C_{27}H_{30}F_2N_4O_6S_2$ 608.2, m/z found 609.2 [M+H]$^+$. $^1$H NMR (400 MHz, CD$_3$OD) δ 7.89 (d, J=2.0 Hz, 1H), 7.73 (d, J=2.8 Hz, 1H), 7.15-6.98 (m, 2H), 5.86 (s, 1H), 4.07-3.78 (m, 6H), 3.21-3.13 (m, 1H), 2.99-2.89 (m, 2H), 2.72-2.54 (m, 4H), 2.49 (s, 3H), 2.18-1.57 (m, 4H), 1.12 (t, J=7.2 Hz, 3H).

Compound 345A: (trans)-(R*)-4-(6-(2-Chloro-3,4-difluorophenyl)-5-(ethoxycarbonyl)-2-(thiazol-2-yl)-3,6-dihydropyrimidin-4-yl)cyclohexanecarboxylic Acid purified by Prep. HPLC (Column: Gilson X-bridge C18 (5 µm 19*150 mm), Mobile Phase A: water (0.1% ammonium bicarbonate), Mobile Phase B: acetonitrile, UV: 214 nm, Flow rate: 15 mL/min, Gradient: 25-70% (% B)) to give the title compound (110 mg, 66% yield, 100% stereopure) as yellow solids. LC-MS (ESI): $R_T$=3.766 min, mass calcd. for $C_{23}H_{22}ClF_2N_3O_4S$ 509.1, m/z found 510.0 [M+H]$^+$. Chiral analysis (Column: Chiralpak IE 5 µm 4.6*250 mm; Mobile Phase: Hex:EtOH:TFA=85:15:0.2 at 1.0 mL/min; Temp: 30° C.; Wavelength: 230 nm, $R_T$=8.775 min). $^1$H NMR (400 MHz, DMSO-$d_6$) δ 8.91 (br s, 1H), 8.03-7.98 (m, 1.5H), 7.94 (d, J=3.2 Hz, 0.5H), 7.49-7.42 (m, 1H), 7.20-7.16 (m, 1H), 6.02 (s, 0.4H), 5.92 (s, 0.6H), 4.00-3.94 (m, 2H), 3.86-3.80 (m, 0.5H), 3.60-3.57 (m, 0.5H), 2.39-2.33 (m, 0.5H), 2.24-2.17 (m, 0.5H), 2.05-1.97 (m, 2H), 1.87-1.63 (m, 4H), 1.43-1.35 (m, 2H), 1.10-1.03 (m, 3H).

Compound 347B: (trans)-4-(6-(2-bromo-3,4-difluorophenyl)-5-(ethoxycarbonyl)-2-(thiazol-2-yl)-3,6-dihydropyrimidin-4-yl)cyclohexanecarboxylic Acid purified by Prep. HPLC (Column: Gilson X-bridge C18 (5 µm 19*150 mm), Mobile Phase A: water (0.1% ammonium bicarbonate), Mobile Phase B: acetonitrile, UV: 214 nm, Flow rate: 15 mL/min, Gradient: 30-70% (% B)) to give the title compound (6.5 mg, 3% yield) as yellow solids. LC-MS (ESI): $R_T$=3.672 min, mass calcd. for $C_{23}H_{22}BrF_2N_3O_4S$ 553.1, m/z found 556.1 [M+H]$^+$. $^1$H NMR (400 MHz, DMSO-d$_6$) δ 9.45 (s, 0.5H), 8.90 (s, 0.5H), 7.99 (d, J=2.4 Hz, 1.5H), 7.93 (s, 0.5H), 7.53-7.45 (m, 1H), 7.21-7.12 (m, 1H), 6.00 (s, 0.5H), 5.91 (s, 0.5H), 4.02-3.95 (m, 2H), 3.86-3.80 (m, 0.5H), 3.64-3.45 (m, 0.5H), 2.40-2.34 (m, 0.5H), 2.26-2.20 (m, 0.5H), 2.04-1.94 (m, 2H), 1.89-1.64 (m, 4H), 1.50-1.35 (m, 2H), 1.08-1.05 (m, 3H).

Compound 352B: (trans)-3-(4-6-(2-Chloro-3,4-difluorophenyl)-2-(3,5-difluoropyridin-2-yl)-5-(ethoxycarbonyl)-3,6-dihydropyrimidin-4-yl)piperidin-1-yl)sulfonyl)cyclobutanecarboxylic Acid LC-MS (ESI): $R_T$=3.229 min, mass calcd. for $C_{28}H_{27}ClF_4N_4O_6S$ 658.1, m/z found 658.9 [M+H]$^+$. Chiral analysis (Column: Chiralpak IA 5 µm 4.6*250 mm; Mobile Phase: Hex:EtOH:TFA=85:15:0.2 at 1.0 mL/min; Temp: 30° C.; Wavelength: 230 nm; $R_T$=18.175 min). $^1$H NMR (400 MHz, CD$_3$OD) δ 8.43 (s, 1H), 7.71-7.67 (m, 1H), 7.24-7.22 (m, 2H), 6.15 (s, 1H), 4.12-3.97 (m, 4H), 3.94-3.88 (m, 2H), 3.24-3.17 (m, 1H), 3.00-2.92 (m, 2H), 2.74-2.58 (m, 4H), 2.03-1.79 (m, 4H), 1.13 (t, J=7.2 Hz, 3H).

Compound 354B: (cis)-4-((4-(6-(2-Chloro-3,4-difluorophenyl)-5-(ethoxycarbonyl)-2-(thiazol-2-yl)-3,6-dihydropyrimidin-4-yl)piperidin-1-yl)sulfonyl)cyclohexane-carboxylic Acid LC-MS (ESI): $R_T$=3.622 min, mass calcd. for $C_{28}H_{31}ClF_2N_4O_6S_2$ 656.1, m/z found 656.9 [M+H]$^+$. $^1$H NMR (400 MHz, CD$_3$OD) δ 7.89 (br s, 1H), 7.75 (s, 1H), 7.28-7.21 (m, 2H), 6.17 (s, 0.3H), 6.09 (s, 0.7H), 4.19-4.11 (m, 0.3H), 4.07-4.02 (m, 2H), 3.99-3.85 (m, 2.7H), 3.15-2.98 (m, 3H), 2.46 (br s, 1H), 2.32-2.29 (m, 2H), 2.13-1.52 (m, 10H), 1.14-1.11 (m, 3H).

Compound 354C: (trans)-4-((4-(6-(2-Chloro-3,4-difluorophenyl)-5-(ethoxycarbonyl)-2-(thiazol-2-yl)-3,6-dihydropyrimidin-4-yl)piperidin-1-yl)sulfonyl)cyclohexane-carboxylic Acid LC-MS (ESI): $R_T$=3.909 min, mass calcd. for $C_{28}H_{31}ClF_2N_4O_6S_2$ 656.1, m/z found 656.9 [M+H]$^+$. $^1$H NMR (400 MHz, CD$_3$OD) δ 7.94-7.89 (m, 1H), 7.75 (br s, 1H), 7.23-7.22 (m, 2H), 6.15 (s, 0.3H), 6.09 (s, 0.7H), 4.21-4.11 (m, 0.4H), 4.09-4.01 (m, 2H), 3.99-3.84 (m, 2.6H), 3.15-2.99 (m, 3H), 2.33-1.84 (m, 8.3H), 1.69-1.46 (m, 4.7H), 1.14-1.11 (m, 3H).

Compound 363E: (trans)-6-(–6-(2-Chloro-4-fluorophenyl)-5-(ethoxycarbonyl)-2-(thiazol-2-yl)-3,6-dihydropyrimidin-4-yl)tetrahydro-2H-pyran-3-carboxylic Acid LC-MS (ESI): $R_T$=2.392 min, mass calcd. for $C_{22}H_{21}ClFN_3O_5S$ 493.1, m/z found 494.2 [M+H]$^+$. Chiral analysis (Column: Chiralpak IC 5 µm 4.6*250 mm; Mobile Phase: Hex:EtOH:TFA=90:10:0.2 at 1.0 mL/min; Temp: 30° C.; Wavelength: 230 nm, $R_T$=5.908 min). $^1$H NMR (400 MHz, CDCl$_3$) δ 9.30 (br s, 1H), 8.00 (s, 1H), 7.69 (br s, 1H), 7.47-7.44 (m, 1H), 7.15 (dd, J=8.8, 2.4 Hz, 1H), 6.99-6.95 (m, 1H), 6.29 (s, 1H), 5.28 (d, J=10.4 Hz, 1H), 4.46-4.42 (m, 1H), 4.11-4.02 (m, 2H), 3.74-3.68 (m, 1H), 2.87-2.78 (m, 1H), 2.32-2.29 (m, 1H), 2.21-2.18 (m, 1H), 1.99-1.88 (m, 1H), 1.60-1.50 (m, 1H), 1.15 (t, J=7.2 Hz, 3H).

Compound 363H: (trans)-6-(6-(2-Chloro-4-fluorophenyl)-5-(ethoxycarbonyl)-2-(thiazol-2-yl)-3,6-dihydropyrimidin-4-yl)tetrahydro-2H-pyran-3-carboxylic Acid LC-MS (ESI): $R_T$=2.623 min, mass calcd. for $C_{22}H_{21}ClFN_3O_5S$ 493.1, m/z found 493.9 [M+H]$^+$. Chiral analysis (Column: Chiralpak IA 5 µm 4.6*250 mm; Mobile Phase: Hex:EtOH:TFA=85:15:0.2 at 1.0 mL/min; Temp: 30° C.; Wavelength: 230 nm, $R_T$=6.854 min). $^1$H NMR (400 MHz, CDCl$_3$) δ 9.18 (br s, 1H), 7.98-7.96 (m, 1H), 7.64-7.42 (m, 2H), 7.14 (d, J=6.4 Hz, 1H), 6.99-6.95 (m, 1H), 6.30-6.29 (m, 1H), 5.25 (br s, 1H), 4.43 (br s, 1H), 4.06 (br s, 2H), 3.71-3.68 (m, 1H), 2.84-2.81 (m, 1H), 2.30 (br s, 2H), 2.04-1.96 (m, 1H), 1.73 (br s, 1H), 1.17 (s, 3H).

Compound 367A: (trans)-3-((3-(6-(2-chloro-4-fluorophenyl)-5-(methoxycarbonyl)-2-(thiazol-2-yl)-3,6-dihydropyrimidin-4-yl)pyrrolidin-1-yl)sulfonyl)cyclobutanecarboxylic Acid LC-MS (ESI): $R_T$=2.980 min, mass calcd. for $C_{24}H_{24}ClFN_4O_6S_2$ 582.1, m/z found 582.8 [M+H]$^+$. $^1$H NMR (400 MHz, CD$_3$OD) δ 7.89 (d, J=2.8 Hz, 1H), 7.77 (d, J=2.8 Hz, 1H), 7.40-7.37 (m, 1H), 7.24-7.21 (m, 1H), 7.10-7.05 (m, 1H), 6.09 (s, 1H), 4.56-4.46 (m, 1H), 4.20-4.12 (m, 1H), 3.76-3.66 (m, 3H), 3.60 (s, 3H), 3.50-3.44 (m, 1H), 3.24-3.16 (m, 1H), 2.81-2.73 (m, 2H), 2.69-2.62 (m, 2H), 2.31-2.20 (m, 1H), 2.14-2.03 (m, 1H).

Compound 367B: (cis)-3-((3-(6-(2-chloro-4-fluorophenyl)-5-(methoxycarbonyl)-2-(thiazol-2-yl)-3,6-dihydropyrimidin-4-yl)pyrrolidin-1-yl)sulfonyl)cyclobutanecarboxylic Acid LC-MS (ESI): $R_T$=3.627 min, mass calcd. for $C_{24}H_{24}ClFN_4O_6S_2$ 582.1, m/z found 582.9 [M+H]$^+$. $^1$H NMR (400 MHz, CD$_3$OD) δ 7.90 (d, J=2.8 Hz, 1H), 7.77 (d, J=3.2 Hz, 1H), 7.40-7.36 (m, 1H), 7.24-7.21 (m, 1H), 7.10-7.05 (m, 1H), 6.10 (s, 1H), 4.52 (s, 1H), 4.08-4.00 (m, 1H), 3.75-3.64 (m, 3H), 3.60 (s, 3H), 3.48-3.42 (m, 1H), 3.15-3.05 (m, 1H), 2.77-2.69 (m, 2H), 2.60-2.53 (m, 2H), 2.33-2.23 (m, 1H), 2.16-2.03 (m, 1H).

Compound 410C: trans-3-((4-(6-(2-Bromo-4-fluorophenyl)-5-(methoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.397 min, mass calcd. for $C_{26}H_{28}BrFN_4O_6S_2$ 654.1, m/z found 655.1 [M+H]$^+$. Chiral analysis (Column: Chiralpak IA 250 mm*4.6 mm 5 um; Mobile Phase: Hex:EtOH:TFA=80:20:0.2 at 1.0 mL/min; Temp: 30° C.; Wavelength: 254 nm, $R_T$=10.874 min). $^1$H NMR (400 MHz, DMSO-d$_6$) δ 8.00 (s, 1.8H), 7.93 (m, 0.2H), 7.56 (dd, J=8.4, 2.4 Hz, 1H), 7.36-7.27 (m, 1H), 7.26-7.23 (m, 1H), 5.98 (s, 0.2H), 5.89 (s, 0.8H), 3.96-3.87 (m, 1.3H), 3.75-3.67 (m, 2.7H), 3.53 (s, 3H), 2.90-2.81 (m, 2H), 2.76-2.71 (m, 2H), 2.23-2.18 (m, 2H), 2.05-1.91 (m, 1H), 1.84-1.74 (m, 2.2H), 1.60-1.57 (m, 0.8H), 1.31 (s, 3H).

Compound 410D: cis-3-((4-(6-(2-Bromo-4-fluorophenyl)-5-(methoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.727 min, mass calcd. for $C_{26}H_{28}BrFN_4O_6S_2$ 654.1, m/z found 654.9 [M+H]$^+$. Chiral analysis (Column: Chiralpak IA 250 mm*4.6 mm 5 um; Mobile Phase: Hex:EtOH:TFA=70:30:0.2 at 1.0 mL/min; Temp: 30° C.; Wavelength: 254 nm, $R_T$=10.417 min). $^1$H NMR (400 MHz, DMSO-$d_6$) δ 9.25 (br s, 1H), 8.02-8.00 (m, 2H), 7.57 (dd, J=8.8, 2.8 Hz, 1H), 7.38-7.35 (m, 1H), 7.28-7.26 (m, 1H), 5.98 (br s, 0.2H), 5.90 (s, 0.8H), 4.13-4.04 (m, 1H), 3.96-3.87 (m, 0.3H), 3.73-3.71 (m, 2.7H), 3.53 (s, 3H), 2.90-2.81 (m, 2H), 2.67-2.62 (m, 2H), 2.14-2.09 (m, 2H), 1.97-1.94 (m, 1H), 1.81-1.78 (m, 2.2H), 1.60-1.58 (m, 0.8H), 1.39 (s, 3H).

Compound 414C: (trans)-3-((4-(6-(2-Bromo-3-fluorophenyl)-5-(ethoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.458 min, mass calcd. for $C_{27}H_{30}BrFN_4O_6S_2$ 668.1, m/z found 671.0 [M+H]$^+$. Chiral analysis (Column: Chiralpak IA 5 μm 4.6*250 mm; Mobile Phase: Hex:EtOH:TFA=80:20:0.2 at 1.0 mL/min; Temp: 30° C.; Wavelength: 254 nm, $R_T$=9.867 min). $^1$H NMR (400 MHz, DMSO-$d_6$) δ 10.04 (br s, 1H), 8.01-7.99 (m, 1.8H), 7.93 (br s, 0.2H), 7.42 (dd, J=13.6, 8.0 Hz, 1H), 7.29 (t, J=8.4 Hz, 1H), 7.21 (d, J=7.6 Hz, 1H), 6.07 (br s, 0.2H), 5.98 (s, 0.8H), 4.14-4.05 (m, 1H), 3.97 (dd, J=13.2, 6.4 Hz, 2H), 3.74-3.67 (m, 3H), 2.89-2.81 (m, 2H), 2.68-2.63 (m, 2H), 2.12 (t, J=10.4 Hz, 2H), 2.01-1.77 (m, 3H), 1.62-1.59 (m, 1H), 1.40 (s, 3H), 1.06 (t, J=6.8 Hz, 3H).

Compound 414D: (cis)-3-((4-(6-(2-Bromo-3-fluorophenyl)-5-(ethoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.458 min, mass calcd. for $C_{27}H_{30}BrFN_4O_6S_2$ 668.1, m/z found 671.0 [M+H]$^+$. Chiral analysis (Column: Chiralpak IA 5 μm 4.6*250 mm; Mobile Phase: Hex:EtOH:TFA=80:20:0.2 at 1.0 mL/min; Temp: 30° C.; Wavelength: 254 nm, $R_T$=15.337 min). $^1$H NMR (400 MHz, DMSO-$d_6$) 9.10 (br s, 1H), 8.02-8.00 (m, 1.8H), 7.93 (br s, 0.2H), 7.41 (dd, J=14.0, 8.0 Hz, 1H), 7.30 (t, J=8.4 Hz, 1H), 7.21 (d, J=7.6 Hz, 1H), 6.07 (s, 0.2H), 5.98 (s, 0.8H), 4.15-4.07 (m, 1H), 4.00-3.95 (m, 2H), 3.77-3.67 (m, 3H), 2.89-2.81 (m, 2H), 2.68-2.63 (m, 2H), 2.13 (t, J=10.4 Hz, 2H), 2.01-1.77 (m, 3H), 1.61 (d, J=14.0 Hz, 1H), 1.40 (s, 3H), 1.06 (t, J=7.2 Hz, 3H).

Compound 420A: (trans)-3-((4-(5-(Ethoxycarbonyl)-6-(4-fluoro-2-methylphenyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=2.813 min, mass calcd. for $C_{28}H_{33}FN_4O_6S_2$ 604.2, m/z found 605.0 [M+H]$^+$. $^1$H NMR (400 MHz, CD$_3$OD) δ 7.88 (br s, 1H), 7.73 (s, 1H), 7.33-7.30 (m, 1H), 6.91-6.83 (m, 2H), 5.85 (br s, 1H), 4.06-3.82 (m, 6H), 2.97-2.81 (m, 4H), 2.59-2.53 (m, 3H), 2.39-2.34 (m, 2H), 2.07-1.84 (m, 3.4H), 1.66-1.64 (m, 0.6H), 1.41 (s, 3H), 1.11 (t, J=7.2 Hz, 3H).

Compound 422: trans-4-(((4-(6-(2-chloro-4-fluorophenyl)-5-(methoxycarbonyl)-2-(thiazol-2-yl)-3,6-dihydropyrimidin-4-yl)piperidinyl)sulfonyl)methyl)cyclohexane-1-carboxylic Acid LC-MS (ESI): $R_T$=2.83 min, mass calcd. for $C_{28}H_{32}ClFN_4O_6S_2$ 638.1, m/z found 639.2 [M+H]$^+$. $^1$H NMR (400 MHz, CD$_3$OD) δ 8.06-8.05 (m, 1H), 7.97-7.96 (m, 1H), 7.48-7.45 (m, 1H), 7.31 (dd, J=2.6, J=8.6 Hz, 1H), 7.15-7.10 (m, 1H), 6.19 (s, 1H), 4.04-3.79 (m, 3H), 3.64 (s, 3H), 2.98-2.85 (m, 4H), 2.31-2.22 (m, 1H), 2.19-1.91 (m, 8H), 1.84-1.83 (m, 1H), 1.56-1.41 (m, 2H), 1.28-1.14 (m, 2H).

Compound 424: trans-4-(((4-(6-(2-chloro-3,4-difluorophenyl)-5-(ethoxycarbonyl)-2-(thiazol-2-yl)-3,6-dihydropyrimidin-4-yl)piperidinyl)sulfonyl)methyl)cyclohexane-1-carboxylic Acid LC-MS (ESI): $R_T$=2.99 min, mass calcd. for $C_{29}H_{33}ClF_2N_4O_6S_2$ 670.1, m/z found 670.5 [M+H]$^+$. $^1$H NMR (400 MHz, DMSO-$d_6$) δ 12.44-11.8 (brs, 0.3H), 9.64 (s, 0.8H), 9.14 (s, 0.2H), 8.09-7.91 (m, 2H), 7.51-7.42 (m, 1H), 7.26-7.16 (m, 1H), 6.04 (m, 0.2H), 5.94 (s, 0.8H), 4.04-3.91 (m, 2H), 3.78-3.61 (m, 3H), 2.95-2.94 (d, J=6.4 Hz, 2H), 2.86-2.77 (m, 2H), 2.18-2.08 (m, 1H), 2.03-1.77 (m, 8H), 1.66-1.63 (m, 1H), 1.40-1.22 (m, 2H), 1.18-0.97 (m, 5H).

Compound 425: trans-4-(((4-(6-(2-chloro-3,4-difluorophenyl)-5-(methoxycarbonyl)-2-(thiazol-2-yl)-3,6-dihydropyrimidin-4-yl)piperidinyl)sulfonyl)methyl)cyclohexane-1-carboxylic Acid LC-MS (ESI): $R_T$=2.89 min, mass calcd. for $C_{28}H_{31}ClF_2N_4O_6S_2$ 656.1, m/z found 656.5 [M+H]$^+$. $^1$H NMR (400 MHz, DMSO-$d_6$) δ 9.68-9.20 (brs, 1H), 8.04-7.94 (m, 2H), 7.50-7.40 (m, 1H), 7.27-7.14 (m, 1H), 6.03 (s, 0.2H), 5.94 (s, 0.8H), 3.78-3.62 (m, 3H), 3.53 (s, 3H), 2.94 (d, J=6.4 Hz, 2H), 2.86-2.79 (m, 2H), 2.15-2.08 (m, 1H), 2.03-1.76 (m, 8H), 1.71-1.60 (m, 1H), 1.39-1.21 (m, 2H), 1.20-0.94 (m, 2H).

Compound 429C: (trans)-3-((4-(-5-(Ethoxycarbonyl)-6-(3-fluoro-2-methylphenyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.097 min, mass calcd. for $C_{28}H_{33}FN_4O_6S_2$ 604.2, m/z found 605.0 [M+H]$^+$. $^1$H NMR (400 MHz, CD$_3$OD) δ 7.88 (s, 1H), 7.73 (d, J=2.8 Hz, 1H), 7.16-7.11 (m, 2H), 6.96-6.91 (m, 1H), 5.90 (s, 1H), 4.06-3.84 (m, 6H), 2.99-2.81 (m, 4H), 2.43-2.36 (m, 5H), 2.10-1.84 (m, 3.4H), 1.66-1.61 (m, 0.6H), 1.42 (s, 3H), 1.11 (t, J=7.2 Hz, 3H).

Compound 429D: (cis)-3-((4-(-5-(Ethoxycarbonyl)-6-(3-fluoro-2-methylphenyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.025 min, mass calcd. for $C_{28}H_{33}FN_4O_6S_2$ 604.2, m/z found 605.0 [M+H]$^+$. $^1$H NMR (400 MHz, CD$_3$OD) δ 7.88 (d, J=2.4 Hz, 1H), 7.73 (d, J=3.2

Hz, 1H), 7.14-7.10 (m, 2H), 6.96-6.91 (m, 1H), 5.91 (s, 1H), 4.06-3.86 (m, 6H), 2.99-2.83 (m, 4H), 2.44 (s, 3H), 2.24-2.19 (m, 2H), 2.08-1.86 (m, 3.4H), 1.70-1.64 (m, 0.6H), 1.48 (s, 3H), 1.11 (t, J=7.2 Hz, 3H).

Compound 439B: (trans)-3-((4-(6-(2-Bromo-3-fluorophenyl)-5-(methoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=3.082 min, mass calcd. for $C_{25}H_{26}BrFN_4O_6S_2$ 640.1, m/z found 640.8 [M+H]$^+$. Chiral analysis (Column: Chiralpak IE 5 μm 4.6*250 mm; Mobile Phase: Hex:EtOH:TFA=70:30:0.2 at 1.0 mL/min; Temp: 30° C.; Wavelength: 230 nm, $R_T$=17.633 min). $^1$H NMR (400 MHz, DMSO-d$_6$) δ 8.00 (s, 1.8H), 7.93 (s, 0.2H), 7.43-7.38 (m, 1H), 7.29 (t, J=8.4 Hz, 1H), 7.21 (d, J=7.2 Hz, 0.8H), 7.15 (d, J=7.2 Hz, 0.2H), 6.06 (s, 0.2H), 5.97 (s, 0.8H), 4.03-3.95 (m, 1H), 3.77-3.71 (m, 3H), 3.52 (s, 3H), 3.14-3.06 (m, 1H), 2.92-2.83 (m, 2H), 2.57-2.53 (m, 4H), 2.08-1.75 (m, 3.2H), 1.61-1.59 (m, 0.8H).

Compound 439D: (cis)-3-((4-(6-(2-Bromo-3-fluorophenyl)-5-(methoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=3.213 min, mass calcd. for $C_{25}H_{26}BrFN_4O_6S_2$ 640.1, m/z found 643.0 [M+H]$^+$. Chiral analysis (Column: Chiralpak IE 5 μm 4.6*250 mm; Mobile Phase: Hex:EtOH:TFA=60:40:0.2 at 1.0 mL/min; Temp: 30° C.; Wavelength: 230 nm, $R_T$=13.828 min). $^1$H NMR (400 MHz, DMSO-d$_6$) δ 8.00 (s, 1.8H), 7.93 (br s, 0.2H), 7.43-7.38 (m, 1H), 7.28 (t, J=8.8 Hz, 1H), 7.20 (d, J=7.2 Hz, 1H), 6.05 (br s, 0.2H), 5.97 (s, 0.8H), 3.98-3.89 (m, 1H), 3.74-3.67 (m, 3H), 3.52 (s, 3H), 3.09-3.00 (m, 1H), 2.89-2.80 (m, 2H), 2.51-2.44 (m, 4H), 2.01-1.76 (m, 3.2H), 1.62-1.59 (m, 0.8H).

Compound 444b: (trans)-4-(((4-(6-(3-Fluoro-2-methylphenyl)-5-(methoxycarbonyl)-2-(thiazol-2-yl)-3,6-dihydropyrimidin-4-yl)piperidin-1-yl)sulfonyl)methyl)cyclohexanecarboxylic Acid LC-MS (ESI): $R_T$=4.233 min, mass calcd. for $C_{29}H_{35}FN_4O_6S_2$ 618.2, m/z found 619.0 [M+H]$^+$. $^1$H NMR (400 MHz, DMSO-d$_6$) δ 8.00-7.97 (m, 1.8H), 7.92-7.91 (m, 0.2H), 7.23-7.13 (m, 1.9H), 7.07-6.99 (m, 1.1H), 5.87 (s, 0.1H), 5.74 (s, 0.9H), 4.03-3.95 (m, 0.2H), 3.77-3.66 (m, 2.8H), 3.53 (s, 0.5H), 3.52 (s, 2.5H), 2.93 (d, J=6.4 Hz, 2H), 2.87-2.78 (m, 2H), 2.45 (br s, 0.4H), 2.39 (s, 2.6H), 2.18-1.77 (m, 9.2H), 1.65-1.61 (m, 0.8H), 1.38-1.28 (m, 2H), 1.17-1.06 (m, 2H).

Compound 447C: (trans)-3-((4-(6-(4-Fluoro-2-methylphenyl)-5-(methoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=2.727 min, mass calcd. for $C_{27}H_{31}FN_4O_6S_2$ 590.2, m/z found 591.0 [M+H]$^+$. $^1$H NMR (400 MHz, DMSO-d$_6$) δ 9.56 (br s, 1H), 8.01-7.99 (m, 1.9H), 7.91 (d, J=3.2 Hz, 0.1H), 7.28-7.24 (m, 1H), 7.02-6.95 (m, 2H), 5.80 (s, 0.1H), 5.67 (s, 0.9H), 3.95-3.87 (m, 1H), 3.75-3.68 (m, 3H), 3.51 (s, 3H), 2.87-2.78 (m, 2H), 2.75-2.70 (m, 2H), 2.51 (s, 3H), 2.21-2.16 (m, 2H), 2.01-1.92 (m, 1H), 1.85-1.72 (m, 2H), 1.59-1.56 (m, 1H), 1.31 (s, 3H).

Compound 447D: (cis)-3-((4-(6-(4-fluoro-2-methylphenyl)-5-(methoxycarbonyl)-2-(thiazol-2-yl)-3,6-dihydropyrimidin-4-yl)piperidin-1-yl)sulfonyl)-1-methylcyclobutanecarboxylic Acid LC-MS (ESI): $R_T$=3.919 min, mass calcd. for $C_{27}H_{31}FN_4O_6S_2$ 590.2, m/z found 591.0 [M+H]$^+$. $^1$H NMR (400 MHz, DMSO-d$_6$) δ 8.00-7.99 (m, 2H), 7.28-7.25 (m, 1H), 7.01-6.95 (m, 2H), 5.68 (s, 1H), 4.08-3.99 (m, 1H), 3.74-3.66 (m, 3H), 3.52 (s, 3H), 2.89-2.80 (m, 2H), 2.68-2.63 (m, 2H), 2.50 (s, 3H), 2.08-2.03 (m, 2H), 1.98-1.92 (m, 1H), 1.87-1.73 (m, 2H), 1.60-1.57 (m, 1H), 1.37 (s, 3H).

Compound 450A: (cis)-4-(((4-(6-(2-Chloro-4-fluorophenyl)-5-(methoxycarbonyl)-2-(thiazol-2-yl)-3,6-dihydropyrimidin-4-yl)piperidin-1-yl)sulfonyl)methyl)-4-methylcyclohexanecarboxylic Acid LC-MS (ESI): $R_T$=4.473 min, mass calcd. for $C_{29}H_{34}ClFN_4O_6S_2$ 652.2, m/z found 653.0 [M+H]$^+$. Chiral analysis (Column: Chiralpak IE 5 μm 4.6*250 mm; Mobile Phase: Hex:EtOH:TFA=60:40:0.2 at 1.0 mL/min; Temp: 30° C.; Wavelength: 254 nm, $R_T$=12.154 min). $^1$H NMR (400 MHz, DMSO-d$_6$) δ 8.01-7.99 (m, 1.8H), 7.93 (d, J=3.2 Hz, 0.2H), 7.42 (dd, J=8.8, 2.8 Hz, 1H), 7.39-7.31 (m, 1H), 7.22 (td, J=8.8, 2.8 Hz, 1H), 6.02 (s, 0.2H), 5.92 (s, 0.8H), 3.99-3.93 (m, 0.2H), 3.73-3.66 (m, 2.8H), 3.53 (s, 2.1H), 3.52 (s, 0.9H), 3.00 (s, 2H), 2.90-2.82 (m, 2H), 2.22-2.14 (m, 1H), 2.05-1.96 (m, 1H), 1.90-1.81 (m, 4H), 1.72-1.53 (m, 5H), 1.25-1.19 (m, 2H), 1.17 (s, 3H).

Compound 450B: (trans)-4-(((4-(6-(2-Chloro-4-fluorophenyl)-5-(methoxycarbonyl)-2-(thiazol-2-yl)-3,6-dihydropyrimidin-4-yl)piperidin-1-yl)sulfonyl)methyl)-4-methylcyclohexanecarboxylic Acid LC-MS (ESI): $R_T$=4.402 min, mass calcd. for $C_{29}H_{34}ClFN_4O_6S_2$ 652.2, m/z found 652.9 [M+H]$^+$. Chiral analysis (Column: Chiralpak IE 5 μm 4.6*250 mm; Mobile Phase: Hex:EtOH:TFA=60:40:0.2 at 1.0 mL/min; Temp: 30° C.; Wavelength: 254 nm, $R_T$=14.009 min). $^1$H NMR (400 MHz, DMSO-d$_6$) δ 8.01 (s, 1.6H), 7.93 (br s, 0.4H), 7.43 (dd, J=8.8, 2.4 Hz, 1H), 7.38-7.35 (m, 1H), 7.22 (td, J=8.8, 2.8 Hz, 1H), 6.01 (br s, 0.2H), 5.92 (s, 0.8H), 3.95 (br s, 0.2H), 3.74-3.67 (m, 2.8H), 3.53 (s, 3H), 2.94 (s, 2H), 2.85-2.77 (m, 2H), 2.15-2.08 (m, 1H), 2.03-1.97 (m, 1H), 1.90-1.79 (m, 2H), 1.73-1.62 (m, 5H), 1.57-1.40 (m, 4H), 1.15 (s, 3H).

Compound 452A: (cis)-4-(((4-(6-(2-Chloro-3,4-difluorophenyl)-5-(methoxycarbonyl)-2-(thiazol-2-yl)-3,6-dihydropyrimidin-4-yl)piperidin-1-yl)sulfonyl)methyl)-4-methylcyclohexanecarboxylic Acid LC-MS (ESI): $R_T$=3.659 min, mass calcd. for $C_{29}H_{33}ClF_2N_4O_6S_2$ 670.2, m/z found 671.0 [M+H]$^+$. $^1$H NMR (400 MHz, DMSO-d$_6$) δ 8.02 (s, 1.6H), 7.94 (s, 0.4H), 7.50-7.43 (m, 1H), 7.23-7.16 (m, 1H), 6.02 (s, 0.2H), 5.93 (s, 0.8H), 4.01-3.94 (m, 0.2H), 3.76-3.66 (m, 2.8H), 3.53 (s, 3H), 3.00 (s, 2H), 2.91-2.83 (m, 2H), 2.21-2.14 (m, 1H), 2.02-1.97 (m, 1H), 1.90-1.77 (m, 4H), 1.71-1.53 (m, 5H), 1.25-1.19 (m, 2H), 1.16 (s, 3H).

Compound 452B: (trans)-4-(((4-(6-(2-Chloro-3,4-difluorophenyl)-5-(methoxycarbonyl)-2-(thiazol-2-yl)-3,6-dihydropyrimidin-4-yl)piperidin-1-yl)sulfonyl)methyl)-4-methylcyclohexanecarboxylic Acid LC-MS (ESI): $R_T$=3.603 min, mass calcd. for $C_{29}H_{33}ClF_2N_4O_6S_2$ 670.2, m/z found 670.9 [M+H]$^+$. $^1$H NMR (400 MHz, DMSO-d$_6$) δ 12.00 (br s, 1H), 9.66 (br s, 0.8H), 9.26 (s, 0.2H), 8.03-7.99 (m, 1.7H), 7.94 (d, J=3.2 Hz, 0.3H), 7.50-7.43 (m, 1H), 7.23-7.15 (m, 1H), 6.02 (s, 0.2H), 5.93 (s, 0.8H), 4.00-3.94 (m, 0.2H), 3.73-3.66 (m, 2.8H), 3.53 (s, 3H), 2.94 (s, 2H), 2.85-2.76 (m, 2H), 2.18-2.13 (m, 1H), 2.02-1.96 (m, 1H), 1.90-1.71 (m, 4H), 1.65-1.62 (m, 3H), 1.55-1.43 (m, 4H), 1.15 (s, 3H).

Compound 454: (trans)-4-(((4-(6-(2-Chloro-3-fluorophenyl)-5-(methoxycarbonyl)-2-(thiazol-2-yl)-3,6-dihydropyrimidin-4-yl)piperidin-1-yl)sulfonyl)methyl)-cyclohexanecarboxylic Acid LC-MS (ESI): $R_T$=3.612 min, mass calcd. for $C_{28}H_{32}ClFN_4O_6S_2$ 638.1, m/z found mass 639.2 [M+H]$^+$. $^1$H NMR (400 MHz, DMSO-d$_6$) δ 9.67 (br s, 0.8H), 9.21 (br s, 0.2H), 8.01-7.99 (m, 1.7H), 7.94 (d, J=3.2 Hz, 0.3H), 7.41-7.32 (m, 2H), 7.23-7.16 (m, 1H), 6.07 (s, 0.2H), 5.98 (s, 0.8H), 4.00-3.94 (m, 0.3H), 3.77-3.67 (m, 2.7H), 3.53 (s, 3H), 2.94 (d, J=6.4 Hz, 2H), 2.86-2.78 (m, 2H), 2.16-2.09 (m, 1H), 2.00-1.78 (m, 8H), 1.66-1.62 (m, 1H), 1.39-1.28 (m, 2H), 1.16-1.07 (m, 2H)

Compound 456: 3-(((4-(6-(2-Chloro-3,4-difluorophenyl)-5-(methoxycarbonyl)-2-(thiazol-2-yl)-3,6-dihydropyrimidin-4-yl)piperidin-1-yl)sulfonyl)methyl)bicyclo[1.1.1]pentane-1-carboxylic Acid LC-MS (ESI): $R_T$=3.237 min, mass calcd. for $C_{27}H_{27}ClF_2N_4O_6S_2$ 640.1, m/z found 641.2 [M+H]$^+$. $^1$H NMR (400 MHz, DMSO-d$_6$) δ 12.35 (br s, 1H), 9.67 (s, 0.8H), 9.25 (s, 0.2H), 8.02-7.99 (m, 1.8H), 7.94 (d, J=2.8 Hz, 0.2H), 7.49-7.42 (m, 1H), 7.23-7.14 (m, 1H), 6.02 (s, 0.2H), 5.93 (d, J=1.6 Hz, 0.8H), 3.98-3.92 (m, 0.2H), 3.75-3.66 (m, 2.8H), 3.53 (s, 2.5H), 3.52 (s, 0.5H), 3.35-3.32 (m, 2H), 2.87-2.75 (m, 2H), 2.07 (s, 6H), 2.06-2.00 (m, 1H), 1.94-1.76 (m, 2.2H), 1.64-1.61 (m, 0.8H).

Compound 470: (trans)-3-(4-((4-(6-(2-Chloro-4-fluorophenyl)-5-(methoxycarbonyl)-2-(thiazol-2-yl)-3,6-dihydropyrimidin-4-yl)piperidin-1-yl)sulfonyl)-1H-pyrazol-1-yl)cyclobutanecarboxylic Acid LC-MS (ESI): $R_T$=2.100 min, mass calcd. for $C_{28}H_{28}ClFN_6O_6S_2$ 662.1, m/z found 662.9 [M+H]$^+$. $^1$H NMR (400 MHz, CD$_3$OD) 8.26 (s, 1H), 7.94 (br s, 1H), 7.87 (s, 1H), 7.76 (d, J=2.4 Hz, 1H), 7.39-7.35 (m, 1H), 7.24-7.21 (m, 1H), 7.06-7.01 (m, 1H), 6.05 (br s, 1H), 5.19-5.11 (m, 1H), 3.94-3.78 (m, 2H), 3.76-3.61 (m, 1H), 3.54 (s, 3H), 3.25-3.15 (m, 1H), 2.95-2.85 (m, 2H), 2.81-2.72 (m, 2H), 2.45-2.34 (m, 2H), 2.24-1.84 (m, 3.4H), 1.77-1.63 (m, 0.6H).

Compound 476A: (trans)-2-(4-((4-(6-(2-Chloro-4-fluorophenyl)-5-(methoxycarbonyl)-2-(thiazol-2-yl)-3,6-dihydropyrimidin-4-yl)piperidin-1-yl)sulfonyl) cyclohexyl)acetic Acid LC-MS (ESI): $R_T$=3.658 min, mass calcd. for $C_{28}H_{32}ClFN_4O_6S_2$ 638.1, m/z found 639.0 [M+H]$^+$. $^1$H NMR (400 MHz, CD$_3$OD) δ 7.90 (d, J=3.2 Hz, 1H), 7.77 (d, J=3.2 Hz, 1H), 7.39 (dd, J=8.8, 6.0 Hz, 1H), 7.23 (dd, J=8.8, 2.8 Hz, 1H), 7.08-7.03 (m, 1H), 6.09 (s, 1H), 4.01-3.88 (m, 3H), 3.59 (s, 3H), 3.09-3.00 (m, 3H), 2.18-2.15 (m, 2H), 2.10-2.06 (m, 3H), 1.98-1.87 (m, 4H), 1.82-1.68 (m, 2H), 1.64-1.54 (m, 2H), 1.11-1.07 (m, 2H).

Compound 476B: (cis)-2-(4-((4-(6-(2-Chloro-4-fluorophenyl)-5-(methoxycarbonyl)-2-(thiazol-2-yl)-3,6-dihydropyrimidin-4-yl)piperidin-1-yl)sulfonyl) cyclohexyl)acetic Acid LC-MS (ESI): $R_T$=3.647 min, mass calcd. for $C_{28}H_{32}ClFN_4O_6S_2$ 638.1, m/z found 639.0 [M+H]$^+$. $^1$H NMR (400 MHz, CD$_3$OD) δ 7.90 (d, J=3.2 Hz, 1H), 7.75 (d, J=2.8 Hz, 1H), 7.39 (dd, J=8.8, 6.0 Hz, 1H), 7.23 (dd, J=8.8, 2.4 Hz, 1H), 7.08-7.03 (m, 1H), 6.09 (s, 1H), 4.00-3.89 (m, 3H), 3.59 (s, 3H), 3.16-3.13 (m, 1H), 3.10-3.00 (m, 2H), 2.25-2.23 (m, 2H), 2.18-1.89 (m, 8H), 1.81-1.71 (m, 3H), 1.67-1.59 (m, 2H).

Compound 476: 2-(4-((4-(6-(2-Chloro-3,4-difluorophenyl)-5-(methoxycarbonyl)-2-(thiazol-2-yl)-3,6-dihydropyrimidin-4-yl)piperidin-1-yl)sulfonyl)cyclohexyl)acetic Acid LC-MS (ESI): $R_T$=4.253 min, mass calcd. for $C_{28}H_{31}ClF_2N_4O_6S_2$ 656.1, m/z found 656.9 [M+H]$^+$. $^1$H NMR (400 MHz, DMSO-d$_6$) δ 12.07 (br s, 0.4H), 9.65 (br s, 0.4H), 9.26 (br s, 0.2H), 8.01-7.99 (m, 1.8H), 7.94-7.93 (m, 0.2H), 7.49-7.42 (m, 1H), 7.23-7.14 (m, 1H), 6.02 (s, 0.2H), 5.92 (s, 0.8H), 4.02-3.96 (m, 0.2H), 3.79-3.72 (m, 2.8H), 3.53 (s, 3H), 3.22-3.16 (m, 0.4H), 3.10-3.04 (m, 0.6H), 3.00-2.91 (m, 2H), 2.25 (d, J=7.6 Hz, 0.8H), 2.11 (d, J=6.8 Hz, 1.2H), 2.07-2.01 (m, 2H), 1.98-1.91 (m, 1H), 1.84-1.59 (m, 7H), 1.47-1.40 (m, 1H), 1.31-1.26 (m, 0.6H), 1.11-1.02 (m, 1H), 0.88-0.84 (m, 0.4H).

Compound 478: 2-(4-((4-(6-(2-Chloro-3,4-difluorophenyl)-5-(methoxycarbonyl)-2-(thiazol-2-yl)-3,6-dihydropyrimidin-4-yl)piperidin-1-yl)sulfonyl)cyclohexyl)acetic Acid LC-MS (ESI): $R_T$=4.253 min, mass calcd. for $C_{28}H_{31}ClF_2N_4O_6S_2$ 656.1, m/z found 656.9 [M+H]$^+$. $^1$H NMR (400 MHz, DMSO-d$_6$) δ 12.07 (br s, 0.4H), 9.65 (br s, 0.4H), 9.26 (br s, 0.2H), 8.01-7.99 (m, 1.8H), 7.94-7.93 (m, 0.2H), 7.49-7.42 (m, 1H), 7.23-7.14 (m, 1H), 6.02 (s, 0.2H), 5.92 (s, 0.8H), 4.02-3.96 (m, 0.2H), 3.79-3.72 (m, 2.8H), 3.53 (s, 3H), 3.22-3.16 (m, 0.4H), 3.10-3.04 (m, 0.6H), 3.00-2.91 (m, 2H), 2.25 (d, J=7.6 Hz, 0.8H), 2.11 (d, J=6.8 Hz, 1.2H), 2.07-2.01 (m, 2H), 1.98-1.91 (m, 1H), 1.84-1.59 (m, 7H), 1.47-1.40 (m, 1H), 1.31-1.26 (m, 0.6H), 1.11-1.02 (m, 1H), 0.88-0.84 (m, 0.4H).

Compound 478A: (trans)-2-(4-((4-(6-(2-Chloro-3,4-difluorophenyl)-5-(methoxycarbonyl)-2-(thiazol-2-yl)-3,6-dihydropyrimidin-4-yl)piperidin-1-yl)sulfonyl)cyclohexyl)acetic Acid LC-MS (ESI): $R_T$=3.397 min, mass calcd. for $C_{28}H_{31}ClF_2N_4O_6S_2$ 656.1, m/z found 656.9 [M+H]$^+$. $^1$H NMR (400 MHz, DMSO-d$_6$) δ 12.08 (s, 1H), 9.66 (d, J=2.8 Hz, 0.8H), 9.27 (s, 0.2H), 8.01-7.99 (m, 1.8H), 7.93 (d, J=3.2 Hz, 0.2H), 7.49-7.42 (m, 1H), 7.23-7.14 (m, 1H), 6.02 (s, 0.2H), 5.92 (d, J=3.2 Hz, 0.8H), 4.02-3.96 (m, 0.2H), 3.79-3.72 (m, 2.8H), 3.53 (s, 3H), 3.10-3.04 (m, 1H), 3.00-2.92 (m, 2H), 2.12-2.04 (m, 4H), 1.98-1.91 (m, 1H), 1.84-1.57 (m, 6H), 1.48-1.39 (m, 2H), 1.11-1.01 (m, 2H).

Compound 480B: 3-(((4-(6-(2-Chloro-3,4-difluorophenyl)-5-(ethoxycarbonyl)-2-(thiazol-2-yl)-3,6-dihydropyrimidin-4-yl)piperidin-1-yl)sulfonyl)methyl)cyclobutanecarboxylic Acid LC-MS (ESI): $R_T$=3.418 min, mass calcd. for $C_{27}H_{29}ClF_2N_4O_6S_2$ 642.1, m/z found 642.9 [M+H]$^+$. Chiral analysis (Column: Chiralpak IA 5 μm 4.6*250 mm; Mobile Phase: Hex:EtOH:TFA=70:30:0.2 at 1.0 mL/min; Temp: 30° C.; Wavelength: 254 nm, $R_T$=11.747 min). $^1$H NMR (400 MHz, DMSO-d$_6$+one drop of D$_2$O) δ 8.00 (d, J=3.2 Hz, 1H), 7.97 (d, J=3.2 Hz, 0.8H), 7.91 (d, J=3.2 Hz, 0.2H), 7.49-7.42 (m, 1H), 7.24-7.19 (m, 1H), 6.04 (s, 0.2H), 5.95 (s, 0.8H), 4.01-3.95 (m, 2.2H), 3.76-3.67 (m, 2.8H), 3.17 (d, J=7.2 Hz, 2H), 3.05-2.96 (m, 1H), 2.85-2.77 (m, 2H), 2.68-2.60 (m, 1H), 2.38-2.32 (m, 2H), 2.05-1.97 (m, 3H), 1.90-1.78 (m, 2.2H), 1.65-1.62 (m, 0.8H), 1.10-1.04 (m, 3H).

Compound 480Y: 3-(((4-(6-(2-Chloro-3,4-difluorophenyl)-5-(ethoxycarbonyl)-2-(thiazol-2-yl)-3,6-dihydropyrimidin-4-yl)piperidin-1-yl)sulfonyl)methyl)cyclobutanecarboxylic Acid LC-MS (ESI): $R_T$=3.388 min, mass calcd. for $C_{27}H_{29}ClF_2N_4O_6S_2$ 642.1, m/z found 642.9 [M+H]$^+$. Chiral analysis (Column: Chiralpak ID 5 μm 4.6*250 mm; Mobile Phase: Hex:EtOH:TFA=70:30:0.2 at 1.0 mL/min; Temp: 30° C.; Wavelength: 254 nm, $R_T$=13.820 min). $^1$H NMR (400 MHz, DMSO-d$_6$+one drop of D$_2$O) δ 8.00 (d, J=3.2 Hz, 1H), 7.96 (d, J=3.2 Hz, 0.8H), 7.90 (d, J=3.2 Hz, 0.2H), 7.49-7.42 (m, 1H), 7.24-7.19 (m, 1H), 6.04 (s, 0.2H), 5.95 (s, 0.8H), 4.01-3.95 (m, 2.2H), 3.76-3.66 (m, 2.8H), 3.26 (d, J=7.2 Hz, 2H), 3.12-3.04 (m, 1H), 2.86-2.76 (m, 3H), 2.37-2.31 (m, 2H), 2.18-2.11 (m, 2H), 2.05-1.96 (m, 1H), 1.91-1.79 (m, 2.2H), 1.66-1.63 (m, 0.8H), 1.10-1.04 (m, 3H).

Compound 482A: 2-(3-((4-(6-(2-Chloro-3,4-difluorophenyl)-5-(ethoxycarbonyl)-2-(thiazol-2-yl)-3,6-dihydropyrimidin-4-yl)piperidin-1-yl)sulfonyl)cyclobutyl)acetic Acid LC-MS (ESI): $R_T$=3.832 min, mass calcd. for $C_{27}H_{29}ClF_2N_4O_6S_2$ 642.1, m/z found 642.9 [M+H]$^+$. $^1$H NMR (400 MHz, CD$_3$OD) δ 7.96-7.89 (m, 1H), 7.76 (s, 1H), 7.27-7.19 (m, 2H), 6.16 (br s, 0.3H), 6.08 (s, 0.7H), 4.14-3.98 (m, 3.4H), 3.95-3.85 (m, 2.6H), 2.99-2.89 (m, 2H), 2.86-2.77 (m, 1H), 2.72-2.65 (m, 2H), 2.54 (d, J=7.6 Hz, 2H), 2.23-1.81 (m, 5.3H), 1.71-1.63 (m, 0.7H), 1.12 (t, J=7.2 Hz, 3H).

Compound 482B: 2-(3-((4-(6-(2-Chloro-3,4-difluorophenyl)-5-(ethoxycarbonyl)-2-(thiazol-2-yl)-3,6-dihydropyrimidin-4-yl)piperidin-1-yl)sulfonyl)cyclobutyl)acetic Acid LC-MS (ESI): $R_T$=3.831 min, mass calcd. for $C_{27}H_{29}ClF_2N_4O_6S_2$ 642.1, m/z found 642.9 [M+H]$^+$. $^1$H NMR (400 MHz, CD$_3$OD) δ 7.94-7.90 (m, 1H), 7.76 (br s, 1H), 7.28-7.22 (m, 2H), 6.16-6.09 (m, 1H), 4.12-4.02 (m, 3.4H), 3.95-3.83 (m, 2.6H), 2.98-2.89 (m, 2H), 2.76-2.86 (m, 1H), 2.60-2.53 (m, 2H), 2.46 (d, J=7.6 Hz, 2H), 2.22-1.82 (m, 5.3H), 1.70-1.65 (m, 0.7H), 1.13 (t, J=7.2 Hz, 3H).

Compound 370B: (trans)-3-((4-(6-(2-Chloro-3,4-difluorophenyl)-5-(ethoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=2.546 min, mass calcd. for $C_{26}H_{27}ClF_2N_4O_6S_2$ 628.1, m/z found 629.1 [M+H]$^+$. $^1$H NMR (400 MHz, DMSO-d$_6$) δ 12.25 (br s, 1H), 9.61 (s, 0.8H), 9.11 (s, 0.2H), 8.01-7.93 (m, 2H), 7.49-7.42 (m, 1H), 7.23-7.17 (m, 1H), 6.03 (s, 0.2H), 5.93 (s, 0.8H), 4.05-3.94 (m, 3.2H), 3.78-3.70 (m, 2.8H), 3.19-3.11 (m, 1H), 2.92-2.82 (m, 2H), 2.59-2.53 (m, 4H), 2.07-1.59 (m, 4H), 1.09-1.03 (m, 3H).

Compound 370D: (cis)-3-((4-(6-(2-Chloro-3,4-difluorophenyl)-5-(ethoxycarbonyl)-2-(thiazol-2-yl)-3,6-dihydropyrimidin-4-yl)piperidin-1-yl)sulfonyl)cyclobutanecarboxylic Acid LC-MS (ESI): $R_T$=3.478 min, mass calcd. for $C_{26}H_{27}ClF_2N_4O_6S_2$ 628.1, m/z found 629.1 [M+H]$^+$. $^1$H NMR (400 MHz, DMSO-d$_6$) δ 8.00-7.93 (m, 2H), 7.49-7.42 (m, 1H), 7.22-7.19 (m, 1H), 6.03 (s, 0.2H), 5.94 (s, 0.8H), 4.00-3.91 (m, 3H), 3.74-3.68 (m, 3H), 3.11-3.02 (m, 1H), 2.88-2.79 (m, 2H), 2.47-2.42 (m, 4H), 1.97-1.60 (m, 4H), 1.07 (t, J=7.2 Hz, 3H).

Section V: Miscellaneous Conversion of Primary Dihydropyrimidines of General Formula I Compound 131: Methyl 6-(1-(2-(tert-butoxy)-2-oxoethyl)piperidin-3-yl)-4-(2-chloro-3-fluorophenyl)-2-(thiazol-2-yl)-1,4-dihydropyrimidine-5-carboxylate (a Mixture of 4 Stereoisomers)

To a solution of methyl 6-(1-(tert-butoxycarbonyl)piperidin-3-yl)-4-(2-chloro-3-fluorophenyl)-2-(thiazol-2-yl)-1,4-dihydropyrimidine-5-carboxylate Compound 30 (315 mg, 0.59 mmol) in methanol (10 mL) was added 4 M hydrochloride acid in methanol (10 mL, 40 mmol) at room temperature. After stirred at room temperature for 20 minutes, the mixture was concentrated to leave a residue (355 mg crude), which was dissolved in N,N-dimethylformamide (15 mL). To above solution was added tert-butyl 2-bromoacetate (115 mg, 0.59 mmol) and triethylamine (149 mg, 1.48 mmol) under nitrogen atmosphere. After stirred at room temperature overnight, the reaction mixture was poured into water (30 mL) and extracted with ethyl acetate (30 mL) for three times. The combined organic layers were washed with water (40 mL) and brine (40 mL), dried over Na$_2$SO$_{4(s)}$, then concentrated to give a residue, which was purified by C18 column (acetonitrile:water=65% to 85%) and Prep. HPLC (Column: Xbridge C18 5 m 19*150 mm, Mobile Phase A: water (0.1% ammonium bicarbonate), Mobile Phase B: acetonitrile, Flow rate: 20 mL/min, Gradient: 60-90% (% B)) to give two fractions Fraction A (83 mg, 26% yield, a mixture of 2 stereoisomers) and Fraction B (43 mg, 13% yield, a mixture of 2 stereoisomers) as yellow solids.

Fraction B (43 mg, 0.08 mmol) was further separated by chiral Prep. HPLC (separation condition: Column: Chiralpak ID 5 μm 20*250 mm; Mobile Phase: Hex:IPA=70:30 at 13 mL/min; Temp: 30° C.; Wavelength: 230 nm) to afford stereoisomers Compound 131M (24.0 mg, 56% yield) and Compound 131N (18.0 mg, 42% yield). Compound 131N: LC-MS (ESI): $R_T$=4.354 min, mass calcd. for $C_{26}H_{30}ClFN_4O_4S$ 548.2, m/z found 549.0 [M+H]$^+$. Chiral HPLC (Column: Chiralpak ID 5 μm 4.6*250 mm; Mobile Phase: Hex:IPA=70:30 at 1.0 mL/min; Temp: 30° C.; Wavelength: 230 nm, $R_T$=6.639 min). $^1$H NMR (400 MHz, DMSO-$d_6$) δ 11.9 (s, 0.9H), 9.51 (s, 0.1H), 7.99 (s, 0.3H), 7.88 (d, J=3.2 Hz, 0.85H), 7.87 (d, J=3.2 Hz, 0.85H), 7.41-7.27 (m, 2H), 7.20-7.15 (m, 1H), 6.10 (s, 0.9H), 5.97 (d, J=2.8 Hz, 0.1H), 4.00 (s, 0.9H), 3.81 (s, 0.1H), 3.53-3.48 (m, 3H), 3.38-3.30 (m, 2H), 3.31-3.29 (m, 1H), 3.12 (d, J=12.8 Hz, 1H), 3.02 (d, J=10.4 Hz, 0.9H), 2.87-2.81 (m, 0.1H), 2.73 (dd, J=11.6, 3.2 Hz, 1H), 1.93-1.83 (m, 1H), 1.82-1.70 (m, 3H), 1.42-1.37 (m, 9H).

Compound 132: trans-Ethyl 4-(2-chloro-4-fluorophenyl)-6-(4-(methylcarbamoyl)-cyclohexyl)-2-(thiazol-2-yl)-1,4-dihydropyrimidine-5-carboxylate The solution of trans-ethyl 4-(2-chloro-4-fluorophenyl)-6-(4-(methoxycarbonyl)-cyclohexyl)-2-(thiazol-2-yl)-1,4-dihydropyrimidine-5-carboxylate Compound 20 (100 mg, 0.20 mmol) in methylamine in alcohol solution (10 mL) was stirred in sealed tube at 45° C. overnight. After cooling down to room temperature, the mixture was concentrated to give a residue, which was purified by C18 column (acetonitrile:water=45% to 55%) to give the title compound (70 mg, 70% yield) as yellow solids.

Compound 132 (250 mg, 0.500 mmol) was further separated by SFC (Column: Chiralpak IC 5 μm 20*250 mm; Mobile Phase: $CO_2$: EtOH=60:40 at 45 g/min; Col. Temp: 40° C.; Wavelength: 214 nm, Back pressure: 100 bar) to afford stereoisomers Compound 132A (92 mg, 37% yield) and Compound 132B (96 mg, 38% yield) as yellow solids.

Compound 132A: LC-MS (ESI): $R_T$=3.670 min, mass calcd. for $C_{24}H_{26}ClFN_4O_3S$ 504.1, m/z found 505.0 [M+H]$^+$. SFC analytical condition: (Column: Chiralpak IC 5 m 4.6*250 mm; Mobile Phase: $CO_2$:MeOH=60:40 at 3.0 mL/min; Col. Temp: 40° C.; Wavelength: 214 nm, Back pressure: 100 bar, $R_T$=2.66 min). $^1$H NMR (400 MHz, CDCl$_3$) δ 8.08 (br s, 0.5H), 7.83-7.80 (m, 1H), 7.48 (d, J=3.2 Hz, 0.5H), 7.44 (d, J=2.8 Hz, 0.5H), 7.34-7.28 (m, 1.5H), 7.14-7.11 (m, 1H), 6.96-6.88 (m, 1H), 6.20 (s, 0.5H), 6.06 (d, J=2.0 Hz, 0.5H), 5.49 (br s, 1H), 4.06 (q, J=7.2 Hz, 2H), 4.02-3.97 (m, 0.5H), 3.80-3.73 (m, 0.5H), 2.84 (d, J=4.4 Hz, 3H), 2.26-1.91 (m, 5H), 1.80-1.64 (m, 2.8H), 1.58-1.46 (m, 1.2H), 1.14 (t, J=7.2 Hz, 3H).

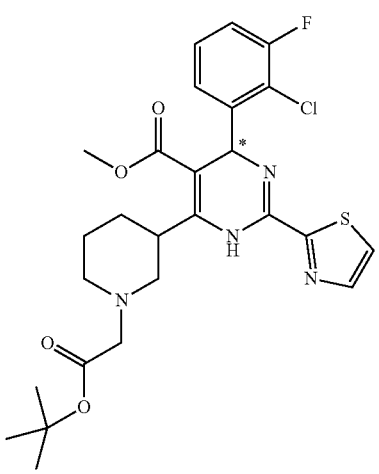

Compound 131N

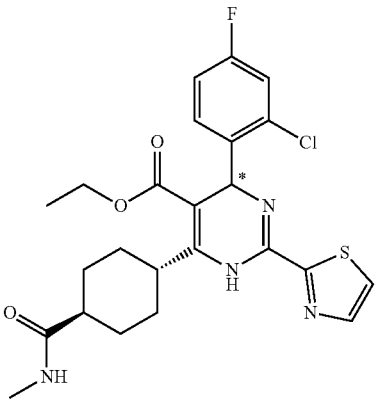

Compound 132A

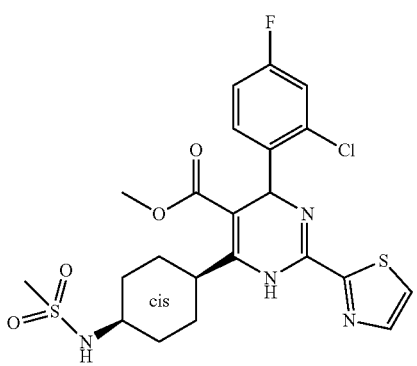

Compound 128

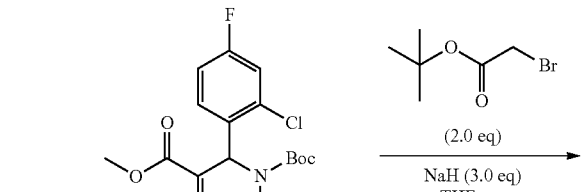

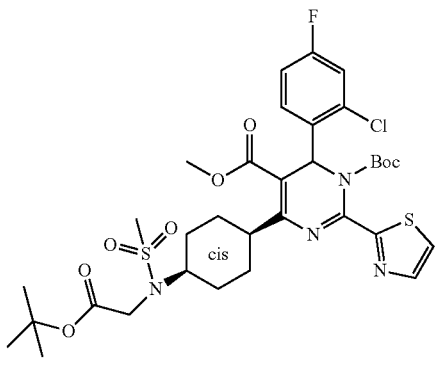

Compound 133

Compound 134

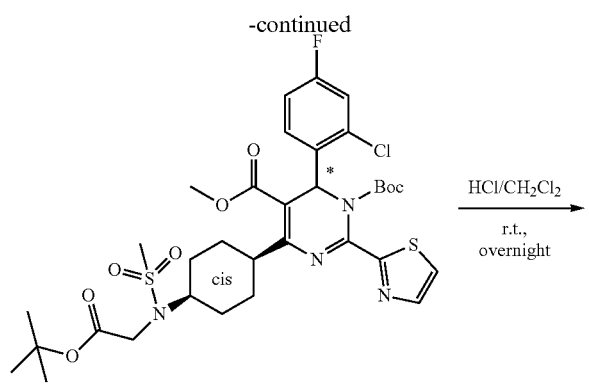

Compound 134B

Compound 133: 1-Tert-butyl 5-methyl 6-(2-chloro-4-fluorophenyl)-4-(cis-4-(methylsulfonamido)cyclohexyl)-2-(thiazol-2-yl)pyrimidine-1,5(6H)-dicarboxylate To a solution of methyl 4-(2-chloro-4-fluorophenyl)-6-(cis-4-(methylsulfonamido)-cyclohexyl)-2-(thiazol-2-yl)-1,4-dihydropyrimidine-5-carboxylate Compound 128 (70 mg, 0.133 mmol) in tetrahydrofuran (5 mL) was added 4-dimethylaminopyridine (20 mg, 0.160 mmol) and di-tert-butyl dicarbonate (35 mg, 0.160 mmol) at room temperature. The mixture was stirred at 60° C. overnight under nitrogen atmosphere. After cooling down to room temperature, the mixture was concentrated under reduced pressure to give a residue, which was purified by prep-TLC (petroleum ether:ethyl acetate=1:1) to give the title compound (60 mg, 72% yield) as yellow solids. LC-MS (ESI): $R_T$=2.590 min, mass calcd. for $C_{27}H_{32}ClFN_4O_6S_2$ 626.1, m/z found 626.7 [M+H]$^+$. H NMR (400 MHz, CDCl$_3$) δ 7.89 (d, J=3.2 Hz, 1H), 7.50 (d, J=3.2 Hz, 1H), 7.12 (dd, J=8.4, 2.4 Hz, 1H), 7.07-7.03 (m, 1H), 6.79 (td, J=8.4, 2.4 Hz, 1H), 6.70 (s, 1H), 4.96 (d, J=7.6 Hz, 1H), 3.84-3.82 (m, 1H), 3.71 (s, 3H), 3.69-3.65 (m, 1H), 3.03 (s, 3H), 2.02-1.74 (m, 7H), 1.56-1.52 (m, 1H), 1.24 (s, 9H).

Compound 134: 1-Tert-butyl 5-methyl 4-(trans-4-(N-(2-(tert-butoxy)-2-oxoethyl)-methylsulfonamido)cyclohexyl)-6-(2-chloro-4-fluorophenyl)-2-(thiazol-2-yl)-pyrimidine-1,5(6H)-dicarboxylate To a solution of 1-tert-butyl 5-methyl 6-(2-chloro-4-fluorophenyl)-4-((cis)-4-(methyl-sulfonamido)cyclohexyl)-2-(thiazol-2-yl)pyrimidine-1,5(6H)-dicarboxylate Compound 133 (60 mg, 0.0958 mmol) in tetrahydrofuran (5 mL) was added 60% wt sodium hydride in mineral oil (11 mg, 0.287 mmol) at 0° C. under nitrogen atmosphere. After stirred at room temperature for 30 minutes, the mixture was added dropwise tert-butyl 2-bromoacetate (37 mg, 0.192 mmol) at 0° C. Having stirred at room temperature overnight under nitrogen atmosphere, the mixture was added dropwise 1 M hydrochloric acid aqueous solution to adjust the pH value to 4-5. The separated aqueous solution was extracted with ethyl acetate (20 mL) for three times. The combined organic layers were washed with brine (20 mL) twice, dried over $Na_2SO_{4(s)}$ and filtered. The filtrate was concentrated under reduced pressure to give a residue, which was purified by Prep. TLC (petroleum ether:ethyl acetate=3:1) to give the title compound (35 mg, 49% yield) as yellow solids.

A mixture of Compound 134 (790 mg, 1.07 mmol) was separated by chiral Prep. HPLC (separation condition: Column: Chiralpak IC 5 μm 30*250 mm; Mobile Phase: Hex:EtOH=80:20 at 20 mL/min; Temp: 30° C.; Wavelength: 214 nm) to afford the title compounds Compound 134A (210 mg, 27% yield) and Compound 134B (280 mg, 35% yield).

Compound 134B: LC-MS (ESI): $R_T$=2.26 min, mass calcd. for $C_{33}H_{42}ClFN_4O_8S_2$ 740.2, m/z found 741.2 [M+H]$^+$. Chiral HPLC (Column: Chiralpak IC 5 μm 4.6*250 mm; Mobile Phase: Hex:EtOH=80:20 at 1.0 mL/min; Temp: 30° C.; Wavelength: 230 nm, $R_T$=11.705 min). $^1$H NMR (400 MHz, CDCl$_3$) δ 7.91 (d, J=3.2 Hz, 0.8H), 7.89 (d, J=3.2 Hz, 0.2H), 7.50-7.48 (m, 1H), 7.14-7.10 (m, 1H), 7.07-7.02 (m, 1H), 6.78 (td, J=8.0, 2.4 Hz, 1H), 6.69 (s, 0.2H), 6.68 (s, 0.8H), 4.17 (d, J=18.4 Hz, 0.8H), 4.09 (d, J=18.4 Hz, 0.8H), 3.97-3.96 (m, 0.4H), 3.92-3.88 (m, 1H), 3.79-3.74 (m, 1H), 3.71 (s, 0.7H), 3.70 (s, 2.3H), 3.15 (s, 0.7H), 3.11 (s, 2.3H), 2.24-2.19 (m, 1.5H), 2.14-2.05 (m, 1.5H), 1.98-1.81 (m, 4.7H), 1.71-1.67 (m, 0.3H), 1.48 (s, 2H), 1.39 (s, 7H), 1.25 (s, 7H), 1.23 (s, 2H).

Compound 135: 2-(N-(cis-4-(6-(2-chloro-4-fluorophenyl)-5-(methoxycarbonyl)-2-(thiazol-2-yl)-3,6-dihydropyrimidin-4-yl)cyclohexyl)methylsulfonamido)acetic Acid A solution of 1-tert-butyl 5-methyl 4-((cis)-4-(N-(2-(tert-butoxy)-2-oxoethyl)methylsulfonamido)cyclohexyl)-6-(2-chloro-4-fluorophenyl)-2-(thiazol-2-yl)pyrimidine-1,5(6H)-dicarboxylate Compound 134B (280 mg, 0.378 mmol) in 1M hydrochloric acid in dichloromethane (10 mL, 10 mmol) was stirred at room temperature overnight under nitrogen atmosphere. Then the reaction mixture was concentrated to give a residue, which was purified by Prep. HPLC (Column: waters 2-Atlantis T3 5 m 19*150 mm, Flow rate: 15 mL/min, Mobile Phase A: Water (0.1% hydrochloric acid), Mobile Phase B: Acetonitrile, Gradient: 20%-85% (% B)) to give the title compound (30 mg, 14% yield, 90.3% ee) as yellow solids. LC-MS (ESI): $R_T$=3.334 min, mass calcd. for $C_{24}H_{26}ClFN_4O_6S_2$ 584.1, m/z found 584.9 [M+H]$^+$. Chiral HPLC (Column: Chiralpak IG 5 μm 4.6*250 mm; Mobile Phase: Hex:EtOH:TFA=70:30:0.2 at 1.0 mL/min; Temp: 30° C.; Wavelength: 230 nm, $R_T$=8.969 min). $^1$H NMR (400 MHz, a drop of D$_2$O in DMSO-d$_6$) δ 8.02-7.99 (m, 2H), 7.44-7.41 (m, 1H), 7.36-7.32 (m, 1H), 7.23-7.18 (m, 1H), 5.95 (s, 1H), 3.97 (s, 2H), 3.72-3.63 (m, 2H), 3.52 (s, 3H), 3.07 (s, 3H), 2.02-1.92 (m, 1H), 1.89-1.76 (m, 4H), 1.68-1.65 (m, 1H), 1.59-1.47 (m, 2H).

Compound 139

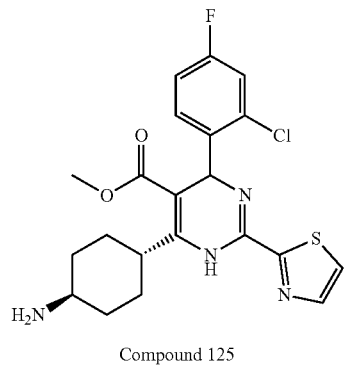

Compound 125

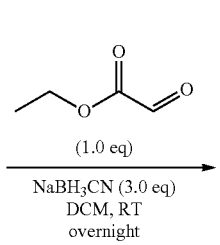

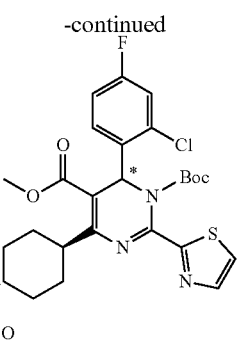

Compound 138B

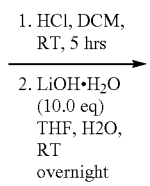

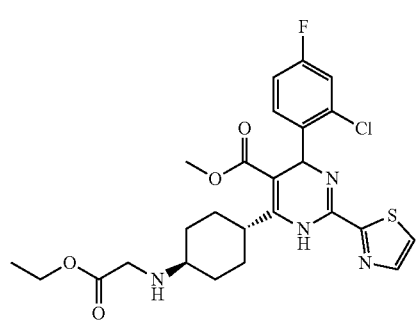

Compound 136

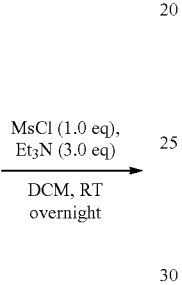

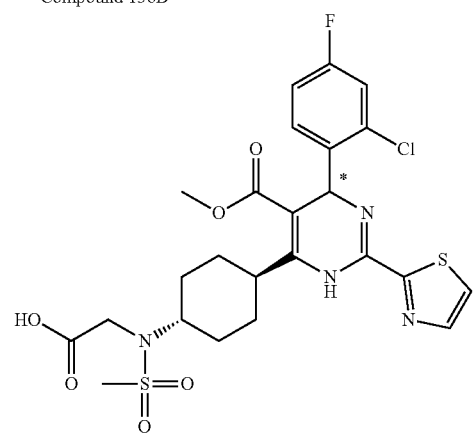

Compound 139

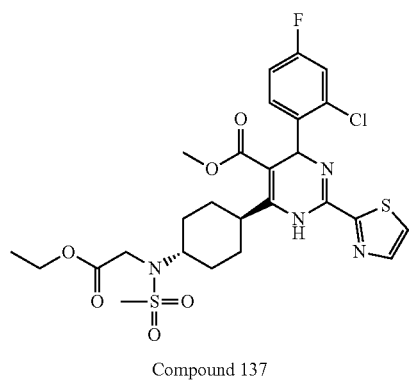

Compound 137

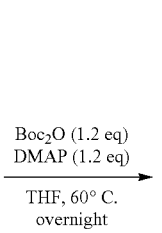

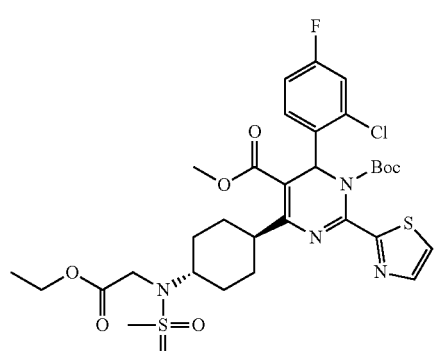

Compound 138

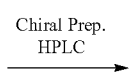

Compound 136: Methyl 4-(2-chloro-4-fluorophenyl)-6-(trans-4-((2-ethoxy-2-oxoethyl)amino)cyclohexyl)-2-(thiazol-2-yl)-1,4-dihydropyrimidine-5-carboxylate To a solution of methyl 6-(trans-4-aminocyclohexyl)-4-(2-chloro-4-fluorophenyl)-2-(thiazol-2-yl)-1,4-dihydropyrimidine-5-carboxylate Compound 125 (800 mg, 1.78 mmol) in dichloromethane (20 mL) was added ethyl 2-oxoacetate (363 mg, 50 wt % in toluene, 1.78 mmol) at room temperature. After stirring at room temperature overnight under nitrogen atmosphere, sodium cyanoborohydride (336 mg, 5.34 mmol) was added. The mixture was stirred at room temperature for another 2 hours and subsequently quenched with saturated sodium bicarbonate aqueous solution (30 mL). The separated aqueous solution was extracted with dichloromethane (30 mL) for three times. The combined organic layers were washed with brine (20 mL) twice, dried over $Na_2SO_{4(s)}$ and filtered. The filtrate was concentrated under reduced pressure to give a residue, which was purified by silica gel column chromatography (petroleum ether:ethyl acetate:ammonium hydroxide=10:1:0.02) to give a residue, which was further purified by C18 (acetonitrile: water (+0.1% trifluoroacetic acid)=5% to 95%) to give the title compound (200 mg, 21% yield) as yellow solids. LC-MS (ESI): $R_T$=2.03 min, mass calcd. for $C_{25}H_{28}ClFN_4O_4S$ 534.2, m/z found 535.2 [M+H]$^+$. $^1$H NMR (300 MHz, CDCl$_3$) δ 8.11 (br s, 0.6H), 7.82-7.80 (m, 1H), 7.46 (dd, J=13.2, 3.0 Hz, 1H), 7.40 (br s, 0.4H), 7.30-7.28 (m, 1H), 7.14-7.11 (m, 1H), 6.95-6.86 (m, 1H), 6.17 (s, 0.6H), 6.03 (d, J=2.4 Hz, 0.4H), 4.21 (q, J=7.2 Hz, 2H), 3.95 (t, J=12.0 Hz, 0.6H), 3.71 (br s, 0.4H), 3.60-3.59 (m, 3H), 3.48-3.47 (m, 2H), 2.60-2.52 (m, 1H), 2.11-1.90 (m, 4H), 1.79-1.71 (m, 1H), 1.60-1.40 (m, 4H), 1.30 (t, J=7.2 Hz, 3H).

Compound 137: Methyl 4-(2-chloro-4-fluorophenyl)-6-(trans-4-(N-(2-ethoxy-2-oxoethyl)methylsulfonamido)cyclohexyl)-2-(thiazol-2-yl)-1,4-dihydro-pyrimidine-5-carboxylate To a solution of methyl 4-(2-chloro-4-fluorophenyl)-6-(trans-4-((2-ethoxy-2-oxoethyl)-amino)cyclohexyl)-2-(thiazol-2-yl)-1,4-dihydropyrimidine-5-carboxylate Compound 136 (200 mg, 0.374 mmol) in dichloromethane (10 mL) were added triethylamine (113 mg, 1.12 mmol) and methanesulfonyl chloride (43 mg, 0.374 mmol) at room temperature. After stirred at room temperature overnight under nitrogen atmosphere, the mixture was quenched with saturated sodium bicarbonate aqueous solution (20 mL). The separated aqueous solution was then extracted with dichloromethane (20 mL) for three times. The combined organic layers were washed with brine (20 mL) twice, dried over $Na_2SO_{4(s)}$ and filtered. The filtrate was concentrated under reduced pressure to give a residue, which was purified by prep-TLC (dichloromethane:methanol=20:1) to give the title compound (85 mg, 37% yield) as yellow solids. LC-MS (ESI): $R_T$=4.211 min, mass calcd. for $C_{26}H_{30}ClFN_4O_6S_2$ 612.1, m/z found 612.9 [M+H]$^+$. $^1$H NMR (400 MHz, DMSO-d$_6$) δ 9.44 (d, J=4.0 Hz, 0.6H), 9.04 (s, 0.4H), 7.99 (s, 1H), 7.98-7.93 (m, 1H), 7.44-7.40 (m, 1H), 7.35-7.29 (m, 1H), 7.23-7.17 (m, 1H), 5.99 (s, 0.4H), 5.90 (d, J=3.6 Hz, 0.6H), 4.13 (q, J=7.2 Hz, 2H), 4.06 (s, 2H), 3.87-3.78 (m, 1H), 3.67-3.60 (m, 0.6H), 3.55 (s, 0.4H), 3.52-3.510 (m, 3H), 3.09-3.07 (m, 3H), 2.08-2.02 (m, 0.4H), 1.93-1.70 (m, 5H), 1.63-1.50 (m, 2.6H), 1.22 (t, J=7.2 Hz, 3H).

Compound 138: 1-tert-butyl 5-methyl 6-(2-chloro-4-fluorophenyl)-4-(trans-4-(N-(2-ethoxy-2-oxo-ethyl)-methyl-sulfonamido)-cyclohexyl)-2-(thiazol-2-yl)-pyrimidine-1,5(6H)-dicarboxylate (a Mixture of 2 Stereoisomers)

To a solution of methyl 4-(2-chloro-4-fluorophenyl)-6-(trans-4-(N-(2-ethoxy-2-oxoethyl)methylsulfonamido)cyclohexyl)-2-(thiazol-2-yl)-1,4-dihydropyrimidine-5-carboxylate Compound 137 (240 mg, 0.392 mmol) in tetrahydrofuran (5 mL) was added 4-dimethylaminopyridine (57 mg, 0.47 mmol) and di-tert-butyl dicarbonate (103 mg, 0.470 mmol) at room temperature. The mixture was stirred at 60° C. overnight under nitrogen atmosphere. After cooling down to room temperature, the mixture was concentrated under reduced pressure to give a residue, which was purified by C18 (acetonitrile:water=30% to 85%) to give the title compound (200 mg, 72% yield) as yellow solids.

Compound 138 (200 mg, 0.281 mmol) was further separated by chiral Prep. HPLC (separation condition: Column: Chiralpak IC 5 um 20*250 mm; Mobile Phase: Hex:EtOH:DEA=80:20:0.3 at 15 mL/min; Temp: 30° C.; Wavelength: 214 nm) to afford stereoisomers Compound 138A (88 mg, 44% yield) and Compound 138B (85 mg, 43% yield).

Compound 138B: LC-MS (ESI): $R_T$=2.20 min, mass calcd. for $C_{31}H_{38}ClFN_4O_8S_2$ 712.2, m/z found 713.1 [M+H]$^+$. Chiral HPLC (Column: Chiralpak IC 5 um 4.6*250 mm; Mobile Phase: Hex:EtOH:DEA=80:20:0.2 at 1.0 mL/min; Temp: 30° C.; Wavelength: 210 nm, 100% ee, Rt=21.183 min). $^1$H NMR (400 MHz, CDCl$_3$) δ 7.89 (d, J=3.2 Hz, 1H), 7.50 (d, J=3.2 Hz, 1H), 7.11 (dd, J=8.6, 2.6 Hz, 1H), 7.05-7.02 (m, 1H), 6.78 (td, J=8.4, 2.4 Hz, 1H), 6.69 (s, 1H), 4.20 (q, J=7.2 Hz, 2H), 4.11 (d, J=18.8 Hz, 1H), 4.04 (d, J=18.4 Hz, 1H), 3.83-3.77 (m, 1H), 3.71 (s, 3H), 3.59-3.53 (m, 1H), 3.15 (s, 3H), 2.06-1.87 (m, 5H), 1.71-1.68 (m, 1H), 1.54-1.46 (m, 2H), 1.31 (t, J=7.2 Hz, 3H), 1.23 (s, 9H).

Compound 139: 2-(N-(trans-4-(6-(2-chloro-4-fluorophenyl)-5-(methoxycarbonyl)-2-(thiazol-2-yl)-3,6-dihydropyrimidin-4-yl)cyclohexyl)methylsulfonamido)acetic Acid A solution of 1-tert-butyl 5-methyl 6-(2-chloro-4-fluorophenyl)-4-(trans-4-(N-(2-ethoxy-2-oxoethyl)methylsulfonamido)cyclohexyl)-2-(thiazol-2-yl)pyrimidine-1,5 (6H)-dicarboxylate Compound 138B (85 mg, 0.119 mmol) in 1M hydrochloric acid in dichloromethane (5 mL, 5 mmol) at room temperature. After stirred at room temperature for 5 hours under nitrogen atmosphere, the reaction mixture was concentrated to give a residue, which was dissolved in tetrahydrofuran (2 mL) and water (2 mL) and added lithium hydroxide (50 mg, 1.19 mmol) at room temperature. After stirring at room temperature overnight under nitrogen atmosphere, the mixture was added dropwise 1 N hydrochloride aqueous solution to adjust the pH value to 3-4. The separated aqueous solution was extracted with ethyl acetate (20 mL) for three times. The combined organic layers were washed with brine (20 mL) twice, dried over $Na_2SO_{4(s)}$ and filtered. The filtrate was concentrated under reduced pressure to give a residue, which was purified by C18 (acetonitrile:water=5% to 95%) to give the title compound (30 mg, 43% yield) as yellow solids. LC-MS (ESI): $R_T$=3.822 min, mass calcd. for $C_{24}H_{26}ClFN_4O_6S_2$ 584.1, m/z found 584.9 [M+H]$^+$. Chiral HPLC (Column: Chiralpak IG 5 um 4.6*250 mm; Mobile Phase: Hex:EtOH:TFA=70:30:0.2 at 1.0 mL/min; Temp: 30° C.; Wavelength: 230 nm, $R_T$=9.786 min). $^1$H NMR (400 MHz, DMSO-d$_6$) δ 12.73 (br s, 1H), 9.46 (d, J=3.2 Hz, 0.6H), 9.06 (s, 0.4H), 7.99-7.94 (m, 2H), 7.46-7.41 (m, 1H), 7.35-7.29 (m, 1H), 7.25-7.17 (m, 1H), 5.99 (s, 0.4H), 5.89 (d, J=3.2 Hz, 0.6H), 3.97 (s, 2H), 3.84-3.79 (m, 1H), 3.64-3.58 (m, 1H), 3.52-3.51 (m, 3H), 3.10-3.08 (m, 3H), 1.92-1.70 (m, 5H), 1.63-1.46 (m, 3H).

Compound 474: methyl 4-(2-chloro-3,4-difluorophenyl)-6-(1-(((2-hydroxyethyl)sulfonyl)piperidin-4-yl)-2-(thiazol-2-yl)-1,4-dihydropyrimidine-5-carboxylate

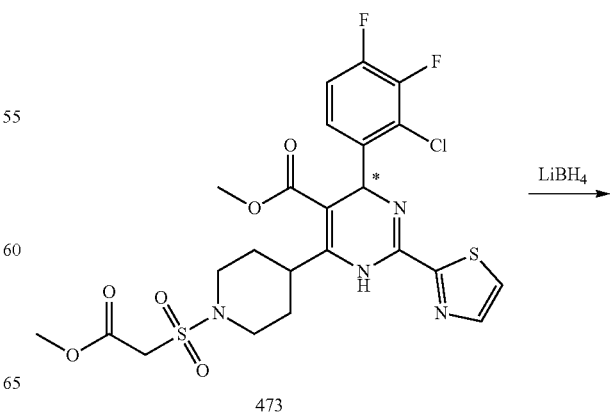

473

541

-continued

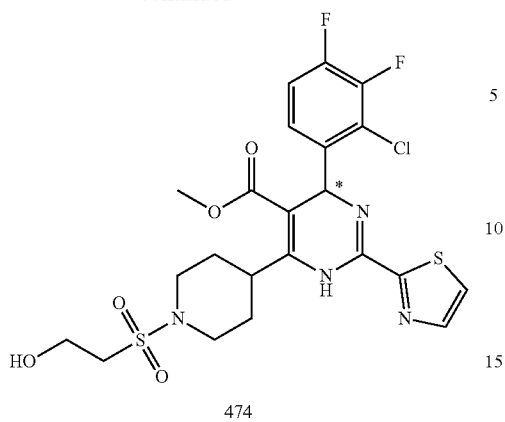

474

To a solution of methyl 4-(2-chloro-3,4-difluorophenyl)-6-(1-((2-methoxy-2-oxoethyl)sulfonyl)piperidin-4-yl)-2-(thiazol-2-yl)-1,4-dihydropyrimidine-5-carboxylate compound 473 (45 mg, 0.076 mmol) in tetrahydrofuran (2 mL) was added lithium borohydride (5.0 mg, 0.23 mmol) at 0° C., the mixture was stirred at 0° C. for 1 hour. The mixture was concentrated under reduced pressure at room temperature to give a residue, which was purified by Prep. HPLC (Column: gilson X-bridge C18 (5 μm 19*150 mm), Mobile phase A: water (+0.1% ammonium bicarbonate), Mobile phase B: acetonitrile, UV: 214 nm, Flow rate: 15 mL/min, Gradient: 40-70% (% B)) to afford the title compound 474 (21 mg, 49% yield) as yellow solids. LC-MS (ESI): $R_T$=4.021 min, mass calcd. for $C_{22}H_{23}ClFN_4O_5S_2$ 560.1, m/z found 561.1 [M+H]$^+$. $^1$H NMR (400 MHz, DMSO-d$_6$) δ 9.62 (s, 0.8H), 9.21 (s, 0.2H), 7.99-7.93 (m, 2H), 7.48-7.41 (m, 1H), 7.23-7.14 (m, 1H), 6.02 (s, 0.2H), 5.93 (s, 0.8H), 5.05-5.00 (m, 1H), 4.02-3.92 (m, 0.3H), 3.80-3.65 (m, 4.7H), 3.58 (s, 3H), 3.24-3.19 (m, 2H), 2.94-2.84 (m, 2H), 2.12-1.76 (m, 3.2H), 1.65-1.62 (m, 0.8H).

Compound 158: Methyl 4-(2-chloro-3-fluorophenyl)-6-(1-((1-(oxazol-2-ylmethyl)-1H-pyrazol-4-yl)sulfonyl)piperidin-4-yl)-2-(thiazol-2-yl)-1,4-dihydropyrimidine-5-carboxylate

542

-continued

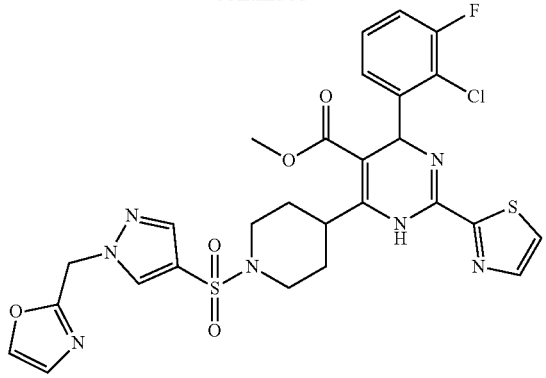

158

To a solution of methyl 6-(1-(((1H-pyrazol-4-yl)sulfonyl)piperidin-4-yl)-4-(2-chloro-3-fluorophenyl)-2-(thiazol-2-yl)-1,4-dihydropyrimidine-5-carboxylate 158A (80.0 mg, 0.142 mmol) in N,N-dimethylformamide (2 mL) was added potassium carbonate (39.0 mg, 0.284 mmol) and sodium iodide (21.0 mg, 0.142 mmol) at room temperature. After stirred at room temperature for 5 minutes, 2-(chloromethyl) oxazole (15.0 mg, 0.123 mmol) in N,N-dimethylformamide (1 mL). After stirred at room temperature overnight, the reaction mixture was poured into water (10 mL) and extracted with ethyl acetate (10 mL) twice. The combined organic layers were washed with water (10 mL) twice, brine (10 mL) twice, dried over $Na_2SO_{4(s)}$ and filtered. The filtrate was concentrated under reduced pressure to give a residue, which was purified by Prep. HPLC (Column: waters Kinete EVO C18 (5 μm 21.2*150 mm), Mobile phase A: water (+0.1% ammonium bicarbonate), Mobile phase B: acetonitrile, UV: 214 nm, Flow rate: 15 mL/min, Gradient: 30-80% (% B)) to give the title compound (25 mg, 27% yield) as yellow solids. LC-MS (ESI): $R_T$=4.318 min, mass calcd. for $C_{27}H_{25}ClFN_7O_5S_2$ 645.1, m/z found 646.1 [M+H]$^+$. $^1$H NMR (400 MHz, CDCl$_3$) δ 8.19 (s, 0.3H), 7.95 (d, J=2.8 Hz, 1H), 7.84-7.79 (m, 2H), 7.71 (s, 1H), 7.53 (d, J=3.2 Hz, 0.7H), 7.46-7.45 (m, 1H), 7.24-7.02 (m, 4H), 6.23 (s, 0.3H), 6.10 (d, J=2.8 Hz, 0.7H), 5.50 (s, 2H), 4.03-3.85 (m, 2.3H), 3.77-3.72 (m, 0.7H), 3.56-3.55 (m, 3H), 2.48-1.91 (m, 5.3H), 1.73-1.70 (m, 0.7H).

Compound 173: Methyl 4-(2-chloro-4-fluorophenyl)-6-((cis)-3-(hydroxymethyl) cyclohexyl)-2-(thiazol-2-yl)-1,4-dihydropyrimidine-5-carboxylate

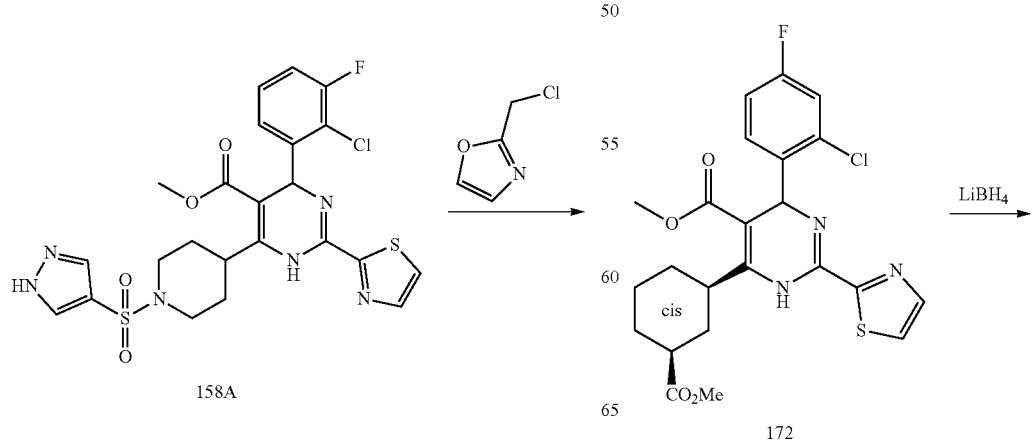

172

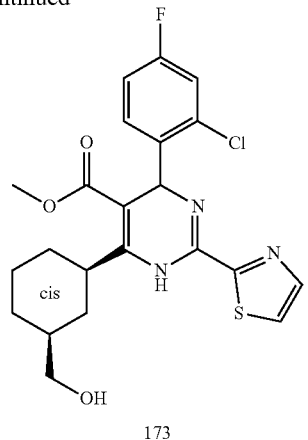
173

To a solution of methyl 4-(2-chloro-4-fluorophenyl)-6-((cis)-3-(methoxycarbonyl) cyclohexyl)-2-(thiazol-2-yl)-1,4-dihydropyrimidine-5-carboxylate compound 172 (100 mg, 0.200 mmol) in tetrahydrofuran (3 mL) was added lithium borohydride (22 mg, 1.0 mmol) at room temperature. After stirring overnight at room temperature, the suspension was quenched with water (20 mL) and extracted with ethyl acetate (20 mL) for three times. The combined organic layers were washed with brine (20 mL), dried over $Na_2SO_{4(s)}$ and filtered. The filtrate was concentrated under reduced pressure to give a residue, which was purified by Prep. HPLC (Column: gilson X-bridge C18 (5 μm 19*150 mm), Mobile Phase A: water (+0.1% ammonium bicarbonate), Mobile Phase B: acetonitrile, UV: 214 nm, Flow rate: 15 mL/min, Gradient: 35-90% (% B)) to give the title compound (90 mg, 96% yield) as yellow solids. LC-MS (ESI): $R_T$=3.055 min, mass calcd. for $C_{22}H_{23}ClFN_3O_3S$ 463.1, m/z found 464.2 [M+H]$^+$. $^1$H NMR (400 MHz, CDCl$_3$) δ 8.15 (s, 0.6H), 7.82 (d, J=2.8 Hz, 1H), 7.49 (d, J=3.6 Hz, 0.3H), 7.44 (d, J=3.6 Hz, 0.7H), 7.40 (br s, 0.4H), 7.33-7.29 (m, 1H), 7.15-7.11 (m, 1H), 6.96-6.87 (m, 1H), 6.18 (d, J=1.6 Hz, 0.7H), 6.04 (d, J=2.4 Hz, 0.3H), 4.08-4.01 (m, 0.7H), 3.86-3.79 (m, 0.3H), 3.61-3.53 (m, 5H), 2.12-1.62 (m, 5H), 1.58-1.02 (m, 5H).

Compound 173A and 173C: Methyl 4-(2-chloro-4-fluorophenyl)-6-((cis)-3-(hydroxymethyl)cyclohexyl)-2-(thiazol-2-yl)-1,4-dihydropyrimidine-5-carboxylate Racemic compound 173 (300 mg, 0.650 mmol) was separated by chiral Prep. HPLC (the first separation: (Column: Chiralpak IC 5 μm 50*250 mm; Mobile Phase: Hex:IPA:DEA=85:15:0.1 at 60 mL/min; Temp: 30° C.; Wavelength: 254 nm) and the second separation (Column: Chiralpak IC 5 μm 50*250 mm; Mobile Phase: Hex:EtOH=90:10:0.1 at 60 mL/min; Temp: 30° C.; Wavelength: 254 nm)) followed by purified by C18 column (acetonitrile:water=40% to 95%) to afford the title compounds 173A (42.0 mg, 14% yield, 96.2% stereopure), 173B (38.4 mg, 13% yield, 94.0% stereopure), 173C (38.7 mg, 13% yield, 100% stereopure) and 173D (43.9 mg, 15% yield, 100% stereopure) as yellow solids.

Compound 173A: LC-MS (ESI): $R_T$=4.063 min, mass calcd. for $C_{22}H_{23}ClFN_3O_3S$ 463.1, m/z found 463.9 [M+H]$^+$. Chiral HPLC (Column: Chiralpak IG 5 μm 4.6*250 mm; Mobile Phase: Hex:EtOH:DEA=90:10:0.2 at 1 mL/min; Temp: 30° C.; Wavelength: 230 nm, $R_T$=11.411 min). $^1$H NMR (400 MHz, CDCl$_3$) δ 8.15 (s, 0.7H), 7.83-7.81 (m, 1H), 7.48 (d, J=3.2 Hz, 0.3H), 7.44 (d, J=3.6 Hz, 0.7H), 7.39 (br s, 0.3H), 7.33-7.29 (m, 1H), 7.15-7.11 (m, 1H), 6.97-6.89 (m, 1H), 6.19 (s, 0.7H), 6.05 (d, J=2.4 Hz, 0.3H), 4.07-4.00 (m, 0.7H), 3.85-3.79 (m, 0.3H), 3.61-3.53 (m, 5H), 2.12-2.09 (m, 1H), 1.99-1.76 (m, 4H), 1.67-1.60 (m, 1H), 1.55-1.46 (m, 1H), 1.41-1.34 (m, 1H), 1.30-1.21 (m, 1H), 1.13-1.05 (m, 1H).

Compound 173C: LC-MS (ESI): $R_T$=4.044 min, mass calcd. for $C_{22}H_{23}ClFN_3O_3S$ 463.1, m/z found 463.9 [M+H]$^+$. Chiral HPLC (Column: Chiralpak IC 5 μm 4.6*250 mm; Mobile Phase: Hex:IPA:DEA=90:10:0.2 at 1 mL/min; Temp: 30° C.; Wavelength: 230 nm, $R_T$=15.756 min). $^1$H NMR (400 MHz, CDCl$_3$) δ 8.14 (s, 0.6H), 7.82-7.81 (m, 1H), 7.48 (d, J=2.8 Hz, 0.3H), 7.44 (d, J=2.8 Hz, 0.7H), 7.39 (br s, 0.4H), 7.32-7.29 (m, 1H), 7.15-7.11 (m, 1H), 6.95-6.87 (m, 1H), 6.18 (s, 0.7H), 6.04 (d, J=2.8 Hz, 0.3H), 4.08-4.01 (m, 0.7H), 3.86-3.79 (m, 0.3H), 3.61 (s, 0.9H), 3.59 (s, 2.1H), 3.58-3.50 (m, 2H), 2.05-1.98 (m, 2H), 1.90-1.70 (m, 3H), 1.55-1.41 (m, 2H), 1.36-1.27 (m, 1H), 1.21-1.03 (m, 2H).

Compound 180B: (cis)-Methyl 4-(2-chloro-4-fluorophenyl)-6-(4-(N-(2-hydroxyethyl)methylsulfonamido)cyclohexyl)-2-(thiazol-2-yl)-1,4-dihydro-pyrimidine-5-carboxylate

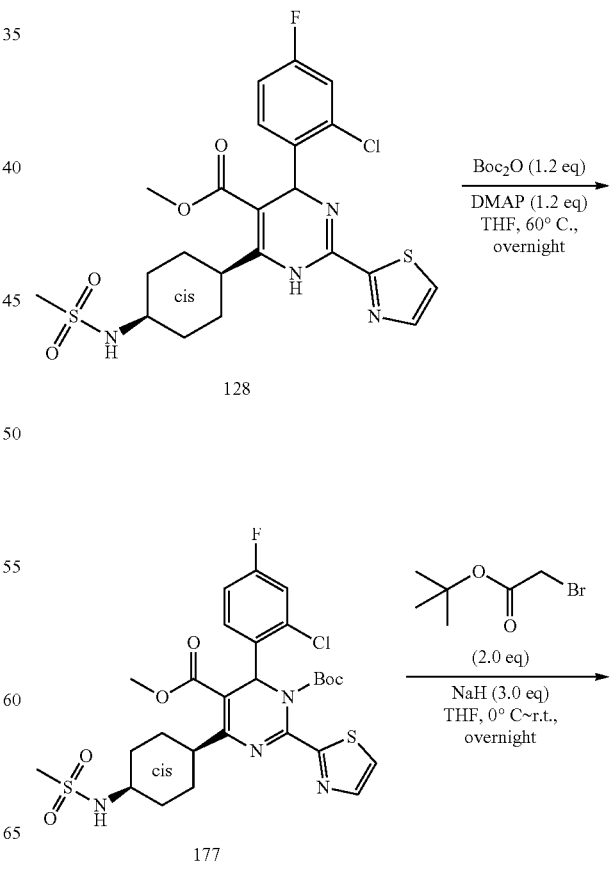
128

177

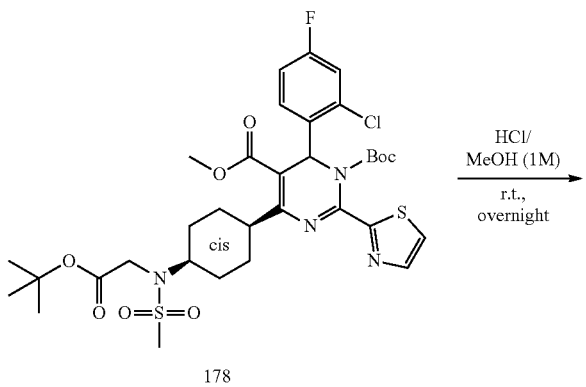

178

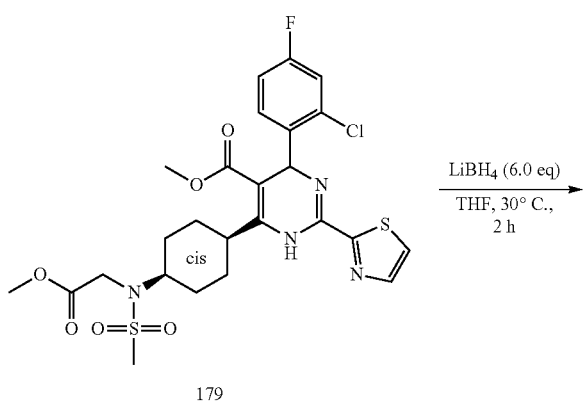

179

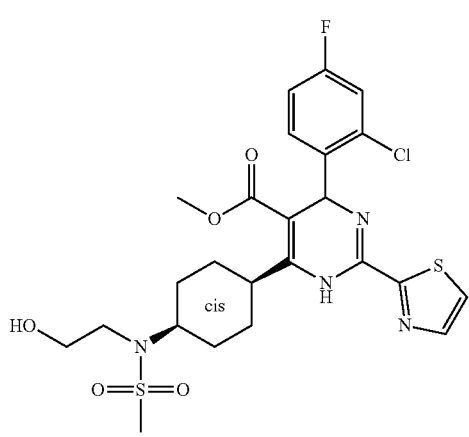

180

Compound 177: (cis)-1-tert-Butyl 5-methyl 6-(2-chloro-4-fluorophenyl)-4-(4-(methylsulfonamido)cyclohexyl)-2-(thiazol-2-yl)pyrimidine-1,5(6H)-dicarboxylate To a solution of (cis)-methyl 4-(2-chloro-4-fluorophenyl)-6-(4-(methylsulfonamido)-cyclohexyl)-2-(thiazol-2-yl)-1,4-dihydropyrimidine-5-carboxylate 128 (1.40 g, 2.66 mmol) in tetrahydrofuran (14 mL) were added N,N-dimethylpyridin-4-amine (389 mg, 3.19 mmol) and di-tert-butyl dicarbonate (696 mg, 3.19 mmol) at room temperature. After stirred at 60° C. overnight, the mixture was concentrated under reduced pressure to give a residue, which was purified by silica gel column chromatography (petroleum ether:ethyl acetate:tetrahydrofuran=10:1:1 to 5:1:1) to give the title compound (1.30 g, 78% yield) as yellow solids. $^1$H NMR (300 MHz, CDCl$_3$) δ 7.89 (d, J=2.4 Hz, 1H), 7.49 (d, J=2.1 Hz, 1H), 7.14-7.10 (m, 1H), 7.07-7.02 (m, 1H), 6.83-6.75 (m, 1H), 6.71-6.69 (m, 1H), 5.01-4.93 (m, 1H), 3.86-3.78 (m, 1H), 3.71 (s, 3H), 3.68-3.57 (m, 1H), 3.02 (s, 3H), 2.02-1.74 (m, 7H), 1.57-1.51 (m, 1H), 1.23 (s, 9H).

Compound 178: (cis)-1-tert-Butyl 5-methyl 4-(4-(N-(2-(tert-butoxy)-2-oxoethyl)methylsulfonamido)cyclohexyl)-6-(2-chloro-4-fluorophenyl)-2-(thiazol-2-yl)pyrimidine-1,5(6H)-dicarboxylate To a solution of (cis)-1-tert-butyl 5-methyl 6-(2-chloro-4-fluorophenyl)-4-(4-(methylsulfonamido)cyclohexyl)-2-(thiazol-2-yl)pyrimidine-1,5(6H)-dicarboxylate 177 (1.0 g, 1.60 mmol) in tetrahydrofuran (10 mL) was added 60% wt. sodium hydride in mineral oil (192 mg, 4.80 mmol) at 0° C. After stirring at room temperature for 30 minutes, tert-butyl 2-bromoacetate (623 mg, 3.19 mmol) was added at 0° C. After stirred at room temperature overnight, the reaction mixture was quenched with saturated sodium bicarbonate aqueous solution (20 mL) and extracted with ethyl acetate (20 mL) twice. The combined organic layers were washed with brine (20 mL), dried over Na$_2$SO$_{4(s)}$ and filtered. The filtrate was concentrated under reduced pressure to give a residue, which was purified by silica gel column chromatography (petroleum ether:ethyl acetate:tetrahydrofuran=10:1:1 to 5:1:1) to give the title compound (430 mg, 36% yield) as yellow solids. $^1$H NMR (300 MHz, CDCl$_3$) δ 7.92-7.88 (m, 1H), 7.51-7.47 (m, 1H), 7.15-7.09 (m, 1H), 7.07-7.01 (m, 1H), 6.82-6.74 (m, 1H), 6.70-6.67 (m, 1H), 4.20-4.05 (m, 1.6H), 3.98-3.95 (m, 0.6H), 3.94-3.89 (m, 0.8H), 3.80-3.76 (m, 0.5H), 3.71 (s, 1H), 3.69 (s, 2H), 3.62-3.52 (m, 0.5H), 3.15 (s, 1H), 3.11 (s, 2H), 2.24-2.17 (m, 1H), 2.14-2.00 (m, 2H), 1.95-1.75 (m, 4H), 1.71-1.59 (m, 1H), 1.48 (s, 3H), 1.38 (s, 6H), 1.24 (s, 6H), 1.22 (s, 3H).

Intermediate 179: (cis)-Methyl 4-(2-chloro-4-fluorophenyl)-6-(4-(N-(2-methoxy-2-oxoethyl)methylsulfonamido)cyclohexyl)-2-(thiazol-2-yl)-1,4-dihydropyrimidine-5-carboxylate To a solution of 1 M hydrochloride in methanol (10 mL, 10 mmol) was added (cis)-1-tert-butyl 5-methyl 4-(4-(N-(2-(tert-butoxy)-2-oxoethyl)methylsulfonamido)-cyclohexyl)-6-(2-chloro-4-fluorophenyl)-2-(thiazol-2-yl)pyrimidine-1,5(6H)-dicarboxylate 178 (430 mg, 0.580 mmol). After stirred at room temperature overnight, the mixture was concentrated under reduced pressure to give a residue, which was dissolved in dichloromethane (20 mL), washed with saturated sodium bicarbonate aqueous solution (20 mL). The separated aqueous phase was extracted with dichloromethane (20 mL) for three times. The combined organic layers were washed with brine (20 mL) twice, dried over $Na_2SO_{4(s)}$ and filtered. The filtrate was concentrated under reduced pressure to give a residue, which was purified by silica gel column chromatography (petroleum ether:ethyl acetate:tetrahydrofuran=20:1:1) to give the title compound (340 mg, 98% yield) as yellow solids. $^1$H NMR (300 MHz, CDCl$_3$) δ 7.85-7.80 (m, 1H), 7.47-7.45 (m, 1H), 7.32-7.29 (m, 1H), 7.19-7.15 (m, 1H), 7.06-7.01 (m, 1H), 6.96-6.89 (m, 1H), 6.19-6.15 (m, 0.3H), 6.08-6.01 (m, 0.7H), 4.10 (s, 2H), 3.99-3.95 (m, 1H), 3.89-3.85 (m, 1H), 3.72 (s, 3H), 3.58 (s, 3H), 3.14 (s, 3H), 2.09-2.00 (m, 5H), 1.78-1.58 (m, 3H).

Compound 180: (cis)-Methyl 4-(2-chloro-4-fluorophenyl)-6-(4-(N-(2-hydroxy-ethyl)methylsulfonamido)cyclohexyl)-2-(thiazol-2-yl)-1,4-dihydropyrimidine-5-carboxylate To a solution of (cis)-methyl 4-(2-chloro-4-fluorophenyl)-6-(4-(N-(2-methoxy-2-oxoethyl)methylsulfonamido)cyclohexyl)-2-(thiazol-2-yl)-1,4-dihydropyrimidine-5-carboxylate 179 (320 mg, 0.534 mmol) in tetrahydrofuran (5 mL) was added lithium tetrahydroborate (71 mg, 3.21 mmol) at 0° C. After stirred at 30° C. for 2 hours under nitrogen atmosphere, the reaction mixture was quenched with 1 M hydrochloride aqueous solution (20 mL) slowly and extracted with dichloromethane (20 mL) for three times. The combined organic layers were washed with brine (20 mL), dried over $Na_2SO_{4(s)}$ and filtered. The filtrate was concentrated under reduced pressure to give a residue, which was purified by Prep. HPLC (Column: Gilson X-bridge C18 (5 μm 19*150 mm), Mobile Phase A: water (0.2% ammonium acetate), Mobile Phase B: acetonitrile, UV: 214 nm, Flow rate: 15 mL/min, Gradient: 30-70% (% B)) to give the title compound (110 mg, 36% yield) as yellow solids. LC-MS (ESI): $R_T$=4.007 min, mass calcd. for $C_{24}H_{28}ClFN_4O_5S_2$ 570.1, m/z found 571.1 [M+H]$^+$.

Compound 180B: (cis)-Methyl 4-(2-chloro-4-fluorophenyl)-6-(4-(N-(2-hydroxy-ethyl)methylsulfonamido)cyclohexyl)-2-(thiazol-2-yl)-1,4-dihydropyrimidine-5-carboxylate Racemic (cis)-methyl 4-(2-chloro-4-fluorophenyl)-6-(4-(N-(2-hydroxyethyl)-methylsulfonamido)cyclohexyl)-2-(thiazol-2-yl)-1,4-dihydropyrimidine-5-carboxylate 180 (110 mg, 0.193 mmol) was separated by chiral Prep. HPLC (the first separation condition: Column: Chiralpak IA 5 μm 20*250 mm; Mobile Phase: Hex:EtOH:DEA=70:30:0.3 at 22 mL/min; Temp: 30° C.; Wavelength: 230 nm; the second separation condition: Column: Chiralpak AD-H 5 μm 20*250 mm; Mobile Phase: Hex:EtOH:DEA=85:15:0.3 at 15 mL/min; Temp: 30° C.; Wavelength: 214 nm) to afford the title compounds 180A (15 mg, 14% yield, 100% stereopure) as yellow solids and 180B (30 mg, 27% yield, 100% stereopure) as yellow solids. Compound 180B: LC-MS (ESI): $R_T$=3.946 min, mass calcd. for $C_{24}H_{28}ClFN_4O_5S_2$ 570.1, m/z found 570.9 [M+H]$^+$. Chiral analysis (Column: Chiralpak IA 5 μm 4.6*250 mm; Mobile Phase: Hex:EtOH:DEA=70:30:0.2 at 1.0 mL/min; Temp: 30° C.; Wavelength: 230 nm, $R_T$=7.725 min). $^1$H NMR (400 MHz, DMSO-d$_6$) δ 9.43 (br s, 0.6H), 9.10 (br s, 0.4H), 8.01-7.97 (m, 1.5H), 7.95-7.92 (m, 0.5H), 7.44-7.40 (m, 1H), 7.36-7.30 (m, 1H), 7.24-7.17 (m, 1H), 6.00 (s, 0.4H), 5.91 (s, 0.6H), 4.79-4.73 (m, 1H), 3.86-3.74 (m, 1H), 3.59-3.55 (m, 1H), 3.53 (s, 1.7H), 3.51 (s, 1.3H), 3.50-3.47 (m, 2H), 3.17 (t, J=7.2 Hz, 2H), 2.97 (s, 1.7H), 2.96 (s, 1H), 2.95 (s, 0.3H), 2.11-2.03 (m, 0.4H), 1.92-1.73 (m, 5H), 1.66-1.56 (m, 2.6H).

Compound 182A: (trans)Methyl 4-(2-chloro-4-fluorophenyl)-6-(4-(2-methoxyethylsulfonamido)cyclohexyl)-2-(thiazol-2-yl)-1,4-dihydropyrimidine-5-carboxylate

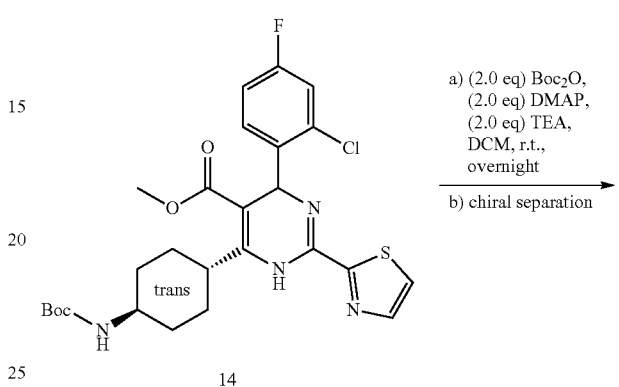

Compound 181A: (trans)-1-tert-Butyl 5-methyl 4-(4-((tert-butoxycarbonyl)amino)-cyclohexyl)-6-(2-chloro-4-fluorophenyl)-2-(thiazol-2-yl)pyrimidine-1,5(6H)-dicarboxylate To a solution of (trans)-methyl 6-(4-((tert-butoxycarbonyl)amino)cyclohexyl)-4-(2-chloro-4-fluorophenyl)-2-(thiazol-2-yl)-1,4-dihydropyrimidine-5-carboxylate 14 (500 mg, 0.910 mmol) in dichloromethane (5 mL) were added di-tert-butyl dicarbonate (398 mg, 1.82 mmol) and triethylamine (184 mg, 1.82 mmol) at room temperature. After stirred for 30 minutes, N,N-dimethylpyridin-4-amine (222 mg, 1.82 mmol) was added. Then the mixture was stirred at room temperature overnight. The solvent was removed under reduced pressure and the obtained residue was purified by silica gel column chromatography (ethyl acetate:petroleum ether=1:5) to give a yellow solid (400 mg), which was separated by chiral Prep. SFC (Column: Chiralpak IE 5 μm 20*250 mm; Mobile Phase: $CO_2$: IPA=75:25 at 50 g/min; Col. Temp: 40° C.; Wavelength: 214 nm, Back pressure: 100 bar) to afford 181A (80 mg, 14% yield, 99.4% stereopure) and 181B (90 mg, 15% yield, 96.9% stereopure) as yellow solids.

Compound 181A: Chiral analysis (Column: Chiralpak IE 5 μm 4.6*250 mm, Mobile Phase: $CO_2$: IPA=75:25 at 3.0 g/min; Col. Temp: 39.6° C.; Wavelength: 230 nm, Back pressure: 100 bar, $R_T$=2.89 min). $^1$H NMR (400 MHz, DMSO-$d_6$) δ 8.00-7.99 (m, 1H), 7.47 (dd, J=9.2, 2.4 Hz, 1H), 7.14 (td, J=8.0, 2.0 Hz, 1H), 7.05-7.01 (m, 1H), 6.83 (d, J=8.4 Hz, 1H), 6.55 (s, 1H), 3.66 (s, 3H), 3.45-3.40 (m, 1H), 3.31-3.24 (m, 1H), 1.94-1.82 (m, 3H), 1.88-1.60 (m, 2H), 1.54-1.50 (m, 1H), 1.40 (s, 9H), 1.32-1.24 (m, 2H), 1.15 (s, 9H).

Compound 182A: (trans)Methyl 4-(2-chloro-4-fluorophenyl)-6-(4-(2-methoxyethylsulfonamido)cyclohexyl)-2-(thiazol-2-yl)-1,4-dihydropyrimidine-5-carboxylate To a solution of 4 N hydrochloride in methanol (5 mL) was added (trans)-1-tert-butyl 5-methyl 4-(4-((tert-butoxycarbonyl)amino)cyclohexyl)-6-(2-chloro-4-fluorophenyl)-2-(thiazol-2-yl)pyrimidine-1,5(6H)-dicarboxylate 181A (100 mg, 0.154 mmol) at room temperature. After stirred overnight, the reaction mixture was concentrated to give a residue, which was dissolved in tetrahydrofuran (10 mL). To this solution was added triethylamine (92 mg, 0.912 mmol) at 0° C. After stirred at room temperature for 30 minutes. 2-methoxyethanesulfonyl chloride (96 mg, 0.610 mmol) was added and the mixture was stirred at 0° C. for 2 hours. Then it was concentrated to give a residue, which was purified by prep-thin layer chromatography (petroleum ether:ethyl acetate=1:1) to give the title compound (22 mg, 25% yield, 98.2% stereopure) as yellow solids. LC-MS (ESI): $R_T$=4.004 min, mass calcd. for $C_{24}H_{28}ClFN_4O_5S_2$ 570.1, m/z found 570.9 [M+H]$^+$. Chiral analysis (Column: Chiralpak IC 5 μm 4.6*250 mm; Mobile Phase: Hex:EtOH=70:30 at 1.0 mL/min; Temp: 30° C.; Wavelength: 230 nm, $R_T$=17.095 min). 1H NMR (400 MHz, DMSO-$d_6$) δ 9.46 (d, J=3.2 Hz, 0.6H), 9.00 (s, 0.4H), 8.00-7.98 (m, 1.6H), 7.94-7.93 (m, 0.4H), 7.44-7.41 (m, 1H), 7.35-7.29 (m, 1H), 7.24-7.14 (m, 2H), 6.00 (s, 0.4H), 5.90 (d, J=3.6 Hz, 0.6H), 3.83-3.76 (m, 0.4H), 3.69-3.65 (m, 2H), 3.58-3.55 (m, 0.6H), 3.52 (s, 1.8H), 3.50 (s, 1.2H), 3.31-3.28 (m, 5.4H), 3.16-3.08 (m, 0.6H), 2.05-1.96 (m, 2.4H), 1.88-1.66 (m, 3H), 1.60-1.57 (m, 0.6H), 1.38-1.22 (m, 2H).

Compound 185B: Methyl 4-(2-chloro-4-fluorophenyl)-6-(1-((2-hydroxyethyl)sulfonyl)piperidin-4-yl)-2-(thiazol-2-yl)-1,4-dihydropyrimidine-5-carboxylate

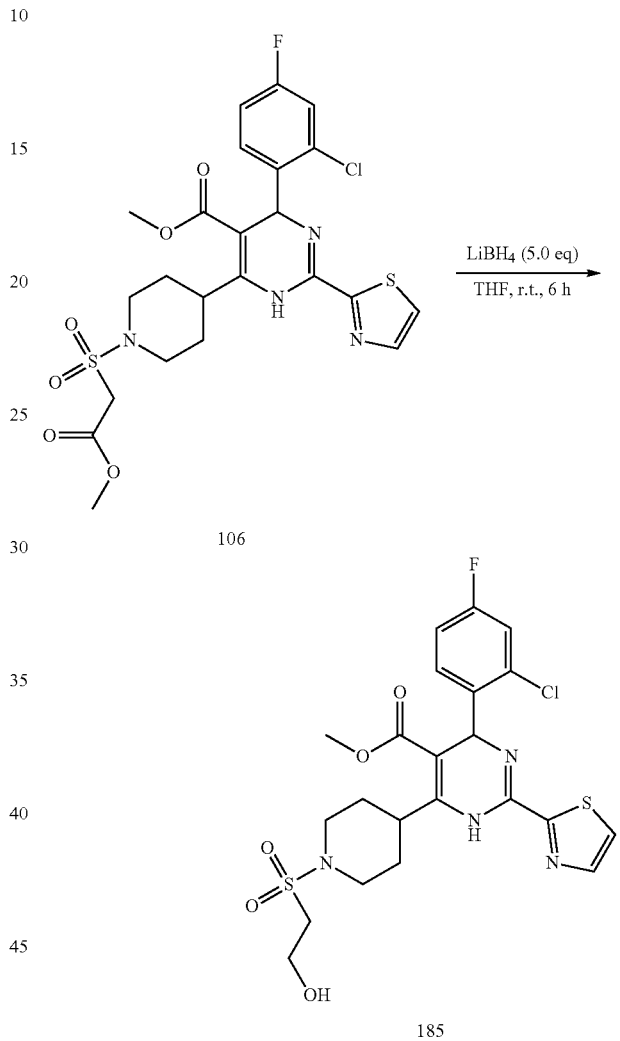

To a solution of methyl 4-(2-chloro-4-fluorophenyl)-6-(1-((2-methoxy-2-oxoethyl) sulfonyl)piperidin-4-yl)-2-(thiazol-2-yl)-1,4-dihydropyrimidine-5-carboxylate compound 106 (140 mg, 0.250 mmol) in tetrahydrofuran (40 mL) was added lithium borohydride (27.0 mg, 1.25 mmol) at 0° C. After stirred at room temperature for 6 hours, the mixture was added water (30 mL), extracted with ethyl acetate (30 mL) for three times. The separated organic layers were washed with brine (30 mL), dried over $Na_2SO_{4(s)}$ and filtered. The filtrate was concentrated to give a residue, which was purified by Prep. HPLC (Column: gilson, x-bridge C18 (5 μm 19*150 mm, Mobile Phase A: Water (+0.1% ammonium bicarbonate), Mobile Phase B: acetonitrile, UV: 214 nm, Flow rate: 15 mL/min, Gradient: 30-80% (% B)) to give the title compound compound 185 (60 mg, 45% yield) as yellow solids. LC-MS (ESI): $R_T$=3.962 min, mass calcd. for $C_{22}H_{24}ClFN_4O_5S_2$ 542.1, m/z found 543.2

[M+H]$^+$. $^1$H NMR (400 MHz, CDCl$_3$) δ 8.20 (s, 0.2H), 7.84-7.81 (m, 1H), 7.52 (d, J=3.2 Hz, 0.8H), 7.46-7.44 (m, 1H), 7.30-7.27 (m, 0.8H), 7.26-7.25 (m, 0.2H), 7.16-7.12 (m, 1H), 6.98-6.89 (m, 1H), 6.19 (s, 0.2H), 6.07 (d, J=2.8 Hz, 0.8H), 4.23-4.15 (m, 0.2H), 4.12-4.01 (m, 2H), 3.93-3.89 (m, 2.8H), 3.60 (s, 2H), 3.59 (s, 1H), 3.22-3.19 (m, 2H), 3.02-2.90 (m, 2H), 2.79-2.73 (m, 1H), 2.31-2.28 (m, 0.8H), 2.21-2.03 (m, 1H), 1.97-1.85 (m, 1.2H), 1.83-1.72 (m, 1H).

Racemic compound 185 (127 mg, 0.200 mmol) was separated by chiral Prep. HPLC (Column: Chiralpak IA 5 μm 20*250 mm; Mobile Phase: Hex:EtOH:DEA=70:30:0.3 at 25 mL/min; Temp: 30° C.; Wavelength: 230 nm) to give the title compounds compound 185A (51.6 mg, 41% yield, 100% stereopure) and compound 185B (59.2 mg, 47% yield, 98.4% stereopure) as yellow solids.

Compound 185A: LC-MS (ESI): R$_T$=3.954 min, mass calcd. for C$_{22}$H$_{24}$ClFN$_4$O$_5$S$_2$ 542.1, m/z found 543.1 [M+H]$^+$. Chiral HPLC (Column: Chiralpak IA 5 μm 4.6*250 mm; Mobile Phase: Hex:EtOH:DEA=70:30:0.2 at 1.0 mL/min; Temp: 30° C.; Wavelength: 230 nm; R$_T$=7.832 min). $^1$H NMR (400 MHz, CDCl$_3$) δ 8.16 (s, 0.2H), 7.89-7.77 (m, 1H), 7.54 (d, J=12.0 Hz, 0.8H), 7.49 (d, J=7.6 Hz, 0.2H), 7.44 (br s, 0.8H), 7.32-7.25 (m, 0.6H), 7.25-7.23 (m, 0.4H), 7.19-7.14 (m, 1H), 7.01-6.87 (m, 1H), 6.19 (s, 0.2H), 6.07 (d, J=2.4 Hz, 0.8H), 4.28-4.16 (m, 0.2H), 4.16-4.06 (m, 2H), 4.05-3.87 (m, 2.8H), 3.60 (s, 2H), 3.59 (s, 1H), 3.25-3.19 (m, 2H), 3.07-2.87 (m, 2H), 2.80-2.67 (m, 1H), 2.36-2.18 (m, 0.7H), 2.16-2.10 (m, 1H), 1.99-1.81 (m, 1.3H), 1.76-1.68 (m, 1H).

Compound 185B LC-MS (ESI): R$_T$=3.951 min, mass calcd. for C$_{22}$H$_{24}$ClFN$_4$O$_5$S$_2$ 542.1, m/z found 543.1 [M+H]$^+$. Chiral HPLC (Column: Chiralpak IA 5 μm 4.6*250 mm; Mobile Phase: Hex:EtOH:DEA=70:30:0.2 at 1.0 mL/min; Temp: 30° C.; Wavelength: 230 nm; R$_T$=11.235 min). $^1$H NMR (400 MHz, CDCl$_3$) δ 8.19 (br s, 0.2H), 7.88-7.78 (m, 1H), 7.54 (d, J=14.0 Hz, 0.8H), 7.48 (d, J=15.2 Hz, 0.2H), 7.39 (br s, 0.8H), 7.32-7.30 (m, 0.7H), 7.25-7.23 (m, 0.3H), 7.19-7.13 (m, 1H), 7.03-6.85 (m, 1H), 6.19 (s, 0.2H), 6.07 (d, J=2.8 Hz, 0.8H), 4.27-4.17 (m, 0.2H), 4.17-4.07 (m, 2H), 4.02-3.87 (m, 2.8H), 3.60 (s, 2H), 3.59 (s, 1H), 3.27-3.13 (m, 2H), 3.02-2.83 (m, 2H), 2.78-2.67 (m, 1H), 2.35-2.16 (m, 0.7H), 2.11-2.04 (m, 1H), 2.00-1.88 (m, 1.3H), 1.80-1.67 (m, 1H).

Compound 186A: (trans)-Methyl 4-(2-chloro-4-fluorophenyl)-6-(4-(propyl-sulfonamido)cyclohexyl)-2-(thiazol-2-yl)-1,4-dihydropyrimidine-5-carboxylate

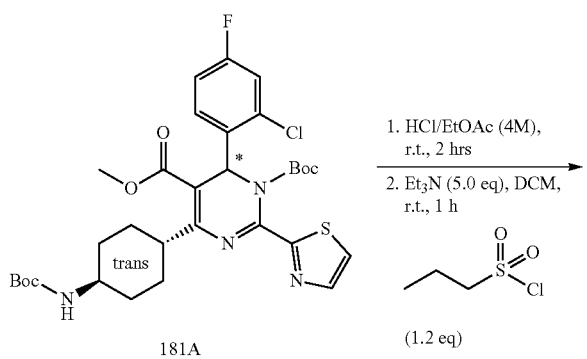

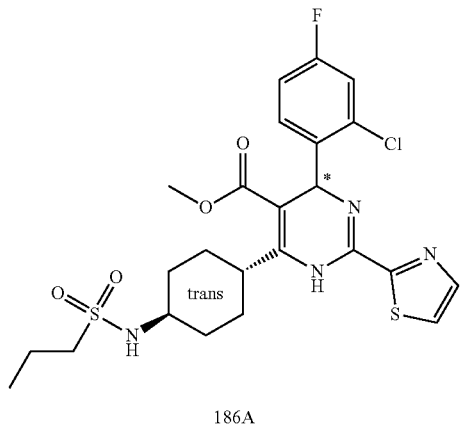

186A

A solution of (trans)-1-tert-butyl 5-methyl 4-(4-((tert-butoxycarbonyl) amino)cyclohexyl)-6-(2-chloro-4-fluorophenyl)-2-(thiazol-2-yl)pyrimidine-1,5(6H)-dicarboxylate 181A (100 mg, 0.154 mmol) in 4 M hydrochloride in ethyl acetate (5 mL, 20 mmol) was stirred at room temperature for 2 hours. Then the mixture was concentrated under reduced pressure to give a residue, which was dissolved in dichloromethane (5 mL). To this solution, triethylamine (78 mg, 0.770 mmol) and propane-1-sulfonyl chloride (26 mg, 0.185 mmol) were added. After stirred at room temperature for 2 hours, the mixture was quenched with saturated sodium bicarbonate aqueous solution (20 mL), extracted with dichloromethane (20 mL) for three times. The combined organic layers were washed with brine (20 mL) twice, dried over Na$_2$SO$_{4(s)}$ and filtered. The filtrate was concentrated under reduced pressure to give a residue, which was purified by prep. thin layer chromatography (petroleum ether:ethyl acetate=3:2) to give the title compound (40 mg, 47% yield, 98.1% stereopure) as yellow solids. LC-MS (ESI): R$_T$=3.988 min, mass calcd. for C$_{24}$H$_{28}$ClFN$_4$O$_4$S$_2$ 554.1, m/z found 554.9 [M+H]$^+$. Chiral analysis (Column: Chiralpak IA 5 μm 4.6*250 mm; Mobile Phase: Hex:EtOH:DEA=70:30:0.2 at 1.0 mL/min; Temp: 30° C.; Wavelength: 230 nm, R$_T$=8.095 min). $^1$H NMR (400 MHz, DMSO-d$_6$) δ 9.45 (br s, 0.6H), 9.01 (br s, 0.4H), 7.99-7.97 (m, 1.5H), 7.94-7.93 (m, 0.5H), 7.44-7.40 (m, 1H), 7.35-7.29 (m, 1H), 7.23-7.18 (m, 1H), 7.12-7.08 (m, 1H), 6.00 (s, 0.4H), 5.90 (d, J=3.6 Hz, 0.6H), 3.82-3.77 (m, 0.4H), 3.57-3.56 (m, 0.6H), 3.51 (s, 1.6H), 3.50 (s, 1.4H), 3.30-3.24 (m, 0.4H), 3.10-3.07 (m, 0.6H), 3.02-2.96 (m, 2H), 1.99-1.94 (m, 2H), 1.86-1.78 (m, 2H), 1.72-1.66 (m, 3H), 1.64-1.56 (m, 1H), 1.39-1.30 (m, 2H), 1.01-0.97 (m, 3H).

Compound 187B: (trans)-Methyl 4-(2-chloro-4-fluorophenyl)-6-(4-(2-hydroxyethylsulfonamido)cyclohexyl)-2-(thiazol-2-yl)-1,4-dihydropyrimidine-5-carboxylate

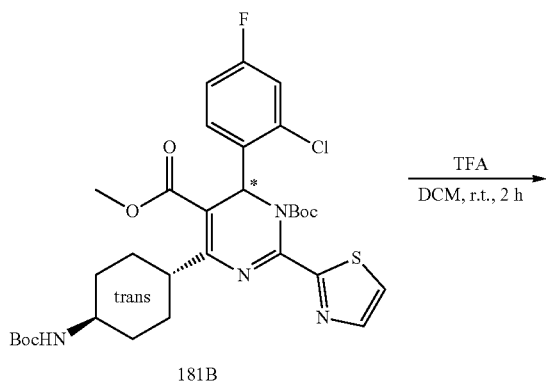

181B

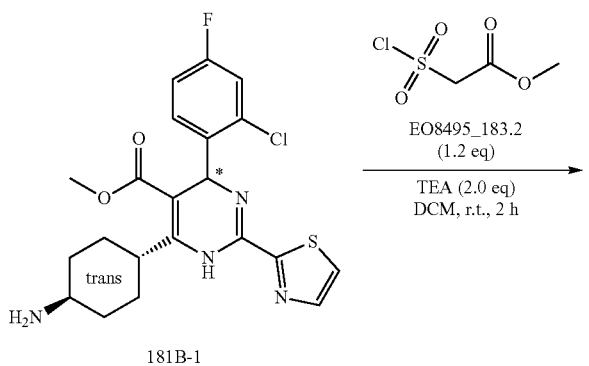

181B-1

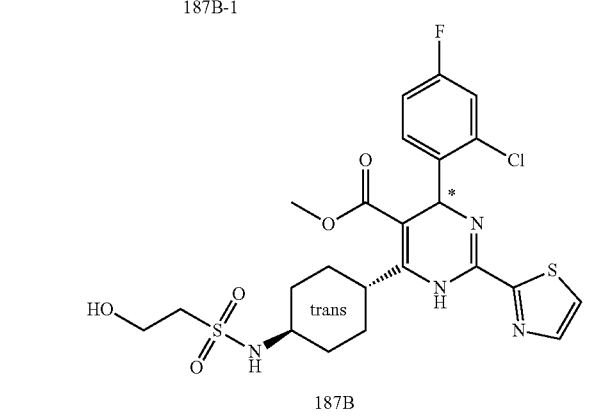

187B-1

187B

Compound 181B-1: (trans)-Methyl 6-(4-aminocyclohexyl)-4-(2-chloro-4-fluorophenyl)-2-(thiazol-2-yl)-1,4-dihydropyrimidine-5-carboxylate To a solution of (trans)-1-tert-butyl 5-methyl 4-(4-((tert-butoxycarbonyl)amino)cyclohexyl)-6-(2-chloro-4-fluorophenyl)-2-(thiazol-2-yl)pyrimidine-1,5(6H)-dicarboxylate compound 181B (200 mg, 0.31 mmol) in dichloromethane (8 mL) was added trifluoroacetic acid (5 mL) under nitrogen atmosphere. After stirred at room temperature for 2 hours, the mixture was concentrated under reduced pressure to give a residue, which was basified with saturated sodium carbonate aqueous solution to pH=8. Then the aqueous phase was extracted with ethyl acetate (10 mL) for three times. The combined organic layers were dried over anhydrous $Na_2SO_{4(s)}$, filtered and concentrated to give the desired compound 181B-1 (140 mg, 99% yield) as yellow solids. LC-MS (ESI): $R_T$=2.159 min, mass calcd. for $C_{21}H_{22}ClFN_4O_2S$ 448.1, m/z found 449.1 $[M+H]^+$.

Compound 187B-1: (trans)-Methyl 4-(2-chloro-4-fluorophenyl)-6-(4-(2-methoxy-2-oxoethylsulfonamido) cyclohexyl)-2-(thiazol-2-yl)-1,4-dihydropyrimidine-5-carboxylate To a solution of (trans)-methyl 6-(4-aminocyclohexyl)-4-(2-chloro-4-fluorophenyl)-2-(thiazol-2-yl)-1,4-dihydropyrimidine-5-carboxylate 181B-1 (100 mg, 0.23 mmol) and triethylamine (47 mg, 0.46 mmol) in dichloromethane (6 mL) was added methyl 2-(chlorosulfonyl)acetate (48 mg, 0.27 mmol) under nitrogen atmosphere. After stirred at room temperature for 2 hours, the mixture was concentrated to give a residue, which was purified by C18 column (acetonitrile:water=40% to 80%) to give the title compound 187B-1 (100 mg, 75% yield) as yellow solids. LC-MS (ESI): $R_T$=4.022 min, mass calcd. for $C_{24}H_{26}ClFN_4O_6S_2$ 584.1, m/z found 584.9 $[M+H]^+$. $^1H$ NMR (400 MHz, $CDCl_3$) δ 8.12 (s, 0.4H), 7.83-7.82 (m, 1H), 7.51 (d, J=2.8 Hz, 0.6H), 7.45 (d, J=2.8 Hz, 0.4H), 7.41 (s, 0.6H), 7.31-7.24 (m, 1H), 7.15-7.11 (m, 1H), 6.96-6.88 (m, 1H), 6.18 (s, 0.4H), 6.04 (d, J=2.4 Hz, 0.6H), 4.75-4.70 (m, 1H), 4.07-4.06 (m, 2H), 4.01-3.94 (m, 0.4H), 3.83 (s, 3H), 3.78-3.70 (m, 0.6H), 3.60 (s, 1.8H), 3.59 (s, 1.2H), 3.44-3.39 (m, 1H), 2.32-2.17 (m, 2H), 2.13-1.93 (m, 2H), 1.90-1.67 (m, 1.5H), 1.57-1.40 (m, 2.5H).

Compound 187B: (trans)-Methyl 4-(2-chloro-4-fluorophenyl)-6-(4-(2-hydroxyethylsulfonamido)cyclohexyl)-2-(thiazol-2-yl)-1,4-dihydropyrimidine-5-carboxylate To a solution of (trans)-methyl 4-(2-chloro-4-fluorophenyl)-6-(4-(2-methoxy-2-oxoethylsulfonamido)cyclohexyl)-2-(thiazol-2-yl)-1,4-dihydropyrimidine-5-carboxylate 187B-1 (100 mg, 0.17 mmol) in tetrahydrofuran (10 mL) was added lithium borohydride (20 mg, 0.85 mmol) under nitrogen atmosphere. After stirred at room temperature overnight, the reaction mixture was diluted with water (10 mL) and extracted by ethyl acetate (10 mL) for three times. The combined organic layers were washed with brine (10 mL), dried over $Na_2SO_{4(s)}$ and filtered. The filtrate was concentrated under reduced pressure to give a residue, which was purified by C18 column (acetonitrile:water=35% to 80%) to give the title compound 187B (51 mg, 55% yield) as pale yellow solids. LC-MS (ESI): $R_T$=3.626 min, mass calcd. for $C_{23}H_{26}ClFN_4O_5S_2$ 556.1, m/z found 556.9 $[M+H]^+$. $^1H$ NMR (400 MHz, $CDCl_3$) δ 8.12 (s, 0.4H), 7.83-7.82 (m, 1H), 7.51 (d, J=2.8 Hz, 0.6H), 7.45 (d, J=3.2 Hz, 0.4H), 7.41 (s, 0.6H), 7.29-7.23 (m, 1H), 7.15-7.11 (m, 1H), 6.96-6.87 (m, 1H), 6.18 (s, 0.4H), 6.04 (d, J=2.4 Hz, 0.6H), 4.34-4.27 (m, 1H), 4.12-4.08 (m, 2H), 4.01-3.94 (m, 0.4H), 3.78-3.70 (m, 0.6H), 3.60 (s, 1.8H), 3.59 (s, 1.2H), 3.48-3.40 (m, 1H), 3.33-3.29 (m, 2H), 2.67 (t, J=6.0 Hz, 0.6H), 2.58 (t, J=6.0 Hz, 0.4H), 2.32-2.15 (m, 2H), 2.13-1.96 (m, 2H), 1.93-1.60 (m, 2H), 1.55-1.37 (m, 2H).

Compound 205: methyl 4-(2-chloro-3,4-difluorophenyl)-6-(1-(S-methylsulfonimidoyl)piperidin-4-yl)-2-(thiazol-2-yl)-1,4-dihydropyrimidine-5-carboxylate

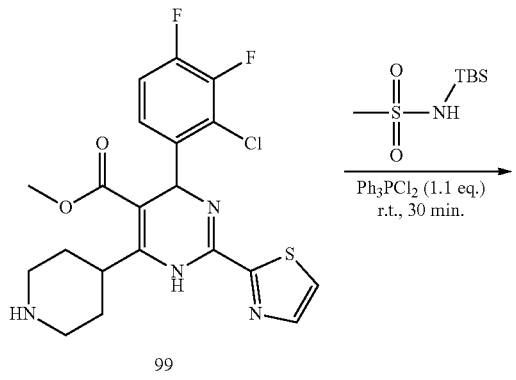

Compound 205P: methyl 6-(1-(N-(tert-butyldimethylsilyl)-S-methylsulfonimidoyl)piperidin-4-yl)-4-(2-chloro-3,4-difluorophenyl)-2-(thiazol-2-yl)-1,4-dihydropyrimidine-5-carboxylate To a stirred solution of triphenylphosphine dichloride (2.40 g, 7.20 mmol) in dry chloroform (10 mL) under nitrogen atmosphere was added triethylamine (1.00 g, 9.90 mmol) at 0° C. After stirred at room temperature for 10 minutes, the reaction mixture was cooled down to 0° C. and a solution of N-(tert-butyldimethylsilyl)-methanesulfonamide (1.40 g, 6.60 mmol) in dry chloroform (3 mL) was added. After stirring at 0° C. for 20 minutes, a solution of methyl 4-(2-chloro-3,4-difluorophenyl)-6-(piperidin-4-yl)-2-(thiazol-2-yl)-1,4-dihydropyrimidine-5-carboxylate compound 99 (300 mg, 0.660 mmol) in chloroform (2 mL) was added. After stirred at 0° C. for 30 minutes, the reaction mixture was concentrated under reduced pressure to give a residue, which was purified by silica gel column chromatography (petroleum ether:ethyl acetate:dichloromethane=10:1:1) to give 205P1 (60 mg, 9% yield) and 205P2 (40 mg, 14% yield) as yellow solids.

Compound 205P1: LC-MS (ESI): $R_T$=2.864 min, mass calcd. for $C_{27}H_{36}ClF_2N_5O_3S_2Si$ 643.2, m/z found 644.2 [M+H]$^+$. $^1$H NMR (400 MHz, CDCl$_3$) δ 8.21 (s, 0.4H), 7.83 (d, J=3.2 Hz, 1H), 7.53 (d, J=2.8 Hz, 0.6H), 7.46 (d, J=3.2 Hz, 0.4H), 7.40 (br s, 0.6H), 7.09-7.02 (m, 2H), 6.19 (s, 0.4H), 6.06 (d, J=2.4 Hz, 0.6H), 4.12-3.86 (m, 3H), 3.61 (s, 1.6H), 3.59 (s, 1.4H), 2.76 (s, 1.6H), 2.75 (s, 1.4H), 2.68-2.63 (m, 2H), 2.31-2.22 (m, 0.6H), 2.07-1.98 (m, 1.4H), 1.93-1.86 (m, 1H), 1.77-1.71 (m, 1H), 0.93 (s, 5H), 0.92 (s, 4H), 0.16-0.11 (m, 6H).

Compound 205P2: LC-MS (ESI): $R_T$=2.848 min, mass calcd. for $C_{27}H_{36}ClF_2N_5O_3S_2Si$ 643.2, m/z found 644.2 [M+H]$^+$. $^1$H NMR (400 MHz, CDCl$_3$) δ 8.21 (s, 0.4H), 7.83 (d, J=3.2 Hz, 1H), 7.53 (d, J=3.2 Hz, 0.6H), 7.46 (d, J=2.8 Hz, 0.4H), 7.41 (d, J=1.6 Hz, 0.6H), 7.08-6.99 (m, 2H), 6.19 (s, 0.4H), 6.07 (d, J=2.8 Hz, 0.6H), 4.13-3.83 (m, 3H), 3.61 (s, 1.6H), 3.59 (s, 1.4H), 2.76 (s, 1.6H), 2.75 (s, 1.4H), 2.73-2.63 (m, 2H), 2.29-2.19 (m, 0.5H), 2.14-2.04 (m, 1H), 2.04-1.95 (m, 1H), 1.91-1.81 (m, 1H), 1.73-1.70 (m, 0.5H), 0.94 (s, 5H), 0.93 (s, 4H), 0.17-0.14 (m, 6H).

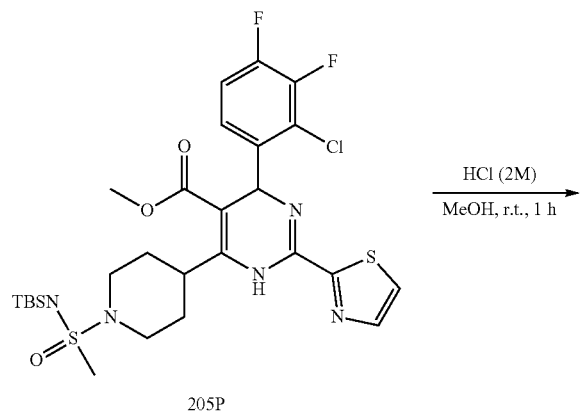

Compound 205: methyl 4-(2-chloro-3,4-difluorophenyl)-6-(1-(S-methylsulfonimidoyl)piperidin-4-yl)-2-(thiazol-2-yl)-1,4-dihydropyrimidine-5-carboxylate To a solution of 205P2 (40 mg, 0.060 mmol) in methanol (2 mL) was added 2 M hydrochloride aqueous solution (0.5 mL) at room temperature. After stirred at room temperature for 1 hour, the reaction mixture was concentrated under reduced pressure to give a residue, which was dissolved in water (10 mL). The mixture was adjusted to pH=9-10 with 28% ammonia solution (0.5 mL), and concentrated under reduced pressure to give a residue, which was purified by Prep. HPLC (Column: Xbridge C18 HILIC (5 μm 10*190 mm), Mobile phase A: water, Mobile phase B: acetonitrile, UV: 214 nm, Flow rate: 50 mL/min, Gradient: 20-95% (% B)) to give compound 205A (20.8 mg, 65% yield) as yellow solids. LC-MS (ESI): $R_T$=3.418 min, mass calcd. for $C_{21}H_{22}ClF_2N_5O_3S_2$ 529.1, m/z found 529.9 [M+H]$^+$. Chiral analysis (Column: Chiralpak IC 5 μm 4.6*250 mm; Mobile Phase: CO$_2$:MeOH=60:40 at 2.999 g/min; Col. Temp: 39.3° C.; Wavelength: 214 nm, Back pressure: 100 bar, $R_T$=6.14 min and 6.84 min). $^1$H NMR (400 MHz, CDCl$_3$) δ 8.19 (s, 0.4H), 7.84-7.83 (m, 1H), 7.53 (d, J=3.2 Hz, 0.6H), 7.47 (d,

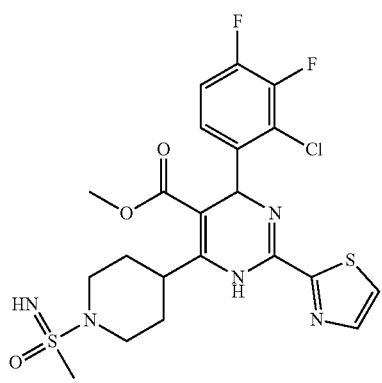

J=3.2 Hz, 0.4H), 7.43 (br s, 0.6H), 7.09-7.02 (m, 2H), 6.19 (s, 0.4H), 6.07 (d, J=2.4 Hz, 0.6H), 4.14-4.03 (m, 2.4H), 3.92-3.86 (m, 0.6H), 3.61 (s, 1.8H), 3.59 (s, 1.2H), 2.86 (s, 1.8H), 2.84 (s, 1.2H), 2.81-2.74 (m, 2H), 2.31-2.20 (m, 0.7H), 2.17-2.00 (m, 2.3H), 1.95-1.74 (m, 2H).

Compound 205B was prepared analogous to 205A from 205P1, $^1$H NMR (400 MHz, CDCl$_3$) δ 8.19 (s, 0.4H), 7.84-7.82 (m, 1H), 7.53 (d, J=3.2 Hz, 0.6H), 7.47 (d, J=3.6 Hz, 0.4H), 7.43 (d, J=1.6 Hz, 0.6H), 7.08-7.01 (m, 2H), 6.19 (s, 0.4H), 6.07 (d, J=2.8 Hz, 0.6H), 4.17-4.00 (m, 2.3H), 3.93-3.86 (m, 0.7H), 3.61 (s, 1.9H), 3.59 (s, 1.1H), 2.86 (s, 1.9H), 2.84 (s, 1.1H), 2.83-2.73 (m, 2H), 2.28-2.22 (m, 0.7H), 2.17-2.06 (m, 2H), 2.02-1.94 (m, 1H), 1.89-1.80 (m, 0.7H), 1.75-1.72 (m, 0.6H).

Compound 207C: methyl 4-(2-chloro-4-fluorophenyl)-6-(–1-methylpyrrolidin-3-yl)-2-(thiazol-2-yl)-1,4-dihydropyrimidine-5-carboxylate

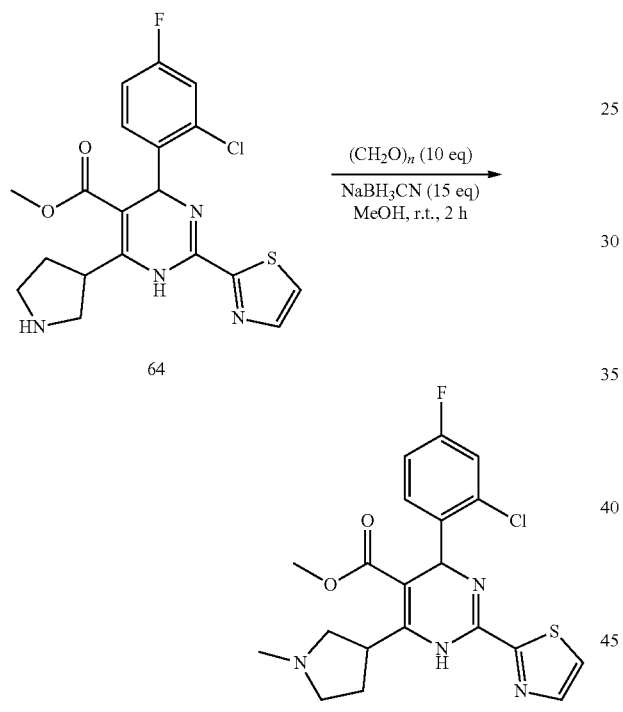

To a solution of methyl 4-(2-chloro-4-fluorophenyl)-6-(pyrrolidin-3-yl)-2-(thiazol-2-yl)-1,4-dihydropyrimidine-5-carboxylate 64 (220 mg, 0.524 mmol) and paraformaldehyde (157 mg, 5.23 mmol) in methanol (8 mL) was added sodium cyanoborohydride (494 mL, 7.87 mmol). The mixture was stirred at room temperature for 2 hours. The mixture was concentrated to give a residue, which was purified by Prep.

HPLC (Column: gilson C18 5 m 19*150 mm, Flow rate: 20 ml/min, Mobile Phase A: Water (0.1% ammonium bicarbonate), Mobile Phase B: Acetonitrile, Gradient: 15-60% (% B)) to give the title compound (90 mg, 40% yield) as yellow solids. LC-MS (ESI): R$_T$=3.328 min, mass calcd. for C$_{20}$H$_{20}$ClFN$_4$O$_2$S 434.1, m/z found 435.0 [M+H]$^+$. $^1$H NMR (400 MHz, DMSO-d$_6$) δ 10.59 (s, 0.5H), 10.55 (s, 0.5H), 7.97 (d, J=2.8 Hz, 1H), 7.91 (s, 1H), 7.44-7.34 (m, 2H), 7.22-7.15 (m, 1H), 6.00 (s, 0.5H), 5.96 (s, 0.5H), 4.52 (s, 1H), 3.51 (s, 1.5H), 3.50 (s, 1.5H), 3.17-2.93 (m, 2H), 2.44 (s, 1.5H), 2.42 (s, 1.5H), 2.33-1.71 (m, 4H).

A mixture of 207 (90 mg, 0.21 mmol) was separated by chiral Prep. HPLC (Column: Chiralpak IE 5 μm 20*250 mm, Mobile Phase: Hex:EtOH:DEA=90:10:0.3 at 15 mL/min, Temp: 30° C., Wavelength: 230 nm) to afford the title compounds 207C (6.3 mg, 7% yield, 97.0% de), 207D (9.3 mg, 10% yield, 98.2% de), and a mixture of 207A and 207B.

Compound 207C: LC-MS (ESI): R$_T$=3.329 min, mass calcd. for C$_{20}$H$_{20}$ClFN$_4$O$_2$S 434.1, m/z found 434.9 [M+H]$^+$. Chiral HPLC (Column: Chiralpak IE 5 μm 4.6*250 mm; Mobile Phase: Hex:EtOH:DEA=90:10:0.2 at 1.0 mL/min; Temp: 30° C.; Wavelength: 230 nm, R$_T$=9.672 min). $^1$H NMR (400 MHz, CDCl$_3$) δ 10.61 (s, 1H), 7.81 (d, J=2.8 Hz, 1H), 7.39 (d, J=3.2 Hz, 1H), 7.33 (dd, J=8.8, 6.4 Hz, 1H), 7.12 (dd, J=8.8, 2.8 Hz, 1H), 6.92-6.88 (m, 1H), 6.13 (s, 1H), 4.67-4.63 (m, 1H), 3.59 (s, 3H), 3.21 (t, J=8.8 Hz, 1H), 3.09 (d, J=10.0 Hz, 1H), 2.50 (s, 3H), 2.46-2.35 (m, 2H), 2.15 (q, J=8.8 Hz, 1H), 1.87-1.79 (m, 1H).

Compound 219: Methyl 4-(2-chloro-3-fluorophenyl)-6-(5-(hydroxymethyl)-tetrahydrofuran-3-yl)-2-(thiazol-2-yl)-1,4-dihydropyrimidine-5-carboxylate

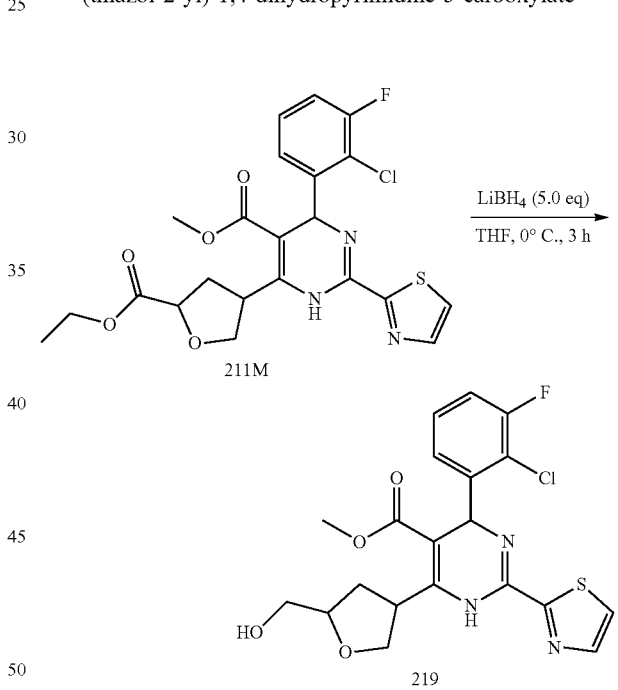

To a solution of methyl 4-(2-chloro-3-fluorophenyl)-6-(5-(ethoxycarbonyl)-tetrahydrofuran-3-yl)-2-(thiazol-2-yl)-1,4-dihydropyrimidine-5-carboxylate 211M (1.33 g, 2.70 mmol) in tetrahydrofuran (45 mL) was added lithium borohydride (297 mg, 13.5 mmol) at 0° C. under nitrogen atmosphere. After stirring at 0° C. for 3 hours, the reaction mixture was quenched by water (25 mL) and 0.6 M hydrochloride aqueous solution (6 mL), and extracted with ethyl acetate (40 mL) for three times. The combined organic layers were washed with water (20 mL) twice, dried over Na$_2$SO$_{4(s)}$, filtered and concentrated to give a residue, which was purified by Prep. HPLC (Column: Waters X-bridge C18 (5 μm 19*150 mm), Mobile phase A: water (0.1% ammonium bicarbonate), Mobile phase B: acetonitrile, UV: 214 nm, Flow rate: 15 mL/min, Gradient: 30-80% (% B)) to afford the title compound 219 (960 mg, 79% yield) as yellow solids. LC-MS (ESI): $R_T$=3.126 min, mass calcd. for $C_{20}H_{19}ClFN_3O_4S$ 451.1, m/z found 451.9 [M+H]$^+$. $^1$H NMR (400 MHz, DMSO-d$_6$) δ 9.65-9.62 (m, 0.3H), 9.61-9.56 (m, 0.3H), 9.24 (s, 0.1H), 9.16 (s, 0.1H), 9.11 (s, 0.1H), 9.04 (s, 0.1H), 8.01 (s, 1H), 7.97-7.91 (m, 1H), 7.41-7.33 (m, 2H), 7.27-7.16 (m, 1H), 6.09-6.05 (m, 0.4H), 6.00-5.96 (m, 0.6H), 5.03-4.86 (m, 0.2H), 4.74-4.59 (m, 0.8H), 4.43-4.33 (m, 0.5H), 4.21-4.11 (m, 0.5H), 4.04-3.97 (m, 1H), 3.90-3.76 (m, 1H), 3.68-3.64 (m, 0.4H), 3.60-3.57 (m, 0.6H), 3.53-3.52 (m, 2H), 3.51-3.46 (m, 1H), 3.43-3.41 (m, 1H), 2.40-2.33 (m, 0.4H), 2.23-2.13 (m, 0.6H), 2.03-1.87 (m, 0.7H), 1.78-1.68 (m, 0.3H).

Racemic 219 (1.00 g, 2.20 mmol) was separated by chiral Prep. HPLC (Column: Chiralpak AD-H 5 μm 20*250 mm; Mobile Phase: Hex:EtOH:DEA=70:30:0.3 at 15 mL/min; Temp: 30° C.; Wavelength: 214 nm) to afford the title compounds 219D (19.7 mg, 2% yield, 100% stereopure), 219F (19.9 mg, 2% yield, 100% stereopure), 219H (19.5 mg, 2% yield, 100% stereopure) and a mixture of five isomers (600 mg, 60% yield). The mixture (600 mg, 1.33 mmol) was separated by chiral Prep. HPLC (Column: Chiralpak OD-H 5 Lm 20*250 mm; Mobile Phase: Hex:EtOH:DEA=90:10:0.3 at 15 mL/min; Temp: 30° C.; Wavelength: 214 nm) to afford the title compounds 219B (19.6 mg, 2% yield, 100% stereopure), Fraction 1 (230 mg, 23% yield) and Fraction 2 (170 mg, 17% yield). Fraction 1 (230 mg, 0.51 mmol) was further separated by chiral SFC (Column: Chiralpak IG 5 μm 20*250 mm; Mobile Phase: CO$_2$:MeOH:DEA=75:25:0.3 at 50 g/min; Col. Temp: 40° C.; Wavelength: 214 nm, Back pressure: 100 bar) to afford the title compounds 219A (19.5 mg, 2% yield, 100% stereopure) and 219C (19.2 mg, 2% yield, 100% stereopure). Fraction 2 (170 mg, 0.38 mmol) was further separated by chiral SFC (Column: Chiralpak IG 5 Lm 20*250 mm; Mobile Phase: CO$_2$:IPA:DEA=70:30:0.3 at 50 g/min; Col. Temp: 40° C.; Wavelength: 214 nm, Back pressure: 100 bar) to afford the title compounds 219E (19.7 mg, 2% yield, 100% stereopure) and 219G (20.0 mg, 2% yield, 100% stereopure).

Compound 219A: LC-MS (ESI): $R_T$=3.308 min, mass calcd. for $C_{20}H_{19}ClFN_3O_4S$ 451.1, m/z found 452.1 [M+H]$^+$. Chiral analysis (Column: Chiralpak OD-H 5 μm 4.6*250 mm; Mobile Phase: Hex:EtOH:DEA=90:10:0.2 at 1.0 mL/min; Temp: 30° C.; Wavelength: 230 nm, $R_T$=10.908 min). $^1$H NMR (400 MHz, DMSO-d$_6$) δ 9.63 (d, J=3.6 Hz, 0.7H), 9.04 (s, 0.3H), 8.03-8.00 (m, 1H), 7.94 (d, J=3.2 Hz, 0.4H), 7.41-7.29 (m, 2H), 7.24-7.22 (m, 1H), 6.09 (s, 0.3H), 5.96 (d, J=4.0 Hz, 0.7H), 4.87-4.84 (m, 0.3H), 4.70-4.67 (m, 0.7H), 4.65-4.60 (m, 0.3H), 4.44-4.36 (m, 0.7H), 4.32-4.26 (m, 0.3H), 4.18-4.13 (m, 0.7H), 4.04-3.96 (m, 1H), 3.89-3.85 (m, 0.3H), 3.68-3.65 (m, 0.7H), 3.53 (s, 2H), 3.51 (s, 1H), 3.45-3.42 (m, 2H), 2.41-2.34 (m, 0.7H), 2.23-2.20 (m, 0.6H), 1.92-1.85 (m, 0.7H).

Compound 219C: LC-MS (ESI): $R_T$=3.319 min, mass calcd. for $C_{20}H_{19}ClFN_3O_4S$ 451.1, m/z found 452.1 [M+H]$^+$. Chiral analysis (Column: Chiralpak AD-H 5 μm 4.6*250 mm; Mobile Phase: Hex:EtOH:DEA=50:50:0.2 at 0.5 mL/min; Temp: 30° C.; Wavelength: 254 nm, $R_T$=4.358 min). $^1$H NMR (400 MHz, DMSO-d$_6$) δ 9.61-9.56 (m, 0.7H), 9.13-9.08 (m, 0.3H), 8.01 (s, 1.6H), 7.95 (s, 0.4H), 7.41-7.26 (m, 2.3H), 7.18 (d, J=7.2 Hz, 0.7H), 6.06 (s, 0.4H), 5.90 (d, J=2.8 Hz, 0.6H), 4.89-4.76 (m, 0.3H), 4.70-4.54 (m, 0.7H), 4.41-4.31 (m, 0.7H), 4.26-4.22 (m, 0.3H), 4.21-4.10 (m, 1.6H), 3.97-3.89 (m, 0.4H), 3.82-3.78 (m, 0.7H), 3.52 (s, 3H), 3.43 (s, 1.3H), 3.42 (s, 1H), 2.28-2.15 (m, 1H), 2.09-2.00 (m, 0.4H), 1.80-1.71 (m, 0.6H). $^1$H NMR (400 MHz, CD$_3$OD+0.6 M HCl aqueous solution (1 drop)) δ 8.00 (d, J=3.2 Hz, 1H), 7.90 (d, J=2.8 Hz, 1H), 7.34-7.31 (m, 1H), 7.28-7.26 (m, 1H), 7.22-7.17 (m, 1H), 6.22 (s, 1H), 4.70-4.60 (m, 1H), 4.41-4.38 (m, 1H), 4.18-4.11 (m, 2H), 3.65-3.58 (m, 5H), 2.30-2.25 (m, 1H), 2.15-2.10 (m, 1H).

Compound 219E: LC-MS (ESI): $R_T$=2.601 min, mass calcd. for $C_{20}H_{19}ClFN_3O_4S$ 451.1, m/z found 451.9 [M+H]$^+$. Chiral analysis (Column: Chiralpak AD-H 5 μm 4.6*250 mm; Mobile Phase: Hex:EtOH:DEA=70:30:0.2 at 1.0 mL/min; Temp: 30° C.; Wavelength: 230 nm, $R_T$=5.603 min). $^1$H NMR (400 MHz, DMSO-d$_6$) δ 9.62 (d, J=3.6 Hz, 0.5H), 9.24 (s, 0.5H), 8.01 (s, 1H), 7.96 (d, J=3.2 Hz, 0.5H), 7.91 (d, J=2.8 Hz, 0.5H), 7.41-7.29 (m, 2H), 7.21 (d, J=7.6 Hz, 1H), 6.06 (s, 0.5H), 5.97 (d, J=3.2 Hz, 0.5H), 5.04 (t, J=5.2 Hz, 0.5H), 4.73-4.67 (m, 1H), 4.45-4.36 (m, 0.5H), 4.04-3.97 (m, 1.5H), 3.89-3.80 (m, 1.5H), 3.76-3.68 (m, 0.5H), 3.63-3.56 (m, 1H), 3.54 (s, 1.5H), 3.51 (s, 1.5H), 3.50-3.46 (m, 0.5H), 2.47-2.44 (m, 0.5H), 2.18-2.09 (m, 1H), 1.97-1.91 (m, 0.5H).

Compound 219H: LC-MS (ESI): $R_T$=3.051 min, mass calcd. for $C_{20}H_{19}ClFN_3O_4S$ 451.1, m/z found 451.9 [M+H]$^+$. Chiral analysis (Column: Chiralpak AD-H 5 μm 4.6*250 mm; Mobile Phase: Hex:EtOH:DEA=70:30:0.2 at 1.0 mL/min; Temp: 30° C.; Wavelength: 230 nm, $R_T$=14.702 min). $^1$H NMR (400 MHz, DMSO-d$_6$) δ 9.62-9.57 (m, 0.5H), 9.16 (s, 0.5H), 8.01 (s, 1H), 7.96 (d, J=2.8 Hz, 0.5H), 7.92 (d, J=3.2 Hz, 0.5H), 7.40-7.30 (m, 2H), 7.28-7.16 (m, 1H), 6.09-6.05 (m, 0.5H), 5.99-5.95 (m, 0.5H), 4.91 (t, J=5.2 Hz, 0.5H), 4.68-4.66 (m, 1H), 4.42-4.33 (m, 0.5H), 4.21-4.18 (m, 0.5H), 4.03-3.94 (m, 1.5H), 3.93-3.79 (m, 1H), 3.62-3.55 (m, 1.4H), 3.53 (s, 1.4H), 3.52 (s, 1.6H), 3.48-3.44 (m, 0.6H), 2.46-2.40 (m, 0.6H), 2.01 (t, J=8.4 Hz, 1H), 1.74-1.67 (m, 0.4H). $^1$H NMR (400 MHz, CD$_3$OD+0.6 M HCl aqueous solution (1 drop)) δ 8.23-8.19 (m, 2H), 7.45-7.40 (m, 2.2H), 7.35-7.31 (m, 0.8H), 6.35-6.33 (m, 1H), 4.73-4.69 (m, 1H), 4.26-4.19 (m, 2H), 4.07-4.03 (m, 1H), 3.97-3.93 (m, 1H), 3.81 (d, J=4.0 Hz, 0.6H), 3.78 (d, J=3.6 Hz, 0.4H), 3.67 (s, 0.3H), 3.64 (s, 2.7H), 2.55-2.47 (m, 1H), 2.14-2.11 (m, 1H).

Compound 221: (cis)-Methyl 4-(2-chloro-3-fluorophenyl)-6-(4-(hydroxymethyl)tetrahydrofuran-2-yl)-2-(thiazol-2-yl)-1,4-dihydropyrimidine-5-carboxylate

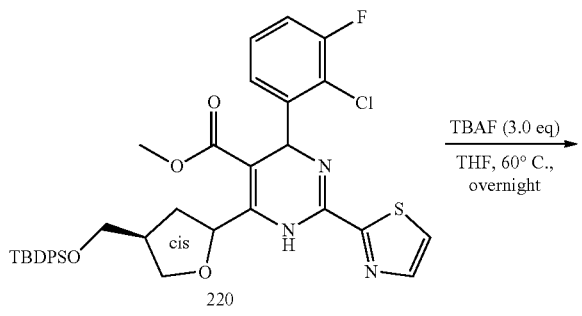

220

561
-continued

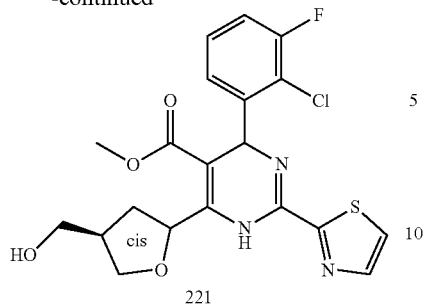

221

To a solution of (cis)-methyl 6-(4-(((tert-butyldiphenylsilyl)oxy)methyl)-tetrahydrofuran-2-yl)-4-(2-chloro-3-fluorophenyl)-2-(thiazol-2-yl)-1,4-dihydropyrimidine-5-carboxylate 220 (2.20 g, 3.19 mmol) in tetrahydrofuran (25 mL) was added tetrabutylammonium fluoride trihydrate (3.03 g, 9.60 mmol) at room temperature under nitrogen atmosphere. After stirred at 60° C. under nitrogen atmosphere overnight. Then it was cooled down to room temperature and concentrated under reduced pressure to give a residue, which was purified by C18 column (acetonitrile:water=5% to 95%) to give the title compound (1.13 g, 78% yield) as yellow solids. LC-MS (ESI): $R_T$=3.277 and 3.326 min, mass calcd. for $C_{20}H_{19}ClFN_3O_4S$ 451.1, m/z found 452.1 [M+H]$^+$. $^1$H NMR (400 MHz, CDCl$_3$) δ 9.13 (s, 0.5H), 9.06 (s, 0.5H), 7.83 (dd, J=10.0, 3.2 Hz, 1H), 7.43 (d, J=3.2 Hz, 1H), 7.23-7.02 (m, 3H), 6.27 (s, 0.5H), 6.22 (s, 0.5H), 5.62-5.53 (m, 1H), 4.14-4.02 (m, 2H), 4.01-3.71 (m, 0.3H), 3.70-3.66 (m, 1.7H), 3.63-3.62 (m, 1H), 3.58 (s, 3H), 2.91-2.86 (m, 1H), 2.71-2.66 (m, 1H), 1.68-1.65 (m, 0.5H), 1.56-1.53 (m, 0.5H).

A racemic mixture of 221 (1.13 g, 2.50 mmol) was separated by chiral Prep. HPLC (Column: Chiralpak IE 5 μm 20*250 mm; Mobile Phase: Hex:EtOH:DEA=80:20:0.2 at 15 mL/min; Temp: 30° C.; Wavelength: 214 nm) to afford 221D (251 mg, 22% yield, 100% stereopure) and Fraction 1 (800 mg). Fraction 1 (800 mg, 1.77 mmol) was further separated by chiral Prep. HPLC (Column: Chiralpak IG 5 μm 20*250 mm; Mobile Phase: Hex:EtOH=80:20 at 15 mL/min; Temp: 30° C.; Wavelength: 214 nm) to afford 221A (161 mg, 14% yield, 100% stereopure) and Fraction 2 (444 mg).

Fraction 2 (444 mg, 0.984 mmol) was further separated by chiral Prep. HPLC (Column: Chiralpak IC 5 μm 20*250 mm; Mobile Phase: Hex:IPA=80:20 at 15 mL/min; Temp: 30° C.; Wavelength: 214 nm) to afford 221B (182 mg, 16% yield, 100% stereopure) and 221C (181 mg, 16% yield, 96.9% stereopure).

Compound 221D: LC-MS (ESI): $R_T$=3.123 min, mass calcd. for $C_{20}H_{19}ClFN_3O_4S$ 451.1, m/z found 451.9 [M+H]$^+$. Chiral analysis (Column: Chiralpak IE 5 μm 4.6*250 mm; Mobile Phase: Hex:EtOH:DEA=80:20:0.2 at 1.0 mL/min; Temp: 30° C.; Wavelength: 230 nm, $R_T$=11.164 min). $^1$H NMR (400 MHz, CD$_3$OD) δ 7.91 (d, J=3.2 Hz, 1H), 7.73 (d, J=2.8 Hz, 1H), 7.29-7.26 (m, 1H), 7.20-7.11 (m, 2H), 6.22 (s, 1H), 5.55-5.51 (m, 1H), 4.05-4.03 (m, 2H), 3.61-3.58 (m, 5H), 2.84-2.81 (m, 1H), 2.65-2.61 (m, 1H), 1.72-1.69 (m, 1H).

562
Compound 243A and 243B: (trans)-Methyl 4-(2-chloro-4-fluorophenyl)-6-(1-((3-(methoxycarbonyl)cyclobutyl)sulfonyl)piperidin-4-yl)-2-(thiazol-2-yl)-1,4-dihydropyrimidine-5-carboxylate and (cis)-methyl 4-(2-chloro-4-fluorophenyl)-6-(1-((3-(methoxycarbonyl)cyclobutyl)sulfonyl)piperidin-4-yl)-2-(thiazol-2-yl)-1,4-dihydropyrimidine-5-carboxylate

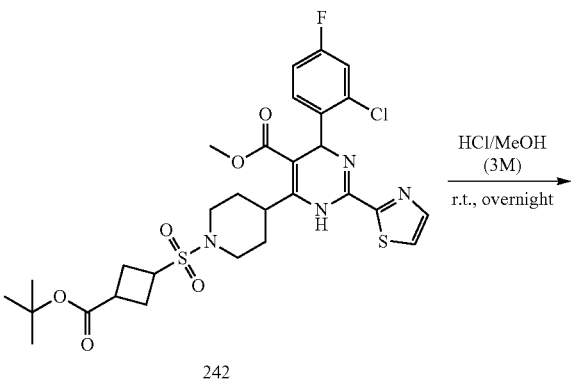

242

$\xrightarrow{\text{HCl/MeOH (3M)}}_{\text{r.t., overnight}}$

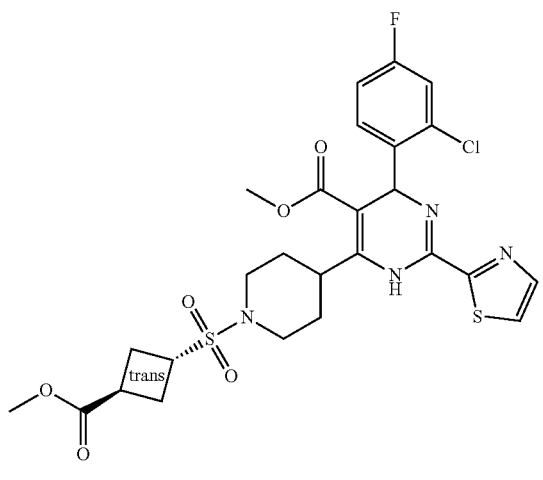

243A

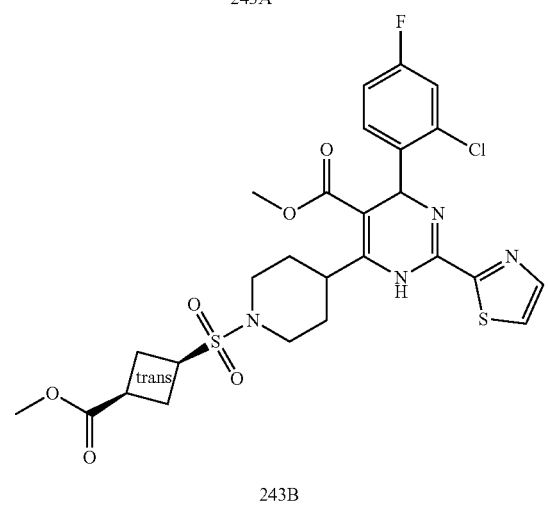

243B

To a solution of methyl 6-(1-((3-(tert-butoxycarbonyl)cyclobutyl)sulfonyl)piperidin-4-yl)-4-(2-chloro-4-fluorophenyl)-2-(thiazol-2-yl)-1,4-dihydropyrimidine-5-carboxylate compound 242 (670 mg, 1.03 mmol) in 3 M hydrochloride in methanol (10 mL, 30 mmol). After stirred at room temperature overnight, the mixture was concentrated under reduced pressure to give a residue, which was dissolved in dichloromethane (20 mL). To above solution was added saturated sodium bicarbonate aqueous solution (20 mL), and extracted with dichloromethane (20 mL) for three times. The combined organic layers were washed with brine (20 mL) twice, dried over $Na_2SO_{4(s)}$ and filtered. The filtrate was concentrated under reduced pressure to give a residue, which was purified by Prep. TLC (petroleum ether:ethyl acetate=2:1) to give the title compounds 243A (200 mg, 32% yield) as yellow solids and 243B (180 mg, 29% yield) as yellow solids.

Compound 243A: $^1$H NMR (300 MHz, DMSO-d$_6$) δ 9.52-9.51 (m, 0.8H), 9.12 (br s, 0.2H), 8.04-7.98 (m, 1.8H), 7.94-7.92 (m, 0.2H), 7.43-7.33 (m, 2H), 7.24-7.15 (m, 1H), 6.01 (s, 0.2H), 5.92 (d, J=3.3 Hz, 0.8H), 4.08-4.00 (m, 1H), 3.78-3.69 (m, 3H), 3.65 (s, 3H), 3.53 (s, 3H), 3.29-3.21 (m, 1H), 2.93-2.82 (m, 2H), 2.62-2.57 (m, 4H), 1.97-1.73 (m, 3H), 1.64-1.54 (m, 1H).

Compound 243B: $^1$H NMR (300 MHz, DMSO-d$_6$) δ 9.55-9.49 (m, 0.8H), 9.12 (br s, 0.2H), 8.00-7.89 (m, 2H), 7.43-7.33 (m, 2H), 7.24-7.17 (m, 1H), 6.01 (s, 0.2H), 5.94-5.90 (m, 0.8H), 4.05-3.94 (m, 1H), 3.74-3.67 (m, 3H), 3.63 (s, 3H), 3.53 (s, 3H), 3.24-3.16 (m, 1H), 2.90-2.79 (m, 2H), 2.59-2.53 (m, 4H), 2.02-1.75 (m, 3H), 1.65-1.55 (m, 1H).

Compound 244X: (trans)-Methyl 4-(2-chloro-4-fluorophenyl)-6-(1-((3-(2-hydroxypropan-2-yl)cyclobutyl)sulfonyl)piperidin-4-yl)-2-(thiazol-2-yl)-1,4-dihydropyrimidine-5-carboxylate

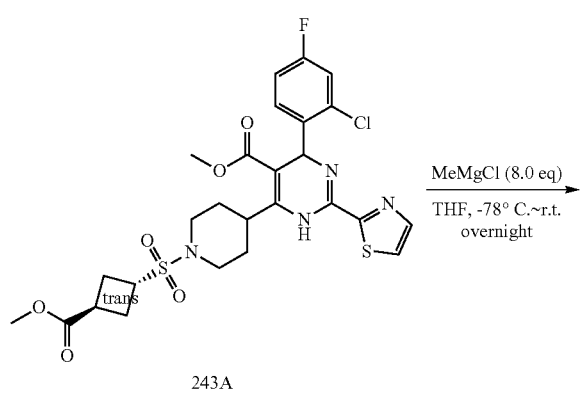

243A

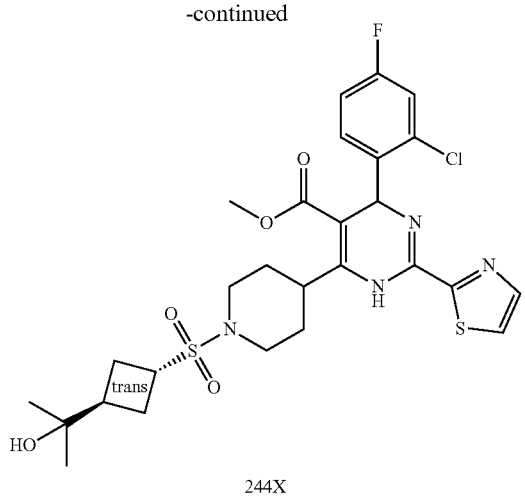

244X

To a solution of (trans)-methyl 4-(2-chloro-4-fluorophenyl)-6-(1-((3-(methoxycarbonyl)cyclobutyl)sulfonyl)piperidin-4-yl)-2-(thiazol-2-yl)-1,4-dihydropyrimidine-5-carboxylate 243A (281 mg, 0.46 mmol) in tetrahydrofuran (6 mL) was added dropwise 3.0 M methylmagnesium chloride in tetrahydrofuran (1.2 mL, 3.6 mmol) at −78° C. After stirred at room temperature overnight, the reaction mixture was quenched with saturated ammonium chloride aqueous solution (20 mL), and extracted with ethyl acetate (20 mL) twice. The combined organic layers were washed with brine (20 mL), dried over $Na_2SO_{4(s)}$ and filtered. The filtrate was concentrated under reduced pressure to give a residue, which was purified by Prep. TLC (petroleum ether:ethyl acetate=3:2) to give the impure title compound, which was further purified by Prep. HPLC (Column: Xbridge C18 (5 μm 10*190 mm), Mobile Phase A: water (0.1% ammonium bicarbonate), Mobile Phase B: acetonitrile, Flow rate: 15 mL/min, Gradient: 40-75% (% B)) to give the title compound (220 mg, 78% yield) as yellow solids. LC-MS (ESI): R$_T$=4.313 min, mass calcd. for $C_{27}H_{32}ClFN_4O_5S_2$ 610.2, m/z found 611.0 [M+H]$^+$. $^1$H NMR (400 MHz, DMSO-d$_6$) δ 9.52 (d, J=3.6 Hz, 0.8H), 9.10 (br s, 0.2H), 8.01-7.98 (m, 1.8H), 7.93 (d, J=3.2 Hz, 0.2H), 7.44-7.40 (m, 1H), 7.37-7.31 (m, 1H), 7.23-7.17 (m, 1H), 6.01 (s, 0.2H), 5.92 (d, J=4.0 Hz, 0.8H), 4.36 (s, 1H), 3.97-3.90 (m, 0.2H), 3.78-3.71 (m, 3.8H), 3.53 (s, 2.3H), 3.52 (s, 0.7H), 2.88-2.79 (m, 2H), 2.40-2.26 (m, 5H), 2.02-1.91 (m, 1H), 1.83-1.74 (m, 2H), 1.63-1.55 (m, 1H), 1.02 (s, 6H).

A racemic mixture of 244X (200 mg, 0.327 mmol) was separated by chiral Prep. SFC (separation condition: Column: Chiralpak IF 5 μm 20*250 mm; Mobile Phase: CO$_2$:MeOH=60:40 at 50 g/min; Col. Temp: 39.8° C.; Wavelength: 214 nm; Back pressure: 100 bar) to afford 244A (70 mg, 35% yield, 100% stereopure) as yellow solids and 244B (75 mg, 38% yield, 100% stereopure) as yellow solids.

Compound 244A: LC-MS (ESI): R$_T$=4.342 min, mass calcd. for $C_{27}H_{32}ClFN_4O_5S_2$ 610.2, m/z found 611.1 [M+H]$^+$. Chiral analysis (Column: Chiralpak IF 5 μm 4.6*250 mm; Mobile Phase: CO$_2$: EtOH=60:40 at 2.999 g/min; Col. Temp: 40.1° C.; Wavelength: 230 nm, Back pressure: 100 bar, R$_T$=4.95 min). $^1$H NMR (400 MHz, DMSO-d$_6$) δ 9.48 (br s, 0.8H), 9.16-9.03 (m, 0.2H), 8.06-7.90 (m, 2H), 7.43-7.40 (m, 1H), 7.37-7.31 (m, 1H), 7.23-7.18 (m, 1H), 6.02-5.97 (m, 0.2H), 5.92 (s, 0.8H), 4.35 (s, 1H), 3.96-3.89 (m, 0.2H), 3.78-3.69 (m, 3.8H), 3.52 (s, 3H), 2.89-2.80 (m, 2H), 2.40-2.26 (m, 5H), 2.00-1.92 (m, 1H), 1.85-1.74 (m, 2H), 1.64-1.55 (m, 1H), 1.02 (s, 6H).

Compound 244B: LC-MS (ESI): $R_T$=4.308 min, mass calcd. for $C_{27}H_{32}ClFN_4O_5S_2$ 610.2, m/z found 611.1 [M+H]$^+$. Chiral analysis (Column: Chiralpak IF 5 μm 4.6*250 mm; Mobile Phase: $CO_2$: EtOH=60:40 at 2.999 g/min; Col. Temp: 40° C.; Wavelength: 230 nm, Back pressure: 100 bar, $R_T$=6.15 min). $^1$H NMR (400 MHz, DMSO-d$_6$) δ 9.51 (d, J=3.6 Hz, 0.8H), 9.09 (br s, 0.2H), 8.01-7.98 (m, 1.8H), 7.94-7.91 (m, 0.2H), 7.44-7.40 (m, 1H), 7.38-7.31 (m, 1H), 7.23-7.18 (m, 1H), 6.01 (s, 0.2H), 5.92 (d, J=3.6 Hz, 0.8H), 4.35 (s, 1H), 3.99-3.91 (m, 0.2H), 3.78-3.71 (m, 3.8H), 3.53 (s, 2.3H), 3.52 (s, 0.7H), 2.88-2.80 (m, 2H), 2.40-2.25 (m, 5H), 2.02-1.91 (m, 1H), 1.86-1.74 (m, 2H), 1.63-1.55 (m, 1H), 1.02 (s, 6H).

Compound 244Y: (cis)-Methyl 4-(2-chloro-4-fluorophenyl)-6-(1-((3-(2-hydroxypropan-2-yl)cyclobutyl)sulfonyl)piperidin-4-yl)-2-(thiazol-2-yl)-1,4-dihydropyrimidine-5-carboxylate

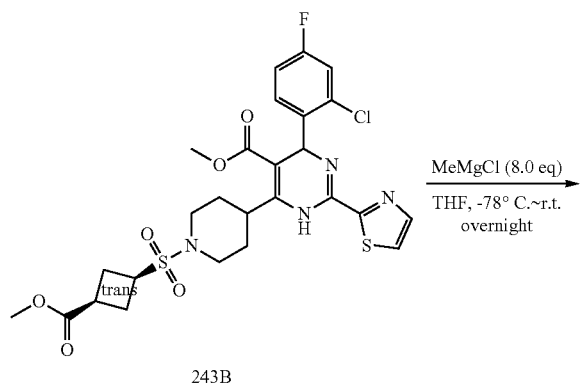

To a solution of (cis)-methyl 4-(2-chloro-4-fluorophenyl)-6-(1-((3-(methoxycarbonyl)cyclobutyl)sulfonyl)piperidin-4-yl)-2-(thiazol-2-yl)-1,4-dihydropyrimidine-5-carboxylate 243B (200 mg, 0.327 mmol) in tetrahydrofuran (4 mL) was added dropwise 3.0 M methylmagnesium chloride in tetrahydrofuran (0.9 mL, 2.7 mmol) at −78° C. After stirred at room temperature overnight, the reaction mixture was quenched with saturated ammonium chloride aqueous solution (20 mL), and extracted with ethyl acetate (20 mL) twice. The combined organic layers were washed with brine (20 mL), dried over $Na_2SO_{4(s)}$ and filtered. The filtrate was concentrated to dryness under reduced pressure to give a residue, which was purified by Prep. TLC (petroleum ether: ethyl acetate=1:1) to give the impure title compound, which was further purified by Prep. HPLC (Column: Xbridge C18 5 m 10*190 mm, Flow rate: 15 mL/min, Mobile Phase A: water (0.1% ammonium bicarbonate), Mobile Phase B: acetonitrile, Gradient: 40%-75% (% B)) to give the title compound (130 mg, 65% yield) as yellow solids. LC-MS (ESI): $R_T$=4.314 min, mass calcd. for $C_{27}H_{32}ClFN_4O_5S_2$ 610.2, m/z found 611.0 [M+H]$^+$. $^1$H NMR (400 MHz, DMSO-d$_6$) δ 9.51 (d, J=3.6 Hz, 0.8H), 9.08 (br s, 0.2H), 8.01-7.98 (m, 1.8H), 7.93 (d, J=2.8 Hz, 0.2H), 7.44-7.40 (m, 1H), 7.38-7.31 (m, 1H), 7.23-7.17 (m, 1H), 6.02 (s, 0.2H), 5.92 (d, J=3.2 Hz, 0.8H), 4.28 (s, 0.2H), 4.26 (s, 0.8H), 3.98-3.91 (m, 0.2H), 3.77-3.68 (m, 3.8H), 3.53 (s, 2.3H), 3.52 (s, 0.7H), 2.89-2.81 (m, 2H), 2.33-2.27 (m, 2H), 2.24-2.20 (m, 1H), 2.12-2.06 (m, 2H), 2.00-1.91 (m, 1H), 1.87-1.74 (m, 2H), 1.63-1.54 (m, 1H), 0.98 (s, 6H).

A racemic mixture of 244Y (110 mg, 0.180 mmol) was separated by chiral Prep. HPLC (separation condition: Column: Chiralpak IE 5 μm 20*250 mm; Mobile Phase: Hex: EtOH:DEA=50:50:0.3 at 9 mL/min; Temp: 30° C.; Wavelength: 230 nm) to afford the title compounds 244C (43 mg, 39% yield, 100% stereopure) as yellow solids and 244D (42 mg, 38% yield, 100% stereopure) as yellow solids.

Compound 244C: LC-MS (ESI): $R_T$=4.328 min, mass calcd. for $C_{27}H_{32}ClFN_4O_5S_2$ 610.2, m/z found 611.1 [M+H]$^+$. Chiral analysis (Column: Chiralpak IE 5 μm 4.6*250 mm; Mobile Phase: Hex:EtOH:DEA=50:50:0.2 at 1.0 mL/min; Temp: 30° C.; Wavelength: 230 nm, $R_T$=10.291 min). $^1$H NMR (400 MHz, DMSO-d$_6$) δ 9.52 (d, J=3.2 Hz, 0.8H), 9.09 (br s, 0.2H), 8.01-7.98 (m, 1.8H), 7.93 (d, J=3.2 Hz, 0.2H), 7.44-7.40 (m, 1H), 7.37-7.31 (m, 1H), 7.23-7.17 (m, 1H), 6.01 (s, 0.2H), 5.92 (d, J=2.8 Hz, 0.8H), 4.29 (s, 0.2H), 4.26 (s, 0.8H), 3.97-3.91 (m, 0.2H), 3.77-3.67 (m, 3.8H), 3.53 (s, 2.3H), 3.52 (s, 0.7H), 2.89-2.80 (m, 2H), 2.33-2.26 (m, 2H), 2.24-2.20 (m, 1H), 2.12-2.06 (m, 2H), 2.01-1.91 (m, 1H), 1.86-1.74 (m, 2H), 1.62-1.55 (m, 1H), 0.98 (s, 6H).

Compound 244D: LC-MS (ESI): $R_T$=4.328 min, mass calcd. for $C_{27}H_{32}ClFN_4O_5S_2$ 610.2, m/z found 611.1 [M+H]$^+$. Chiral analysis (Column: Chiralpak IE 5 μm 4.6*250 mm; Mobile Phase: Hex:EtOH:DEA=50:50:0.2 at 1.0 mL/min; Temp: 30° C.; Wavelength: 230 nm, $R_T$=10.635 min). $^1$H NMR (400 MHz, DMSO-d$_6$) δ 9.52 (d, J=3.2 Hz, 0.8H), 9.09 (br s, 0.2H), 8.03-7.98 (m, 1.8H), 7.93 (d, J=3.6 Hz, 0.2H), 7.44-7.40 (m, 1H), 7.38-7.31 (m, 1H), 7.23-7.17 (m, 1H), 6.02 (s, 0.2H), 5.92 (d, J=3.2 Hz, 0.8H), 4.29 (s, 0.3H), 4.26 (s, 0.7H), 3.98-3.92 (m, 0.2H), 3.77-3.67 (m, 3.8H), 3.53 (s, 3H), 2.89-2.80 (m, 2H), 2.33-2.27 (m, 2H), 2.24-2.20 (m, 1H), 2.12-2.06 (m, 2H), 2.01-1.91 (m, 1H), 1.86-1.74 (m, 2H), 1.63-1.55 (m, 1H), 0.98 (s, 6H).

Compound 245: (trans)-Methyl 4-(2-chloro-3,4-difluorophenyl)-6-(4-(N—((R)-2-hydroxy-3-methoxypropyl)methylsulfonamido)cyclohexyl)-2-(thiazol-2-yl)-1,4-dihydropyrimidine-5-carboxylate

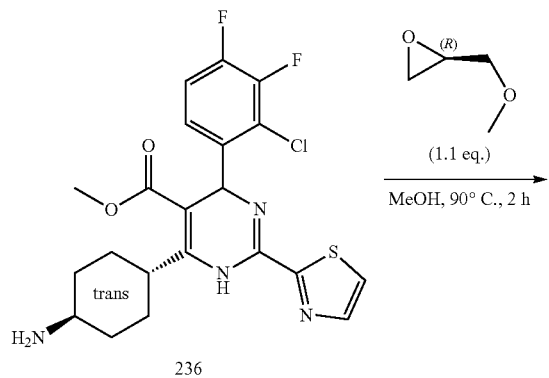

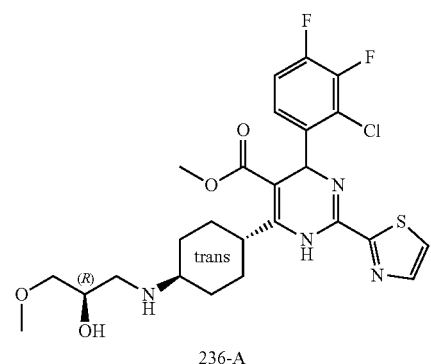

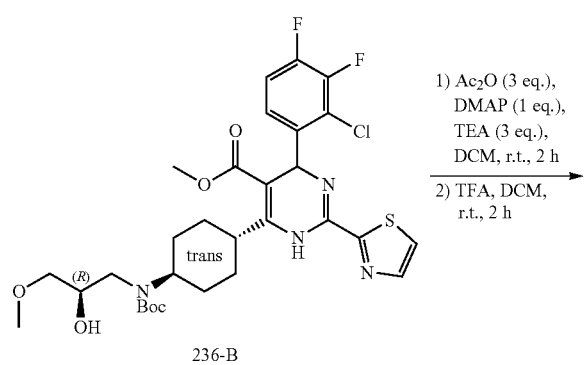

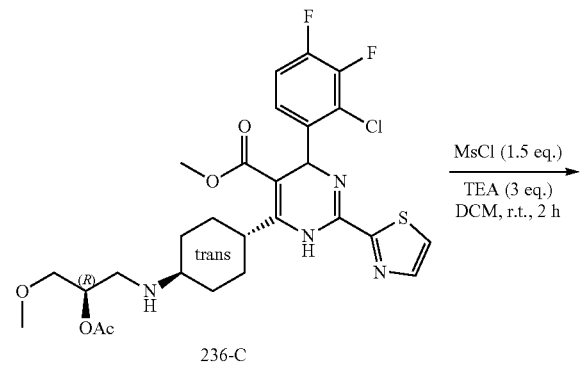

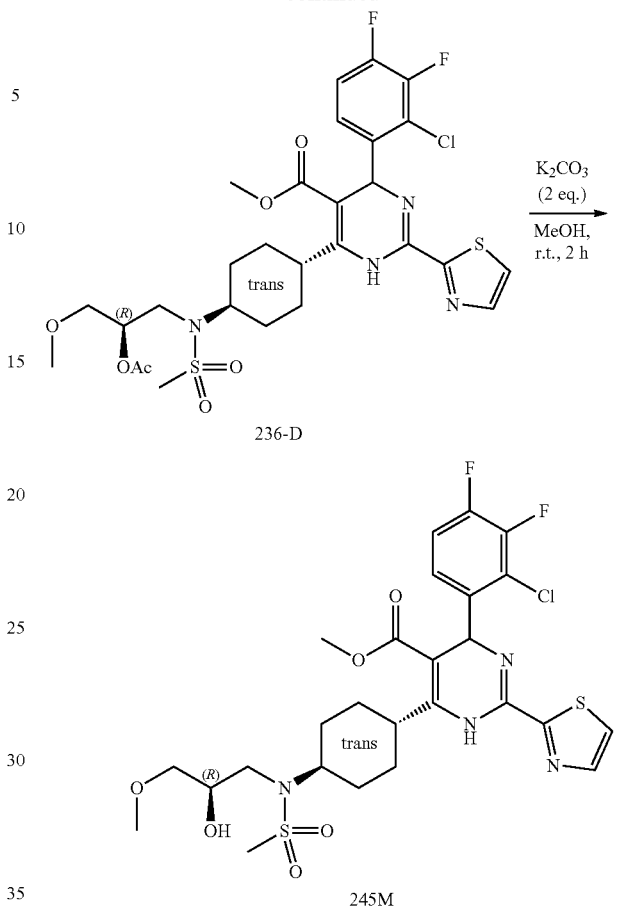

Compound 236-A: (trans)-Methyl 4-(2-chloro-3,4-difluorophenyl)-6-(4-(((R)-2-hydroxy-3-methoxypropyl)amino)cyclohexyl)-2-(thiazol-2-yl)-1,4-dihydropyrimidine-5-carboxylate To a solution of (trans)-methyl 6-(4-aminocyclohexyl)-4-(2-chloro-3,4-difluorophenyl)-2-(thiazol-2-yl)-1,4-dihydropyrimidine-5-carboxylate 236 (200 mg, 0.430 mmol) in methanol (4 mL) was added (R)-2-(methoxymethyl)oxirane (40 mg, 0.470 mmol). After stirred at 90° C. for 2 hours in a microwave reactor, the reaction mixture was cooled down to room temperature, diluted with water (10 mL) and extracted with ethyl acetate (10 mL) for three times. The combined organic layers were washed with brine (10 mL), dried over $Na_2SO_{4(s)}$ and filtered. The filtrate was concentrated under reduced pressure to give a crude product, which was purified by C18 column (acetonitrile:water=40% to 80%) to give the title compound (200 mg, 84% yield) as yellow solids. LC-MS (ESI): $R_T$=2.161 min, mass calcd. for $C_{25}H_{29}ClF_2N_4O_4S$ 554.2, m/z found 554.9 [M+H]⁺. $^1$H NMR (400 MHz, CDCl₃) δ 8.15 (s, 0.5H), 7.83-7.81 (m, 1H), 7.50 (d, J=3.2 Hz, 0.5H), 7.45 (d, J=3.2 Hz, 0.5H), 7.39 (s, 0.5H), 7.09-6.98 (m, 2H), 6.17 (s, 0.6H), 6.04 (s, 0.4H), 4.20-4.13 (m, 0.5H), 4.00-3.93 (m, 1H), 3.81-3.71 (m, 0.5H), 3.61-3.59 (m, 3H), 3.50-3.41 (m, 2H), 3.40 (s, 3H), 3.12-3.09 (m, 1H), 2.96-2.88 (m, 2H), 2.28-1.99 (m, 4H), 1.84-1.39 (m, 4H).

Compound 236-B: (trans)-Methyl 6-(4-((tert-butoxycarbonyl)((R)-2-hydroxy-3-methoxypropyl)amino)cyclohexyl)-4-(2-chloro-3,4-difluorophenyl)-2-(thiazol-2-yl)-1,4-dihydropyrimidine-5-carboxylate To a solution of (trans)-methyl 4-(2-chloro-3,4-difluorophenyl)-6-(4-(((R)-2-hydroxy-3-methoxypropyl)amino)cyclohexyl)-2-(thiazol-2-yl)-1,4-dihydropyrimidine-5-carboxylate 236-A (150 mg, 0.270 mmol) in dichloromethane (8 mL) was added di-tert-butyl pyrocarbonate (177 mg, 0.810 mmol) and triethylamine (90 mg, 0.810 mmol) under nitrogen atmosphere. After stirred at room temperature for 2 hours, the reaction mixture was diluted with water (10 mL) and extracted with ethyl acetate (10 mL) for three times. The combined organic layers were washed with brine (40 mL), dried over $Na_2SO_{4(s)}$ and filtered. The filtrate was concentrated under reduced pressure to give the title compound (180 mg, 99% yield) as yellow oil. LC-MS (ESI): $R_T$=2.517 min, mass calcd. for $C_{30}H_{37}ClF_2N_4O_6S$ 654.2, m/z found 655.0 [M+H]$^+$. $^1$H NMR (400 MHz, CDCl$_3$) δ 8.17 (s, 0.6H), 7.83 (d, J=3.2 Hz, 1H), 7.51 (d, J=2.8 Hz, 0.4H), 7.45 (d, J=2.8 Hz, 0.6H), 7.39 (s, 0.4H), 7.07-6.98 (m, 2H), 6.17 (s, 0.7H), 6.04 (s, 0.3H), 3.99-3.83 (m, 2H), 3.61-3.59 (m, 3H), 3.41-3.24 (m, 8H), 2.14-1.70 (m, 8H), 1.52 (s, 9H).

Compound 236-C: (trans)-Methyl 6-(4-(((R)-2-acetoxy-3-methoxypropyl)-amino)cyclohexyl)-4-(2-chloro-3,4-difluorophenyl)-2-(thiazol-2-yl)-1,4-dihydropyrimidine-5-carboxylate To a solution of (trans)-methyl 6-(4-((tert-butoxycarbonyl)((R)-2-hydroxy-3-methoxypropyl)amino)cyclohexyl)-4-(2-chloro-3,4-difluorophenyl)-2-(thiazol-2-yl)-1,4 dihydropyrimidine-5-carboxylate 236-B (130 mg, 0.200 mmol) in dichloromethane (10 mL) was added acetic anhydride (61 mg, 0.600 mmol), 4-dimethylaminopyridine (24 mg, 0.200 mmol) and triethylamine (60 mg, 0.600 mmol) under nitrogen atmosphere. After stirred at room temperature for 2 hours, the reaction mixture was diluted with water (10 mL) and extracted with ethyl acetate (10 mL) for three times. The combined organic layers were washed with 1 M hydrochloride aqueous solution (10 mL), dried over $Na_2SO_{4(s)}$ and filtered. The filtrate was concentrated under reduced pressure to give the crude compound (150 mg) as colorless oil which was dissolved in dichloromethane (10 mL). To the above solution was added trifluoroacetic acid (5 ml) under nitrogen atmosphere. After stirred at room temperature for 2 hours, the reaction mixture was diluted with water (10 mL) and extracted with ethyl acetate (10 mL) for three times. The combined organic layers were washed with brine (10 mL), dried over $Na_2SO_{4(s)}$ and filtered. The filtrate was concentrated under reduced pressure to give the crude compound (140 mg, 99% yield) as colorless oil. LC-MS (ESI): $R_T$=2.402 min, mass calcd. for $C_{27}H_{31}ClF_2N_4O_5S$ 596.2, m/z found 596.8 [M+H]$^+$.

Compound 236-D: (trans)-Methyl 6-(4-(N—((R)-2-acetoxy-3-methoxypropyl)methylsulfonamido)cyclohexyl)-4-(2-chloro-3,4-difluorophenyl)-2-(thiazol-2-yl)-1,4-dihydropyrimidine-5-carboxylate To a solution of (trans)-methyl 6-(4-(((R)-2-acetoxy-3-methoxypropyl)amino)-cyclohexyl)-4-(2-chloro-3,4-difluorophenyl)-2-(thiazol-2-yl)-1,4-dihydropyrimidine-5-carboxylate 236-C (140 mg, 0.230 mmol) in dichloromethane (10 mL) was added methanesulfonyl chloride (40 mg, 0.350 mmol) and triethylamine (70 mg, 0.700 mmol) under nitrogen atmosphere. After stirred at room temperature for 2 hours, the reaction mixture was diluted with water (10 mL) and extracted with ethyl acetate (10 mL) for three times. The combined organic layers were washed with brine (10 mL), dried over $Na_2SO_{4(s)}$ and filtered. The filtrate was concentrated under reduced pressure to give a residue, which was purified by C18 column (acetonitrile:water=40% to 80%) to give the title compound (75 mg, 50% yield) as yellow solids. LC-MS (ESI): $R_T$=1.837 min, mass calcd. for $C_{28}H_{33}ClF_2N_4O_7S_2$ 674.1, m/z found 674.9 [M+H]$^+$. $^1$H NMR (400 MHz, CDCl$_3$) δ 8.16 (s, 0.5H), 7.84-7.83 (m, 1H), 7.56-7.41 (m, 1.5H), 7.05 (br s, 2H), 6.17 (s, 0.5H), 6.05 (s, 0.5H), 4.00-3.90 (m, 1H), 3.61-3.50 (m, 6H), 3.38 (s, 3H), 3.14 (s, 3H), 2.93 (s, 3H), 2.12 (s, 3H), 2.05-1.72 (m, 8H).

Compound 245M: (trans)-Methyl 4-(2-chloro-3,4-difluorophenyl)-6-(4-(N—((R)-2-hydroxy-3-methoxypropyl)methylsulfonamido)cyclohexyl)-2-(thiazol-2-yl)-1,4-dihydropyrimidine-5-carboxylate To a solution of (trans)-methyl 6-(4-(N—((R)-2-acetoxy-3-methoxypropyl)methylsulfonamido)cyclohexyl)-4-(2-chloro-3,4-difluorophenyl)-2-(thiazol-2-yl)-1,4-dihydropyrimidine-5-carboxylate 236-D (110 mg, 0.160 mmol) in methanol (8 mL) was added potassium carbonate (44 mg, 0.320 mmol) under nitrogen atmosphere. After stirred at room temperature for 2 hours, the reaction mixture was diluted with water (10 mL) and extracted with ethyl acetate (10 mL) for three times. The combined organic layers were washed with brine (10 mL), dried over $Na_2SO_{4(s)}$ and filtered. The filtrate was concentrated to give a residue, which was purified by C18 column (acetonitrile:water=40% to 80%) to give the title compound (40 mg, 41% yield) as yellow solids. LC-MS (ESI): $R_T$=1.739 min, mass calcd. for $C_{26}H_{31}ClF_2N_4O_6S_2$ 632.1, m/z found 632.9 [M+H]$^+$. $^1$H NMR (400 MHz, CDCl$_3$) δ 8.17 (s, 0.5H), 7.83 (d, J=4.0 Hz, 1H), 7.53 (d, J=2.8 Hz, 0.5H), 7.46 (d, J=2.8 Hz, 0.5H), 7.39 (s, 0.5H), 7.08-6.99 (m, 2H), 6.17 (s, 0.5H), 6.04 (d, J=2.8 Hz, 0.5H), 4.00-3.94 (m, 1.5H), 3.85-3.70 (m, 1.5H), 3.61-3.59 (m, 3H), 3.46-3.38 (m, 5H), 3.34-3.31 (m, 2H), 2.98-2.96 (m, 3.5H), 2.89-2.85 (m, 0.5H), 2.15-1.94 (m, 4H), 1.90-1.64 (m, 4H).

Racemic 245M (80 mg, 0.13 mmol) was separated by chiral Prep. HPLC (Column: Chiralpak IA 5 μm 20*250 mm; Mobile Phase: Hex:EtOH:DEA=80:20:0.3 at 25 mL/min; Temp: 30° C.; Wavelength: 214 nm) to afford the title compounds 245A (40 mg, 50% yield, 100% stereopure) and 245B (40 mg, 50% yield, 100% stereopure) as yellow solids.

Compound 245A: LC-MS (ESI): $R_T$=2.135 min, mass calcd. for $C_{26}H_{31}ClF_2N_4O_6S_2$ 632.1, m/z found 632.9 [M+H]$^+$. Chiral analysis (Column: Chiralpak IG 5 μm 4.6*250 mm; Mobile Phase: Hex:EtOH:DEA=50:50:0.2 at 1.0 mL/min; Temp: 30° C.; Wavelength: 230 nm, $R_T$=8.105 min). $^1$H NMR (400 MHz, CDCl$_3$) δ 8.17 (s, 0.5H), 7.83 (d, J=3.2 Hz, 1H), 7.52 (d, J=3.2 Hz, 0.5H), 7.46 (d, J=3.2 Hz, 0.5H), 7.41 (s, 0.5H), 7.07-6.98 (m, 2H), 6.17 (s, 0.5H), 6.04 (d, J=2.8 Hz, 0.5H), 4.01-3.93 (m, 1.5H), 3.85-3.68 (m, 1.5H), 3.61-3.59 (m, 3H), 3.46-3.41 (m, 5H), 3.42-3.31 (m, 2H), 2.98-2.96 (m, 3.5H), 2.88-2.87 (m, 0.5H), 2.16-1.96 (m, 4H), 1.92-1.67 (m, 4H).

Compound 245B: LC-MS (ESI): $R_T$=2.123 min, mass calcd. for $C_{26}H_{31}ClF_2N_4O_6S_2$ 632.1, m/z found 632.9 [M+H]$^+$. Chiral analysis (Column: Chiralpak IG 5 μm 4.6*250 mm; Mobile Phase: Hex:EtOH:DEA=50:50:0.2 at 1.0 mL/min; Temp: 30° C.; Wavelength: 230 nm, $R_T$=10.000 min). $^1$H NMR (400 MHz, CDCl$_3$) δ 8.17 (s, 0.5H), 7.83 (d, J=3.2 Hz, 1H), 7.52 (d, J=3.2 Hz, 0.5H), 7.46 (d, J=3.2 Hz, 0.5H), 7.40 (s, 0.5H), 7.07-6.98 (m, 2H), 6.17 (s, 0.5H), 6.04 (d, J=2.8 Hz, 0.5H), 4.01-3.93 (m, 1.5H), 3.85-3.69 (m, 1.5H), 3.61-3.59 (m, 3H), 3.46-3.39 (m, 5H), 3.34-3.24 (m, 2H), 3.01-2.98 (m, 3.5H), 2.90-2.89 (m, 0.5H), 2.16-1.93 (m, 4H), 1.90-1.63 (m, 4H).

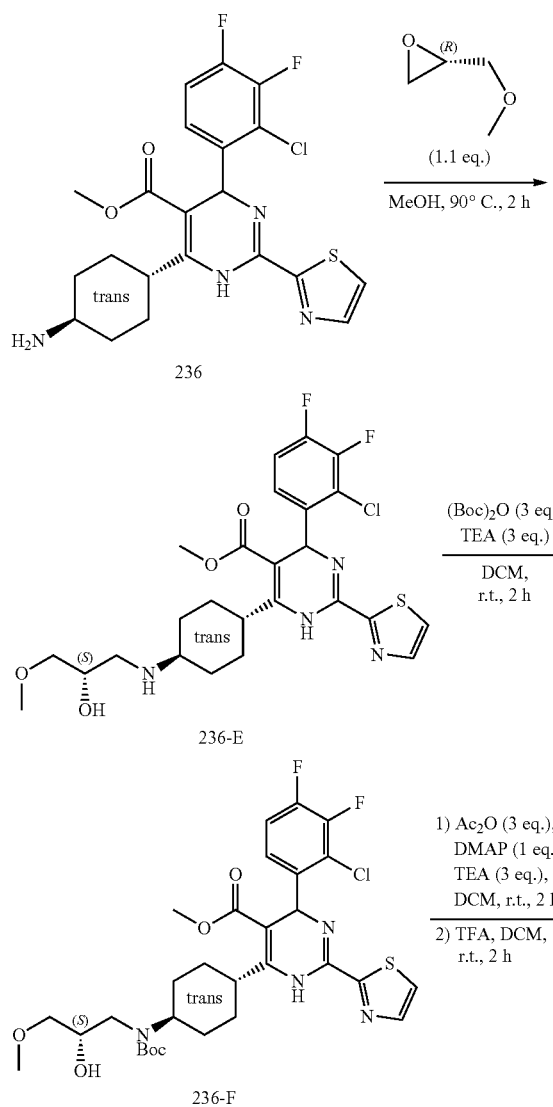

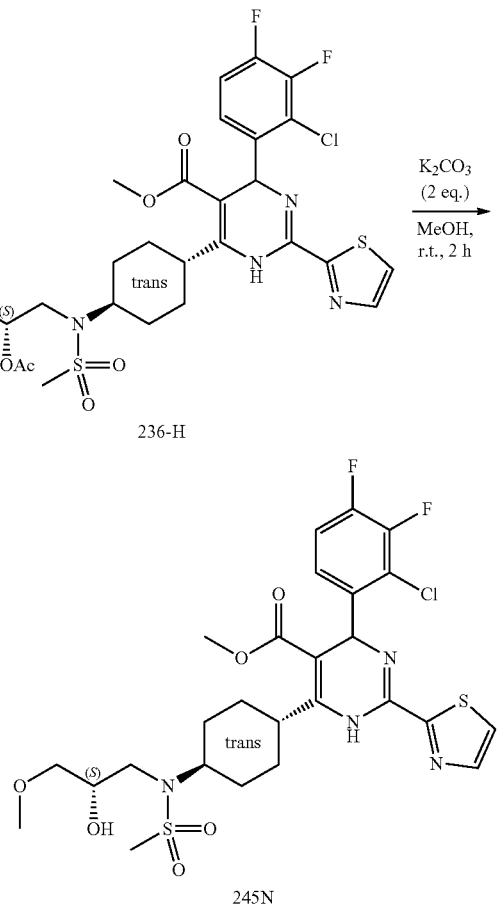

Compound 236-E: (trans)-Methyl 4-(2-chloro-3,4-difluorophenyl)-6-(4-(((S)-2-hydroxy-3-methoxypropyl)amino)cyclohexyl)-2-(thiazol-2-yl)-1,4-dihydropyrimidine-5-carboxylate To a solution of (trans)-methyl 6-(4-aminocyclohexyl)-4-(2-chloro-3,4-difluorophenyl)-2-(thiazol-2-yl)-1,4-dihydropyrimidine-5-carboxylate 236 (200 mg, 0.430 mmol) in methanol (4 mL) was added (S)-2-(methoxymethyl)oxirane (42 mg, 0.470 mmol). After stirred at 85° C. for 2 hours in a microwave reactor, the reaction mixture was cooled down to room temperature, diluted with water (10 mL) and extracted with ethyl acetate (10 mL) for three times. The combined organic layers were washed with brine (10 mL), dried over Na$_2$SO$_{4(s)}$ and filtered. The filtrate was concentrated under reduced pressure to give a crude product, which was purified by C18 column (acetonitrile:water=40% to 80%) to give the title compound (170 mg, 71% yield) as yellow solids. LC-MS (ESI): $R_T$=2.169 min, mass calcd. for C$_{25}$H$_{29}$ClF$_2$N$_4$O$_4$S 554.2, m/z found 554.9 [M+H]$^+$. $^1$H NMR (400 MHz, CDCl$_3$) δ 8.15 (s, 0.5H), 7.83-7.81 (m, 1H), 7.50 (d, J=3.2 Hz, 0.5H), 7.45 (d, J=3.2 Hz, 0.5H), 7.39 (s, 0.5H), 7.08-6.98 (m, 2H), 6.17 (s, 0.6H), 6.04 (s, 0.4H), 4.21-4.14 (m, 0.5H), 3.98-3.93 (m, 1H), 3.80-3.72 (m, 0.5H), 3.61-3.59 (m, 3H), 3.50-3.41 (m, 2H), 3.40 (s, 3H), 3.13-3.08 (m, 1H), 2.97-2.88 (m, 2H), 2.33-1.98 (m, 4H), 1.82-1.42 (m, 4H).

Compound 236-F: (trans)-Methyl 6-(4-(((tert-butoxycarbonyl)((S)-2-hydroxy-3-methoxypropyl)amino)cyclohexyl)-4-(2-chloro-3,4-difluorophenyl)-2-(thiazol-2-yl)-1,4-dihydropyrimidine-5-carboxylate To a solution of (trans)-methyl 4-(2-chloro-3,4-difluorophenyl)-6-(4-(((S)-2-hydroxy-3-methoxypropyl)amino)cyclohexyl)-2-(thiazol-2-yl)-1,4-dihydropyrimidine-5-carboxylate 236-E (170 mg, 0.300 mmol) in dichloromethane (10 mL) was added di-tert-butyl pyrocarbonate (200 mg, 0.920 mmol) and triethylamine (93 mg, 0.920 mmol) under nitrogen atmosphere. After stirred at room temperature for 2 hours, the reaction mixture was diluted with water (10 mL) and extracted with ethyl acetate (10 mL) for three times. The combined organic layers were washed with brine (40 mL), dried over $Na_2SO_{4(s)}$ and filtered. The filtrate was concentrated under reduced pressure to give the title compound (200 mg, 99% yield) as yellow oil. LC-MS (ESI): $R_T$=1.945 min, mass calcd. for $C_{30}H_{37}ClF_2N_4O_6S$ 654.2, m/z found 654.9 [M+H]$^+$. $^1$H NMR (400 MHz, CDCl$_3$) δ 8.17 (s, 0.6H), 7.83-7.82 (m, 1H), 7.51 (d, J=2.8 Hz, 0.4H), 7.45 (d, J=2.8 Hz, 0.6H), 7.39 (s, 0.4H), 7.07-6.98 (m, 2H), 6.17 (s, 0.7H), 6.04 (s, 0.3H), 3.99-3.83 (m, 2H), 3.61-3.59 (m, 3H), 3.41-3.24 (m, 8H), 2.14-1.70 (m, 8H), 1.51 (s, 9H).

Compound 236-G: (trans)-Methyl 6-(4-(((S)-2-acetoxy-3-methoxypropyl)(tert-butoxycarbonyl)amino)cyclohexyl)-4-(2-chloro-3,4-difluorophenyl)-2-(thiazol-2-yl)-1,4-dihydropyrimidine-5-carboxylate To a solution of (trans)-methyl 6-(4-((tert-butoxycarbonyl)((S)-2-hydroxy-3-methoxypropyl)amino)cyclohexyl)-4-(2-chloro-3,4-difluorophenyl)-2-(thiazol-2-yl)-1,4 dihydropyrimidine-5-carboxylate 236-F (200 mg, 0.310 mmol) in dichloromethane (10 mL) was added acetic anhydride (94 mg, 0.930 mmol), 4-dimethylaminopyridine (40 mg, 0.310 mmol) and triethylamine (83 mg, 0.930 mmol) under nitrogen atmosphere. After stirred at room temperature for 2 hours, the reaction mixture was diluted with water (10 mL) and extracted with ethyl acetate (10 mL) for three times. The combined organic layers were washed with 1 M hydrochloride aqueous solution (10 mL), dried over $Na_2SO_{4(s)}$ and filtered. The filtrate was concentrated under reduced pressure to give the crude compound (220 mg, 99% yield) as colorless oil. LC-MS (ESI): $R_T$=2.121 min, mass calcd. for $C_{32}H_{39}ClF_2N_4O_7S$ 696.2, m/z found 696.9 [M+H]$^+$.

Compound 236-H: (trans)-Methyl 6-(4-(N—((S)-2-acetoxy-3-methoxypropyl)methylsulfonamido)cyclohexyl)-4-(2-chloro-3,4-difluorophenyl)-2-(thiazol-2-yl)-1,4-dihydropyrimidine-5-carboxylate To a solution of (trans)-methyl 6-(4-(((S)-2-acetoxy-3-methoxypropyl)(tert-butoxycarbonyl)amino)cyclohexyl)-4-(2-chloro-3,4-difluorophenyl)-2-(thiazol-2-yl)-1,4-dihydropyrimidine-5-carboxylate 236-G (220 mg, 0.310 mmol) in dichloromethane (10 mL) was added trifluoroacetic acid (5 ml) under nitrogen atmosphere. After stirred at room temperature for 2 hours, the reaction mixture was diluted with water (10 mL) and extracted with ethyl acetate (10 mL) for three times. The combined organic layers were washed with brine (10 mL), dried over $Na_2SO_{4(s)}$ and filtered. The filtrate was concentrated under reduced pressure to give the crude compound (230 mg) which was dissolved in dichloromethane (10 mL). To the above solution was added methanesulfonyl chloride (53 mg, 0.470 mmol) and triethylamine (90 mg, 0.900 mmol) under nitrogen atmosphere. After stirred at room temperature for 2 hours, the reaction mixture was diluted with water (10 mL) and extracted with ethyl acetate (10 mL) for three times. The combined organic layers were washed with brine (10 mL), dried over $Na_2SO_{4(s)}$ and filtered. The filtrate was concentrated under reduced pressure to give a residue, which was purified by C18 column (acetonitrile:water=40% to 80%) to give the title compound (150 mg, 75% yield) as yellow solids. LC-MS (ESI): $R_T$=1.855 min, mass calcd. for $C_{28}H_{33}ClF_2N_4O_7S_2$ 674.1, m/z found 674.9 [M+H]$^+$. $^1$H NMR (400 MHz, CDCl$_3$) δ 8.16 (s, 0.5H), 7.84-7.83 (m, 1H), 7.56-7.41 (m, 1.5H), 7.05 (br s, 2H), 6.17 (s, 0.5H), 6.05 (s, 0.5H), 4.00-3.90 (m, 1H), 3.61-3.50 (m, 6H), 3.38 (s, 3H), 3.14 (s, 3H), 2.93 (s, 3H), 2.12 (s, 3H), 2.05-1.72 (m, 8H).

Compound 245N: (trans)-Methyl 4-(2-chloro-3,4-difluorophenyl)-6-(4-(N—((S)-2-hydroxy-3-methoxypropyl)methylsulfonamido)cyclohexyl)-2-(thiazol-2-yl)-1,4-dihydropyrimidine-5-carboxylate To a solution of (trans)-methyl 6-(4-(N—((S)-2-acetoxy-3-methoxypropyl)methylsulfonamido)cyclohexyl)-4-(2-chloro-3,4-difluorophenyl)-2-(thiazol-2-yl)-1,4-dihydropyrimidine-5-carboxylate 236-H (150 mg, 0.220 mmol) in methanol (5 mL) was added potassium carbonate (60 mg, 0.440 mmol) under nitrogen atmosphere. After stirred at room temperature for 2 hours, the reaction mixture was diluted with water (10 mL) and extracted with ethyl acetate (10 mL) for three times. The combined organic layers were washed with brine (10 mL), dried over $Na_2SO_{4(s)}$ and filtered. The filtrate was concentrated to give a residue, which was purified by C18 column (acetonitrile:water=40% to 80%) to give the title compound (85 mg, 60% yield) as yellow solids. LC-MS (ESI): $R_T$=2.456 min, mass calcd. for $C_{26}H_{31}ClF_2N_4O_6S_2$ 632.1, m/z found 632.8 [M+H]$^+$. $^1$H NMR (400 MHz, CDCl$_3$) δ 8.17 (s, 0.5H), 7.84-7.83 (m, 1H), 7.53 (d, J=3.2 Hz, 0.5H), 7.46 (d, J=3.2 Hz, 0.5H), 7.41 (s, 0.5H), 7.06-6.98 (m, 2H), 6.17 (s, 0.5H), 6.04 (d, J=2.8 Hz, 0.5H), 4.03-3.91 (m, 1.5H), 3.80-3.68 (m, 1.5H), 3.65-3.59 (m, 3H), 3.51-3.41 (m, 5H), 3.34-3.31 (m, 2H), 3.04-2.98 (m, 3.5H), 2.92-2.86 (m, 0.5H), 2.18-1.91 (m, 4H), 1.80-1.65 (m, 4H).

Racemic 245N (150 mg, 0.240 mmol) was separated by chiral Prep. HPLC (Column: Chiralpak IA 5 μm 20*250 mm; Mobile Phase: Hex:EtOH:DEA=60:40:0.2 at 25 mL/min; Temp: 30° C.; Wavelength: 214 nm) to afford the title compounds 245C (75 mg, 50% yield, 100% stereopure) and 245D (75 mg, 50% yield, 99.7% stereopure) as yellow solids.

Compound 245C: LC-MS (ESI): $R_T$=2.124 min, mass calcd. for $C_{26}H_{31}ClF_2N_4O_6S_2$ 632.1, m/z found 632.9 [M+H]$^+$. Chiral analysis (Column: Chiralpak IA 5 μm 4.6*250 mm; Mobile Phase: Hex:EtOH:DEA=60:40:0.2 at 1.0 mL/min; Temp: 30° C.; Wavelength: 230 nm, $R_T$=5.708 min). $^1$H NMR (400 MHz, CDCl$_3$) δ 8.17 (s, 0.5H), 7.83 (d, J=2.8 Hz, 1H), 7.52 (d, J=3.2 Hz, 0.5H), 7.46 (d, J=3.2 Hz, 0.5H), 7.40 (s, 0.5H), 7.07-6.98 (m, 2H), 6.17 (s, 0.5H), 6.04 (d, J=2.4 Hz, 0.5H), 4.02-3.92 (m, 1.5H), 3.86-3.69 (m, 1.5H), 3.61-3.59 (m, 3H), 3.46-3.39 (m, 5H), 3.34-3.30 (m, 2H), 2.99-2.98 (m, 3.5H), 2.90-2.89 (m, 0.5H), 2.17-1.96 (m, 4H), 1.90-1.63 (m, 4H).

Compound 245D: LC-MS (ESI): $R_T$=2.103 min, mass calcd. for $C_{26}H_{31}ClF_2N_4O_6S_2$ 632.1, m/z found 632.8 [M+H]$^+$. Chiral analysis (Column: Chiralpak IA 5 μm 4.6*250 mm; Mobile Phase: Hex:EtOH:DEA=60:40:0.2 at 1.0 mL/min; Temp: 30° C.; Wavelength: 230 nm, $R_T$=6.282 min). 1H NMR (400 MHz, CDCl$_3$) δ 8.17 (s, 0.5H), 7.83 (d, J=2.8 Hz, 1H), 7.52 (d, J=2.8 Hz, 0.5H), 7.46 (d, J=3.2 Hz, 0.5H), 7.40 (s, 0.5H), 7.07-6.98 (m, 2H), 6.17 (s, 0.5H), 6.04 (d, J=2.4 Hz, 0.5H), 4.02-3.94 (m, 1.5H), 3.85-3.70 (m, 1.5H), 3.61-3.59 (m, 3H), 3.48-3.38 (m, 5H), 3.34-3.31 (m, 2H), 2.98-2.96 (m, 3.5H), 2.87-2.86 (m, 0.5H), 2.16-1.92 (m, 4H), 1.89-1.63 (m, 4H).

Compound 248: Methyl 6-(1-((1-(2-(tert-butoxy)ethyl)azetidin-3-yl)sulfonyl)piperidin-4-yl)-4-(2-chloro-3,4-difluorophenyl)-2-(thiazol-2-yl)-1,4-dihydropyrimidine-5-carboxylate

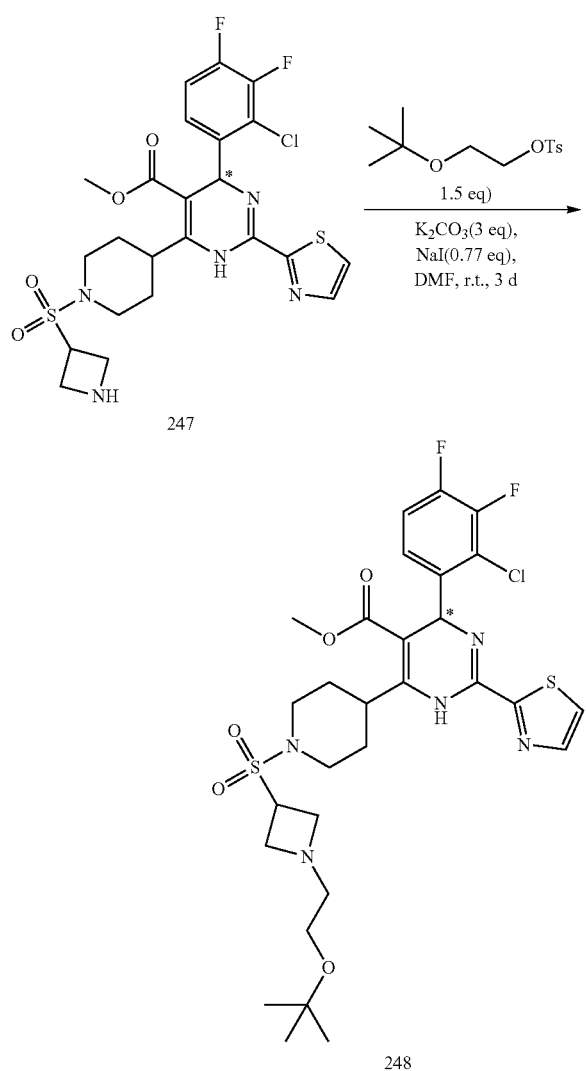

To a solution of methyl 6-(1-(azetidin-3-ylsulfonyl)piperidin-4-yl)-4-(2-chloro-3,4-difluorophenyl)-2-(thiazol-2-yl)-1,4-dihydropyrimidine-5-carboxylate compound 247 (150 mg, crude, 0.250 mmol (quantitative according to 246)), potassium carbonate (100 mg, 0.780 mmol) and sodium iodide (30 mg, 0.200 mmol) in N,N-dimethylformamide (9 mL) was added a solution of 2-(tert-butoxy)ethyl 4-methylbenzenesulfonate (100 mg, 0.390 mmol) in N,N-dimethylformamide (1 mL) under nitrogen atmosphere. After stirred at room temperature for 3 days, the mixture was diluted in water (30 mL), extracted with ethyl acetate (10 mL) for three times. The combined organic layers were washed with brine (10 mL) for three times, dried over Na$_2$SO$_{4(s)}$, filtered and concentrated under reduced pressure to give a residue, which was purified by Prep. TLC (petroleum ether:ethyl acetate=1:1) to give the title compound 248 (10 mg, 6% yield) as yellow solids. LC-MS (ESI): R$_T$=9.582 min, mass calcd. for C$_{29}$H$_{36}$ClF$_2$N$_5$O$_5$O$_5$S$_2$ 671.2, m/z found 672.3 [M+H]$^+$. $^1$H NMR (400 MHz, CDCl$_3$) δ 8.19 (s, 0.5H), 7.83 (dd, J=3.2, 1.2 Hz, 1H), 7.53 (d, J=2.8 Hz, 0.5H), 7.46 (d, J=3.2 Hz, 0.5H), 7.42 (br s, 0.5H), 7.10-6.99 (m, 2H), 6.18 (s, 0.4H), 6.06 (d, J=2.4 Hz, 0.6H), 4.20-4.13 (m, 0.3H), 4.04-3.87 (m, 3.7H), 3.78-3.69 (m, 2H), 3.60-3.58 (m, 3H), 3.56-3.52 (m, 2H), 3.38 (t, J=5.2 Hz, 2H), 2.96-2.83 (m, 2H), 2.68 (q, J=5.6 Hz, 2H), 2.24-1.67 (m, 4H), 1.17 (s, 9H).

Compound 251: (trans)-Methyl 4-(2-chloro-3,4-difluorophenyl)-6-(4-(1-methylazetidine-3-sulfonamido)cyclohexyl)-2-(thiazol-2-yl)-1,4-dihydropyrimidine-5-carboxylate

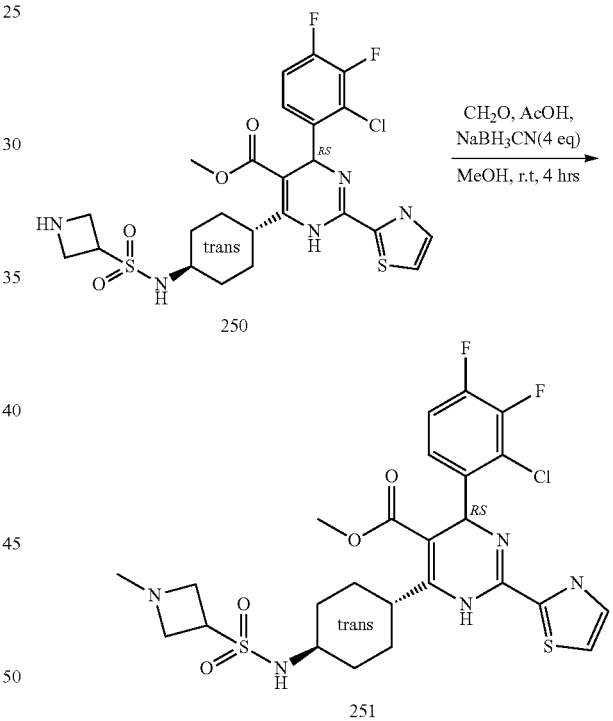

To the solution of (trans)-methyl 6-(4-(azetidine-3-sulfonamido)cyclohexyl)-4-(2-chloro-3,4-difluorophenyl)-2-(thiazol-2-yl)-1,4-dihydropyrimidine-5-carboxylate 250 (210 mg, 0.340 mmol) and formaldehyde (1.5 mL) in methanol (10 mL) was added acetic acid (5 drops) at room temperature under nitrogen atmosphere. After stirred at room temperature for 1 hour, the mixture was added sodium cyanoborohydride (90 mg, 1.36 mmol) and stirred at room temperature for 3 hours. Then, the mixture was quenched with water (10 mL), concentrated under reduced pressure to remove methanol and extracted with dichloromethane (10 mL) for three times. The combined organic layers were washed with brine (20 mL), dried over Na$_2$SO$_{4(s)}$, filtered and concentrated under reduced pressure to give a residue, which was purified by C18 column (acetonitrile:water=5% to 100%) to give the title compound (130 mg, 60% yield) as yellow solids. LC-MS (ESI): $R_T$=1.677 min, mass calcd. for $C_{25}H_{28}ClF_2N_5O_4S_2$ 599.1, m/z found 599.9 [M+H]$^+$. $^1$H NMR (400 MHz, CDCl$_3$) δ 8.14 (s, 0.5H), 7.84-7.82 (m, 1H), 7.52 (d, J=3.2 Hz, 0.5H), 7.46 (d, J=3.2 Hz, 0.5H), 7.39 (s, 0.5H), 7.07-6.98 (m, 2H), 6.17 (s, 0.5H), 6.04 (d, J=2.4 Hz, 0.5H), 4.09 (s, 1H), 4.01-3.92 (m, 1.5H), 3.77-3.69 (m, 0.5H), 3.68-3.63 (m, 2H), 3.60 (s, 1.5H), 3.58 (s, 1.5H), 3.49-3.43 (m, 2H), 3.39-3.36 (m, 1H), 2.38 (d, J=1.6 Hz, 3H), 2.25-1.90 (m, 4.3H), 1.85-1.66 (m, 1.7H), 1.53-1.36 (m, 2H).

Racemic 251 (130 mg, 0.220 mmol) was separated by chiral Prep. HPLC (separation condition: Column: Chiralpak IE 5 μm 20*250 mm; Mobile Phase: Hex:EtOH: DEA=50:50:0.3 at 10 mL/min; Temp: 30° C.; Wavelength: 230 nm) to afford the title compounds 251A (30 mg, 23% yield, 100% stereopure) as yellow solids and 251B (30 mg, 31% yield, 99.6% stereopure) as yellow solids.

Compound 251A: LC-MS (ESI): $R_T$=8.952 min, mass calcd. for $C_{25}H_{28}ClF_2N_5O_4S_2$ 599.1, m/z found 600.2 [M+H]$^+$. Chiral analysis (Column: Chiralpak IE 5 μm 4.6*250 mm; Mobile Phase: Hex:EtOH:DEA=50:50:0.2 at 1.0 mL/min; Temp: 30° C.; Wavelength: 230 nm, $R_T$=10.756 min). $^1$H NMR (400 MHz, CDCl$_3$) δ 8.14 (s, 0.5H), 7.83-7.82 (m, 1H), 7.52 (d, J=3.2 Hz, 0.5H), 7.46 (d, J=3.2 Hz, 0.5H), 7.39 (s, 0.5H), 7.07-6.98 (m, 2H), 6.17 (s, 0.5H), 6.04 (d, J=2.4 Hz, 0.5H), 4.15-4.08 (m, 1H), 4.02-3.92 (m, 1.5H), 3.77-3.71 (m, 0.5H), 3.66 (q, J=7.6 Hz, 2H), 3.60 (s, 1.5H), 3.58 (s, 1.5H), 3.48-3.43 (m, 2H), 3.42-3.34 (m, 1H), 2.38 (d, J=2.4 Hz, 3H), 2.25-1.90 (m, 4.4H), 1.84-1.66 (m, 1.6H), 1.59-1.34 (m, 2H).

Compound 251B: LC-MS (ESI): $R_T$=3.687 min, mass calcd. for $C_{25}H_{28}ClF_2N_5O_4S_2$ 599.1, m/z found 600.2 [M+H]$^+$. Chiral analysis (Column: Chiralpak IE 5 μm 4.6*250 mm; Mobile Phase: Hex:EtOH:DEA=50:50:0.2 at 1.0 mL/min; Temp: 30° C.; Wavelength: 230 nm, $R_T$=14.460 min). $^1$H NMR (400 MHz, CDCl$_3$) δ 8.14 (s, 0.5H), 7.83 (t, J=2.4 Hz, 1H), 7.52 (d, J=3.2 Hz, 0.5H), 7.46 (d, J=3.2 Hz, 0.5H), 7.39 (s, 0.5H), 7.09-6.98 (m, 2H), 6.17 (s, 0.5H), 6.04 (d, J=2.4 Hz, 0.5H), 4.11-4.05 (m, 1H), 4.01-3.91 (m, 1.6H), 3.78-3.71 (m, 0.4H), 3.65 (q, J=8.0 Hz, 2H), 3.60 (s, 1.5H), 3.58 (s, 1.5H), 3.49-3.43 (m, 2H), 3.40-3.34 (m, 1H), 2.38 (d, J=1.2 Hz, 3H), 2.25-1.94 (m, 4H), 1.91-1.78 (m, 0.8H), 1.73-1.62 (m, 1.2H), 1.56-1.33 (m, 2H).

Compound 253B: (trans)-Methyl 4-(2-chloro-3,4-difluorophenyl)-6-(4-(3-hydroxypropylsulfonamido) cyclohexyl)-2-(thiazol-2-yl)-1,4-dihydropyrimidine-5-carboxylate

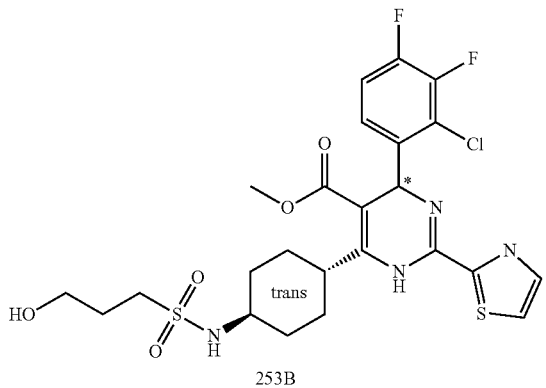

253B

To a solution of (trans)-methyl 4-(2-chloro-3,4-difluorophenyl)-6-(4-(3-methoxy-3-oxopropylsulfonamido)cyclohexyl)-2-(thiazol-2-yl)-1,4-dihydropyrimidine-5-carboxylate 252Y (100 mg, 0.160 mmol) in tetrahydrofuran (8 mL) was added lithium borohydride (15 mg, 0.640 mmol) under nitrogen atmosphere. After stirred at room temperature overnight, the reaction mixture was diluted with water (10 mL) and extracted with ethyl acetate (10 mL) for three times. The combined organic layers were washed with brine (10 mL), dried over Na$_2$SO$_{4(s)}$ and filtered. The filtrate was concentrated under reduced pressure to give a crude product, which was purified by C18 column (acetonitrile:water=35% to 80%) to give the title compound (50 mg, 53% yield) as pale yellow solids. LC-MS (ESI): $R_T$=3.941 min, mass calcd. for $C_{24}H_{27}ClF_2N_4O_5S_2$ 588.1, m/z found 588.9 [M+H]$^+$. $^1$H NMR (400 MHz, CDCl$_3$) δ 8.15 (s, 0.5H), 7.83-7.82 (m, 1H), 7.52 (d, J=3.2 Hz, 0.5H), 7.45 (d, J=3.2 Hz, 0.5H), 7.40 (s, 0.5H), 7.07-6.98 (m, 2H), 6.17 (s, 0.5H), 6.04 (d, J=2.4 Hz, 0.5H), 4.31-4.29 (m, 0.5H), 4.24-4.22 (m, 0.5H), 4.01-3.94 (m, 0.5H), 3.84-3.82 (m, 2H), 3.76-3.69 (m, 0.5H), 3.60-3.59 (m, 3H), 3.45-3.37 (m, 1H), 3.24-3.20 (m, 2H), 2.31-2.17 (m, 2H), 2.14-1.83 (m, 4H), 1.82-1.65 (m, 2H), 1.55-1.39 (m, 2H).

Compound 268: Methyl 4-(2-chloro-4-fluorophenyl)-6-(1-(N-(2-methoxyethyl)-sulfamoyl)piperidin-4-yl)-2-(thiazol-2-yl)-1,4-dihydropyrimidine-5-carboxylate

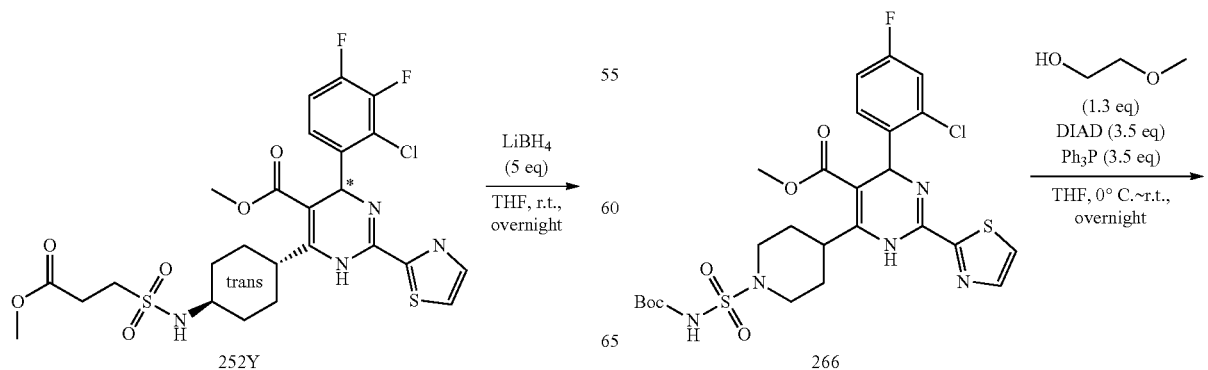

-continued

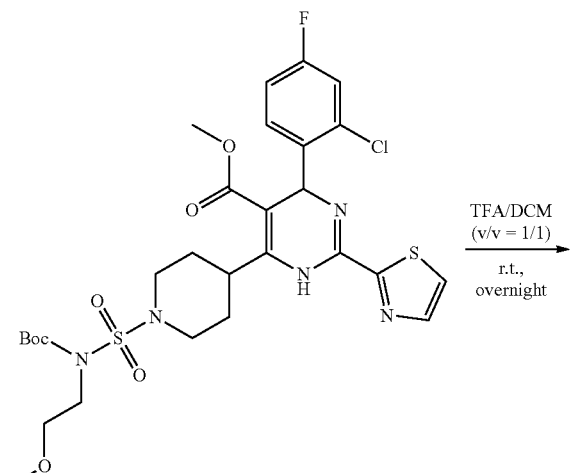

267

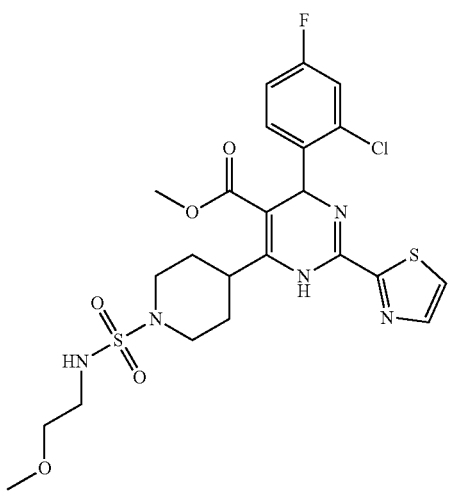

268

Compound 267: Methyl 6-(1-(N-(tert-butoxycarbonyl)-N-(2-methoxyethyl)-sulfamoyl)piperidin-4-yl)-4-(2-chloro-4-fluorophenyl)-2-(thiazol-2-yl)-1,4-dihydropyrimidine-5-carboxylate To a solution of methyl 6-(1-(N-(tert-butoxycarbonyl) sulfamoyl)piperidin-4-yl)-4-(2-chloro-4-fluorophenyl)-2-(thiazol-2-yl)-1,4-dihydropyrimidine-5-carboxylate compound 266 (307 mg, 0.500 mmol), 2-methoxyethanol (49 mg, 0.65 mmol) and triphenylphosphine (460 mg, 1.75 mmol) in tetrahydrofuran (10 mL) was added 1.9 M diisopropyl azodicarboxylate in tetrahydrofuran (0.9 mL, 1.75 mmol) at 0° C. After stirred at room temperature overnight, the reaction mixture was concentrated under reduced pressure to give a residue, which was purified by C18 column (acetonitrile: water=60% to 80%) to give the title compound (170 mg, 50% yield) as yellow solids. LC-MS (ESI): $R_T$=2.776 min, mass calcd. for $C_{28}H_{35}ClFN_5O_7S_2$ 671.2, m/z found 672.2 [M+H]$^+$. $^1$H NMR (400 MHz, DMSO-$d_6$) δ 9.55 (d, J=3.6 Hz, 0.8H), 9.15 (s, 0.2H), 8.01-7.93 (m, 2H), 7.44-7.31 (m, 2H), 7.23-7.19 (m, 1H), 6.02 (s, 0.2H), 5.92 (d, J=3.6 Hz, 0.8H), 3.96-3.78 (m, 4H), 3.74-3.67 (m, 1H), 3.53 (s, 3H), 3.49 (t, J=6.0 Hz, 2H), 3.27 (s, 3H), 2.98-2.87 (m, 2H), 2.03-1.76 (m, 3H), 1.64-1.61 (m, 1H), 1.49 (s, 9H).

Compound 268: Methyl 4-(2-chloro-4-fluorophenyl)-6-(1-(N-(2-methoxyethyl)-sulfamoyl)piperidin-4-yl)-2-(thiazol-2-yl)-1,4-dihydropyrimidine-5-carboxylate To a solution of methyl 6-(1-(N-(tert-butoxycarbonyl)-N-(2-methoxyethyl)sulfamoyl)piperidin-4-yl)-4-(2-chloro-4-fluorophenyl)-2-(thiazol-2-yl)-1,4-dihydropyrimidine-5-carboxylate Compound 267 (160 mg, 0.238 mmol) in dichloromethane (10 mL) was added trifluoroacetic acid (10 mL) at 0° C. After stirred at room temperature overnight, the reaction mixture was concentrated under reduced pressure, basified with saturated sodium carbonate aqueous solution to pH 7-8 and extracted with ethyl acetate (30 mL) twice. The combined organic layers were washed with brine (20 mL) twice, dried over $Na_2SO_{4(s)}$ and filtered. The filtrate was concentrated under reduced pressure to give the crude product, which was purified by C18 column (acetonitrile: water=65% to 85%) to give the title compound (120 mg, 88% yield) as yellow solids. LC-MS (ESI): $R_T$=3.148 min, mass calcd. for $C_{23}H_{27}ClFN_5O_5S_2$ 571.1, m/z found 571.9 [M+H]$^+$. $^1$H NMR (400 MHz, DMSO-$d_6$) δ 9.53 (d, J=2.4 Hz, 0.8H), 9.03 (s, 0.2H), 8.01-7.99 (m, 1.8H), 7.94-7.93 (m, 0.2H), 7.43 (dd, J=8.8, 2.4 Hz, 1H), 7.38-7.29 (m, 2H), 7.21-7.19 (m, 1H), 6.02 (s, 0.2H), 5.92 (d, J=3.6 Hz, 0.8H), 3.70-3.60 (m, 3H), 3.53 (s, 3H), 3.41 (t, J=5.6 Hz, 2H), 3.28 (s, 3H), 3.09 (q, J=6.0 Hz, 2H), 2.73-2.65 (m, 2H), 2.04-1.96 (m, 1H), 1.88-1.76 (m, 2H), 1.63-1.60 (m, 1H).

Racemic 268 (100 mg, 0.175 mmol) was separated by chiral Prep. HPLC (Column: Chiralpak IA 5 μm 20*250 mm; Mobile Phase: Hex:EtOH:DEA=80:20:0.3 at 10 mL/min; Temp: 30° C.; Wavelength: 214 nm) to afford the title compounds 268A (17.5 mg, 17.5% yield, 100% stereopure) and 268B (15.3 mg, 15.3% yield, 96.8% stereopure) as yellow solids.

Compound 268A: LC-MS (ESI): $R_T$=3.652 min, mass calcd. for $C_{23}H_{27}ClFN_5O_5S_2$ 571.1, m/z found 571.9 [M+H]$^+$. Chiral analysis (Column: Chiralpak IA 5 μm 4.6*250 mm; Mobile Phase: Hex:EtOH:DEA=80:20:0.2 at 1.0 mL/min; Temp: 30° C.; Wavelength: 230 nm, $R_T$=11.598 min). $^1$H NMR (400 MHz, DMSO-$d_6$) δ 9.55 (s, 0.8H), 9.04 (s, 0.2H), 8.00-7.95 (m, 2H), 7.44-7.42 (m, 1H), 7.37-7.31 (m, 2H), 7.23-7.18 (m, 1H), 6.01-5.92 (m, 1H), 3.68-3.65 (m, 3H), 3.53 (s, 3H), 3.42-3.40 (m, 2H), 3.28 (s, 3H), 3.12-3.09 (m, 2H), 2.71-2.68 (m, 2H), 2.03-2.00 (m, 1H), 1.89-1.76 (m, 2H), 1.63-1.60 (m, 1H).

Compound 268B: LC-MS (ESI): $R_T$=3.652 min, mass calcd. for $C_{23}H_{27}ClFN_5O_5S_2$ 571.1, m/z found 571.9 [M+H]$^+$. Chiral analysis (Column: Chiralpak IA 5 μm 4.6*250 mm; Mobile Phase: Hex:EtOH:DEA=80:20:0.2 at 1.0 mL/min; Temp: 30° C.; Wavelength: 230 nm, $R_T$=13.014 min). $^1$H NMR (400 MHz, DMSO-$d_6$) δ 9.54 (s, 0.8H), 9.03 (s, 0.2H), 8.00-7.94 (m, 2H), 7.44-7.42 (m, 1H), 7.34-7.31 (m, 2H), 7.23-7.19 (m, 1H), 6.01-5.92 (m, 1H), 3.68-3.65 (m, 3H), 3.53 (s, 3H), 3.42-3.40 (m, 2H), 3.28 (s, 3H), 3.09 (q, J=6.0 Hz, 2H), 2.71-2.68 (m, 2H), 2.02-1.99 (m, 1H), 1.89-1.76 (m, 2H), 1.63-1.61 (m, 1H).

Compound 284: methyl 4-(2-chloro-3-fluorophenyl)-6-(−5-oxopyrrolidin-3-yl)-2-(thiazol-2-yl)-1,4-dihydropyrimidine-5-carboxylate

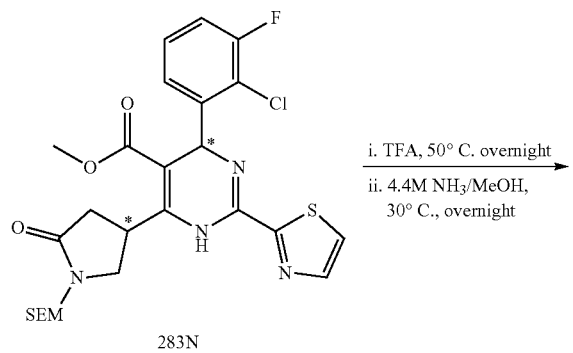

To a solution of compound 283N (530 mg, 0.94 mmol) in trifluoroacetic acid (22 mL) was stirred at 50° C. under nitrogen atmosphere overnight. The mixture was concentrated to give a residue, which was diluted with dichloromethane (10 mL) and washed with saturated sodium bicarbonate aqueous solution (5 mL). The organic layer was dried over $Na_2SO_{4(s)}$ and filtered. The filtrate was concentrated to give a residue, which was diluted with 4.4 M ammonia in methanol (20 mL) and stirred at 30° C. under nitrogen atmosphere overnight. Then it was concentrated to give a residue, which was purified by C18 column (acetonitrile:water=5% to 100%) to give the title compound (210 mg, 41% yield) as yellow solids. LC-MS (ESI): $R_T$=2.135 min, mass calcd. for $C_{19}H_{16}ClFN_4O_3S$ 434.1, m/z found 435.1 [M+H]$^+$. $^1$H NMR (400 MHz, CDCl$_3$) δ 7.83 (d, J=2.8 Hz, 1H), 7.55-7.52 (m, 2H), 7.27-7.20 (m, 1H), 7.12-7.07 (m, 2H), 6.26-6.12 (m, 1H), 5.8-5.76 (m, 1H), 4.97-4.84 (m, 1H), 3.81 (t, J=8.4 Hz, 0.3H), 3.73-3.62 (m, 0.7H), 3.61 (s, 3H), 3.53-3.49 (m, 1H), 3.07-3.01 (m, 0.7H), 2.90-2.84 (m, 0.3H), 2.65-2.59 (m, 0.8H), 2.50-2.44 (m, 0.2H).

A racemic mixture of compound 284N (210 mg, 0.48 mmol) was separated by chiral prep. HPLC (the first separation condition: Column: Chiralpak IA 5 μm 20*250 mm; Mobile Phase: Hex:EtOH:DEA=80:20:0.3 at 13 mL/min; Temp: 30° C.; Wavelength: 230 nm; the second separation condition: Column: Chiralpak IB 5 μm 20*250 mm; Mobile Phase: Hex:IPA:DEA=80:20:0.3 at 16 mL/min; Temp: 30° C.; Wavelength: 214 nm; the third separation condition: Column: Chiralpak AD-H 5 μm 20*250 mm; Mobile Phase: Hex:EtOH=60:40 at 13 mL/min; Temp: 30° C.; Wavelength: 214 nm) to afford the title compounds 284C (22.6 mg, 31% yield, 100% stereopure) and 284D (17.9 mg, 22% yield, 94.4% stereopure) as yellow solids. Compound 284C: LC-MS (ESI): $R_T$=3.562 min, mass calcd. for $C_{19}H_{16}ClFN_4O_3S$ 434.1, m/z found 435.1 [M+H]$^+$. Chiral analysis (Column: Chiralpak IA 5 μm 4.6*250 mm; Mobile Phase: Hex:EtOH:DEA=80:20:0.2 at 1.0 mL/min; Temp: 30° C.; Wavelength: 254 nm, $R_T$=12.940 min). $^1$H NMR (400 MHz, CDCl$_3$) δ 8.35 (s, 0.1H), 7.84-7.80 (m, 0.9H), 7.54-7.52 (m, 1.9H), 7.46 (s, 0.1H), 7.27-7.22 (m, 1H), 7.13-7.09 (m, 2H), 6.26 (s, 0.1H), 6.13 (d, J=2.0 Hz, 0.9H), 5.95 (s, 0.1H), 5.65 (s, 0.9H), 5.18 (s, 0.1H), 4.96-4.89 (m, 0.9H), 3.83-3.75 (m, 0.2H), 3.68-3.63 (m, 3.8H), 3.53-3.49 (m, 1H), 3.07-3.01 (m, 0.9H), 2.90-2.83 (m, 0.1H), 2.65-2.59 (m, 1H). Compound 284D: LC-MS (ESI): $R_T$=3.567 min, mass calcd. for $C_{19}H_{16}ClFN_4O_3S$ 434.1, m/z found 435.1 [M+H]$^+$. Chiral analysis (Column: Chiralpak IA 5 μm 4.6*250 mm; Mobile Phase: Hex:EtOH:DEA=80:20:0.2 at 1.0 mL/min; Temp: 30° C.; Wavelength: 254 nm, $R_T$=15.428 min). $^1$H NMR (400 MHz, CDCl$_3$) δ 8.35 (s, 0.1H), 7.84-7.80 (m, 0.9H), 7.52 (d, J=3.6 Hz, 1.9H), 7.46 (d, J=2.8 Hz, 0.1H), 7.27-7.20 (m, 1H), 7.11 (t, J=7.2 Hz, 2H), 6.26 (s, 0.1H), 6.13 (d, J=2.4 Hz, 0.9H), 5.85 (s, 0.1H), 5.58 (s, 0.9H), 5.18 (s, 0.1H), 4.96-4.89 (m, 0.9H), 3.83-3.78 (m, 0.2H), 3.68-3.61 (m, 3.8H), 3.51 (t, J=7.2 Hz, 1H), 3.07-3.01 (m, 1H), 2.65-2.59 (m, 1H).

Compound 287: Methyl 4-(2-chloro-4-fluorophenyl)-6-((trans)-4-(methylsulfonoimidamido)cyclohexyl)-2-(thiazol-2-yl)-1,4-dihydropyrimidine-5-carboxylate

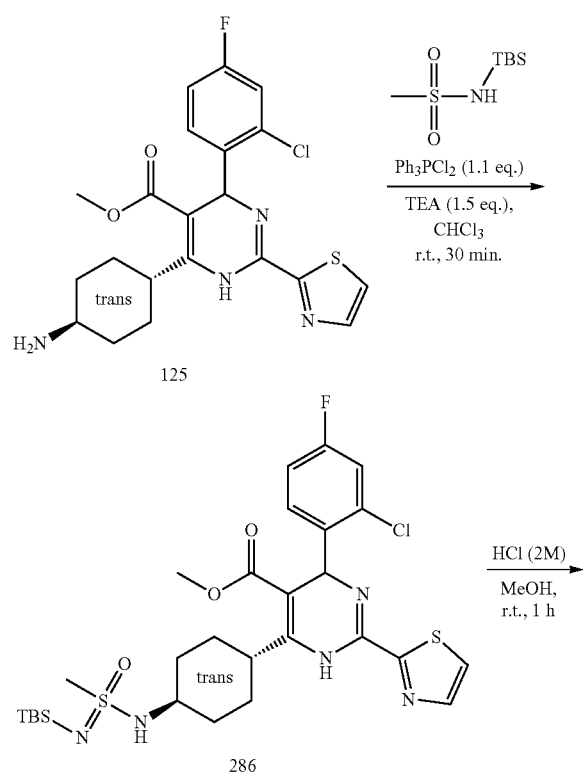

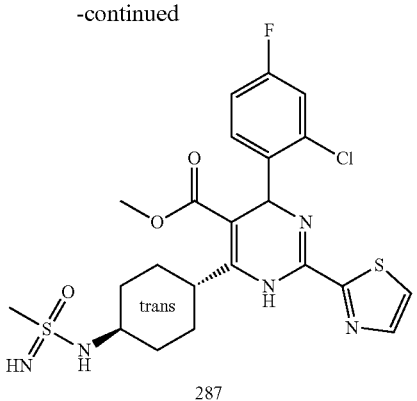

Compound 286: Methyl 6-((trans)-4-(N'-(tert-butyldimethylsilyl)-methylsulfonoimidamido)cyclohexyl)-4-(2-chloro-4-fluorophenyl)-2-(thiazol-2-yl)-1,4-dihydropyrimidine-5-carboxylate To a stirred solution of triphenylphosphine dichloride (2.0 g, 6.0 mmol) in dry chloroform (10 mL) under nitrogen atmosphere was added triethylamine (827 mg, 8.20 mmol) at 0° C. After stirred at room temperature for 10 minutes, the reaction mixture was cooled down to 0° C. and a solution of N-(tert-butyldimethylsilyl)-methanesulfonamide (1.15 g, 5.50 mmol) in dry chloroform (3 mL) was added. The reaction mixture was stirred at 0° C. for 20 minutes, after that a solution of methyl 6-((trans)-4-aminocyclohexyl)-4-(2-chloro-4-fluorophenyl)-2-(thiazol-2-yl)-1,4-dihydropyrimidine-5-carboxylate compound 125 (300 mg, 0.53 mmol) in chloroform (2 mL) was added. After stirred at 0° C. for 30 minutes, the reaction mixture was concentrated under reduced pressure to give a residue, which was purified by silica gel column chromatography (petroleum ether:ethyl acetate=5:1) to give the title compound (55 mg, 16% yield) as yellow solids. $^1$H NMR (400 MHz, CDCl$_3$) δ 8.13 (s, 0.4H), 7.83-7.82 (m, 1H), 7.51 (d, J=2.8 Hz, 0.5H), 7.45 (d, J=2.8 Hz, 0.5H), 7.40 (br s, 0.6H), 7.29-7.28 (m, 1H), 7.15-7.11 (m, 1H), 6.96-6.88 (m, 1H), 6.18 (s, 0.4H), 6.04 (d, J=2.8 Hz, 0.6H), 3.98-3.92 (m, 0.5H), 3.84-3.81 (m, 1H), 3.75-3.70 (m, 0.5H), 3.60 (s, 1.6H), 3.59 (s, 1.4H), 3.41-3.31 (m, 1H), 3.01 (s, 1.6H), 3.00 (s, 1.4H), 2.32-2.19 (m, 1.5H), 2.15-2.11 (m, 1H), 2.09-1.97 (m, 1.5H), 1.91-1.84 (m, 0.7H), 1.78-1.62 (m, 1.3H), 1.55-1.35 (m, 2H), 0.93 (s, 5H), 0.92 (s, 4H), 0.14-0.12 (m, 6H).

Compound 287: Methyl 4-(2-chloro-4-fluorophenyl)-6-((trans)-4-(methylsulfonoimidamido)cyclohexyl)-2-(thiazol-2-yl)-1,4-dihydropyrimidine-5-carboxylate To a solution of methyl 6-((trans)-4-(N'-(tert-butyldimethylsilyl)methylsulfonoimidamido)cyclohexyl)-4-(2-chloro-4-fluorophenyl)-2-(thiazol-2-yl)-1,4-dihydropyrimidine-5-carboxylate compound 286 (50 mg, 0.080 mmol) in methanol (2 mL) was added 2 M hydrochloride aqueous solution (1 mL) at room temperature. After stirred at room temperature for 1 hour, the reaction mixture was concentrated under reduced pressure to give a residue, which was dissolved in water (10 mL). The mixture was adjusted to pH=9-10 with 28% ammonia solution (1 mL), and concentrated under reduced pressure to give a residue, which was purified by Prep. HPLC (Column: Xbridge C18 HILIC (5 μm 10*190 mm), Mobile phase A: water, Mobile phase B: acetonitrile, UV: 214 nm, Flow rate: 50 mL/min, Gradient: 20-95% (% B)) to give the title compound 287 (25.0 mg, 74% yield) as yellow solids. LC-MS (ESI): R$_T$=3.364 min, mass calcd. for C$_{22}$H$_{25}$ClFN$_5$O$_3$S$_2$ 525.1, m/z found 526.2 [M+H]$^+$. $^1$H NMR (400 MHz, CDCl$_3$) δ 8.14 (s, 0.4H), 7.83-7.82 (m, 1H), 7.52 (d, J=3.2 Hz, 0.6H), 7.46 (d, J=3.2 Hz, 0.4H), 7.43 (br s, 0.6H), 7.30-7.25 (m, 1H), 7.15-7.12 (m, 1H), 6.95-6.88 (m, 1H), 6.18 (s, 0.4H), 6.04 (d, J=2.8 Hz, 0.6H), 4.00-3.94 (m, 0.4H), 3.76-3.71 (m, 0.6H), 3.60 (s, 1.6H), 3.59 (s, 1.4H), 3.43-3.38 (m, 1H), 3.10 (s, 1.6H), 3.09 (s, 1.4H), 2.23-2.09 (m, 2H), 2.05-1.80 (m, 2H), 1.74-1.55 (m, 2H), 1.48-1.41 (m, 2H).

A racemic mixture of compound 287 (220 mg, 0.344 mmol) was separated by chiral Prep. HPLC (Column: Chiralpak IC 5 μm 20*250 mm; Mobile Phase: Hex:EtOH:DEA=60:40:0.3 at 12 mL/min, Temp: 30° C.; Wavelength: 230 nm) to afford Group 1 (70 mg) and Group 2 (30 mg).

Group 1 (70 mg, 0.13 mmol) was separated by chiral Prep. HPLC (Column: Chiralpak AD-H 5 μm 20*250 mm; Mobile Phase: Hex:EtOH:DEA=70:30:0.3 at 15 mL/min, Temp: 30° C.; Wavelength: 214 nm) to give the title compounds 287A (20.4 mg, 29% yield, 100% ee) and 287B (19.2 mg, 27% yield, 100% ee) as yellow solids. Group 2 (30 mg, 0.060 mmol) was separated by chiral Prep. HPLC (Column: Chiralpak IC 5 μm 20*250 mm; Mobile Phase: Hex:EtOH:DEA=60:40:0.3 at 10 mL/min, Temp: 30° C.; Wavelength: 230 nm) to give the title compounds 287C (11.0 mg, 37% yield, 100% ee) and 287D (9.8 mg, 33% yield, 97.2% ee) as yellow solids.

Compound 287A: LC-MS (ESI): R$_T$=2.522 min, mass calcd. for C$_{22}$H$_{25}$ClFN$_5$O$_3$S$_2$ 525.1, m/z found 525.9 [M+H]$^+$. Chiral HPLC (Column: Chiralpak IC 5 μm 4.6*250 mm; Mobile Phase: Hex:EtOH:DEA=60:40:0.2 at 1.0 mL/min; Temp: 30° C.; Wavelength: 230 nm, R$_T$=10.044 min). $^1$H NMR (400 MHz, CDCl$_3$) δ 8.13 (s, 0.4H), 7.83-7.82 (m, 1H), 7.51 (d, J=2.8 Hz, 0.6H), 7.45 (d, J=3.2 Hz, 0.4H), 7.41 (d, J=1.6 Hz, 0.6H), 7.29-7.27 (m, 0.7H), 7.26-7.25 (m, 0.3H), 7.15-7.11 (m, 1H), 6.96-6.88 (m, 1H), 6.18 (s, 0.4H), 6.04 (d, J=2.8 Hz, 0.6H), 4.01-3.94 (m, 0.4H), 3.76-3.71 (m, 0.6H), 3.60 (s, 1.6H), 3.59 (s, 1.4H), 3.43-3.38 (m, 1H), 3.10 (s, 1.6H), 3.09 (s, 1.4H), 2.23-2.16 (m, 2H), 2.09-1.97 (m, 2H), 1.96-1.69 (m, 2H), 1.62-1.35 (m, 2H).

Compound 287B: LC-MS (ESI): R$_T$=2.876 min, mass calcd. for C$_{22}$H$_{25}$ClFN$_5$O$_3$S$_2$ 525.1, m/z found 525.9 [M+H]$^+$. Chiral HPLC (Column: Chiralpak IC 5 μm 4.6*250 mm; Mobile Phase: Hex:EtOH:DEA=60:40:0.2 at 1.0 mL/min; Temp: 30° C.; Wavelength: 230 nm, R$_T$=10.327 min). $^1$H NMR (400 MHz, CDCl$_3$) δ 8.13 (s, 0.4H), 7.83-7.82 (m, 1H), 7.51 (d, J=2.8 Hz, 0.6H), 7.45 (d, J=3.6 Hz, 0.4H), 7.41 (br s, 0.6H), 7.29-7.28 (m, 0.6H), 7.26-7.25 (m, 0.4H), 7.15-7.11 (m, 1H), 6.95-6.88 (m, 1H), 6.18 (s, 0.4H), 6.04 (d, J=2.4 Hz, 0.6H), 4.01-3.95 (m, 0.4H), 3.76-3.72 (m, 0.6H), 3.60 (s, 1.6H), 3.59 (s, 1.4H), 3.43-3.38 (m, 1H), 3.10 (s, 1.6H), 3.09 (s, 1.4H), 2.26-2.09 (m, 2.3H), 2.05-1.96 (m, 1.7H), 1.93-1.86 (m, 0.9H), 1.78-1.66 (m, 1.1H), 1.55-1.37 (m, 2H).

Compound 287C: LC-MS (ESI): R$_T$=2.556 min, mass calcd. for C$_{22}$H$_{25}$ClFN$_5$O$_3$S$_2$ 525.1, m/z found 526.1 [M+H]$^+$. Chiral HPLC (Column: Chiralpak IC 5 μm 4.6*250 mm; Mobile Phase: Hex:EtOH:DEA=60:40:0.2 at 1.0 mL/min; Temp: 30° C.; Wavelength: 230 nm, R$_T$=13.442 min). $^1$H NMR (400 MHz, CD$_3$OD) δ 7.92 (d, J=3.6 Hz, 0.5H), 7.88 (d, J=3.2 Hz, 0.5H), 7.75-7.73 (m, 1H), 7.39-7.35 (m, 1H), 7.24-7.20 (m, 1H), 7.07-7.00 (m, 1H), 6.13 (s, 0.5H), 6.05 (s, 0.5H), 3.96-3.89 (m, 0.5H), 3.72-3.66 (m, 0.5H), 3.58 (s, 3H), 3.40-3.31 (m, 1H), 3.04 (s, 3H), 2.19-2.13 (m, 2H), 2.03-1.99 (m, 1H), 1.92-1.87 (m, 1.5H), 1.80-1.77 (m, 0.8H), 1.73-1.67 (m, 0.7H), 1.51-1.42 (m, 2H).

Compound 287D: LC-MS (ESI): $R_T$=2.558 min, mass calcd. for $C_{22}H_{25}ClFN_5O_3S_2$ 525.1, m/z found 526.2 [M+H]$^+$. Chiral HPLC (Column: Chiralpak IC 5 μm 4.6*250 mm; Mobile Phase: Hex:EtOH:DEA=60:40:0.2 at 1.0 mL/min; Temp: 30° C.; Wavelength: 230 nm, $R_T$=15.164 min). $^1$H NMR (400 MHz, CD$_3$OD) δ 7.92 (d, J=2.8 Hz, 0.5H), 7.88 (d, J=3.2 Hz, 0.5H), 7.75-7.73 (m, 1H), 7.39-7.35 (m, 1H), 7.24-7.20 (m, 1H), 7.07-7.00 (m, 1H), 6.13 (s, 0.5H), 6.05 (s, 0.5H), 3.96-3.90 (m, 0.5H), 3.71-3.65 (m, 0.5H), 3.59 (s, 3H), 3.40-3.35 (m, 0.7H), 3.30-3.27 (m, 0.3H), 3.04 (s, 3H), 2.21-2.11 (m, 2H), 2.08-1.96 (m, 1H), 1.93-1.86 (m, 1.5H), 1.83-1.77 (m, 0.8H), 1.72-1.67 (m, 0.7H), 1.53-1.41 (m, 2H).

Compound 291: (trans)-Methyl 4-(2-chloro-3,4-difluorophenyl)-6-(4-(N-(2-hydroxyethyl)sulfamoyl)cyclohexyl)-2-(thiazol-2-yl)-1,4-dihydropyrimidine-5-carboxylate

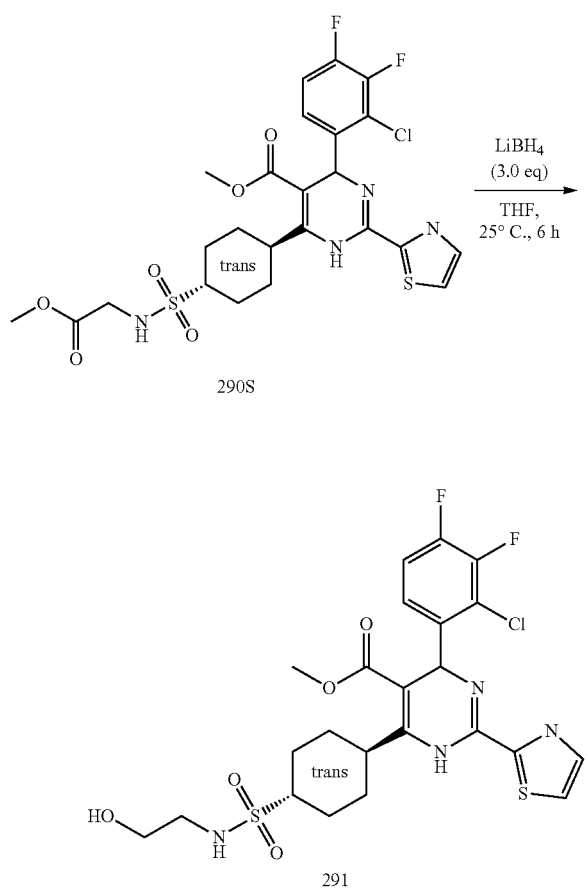

To a solution of (trans)-methyl 4-(2-chloro-3,4-difluorophenyl)-6-(4-(N-(2-ethoxy-2-oxoethyl)sulfamoyl)cyclohexyl)-2-(thiazol-2-yl)-1,4-dihydropyrimidine-5-carboxylate compound 290S (308 mg, 0.500 mmol) in tetrahydrofuran (20 mL) was added lithium borohydride (33 mg, 1.50 mmol) at 0° C. After stirred at 25° C. under nitrogen atmosphere for 6 hours, the mixture was diluted with ethyl acetate (200 mL) and brine (100 mL). The organic layer was separated, dried over Na$_2$SO$_{4(s)}$ and filtered. The filtrate was concentrated and purified by silica gel column chromatography (petroleum ether:ethyl acetate=4:1 to 2:1) to give the title compound (140 mg, 78% yield) as light yellow solids. LC-MS (ESI): $R_T$=3.357 min, mass calcd. for $C_{23}H_{25}ClF_2N_4O_5S_2$ 574.1, m/z found 575.0 [M+H]$^+$. $^1$H NMR (400 MHz, DMSO-d$_6$) δ 9.57 (d, J=3.2 Hz, 0.6H), 8.98 (s, 0.4H), 8.00-7.99 (m, 1.6H), 7.95-7.94 (m, 0.4H), 7.49-7.41 (m, 1H), 7.21-7.14 (m, 1H), 7.06 (t, J=6.0 Hz, 0.4H), 6.98 (t, J=6.0 Hz, 0.6H), 6.01 (s, 0.4H), 5.92 (d, J=3.6 Hz, 0.6H), 4.77-4.71 (m, 1H), 3.89-3.81 (m, 0.4H), 3.61-3.56 (m, 0.6H), 3.53 (s, 1.8H), 3.52 (s, 1.2H), 3.48-3.42 (m, 2H), 3.19-3.13 (m, 0.4H), 3.06-3.00 (m, 2.6H), 2.21-2.14 (m, 2H), 1.99-1.94 (m, 1H), 1.87-1.77 (m, 2H), 1.73-1.69 (m, 1H), 1.55-1.45 (m, 2H).

The racemic mixture of (trans)-methyl 4-(2-chloro-3,4-difluorophenyl)-6-(4-(N-(2-hydroxyethyl) sulfamoyl)cyclohexyl)-2-(thiazol-2-yl)-1,4-dihydropyrimidine-5-carboxylate 291 (140 mg, 0.243 mmol) was separated by chiral Prep. SFC (separation condition: Column: Chiralpak IA 5 Lm 20*250 mm; Mobile Phase: CO$_2$:MeOH=70:30 at 45 g/min; Col. Temp: 40.2° C.; Wavelength: 214 nm, Back pressure: 100 bar) to afford the title compounds 291C (43.2 mg, 20% yield, 98.3% stereopure) and 291D (38.5 mg, 18% yield, 94.4% stereopure) as yellow solids.

Compound 291C: LC-MS (ESI): $R_T$=4.541 min, mass calcd. for $C_{23}H_{25}ClF_2N_4O_5S_2$ 574.1, m/z found 575.0 [M+H]$^+$. Chiral analysis (Column: Chiralpak IA 5 μm 4.6*250 mm; Mobile Phase: CO$_2$:MeOH=70:30 at 2.999 g/min; Col. Temp: 40.2° C.; Wavelength: 214 nm, Back pressure: 100 bar, $R_T$=3.96 min). $^1$H NMR (400 MHz, DMSO-d$_6$) δ 9.57 (br s, 0.6H), 8.98 (br s, 0.4H), 8.00-7.99 (m, 1.6H), 7.95 (d, J=3.2 Hz, 0.4H), 7.49-7.41 (m, 1H), 7.21-7.15 (m, 1H), 7.06 (t, J=6.0 Hz, 0.4H), 6.98 (t, J=6.0 Hz, 0.6H), 6.01 (s, 0.4H), 5.92 (s, 0.6H), 4.77-4.71 (m, 1H), 3.89-3.82 (m, 0.4H), 3.60-3.56 (m, 0.6H), 3.53 (s, 1.8H), 3.52 (s, 1.2H), 3.48-3.42 (m, 2H), 3.19-3.13 (m, 0.4H), 3.06-2.99 (m, 2.6H), 2.22-2.14 (m, 2H), 1.99-1.94 (m, 1H), 1.87-1.81 (m, 2H), 1.73-1.70 (m, 1H), 1.53-1.45 (m, 2H).

Compound 291D: LC-MS (ESI): $R_T$=4.535 min, mass calcd. for $C_{23}H_{25}ClF_2N_4O_5S_2$ 574.1, m/z found 575.0 [M+H]$^+$. Chiral analysis (Column: Chiralpak IA 5 μm 4.6*250 mm; Mobile Phase: CO$_2$:MeOH=70:30 at 2.999 g/min; Col. Temp: 40.1° C.; Wavelength: 214 nm, Back pressure: 100 bar, $R_T$=4.82 min). $^1$H NMR (400 MHz, DMSO-d$_6$) δ 9.57 (d, J=4.0 Hz, 0.6H), 8.98 (br s, 0.4H), 8.00-7.99 (m, 1.6H), 7.94 (d, J=3.2 Hz, 0.4H), 7.49-7.41 (m, 1H), 7.21-7.14 (m, 1H), 7.06 (d, J=6.0 Hz, 0.4H), 6.98 (d, J=6.0 Hz, 0.6H), 6.01 (s, 0.4H), 5.92 (d, J=3.2 Hz, 0.6H), 4.77-4.71 (m, 1H), 3.89-3.82 (m, 0.4H), 3.61-3.58 (m, 0.6H), 3.53 (s, 1.8H), 3.52 (s, 1.2H), 3.48-3.43 (m, 2H), 3.19-3.13 (m, 0.4H), 3.06-2.99 (m, 2.6H), 2.21-2.14 (m, 2H), 1.99-1.94 (m, 1H), 1.88-1.78 (m, 2H), 1.73-1.70 (m, 1H), 1.55-1.43 (m, 2H).

587

Compound 295: Methyl 4-(2-chloro-4-fluorophenyl)-6-(3-hydroxycyclobutyl)-2-(thiazol-2-yl)-1,4-dihydropyrimidine-5-carboxylate

588

Compound 303: Methyl 6-(1-carbamoylpiperidin-4-yl)-4-(2-chloro-4-fluorophenyl)-2-(thiazol-2-yl)-1,4-dihydropyrimidine-5-carboxylate

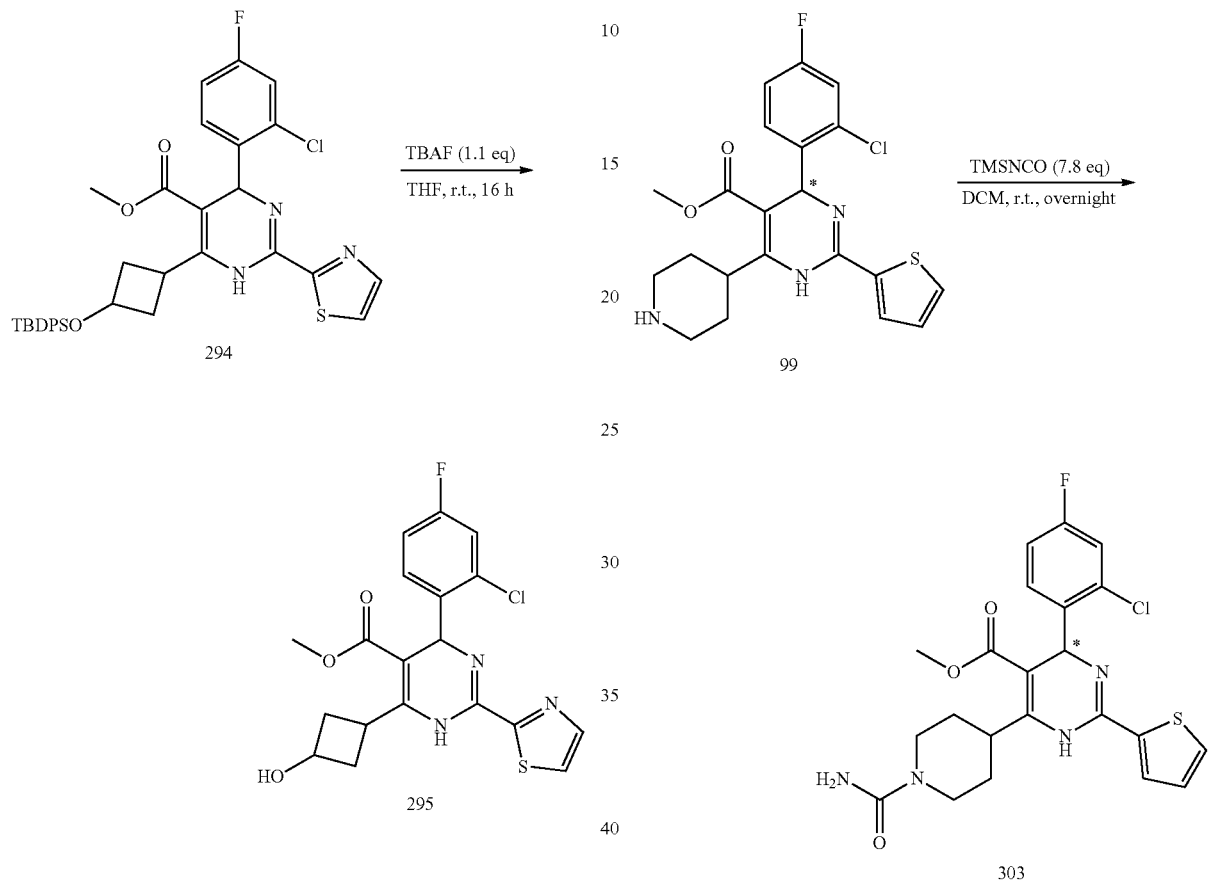

To a solution of methyl 6-(3-((tert-butyldiphenylsilyl)oxy)cyclobutyl)-4-(2-chloro-4-fluorophenyl)-2-(thiazol-2-yl)-1,4-dihydropyrimidine-5-carboxylate compound 294 (100 mg, 0.15 mmol) in tetrahydrofuran (5 mL) was added 1 M tetrabutylammonium fluoride in tetrahydrofuran (0.17 mL, 0.17 mmol) at 0° C. After stirred at room temperature for 16 hours, the mixture was diluted with ethyl acetate (50 mL), washed with water (50 mL) and brine (50 mL), dried over $Na_2SO_{4(s)}$ and filtered. The filtrate was concentrated under reduced pressure to give a residue, which was purified by C18 column (acetonitrile:water (+0.1% ammonium bicarbonate)=35% to 65%) to give the title compound (33.2 mg, 52% yield) as yellow solids. LC-MS (ESI): $R_T$=3.828 min, mass calcd. for $C_{19}H_{17}ClFN_3O_3S$ 421.1, m/z found 422.0 [M+H]$^+$. $^1$H NMR (400 MHz, DMSO-d$_6$) δ 9.50-9.46 (m, 0.6H), 8.99 (m, 0.4H), 8.02-8.00 (m, 1.6H), 7.96-7.95 (m, 0.4H), 7.43-7.39 (m, 1H), 7.33-7.29 (m, 1H), 7.24-7.17 (m, 1H), 6.00 (s, 0.4H), 5.90-5.89 (m, 0.5H), 5.42-5.40 (m, 0.4H), 5.07-5.05 (m, 0.5H), 4.98-4.97 (m, 0.1H), 4.56-4.51 (m, 0.1H), 4.26-4.22 (m, 0.1H), 4.12-3.98 (m, 1.2H), 3.78-3.69 (m, 0.6H), 3.51 (s, 3H), 2.67-2.61 (m, 0.5H), 2.42-2.36 (m, 0.7H), 2.29-2.22 (m, 2H), 2.08-1.93 (m, 0.8H).

To a solution of methyl 4-(2-chloro-4-fluorophenyl)-6-(piperidin-4-yl)-2-(thiazol-2-yl)-1,4-dihydropyrimidine-5-carboxylate compound 99 (100 mg, 0.230 mmol) in dichloromethane (2 mL) was added isocyanatotrimethylsilane (200 mg, 1.80 mmol) at room temperature under nitrogen atmosphere. After stirred at room temperature overnight, the mixture was concentrated under reduced pressure to give a residue, which was purified by Prep. HPLC (Column: Gilson X-bridge C18 (5 μm 19*150 mm), Mobile Phase A: water (+0.1% trifluoroacetic acid), Mobile Phase B: acetonitrile, UV: 214 nm, Flow rate: 20 mL/min, Gradient: 40-60% (% B)) to give the title compound (30 mg, 27% yield) as yellow solids. LC-MS (ESI): $R_T$=4.233 min, mass calcd. for $C_{21}H_{21}ClFN_5O_3S$ 477.1, m/z found 478.0 [M+H]$^+$. $^1$H NMR (400 MHz, DMSO-d$_6$) δ 9.47 (d, J=3.2 Hz, 0.7H), 9.10 (s, 0.3H), 8.00-7.98 (m, 1.7H), 7.92 (d, J=3.2 Hz, 0.3H), 7.44-7.31 (m, 2H), 7.24-7.17 (m, 1H), 6.01-5.91 (m, 3H), 4.16-3.98 (m, 2.3H), 3.79-3.72 (m, 0.7H), 3.53 (s, 2H), 3.52 (s, 1H), 2.76-2.64 (m, 2H), 1.96-1.59 (m, 3.3H), 1.49-1.46 (m, 0.7H).

Compound 305: Methyl 4-(2-chloro-4-fluorophenyl)-6-(1-((2,3-dihydroxypropyl)sulfonyl)piperidin-4-yl)-2-(thiazol-2-yl)-1,4-dihydropyrimidine-5-carboxylate

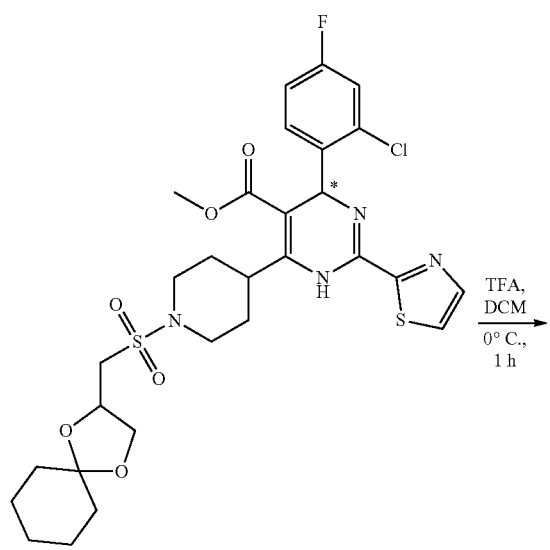

304A

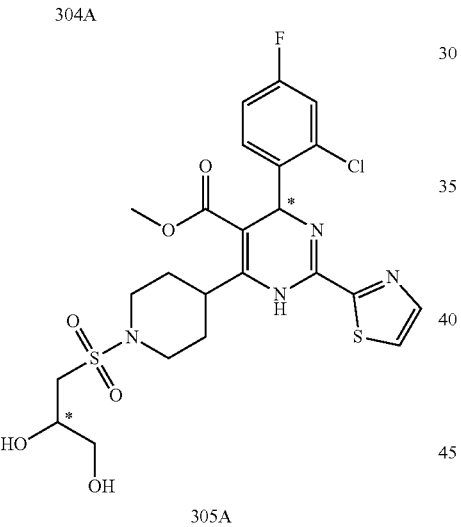

305A

To a solution of methyl 6-(1-((1,4-dioxaspiro[4.5]decan-2-ylmethyl) sulfonyl)piperidin-4-yl)-4-(2-chloro-4-fluorophenyl)-2-(thiazol-2-yl)-1,4-dihydropyrimidine-5-carboxylate compound 304A (45 mg, 0.070 mmol) in dichloromethane (2 mL) was added trifluoroacetic acid (1 mL) dropwise at 0° C. After stirred at room temperature for 1 hour, the mixture was washed with saturated sodium bicarbonate aqueous (10 mL) for three times, followed by water (10 mL). The separated organic layer was concentrated under reduced pressure to give a residue, which was purified by C18 column (acetonitrile:water (0.1% ammonium bicarbonate)=5% to 80%) to give the title compound 305A (10 mg, 25% yield, 100% stereopure) as yellow solids. LC-MS (ESI): $R_T$=3.984 min, mass calcd. for $C_{23}H_{26}ClFN_4O_6S_2$ 572.1, m/z found 573.1 [M+H]$^+$. Chiral analysis (Column: Chiralpak IA 5 μm 4.6*250 mm; Mobile Phase: Hex:EtOH:TFA=70:30:0.2 at 1.0 mL/min; Temp: 30° C.; Wavelength: 230 nm, $R_T$=12.191 min). $^1$H NMR (400 MHz, DMSO-d$_6$) δ 9.56 (s, 0.8H), 9.19 (s, 0.2H), 8.04-7.98 (m, 1.8H), 7.93 (d, J=3.2 Hz, 0.2H), 7.46-7.40 (m, 1H), 7.38-7.31 (m, 1H), 7.25-7.18 (m, 1H), 6.02 (s, 0.2H), 5.92 (s, 0.8H), 5.16-5.12 (m, 1H), 4.88-4.82 (m, 1H), 3.98-3.86 (m, 1.2H), 3.77-3.64 (m, 2.8H), 3.55 (s, 2.1H), 3.53 (s, 0.9H), 3.43-3.38 (m, 1H), 3.32-3.20 (m, 2H), 3.06-2.82 (m, 3H), 2.16-2.07 (m, 0.2H), 2.05-1.92 (m, 1H), 1.90-1.73 (m, 2H), 1.66-1.59 (m, 0.8H).

Compound 304B was converted to compound 305B using similar condition.

Compound 305B: Methyl 4-(2-chloro-4-fluorophenyl)-6-(1-((2,3-dihydroxypropyl)sulfonyl) piperidin-4-yl)-2-(thiazol-2-yl)-1,4-dihydropyrimidine-5-carboxylate LC-MS (ESI): $R_T$=3.640 min, mass calcd. for $C_{23}H_{26}ClFN_4O_6S_2$ 572.1, m/z found 573.1 [M+H]$^+$. Chiral analysis (Column: Chiralpak IA 5 μm 4.6*250 mm; Mobile Phase: Hex:EtOH:TFA=70:30:0.2 at 1.0 mL/min; Temp: 30° C.; Wavelength: 230 nm, $R_T$=15.002 min). $^1$H NMR (400 MHz, DMSO-d$_6$) δ 9.53 (s, 0.8H), 9.16 (s, 0.2H), 8.04-7.96 (m, 1.8H), 7.95-7.91 (m, 0.2H), 7.46-7.40 (m, 1H), 7.38-7.30 (m, 1H), 7.25-7.16 (m, 1H), 6.02 (s, 0.2H), 5.92 (d, J=3.2 Hz, 0.8H), 5.12 (br s, 1H), 4.83 (br s, 1H), 3.99-3.86 (m, 1.2H), 3.79-3.61 (m, 2.8H), 3.53 (s, 3H), 3.44-3.39 (m, 1H), 3.29-3.21 (m, 2H), 3.07-2.93 (m, 2H), 2.88-2.77 (m, 1H), 2.17-2.06 (m, 0.2H), 2.04-1.93 (m, 1H), 1.90-1.73 (m, 2H), 1.67-1.58 (m, 0.8H).

Compound 315: (trans)-Methyl 4-(2-chloro-3,4-difluorophenyl)-6-(4-(N-(2-hydroxyethyl)methylsulfonamido)cyclohexyl)-2-(thiazol-2-yl)-1,4-dihydropyrimidine-5-carboxylate

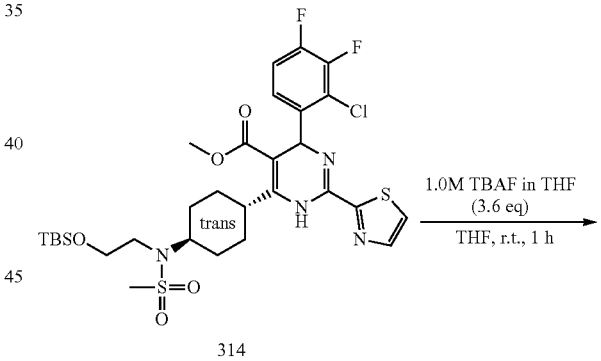

314

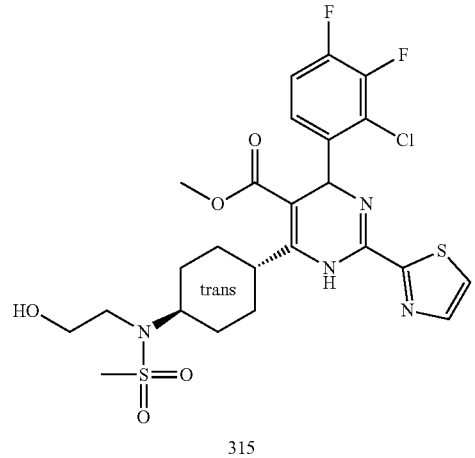

315

To a solution of (trans)-methyl 6-(4-(N-(2-((tert-butyldimethylsilyl)oxy)ethyl)methylsulfonamido)cyclohexyl)-4-(2-chloro-3,4-difluorophenyl)-2-(thiazol-2-yl)-1,4-dihydropyrimidine-5-carboxylate compound 314 (200 mg, 0.280 mmol) in dry tetrahydrofuran (10 mL) was added 1 M tetrabutylammonium fluoride in tetrahydrofuran (1 mL, 1.0 mmol) at 0° C. under nitrogen atmosphere. After stirred at room temperature for 1 hour, the mixture was quenched with water (20 mL) and extracted with ethyl acetate (20 mL) for three times. The combined organic layers were washed with brine (20 mL), dried over $Na_2SO_{4(s)}$ and filtered. The filtrate was concentrated under reduced pressure to give a residue, which was purified by C18 column (acetonitrile:water=45% to 60%) to give the title compound (150 mg, 90% yield) as yellow solids. LC-MS (ESI): $R_T$=3.550 min, mass calcd. for $C_{24}H_{27}ClF_2N_4O_5S_2$ 588.1, m/z found 588.9 [M+H]$^+$. $^1$H NMR (400 MHz, CDCl$_3$) δ 8.16 (s, 0.5H), 7.83 (d, J=3.2 Hz, 1H), 7.53 (d, J=3.2 Hz, 0.5H), 7.46 (d, J=2.8 Hz, 0.5H), 7.40 (s, 0.5H), 7.07-6.99 (m, 2H), 6.17 (s, 0.5H), 6.04 (d, J=2.8 Hz, 0.5H), 3.99-3.94 (m, 0.5H), 3.89-3.85 (m, 1H), 3.83-3.78 (m, 2H), 3.75-3.69 (m, 0.5H), 3.60 (s, 1.5H), 3.59 (s, 1.5H), 3.41-3.37 (m, 2H), 2.97 (s, 3H), 2.35 (t, J=5.6 Hz, 0.5H), 2.26-2.24 (m, 0.5H), 2.16-1.84 (m, 5H), 1.78-1.61 (m, 3H).

Racemic compound 315 (150 mg, 0.230 mmol) was separated by chiral Prep. HPLC (separation condition: Column: Chiralpak IA 5 μm 20*250 mm; Mobile Phase: Hex:EtOH=70:30 at 25 mL/min; Temp: 30° C.; Wavelength: 214 nm) to afford the title compounds 315C (13.8 mg, 9% yield, 100% stereopure) and 315D (11.1 mg, 7% yield, 99.0% stereopure) as yellow solids.

Compound 315C: LC-MS (ESI): $R_T$=3.302 min, mass calcd. for $C_{24}H_{27}ClF_2N_4O_5S_2$ 588.1, m/z found 589.2 [M+H]$^+$. Chiral analysis (Column: Chiralpak IA 5 μm 4.6*250 mm; Mobile Phase: Hex:EtOH=70:30 at 1.0 mL/min; Temp: 30° C.; Wavelength: 230 nm, $R_T$=6.533 min). $^1$H NMR (400 MHz, CDCl$_3$) δ 8.17 (s, 0.5H), 7.83 (d, J=2.8 Hz, 1H), 7.53 (d, J=2.8 Hz, 0.5H), 7.46 (d, J=2.8 Hz, 0.5H), 7.40 (s, 0.5H), 7.07-6.98 (m, 2H), 6.17 (s, 0.5H), 6.04 (d, J=2.4 Hz, 0.5H), 4.00-3.94 (m, 0.5H), 3.87-3.69 (m, 3.5H), 3.60 (s, 1.5H), 3.59 (s, 1.5H), 3.40-3.37 (m, 2H), 2.97 (s, 3H), 2.37 (d, J=6.0 Hz, 0.5H), 2.30-2.27 (m, 0.5H), 2.15-1.87 (m, 5H), 1.80-1.64 (m, 3H).

Compound 315D: LC-MS (ESI): $R_T$=4.127 min, mass calcd. for $C_{24}H_{27}ClF_2N_4O_5S_2$ 588.1, m/z found 589.2 [M+H]$^+$. Chiral analysis (Column: Chiralpak IA 5 μm 4.6*250 mm; Mobile Phase: Hex:EtOH=70:30 at 1.0 mL/min; Temp: 30° C.; Wavelength: 230 nm, $R_T$=8.328 min). $^1$H NMR (400 MHz, CDCl$_3$) δ 8.16 (s, 0.5H), 7.83 (d, J=2.8 Hz, 1H), 7.53 (d, J=3.2 Hz, 0.5H), 7.46 (d, J=2.8 Hz, 0.5H), 7.40 (s, 0.5H), 7.06-6.98 (m, 2H), 6.17 (s, 0.5H), 6.04 (d, J=3.2 Hz, 0.5H), 3.99-3.94 (m, 0.5H), 3.88-3.70 (m, 3.5H), 3.60 (s, 1.5H), 3.59 (s, 1.5H), 3.40-3.37 (m, 2H), 2.97 (s, 3H), 2.36 (d, J=6.0 Hz, 0.5H), 2.29-2.25 (m, 0.5H), 2.16-1.93 (m, 4.5H), 1.80-1.64 (m, 3.5H).

Compound 325: Methyl 4-(2-chloro-3,4-difluorophenyl)-2-(thiazol-2-yl)-6-(1-((1-(3,3,3-trifluoro-2-hydroxypropyl)-1H-pyrazol-4-yl)sulfonyl)piperidin-4-yl)-1,4-dihydropyrimidine-5-carboxylate

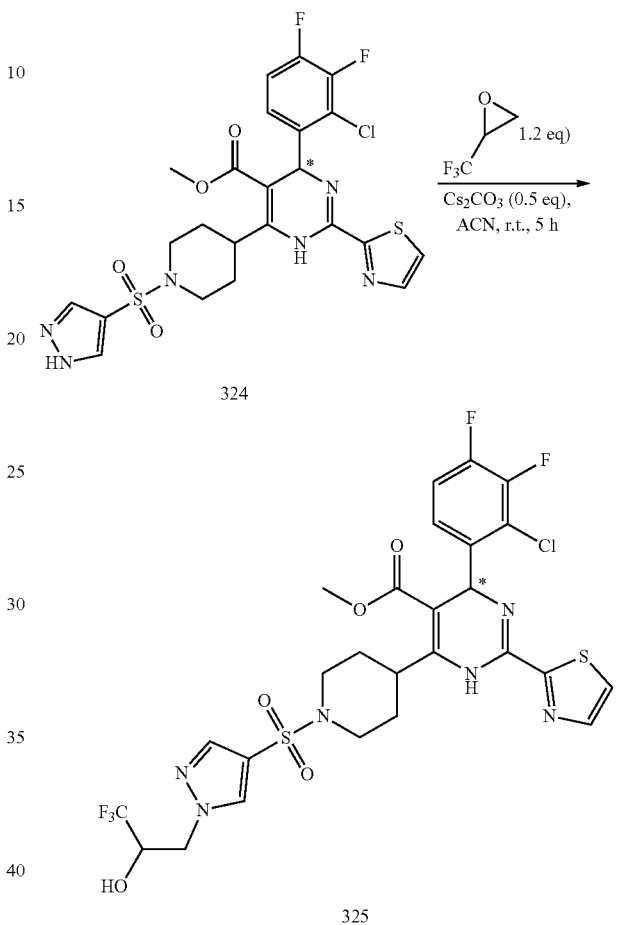

324

325

To a solution of methyl 6-(1-((1H-pyrazol-4-yl)sulfonyl)piperidin-4-yl)-4-(2-chloro-3,4-difluorophenyl)-2-(thiazol-2-yl)-1,4-dihydropyrimidine-5-carboxylate compound 324 (80 mg, 0.14 mmol) and 2-(trifluoromethyl)oxirane (18 mg, 0.17 mmol) in acetonitrile (2 mL) was added caesium carbonate (22 mg, 0.069 mmol). After stirred at room temperature under nitrogen atmosphere for 5 hours, the mixture was quenched with the addition of water (20 mL), then extracted with ethyl acetate (20 mL) twice. The combined organic layers were washed with water (15 mL), brine (15 mL), dried over $Na_2SO_{4(s)}$ and filtered. The filtrate was concentrated under reduced pressure to give a residue, which was purified by Prep. HPLC (Column: gilson X-bridge C18 (5 μm 19*150 mm), Mobile phase A: water (+0.1% ammonium bicarbonate), Mobile phase B: acetonitrile, UV: 214 nm, Flowrate: 15 mL/min, Gradient: 70-80% (% B)) to give the title compound (36 mg, 99.3% purity, 38% yield) as yellow solids. LC-MS (ESI): $R_T$=3.915 min, mass calcd. for $C_{26}H_{24}ClF_5N_6O_5S_2$ 694.1, m/z found 695.1 [M+H]$^+$. $^1$H NMR (400 MHz, DMSO-d$_6$) δ 9.65 (d, J=3.2 Hz, 0.8H), 9.25 (s, 0.2H), 8.43 (s, 0.2H), 8.41 (s, 0.8H), 8.05-7.99 (m, 1.8H), 7.94 (d, J=3.2 Hz, 0.2H), 7.91 (s, 0.2H), 7.90 (s, 0.8H), 7.49-7.39 (m, 1H), 7.23-7.12 (m, 1H), 6.80 (d, J=6.4

Hz, 1H), 6.01 (s, 0.2H), 5.91 (d, J=3.2 Hz, 0.8H), 4.57-4.45 (m, 2H), 4.41-4.32 (m, 1H), 3.80-3.64 (m, 2.2H), 3.58-3.50 (m, 0.8H), 3.48 (s, 2.4H), 3.47 (s, 0.6H), 2.21-2.16 (m, 2.2H), 2.12-2.01 (m, 1H), 1.98-1.85 (m, 1H), 1.84-1.75 (m, 1H), 1.69-1.61 (m, 0.8H).

Compound 335: Methyl 4-(2-chloro-4-fluorophenyl)-6-(1-((3-hydroxycyclobutyl)sulfonyl)piperidin-4-yl)-2-(thiazol-2-yl)-1,4-dihydropyrimidine-5-carboxylate

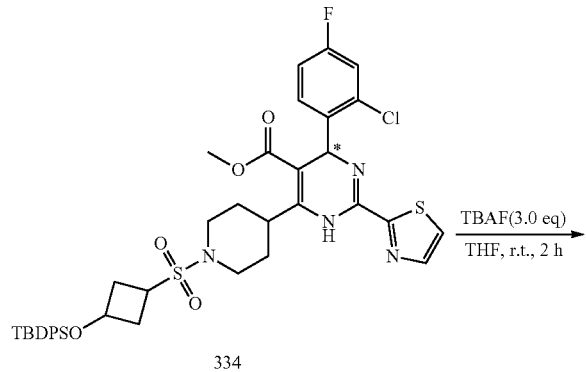

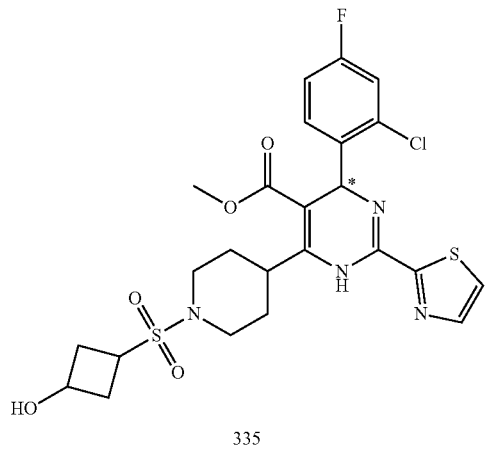

To a solution of methyl 6-(1-((3-((tert-butyldiphenylsilyl)oxy)cyclobutyl)-sulfonyl)piperidin-4-yl)-4-(2-chloro-4-fluorophenyl)-2-(thiazol-2-yl)-1,4-dihydropyrimidine-5-carboxylate 334 (260 mg, 0.320 mmol) in tetrahydrofuran (5 mL) was added 1 M tetrabutylammonium fluoride in tetrahydrofuran (1 mL, 1.0 mmol) at 0° C. After stirred at room temperature for 2 hours, the mixture was diluted in ethyl acetate (150 mL), washed with water (50 mL) and brine (50 mL), dried over $Na_2SO_{4(s)}$ and filtered. The filtrate was concentrated under reduced pressure to give a residue, which was purified by C18 column (acetonitrile:water (0.1% ammonium bicarbonate)=5% to 80%) to give the title compound (200 mg, purity 90%, 99% yield) as yellow solids. LC-MS (ESI): $R_T$=1.61 min, mass calcd. for $C_{24}H_{26}ClFN_4O_5S_2$ 568.1, m/z found 569.3 [M+H]$^+$.

Racemic 335 (200 mg, purity 90%, 0.316 mmol) was separated by chiral Prep. HPLC (Column: Chiralpak IC 5 μm 20*250 mm; Mobile Phase: Hex:EtOH:DEA=60:40:0.2 at 15 mL/min; Temp: 30° C.; Wavelength: 214 nm) to afford the title compounds 335A (cis isomer) (55.0 mg, 31% yield, 100% stereopure) and 335B (50.0 mg, 28% yield, 100% stereopure) as yellow solids.

Compound 335A (cis isomer): LC-MS (ESI): $R_T$=4.005 min, mass calcd. for $C_{24}H_{26}ClFN_4O_5S_2$ 568.1, m/z found 569.1 [M+H]$^+$. Chiral analysis (Column: Chiralpak IC 5 μm 4.6*250 mm; Mobile Phase: Hex:EtOH:DEA=60:40:0.2 at 1.0 mL/min; Temp: 30° C.; Wavelength: 230 nm, $R_T$=7.531 min). $^1$H NMR (400 MHz, DMSO-d$_6$) δ 9.49 (br s, 0.8H), 9.12 (br s, 0.2H), 8.00-7.99 (m, 1.8H), 7.93-7.92 (m, 0.2H), 7.43-7.40 (m, 1H), 7.38-7.31 (m, 1H), 7.23-7.18 (m, 1H), 6.05 (s, 0.2H), 5.92 (s, 0.8H), 5.37-5.34 (m, 1H), 4.38-4.30 (m, 1H), 3.96-3.94 (m, 0.2H), 3.92-3.85 (m, 1H), 3.78-3.68 (m, 2.8H), 3.53 (s, 2.4H), 3.52 (s, 0.6H), 2.89-2.80 (m, 2H), 2.60-2.54 (m, 2H), 2.31-2.24 (m, 2H), 2.07-2.04 (m, 0.2H), 2.00-1.74 (m, 3H), 1.61-1.57 (m, 0.8H).

Compound 335B (trans isomer): LC-MS (ESI): $R_T$=3.920 min, mass calcd. for $C_{24}H_{26}ClFN_4O_5S_2$ 568.1, m/z found 569.1 [M+H]$^+$. Chiral analysis (Column: Chiralpak IC 5 μm 4.6*250 mm; Mobile Phase: Hex:EtOH:DEA=60:40:0.2 at 1.0 mL/min; Temp: 30° C.; Wavelength: 230 nm, $R_T$=10.464 min). $^1$H NMR (400 MHz, DMSO-d$_6$) δ 9.53 (d, J=3.2 Hz, 0.8H), 9.14 (s, 0.2H), 8.02-7.99 (m, 1.8H), 7.93-7.92 (m, 0.2H), 7.44-7.41 (m, 1H), 7.38-7.31 (m, 1H), 7.23-7.17 (m, 1H), 6.01 (s, 0.2H), 5.92 (d, J=3.6 Hz, 0.8H), 5.46-5.44 (m, 1H), 4.07-3.98 (m, 1H), 3.94-3.90 (m, 0.2H), 3.75-3.65 (m, 2.8H), 3.53 (s, 2.4H), 3.52 (s, 0.6H), 3.50-3.43 (m, 1H), 2.86-2.76 (m, 2H), 2.59-2.51 (m, 2H), 2.18-2.14 (m, 2H), 2.11-1.75 (m, 3.2H), 1.62-1.59 (m, 0.8H).

Compound 348: Methyl 4-(2-chloro-4-fluorophenyl)-6-(3-(1-hydroxyethyl)bicyclo[1.1.1]pentan-1-yl)-2-(thiazol-2-yl)-1,4-dihydropyrimidine-5-carboxylate

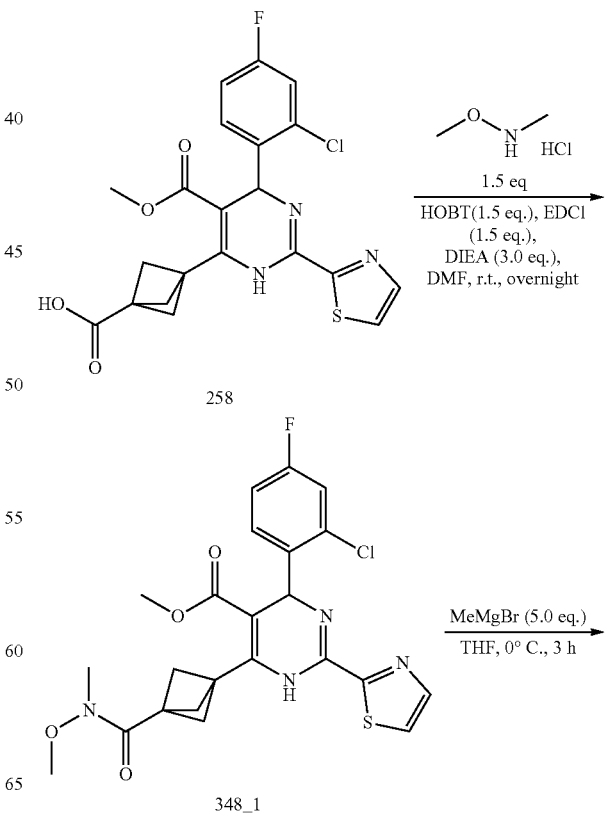

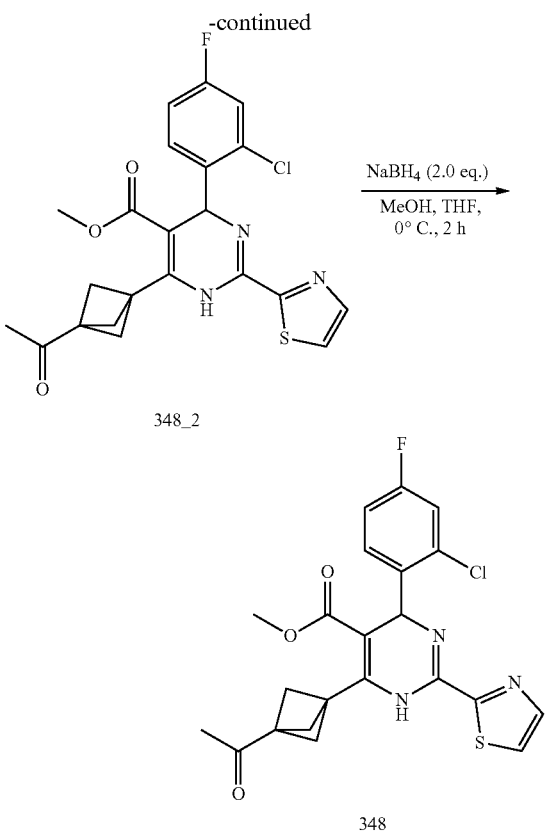

348_2

348

Compound 348_1: Methyl 4-(2-chloro-4-fluorophenyl)-6-(3-(methoxy(methyl)carbamoyl)bicyclo[1.1.1]pentan-1-yl)-2-(thiazol-2-yl)-1,4-dihydropyrimidine-5-carboxylate To a solution of 3-(6-(2-chloro-4-fluorophenyl)-5-(methoxycarbonyl)-2-(thiazol-2-yl)-3,6-dihydropyrimidin-4-yl)bicyclo[1.1.1]pentane-1-carboxylic acid 258 (380 mg, 90% purity, 0.740 mmol), 1-hydroxybenzotriazole (150 mg, 1.11 mmol) and N-((ethylimino)methylene)-N,N-dimethylpropane-1,3-diamine hydrochloride (213 mg, 1.11 mmol) in N,N-dimethylformamide (10 mL) was added ethyldiisopropylamine (287 mg, 2.22 mmol) and N,O-dimethylhydroxylamine hydrochloride (108 mg, 1.11 mmol) at room temperature. After stirred at room temperature overnight, the mixture was quenched with water (40 mL) and extracted with ethyl acetate (40 mL) for three times. The combined organic layers were washed with 1 M hydrochloride aqueous solution (30 mL), water (30 mL), brine (30 mL), dried over $Na_2SO_{4(s)}$ and filtered. The filtrate was concentrated under reduced pressure to give the title compound (340 mg, 90% purity from $^1$H NMR, 82% yield) as yellow solids. LC-MS (ESI): $R_T$=1.54 min, mass calcd. for $C_{23}H_{22}ClFN_4O_4S$ 504.1, m/z found 505.5 [M+H]$^+$. $^1$H NMR (400 MHz, CDCl$_3$) δ 7.90 (s, 0.7H), 7.82 (d, J=3.2 Hz, 1H), 7.49-7.40 (m, 1.3H), 7.30-7.28 (m, 1H), 7.14-7.11 (m, 1H), 6.97-6.89 (m, 1H), 6.16 (s, 0.7H), 6.04 (s, 0.3H), 3.73 (s, 3H), 3.61 (s, 3H), 3.23 (s, 3H), 2.61 (s, 6H).

Compound 348_2: Methyl 6-(3-acetylbicyclo[1.1.1]pentan-1-yl)-4-(2-chloro-4-fluorophenyl)-2-(thiazol-2-yl)-1,4-dihydropyrimidine-5-carboxylate To a solution of methyl 4-(2-chloro-4-fluorophenyl)-6-(3-(methoxy(methyl)carbamoyl)bicyclo[1.1.1]pentan-1-yl)-2-(thiazol-2-yl)-1,4-dihydropyrimidine-5-carboxylate 348_1 (340 mg, 90% purity, 0.606 mmol) in tetrahydrofuran (8 mL) was dropwise added 2 M methyl magnesium bromide in tetrahydrofuran (1.5 mL, 3.00 mmol) at 0° C. After stirred at 0° C. for 3 hours, the mixture was quenched with water (10 mL) and extracted with ethyl acetate (10 mL) for three times. The combined organic layers were washed with brine (20 mL), dried over $Na_2SO_{4(s)}$ and filtered. The filtrate was concentrated under reduced pressure to give a residue, which was purified by C18 column (acetonitrile:water=60% to 90%) to give the title compound (185 mg, 90% purity from $^1$H NMR, 60% yield) as yellow solids. LC-MS (ESI): $R_T$=1.61 min, mass calcd. for $C_{22}H_{19}ClFN_3O_3S$ 459.1, m/z found 460.4 [M+H]$^+$. $^1$H NMR (400 MHz, CDCl$_3$) δ 7.89 (s, 0.7H), 7.83-7.81 (m, 1H), 7.50 (d, J=3.2 Hz, 0.4H), 7.45 (d, J=3.2 Hz, 0.6H), 7.42 (s, 0.3H), 7.31-7.28 (m, 1H), 7.15-7.12 (m, 1H), 6.98-6.90 (m, 1H), 6.17 (s, 0.6H), 6.03 (d, J=2.8 Hz, 0.4H), 3.64 (s, 1.1H), 3.61 (s, 1.9H), 2.54 (s, 3.8H), 2.48 (s, 2.2H), 2.20 (s, 3H).

Racemic 348_2 (180 mg, 90% purity, 0.352 mmol) was separated by chiral Prep. HPLC (separation condition: Column: Chiralpak IG 5 μm 20*250 mm; Mobile Phase: Hex:EtOH:DEA=85:15:0.3 at 15 mL/min; Temp: 30° C.; Wavelength: 230 nm) to afford the title compounds 348_2A (78 mg, 90% purity from $^1$H NMR, 43% yield, 100% stereopure) and 348_2B (76 mg, 90% purity from $^1$H NMR, 42% yield, 100% stereopure) as yellow solids.

Compound 348_2A: LC-MS (ESI): $R_T$=1.58 min, mass calcd. for $C_{22}H_{19}ClFN_3O_3S$ 459.1, m/z found 460.4 [M+H]$^+$. Chiral analysis (Column: Chiralpak IG 5 μm 4.6*250 mm; Mobile Phase: Hex:EtOH:DEA=85:15:0.2 at 1.0 mL/min; Temp: 30° C.; Wavelength: 230 nm, $R_T$=10.906 min). $^1$H NMR (400 MHz, DMSO-d$_6$) δ 9.44 (d, J=3.2 Hz, 0.6H), 8.34 (s, 0.4H), 8.01-7.99 (m, 1.6H), 7.96-7.95 (m, 0.4H), 7.46-7.41 (m, 1H), 7.35-7.31 (m, 1H), 7.25-7.20 (m, 1H), 5.98 (s, 0.4H), 5.88 (d, J=2.8 Hz, 0.6H), 3.56 (s, 1.8H), 3.55 (s, 1.2H), 2.45 (s, 2.5H), 2.30 (s, 3.5H), 2.15 (s, 1.2H), 2.13 (s, 1.8H).

Compound 348_2B: LC-MS (ESI): $R_T$=1.58 min, mass calcd. for $C_{22}H_{19}ClFN_3O_3S$ 459.1, m/z found 460.3 [M+H]$^+$. Chiral analysis (Column: Chiralpak IG 5 μm 4.6*250 mm; Mobile Phase: Hex:EtOH:DEA=85:15:0.2 at 1.0 mL/min; Temp: 30° C.; Wavelength: 230 nm, $R_T$=12.902 min). $^1$H NMR (400 MHz, DMSO-d$_6$) δ 9.44 (d, J=3.2 Hz, 0.6H), 8.34 (s, 0.4H), 8.01-7.99 (m, 1.6H), 7.96-7.95 (m, 0.4H), 7.45-7.40 (m, 1H), 7.35-7.31 (m, 1H), 7.25-7.19 (m, 1H), 5.98 (s, 0.4H), 5.88 (d, J=3.6 Hz, 0.6H), 3.56 (s, 1.8H), 3.55 (s, 1.2H), 2.45 (s, 2.5H), 2.30 (s, 3.5H), 2.15 (s, 1.3H), 2.13 (s, 1.7H).

Compound 348B: Methyl 4-(2-chloro-4-fluorophenyl)-6-(3-(1-hydroxyethyl)bicyclo[1.1.1]pentan-1-yl)-2-(thiazol-2-yl)-1,4-dihydropyrimidine-5-carboxylate To a solution of methyl 6-(3-acetylbicyclo[1.1.1]pentan-1-yl)-4-(2-chloro-4-fluorophenyl)-2-(thiazol-2-yl)-1,4-dihydropyrimidine-5-carboxylate 348_2B (70 mg, 90% purity, 0.14 mmol) in methanol (0.8 mL) and tetrahydrofuran (1.6 mL) was added sodium borohydride (11 mg, 0.27 mmol) at 0° C. The reaction mixture was stirred at 0° C. for 2 hours. The mixture was added water (10 mL) slowly and concentrated to give a residue, which was extracted with ethyl acetate (10 mL) for three times. The combined organic layers were washed with brine (20 mL), dried over $Na_2SO_4$ (s) and filtered. The filtrate was concentrated under reduced pressure to give a residue, which was purified by Prep.

HPLC (Column: water X-bridge C18 (5 μm 19*150 mm), Mobile Phase A: water (+0.1% ammonium bicarbonate), Mobile Phase B: acetonitrile, UV: 214 nm, Flow rate: 15 mL/min, Gradient: 30-95% (% B)) to give the title compound (20 mg, 99.2% purity, 31% yield) as yellow solids. LC-MS (ESI): $R_T$=3.347 min, mass calcd. for $C_{22}H_{21}ClFN_3O_3S$ 461.1, m/z found 462.1 [M+H]$^+$. $^1$H NMR (400 MHz, CDCl$_3$) δ 7.92 (s, 0.8H), 7.82-7.80 (m, 1H), 7.48 (d, J=3.2 Hz, 0.2H), 7.44 (d, J=3.2 Hz, 0.8H), 7.40 (s, 0.2H), 7.33-7.28 (m, 1H), 7.14-7.11 (m, 1H), 6.97-6.89 (m, 1H), 6.16 (s, 0.8H), 6.01 (d, J=2.8 Hz, 0.2H), 3.95-3.87 (m, 1H), 3.63 (s, 0.5H), 3.60 (s, 2.5H), 2.24-2.09 (m, 6H), 1.34 (d, J=3.2 Hz, 1H), 1.19 (d, J=6.4 Hz, 3H).

Compound 356: Ethyl 4-(2-chloro-3,4-difluorophenyl)-6-(1-((2-hydroxyethyl)sulfonyl)piperidin-4-yl)-2-(thiazol-2-yl)-1,4-dihydropyrimidine-5-carboxylate

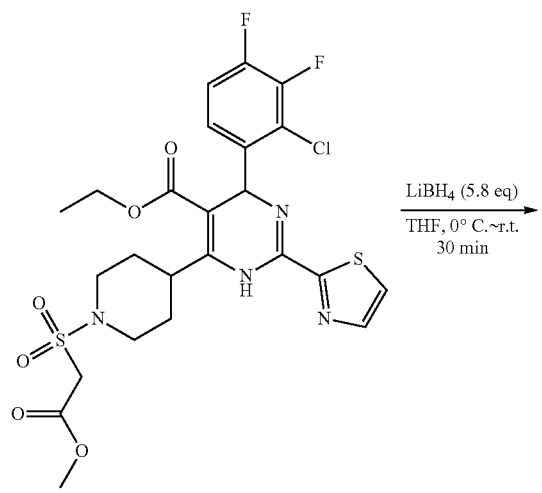

To a solution of ethyl 4-(2-chloro-3,4-difluorophenyl)-6-(1-((2-methoxy-2-oxoethyl)sulfonyl)piperidin-4-yl)-2-(thiazol-2-yl)-1,4-dihydropyrimidine-5-carboxylate 355 (320 mg, 99% purity, 0.525 mmol) in tetrahydrofuran (5 mL) was added lithium tetrahydroborate (70 mg, 96% purity, 3.1 mmol) at 0° C. under nitrogen atmosphere. After stirred at room temperature for 30 minutes, the reaction mixture was quenched with saturated aqueous sodium bicarbonate solution (20 mL) slowly and extracted with ethyl acetate (20 mL) for three times. The combined organic layers were washed with brine (20 mL), dried over Na$_2$SO$_{4(s)}$, filtered and concentrated under reduced pressure to give a residue, which was purified by silica gel column chromatography (dichloromethane:methanol=200:1 to 100:1) to give the title compound (250 mg, 99.7% purity, 80% yield) as yellow solids. LC-MS (ESI): $R_T$=3.809 min, mass calcd. for $C_{23}H_{25}ClF_2N_4O_5S_2$ 574.1, m/z found 574.9 [M+H]$^+$. $^1$H NMR (400 MHz, DMSO-d$_6$) δ 9.62 (br s, 0.8H), 9.16 (br s, 0.2H), 8.06-7.97 (m, 1.8H), 7.95-7.92 (m, 0.2H), 7.49-7.43 (m, 1H), 7.23-7.17 (m, 1H), 6.03 (s, 0.2H), 5.94 (s, 0.8H), 5.34-5.31 (m, 0.1H), 5.06-5.02 (m, 0.9H), 3.98 (q, J=6.8 Hz, 2H), 3.79-3.65 (m, 5H), 3.24-3.19 (m, 2H), 2.92-2.83 (m, 2H), 2.16-2.08 (m, 0.2H), 2.03-1.94 (m, 1H), 1.87-1.78 (m, 2H), 1.68-1.59 (m, 0.8H), 1.09-1.03 (m, 3H).

Racemic 356 (240 mg, 0.405 mmol) was separated by chiral Prep. HPLC (Column: Chiralpak ID 5 Lm 20*250 mm; Mobile Phase: Hex:EtOH:DEA=70:30:0.3 at 15 mL/min; Temp: 30° C.; Wavelength: 214 nm) to afford the title compounds 356A (80 mg, 99.9% purity, 34% yield, 100% stereopure) and 356B (65 mg, 99.0% purity, 28% yield, 98.1% stereopure) as yellow solids.

Compound 356A: LC-MS (ESI): $R_T$=3.846 min, mass calcd. for $C_{23}H_{25}ClF_2N_4O_5S_2$ 574.1, m/z found 574.9 [M+H]$^+$. Chiral analysis (Column: Chiralpak ID 5 μm 4.6*250 mm; Mobile Phase: Hex:EtOH:DEA=70:30:0.2 at 1.0 mL/min; Temp: 30° C.; Wavelength: 230 nm, $R_T$=9.363 min). $^1$H NMR (400 MHz, DMSO-d$_6$) δ 9.40 (br s, 1H), 8.00-7.96 (m, 2H), 7.48-7.42 (m, 1H), 7.26-7.19 (m, 1H), 5.96 (s, 1H), 5.02 (br s, 1H), 3.97 (q, J=7.2 Hz, 2H), 3.79-3.67 (m, 5H), 3.21 (t, J=6.4 Hz, 2H), 2.92-2.84 (m, 2H), 2.05-1.97 (m, 1H), 1.88-1.79 (m, 2H), 1.71-1.62 (m, 1H), 1.07 (t, J=7.2 Hz, 3H).

Compound 356B: LC-MS (ESI): $R_T$=3.847 min, mass calcd. for $C_{23}H_{25}ClF_2N_4O_5S_2$ 574.1, m/z found 574.9 [M+H]$^+$. Chiral analysis (Column: Chiralpak ID 5 μm 4.6*250 mm; Mobile Phase: Hex:EtOH:DEA=70:30:0.2 at 1.0 mL/min; Temp: 30° C.; Wavelength: 230 nm, $R_T$=11.939 min). $^1$H NMR (400 MHz, DMSO-d$_6$) δ 8.74 (br s, 1H), 8.04-7.94 (m, 2H), 7.49-7.42 (m, 1H), 7.22-7.17 (m, 1H), 5.96 (s, 1H), 5.03 (br s, 1H), 3.97 (q, J=6.8 Hz, 2H), 3.77-3.67 (m, 5H), 3.21 (t, J=6.0 Hz, 2H), 2.92-2.84 (m, 2H), 2.04-1.96 (m, 1H), 1.87-1.79 (m, 2H), 1.69-1.62 (m, 1H), 1.07 (t, J=6.8 Hz, 3H).

Compound 357A: (trans)-Methyl 4-(2-chloro-4-fluorophenyl)-6-(1-((3-(hydroxymethyl)cyclobutyl)sulfonyl)piperidin-4-yl)-2-(thiazol-2-yl)-1,4-dihydropyrimidine-5-carboxylate

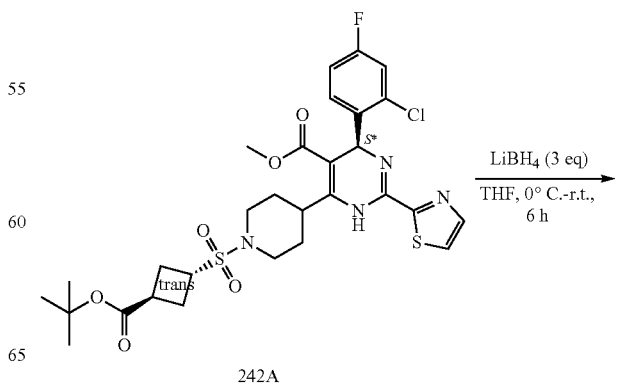

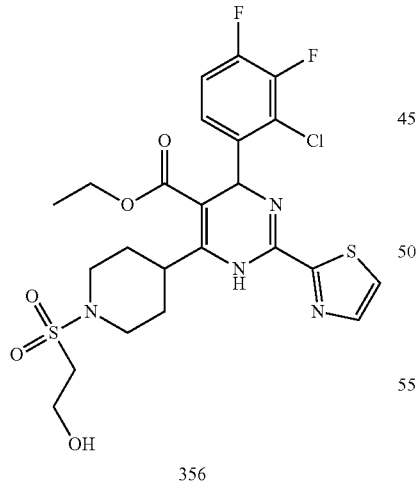

-continued

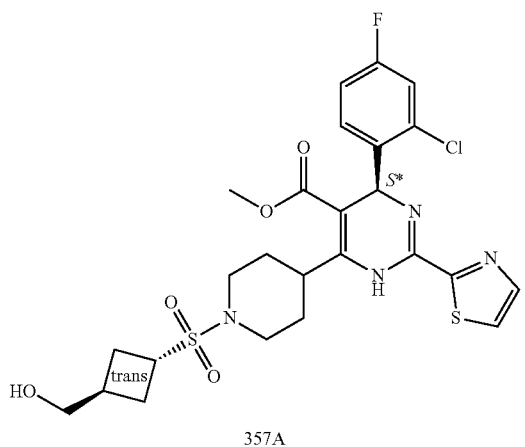

357A

To a solution of (trans)-methyl 6-(1-((3-(tert-butoxycarbonyl)cyclobutyl)sulfon yl)piperidin-4-yl)-4-(2-chloro-4-fluorophenyl)-2-(thiazol-2-yl)-1,4-dihydropyrimidine-5-carboxylate 242A (210 mg, 0.322 mmol) in tetrahydrofuran (15 mL) was added lithium borohydride (21 mg, 0.966 mmol) at 0° C. After stirred at room temperature for 6 hours, the mixture was quenched with water (40 mL) at 0° C., concentrated under reduced pressure and extracted with ethyl acetate (40 mL) twice. The combined organic layers were dried over $Na_2SO_{4(s)}$ and concentrated to give a residue, which was purified by C18 column (acetonitrile:water=50% to 58%) to give the title compound (50 mg, 22% yield, 99.9% stereopure) as yellow solids. LC-MS (ESI): $R_T$=3.848 min, mass calcd. for $C_{25}H_{28}ClFN_4O_5S_2$ 582.1, m/z found 582.9 [M+H]$^+$. Chiral analysis (Column: Chiralpak IG 5 μm 4.6*250 mm; Mobile Phase: CO2:MeOH=70:30 at 2.999 g/min; Col. Temp: 39.9° C.; Wavelength: 230 nm, Back pressure: 100 bar, $R_T$=3.79 min). $^1$H NMR (400 MHz, DMSO-d$_6$) δ 9.53 (d, J=3.6 Hz, 0.8H), 9.12 (s, 0.2H), 8.01-7.93 (m, 2H), 7.45-7.41 (m, 1H), 7.38-7.31 (m, 1H), 7.23-7.18 (m, 1H), 6.01 (s, 0.2H), 5.92 (d, J=3.2 Hz, 0.8H), 4.66 (t, J=4.8 Hz, 1H), 4.03-3.95 (m, 1H), 3.76-3.69 (m, 3H), 3.53 (s, 2.4H), 3.52 (s, 0.6H), 3.47 (s, 2H), 2.87-2.79 (m, 2H), 2.40-2.33 (m, 3H), 2.14-1.74 (m, 5.2H), 1.61-1.58 (m, 0.8H).

Compound 357B: (cis)-Methyl 4-(2-chloro-4-fluorophenyl)-6-(1-((3-(hydroxymethyl)cyclobutyl) sulfonyl)piperidin-4-yl)-2-(thiazol-2-yl)-1,4-dihydropyrimidine-5-carboxylate compound 357B was prepared analogously to compound 357A from compound 242B, LC-MS (ESI): $R_T$=3.635 min, mass calcd. for $C_{25}H_{28}ClFN_4O_5S_2$ 582.1, m/z found 583.1 [M+H]$^+$. Chiral analysis (Column: Chiralpak IG 5 μm 4.6*250 mm; Mobile Phase: CO2:MeOH=70:30 at 2.999 g/min; Col. Temp: 39.9° C.; Wavelength: 230 nm, Back pressure: 100 bar, $R_T$=3.79 min). $^1$H NMR (400 MHz, DMSO-d$_6$) δ 8.01-7.93 (m, 2H), 7.45-7.31 (m, 2H), 7.24-7.18 (m, 1H), 6.01 (s, 0.2H), 5.92 (s, 0.8H), 4.61 (t, J=5.6 Hz, 1H), 3.95-3.86 (m, 1.2H), 3.77-3.66 (m, 2.8H), 3.53 (s, 2.4H), 3.52 (s, 0.6H), 3.40-3.35 (m, 2H), 2.87-2.79 (m, 2H), 2.42-2.25 (m, 3H), 2.12-1.74 (m, 5H), 1.62-1.57 (m, 1H).

Compound 358B: (trans)-Methyl 4-(2-chloro-3,4-difluorophenyl)-6-(4-(N-(3-hydroxy-3-methylbutyl) sulfamoyl)cyclohexyl)-2-(thiazol-2-yl)-1,4-dihydropyrimidine-5-carboxylate

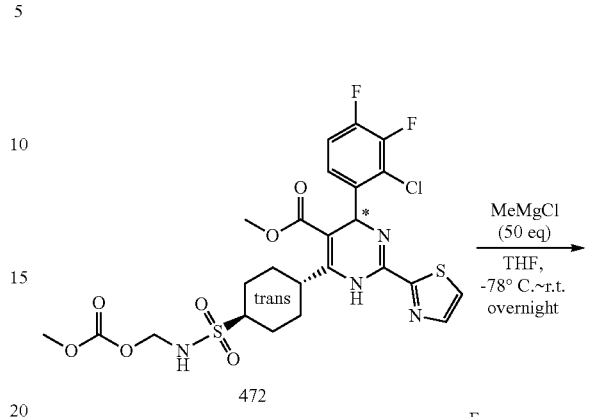

472

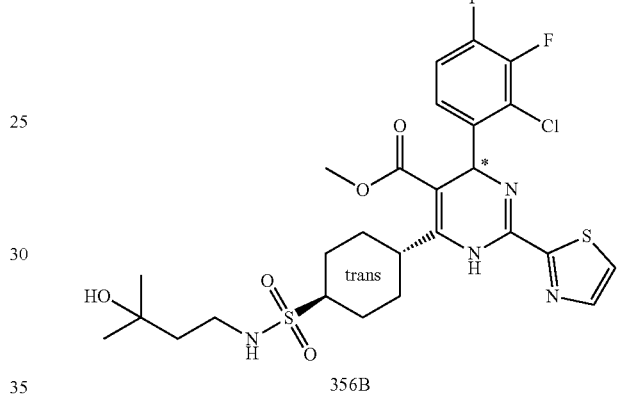

356B

To a solution of (trans)-methyl 4-(2-chloro-3,4-difluorophenyl)-6-(4-(N-(3-methoxy-3-oxopropyl)sulfamoyl)cyclohexyl)-2-(thiazol-2-yl)-1,4-dihydropyrimidine-5-carboxylate 252Y (60 mg, 97.2 μmol) in tetrahydrofuran (4 mL) were added dropwise 3.0 M methylmagnesium chloride in tetrahydrofuran (1.6 mL, 4.8 mmol) at −78° C. After stirred at room temperature overnight, the reaction mixture was quenched with saturated ammonium chloride aqueous solution (20 mL), and extracted with ethyl acetate (20 mL) twice. The combined organic layers were washed with brine (20 mL), dried over $Na_2SO_{4(s)}$ and filtered. The filtrate was concentrated under reduced pressure to give a residue, which was purified by Prep. TLC (dichloromethane:methanol=20:1) to give an impure compound, which was further purified by Prep. HPLC (Column: X-bridge C18 (5 μm 19*150 mm), Mobile Phase A: water (+0.1% ammonium bicarbonate), Mobile Phase B: acetonitrile, UV: 214 nm, Flow rate: 15 mL/min, Gradient: 45-70% (% B)) to give the title compound (25 mg, 36% yield, 99.0% stereopure) as yellow solids. LC-MS (ESI): $R_T$=3.690 min, mass calcd. for $C_{26}H_{31}ClF_2N_4O_5S_2$ 616.1, m/z found 617.1 [M+H]$^+$. Chiral analysis (Column: Chiralpak IE 5 μm 4.6*250 mm; Mobile Phase: Hex:EtOH:DEA=50:50:0.2 at 1.0 mL/min; Temp: 30° C.; Wavelength: 230 nm, $R_T$=9.331 min). $^1$H NMR (400 MHz, DMSO-d$_6$) δ 9.55 (d, J=2.8 Hz, 0.6H), 8.98 (br s, 0.4H), 8.07-7.98 (m, 1.6H), 7.94 (d, J=2.8 Hz, 0.4H), 7.48-7.41 (m, 1H), 7.21-7.15 (m, 1H), 6.92 (t, J=6.4 Hz, 0.4H), 6.85 (t, J=5.6 Hz, 0.6H), 6.01 (s, 0.4H), 5.92 (d, J=3.2 Hz, 0.6H), 4.34 (s, 0.4H), 4.32 (s, 0.6H), 3.90-3.82 (m, 0.4H), 3.62-3.58 (m, 0.6H), 3.53 (s, 1.8H), 3.52 (s, 1.2H), 3.18-3.12 (m, 0.5H), 3.08-3.04 (m, 2H), 2.99-2.95 (m, 0.5H), 2.22-2.12 (m, 2H), 2.01-1.82 (m, 3H), 1.75-1.70 (m, 1H), 1.61-1.56 (m, 2H), 1.53-1.43 (m, 2H), 1.10 (s, 6H).

Compound 360C: methyl 4-(2-chloro-4-fluorophenyl)-6-(1-((1-(((R)-2-hydroxypropyl)-1H-pyrazol-4-yl)sulfonyl)piperidin-4-yl)-2-(thiazol-2-yl)-1,4-dihydropyrimidine-5-carboxylate

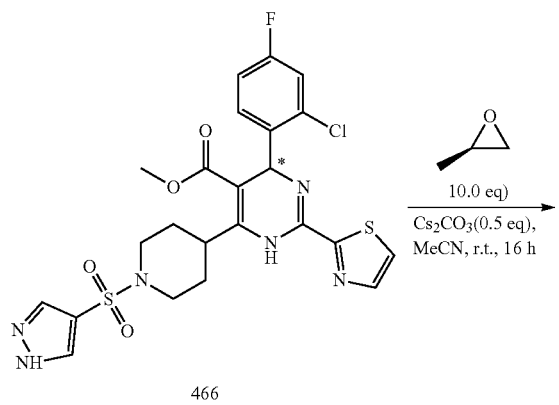

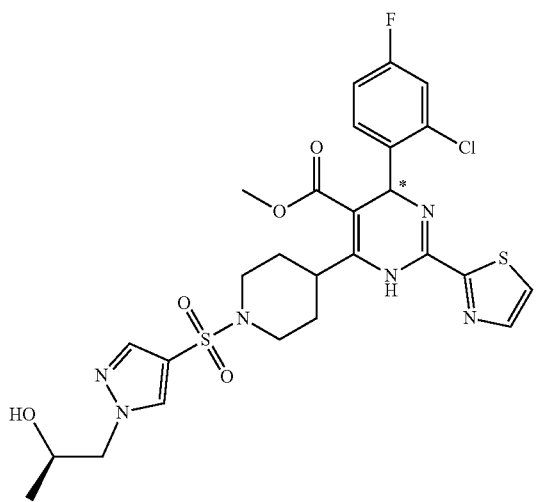

360C

To a solution of methyl 6-(1-((1H-pyrazol-4-yl)sulfonyl)piperidin-4-yl)-4-(2-chloro-4-fluorophenyl)-2-(thiazol-2-yl)-1,4-dihydropyrimidine-5-carboxylate 466 (100 mg, 0.177 mmol) and (R)-2-methyloxirane (103 mg, 1.77 mmol) in acetonitrile (2 mL) was added caesium carbonate (29 mg, 0.089 mmol). After stirred at room temperature under nitrogen atmosphere for 16 hours, the mixture was diluted with water (20 mL) and extracted with ethyl acetate (20 mL) twice. The combined organic layers were washed with water (15 mL), brine (15 mL), dried over Na$_2$SO$_{4(s)}$ and filtered. The filtrate was concentrated under reduced pressure to give a residue, which was purified by Prep. HPLC (Column: Gilson X-bridge C18 (5 μm 19*150 mm), Mobile phase A: water (0.1% ammonium bicarbonate), Mobile phase B: acetonitrile, UV: 214 nm, Flowrate: 15 mL/min, Gradient: 50-55% (% B)) to give the title compound (45.0 mg, 95.1% purity, 41% yield) as yellow solids. LC-MS (ESI): R$_T$=2.611 min, mass calcd. for C$_{26}$H$_{28}$ClFN$_6$O$_5$S$_2$ 622.1, m/z found 622.9 [M+H]$^+$. $^1$H NMR (400 MHz, DMSO-d$_6$) δ 9.51 (d, J=3.6 Hz, 0.8H), 9.15 (s, 0.2H), 8.28 (s, 0.2H), 8.27 (s, 0.8H), 8.04-7.98 (m, 1.8H), 7.93 (d, J=3.2 Hz, 0.2H), 7.83 (s, 0.2H), 7.82 (s, 0.8H), 7.44-7.38 (m, 1H), 7.37-7.29 (m, 1H), 7.24-7.16 (m, 1H), 6.00 (s, 0.2H), 5.90 (d, J=3.2 Hz, 0.8H), 4.99 (d, J=4.4 Hz, 1H), 4.17-3.98 (m, 3H), 3.79-3.63 (m, 2.2H), 3.58-3.50 (m, 0.8H), 3.48 (s, 2.4H), 3.47 (s, 0.6H), 2.30-2.17 (m, 2.2H), 2.11-2.00 (m, 1H), 1.97-1.87 (m, 1H), 1.84-1.75 (m, 1H), 1.68-1.60 (m, 0.8H), 1.05 (d, J=6.0 Hz, 3H).

Compound 360D: methyl 4-(2-chloro-4-fluorophenyl)-6-(1-(((1-(((S)-2-hydroxypropyl)-1H-pyrazol-4-yl)sulfonyl)piperidin-4-yl)-2-(thiazol-2-yl)-1,4-dihydropyrimidine-5-carboxylate Compound 360D was prepared analogously to compound 360C from compound 466, purified by Prep. HPLC (Column: Gilson X-bridge C18 (5 μm 19*150 mm), Mobile phase A: water (0.1% ammonium bicarbonate), Mobile phase B: acetonitrile, UV: 214 nm, Flowrate: 15 mL/min, Gradient: 50-55% (% B)) to give the title compound (65.0 mg, 98.2% purity, 59% yield) as yellow solids. LC-MS (ESI): R$_T$=2.557 min, mass calcd. for C$_{26}$H$_{28}$ClFN$_6$O$_5$S$_2$ 622.1, m/z found 622.9 [M+H]$^+$. $^1$H NMR (400 MHz, DMSO-d$_6$) δ 9.51 (d, J=3.6 Hz, 0.8H), 9.15 (s, 0.2H), 8.28 (s, 0.2H), 8.27 (s, 0.8H), 8.04-7.98 (m, 1.8H), 7.92 (d, J=2.8 Hz, 0.2H), 7.83 (s, 0.2H), 7.82 (s, 0.8H), 7.44-7.38 (m, 1H), 7.37-7.30 (m, 1H), 7.23-7.16 (m, 1H), 6.00 (s, 0.2H), 5.90 (d, J=3.6 Hz, 0.8H), 4.99 (d, J=4.8 Hz, 1H), 4.17-3.98 (m, 3H), 3.79-3.63 (m, 2.2H), 3.57-3.50 (m, 0.8H), 3.48 (s, 2.4H), 3.47 (s, 0.6H), 2.30-2.17 (m, 2.2H), 2.12-1.99 (m, 1H), 1.97-1.85 (m, 1H), 1.84-1.75 (m, 1H), 1.68-1.60 (m, 0.8H), 1.05 (d, J=6.0 Hz, 3H).

Compound 376: Methyl 4-(2-chloro-4-fluorophenyl)-6-(3-(N—((R)-2,3-dihydroxypropyl)methylsulfonamido)bicyclo[1.1.1]pentan-1-yl)-2-(thiazol-2-yl)-1,4-dihydropyrimidine-5-carboxylate

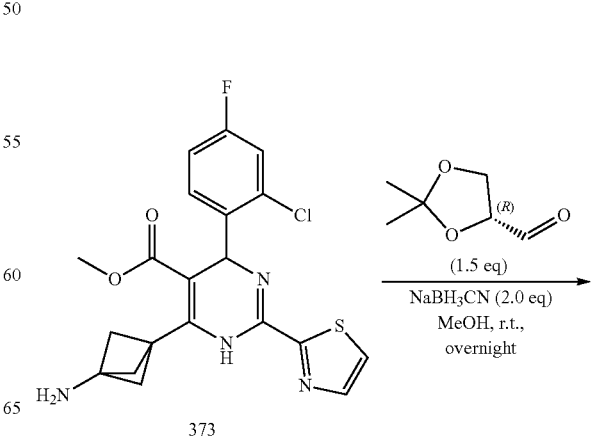

373

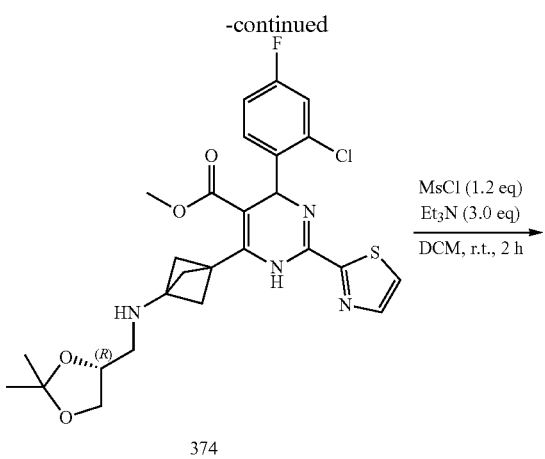

374

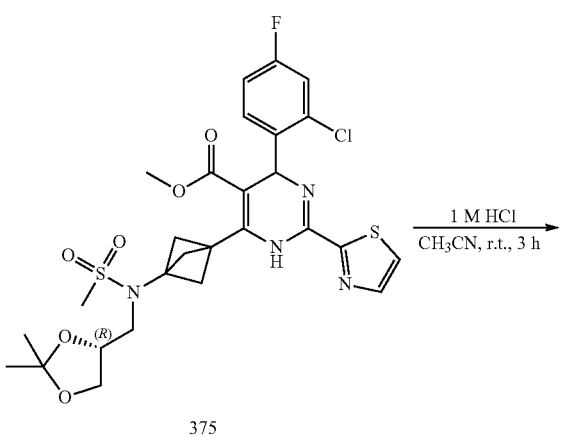

375

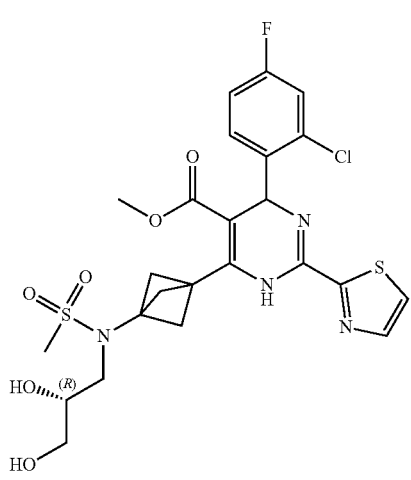

376

Compound 374: Methyl 4-(2-chloro-4-fluorophenyl)-6-(3-((((R)-2,2-dimethyl-1,3-dioxolan-4-yl)methyl)amino)bicyclo[1.1.1]pentan-1-yl)-2-(thiazol-2-yl)-1,4-dihydropyrimidine-5-carboxylate To a solution of methyl 6-(3-aminobicyclo[1.1.1]pentan-1-yl)-4-(2-chloro-4-fluorophenyl)-2-(thiazol-2-yl)-1,4-dihydropyrimidine-5-carboxylate 373 (250 mg, 0.579 mmol) in methanol (8 mL) was added (R)-2,2-dimethyl-1,3-dioxolane-4-carbaldehyde (113 mg, 0.859 mmol) at room temperature. After stirring at room temperature for 1.5 hours, sodium cyanoborohydride (73 mg, 1.16 mmol) was added at room temperature. After stirred at room temperature overnight, the reaction mixture was poured into water (10 mL) and extracted with ethyl acetate (20 mL) twice. The combined organic layers were washed with brine (20 mL) twice, dried over $Na_2SO_{4(s)}$ and filtered. The filtrate was concentrated under reduced pressure to give a residue, which was purified by Prep. HPLC (Column: X-bridge C18 (5 μm 19*150 mm), Mobile phase A: water (0.1% ammonium bicarbonate), Mobile phase B: acetonitrile, UV: 214 nm, Flow rate: 15 mL/min, Gradient: 60-90% (% B)) to give the title compound (150 mg, 48% yield) as yellow solids. $^1$H NMR (300 MHz, $CDCl_3$) δ 7.88-7.80 (m, 2H), 7.49-7.40 (m, 1.3H), 7.33-7.28 (m, 0.7H), 7.14-7.11 (m, 1H), 6.95-6.89 (m, 1H), 6.16 (s, 0.9H), 6.04 (s, 0.1H), 4.29-4.21 (m, 1H), 4.09-4.04 (m, 1H), 3.72-3.67 (m, 1H), 3.63-3.60 (m, 3H), 2.81-2.77 (m, 2H), 2.30-2.24 (m, 7H), 1.44 (s, 3H), 1.37 (s, 3H).

Compound 375: Methyl 4-(2-chloro-4-fluorophenyl)-6-(3-(N—(((R)-2,2-dimethyl-1,3-dioxolan-4-yl)methyl)methylsulfonamido)bicyclo[1.1.1]pentan-1-yl)-2-(thiazol-2-yl)-1,4-dihydropyrimidine-5-carboxylate To a solution of methyl 4-(2-chloro-4-fluorophenyl)-6-(3-((((R)-2,2-dimethyl-1,3-dioxolan-4-yl)methyl)amino)bicyclo[1.1.1]pentan-1-yl)-2-(thiazol-2-yl)-1,4-dihydropyrimidine-5-carboxylate 374 (150 mg, 0.275 mmol) in dichloromethane (5 mL) was added methanesulfonyl chloride (38 mg, 0.330 mmol) and triethylamine (83 mg, 0.825 mmol) at 0° C. After stirred at room temperature for 2 hours, the mixture was diluted with water (10 mL), extracted with dichloromethane (10 mL) twice. The combined organic layers were washed with brine (15 mL) twice, dried over $Na_2SO_{4(s)}$ and filtered. The filtrate was concentrated under reduced pressure to give a residue, which was purified by C18 column (acetonitrile:water=05% to 80%) to give the title compound (160 mg, 93% yield) as yellow solids. $^1$H NMR (400 MHz, DMSO-$d_6$) δ 9.45-9.44 (m, 0.6H), 8.38 (s, 0.4H), 8.00-7.95 (m, 2H), 7.44-7.41 (m, 1H), 7.35-7.31 (m, 1H), 7.24-7.18 (m, 1H), 5.97 (s, 0.5H), 5.88 (d, J=3.2 Hz, 0.5H), 4.22-4.18 (m, 1H), 4.03-4.00 (m, 1H), 3.74-3.70 (m, 1H), 3.55-3.54 (m, 3H), 3.29-3.23 (m, 2H), 3.03-2.99 (m, 3H), 2.56 (s, 3H), 2.39 (s, 3H), 1.37 (s, 3H), 1.28 (s, 3H).

Racemic 375 (160 mg, 0.256 mmol) was separated by chiral Prep. SFC (Column: Chiralpak IG 5 μm 20*250 mm; Mobile Phase: $CO_2$:MeOH:DEA=75:25:0.3 at 50 g/min; Col. Temp 41.1° C.; Wavelength: 254 nm; Back pressure: 100 bar) to afford the title compounds 375C (50 mg, 31% yield, 100% stereopure) and 375D (60 mg, 38% yield, 100% stereopure) as yellow solids.

Compound 375C: Chiral analysis (Column: Chiralpak IG 5 μm 4.6*250 mm; Mobile Phase: $CO_2$:MeOH:DEA=75:25:0.2 at 3.0 g/min; Col. Temp: 40° C.; Wavelength: 230 nm, $R_T$=6.14 min). $^1$H NMR (400 MHz, DMSO-$d_6$) δ 9.44 (s, 0.5H), 8.38 (s, 0.5H), 8.01-7.95 (m, 2H), 7.45-7.40 (m, 1H), 7.35-7.30 (m, 1H), 7.24-7.19 (m, 1H), 5.97 (s, 0.5H), 5.88 (s, 0.5H), 4.22-4.18 (m, 1H), 4.04-4.00 (m, 1H), 3.73-3.70 (m, 1H), 3.55-3.54 (m, 3H), 3.29-3.26 (m, 2H), 3.03-2.99 (m, 3H), 2.56 (s, 3H), 2.39 (s, 3H), 1.37 (s, 3H), 1.28 (s, 3H).

Compound 375D: Chiral analysis (Column: Chiralpak IG 5 μm 4.6*250 mm; Mobile Phase: CO$_2$:MeOH:DEA=75:25:0.2 at 3.0 g/min; Col. Temp: 40° C.; Wavelength: 230 nm, $R_T$=7.18 min). $^1$H NMR (400 MHz, DMSO-d$_6$) δ 9.45-9.44 (m, 0.6H), 8.37 (s, 0.4H), 8.01-7.95 (m, 2H), 7.45-7.41 (m, 1H), 7.35-7.30 (m, 1H), 7.24-7.18 (m, 1H), 5.97 (s, 0.5H), 5.89-5.88 (m, 0.5H), 4.23-4.17 (m, 1H), 4.03-4.00 (m, 1H), 3.73-3.70 (m, 1H), 3.55-3.54 (m, 3H), 3.29-3.26 (m, 2H), 3.03-2.99 (m, 3H), 2.56 (s, 3H), 2.39 (s, 3H), 1.37 (s, 3H), 1.28 (s, 3H).

Compound 376C: Methyl 4-(2-chloro-4-fluorophenyl)-6-(3-(N—((R)-2,3-dihydroxypropyl)methylsulfonamido)bicyclo[1.1.1]pentan-1-yl)-2-(thiazol-2-yl)-1,4-dihydropyrimidine-5-carboxylate To a solution of methyl 4-(2-chloro-4-fluorophenyl)-6-(3-(N—(((R)-2,2-dimethyl-1,3-dioxolan-4-yl)methyl)methylsulfonamido)bicyclo[1.1.1]pentan-1-yl)-2-(thiazol-2-yl)-1,4-dihydropyrimidine-5-carboxylate 375C (30 mg, 0.048 mmol) in acetonitrile (3 mL) was added 1 M hydrochloride aqueous solution (2 mL) at 0° C. After stirred at room temperature for 3 hours, the mixture was concentrated under reduced pressure to give a residue, which was diluted with water (10 mL) and extracted with ethyl acetate (10 mL) twice. The combined organic layers were washed with brine (10 mL) twice, dried over Na$_2$SO$_{4(s)}$ and filtered. The filtrate was concentrated under reduced pressure to give a residue, which was purified by Prep. HPLC (Column: Gilson X-bridge C18 (5 μm 19*150 mm), Mobile phase A: water (0.1% ammonium bicarbonate), Mobile phase B: acetonitrile, UV: 214 nm, Flow rate: 15 mL/min, Gradient: 10-70% (% B)) to give the title compound (8 mg, 29% yield) as yellow solids. LC-MS (ESI): $R_T$=3.876 min, mass calcd. for C$_{24}$H$_{26}$ClFN$_4$O$_6$S$_2$ 584.1, m/z found 585.1 [M+H]$^+$. $^1$H NMR (400 MHz, DMSO-d$_6$) δ 9.44-9.40 (m, 0.5H), 8.35 (s, 0.5H), 8.01-7.99 (m, 1.5H), 7.96-7.95 (m, 0.5H), 7.45-7.41 (m, 1H), 7.35-7.30 (m, 1H), 7.25-7.18 (m, 1H), 5.97 (s, 0.5H), 5.88-5.87 (m, 0.5H), 4.85-4.79 (m, 1H), 4.60-4.54 (m, 1H), 3.67-3.63 (m, 1H), 3.55-3.54 (m, 3H), 3.39-3.34 (m, 1H), 3.30-3.21 (m, 2H), 3.13-3.08 (m, 1H), 3.02-2.98 (m, 3H), 2.55-2.54 (m, 3H), 2.38 (s, 3H).

Compound 376D: Methyl 4-(2-chloro-4-fluorophenyl)-6-(3-(N—((R)-2,3-dihydroxypropyl)methylsulfonamido)bicyclo[1.1.1]pentan-1-yl)-2-(thiazol-2-yl)-1,4-dihydropyrimidine-5-carboxylate Compound 376D was prepared analogously to compound 376C from compound 375D, LC-MS (ESI): $R_T$=3.701 min, mass calcd. for C$_{24}$H$_{26}$ClFN$_4$O$_6$S$_2$ 584.1, m/z found 585.1 [M+H]$^+$. $^1$H NMR (400 MHz, DMSO-d$_6$) δ 9.43 (s, 0.5H), 8.35 (s, 0.5H), 8.01-7.99 (m, 1.5H), 7.96-7.95 (m, 0.5H), 7.45-7.41 (m, 1H), 7.35-7.30 (m, 1H), 7.25-7.18 (m, 1H), 5.97 (s, 0.5H), 5.88 (s, 0.5H), 4.85-4.79 (m, 1H), 4.60-4.54 (m, 1H), 3.65-3.64 (m, 1H), 3.55-3.54 (m, 3H), 3.38-3.35 (m, 1H), 3.30-3.21 (m, 2H), 3.13-3.08 (m, 1H), 3.02-2.98 (m, 3H), 2.54 (s, 3H), 2.39-2.38 (m, 3H).

Compound 379N: ethyl 4-(2-chloro-4-fluorophenyl)-6-((trans)-2-(hydroxymethyl)-1-(methylsulfonyl)piperidin-4-yl)-2-(thiazol-2-yl)-1,4-dihydropyrimidine-5-carboxylate

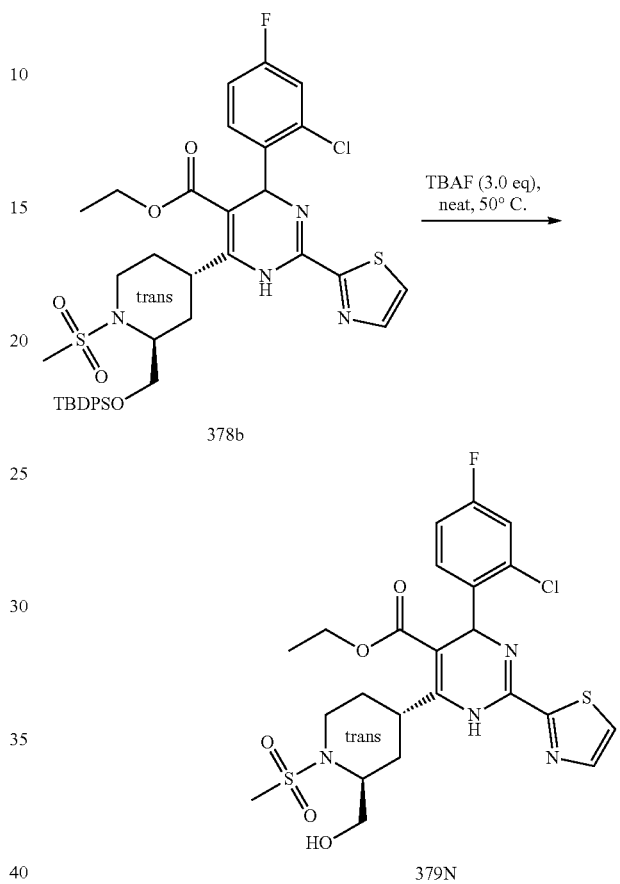

A mixture of compound 378b (520 mg, 0.655 mmol) and tetrabutylammonium fluoride (601 mg, 2.30 mmol) was stirred at 50° C. under nitrogen atmosphere overnight. Then the mixture was allowed to cool down to room temperature and purified by C18 column (acetonitrile:water=40% to 95%) to afford the crude product, which was further purified by Prep. HPLC (Column: X-bridge C18 (5 μm 21.2*150 mm), Mobile phase A: water (0.1% ammonium bicarbonate), Mobile phase B: acetonitrile, UV: 214 nm, Flowrate: 15 mL/min, Gradient: 35-80% (% B)) to afford compound 379N (170 mg, 47% yield) as light yellow solids. LC-MS (ESI): $R_T$=2.853 min, mass calcd. for C$_{23}$H$_{26}$ClFN$_4$O$_5$S$_2$ 556.1, m/z found 557.2 [M+H]$^+$. $^1$H NMR (400 MHz, DMSO-d$_6$) δ 9.51 (d, J=2.0 Hz, 0.8H), 9.12 (s, 0.2H), 7.99 (s, 1.7H), 7.93 (d, J=3.2 Hz, 0.3H), 7.42 (dd, J=8.8, 2.4 Hz, 1H), 7.37-7.32 (m, 1H), 7.24-7.20 (m, 1H), 6.03 (s, 0.2H), 5.93 (d, J=2.8 Hz, 0.8H), 4.95-4.91 (m, 1H), 4.05-3.95 (m, 4H), 3.77-3.68 (m, 2H), 3.59-3.54 (m, 1H), 3.10-3.07 (m, 1H), 3.03 (s, 3H), 2.10-2.02 (m, 1H), 1.88-1.79 (m, 2H), 1.70-1.63 (m, 0.3H), 1.53-1.47 (m, 0.7H), 1.12-1.05 (m, 3H).

Racemic 379N (170 mg, 0.306 mmol) was separated by chiral Prep. HPLC (Column: Chiralpak IF 5 μm 20*250 mm; Mobile Phase: Hex:EtOH:DEA=60:40:0.3 at 11 mL/min; Temp: 30° C.; Wavelength: 214 nm) to afford the title compounds 379C (41 mg, 24% yield, 100% stereopure) and 379D (38 mg, 22% yield, 97.2% stereopure) as yellow solids.

Compound 379C: LC-MS (ESI): $R_T$=2.559 min, mass calcd. for $C_{23}H_{26}ClFN_4O_5S_2$ 556.1, m/z found 556.9 [M+H]$^+$. Chiral analysis (Column: Chiralpak IF 5 μm 4.6*250 mm; Mobile Phase: Hex:EtOH:DEA=70:30:0.2 at 1.0 mL/min; Temp: 30° C.; Wavelength: 230 nm, $R_T$=10.071 min). $^1$H NMR (400 MHz, DMSO-d$_6$) δ 9.52 (d, J=3.2 Hz, 0.8H), 9.14 (s, 0.2H), 7.99 (s, 1.8H), 7.93 (d, J=3.2 Hz, 0.2H), 7.43 (dd, J=8.8, 2.4 Hz, 1H), 7.37-7.32 (m, 1H), 7.25-7.20 (m, 1H), 6.03 (s, 0.2H), 5.92 (d, J=3.6 Hz, 0.8H), 4.96-4.91 (m, 1H), 4.07-3.95 (m, 4H), 3.78-3.67 (m, 2H), 3.59-3.53 (m, 1H), 3.12-3.06 (m, 1H), 3.04 (s, 0.5H), 3.03 (s, 2.5H), 2.20-2.15 (m, 0.2H), 2.12-2.01 (m, 0.8H), 1.87-1.75 (m, 2H), 1.69-1.63 (m, 0.2H), 1.53-1.47 (m, 0.8H), 1.12-1.05 (m, 3H).

Compound 379D: LC-MS (ESI): $R_T$=2.290 min, mass calcd. for $C_{23}H_{26}ClFN_4O_5S_2$ 556.1, m/z found 556.9 [M+H]$^+$. Chiral analysis (Column: Chiralpak IF 5 μm 4.6*250 mm; Mobile Phase: Hex:EtOH:DEA=70:30:0.2 at 1.0 mL/min; Temp: 30° C.; Wavelength: 230 nm, $R_T$=13.403 min). $^1$H NMR (400 MHz, DMSO-d$_6$) δ 9.52 (d, J=3.2 Hz, 0.8H), 9.14 (s, 0.2H), 7.99 (s, 1.8H), 7.93 (d, J=2.4 Hz, 0.2H), 7.43 (dd, J=8.8, 2.4 Hz, 1H), 7.37-7.32 (m, 1H), 7.25-7.20 (m, 1H), 6.03 (s, 0.2H), 5.93 (d, J=3.2 Hz, 0.8H), 4.97-4.91 (m, 1H), 4.05-3.95 (m, 4H), 3.75-3.68 (m, 2H), 3.60-3.53 (m, 1H), 3.12-3.06 (m, 1H), 3.03 (s, 3H), 2.21-2.17 (m, 0.1H), 2.14-2.01 (m, 0.9H), 1.85-1.75 (m, 2H), 1.68-1.65 (m, 0.2H), 1.52-1.48 (m, 0.8H), 1.12-1.05 (m, 3H).

Compound 381: (trans)-Methyl 4-(2-chloro-3-fluorophenyl)-6-(4-hydroxycyclohexyl)-2-(thiazol-2-yl)-1,4-dihydropyrimidine-5-carboxylate

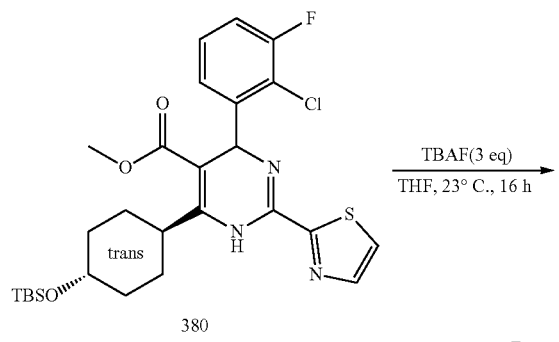

380

To a mixture of (trans)-methyl 6-(4-((tert-butyldimethylsilyl)oxy)cyclohexyl)-4-(2-chloro-3-fluorophenyl)-2-(thiazol-2-yl)-1,4-dihydropyrimidine-5-carboxylate 380 (200 mg, 0.350 mmol) in tetrahydrofuran (10 mL) was added tetrabutylammonium fluoride (262 mg, 1.05 mmol) at 0° C. After being stirred at 23° C. for 16 hours, the mixture was quenched with water (10 mL) and extracted with ethyl acetate (30 mL) for three times. The combined organic layers were washed with water (20 mL) twice, dried over Na$_2$SO$_{4(s)}$ and concentrated to give a residue, which was purified by Prep. TLC (petroleum ether:ethyl acetate=2:3) to give compound 381 (64 mg, 44% yield) as yellow solids. LC-MS (ESI): $R_T$=3.418 min, mass calcd. for $C_{21}H_{21}ClFN_3O_3S$ 449.1, m/z found 450.2 [M+H]$^+$. $^1$H NMR (400 MHz, CD$_3$OD) δ 7.92 (d, J=3.2 Hz, 0.6H), 7.88 (d, J=3.2 Hz, 0.4H), 7.74-7.73 (m, 1H), 7.29-7.24 (m, 1H), 7.21-7.11 (m, 2H), 6.18 (s, 0.6H), 6.10 (s, 0.4H), 3.94-3.92 (m, 0.6H), 3.69-3.63 (m, 1.4H), 3.59 (s, 1.2H), 3.58 (s, 1.8H), 2.09-2.03 (m, 2.1H), 1.99-1.82 (m, 2.1H), 1.79-1.64 (m, 1.8H), 1.47-1.29 (m, 2H).

Racemic 381 (180 mg, 0.400 mmol) was separated by chiral Prep. HPLC (separation condition: column: Chiralpak OJ-H 5 μm 20*250 mm; Mobile Phase: Hex:EtOH: DEA=90:10:0.3 at 18 mL/min, Temp: 30° C., Wavelength: 214 nm) to afford the title compounds 381A (23.7 mg, 13% yield, 100% stereopure) and 381B (19.9 mg, 122% yield, 100% stereopure) as yellow solids.

Compound 381A: LC-MS (ESI): $R_T$=3.407 min, mass calcd. for $C_{21}H_{21}ClFN_3O_3S$ 449.1, m/z found 450.2 [M+H]$^+$. Chiral analysis (Column: Chiralpak OJ-H 5 μm 4.6*250 mm; Mobile Phase: Hex:EtOH:DEA=85:15:0.2 at 1.0 mL/min; Temp: 30° C.; Wavelength: 230 nm, $R_T$=11.545 min). $^1$H NMR (400 MHz, CD$_3$OD) δ 7.92 (d, J=3.2 Hz, 0.6H), 7.88 (d, J=3.2 Hz, 0.4H), 7.74-7.73 (m, 1H), 7.29-7.20 (m, 1H), 7.19-7.11 (m, 2H), 6.18 (s, 0.6H), 6.10 (s, 0.4H), 3.94-3.93 (m, 0.6H), 3.69-3.65 (m, 1.4H), 3.58 (s, 1.2H), 3.56 (s, 1.8H), 2.15-2.02 (m, 2H), 1.98-1.87 (m, 2.2H), 1.79-1.65 (m, 1.8H), 1.46-1.29 (m, 2H).

Compound 381B: LC-MS (ESI): $R_T$=3.387 min, mass calcd. for $C_{21}H_{21}ClFN_3O_3S$ 449.1, m/z found 450.2 [M+H]$^+$. Chiral analysis (Column: Chiralpak OJ-H 5 μm 4.6*250 mm; Mobile Phase: Hex:EtOH:DEA=85:15:0.2 at 1.0 mL/min; Temp: 30° C.; Wavelength: 230 nm, $R_T$=15.656 min). $^1$H NMR (400 MHz, CD$_3$OD) δ 7.92 (d, J=3.2 Hz, 0.6H), 7.87 (d, J=2.8 Hz, 0.4H), 7.74-7.73 (m, 1H), 7.27-7.24 (m, 1H), 7.20-7.13 (m, 2H), 6.18 (s, 0.6H), 6.10 (s, 0.4H), 3.93-3.92 (m, 0.6H), 3.69-3.64 (m, 1.4H), 3.59 (s, 1.2H), 3.58 (s, 1.8H), 2.11-1.96 (m, 2.6H), 1.88-1.64 (m, 3.4H), 1.46-1.29 (m, 2H).

Compound 388: (trans)-Methyl 4-(2-chloro-4-fluorophenyl)-6-(4-(N-methylmethylsulfonamido)cyclohexyl)-2-(thiazol-2-yl)-1,4-dihydropyrimidine-5-carboxylate

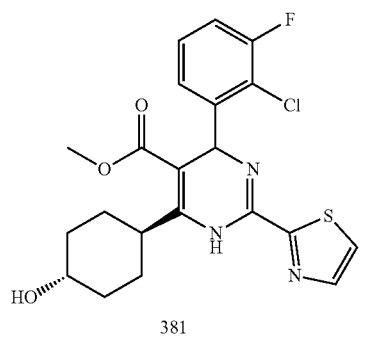

381

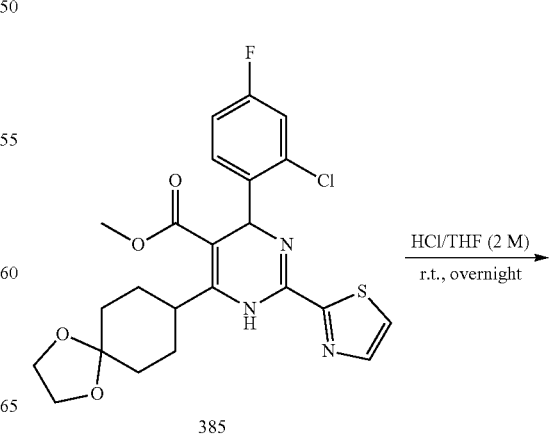

385

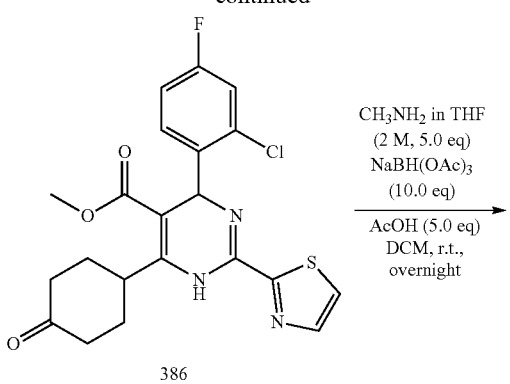

386

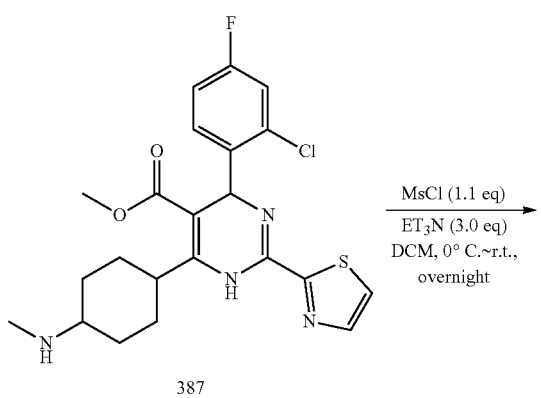

387

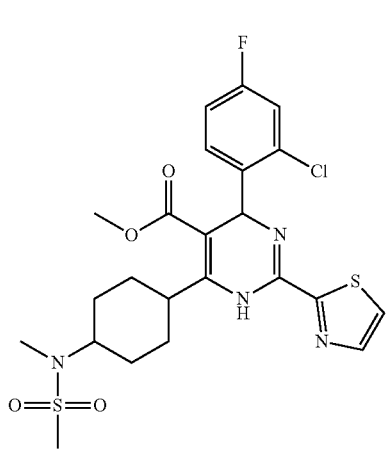

388

Compound 386: Methyl 4-(2-chloro-4-fluorophenyl)-6-(4-oxocyclohexyl)-2-(thiazol-2-yl)-1,4-dihydropyrimidine-5-carboxylate To a mixture of methyl 4-(2-chloro-4-fluorophenyl)-6-(1,4-dioxaspiro[4.5]decan-8-yl)-2-(thiazol-2-yl)-1,4-dihydropyrimidine-5-carboxylate 385 (4.90 g, 80% purity from $^1$H NMR, 7.97 mmol) in tetrahydrofuran (49 mL) was added 2 M hydrochloride in tetrahydrofuran (49 mL, 98 mmol). After stirred at room temperature overnight, the mixture was concentrated to give a residue, which was dissolved in ethyl acetate (50 mL), diluted with saturated sodium bicarbonate aqueous solution (50 mL) and extracted with ethyl acetate (50 mL) for three times. The combined organic layers were washed with brine (50 mL) twice, dried over $Na_2SO_{4(s)}$ and filtered. The filtrate was concentrated under reduced pressure to give a residue, which was purified by silica gel column chromatography (petroleum ether:ethyl acetate:tetrahydrofuran=10:1:0 to 10:1:1) to give the title compound (2.90 g, 81% yield) as yellow solids. $^1$H NMR (300 MHz, CDCl$_3$) δ 8.12 (br s, 0.2H), 7.82-7.79 (m, 1H), 7.50-7.49 (m, 0.8H), 7.45 (s, 1H), 7.31-7.28 (m, 1H), 7.16-7.12 (m, 1H), 6.98-6.88 (m, 1H), 6.20 (s, 0.3H), 6.07 (d, J=2.1 Hz, 0.7H), 4.54-4.46 (m, 0.3H), 4.31-4.23 (m, 0.7H), 3.62 (s, 3H), 2.57-2.49 (m, 4H), 2.39-2.32 (m, 1H), 2.25-2.14 (m, 2H), 1.99-1.89 (m, 1H).

Compound 387: (cis)-Methyl 4-(2-chloro-4-fluorophenyl)-6-(4-(methylamino)cyclohexyl)-2-(thiazol-2-yl)-1,4-dihydropyrimidine-5-carboxylate and (trans)-methyl 4-(2-chloro-4-fluorophenyl)-6-(4-(methylamino)cyclohexyl)-2-(thiazol-2-yl)-1,4-dihydropyrimidine-5-carboxylate To a solution of methyl 4-(2-chloro-4-fluorophenyl)-6-(4-oxocyclohexyl)-2-(thiazol-2-yl)-1,4-dihydropyrimidine-5-carboxylate 386 (600 mg, 1.34 mmol) in dichloromethane (12 mL) were added 2 M methanamine in tetrahydrofuran (3.4 mL, 6.80 mmol), sodium triacetoxyhydroborate (2.84 g, 13.4 mmol) and acetic acid (402 mg, 6.70 mmol) at 0° C. under nitrogen atmosphere. After stirred at room temperature overnight, the reaction mixture was quenched with saturated sodium bicarbonate aqueous solution (30 mL) slowly and extracted with dichloromethane (30 mL) for three times. The combined organic layers were washed with brine (30 mL), dried over $Na_2SO_{4(s)}$ and filtered. The filtrate was concentrated under reduced pressure to give a residue, which was purified by silica gel column chromatography (dichloromethane:methanol:ammonium hydroxide=100:1:0.02 to 50:1:0.02) to give the title compounds 387A (260 mg, 42% yield) as yellow solids and 387B (250 mg, 40% yield) as yellow solids.

Intermediate 387A: $^1$H NMR (400 MHz, DMSO-d$_6$) δ 8.00-7.93 (m, 2H), 7.42-7.40 (m, 1H), 7.34-7.31 (m, 1H), 7.22-7.18 (m, 1H), 6.01 (s, 0.7H), 5.90 (s, 0.3H), 3.89-3.83 (m, 0.7H), 3.61-3.58 (m, 0.3H), 3.50 (s, 3H), 2.74-2.70 (m, 1H), 2.33 (s, 3H), 2.01-1.84 (m, 4H), 1.59-1.42 (m, 4H).

Intermediate 387B: $^1$H NMR (400 MHz, DMSO-d$_6$) δ 8.85 (br s, 1H), 7.99-7.93 (m, 2H), 7.44-7.40 (m, 1H), 7.38-7.30 (m, 1H), 7.23-7.16 (m, 1H), 6.00 (s, 0.4H), 5.90 (s, 0.6H), 3.82-3.75 (m, 0.6H), 3.62-3.59 (m, 0.4H), 3.51 (s, 3H), 2.35-2.26 (m, 4H), 2.02-1.96 (m, 2H), 1.85-1.67 (m, 3H), 1.58-1.55 (m, 1H), 1.10-1.02 (m, 2H).

Compound 388: (trans)-Methyl 4-(2-chloro-4-fluorophenyl)-6-(4-(N-methylmethylsulfonamido)cyclohexyl)-2-(thiazol-2-yl)-1,4-dihydropyrimidine-5-carboxylate To a solution of (trans)-methyl 4-(2-chloro-4-fluorophenyl)-6-(4-(methylamino)cyclohexyl)-2-(thiazol-2-yl)-1,4-dihydropyrimidine-5-carboxylate 387B (250 mg, 0.540 mmol) in dichloromethane (5 mL) were added triethylamine (164 mg, 1.62 mmol) and methanesulfonyl chloride (68 mg, 0.594 mmol) at 0° C. under nitrogen atmosphere. After stirred at room temperature overnight, the reaction mixture was quenched with saturated sodium bicarbonate aqueous solution (20 mL) slowly and extracted with dichloromethane (20 mL) for three times. The combined organic layers were washed with brine (20 mL), dried over $Na_2SO_{4(s)}$ and filtered. The filtrate was concentrated under reduced pressure to give a residue, which was purified by C18 column (acetonitrile:water=40% to 95%) to give the title compound (120 mg, 41% yield) as yellow solids. LC-MS (ESI): $R_T$=3.751 min, mass calcd. for $C_{23}H_{26}ClFN_4O_4S_2$ 540.1, m/z found 540.7 $[M+H]^+$. $^1$H NMR (400 MHz, DMSO-$d_6$) δ 9.45 (d, J=3.2 Hz, 0.6H), 9.16 (br s, 0.4H), 7.99-7.98 (m, 1.6H), 7.93-7.92 (m, 0.4H), 7.43-7.41 (m, 1H), 7.36-7.29 (m, 1H), 7.23-7.19 (m, 1H), 6.00 (s, 0.4H), 5.90 (d, J=3.2 Hz, 0.6H), 3.85-3.82 (m, 1H), 3.66-3.57 (m, 1H), 3.53 (s, 1.7H), 3.51 (s, 1.3H), 2.92 (s, 3H), 2.73 (s, 3H), 2.07-1.97 (m, 0.5H), 1.93-1.73 (m, 5H), 1.66-1.59 (m, 2.5H).

Racemic 388 (100 mg, 0.185 mmol) was separated by chiral Prep. HPLC (separation condition: Column: Chiralpak IA 5 μm 20*250 mm; Mobile Phase: Hex:EtOH:DEA=70:30:0.3 at 20 mL/min; Temp: 30° C.; Wavelength: 230 nm) to afford the title compounds 388A (32 mg, 32% yield, 100% stereopure) as yellow solids and 388B (28 mg, 28% yield, 100% stereopure) as yellow solids.

Compound 388A: LC-MS (ESI): $R_T$=2.462 min, mass calcd. for $C_{23}H_{26}ClFN_4O_4S_2$ 540.1, m/z found 541.1 $[M+H]^+$. Chiral analysis (Column: Chiralpak IA 5 μm 4.6*250 mm; Mobile Phase: Hex:EtOH:DEA=70:30:0.2 at 1.0 mL/min; Temp: 30° C.; Wavelength: 230 nm, $R_T$=7.008 min). $^1$H NMR (400 MHz, DMSO-$d_6$) δ 9.43 (d, J=3.6 Hz, 0.6H), 9.15 (br s, 0.4H), 8.00-7.97 (m, 1.6H), 7.93-7.92 (m, 0.4H), 7.43-7.40 (m, 1H), 7.36-7.29 (m, 1H), 7.23-7.17 (m, 1H), 6.00 (s, 0.4H), 5.91 (d, J=3.6 Hz, 0.6H), 3.89-3.78 (m, 1H), 3.67-3.57 (m, 1H), 3.53 (s, 1.7H), 3.51 (s, 1.3H), 2.92 (d, J=2.8 Hz, 3H), 2.73 (s, 3H), 2.14-2.05 (m, 0.5H), 1.97-1.73 (m, 5H), 1.66-1.59 (m, 2.5H).

Compound 388B: LC-MS (ESI): $R_T$=2.459 min, mass calcd. for $C_{23}H_{26}ClFN_4O_4S_2$ 540.1, m/z found 541.0 $[M+H]^-$. Chiral analysis (Column: Chiralpak IA 5 μm 4.6*250 mm; Mobile Phase: Hex:EtOH:DEA=70:30:0.2 at 1.0 mL/min; Temp: 30° C.; Wavelength: 230 nm, $R_T$=8.755 min). $^1$H NMR (400 MHz, DMSO-$d_6$) δ 9.44 (d, J=3.6 Hz, 0.6H), 9.16 (br s, 0.4H), 8.00-7.98 (m, 1.6H), 7.93-7.92 (m, 0.4H), 7.44-7.40 (m, 1H), 7.36-7.29 (m, 1H), 7.23-7.17 (m, 1H), 6.00 (s, 0.4H), 5.90 (d, J=3.6 Hz, 0.6H), 3.88-3.79 (m, 1H), 3.66-3.56 (m, 1H), 3.52 (s, 1.8H), 3.51 (s, 1.2H), 2.92 (d, J=2.4 Hz, 3H), 2.73 (s, 3H), 2.11-2.04 (m, 0.5H), 1.97-1.73 (m, 5H), 1.66-1.57 (m, 2.5H).

Compound 390B: Methyl 4-(2-chloro-4-fluorophenyl)-6-(3-(2-hydroxyethylsulfonamido)bicyclo[1.1.1]pentan-1-yl)-2-(thiazol-2-yl)-1,4-dihydropyrimidine-5-carboxylate

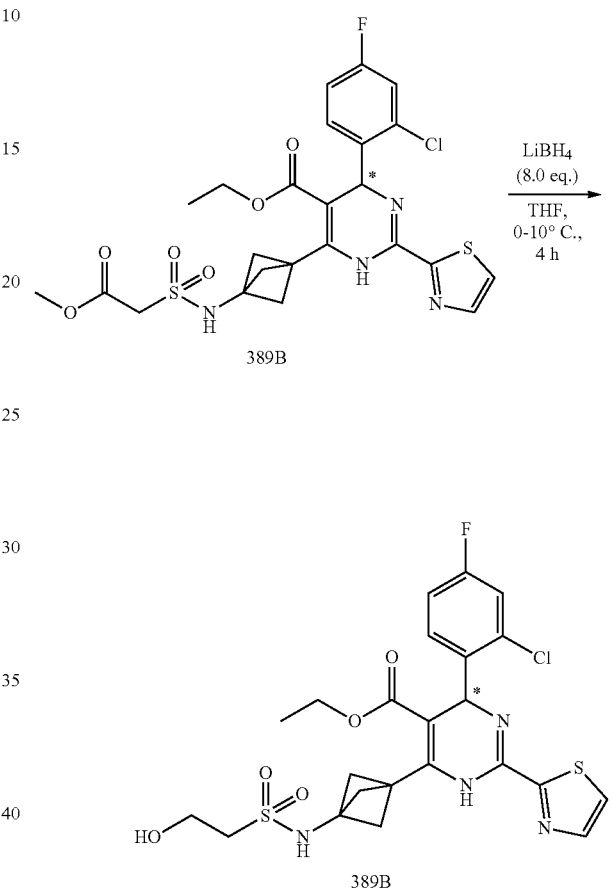

389B

To a solution of methyl 4-(2-chloro-4-fluorophenyl)-6-(3-(2-methoxy-2-oxoethyl sulfonamido)bicyclo[1.1.1]pentan-1-yl)-2-(thiazol-2-yl)-1,4-dihydropyrimidine-5-carboxylate compound 389B (40 mg, 0.070 mmol) in tetrahydrofuran (1 mL) was added lithium borohydride (12 mg, 0.56 mmol) at 0° C. After stirred at the temperature between 0° C. to 10° C. for 4 hours, the mixture was concentrated under reduced pressure to give a residue, which was purified by C18 column (acetonitrile:water=50-60%) to afford the title compound (18 mg, 47% yield) as yellow solids. LC-MS (ESI): $R_T$=3.976 min, mass calcd. for $C_{22}H_{22}ClFN_4O_5S_2$ 540.1, m/z found 541.1 $[M+H]^+$. $^1$H NMR (400 MHz, DMSO-$d_6$) 9.44 (s, 0.5H), 8.35 (s, 0.5H), 8.01-7.97 (m, 1.5H), 7.95 (d, J=2.8 Hz, 0.5H), 7.45-7.40 (m, 1H), 7.34-7.30 (m, 1H), 7.24-7.18 (m, 1H), 5.96 (s, 0.5H), 5.86 (s, 0.5H), 4.90 (s, 1H), 3.77-3.74 (m, 2H), 3.54 (s, 1.5H), 3.53 (s, 1.5H), 3.22-3.16 (m, 2H), 2.43 (s, 3H), 2.27 (s, 3H).

Compound 393B: Methyl 4-(2-chloro-4-fluorophenyl)-6-(3-(2,3-dihydroxypropylsulfonamido)bicyclo[1.1.1]pentan-1-yl)-2-(thiazol-2-yl)-1,4-dihydropyrimidine-5-carboxylate

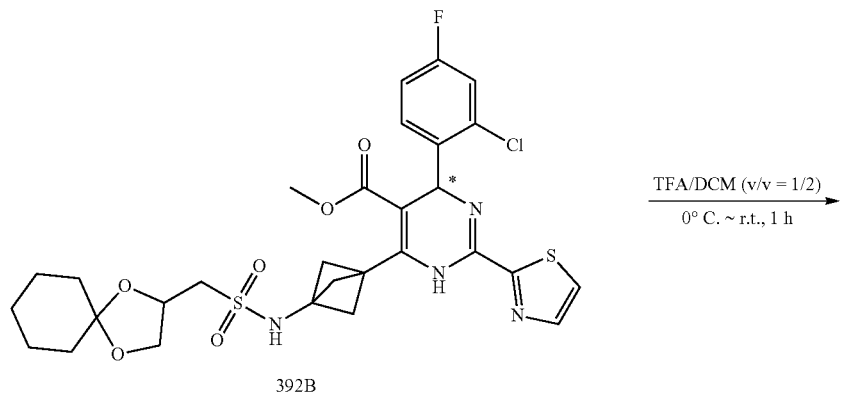

To a solution of methyl 6-(3-(1,4-dioxaspiro[4.5]decan-2-ylmethylsulfonamido)bicyclo[1.1.1]pentan-1-yl)-4-(2-chloro-4-fluorophenyl)-2-(thiazol-2-yl)-1,4-dihydropyrimidine-5-carboxylate 392B (30 mg, 0.050 mmol) in dichloromethane (2 mL) was added trifluoroacetic acid (1 mL) dropwise at 0° C. After stirred at room temperature for 1 hour, the mixture was washed with saturated sodium bicarbonate aqueous solution (10 mL) for three times, followed by water (10 mL). The separated organic phase was concentrated under reduced pressure to give a residue, which was purified by C18 column (acetonitrile: water (0.1% ammonium bicarbonate)=5% to 80%) to give the title compound (10 mg, 40% yield) as yellow solids. LC-MS (ESI): $R_T$=3.624 min, mass calcd. for $C_{23}H_{24}ClFN_4O_6S_2$ 570.1, m/z found 571.1 [M+H]$^+$. 1H NMR (400 MHz, DMSO-d$_6$) δ 8.00-7.99 (m, 1H), 7.92-7.87 (m, 1H), 7.42 (d, J=2.4 Hz, 0.5H), 7.40 (d, J=2.8 Hz, 0.5H), 7.36-7.32 (m, 1H), 7.22-7.17 (m, 1H), 5.97-5.91 (m, 1H), 3.98-3.94 (m, 1H), 3.56 (s, 3H), 3.48-3.44 (m, 1H), 3.41-3.36 (m, 1H), 3.31-3.30 (m, 0.5H), 3.27-3.26 (m, 0.5H), 3.09-3.03 (m, 1H), 2.46-2.31 (m, 6H).

Compound 401: Methyl 4-(2-chloro-4-fluorophenyl)-6-(1-(S-methylsulfonimidoyl)piperidin-4-yl)-2-(thiazol-2-yl)-1,4-dihydropyrimidine-5-carboxylate

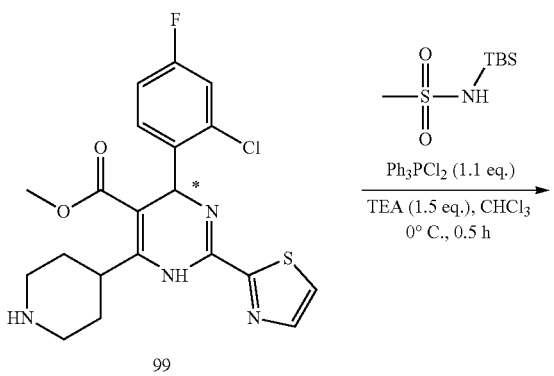

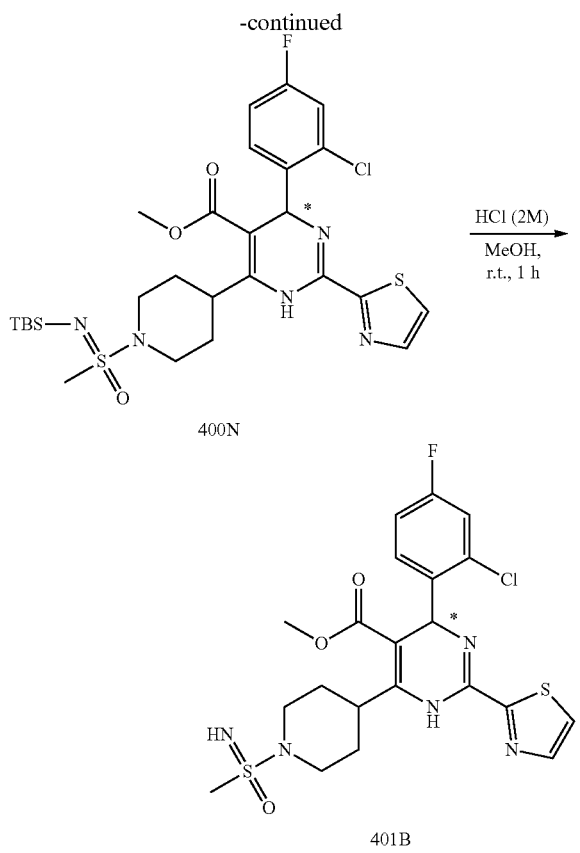

400N

HCl (2M)
MeOH,
r.t., 1 h

401B

Compound 400N: Methyl 6-(1-(N-(tert-butyldimethylsilyl)-S-methylsulfonimidoyl)piperidin-4-yl)-4-(2-chloro-4-fluorophenyl)-2-(thiazol-2-yl)-1,4-dihydropyrimidine-5-carboxylate To a stirred solution of methanesulfonamide (2.00 g, 21.0 mmol) and tert-butylchlorodimethylsilane (4.80 g, 31.6 mmol) in chloroform (30 mL) was added triethylamine (3.20 g, 31.6 mmol) at 0° C. After stirred at room temperature overnight for 16 hours, the mixture was concentrated under reduced pressure to give a residue, which was diluted with water (100 mL), and extracted with ethyl acetate (30 mL) twice. The combined organic layers were dried over $Na_2SO_4$ (s) and filtered. The filtrate was concentrated under reduced pressure to give N-(tert-Butyldimethylsilyl)-methanesulfonamide (3.20 g, 73% yield) as white solids.

To a stirred solution of triphenylphosphine dichloride (1.7 g, 5.1 mmol) in dry chloroform (10 mL) under nitrogen atmosphere was added triethylamine (697 mg, 6.90 mmol) at 0° C. After stirred at room temperature for ten minutes, the reaction mixture was cooled down to 0° C. and a solution of N-(tert-butyldimethylsilyl)-methanesulfonamide (970 mg, 5.50 mmol) in dry chloroform (3 mL) was added. After stirring at 0° C. for 20 minutes, a solution of (S*)-methyl 4-(2-chloro-4-fluorophenyl)-6-(piperidin-4-yl)-2-(thiazol-2-yl)-1,4-dihydropyrimidine-5-carboxylate compound 99 (150 mg, 0.350 mmol, 100% stereopure) in chloroform (1 mL) was added. After stirred at room temperature for 30 minutes, the reaction mixture was concentrated under reduced pressure to give a residue, which was purified by silica gel column chromatography (petroleum ether:ethyl acetate:dichloromethane=10:1:1) to give the title compound (150 mg, 69% yield over two steps) as yellow solids. LC-MS (ESI): $R_T$=2.867 min, mass calcd. for $C_{27}H_{37}ClFN_5O_3S_2Si$ 625.2, m/z found 626.2 [M+H]$^+$. $^1$H NMR (400 MHz, CDCl$_3$) δ 8.20 (s, 0.3H), 7.83 (d, J=2.8 Hz, 1H), 7.52 (d, J=2.8 Hz, 0.7H), 7.45 (d, J=3.6 Hz, 0.3H), 7.44 (br s, 0.7H), 7.31-7.28 (m, 1H), 7.16-7.12 (m, 1H), 6.98-6.89 (m, 1H), 6.20 (d, J=2.8 Hz, 0.3H), 6.07 (s, 0.7H), 4.13-3.93 (m, 2.3H), 3.90-3.83 (m, 0.7H), 3.61 (s, 1.8H), 3.60 (s, 1.2H), 2.77 (s, 1.8H), 2.76 (s, 1.2H), 2.71-2.61 (m, 2H), 2.33-2.20 (m, 0.8H), 2.15-1.70 (m, 3.2H), 0.94 (s, 4H), 3.93 (s, 5H), 0.17-0.13 (m, 6H).

Compound 401B: Methyl 4-(2-chloro-4-fluorophenyl)-6-(1-(S-methylsulfonimidoyl)piperidin-4-yl)-2-(thiazol-2-yl)-1,4-dihydropyrimidine-5-carboxylate To a solution of methyl 6-(1-(N-(tert-butyldimethylsilyl)-S-methylsulfonimidoyl)piperidin-4-yl)-4-(2-chloro-4-fluorophenyl)-2-(thiazol-2-yl)-1,4-dihydropyrimidine-5-carboxylate 400N (150 mg, 0.240 mmol) in methanol (2 mL) was added 2 M hydrochloride aqueous solution (2 mL) at room temperature. After stirred at room temperature for 1 hour, the reaction mixture was concentrated under reduced pressure to give a residue, which was dissolved in water (10 mL), adjusted to pH=9-10 with 28% ammonia solution (1 mL), and concentrated under reduced pressure to give a residue, which was purified by Prep. HPLC (Column: Xbridge C18 HILIC (5 m 10*190 mm), Mobile phase A: water, Mobile phase B: acetonitrile, UV: 214 nm, Flow rate: 50 mL/min, Gradient: 20-95% (% B)) to give the title compound 401B (101.0 mg, 83% yield) as yellow solids. LC-MS (ESI): $R_T$=3.149 min, mass calcd. for $C_{21}H_{23}ClFN_5O_3S_2$ 511.1, m/z found 511.9 [M+H]$^+$. $^1$H NMR (400 MHz, CD$_3$OD) δ 7.92 (d, J=3.2 Hz, 0.3H), 7.89 (d, J=3.2 Hz, 0.7H), 7.76-7.73 (m, 1H), 7.41-7.37 (m, 1H), 7.25-7.22 (m, 1H), 7.08-7.04 (m, 1H), 6.15 (s, 0.3H), 6.07 (s, 0.7H), 4.11-3.95 (m, 2.1H), 3.89-3.83 (m, 0.9H), 3.59 (s, 3H), 2.88 (s, 3H), 2.85-2.78 (m, 2H), 2.24-2.14 (m, 0.7H), 2.11-2.01 (m, 1H), 1.98-1.91 (m, 1.5H), 1.75-1.71 (m, 0.8H). Racemic 401B (60 mg, 0.12 mmol) was separated by chiral Prep. SFC (Column: Chiralpak IF 5 μm 20*250 mm; Mobile Phase: CO$_2$:MeOH=60:40 at 50 g/min; Temp: 30° C.; Wavelength: 230 nm, Back pressure: 100 bar) to afford the title compounds 401X (7.7 mg, 13% yield, 100% stereopure) and 401Y (33.1 mg, 55% yield, 100% stereopure) as yellow solids.

Compound 401X: LC-MS (ESI): $R_T$=3.621 min, mass calcd. for $C_{21}H_{23}ClFN_5O_3S_2$ 511.1, m/z found 511.9 [M+H]$^+$. Chiral analysis (Column: Chiralpak IF 5 μm 4.6*250 mm; Mobile Phase: CO$_2$: EtOH=60:40 at 2.999 g/min; Col. Temp: 40° C.; Wavelength: 214 nm, Back pressure: 100 bar, $R_T$=4.52 min). $^1$H NMR (400 MHz, CD$_3$OD) δ 7.92 (d, J=2.8 Hz, 0.3H), 7.89 (d, J=3.2 Hz, 0.7H), 7.76-7.74 (m, 1H), 7.41-7.37 (m, 1H), 7.25-7.21 (m, 1H), 7.08-7.03 (m, 1H), 6.15 (s, 0.3H), 6.08 (s, 0.7H), 4.12-3.92 (m, 1.6H), 3.90-3.83 (m, 1.4H), 3.59 (s, 3H), 2.88 (s, 3H), 2.85-2.79 (m, 2H), 2.27-2.20 (m, 0.8H), 2.17-2.01 (m, 1.2H), 1.94-1.92 (m, 1.3H), 1.74-1.70 (m, 0.7H).

Compound 401Y: LC-MS (ESI): $R_T$=3.053 min, mass calcd. for $C_{21}H_{23}ClFN_5O_3S_2$ 511.1, m/z found 511.9 [M+H]$^+$. Chiral analysis (Column: Chiralpak IF 5 μm 4.6*250 mm; Mobile Phase: CO$_2$: EtOH=60:40 at 2.999 g/min; Col. Temp: 40° C.; Wavelength: 214 nm, Back pressure: 100 bar, $R_T$=5.7 min). $^1$H NMR (400 MHz, CD$_3$OD) δ 7.92 (d, J=3.2 Hz, 0.3H), 7.89 (d, J=3.2 Hz, 0.7H), 7.76-7.74 (m, 1H), 7.41-7.37 (m, 1H), 7.25-7.22 (m, 1H), 7.08-7.03 (m, 1H), 6.15 (s, 0.3H), 6.07 (s, 0.7H), 4.09-3.95 (m, 2.3H), 3.88-3.83 (m, 0.7H), 3.59 (s, 3H), 2.88 (s, 3H), 2.86-2.78 (m, 2H), 2.24-2.17 (m, 0.8H), 2.13-2.04 (m, 1H), 1.94-1.90 (m, 1.5H), 1.75-1.72 (m, 0.7H).

Compound 404N: ethyl 4-(2-chloro-4-fluorophenyl)-6-((trans)-2-(fluoromethyl)-1-(methylsulfonyl)piperidin-4-yl)-2-(thiazol-2-yl)-1,4-dihydropyrimidine-5-carboxylate

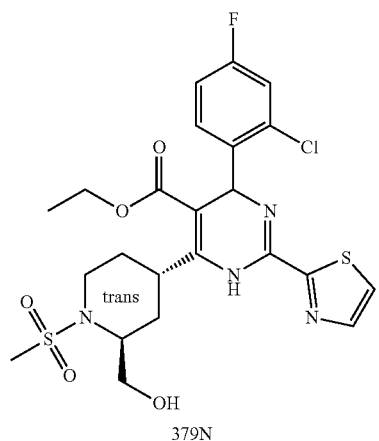

379N (Boc)₂O (1.2 eq)
DMAP (1.2 eq)
⟶
THF, 60° C.
overnight

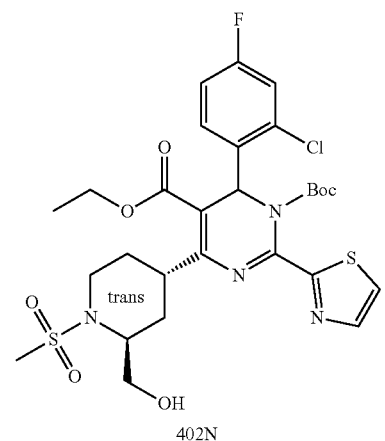

402N

DAST (3.0 eq)
⟶
DCM, -78° C., 2 h
r.t., overnight

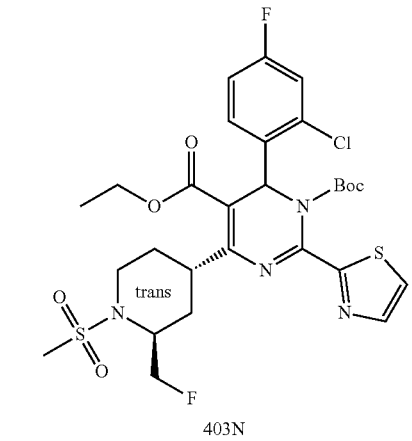

403N

TFA/DCM
⟶

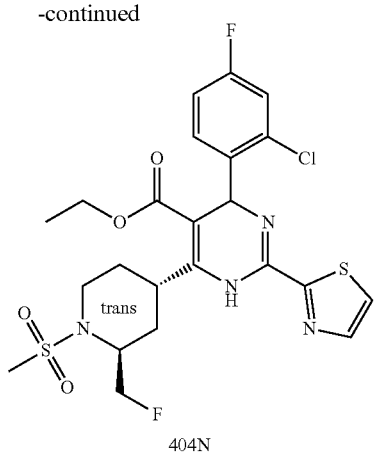

404N

Compound 402N: 1-tert-butyl 5-ethyl 6-(2-chloro-4-fluorophenyl)-4-((trans)-2-(hydroxymethyl)-1-(methylsulfonyl)piperidin-4-yl)-2-(thiazol-2-yl)pyrimidine-1,5(6H)-dicarboxylate To a solution of compound 379N (1.44 g, 2.59 mmol) in tetrahydrofuran (50 mL) were added 4-dimethylaminopyridine (379 mg, 3.11 mmol) and di-tert-butyl dicarbonate (671 mg, 3.11 mmol) at room temperature. After stirring at 60° C. overnight under nitrogen, it was cooled down to room temperature and concentrated to give a residue, which was purified by C18 column (acetonitrile:water=30% to 95%) to afford the title compound (900 mg, 53% yield) as yellow solids. LC-MS (ESI): $R_T$=0.765 min, mass calcd. for $C_{28}H_{34}ClFN_4O_7S_2$ 656.2, m/z found 656.8 [M+H]⁺.

Compound 403N: 1-tert-butyl 5-ethyl 6-(2-chloro-4-fluorophenyl)-4-((trans)-2-(fluoromethyl)-1-(methylsulfonyl)piperidin-4-yl)-2-(thiazol-2-yl)pyrimidine-1,5(6H)-dicarboxylate To a solution of compound 402N (200 mg, 0.305 mmol) in dichloromethane (2 mL) was added diethylaminosulfur trifluoride (147 mg, 0.915 mmol) at -78° C. After stirred at room temperature under nitrogen atmosphere overnight, the reaction mixture was diluted with water (2 mL) and extracted with dichloromethane (10 mL) for three times. The combined organic layers were washed with cold brine (20 mL) for three times, dried over $Na_2SO_{4(s)}$, filtered and concentrated to give a residue, which was further purified by Prep. HPLC (Column: Waters X-bridge C18 (5 μm 19*150 mm), Mobile Phase A: water (0.1% ammonium bicarbonate), Mobile Phase B: acetonitrile, UV: 214 nm, Flow rate: 15 mL/min, Gradient: 40-85% (% B)) to give the title compound (64.0 mg, 53% yield) as yellow solids. ¹H NMR (300 MHz, CDCl₃) δ 7.90 (d, J=1.5 Hz, 1H), 7.50 (d, J=3.0 Hz, 1H), 7.16-7.04 (m, 2H), 6.85-6.78 (m, 1H), 6.74 (d, J=3.6 Hz, 1H), 5.16 (br s, 0.5H), 5.02 (br s, 0.5H), 4.28-4.14 (m, 3H), 3.91-3.58 (m, 4H), 3.03 (s, 3H), 2.44-2.12 (m, 4H), 1.26 (s, 12H).

Compound 404N: ethyl 4-(2-chloro-4-fluorophenyl)-6-((trans)-2-(fluoromethyl)-1-(methylsulfonyl)piperidin-4-yl)-2-(thiazol-2-yl)-1,4-dihydropyrimidine-5-carboxylate To a solution of compound 403N (64.0 mg, 0.097 mmol) in dichloromethane (1.5 mL) was added trifluoroacetic acid (1.5 mL) at room temperature under nitrogen atmosphere. After stirring at room temperature for 1 hour, the mixture was concentrated under reduced pressure to give a residue, which was further purified by Prep. HPLC (Column: Gilson X-bridge C18 (5 μm 19*150 mm), Mobile Phase A: water (0.1% ammonium bicarbonate), Mobile Phase B: acetonitrile, UV: 214 nm, Flow rate: 15 mL/min, Gradient: 35-85% (% B)) to give the title compound (32.0 mg, 59% yield) as yellow solids. LC-MS (ESI): $R_T$=3.980 min, mass calcd. for $C_{23}H_{25}ClF_2N_4O_4S_2$ 558.1, m/z found 559.2 [M+H]$^+$. $^1$H NMR (400 MHz, DMSO-d$_6$) δ 9.45 (s, 0.7H), 9.30 (s, 0.3H), 7.99-7.92 (m, 2H), 7.44-7.41 (m, 1H), 7.38-7.32 (m, 1H), 7.25-7.21 (m, 1H), 6.04 (s, 0.3H), 5.95 (d, J=3.6 Hz, 0.7H), 5.10 (s, 0.5H), 4.98 (s, 0.5H), 4.51 (s, 0.2H), 4.21-4.18 (m, 0.8H), 4.02-3.95 (m, 2H), 3.77-3.66 (m, 0.4H), 3.63-3.60 (m, 0.6H), 3.55-3.53 (m, 0.8H), 3.51-3.41 (m, 1.2H), 3.39-3.36 (m, 1H), 2.99 (s, 3H), 2.28-1.98 (m, 4H), 1.09-1.04 (m, 3H).

Compound 416: Methyl 4-(2-chloro-3,4-difluorophenyl)-6-(1-sulfamoyl)piperidin-4-yl)-2-(thiazol-2-yl)-1,4-dihydropyrimidine-5-carboxylate

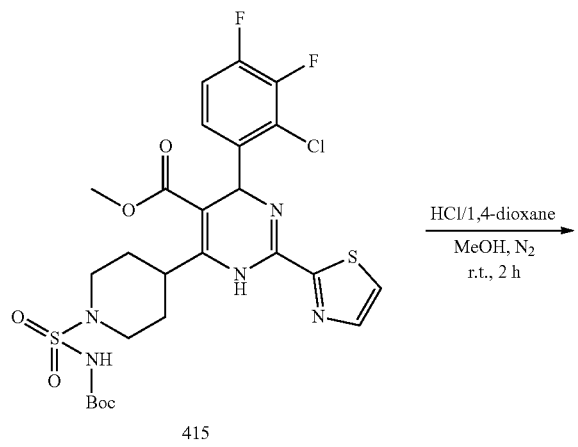

To a solution of methyl 6-(1-(-(tert-butoxycarbonyl)sulfamoyl)piperidin-4-yl)-4-(2-chloro-3,4-difluorophenyl)-2-(thiazol-2-yl)-1,4-dihydropyrimidine-5-carboxylate compound 415 (440 mg, 0.69 mmol) in methanol (10 mL) was added 4 N hydrochloride in 1,4-dioxane (3.0 mL, 12 mmol) at room temperature under nitrogen atmosphere. After stirred at room temperature for 4 hours, the mixture was concentrated under reduced pressure to give a residue, which was purified by silica gel column chromatography (petroleum ether:ethyl acetate=4:1 to 1:1) to afford the title compound (225 mg, 61% yield) as yellow solids. LC-MS (ESI): $R_T$=3.366 min, mass calcd. for $C_{20}H_{20}ClF_2N_5O_4S_2$ 531.1, m/z found 532.0 [M+H]$^+$. $^1$H NMR (400 MHz, DMSO-d$_6$) δ 9.61 (s, 0.8H), 9.08 (s, 0.2H), 8.01-7.99 (m, 1.8H), 7.94 (d, J=3.2 Hz, 0.2H), 7.48-7.42 (m, 1H), 7.23-7.16 (m, 1H), 6.77-6.74 (m, 2H), 6.03 (s, 0.2H), 5.93 (s, 0.8H), 3.92-3.53 (m, 6H), 2.67-2.54 (m, 2H), 2.12-2.00 (m, 1H), 1.93-1.88 (m, 1H), 1.87-1.78 (m, 1H), 1.66-1.63 (m, 1H).

Racemic 416 (225 mg, 0.422 mmol) was separated by Chiral Prep. HPLC (separation condition: Column: Chiralpak IE 5 Lm 20*250 mm; Mobile Phase: Hex:EtOH:DEA=70:30:0.3 at 12 mL/min; Temp: 30° C.; Wavelength: 214 nm) to give the title compounds 416A (6.4 mg, 3% yield, 100% stereopure) and 416B (5.3 mg, 2% yield, 100% stereopure) as yellow solids.

Compound 416A: LC-MS (ESI): $R_T$=7.703 min, mass calcd. for $C_{20}H_{20}ClF_2N_5O_4S_2$ 531.1, m/z found 532.0 [M+H]$^+$. Chiral analysis (Column: Chiralpak IE 5 μm 4.6*250 mm; Mobile Phase: Hex:EtOH:DEA=70:30:0.2 at 1.0 mL/min; Temp: 30° C.; Wavelength: 230 nm, $R_T$=11.086 min). $^1$H NMR (400 MHz, DMSO-d$_6$) δ 9.62 (d, J=3.2 Hz, 0.8H), 9.09 (s, 0.2H), 8.01-7.99 (m, 1.8H), 7.94 (d, J=3.2 Hz, 0.2H), 7.49-7.41 (m, 1H), 7.23-7.15 (m, 1H), 6.77-6.74 (m, 2H), 6.03 (s, 0.2H), 5.93 (d, J=3.2 Hz, 0.8H), 3.92-3.58 (m, 3H), 3.53 (s, 3H), 2.67-2.54 (m, 2H), 2.13-2.00 (m, 1H), 1.95-1.87 (m, 1H), 1.81-1.78 (m, 1H), 1.67-1.63 (m, 1H).

Compound 416B: LC-MS (ESI): $R_T$=4.704 min, mass calcd. for $C_{20}H_{20}ClF_2N_5O_4S_2$ 531.1, m/z found 532.0 [M+H]$^+$. Chiral analysis (Column: Chiralpak IE 5 μm 4.6*250 mm; Mobile Phase: Hex:EtOH:DEA=70:30:0.2 at 1.0 mL/min; Temp: 30° C.; Wavelength: 230 nm, $R_T$=14.628 min). $^1$H NMR (400 MHz, DMSO-d$_6$) δ 9.62 (s, 0.8H), 9.09 (br s, 0.2H), 8.01 (s, 1.8H), 7.94 (br s, 0.2H), 7.48-7.41 (m, 1H), 7.21 (br s, 1H), 6.74 (s, 2H), 6.02 (br s, 0.2H), 5.93 (s, 0.8H), 3.89-3.58 (m, 3H), 3.53 (s, 3H), 2.66-2.54 (m, 2H), 2.09-2.00 (m, 1H), 1.93-1.87 (m, 1H), 1.81-1.78 (m, 1H), 1.66-1.63 (m, 1H).

Compound 431: (trans)-Methyl 4-(2-chloro-4-fluorophenyl)-6-(4-(N-(3-hydroxypropyl)methylsulfonamido)cyclohexyl)-2-(thiazol-2-yl)-1,4-dihydropyrimidine-5-carboxylate

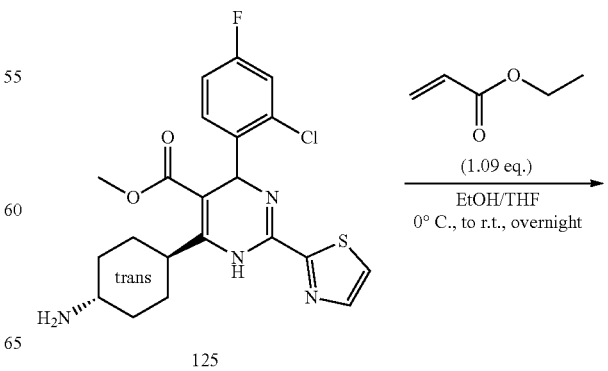

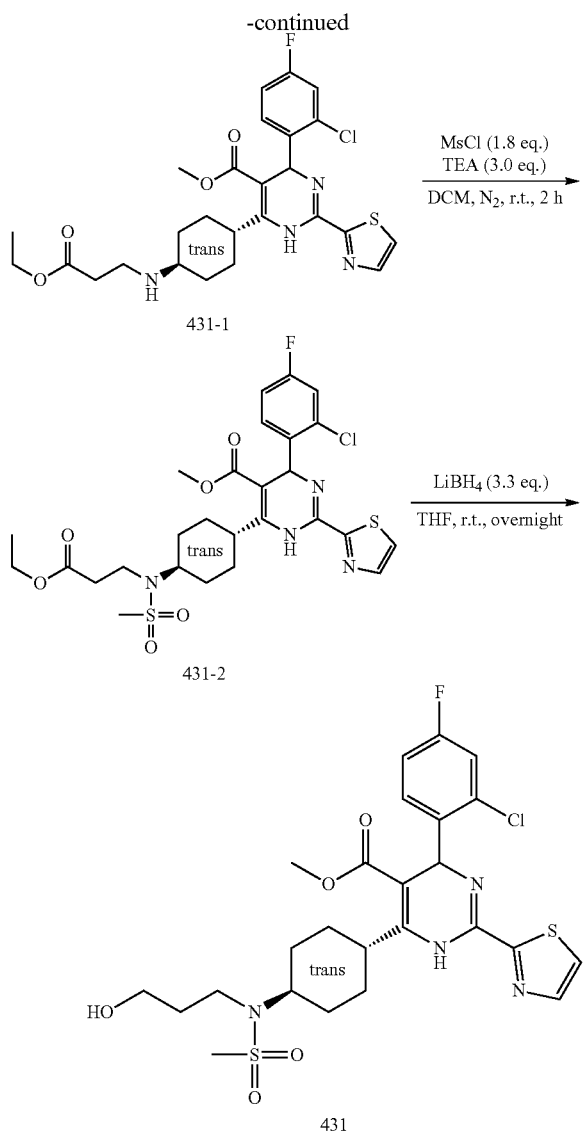

Compound 431-1: (trans)-Methyl 4-(2-chloro-4-fluorophenyl)-6-(4-((3-ethoxy-3-oxopropyl)amino)cyclohexyl)-2-(thiazol-2-yl)-1,4-dihydropyrimidine-5-carboxylate To a solution of (trans)-methyl 6-(4-aminocyclohexyl)-4-(2-chloro-4-fluorophenyl)-2-(thiazol-2-yl)-1,4-dihydropyrimidine-5-carboxylate compound 125 (1.67 g, 97% purity, 2.87 mmol) in ethanol (3 mL) and tetrahydrofuran (3 mL) was added ethyl acrylate (323 mg, 97% purity, 3.13 mmol) at 0° C. under nitrogen atmosphere. After stirred at room temperature overnight, the mixture was concentrated under reduced pressure to give a residue, which was purified by silica gel column chromatography (petroleum ether:ethyl acetate=8:1) to afford the title compound 431-1 (1.11 g, 68% yield) as yellow solids. LC-MS (ESI): $R_T$=1.67 min, mass calcd. for $C_{26}H_{30}ClFN_4O_4S$ 548.2, m/z found 549.5 [M+H]$^+$. $^1$H NMR (400 MHz, DMSO-d$_6$) δ 9.40 (br s, 0.3H), 8.87 (s, 0.7H), 8.03-7.96 (m, 1.7H), 7.94 (s, 0.3H), 7.46-7.43 (m, 1H), 7.40-7.30 (m, 1H), 7.25-7.17 (m, 1H), 6.01 (s, 0.41H), 5.94-5.90 (m, 0.6H), 4.12-4.04 (m, 2H), 3.85-3.75 (m, 0.5H), 3.62-3.52 (m, 0.5H), 3.51 (s, 3H), 2.94-2.84 (m, 2H), 2.65-2.57 (m, 1H), 2.05-1.96 (m, 2H), 1.89-1.56 (m, 5H), 1.23-1.07 (m, 6H).

Compound 431-2: (trans)-Methyl 4-(2-chloro-4-fluorophenyl)-6-(4-(N-(3-ethoxy-3-oxopropyl)methylsulfonamido)cyclohexyl)-2-(thiazol-2-yl)-1,4-dihydropyrimidine-5-carboxylate To a solution of (trans)-methyl 4-(2-chloro-4-fluorophenyl)-6-(4-((3-ethoxy-3-oxopropyl)amino)cyclohexyl)-2-(thiazol-2-yl)-1,4-dihydropyrimidine-5-carboxylate compound 431-1 (1.11 g, 1.96 mmol) in dichloromethane (30 mL) was added triethylamine (614 mg, 99% purity, 6.00 mmol) and methanesulfonyl chloride (421 mg, 98% purity, 3.60 mmol) at room temperature under nitrogen atmosphere. After stirred at room temperature for 2 hours, the mixture was concentrated under reduced pressure to give a residue, which was purified by silica gel column chromatography (petroleum ether:ethyl acetate=2:1) to afford the title compound 431-2 (1.08 g, 95% purity, 86% yield) as yellow solids. LC-MS (ESI): $R_T$=4.286 min, mass calcd. for $C_{27}H_{32}ClFN_4O_6S_2$ 626.1, m/z found 627.1 [M+H]$^+$. $^1$H NMR (400 MHz, DMSO-d$_6$) δ 9.43 (d, J=4.0 Hz, 0.6H), 9.09 (s, 0.4H), 8.00-7.98 (m, 1.5H), 7.93 (d, J=3.6 Hz, 0.5H), 7.44-7.40 (m, 1H), 7.37-7.30 (m, 1H), 7.24-7.18 (m, 1H), 6.01 (s, 0.4H), 5.91 (d, J=3.6 Hz, 0.6H), 4.08 (q, J=7.2 Hz, 2H), 3.87-3.75 (m, 1H), 3.60-3.51 (m, 4H), 3.41 (t, J=7.6 Hz, 2H), 2.98 (d, J=3.6 Hz, 3H), 2.61 (t, J=8.0 Hz, 2H), 2.08-1.56 (m, 8H), 1.21 (t, J=7.2 Hz, 3H).

Compound 431: (trans)-Methyl 4-(2-chloro-4-fluorophenyl)-6-(4-(N-(3-hydroxypropyl)methylsulfonamido)cyclohexyl)-2-(thiazol-2-yl)-1,4-dihydropyrimidine-5-carboxylate To a solution of (trans)-methyl 4-(2-chloro-4-fluorophenyl)-6-(4-(N-(3-ethoxy-3-oxopropyl)methylsulfonamido)cyclohexyl)-2-(thiazol-2-yl)-1,4-dihydropyrimidine-5-carboxylate compound 431-2 (520 mg, 95% purity, 0.788 mmol) in tetrahydrofuran (6 mL) was added lithium borohydride (56 mg, 97% purity, 2.59 mmol) at 0° C. under nitrogen atmosphere. After stirred at room temperature overnight, the mixture was cooled down to 0° C., quenched with water (100 mL) and extracted with ethyl acetate (50 mL) for three times. The combined organic layers were washed with brine (50 mL), dried over $Na_2SO_{4(s)}$, filtered and concentrated to give a residue, which was purified by silica gel column chromatography (petroleum ether:ethyl acetate=1:2) to afford the title compound 431 (300 mg, 96% purity, 63% yield) as yellow solids. LC-MS (ESI): $R_T$=3.992 min, mass calcd. for $C_{25}H_{30}ClFN_4O_5S_2$ 584.1, m/z found 585.1 [M+H]$^+$. $^1$H NMR (400 MHz, DMSO-d$_6$) δ 9.43 (d, J=3.2 Hz, 0.6H), 9.10 (s, 0.4H), 8.00-7.98 (m, 1.5H), 7.93 (d, J=3.6 Hz, 0.5H), 7.44-7.40 (m, 1H), 7.36-7.30 (m, 1H), 7.23-7.17 (m, 1H), 6.00 (s, 0.4H), 5.91 (d, J=3.6 Hz, 0.6H), 4.49-4.47 (m, 1H), 3.86-3.75 (m, 1H), 3.60-3.55 (m, 2H), 3.52 (s, 1.8H), 3.51 (s, 1.2H), 3.45-3.41 (m, 2H), 3.20-3.16 (m, 2H), 2.93 (d, J=2.8 Hz, 3H), 1.95-1.60 (m, 10H).

Racemic 431 (300 mg, 96% purity, 0.492 mmol) was separated by chiral Prep. HPLC (Column: Chiralpak IA 5 μm 20*250 mm; Mobile Phase: Hex:EtOH:DEA=80:20:0.3 at 25 mL/min; Temp: 30° C.; Wavelength: 230 nm) to give the title compounds 431A (64.4 mg, 98.6% purity, 22% yield, 100% stereopure) and 431B (63.4 mg, 99.8% purity, 22% yield, 98.8% stereopure) as yellow solids.

Compound 431A: LC-MS (ESI): $R_T$=3.689 min, mass calcd. for $C_{25}H_{30}ClFN_4O_5S_2$ 584.1, m/z found 584.7

[M+H]⁺. Chiral analysis (Column: Chiralpak IA 5 μm 4.6*250 mm; Mobile Phase: Hex:EtOH:DEA=80:20:0.2 at 1.0 mL/min; Temp: 30° C.; Wavelength: 230 nm, R$_T$=9.607 min). ¹H NMR (400 MHz, DMSO-d$_6$) δ 9.44 (d, J=3.6 Hz, 0.6H), 9.11 (s, 0.4H), 8.00-7.98 (m, 1.5H), 7.93 (d, J=3.6 Hz, 0.5H), 7.44-7.40 (m, 1H), 7.36-7.30 (m, 1H), 7.24-7.18 (m, 1H), 6.01 (s, 0.4H), 5.91 (d, J=3.2 Hz, 0.6H), 4.49 (t, J=4.8 Hz, 1H), 3.86-3.75 (m, 1H), 3.61-3.56 (m, 1H), 3.53 (s, 1.8H), 3.51 (s, 1.2H), 3.44 (q, J=5.6 Hz, 2H), 3.20-3.16 (m, 2H), 2.94 (d, J=2.8 Hz, 3H), 2.11-1.76 (m, 5H), 1.73-1.61 (m, 5H).

Compound 431B: LC-MS (ESI): R$_T$=3.690 min, mass calcd. for C$_{25}$H$_{30}$ClFN$_4$O$_5$S$_2$ 584.1, m/z found 584.7 [M+H]⁺. Chiral analysis (Column: Chiralpak IA 5 μm 4.6*250 mm; Mobile Phase: Hex:EtOH:DEA=80:20:0.2 at 1.0 mL/min; Temp: 30° C.; Wavelength: 230 nm, R$_T$=11.156 min). ¹H NMR (400 MHz, DMSO-d$_6$) δ 9.44 (d, J=3.6 Hz, 0.6H), 9.11 (s, 0.4H), 8.00-7.98 (m, 1.5H), 7.93 (d, J=3.2 Hz, 0.5H), 7.44-7.40 (m, 1H), 7.36-7.30 (m, 1H), 7.23-7.17 (m, 1H), 6.00 (s, 0.4H), 5.91 (d, J=3.6 Hz, 0.6H), 4.48 (t, J=5.2 Hz, 1H), 3.86-3.75 (m, 1H) 3.60-3.55 (m, 1H), 3.52 (s, 1.8H), 3.51 (s, 1.2H), 3.44 (q, J=5.6 Hz, 2H), 3.18 (t, J=7.6 Hz, 2H), 2.94 (s, 1.5H), 2.93 (s, 1.5H), 2.1.2-1.76 (m, 5H), 1.73-1.61 (m, 5H).

Compound 433: (trans)-Methyl 4-(2-chloro-3,4-difluorophenyl)-6-(4-(N-(2-hydroxyethyl)acetamido)cyclohexyl)-2-(thiazol-2-yl)-1,4-dihydropyrimidine-5-carboxylate

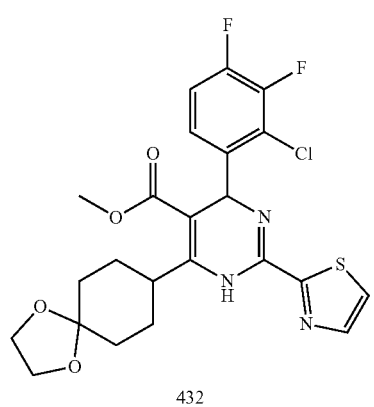

432

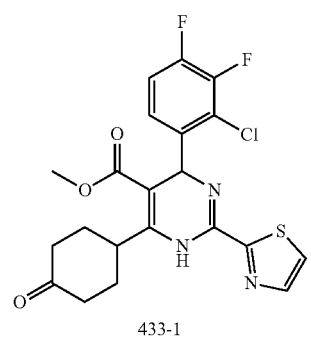

433-1

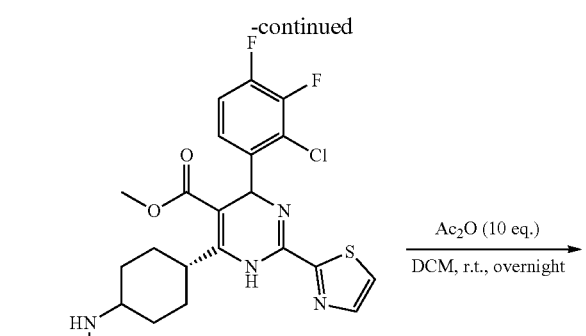

433-2

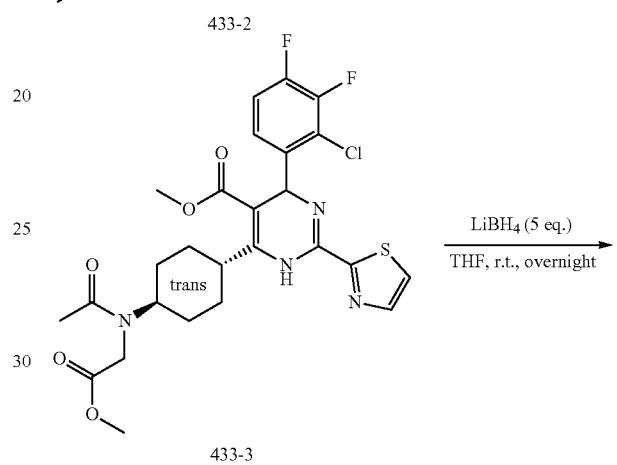

433-3

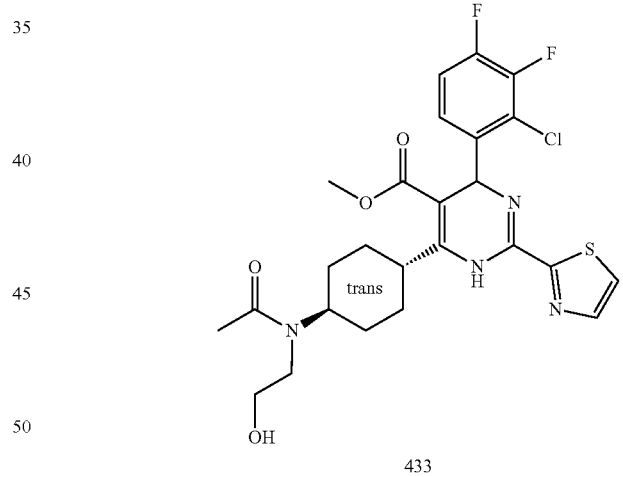

433

Compound 433-1: Methyl 4-(2-chloro-3,4-difluorophenyl)-6-(4-oxocyclohexyl)-2-(thiazol-2-yl)-1,4-dihydropyrimidine-5-carboxylate To a solution of 4-(2-chloro-3,4-difluorophenyl)-6-(1,4-dioxaspiro[4.5]decan-8-yl)-2-(thiazol-2-yl)-1,4-dihydropyrimidine-5-carboxylate compound 432 (2.85 g, 5.58 mmol) in dichloromethane (25 mL) was added trifluoroacetic acid (25 mL) at 0° C. After stirred at room temperature for 1 hour, the mixture was concentrated under reduced pressure to give a residue, which was dissolved in dichloromethane (250 mL) and washed with saturated sodium bicarbonate aqueous solution (200 mL) twice, brine (200 mL), dried over Na$_2$SO$_4$ (s) and filtered. The filtrate was concentrated under reduced pressure to give the title compound (1.72 g, 66% yield) as yellow solids. $^1$H NMR (400 MHz, DMSO-$d_6$) δ 9.63 (s, 0.7H), 9.25 (br s, 0.3H), 8.00-7.93 (m, 2H), 7.45 (q, J=8.8 Hz, 1H), 7.24-7.21 (m, 1H), 6.04-5.95 (m, 1H), 4.13-4.00 (m, 1H), 3.56 (s, 3H), 2.59-2.51 (m, 1H), 2.36-2.29 (m, 3H), 2.17-2.10 (m, 2H), 2.02-1.94 (m, 2H).

Compound 433-2: Methyl 4-(2-chloro-3,4-difluorophenyl)-6-(4-((2-methoxy-2-oxoethyl)amino)cyclohexyl)-2-(thiazol-2-yl)-1,4-dihydropyrimidine-5-carboxylate To a solution of methyl 4-(2-chloro-3,4-difluorophenyl)-6-(4-oxocyclohexyl)-2-(thiazol-2-yl)-1,4-dihydropyrimidine-5-carboxylate compound 433-1 (1.98 g, 4.24 mmol) and methyl 2-aminoacetate hydrochloride (1.64 g, 12.7 mmol) in methanol (50 mL) was added sodium acetate (1.60 g, 19.1 mmol) and sodium cyanoborohydride (1.31 g, 20.4 mmol). After stirred at room temperature overnight, the mixture was quenched with water (100 mL) and extracted with dichloromethane (100 mL) for three times. The combined organic layers were washed with brine (50 mL), dried over Na$_2$SO$_{4(s)}$ and filtered. The filtrate was concentrated to give the residue, which was purified by silica gel column chromatography (petroleum ether:ethyl acetate=3:1 to 1:1) to afford the title compounds 433-2A (1.30 g, 54% yield) and 433-2B (500 mg, 21% yield) as yellow solids.

Compound 433-2A (trans): $^1$H NMR (400 MHz, CDCl$_3$) δ 8.14-8.11 (m, 0.7H), 7.81 (s, 1H), 7.50-7.45 (m, 1.3H), 7.08-6.96 (m, 2H), 6.17 (s, 0.71), 6.03 (s, 0.3H), 4.00-3.91 (m, 1H), 3.76-3.73 (m, 4H), 3.61-3.59 (m, 3H), 3.52-3.46 (m, 2H), 2.62-2.54 (m, 1H), 2.35 (br s, 2H), 1.99-1.90 (m, 2H), 1.80-1.71 (m, 1H), 1.44-1.34 (m, 2H).

Compound 433-2B (cis): $^1$H NMR (400 MHz, CDCl$_3$) δ 8.46-8.42 (m, 0.8H), 7.83-7.82 (m, 1H), 7.51-7.44 (m, 1.2H), 7.10-6.96 (m, 2H), 6.20-6.18 (m, 0.8H), 6.05 (br s, 0.2H), 4.04-3.96 (m, 1H), 3.77 (s, 3H), 3.59 (s, 3H), 3.52-3.45 (m, 2H), 2.95-2.89 (m, 1H), 2.22-1.87 (m, 6H), 1.77-1.70 (m, 2H).

Compound 433-3: (trans)-Methyl 4-(2-chloro-3,4-difluorophenyl)-6-(4-(N-(2-methoxy-2-oxoethyl)acetamido)cyclohexyl)-2-(thiazol-2-yl)-1,4-dihydropyrimidine-5-carboxylate To a solution of (trans)-methyl 4-(2-chloro-3,4-difluorophenyl)-6-(4-((2-methoxy-2-oxoethyl)amino)cyclohexyl)-2-(thiazol-2-yl)-1,4-dihydropyrimidine-5-carboxylate 433-2A (475 mg, 0.870 mmol) in dichloromethane (10 mL) was added acetic anhydride (903 mg, 8.70 mmol) at 0° C. After stirred at room temperature overnight, the mixture was concentrated under reduced pressure to give a residue, which was dissolved in dichloromethane (200 mL), washed with saturated sodium bicarbonate aqueous solution (10 mL) twice and brine (10 mL), dried over Na$_2$SO$_{4(s)}$ and filtered. The filtrate was concentrated under reduced pressure to give a residue, which was purified by silica gel column chromatography (petroleum ether:ethyl acetate=3:1 to 1:1) to afford the title compound (340 mg, 55% yield) as yellow solids. $^1$H NMR (400 MHz, DMSO-$d_6$) δ 9.54 (d, J=3.6 Hz, 0.5H), 9.28 (s, 0.2H), 8.95 (s, 0.3H), 8.00-7.99 (m, 1.5H), 7.95 (d, J=3.2 Hz, 0.3H), 7.93 (d, J=3.2 Hz, 0.2H), 7.49-7.41 (m, 1H), 7.20-7.12 (m, 1H), 6.01 (d, J=6.0 Hz, 0.5H), 5.91 (t, J=4.0 Hz, 0.5H), 4.57-4.51 (m, 0.2H), 437-4.31 (m, 0.2H), 4.20 (s, 0.6H), 3.96 (s, 1H), 3.91-3.79 (m, 1H), 3.71 (s, 1.5H), 3.61 (s, 2H), 3.53-3.51 (m, 3.5H), 3.32 (s, 3H), 2.13 (s, 2H), 1.93-1.82 (m, 4H), 1.63-1.55 (m, 2H).

Compound 433: (trans)-Methyl 4-(2-chloro-3,4-difluorophenyl)-6-(4-(N-(2-hydroxyethyl)acetamido)cyclohexyl)-2-(thiazol-2-yl)-1,4-dihydropyrimidine-5-carboxylate To a solution of (trans)-methyl 4-(2-chloro-3,4-difluorophenyl)-6-(4-(N-(2-methoxy-2-oxoethyl)acetamido)cyclohexyl)-2-(thiazol-2-yl)-1,4-dihydropyrimidine-5-carboxylate 433-2A (270 mg, 0.460 mmol) in tetrahydrofuran (2 mL) was added lithium borohydride (52 mg, 2.32 mmol). After stirred at room temperature overnight, the mixture was quenched with water (10 mL) and extracted with ethyl acetate (10 mL) for three times. The combined organic layers were washed with brine (5 mL), dried over Na$_2$SO$_{4(s)}$ and filtered. The filtrate was concentrated to give a residue, which was purified by silica gel column chromatography (petroleum ether:ethyl acetate=1:1 to 1:2) to afford the title compound 433 (200 mg, 99.8% yield) as yellow solids. LC-MS (ESI): R$_T$=4.557 min, mass calcd. for C$_{25}$H$_{27}$ClF$_2$N$_4$O$_4$S 552.1, m/z found 553.1 [M+H]$^+$. $^1$H NMR (400 MHz, DMSO-$d_6$) δ 9.55 (t, J=3.6 Hz, 0.5H), 9.25 (s, 0.3H), 8.99 (s, 0.2H), 8.00-7.99 (m, 1.5H), 7.95-7.93 (m, 0.5H), 7.48-7.42 (m, 1H), 7.21-7.12 (m, 1H), 6.01 (d, J=4.8 Hz, 0.5H), 5.92 (t, J=3.6 Hz, 0.5H), 4.86-4.83 (m, 0.5H), 4.66-4.63 (m, 0.5H), 4.34-4.27 (m, 0.2H), 4.17-4.11 (m, 0.3H), 3.86-3.79 (m, 0.5H), 3.62-3.47 (m, 5H), 3.43-3.38 (m, 1H), 3.30-3.28 (m, 1H), 3.25-3.23 (m, 1H), 2.09-2.05 (m, 3H), 1.96-1.75 (m, 4H), 1.70-1.57 (m, 4H).

Racemic 433 (200 mg, 0.362 mmol) was separated by chiral Prep. HPLC (Column: Chiralpak AD-H 5 μm 20*250 mm; Mobile Phase: Hex:EtOH:DEA=70:30:0.3 at 13 mL/min; Temp: 30° C.; Wavelength: 214 nm) to afford the title compound 433A (54.5 mg, 27% yield, 100% stereopure) and 433B (37.5 mg, 12% yield, 100% stereopure) as yellow solids.

Compound 433A: LC-MS (ESI): R$_T$=4.554 min, mass calcd. for C$_{25}$H$_{27}$ClF$_2$N$_4$O$_4$S 552.1, m/z found 553.1 [M+H]$^+$. Chiral analysis (Column: Chiralpak AD-H 5 μm 4.6*250 mm; Mobile Phase: Hex:EtOH:DEA=70:30:0.2 at 1.0 mL/min; Temp: 30° C.; Wavelength: 230 nm, R$_T$=4.737 min). $^1$H NMR (400 MHz, DMSO-$d_6$) δ 9.55 (s, 0.5H), 9.24 (s, 0.3H), 8.99 (s, 0.2H), 8.00-7.99 (m, 1.5H), 7.95-7.92 (m, 0.5H), 7.49-7.42 (m, 1H), 7.21-7.13 (m, 1H), 6.01 (d, J=4.8 Hz, 0.4H), 5.93-5.92 (m, 0.6H), 4.88-4.85 (m, 0.5H), 4.66 (t, J=5.6 Hz, 0.5H), 4.33-4.27 (m, 0.2H), 4.17-4.11 (m, 0.3H), 3.87-3.76 (m, 0.5H), 3.59-3.49 (m, 5H), 3.41-3.38 (m, 1H), 3.32-3.30 (m, 1H), 3.25-3.24 (m, 1H), 2.09-2.05 (m, 3H), 1.95-1.75 (m, 4H), 1.66-1.57 (m, 4H).

Compound 433B: LC-MS (ESI): R$_T$=4.554 min, mass calcd. for C$_{25}$H$_{27}$ClF$_2$N$_4$O$_4$S 552.1, m/z found 553.1 [M+H]$^+$. Chiral analysis (Column: Chiralpak AD-H 5 μm 4.6*250 mm; Mobile Phase: Hex:EtOH:DEA=70:30:0.2 at 1.0 mL/min; Temp: 30° C.; Wavelength: 230 nm, R$_T$=11.148 min). $^1$H NMR (400 MHz, DMSO-$d_6$) δ 9.55 (s, 0.5H$_{11}$), 9.25 (s, 0.3H), 8.99 (s, 0.2-1), 8.00 (s, 1.5H), 7.95-7.93 (m, 0.5H), 7.49-7.42 (m, 1H), 7.21-7.13 (m, 1H), 6.02 (d, J=4.8 Hz, 0.5H), 5.92 (t, J=3.2 Hz, 0.5H), 4.88-4.85 (m, 0.5H), 4.67-4.64 (m, 0.5H), 4.31 (br s, 0.2H), 4.14 (br s, 0.3H), 3.89-3.76 (m, 0.5H), 3.61-3.49 (m, 5H), 3.43-3.38 (m, 1H), 3.32-3.28 (m, 1H), 3.25-3.22 (m, 1H), 2.09-2.05 (m, 3H), 1.96-1.75 (m, 4H), 1.70-1.57 (m, 4H).

Compound 434: (trans)-Methyl 4-(2-chloro-3,4-difluorophenyl)-6-(4-((2-hydroxyethyl)(2,2,2-trifluoroethyl)amino)cyclohexyl)-2-(thiazol-2-yl)-1,4-dihydropyrimidine-5-carboxylate

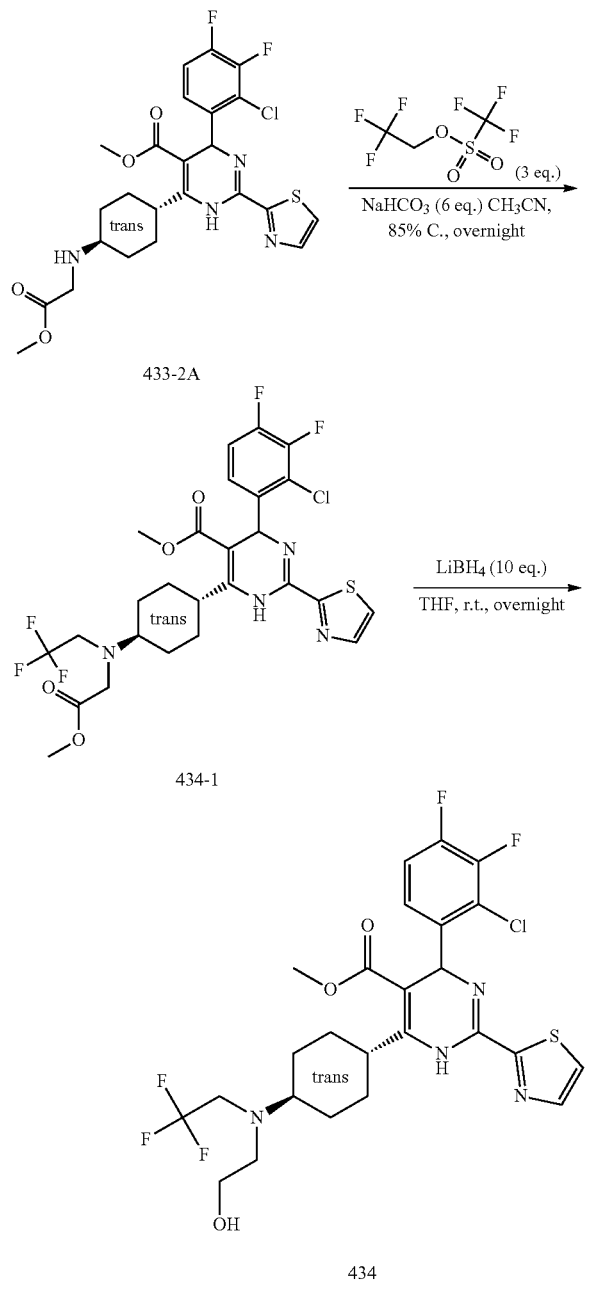

Compound 434-1: (trans)-Methyl 4-(2-chloro-3,4-difluorophenyl)-6-(4-((2-methoxy-2-oxoethyl)(2,2,2-trifluoroethyl)amino)cyclohexyl)-2-(thiazol-2-yl)-1,4-dihydropyrimidine-5-carboxylate To a solution of (trans)-methyl 4-(2-chloro-3,4-difluorophenyl)-6-(4-((2-methoxy-2-oxoethyl)amino)cyclohexyl)-2-(thiazol-2-yl)-1,4-dihydropyrimidine-5-carboxylate 433-2A (340 mg, 0.610 mmol) in acetonitrile (2 mL) was added sodium bicarbonate (310 mg, 3.66 mmol) and 2,2,2-trifluoroethyl trifluoromethanesulfonate (438 mg, 1.83 mmol). After stirred at 85° C. overnight, the mixture was quenched with water (10 mL) and extracted with ethyl acetate (10 mL) for three times. The combined organic layers were washed with brine (5 mL), dried over $Na_2SO_{4(s)}$ and filtered. The filtrate was concentrated to give a residue, which was purified by silica gel column chromatography (petroleum ether:ethyl acetate=3:1 to 1:1) to afford the title compound 434-1 (320 mg, 52% yield) as yellow solids. $^1$H NMR (400 MHz, DMSO-$d_6$) δ 9.53 (d, J=3.6 Hz, 0.6H), 9.01 (s, 0.4H), 8.00-7.98 (m, 1.5H), 7.94 (d, J=3.2 Hz, 0.5H), 7.48-7.41 (m, 1H), 7.20-7.12 (m, 1H), 6.00 (s, 0.4H), 5.90 (d, J=3.2 Hz, 0.6H), 3.82-3.74 (m, 0.6H), 369-3.61 (m, 3.4H), 3.58 (s, 21H), 3.52 (s, 1.8H), 3.51 (s, 1.2H), 3.48-3.43 (m, 2H), 2.84-2.78 (m, 0.4H), 2.71-2.65 (m, 0.6H), 1.92-1.85 (m, 3H), 1.81-1.72 (m, 2H), 1.68-1.59 (m, 1H), 1.33-1.23 (m, 2H).

Compound 434: (trans)-Methyl 4-(2-chloro-3,4-difluorophenyl)-6-(4-((2-hydroxyethyl)(2,2,2-trifluoroethyl)amino)cyclohexyl)-2-(thiazol-2-yl)-1,4-dihydropyrimidine-5-carboxylate To a solution of (trans)-methyl 4-(2-chloro-3,4-difluorophenyl)-6-(4-((2-methoxy-2-oxoethyl)(2,2,2-trifluoroethyl)amino)cyclohexyl)-2-(thiazol-2-yl)-1,4-dihydropyrimidine-5-carboxylate 434-1 (247 mg, 0.398 mmol) in tetrahydrofuran (2 mL) was added lithium borohydride (90 mg, 4.13 mmol). After stirring at room temperature overnight, the mixture was quenched with water (10 mL) and extracted with ethyl acetate (10 mL) for three times. The combined organic layers were washed with brine (5 mL), dried over $Na_2SO_{4(s)}$ and filtered. The filtrate was concentrated to give a residue, which was purified by silica gel column chromatography (petroleum ether:ethyl acetate=1:1 to 1:2) to afford the title compound 434 (70 mg, 24% yield) as yellow solids. LC-MS (ESI): $R_T$=4.187 min, mass calcd. for $C_{25}H_{26}ClF_5N_4O_3S$ 592.1, m/z found 593.2 [M+H]$^+$. $^1$H NMR (400 MHz, DMSO-$d_6$) δ 9.52 (d, J=3.2 Hz, 0.5H), 8.99 (s, 0.5H), 8.00-7.97 (m, 1.5H), 7.94 (d, J=2.8 Hz, 0.5H), 7.49-7.41 (m, 1H), 7.20-7.13 (m, 1H), 6.01 (s, 0.4H), 5.91 (d, J=3.6 Hz, 0.6H), 4.43-4.39 (m, 1H), 3.83-3.75 (m, 0.5H), 3.52-3.51 (m, 3.5H), 3.46-3.40 (m, 2H), 3.30-3.26 (m, 2H), 2.70 (t, J=6.8 Hz, 2H), 2.59-2.56 (m, 1H), 1.91-1.79 (m, 5H), 1.75-1.64 (m, 1H), 1.39-1.29 (m, 2H).

Racemic 434 (70 mg, 0.12 mmol) was separated by chiral Prep. SFC (Column: Chiralpak IG 5 μm 20*250 mm; Mobile Phase: CO$_2$:MeOH=70:30 at 50 g/min; Col. Temp: 30° C.; Wavelength: 230 nm, Back pressure: 100 bar) to afford the title compounds 434A (19.1 mg, 27% yield, 100% stereopure) and 434B (19.8 mg, 28% yield, 100% stereopure) as yellow solids.

Compound 434A: LC-MS (ESI): $R_T$=4.165 min, mass calcd. for $C_{25}H_{26}ClF_5N_4O_3S$ 592.1, m/z found 593.0 [M+H]$^+$. Chiral analysis (Column: Chiralpak IE 5 μm 4.6*250 mm; Mobile Phase: Hex:EtOH:DEA=90:10:0.2 at 1.0 mL/min; Temp: 30° C.; Wavelength: 230 nm, $R_T$=10.689 min). $^1$H NMR (400 MHz, DMSO-$d_6$) δ 9.52 (d, J=3.2 Hz, 0.5H), 8.98 (s, 0.5H), 8.00-7.97 (m, 1.5H), 7.94 (d, J=3.6 Hz, 0.5H), 7.49-7.41 (m, 1H), 7.20-7.13 (m, 1H), 6.01 (s, 0.5H), 5.91 (d, J=3.2 Hz, 0.5H), 4.43-4.39 (m, 1H), 3.81-3.70 (m, 0.6H), 3.53-3.52 (m, 3.4H), 3.46-3.41 (m, 2H), 3.28-3.26 (m, 2H), 2.72-2.68 (m, 2H), 2.60-2.56 (m, 1H), 1.90-1.74 (m, 5H), 1.70-1.64 (m, 1H), 1.40-1.29 (m, 2H).

Compound 434B: LC-MS (ESI): $R_T$=4.169 min, mass calcd. for $C_{25}H_{26}ClF_5N_4O_3S$ 592.1, m/z found 593.0 [M+H]$^+$. Chiral analysis (Column: Chiralpak IE 5 μm 4.6*250 mm; Mobile Phase: Hex:EtOH:DEA=90:10:0.2 at 1.0 mL/min; Temp: 30° C.; Wavelength: 230 nm, $R_T$=12.458 min). $^1$H NMR (400 MHz, DMSO-$d_6$) δ 9.52 (d, J=3.6 Hz, 0.5H), 8.98 (s, 0.5H), 8.00-7.97 (m, 1.5H), 7.94 (d, J=3.2 Hz, 0.5H), 7.49-7.41 (m, 1H), 7.20-7.13 (m, 1H), 6.01 (s, 0.4H), 5.91 (d, J=3.2 Hz, 0.6H), 4.44-4.40 (m, 1H), 3.81-3.76 (m, 0.6H), 3.53-3.52 (m, 3.4H), 3.46-3.42 (m, 2H), 3.28-3.26 (m, 2H), 2.71-2.68 (m, 2H), 2.59-2.56 (m, 1H), 1.88-1.73 (m, 5H), 1.69-1.63 (m, 1H), 1.40-1.29 (m, 2H).

Compound 448: (trans)-Methyl 4-(2-chloro-4-fluorophenyl)-6-(4-(N-(cyanomethyl)methylsulfonamido)cyclohexyl)-2-(thiazol-2-yl)-1,4-dihydropyrimidine-5-carboxylate

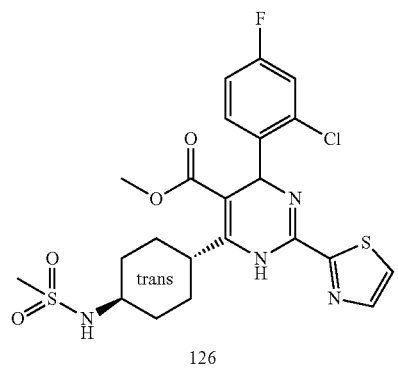

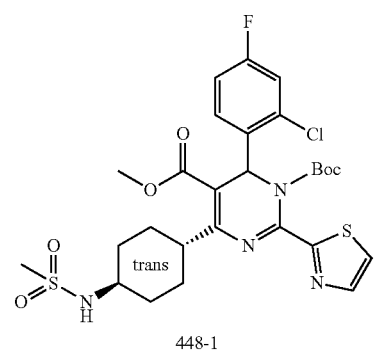

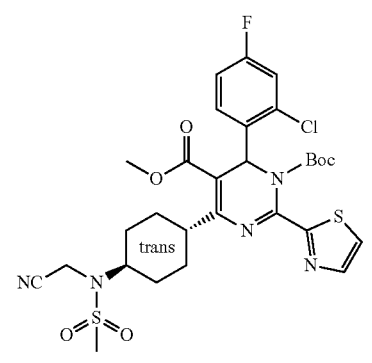

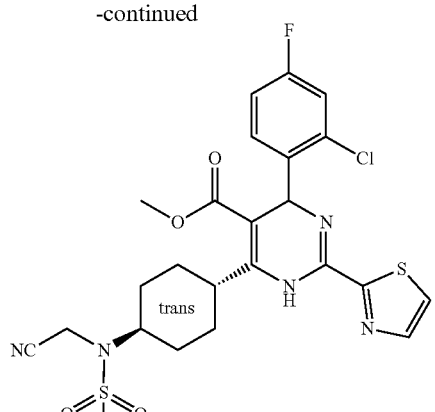

Compound 448-1: (trans)-1-tert-Butyl 5-methyl 6-(2-chloro-4-fluorophenyl)-4-(4-(methylsulfonamido)cyclohexyl)-2-(thiazol-2-yl)pyrimidine-1,5(6H)-dicarboxylate The mixture of (trans)-methyl 4-(2-chloro-4-fluorophenyl)-6-(4-(methylsulfonamido)cyclohexyl)-2-(thiazol-2-yl)-1,4-dihydropyrimidine-5-carboxylate 126 (1.44 g, 2.73 mmol), di-tert-butyl dicarbonate (631 mg, 2.89 mmol) and N,N-dimethylpyridin-4-amine (136 mg, 1.11 mmol) in tetrahydrofuran (10 mL) was stirred at 60° C. overnight. After cooled down to room temperature and quenched with water (100 mL), the mixture was extracted with dichloromethane (100 mL) for three times. The combined organic layers were washed with saturated sodium sulfite aqueous solution (50 mL), dried over $Na_2SO_{4(s)}$ and filtered. The filtrate was concentrated to give a residue, which was purified by silica gel column chromatography (petroleum ether:ethyl acetate=3:1 to 1:1) to afford the title compound 448-1 (990 mg, 58% yield) as yellow solids. LC-MS (ESI): $R_T$=1.82 min, mass calcd. for $C_{27}H_{32}ClFN_4O_6S_2$ 626.1, m/z found 627.4 [M+H]$^+$.

Compound 448-2: (trans)-1-tert-Butyl 5-methyl 6-(2-chloro-4-fluorophenyl)-4-(4-(N-(cyanomethyl)methylsulfonamido)cyclohexyl)-2-(thiazol-2-yl)pyrimidine-1,5(6H)-dicarboxylate To a solution of (trans)-1-tert-butyl 5-methyl 6-(2-chloro-4-fluorophenyl)-4-(4-(methylsulfonamido)cyclohexyl)-2-(thiazol-2-yl)pyrimidine-1,5(6H)-dicarboxylate 448-1 (830 mg, 1.32 mmol) in tetrahydrofuran (6 mL) was added 60% wt. sodium hydride in mineral oil (160 mg, 3.97 mmol) at 0° C. After stirred for 1 hour at room temperature, the mixture was cooled down to 0° C. and 2-bromoacetonitrile (634 mg, 5.28 mmol) was added. After stirred at room temperature overnight, the mixture was diluted with water (100 mL), extracted with ethyl acetate (50 mL) for three times. The combined organic layers were washed with brine (50 mL), dried over $Na_2SO_{4(s)}$ and filtered. The filtrate was concentrated to give a residue, which was purified by silica gel column chromatography (petroleum ether:ethyl acetate=3:1 to 1:1) to afford the title compound 448-2 (550 mg, 63% yield) as yellow solids. $^1$H NMR (300 MHz, DMSO-$d_6$) δ 8.00 (s, 2H), 7.48 (dd, J=8.4, 2.4 Hz, 1H), 7.17-7.11 (m, 1H), 7.07-7.00 (m, 1H), 6.55 (s, 1H), 4.46 (s, 2l-), 3.79-3.71 (m, 1H), 3.68 (s, 3H), 3.49 (br s, 1H), 3.12 (s, 3H), 2.06-2.01 (m, 1H), 1.91-1.62 (m, 6H), 1.59 (br s, 1H), 1.15 (s, 9H).

Compound 448: (trans)-Methyl 4-(2-chloro-4-fluorophenyl)-6-(4-(N-(cyanomethyl)methylsulfonamido)cyclohexyl)-2-(thiazol-2-yl)-1,4-dihydropyrimidine-5-carboxylate To a solution of (trans)-1-tert-butyl 5-methyl 6-(2-chloro-4-fluorophenyl)-4-(4-(N-(cyanomethyl)methylsulfonamido)cyclohexyl)-2-(thiazol-2-yl)pyrimidine-1,5(6H)-dicarboxylate 448-2 (500 mg, 0.750 mmol) in dichloromethane (2 mL) was added trifluoroacetic acid (1 mL) at 0° C. After stirred at room temperature overnight, the mixture was concentrated under reduced pressure to give a residue, which was dissolved in dichloromethane (5 mL), washed with saturated sodium bicarbonate aqueous solution (3 mL) twice, brine (3 mL), dried over $Na_2SO_{4(s)}$ and filtered. The filtrate was concentrated under reduced pressure to give a residue, which was purified by silica gel column chromatography (petroleum ether:ethyl acetate=3:1 to 1:1) to afford the title compound 448 (280 mg, 66% yield) as yellow solids. LC-MS (ESI): $R_T$=4.278 min, mass calcd. for $C_{24}H_{25}ClFN_5O_4S_2$ 565.1, m/z found 566.0 $[M+H]^+$. $^1H$ NMR (400 MHz, DMSO-$d_6$) δ 9.43 (d, J=3.2 Hz, 0.6H), 9.09 (s, 0.4H), 8.00-7.93 (m, 2H), 7.44-7.40 (m, 1H), 7.37-7.30 (m, 1H), 7.24-7.18 (m, 1H), 6.01 (s, 0.4H), 5.91 (d, J=3.2 Hz, 0.6H), 4.45 (s, 2H$_1$), 3.97-3.84 (m, 1H), 3.74-3.68 (m, 0.5H), 3.62-3.59 (m, 0.5H), 3.54 (s, 1.5H), 3.52 (s, 1.5H), 3.11 (s, 1.5H), 3.09 (s, 1.5H), 1.99-1.66 (m, 8H).

Racemic 448 (280 mg, 0.495 mmol) was separated by chiral Prep. HPLC (Column: Chiralpak IC 5 μm 20*250 mm; Mobile Phase: Hex:EtOH=70:30 at 25 mL/min; Temp: 30° C.; Wavelength: 214 nm) to afford the title compounds 448A (52.6 mg, 99.5% purity, 19% yield, 100% stereopure) and 448B (46.1 mg, 99.4% purity, 16% yield, 100% stereopure) as yellow solids.

Compound 448A: LC-MS (ESI): $R_T$=4.058 min, mass calcd. for $C_{24}H_{25}ClFN_5O_4S_2$ 565.1, m/z found 566.1 $[M+H]^+$. Chiral analysis (Column: Chiralpak IC 5 μm 4.6*250 mm; Mobile Phase: Hex:EtOH=70:30 at 1.0 mL/min; Temp: 30° C.; Wavelength: 230 nm, $R_T$=12.949 min). $^1H$ NMR (400 MHz, DMSO-$d_6$) δ 9.43 (d, J=3.2 Hz, 0.6H), 9.08 (s, 0.4H), 8.00-7.93 (m, 2H), 7.43-7.41 (m, 1H), 7.37-7.31 (m, 1H), 7.24-7.17 (m, 1H), 6.01 (s, 0.4H), 5.91 (d, J=3.2 Hz, 0.6H), 4.45 (s, 2H), 3.97-3.84 (m, 1H), 3.74-3.68 (m, 0.5H), 3.61-3.59 (m, 0.5H), 3.54 (s, 1.5H), 3.52 (s, 1.5H), 3.11 (s, 1.5H), 3.09 (s, 1.5H), 2.11-1.95 (m, 1H), 1.92-1.69 (m, 7H).

Compound 448B: LC-MS (ESI): $R_T$=4.063 min, mass calcd. for $C_{24}H_{25}ClFN_5O_4S_2$ 565.1, m/z found 566.1 $[M+H]^+$. Chiral analysis (Column: Chiralpak IC 5 μm 4.6*250 mm; Mobile Phase: Hex:EtOH=70:30 at 1.0 mL/min; Temp: 30° C.; Wavelength: 230 nm, $R_T$=15.940 min). H NMR (400 MHz, DMSO-$d_6$) δ 9.43 (s, 0.6H), 9.09 (s, 0.4H), 7.99-7.93 (m, 2H), 7.43-7.31 (m, 2H), 7.23-7.20 (m, 1H), 6.01 (s, 0.4H), 5.92 (s, 0.6H), 4.46 (s, 2H), 3.96-3.85 (m, 1H), 3.74-3.69 (m, 0.5H), 3.62-3.59 (m, 0.5H), 3.54 (s, 1.5H), 3.53 (s, 1.5H), 3.11 (s, 1.5H), 3.10 (s, 1.5H), 2.12-1.96 (m, 1H), 1.92-1.69 (m, 7H).

Compound 457: Methyl 6-(1-((3-amino-3-oxopropyl)sulfonyl)piperidin-4-yl)-4-(2-chloro-4-fluorophenyl)-2-(thiazol-2-yl)-1,4-dihydropyrimidine-5-carboxylate

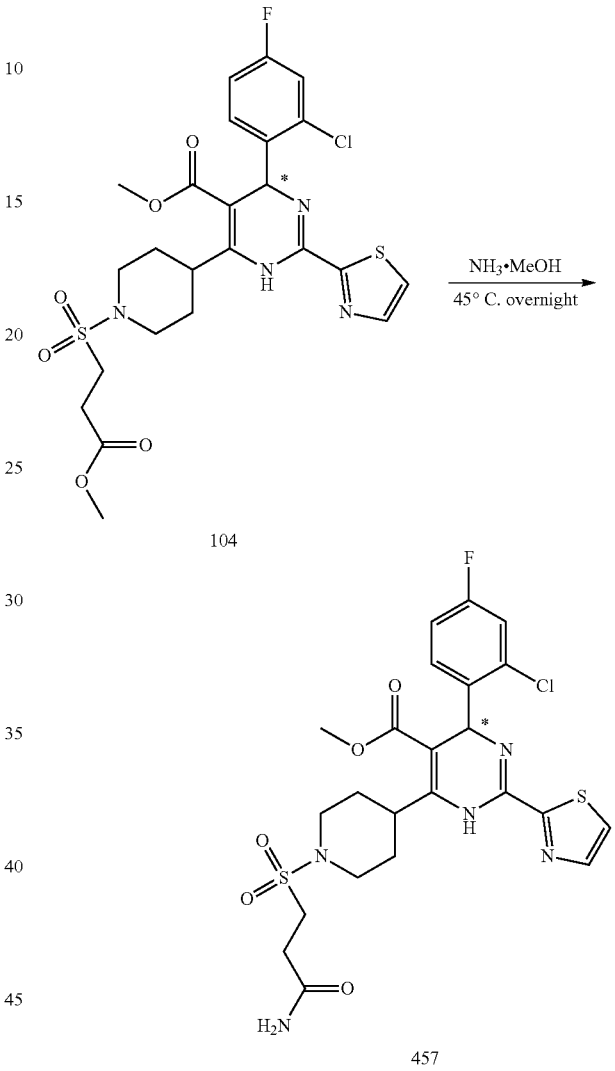

A suspension of methyl 4-(2-chloro-4-fluorophenyl)-6-(1-((3-methoxy-3-oxopropyl) sulfonyl)piperidin-4-yl)-2-(thiazol-2-yl)-1,4-dihydropyrimidine-5-carboxylate 104 (130 mg, 0.222 mmol) in 3 M ammonia in methanol (3 mL, 9.00 mmol) in a steal tube was stirred at 45° C. overnight. After cooled down to room temperature, the mixture was concentrated under reduced pressure to give a residue, which was purified by Prep. HPLC (Column: Waters kinete EVO C18 (5 μm 21.2*150 mm), Mobile phase A: water (0.1% ammonium bicarbonate), Mobile phase B: acetonitrile, UV: 214 nm, Flow rate: 15 mL/min, Gradient: 20-80% (% B)) to give the title compound 457 (42.8 mg, 99.2% purity, 34% yield) as yellow solids. LC-MS (ESI): $R_T$=3.767 min, mass calcd. for $C_{23}H_{25}ClFN_5O_5S_2$ 569.1, m/z found 569.9 $[M+H]^+$. $^1H$ NMR (400 MHz, DMSO-$d_6$) δ 9.55 (d, J=3.6 Hz, 0.8H), 9.18 (s, 0.2H), 8.00-7.99 (m, 1.8H), 7.94-7.93 (m, 0.2H), 7.53 (br s, 1H), 7.45-7.41 (m, 1H), 7.38-7.31 (m, 1H), 7.24-7.19 (m, 1H), 7.04 (br s, 1H), 6.02 (s, 0.2H), 5.92 (d, J=3.2 Hz, 0.8H), 4.00-3.92 (m, 0.2H), 3.78-3.67 (m, 2.8H), 3.53 (s, 3H), 3.30-3.24 (m, 2H), 2.93-2.84 (m, 2H), 2.54-2.52 (m, 2H), 2.12-1.75 (m, 3.2H), 1.64-1.62 (m, 0.8H).

Compound 462: 6-(4-((4-(6-(2-Chloro-3,4-difluoro-phenyl)-5-(ethoxycarbonyl)-2-(thiazol-2-yl)-3,6-dihydropyrimidin-4-yl)piperidin-1-yl)sulfonyl)-1H-pyrazol-1-yl)hexanoic Acid 0.436 mmol). After stirred at 60° C. overnight, the mixture was diluted with water (30 mL) and extracted with ethyl acetate (30 mL) for three times. The combined organic phases were washed with water (20 mL) for three times, brine (20 mL), dried over $Na_2SO_{4(s)}$ and filtered. The filtrate was concentrated in vacuo to give a residue, which was purified by Prep. HPLC (Column: Waters Xbridge C18 (5 um 19*150 mm), mobile phase A: water (0.1% ammonium bicarbonate), mobile phase B: acetonitrile, UV: 214 nm,

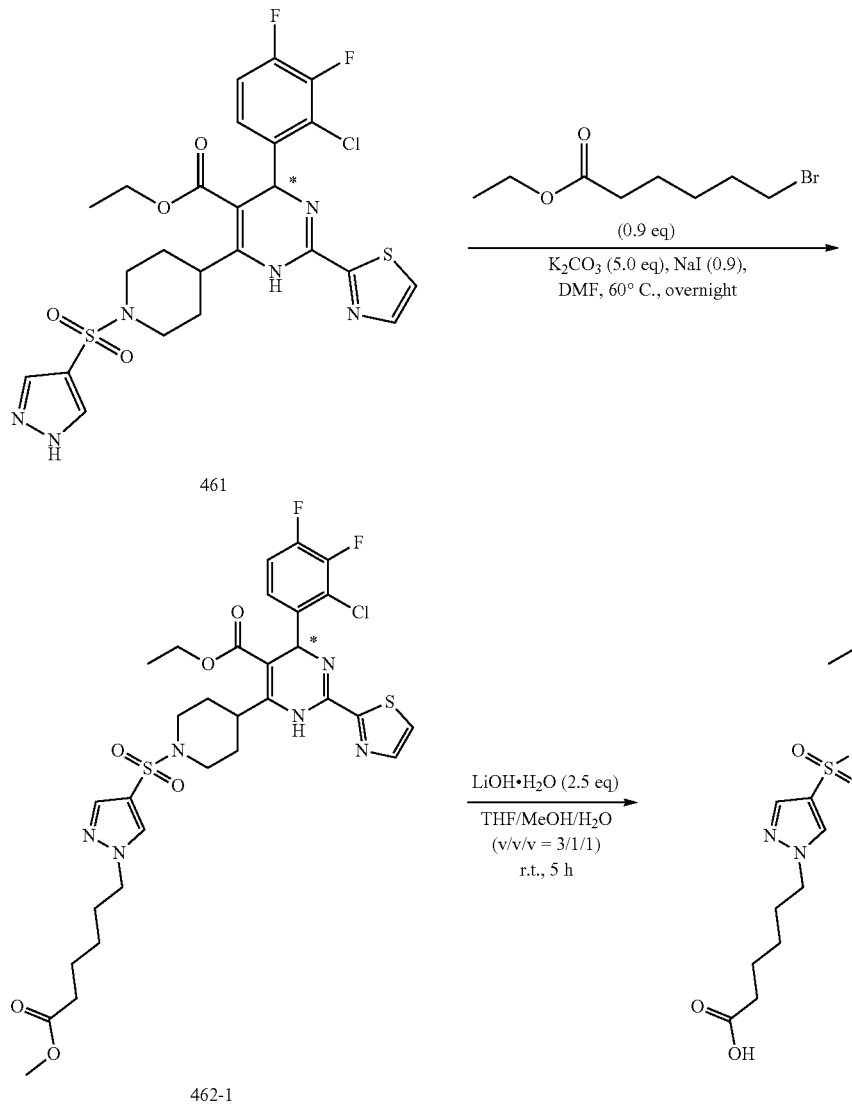

Compound 462-1: Ethyl 4-(2-chloro-3,4-difluoro-phenyl)-6-(1-((1-(6-ethoxy-6-oxohexyl)-1H-pyrazol-4-yl)sulfonyl)piperidin-4-yl)-2-(thiazol-2-yl)-1,4-dihydropyrimidine-5-carboxylate To a solution of ethyl 6-(1-(((1H-pyrazol-4-yl)sulfonyl) piperidin-4-yl)-4-(2-chloro-3,4-difluorophenyl)-2-(thiazol-2-yl)-1,4-dihydropyrimidine-5-carboxylate 461 (360 mg, 80% purity, 0.482 mmol) in N,N-dimethylformamide (10 mL) was added ethyl 6-bromohexanoate (98 mg, 99% purity, 0.435 mmol), potassium carbonate (340 mg, 99% purity, 2.44 mmol) and sodium iodide (66 mg, 99% purity, Flowrate: 15 mL/min, Gradient: 65-85% (% B)) to give the title Compound 462-1 (165 mg, 98.7% purity, 46% yield) as yellow solids. LC-MS (ESI): $R_T$=3.076 min, mass calcd. for $C_{32}H_{37}ClF_2N_6O_6S_2$ 738.2, m/z found 739.3 $[M+H]^+$. $^1H$ NMR (400 MHz, $CDCl_3$) δ 8.18 (s, 0.3H), 7.86-7.81 (m, 1H), 7.78-7.73 (m, 2H), 7.56-7.51 (m, 0.7H), 7.48-7.45 (m, 0.4H), 7.36-7.32 (m, 0.6H), 7.09-7.01 (m, 2H), 6.18 (s, 0.4H), 6.08-6.06 (m, 0.6H), 4.21-4.09 (m, 4H), 4.04-3.85 (m, 4.4H), 3.79-3.69 (m, 0.6H), 2.46-2.35 (m, 2H), 2.34-2.29 (m, 2H), 2.00-1.88 (m, 4H), 1.73-1.66 (m, 2H), 1.55-1.52 (m, 2H), 1.42-1.33 (m, 2H), 1.28-1.23 (m, 3H), 1.12-1.04 (m, 3H).

Compound 462: 6-(4-((4-(6-(2-Chloro-3,4-difluorophenyl)-5-(ethoxycarbonyl)-2-(thiazol-2-yl)-3,6-dihydropyrimidin-4-yl)piperidin-1-yl)sulfonyl)-1H-pyrazol-1-yl)hexanoic Acid To a solution of ethyl 4-(2-chloro-3,4-difluorophenyl)-6-(1-((1-(6-ethoxy-6-oxohexyl)-1H-pyrazol-4-yl) sulfonyl)piperidin-4-yl)-2-(thiazol-2-yl)-1,4-dihydropyrimidine-5-carboxylate 462-1 (159 mg, 98.7% purity, 0.212 mmol) in methanol (2 mL), water (2 mL) and tetrahydrofuran (6 mL) was added lithium hydroxide monohydrate (22 mg, 0.524 mmol) at 0° C. After stirred at room temperature for 5 hours, the mixture was diluted by water (10 mL), acidified with 1 M hydrochloride aqueous solution to pH~2 and extracted with ethyl acetate (15 mL) for three times. The combined organic phases were washed with water (15 mL), brine (15 mL), dried over $Na_2SO_{4(s)}$, filtered and concentrated in vacuo to give a residue, which was purified by C18 column (acetonitrile:water=10% to 95%) to give the title Compound 462 (90 mg, 97% purity, 58% yield) as yellow solids. LC-MS (ESI): $R_T$=3.907 min, mass calcd. for $C_{30}H_{33}ClF_2N_6O_6S_2$ 710.2, m/z found 710.9 [M+H]$^+$. $^1$H NMR (400 MHz, DMSO-d$_6$) δ 8.41 (s, 1H), 8.07-7.98 (m, 1.8H), 7.94 (s, 0.2H), 7.82 (s, 1H), 7.45 (dd, J=9.2, 16.8 Hz, 1H), 7.24-7.15 (m, 1H), 6.01 (br s, 0.2H), 5.91 (s, 0.8H), 4.18 (t, J=6.8 Hz, 2H), 3.92 (q, J=6.8 Hz, 2H), 3.75-3.64 (m, 2.2H), 3.56-3.51 (m, 0.8H), 2.33-2.12 (m, 4H), 2.10-1.97 (m, 1H), 1.92-1.89 (m, 4H), 1.70-1.59 (m, 0.8H), 1.55-1.43 (m, 2H), 1.25-1.14 (m, 2.2H), 1.05-0.95 (m, 3H).

Compound 463: 5-(4-((4-(6-(2-Chloro-3,4-difluorophenyl)-5-(ethoxycarbonyl)-2-(thiazol-2-yl)-3,6-dihydropyrimidin-4-yl)piperidin-1-yl)sulfonyl)-1H-pyrazol-1-yl)pentanoic acid

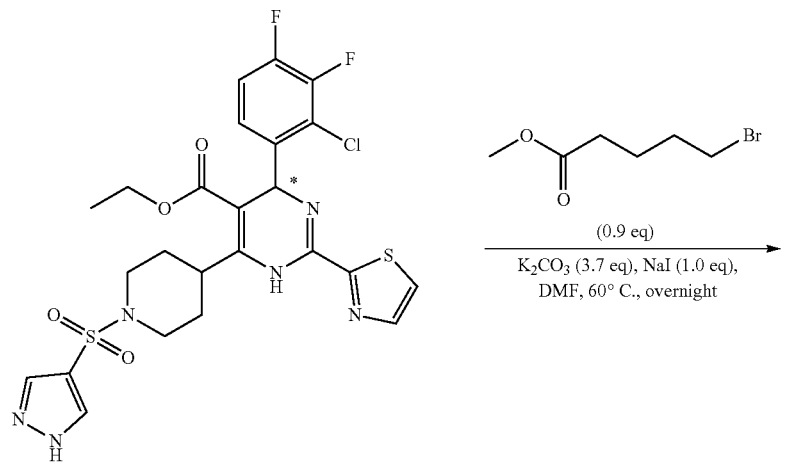

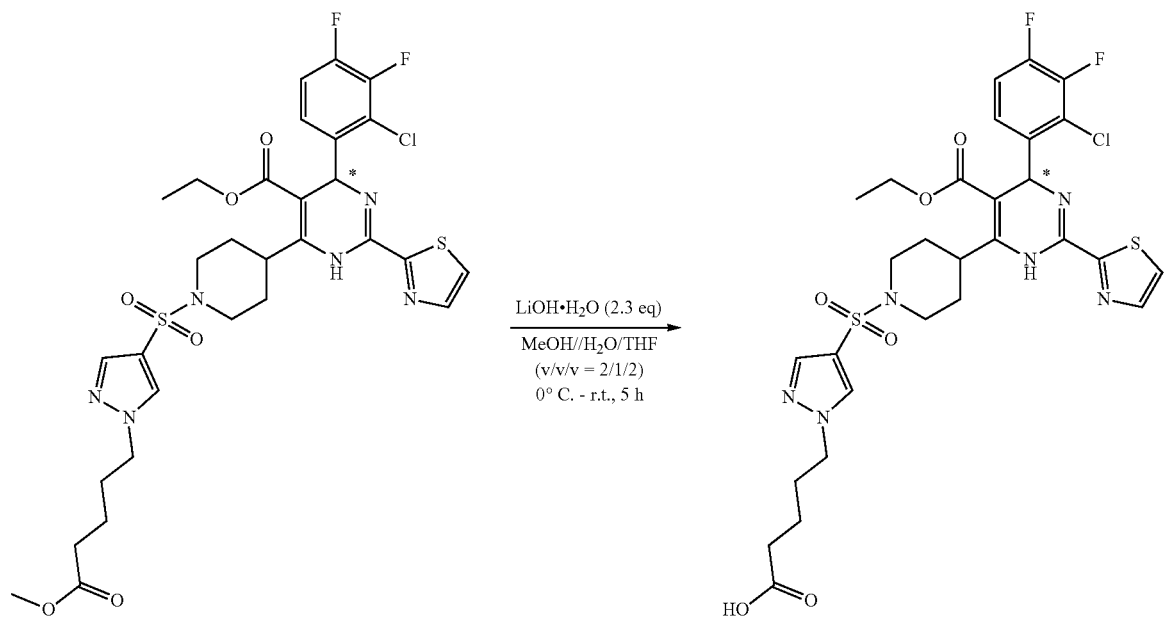

Compound 463-1: Ethyl 4-(2-chloro-3,4-difluorophenyl)-6-(1-((1-(5-methoxy-5-oxopentyl)-1H-pyrazol-4-yl)sulfonyl)piperidin-4-yl)-2-(thiazol-2-yl)-1,4-dihydropyrimidine-5-carboxylate To a solution of ethyl 6-(1-(((1H-pyrazol-4-yl)sulfonyl)piperidin-4-yl)-4-(2-chloro-3,4-difluorophenyl)-2-(thiazol-2-yl)-1,4-dihydropyrimidine-5-carboxylate 461 (300 mg, 75% purity, 0.377 mmol) in N,N-dimethylformamide (5 mL) was added methyl 5-bromopentanoate (67 mg, 0.344 mmol), potassium carbonate (194 mg, 1.41 mmol) and sodium iodide (58 mg, 0.387 mmol) at room temperature. After stirred at 60° C. overnight, the mixture was dissolved in ethyl acetate (40 mL) and washed with water (100 mL) twice. The combined aqueous layers were extracted with ethyl acetate (60 mL) twice. The combined organic layers were washed with water (30 mL) twice and brine (30 mL), dried over $Na_2SO_{4(s)}$ and filtered. The filtrate was concentrated under reduced pressure to afford a residue, which was purified by prep. HPLC (Column: Gilson Gemini C18 (5 μm 19*150 mm), Mobile phase A: water (0.1% ammonium bicarbonate), B: acetonitrile, UV: 214 nm, Flowrate 15 mL/min, Gradient: 55-70% (% B)) to give the title Compound 463-1 (150 mg, 99% purity, 56% yield) as yellow solids. LC-MS (ESI): $R_T$=4.243 min, mass calcd. for $C_{30}H_{33}ClF_2N_6O_6S_2$ 710.2, m/z found 710.8 $[M+H]^+$. $^1H$ NMR (400 MHz, DMSO-$d_6$) δ 9.64 (d, J=3.6 Hz, 0.8H), 9.18 (s, 0.2H), 8.43-8.42 (m, 1H), 8.04-7.93 (m, 2H), 7.84 (d, J=4.8 Hz, 1H), 7.44 (q, J=8.8 Hz, 1H), 7.22-7.18 (m, 1H), 6.01 (s, 0.2H), 5.91 (d, J=3.2 Hz, 0.8H), 4.20 (t, J=6.8 Hz, 2H), 3.95-3.89 (m, 2H), 3.75-3.65 (m, 2.3H), 3.56 (s, 3H), 3.53-3.49 (m, 0.7H), 2.35-2.30 (m, 2H), 2.26-2.17 (m, 2H), 2.09-2.03 (m, 1H), 1.95-1.77 (m, 4H), 1.66-1.63 (m, 1H), 1.48-1.40 (m, 2H), 1.03-0.96 (m, 3H).

Compound 463: 5-(4-((4-(6-(2-Chloro-3,4-difluorophenyl)-5-(ethoxycarbonyl)-2-(thiazol-2-yl)-3,6-dihydropyrimidin-4-yl)piperidin-1-yl)sulfonyl)-1H-pyrazol-1-yl)pentanoic Acid To a solution of ethyl 4-(2-chloro-3,4-difluorophenyl)-6-(1-((1-(5-methoxy-5-oxopentyl)-1H-pyrazol-4-yl)sulfonyl)piperidin-4-yl)-2-(thiazol-2-yl)-1,4-dihydropyrimidine-5-carboxylate Compound 463-1 (50 mg, 99% purity, 0.070 mmol) in tetrahydrofuran (1 mL) and ethanol (1 mL) was added a solution of lithium hydroxide hydrate (7 mg, 0.163 mmol) in water (0.5 mL). After stirred at room temperature for 5 hours, the mixture was concentrated to give a residue, which was diluted water (10 mL), acidified with 1 M hydrochloride aqueous solution (1 mL) to pH 4-5, and extracted with ethyl acetate (20 mL) twice. The combined organic layers were washed with water (10 mL) twice and brine (10 mL), dried over $Na_2SO_{4(s)}$ and filtered. The filtrate was concentrated under reduced pressure to afford a residue, which was purified by prep. HPLC (Column: Gilson Gemini C18 (5 μm 19*150 mm), Mobile phase A: water (0.1% ammonium bicarbonate), B: acetonitrile, UV: 214 nm, Flowrate 15 mL/min, Gradient: 05-80% (% B)) to give the title Compound 463 (40 mg, 99.5% purity, 82% yield) as yellow solids. LC-MS (ESI): $R_T$=3.667 min, mass calcd. for $C_{29}H_{31}ClF_2N_6O_6S_2$ 696.1, m/z found 697.1 $[M+H]^+$. $^1H$ NMR (400 MHz, DMSO-$d_6$) δ 8.41 (s, 1H), 8.03-7.94 (m, 2H), 7.83 (s, 1H), 7.43 (q, J=9.2 Hz, 1H), 7.21-7.18 (m, 1H), 6.01 (s, 0.2H), 5.91 (s, 0.8H), 4.20 (t, J=7.2 Hz, 2H), 3.92 (q, J=7.2 Hz, 2H), 3.75-3.65 (m, 2.2H), 3.56-3.50 (m, 0.8H), 2.26-2.17 (m, 4H), 2.09-2.00 (m, 1H), 1.92-1.77 (m, 4H), 1.66-1.63 (m, 1H), 1.45-1.38 (m, 2H), 1.03-0.97 (m, 3H).

Compound 465: Methyl 4-(2-chloro-3,4-difluorophenyl)-6-(1-((1-(oxazol-2-ylmethyl)-1H-pyrazol-4-yl)sulfonyl)piperidin-4-yl)-2-(thiazol-2-yl)-1,4-dihydropyrimidine-5-carboxylate

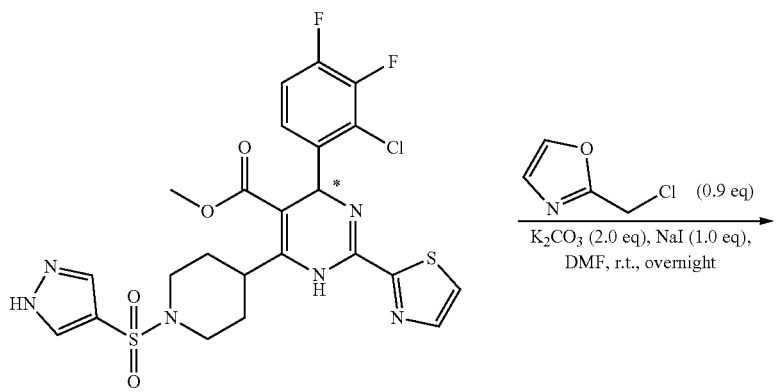

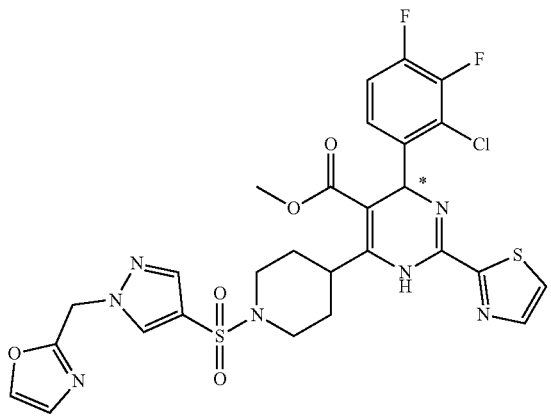

465

To a solution of methyl 6-(1-((1H-pyrazol-4-yl) sulfonyl) piperidin-4-yl)-4-(2-chloro-3,4-difluorophenyl)-2-(thiazol-2-yl)-1,4-dihydropyrimidine-5-carboxylate 324 (90 mg, 0.154 mmol) in N,N-dimethylformamide (3 mL) was added 2-(chloromethyl)oxazole (16 mg, 0.136 mmol), potassium carbonate (43 mg, 0.312 mmol) and sodium iodide (23 mg, 0.153 mmol) at 0° C. After stirred at room temperature under nitrogen atmosphere overnight, the mixture was diluted with ethyl acetate (20 mL) and washed with water (15 mL). The aqueous layer was extracted with ethyl acetate (10 mL) for three times. The combined organic layers were washed with brine (10 mL), dried over $Na_2SO_{4(s)}$ and filtered. The filtrate was concentrated under reduced pressure to give a residue, which was purified by silica gel column chromatography (petroleum ether:ethyl acetate=3:2), and then further purified by Prep. HPLC (Column: Waters Xbridge C18 (5 μm 19*150 mm), Mobile phase A: water (0.1% ammonium bicarbonate), Mobile phase B: acetonitrile, UV: 214 nm, Flow rate: 15 mL/min, Gradient: 20-95% (% B)) to afford the title compound 465 (45 mg, 98.6% purity, 43% yield) as yellow solids. LC-MS (ESI): $R_T$=3.869 min, mass calcd. for $C_{27}H_{24}ClF_2N_7O_5S_2$ 663.1, m/z found 664.1 [M+H]$^+$. $^1$H NMR (400 MHz, CDCl$_3$) δ 8.20 (s, 0.3H), 7.95 (d, J=3.2 Hz, 1H), 7.84-7.83 (m, 1H), 7.80-7.79 (s, 1H), 7.71 (s, 1H), 7.54 (d, J=2.8 Hz, 0.6H), 7.46 (d, J=2.8 Hz, 0.4H), 7.43 (s, 0.7H), 7.18 (s, 1H), 7.08-7.01 (m, 2H), 6.16 (s, 0.3H), 6.05 (d, J=2.8 Hz, 0.7H), 5.50 (s, 2H), 4.02-3.91 (m, 2H), 3.88-3.85 (m, 0.3H), 3.76-3.70 (m, 0.7H), 3.56 (s, 2H), 3.55 (s, 1H), 2.47-2.40 (m, 2H), 2.32-2.14 (m, 1H), 2.06-1.87 (m, 2.2H), 1.73-1.70 (m, 0.8H).

Compound 468: Methyl 4-(2-chloro-4-fluorophenyl)-6-(1-((2-(2-(2-hydroxyethoxy)ethoxy)ethyl)sulfonyl)piperidin-4-yl)-2-(thiazol-2-yl)-1,4-dihydropyrimidine-5-carboxylate

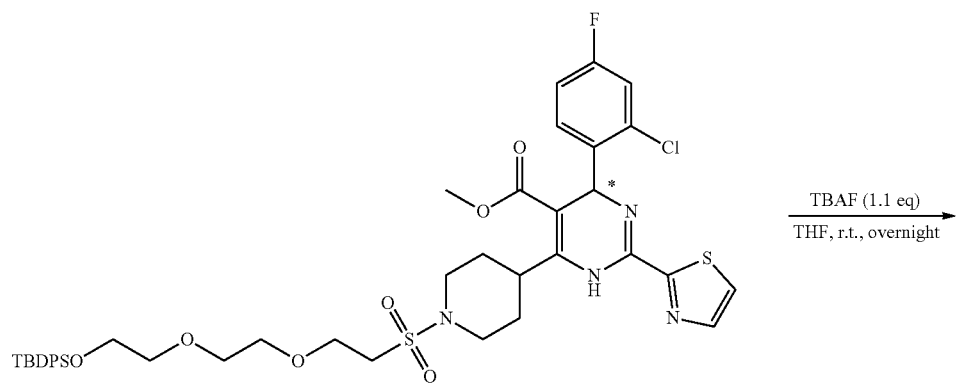

467

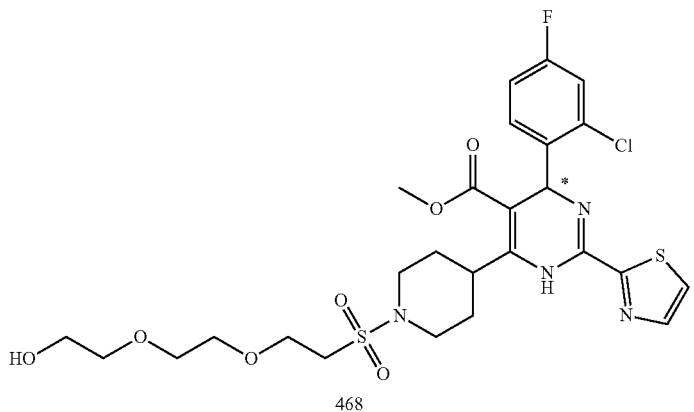

To a solution of methyl 4-(2-chloro-4-fluorophenyl)-6-(1-((2,2-dimethyl-3,3-di phenyl-4,7,10-trioxa-3-siladodecan-12-yl)sulfonyl)piperidin-4-yl)-2-(thiazol-2-yl)-1,4-dihydropyrimidine-5-carboxylate 467 (150 mg, 0.173 mmol) in tetrahydrofuran (3 mL) was added tetrabutylammonium fluoride in tetrahydrofuran (0.19 mL, 0.190 mmol) at room temperature. After stirred at room temperature overnight, the mixture was quenched with water (30 mL) and extracted with ethyl acetate (30 mL) twice, the combined organic layers were washed with brine (20 mL), dried over $Na_2SO_4$ (s), filtered and concentrated to give a residue, which was purified by silica gel column chromatography (petroleum ether:ethyl acetate=1:2 to 1:3), then further purified by C18 column (acetonitrile:water=54% to 70%) to give the title compound 468 (40 mg, 37% yield) as yellow solids. LC-MS (ESI): $R_T$=3.170 min, mass calcd. for $C_{26}H_{32}ClFN_4O_7S_2$ 630.1, m/z found 631.2 [M+H]$^+$. $^1$H NMR (400 MHz, DMSO-$d_6$) δ 9.51 (d, J=3.6 Hz, 0.8H), 9.15 (s, 0.2H), 8.00-7.98 (m, 1.8H), 7.93 (d, J=3.2 Hz, 0.2H), 7.43-7.35 (m, 2H), 7.23-7.18 (m, 1H), 6.02 (s, 0.2H), 5.92 (d, J=3.6 Hz, 0.8H), 4.56 (t, J=5.2 Hz, 1H), 3.98-3.91 (m, 0.2H), 3.78-3.65 (m, 4.8H), 3.59-3.53 (m, 9H), 3.47-3.45 (m, 2H), 3.43-3.42 (m, 2H), 2.92-2.84 (m, 2H), 2.12-1.61 (m, 4H).

Compound 471: 5-(4-((4-(6-(2-Chloro-4-fluorophenyl)-5-(methoxycarbonyl)-2-(thiazol-2-yl)-3,6-dihydropyrimidin-4-yl)piperidin-1-yl)sulfonyl)-1H-pyrazol-1-yl)pentanoic Acid

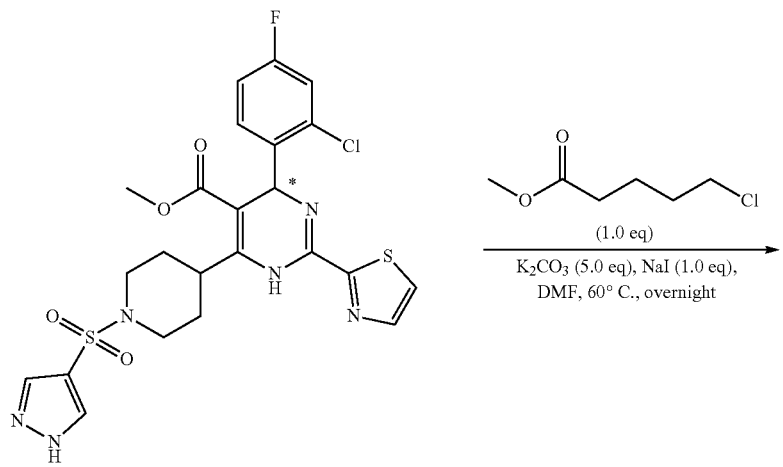

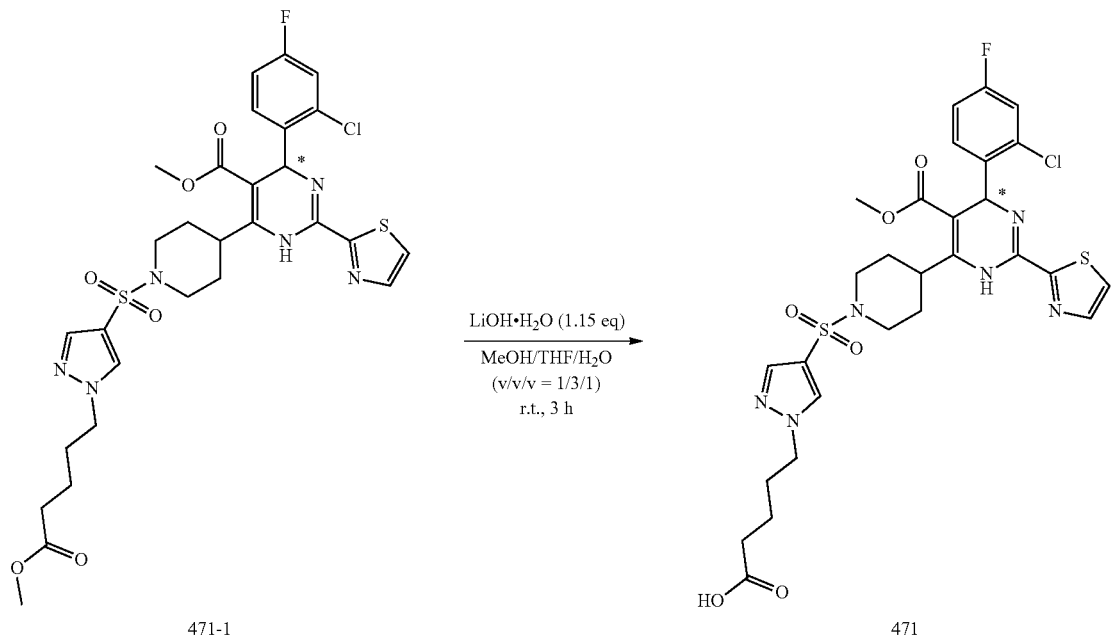

Compound 471-1: Methyl 6-(1-((1H-pyrazol-4-yl)sulfonyl)piperidin-4-yl)-4-(2-chloro-4-fluorophenyl)-2-(thiazol-2-yl)-1,4-dihydropyrimidine-5-carboxylate To a solution of methyl 6-(1-((1H-pyrazol-4-yl)sulfonyl)piperidin-4-yl)-4-(2-chloro-4-fluorophenyl)-2-(thiazol-2-yl)-1,4-dihydropyrimidine-5-carboxylate 466 (100 mg, 0.177 mmol) and methyl 5-chloropentanoate (27 mg, 0.177 mmol) in N,N-dimethylformamide (5 mL) was added potassium carbonate (122 mg, 0.884 mmol) and sodium iodide (27 mg, 0.177 mmol) at room temperature. After stirred at 60° C. overnight, the mixture was diluted with water (20 mL), extracted with ethyl acetate (20 mL) twice. The combined organic layers were washed with brine (20 mL), dried over $Na_2SO_4$ (s) and filtered. The filtrate was concentrated under reduced pressure to give a residue, which was purified by silica gel column chromatography (petroleum ether:ethyl acetate=5:1) to give the title Compound 471-1 (115 mg, 96% yield). LC-MS (ESI): $R_T$=2.262 min, mass calcd. for $C_{29}H_{32}ClFN_6O_6S_2$ 678.2, m/z found 679.0 [M+H]$^+$. $^1$H NMR (400 MHz, CDCl$_3$) δ 7.87-7.72 (m, 4H), 7.57-7.50 (m, 1H), 7.50-7.40 (m, 1H), 7.17-7.10 (m, 1H), 6.99-6.88 (m, 1H), 6.16 (s, 0.2H), 6.05 (s, 0.8H), 4.19 (t, J=7.2 Hz, 2H), 4.00-3.82 (m, 3H), 3.68 (s, 3H), 3.55 (s, 3H), 2.47-2.33 (m, 6H), 1.99-1.94 (m, 3H), 1.73-1.63 (m, 3H).

Compound 471: 5-(4-((4-(6-(2-Chloro-4-fluorophenyl)-5-(methoxycarbonyl)-2-(thiazol-2-yl)-3,6-dihydropyrimidin-4-yl)piperidin-1-yl)sulfonyl)-1H-pyrazol-1-yl)pentanoic Acid To a solution of methyl 6-(1-((1H-pyrazol-4-yl)sulfonyl)piperidin-4-yl)-4-(2-chloro-4-fluorophenyl)-2-(thiazol-2-yl)-1,4-dihydropyrimidine-5-carboxylate Compound 471-1 (112 mg, 0.165 mmol) in methanol (0.45 mL), water (0.45 mL) and tetrahydrofuran (1.35 mL) was added lithium hydroxide monohydrate (8.0 mg, 0.190 mmol) at 0° C. After stirred at room temperature for 3 hours, the mixture was diluted by water (10 mL), acidified with 1 M hydrochloride aqueous solution to pH~2, and extracted with ethyl acetate (15 mL) for three times. The combined organic phases were washed with water (15 mL), brine (15 mL), dried over $Na_2SO_{4(s)}$ and filtered. The filtrate was concentrated in vacuo to give a residue, which was purified by C18 column (acetonitrile:water=10% to 95%) to give the title Compound 471 (53 mg, 97% purity, 48% yield) as yellow solids. LC-MS (ESI): $R_T$=3.530 min, mass calcd. for $C_{28}H_{30}ClFN_6O_6S_2$ 664.1, m/z found 665.2 [M+H]$^+$. $^1$H NMR (400 MHz, CD$_3$OD) δ 8.21 (s, 1H), 7.97-7.87 (m, 1H), 7.80 (s, 1H), 7.78-7.71 (m, 1H), 7.41-7.33 (m, 1H), 7.26-7.19 (m, 1H), 7.08-7.00 (m, 1H), 6.11 (s, 0.2H), 6.05 (s, 0.8H), 4.25 (t, J=7.2 Hz, 2H), 3.95-3.75 (m, 2.5H), 3.70-3.66 (m, 0.5H), 3.54 (s, 3H), 2.46-2.34 (m, 2H), 2.33-2.27 (m, 2H), 2.24-2.12 (m, 1H), 2.09-2.01 (m, 1H), 1.97-1.88 (m, 3H), 1.76-1.66 (m, 1H), 1.63-1.53 (m, 2H).

Compound 484: Methyl 4-(2-chloro-4-fluorophenyl)-6-(1-((2-(2-hydroxyethoxy)ethyl)sulfonyl)piperidin-4-yl)-2-(thiazol-2-yl)-1,4-dihydropyrimidine-5-carboxylate

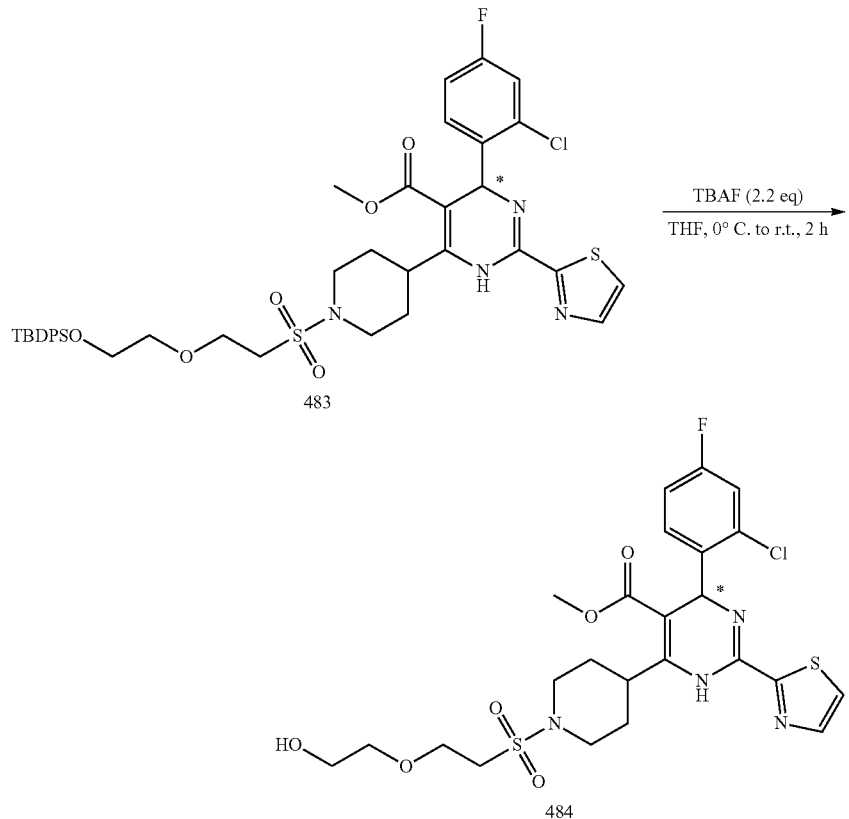

To a solution of methyl 6-(1-((2-(2-((tert-butyldiphenylsilyl)oxy)ethoxy)ethyl) sulfonyl)piperidin-4-yl)-4-(2-chloro-4-fluorophenyl)-2-(thiazol-2-yl)-1,4-dihydropyrimidine-5-carboxylate 483 (160 mg, 95% purity, 0.184 mmol) in tetrahydrofuran (2 mL) was added dropwise 1 M tetrabutylammonium fluoride in tetrahydrofuran (0.4 mL, 0.400 mmol) at 0° C. After stirred at room temperature for 2 hours, the reaction mixture was quenched with saturated ammonium chloride aqueous solution (5 mL) and water (5 mL), then extracted with ethyl acetate (10 mL) for three times. The combined organic layers were washed with brine (10 mL), dried over $Na_2SO_{4(s)}$ and filtered. The filtrate was concentrated under reduced pressure to give a residue, which was purified by silica gel column chromatography (dichloromethane:methanol=1:0 to 30:1) to give a crude product, which was further purified by Prep. HPLC (Column: Water Xbridge C18 (5 m 19*150 mm), Mobile Phase A: water (0.1% ammonium bicarbonate), Mobile Phase B: acetonitrile, UV: 214 nm, Flow rate: 15 mL/min, Gradient: 30-95% (% B)) to give the title compound 484 (60.0 mg, 98.5% purity, 55% yield) as yellow solids. LC-MS (ESI): $R_T$=3.803 min, mass calcd. for $C_{24}H_{28}ClFN_4O_6S_2$ 586.1, m/z found 586.9 [M+H]$^+$. H NMR (400 MHz, CDCl$_3$) δ 8.20 (s, 0.3H), 7.83-7.81 (m, 1H), 7.53-7.52 (m, 0.7H), 7.45-7.44 (m, 1H), 7.29-7.27 (m, 1H), 7.15-7.11 (m, 1H), 6.97-6.88 (m, 1H), 6.18 (s, 0.3H), 6.06 (d, J=2.8 Hz, 0.7H), 4.21-4.13 (m, 0.3H), 3.98-3.89 (m, 4.7H), 3.83-3.77 (m, 2H), 3.65-3.62 (m, 2H), 3.59-3.58 (m, 3H), 3.29-3.24 (m, 2H), 3.09-2.92 (m, 2H), 2.84-2.81 (m, 0.3H), 2.47-2.44 (m, 0.7H), 2.30-2.19 (m, 0.7H), 2.12-2.00 (m, 1H), 1.94-1.84 (m, 1.6H), 1.73-1.69 (m, 0.7H).

Example 1: HBV Assembly Assay

The interference of compounds from this invention with HBV capsid assembly could be measured using an in vitro assembly assay based on fluorescence quenching, which was developed according to a method described by Zlotnick and coworkers (Nature Biotechnology 2006, 24:358). In a typical assay, a mutant HBV C150 protein (amino acids 1-150, C49A, C61A, C107A, 150C) is cloned into a T7 RNA-polymerase based expression vector, expressed in E. coli and purified to homogeneity as a dimer. The purified HBV core protein is desalted and labeled with BODIPY-FL Dye.

In a non-limiting embodiment, the assembly assay is conducted in 96-well plate format. The assembly reactions are carried out in 50 mM Hepes buffer, pH 7.5 and 150 mM NaCl. The compounds are pre-incubated with the HBV CA protein for 15 min, and the assembly reactions are initiated by addition of NaCl. The reaction is allowed to continue for 1 hour at room temperature. The changes in fluorescence between DMSO treated and compound treated samples are recorded and analyzed for assembly modulation.

Example 2: HBV Inhibitory Activity and Cytotoxicity Determination

HBV replication inhibition by the compounds of this invention as well as cytotoxicity determination was determined in cells infected or transfected with HBV, or cells with stably integrated HBV, such as HepG2.2.15 cells (Sells et al. 1987). The method used herein is as follows.

The HepG2.2.15 cells were seeded into 96-well plate in 2% FBS (Fetal bovine serum) culture medium at the density of 40,000 cells/well and 5,000 cells/well for HBV inhibitory activity and cytotoxicity determination, respectively. After seeding, the cell plates were incubated at 37° C., 5% $CO_2$ overnight. The next day, medium containing compounds were added to treat the cells for 6 days with medium refreshed once in the middle of the treatment. Eight dose points with 3 folds dilution of each compound were adopted and the highest concentration of the compounds was 10 μM and 100 μM for HBV inhibitory activity and cytotoxicity determination, respectively.

After 6 days of compounds treatment, 20 μl CCK-8 (Cell Counting Kit-8 (Tianjin Biolite company)) reagents were added to each well of cytotoxicity assay plates, the plate was incubated at 37° C., 5% $CO_2$ for 2.5 hours and the absorbance at 450 nm wavelength was measured, at the same time the absorbance at 630 nm wavelength was read as reference.

The HBV DAN change in the cell culture medium induced by the compounds was measured by q-PCR (quantitative polymerase chain reaction) method. The HBV DNA in the culture medium was extracted using QIAamp 96 DNA Blood Kit according to the manual and then quantified by q-PCR using the primers and probe in the table below:

| Primers or Probe | Sequence | Reporter | Quencher |
|---|---|---|---|
| HBV-Fw | GTGTCTGCGGCGTTTTATCA (SEQ ID. No. 1) | | |
| HBV-Rev | GACAAACGGGCAACATACCTT (SEQ ID. No. 2) | | |
| HBV-Probe | CCTCTKCATCCTGCTGCTATGCCTCATC (SEQ ID. No. 3) | Fam | BHQ1 |

EC50 and CC50 values are calculated by the GraphPad Prism software and are averages where multiple measurements were made. The EC50 and CC50 values for those exemplified compounds with an EC50 value of lower than 1 μM are shown in Table 4. EC50 values for the other exemplified compounds were either not measured or higher than 1 μM.

TABLE 4

Activity DATA

| Compound number | EC50 (μM) | CC50 (μM) |
|---|---|---|
| 1A | 0.386 | 90.2 |
| 1B | 0.096 | 13.6 |
| 2 | 0.232 | 98.4 |
| 2B | 0.338 | >100 |
| 3 | 0.038 | 32.8 |
| 3A | 0.126 | 35.9 |
| 3C | 0.132 | 5.6 |
| 4B | 0.351 | >10 |
| 7 | 0.168 | >100 |
| 16X | 0.049 | 29.3 |
| 17 | 0.3 | 93.8 |
| 18X | 0.042 | 27.9 |
| 19 | 0.062 | 8.7 |
| 20X | 0.052 | 27.2 |
| 21 | 0.031 | 9.9 |
| 22Y | 0.224 | 75.9 |
| 23 | 0.566 | 47.5 |
| 24Q | 0.964 | 3.52 |
| 25 | 0.165 | 35.3 |
| 28 | 0.407 | 49.3 |
| 29 | 0.123 | 33.6 |
| 33A | 0.19 | 78.1 |
| 33C | 0.484 | 37.7 |
| 36 | 0.153 | 20.7 |
| 37B | 0.129 | 5.9 |
| 38B | 0.239 | 34.1 |
| 39B | 0.101 | 30.6 |
| 41A | 0.514 | 11.6 |
| 47A | 0.276 | 30.9 |
| 48A | 0.565 | 46.9 |
| 48D | 0.21 | >100 |
| 49C | 0.202 | 84.6 |
| 50B | 0.27 | 35.6 |
| 51 | 0.112 | 9.9 |
| 51B | 0.467 | >100 |
| 54A | 0.019 | 31.2 |
| 56A | 0.513 | >10 |
| 59B | 0.388 | 27.9 |
| 61B | 0.333 | >20 |
| 61D | 0.035 | 33.4 |
| 61E | 0.358 | 21.7 |
| 61G | 0.423 | >10 |
| 62B | 0.063 | 22.9 |
| 62D | 0.892 | 75.1 |
| 62G | 0.119 | 37.1 |
| 65A | 0.425 | 69.1 |
| 65C | 0.378 | 19.5 |
| 68 | 0.581 | 72.9 |
| 69C | 0.448 | 11.9 |
| 70D | 0.14 | 22.6 |
| 72C | 0.475 | 22.1 |
| 72F | 0.058 | 30 |
| 73H | 0.35 | 32.9 |
| 74A | 0.088 | 33 |
| 74C | 0.249 | 86.5 |
| 74D | 0.303 | 84.5 |
| 75A | 0.213 | 32.3 |
| 75D | 0.045 | 10.2 |
| 77 | 0.071 | 34.2 |

TABLE 4-continued

Activity DATA

| Compound number | EC50 (μM) | CC50 (μM) |
|---|---|---|
| 80 | 0.107 | 6.3 |
| 81 | 0.119 | 10.5 |
| 82 | 0.197 | 6.9 |
| 84A | 0.118 | 29 |
| 85C | 0.6 | 95.4 |
| 86 | 0.11 | 21.6 |
| 89R | 0.112 | 17.2 |
| 90A | 0.023 | 26.7 |
| 92 | 0.326 | 99 |
| 93 | 0.507 | 92.5 |
| 95A | 0.101 | 100 |
| 95C | 0.117 | 33.1 |
| 95E | 0.141 | 75 |
| 95F | 0.156 | 80 |
| 96B | 0.13 | 21.2 |
| 97B | 0.047 | >100 |
| 98A | 0.27 | 11.4 |
| 100 | 0.166 | 7.2 |
| 101 | 0.21 | 38 |
| 102 | 0.13 | 57 |
| 103 | 0.501 | 87 |
| 105 | 0.15 | 14.4 |
| 107 | 0.248 | 51.4 |
| 108 | 0.077 | 26.9 |
| 110B | 0.798 | >10 |
| 112 | 0.293 | 43.2 |
| 112B | 0.95 | 8.2 |
| 113Y | 0.966 | 11.8 |
| 114 | 0.04 | 27.5 |
| 115B | 0.342 | 19.1 |
| 116B | 0.207 | 71.3 |
| 118 | 0.015 | 59.1 |
| 120A | 0.35 | 31.7 |
| 120B | 0.154 | 16.3 |
| 122 | 0.394 | 5.1 |
| 122B | 0.057 | 31.6 |
| 124B | 0.085 | 6.6 |
| 126B | 0.343 | 31.8 |
| 128D | 0.017 | 22.8 |
| 129 | 0.055 | 28.2 |
| 130A | 0.317 | >10 |
| 130 | 0.550 | >10 |
| 132A | 0.472 | 23.9 |
| 135 | 0.346 | 62.5 |
| 139 | 0.112 | 75.6 |
| 141 | 0.051 | 30.7 |
| 142 | 0.089 | 37.6 |
| 146 | 0.068 | 42.1 |
| 148A | 0.097 | 29.4 |
| 150A | 0.071 | 28.1 |
| 152A | 0.092 | 39.5 |
| 154A | 0.071 | 30.7 |
| 156 | 0.071 | 34.9 |
| 157A | 0.085 | 80.0 |
| 158A | 0.009 | 12.7 |
| 162 | 0.059 | 34.5 |
| 163 | 0.065 | 23.9 |
| 164 | 0.058 | 57.4 |
| 165 | 0.012 | >100 |
| 166A | 0.061 | >50 |
| 167A | 0.034 | 11.6 |
| 168A | 0.006 | 12.5 |
| 169A | 0.056 | >100 |
| 170 | 0.533 | 14.9 |
| 171 | 0.124 | 15.5 |
| 173A | 0.076 | 18.6 |
| 173C | 0.107 | 9.9 |
| 174A | 0.128 | 19.4 |
| 176A | 0.069 | 19.9 |
| 176D | 0.700 | 11.0 |
| 180B | 0.024 | 22.1 |
| 182A | 0.093 | 33.6 |
| 185B | 0.018 | 26.2 |
| 186A | 0.097 | 83.1 |
| 187B | 0.032 | 18.9 |
| 190 | 0.078 | 15.0 |
| 195A | 0.084 | 43.9 |
| 199A | 0.056 | 35.8 |
| 199B | <0.0046 | 14.2 |
| 200A | 0.102 | >100 |
| 201A | 0.053 | 15.7 |
| 204A | 0.007 | 23.8 |
| 205A | 0.007 | 42.3 |
| 205B | 0.189 | 40.5 |
| 206B | 0.108 | 26.1 |
| 206D | 0.389 | 39.2 |
| 207C | 0.753 | >20 |
| 208B | 0.280 | >100 |
| 210A | 0.024 | 6.0 |
| 210B | 0.044 | 9.7 |
| 212A | 1.012 | >100 |
| 214A | 0.196 | >100 |
| 214C | 0.784 | >100 |
| 215 | 0.051 | 52.7 |
| 216 | 0.090 | >100 |
| 217 | 0.511 | 29.6 |
| 218 | 0.148 | 29.7 |
| 219A | 0.192 | 35.3 |
| 219C | 0.176 | 10.3 |
| 219E | 0.134 | 51.4 |
| 219H | 0.334 | 1.5 |
| 221 | 0.053 | 47.1 |
| 223 | 0.145 | 50.0 |
| 224 | 0.071 | 28.4 |
| 225 | 0.087 | 100.0 |
| 227A | 0.096 | 37.6 |
| 229B | 0.011 | 32.1 |
| 230 | 0.146 | >100 |
| 232B | 0.057 | 60.0 |
| 232D | 0.030 | 39.6 |
| 232X | 0.105 | 70.0 |
| 233B | 0.056 | 6.3 |
| 233C | 0.013 | 5.6 |
| 234B | 0.113 | 16.3 |
| 234D | 0.013 | 4.2 |
| 238 | 0.053 | 13.4 |
| 239X | 0.149 | 14.8 |
| 241B | 0.120 | 60.0 |
| 244B | 0.006 | 12.3 |
| 244D | 0.107 | 60.0 |
| 245B | 0.049 | 12.3 |
| 245D | 0.015 | 12.5 |
| 248 | 0.056 | 3.5 |
| 251B | 0.103 | 8.7 |
| 253B | 0.008 | 13.7 |
| 254 | 0.047 | >100 |
| 255 | 0.049 | 24.1 |
| 256A | 0.082 | >100 |
| 256D | 0.964 | 22.9 |
| 258B | 0.401 | 27.4 |
| 259C | 0.036 | 12.7 |
| 259E | 0.028 | 22.7 |
| 261 | 0.142 | 37.5 |
| 262 | 0.400 | 75.8 |
| 263 | 0.150 | 81.1 |
| 265E | 0.978 | 92.3 |
| 265H | 0.214 | >100 |
| 268B | 0.059 | 30.7 |
| 270A | 0.012 | 9.2 |
| 270B | 0.017 | 10.3 |
| 272A | 0.017 | 16.6 |
| 272B | 0.047 | 20.1 |
| 274A | 0.042 | 31.4 |
| 278C | 0.045 | 18.9 |
| 282C | 0.015 | 15.7 |
| 282D | 0.039 | 11.2 |
| 284 | 0.226 | 21.1 |
| 285A | 0.024 | 67.2 |
| 287B | 0.072 | 23.1 |
| 287D | 0.067 | 60.0 |

TABLE 4-continued

Activity DATA

| Compound number | EC50 (μM) | CC50 (μM) |
| --- | --- | --- |
| 288M | 0.063 | 20.0 |
| 289A | 0.015 | 24.2 |
| 291C | 0.016 | 12.0 |
| 293C | 0.150 | 85.7 |
| 295 | 0.215 | 64.2 |
| 298B | 0.017 | 13.2 |
| 300B | 0.013 | 28.6 |
| 300D | 0.014 | 12.6 |
| 300G | 0.122 | 23.9 |
| 302A | 0.024 | 15.2 |
| 302C | 0.050 | 10.2 |
| 302E | 0.025 | 14.6 |
| 302F | 0.037 | 10.3 |
| 303 | 0.054 | >100 |
| 305A | 0.047 | 36.2 |
| 305B | 0.025 | 34.5 |
| 309C | 0.047 | 36.2 |
| 311A | 0.089 | >100 |
| 311B | 0.097 | >100 |
| 312X | 0.097 | >100 |
| 313A | 0.058 | 35.0 |
| 313B | 0.011 | 34.6 |
| 315D | 0.025 | 12.6 |
| 319B | 0.102 | 31.3 |
| 321A | 0.012 | 17.2 |
| 321B | 0.060 | 15.8 |
| 323C | 0.010 | 24.1 |
| 323D | 0.030 | 28.6 |
| 324 | 0.005 | 9.8 |
| 325 | 0.005 | 7.9 |
| 329B | 0.069 | 60.0 |
| 331C | 0.192 | >100 |
| 333B | 0.035 | 33.1 |
| 335A | 0.020 | 12.2 |
| 335B | 0.013 | 15.2 |
| 339B | 0.010 | 13.4 |
| 339D | 0.099 | 32.7 |
| 343A | 0.089 | 40.8 |
| 343C | 0.014 | 25.2 |
| 343D | 0.053 | 24.0 |
| 345A | 0.044 | 34.1 |
| 347B | 0.110 | 31.4 |
| 348B | 0.063 | 25.0 |
| 352B | 0.011 | 29.4 |
| 354B | 0.018 | 7.0 |
| 354C | 0.015 | 7.9 |
| 356B | 0.006 | 12.2 |
| 357A | 0.037 | 13.6 |
| 357B | 0.036 | 15.4 |
| 358B | 0.059 | 12.5 |
| 359B | 0.055 | 10.5 |
| 359D | 0.005 | 12.0 |
| 360C | 0.017 | 17.0 |
| 360D | 0.105 | 20.4 |
| 361X | 0.087 | >100 |
| 363E | 0.296 | >100 |
| 363H | 0.650 | >100 |
| 364 | 0.208 | >100 |
| 365 | 0.061 | 21.8 |
| 399 | 0.033 | 36.8 |
| 367A | 0.303 | 33.4 |
| 367B | 0.800 | >100 |
| 370B | 0.004 | 23.2 |
| 370D | 0.040 | 26.3 |
| 372Y | 0.015 | 31.8 |
| 376C | 0.075 | 95.0 |
| 376D | 0.035 | 97.3 |
| 379C | 0.055 | 32.6 |
| 381A | 0.070 | 28.5 |
| 383A | 0.087 | 32.9 |
| 383D | 0.148 | 31.5 |
| 384B | 0.065 | 34.0 |
| 388B | 0.028 | 27.8 |
| 390B | 0.054 | 45.3 |
| 391B | 0.068 | 46.8 |
| 393B | 0.100 | 85.0 |
| 396B | 0.020 | 22.5 |
| 401B | 0.029 | 56.2 |
| 401Y | 0.024 | 60.0 |
| 404N | 0.155 | 17.7 |
| 406 | 0.600 | 5.6 |
| 410C | 0.016 | 24.7 |
| 410D | 0.043 | 23.7 |
| 414C | 0.019 | 17.3 |
| 414D | 0.039 | 16.3 |
| 416B | 0.006 | 13.5 |
| 420A | 0.076 | 20.8 |
| 422 | 0.027 | 26.9 |
| 424 | 0.007 | 8.2 |
| 425 | 0.006 | 13.3 |
| 429C | 0.066 | 25.5 |
| 429D | 0.049 | 16.0 |
| 430 | 0.015 | 15.1 |
| 431B | 0.052 | 28.1 |
| 433B | 0.059 | 17.4 |
| 434B | 0.128 | 6.8 |
| 437 | 0.404 | 4.0 |
| 437A | 0.600 | 10.4 |
| 439B | 0.066 | 53.8 |
| 440b | 0.013 | 82.9 |
| 444b | 0.059 | 8.3 |
| 447C | 0.080 | 48.2 |
| 448A | 0.008 | >100 |
| 450A | 0.017 | 12.8 |
| 450B | 0.007 | 14.0 |
| 452A | 0.006 | 9.7 |
| 452B | 0.005 | 7.7 |
| 454 | 0.037 | 12.0 |
| 456 | 0.043 | 19.5 |
| 457 | 0.054 | 63.4 |
| 458 | <0.0046 | 15.5 |
| 459 | 0.041 | 93.5 |
| 460 | 0.008 | 19.9 |
| 462 | 0.024 | 6.6 |
| 463 | 0.031 | 12.2 |
| 464 | <0.0046 | 29.4 |
| 465 | 0.009 | 35.2 |
| 468 | 0.009 | 42.9 |
| 470 | 0.056 | 20.1 |
| 471 | 0.053 | 32.3 |
| 474 | 0.007 | 18.3 |
| 476A | 0.014 | 30.4 |
| 476B | 0.044 | 30.2 |
| 478 | 0.006 | 23.4 |
| 478A | 0.021 | 9.9 |
| 480B | 0.022 | 9.9 |
| 480Y | 0.011 | 10.2 |
| 482A | 0.006 | 15.3 |
| 482B | 0.011 | 11.3 |
| 484 | 0.005 | 47.0 |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A compound of Formula I

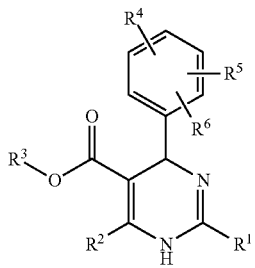

(I)

or a deuterated isomer, stereoisomer, or tautomeric form thereof, wherein:

$R^1$ is selected from aryl or heteroaryl, each optionally substituted with one or more halogen;

$R^2$ is selected from the group consisting of a 4-7 membered substituted saturated ring and a 5-12 membered fused, spiro or bridged bicyclic substituted saturated ring, such saturated rings each optionally comprising one or more heteroatoms and wherein said substituted saturated rings are substituted with one or more substituents each independently selected from the group consisting of halogen, oxo, $C_1$-$C_3$alkyl, hydroxy$C_1$-$C_3$ alkyl or —X—$R^7$;

$R^3$ is $C_1$-$C_4$alkyl;

$R^4$, $R^5$ and $R^6$ independently are selected from the group consisting of hydrogen, $C_1$-$C_3$alkyl and halogen;

—X—$R^7$ is selected from the group consisting of —SO$_2$—$R^7$, —SO$_2$—$R^8$—(CH$_2$)$_n$—$R^7$, —SO$_2$NR$^8$R$^7$, —NR$^8$S(=O)(=NH)—$R^7$, —NR$^8$S(=O)NR$^8$—$R^7$, —NR$^8$C(=O)NR$^8$—$R^7$, —S(=O)(=NH)NR$^8$—$R^7$, —S(=O)(=NH)—$R^7$, —NR$^8$—(CH$_2$)$_n$—SO$_2$—$R^7$, —NR$^8$SO$_2$—NR$^8$R$^7$, —OC(=O)—$R^7$, —C(=O)—$R^7$, —NR$^8$C(=O)—$R^7$, —NR$^8$C(=O)O—$R^7$, —OC(=O)NR$^8$—$R^7$ and —NR$^8$—$R^7$;

$R^7$ and $R^8$ each independently are selected from hydrogen or a substituent selected from the group consisting of $C_1$-$C_4$alkyl, aryl, heteroaryl and a 3-7 membered saturated ring optionally containing one or more heteroatoms, each of such substituents from this group may optionally be substituted with one or more $R^9$ and $R^{10}$;

or $R^7$ and $R^8$ when attached to a nitrogen can be taken together to form a 3-7 membered saturated ring;

$R^9$ and $R^{10}$ each independently are selected from —OR$^{11}$, oxo, $C_1$-$C_4$alkyl optionally substituted with one or two $R^{11}$, —NHC(=O)OR$^{11}$, —C(=O)R$^{11}$, —(CH$_2$)$_n$—C(=O)OR$^{11}$, —C(=O)NH$_2$, —CN, halogen, or phenyl;

each $R^{11}$ independently is $C_1$-$C_4$ alkyl, —(CH$_2$)$_n$—OR$^{11}$, or hydrogen;

each n independently being an integer from 0 to 4;

or a pharmaceutically acceptable salt thereof or a solvate thereof.

2. The compound according to claim 1, wherein —X—$R^7$ represents —SO$_2$—$R^7$ or —SO$_2$NH—$R^7$.

3. The compound according to claim 1, wherein $R^4$, $R^5$ and $R^6$ are independently selected from fluoro, chloro or bromo.

4. The compound according to claim 3, wherein at least one of $R^4$ and $R^5$ is fluoro.

5. The compound according to claim 1, wherein $R^1$ is thiazolyl.

6. The compound according to claim 1, wherein $R^2$ is a 4-7 membered saturated ring optionally containing one or more heteroatoms and substituted with one or more halogen, oxo, or —X—$R^7$.

7. The compound according to claim 1, wherein $R^2$ is a 4-6 membered saturated ring optionally containing one or more heteroatoms and substituted with one or more halogen, oxo, or —X—$R^7$.

8. The compound according to claim 1, wherein $R^2$ is a 5 or 6 membered saturated ring optionally containing one or more heteroatoms, wherein said 5 or 6 membered saturated ring is further substituted with —X—$R^7$.

9. The compound according to claim 8, wherein said 5 or 6 membered saturated ring contains a nitrogen or an oxygen.

10. The compound according to claim 1, wherein $R^3$ is methyl.

11. A pharmaceutical composition comprising a compound of Formula I

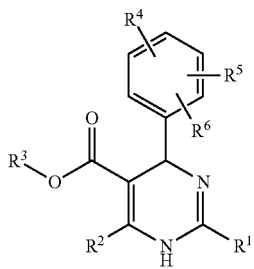

(I)

or a deuterated isomer, stereoisomer, or tautomeric form thereof, wherein:
$R^1$ is selected from aryl or heteroaryl, each optionally substituted with one or more halogen;
$R^2$ is selected from the group consisting of a 4-7 membered substituted saturated ring and a 5-12 membered fused, spiro or bridged bicyclic substituted saturated ring, such saturated rings each optionally comprising one or more heteroatoms and wherein said substituted saturated rings are substituted with one or more substituents each independently selected from the group consisting of halogen, oxo, $C_1$-$C_3$alkyl, hydroxy$C_1$-$C_3$alkyl or —X—$R^7$;
$R^3$ is $C_1$-$C_4$alkyl;
$R^4$, $R^5$ and $R^6$ independently are selected from the group consisting of hydrogen, $C_1$-$C_3$alkyl and halogen;
—X—$R^7$ is selected from the group consisting of —SO$_2$—$R^7$, —SO$_2$—$R^8$—(CH$_2$)$_n$—$R^7$, —SO$_2$NR$^8$R$^7$, —NR$^8$S(=O)(=NH)—$R^7$, —NR$^8$S(=O)NR$^8$—$R^7$, —NR$^8$C(=O)NR$^8$—$R^7$, —S(=O)(=NH)NR$^8$—$R^7$, —S(=O)(=NH)—$R^7$, —NR$^8$—(CH$_2$)$_n$—SO$_2$—$R^7$, —NR$^8$SO$_2$—NR$^8$R$^7$, —OC(=O)—$R^7$, —C(=O)—$R^7$, —NR$^8$C(=O)—$R^7$, —NR$^8$C(=O)O—$R^7$, —OC(=O)NR$^8$—$R^7$ and —NR$^8$—$R^7$;
$R^7$ and $R^8$ each independently are selected from hydrogen or a substituent selected from the group consisting of $C_1$-$C_4$alkyl, aryl, heteroaryl and a 3-7 membered saturated ring optionally containing one or more heteroatoms, each of such substituents from this group may optionally be substituted with one or more $R^9$ and $R^{10}$;
or $R^7$ and $R^8$ when attached to a nitrogen can be taken together to form a 3-7 membered saturated ring;

$R^9$ and $R^{10}$ each independently are selected from —OR$^{11}$, oxo, $C_1$-$C_4$alkyl optionally substituted with one or two $R^{11}$, —NHC(=O)OR$^{11}$, —C(=O)R$^{11}$, —(CH$_2$)$_n$—C(=O)OR$^{11}$, —C(=O)NH$_2$, —CN, halogen, or phenyl;
each $R^{11}$ independently is $C_1$-$C_4$ alkyl, —(CH$_2$)$_n$—OR$^{11}$, or hydrogen;
each n independently being an integer from 0 to 4;
or a pharmaceutically acceptable salt thereof or a solvate thereof, and a pharmaceutically acceptable carrier.

12. A method for treating an HBV infection in a mammal comprising administering to said mammal a therapeutically effective amount of a pharmaceutical composition according to claim 11.

13. A method for treating an HBV infection in a mammal comprising administering to said mammal a therapeutically effective amount of a compound according to claim 1.

14. The compound according to claim 1, selected from the group consisting of

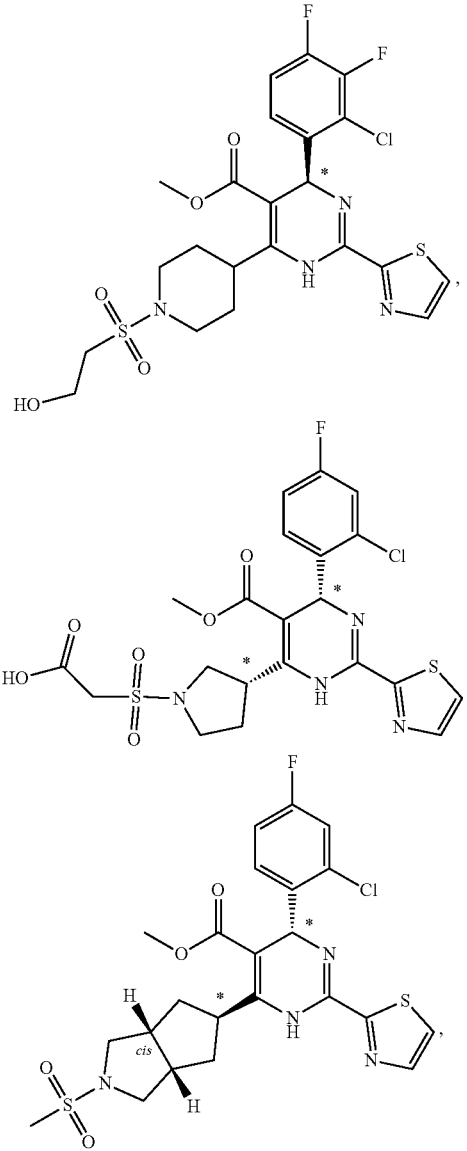

657
-continued
658
-continued
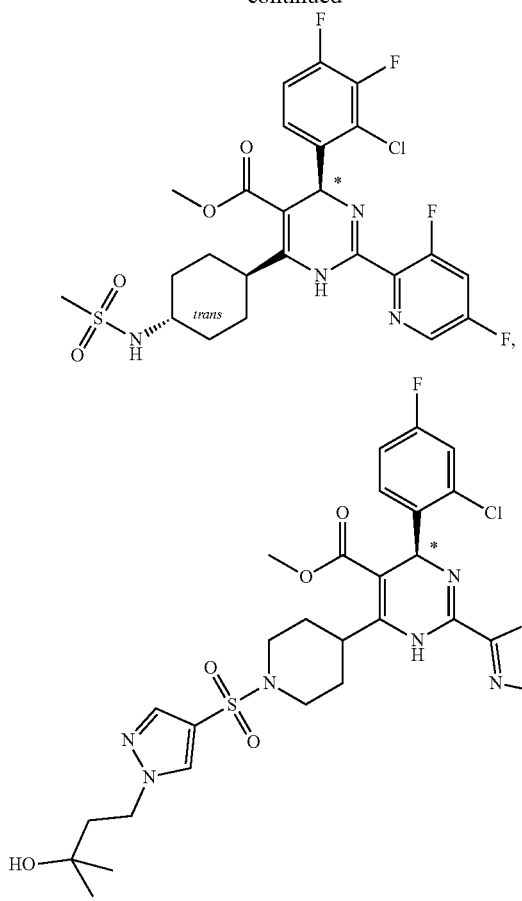
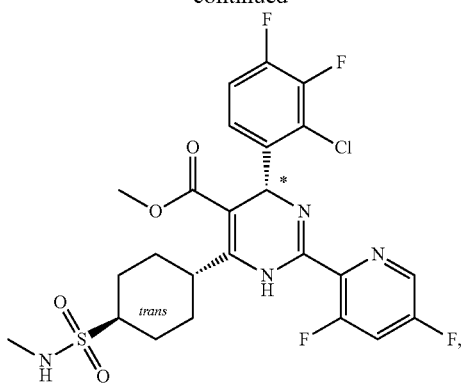
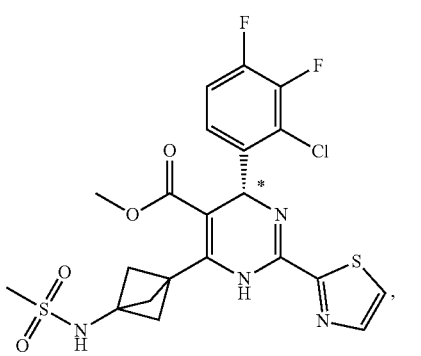
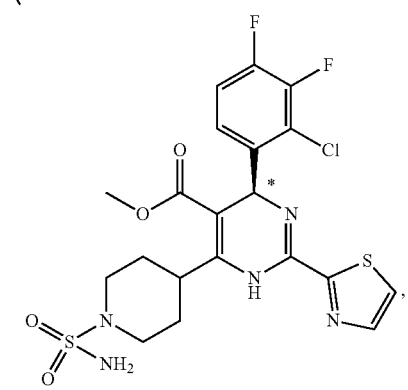
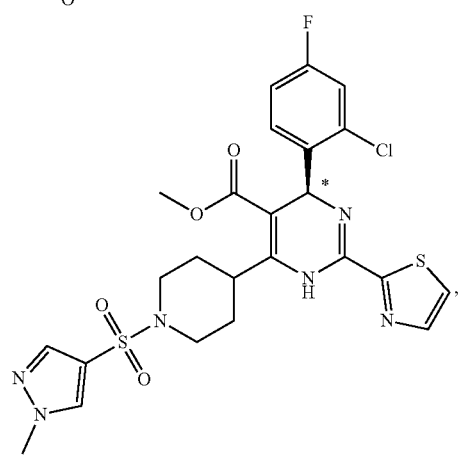
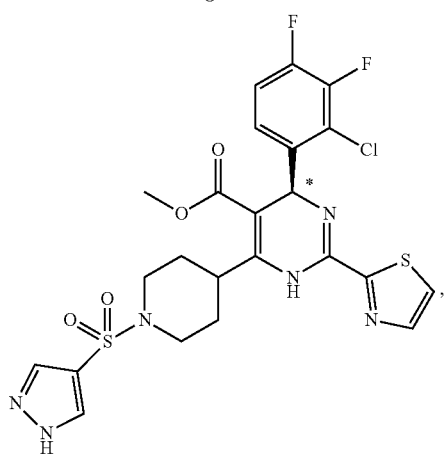

659
-continued
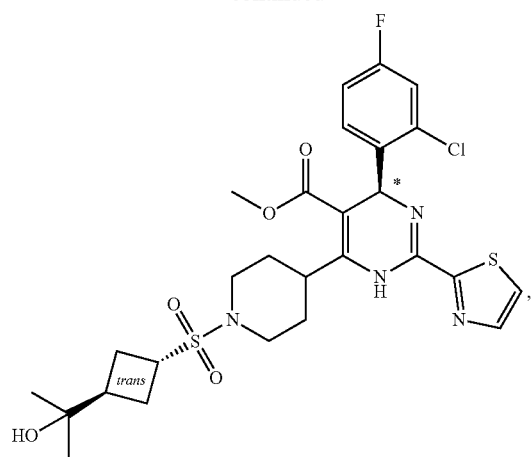
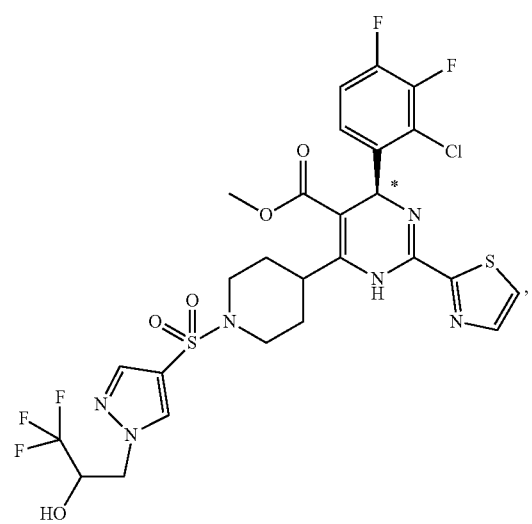
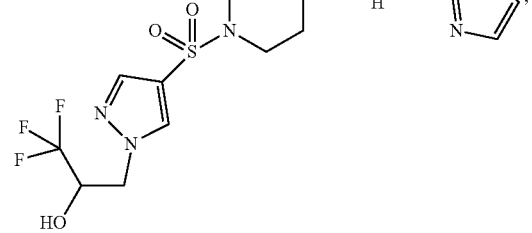
660
-continued
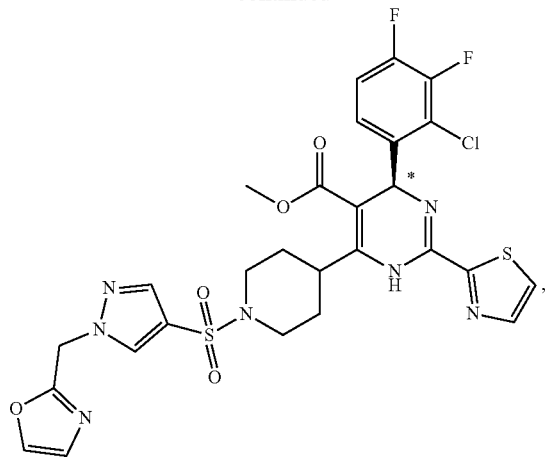
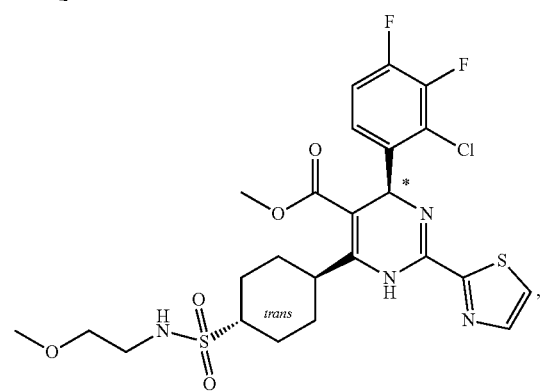
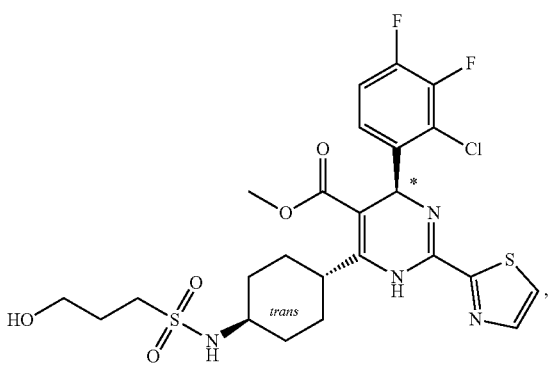
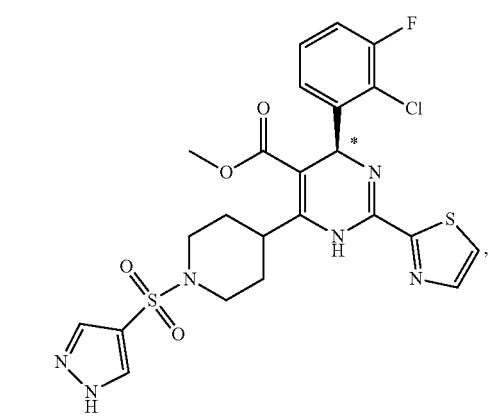
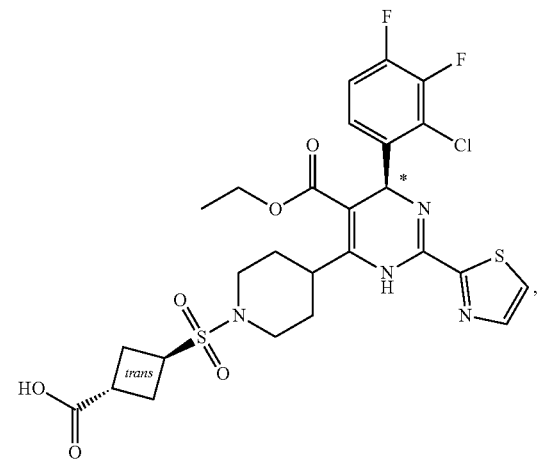

661
-continued
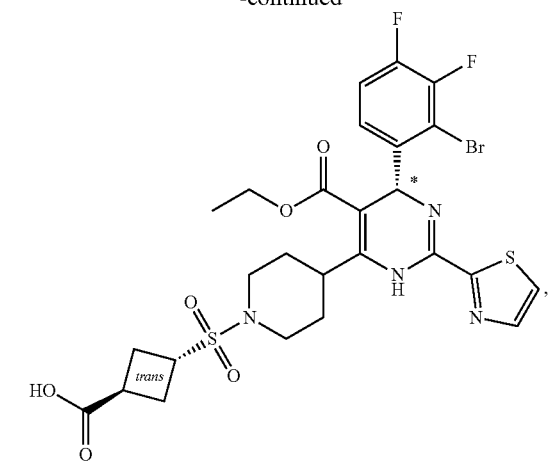
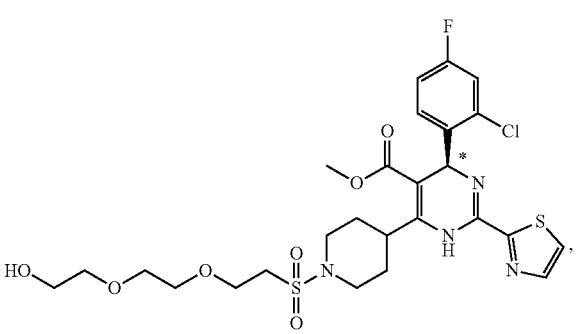
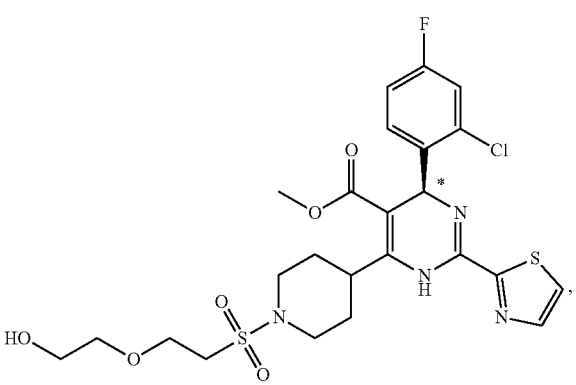
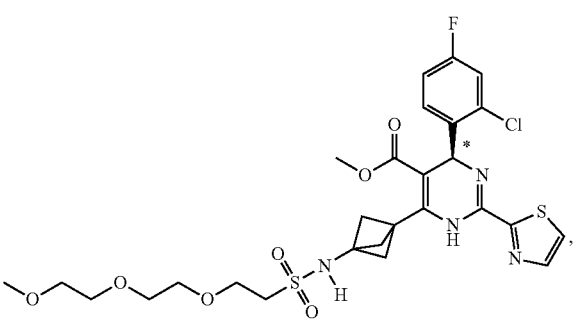
662
-continued
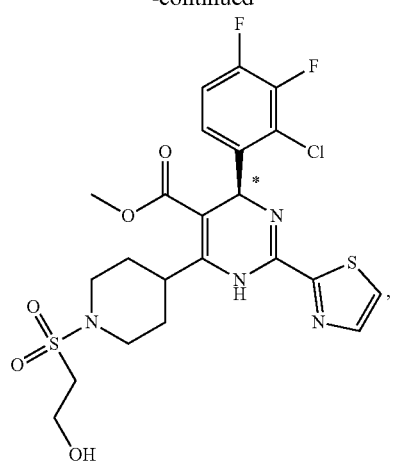
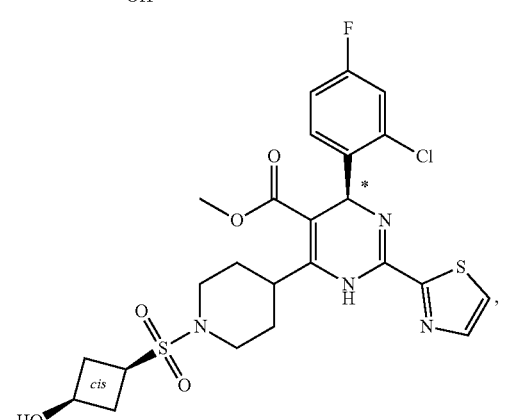
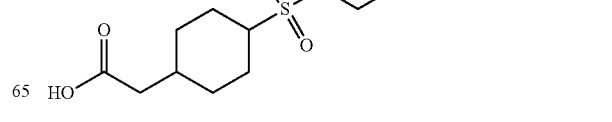

663
-continued
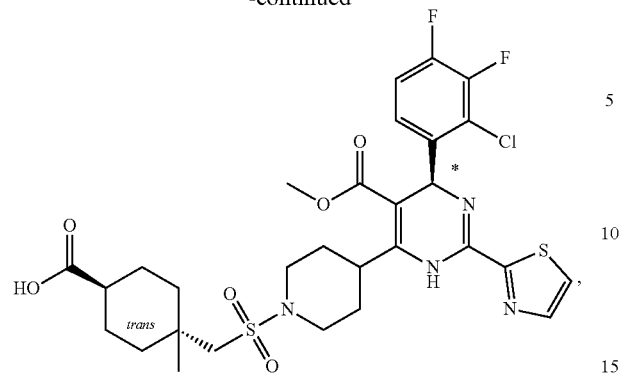
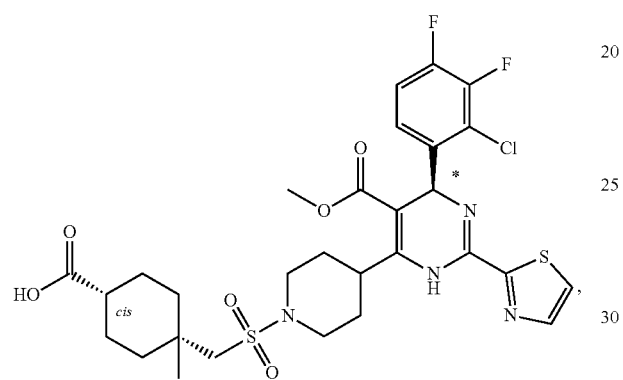
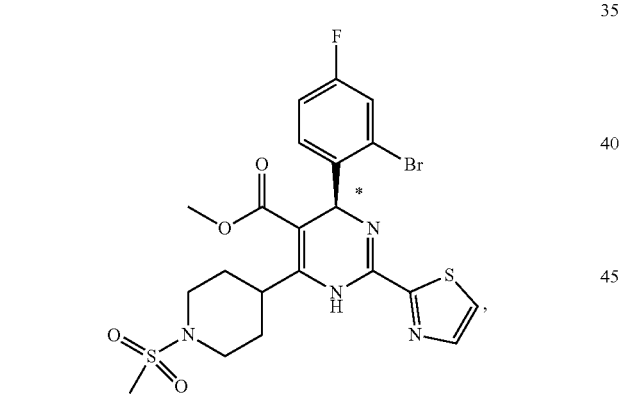
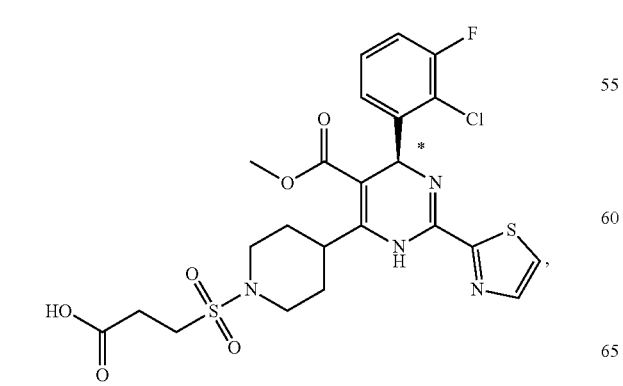
664
-continued
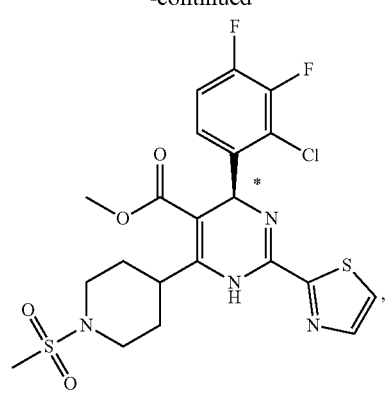
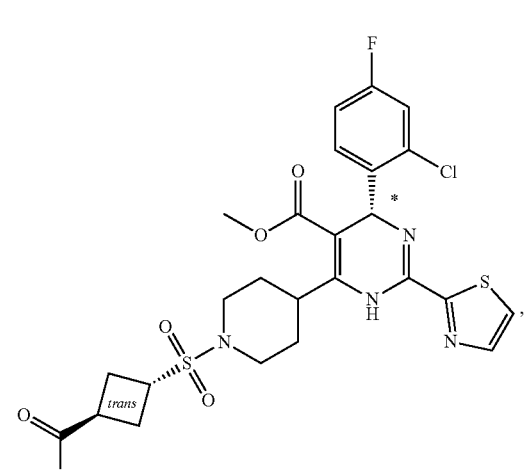

665
-continued
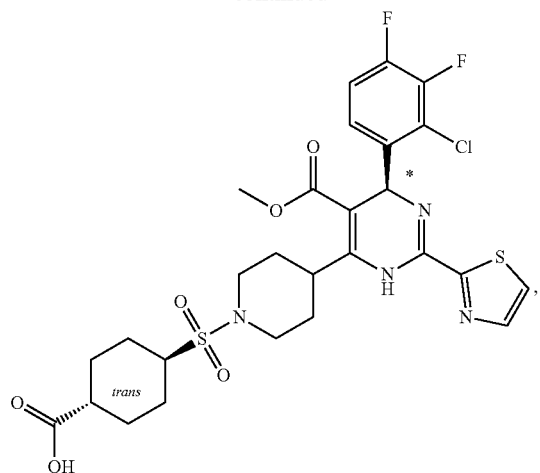
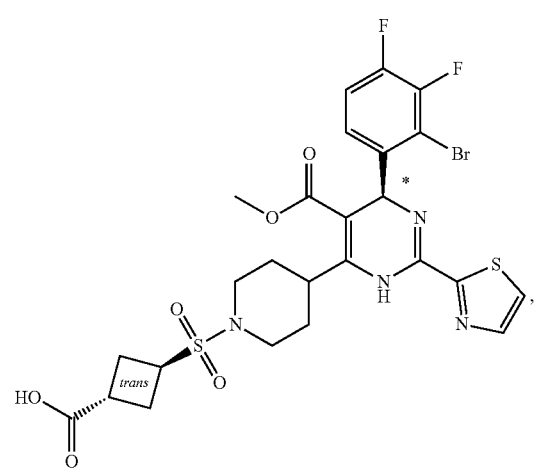
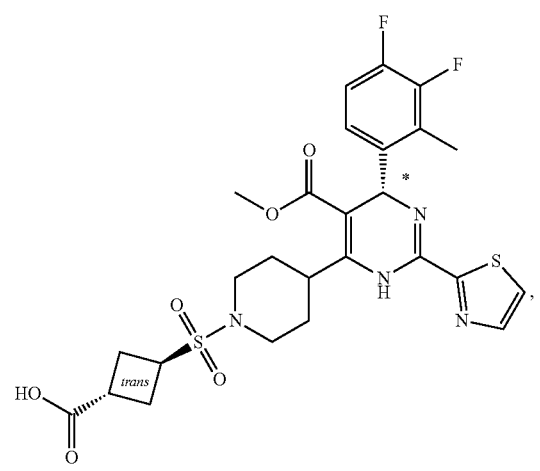
666
-continued
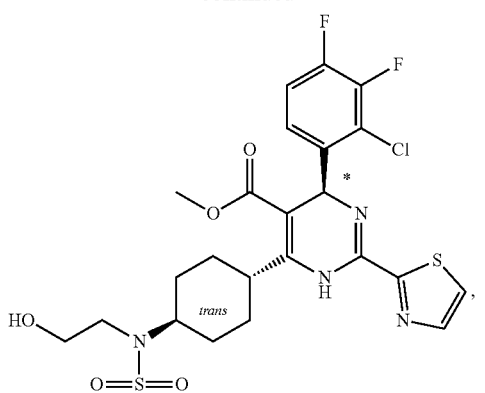
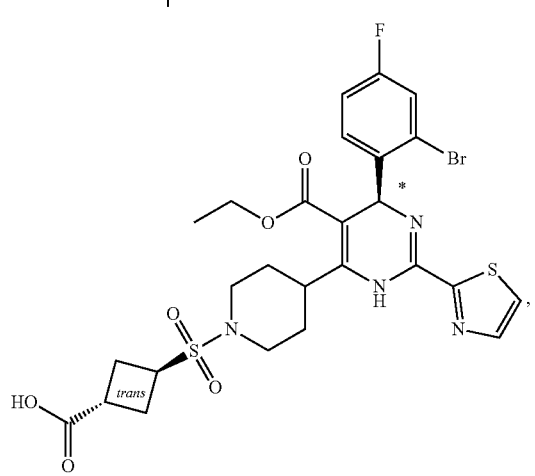
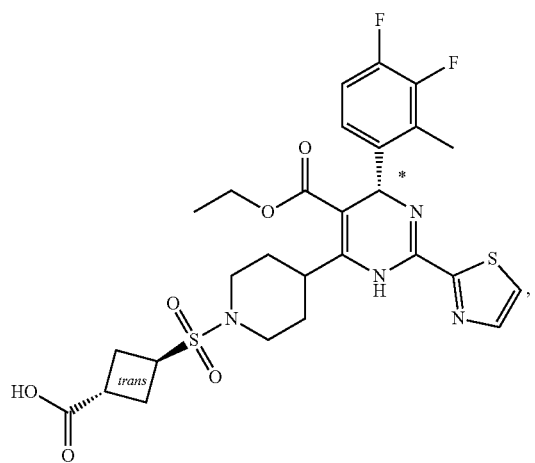
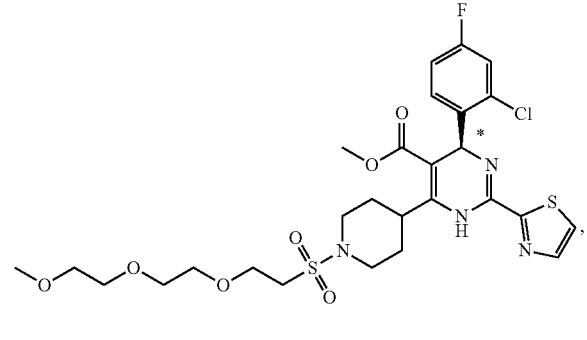

667
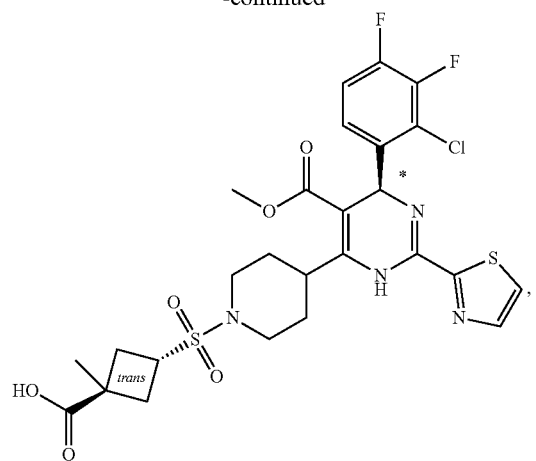
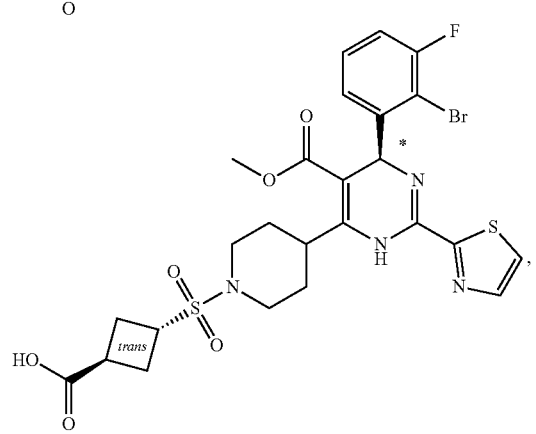
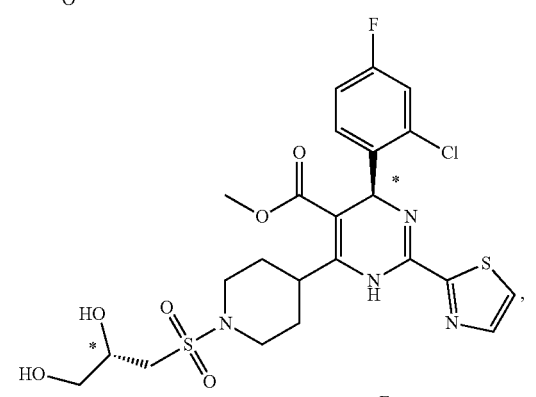
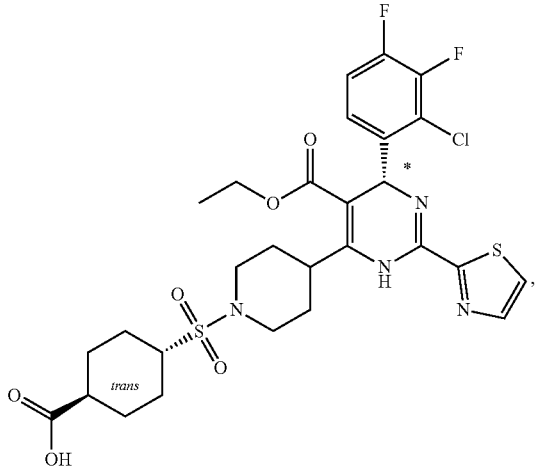
668
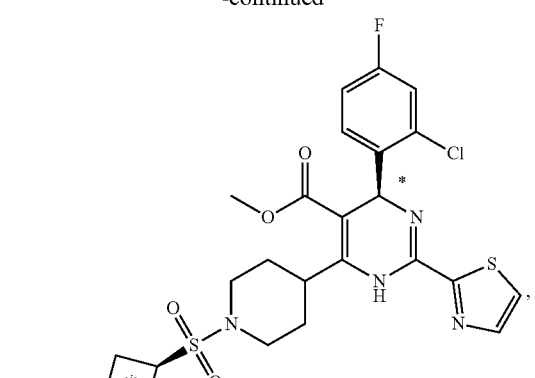
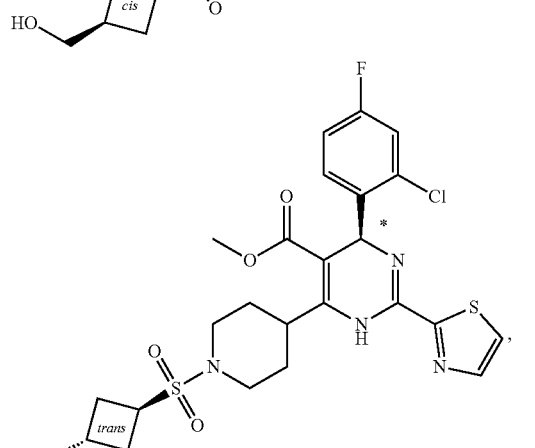
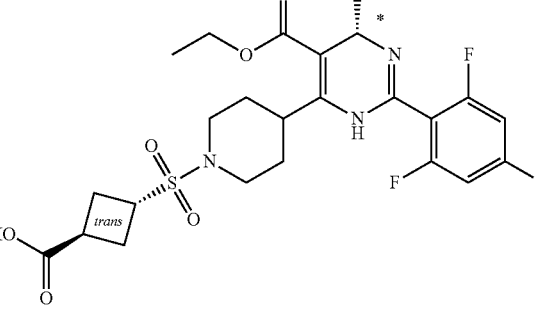
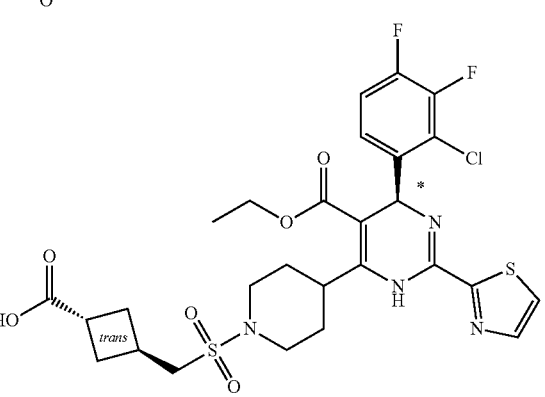

669
-continued
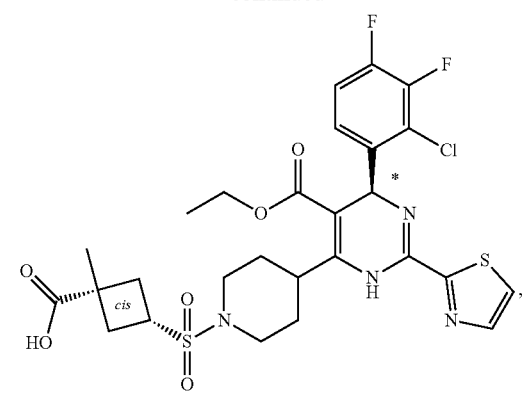
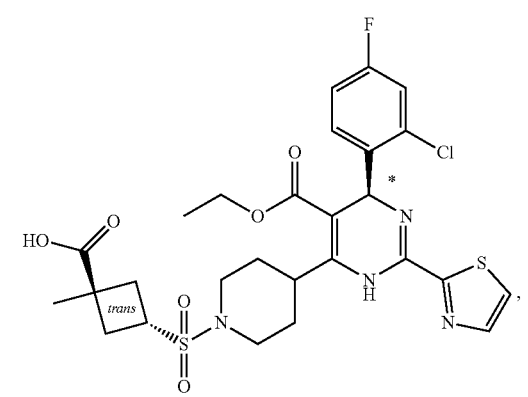
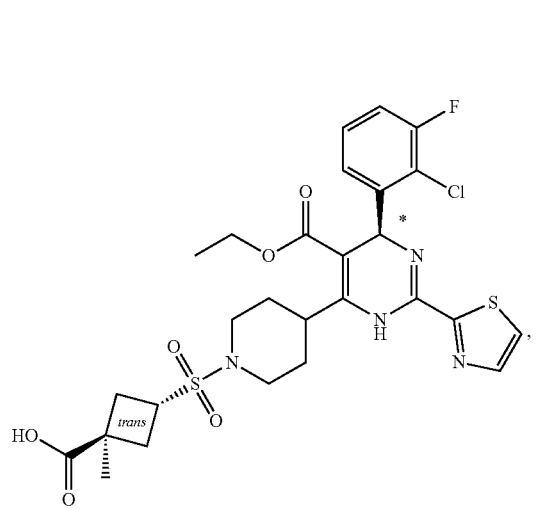
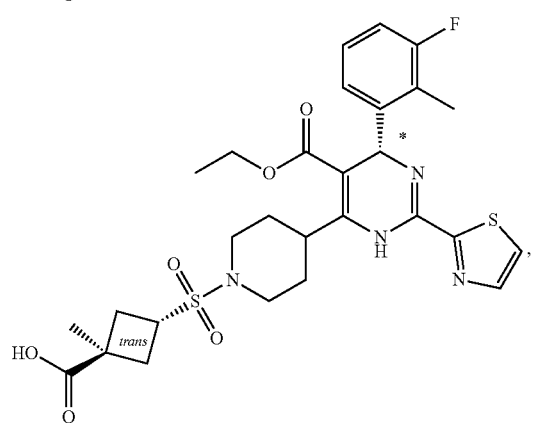
670
-continued
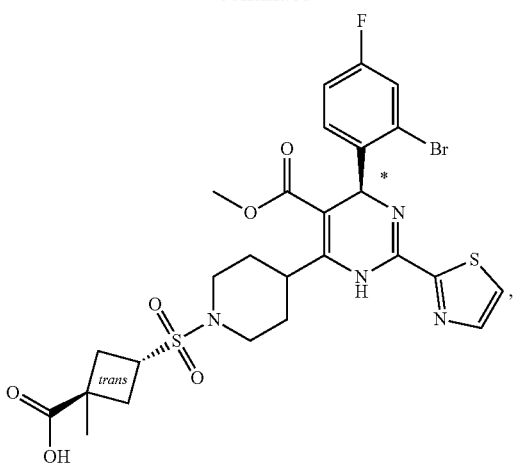
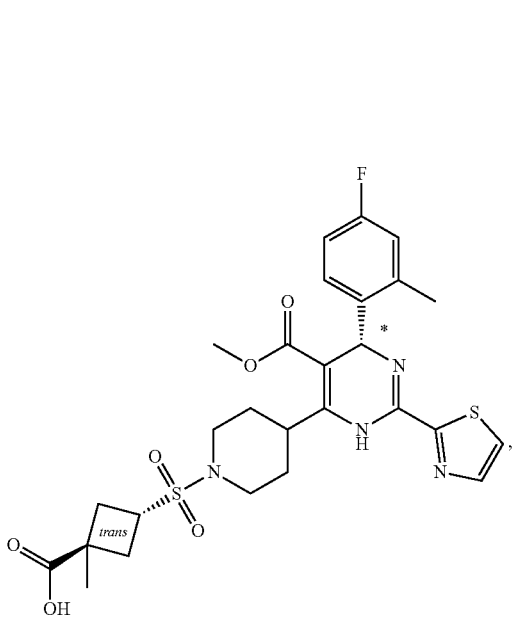
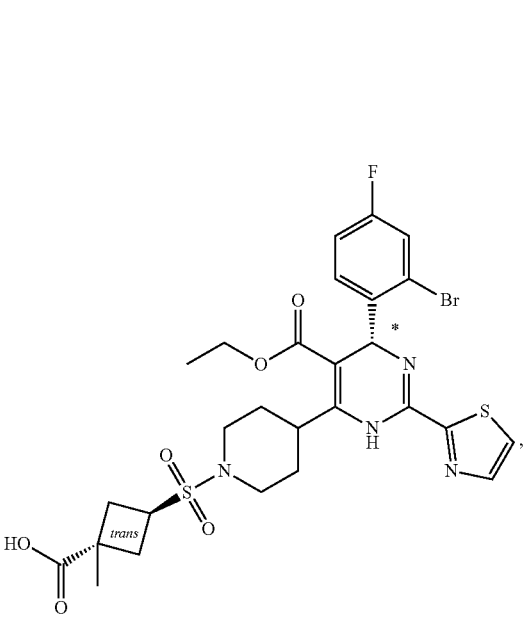

671
-continued
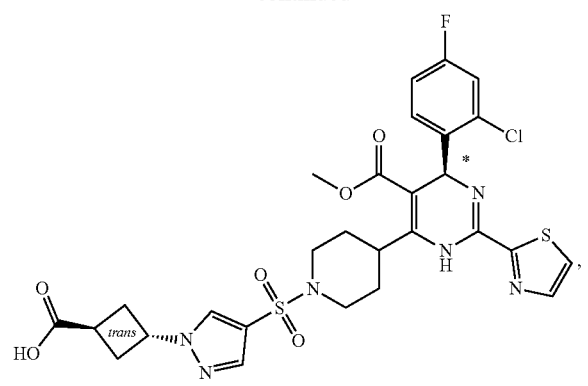
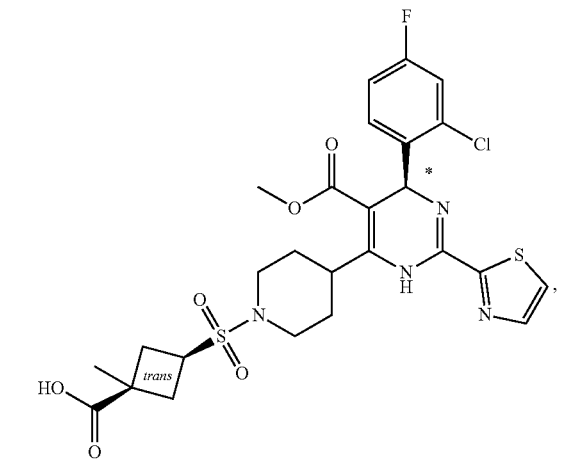
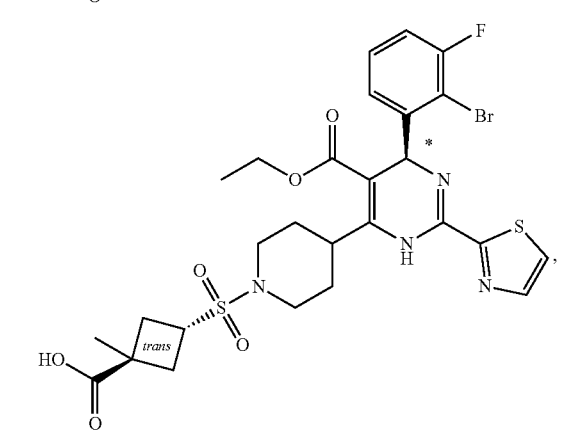
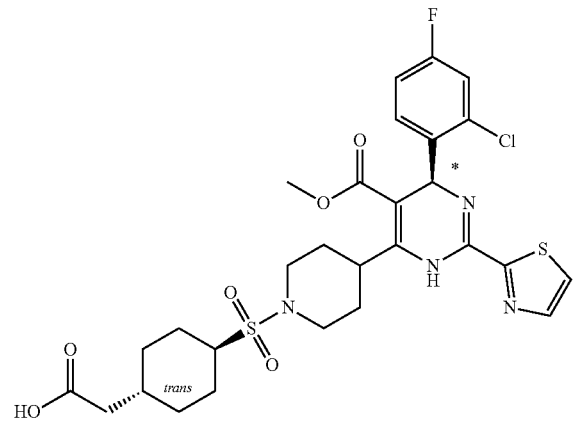
672
-continued
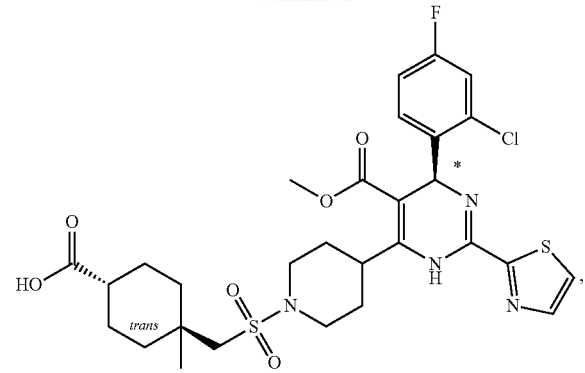
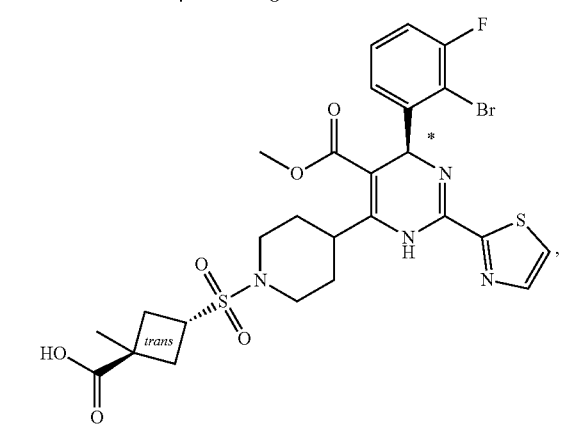
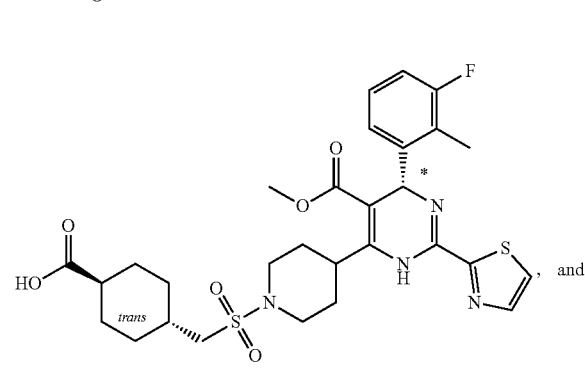
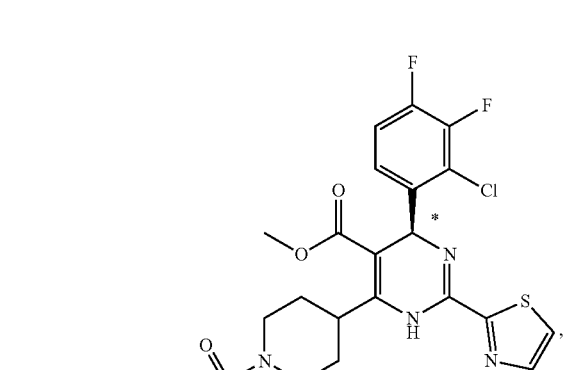
, and
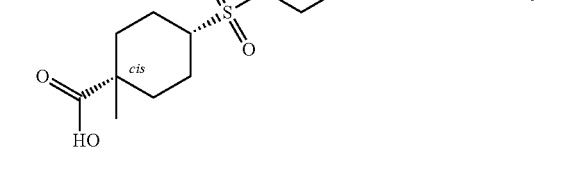
and pharmaceutically acceptable salts thereof.

15. The compound according to claim 1, wherein the compound is

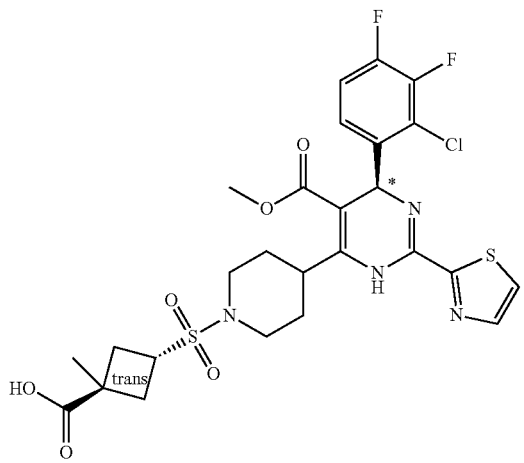 [SMILES: COC(=O)C1=C(C2CCN(S(=O)(=O)[C@H]3C[C@](C)(C(=O)O)C3)CC2)NC(c2nccs2)=N[C@@H]1c1ccc(F)c(F)c1Cl]

or a pharmaceutically acceptable salt thereof.

16. The compound according to claim 1, wherein the compound is

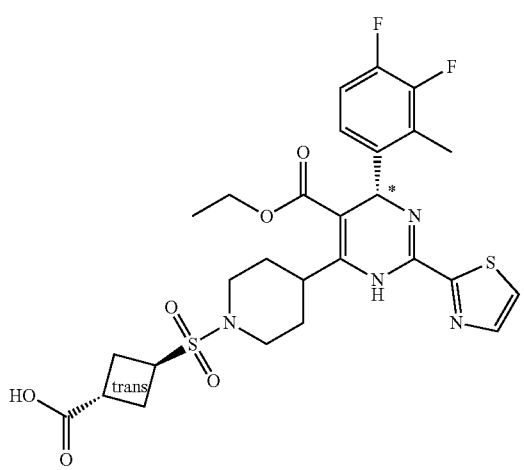 [SMILES: CCOC(=O)C1=C(C2CCN(S(=O)(=O)[C@H]3C[C@H](C(=O)O)C3)CC2)NC(c2nccs2)=N[C@H]1c1ccc(F)c(F)c1C]

or a pharmaceutically acceptable salt thereof.

17. The compound according to claim 1, wherein the compound is

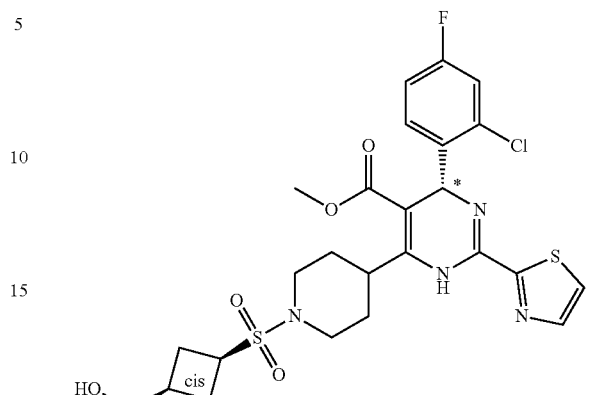

or a pharmaceutically acceptable salt thereof.

18. The compound according to claim 1, wherein the compound is

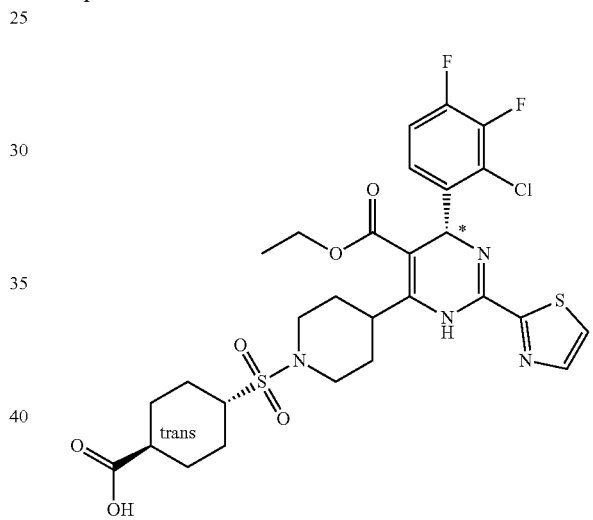

or a pharmaceutically acceptable salt thereof.

19. The compound according to claim 1, wherein the compound is

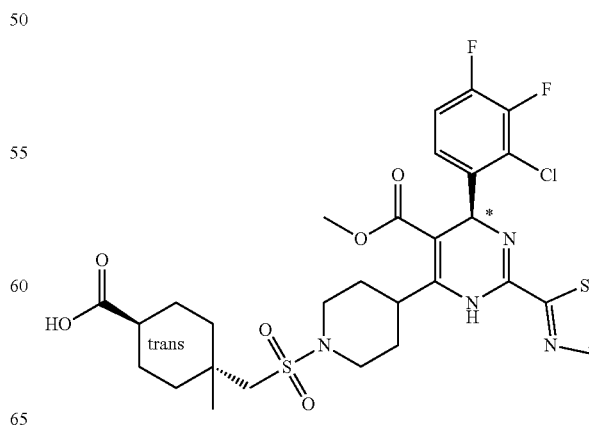

or a pharmaceutically acceptable salt thereof.

20. The compound according to claim 1, wherein the compound is

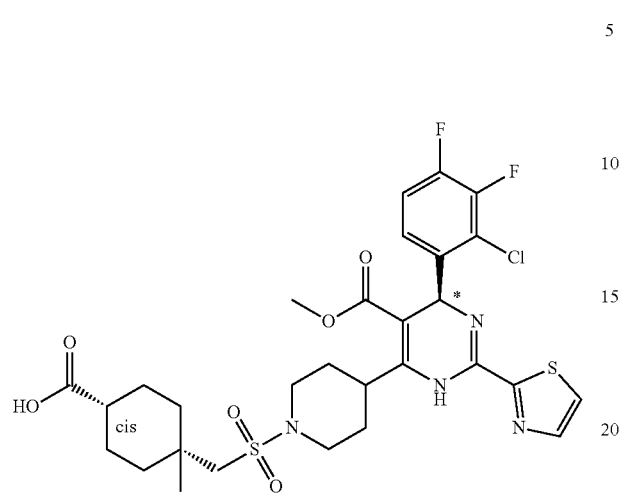

or a pharmaceutically acceptable salt thereof.

21. The compound according to claim 1, wherein the compound is

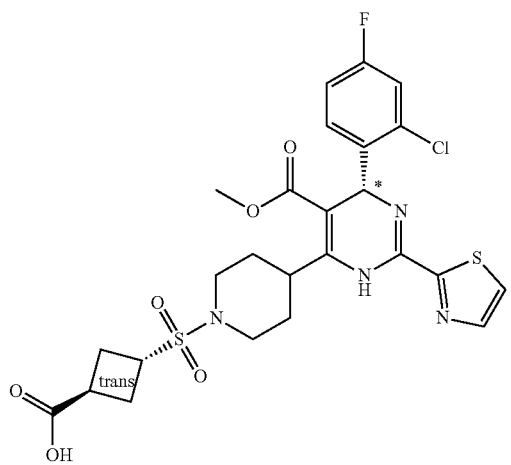 [SMILES: COC(=O)C1=C(C2CCN(S(=O)(=O)[C@H]3C[C@H](C(=O)O)C3)CC2)NC(c2nccs2)=N[C@H]1c1ccc(F)cc1Cl]

or a pharmaceutically acceptable salt thereof.

22. The pharmaceutical composition according to claim 11, wherein $R^4$, $R^5$ and $R^6$ are independently selected from fluoro, chloro or bromo.

23. The pharmaceutical composition according to claim 11, wherein $R^2$ is a 4-7 membered substituted saturated ring optionally containing one or more heteroatoms.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
gtgtctgcgg cgttttatca                                                  20

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
gacaaacggg caacatacct t                                                21

<210> SEQ ID NO 3
<211> LENGTH: 28
<212> TYPE: DNA
<213> ORGANISM: Artificial Sequence
<220> FEATURE:
<223> OTHER INFORMATION: probe

<400> SEQUENCE: 3
cctctkcatc ctgctgctat gcctcatc                                         28
```